US012759982B2

(12) United States Patent
Sugiyama et al.

(10) Patent No.: US 12,759,982 B2
(45) Date of Patent: Oct. 13, 2026

(54) ARYL OR HETEROARYL DERIVATIVE

(71) Applicant: Teijin Pharma Limited, Tokyo (JP)

(72) Inventors: Sakae Sugiyama, Tokyo (JP); Takuya Yokosaka, Tokyo (JP); Kunio Minamizono, Tokyo (JP); Asahi Kawana, Tokyo (JP); Toshiyuki Kaneko, Tokyo (JP); Akinobu Maruyama, Tokyo (JP); Kosuke Sasaki, Tokyo (JP); Shinnosuke Hosoda, Tokyo (JP); Masaki Koshimizu, Tokyo (JP); Susumu Takeuchi, Tokyo (JP); Kenta Kato, Tokyo (JP); Nagasree Chakka, Lexington, MA (US); Brett M. Johnson, South Weymouth, MA (US); Ryan D. White, Somerville, MA (US); Wei Zhao, Westford, MA (US)

(73) Assignee: Teijin Pharma Limited, Tokyo (JP)

( * ) Notice: Subject to any disclaimer, the term of this patent is extended or adjusted under 35 U.S.C. 154(b) by 806 days.

(21) Appl. No.: 17/919,186

(22) PCT Filed: Apr. 15, 2021

(86) PCT No.: PCT/JP2021/015607

§ 371 (c)(1),
(2) Date: Oct. 14, 2022

(87) PCT Pub. No.: WO2021/210650

PCT Pub. Date: Oct. 21, 2021

(65) Prior Publication Data

US 2023/0167073 A1 Jun. 1, 2023

(30) Foreign Application Priority Data

Apr. 16, 2020 (JP) ................................ 2020-073699

(51) Int. Cl.
*C07D 239/42* (2006.01)
*C07D 213/30* (2006.01)
(Continued)

(52) U.S. Cl.
CPC ......... *C07D 239/42* (2013.01); *C07D 213/30* (2013.01); *C07D 231/20* (2013.01);
(Continued)

(58) Field of Classification Search
CPC .. C07D 239/42; C07D 213/30; C07D 231/20; C07D 237/14; C07D 237/22; C07D 239/34; C07D 239/47; C07D 239/48; C07D 239/52; C07D 401/04; C07D 401/12; C07D 401/14; C07D 403/04; C07D 403/12; C07D 403/14; C07D 405/04; C07D 405/12; C07D 405/14; C07D 409/04; C07D 409/12; C07D 413/04; C07D 413/12; C07D 413/14; C07D 417/04; C07D 417/12; C07D 417/14; C07D 471/04; C07D 487/04; C07D 487/12; C07D 491/052; C07D 491/107; C07D 498/08
See application file for complete search history.

(56) References Cited

U.S. PATENT DOCUMENTS 4,044,129 A * 8/1977 Kuwada .................. A61P 25/08 514/315
4,315,926 A 2/1982 Gschwend
(Continued)

FOREIGN PATENT DOCUMENTS

CN 104292233 A 1/2015
CN 106317050 A 1/2017
(Continued)

OTHER PUBLICATIONS

Marinho et al., Tetrahedron, 2010, 66:8681-8689 (Year: 2010).*
(Continued)

*Primary Examiner* — Andrew D Kosar
*Assistant Examiner* — Jonathan D Mahlum
(74) *Attorney, Agent, or Firm* — McCarter & English, LLP; Xin Zhang; Zhongyu "Alex" Wang

(57) ABSTRACT

A compound indicated by formula (I) or a pharmacologically acceptable salt thereof is provided as a compound that can be a therapeutic or prophylactic drug for TRPC6-related diseases, such as nephrotic syndrome, membranous nephropathy, acute renal failure, septicemia, chronic renal failure, diabetic nephropathy, pulmonary hypertension, acute lung injury, heart failure, malignant tumor, and muscular dystrophy. (In the formula, $Ar^1$, $Ar^2$, $X^1$-$X^3$, $R^1$, $R^3$, $R^7$, $R^8$, $L^1$, and $L^2$ are as defined in the specifications.)

(I)

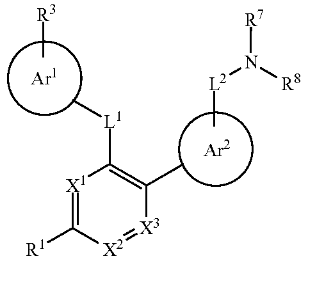

21 Claims, No Drawings

(51) Int. Cl.

| | |
|---|---|
| ***C07D 231/20*** | (2006.01) |
| ***C07D 237/14*** | (2006.01) |
| ***C07D 237/22*** | (2006.01) |
| ***C07D 239/34*** | (2006.01) |
| ***C07D 239/47*** | (2006.01) |
| ***C07D 239/48*** | (2006.01) |
| ***C07D 239/52*** | (2006.01) |
| ***C07D 401/04*** | (2006.01) |
| ***C07D 401/12*** | (2006.01) |
| ***C07D 401/14*** | (2006.01) |
| ***C07D 403/04*** | (2006.01) |
| ***C07D 403/12*** | (2006.01) |
| ***C07D 403/14*** | (2006.01) |
| ***C07D 405/04*** | (2006.01) |
| ***C07D 405/12*** | (2006.01) |
| ***C07D 405/14*** | (2006.01) |
| ***C07D 409/04*** | (2006.01) |
| ***C07D 409/12*** | (2006.01) |
| ***C07D 413/04*** | (2006.01) |
| ***C07D 413/12*** | (2006.01) |
| ***C07D 413/14*** | (2006.01) |
| ***C07D 417/04*** | (2006.01) |
| ***C07D 417/12*** | (2006.01) |
| ***C07D 417/14*** | (2006.01) |
| ***C07D 471/04*** | (2006.01) |
| ***C07D 487/04*** | (2006.01) |
| ***C07D 487/12*** | (2006.01) |
| ***C07D 491/052*** | (2006.01) |
| ***C07D 491/107*** | (2006.01) |
| ***C07D 498/08*** | (2006.01) |

(52) U.S. Cl.

CPC ......... *C07D 237/14* (2013.01); *C07D 237/22* (2013.01); *C07D 239/34* (2013.01); *C07D 239/47* (2013.01); *C07D 239/48* (2013.01); *C07D 239/52* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 405/04* (2013.01); *C07D 405/12* (2013.01); *C07D 405/14* (2013.01); *C07D 409/04* (2013.01); *C07D 409/12* (2013.01); *C07D 413/04* (2013.01); *C07D 413/12* (2013.01); *C07D 413/14* (2013.01); *C07D 417/04* (2013.01); *C07D 417/12* (2013.01); *C07D 417/14* (2013.01); *C07D 471/04* (2013.01); *C07D 487/04* (2013.01); *C07D 487/12* (2013.01); *C07D 491/052* (2013.01); *C07D 491/107* (2013.01); *C07D 498/08* (2013.01)

(56) References Cited

U.S. PATENT DOCUMENTS

| | | | |
|---|---|---|---|
| 2013/0131034 | A1 | 5/2013 | Follmann et al. |
| 2015/0038503 | A1 | 2/2015 | Bourotte et al. |
| 2016/0102095 | A1 | 4/2016 | Wang et al. |
| 2019/0263800 | A1 | 8/2019 | Zhang et al. |

FOREIGN PATENT DOCUMENTS

| | | | | | |
|---|---|---|---|---|---|
| CN | 107250134 | A | | 10/2017 | |
| CN | 107253952 | A | | 10/2017 | |
| GB | 1497827 | A | * | 1/1978 | .............. A61P 25/08 |
| GB | 1518693 | A | * | 7/1978 | ........... C07D 249/08 |
| JP | 5283850 | A | * | 7/1977 | ........... C07D 401/10 |
| WO | WO-2010026214 | A1 | * | 3/2010 | ................ A61P 9/00 |
| WO | 2011/107474 | A1 | | 9/2011 | |
| WO | 2012/037349 | A2 | | 3/2012 | |
| WO | 2012/037351 | A1 | | 3/2012 | |
| WO | WO-2013045519 | A1 | * | 4/2013 | ................ A61P 9/00 |
| WO | 2014/016766 | A1 | | 1/2014 | |
| WO | WO-2014151871 | A2 | * | 9/2014 | ................ A61P 9/10 |
| WO | 2014/192865 | A1 | | 12/2014 | |
| WO | WO-2016149315 | A1 | * | 9/2016 | ........... C07D 417/14 |
| WO | 2019/079578 | A1 | | 4/2019 | |
| WO | 2019/081637 | A1 | | 5/2019 | |
| WO | 2019/118313 | A1 | | 6/2019 | |
| WO | 2019/158572 | A1 | | 8/2019 | |
| WO | 2019/161010 | A1 | | 8/2019 | |
| WO | 2019/208812 | A1 | | 10/2019 | |
| WO | 2020/231990 | A1 | | 11/2020 | |
| WO | 2021/211864 | A1 | | 10/2021 | |

OTHER PUBLICATIONS

Zhang et al., ACS Catalysis, 2018, 8:8324-8335 (Year: 2018).*

Hirai et al., Chem Informationsdienst, 1983, 14 (issue 30):88-89 (Year: 1983).*

Koichiro Kuwahara et al., "TRPC6 fulfills a calcineurin signaling circuit during pathologic cardiac remodeling", The Journal of Clinical Investigation, Dec 2006, vol. 116, No. 12, pp. 3114-3126 (13 pages total).

Jennifer Davis et al., "A TRPC6-dependent pathway for myofibroblast transdifferentiation and wound healing in vivo", Dev Cell, Oct. 16, 2012, vol. 23(4), pp. 705-715 (22 pages total).

Kinya Seo et al., "Hyperactive Adverse Mechanical Stress Responses in Dystrophic Heart Are Coupled to Transient Receptor Potential Canonical 6 and Blocked by cGMP—Protein Kinase G Modulation", Circulation Research, Feb. 28, 2014, pp. 823-832 (20 pages total).

Norbert Weissmann et al., "Classical transient receptor potential channel 6 (TRPC6) is essential for hypoxic pulmonary vasoconstriction and alveolar gas exchange", PNAS, Dec 12, 2006, vol. 103, No. 50, pp. 19093-19098 (6 pages total).

Annemarieke E. Loot et al., "Cytochrome P450-Derived Epoxyeicosatrienoic Acids and Pulmonary Hypertension: Central Role of Transient Receptor Potential C6 Channels", J Cardiovasc Pharmacol, Feb. 2011, vol. 57, No. 2, pp. 140-147 (8 pages total).

Yang Xia et al., "Classical Transient Receptor Potential 1 and 6 Contribute to Hypoxic Pulmonary Hypertension Through Differential Regulation of Pulmonary Vascular Functions", Hypertension, Jan. 2014, pp. 173-180 (18 pages total).

S. Sel et al., "Loss of classical transient receptor potential 6 channel reduces allergic airway response", Clinical and Experimental Allergy, 2008, vol. 38, pp. 1548-1558 (11 pages total).

N. Damann et al., "The calcium-conducting ion channel transient receptor potential canonical 6 is involved in macrophage inflammatory protein-2-induced migration of mouse neutrophils", Acta Physiol, 2009, vol. 195, pp. 3-11 (9 pages total).

Mohammad Tauseef et al., "TLR4 activation of TRPC6-dependent calcium signaling mediates endotoxin-induced lung vascular permeability and inflammation", J. Exp. Med., 2012, vol. 209, No. 11, pp. 1953-1968 (16 pages total).

Wen Chen et al., "Atrial Natriuretic Peptide-Mediated Inhibition of Microcirculatory Endothelial $Ca^{2+}$ and Permeability Response to Histamine Involves cGMP-Dependent Protein Kinase I and TRPC6 Channels", Arterioscler Thromb Vasc Biol, Sep. 2013, pp. 2121-2129 (15 pages total).

Paola Krall et al., "Podocyte-Specific Overexpression of Wild Type or Mutant Trpc6 in Mice Is Sufficient to Cause Glomerular Disease", PLoS One, Sep. 2010, vol. 5, Issue 9, e12859, pp. 1-11 (11 pages total).

Xia Ding et al., "Targeting TRPC6 channels in oesophageal carcinoma growth", Expert Opin. Ther. Targets, 2010, vol. 14(5), pp. 513-527 (15 pages total).

Sandra Bernaldo De Quiros et al., "Identification of TRPC6 as a possible candidate target gene within an amplicon at 11q21-q22.2 for migratory capacity in head and neck squamous cell carcinomas", BMC Cancer, 2013, vol. 13:116, pp. 1-11 (11 pages total).

(56) References Cited

OTHER PUBLICATIONS

Michelle P. Winn et al., "A Mutation in the TRPC6 Cation Channel Causes Familial Focal Segmental Glomerulosclerosis", Science, Jun. 17, 2005, vol. 308, pp. 1801-1804 (5 pages total).
Jochen Reiser et al., "TRPC6 is a glomerular slit diaphragm-associated channel required for normal renal function", Nat Genet., Jul. 2005, vol. 37(7), pp. 739-744 (15 pages total).
Saskia F. Heeringa et al., "A Novel TRPC6 Mutation That Causes Childhood FSGS", PLoS One, Nov. 2009, vol. 4, Issue 11, e7771, pp. 1-8 (8 pages total).
Sheila Santin et al., "Clinical Utility of Genetic Testing in Children and Adults with Steroid-Resistant Nephrotic Syndrome", Clinical Journal of the American Society of Nephrology, May 2011, vol. 6, pp. 1139-1148 (10 pages total).
Shoichiro Kanda et al., "Tyrosine phosphorylation-dependent activation of TRPC6 regulated by PLC-γ1 and nephrin: effect of mutations associated with focal segmental glomerulosclerosis", Molecular Biology of the Cell, Jun. 1, 2011, vol. 22, pp. 1824-1835 (12 pages total).
Amy K Mottl et al., "A novel TRPC6 mutation in a family with podocytopathy and clinical variability", BMC Nephrology, 2013, vol. 14:104 (12 pages total).
Xin-Yu Kuang et al., "254C>G: a TRPC6 promoter variation associated with enhanced transcription and steroid-resistant nephrotic syndrome in Chinese children", Pediatric Research, Nov. 2013, vol. 74, No. 5, pp. 511-516 (6 pages total).
Julia M. Hofstra et al., "New TRPC6 gain-of-function mutation in a non-consanguineous Dutch family with late-onset focal segmental glomerulosclerosis", Nephrol Dial Transplant, 2013, vol. 28, pp. 1830-1838 (9 pages total).
Ying Yu et al., "A Functional Single-Nucleotide Polymorphism in the TRPC6 Gene Promoter Associated With Idiopathic Pulmonary Arterial Hypertension", Circulation, May 5, 2009, pp. 2313-2322 (25 pages total).
Clemens C. Möller et al., "Induction of TRPC6 Channel in Acquired Forms of Proteinuric Kidney Disease", J Am Soc Nephrol, 2007, vol. 18, pp. 29-36 (8 pages total).
Yanqin Fu et al., "Increased TRPC6 expression is associated with tubular epithelial cell proliferation and inflammation in diabetic nephropathy", Molecular Immunology, 2018, vol. 94, pp. 75-81 (7 pages total).
Luoqiang Zhang et al., Experimental and Theoretical Studies on Ru(II)-Catalyzed Oxidative C—H/C—H Coupling of Phenols with Aromatic Amides Using Air as Oxidant: Scope, Synthetic Applications, and Mechanistic Insights, ACS Catal., 2018, vol. 8, pp. 8324-8335 (12 pages total).
Elina Marinho et al., "The reaction of anthranilonitrile and triethylorthoformate revisited: formation of dimeric and trimeric species", Tetrahedron, 2010, vol. 66, pp. 8681-8689 (9 pages total).
International Search Report dated Jun. 1, 2021 issued by the International Searching Authority in Application No. PCT/JP2021/015607.
Written Opinion dated Jun. 1, 2021 issued by the International Searching Authority in Application No. PCT/JP2021/015607.
Zhang et al., Highly Regio- and Chemoselective Oxidative C—H/C—H Cross-Couplings of Anilines and Phenols Enabled by a Co-Oxidant-Free Rh(1)/Zn(NTf2)2/Air Catalytic System. ACS Catal. 2019;9:5358-5364.

* cited by examiner

ARYL OR HETEROARYL DERIVATIVE

CROSS REFERENCE TO RELATED APPLICATIONS

This application is a National Stage of International Application No. PCT/JP2021/015607 filed Apr. 15, 2021, claiming priority based on Japanese Patent Application No. 2020-073699 filed Apr. 16, 2020.

TECHNICAL FIELD

The present invention relates to aryl or heteroaryl derivatives useful as pharmaceutical agents. More specifically, the present invention relates to aryl or heteroaryl derivatives or pharmaceutically acceptable salts thereof useful for the treatment or prevention of diseases in which a TRPC6 inhibitor may be involved, such as nephrotic syndrome, membranous nephropathy, acute renal failure, sepsis, chronic renal failure, diabetic nephropathy, pulmonary hypertension, acute lung injury, heart failure, malignant tumor, or muscular dystrophy.

BACKGROUND ART

The TRPC6 channel, a member of the Transient receptor potential (TRP) family, which is a non-selective cation-permeable channel, is activated by diacylglycerol and the like produced by activation of phospholipase C and exerts physiological and pathophysiological effects. TRPC6 has effects such as pathological cardiac hypertrophy and fibrosis, progression of myocardial damage in muscular dystrophy, acute pulmonary vasoconstriction, pathological progression associated with chronic hypoxia-induced pulmonary hypertension, allergic immune response, migration of cells such as neutrophils, increased endothelial permeability on inflammation, pathological flattening of podocytes foot processes and following progression of glomerular injury, and proliferation or infiltration of malignant tumors, and is diversely distributed in the brain, heart, lungs, kidneys, placenta, ovaries, spleen, and the like (NPLs 1 to 13). In familial focal segmental glomerulosclerosis (FSGS), a gain-of-function mutant of TRPC6 has been identified, and in idiopathic nephrotic syndrome or idiopathic pulmonary arterial hypertension patients, a variant in the promoter region that increases mRNA expression of TRPC6 has been identified. Thus, it is considered that enhanced activation or increased expression of TRPC6 contributes to pathological progression of nephrotic syndrome, pulmonary hypertension, and the like (NPLs 14 to 22). Furthermore, increased expression of TRPC6 has been reported in minimal change nephrotic syndrome, membranous nephropathy, and diabetic nephropathy (NPLs 23 to 24). Thus, TRPC6 inhibitors, which inhibit ion influx via the TRPC6 channel, are expected to be useful for prevention and/or treatment of such as nephrotic syndrome, membranous nephropathy, acute renal failure, sepsis, chronic renal failure, diabetic nephropathy, pulmonary hypertension, acute lung injury, heart failure, malignant tumor, muscular dystrophy or the like. Compounds inhibiting TRPC6 are described in PLTs 1 to 11.

CITATION LIST

Patent Literature

[PTL 1] WO2011/107474
[PTL 2] WO2012/037349
[PTL 3] WO2012/037351
[PTL 4] WO2014/016766
[PTL 5] Chinese Patent Application Publication No. 104292233
[PTL 6] Chinese Patent Application Publication No. 106317050
[PTL 7] Chinese Patent Application Publication No. 107253952
[PTL 8] WO2019/079578
[PTL 9] WO2019/081637
[PTL 10] WO2019/158572
[PTL 11] WO2019/161010

Non Patent Literature

[NPL 1] J. Clin. Invest. 116: 3114-3126, 2006
[NPL 2] Dev. Cell. 23: 705-715, 2012
[NPL 3] Circ. Res. 114: 823-832, 2014
[NPL 4] Proc. Natl. Acd. Sci. USA 103: 19093-19098, 2006
[NPL 5] J. Cardiovasc. Pharmacol. 57: 140-147, 2011
[NPL 6] Hypertension 63: 173-80, 2014
[NPL 7] Clin. Exp. Allergy 38: 1548-1558, 2008
[NPL 8] Acta. Physiol. 195: 3-11, 2009
[NPL 9] J. Exp. Med. 209: 1953-1968, 2011
[NPL 10] Arterioscler. Thromb. Vasc. Biol. 33: 2121-2129, 2013
[NPL 11] PLoS ONE 5: e12859, 2010
[NPL 12] Expert. Opin. Ther. Targets. 14: 513-27, 2010
[NPL 13] BMC Cancer 13:116, 2013
[NPL 14] Science 308: 1801-1804, 2005
[NPL 15] Nat. Genet. 37: 739-744, 2005
[NPL 16] PLoS One 4: e7771, 2009
[NPL 17] Clin. J. Am. Soc. Nephrol. 6: 1139-1148, 2011
[NPL 18] Mol. Biol. Cell. 22: 1824-1835, 2011
[NPL 19] BMC Nephrol. 14:104, 2013
[NPL 20] Pediatr. Res. 74: 511-516, 2013
[NPL 21] Nephrol. Dial. Transplant. 28: 1830-1838, 2013
[NPL 22] Circulation 119: 2313-2322, 2009
[NPL 23] J. Am. Soc. Nephrol. 18: 29-36, 2007
[NPL 24] Mol Immunol. February; 94:75-81, 2018.

SUMMARY OF INVENTION

Technical Problem

An object of the present invention is to provide a novel compound having a TRPC6-inhibitory effect or a pharmaceutically acceptable salt thereof, a pharmaceutical composition comprising the compound, and a therapeutic agent or prophylactic agent for diseases associated with TRPC6.

Solution to Problem

As a result of diligent studies for the above-mentioned purpose, the present inventors arrived at the following invention.

[1] A compound represented by the formula (I) or a pharmaceutically acceptable salt thereof.

[Chem. 1]

(I)

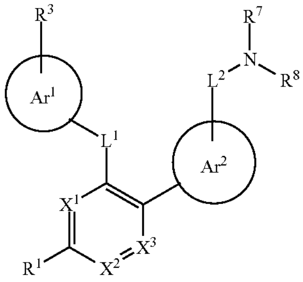

[wherein, $X^1$, $X^2$, and $X^3$ are independently CH, N, or CY;

At least one of $X^1$, $X^2$, and $X^3$ is CH or CY;

Y is a halogen atom, or a $C_{1-3}$ alkyl group optionally substituted with 1 to 3 halogen atoms;

$R^1$ is a cyano group, a fluorine atom, or a chlorine atom;

$L^1$ is —O—, —S—, —SO—, —CH($R^{11}$)—, —C(═$CH_2$)—, —CO—, 1,1-cyclopropylidene group, or —$NR^{12}$—;

$R^{11}$ is a hydrogen atom, a hydroxy group, a $C_{1-3}$ alkyl group optionally substituted with 1 to 3 halogen atoms, or a $C_{1-3}$ alkoxy group optionally substituted with 1 to 2 cyano groups;

$R^{12}$ is a hydrogen atom, or a $C_{1-3}$ alkyl group optionally substituted with 1 to 3 halogen atoms;

$Ar^1$ is a nitrogen-containing heteroaryl ring optionally substituted with 1 to 3 $R^2$.

$R^2$ is independently a halogen atom, a cyano group, or a $C_{1-4}$ alkyl group optionally substituted with 1 to 3 halogen atoms;

$R^3$ is a hydrogen atom, a halogen atom, an amino group, a cyano group, a carboxy group, a ($C_{1-3}$ alkylcarbonyl) amino group, a ($C_{1-6}$ alkylamino)carbonyl group, a di($C_{1-3}$ alkyl)aminocarbonyl group, a ($C_{1-3}$ alkoxy)carbonyl group, a ($C_{3-8}$ cycloalkyl)amino group, a ($C_{3-8}$ heterocycloalkyl)amino group, a $C_{3-8}$ cycloalkyl group, a 3- to 8-membered heterocycloalkyloxy group, a $C_{3-8}$ cycloalkyloxy group optionally substituted with 1 to 6 $R^{31}$, a $C_{1-6}$ alkyl group optionally substituted with 1 to 6 $R^{31}$, a $C_{1-6}$ alkoxy group optionally substituted with 1 to 6 $R^3$, a di($C_{1-6}$ alkyl)amino group optionally substituted with 1 to 6 $R^{31}$, a ($C_{1-6}$ alkyl)amino group optionally substituted with 1 to 6 $R^{31}$, a 3- to 8-membered heterocycloalkyl group optionally substituted with 1 to 4 $R^{32}$, an aryl group optionally substituted with 1 to 4 $R^{32}$, or a heteroaryl group optionally substituted with 1 to 4 $R^{32}$;

$R^{31}$ is independently a halogen atom, a hydroxy group, a cyclopropylidene group, a $C_{3-8}$ cycloalkyl group optionally substituted with 1 to 3 halogen atoms, a 3- to 8-membered heterocycloalkyl group, an oxetanylidene group, a $C_{1-4}$ alkoxy group, or a 3- to 8-membered cycloalkyloxy group;

$R^{32}$ is independently a halogen atom, a hydroxy group, an acetylamino group, a $C_{1-3}$ alkyl group optionally substituted with 1 to 3 halogen atoms, a $C_{1-3}$ alkoxy group optionally substituted with 1 to 3 halogen atoms, an oxo group, a cyano group, a carboxy group, a ($C_{1-3}$ alkoxy) carbonyl group, a ($C_{1-3}$ alkyl)sulfonyl group, a carboxamide group, or a benzyloxy group;

when $R^2$ and $R^3$ are bonded to atoms adjacent to each other on $Ar^1$, $R^2$ and $R^3$ may be bonded via a single bond or —O— to form a 5- to 7-membered ring together with the atoms of $Ar^1$ to which they are bonded;

$Ar^2$ is an aryl ring optionally substituted with 1 to 4 $R^4$, or a heteroaryl ring optionally substituted with 1 to 4 $R^4$;

$R^4$ is independently a halogen atom, a hydroxy group, a carboxy group, a cyano group, a cyanomethyl group, an amino group, a di($C_{1-3}$ alkyl)amino group, a $C_{1-3}$ alkyl group optionally substituted with 1 to 3 halogen atoms, or $C_{1-3}$ alkoxy group;

$L^2$ is a single bond, a $C_{1-6}$ alkylene group optionally substituted with 1 to 3 $R^{21}$, a $C_{3-8}$ cycloalkylene group optionally substituted with 1 to 3 $R^{21}$, or a 4- to 8-membered heterocycloalkylene group optionally substituted with 1 to 3 $R^{21}$;

$L^2$ may be bonded at any position to $Ar^2$ or —$NR^7R^8$ which is located at either end of it;

One $sp^3$ carbon atom at any position of $L^2$ may be replaced by a structure of —O or —$NR^{22}$—;

$R^{21}$ is independently a halogen atom, a hydroxy group, an oxo group, a cyano group, a 1,1-cyclopropylidene group, an oxetanylidene group, a carboxy group, a carboxamide group, a $C_{1-6}$ alkyl group optionally substituted with 1 to 3 halogen atoms, a $C_{3-8}$ cycloalkyl group, a $C_{1-6}$ alkoxy group, a ($C_{1-3}$ alkoxy)$C_{1-3}$ alkyl group, a ($C_{1-3}$ alkoxy)$C_{1-3}$ alkoxy group, a (hydroxy) $C_{1-6}$ alkyl group, a (carboxy)$C_{1-3}$ alkyl group, a (carboxy)$C_{1-3}$ alkoxy group, a ($C_{1-3}$ alkoxy)carbonyl group, a ($C_{1-3}$ alkoxycarbonyl)$C_{1-3}$ alkyl group, a ($C_{1-6}$ alkylamino)carbonyl group, a di($C_{1-3}$ alkyl)aminocarbonyl group, a phenyl group optionally substituted with 1 to 3 halogen atoms, a heteroaryl group optionally substituted with 1 to 3 halogen atoms, or a phenoxy group optionally substituted with 1 to 3 halogen atoms;

$R^{22}$ is a hydrogen atom or a $C_{1-3}$ alkyl group;

$L^2$ and $R^7$ may be bonded via a single bond, —O—, —S(═O)$_n$—, or —$NR^{23}$— to form a 4- to 8-membered ring containing a nitrogen atom to which $L^2$ and $R^7$ are bonded, and the ring is optionally substituted with 1 to 3 halogen atoms or 1 to 2 hydroxy groups;

n represents an integer from 0 to 2;

$R^{23}$ is a hydrogen atom or a $C_{1-3}$ alkyl group;

when $L^2$ and $R^4$ are bonded to atoms adjacent to each other on $Ar^2$, they may be bonded via a single-bond or —O— to form a 5- to 8-membered ring together with the atoms of $Ar^2$ to which they are bonded;

$R^7$ is a hydrogen atom, or $C_{1-3}$ alkyl group;

$R^7$ and an atom of $Ar^2$ may be bonded via a single bond to form a 5- to 8-membered ring;

$R^8$ is a hydrogen atom, a $C_{1-6}$ alkyl group, an adamantyl group, a $C_{1-6}$ cycloalkyl group, a cyanomethyl group, an oxetanyl group, a ($C_{1-3}$ alkylamino)carbonylmethyl group, a di($C_{1-3}$ alkyl)aminocarbonylmethyl group, a ($C_{1-3}$ alkylamino)$C_{1-8}$ alkyl group, a di($C_{1-3}$ alkyl)amino$C_{1-8}$ alkyl group, a (hydroxy)$C_{1-8}$ alkyl group, a (carboxy)$C_{1-3}$ alkyl group, a ($C_{1-3}$ alkoxycarbonyl)$C_{1-3}$ alkyl group, or a ($C_{1-3}$ alkoxy)$C_{1-3}$ alkyl group;

$R^7$ and $R^8$ may be bonded each other via a single bond, —O—, —S(═O)$_m$—, or —$NR^{41}$— to form a 3- to 8-membered ring, and further, the ring is optionally substituted with an amino group, an oxo group, or a $C_{1-3}$ alkyl group;

m represents an integer from 0 to 2;

$R^{41}$ is a hydrogen atom or a $C_{1-3}$ alkyl group.]

[2] The compound according to [1] or a pharmaceutically acceptable salt thereof, wherein $X^1$, $X^2$, and $X^3$ are CH.

[3] The compound according to [1] or [2] or a pharmaceutically acceptable salt thereof, wherein $R^1$ is a cyano group.

[4] The compound according to [1] or [2] or a pharmaceutically acceptable salt thereof, wherein $R^1$ is a fluorine atom.

[5] The compound according to any one of [1] to [4] or a pharmaceutically acceptable salt thereof, wherein the nitrogen-containing heteroaryl ring of $Ar^1$ is one of the following groups:

[Chem. 2]

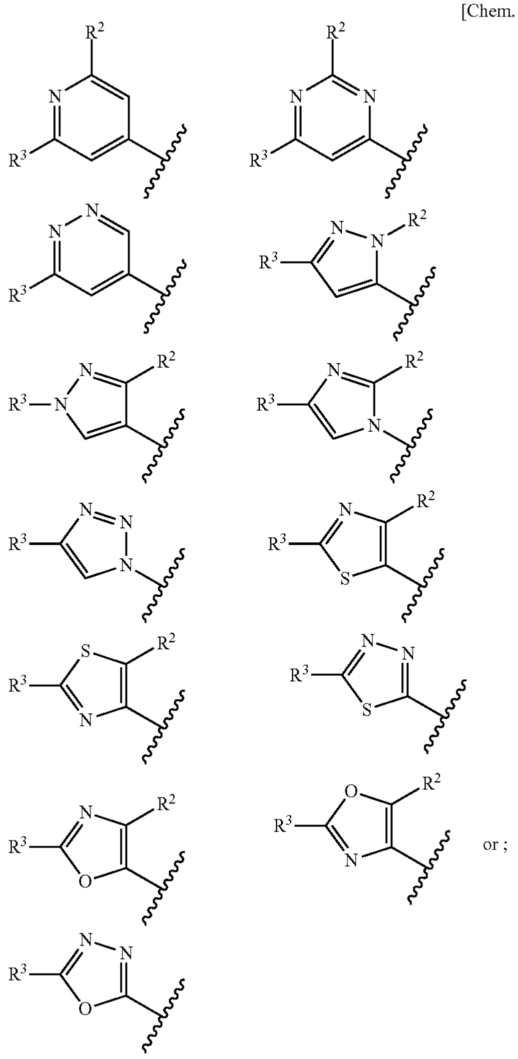

or ;

[6] The compound according to any one of [1] to [5] or a pharmaceutically acceptable salt thereof, wherein $L^1$ is —O—.

[7] The compound according to any one of [1] to [5] or a pharmaceutically acceptable salt thereof, wherein $L^1$ is —CO—.

[8] The compound according to any one of [1] to [5] or a pharmaceutically acceptable salt thereof, wherein $L^1$ is —$CH_2$—.

[9] The compound according to any one of [1] to [8] or a pharmaceutically acceptable salt thereof, wherein $R^2$ is a methyl group.

[10] The compound according to any one of [1] to [9] or a pharmaceutically acceptable salt thereof, wherein $R^3$ is a $C_{3-8}$ cycloalkyl group, a 3- to 8-membered heterocycloalkyloxy group, a $C_{3-8}$ cycloalkyloxy group optionally substituted with 1 to 6 $R^{31}$, a $C_{1-6}$ alkyl group optionally substituted with 1 to 6 $R^{31}$, a $C_{1-6}$ alkoxy group optionally substituted with 1 to 6 $R^{31}$, a di($C_{1-4}$ alkyl)amino group optionally substituted with 1 to 6 $R^{31}$, a ($C_{1-6}$ alkyl)amino group optionally substituted with 1 to 6 $R^{31}$, a 3- to 8-membered heterocycloalkyl group optionally substituted with 1 to 4 $R^{32}$, an aryl group optionally substituted with 1 to 4 $R^{32}$, or a heteroaryl group optionally substituted with 1 to 4 $R^{32}$.

[11] The compound according to any one of [1] to [10] or a pharmaceutically acceptable salt thereof, wherein $R^{31}$ is a halogen atom, a cyclopropylidene group, or a $C_{1-4}$ alkoxy group.

[12] The compound according to any one of [1] to [11] or a pharmaceutically acceptable salt thereof, wherein $R^{32}$ is a halogen atom, a $C_{1-3}$ alkyl group optionally substituted with 1 to 3 halogen atoms, a $C_{1-3}$ alkoxy group optionally substituted with 1 to 3 halogen atoms, an oxo group or a cyano group.

[13] The compound according to any one of [1] to [12] or a pharmaceutically acceptable salt thereof, wherein the heteroaryl ring of $Ar^2$ is

[Chem. 3]

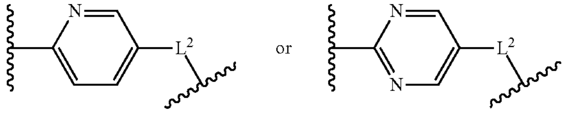

[14] The compound according to any one of [1] to [13] or a pharmaceutically acceptable salt thereof, wherein $L^2$ is a $C_{1-3}$ alkylene group optionally substituted with 1 to 2 $R^{21}$.

[15] The compound according to any one of [1] to [13] or a pharmaceutically acceptable salt thereof, wherein $L^2$ is —$CH_2$—.

[16] The compound according to any one of [1] to [13] or a pharmaceutically acceptable salt thereof, wherein $L^2$ is —$CH_2CH_2$—.

[17] The compound according to any one of [1] to [16] or a pharmaceutically acceptable salt thereof, wherein $R^7$ is a hydrogen atom.

[18] The compound according to any one of [1] to [17] or a pharmaceutically acceptable salt thereof, wherein $R^8$ is a hydrogen atom.

[19] The compound according to [1] or a pharmaceutically acceptable salt thereof, wherein the compound represented by the formula (I) is selected from the following (1) to (150):

(1) 4-[5-(2-aminoethyl)pyridin-2-yl]-3-(2-methyl-6-morpholin-4-ylpyridin-4-yl)oxybenzonitrile (2) 4-[5-(2-aminoethyl)pyridin-2-yl]-3-(2-methyl-5-phenylpyrazol-3-yl)oxybenzonitrile (3) 4-[5-(2-aminoethyl)pyridin-2-yl]-3-(2-methyl-5-pyridin-2-ylpyrazol-3-yl)oxybenzonitrile (4) 4-[5-(2-aminoethyl)pyridin-2-yl]-3-[2-methyl-5-(5-methylpyridin-2-yl)pyrazol-3-yl]oxybenzonitrile (5) 4-[5-(2-aminoethyl)pyridin-2-yl]-3-[5-(4-fluorophenyl)-2-methylpyrazol-3-yl]oxybenzonitrile (6) 4-[5-(2-aminoethyl)pyridin-2-yl]-3-[5-(3-fluorophenyl)-2-methylpyrazol-3-yl]oxybenzonitrile
(7) 4-[5-(2-aminoethyl)pyridin-2-yl]-3-(5-cyclopropyl-2-methylpyrazol-3-yl)oxybenzonitrile
(8) 4-[5-(2-aminoethyl)pyridin-2-yl]-3-[2-methyl-5-(2-methylpropyl)pyrazol-3-yl]oxybenzonitrile
(9) 4-[5-(2-aminoethyl)pyridin-2-yl]-3-(2-methyl-5-propan-2-ylpyrazol-3-yl)oxybenzonitrile
(10) 4-[5-(2-aminoethyl)pyridin-2-yl]-3-(2-methyl-5-propylpyrazol-3-yl)oxybenzonitrile
(11) 4-[5-(2-aminoethyl)pyridin-2-yl]-3-(5-cyclobutyl-2-methylpyrazol-3-yl)oxybenzonitrile
(12) 4-[5-(2-aminoethyl)pyrimidin-2-yl]-3-(2-methyl-6-morpholin-4-ylpyridin-4-yl)oxybenzonitrile
(13) 4-[5-(2-aminoethyl)pyridin-2-yl]-3-(2-methyl-6-pyrrolidin-1-ylpyridin-4-yl)oxybenzonitrile
(14) 4-[5-(2-aminoethyl)pyridin-2-yl]-3-(2-methyl-6-pyridin-2-ylpyridin-4-yl)oxybenzonitrile
(15) 4-[5-(2-aminoethyl)pyrimidin-2-yl]-3-(2-methyl-5-propylpyrazol-3-yl)oxybenzonitrile
(16) 4-[5-(2-aminoethyl)pyrimidin-2-yl]-3-(2-methyl-5-propan-2-ylpyrazol-3-yl)oxybenzonitrile
(17) 4-[5-(2-aminoethyl)pyrimidin-2-yl]-3-(2-methyl-6-pyrrolidin-1-ylpyridin-4-yl)oxybenzonitrile
(18) 4-[5-(2-aminoethyl)pyridin-2-yl]-3-[2-methyl-5-(trifluoromethyl)pyrazol-3-yl]oxybenzonitrile
(19) 4-[5-(2-aminoethyl)pyrimidin-2-yl]-3-(5-cyclobutyl-2-methylpyrazol-3-yl)oxybenzonitrile
(20) 4-[5-(2-aminoethyl)pyrimidin-2-yl]-3-(2-methyl-5-phenylpyrazol-3-yl)oxybenzonitrile
(21) 4-[5-(2-aminoethyl)pyrimidin-2-yl]-3-(2-methyl-6-phenylpyrimidin-4-yl)oxybenzonitrile
(22) 4-[5-(2-aminoethyl)pyrimidin-2-yl]-3-(6-phenylpyridazin-4-yl)oxybenzonitrile
(23) 4-[5-(2-aminoethyl)pyrimidin-2-yl]-3-(2-methyl-5-pyridin-2-ylpyrazol-3-yl)oxybenzonitrile
(24) 4-[5-(2-aminoethyl)pyridin-2-yl]-3-(5-ethyl-2-methylpyrazol-3-yl)oxybenzonitrile
(25) 4-[5-(aminomethyl)pyridin-2-yl]-3-(2-methyl-5-phenylpyrazol-3-yl)oxybenzonitrile
(26) 4-[5-(2-aminoethyl)pyrimidin-2-yl]-3-(5-ethyl-2-methylpyrazol-3-yl)oxybenzonitrile
(27) 4-[5-(2-aminoethyl)pyrimidin-2-yl]-3-[6-(2-cyanophenyl)-2-methylpyrimidin-4-yl]oxybenzonitrile
(28) 4-[5-(2-aminoethyl)pyridin-2-yl]-3-(2,5-dimethylpyrazol-3-yl)oxybenzonitrile
(29) 4-[5-(aminomethyl)pyrimidin-2-yl]-3-(2-methyl-5-phenylpyrazol-3-yl)oxybenzonitrile
(30) 4-[5-(2-aminoethyl)pyrimidin-2-yl]-3-(5-cyclopropyl-2-methylpyrazol-3-yl)oxybenzonitrile
(31) 4-[5-(2-aminoethyl)pyrimidin-2-yl]-3-(5-butyl-2-methylpyrazol-3-yl)oxybenzonitrile
(32) 4-[5-(aminomethyl)pyrimidin-2-yl]-3-(5-ethyl-2-methylpyrazol-3-yl)oxybenzonitrile
(33) 4-[5-(aminomethyl)pyrimidin-2-yl]-3-(5-cyclopropyl-2-methylpyrazol-3-yl)oxybenzonitrile
(34) 4-[5-(aminomethyl)pyridin-2-yl]-3-(5-ethyl-2-methylpyrazol-3-yl)oxybenzonitrile
(35) 4-[5-(aminomethyl)pyridin-2-yl]-3-(5-cyclopropyl-2-methylpyrazol-3-yl)oxybenzonitrile
(36) 4-[5-(aminomethyl)pyrimidin-2-yl]-3-(2-methyl-6-morpholin-4-ylpyridin-4-yl)oxybenzonitrile
(37) 4-[5-(aminomethyl)pyridin-2-yl]-3-(2-methyl-6-morpholin-4-ylpyridin-4-yl)oxybenzonitrile
(38) 4-[5-(aminomethyl)pyridin-2-yl]-3-(2-methyl-5-propylpyrazol-3-yl)oxybenzonitrile
(39) 4-[5-(aminomethyl)pyridin-2-yl]-3-(2-methyl-5-propan-2-ylpyrazol-3-yl)oxybenzonitrile
(40) 4-[5-(aminomethyl)pyrimidin-2-yl]-3-(2-methyl-5-propylpyrazol-3-yl)oxybenzonitrile
(41) 4-[5-(aminomethyl)pyrimidin-2-yl]-3-(2-methyl-5-propan-2-ylpyrazol-3-yl)oxybenzonitrile
(42) 4-[5-(2-aminoethyl)pyrimidin-2-yl]-3-(5-tert-butyl-2-methylpyrazol-3-yl)oxybenzonitrile
(43) 4-[5-(2-aminoethyl)pyrimidin-2-yl]-3-(2-methyl-6-pyridin-2-ylpyridin-4-yl)oxybenzonitrile
(44) 4-[5-(2-aminoethyl)pyridin-2-yl]-3-[2-methyl-5-(1,3-thiazol-2-yl)pyrazol-3-yl]oxybenzonitrile
(45) 4-[5-(2-aminoethyl)pyrimidin-2-yl]-3-[2-methyl-5-(1,3-thiazol-2-yl)pyrazol-3-yl]oxybenzonitrile
(46) 4-[5-(2-aminoethyl)pyrimidin-2-yl]-3-(5-cyclopentyl-2-methylpyrazol-3-yl)oxybenzonitrile
(47) 4-[5-(aminomethyl)pyrimidin-2-yl]-3-(2-methyl-5-pyridin-2-ylpyrazol-3-yl)oxybenzonitrile
(48) 4-[5-(2-aminoethyl)pyrimidin-2-yl]-3-[5-(3-fluorophenyl)-2-methylpyrazol-3-yl]oxybenzonitrile
(49) 4-[5-(2-aminoethyl)pyrimidin-2-yl]-3-[2-[(2S)-2-(difluoromethyl)morpholin-4-yl]-6-methylpyridin-4-yl]oxybenzonitrile
(50) 4-[5-(aminomethyl)pyridin-2-yl]-3-[2-methyl-5-(oxan-4-yl)pyrazol-3-yl]oxybenzonitrile
(51) 4-[5-(2-aminoethyl)pyrimidin-2-yl]-3-[2-[(2R)-2-(difluoromethyl)morpholin-4-yl]-6-methylpyridin-4-yl]oxybenzonitrile
(52) 4-[5-(2-aminoethyl)pyrimidin-2-yl]-3-[2-methyl-6-(3-oxa-8-azabicyclo[3.2.1]octan-8-yl)pyridin-4-yl]oxybenzonitrile
(53) 4-[5-(2-aminoethyl)pyrimidin-2-yl]-3-(2-methyl-6-piperidin-1-ylpyrimidin-4-yl)oxybenzonitrile
(54) 4-[5-(2-aminoethyl)pyrimidin-2-yl]-3-(2-methyl-6-pyrrolidin-1-ylpyrimidin-4-yl)oxybenzonitrile
(55) 4-[5-(2-aminoethyl)pyrimidin-2-yl]-3-[2-methyl-6-(8-oxa-3-azabicyclo[3.2.1]octan-3-yl)pyridin-4-yl]oxybenzonitrile
(56) 4-[5-(2-aminoethyl)pyridin-2-yl]-3-[2-[2-methoxyethyl(methyl)amino]-6-methylpyridin-4-yl]oxybenzonitrile
(57) 4-[5-(2-aminoethyl)pyrimidin-2-yl]-3-[2-methyl-6-(propan-2-ylamino)pyridin-4-yl]oxybenzonitrile
(58) 4-[5-(2-aminoethyl)pyrimidin-2-yl]-3-[2-methyl-6-[(3R)-3-methylmorpholin-4-yl]pyridin-4-yl]oxybenzonitrile
(59) 4-[5-(2-aminoethyl)pyrimidin-2-yl]-3-[2-methyl-6-[(3S)-3-methylmorpholin-4-yl]pyridin-4-yl]oxybenzonitrile
(60) 4-[5-(2-aminoethyl)pyridin-2-yl]-3-(2-methyl-5-piperidin-1-ylpyrazol-3-yl)oxybenzonitrile
(61) 4-[5-(2-aminoethyl)pyridin-2-yl]-3-(2-methyl-5-pyrrolidin-1-ylpyrazol-3-yl)oxybenzonitrile
(62) 4-[5-(2-aminoethyl)pyridin-2-yl]-3-[5-(dimethylamino)-2-methylpyrazol-3-yl]oxybenzonitrile
(63) 4-[5-(aminomethyl)pyrimidin-2-yl]-3-[2-methyl-5-(1,3-thiazol-2-yl)pyrazol-3-yl]oxybenzonitrile
(64) 4-[5-(2-aminoethyl)pyrimidin-2-yl]-3-(2-methyl-6-pyridin-2-ylpyrimidin-4-yl)oxybenzonitrile
(65) 4-[5-(aminomethyl)pyridin-2-yl]-3-(2-methyl-5-pyridin-2-ylpyrazol-3-yl)oxybenzonitrile
(66) 4-[5-(aminomethyl)pyridin-2-yl]-3-(2-methyl-5-piperidin-1-ylpyrazol-3-yl)oxybenzonitrile
(67) 4-[5-(aminomethyl)pyridin-2-yl]-3-(2-methyl-5-pyrrolidin-1-ylpyrazol-3-yl)oxybenzonitrile
(68) 4-[5-(aminomethyl)pyridin-2-yl]-3-[5-(dimethylamino)-2-methylpyrazol-3-yl]oxybenzonitrile

(69) 4-[5-(aminomethyl)pyrimidin-2-yl]-3-[2-methyl-5-(4-methylpyridin-2-yl)pyrazol-3-yl]oxybenzonitrile
(70) 4-[5-(aminomethyl)pyrimidin-2-yl]-3-[5-(diethylamino)-2-methylpyrazol-3-yl]oxybenzonitrile
(71) 4-[5-(2-aminoethyl)pyrimidin-2-yl]-3-[5-(diethylamino)-2-methylpyrazol-3-yl]oxybenzonitrile
(72) 4-[5-(aminomethyl)pyridin-2-yl]-3-(2-methyl-6-pyrrolidin-1-ylpyrimidin-4-yl)oxybenzonitrile
(73) 4-[5-(aminoethyl)pyrimidin-2-yl]-3-[2-methyl-6-pyrrolidin-1-ylpyrimidin-4-yl]oxybenzonitrile
(74) 4-[5-(2-aminoethyl)pyrimidin-2-yl]-3-[6-(7-azabicyclo[2.2.1]heptan-7-yl)-2-methylpyrimidin-4-yl]oxybenzonitrile
(75) 4-[5-(aminomethyl)pyrimidin-2-yl]-3-[6-(7-azabicyclo[2.2.1]heptan-7-yl)-2-methylpyrimidin-4-yl]oxybenzonitrile
(76) 4-[5-(aminomethyl)pyridin-2-yl]-3-(6-piperidin-1-ylpyridazin-4-yl)oxybenzonitrile
(77) 4-[5-(2-aminoethyl)pyrimidin-2-yl]-3-[(5-phenyl-1,3,4-thiadiazol-2-yl)oxy]benzonitrile
(78) 4-[5-(2-aminoethyl)pyridin-2-yl]-3-[5-(diethylamino)-2-methylpyrazol-3-yl]oxybenzonitrile
(79) 4-[5-(2-aminoethyl)pyrimidin-2-yl]-3-[2-methyl-5-[methyl(2-methylpropyl)amino]pyrazol-3-yl]oxybenzonitrile
(80) 4-[5-(2-aminoethyl)pyrimidin-2-yl]-3-[5-[cyclopropylmethyl(methyl)amino]-2-methylpyrazol-3-yl]oxybenzonitrile
(81) 4-[5-(2-aminoethyl)pyrimidin-2-yl]-3-[2-methyl-5-[methyl(propyl)amino]pyrazol-3-yl]oxybenzonitrile
(82) 4-[5-(aminomethyl)pyridin-2-yl]-3-(2-methyl-5-morpholin-4-ylpyrazol-3-yl)oxybenzonitrile
(83) 4-[5-(2-aminoethyl)pyrimidin-2-yl]-3-[2-methyl-5-[methyl(propan-2-yl)amino]pyrazol-3-yl]oxybenzonitrile
(84) 4-[5-(2-aminoethyl)pyrimidin-2-yl]-3-[5-[2,2-difluoroethyl(methyl)amino]-2-methylpyrazol-3-yl]oxybenzonitrile
(85) 4-[5-(2-aminoethyl)pyrimidin-2-yl]-3-[2-methyl-5-[methyl(2,2,2-trifluoroethyl)amino]pyrazol-3-yl]oxybenzonitrile
(86) 4-[5-(aminomethyl)pyrimidin-2-yl]-3-[2-methyl-6-[(2S)-2-methylpyrrolidin-1-yl]pyrimidin-4-yl]oxybenzonitrile
(87) 4-[5-(2-aminoethyl)pyrimidin-2-yl]-3-[3-methyl-1-(2-methylpropyl)pyrazol-4-yl]oxybenzonitrile
(88) 4-[5-(aminomethyl)pyrimidin-2-yl]-3-[3-methyl-1-(2-methylpropyl)pyrazol-4-yl]oxybenzonitrile
(89) 4-[5-(aminomethyl)pyridin-2-yl]-3-[2-methyl-5-(trifluoromethyl)pyrazol-3-yl]oxybenzonitrile
(90) 4-[5-(aminomethyl)pyrimidin-2-yl]-3-[2-methyl-5-(trifluoromethyl)pyrazol-3-yl]oxybenzonitrile
(91) 4-[5-(2-aminoethyl)pyrimidin-2-yl]-3-[2-methyl-5-(trifluoromethyl)pyrazol-3-yl]oxybenzonitrile
(92) 4-[5-(aminomethyl)pyrimidin-2-yl]-3-[2-(7-azabicyclo[2.2.1]heptan-7-yl)-6-methylpyridin-4-yl]oxybenzonitrile
(93) 4-[5-(2-aminoethyl)pyrimidin-2-yl]-3-[2-(7-azabicyclo[2.2.1]heptan-7-yl)-6-methylpyridin-4-yl]oxybenzonitrile
(94) 4-[5-(2-aminoethyl)pyrimidin-2-yl]-3-(3-methyl-1-pyridin-2-ylpyrazol-4-yl)oxybenzonitrile
(95) 4-[5-(aminomethyl)pyrimidin-2-yl]-3-(3-methyl-1-pyridin-2-ylpyrazol-4-yl)oxybenzonitrile
(96) 4-[5-(aminomethyl)pyrimidin-2-yl]-3-[3-methyl-1-(2,2,2-trifluoroethyl)pyrazol-4-yl]oxybenzonitrile
(97) 4-[5-(2-aminoethyl)pyrimidin-2-yl]-3-[5-[ethyl(propan-2-yl)amino]-2-methylpyrazol-3-yl]oxybenzonitrile
(98) 4-[5-(2-aminoethyl)pyrimidin-2-yl]-3-[2-methyl-6-(2-methylpropoxy)pyrimidin-4-yl]oxybenzonitrile
(99) 4-[5-(2-aminoethyl)pyrimidin-2-yl]-3-[6-(diethylamino)-2-methylpyrimidin-4-yl]oxybenzonitrile
(100) 4-[5-(2-aminoethyl)pyrimidin-2-yl]-3-[2-methyl-6-[methyl(propan-2-yl)amino]pyrimidin-4-yl]oxybenzonitrile
(101) 4-[5-(2-aminoethyl)pyrimidin-2-yl]-3-[2-methyl-6-[(2R)-2-methylpyrrolidin-1-yl]pyrimidin-4-yl]oxybenzonitrile
(102) 4-[5-(2-aminoethyl)pyrimidin-2-yl]-3-[2-methyl-6-[(2S)-2-methylpyrrolidin-1-yl]pyrimidin-4-yl]oxybenzonitrile
(103) 4-[5-(aminomethyl)pyrimidin-2-yl]-3-[2-methyl-5-(3,3,4,5-tetrafluoropyrrolidin-1-yl)pyrazol-3-yl]oxybenzonitrile
(104) 4-[5-(aminomethyl)pyrimidin-2-yl]-3-[5-[2,2-difluoroethyl(ethyl)amino]-2-methylpyrazol-3-yl]oxybenzonitrile
(105) 4-[5-(2-aminoethyl)pyrimidin-2-yl]-3-[5-[2,2-difluoroethyl(ethyl)amino]-2-methylpyrazol-3-yl]oxybenzonitrile
(106) 4-[5-(2-aminoethyl)pyrimidin-2-yl]-3-[2-methyl-5-(3,3,4,4-tetrafluoropyrrolidin-1-yl)pyrazol-3-yl]oxybenzonitrile
(107) 4-[5-(2-aminoethyl)pyrimidin-2-yl]-3-[I-(2-methylpropyl)pyrazol-4-yl]oxybenzonitrile
(108) 4-[5-(2-aminoethyl)pyrimidin-2-yl]-3-(1-pyridin-2-ylpyrazol-4-yl)oxybenzonitrile
(109) 4-[5-(2-aminoethyl)pyrimidin-2-yl]-3-[1-(2,2-dimethylpropyl)-3-methylpyrazol-4-yl]oxybenzonitrile
(110) 4-[5-(aminomethyl)pyrimidin-2-yl]-3-[2-methyl-5-(1,3-thiazol-4-yl)pyrazol-3-yl]oxybenzonitrile
(111) 4-[5-(2-aminoethyl)pyrimidin-2-yl]-3-[3-ethyl-1-(2-methylpropyl)pyrazol-4-yl]oxybenzonitrile
(112) 4-[5-(2-aminoethyl)pyrimidin-2-yl]-3-[1-(2-methylpropyl)-3-(trifluoromethyl)pyrazol-4-yl]oxybenzonitrile
(113) 4-[5-(aminomethyl)pyrimidin-2-yl]-3-[2-methyl-5-(4-methyl-1,3-thiazol-5-yl)pyrazol-3-yl]oxybenzonitrile
(114) 4-[5-(aminomethyl)pyrimidin-2-yl]-3-[2-methyl-5-(5-methyl-1,3-thiazol-4-yl)pyrazol-3-yl]oxybenzonitrile
(115) 2-[2-[4-fluoro-2-[3-methyl-1-(2-methylpropyl)pyrazol-4-yl]oxyphenyl]pyrimidin-5-yl]ethanamine
(116) 5-[2-[5-(2-aminoethyl)pyrimidin-2-yl]-5-fluorophenoxy]-N,N-diethyl-1-methylpyrazole-3-amine
(117) 2-[6-[4-fluoro-2-(2-methyl-5-morpholin-4-ylpyrazol-3-yl)oxyphenyl]pyridin-3-yl]ethanamine
(118) 2-[2-[4-fluoro-2-(2-methyl-5-pyridin-2-ylpyrazol-3-yl)oxyphenyl]pyrimidin-5-yl]ethanamine
(119) 2-[2-[4-fluoro-2-(2-methyl-5-pyrrolidin-1-ylpyrazol-3-yl)oxyphenyl]pyrimidin-5-yl]ethanamine
(120) 2-[6-[4-fluoro-2-(2-methyl-5-pyrrolidin-1-ylpyrazol-3-yl)oxyphenyl]pyridin-3-yl]ethanamine
(121) 5-[2-[5-(2-aminoethyl)pyrimidin-2-yl]-5-fluorophenoxy]-N-(2,2-difluoroethyl)-N,1-dimethylpyrazole-3-amine
(122) 5-[2-[5-(2-aminoethyl)pyridin-2-yl]-5-fluorophenoxy]-N-(2,2-difluoroethyl)-N,1-dimethylpyrazole-3-amine
(123) 5-[2-[5-(2-aminoethyl)pyrimidin-2-yl]-5-fluorophenoxy]-N-(2,2-difluoroethyl)-N-ethyl-1-methylpyrazole-3-amine
(124) 5-[2-[5-(2-aminoethyl)pyridin-2-yl]-5-fluorophenoxy]-N-(2,2-difluoroethyl)-N-ethyl-1-methylpyrazole-3-amine
(125) 5-[2-[5-(2-aminoethyl)pyridin-2-yl]-5-fluorophenoxy]-N,N-diethyl-1-methylpyrazole-3-amine
(126) 5-[2-[5-(2-aminoethyl)pyridin-2-yl]-5-fluorophenoxy]-N,N,1-trimethylpyrazole-3-amine (127) 2-[6-[4-fluoro-2-[2-methyl-5-(oxan-4-yl)pyrazol-3-yl]oxyphenyl]pyridin-3-yl]ethanamine
(128) [2-[4-fluoro-2-(2-methyl-5-propan-2-ylpyrazol-3-yl)oxyphenyl]pyrimidin-5-yl]methanamine
(129) 2-[2-[4-fluoro-2-(2-methyl-5-propan-2-ylpyrazol-3-yl)oxyphenyl]pyrimidin-5-yl]ethanamine
(130) 2-[6-[4-fluoro-2-(2-methyl-5-propan-2-ylpyrazol-3-yl)oxyphenyl]pyridin-3-yl]ethanamine
(131) 2-[6-[2-(5-cyclopropyl-2-methylpyrazol-3-yl)oxy-4-fluorophenyl]pyridin-3-yl]ethanamine
(132) 4-[5-(2-aminoethyl)pyrimidin-2-yl]-3-(5-ethyl-2-methylpyrazole-3-carbonyl)benzonitrile
(133) 4-[5-(aminomethyl)pyrimidin-2-yl]-3-(5-ethyl-2-methylpyrazole-3-carbonyl)benzonitrile
(134) 4-[5-(2-aminoethyl)pyrimidin-2-yl]-3-(2-methyl-5-morpholin-4-ylpyrazole-3-carbonyl)benzonitrile
(135) 4-[5-(aminomethyl)pyrimidin-2-yl]-3-(2-methyl-5-morpholin-4-ylpyrazole-3-carbonyl)benzonitrile
(136) 4-[5-(aminomethyl)pyridin-2-yl]-3-(2-methyl-5-morpholin-4-ylpyrazole-3-carbonyl)benzonitrile
(137) 4-[5-(aminomethyl)pyrimidin-2-yl]-3-(5-tert-butyl-2-methylpyrazole-3-carbonyl)benzonitrile
(138) 4-[5-(2-aminoethyl)pyrimidin-2-yl]-3-(5-tert-butyl-2-methylpyrazole-3-carbonyl)benzonitrile
(139) 4-[5-(2-aminoethyl)pyrimidin-2-yl]-3-[5-(diethylamino)-2-methylpyrazole-3-carbonyl]benzonitrile
(140) 4-[5-(2-aminoethyl)pyrimidin-2-yl]-3-(1-pyridin-2-ylpyrazole-4-carbonyl)benzonitrile
(141) 4-[5-(2-aminoethyl)pyrimidin-2-yl]-3-(2-methyl-6-morpholin-4-ylpyridine-4-carbonyl)benzonitrile
(142) 4-[5-(2-aminoethyl)pyrimidin-2-yl]-3-[5-(dimethylamino)-2-methylpyrazole-3-carbonyl]benzonitrile
(143) 4-[5-(aminomethyl)pyrimidin-2-yl]-3-[5-(dimethylamino)-2-methylpyrazole-3-carbonyl]benzonitrile
(144) 4-[5-(aminomethyl)pyrimidin-2-yl]-3-[5-(diethylamino)-2-methylpyrazole-3-carbonyl]benzonitrile
(145) 4-[5-(2-aminoethyl)pyrimidin-2-yl]-3-(2-methyl-5-piperidin-1-ylpyrazole-3-carbonyl)benzonitrile
(146) 4-[5-(aminomethyl)pyrimidin-2-yl]-3-(2-methyl-5-piperidin-1-ylpyrazole-3-carbonyl)benzonitrile
(147) 4-[5-(2-aminoethyl)pyrimidin-2-yl]-3-(2-methyl-5-pyrrolidin-1-ylpyrazole-3-carbonyl)benzonitrile
(148) 4-[5-(aminomethyl)pyrimidin-2-yl]-3-(2-methyl-5-pyrrolidin-1-ylpyrazole-3-carbonyl)benzonitrile
(149) 4-[5-(2-aminoethyl)pyrimidin-2-yl]-3-[5-[2,2-difluoroethyl(ethyl)amino]-2-methylpyrazole-3-carbonyl]benzonitrile
(150) 4-[5-(aminomethyl)pyrimidin-2-yl]-3-[5-[2,2-difluoroethyl(ethyl)amino]-2-methylpyrazole-3-carbonyl]benzonitrile.

[20] pharmaceutical composition comprising the compound according to any one of [1] to [19] or a pharmaceutically acceptable salt thereof.

[21] A pharmaceutical composition having TRPC6 channel inhibitory activity, comprising the compound according to any one of [1] to [19] or a pharmaceutically acceptable salt thereof.

[12] A therapeutic or prophylactic agent for nephrotic syndrome, membranous nephropathy, acute renal failure, sepsis, chronic renal failure, diabetic nephropathy, pulmonary hypertension, acute lung injury, heart failure, malignant tumors, or muscular dystrophy, comprising the compound according to any one of [1] to [19] or a pharmaceutically acceptable salt thereof.

Advantageous Effects of Invention

The present invention provides a novel compound or a pharmaceutically acceptable salt thereof, having TRPC6 inhibitory activity, and a pharmaceutical composition and a therapeutic or prophylactic drug for the disease associated with TRPC6, including thereof.

DESCRIPTION OF EMBODIMENTS

Terms used alone or in combination in the present description will be explained below. Unless otherwise stated, the explanation of each substituent shall be common to each site. In addition, combinations of substituents and variables are permissible only if such combinations result in chemically stable compounds. When the substituent itself is substituted with two or more groups, these many groups can exist on the same or different carbon atom as long as a stable structure is formed.

In the present invention, the number situated to the right of carbon atom indicates the number of carbon atoms. For example, "$C_{1-6}$" represents having "1 to 6 carbon atoms." For example, a "$C_{1-4}$ alkyl group" means an alkyl group having 1 to 4 carbon atoms. The number of carbon atoms in other groups is handled in the same manner. Incidentally, for example, in an expression such as "($C_{1-3}$ alkyl)carbonyl group", the number of carbon atoms of $C_{1-3}$ represents the number of carbon atoms of the $C_{1-3}$ alkyl in the parentheses, and the carbon in the carbonyl is not considered. The number of carbon atoms in a similar representation is calculated in the same manner. Unless otherwise specified, the method of naming a substituent shall be performed by naming from the terminal portion of the functional group and then naming the functional group adjacent to the binding point.

In the present invention, the "halogen atom" means a fluorine atom, a chlorine atom, a bromine atom, and an iodine atom.

In the present invention, "alkyl group" means a saturated linear or branched aliphatic hydrocarbon group and includes, for example, a methyl group, a ethyl group, an n-propyl group, an n-butyl group, an n-pentyl group, an n-hexyl group, an isopropyl group, an isobutyl group, a sec-butyl group, a tert-butyl group, an isopentyl group, a 2-methylbutyl group, a 3-methylbutyl group, a 1-ethylpropyl group, a 1,1-dimethylpropyl group, a 1,2-dimethylpropyl group, a neopentyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 1-ethylbutyl group, a 2-ethylbutyl group and the like.

In the present invention, the "cycloalkyl group" means a saturated or partially unsaturated monocyclic or polycyclic hydrocarbon group, and includes, for example, a cyclopropyl group, a cyclobutyl group, a cyclopentyl group, a cyclohexyl group, a cycloheptyl group, a cyclooctyl group and the like.

In the present invention, a "heterocycloalkyl group" means a saturated or partially unsaturated monocyclic or polycyclic hydrocarbon ring in which one or more carbon atoms are substituted with a hetero atom selected from O, S and N, and includes, for example, an aziridino group, an azetidino group, an oxetanyl group, a morpholino group, a thiomorpholino group, a pyrrolidinyl group, a piperidinyl group, a piperazinyl group, an imidazolidinyl group, a pyrazolidinyl group, a tetrahydrofuranyl group, a tetrahydropyranyl group and the like.

In the present invention, the "alkoxy group", "cycloalkyloxy group" and "heterocycloalkyloxy group" mean an oxy group substituted with an alkyl group, a cycloalkyl group or a heterocycloalkyl group.

In the present invention, "(alkoxy)alkoxy group" and "(carboxy)alkoxy group" mean an alkoxy group substituted with an alkoxy group or a carboxy group. For example, "($C_{1-3}$ alkoxy)$C_{1-3}$ alkoxy group" means an alkoxy group having 1 to 3 carbon atoms substituted with an alkoxy group having 1 to 3 carbon atoms.

In the present invention, "(alkoxy)carbonyl group" means a carbonyl group substituted with an alkoxy group. For example, "($C_{1-3}$ alkoxy)carbonyl group" means a carbonyl group substituted with an alkoxy group having 1 to 3 carbon atoms.

In the present invention, "(alkyl)amino group", "(cycloalkyl)amino group" and "(heterocycloalkyl)amino group" mean an amino group substituted with one alkyl group, cycloalkyl group and heterocycloalkyl group, respectively. For example, "($C_{3-8}$ heterocycloalkyl)amino group" means an amino group substituted with a 3- to 8-membered heterocycloalkyl group.

In the present invention, "di(alkyl)amino group" means an amino group substituted with two of the same or different alkyl groups. For example, "di($C_{1-6}$ alkyl)amino group" means an amino group substituted with two of the same or different alkyl groups having 1 to 6 carbon atoms.

In the present invention, "(alkylcarbonyl)amino group" means an amino group substituted with one alkylcarbonyl group. For example, "($C_{1-3}$ alkyl)carbonylamino group" means an amino group substituted with one ($C_{1-3}$ alkyl) carbonyl group.

In the present invention, "(alkylamino)carbonyl group" means a carbonyl group substituted with an alkylamino group. Similarly, "di(alkyl)aminocarbonyl group" means a carbonyl group substituted with a di(alkyl)amino group.

In the present invention, "alkoxyalkyl group", "alkoxycarbonylalkyl group", "di(alkyl)aminoalkyl group", "hydroxyalkyl group" and "carboxyalkyl group" mean an alkyl group substituted with an alkoxy group, an alkoxycarbonyl group, a di(alkyl)amino group, a hydroxy group and a carboxy group, respectively. Further, "di(alkyl)aminocarbonylmethyl group" means a methyl group substituted with a di(alkyl)aminocarbonyl group.

In the present invention, "alkylene group" means a divalent group derived by removing one hydrogen atom at an arbitrary position from the "alkyl group", and includes, for example, a methylene group, an ethylene group, an n-propylene group, an isopropylene group, an n-butylene group, an isobutylene group, an n-pentylene group, an n-hexylene group and the like.

In the present invention, "cycloalkylene group" means a divalent group derived by removing one hydrogen atom at an arbitrary position from the "cycloalkyl group", and includes, for example, a cyclopropylene group, a cyclobutylene group, a cyclohexylene group and the like.

In the present invention, "heterocycloalkylene group" means a divalent group derived by removing one hydrogen atom at an arbitrary position from the "heterocycloalkyl group".

In the present invention, "optionally substituted $C_{1-3}$ alkyl group" represents an alkyl group having 1 to 3 carbon atoms which may have one or more substituents at substitutable positions. When a plurality of substituents is present, each substituent may be the same or different. Similar expressions have the same meaning.

In the present invention, "aryl group" means a monocyclic or bicyclic aromatic hydrocarbon group having 6 to 10 carbon atoms, and includes, for example, a phenyl group, a naphthyl group, an indenyl group, an azulenyl group and the like. "Aryl ring" refers to the ring portion of an aryl group.

In the present invention, "heteroaryl group" means a 5- to 10-membered monocyclic or bicyclic aromatic heterocyclic group having 1 to 5 heteroatoms selected from O, S, and N. Heteroaryl group includes a pyridyl group, a pyrazil group, a pyrimidyl group, a pyridalyl group, a furyl group, a thienyl group, an isooxazolyl group, an isothiazolyl group, a benzofuranyl group, a benzothienyl group, a benzothiazolyl group, a benzoimidazolyl group, a benzoxazolyl group, a pyranyl group, a pyrazolyl group, an imidazolyl group, an oxazolyl group, a thiazolyl group, a triazinyl group, a triazolyl group, a benzoxazolyl group, a benzoisoxazolyl group and the like. "Heteroaryl ring" refers to the ring portion of a heteroaryl group. "Nitrogen-containing heteroaryl ring" means a heteroaryl ring containing one or more Ns on the ring.

In the formula (I), $X^1$, $X^2$, and $X^3$ are independently CH, N, or CY, and at least one of $X^1$, $X^2$, and $X^3$ is CH or CY. Preferably, $X^1$, $X^2$, and $X^3$ are CH.

Y is a halogen atom or a methyl group.

In the formula (I), $R^1$ is a cyano group, a fluorine atom, or a chlorine atom, and preferably a cyano group or a fluorine atom.

In the formula (I), linker $L^1$ is —O—, —S—, —SO—, —CH($R^{11}$)—, —C(=$CH_2$)—, —CO—, a 1,1-cyclopropylidene group, or —$NR^{12}$—, preferably, —O—, —S—, —CH($R^{11}$)—, —CO—, or —$NR^{12}$—, and more preferably —O—, —CO—, or —$CH_2$—.

$R^{11}$ is a hydrogen atom, a hydroxy group, a $C_{1-3}$ alkyl group optionally substituted with 1 to 3 halogen atoms, or a $C_{1-3}$ alkoxy group optionally substituted with 1 to 2 cyano groups.

$R^{12}$ is a hydrogen atom or a $C_{1-3}$ alkyl group optionally substituted with 1 to 3 halogen atoms.

In the formula (I), $Ar^1$ is a nitrogen-containing heteroaryl ring optionally substituted with 1 to 3 $R^2$, and preferably has the following structures.

[Chem. 4]

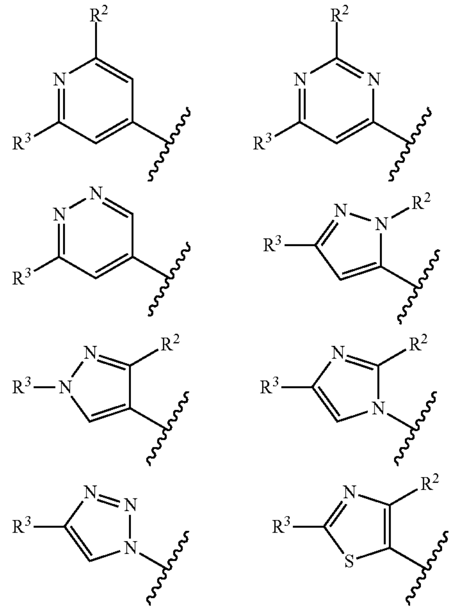

-continued

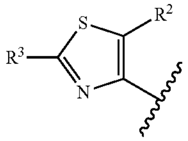

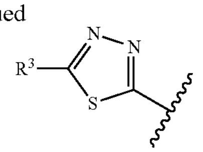

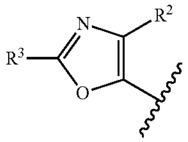

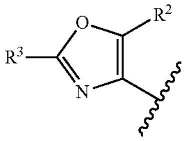

or

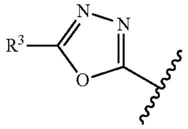

$R^2$ is independently a halogen atom, a cyano group, or a $C_{1-4}$ alkyl group optionally substituted with 1 to 3 halogen atoms, preferably a $C_{1-4}$ alkyl group optionally substituted with 1 to 3 halogen atoms, and more preferably a methyl group. When $R^2$ and $R^3$ are bonded to atoms adjacent to each other on $Ar^1$, $R^2$ and $R^3$ may be bonded via a single bond or —O— to form a 5- to 7-membered ring together with the atoms on $Ar^1$ to which they are bonded.

In the formula (I), $R^3$ is a hydrogen atom, a halogen atom, an amino group, a cyano group, a carboxy group, a ($C_{1-3}$ alkylcarbonyl)amino group, a ($C_{1-6}$ alkylamino)carbonyl group, a di($C_{1-3}$ alkyl)aminocarbonyl group, a ($C_{1-3}$ alkoxy) carbonyl group, a ($C_{3-8}$ cycloalkyl)amino group, a ($C_{3-8}$ heterocycloalkyl)amino group, a $C_{3-8}$ cycloalkyl group, a 3- to 8-membered heterocycloalkyloxy group, a $C_{3-8}$ cycloalkyloxy group optionally substituted with 1 to 6 $R^{31}$, a $C_{1-6}$ alkyl group optionally substituted with 1 to 6 $R^{31}$, a $C_{1-6}$ alkoxy group optionally substituted with 1 to 6 $R^{31}$, a di($C_{1-6}$ alkyl)amino group optionally substituted with 1 to 6 $R^{31}$, a ($C_{1-6}$ alkyl)amino group optionally substituted with 1 to 6 $R^{31}$, a 3- to 8-membered heterocycloalkyl group optionally substituted with 1 to 4 $R^{32}$, an aryl group optionally substituted with 1 to 4 $R^{32}$, or a heteroaryl group optionally substituted with 1 to 4 $R^{32}$.

$R^{31}$ is independently a halogen atom, a hydroxy group, a cyclopropylidene group, a $C_{3-8}$ cycloalkyl group optionally substituted with 1 to 3 halogen atoms, a 3- to 8-membered heterocycloalkyl group, an oxetanylidene group, a $C_{1-4}$ alkoxy group, or a 3- to 8-membered cycloalkyloxy group.

$R^{32}$ is independently a halogen atom, a hydroxy group, an acetylamino group, a $C_{1-3}$ alkyl group optionally substituted with 1 to 3 halogen atoms, a $C_{1-3}$ alkoxy group optionally substituted with 1 to 3 halogen atoms, an oxo group, a cyano group, a carboxy group, a ($C_{1-3}$ alkoxy)carbonyl group, a ($C_{1-3}$ alkyl)sulfonyl group, a carboxamide group, or a benzyloxy group.

In the formula (I), preferred $R^3$ is a $C_{3-8}$ cycloalkyl group, a 3- to 8-membered heterocycloalkyloxy group, a $C_{3-8}$ cycloalkyloxy group optionally substituted with 1 to 6 $R^{31}$, a $C_{1-6}$ alkyl group optionally substituted with 1 to 6 $R^{31}$, a $C_{1-6}$ alkoxy group optionally substituted with 1 to 6 $R^{31}$, a di($C_{1-6}$ alkyl)amino group optionally substituted with 1 to 6 $R^{31}$, a ($C_{1-6}$ alkyl)amino group optionally substituted with 1 to 6 $R^{31}$, a 3- to 8-membered heterocycloalkyl group optionally substituted with 1 to 4 $R^{32}$, an aryl group optionally substituted with 1 to 4 $R^{32}$ or a heteroaryl group optionally substituted with 1 to 4 $R^{32}$.

Preferred $R^{31}$ is a halogen atom, a cyclopropylidene group, or a $C_{1-4}$ alkoxy group.

Preferred $R^{32}$ is a halogen atom, a $C_{1-3}$ alkyl group optionally substituted with 1 to 3 halogen atoms, a $C_{1-3}$ alkoxy group optionally substituted with 1 to 3 halogen atoms, an oxo group, or a cyano group.

In the formula (I), $Ar^2$ is an aryl ring optionally substituted with 1 to 4 $R^4$, or a heteroaryl ring optionally substituted with 1 to 4 $R^4$, preferably a heteroaryl ring optionally substituted with 1 to 4 $R^4$, and more preferably a pyridine ring or a pyrimidine ring having a substitution pattern of the following structure.

[Chem. 5]

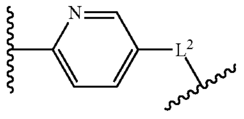

or

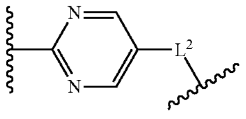

$R^4$ is independently a halogen atom, a hydroxy group, a carboxy group, a cyano group, a cyanomethyl group, an amino group, a di($C_{1-3}$ alkyl)amino group, a $C_{1-3}$ alkyl group optionally substituted with 1 to 3 halogen atoms, or a $C_{1-3}$ alkoxy group.

In the formula (I), $L^2$ is a single bond, a $C_{1-6}$ alkylene group optionally substituted with 1 to 3 $R^{21}$, a $C_{3-8}$ cycloalkylene group optionally substituted with 1 to 3 $R^{21}$, or a 4- to 8-membered heterocycloalkylene group optionally substituted with 1 to 3 $R^{21}$. $L^2$ may be bonded at any position to $Ar^2$ or $—NR^7R^8$ which is located at either end of it. One $sp^3$ carbon atom at any position of $L^2$ may be replaced by a structure of —O— or $—NR^{22}—$. Preferred $L^2$ is a $C_{1-3}$ alkylene group optionally substituted with 1 to 2 $R^{21}$, and more preferably $—CH_2—$ or $—CH_2CH_2—$.

$R^{21}$ is independently a halogen atom, a hydroxy group, an oxo group, a cyano group, a 1,1-cyclopropylidene group, an oxetanylidene group, a carboxy group, a carboxamide group, a $C_{1-6}$ alkyl group optionally substituted with 1 to 3 halogen atoms, a $C_{3-8}$ cycloalkyl group, a $C_{1-6}$ alkoxy group, a ($C_{1-3}$ alkoxy)$C_{1-3}$ alkyl group, a ($C_{1-3}$ alkoxy)$C_{1-3}$ alkoxy group, a (hydroxy) $C_{1-6}$ alkyl group, a (carboxy)$C_{1-3}$ alkyl group, a (carboxy)$C_{1-3}$ alkoxy group, a ($C_{1-3}$ alkoxy)carbonyl group, a ($C_{1-3}$ alkoxycarbonyl)$C_{1-3}$ alkyl group, a ($C_{1-6}$ alkylamino)carbonyl group, a di($C_{1-3}$ alkyl)aminocarbonyl group, a phenyl group optionally substituted with 1 to 3 halogen atoms, a heteroaryl group optionally substituted with 1 to 3 halogen atoms, or a phenoxy group optionally substituted with 1 to 3 halogen atoms. Preferred $R^{21}$ is a halogen atom, a hydroxy group, an oxo group, an oxetanylidene group, or a $C_{1-6}$ alkyl group optionally substituted with 1 to 3 halogen atoms, and more preferred is a halogen atom or a hydroxy group.

$R^{22}$ is a hydrogen atom or a $C_{1-3}$ alkyl group.

$L^2$ and $R^7$ may be bonded via a single bond, —O—, $—S(=O)_n—$, or $—NR^{23}—$ to form a 4- to 8-membered ring containing a nitrogen atom to which $L^2$ and $R^7$ are bonded, and the ring is optionally substituted with 1 to 3 halogen atoms or 1 to 2 hydroxy groups, wherein n represents an integer from 0 to 2.

$R^{23}$ is a hydrogen atom or a $C_{1-3}$ alkyl group.

When $L^2$ and R are bonded to atoms adjacent to each other on $Ar^2$, they may be bonded via a single-bond or —O— to form a 5- to 8-membered ring together with the atoms of $Ar^2$ to which they are bonded.

In the formula (I), $R^7$ is a hydrogen atom or a $C_{1-3}$ alkyl group, and more preferably a hydrogen atom. $R^7$ and an atom of $Ar^2$ may be bonded via a single bond to form a 5- to 8-membered ring.

In the formula (I), $R^8$ is a hydrogen atom, a $C_{1-6}$ alkyl group, an adamantyl group, a $C_{1-6}$ cycloalkyl group, a cyanomethyl group, an oxetanyl group, a ($C_{1-3}$ alkylamino)carbonylmethyl group, a di($C_{1-3}$ alkyl)aminocarbonylmethyl group, a ($C_{1-3}$ alkylamino)$C_{1-8}$ alkyl group, a di($C_{1-3}$ alkyl)amino$C_{1-8}$ alkyl group, a (hydroxy)$C_{1-8}$ alkyl group, a (carboxy)$C_{1-3}$ alkyl group, a ($C_{1-3}$ alkoxycarbonyl)$C_{1-3}$ alkyl group, or a ($C_{1-3}$ alkoxy)$C_{1-3}$ alkyl group. More preferred $R^8$ is a hydrogen atom.

$R^7$ and $R^8$ may be bonded each other via a single bond, —O—, —S(=O)$_m$—, or —$NR^{41}$— to form a 3- to 8-membered ring, and further, the ring is optionally substituted with an amino group, an oxo group, or a $C_{1-3}$ alkyl group, wherein m represents an integer from 0 to 2.

$R^{41}$ is a hydrogen atom or a $C_{1-3}$ alkyl group.

Among the compounds of the present invention, preferable is the following compound group, that is, the compound group in the formula (I), wherein, $X^1$, $X^2$, and $X^3$ are CH, $R^1$ is a cyano group or a fluorine atom, linker $L^1$ is —O—, —CO—, or —$CH_2$—, $Ar^1$ has the following structure,

[Chem. 6]

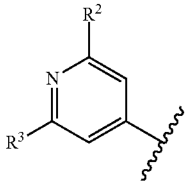

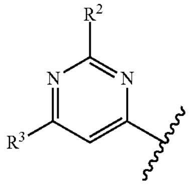

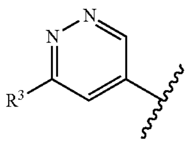

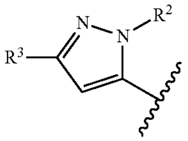

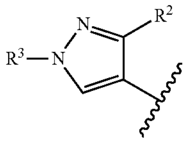

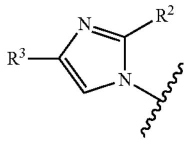

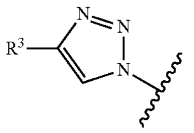

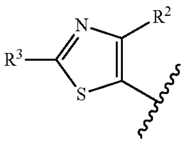

-continued

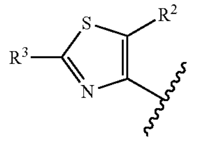

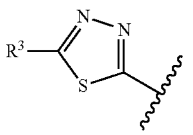

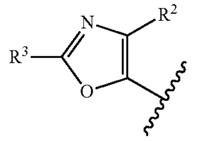

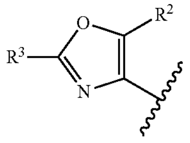

or

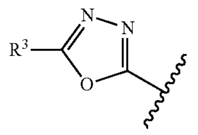

$R^2$ is a methyl group, $R^3$ is a $C_{3-8}$ cycloalkyl group, a 3- to 8-membered heterocycloalkyloxy group, a $C_{3-8}$ cycloalkyloxy group optionally substituted with 1 to 6 $R^{31}$, a $C_{1-6}$ alkyl group optionally substituted with 1 to 6 $R^{31}$, a $C_{1-6}$ alkoxy group optionally substituted with 1 to 6 $R^{31}$, a di($C_{1-6}$ alkyl)amino group optionally substituted with 1 to 6 $R^{31}$, a ($C_{1-6}$ alkyl)amino group optionally substituted with 1 to 6 $R^{31}$, a 3- to 8-membered heterocycloalkyl group optionally substituted with 1 to 4 $R^{32}$, an aryl group optionally substituted with 1 to 4 $R^{32}$ or a heteroaryl group optionally substituted with 1 to 4 $R^{32}$.

$R^{31}$ is a halogen atom, a cyclopropylidene group, or a $C_{1-4}$ alkoxy group, and $R^{32}$ is a halogen atom, a $C_{1-3}$ alkyl group optionally substituted with 1 to 3 halogen atoms, a $C_{1-3}$ alkoxy group optionally substituted with 1 to 3 halogen atoms, an oxo group, or a cyano group.

$Ar^2$ is a pyridine ring or a pyrimidine ring having a substitution pattern of the following structure.

[Chem. 7]

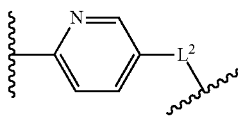

or

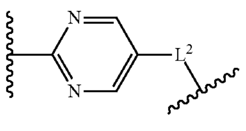

$L^2$ is —$CH_2$— or —$CH_2CH_2$—, $R^7$ is a hydrogen atom, and $R^8$ is a hydrogen atom.

Specific examples of the compound of the formula (I) include the compounds shown in the following Table 1.

TABLE 1
| Compound number | Structural formula | Compound name |
|---|---|---|
| 1 | 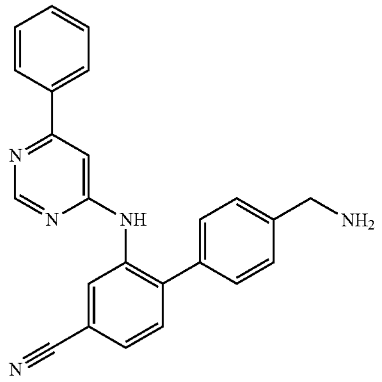 [SMILES: N#Cc1ccc(-c2ccc(CN)cc2)c(Nc2cc(-c3ccccc3)ncn2)c1] | 4-[4-(aminomethyl)phenyl]-3-[(6-phenylpyrimidin-4-yl)amino]benzonitrile |
| 2 | 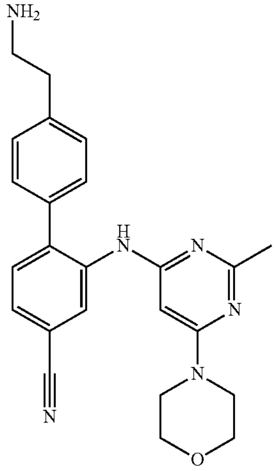 [SMILES: Cc1nc(Nc2cc(C#N)ccc2-c2ccc(CCN)cc2)cc(N2CCOCC2)n1] | 4-[4-(2-aminoethyl)phenyl]-3-[(2-methyl-6-morpholin-4-ylpyrimidin-4-yl)amino]benzonitrile |
| 3 | 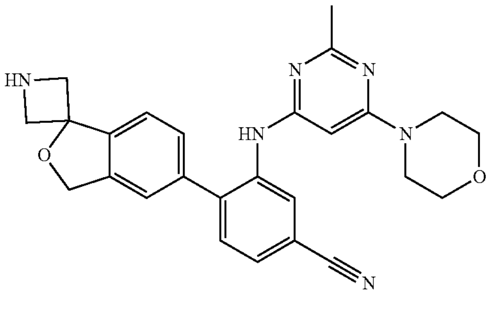 [SMILES: Cc1nc(Nc2cc(C#N)ccc2-c2ccc3c(c2)COC32CNC2)cc(N2CCOCC2)n1] | 3-[(2-methyl-6-morpholin-4-ylpyrimidin-4-yl)amino]-4-spiro[3H-2-benzofuran-1,3'-azetidin]-5-ylbenzonitrile |

TABLE 1-continued
| Compound number | Structural formula | Compound name |
| --- | --- | --- |
| 4 | 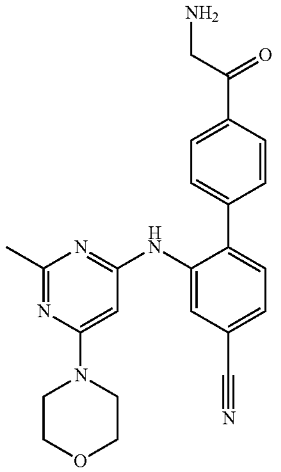 [SMILES: Cc1nc(Nc2cc(C#N)ccc2-c2ccc(C(=O)CN)cc2)cc(N2CCOCC2)n1] | 4-[4-(2-aminoacetyl)phenyl]-3-[(2-methyl-6-morpholin-4-ylpyrimidin-4-yl)amino]benzonitrile |
| 5 | 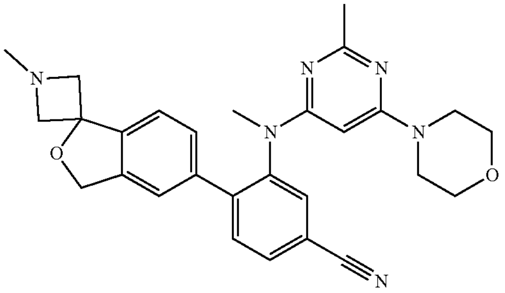 [SMILES: Cc1nc(N2CCOCC2)cc(N(C)c2cc(C#N)ccc2-c2ccc3c(c2)COC32CN(C)C2)n1] | 3-[methyl-(2-methyl-6-morpholin-4-ylpyrimidin-4-yl)amino]-4-(1'-methylspiro[3H-2-benzofuran-1,3'-azetidin]-5-yl)benzonitrile |
| 6 | 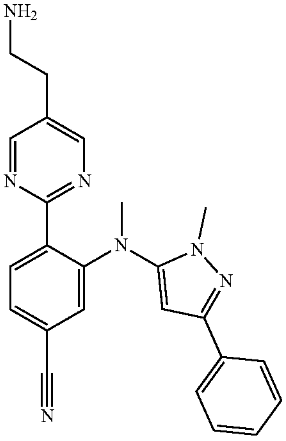 [SMILES: CN(c1cc(C#N)ccc1-c1ncc(CCN)cn1)c1cc(-c2ccccc2)nn1C] | 4-[5-(2-aminoethyl)pyrimidin-2-yl]-3-[methyl-(2-methyl-5-phenylpyrazol-3-yl)amino]benzonitrile |

TABLE 1-continued
| Compound number | Structural formula | Compound name |
| --- | --- | --- |
| 7 | 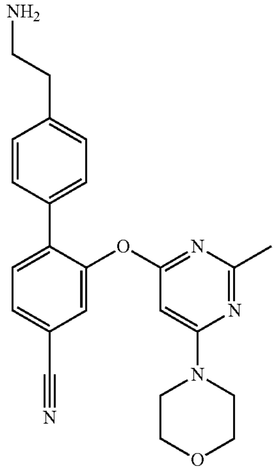 [SMILES: Cc1nc(Oc2cc(C#N)ccc2-c2ccc(CCN)cc2)cc(N2CCOCC2)n1] | 4-[4-(2-aminoethyl)phenyl]-3-(2-methyl-6-morpholin-4-ylpyrimidin-4-yl)oxybenzonitrile |
| 8 | 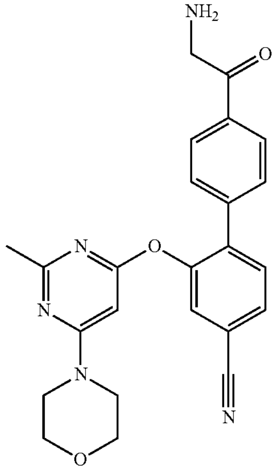 [SMILES: Cc1nc(Oc2cc(C#N)ccc2-c2ccc(C(=O)CN)cc2)cc(N2CCOCC2)n1] | 4-[4-(2-aminoacetyl)phenyl]-3-(2-methyl-6-morpholin-4-ylpyrimidin-4-yl)oxybenzonitrile |
| 9 | 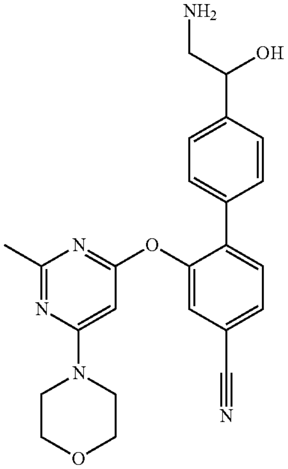 [SMILES: Cc1nc(Oc2cc(C#N)ccc2-c2ccc(C(O)CN)cc2)cc(N2CCOCC2)n1] | 4-[4-(2-amino-1-hydroxyethyl)phenyl]-3-(2-methyl-6-morpholin-4-ylpyrimidin-4-yl)oxybenzonitrile |

TABLE 1-continued
| Compound number | Structural formula | Compound name |
|---|---|---|
| 10 | 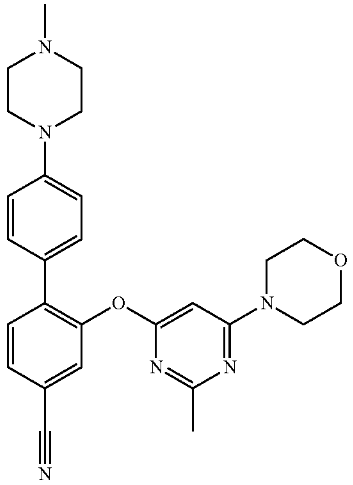 [SMILES: Cc1nc(Oc2cc(C#N)ccc2-c2ccc(N3CCN(C)CC3)cc2)cc(N2CCOCC2)n1] | 3-(2-methyl-6-morpholin-4-ylpyrimidin-4-yl)oxy-4-[4-(4-methylpiperazin-1-yl)phenyl]benzonitrile |
| 11 | 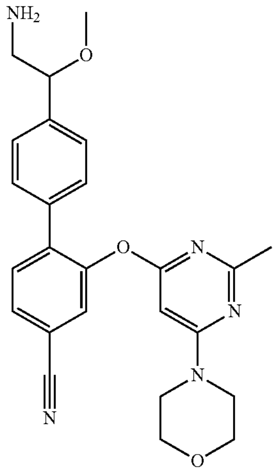 [SMILES: COC(CN)c1ccc(-c2ccc(C#N)cc2Oc2cc(N3CCOCC3)nc(C)n2)cc1] | 4-[4-(2-amino-1-methoxyethyl)phenyl]-3-(2-methyl-6-morpholin-4-ylpyrimidin-4-yl)oxybenzonitrile |
| 12 | 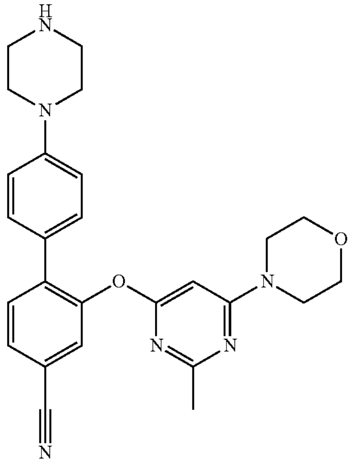 [SMILES: Cc1nc(Oc2cc(C#N)ccc2-c2ccc(N3CCNCC3)cc2)cc(N2CCOCC2)n1] | 3-(2-methyl-6-morpholin-4-ylpyrimidin-4-yl)oxy-4-(4-piperazin-1-ylphenyl)benzonitrile |

TABLE 1-continued
| Compound number | Structural formula | Compound name |
|---|---|---|
| 13 | 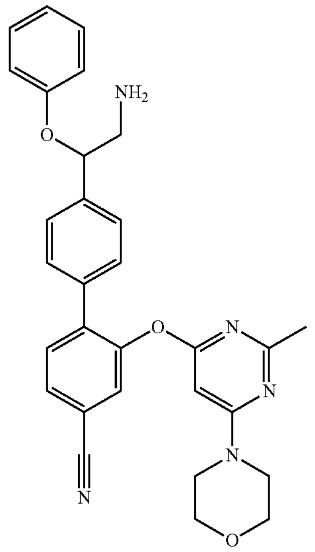 [SMILES: Cc1nc(Oc2cc(C#N)ccc2-c2ccc(C(CN)Oc3ccccc3)cc2)cc(N2CCOCC2)n1] | 4-[4-(2-amino-1-phenoxyethyl)phenyl]-3-(2-methyl-6-morpholin-4-ylpyrimidin-4-yl)oxybenzonitrile |
| 14 | 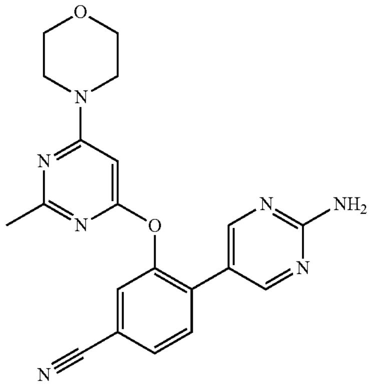 [SMILES: Cc1nc(Oc2cc(C#N)ccc2-c2cnc(N)nc2)cc(N2CCOCC2)n1] | 4-(2-aminopyrimidin-5-yl)-3-(2-methyl-6-morpholin-4-ylpyrimidin-4-yl)oxybenzonitrile |
| 15 | 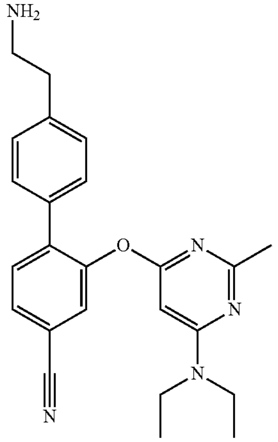 [SMILES: CCN(CC)c1cc(Oc2cc(C#N)ccc2-c2ccc(CCN)cc2)nc(C)n1] | 4-[4-(2-aminoethyl)phenyl]-3-[6-(diethylamino)-2-methylpyrimidin-4-yl]oxybenzonitrile |

TABLE 1-continued
| Compound number | Structural formula | Compound name |
| --- | --- | --- |
| 16 | 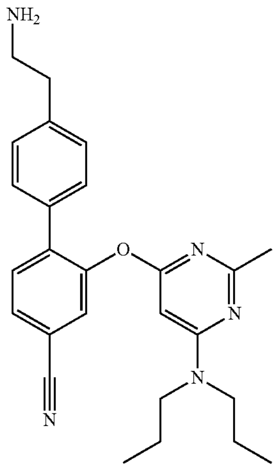 [SMILES: CCCN(CCC)c1cc(Oc2cc(C#N)ccc2-c2ccc(CCN)cc2)nc(C)n1] | 4-[4-(2-aminoethyl)phenyl]-3-[6-(dipropylamino)-2-methylpyrimidin-4-yl]oxybenzonitrile |
| 17 | 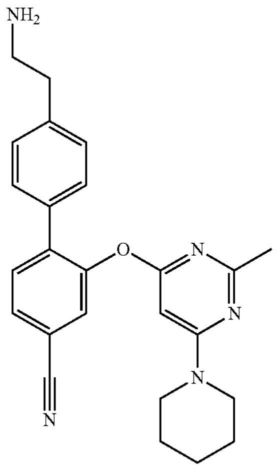 [SMILES: Cc1nc(Oc2cc(C#N)ccc2-c2ccc(CCN)cc2)cc(N2CCCCC2)n1] | 4-[4-(2-aminoethyl)phenyl]-3-(2-methyl-6-piperidin-1-ylpyrimidin-4-yl)oxybenzonitrile |
| 18 | 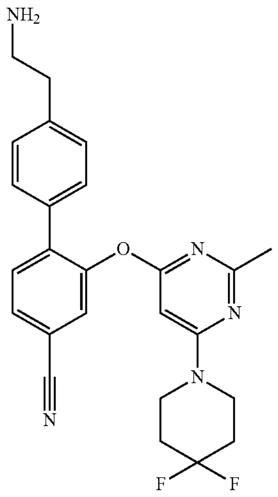 [SMILES: Cc1nc(Oc2cc(C#N)ccc2-c2ccc(CCN)cc2)cc(N2CCC(F)(F)CC2)n1] | 4-[4-(2-aminoethyl)phenyl]-3-[6-(4,4-difluoropiperidin-1-yl)-2-methylpyrimidin-4-yl]oxybenzonitrile |

TABLE 1-continued
| Compound number | Structural formula | Compound name |
|---|---|---|
| 19 | 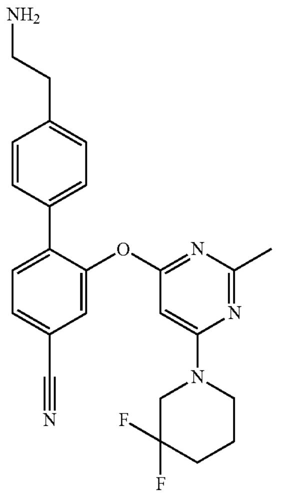 [SMILES: Cc1nc(Oc2cc(C#N)ccc2-c2ccc(CCN)cc2)cc(N2CCCC(F)(F)C2)n1] | 4-[4-(2-aminoethyl)phenyl]-3-[6-(3,3-difluoropiperidin-1-yl)-2-methylpyrimidin-4-yl]oxybenzonitrile |
| 20 | 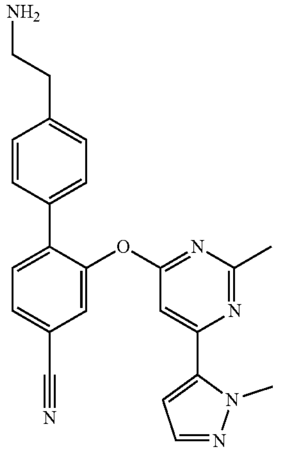 [SMILES: Cc1nc(Oc2cc(C#N)ccc2-c2ccc(CCN)cc2)cc(-c2ccnn2C)n1] | 4-[4-(2-aminoethyl)phenyl]-3-[2-methyl-6-(2-methylpyrazol-3-yl)pyrimidin-4-yl]oxybenzonitrile |
| 21 | 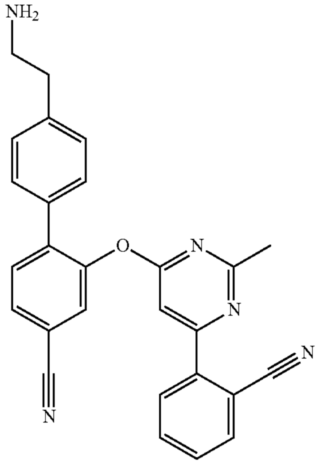 [SMILES: Cc1nc(Oc2cc(C#N)ccc2-c2ccc(CCN)cc2)cc(-c2ccccc2C#N)n1] | 4-[4-(2-aminoethyl)phenyl]-3-[6-(2-cyanophenyl)-2-methylpyrimidin-4-yl]oxybenzonitrile |

TABLE 1-continued
| Compound number | Structural formula | Compound name |
|---|---|---|
| 22 | 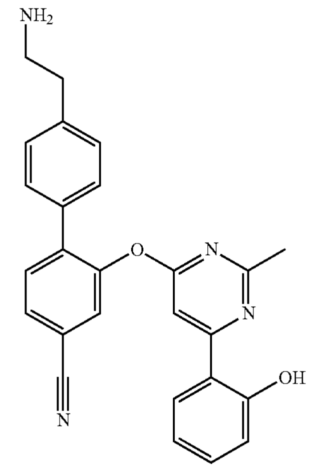 [SMILES: Cc1nc(Oc2cc(C#N)ccc2-c2ccc(CCN)cc2)cc(-c2ccccc2O)n1] | 4-[4-(2-aminoethyl)phenyl]-3-[6-(2-hydroxyphenyl)-2-methylpyrimidin-4-yl]oxybenzonitrile |
| 23 | 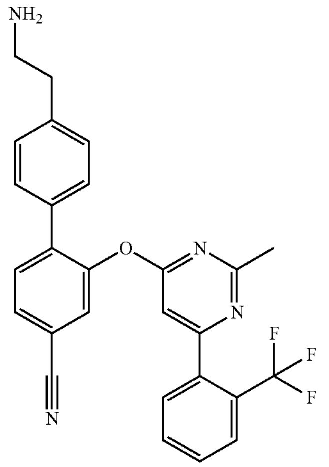 [SMILES: Cc1nc(Oc2cc(C#N)ccc2-c2ccc(CCN)cc2)cc(-c2ccccc2C(F)(F)F)n1] | 4-[4-(2-aminoethyl)phenyl]-3-[2-methyl-6-[2-(trifluoromethyl)phenyl]pyrimidin-4-yl]oxybenzonitrile |
| 24 | 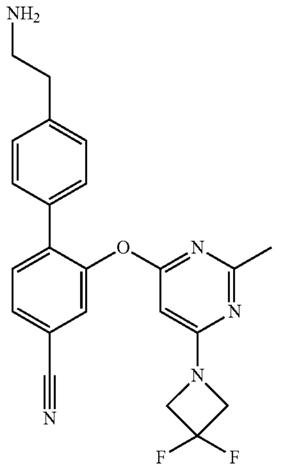 [SMILES: Cc1nc(Oc2cc(C#N)ccc2-c2ccc(CCN)cc2)cc(N2CC(F)(F)C2)n1] | 4-[4-(2-aminoethyl)phenyl]-3-[6-(3,3-difluoroazetidin-1-yl)-2-methylpyrimidin-4-yl]oxybenzonitrile |

TABLE 1-continued
| Compound number | Structural formula | Compound name |
|---|---|---|
| 25 | 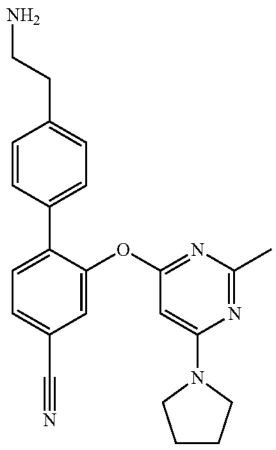 [SMILES: Cc1nc(Oc2cc(C#N)ccc2-c2ccc(CCN)cc2)cc(N2CCCC2)n1] | 4-[4-(2-aminoethyl)phenyl]-3-(2-methyl-6-pyrrolidin-1-ylpyrimidin-4-yl)oxybenzonitrile |
| 26 | 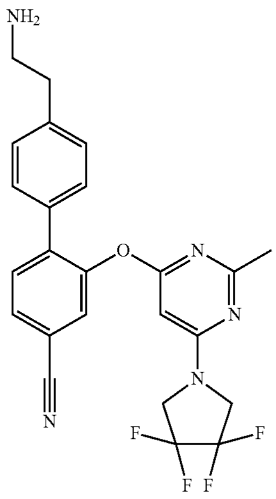 [SMILES: Cc1nc(Oc2cc(C#N)ccc2-c2ccc(CCN)cc2)cc(N2CC(F)(F)C(F)(F)C2)n1] | 4-[4-(2-aminoethyl)phenyl]-3-[2-methyl-6-(3,3,4,4-tetrafluoropyrrolidin-1-yl)pyrimidin-4-yl]oxybenzonitrile |
| 27 | 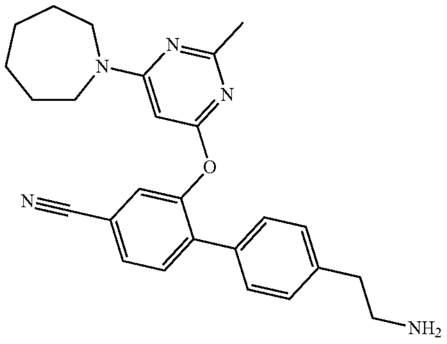 [SMILES: Cc1nc(Oc2cc(C#N)ccc2-c2ccc(CCN)cc2)cc(N2CCCCCC2)n1] | 4-[4-(2-aminoethyl)phenyl]-3-[6-(azepan-1-yl)-2-methylpyrimidin-4-yl]oxybenzonitrile |

TABLE 1-continued
| Compound number | Structural formula | Compound name |
| --- | --- | --- |
| 28 | 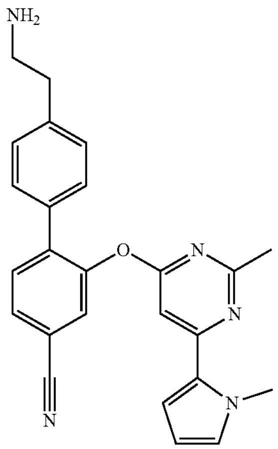 [SMILES: Cc1nc(Oc2cc(C#N)ccc2-c2ccc(CCN)cc2)cc(-c2cccn2C)n1] | 4-[4-(2-aminoethyl)phenyl]-3-[2-methyl-6-(1-methylpyrrol-2-yl)pyrimidin-4-yl]oxybenzonitrile |
| 29 | 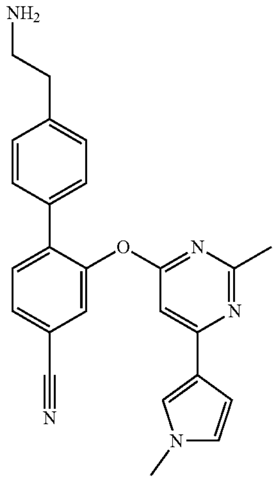 [SMILES: Cc1nc(Oc2cc(C#N)ccc2-c2ccc(CCN)cc2)cc(-c2ccn(C)c2)n1] | 4-[4-(2-aminoethyl)phenyl]-3-[2-methyl-6-(1-methylpyrrol-3-yl)pyrimidin-4-yl]oxybenzonitrile |
| 30 | 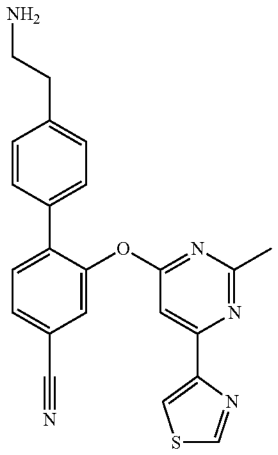 [SMILES: Cc1nc(Oc2cc(C#N)ccc2-c2ccc(CCN)cc2)cc(-c2cscn2)n1] | 4-[4-(2-aminoethyl)phenyl]-3-[2-methyl-6-(1,3-thiazol-4-yl)pyrimidin-4-yl]oxybenzonitrile |

TABLE 1-continued
| Compound number | Structural formula | Compound name |
|---|---|---|
| 31 | 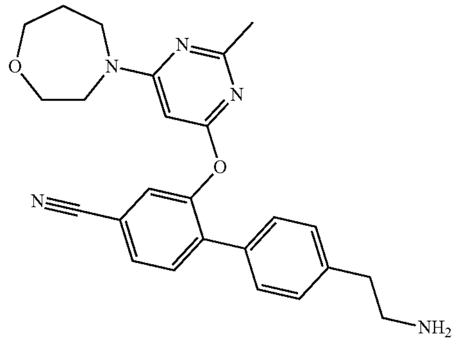 [SMILES: Cc1nc(Oc2cc(C#N)ccc2-c2ccc(CCN)cc2)cc(N2CCCOCC2)n1] | 4-[4-(2-aminoethyl)phenyl]-3-[2-methyl-6-(1,4-oxazepan-4-yl)pyrimidin-4-yl]oxybenzonitrile |
| 32 | 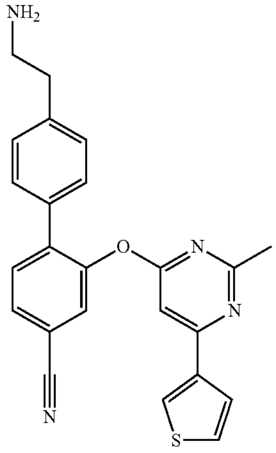 [SMILES: Cc1nc(Oc2cc(C#N)ccc2-c2ccc(CCN)cc2)cc(-c2ccsc2)n1] | 4-[4-(2-aminoethyl)phenyl]-3-(2-methyl-6-thiophen-3-ylpyrimidin-4-yl)oxybenzonitrile |
| 33 | 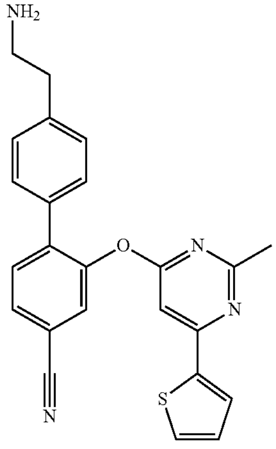 [SMILES: Cc1nc(Oc2cc(C#N)ccc2-c2ccc(CCN)cc2)cc(-c2cccs2)n1] | 4-[4-(2-aminoethyl)phenyl]-3-(2-methyl-6-thiophen-2-ylpyrimidin-4-yl)oxybenzonitrile |

TABLE 1-continued
| Compound number | Structural formula | Compound name |
|---|---|---|
| 34 | 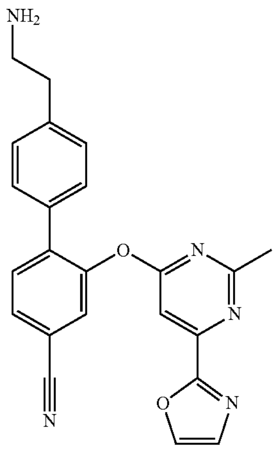 [SMILES: Cc1nc(Oc2cc(C#N)ccc2-c2ccc(CCN)cc2)cc(-c2ncco2)n1] | 4-[4-(2-aminoethyl)phenyl]-3-[2-methyl-6-(1,3-oxazol-2-yl)pyrimidin-4-yl]oxybenzonitrile |
| 35 | 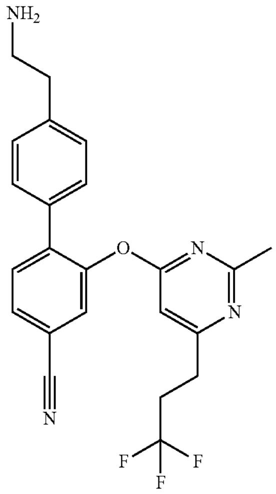 [SMILES: Cc1nc(CCC(F)(F)F)cc(Oc2cc(C#N)ccc2-c2ccc(CCN)cc2)n1] | 4-[4-(2-aminoethyl)phenyl]-3-[2-methyl-6-(2,2,2-trifluoroethoxy)pyrimidin-4-yl]oxybenzonitrile |
| 36 | 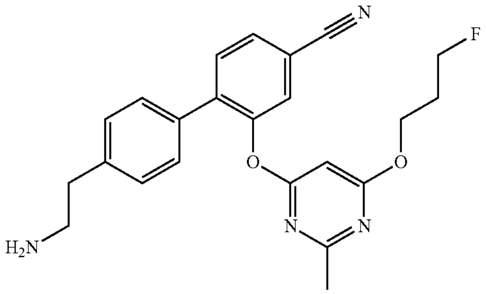 [SMILES: Cc1nc(OCCCF)cc(Oc2cc(C#N)ccc2-c2ccc(CCN)cc2)n1] | 4-[4-(2-aminoethyl)phenyl]-3-[6-(3-fluoropropoxy)-2-methylpyrimidin-4-yl]oxybenzonitrile |

TABLE 1-continued
| Compound number | Structural formula | Compound name |
|---|---|---|
| 37 | 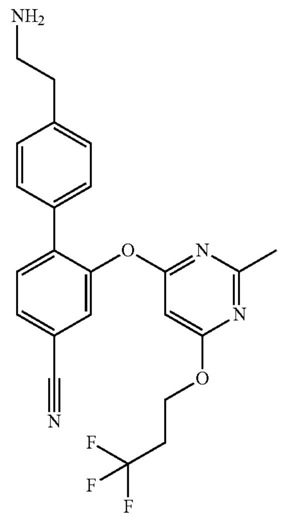 [SMILES: Cc1nc(OCCC(F)(F)F)cc(Oc2cc(C#N)ccc2-c2ccc(CCN)cc2)n1] | 4-[4-(2-aminoethyl)phenyl]-3-[2-methyl-6-(3,3,3-trifluoropropoxy)pyrimidin-4-yl]oxybenzonitrile |
| 38 | 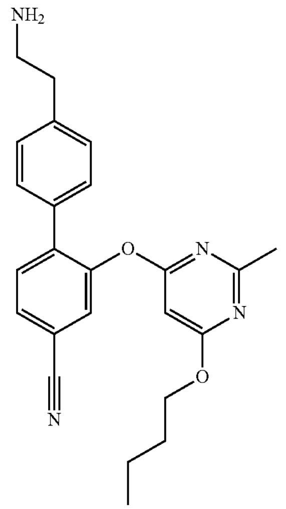 [SMILES: CCCCOc1cc(Oc2cc(C#N)ccc2-c2ccc(CCN)cc2)nc(C)n1] | 4-[4-(2-aminoethyl)phenyl]-3-(6-butoxy-2-methylpyrimidin-4-yl)oxybenzonitrile |
| 39 | 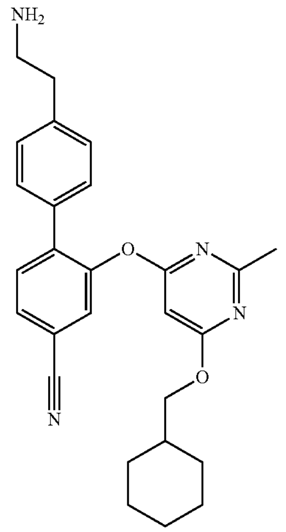 [SMILES: Cc1nc(OCC2CCCCC2)cc(Oc2cc(C#N)ccc2-c2ccc(CCN)cc2)n1] | 4-[4-(2-aminoethyl)phenyl]-3-[6-(cyclohexylmethoxy)-2-methylpyrimidin-4-yl]oxybenzonitrile |

TABLE 1-continued
| Compound number | Structural formula | Compound name |
| --- | --- | --- |
| 40 | 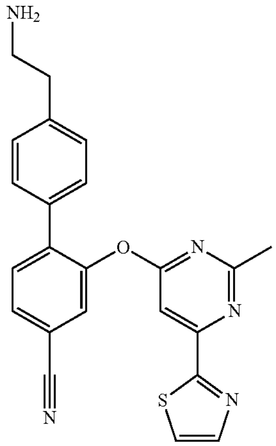 [SMILES: Cc1nc(Oc2cc(C#N)ccc2-c2ccc(CCN)cc2)cc(-c2nccs2)n1] | 4-[4-(2-aminoethyl)phenyl]-3-[2-methyl-6-(1,3-thiazol-2-yl)pyrimidin-4-yl]oxybenzonitrile |
| 41 | 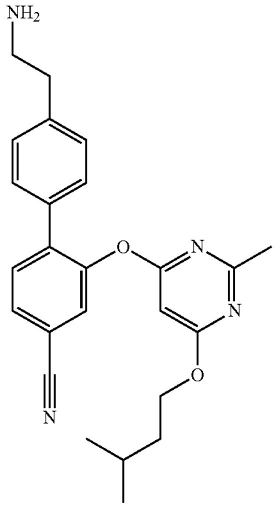 [SMILES: Cc1nc(OCCC(C)C)cc(Oc2cc(C#N)ccc2-c2ccc(CCN)cc2)n1] | 4-[4-(2-aminoethyl)phenyl]-3-[2-methyl-6-(3-methylbutoxy)pyrimidin-4-yl]oxybenzonitrile |
| 42 | 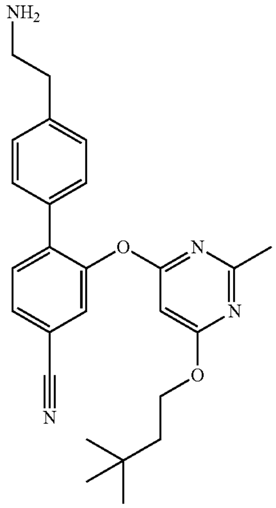 [SMILES: Cc1nc(OCCC(C)(C)C)cc(Oc2cc(C#N)ccc2-c2ccc(CCN)cc2)n1] | 4-[4-(2-aminoethyl)phenyl]-3-[6-(3,3-dimethylbutoxy)-2-methylpyrimidin-4-yl]oxybenzonitrile |

TABLE 1-continued
| Compound number | Structural formula | Compound name |
|---|---|---|
| 43 | 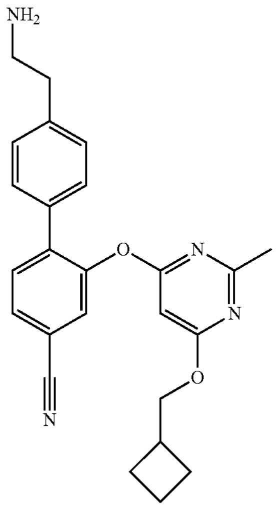 [SMILES: Cc1nc(OCC2CCC2)cc(Oc2cc(C#N)ccc2-c2ccc(CCN)cc2)n1] | 4-[4-(2-aminoethyl)phenyl]-3-[6-(cyclobutylmethoxy)-2-methylpyrimidin-4-yl]oxybenzonitrile |
| 44 | 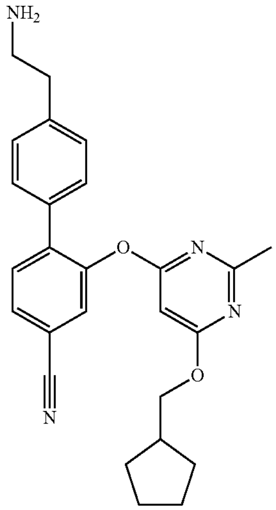 [SMILES: Cc1nc(OCC2CCCC2)cc(Oc2cc(C#N)ccc2-c2ccc(CCN)cc2)n1] | 4-[4-(2-aminoethyl)phenyl]-3-[6-(cyclopentylmethoxy)-2-methylpyrimidin-4-yl]oxybenzonitrile |
| 45 | 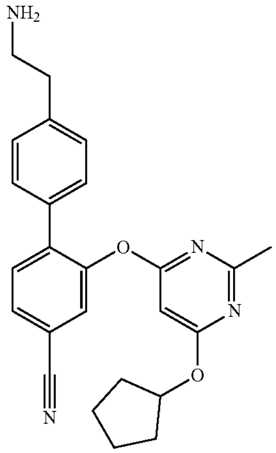 [SMILES: Cc1nc(Oc2cc(C#N)ccc2-c2ccc(CCN)cc2)cc(OC2CCCC2)n1] | 4-[4-(2-aminoethyl)phenyl]-3-(6-cyclopentyloxy-2-methylpyrimidin-4-yl)oxybenzonitrile |

TABLE 1-continued
| Compound number | Structural formula | Compound name |
|---|---|---|
| 46 | 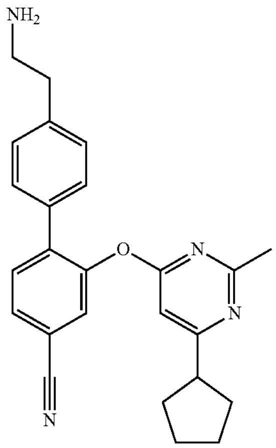 [SMILES: Cc1nc(Oc2cc(C#N)ccc2-c2ccc(CCN)cc2)cc(C2CCCC2)n1] | 4-[4-(2-aminoethyl)phenyl]-3-(6-cyclopentyl-2-methylpyrimidin-4-yl)oxybenzonitrile |
| 47 | 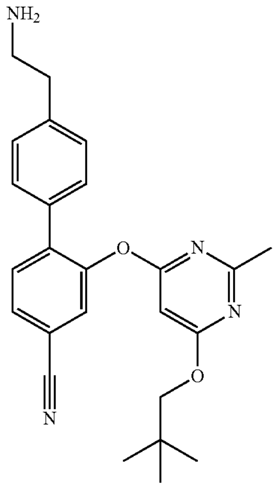 [SMILES: Cc1nc(OCC(C)(C)C)cc(Oc2cc(C#N)ccc2-c2ccc(CCN)cc2)n1] | 4-[4-(2-aminoethyl)phenyl]-3-[6-(2,2-dimethylpropoxy)-2-methylpyrimidin-4-yl]oxybenzonitrile |
| 48 | 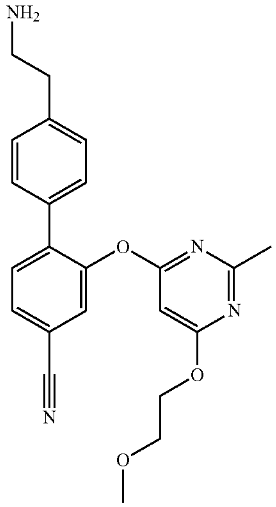 [SMILES: COCCOc1cc(Oc2cc(C#N)ccc2-c2ccc(CCN)cc2)nc(C)n1] | 4-[4-(2-aminoethyl)phenyl]-3-[6-(2-methoxyethoxy)-2-methylpyrimidin-4-yl]oxybenzonitrile |

TABLE 1-continued
| Compound number | Structural formula | Compound name |
|---|---|---|
| 49 | 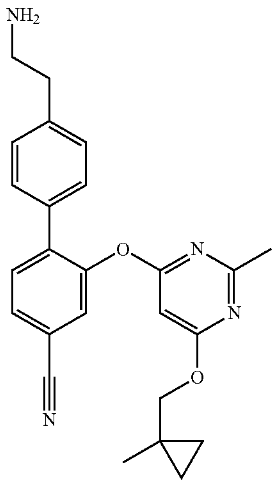 [SMILES: Cc1nc(OCC2(C)CC2)cc(Oc2cc(C#N)ccc2-c2ccc(CCN)cc2)n1] | 4-[4-(2-aminoethyl)phenyl]-3-[2-methyl-6-[(1-methylcyclopropyl)methoxy] pyrimidin-4-yl]oxybenzonitrile |
| 50 | 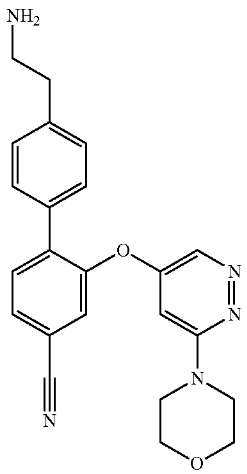 [SMILES: N#Cc1ccc(-c2ccc(CCN)cc2)c(Oc2cnnc(N3CCOCC3)c2)c1] | 4-[4-(2-aminoethyl)phenyl]-3-(6-morpholin-4-ylpyridazin-4-yl)oxybenzonitrile |
| 51 | 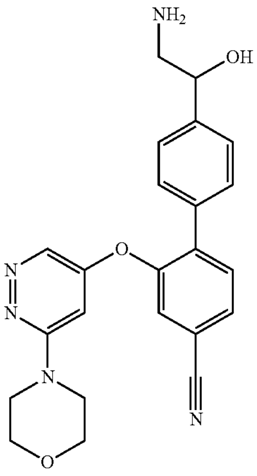 [SMILES: N#Cc1ccc(-c2ccc(C(O)CN)cc2)c(Oc2cnnc(N3CCOCC3)c2)c1] | 4-[4-(2-amino-1-hydroxyethyl)phenyl]-3-(6-morpholin-4-ylpyridazin-4-yl)oxybenzonitrile |

TABLE 1-continued
| Compound number | Structural formula | Compound name |
|---|---|---|
| 52 | 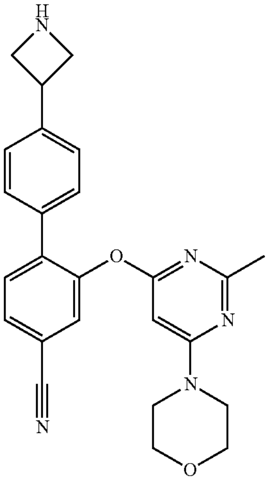 [SMILES: Cc1nc(Oc2cc(C#N)ccc2-c2ccc(C3CNC3)cc2)cc(N2CCOCC2)n1] | 4-[4-(azetidin-3-yl)phenyl]-3-(2-methyl-6-morpholin-4-ylpyrimidin-4-yl)oxybenzonitrile |
| 53 | 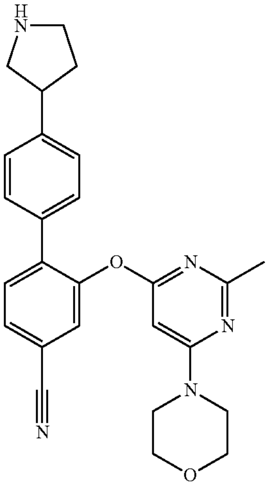 [SMILES: Cc1nc(Oc2cc(C#N)ccc2-c2ccc(C3CCNC3)cc2)cc(N2CCOCC2)n1] | 3-(2-methyl-6-morpholin-4-ylpyrimidin-4-yl)oxy-4-(4-pyrrolidin-3-ylphenyl)benzonitrile |
| 54 | 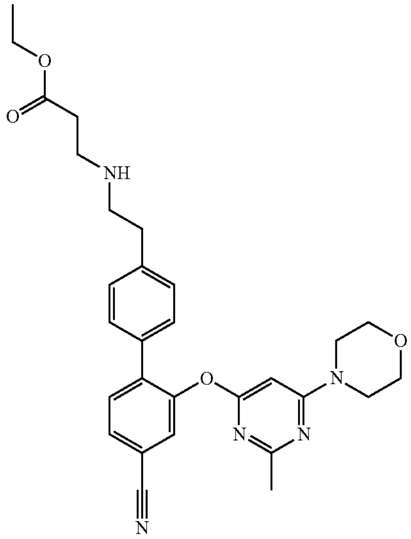 [SMILES: CCOC(=O)CCNCCc1ccc(-c2ccc(C#N)cc2Oc2cc(N3CCOCC3)nc(C)n2)cc1] | ethyl 3-[2-[4-[4-cyano-2-(2-methyl-6-morpholin-4-ylpyrimidin-4-yl)oxyphenyl]phenyl]ethylamino] propanoate |

TABLE 1-continued
| Compound number | Structural formula | Compound name |
|---|---|---|
| 55 | 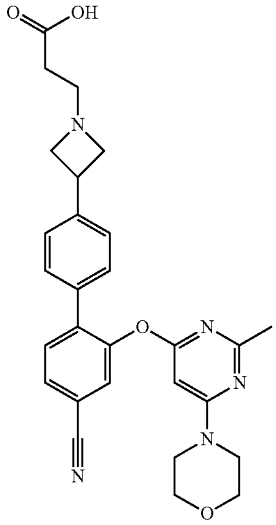 [SMILES: Cc1nc(Oc2cc(C#N)ccc2-c2ccc(C3CN(CCC(=O)O)C3)cc2)cc(N2CCOCC2)n1] | 3-[3-[4-[4-cyano-2-(2-methyl-6-morpholin-4-ylpyrimidin-4-yl)oxyphenyl]phenyl]azetidin-1-yl]propanoic acid |
| 56 | 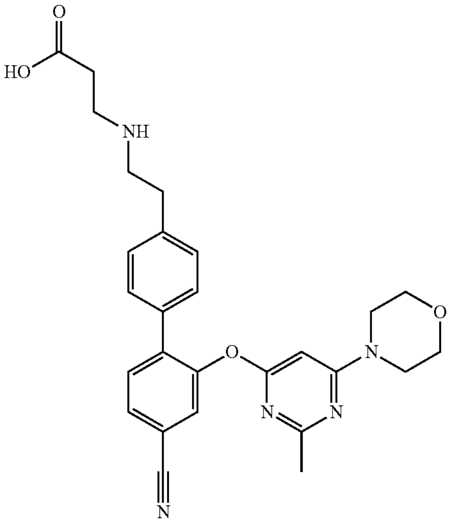 [SMILES: Cc1nc(Oc2cc(C#N)ccc2-c2ccc(CCNCCC(=O)O)cc2)cc(N2CCOCC2)n1] | 3-[2-[4-[4-cyano-2-(2-methyl-6-morpholin-4-ylpyrimidin-4-yl)oxyphenyl]phenyl]ethylamino] propanoic acid |
| 57 | 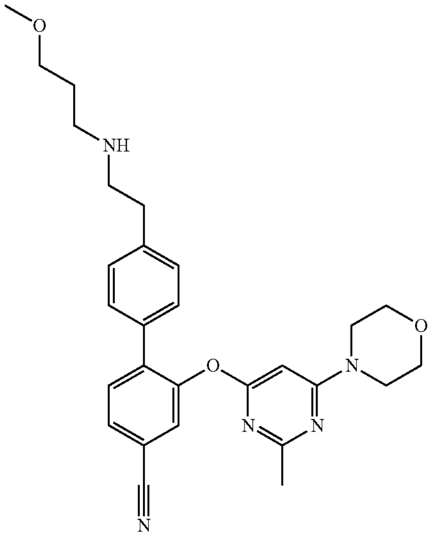 [SMILES: COCCCNCCc1ccc(-c2ccc(C#N)cc2Oc2cc(N3CCOCC3)nc(C)n2)cc1] | 4-[4-[2-(3-methoxypropylamino)ethyl]phenyl]-3-(2-methyl-6-morpholin-4-ylpyrimidin-4-yl)oxybenzonitrile |

TABLE 1-continued
| Compound number | Structural formula | Compound name |
|---|---|---|
| 58 | 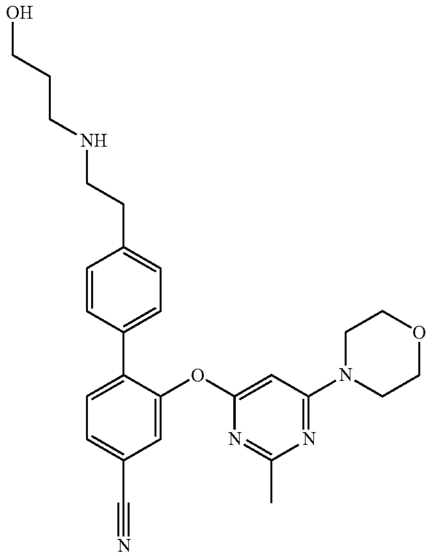 [SMILES: Cc1nc(Oc2cc(C#N)ccc2-c2ccc(CCNCCCO)cc2)cc(N2CCOCC2)n1] | 4-[4-[2-(3-hydroxypropylamino)ethyl]phenyl]-3-(2-methyl-6-morpholin-4-ylpyrimidin-4-yl)oxybenzonitrile |
| 59 | 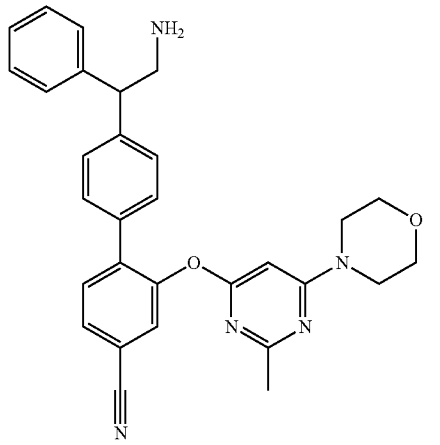 [SMILES: Cc1nc(Oc2cc(C#N)ccc2-c2ccc(C(CN)c3ccccc3)cc2)cc(N2CCOCC2)n1] | 4-[4-(2-amino-1-phenylethyl)phenyl]-3-(2-methyl-6-morpholin-4-ylpyrimidin-4-yl)oxybenzonitrile |
| 60 | 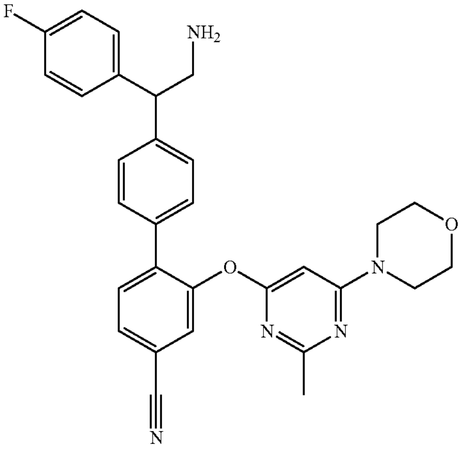 [SMILES: Cc1nc(Oc2cc(C#N)ccc2-c2ccc(C(CN)c3ccc(F)cc3)cc2)cc(N2CCOCC2)n1] | 4-[4-[2-amino-1-(4-fluorophenyl)ethyl]phenyl]-3-(2-methyl-6-morpholin-4-ylpyrimidin-4-yl)oxybenzonitrile |

TABLE 1-continued
| Compound number | Structural formula | Compound name |
|---|---|---|
| 61 | 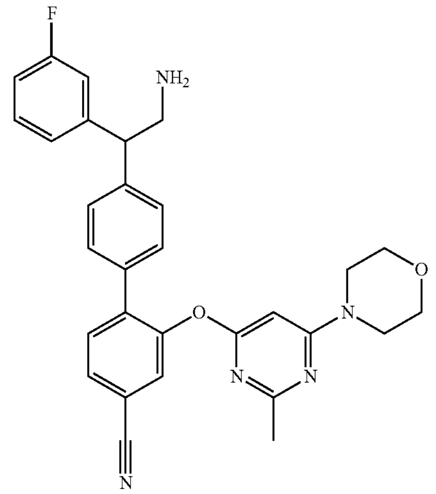 [SMILES: Cc1nc(Oc2cc(C#N)ccc2-c2ccc(C(CN)c3cccc(F)c3)cc2)cc(N2CCOCC2)n1] | 4-[4-[2-amino-1-(3-fluorophenyl)ethyl]phenyl]-3-(2-methyl-6-morpholin-4-ylpyrimidin-4-yl)oxybenzonitrile |
| 62 | 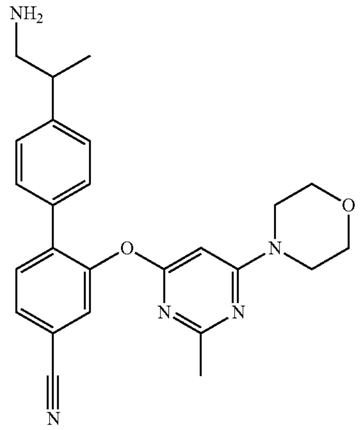 [SMILES: Cc1nc(Oc2cc(C#N)ccc2-c2ccc(C(C)CN)cc2)cc(N2CCOCC2)n1] | 4-[4-(1-aminopropan-2-yl)phenyl]-3-(2-methyl-6-morpholin-4-ylpyrimidin-4-yl)oxybenzonitrile |
| 63 | 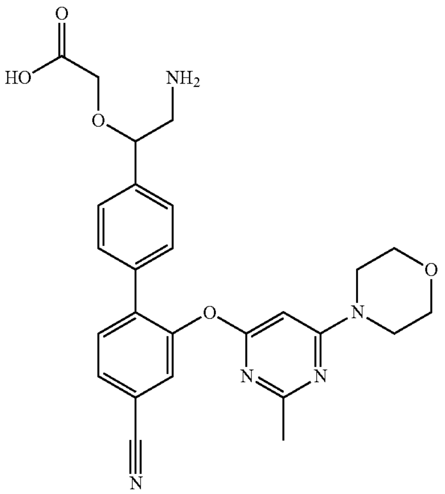 [SMILES: Cc1nc(Oc2cc(C#N)ccc2-c2ccc(C(CN)OCC(=O)O)cc2)cc(N2CCOCC2)n1] | 2-[2-amino-1-[4-[4-cyano-2-(2-methyl-6-morpholin-4-ylpyrimidin-4-yl)oxyphenyl]phenyl]ethoxy] acetic acid |

TABLE 1-continued
| Compound number | Structural formula | Compound name |
|---|---|---|
| 64 | 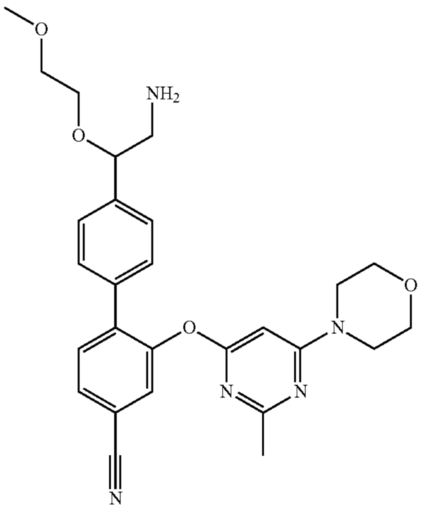 [SMILES: COCCOC(CN)c1ccc(-c2ccc(C#N)cc2Oc2cc(N3CCOCC3)nc(C)n2)cc1] | 4-[4-[2-amino-1-(2-methoxyethoxy)ethyl]phenyl]-3-(2-methyl-6-morpholin-4-ylpyrimidin-4-yl)oxybenzonitrile |
| 65 | 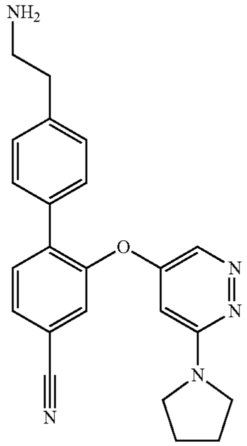 [SMILES: N#Cc1ccc(-c2ccc(CCN)cc2)c(Oc2cnnc(N3CCCC3)c2)c1] | 4-[4-(2-aminoethyl)phenyl]-3-(6-pyrrolidin-1-ylpyridazin-4-yl)oxybenzonitrile |
| 66 | 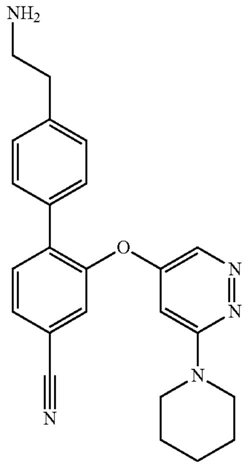 [SMILES: N#Cc1ccc(-c2ccc(CCN)cc2)c(Oc2cnnc(N3CCCCC3)c2)c1] | 4-[4-(2-aminoethyl)phenyl]-3-(6-piperidin-1-ylpyridazin-4-yl)oxybenzonitrile |

TABLE 1-continued
| Compound number | Structural formula | Compound name |
|---|---|---|
| 67 | 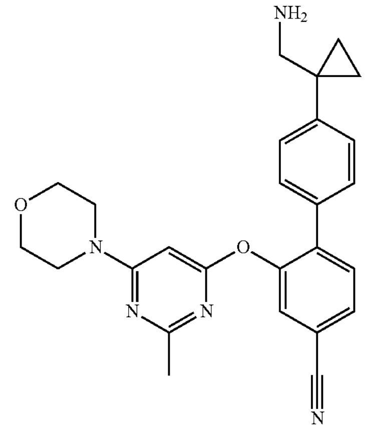 [SMILES: Cc1nc(Oc2cc(C#N)ccc2-c2ccc(C3(CN)CC3)cc2)cc(N2CCOCC2)n1] | 4-[4-[1-(aminomethyl)cyclopropyl]phenyl]-3-(2-methyl-6-morpholin-4-ylpyrimidin-4-yl)oxybenzonitrile |
| 68 | 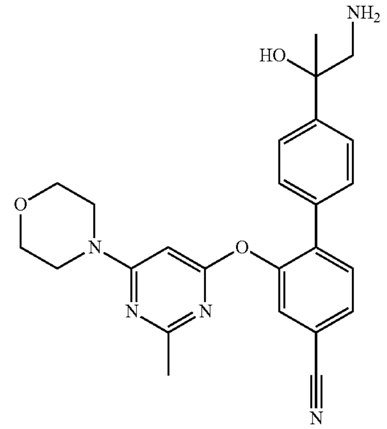 [SMILES: Cc1nc(Oc2cc(C#N)ccc2-c2ccc(C(C)(O)CN)cc2)cc(N2CCOCC2)n1] | 4-[4-(1-amino-2-hydroxypropan-2-yl)phenyl]-3-(2-methyl-6-morpholin-4-ylpyrimidin-4-yl)oxybenzonitrile |
| 69 | 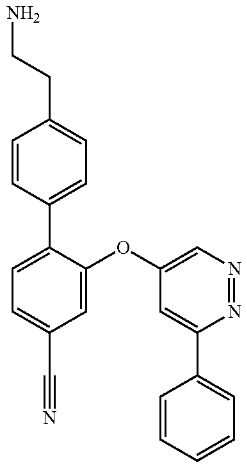 [SMILES: N#Cc1ccc(-c2ccc(CCN)cc2)c(Oc2cnnc(-c3ccccc3)c2)c1] | 4-[4-(2-aminoethyl)phenyl]-3-(6-phenylpyridazin-4-yl)oxybenzonitrile |

TABLE 1-continued
| Compound number | Structural formula | Compound name |
|---|---|---|
| 70 | 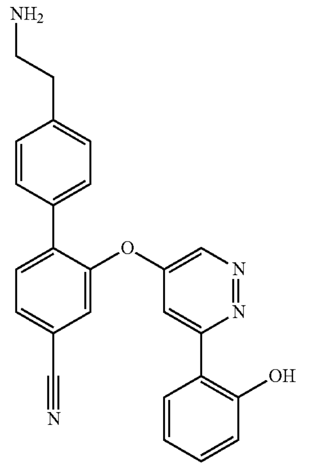 [SMILES: N#Cc1ccc(-c2ccc(CCN)cc2)c(Oc2cnnc(-c3ccccc3O)c2)c1] | 4-[4-(2-aminoethyl)phenyl]-3-[6-(2-hydroxyphenyl)pyridazin-4-yl]oxybenzonitrile |
| 71 | 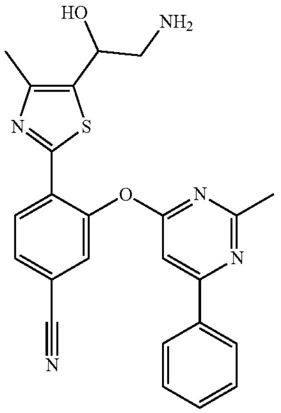 | 4-[5-(2-amino-1-hydroxyethyl)-4-methyl-1,3-thiazol-2-yl]-3-(2-methyl-6-phenylpyrimidin-4-yl)oxybenzonitrile |
| 72 | 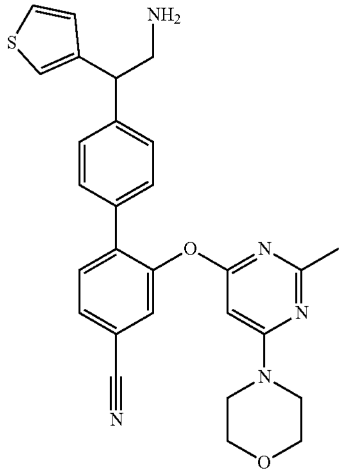 [SMILES: Cc1nc(Oc2cc(C#N)ccc2-c2ccc(C(CN)c3ccsc3)cc2)cc(N2CCOCC2)n1] | 4-[4-(2-amino-1-thiophen-3-ylethyl)phenyl]-3-(2-methyl-6-morpholin-4-ylpyrimidin-4-yl)oxybenzonitrile |

TABLE 1-continued
| Compound number | Structural formula | Compound name |
|---|---|---|
| 73 | 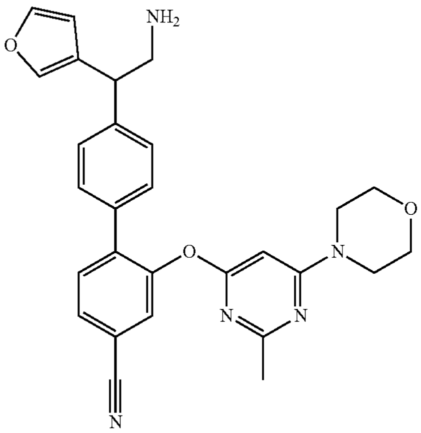 [SMILES: Cc1nc(Oc2cc(C#N)ccc2-c2ccc(C(CN)c3ccoc3)cc2)cc(N2CCOCC2)n1] | 4-[4-[2-amino-1-(furan-3-yl)ethyl]phenyl]-3-(2-methyl-6-morpholin-4-ylpyrimidin-4-yl)oxybenzonitrile |
| 74 | 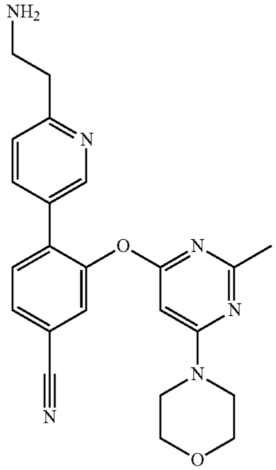 [SMILES: Cc1nc(Oc2cc(C#N)ccc2-c2ccc(CCN)nc2)cc(N2CCOCC2)n1] | 4-[6-(2-aminoethyl)pyridin-3-yl]-3-(2-methyl-6-morpholin-4-ylpyrimidin-4-yl)oxybenzonitrile |
| 75 | 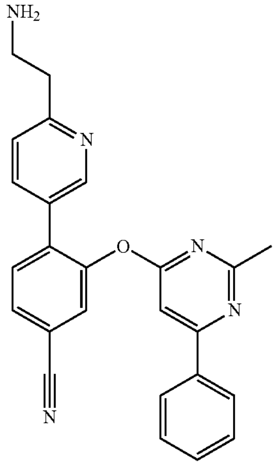 [SMILES: Cc1nc(Oc2cc(C#N)ccc2-c2ccc(CCN)nc2)cc(-c2ccccc2)n1] | 4-[6-(2-aminoethyl)pyridin-3-yl]-3-(2-methyl-6-phenylpyrimidin-4-yl)oxybenzonitrile |

TABLE 1-continued
| Compound number | Structural formula | Compound name |
|---|---|---|
| 76 | 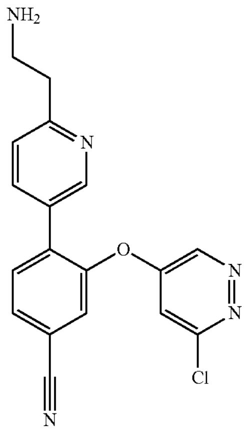 [SMILES: N#Cc1ccc(-c2ccc(CCN)nc2)c(Oc2cnnc(Cl)c2)c1] | 4-[6-(2-aminoethyl)pyridin-3-yl]-3-(6-chloropyridazin-4-yl)oxybenzonitrile |
| 77 | 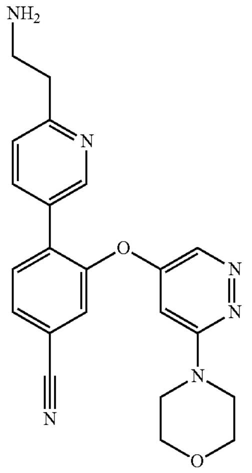 | 4-[6-(2-aminoethyl)pyridin-3-yl]-3-(6-morpholin-4-ylpyridazin-4-yl)oxybenzonitrile |
| 78 | 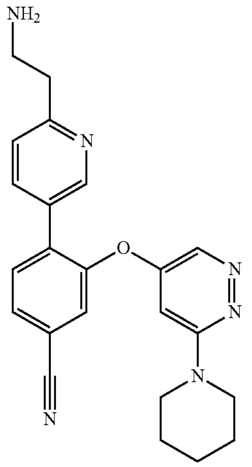 [SMILES: N#Cc1ccc(-c2ccc(CCN)nc2)c(Oc2cnnc(N3CCCCC3)c2)c1] | 4-[6-(2-aminoethyl)pyridin-3-yl]-3-(6-piperidin-1-ylpyridazin-4-yl)oxybenzonitrile |

TABLE 1-continued
| Compound number | Structural formula | Compound name |
|---|---|---|
| 79 | 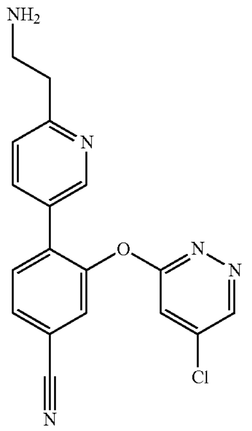 [SMILES: N#Cc1ccc(-c2ccc(CCN)nc2)c(Oc2cc(Cl)cnn2)c1] | 4-[6-(2-aminoethyl)pyridin-3-yl]-3-(5-chloropyridazin-3-yl)oxybenzonitrile |
| 80 | 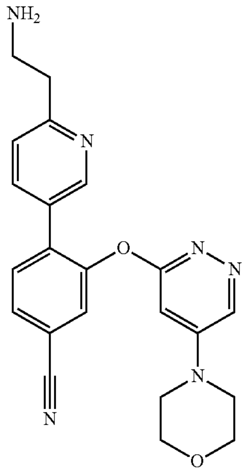 [SMILES: N#Cc1ccc(-c2ccc(CCN)nc2)c(Oc2cc(N3CCOCC3)cnn2)c1] | 4-[6-(2-aminoethyl)pyridin-3-yl]-3-(5-morpholin-4-ylpyridazin-3-yl)oxybenzonitrile |
| 81 | 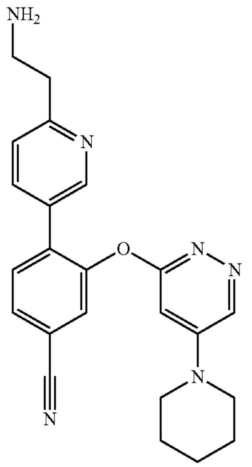 [SMILES: N#Cc1ccc(-c2ccc(CCN)nc2)c(Oc2cc(N3CCCCC3)cnn2)c1] | 4-[6-(2-aminoethyl)pyridin-3-yl]-3-(5-piperidin-1-ylpyridazin-3-yl)oxybenzonitrile |

TABLE 1-continued
| Compound number | Structural formula | Compound name |
|---|---|---|
| 82 | 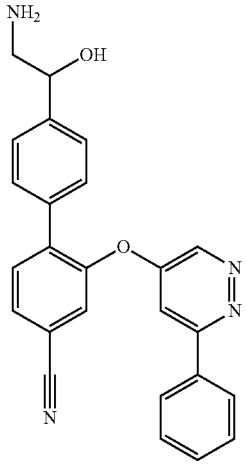 [SMILES: N#Cc1ccc(-c2ccc(C(O)CN)cc2)c(Oc2cnnc(-c3ccccc3)c2)c1] | 4-[4-(2-amino-1-hydroxyethyl)phenyl]-3-(6-phenylpyridazin-4-yl)oxybenzonitrile |
| 83 | 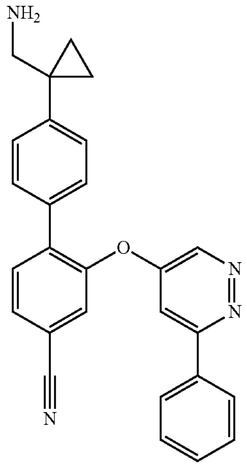 [SMILES: N#Cc1ccc(-c2ccc(C3(CN)CC3)cc2)c(Oc2cnnc(-c3ccccc3)c2)c1] | 4-[4-[1-(aminomethyl)cyclopropyl]phenyl]-3-(6-phenylpyridazin-4-yl)oxybenzonitrile |
| 84 | 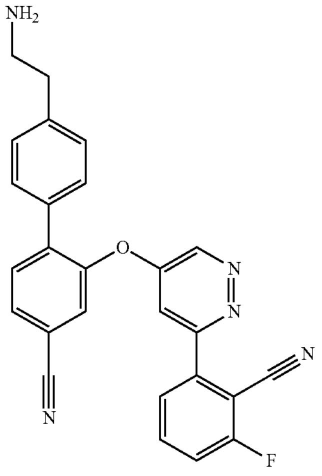 [SMILES: N#Cc1ccc(-c2ccc(CCN)cc2)c(Oc2cnnc(-c3cccc(F)c3C#N)c2)c1] | 2-[5-[2-[4-(2-aminoethyl)phenyl]-5-cyanophenoxy]pyridazin-3-yl]-6-fluorobenzonitrile |

TABLE 1-continued
| Compound number | Structural formula | Compound name |
|---|---|---|
| 85 | 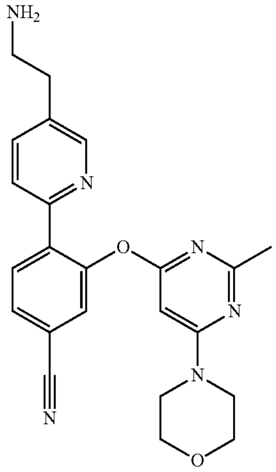 [SMILES: Cc1nc(Oc2cc(C#N)ccc2-c2ccc(CCN)cn2)cc(N2CCOCC2)n1] | 4-[5-(2-aminoethyl)pyridin-2-yl]-3-(2-methyl-6-morpholin-4-ylpyrimidin-4-yl)oxybenzonitrile |
| 86 | 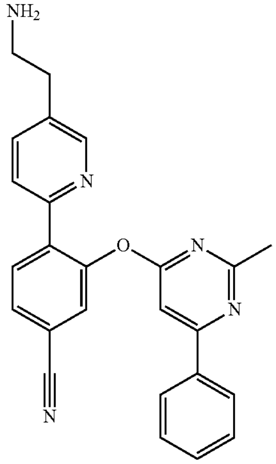 [SMILES: Cc1nc(Oc2cc(C#N)ccc2-c2ccc(CCN)cn2)cc(-c2ccccc2)n1] | 4-[5-(2-aminoethyl)pyridin-2-yl]-3-(2-methyl-6-phenylpyrimidin-4-yl)oxybenzonitrile |
| 87 | 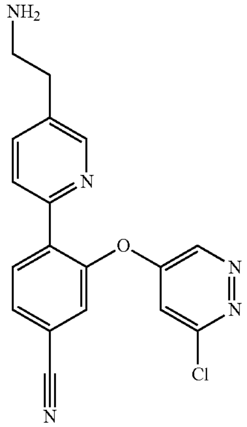 [SMILES: N#Cc1ccc(-c2ccc(CCN)cn2)c(Oc2cnnc(Cl)c2)c1] | 4-[5-(2-aminoethyl)pyridin-2-yl]-3-(6-chloropyridazin-4-yl)oxybenzonitrile |

TABLE 1-continued
| Compound number | Structural formula | Compound name |
| --- | --- | --- |
| 88 | 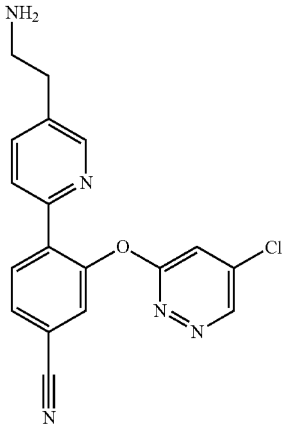 [SMILES: N#Cc1ccc(-c2ccc(CCN)cn2)c(Oc2cc(Cl)cnn2)c1] | 4-[5-(2-aminoethyl)pyridin-2-yl]-3-(5-chloropyridazin-3-yl)oxybenzonitrile |
| 89 | 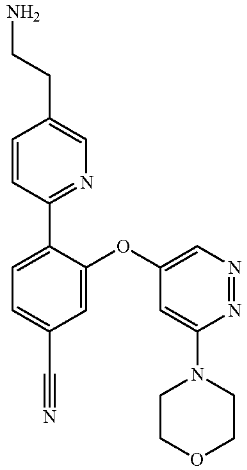 | 4-[5-(2-aminoethyl)pyridin-2-yl]-3-(6-morpholin-4-ylpyridazin-4-yl)oxybenzonitrile |
| 90 | 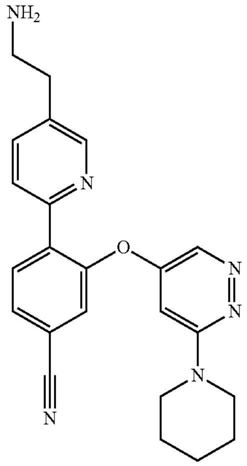 [SMILES: N#Cc1ccc(-c2ccc(CCN)cn2)c(Oc2cnnc(N3CCCCC3)c2)c1] | 4-[5-(2-aminoethyl)pyridin-2-yl]-3-(6-piperidin-1-ylpyridazin-4-yl)oxybenzonitrile |

TABLE 1-continued
| Compound number | Structural formula | Compound name |
|---|---|---|
| 91 | 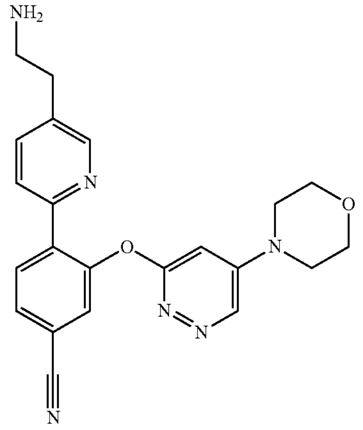 [SMILES: N#Cc1ccc(-c2ccc(CCN)cn2)c(Oc2cc(N3CCOCC3)cnn2)c1] | 4-[5-(2-aminoethyl)pyridin-2-yl]-3-(5-morpholin-4-ylpyridazin-3-yl)oxybenzonitrile |
| 92 | 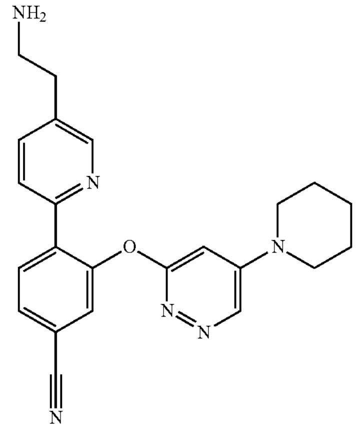 [SMILES: N#Cc1ccc(-c2ccc(CCN)cn2)c(Oc2cc(N3CCCCC3)cnn2)c1] | 4-[5-(2-aminoethyl)pyridin-2-yl]-3-(5-piperidin-1-ylpyridazin-3-yl)oxybenzonitrile |
| 93 | 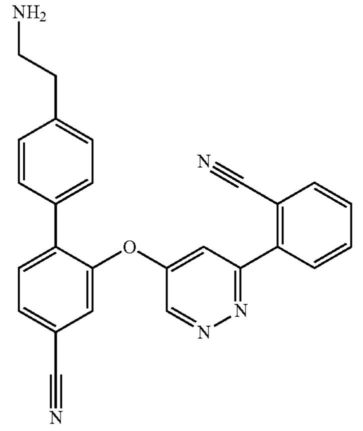 [SMILES: N#Cc1ccc(-c2ccc(CCN)cc2)c(Oc2cnnc(-c3ccccc3C#N)c2)c1] | 4-[4-(2-aminoethyl)phenyl]-3-[6-(2-cyanophenyl)pyridazin-4-yl]oxybenzonitrile |

TABLE 1-continued
| Compound number | Structural formula | Compound name |
|---|---|---|
| 94 | 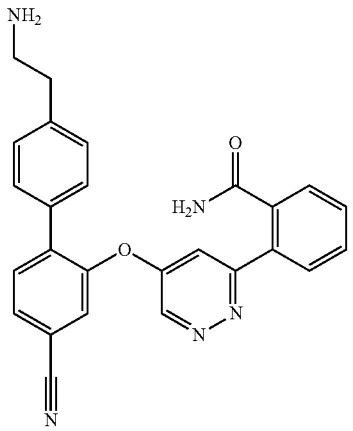 [SMILES: N#Cc1ccc(-c2ccc(CCN)cc2)c(Oc2cnnc(-c3ccccc3C(N)=O)c2)c1] | 2-[5-[2-[4-(2-aminoethyl)phenyl]-5-cyanophenoxy]pyridazin-3-yl]benzamide |
| 95 | 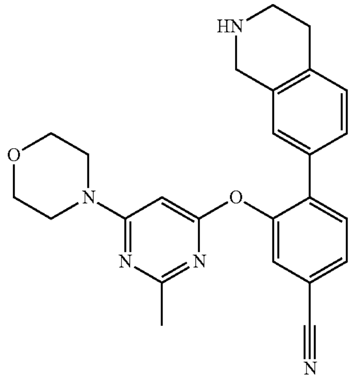 [SMILES: Cc1nc(Oc2cc(C#N)ccc2-c2ccc3c(c2)CNCC3)cc(N2CCOCC2)n1] | 3-(2-methyl-6-morpholin-4-ylpyrimidin-4-yl)oxy-4-(1,2,3,4-tetrahydroisoquinolin-7-yl)benzonitrile |
| 96 | 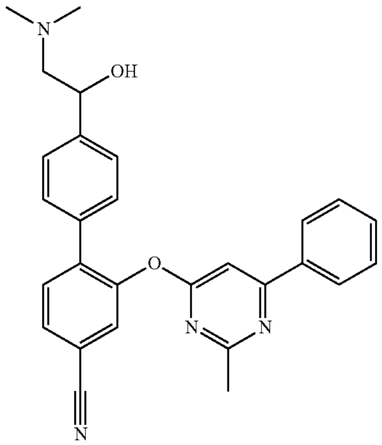 [SMILES: Cc1nc(Oc2cc(C#N)ccc2-c2ccc(C(O)CN(C)C)cc2)cc(-c2ccccc2)n1] | 4-[4-[2-(dimethylamino)-1-hydroxyethyl]phenyl]-3-(2-methyl-6-phenylpyrimidin-4-yl)oxybenzonitrile |

TABLE 1-continued
| Compound number | Structural formula | Compound name |
|---|---|---|
| 97 | 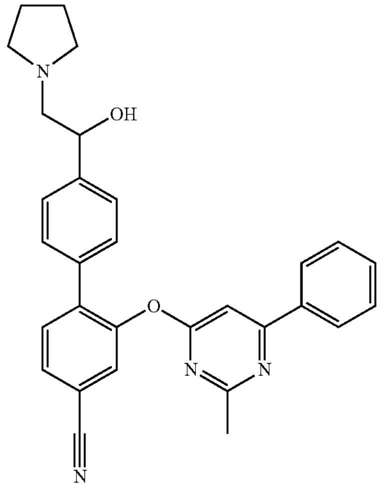 [SMILES: Cc1nc(Oc2cc(C#N)ccc2-c2ccc(C(O)CN3CCCC3)cc2)cc(-c2ccccc2)n1] | 4-[4-(1-hydroxy-2-pyrrolidin-1-ylethyl)phenyl]-3-(2-methyl-6-phenylpyrimidin-4-yl)oxybenzonitrile |
| 98 | 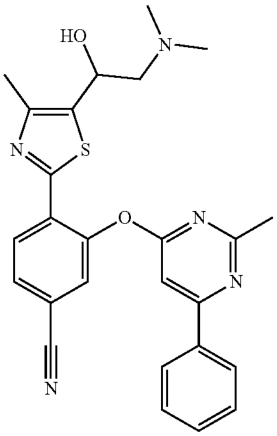 | 4-[5-[2-(dimethylamino)-1-hydroxyethyl]-4-methyl-1,3-thiazol-2-yl]-3-(2-methyl-6-phenylpyrimidin-4-yl)oxybenzonitrile |
| 99 | 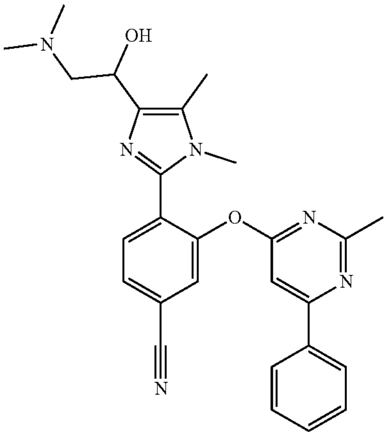 | 4-[4-[2-(dimethylamino)-1-hydroxyethyl]-1,5-dimethylimidazol-2-yl]-3-(2-methyl-6-phenylpyrimidin-4-yl)oxybenzonitrile |

TABLE 1-continued
| Compound number | Structural formula | Compound name |
| --- | --- | --- |
| 100 | 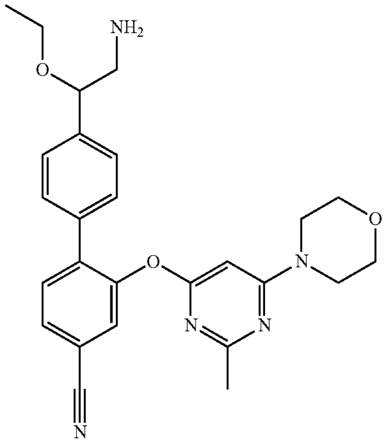 [SMILES: CCOC(CN)c1ccc(-c2ccc(C#N)cc2Oc2cc(N3CCOCC3)nc(C)n2)cc1] | 4-[4-(2-amino-1-ethoxyethyl)phenyl]-3-(2-methyl-6-morpholin-4-ylpyrimidin-4-yl)oxybenzonitrile |
| 101 | 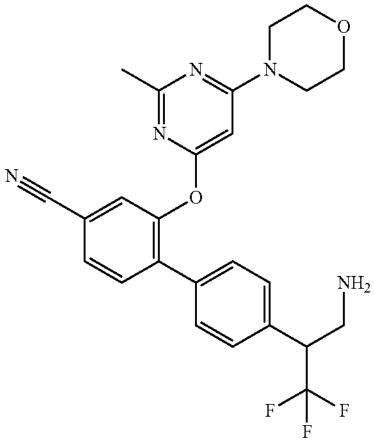 [SMILES: Cc1nc(Oc2cc(C#N)ccc2-c2ccc(C(CN)C(F)(F)F)cc2)cc(N2CCOCC2)n1] | 4-[4-(3-amino-1,1,1-trifluoropropan-2-yl)phenyl]-3-(2-methyl-6-morpholin-4-ylpyrimidin-4-yl)oxybenzonitrile |
| 102 | 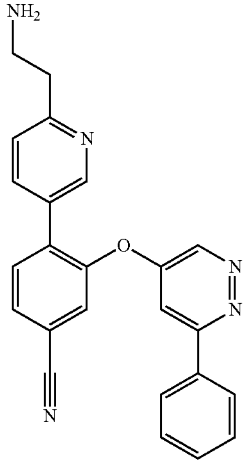 [SMILES: N#Cc1ccc(-c2ccc(CCN)nc2)c(Oc2cnnc(-c3ccccc3)c2)c1] | 4-[6-(2-aminoethyl)pyridin-3-yl]-3-(6-phenylpyridazin-4-yl)oxybenzonitrile |

TABLE 1-continued
| Compound number | Structural formula | Compound name |
| --- | --- | --- |
| 103 | 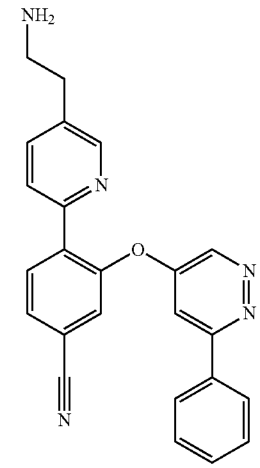 [SMILES: N#Cc1ccc(-c2ccc(CCN)cn2)c(Oc2cnnc(-c3ccccc3)c2)c1] | 4-[5-(2-aminoethyl)pyridin-2-yl]-3-(6-phenylpyridazin-4-yl)oxybenzonitrile |
| 104 | 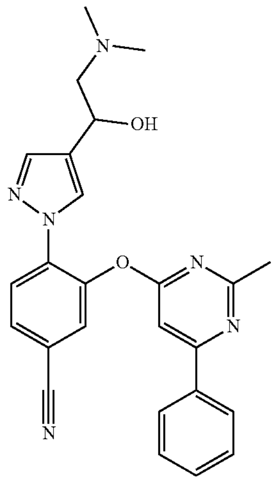 [SMILES: Cc1nc(Oc2cc(C#N)ccc2-n2cc(C(O)CN(C)C)cn2)cc(-c2ccccc2)n1] | 4-[4-[2-(dimethylamino)-1-hydroxyethyl]pyrazol-1-yl]-3-(2-methyl-6-phenylpyrimidin-4-yl)oxybenzonitrile |
| 105 | 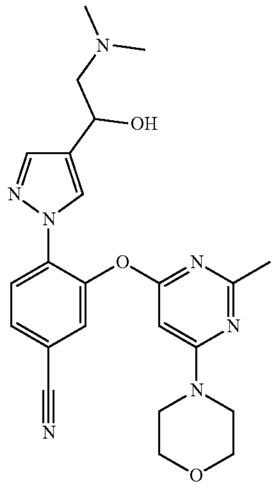 [SMILES: Cc1nc(Oc2cc(C#N)ccc2-n2cc(C(O)CN(C)C)cn2)cc(N2CCOCC2)n1] | 4-[4-[2-(dimethylamino)-1-hydroxyethyl]pyrazol-1-yl]-3-(2-methyl-6-morpholin-4-ylpyrimidin-4-yl)oxybenzonitrile |

TABLE 1-continued
| Compound number | Structural formula | Compound name |
|---|---|---|
| 106 | 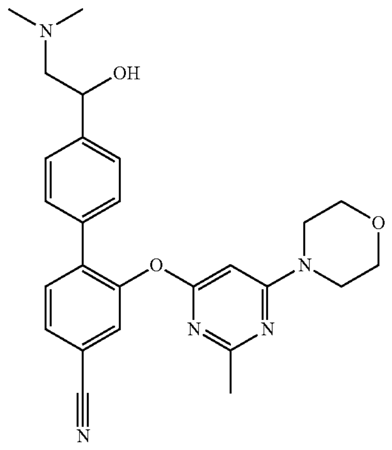 [SMILES: Cc1nc(Oc2cc(C#N)ccc2-c2ccc(C(O)CN(C)C)cc2)cc(N2CCOCC2)n1] | 4-[4-[2-(dimethylamino)-1-hydroxyethyl]phenyl]-3-(2-methyl-6-morpholin-4-ylpyrimidin-4-yl)oxybenzonitrile |
| 107 | 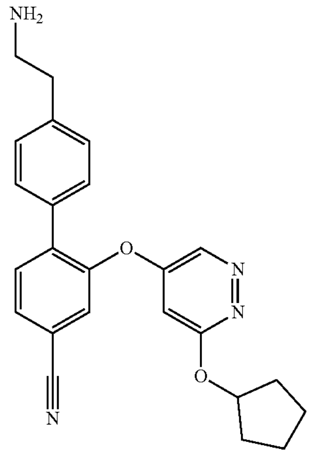 [SMILES: N#Cc1ccc(-c2ccc(CCN)cc2)c(Oc2cnnc(OC3CCCC3)c2)c1] | 4-[4-(2-aminoethyl)phenyl]-3-(6-cyclopentyloxypyridazin-4-yl)oxybenzonitrile |
| 108 | 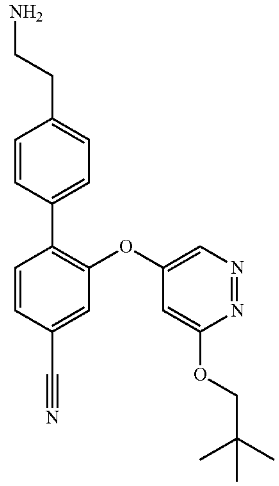 [SMILES: CC(C)(C)COc1cc(Oc2cc(C#N)ccc2-c2ccc(CCN)cc2)cnn1] | 4-[4-(2-aminoethyl)phenyl]-3-[6-(2,2-dimethylpropoxy)pyridazin-4-yl]oxybenzonitrile |

TABLE 1-continued
| Compound number | Structural formula | Compound name |
|---|---|---|
| 109 | 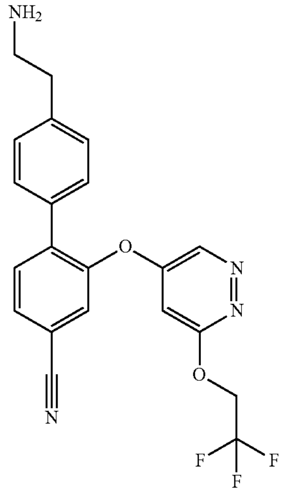 [SMILES: N#Cc1ccc(-c2ccc(CCN)cc2)c(Oc2cnnc(OCC(F)(F)F)c2)c1] | 4-[4-(2-aminoethyl)phenyl]-3-[6-(2,2,2-trifluoroethoxy)pyridazin-4-yl]oxybenzonitrile |
| 110 | 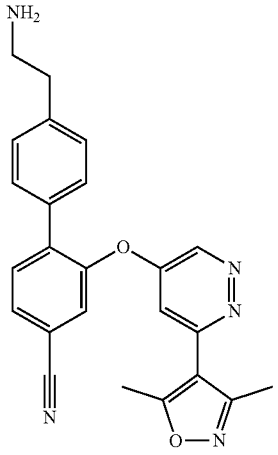 [SMILES: Cc1noc(C)c1-c1cc(Oc2cc(C#N)ccc2-c2ccc(CCN)cc2)cnn1] | 4-[4-(2-aminoethyl)phenyl]-3-[6-(3,5-dimethyl-1,2-oxazol-4-yl)pyridazin-4-yl]oxybenzonitrile |
| 111 | 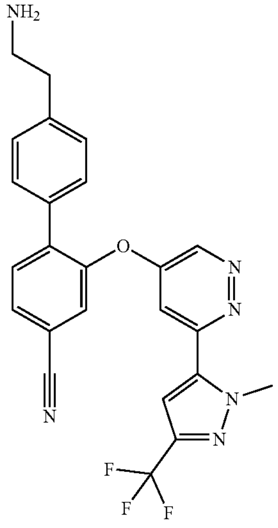 [SMILES: Cn1nc(C(F)(F)F)cc1-c1cc(Oc2cc(C#N)ccc2-c2ccc(CCN)cc2)cnn1] | 4-[4-(2-aminoethyl)phenyl]-3-[6-[2-methyl-5-(trifluoromethyl)pyrazol-3-yl]pyridazin-4-yl]oxybenzonitrile |

TABLE 1-continued
| Compound number | Structural formula | Compound name |
|---|---|---|
| 112 | 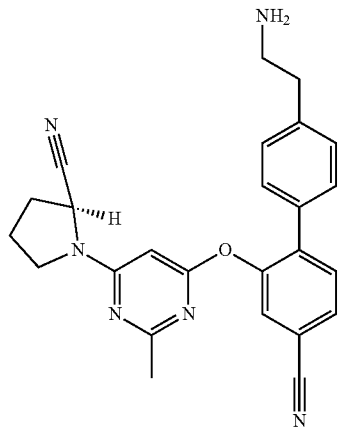 [SMILES: Cc1nc(Oc2cc(C#N)ccc2-c2ccc(CCN)cc2)cc(N2CCC[C@H]2C#N)n1] | (2S)-1-[6-[2-[4-(2-aminoethyl)phenyl]-5-cyanophenoxy]-2-methylpyrimidin-4 yl]pyrrolidine-2-carbonitrile |
| 113 | 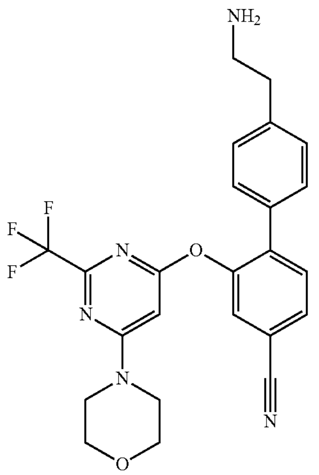 [SMILES: N#Cc1ccc(-c2ccc(CCN)cc2)c(Oc2cc(N3CCOCC3)nc(C(F)(F)F)n2)c1] | 4-[4-(2-aminoethyl)phenyl]-3-[6-morpholin-4-yl-2-(trifluoromethyl)pyrimidin-4-yl]oxybenzonitrile |
| 114 | 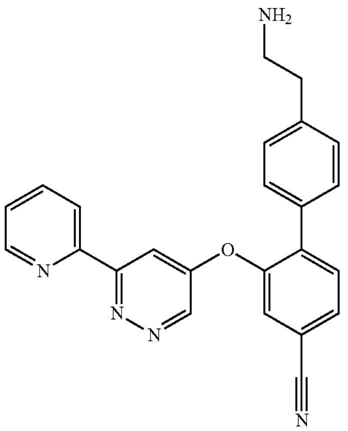 [SMILES: N#Cc1ccc(-c2ccc(CCN)cc2)c(Oc2cnnc(-c3ccccn3)c2)c1] | 4-[4-(2-aminoethyl)phenyl]-3-(6-pyridin-2-ylpyridazin-4-yl)oxybenzonitrile |

TABLE 1-continued
| Compound number | Structural formula | Compound name |
|---|---|---|
| 115 | 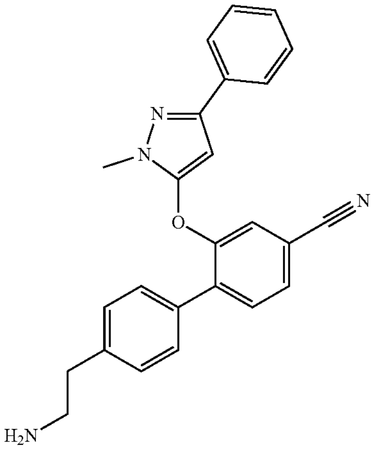 [SMILES: Cn1nc(-c2ccccc2)cc1Oc1cc(C#N)ccc1-c1ccc(CCN)cc1] | 4-[4-(2-aminoethyl)phenyl]-3-(2-methyl-5-phenylpyrazol-3-yl)oxybenzonitrile |
| 116 | 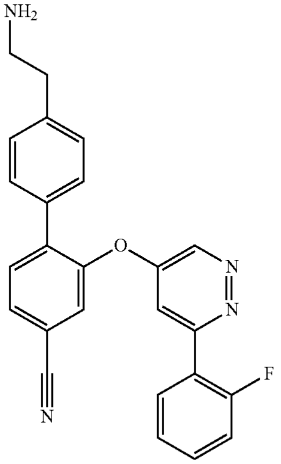 [SMILES: N#Cc1ccc(-c2ccc(CCN)cc2)c(Oc2cnnc(-c3ccccc3F)c2)c1] | 4-[4-(2-aminoethyl)phenyl]-3-[6-(2-fluorophenyl)pyridazin-4-yl]oxybenzonitrile |
| 117 | 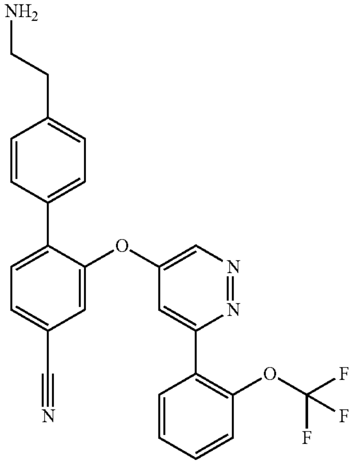 [SMILES: N#Cc1ccc(-c2ccc(CCN)cc2)c(Oc2cnnc(-c3ccccc3OC(F)(F)F)c2)c1] | 4-[4-(2-aminoethyl)phenyl]-3-[6-[2-(trifluoromethoxy)phenyl]pyridazin-4-yl]oxybenzonitrile |

TABLE 1-continued
| Compound number | Structural formula | Compound name |
| --- | --- | --- |
| 118 | 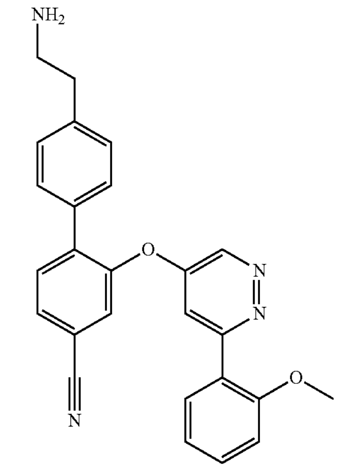 [SMILES: COc1ccccc1-c1cc(Oc2cc(C#N)ccc2-c2ccc(CCN)cc2)cnn1] | 4-[4-(2-aminoethyl)phenyl]-3-[6-(2-methoxypheny)pyridazin-4-yl]oxybenzonitrile |
| 119 | 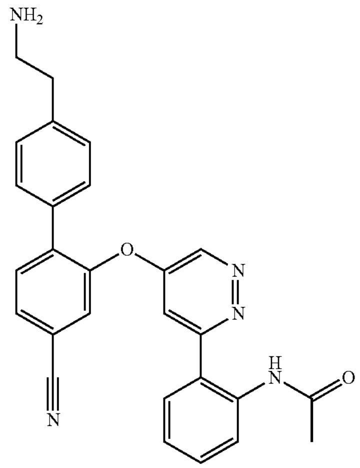 [SMILES: CC(=O)Nc1ccccc1-c1cc(Oc2cc(C#N)ccc2-c2ccc(CCN)cc2)cnn1] | N-[2-[5-[2-[4-(2-aminoethyl)phenyl]-5-cyanophenoxy]pyridazin-3-yl]phenyl]acetamide |
| 120 | 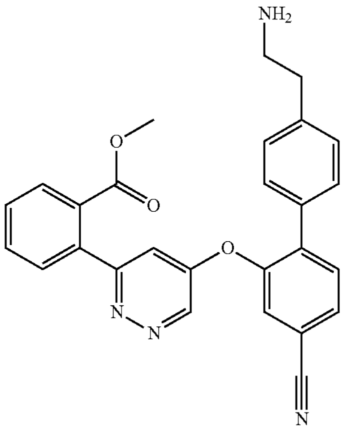 [SMILES: COC(=O)c1ccccc1-c1cc(Oc2cc(C#N)ccc2-c2ccc(CCN)cc2)cnn1] | methyl 2-[5-[2-[4-(2-aminoethyl)phenyl]-5-cyanophenoxy]pyridazin-3-yl]benzoate |

TABLE 1-continued
| Compound number | Structural formula | Compound name |
|---|---|---|
| 121 | 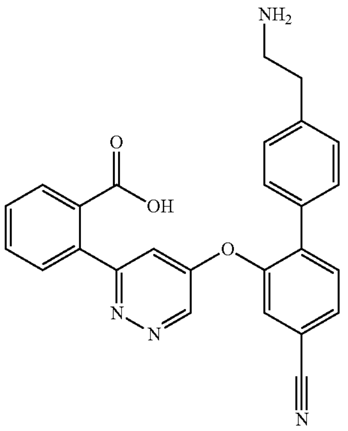 [SMILES: N#Cc1ccc(-c2ccc(CCN)cc2)c(Oc2cnnc(-c3ccccc3C(=O)O)c2)c1] | 2-[5-[2-[4-(2-aminoethyl)phenyl]-5-cyanophenoxy]pyridazin-3-yl]benzoic acid |
| 122 | 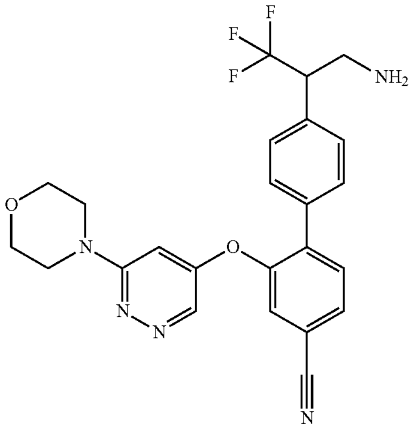 [SMILES: N#Cc1ccc(-c2ccc(C(CN)C(F)(F)F)cc2)c(Oc2cnnc(N3CCOCC3)c2)c1] | 4-[4-(3-amino-1,1,1-trifluoropropan-2-yl)phenyl]-3-(6-morpholin-4-ylpyridazin-4-yl)oxybenzonitrile |
| 123 | 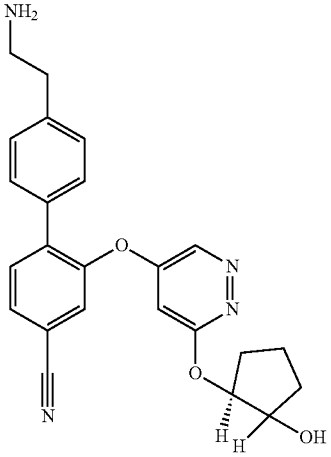 [SMILES: N#Cc1ccc(-c2ccc(CCN)cc2)c(Oc2cnnc(O[C@H]3CCCC3O)c2)c1] | 4-[4-(2-aminoethyl)phenyl]-3-[6-[(1S,2R)-2-hydroxycyclopentyl]oxypyridazin-4-yl]oxybenzonitrile |

TABLE 1-continued
| Compound number | Structural formula | Compound name |
|---|---|---|
| 124 | 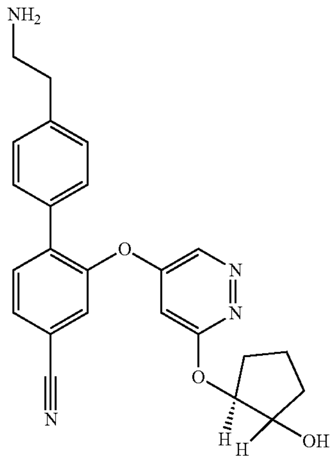 [SMILES: N#Cc1ccc(-c2ccc(CCN)cc2)c(Oc2cnnc(O[C@H]3CCCC3O)c2)c1] | 4-[4-(2-aminoethyl)phenyl]-3[6-[(1S,2S)-2-hydroxycyclopentyl]oxypyridazin-4-yl]oxybenzonitrile |
| 125 | 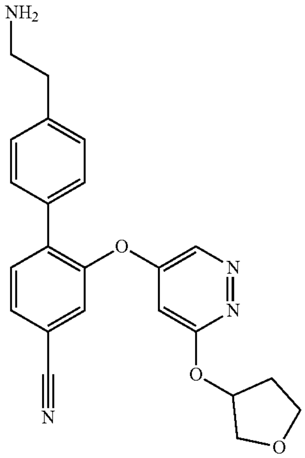 [SMILES: N#Cc1ccc(-c2ccc(CCN)cc2)c(Oc2cnnc(OC3CCOC3)c2)c1] | 4-[4-(2-aminoethyl)phenyl]-3-[6-(oxolan-3-yloxy)pyridazin-4-yl]oxybenzonitrile |
| 126 | 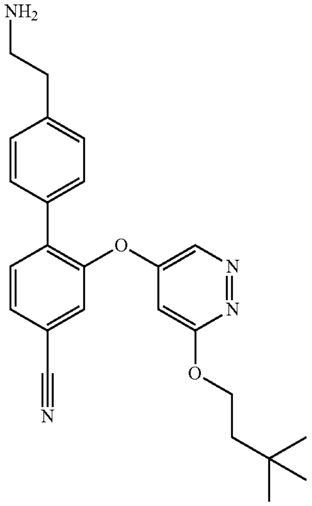 [SMILES: CC(C)(C)CCOc1cc(Oc2cc(C#N)ccc2-c2ccc(CCN)cc2)cnn1] | 4-[4-(2-aminoethyl)phenyl]-3-[6-(3,3-dimethylbutoxy)pyridazin-4-yl]oxybenzonitrile |

TABLE 1-continued
| Compound number | Structural formula | Compound name |
| --- | --- | --- |
| 127 | 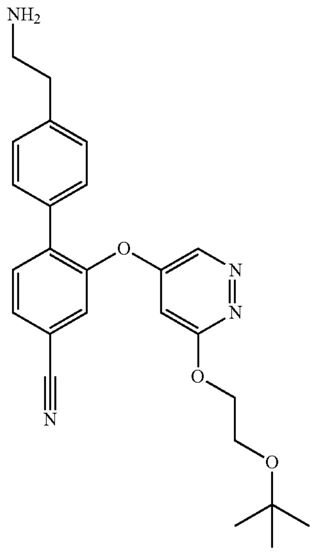 [SMILES: CC(C)(C)OCCOc1cc(Oc2cc(C#N)ccc2-c2ccc(CCN)cc2)cnn1] | 4-[4-(2-aminoethyl)phenyl]-3-[6-[2-[(2-methylpropan-2-yl)oxy]ethoxy]pyridazin-4-yl]oxybenzonitrile |
| 128 | 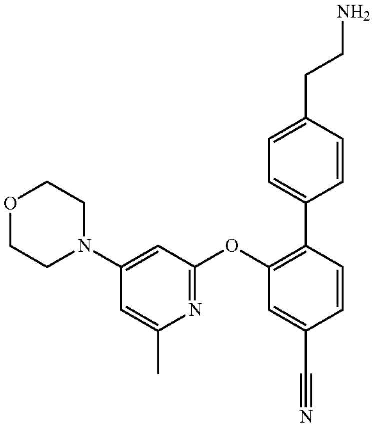 [SMILES: Cc1cc(N2CCOCC2)cc(Oc2cc(C#N)ccc2-c2ccc(CCN)cc2)n1] | 4-[4-(2-aminoethyl)phenyl]-3-(6-methyl-4-morpholin-4-ylpyridin-2-yl)oxybenzonitrile |
| 129 | 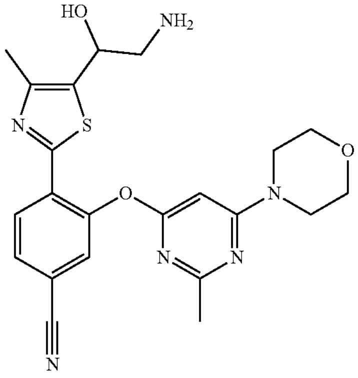 [SMILES: Cc1nc(Oc2cc(C#N)ccc2-c2nc(C)c(C(O)CN)s2)cc(N2CCOCC2)n1] | 4-[5-(2-amino-1-hydroxyethyl)-4-methyl-1,3-thiazol-2-yl]-3-(2-methyl-6-morpholin-4-ylpyrimidin-4-yl)oxybenzonitrile |

TABLE 1-continued
| Compound number | Structural formula | Compound name |
|---|---|---|
| 130 | 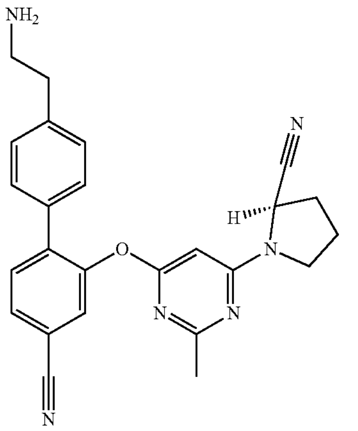 [SMILES: Cc1nc(Oc2cc(C#N)ccc2-c2ccc(CCN)cc2)cc(N2CCC[C@@H]2C#N)n1] | (2R)-1-[6-[2-[4-(2-aminoethyl)phenyl]-5-cyanophenoxy]-2-methylpyrimidin-4-yl]pyrrolidine-2-carbonitrile |
| 131 | 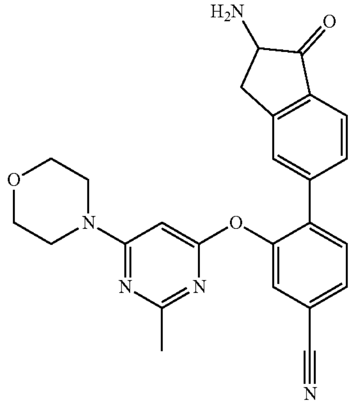 [SMILES: Cc1nc(Oc2cc(C#N)ccc2-c2ccc3c(c2)CC(N)C3=O)cc(N2CCOCC2)n1] | 4-(2-amino-1-oxo-2,3-dihydroinden-5-yl)-3-(2-methyl-6-morpholin-4-ylpyrimidin-4-yl)oxybenzonitrile |
| 132 | 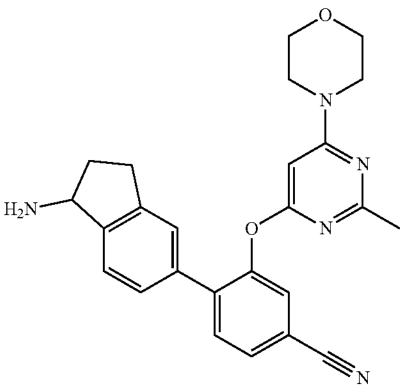 [SMILES: Cc1nc(Oc2cc(C#N)ccc2-c2ccc3c(c2)CCC3N)cc(N2CCOCC2)n1] | 4-(1-amino-2,3-dihydro-1H-inden-5-yl)-3-(2-methyl-6-morpholin-4-ylpyrimidin-4-yl)oxybenzonitrile |

TABLE 1-continued
| Compound number | Structural formula | Compound name |
|---|---|---|
| 133 | 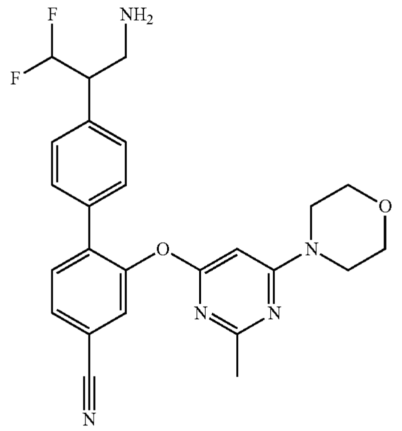 [SMILES: Cc1nc(Oc2cc(C#N)ccc2-c2ccc(C(CN)C(F)F)cc2)cc(N2CCOCC2)n1] | 4-[4-(3-amino-1,1-difluoropropan-2-yl)phenyl]-3-(2-methyl-6-morpholin-4-ylpyrimidin-4-yl)oxybenzonitrile |
| 134 | 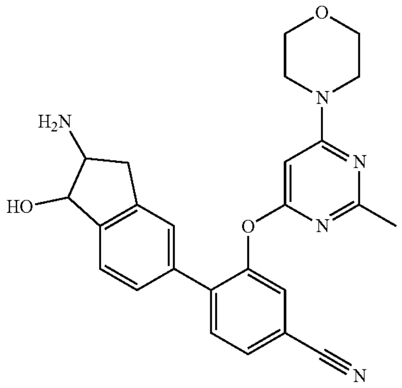 [SMILES: Cc1nc(Oc2cc(C#N)ccc2-c2ccc3c(c2)CC(N)C3O)cc(N2CCOCC2)n1] | 4-(2-amino-1-hydroxy-2,3-dihydro-1H-inden-5-yl)-3-(2-methyl-6-morpholin-4-ylpyrimidin-4-yl)oxybenzonitrile |
| 135 | 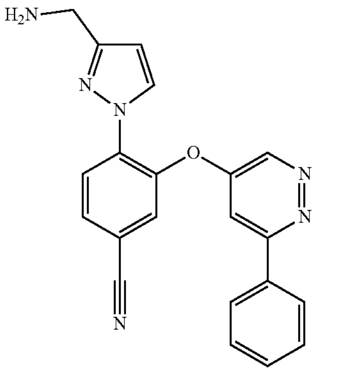 [SMILES: N#Cc1ccc(-n2ccc(CN)n2)c(Oc2cnnc(-c3ccccc3)c2)c1] | 4-[3-(aminomethyl)pyrazol-1-yl]-3-(6-phenylpyridazin-4-yl)oxybenzonitrile |

TABLE 1-continued
| Compound number | Structural formula | Compound name |
|---|---|---|
| 136 | 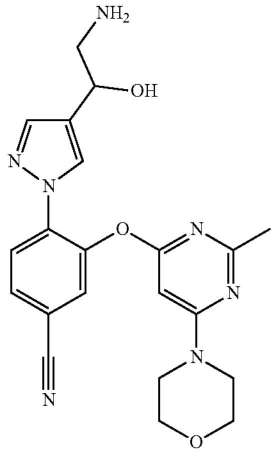 [SMILES: Cc1nc(Oc2cc(C#N)ccc2-n2cc(C(O)CN)cn2)cc(N2CCOCC2)n1] | 4-[4-(2-amino-1-hydroxyethyl)pyrazol-1-yl]-3-(2-methyl-6-morpholin-4-ylpyrimidin-4-yl)oxybenzonitrile |
| 137 | 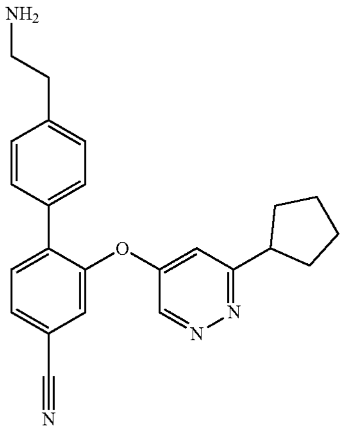 [SMILES: N#Cc1ccc(-c2ccc(CCN)cc2)c(Oc2cnnc(C3CCCC3)c2)c1] | 4-[4-(2-aminoethyl)phenyl]-3-(6-cyclopentylpyridazin-4-yl)oxybenzonitrile |
| 138 | 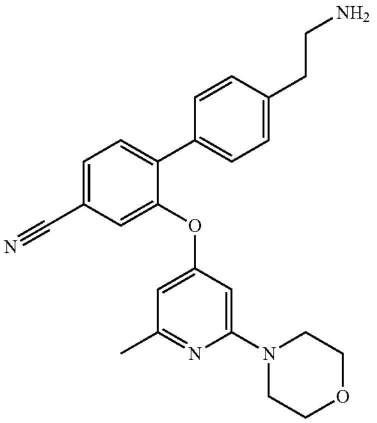 [SMILES: Cc1cc(Oc2cc(C#N)ccc2-c2ccc(CCN)cc2)cc(N2CCOCC2)n1] | 4-[4-(2-aminoethyl)phenyl]-3-(2-methyl-6-morpholin-4-ylpyridin-4-yl)oxybenzonitrile |

TABLE 1-continued

| Compound number | Structural formula | Compound name |
|---|---|---|
| 139 | 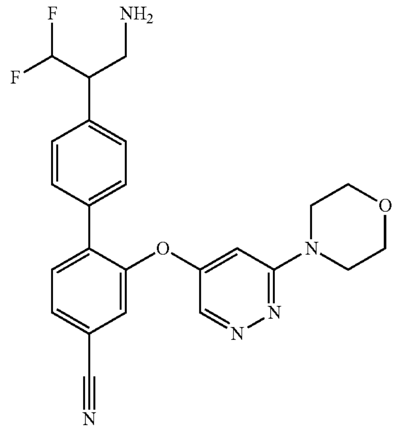 [SMILES: N#Cc1ccc(-c2ccc(C(CN)C(F)F)cc2)c(Oc2cnnc(N3CCOCC3)c2)c1] | 4-[4-(3-amino-1,1-difluoropropan-2-yl)phenyl]-3-(6-morpholin-4 ylpyridazin-4-yl)oxybenzonitrile |
| 140 | 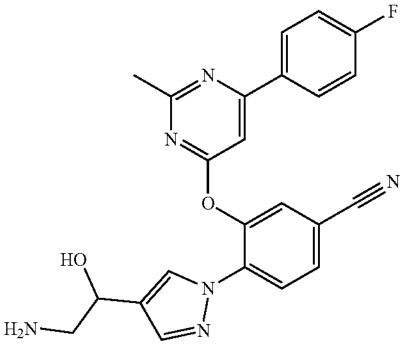 [SMILES: Cc1nc(Oc2cc(C#N)ccc2-n2cc(C(O)CN)cn2)cc(-c2ccc(F)cc2)n1] | 4-[4-(2-amino-1-hydroxyethyl)pyrazol-1-yl]-3-[6-(4-fluorophenyl)-2-methylpyrimidin-4-yl]oxybenzonitrile |
| 141 | 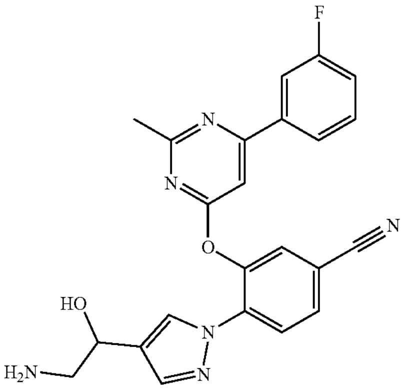 [SMILES: Cc1nc(Oc2cc(C#N)ccc2-n2cc(C(O)CN)cn2)cc(-c2cccc(F)c2)n1] | 4-[4-(2-amino-1-hydroxyethyl)pyrazol-1-yl]-3-[6-(3-fluorophenyl)-2-methylpyrimidin-4-yl]oxybenzonitrile |
| 142 | 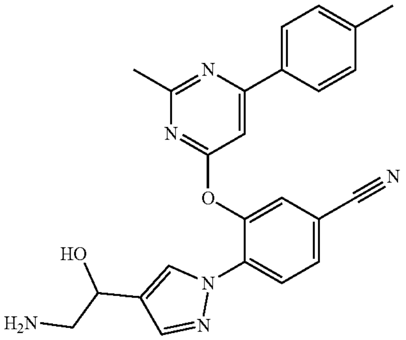 [SMILES: Cc1ccc(-c2cc(Oc3cc(C#N)ccc3-n3cc(C(O)CN)cn3)nc(C)n2)cc1] | 4-[4-(2-amino-1-hydroxyethyl)pyrazol-1-yl]-3-[2-methyl-6-(4-methylphenyl)pyrimidin-4-yl]oxybenzonitrile |

TABLE 1-continued
| Compound number | Structural formula | Compound name |
|---|---|---|
| 143 | 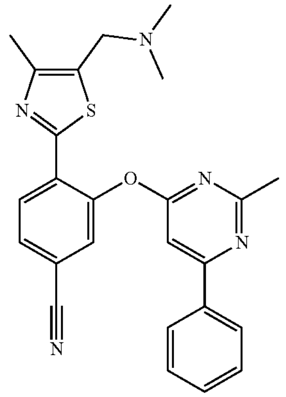 | 4-[5-[(dimethylamino)methyl]-4-methyl-1,3-thiazol-2-yl]-3-(2-methyl-6-phenylpyrimidin-4-yl)oxybenzonitrile |
| 144 | 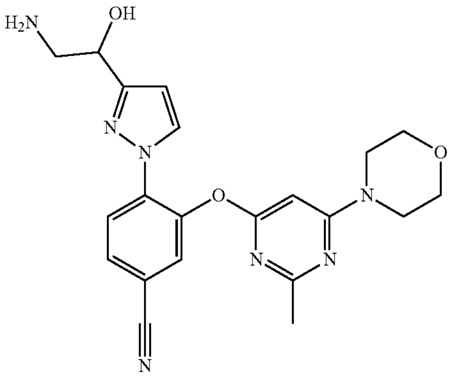 [SMILES: Cc1nc(Oc2cc(C#N)ccc2-n2ccc(C(O)CN)n2)cc(N2CCOCC2)n1] | 4-[3-(2-amino-1-hydroxyethyl)pyrazol-1-yl]-3-(2-methyl-6-morpholin-4-ylpyrimidin-4-yl)oxybenzonitrile |
| 145 | 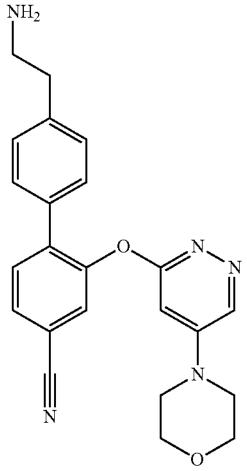 [SMILES: N#Cc1ccc(-c2ccc(CCN)cc2)c(Oc2cc(N3CCOCC3)cnn2)c1] | 4-[4-(2-aminoethyl)phenyl]-3-(5-morpholin-4-ylpyridazin-3-yl)oxybenzonitrile |

TABLE 1-continued
| Compound number | Structural formula | Compound name |
|---|---|---|
| 146 | 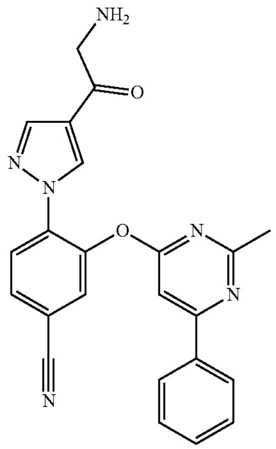 [SMILES: Cc1nc(Oc2cc(C#N)ccc2-n2cc(C(=O)CN)cn2)cc(-c2ccccc2)n1] | 4-[4-(2-aminoacetyl)pyrazol-1-yl]-3-(2-methyl-6-phenylpyrimidin-4-yl)oxybenzonitrile |
| 147 | 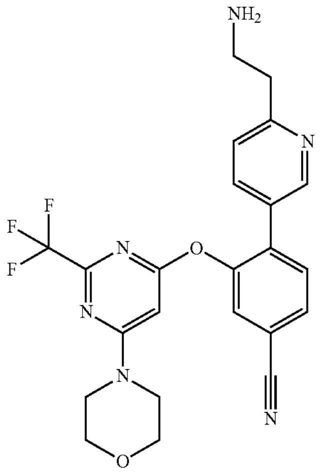 [SMILES: N#Cc1ccc(-c2ccc(CCN)nc2)c(Oc2cc(N3CCOCC3)nc(C(F)(F)F)n2)c1] | 4-[6-(2-aminoethyl)pyridin-3-yl]-3-[6-morpholin-4-yl-2-(trifluoromethyl)pyrimidin-4-yl]oxybenzonitrile |
| 148 | 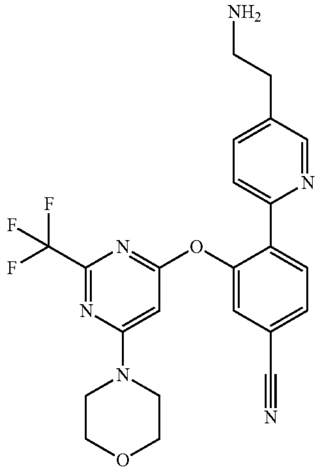 [SMILES: N#Cc1ccc(-c2ccc(CCN)cn2)c(Oc2cc(N3CCOCC3)nc(C(F)(F)F)n2)c1] | 4-[5-(2-aminoethyl)pyridin-2-yl]-3-[6-morpholin-4-yl-2-(trifluoromethyl)pyrimidin-4-yl]oxybenzonitrile |

TABLE 1-continued
| Compound number | Structural formula | Compound name |
|---|---|---|
| 149 | 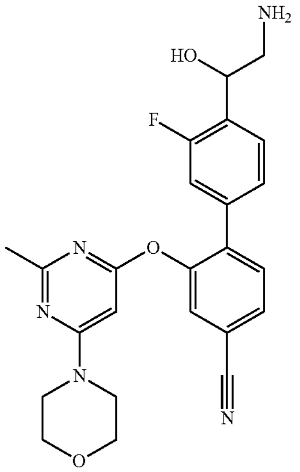 [SMILES: Cc1nc(Oc2cc(C#N)ccc2-c2ccc(C(O)CN)c(F)c2)cc(N2CCOCC2)n1] | 4-[4-(2-amino-1-hydroxyethyl)-3-fluorophenyl]-3-(2-methyl-6-morpholin-4-ylpyrimidin-4-yl)oxybenzonitrile |
| 150 | 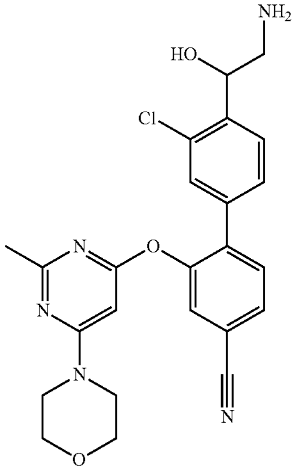 [SMILES: Cc1nc(Oc2cc(C#N)ccc2-c2ccc(C(O)CN)c(Cl)c2)cc(N2CCOCC2)n1] | 4-[4-(2-amino-1-hydroxyethyl)-3-chlorophenyl]-3-(2-methyl-6-morpholin-4-ylpyrimidin-4-yl)oxybenzonitrile |
| 151 | 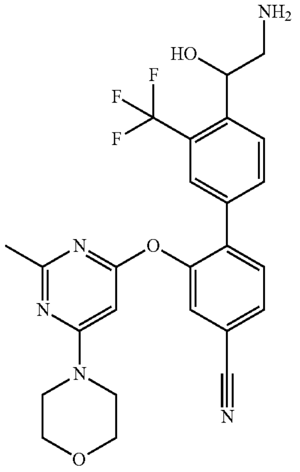 [SMILES: Cc1nc(Oc2cc(C#N)ccc2-c2ccc(C(O)CN)c(C(F)(F)F)c2)cc(N2CCOCC2)n1] | 4-[4-(2-amino-1-hydroxyethyl)-3-(trifluoromethyl)phenyl]-3-(2-methyl-6-morpholin-4-ylpyrimidin-4-yl)oxybenzonitrile |

TABLE 1-continued
| Compound number | Structural formula | Compound name |
|---|---|---|
| 152 | 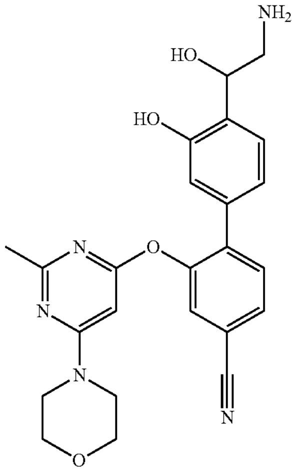 [SMILES: Cc1nc(Oc2cc(C#N)ccc2-c2ccc(C(O)CN)c(O)c2)cc(N2CCOCC2)n1] | 4-[4-(2-amino-1-hydroxyethyl)-3-hydroxyphenyl]-3-(2-methyl-6-morpholin-4-ylpyrimidin-4-yl)oxybenzonitrile |
| 153 | 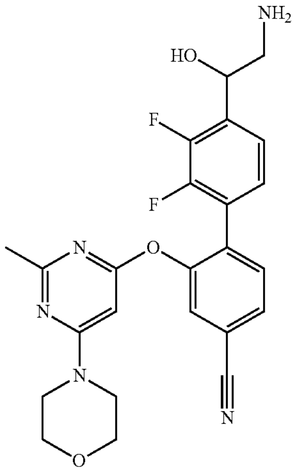 [SMILES: Cc1nc(Oc2cc(C#N)ccc2-c2ccc(C(O)CN)c(F)c2F)cc(N2CCOCC2)n1] | 4-[4-(2-amino-1-hydroxyethyl)-2,3-difluorophenyl]-3-(2-methyl-6-morpholin-4-ylpyrimidin-4-yl)oxybenzonitrile |
| 154 | 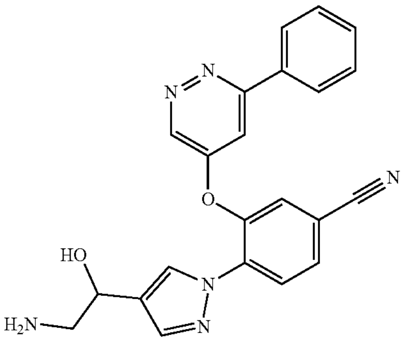 [SMILES: N#Cc1ccc(-n2cc(C(O)CN)cn2)c(Oc2cnnc(-c3ccccc3)c2)c1] | 4-[4-(2-amino-1-hydroxyethyl)pyrazol-1-yl]-3-(6-phenylpyridazin-4-yl)oxybenzonitrile |

TABLE 1-continued
| Compound number | Structural formula | Compound name |
|---|---|---|
| 155 | 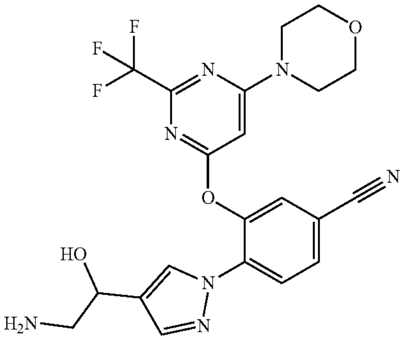 [SMILES: N#Cc1ccc(-n2cc(C(O)CN)cn2)c(Oc2cc(N3CCOCC3)nc(C(F)(F)F)n2)c1] | 4-[4-(2-amino-1-hydroxyethyl)pyrazol-1-yl]-3-[6-morpholin-4-yl-2-(trifluoromethyl)pyrimidin-4-yl]oxybenzonitrile |
| 156 | 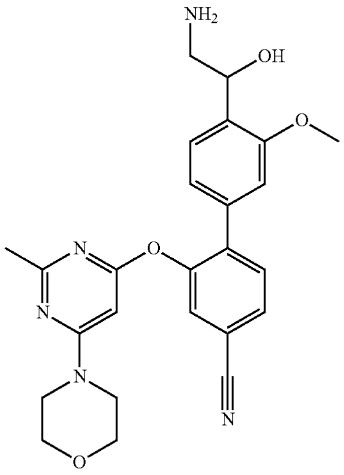 | 4-[4-(2-amino-1-hydroxyethyl)-3-methoxyphenyl]-3-(2-methyl-6-morpholin-4-ylpyrimidin-4-yl)oxybenzonitrile |
| 157 | 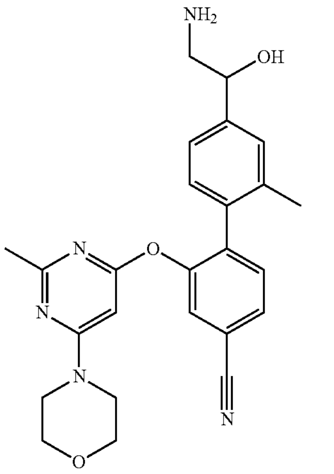 | 4-[4-(2-amino-1-hydroxyethyl)-2-methylphenyl]-3-(2-methyl-6-morpholin-4-ylpyrimidin-4-yl)oxybenzonitrile |

TABLE 1-continued
| Compound number | Structural formula | Compound name |
|---|---|---|
| 158 | 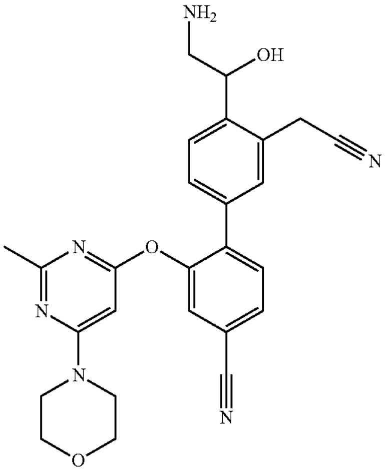 [SMILES: Cc1nc(Oc2cc(C#N)ccc2-c2ccc(C(O)CN)c(CC#N)c2)cc(N2CCOCC2)n1] | 4-[4-(2-amino-1-hydroxyethyl)-3-(cyanomethyl)phenyl]-3-(2-methyl-6-morpholin-4-ylpyrimidin-4-yl)oxybenzonitrile |
| 159 | 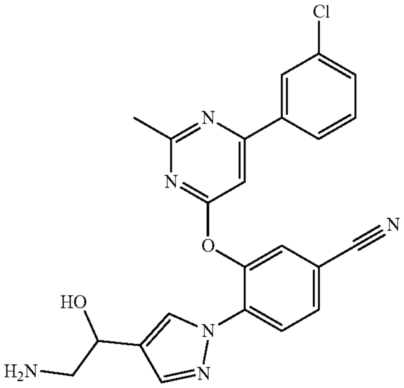 | 4-[4-(2-amino-1-hydroxyethyl)pyrazol-1-yl]-3-[6-(3-chlorophenyl)-2-methylpyrimidin-4-yl]oxybenzonitrile |
| 160 | 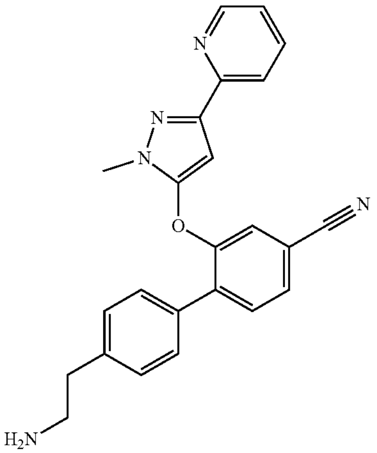 [SMILES: Cn1nc(-c2ccccn2)cc1Oc1cc(C#N)ccc1-c1ccc(CCN)cc1] | 4-[4-(2-aminoethyl)phenyl]-3-(2-methyl-5-pyridin-2-ylpyrazol-3-yl)oxybenzonitrile |

TABLE 1-continued
| Compound number | Structural formula | Compound name |
|---|---|---|
| 161 | 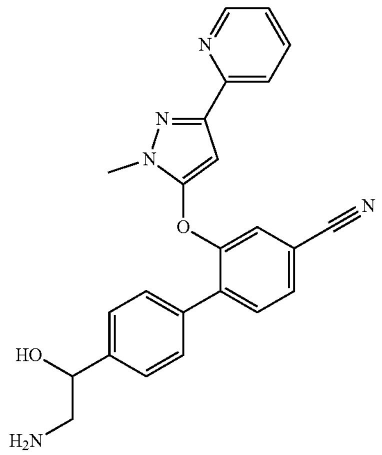 [SMILES: Cn1nc(-c2ccccn2)cc1Oc1cc(C#N)ccc1-c1ccc(C(O)CN)cc1] | 4-[4-(2-amino-1-hydroxyethyl)phenyl]-3-(2-methyl-5-pyridin-2-ylpyrazol-3-yl)oxybenzonitrile |
| 162 | 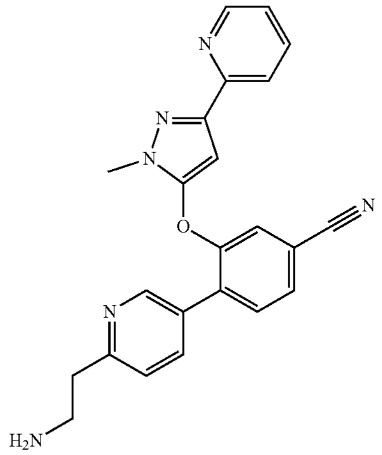 [SMILES: Cn1nc(-c2ccccn2)cc1Oc1cc(C#N)ccc1-c1ccc(CCN)nc1] | 4-[6-(2-aminoethyl)pyridin-3-yl]-3-(2-methyl-5-pyridin-2-ylpyrazol-3-yl)oxybenzonitrile |
| 163 | 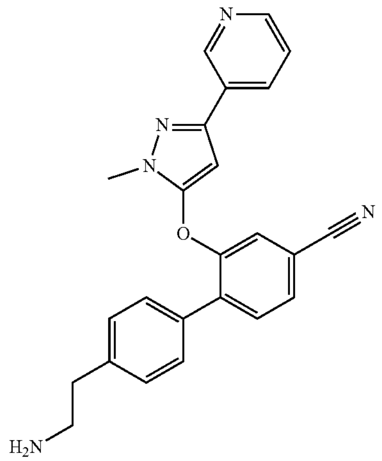 [SMILES: Cn1nc(-c2cccnc2)cc1Oc1cc(C#N)ccc1-c1ccc(CCN)cc1] | 4-[4-(2-aminoethyl)phenyl]-3-(2-methyl-5-pyridin-3-ylpyrazol-3-yl)oxybenzonitrile |

TABLE 1-continued
| Compound number | Structural formula | Compound name |
| --- | --- | --- |
| 164 | 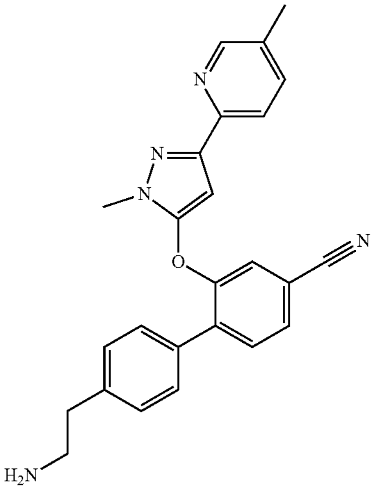 [SMILES: Cc1ccc(-c2cc(Oc3cc(C#N)ccc3-c3ccc(CCN)cc3)n(C)n2)nc1] | 4-[4-(2-aminoethyl)phenyl]-3-[2-methyl-5-(5-methylpyridin-2-yl)pyrazol-3-yl]oxybenzonitrile |
| 165 | 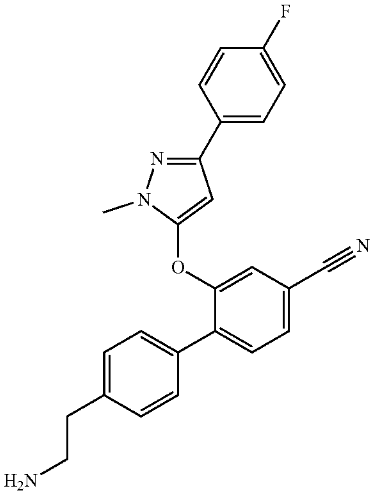 [SMILES: Cn1nc(-c2ccc(F)cc2)cc1Oc1cc(C#N)ccc1-c1ccc(CCN)cc1] | 4-[4-(2-aminoethyl)phenyl]-3-[5-(4-fluorophenyl)-2-methylpyrazol-3-yl]oxybenzonitrile |
| 166 | 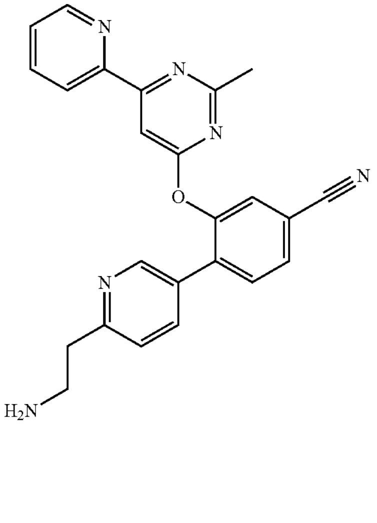 [SMILES: Cc1nc(Oc2cc(C#N)ccc2-c2ccc(CCN)nc2)cc(-c2ccccn2)n1] | 4-[6-(2-aminoethyl)pyridin-3-yl]-3-(2-methyl-6-pyridin-2-ylpyrimidin-4-yl)oxybenzonitrile |

TABLE 1-continued
| Compound number | Structural formula | Compound name |
|---|---|---|
| 167 | 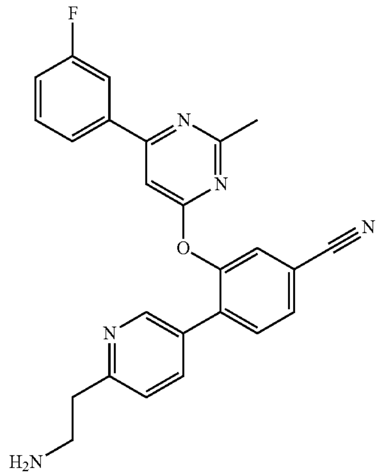 [SMILES: Cc1nc(Oc2cc(C#N)ccc2-c2ccc(CCN)nc2)cc(-c2cccc(F)c2)n1] | 4-[6-(2-aminoethyl)pyridin-3-yl]-3-[6-(3-fluorophenyl)-2-methylpyrimidin-4-yl]oxybenzonitrile |
| 168 | 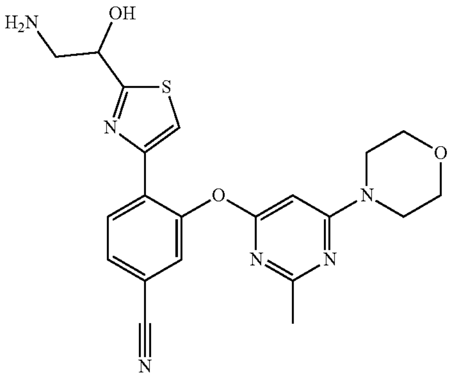 [SMILES: Cc1nc(Oc2cc(C#N)ccc2-c2csc(C(O)CN)n2)cc(N2CCOCC2)n1] | 4-[2-(2-amino-1-hydroxyethyl)-1,3-thiazol-4-yl]-3-(2-methyl-6-morpholin-4-ylpyrimidin-4-yl)oxybenzonitrile |
| 169 | 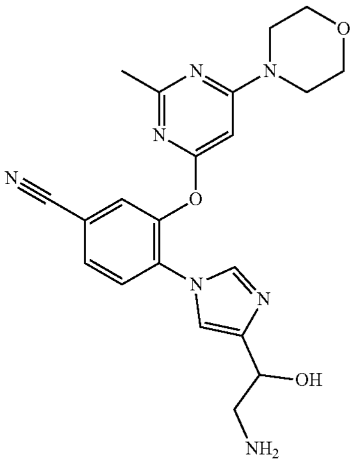 [SMILES: Cc1nc(Oc2cc(C#N)ccc2-n2cnc(C(O)CN)c2)cc(N2CCOCC2)n1] | 4-[4-(2-amino-1-hydroxyethyl)imidazol-1-yl]-3-(2-methyl-6-morpholin-4-ylpyrimidin-4-yl)oxybenzonitrile |

TABLE 1-continued

| Compound number | Structural formula | Compound name |
|---|---|---|
| 170 | 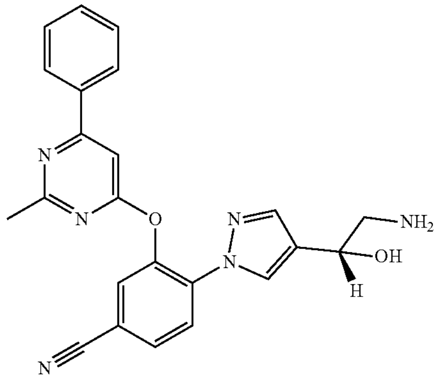 [SMILES: Cc1nc(Oc2cc(C#N)ccc2-n2cc([C@@H](O)CN)cn2)cc(-c2ccccc2)n1] | 4-[4-[(1R)-2-amino-1-hydroxyethyl]pyrazol-1-yl]-3-(2-methyl-6-phenylpyrimidin-4-yl)oxybenzonitrile |
| 171 | 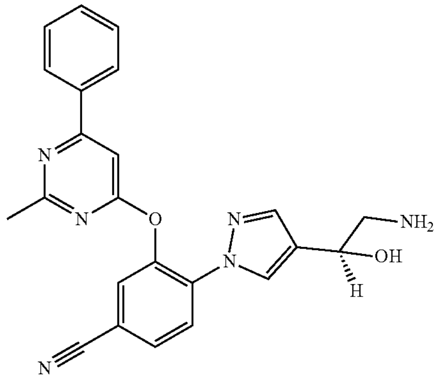 [SMILES: Cc1nc(Oc2cc(C#N)ccc2-n2cc([C@H](O)CN)cn2)cc(-c2ccccc2)n1] | 4-[4-[(1S)-2-amino-1-hydroxyethyl]pyrazol-1-yl]-3-(2-methyl-6-phenylpyrimidin-4-yl)oxybenzonitrile |
| 172 | 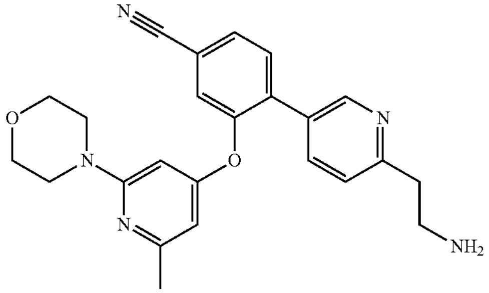 [SMILES: Cc1cc(Oc2cc(C#N)ccc2-c2ccc(CCN)nc2)cc(N2CCOCC2)n1] | 4-[6-(2-aminoethyl)pyridin-3-yl]-3-(2-methyl-6-morpholin-4-ylpyridin-4-yl)oxybenzonitrile |
| 173 | 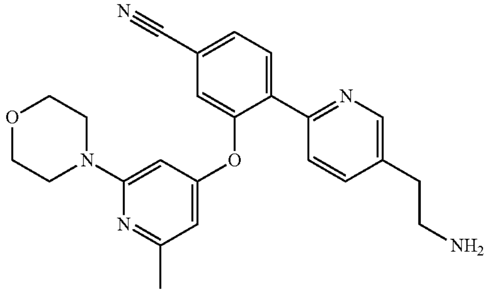 [SMILES: Cc1cc(Oc2cc(C#N)ccc2-c2ccc(CCN)cn2)cc(N2CCOCC2)n1] | 4-[5-(2-aminoethyl)pyridin-2-yl]-3-(2-methyl-6-morpholin-4-ylpyridin-4-yl)oxybenzonitrile |

TABLE 1-continued
| Compound number | Structural formula | Compound name |
| --- | --- | --- |
| 174 | 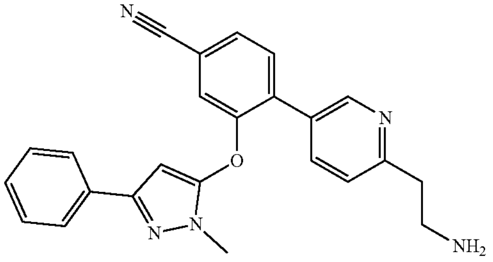 [SMILES: Cn1nc(-c2ccccc2)cc1Oc1cc(C#N)ccc1-c1ccc(CCN)nc1] | 4-[6-(2-aminoethyl)pyridin-3-yl]-3-(2-methyl-5-phenylpyrazol-3-yl)oxybenzonitrile |
| 175 | 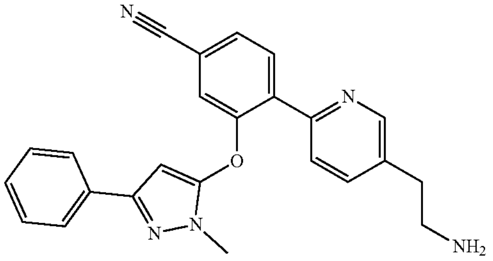 | 4-[5-(2-aminoethyl)pyridin-2-yl]-3-(2-methyl-5-phenylpyrazol-3-yl)oxybenzonitrile |
| 176 | 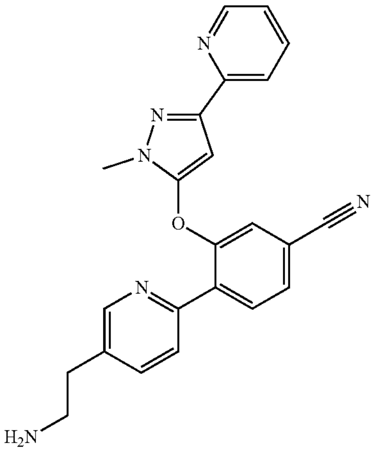 [SMILES: Cn1nc(-c2ccccn2)cc1Oc1cc(C#N)ccc1-c1ccc(CCN)cn1] | 4-[5-(2-aminoethyl)pyridin-2-yl]-3-(2-methyl-5-pyridin-2-ylpyrazol-3-yl)oxybenzonitrile |
| 177 | 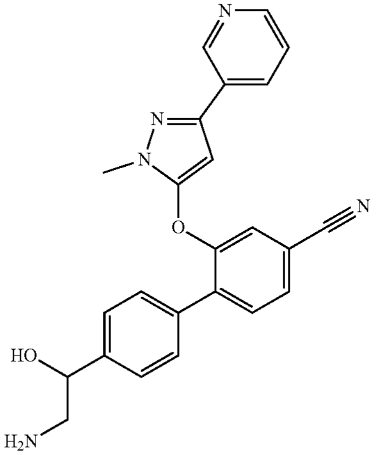 [SMILES: Cn1nc(-c2cccnc2)cc1Oc1cc(C#N)ccc1-c1ccc(C(O)CN)cc1] | 4-[4-(2-amino-1-hydroxyethyl)phenyl]-3-(2-methyl-5-pyridin-3-ylpyrazol-3-yl)oxybenzonitrile |

TABLE 1-continued
| Compound number | Structural formula | Compound name |
|---|---|---|
| 178 | 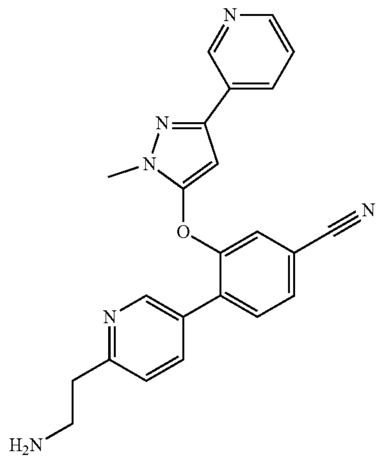 [SMILES: Cn1nc(-c2cccnc2)cc1Oc1cc(C#N)ccc1-c1ccc(CCN)nc1] | 4-[6-(2-aminoethyl)pyridin-3-yl]-3-(2-methyl-5-pyridin-3-ylpyrazol-3-yl)oxybenzonitrile |
| 179 | 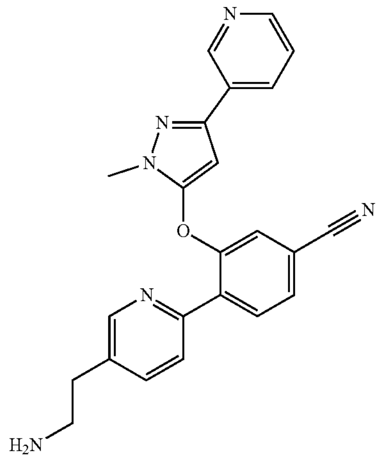 [SMILES: Cn1nc(-c2cccnc2)cc1Oc1cc(C#N)ccc1-c1ccc(CCN)cn1] | 4-[5-(2-aminoethyl)pyridin-2-yl]-3-(2-methyl-5-pyridin-3-ylpyrazol-3-yl)oxybenzonitrile |
| 180 | 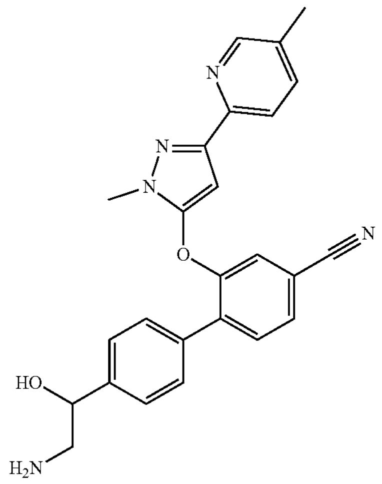 [SMILES: Cc1ccc(-c2cc(Oc3cc(C#N)ccc3-c3ccc(C(O)CN)cc3)n(C)n2)nc1] | 4-[4-(2-amino-1-hydroxyethyl)phenyl]-3-[2-methyl-5-(5-methylpyridin-2-yl)pyrazol-3-yl]oxybenzonitrile |

TABLE 1-continued
| Compound number | Structural formula | Compound name |
|---|---|---|
| 181 | 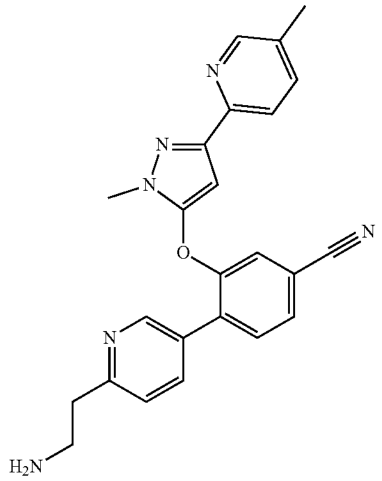 [SMILES: Cc1ccc(-c2cc(Oc3cc(C#N)ccc3-c3ccc(CCN)nc3)n(C)n2)nc1] | 4-[6-(2-aminoethyl)pyridin-3-yl]-3-[2-methyl-5-(5-methylpyridin-2-yl)pyrazol-3-yl]oxybenzonitrile |
| 182 | 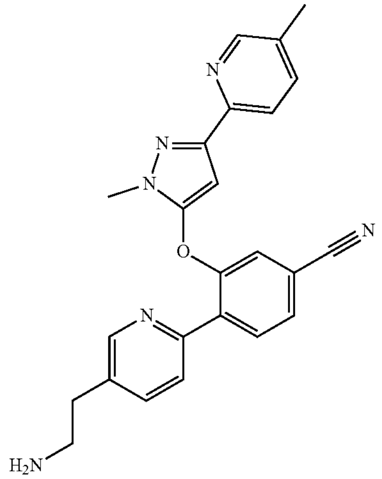 [SMILES: Cc1ccc(-c2cc(Oc3cc(C#N)ccc3-c3ccc(CCN)cn3)n(C)n2)nc1] | 4-[5-(2-aminoethyl)pyridin-2-yl]-3-[2-methyl-5-(5-methylpyridin-2-yl)pyrazol-3-yl]oxybenzonitrile |
| 183 | 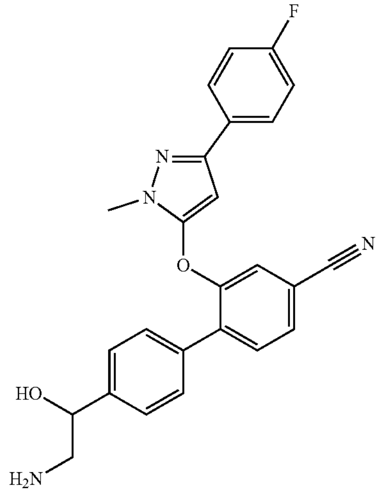 [SMILES: Cn1nc(-c2ccc(F)cc2)cc1Oc1cc(C#N)ccc1-c1ccc(C(O)CN)cc1] | 4-[4-(2-amino-1-hydroxyethyl)phenyl]-3-[5-(4-fluorophenyl)-2-methylpyrazol-3-yl]oxybenzonitrile |

TABLE 1-continued
| Compound number | Structural formula | Compound name |
| --- | --- | --- |
| 184 | 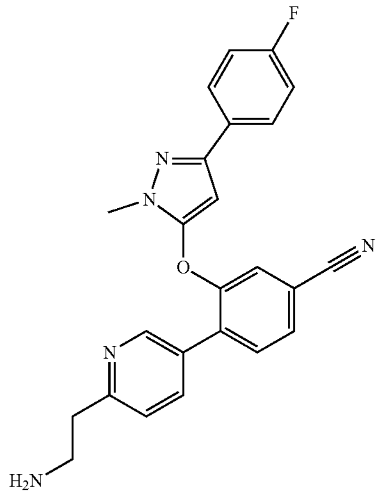 [SMILES: Cn1nc(-c2ccc(F)cc2)cc1Oc1cc(C#N)ccc1-c1ccc(CCN)nc1] | 4-[6-(2-aminoethyl)pyridin-3-yl]-3-[5-(4-fluorophenyl)-2-methylpyrazol-3-yl]oxybenzonitrile |
| 185 | 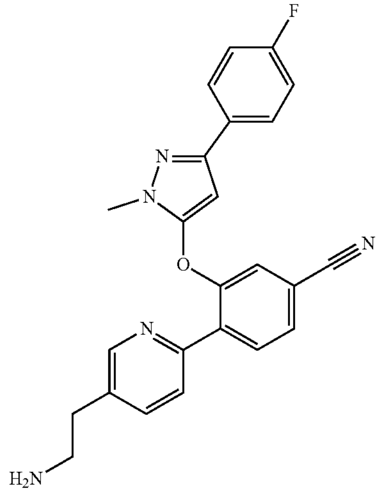 [SMILES: Cn1nc(-c2ccc(F)cc2)cc1Oc1cc(C#N)ccc1-c1ccc(CCN)cn1] | 4-[5-(2-aminoethyl)pyridin-2-yl]-3-[5-(4-fluorophenyl)-2-methylpyrazol-3-yl]oxybenzonitrile |
| 186 | 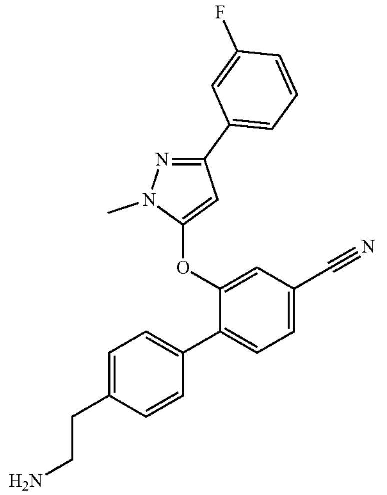 [SMILES: Cn1nc(-c2cccc(F)c2)cc1Oc1cc(C#N)ccc1-c1ccc(CCN)cc1] | 4-[4-(2-aminoethyl)phenyl]-3-[5-(3-fluorophenyl)-2-methylpyrazol-3-yl]oxybenzonitrile |

TABLE 1-continued
| Compound number | Structural formula | Compound name |
| --- | --- | --- |
| 187 | 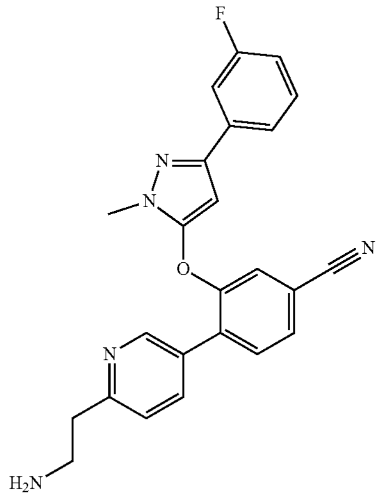 [SMILES: Cn1nc(-c2cccc(F)c2)cc1Oc1cc(C#N)ccc1-c1ccc(CCN)nc1] | 4-[6-(2-aminoethyl)pyridin-3-yl]-3-[5-(3-fluorophenyl)-2-methylpyrazol-3-yl]oxybenzonitrile |
| 188 | 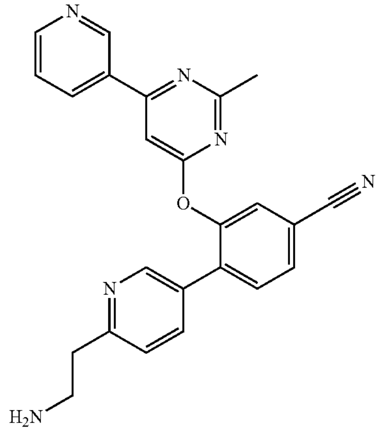 [SMILES: Cc1nc(Oc2cc(C#N)ccc2-c2ccc(CCN)nc2)cc(-c2cccnc2)n1] | 4-[6-(2-aminoethyl)pyridin-3-yl]-3-(2-methyl-6-pyridin-3-ylpyrimidin-4-yl)oxybenzonitrile |
| 189 | 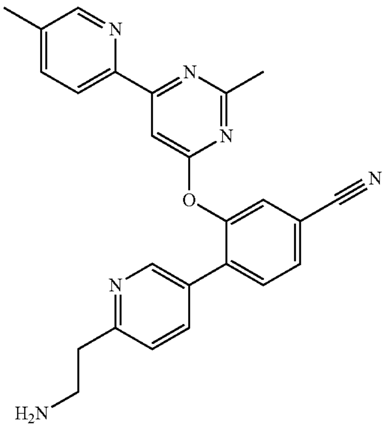 [SMILES: Cc1ccc(-c2cc(Oc3cc(C#N)ccc3-c3ccc(CCN)nc3)nc(C)n2)nc1] | 4-[6-(2-aminoethyl)pyridin-3-yl]-3-[2-methyl-6-(5-methylpyridin-2-yl)pyrimidin-4-yl]oxybenzonitrile |

TABLE 1-continued

| Compound number | Structural formula | Compound name |
| --- | --- | --- |
| 190 | 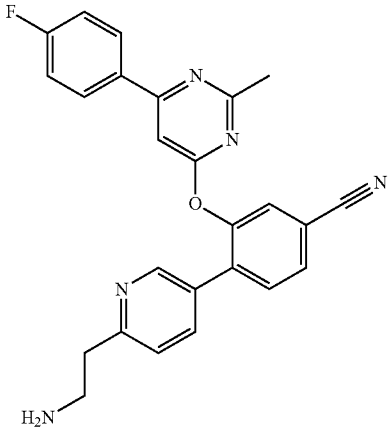 [SMILES: Cc1nc(Oc2cc(C#N)ccc2-c2ccc(CCN)nc2)cc(-c2ccc(F)cc2)n1] | 4-[6-(2-aminoethyl)pyridin-3-yl]-3-[6-(4-fluorophenyl)-2-methylpyrimidin-4-yl]oxybenzonitrile |
| 191 | 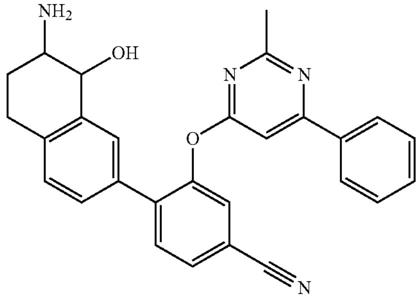 [SMILES: Cc1nc(Oc2cc(C#N)ccc2-c2ccc3c(c2)C(O)C(N)CC3)cc(-c2ccccc2)n1] | 4-(7-amino-8-hydroxy-5,6,7,8-tetrahydronaphthalen-2-yl)-3-(2-methyl-6-phenylpyrimidin-4-yl)oxybenzonitrile |
| 192 | 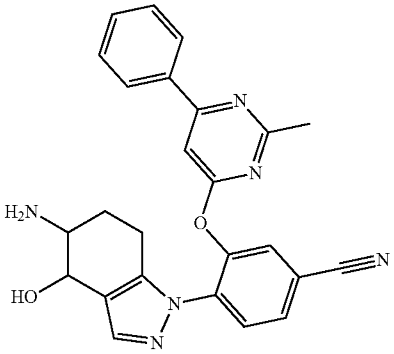 [SMILES: Cc1nc(Oc2cc(C#N)ccc2-n2ncc3c2CCC(N)C3O)cc(-c2ccccc2)n1] | 4-(5-amino-4-hydroxy-4,5,6,7-tetrahydroindazol-1-yl)-3-(2-methyl-6-phenylpyrimidin-4-yl)oxybenzonitrile |
| 193 | 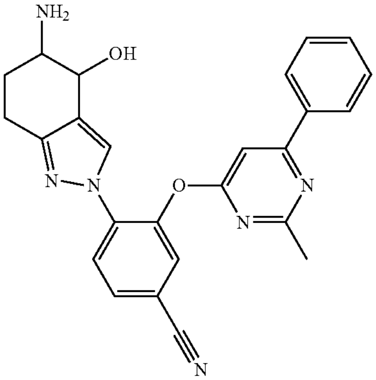 [SMILES: Cc1nc(Oc2cc(C#N)ccc2-n2cc3c(n2)CCC(N)C3O)cc(-c2ccccc2)n1] | 4-(5-amino-4-hydroxy-4,5,6,7-tetrahydroindazol-2-yl)-3-(2-methyl-6-phenylpyrimidin-4-yl)oxybenzonitrile |

TABLE 1-continued

| Compound number | Structural formula | Compound name |
| --- | --- | --- |
| 194 | 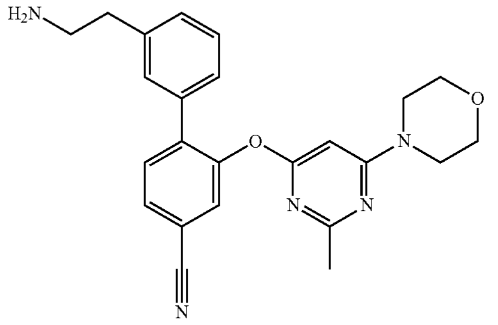 [SMILES: Cc1nc(Oc2cc(C#N)ccc2-c2cccc(CCN)c2)cc(N2CCOCC2)n1] | 4-[3-(2-aminoethyl)phenyl]-3-(2-methyl-6-morpholin-4-ylpyrimidin-4-yl)oxybenzonitrile |
| 195 | 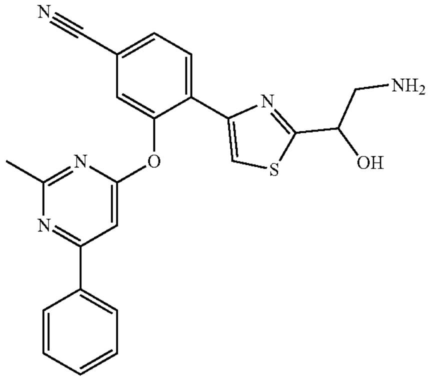 [SMILES: Cc1nc(Oc2cc(C#N)ccc2-c2csc(C(O)CN)n2)cc(-c2ccccc2)n1] | 4-[2-(2-amino-1-hydroxyethyl)-1,3-thiazol-4-yl]-3-(2-methyl-6-phenylpyrimidin-4-yl)oxybenzonitrile |
| 196 | 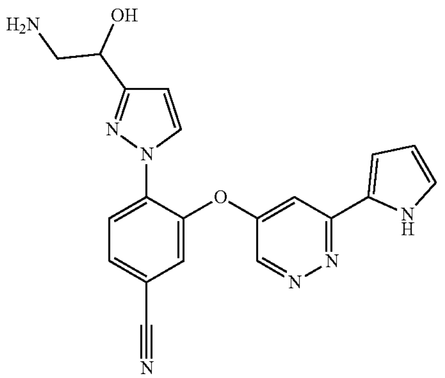 [SMILES: N#Cc1ccc(-n2ccc(C(O)CN)n2)c(Oc2cnnc(-c3ccc[nH]3)c2)c1] | 4-[3-(2-amino-1-hydroxyethyl)pyrazol-1-yl]-3-[6-(1H-pyrrol-2-yl)pyridazin-4-yl]oxybenzonitrile |
| 197 | 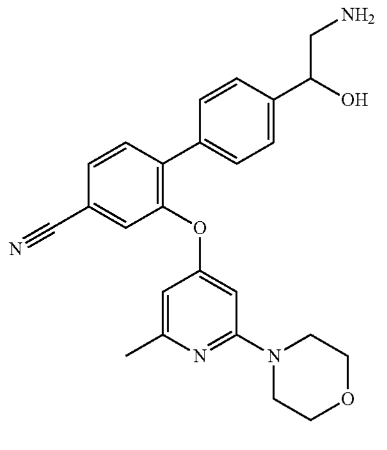 [SMILES: Cc1cc(Oc2cc(C#N)ccc2-c2ccc(C(O)CN)cc2)cc(N2CCOCC2)n1] | 4-[4-(2-amino-1-hydroxyethyl)phenyl]-3-(2-methyl-6-morpholin-4-ylpyridin-4-yl)oxybenzonitrile |

TABLE 1-continued
| Compound number | Structural formula | Compound name |
| --- | --- | --- |
| 198 | 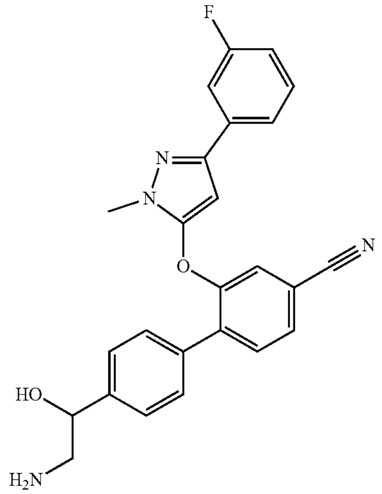 [SMILES: Cn1nc(-c2cccc(F)c2)cc1Oc1cc(C#N)ccc1-c1ccc(C(O)CN)cc1] | 4-[4-(2-amino-1-hydroxyethyl)phenyl]-3-[5-(3-fluorophenyl)-2-methylpyrazol-3-yl]oxybenzonitrile |
| 199 | 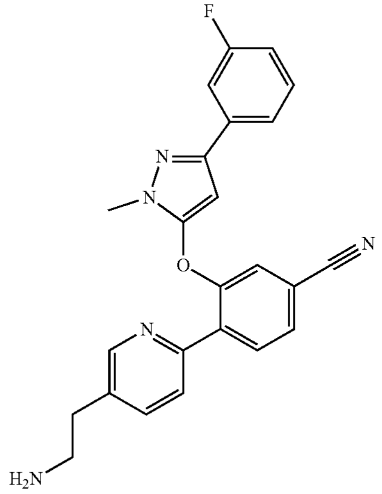 [SMILES: Cn1nc(-c2cccc(F)c2)cc1Oc1cc(C#N)ccc1-c1ccc(CCN)cn1] | 4-[5-(2-aminoethyl)pyridin-2-yl]-3-[5-(3-fluorophenyl)-2-methylpyrazol-3-yl]oxybenzonitrile |
| 200 | 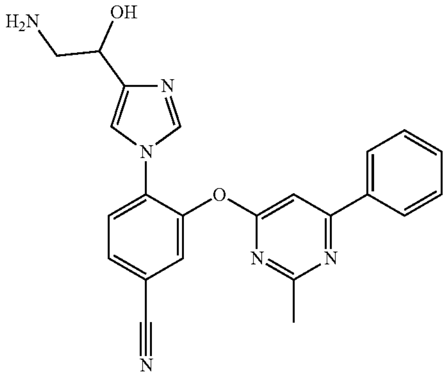 [SMILES: Cc1nc(Oc2cc(C#N)ccc2-n2cnc(C(O)CN)c2)cc(-c2ccccc2)n1] | 4-[4-(2-amino-1-hydroxyethyl)imidazol-1-yl]-3-(2-methyl-6-phenylpyrimidin-4-yl)oxybenzonitrile |

TABLE 1-continued
| Compound number | Structural formula | Compound name |
|---|---|---|
| 201 | 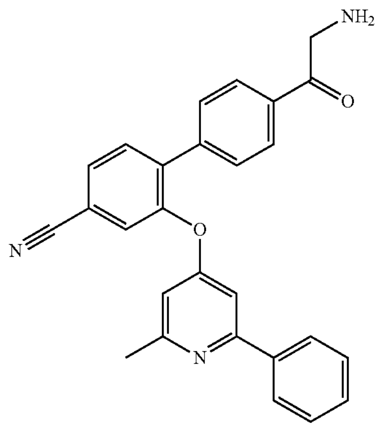 [SMILES: Cc1cc(Oc2cc(C#N)ccc2-c2ccc(C(=O)CN)cc2)cc(-c2ccccc2)n1] | 4-[4-(2-aminoacetyl)phenyl]-3-(2-methyl-6-phenylpyridin-4-yl)oxybenzonitrile |
| 202 | 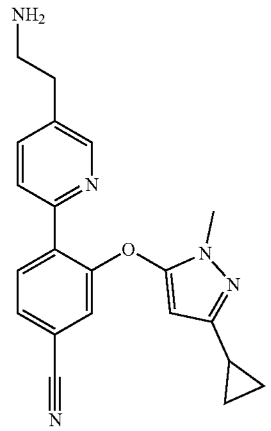 [SMILES: Cn1nc(C2CC2)cc1Oc1cc(C#N)ccc1-c1ccc(CCN)cn1] | 4-[5-(2-aminoethyl)pyridin-2-yl]-3-(5-cyclopropyl-2-methylpyrazol-3-yl)oxybenzonitrile |
| 203 | 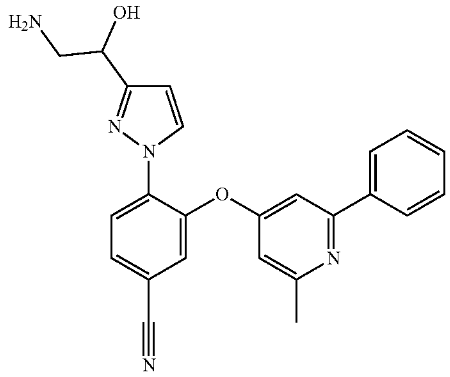 [SMILES: Cc1cc(Oc2cc(C#N)ccc2-n2ccc(C(O)CN)n2)cc(-c2ccccc2)n1] | 4-[3-(2-amino-1-hydroxyethyl)pyrazol-1-yl]-3-(2-methyl-6-phenylpyridin-4-yl)oxybenzonitrile |

TABLE 1-continued
| Compound number | Structural formula | Compound name |
|---|---|---|
| 204 | 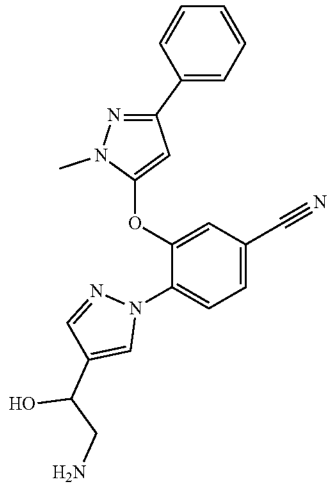 [SMILES: Cn1nc(-c2ccccc2)cc1Oc1cc(C#N)ccc1-n1cc(C(O)CN)cn1] | 4-[4-(2-amino-1-hydroxyethyl)pyrazol-1-yl]-3-(2-methyl-5-phenylpyrazol-3-yl)oxybenzonitrile |
| 205 | 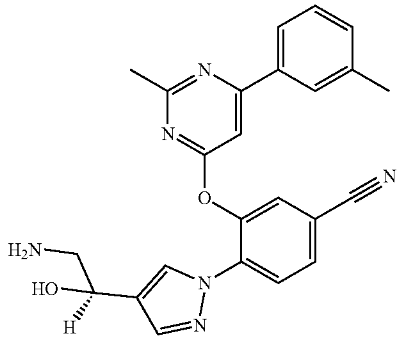 [SMILES: Cc1cccc(-c2cc(Oc3cc(C#N)ccc3-n3cc([C@@H](O)CN)cn3)nc(C)n2)c1] | 4-[4-[(1R)-2-amino-1-hydroxyethyl]pyrazol-1-yl]-3-[2-methyl-6-(3-methylphenyl)pyrimidin-4-yl]oxybenzonitrile |
| 206 | 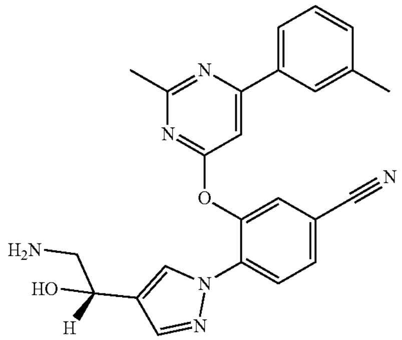 [SMILES: Cc1cccc(-c2cc(Oc3cc(C#N)ccc3-n3cc([C@H](O)CN)cn3)nc(C)n2)c1] | 4-[4-[(1S)-2-amino-1-hydroxyethyl]pyrazol-1-yl]-3-[2-methyl-6-(3-methylphenyl)pyrimidin-4-yl]oxybenzonitrile |

TABLE 1-continued

| Compound number | Structural formula | Compound name |
| --- | --- | --- |
| 207 | 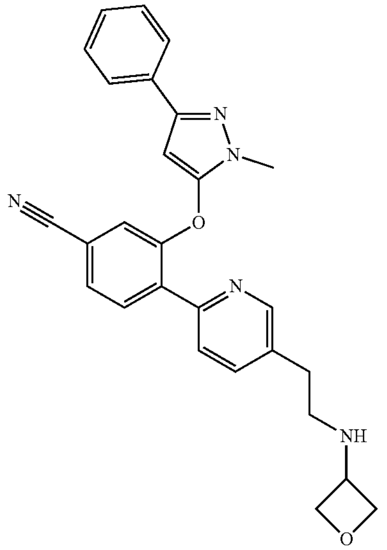 [SMILES: Cn1nc(-c2ccccc2)cc1Oc1cc(C#N)ccc1-c1ccc(CCNC2COC2)cn1] | 3-(2-methyl-5-phenylpyrazol-3-yl)oxy-4-[5-[2-(oxetan-3 ylamino)ethyl]pyridin-2-yl]benzonitrile |
| 208 | 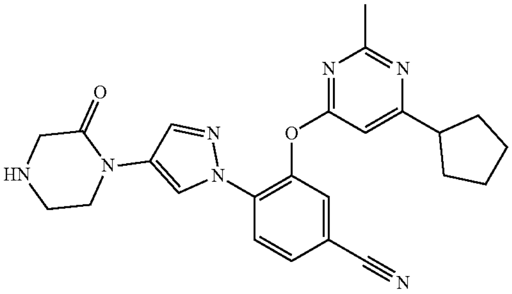 [SMILES: Cc1nc(Oc2cc(C#N)ccc2-n2cc(N3CCNCC3=O)cn2)cc(C2CCCC2)n1] | 3-(6-cyclopentyl-2-methylpyrimidin-4-yl)oxy-4-[4-(2-oxopiperazin-1-yl)pyrazol-1-yl]benzonitrile |
| 209 | 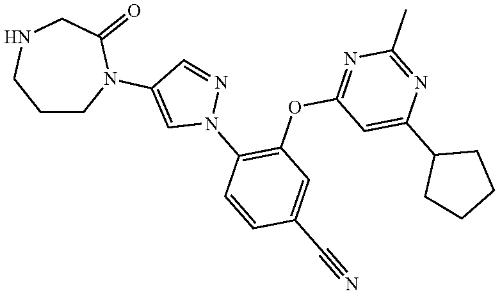 [SMILES: Cc1nc(Oc2cc(C#N)ccc2-n2cc(N3CCCNCC3=O)cn2)cc(C2CCCC2)n1] | 3-(6-cyclopentyl-2-methylpyrimidin-4-yl)oxy-4-[4-(2-oxo-1,4-diazepan-1-yl)pyrazol-1-yl]benzonitrile |
| 210 | 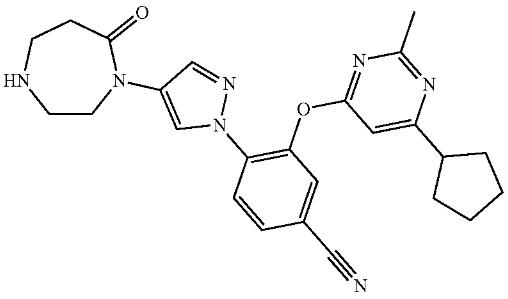 [SMILES: Cc1nc(Oc2cc(C#N)ccc2-n2cc(N3CCNCCC3=O)cn2)cc(C2CCCC2)n1] | 3-(6-cyclopentyl-2-methylpyrimidin-4-yl)oxy-4-[4-(7-oxo-1,4-diazepan-1-yl)pyrazol-1-yl]benzonitrile |

TABLE 1-continued
| Compound number | Structural formula | Compound name |
|---|---|---|
| 211 | 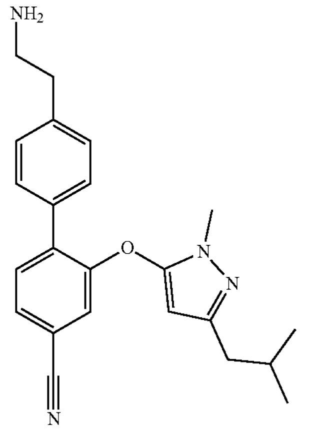 [SMILES: CC(C)Cc1cc(Oc2cc(C#N)ccc2-c2ccc(CCN)cc2)n(C)n1] | 4-[4-(2-aminoethyl)phenyl]-3-[2-methyl-5-(2-methylpropyl)pyrazol-3-yl]oxybenzonitrile |
| 212 | 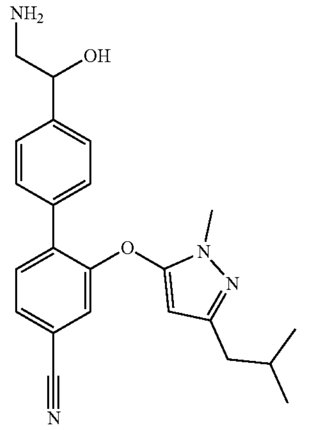 [SMILES: CC(C)Cc1cc(Oc2cc(C#N)ccc2-c2ccc(C(O)CN)cc2)n(C)n1] | 4-[4-(2-amino-1-hydroxyethyl)phenyl]-3-[2-methyl-5 (2-methylpropyl)pyrazol-3-yl]oxybenzonitrile |
| 213 | 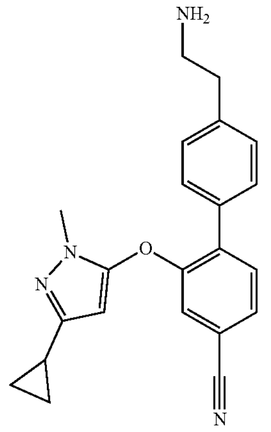 [SMILES: Cn1nc(C2CC2)cc1Oc1cc(C#N)ccc1-c1ccc(CCN)cc1] | 4-[4-(2-aminoethyl)phenyl]-3-(5-cyclopropyl-2-methylpyrazol-3-yl)oxybenzonitrile |

TABLE 1-continued

| Compound number | Structural formula | Compound name |
|---|---|---|
| 214 | 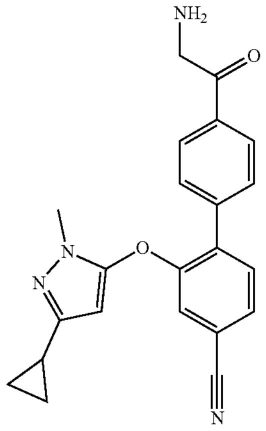 [SMILES: Cn1nc(C2CC2)cc1Oc1cc(C#N)ccc1-c1ccc(C(=O)CN)cc1] | 4-[4-(2-aminoacetyl)phenyl]-3-(5-cyclopropyl-2-methylpyrazol-3-yl)oxybenzonitrile |
| 215 | 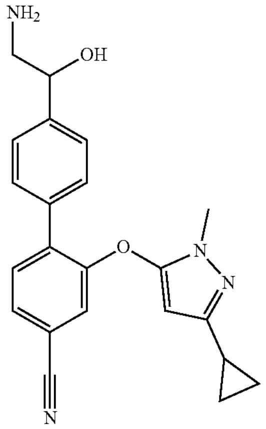 [SMILES: Cn1nc(C2CC2)cc1Oc1cc(C#N)ccc1-c1ccc(C(O)CN)cc1] | 4-[4-(2-amino-1-hydroxyethyl)phenyl]-3-(5-cyclopropyl-2-methylpyrazol-3-yl)oxybenzonitrile |
| 216 | 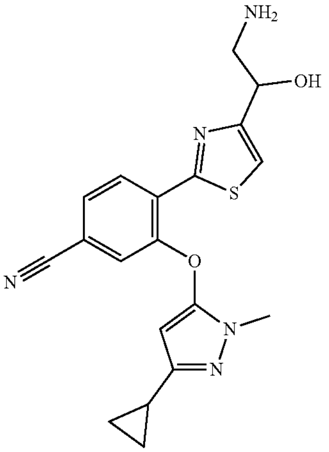 [SMILES: Cn1nc(C2CC2)cc1Oc1cc(C#N)ccc1-c1nc(C(O)CN)cs1] | 4-[4-(2-amino-1-hydroxyethyl)-1,3-thiazol-2-yl]-3-(5-cyclopropyl-2-methylpyrazol-3-yl)oxybenzonitrile |
| 217 | 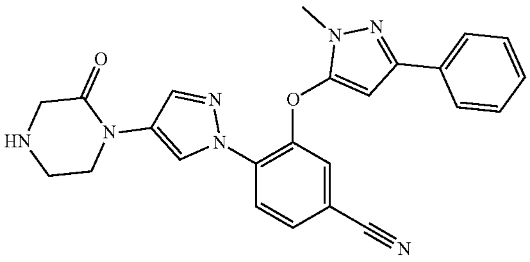 [SMILES: Cn1nc(-c2ccccc2)cc1Oc1cc(C#N)ccc1-n1cc(N2CCNCC2=O)cn1] | 3-(2-methyl-5-phenylpyrazol-3-yl)oxy-4-[4-(2-oxopiperazin-1-yl)pyrazol-1-yl]benzonitrile |

TABLE 1-continued

| Compound number | Structural formula | Compound name |
|---|---|---|
| 218 | 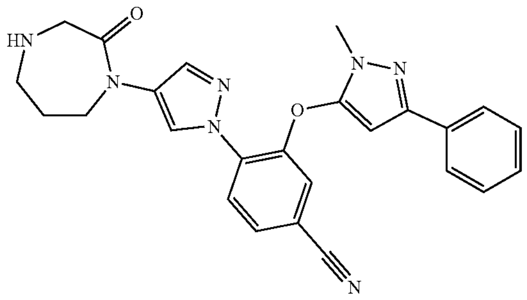 [SMILES: Cn1nc(-c2ccccc2)cc1Oc1cc(C#N)ccc1-n1cc(N2CCCNCC2=O)cn1] | 3-(2-methyl-5-phenylpyrazol-3-yl)oxy-4-[4-(2-oxo-1,4-diazepan-1-yl)pyrazol-1-yl]benzonitrile |
| 219 | 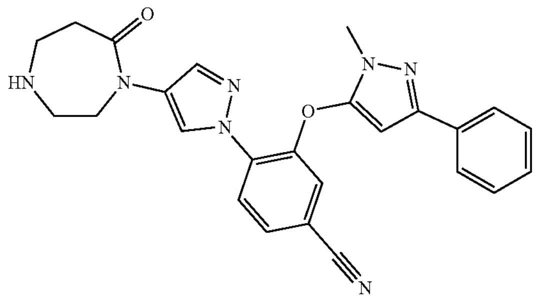 [SMILES: Cn1nc(-c2ccccc2)cc1Oc1cc(C#N)ccc1-n1cc(N2CCNCCC2=O)cn1] | 3-(2-methyl-5-phenylpyrazol-3-yl)oxy-4-[4-(7-oxo-1,4-diazepan-1-yl)pyrazol-1-yl]benzonitrile |
| 220 | 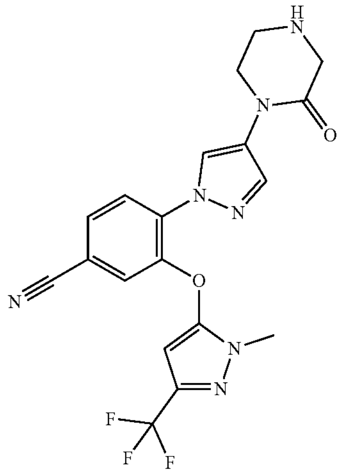 [SMILES: Cn1nc(C(F)(F)F)cc1Oc1cc(C#N)ccc1-n1cc(N2CCNCC2=O)cn1] | 3-[2-methyl-5-(trifluoromethyl)pyrazol-3-yl]oxy-4-[4-(2-oxopiperazin-1-yl)pyrazol-1-yl]benzonitrile |
| 221 | 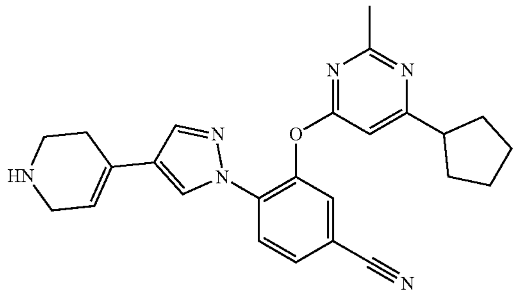 [SMILES: Cc1nc(Oc2cc(C#N)ccc2-n2cc(C3=CCNCC3)cn2)cc(C2CCCC2)n1] | 3-(6-cyclopentyl-2-methylpyrimidin-4-yl)oxy-4-[4-(1,2,3,6-tetrahydropyridin-4-yl)pyrazol-1-yl]benzonitrile |

TABLE 1-continued

| Compound number | Structural formula | Compound name |
| --- | --- | --- |
| 222 | 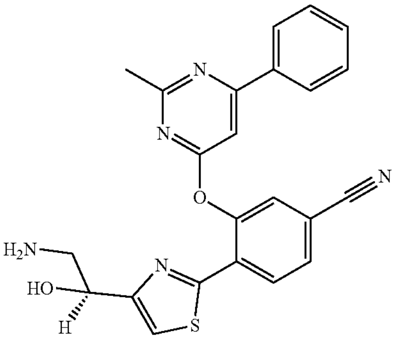 [SMILES: Cc1nc(Oc2cc(C#N)ccc2-c2nc([C@@H](O)CN)cs2)cc(-c2ccccc2)n1] | 4-[4-[(1S)-2-amino-1-hydroxyethyl]-1,3-thiazol-2-yl]-3-(2-methyl-6-phenylpyrimidin-4-yl)oxybenzonitrile |
| 223 | 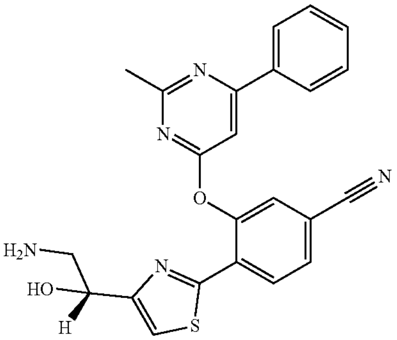 [SMILES: Cc1nc(Oc2cc(C#N)ccc2-c2nc([C@H](O)CN)cs2)cc(-c2ccccc2)n1] | 4-[4-[(1R)-2-amino-1-hydroxyethyl]-1,3-thiazol-2-yl]-3-(2-methyl-6-phenylpyrimidin-4-yl)oxybenzonitrile |
| 224 | 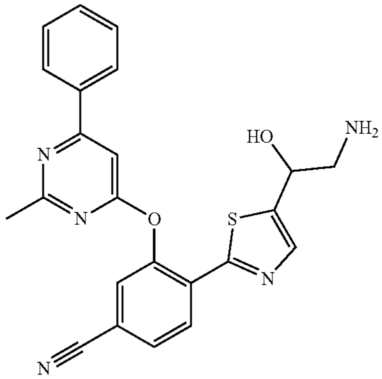 [SMILES: Cc1nc(Oc2cc(C#N)ccc2-c2ncc(C(O)CN)s2)cc(-c2ccccc2)n1] | 4-[5-(2-amino-1-hydroxyethyl)-1,3-thiazol-2-yl]-3-(2-methyl-6-phenylpyrimidin-4-yl)oxybenzonitrile |
| 225 | 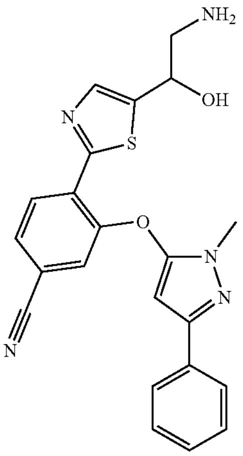 [SMILES: Cn1nc(-c2ccccc2)cc1Oc1cc(C#N)ccc1-c1ncc(C(O)CN)s1] | 4-[5-(2-amino-1-hydroxyethyl)-1,3-thiazol-2-yl]-3-(2-methyl-5-phenylpyrazol-3-yl)oxybenzonitrile |

TABLE 1-continued
| Compound number | Structural formula | Compound name |
|---|---|---|
| 226 | 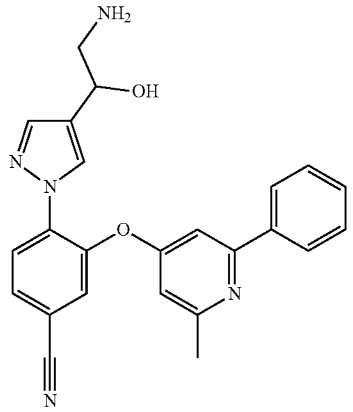 [SMILES: Cc1cc(Oc2cc(C#N)ccc2-n2cc(C(O)CN)cn2)cc(-c2ccccc2)n1] | 4-[4-(2-amino-1-hydroxyethyl)pyrazol-1-yl]-3-(2-methyl-6-phenylpyridin-4-yl)oxybenzonitrile |
| 227 | 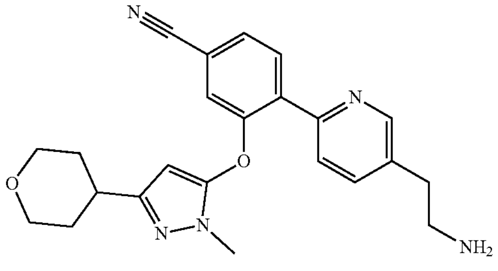 | 4-[5-(2-aminoethyl)pyridin-2-yl]-3-[2-methyl-5-(oxan-4-yl)pyrazol-3-yl]oxybenzonitrile |
| 228 | 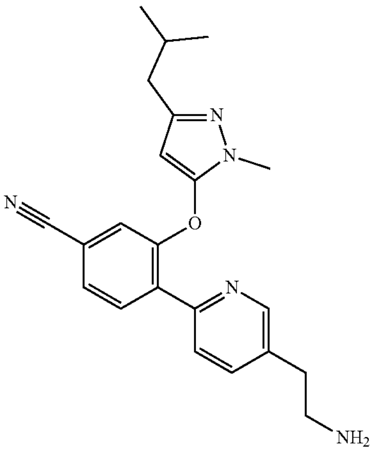 [SMILES: CC(C)Cc1cc(Oc2cc(C#N)ccc2-c2ccc(CCN)cn2)n(C)n1] | 4-[5-(2-aminoethyl)pyridin-2-yl]-3-[2-methyl-5-(2-methylpropyl)pyrazol-3-yl]oxybenzonitrile |
| 229 | 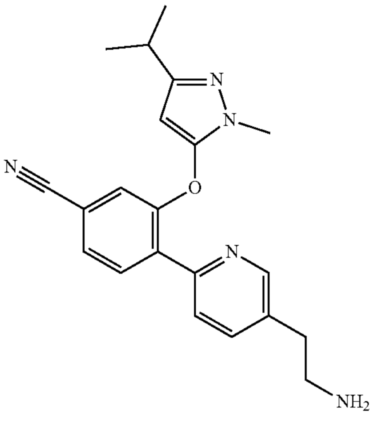 | 4-[5-(2-aminoethyl)pyridin-2-yl]-3-(2-methyl-5-propan-2-ylpyrazol-3-yl)oxybenzonitrile |

TABLE 1-continued

| Compound number | Structural formula | Compound name |
|---|---|---|
| 230 | 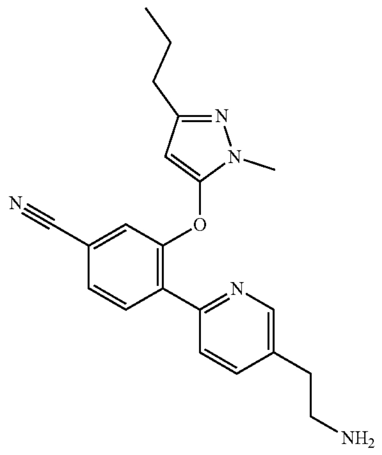 | 4-[5-(2-aminoethyl)pyridin-2-yl]-3-(2-methyl-5-propylpyrazol-3-yl)oxybenzonitrile |
| 231 | 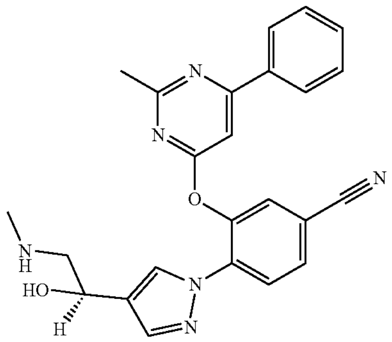 [SMILES: CNC[C@H](O)c1cnn(-c2ccc(C#N)cc2Oc2cc(-c3ccccc3)nc(C)n2)c1] | 4-[4-[(1R)-1-hydroxy-2-(methylamino)ethyl]pyrazol-1-yl]-3-(2-methyl-6-phenylpyrimidin-4-yl)oxybenzonitrile |
| 232 | 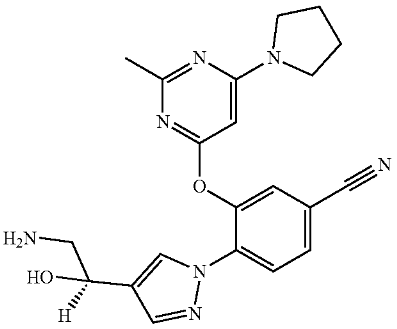 [SMILES: Cc1nc(Oc2cc(C#N)ccc2-n2cc([C@@H](O)CN)cn2)cc(N2CCCC2)n1] | 4-[4-[(1R)-2-amino-1-hydroxyethyl]pyrazol-1-yl]-3-(2-methyl-6-pyrrolidin-1-ylpyrimidin-4-yl)oxybenzonitrile |
| 233 | 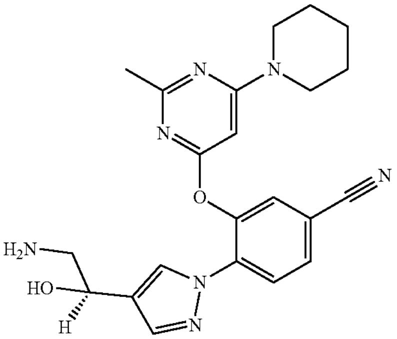 [SMILES: Cc1nc(Oc2cc(C#N)ccc2-n2cc([C@@H](O)CN)cn2)cc(N2CCCCC2)n1] | 4-[4-[(1R)-2-amino-1-hydroxyethyl]pyrazol-1-yl]-3-(2-methyl-6-piperidin-1-ylpyrimidin-4-yl)oxybenzonitrile |

TABLE 1-continued

| Compound number | Structural formula | Compound name |
|---|---|---|
| 234 | 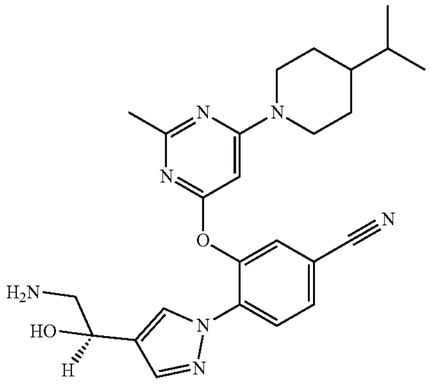 [SMILES: Cc1nc(Oc2cc(C#N)ccc2-n2cc([C@@H](O)CN)cn2)cc(N2CCC(C(C)C)CC2)n1] | 4-[4-[(1R)-2-amino-1-hydroxyethyl]pyrazol-1-yl]-3-[2-methyl-6-(4-propan-2-ylpiperidin-1-yl)pyrimidin-4-yl]oxybenzonitrile |
| 235 | 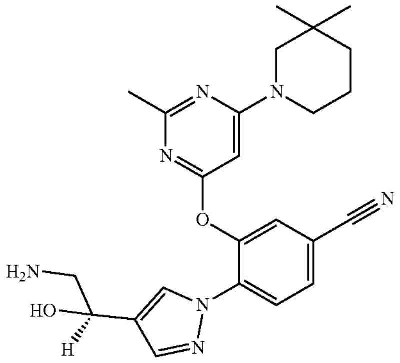 [SMILES: Cc1nc(Oc2cc(C#N)ccc2-n2cc([C@@H](O)CN)cn2)cc(N2CCCC(C)(C)C2)n1] | 4-[4-[(1R)-2-amino-1 hydroxyethyl]pyrazol-1-yl]-3-[6-(3,3-dimethylpiperidin-1-yl)-2-methylpyrimidin-4-yl]oxybenzonitrile |
| 236 | 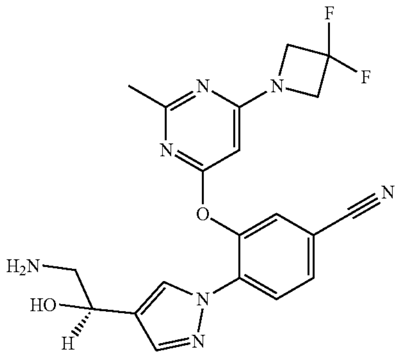 [SMILES: Cc1nc(Oc2cc(C#N)ccc2-n2cc([C@@H](O)CN)cn2)cc(N2CC(F)(F)C2)n1] | 4-[4-[(1R)-2-amino-1-hydroxyethyl]pyrazol-1-yl]-3-[6-(3,3-difluoroazetidin-1-yl)-2-methylpyrimidin-4-yl]oxybenzonitrile |
| 237 | 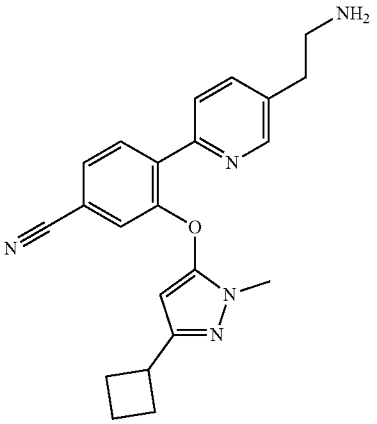 [SMILES: Cn1nc(C2CCC2)cc1Oc1cc(C#N)ccc1-c1ccc(CCN)cn1] | 4-[5-(2-aminoethyl)pyridin-2-yl]-3-(5-cyclobutyl-2-methylpyrazol-3-yl)oxybenzonitrile |

TABLE 1-continued

| Compound number | Structural formula | Compound name |
|---|---|---|
| 238 | 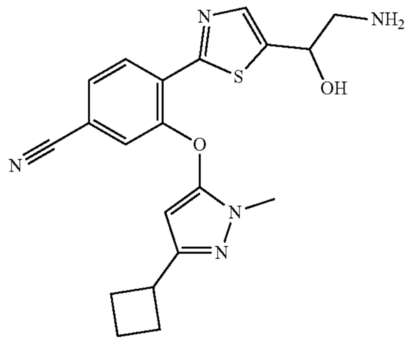 [SMILES: Cn1nc(C2CCC2)cc1Oc1cc(C#N)ccc1-c1ncc(C(O)CN)s1] | 4-[5-(2-amino-1-hydroxyethyl)-1,3-thiazol-2-yl]-3-(5-cyclobutyl-2-methylpyrazol-3-yl)oxybenzonitrile |
| 239 | 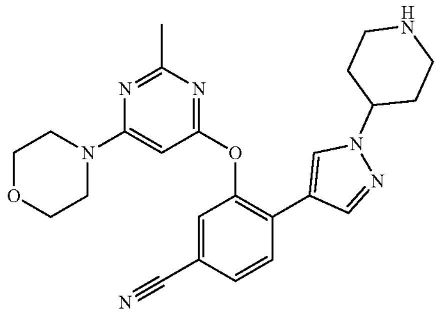 [SMILES: Cc1nc(Oc2cc(C#N)ccc2-c2cnn(C3CCNCC3)c2)cc(N2CCOCC2)n1] | 3-(2-methyl-6-morpholin-4-ylpyrimidin-4-yl)oxy-4-(1-piperidin-4-ylpyrazol-4-yl)benzonitrile |
| 240 | 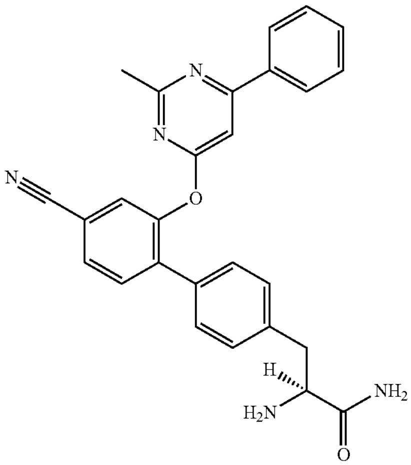 [SMILES: Cc1nc(Oc2cc(C#N)ccc2-c2ccc(C[C@H](N)C(N)=O)cc2)cc(-c2ccccc2)n1] | (2S)-2-amino-3-[4-[4-cyano-2-(2-methyl-6-phenylpyrimidin-4-yl)oxyphenyl]phenyl]propanamide |
| 241 | 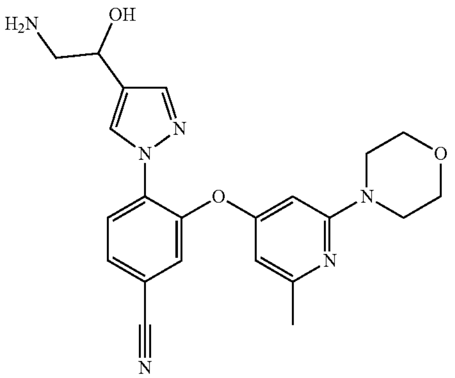 [SMILES: Cc1cc(Oc2cc(C#N)ccc2-n2cc(C(O)CN)cn2)cc(N2CCOCC2)n1] | 4-[4-(2-amino-1-hydroxyethyl)pyrazol-1-yl]-3-(2-methyl-6-morpholin-4-ylpyridin-4-yl)oxybenzonitrile |

TABLE 1-continued
| Compound number | Structural formula | Compound name |
|---|---|---|
| 242 | 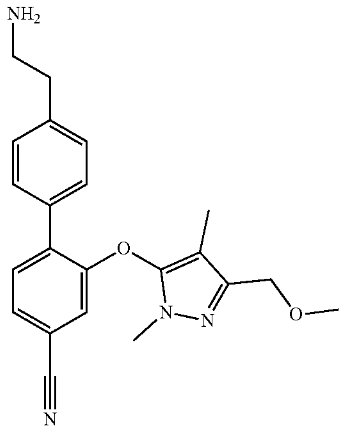 [SMILES: COCc1nn(C)c(Oc2cc(C#N)ccc2-c2ccc(CCN)cc2)c1C] | 4-[4-(2-aminoethyl)phenyl]-3-[5-(methoxymethyl)-2,4-dimethylpyrazol-3-yl]oxybenzonitrile |
| 243 | 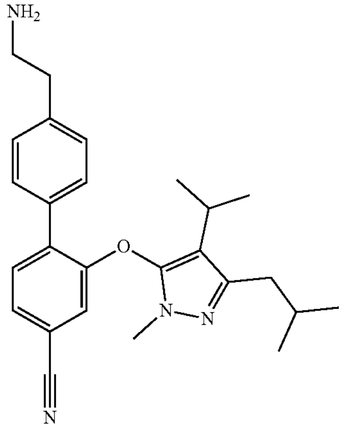 [SMILES: CC(C)Cc1nn(C)c(Oc2cc(C#N)ccc2-c2ccc(CCN)cc2)c1C(C)C] | 4-[4-(2-aminoethyl)phenyl]-3-[2-methyl-5-(2-methylpropyl)-4-propan-2-ylpyrazol-3-yl]oxybenzonitrile |
| 244 | 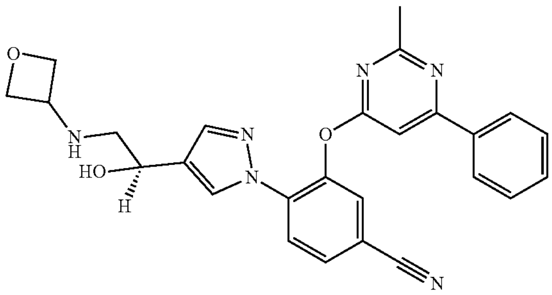 [SMILES: Cc1nc(Oc2cc(C#N)ccc2-n2cc([C@@H](O)CNC3COC3)cn2)cc(-c2ccccc2)n1] | 4-[4-[(1R)-1-hydroxy-2-(oxetan-3-ylamino)ethyl]pyrazol-1-yl]-3-(2-methyl-6-phenylpyrimidin-4-yl)oxybenzonitrile |

TABLE 1-continued
| Compound number | Structural formula | Compound name |
|---|---|---|
| 245 | 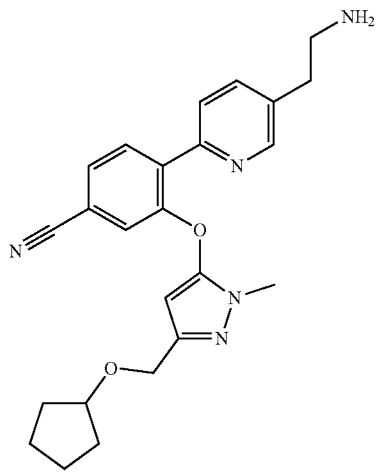 [SMILES: Cn1nc(COC2CCCC2)cc1Oc1cc(C#N)ccc1-c1ccc(CCN)cn1] | 4-[5-(2-aminoethyl)pyridin-2-yl]-3-[5-(cyclopentyloxymethyl)-2-methylpyrazol-3-yl]oxybenzonitrile |
| 246 | 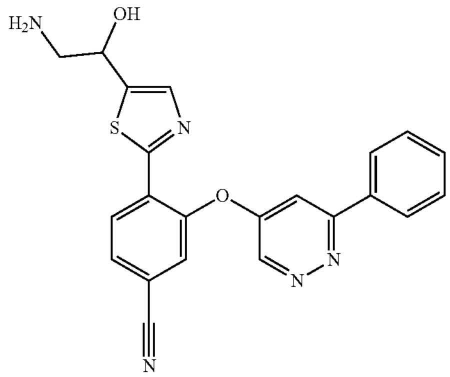 [SMILES: N#Cc1ccc(-c2ncc(C(O)CN)s2)c(Oc2cnnc(-c3ccccc3)c2)c1] | 4-[5-(2-amino-1-hydroxyethyl)-1,3-thiazol-2-yl]-3-(6-phenylpyridazin-4-yl)oxybenzonitrile |
| 247 | 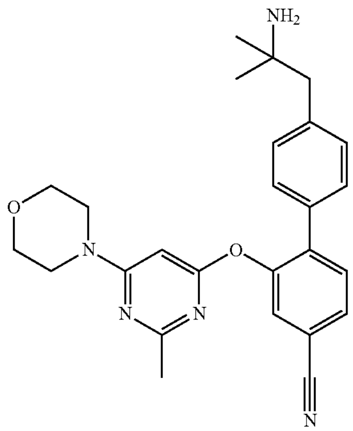 [SMILES: Cc1nc(Oc2cc(C#N)ccc2-c2ccc(CC(C)(C)N)cc2)cc(N2CCOCC2)n1] | 4-[4-(2-amino-2-methylpropyl)phenyl]-3-(2-methyl-6-morpholin-4-ylpyrimidin-4-yl)oxybenzonitrile |

TABLE 1-continued

| Compound number | Structural formula | Compound name |
|---|---|---|
| 248 | 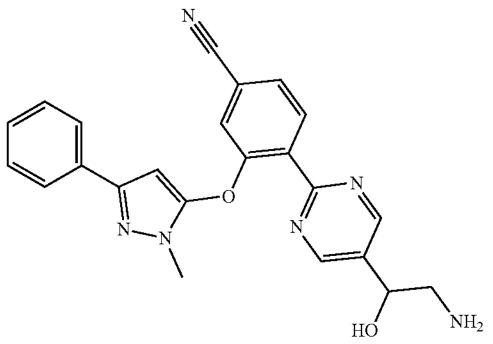 [SMILES: Cn1nc(-c2ccccc2)cc1Oc1cc(C#N)ccc1-c1ncc(C(O)CN)cn1] | 4-[5-(2-amino-1-hydroxyethyl)pyrimidin-2-yl]-3-(2-methyl-5-phenylpyrazol-3-yl)oxybenzonitrile |
| 249 | 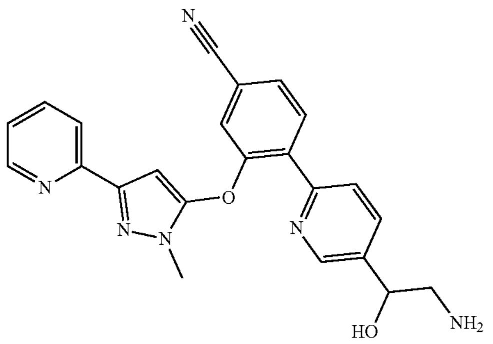 [SMILES: Cn1nc(-c2ccccn2)cc1Oc1cc(C#N)ccc1-c1ccc(C(O)CN)cn1] | 4-[5-(2-amino-1-hydroxyethyl)pyridin-2-yl]-3-(2-methyl-5-pyridin-2-ylpyrazol-3-yl)oxybenzonitrile |
| 250 | 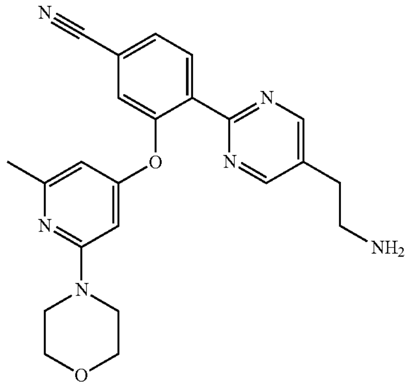 [SMILES: Cc1cc(Oc2cc(C#N)ccc2-c2ncc(CCN)cn2)cc(N2CCOCC2)n1] | 4-[5-(2-aminoethyl)pyrimidin-2-yl]-3-(2-methyl-6-morpholin-4-ylpyridin-4-yl)oxybenzonitrile |
| 251 | 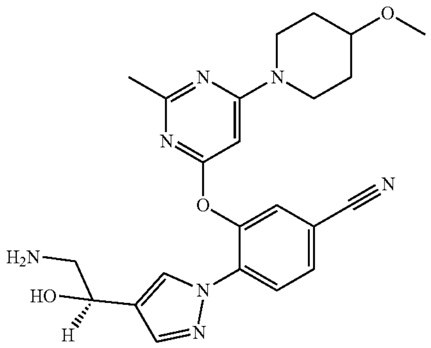 [SMILES: COC1CCN(c2cc(Oc3cc(C#N)ccc3-n3cc([C@@H](O)CN)cn3)nc(C)n2)CC1] | 4-[4-[(1R)-2-amino-1-hydroxyethyl]pyrazol-1-yl]-3-[6-(4-methoxypiperidin-1-yl)-2-methylpyrimidin-4-yl]oxybenzonitrile |

TABLE 1-continued

| Compound number | Structural formula | Compound name |
|---|---|---|
| 252 | 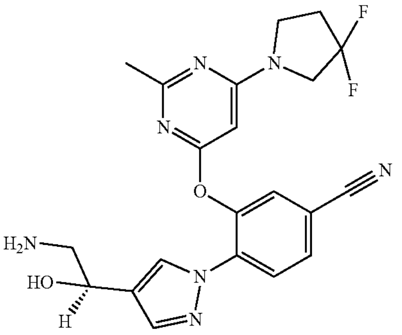 [SMILES: Cc1nc(Oc2cc(C#N)ccc2-n2cc([C@@H](O)CN)cn2)cc(N2CCC(F)(F)C2)n1] | 4-[4-[(1R)-2-amino-1-hydroxyethyl]pyrazol-1-yl]-3-[6-(3,3-difluoropyrrolidin-1-yl)-2-methylpyrimidin-4-yl]oxybenzonitrile |
| 253 | 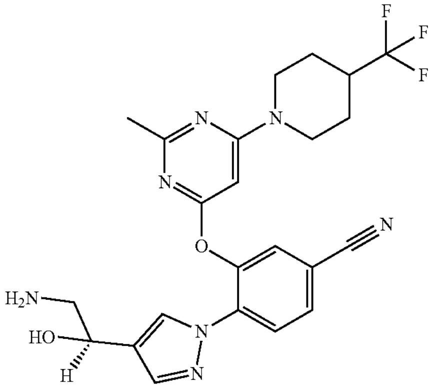 [SMILES: Cc1nc(Oc2cc(C#N)ccc2-n2cc([C@@H](O)CN)cn2)cc(N2CCC(C(F)(F)F)CC2)n1] | 4-[4-[(1R)-2-amino-1-hydroxyethyl]pyrazol-1-yl]-3-[2-methyl-6-[4-(trifluoromethyl)piperidin-1-yl]pyrimidin-4-yl]oxybenzonitrile |
| 254 | 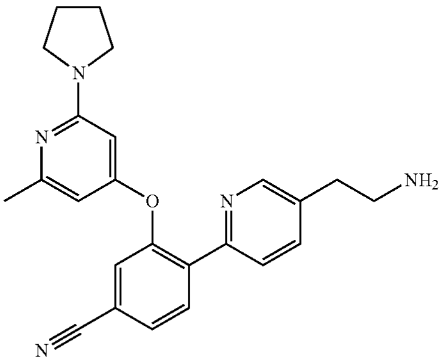 [SMILES: Cc1cc(Oc2cc(C#N)ccc2-c2ccc(CCN)cn2)cc(N2CCCC2)n1] | 4-[5-(2-aminoethyl)pyridin-2-yl]-3-(2-methyl-6-pyrrolidin-1-ylpyridin-4-yl)oxybenzonitrile |
| 255 | 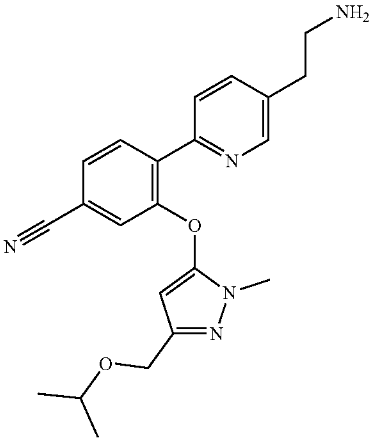 [SMILES: CC(C)OCc1cc(Oc2cc(C#N)ccc2-c2ccc(CCN)cn2)n(C)n1] | 4-[5-(2-aminoethyl)pyridin-2-yl]-3-[2-methyl-5-(propan-2-yloxymethyl)pyrazol-3-yl]oxybenzonitrile |

TABLE 1-continued

| Compound number | Structural formula | Compound name |
|---|---|---|
| 256 | 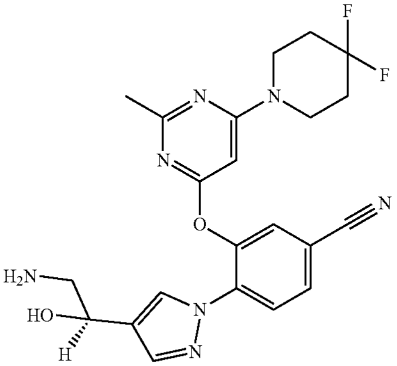 [SMILES: Cc1nc(Oc2cc(C#N)ccc2-n2cc([C@@H](O)CN)cn2)cc(N2CCC(F)(F)CC2)n1] | 4-[4-[(1R)-2-amino-1-hydroxyethyl]pyrazol-1-yl]-3-[6-(4,4-difluoropiperidin-1-yl)-2-methylpyrimidin-4-yl]oxybenzonitrile |
| 257 | 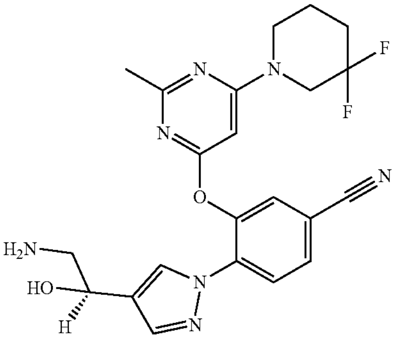 [SMILES: Cc1nc(Oc2cc(C#N)ccc2-n2cc([C@@H](O)CN)cn2)cc(N2CCCC(F)(F)C2)n1] | 4-[4-[(1R)-2-amino-1-hydroxyethyl]pyrazol-1-yl]-3-[6-(3,3-difluoropiperidin-1-yl)-2-methylpyrimidin-4-yl]oxybenzonitrile |
| 258 | 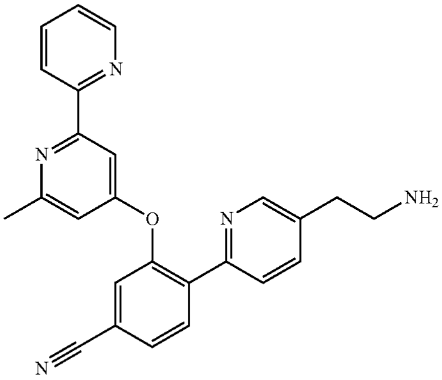 [SMILES: Cc1cc(Oc2cc(C#N)ccc2-c2ccc(CCN)cn2)cc(-c2ccccn2)n1] | 4-[5-(2-aminoethyl)pyridin-2-yl]-3-(2-methyl-6-pyridin-2-ylpyridin-4-yl)oxybenzonitrile |
| 259 | 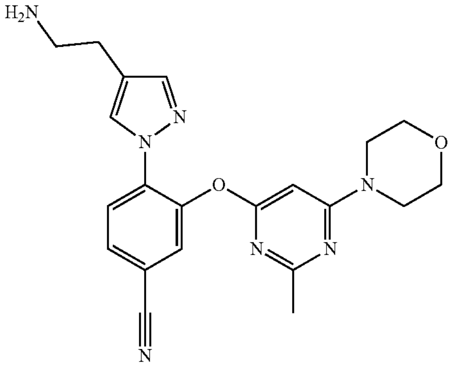 [SMILES: Cc1nc(Oc2cc(C#N)ccc2-n2cc(CCN)cn2)cc(N2CCOCC2)n1] | 4-[4-(2-aminoethyl)pyrazol-1-yl]-3-(2-methyl-6-morpholin-4-ylpyrimidin-4-yl)oxybenzonitrile |

TABLE 1-continued
| Compound number | Structural formula | Compound name |
| --- | --- | --- |
| 260 | 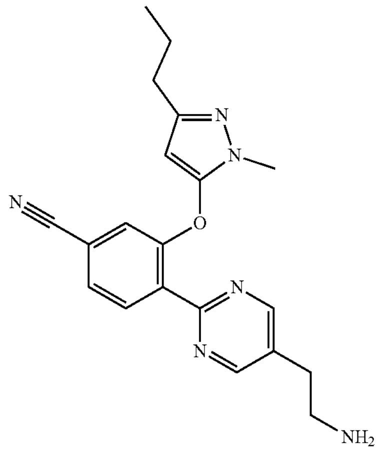 [SMILES: CCCc1cc(Oc2cc(C#N)ccc2-c2ncc(CCN)cn2)n(C)n1] | 4-[5-(2-aminoethyl)pyrimidin-2-yl]-3-(2-methyl-5-propylpyrazol-3-yl)oxybenzonitrile |
| 261 | 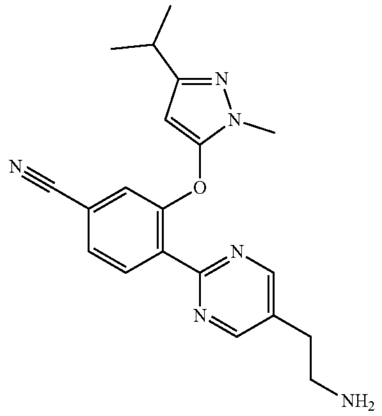 [SMILES: CC(C)c1cc(Oc2cc(C#N)ccc2-c2ncc(CCN)cn2)n(C)n1] | 4-[5-(2-aminoethyl)pyrimidin-2-yl]-3-(2-methyl-5-propan-2-ylpyrazol-3-yl)oxybenzonitrile |
| 262 | 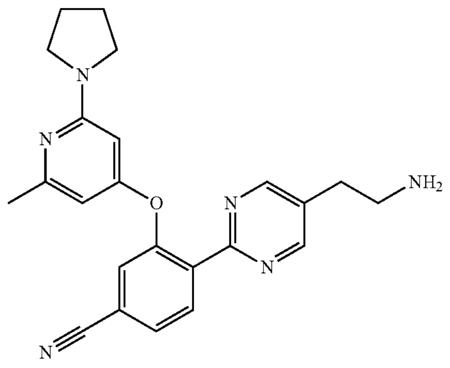 [SMILES: Cc1cc(Oc2cc(C#N)ccc2-c2ncc(CCN)cn2)cc(N2CCCC2)n1] | 4-[5-(2-aminoethyl)pyrimidin-2-yl]-3-(2-methyl-6-pyrrolidin-1-ylpyridin-4-yl)oxybenzonitrile |

TABLE 1-continued

| Compound number | Structural formula | Compound name |
| --- | --- | --- |
| 263 | 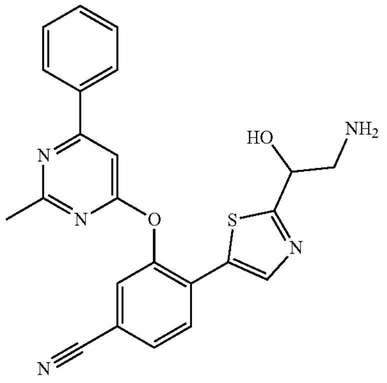 [SMILES: Cc1nc(Oc2cc(C#N)ccc2-c2cnc(C(O)CN)s2)cc(-c2ccccc2)n1] | 4-[2-(2-amino-1-hydroxyethyl)-1,3-thiazol-5-yl]-3-(2-methyl-6-phenylpyrimidin-4-yl)oxybenzonitrile |
| 264 | 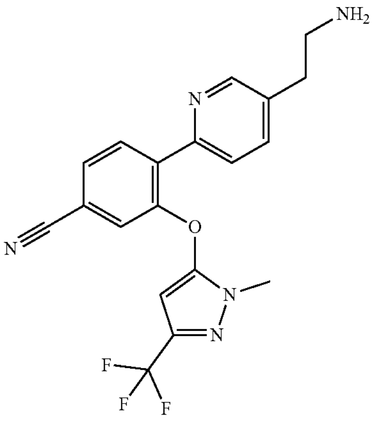 [SMILES: Cn1nc(C(F)(F)F)cc1Oc1cc(C#N)ccc1-c1ccc(CCN)cn1] | 4-[5-(2-aminoethyl)pyridin-2-yl]-3-[2-methyl-5-(trifluoromethyl)pyrazol-3-yl]oxybenzonitrile |
| 265 | 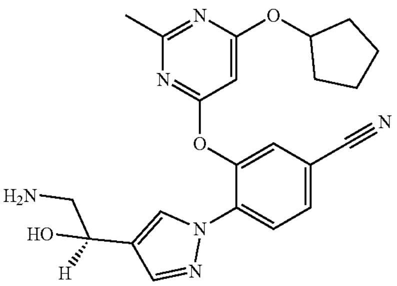 [SMILES: Cc1nc(Oc2cc(C#N)ccc2-n2cc([C@@H](O)CN)cn2)cc(OC2CCCC2)n1] | 4-[4-[(1R)-2-amino-1-hydroxyethyl]pyrazol-1-yl]-3-(6-cyclopentyloxy-2-methylpyrimidin-4-yl)oxybenzonitrile |
| 266 | 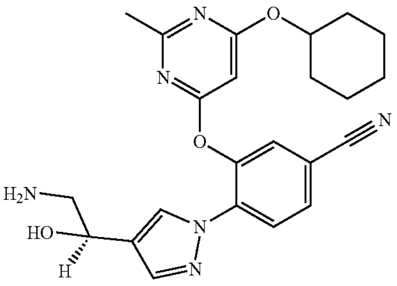 [SMILES: Cc1nc(Oc2cc(C#N)ccc2-n2cc([C@@H](O)CN)cn2)cc(OC2CCCCC2)n1] | 4-[4-[(1R)-2-amino-1-hydroxyethyl]pyrazol-1-yl]-3-(6-cyclohexyloxy-2-methylpyrimidin-4-yl)oxybenzonitrile |

TABLE 1-continued

| Compound number | Structural formula | Compound name |
|---|---|---|
| 267 | 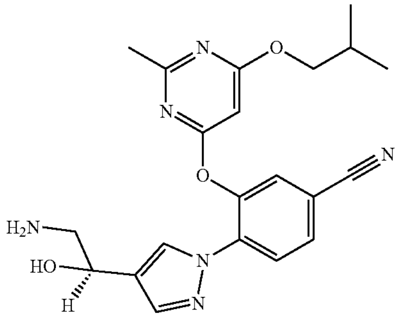 [SMILES: Cc1nc(OCC(C)C)cc(Oc2cc(C#N)ccc2-n2cc([C@@H](O)CN)cn2)n1] | 4-[4-[(1R)-2-amino-1-hydroxyethyl]pyrazol-1-yl]-3-[2-methyl-6-(2-methylpropoxy)pyrimidin-4-yl]oxybenzonitrile |
| 268 | 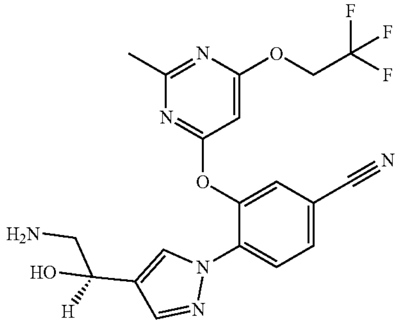 [SMILES: Cc1nc(OCC(F)(F)F)cc(Oc2cc(C#N)ccc2-n2cc([C@@H](O)CN)cn2)n1] | 4-[4-[(1R)-2-amino-1-hydroxyethyl]pyrazol-1-yl]-3-[2-methyl-6-(2,2,2-trifluoroethoxy)pyrimidin-4-yl]oxybenzonitrile |
| 269 | 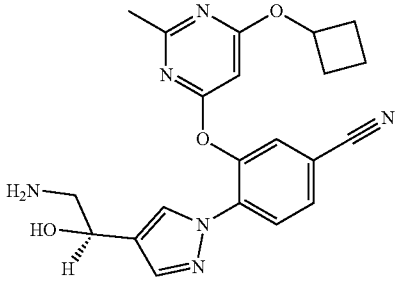 [SMILES: Cc1nc(Oc2cc(C#N)ccc2-n2cc([C@@H](O)CN)cn2)cc(OC2CCC2)n1] | 4-[4-[(1R)-2-amino-1-hydroxyethyl]pyrazol-1-yl]-3-(6-cyclobutyloxy-2-methylpyrimidin-4-yl)oxybenzonitrile |
| 270 | 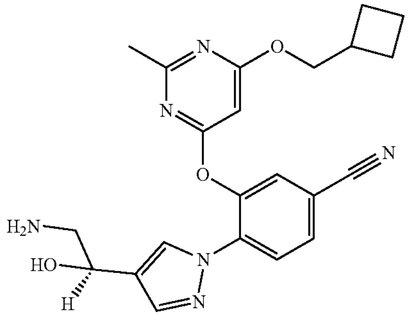 [SMILES: Cc1nc(OCC2CCC2)cc(Oc2cc(C#N)ccc2-n2cc([C@@H](O)CN)cn2)n1] | 4-[4-[(1R)-2-amino-1-hydroxyethyl]pyrazol-1-yl]-3-[6-(cyclobutylmethoxy)-2-methylpyrimidin-4-yl]oxybenzonitrile |
| 271 | 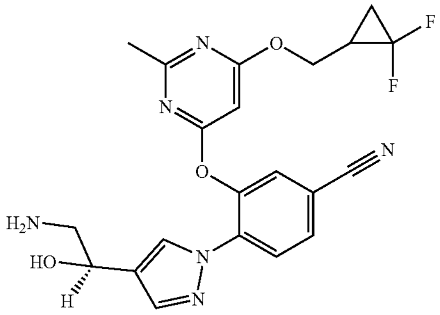 [SMILES: Cc1nc(OCC2CC2(F)F)cc(Oc2cc(C#N)ccc2-n2cc([C@@H](O)CN)cn2)n1] | 4-[4-[(1R)-2-amino-1-hydroxyethyl]pyrazol-1-yl]-3-[6-[(2,2-difluorocyclopropyl)methoxy]-2-methylpyrimidin-4-yl]oxybenzonitrile |

TABLE 1-continued
| Compound number | Structural formula | Compound name |
|---|---|---|
| 272 | 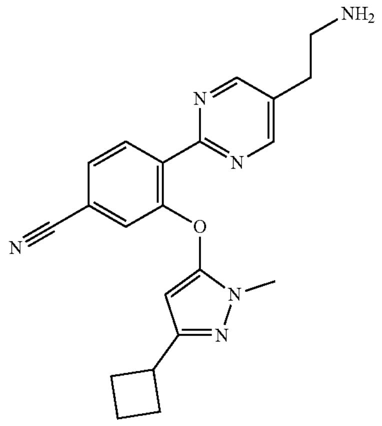 [SMILES: Cn1nc(C2CCC2)cc1Oc1cc(C#N)ccc1-c1ncc(CCN)cn1] | 4-[5-(2-aminoethyl)pyrimidin-2-yl]-3-(5-cyclobutyl-2-methylpyrazol-3-yl)oxybenzonitrile |
| 273 | 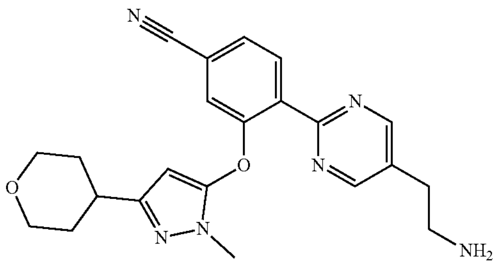 [SMILES: Cn1nc(C2CCOCC2)cc1Oc1cc(C#N)ccc1-c1ncc(CCN)cn1] | 4-[5-(2-aminoethyl)pyrimidin-2-yl]-3-[2-methyl-5-(oxan-4-yl)pyrazol-3-yl]oxybenzonitrile |
| 274 | 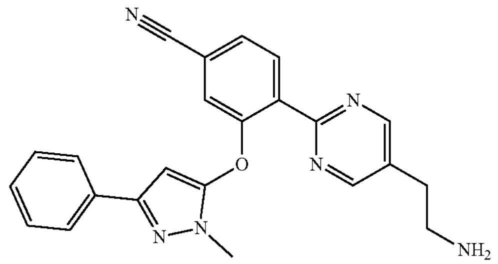 [SMILES: Cn1nc(-c2ccccc2)cc1Oc1cc(C#N)ccc1-c1ncc(CCN)cn1] | 4-[5-(2-aminoethyl)pyrimidin-2-yl]-3-(2-methyl-5-phenylpyrazol-3-yl)oxybenzonitrile |
| 275 | 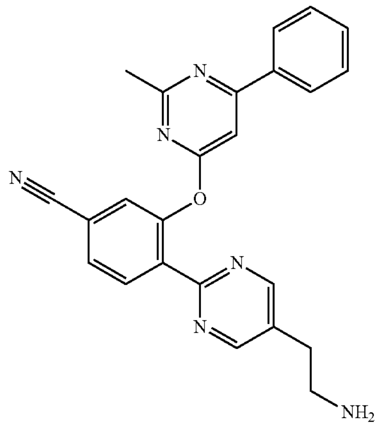 [SMILES: Cc1nc(Oc2cc(C#N)ccc2-c2ncc(CCN)cn2)cc(-c2ccccc2)n1] | 4-[5-(2-aminoethyl)pyrimidin-2-yl]-3-(2-methyl-6-phenylpyrimidin-4-yl)oxybenzonitrile |

TABLE 1-continued
| Compound number | Structural formula | Compound name |
| --- | --- | --- |
| 276 | 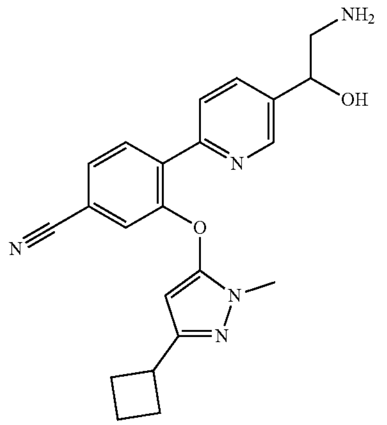 [SMILES: Cn1nc(C2CCC2)cc1Oc1cc(C#N)ccc1-c1ccc(C(O)CN)cn1] | 4-[5-(2-amino-1-hydroxyethyl)pyridin-2-yl]-3-(5-cyclobutyl-2-methylpyrazol-3-yl)oxybenzonitrile |
| 277 | 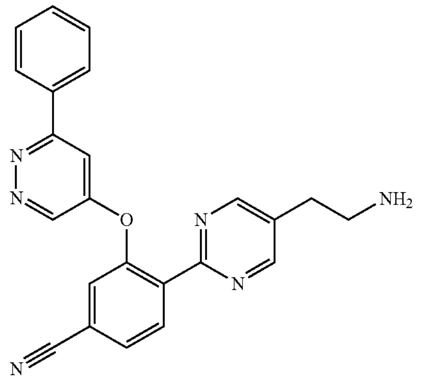 [SMILES: N#Cc1ccc(-c2ncc(CCN)cn2)c(Oc2cnnc(-c3ccccc3)c2)c1] | 4-[5-(2-aminoethyl)pyrimidin-2-yl]-3-(6-phenylpyridazin-4-yl)oxybenzonitrile |
| 278 | 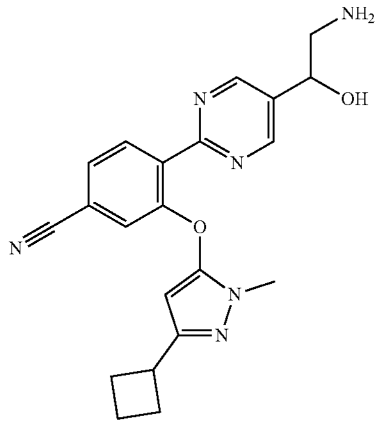 [SMILES: Cn1nc(C2CCC2)cc1Oc1cc(C#N)ccc1-c1ncc(C(O)CN)cn1] | 4-[5-(2-amino-1-hydroxyethyl)pyrimidin-2-yl]-3-(5-cyclobutyl-2-methylpyrazol-3-yl)oxybenzonitrile |

TABLE 1-continued
| Compound number | Structural formula | Compound name |
|---|---|---|
| 279 | 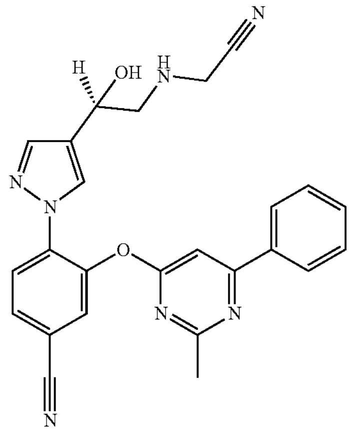 [SMILES: Cc1nc(Oc2cc(C#N)ccc2-n2cc([C@@H](O)CNCC#N)cn2)cc(-c2ccccc2)n1] | 4-[4-[(1R)-2-(cyanomethylamino)-1-hydroxyethyl]pyrazol-1-yl]-3-(2-methyl-6-phenylpyrimidin-4-yl)oxybenzonitrile |
| 280 | 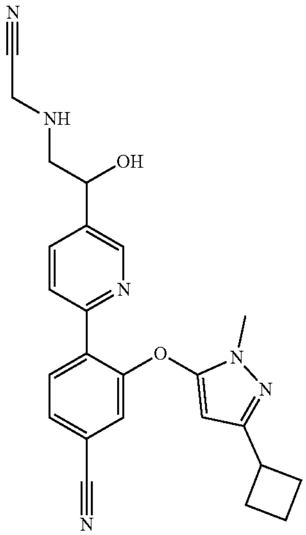 [SMILES: Cn1nc(C2CCC2)cc1Oc1cc(C#N)ccc1-c1ccc(C(O)CNCC#N)cn1] | 4-[5-[2-(cyanomethylamino)-1-hydroxyethyl]pyridin-2-yl]-3-(5-cyclobutyl-2-methylpyrazol-3-yl)oxybenzonitrile |
| 281 | 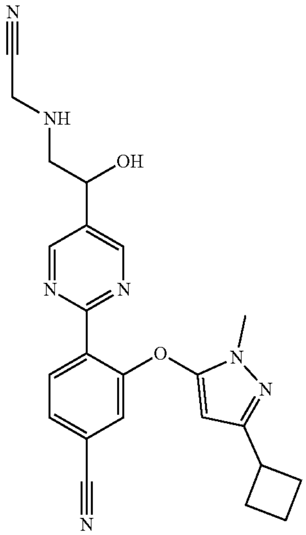 [SMILES: Cn1nc(C2CCC2)cc1Oc1cc(C#N)ccc1-c1ncc(C(O)CNCC#N)cn1] | 4-[5-[2-(cyanomethylamino)-1-hydroxyethyl]pyrimidin-2-yl]-3-(5-cyclobutyl-2-methylpyrazol-3-yl)oxybenzonitrile |

TABLE 1-continued
| Compound number | Structural formula | Compound name |
| --- | --- | --- |
| 282 | 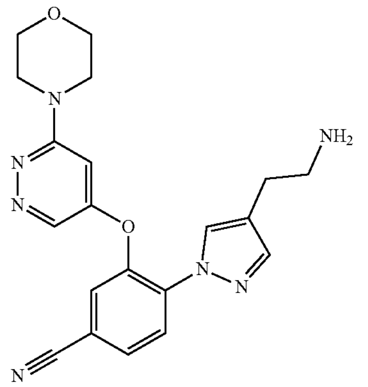 [SMILES: N#Cc1ccc(-n2cc(CCN)cn2)c(Oc2cnnc(N3CCOCC3)c2)c1] | 4-[4-(2-aminoethyl)pyrazol-1-yl]-3-(6-morpholin-4-ylpyridazin-4-yl)oxybenzonitrile |
| 283 | 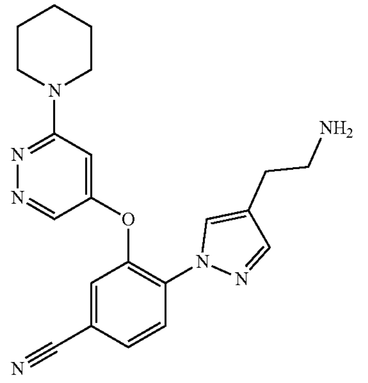 [SMILES: N#Cc1ccc(-n2cc(CCN)cn2)c(Oc2cnnc(N3CCCCC3)c2)c1] | 4-[4-(2-aminoethyl)pyrazol-1-yl]-3-(6-piperidin-1-ylpyridazin-4-yl)oxybenzonitrile |
| 284 | 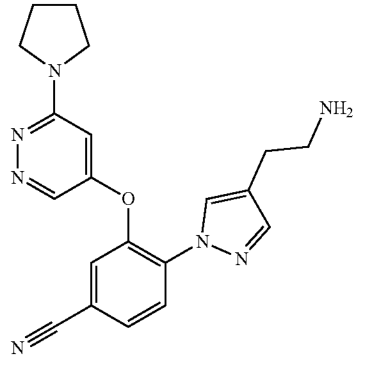 [SMILES: N#Cc1ccc(-n2cc(CCN)cn2)c(Oc2cnnc(N3CCCC3)c2)c1] | 4-[4-(2-aminoethyl)pyrazol-1-yl]-3-(6-pyrrolidin-1-ylpyridazin-4-yl)oxybenzonitrile |
| 285 | 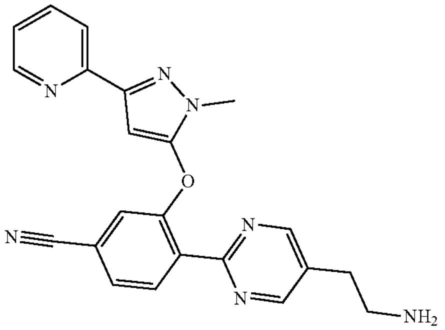 [SMILES: Cn1nc(-c2ccccn2)cc1Oc1cc(C#N)ccc1-c1ncc(CCN)cn1] | 4-[5-(2-aminoethyl)pyrimidin-2-yl]-3-(2-methyl-5-pyridin-2-ylpyrazol-3-yl)oxybenzonitrile |

TABLE 1-continued
| Compound number | Structural formula | Compound name |
|---|---|---|
| 286 | 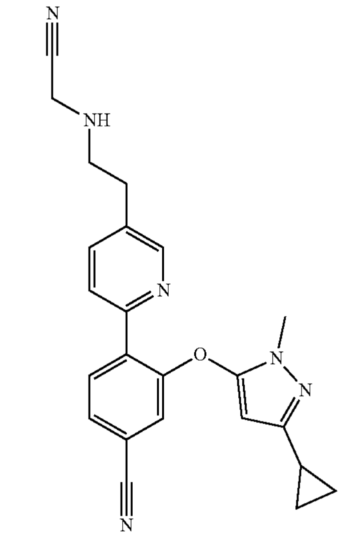 [SMILES: Cn1nc(C2CC2)cc1Oc1cc(C#N)ccc1-c1ccc(CCNCC#N)cn1] | 4-[5-[2-(cyanomethylamino)ethyl]pyridin-2-yl]-3-(5-cyclopropyl-2-methylpyrazol-3-yl)oxybenzonitrile |
| 287 | 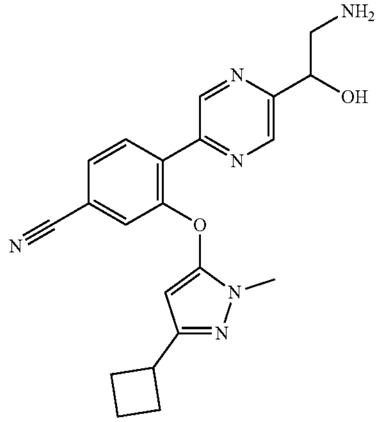 [SMILES: Cn1nc(C2CCC2)cc1Oc1cc(C#N)ccc1-c1cnc(C(O)CN)cn1] | 4-[5-(2-amino-1-hydroxyethyl)pyrazin-2-yl]-3-(5-cyclobutyl-2-methylpyrazol-3-yl)oxybenzonitrile |
| 288 | 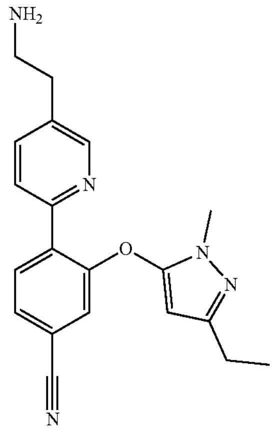 [SMILES: CCc1cc(Oc2cc(C#N)ccc2-c2ccc(CCN)cn2)n(C)n1] | 4-[5-(2-aminoethyl)pyridin-2-yl]-3-(5-ethyl-2-methylpyrazol-3-yl)oxybenzonitrile |

TABLE 1-continued

| Compound number | Structural formula | Compound name |
|---|---|---|
| 289 | 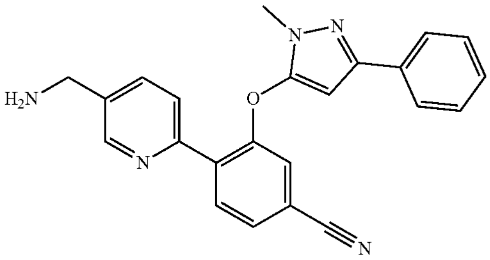 [SMILES: Cn1nc(-c2ccccc2)cc1Oc1cc(C#N)ccc1-c1ccc(CN)cn1] | 4-[5-(aminomethyl)pyridin-2-yl]-3-(2-methyl-5-phenylpyrazol-3-yl)oxybenzonitrile |
| 290 | 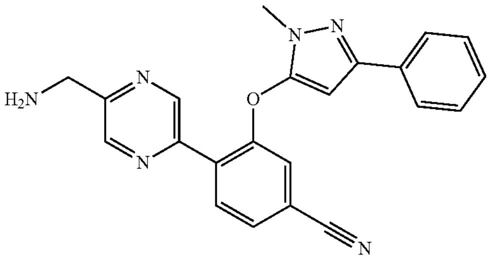 [SMILES: Cn1nc(-c2ccccc2)cc1Oc1cc(C#N)ccc1-c1cnc(CN)cn1] | 4-[5-(aminomethyl)pyrazin-2-yl]-3-(2-methyl-5-phenylpyrazol-3-yl)oxybenzonitrile |
| 291 | 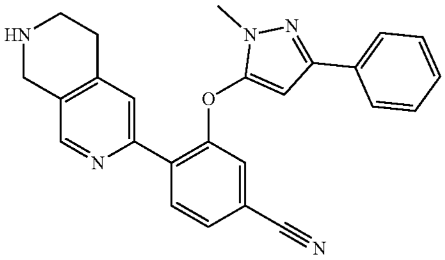 [SMILES: Cn1nc(-c2ccccc2)cc1Oc1cc(C#N)ccc1-c1cc2c(cn1)CNCC2] | 3-(2-methyl-5-phenylpyrazol-3-yl)oxy-4-(5,6,7,8-tetrahydro-2,7-naphthylidin-3-yl)benzonitrile |
| 292 | 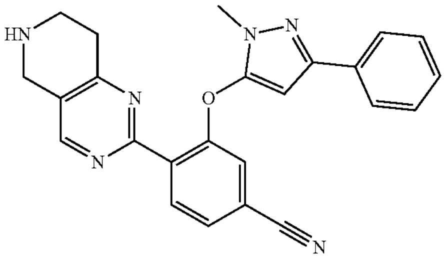 [SMILES: Cn1nc(-c2ccccc2)cc1Oc1cc(C#N)ccc1-c1ncc2c(n1)CCNC2] | 3-(2-methyl-5-phenylpyrazol-3-yl)oxy-4-(5,6,7,8-tetrahydropyrido[4,3-d]pyrimidin-2-yl)benzonitrile |
| 293 | 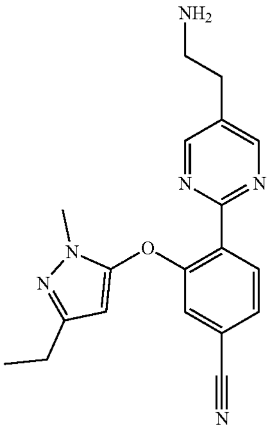 [SMILES: CCc1cc(Oc2cc(C#N)ccc2-c2ncc(CCN)cn2)n(C)n1] | 4-[5-(2-aminoethyl)pyrimidin-2-yl]-3-(5-ethyl-2-methylpyrazol-3-yl)oxybenzonitrile |

TABLE 1-continued
| Compound number | Structural formula | Compound name |
| --- | --- | --- |
| 294 | 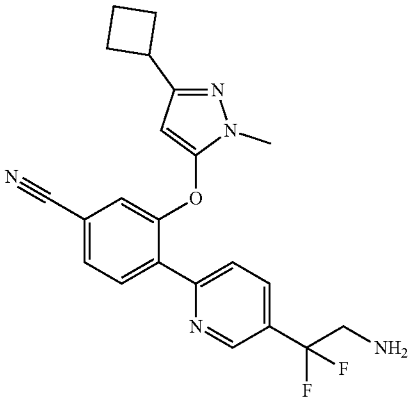 [SMILES: Cn1nc(C2CCC2)cc1Oc1cc(C#N)ccc1-c1ccc(C(F)(F)CN)cn1] | 4-[5-(2-amino-1,1-difluoroethyl)pyridin-2-yl]-3-(5-cyclobutyl-2-methylpyrazol-3-yl)oxybenzonitrile |
| 295 | 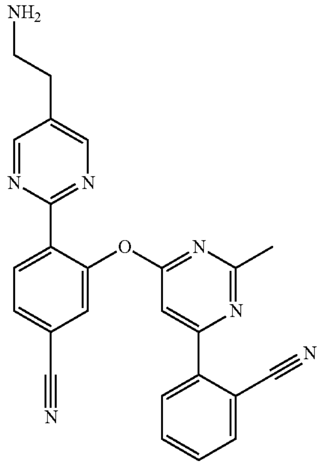 [SMILES: Cc1nc(Oc2cc(C#N)ccc2-c2ncc(CCN)cn2)cc(-c2ccccc2C#N)n1] | 4-[5-(2-aminoethyl)pyrimidin-2-yl]-3-[6-(2-cyanophenyl)-2-methylpyrimidin-4-yl]oxybenzonitrile |
| 296 | 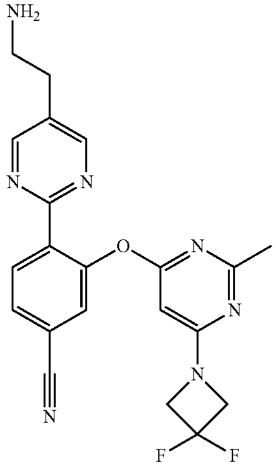 [SMILES: Cc1nc(Oc2cc(C#N)ccc2-c2ncc(CCN)cn2)cc(N2CC(F)(F)C2)n1] | 4-[5-(2-aminoethyl)pyrimidin-2-yl]-3-[6-(3,3-difluoroazetidin-1-yl)-2-methylpyrimidin-4-yl]oxybenzonitrile |

TABLE 1-continued
| Compound number | Structural formula | Compound name |
|---|---|---|
| 297 | 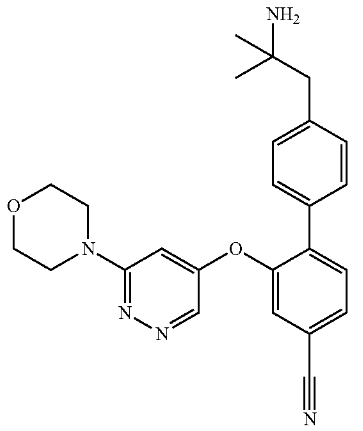 [SMILES: CC(C)(N)Cc1ccc(-c2ccc(C#N)cc2Oc2cnnc(N3CCOCC3)c2)cc1] | 4-[4-(2-amino-2-methylpropyl)phenyl]-3-(6-morpholin-4-ylpyridazin-4-yl)oxybenzonitrile |
| 298 | 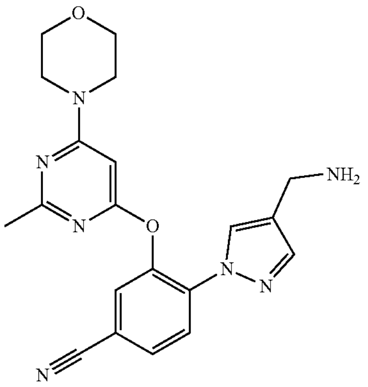 [SMILES: Cc1nc(Oc2cc(C#N)ccc2-n2cc(CN)cn2)cc(N2CCOCC2)n1] | 4-[4-(aminomethyl)pyrazol-1-yl]-3-(2-methyl-6-morpholin-4-ylpyrimidin-4-yl)oxybenzonitrile |
| 299 | 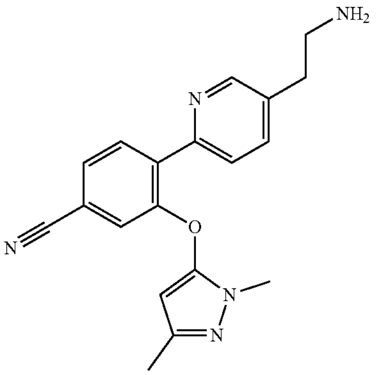 [SMILES: Cc1cc(Oc2cc(C#N)ccc2-c2ccc(CCN)cn2)n(C)n1] | 4-[5-(2-aminoethyl)pyridin-2-yl]-3-(2,5-dimethylpyrazol-3-yl)oxybenzonitrile |
| 300 | 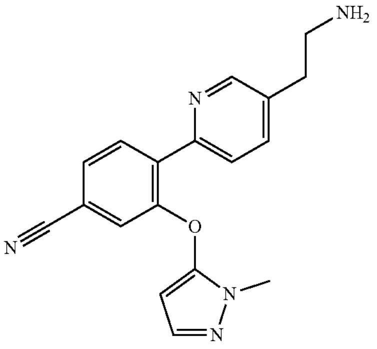 [SMILES: Cn1nccc1Oc1cc(C#N)ccc1-c1ccc(CCN)cn1] | 4-[5-(2-aminoethyl)pyridin-2-yl]-3-(2-methylpyrazol-3-yl)oxybenzonitrile |

TABLE 1-continued

| Compound number | Structural formula | Compound name |
|---|---|---|
| 301 | 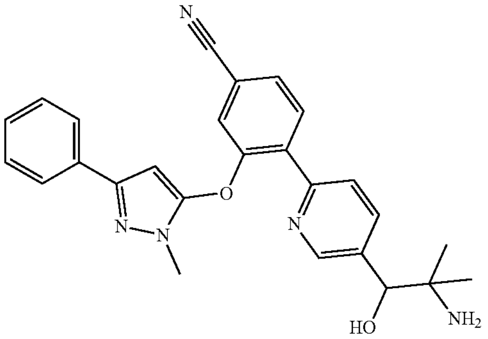 [SMILES: Cn1nc(-c2ccccc2)cc1Oc1cc(C#N)ccc1-c1ccc(C(O)C(C)(C)N)cn1] | 4-[5-(2-amino-1-hydroxy-2-methylpropyl)pyridin-2-yl]-3-(2-methyl-5-phenylpyrazol-3-yl)oxybenzonitrile |
| 302 | 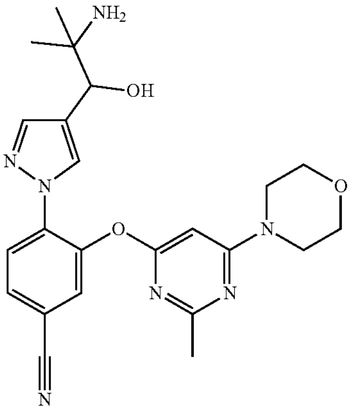 [SMILES: Cc1nc(Oc2cc(C#N)ccc2-n2cc(C(O)C(C)(C)N)cn2)cc(N2CCOCC2)n1] | 4-[4-(2-amino-1-hydroxy-2-methylpropyl)pyrazol-1-yl]-3-(2-methyl-6-morpholin-4-ylpyrimidin-4-yl)oxybenzonitrile |
| 303 | 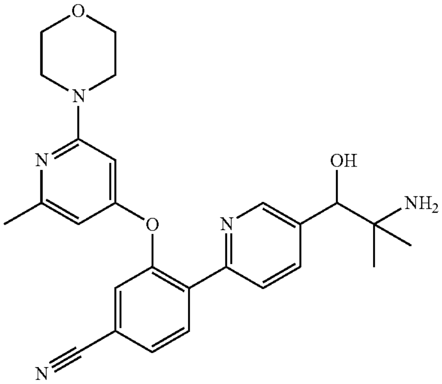 [SMILES: Cc1cc(Oc2cc(C#N)ccc2-c2ccc(C(O)C(C)(C)N)cn2)cc(N2CCOCC2)n1] | 4-[5-(2-amino-1-hydroxy-2-methylpropyl)pyridin-2-yl]-3-(2-methyl-6-morpholin-4-ylpyridin-4-yl)oxybenzonitrile |
| 304 | 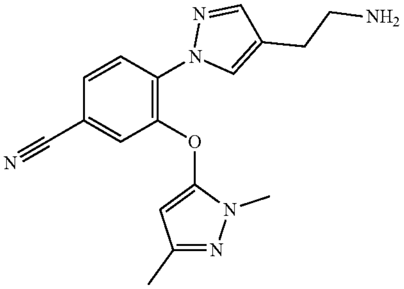 [SMILES: Cc1cc(Oc2cc(C#N)ccc2-n2cc(CCN)cn2)n(C)n1] | 4-[4-(2-aminoethyl)pyrazol-1-yl]-3-(2,5-dimethylpyrazol-3-yl)oxybenzonitrile |

TABLE 1-continued
| Compound number | Structural formula | Compound name |
|---|---|---|
| 305 | 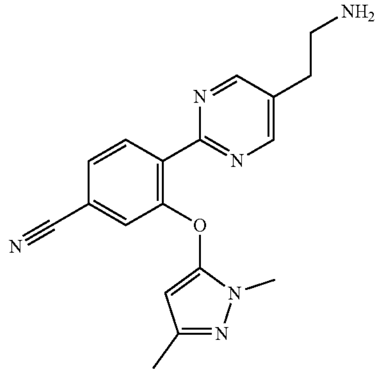 [SMILES: Cc1cc(Oc2cc(C#N)ccc2-c2ncc(CCN)cn2)n(C)n1] | 4-[5-(2-aminoethyl)pyrimidin-2-yl]-3-(2,5-dimethylpyrazol-3-yl)oxybenzonitrile |
| 306 | 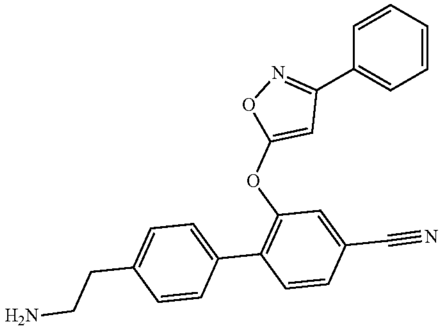 [SMILES: N#Cc1ccc(-c2ccc(CCN)cc2)c(Oc2cc(-c3ccccc3)no2)c1] | 4-[4-(2-aminoethyl)phenyl]-3-[(3-phenyl-1,2-oxazol-5-yl)oxy]benzonitrile |
| 307 | 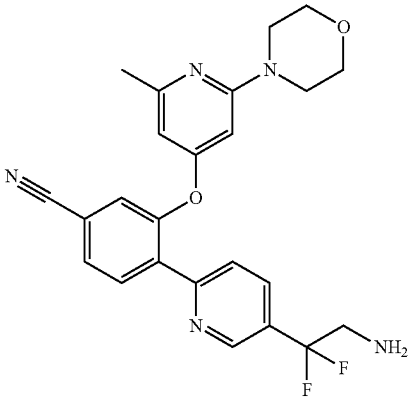 [SMILES: Cc1cc(Oc2cc(C#N)ccc2-c2ccc(C(F)(F)CN)cn2)cc(N2CCOCC2)n1] | 4-[5-(2-amino-1,1-difluoroethyl)pyridin-2-yl]-3-(2-methyl-6-morpholin-4-ylpyridin-4-yl)oxybenzonitrile |
| 308 | 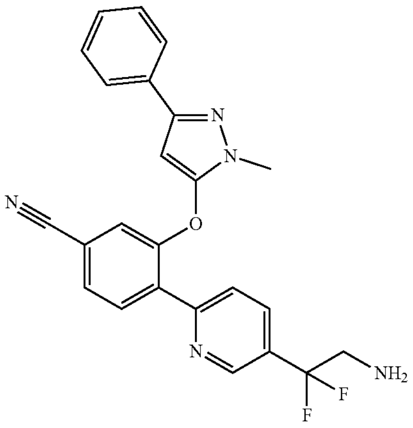 [SMILES: Cn1nc(-c2ccccc2)cc1Oc1cc(C#N)ccc1-c1ccc(C(F)(F)CN)cn1] | 4-[5-(2-amino-1,1-difluoroethyl)pyridin-2-yl]-3-(2-methyl-5-phenylpyrazol-3-yl)oxybenzonitrile |

TABLE 1-continued

| Compound number | Structural formula | Compound name |
|---|---|---|
| 309 | 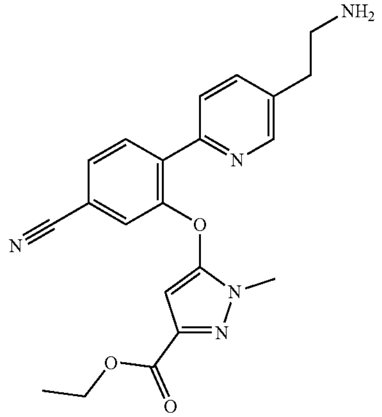 [SMILES: CCOC(=O)c1cc(Oc2cc(C#N)ccc2-c2ccc(CCN)cn2)n(C)n1] | ethyl 5-[2-[5-(2-aminoethyl)pyridin-2-yl]-5-cyanophenoxy]-1-methylpyrazole-3-carboxylate |
| 310 | 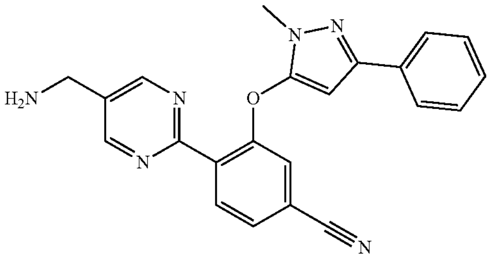 [SMILES: Cn1nc(-c2ccccc2)cc1Oc1cc(C#N)ccc1-c1ncc(CN)cn1] | 4-[5-(aminomethyl)pyrimidin-2-yl]-3-(2-methyl-5-phenylpyrazol-3-yl)oxybenzonitrile |
| 311 | 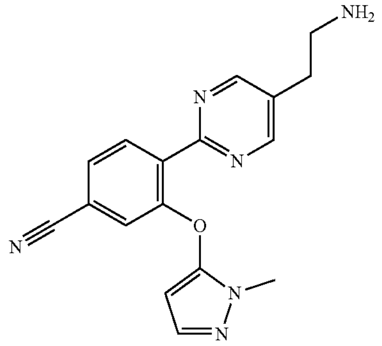 [SMILES: Cn1nccc1Oc1cc(C#N)ccc1-c1ncc(CCN)cn1] | 4-[5-(2-aminoethyl)pyrimidin-2-yl]-3-(2-methylpyrazol-3-yl)oxybenzonitrile |
| 312 | 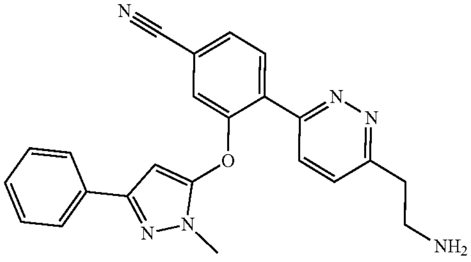 [SMILES: Cn1nc(-c2ccccc2)cc1Oc1cc(C#N)ccc1-c1ccc(CCN)nn1] | 4-[6-(2-aminoethyl)pyridazin-3-yl]-3-(2-methyl-5-phenylpyrazol-3-yl)oxybenzonitrile |
| 313 | 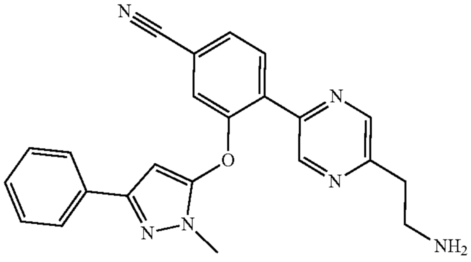 [SMILES: Cn1nc(-c2ccccc2)cc1Oc1cc(C#N)ccc1-c1cnc(CCN)cn1] | 4-[5-(2-aminoethyl)pyrazin-2-yl]-3-(2-methyl-5-phenylpyrazol-3-yl)oxybenzonitrile |

TABLE 1-continued
| Compound number | Structural formula | Compound name |
|---|---|---|
| 314 | 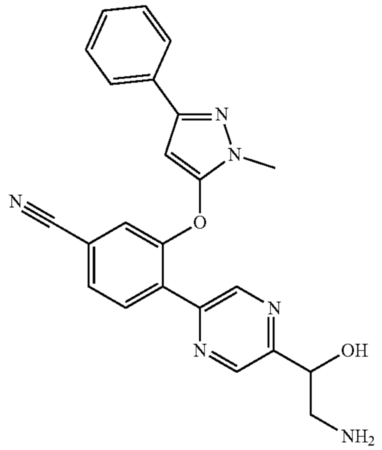 [SMILES: Cn1nc(-c2ccccc2)cc1Oc1cc(C#N)ccc1-c1cnc(C(O)CN)cn1] | 4-[5-(2-amino-1-hydroxyethyl)pyrazin-2-yl]-3-(2-methyl-5-phenylpyrazol-3-yl)oxybenzonitrile |
| 315 | 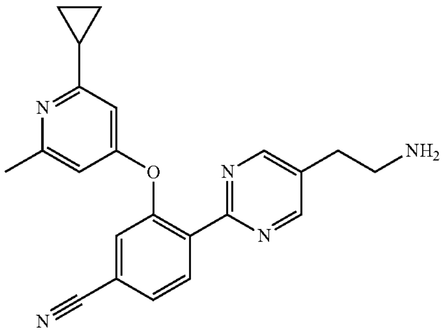 [SMILES: Cc1cc(Oc2cc(C#N)ccc2-c2ncc(CCN)cn2)cc(C2CC2)n1] | 4-[5-(2-aminoethyl)pyrimidin-2-yl]-3-(2-cyclopropyl-6-methylpyridin-4-yl)oxybenzonitrile |
| 316 | 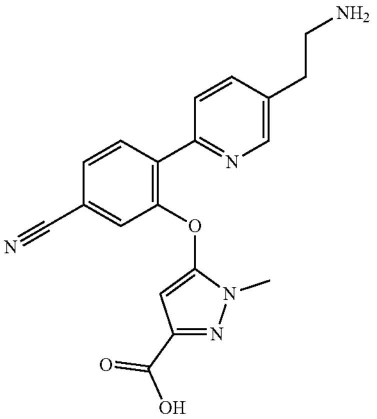 [SMILES: Cn1nc(C(=O)O)cc1Oc1cc(C#N)ccc1-c1ccc(CCN)cn1] | 5-[2-[5-(2-aminoethyl)pyridin-2-yl]-5-cyanophenoxy]-1-methylpyrazole-3-carboxylic acid |

TABLE 1-continued

| Compound number | Structural formula | Compound name |
|---|---|---|
| 317 | 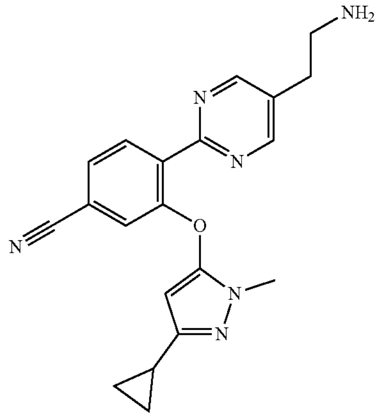 [SMILES: Cn1nc(C2CC2)cc1Oc1cc(C#N)ccc1-c1ncc(CCN)cn1] | 4-[5-(2-aminoethyl)pyrimidin-2-yl]-3-(5-cyclopropyl-2-methylpyrazol-3-yl)oxybenzonitrile |
| 318 | 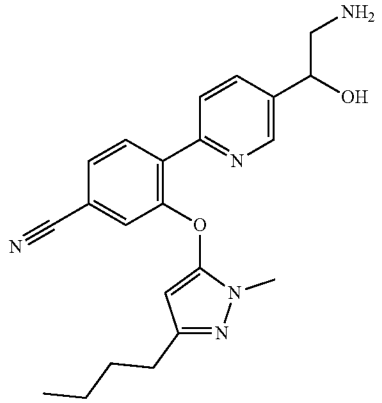 [SMILES: CCCCc1cc(Oc2cc(C#N)ccc2-c2ccc(C(O)CN)cn2)n(C)n1] | 4-[5-(2-amino-1-hydroxyethyl)pyridin-2-yl]-3-(5-butyl-2-methylpyrazol-3-yl)oxybenzonitrile |
| 319 | 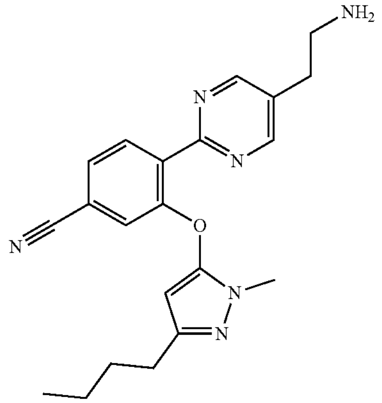 [SMILES: CCCCc1cc(Oc2cc(C#N)ccc2-c2ncc(CCN)cn2)n(C)n1] | 4-[5-(2-aminoethyl)pyrimidin-2-yl]-3-(5-butyl-2-methylpyrazol-3-yl)oxybenzonitrile |
| 320 | 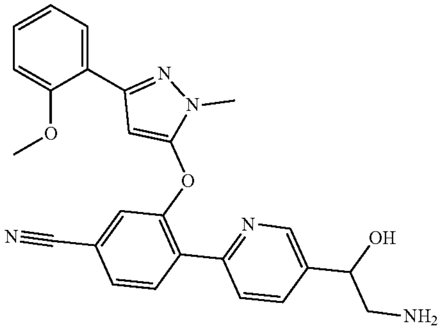 [SMILES: COc1ccccc1-c1cc(Oc2cc(C#N)ccc2-c2ccc(C(O)CN)cn2)n(C)n1] | 4-[5-(2-amino-1-hydroxyethyl)pyridin-2-yl]-3-[5-(2-methoxyphenyl)-2-methylpyrazol-3-yl]oxybenzonitrile |

TABLE 1-continued

| Compound number | Structural formula | Compound name |
| --- | --- | --- |
| 321 | 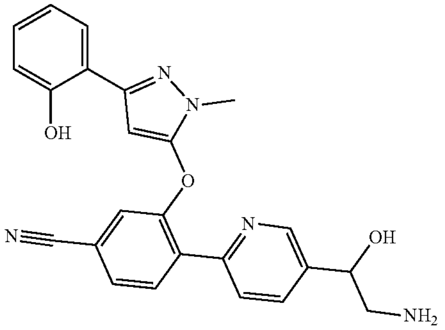 [SMILES: Cn1nc(-c2ccccc2O)cc1Oc1cc(C#N)ccc1-c1ccc(C(O)CN)cn1] | 4-[5-(2-amino-1-hydroxyethyl)pyridin-2-yl]-3-[5-(2-hydroxyphenyl)-2-methylpyrazol-3-yl]oxybenzonitrile |
| 322 | 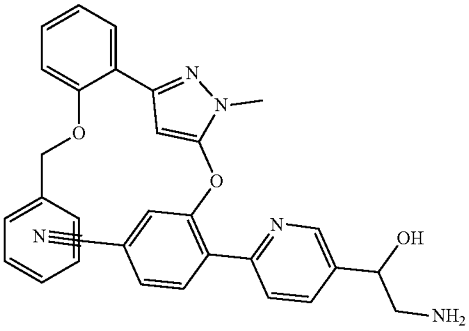 | 4-[5-(2-amino-1-hydroxyethyl)pyridin-2-yl]-3-[2-methyl-5-(2-phenylmethoxyphenyl)pyrazol-3-yl]oxybenzonitrile |
| 323 | 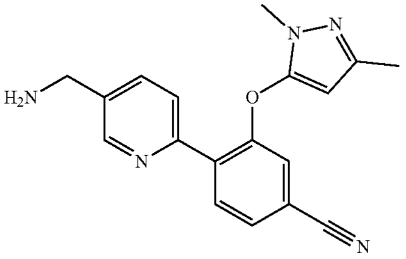 [SMILES: Cc1cc(Oc2cc(C#N)ccc2-c2ccc(CN)cn2)n(C)n1] | 4-[5-(aminomethyl)pyridin-2-yl]-3-(2,5-dimethylpyrazol-3-yl)oxybenzonitrile |
| 324 | 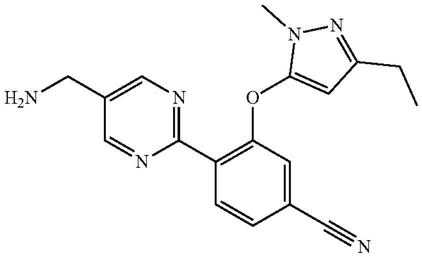 [SMILES: CCc1cc(Oc2cc(C#N)ccc2-c2ncc(CN)cn2)n(C)n1] | 4-[5-(aminomethyl)pyrimidin-2-yl]-3-(5-ethyl-2-methylpyrazol-3-yl)oxybenzonitrile |
| 325 | 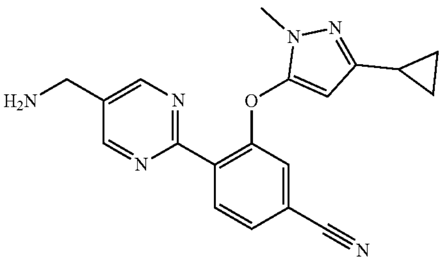 [SMILES: Cn1nc(C2CC2)cc1Oc1cc(C#N)ccc1-c1ncc(CN)cn1] | 4-[5-(aminomethyl)pyrimidin-2-yl]-3-(5-cyclopropyl-2-methylpyrazol-3-yl)oxybenzonitrile |

TABLE 1-continued

| Compound number | Structural formula | Compound name |
|---|---|---|
| 326 | 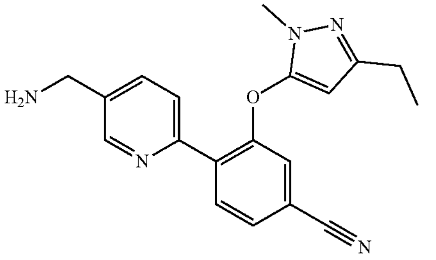 [SMILES: CCc1cc(Oc2cc(C#N)ccc2-c2ccc(CN)cn2)n(C)n1] | 4-[5-(aminomethyl)pyridin-2-yl]-3-(5-ethyl-2-methylpyrazol-3-yl)oxybenzonitrile |
| 327 | 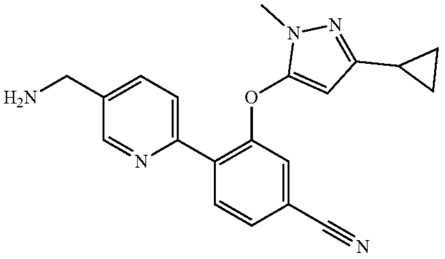 [SMILES: Cn1nc(C2CC2)cc1Oc1cc(C#N)ccc1-c1ccc(CN)cn1] | 4-[5-(aminomethyl)pyridin-2-yl]-3-(5-cyclopropyl-2-methylpyrazol-3-yl)oxybenzonitrile |
| 328 | 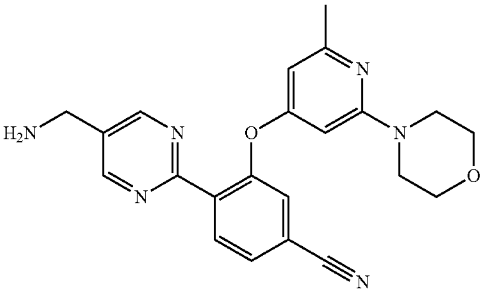 [SMILES: Cc1cc(Oc2cc(C#N)ccc2-c2ncc(CN)cn2)cc(N2CCOCC2)n1] | 4-[5-(aminomethyl)pyrimidin-2-yl]-3-(2-methyl-6-morpholin-4-ylpyridin-4-yl)oxybenzonitrile |
| 329 | 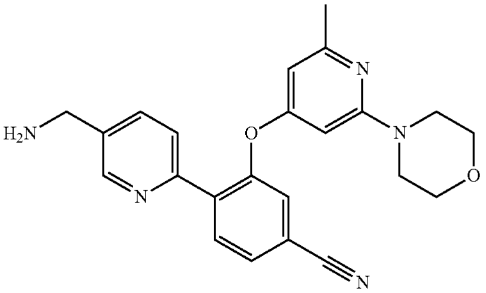 [SMILES: Cc1cc(Oc2cc(C#N)ccc2-c2ccc(CN)cn2)cc(N2CCOCC2)n1] | 4-[5-(aminomethyl)pyridin-2-yl]-3-(2-methyl-6-morpholin-4-ylpyridin-4-yl)oxybenzonitrile |
| 330 | 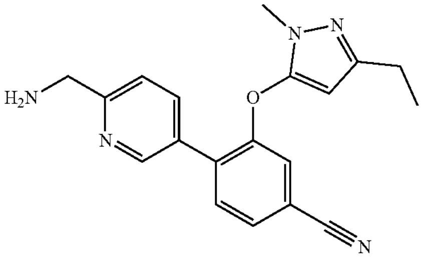 [SMILES: CCc1cc(Oc2cc(C#N)ccc2-c2ccc(CN)nc2)n(C)n1] | 4-[6-(aminomethyl)pyridin-3-yl]-3-(5-ethyl-2-methylpyrazol-3-yl)oxybenzonitrile |

TABLE 1-continued

| Compound number | Structural formula | Compound name |
|---|---|---|
| 331 | 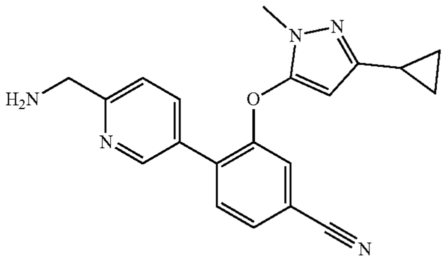 [SMILES: Cn1nc(C2CC2)cc1Oc1cc(C#N)ccc1-c1ccc(CN)nc1] | 4-[6-(aminomethyl)pyridin-3-yl]-3-(5-cyclopropyl-2-methylpyrazol-3-yl)oxybenzonitrile |
| 332 | 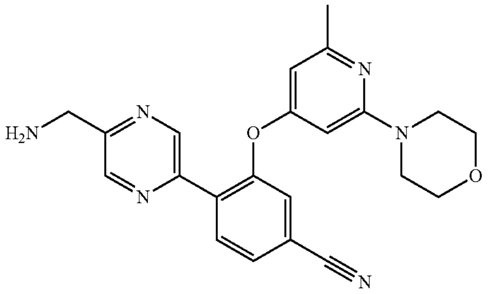 [SMILES: Cc1cc(Oc2cc(C#N)ccc2-c2cnc(CN)cn2)cc(N2CCOCC2)n1] | 4-[5-(aminomethyl)pyrazin-2-yl]-3-(2-methyl-6-morpholin-4-ylpyridin-4-yl)oxybenzonitrile |
| 333 | 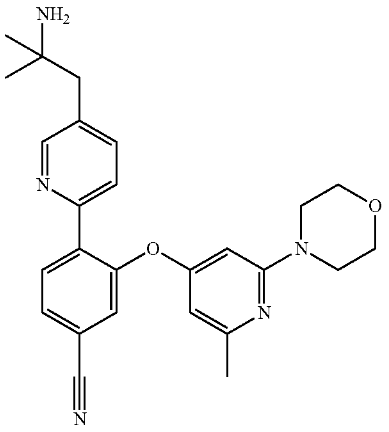 [SMILES: Cc1cc(Oc2cc(C#N)ccc2-c2ccc(CC(C)(C)N)cn2)cc(N2CCOCC2)n1] | 4-[5-(2-amino-2-methylpropyl)pyridin-2-yl]-3-(2-methyl-6-morpholin-4-ylpyridin-4-yl)oxybenzonitrile |
| 334 | 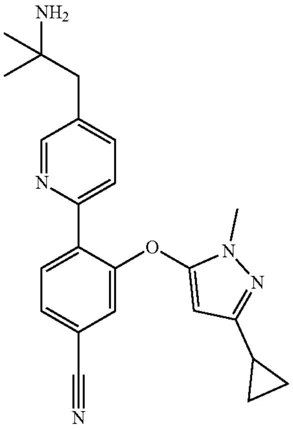 [SMILES: Cn1nc(C2CC2)cc1Oc1cc(C#N)ccc1-c1ccc(CC(C)(C)N)cn1] | 4-[5-(2-amino-2-methylpropyl)pyridin-2-yl]-3-(5-cyclopropyl-2-methylpyrazol-3-yl)oxybenzonitrile |

TABLE 1-continued
| Compound number | Structural formula | Compound name |
|---|---|---|
| 335 | 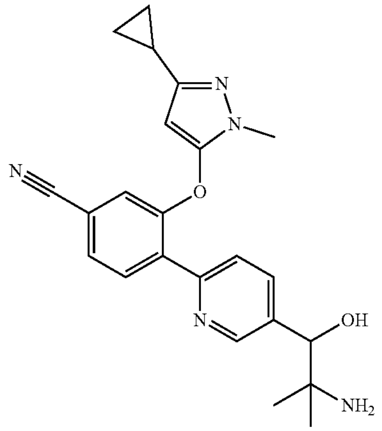 [SMILES: Cn1nc(C2CC2)cc1Oc1cc(C#N)ccc1-c1ccc(C(O)C(C)(C)N)cn1] | 4-[5-(2-amino-1-hydroxy-2-methylpropyl)pyridin-2-yl]-3-(5-cyclopropyl-2-methylpyrazol-3-yl)oxybenzonitrile |
| 336 | 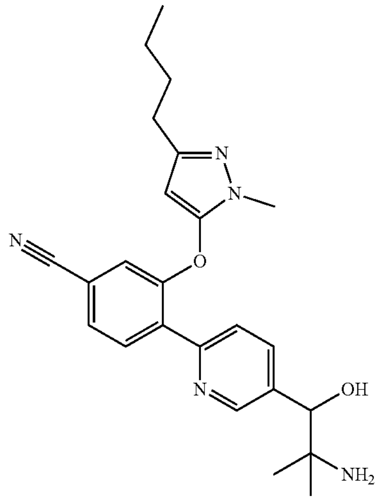 [SMILES: CCCCc1cc(Oc2cc(C#N)ccc2-c2ccc(C(O)C(C)(C)N)cn2)n(C)n1] | 4-[5-(2-amino-1-hydroxy-2-methylpropyl)pyridin-2-yl]-3-(5-butyl-2-methylpyrazol-3-yl)oxybenzonitrile |
| 337 | 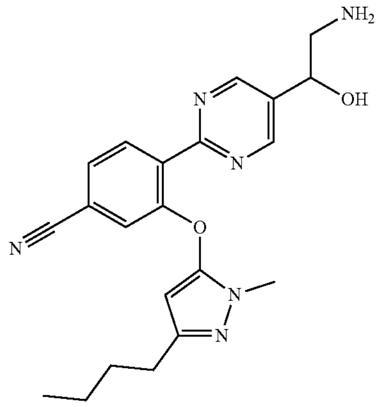 | 4-[5-(2-amino-1-hydroxyethyl)pyrimidin-2-yl]-3-(5-butyl-2-methylpyrazol-3-yl)oxybenzonitrile |

TABLE 1-continued

| Compound number | Structural formula | Compound name |
|---|---|---|
| 338 | 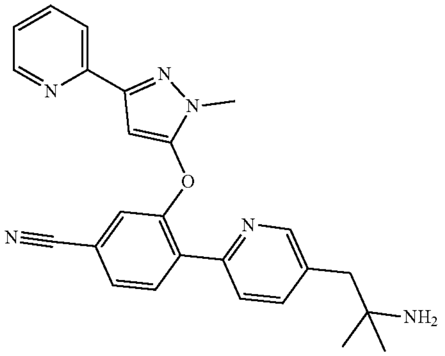 [SMILES: Cn1nc(-c2ccccn2)cc1Oc1cc(C#N)ccc1-c1ccc(CC(C)(C)N)cn1] | 4-[5-(2-amino-2-methylpropyl)pyridin-2-yl]-3-(2-methyl-5-pyridin-2-ylpyrazol-3-yl)oxybenzonitrile |
| 339 | 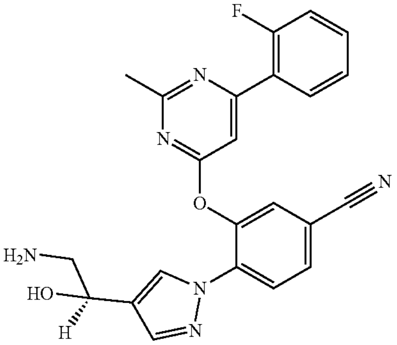 | 4-[4-[(1R)-2-amino-1-hydroxyethyl]pyrazol-1-yl]-3-[6-(2-fluorophenyl)-2-methylpyrimidin-4-yl]oxybenzonitrile |
| 340 | 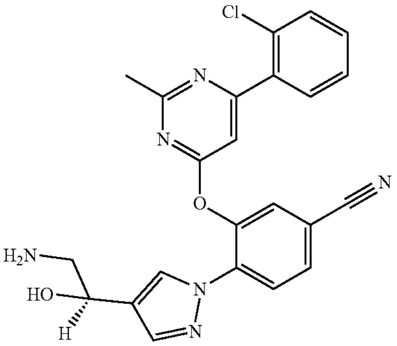 [SMILES: Cc1nc(Oc2cc(C#N)ccc2-n2cc([C@@H](O)CN)cn2)cc(-c2ccccc2Cl)n1] | 4-[4-[(1R)-2-amino-1-hydroxyethyl]pyrazol-1-yl]-3-[6-(2-chlorophenyl)-2-methylpyrimidin-4-yl]oxybenzonitrile |
| 341 | 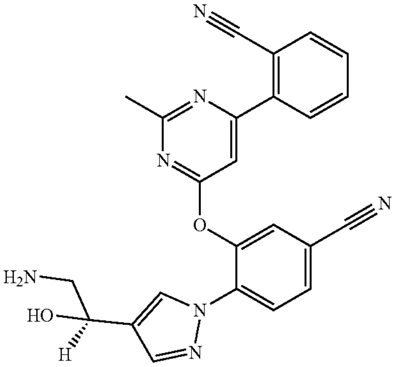 [SMILES: Cc1nc(Oc2cc(C#N)ccc2-n2cc([C@@H](O)CN)cn2)cc(-c2ccccc2C#N)n1] | 4-[4-[(1R)-2-amino-1-hydroxyethyl]pyrazol-1-yl]-3-[6-(2-cyanophenyl)-2-methylpyrimidin-4-yl]oxybenzonitrile |

TABLE 1-continued

| Compound number | Structural formula | Compound name |
|---|---|---|
| 342 | 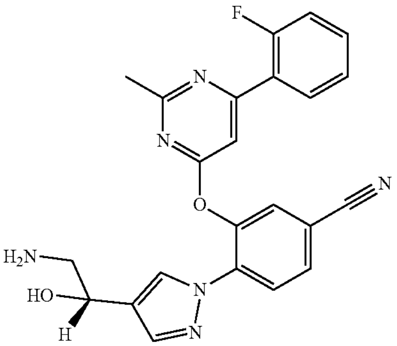 [SMILES: Cc1nc(Oc2cc(C#N)ccc2-n2cc([C@H](O)CN)cn2)cc(-c2ccccc2F)n1] | 4-[4-[(1S)-2-amino-1-hydroxyethyl]pyrazol-1-yl]-3-[6-(2-fluorophenyl)-2-methylpyrimidin-4-yl]oxybenzonitrile |
| 343 | 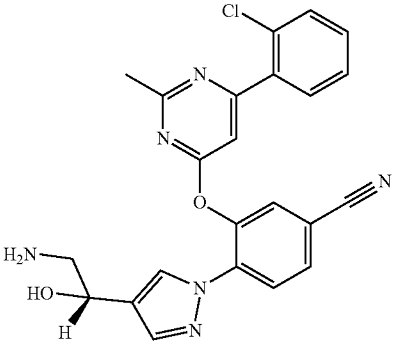 [SMILES: Cc1nc(Oc2cc(C#N)ccc2-n2cc([C@H](O)CN)cn2)cc(-c2ccccc2Cl)n1] | 4-[4-[(1S)-2-amino-1-hydroxyethyl]pyrazol-1-yl]-3-[6-(2-chlorophenyl)-2-methylpyrimidin-4-yl]oxybenzonitrile |
| 344 | 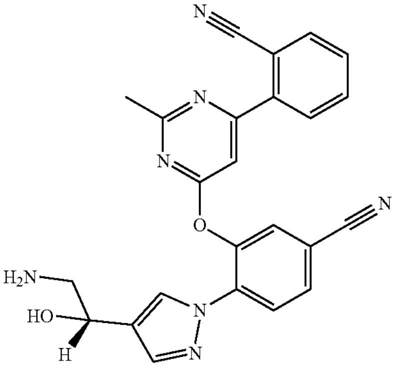 [SMILES: Cc1nc(Oc2cc(C#N)ccc2-n2cc([C@H](O)CN)cn2)cc(-c2ccccc2C#N)n1] | 4-[4-[(1S)-2-amino-1-hydroxyethyl]pyrazol-1-yl]-3-[6-(2-cyanophenyl)-2-methylpyrimidin-4-yl]oxybenzonitrile |
| 345 | 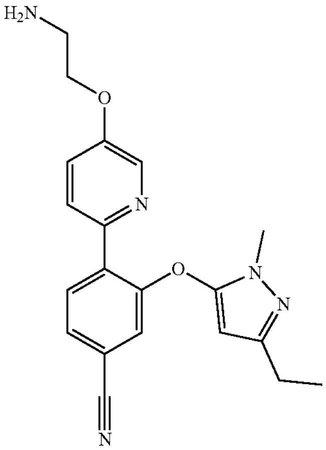 [SMILES: CCc1cc(Oc2cc(C#N)ccc2-c2ccc(OCCN)cn2)n(C)n1] | 4-[5-(2-aminoethoxy)pyridin-2-yl]-3-(5-ethyl-2-methylpyrazol-3-yl)oxybenzonitrile |

TABLE 1-continued
| Compound number | Structural formula | Compound name |
| --- | --- | --- |
| 346 | 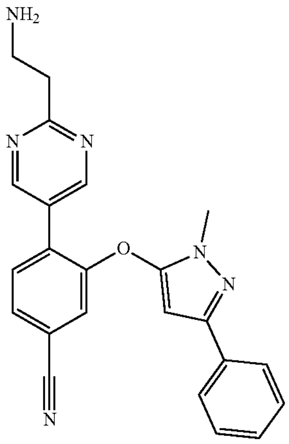 [SMILES: Cn1nc(-c2ccccc2)cc1Oc1cc(C#N)ccc1-c1cnc(CCN)nc1] | 4-[2-(2-aminoethyl)pyrimidin-5-yl]-3 (2-methyl-5-phenylpyrazol-3-yl)oxybenzonitrile |
| 347 | 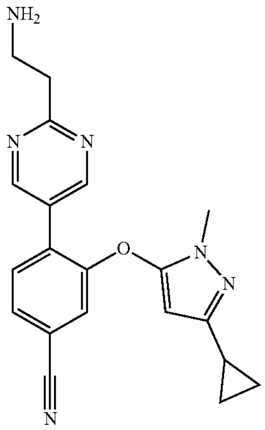 [SMILES: Cn1nc(C2CC2)cc1Oc1cc(C#N)ccc1-c1cnc(CCN)nc1] | 4-[2-(2-aminoethyl)pyrimidin-5-yl]-3-(5-cyclopropyl-2-methylpyrazol-3 yl)oxybenzonitrile |
| 348 | 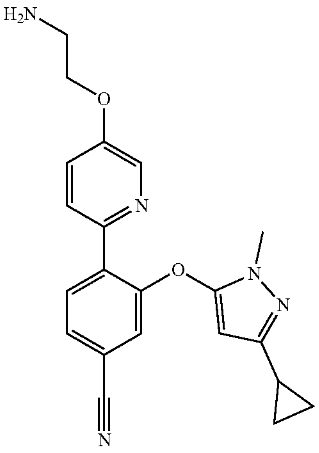 [SMILES: Cn1nc(C2CC2)cc1Oc1cc(C#N)ccc1-c1ccc(OCCN)cn1] | 4-[5-(2-aminoethoxy)pyridin-2-yl]-3-(5-cyclopropyl-2-methylpyrazol-3-yl)oxybenzonitrile |

TABLE 1-continued
| Compound number | Structural formula | Compound name |
|---|---|---|
| 349 | 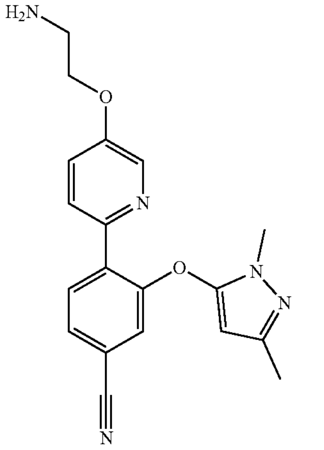 [SMILES: Cc1cc(Oc2cc(C#N)ccc2-c2ccc(OCCN)cn2)n(C)n1] | 4-[5-(2-aminoethoxy)pyridin-2-yl]-3-(2,5-dimethylpyrazol-3-yl)oxybenzonitrile |
| 350 | 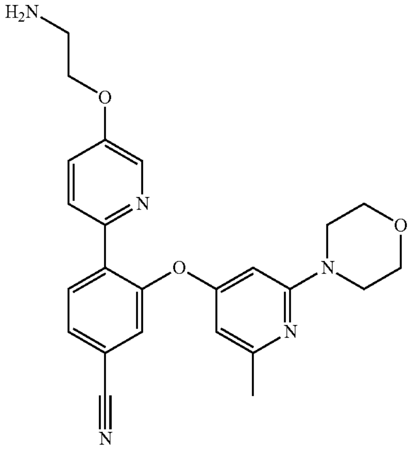 [SMILES: Cc1cc(Oc2cc(C#N)ccc2-c2ccc(OCCN)cn2)cc(N2CCOCC2)n1] | 4-[5-(2-aminoethoxy)pyridin-2-yl]-3-(2-methyl-6-morpholin-4-ylpyridin-4-yl)oxybenzonitrile |
| 351 | 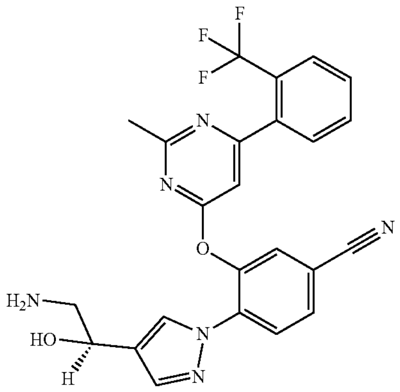 [SMILES: Cc1nc(Oc2cc(C#N)ccc2-n2cc([C@@H](O)CN)cn2)cc(-c2ccccc2C(F)(F)F)n1] | 4-[4-[(1R)-2-amino-1-hydroxyethyl]pyrazol-1-yl]-3-[2-methyl-6-[2-(trifluoromethyl)phenyl]pyrimidin-4-yl]oxybenzonitrile |

TABLE 1-continued

| Compound number | Structural formula | Compound name |
|---|---|---|
| 352 | 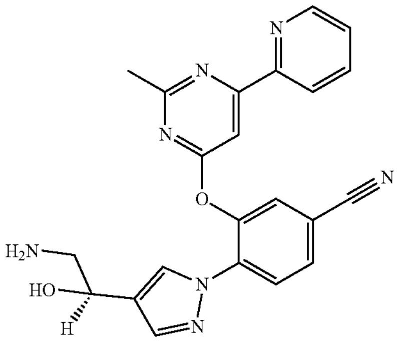 [SMILES: Cc1nc(Oc2cc(C#N)ccc2-n2cc([C@@H](O)CN)cn2)cc(-c2ccccn2)n1] | 4-[4-[(1R)-2-amino-1-hydroxyethyl]pyrazol-1-yl]-3-(2-methyl-6-pyridin-2-ylpyrimidin-4-yl)oxybenzonitrile |
| 353 | 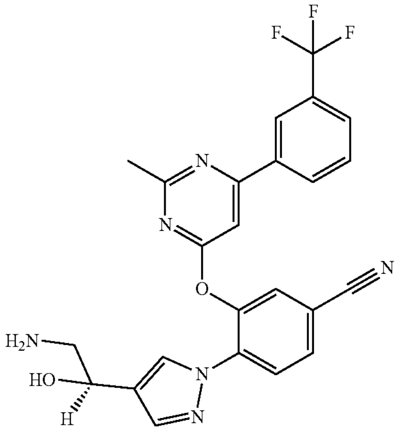 [SMILES: Cc1nc(Oc2cc(C#N)ccc2-n2cc([C@@H](O)CN)cn2)cc(-c2cccc(C(F)(F)F)c2)n1] | 4-[4-[(1R)-2-amino-1-hydroxyethyl]pyrazol-1-yl]-3-[2-methyl-6-[3-(trifluoromethyl)phenyl]pyrimidin-4-yl]oxybenzonitrile |
| 354 | 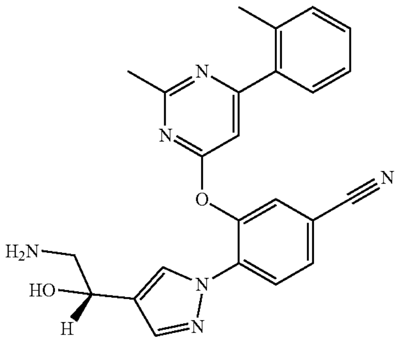 [SMILES: Cc1nc(Oc2cc(C#N)ccc2-n2cc([C@H](O)CN)cn2)cc(-c2ccccc2C)n1] | 4-[4-[(1S)-2-amino-1-hydroxyethyl]pyrazol-1-yl]-3-[2-methyl-6-(2-methylphenyl)pyrimidin-4-yl]oxybenzonitrile |
| 355 | 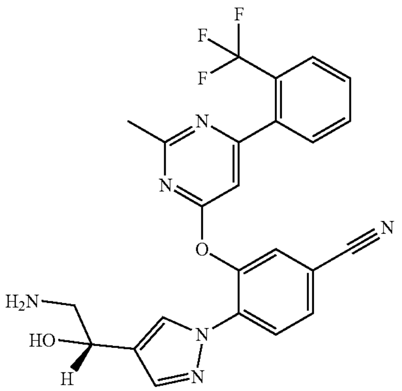 [SMILES: Cc1nc(Oc2cc(C#N)ccc2-n2cc([C@H](O)CN)cn2)cc(-c2ccccc2C(F)(F)F)n1] | 4-[4-[(1S)-2-amino-1-hydroxyethyl]pyrazol-1-yl]-3-[2-methyl-6-[2-(trifluoromethyl)phenyl]pyrimidin-4-yl]oxybenzonitrile |

TABLE 1-continued

| Compound number | Structural formula | Compound name |
|---|---|---|
| 356 | 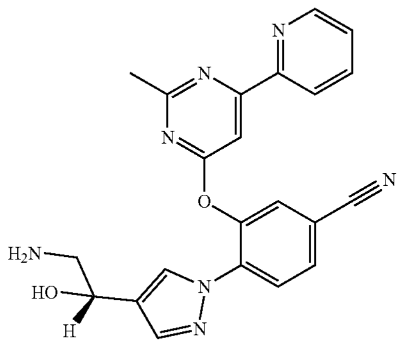 [SMILES: Cc1nc(Oc2cc(C#N)ccc2-n2cc([C@H](O)CN)cn2)cc(-c2ccccn2)n1] | 4-[4-[(1S)-2-amino-1-hydroxyethyl]pyrazol-1-yl]-3-(2-methyl-6-pyridin-2-ylpyrimidin-4-yl)oxybenzonitrile |
| 357 | 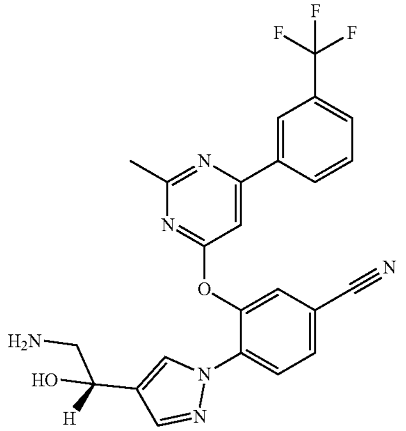 [SMILES: Cc1nc(Oc2cc(C#N)ccc2-n2cc([C@H](O)CN)cn2)cc(-c2cccc(C(F)(F)F)c2)n1] | 4-[4-[(1S)-2-amino-1-hydroxyethyl]pyrazol-1-yl]-3-[2-methyl-6-[3-(trifluoromethyl)phenyl]pyrimidin-4-yl]oxybenzonitrile |
| 358 | 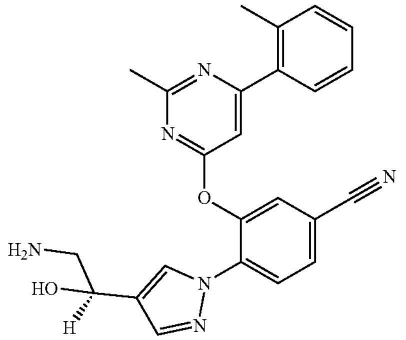 [SMILES: Cc1nc(Oc2cc(C#N)ccc2-n2cc([C@@H](O)CN)cn2)cc(-c2ccccc2C)n1] | 4-[4-[(1R)-2-amino-1-hydroxyethyl]pyrazol-1-yl]-3-[2-methyl-6-(2-methylphenyl)pyrimidin-4-yl]oxybenzonitrile |
| 359 | 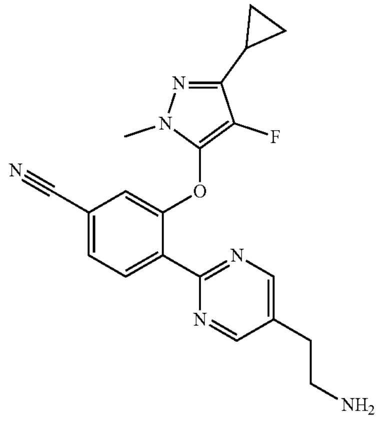 [SMILES: Cn1nc(C2CC2)c(F)c1Oc1cc(C#N)ccc1-c1ncc(CCN)cn1] | 4-[5-(2-aminoethyl)pyrimidin-2-yl]-3-(5-cyclopropyl-4-fluoro-2-methylpyrazol-3-yl)oxybenzonitrile |

TABLE 1-continued

| Compound number | Structural formula | Compound name |
| --- | --- | --- |
| 360 | 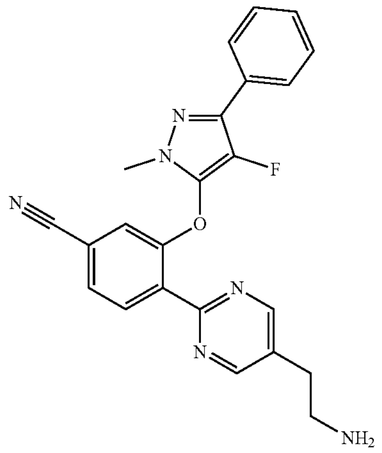 [SMILES: Cn1nc(-c2ccccc2)c(F)c1Oc1cc(C#N)ccc1-c1ncc(CCN)cn1] | 4-[5-(2-aminoethyl)pyrimidin-2-yl]-3-(4-fluoro-2-methyl-5-phenylpyrazol-3-yl)oxybenzonitrile |
| 361 | 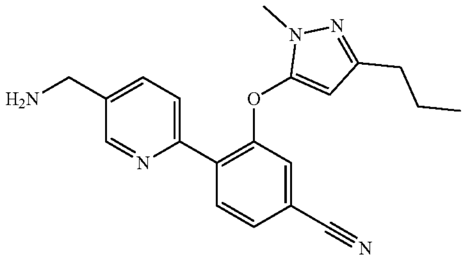 [SMILES: CCCc1cc(Oc2cc(C#N)ccc2-c2ccc(CN)cn2)n(C)n1] | 4-[5-(aminomethyl)pyridin-2-yl]-3-(2-methyl-5-propylpyrazol-3-yl)oxybenzonitrile |
| 362 | 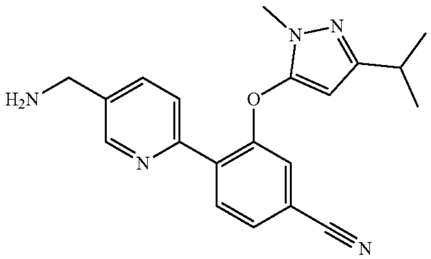 [SMILES: CC(C)c1cc(Oc2cc(C#N)ccc2-c2ccc(CN)cn2)n(C)n1] | 4-[5-(aminomethyl)pyridin-2-yl]-3-(2-methyl-5-propan-2-ylpyrazol-3-yl)oxybenzonitrile |
| 363 | 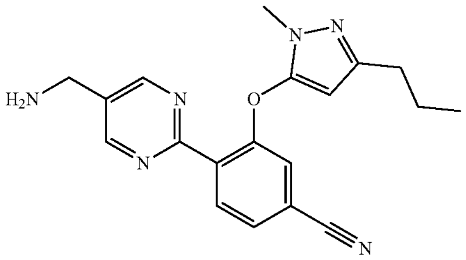 [SMILES: CCCc1cc(Oc2cc(C#N)ccc2-c2ncc(CN)cn2)n(C)n1] | 4-[5-(aminomethyl)pyrimidin-2-yl]-3-(2-methyl-5-propylpyrazol-3-yl)oxybenzonitrile |
| 364 | 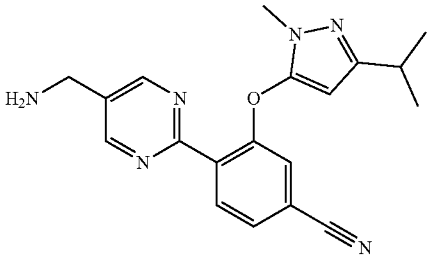 [SMILES: CC(C)c1cc(Oc2cc(C#N)ccc2-c2ncc(CN)cn2)n(C)n1] | 4-[5-(aminomethyl)pyrimidin-2-yl]-3-(2-methyl-5-propan-2-ylpyrazol-3-yl)oxybenzonitrile |

TABLE 1-continued
| Compound number | Structural formula | Compound name |
| --- | --- | --- |
| 365 | 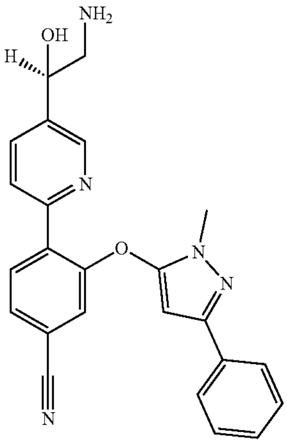 [SMILES: Cn1nc(-c2ccccc2)cc1Oc1cc(C#N)ccc1-c1ccc([C@@H](O)CN)cn1] | 4-[5-[(1R)-2-amino-1-hydroxyethyl]pyridin-2-yl]-3-(2-methyl-5-phenylpyrazol-3-yl)oxybenzonitrile |
| 366 | 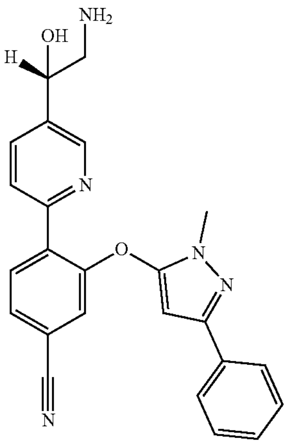 [SMILES: Cn1nc(-c2ccccc2)cc1Oc1cc(C#N)ccc1-c1ccc([C@H](O)CN)cn1] | 4-[5-[(1S)-2-amino-1-hydroxyethyl]pyridin-2-yl]-3-(2-methyl-5-phenylpyrazol-3-yl)oxybenzonitrile |
| 367 | 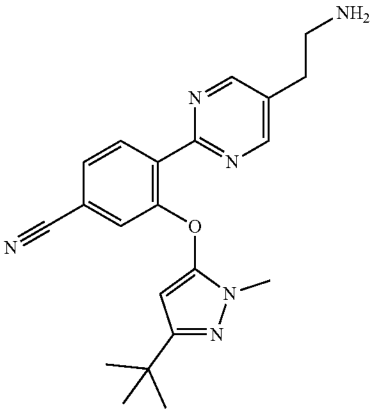 [SMILES: Cn1nc(C(C)(C)C)cc1Oc1cc(C#N)ccc1-c1ncc(CCN)cn1] | 4-[5-(2-aminoethyl)pyrimidin-2-yl]-3-(5-tert-butyl-2-methylpyrazol-3-yl)oxybenzonitrile |

TABLE 1-continued
| Compound number | Structural formula | Compound name |
|---|---|---|
| 368 | 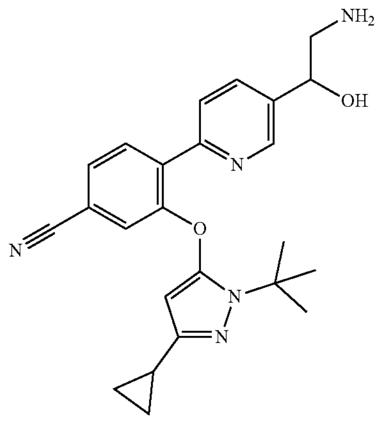 [SMILES: CC(C)(C)n1nc(C2CC2)cc1Oc1cc(C#N)ccc1-c1ccc(C(O)CN)cn1] | 4-[5-(2-amino-1-hydroxyethyl)pyridin-2-yl]-3-(2-tert-butyl-5-cyclopropylpyrazol-3-yl)oxybenzonitrile |
| 369 | 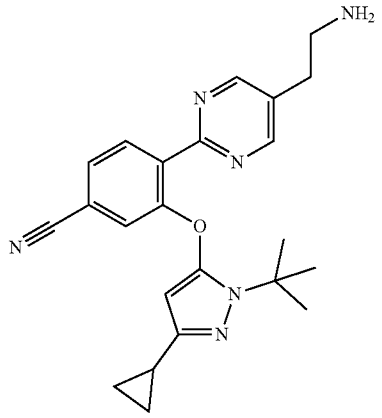 [SMILES: CC(C)(C)n1nc(C2CC2)cc1Oc1cc(C#N)ccc1-c1ncc(CCN)cn1] | 4-[5-(2-aminoethyl)pyrimidin-2-yl]-3-(2-tert-butyl-5-cyclopropylpyrazol-3-yl)oxybenzonitrile |
| 370 | 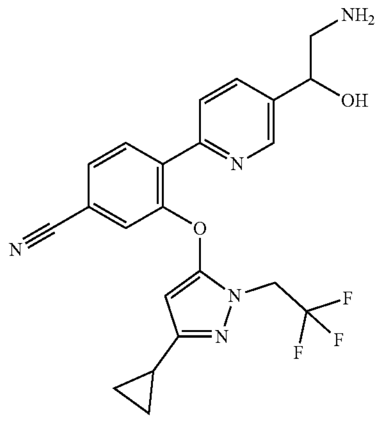 [SMILES: N#Cc1ccc(-c2ccc(C(O)CN)cn2)c(Oc2cc(C3CC3)nn2CC(F)(F)F)c1] | 4-[5-(2-amino-1-hydroxyethyl)pyridin-2-yl]-3-[5-cyclopropyl-2-(2,2,2-trifluoroethyl)pyrazol-3-yl]oxybenzonitrile |

TABLE 1-continued
| Compound number | Structural formula | Compound name |
|---|---|---|
| 371 | 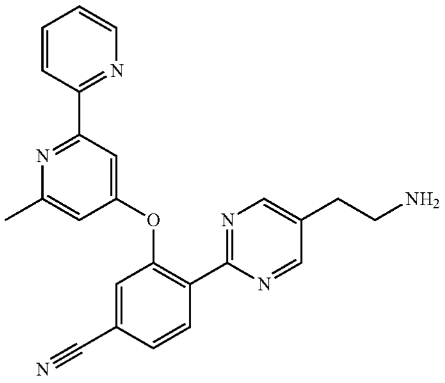 [SMILES: Cc1cc(Oc2cc(C#N)ccc2-c2ncc(CCN)cn2)cc(-c2ccccn2)n1] | 4-[5-(2-aminoethyl)pyrimidin-2-yl]-3-(2-methyl-6-pyridin-2-ylpyridin-4-yl)oxybenzonitrile |
| 372 | 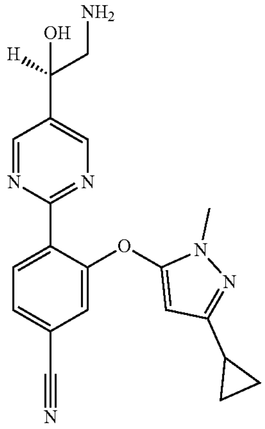 [SMILES: Cn1nc(C2CC2)cc1Oc1cc(C#N)ccc1-c1ncc([C@@H](O)CN)cn1] | 4-[5-[(1R)-2-amino-1-hydroxyethyl]pyrimidin-2-yl]-3-(5-cyclopropyl-2-methylpyrazol-3-yl)oxybenzonitrile |
| 373 | 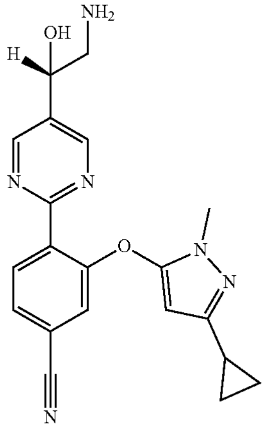 [SMILES: Cn1nc(C2CC2)cc1Oc1cc(C#N)ccc1-c1ncc([C@H](O)CN)cn1] | 4-[5-[(1S)-2-amino-1-hydroxyethyl]pyrimidin-2-yl]-3-(5 cyclopropyl-2-methylpyrazol-3-yl)oxybenzonitrile |

TABLE 1-continued
| Compound number | Structural formula | Compound name |
| --- | --- | --- |
| 374 | 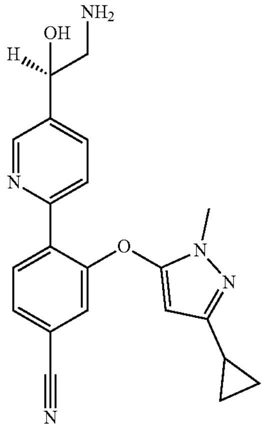 [SMILES: Cn1nc(C2CC2)cc1Oc1cc(C#N)ccc1-c1ccc([C@@H](O)CN)cn1] | 4-[5-[(1R)-2-amino-1-hydroxyethyl]pyridin-2-yl]-3-(5-cyclopropyl-2-methylpyrazol-3-yl)oxybenzonitrile |
| 375 | 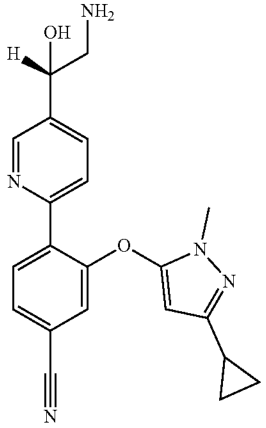 [SMILES: Cn1nc(C2CC2)cc1Oc1cc(C#N)ccc1-c1ccc([C@H](O)CN)cn1] | 4-[5-[(1S)-2-amino-1-hydroxyethyl]pyridin-2-yl]-3-(5-cyclopropyl-2-methylpyrazol-3-yl)oxybenzonitrile |
| 376 | 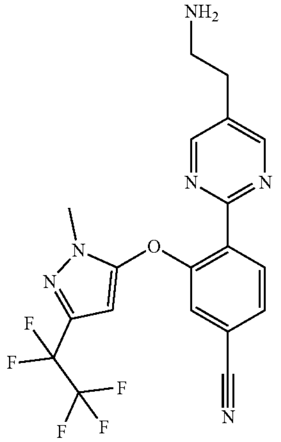 [SMILES: Cn1nc(C(F)(F)C(F)(F)F)cc1Oc1cc(C#N)ccc1-c1ncc(CCN)cn1] | 4-[5-(2-aminoethyl)pyrimidin-2-yl]-3-[2-methyl-5-(1,1,2,2,2-pentafluoroethyl)pyrazol-3-yl]oxybenzonitrile |

TABLE 1-continued
| Compound number | Structural formula | Compound name |
|---|---|---|
| 377 | 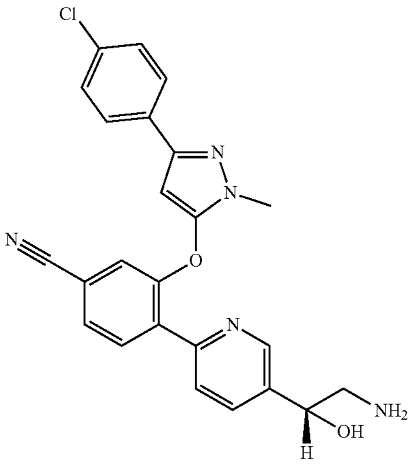 [SMILES: Cn1nc(-c2ccc(Cl)cc2)cc1Oc1cc(C#N)ccc1-c1ccc([C@@H](O)CN)cn1] | 4-[5-[(1R)-2-amino-1-hydroxyethyl]pyridin-2-yl]-3-[5-(4-chlorophenyl)-2-methylpyrazol-3-yl]oxybenzonitrile |
| 378 | 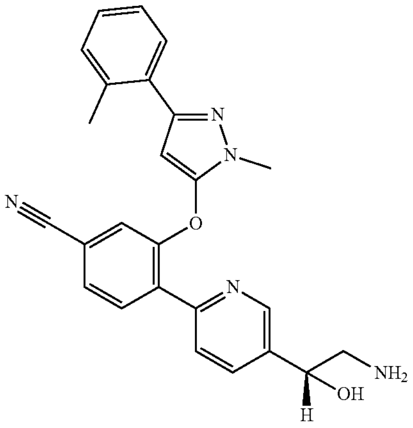 [SMILES: Cc1ccccc1-c1cc(Oc2cc(C#N)ccc2-c2ccc([C@@H](O)CN)cn2)n(C)n1] | 4-[5-[(1R)-2-amino-1-hydroxyethyl]pyridin-2-yl]-3-[2-methyl-5-(2-methylphenyl)pyrazol-3-yl]oxybenzonitrile |
| 379 | 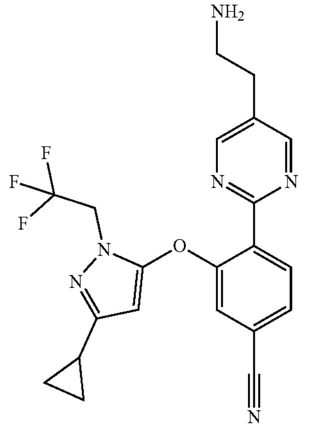 [SMILES: N#Cc1ccc(-c2ncc(CCN)cn2)c(Oc2cc(C3CC3)nn2CC(F)(F)F)c1] | 4-[5-(2-aminoethyl)pyrimidin-2-yl]-3-[5-cyclopropyl-2-(2,2,2-trifluoroethyl)pyrazol-3-yl]oxybenzonitrile |

TABLE 1-continued
| Compound number | Structural formula | Compound name |
|---|---|---|
| 380 | 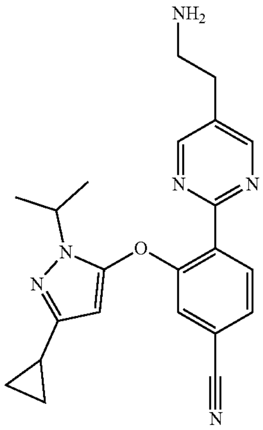 [SMILES: CC(C)n1nc(C2CC2)cc1Oc1cc(C#N)ccc1-c1ncc(CCN)cn1] | 4-[5-(2-aminoethyl)pyrimidin-2-yl]-3-(5-cyclopropyl-2-propan-2-ylpyrazol-3-yl)oxybenzonitrile |
| 381 | 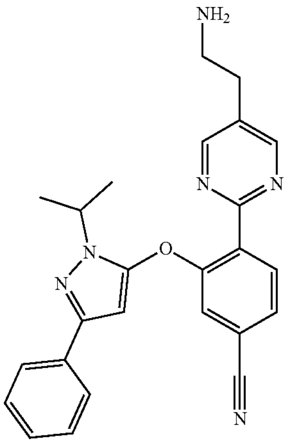 [SMILES: CC(C)n1nc(-c2ccccc2)cc1Oc1cc(C#N)ccc1-c1ncc(CCN)cn1] | 4-[5-(2-aminoethyl)pyrimidin-2-yl]-3-(5-phenyl-2-propan-2-ylpyrazol-3-yl)oxybenzonitrile |
| 382 | 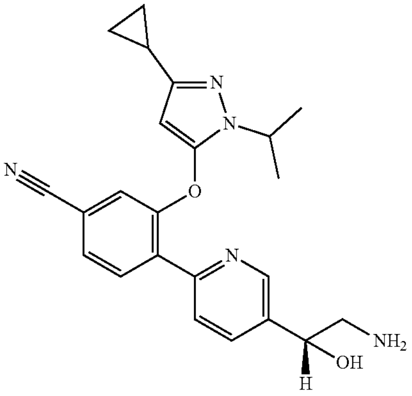 [SMILES: CC(C)n1nc(C2CC2)cc1Oc1cc(C#N)ccc1-c1ccc([C@@H](O)CN)cn1] | 4-[5-[(1R)-2-amino-1-hydroxyethyl]pyridin-2-yl]-3-(5-cyclopropyl-2-propan-2-ylpyrazol-3-yl)oxybenzonitrile |

TABLE 1-continued
| Compound number | Structural formula | Compound name |
| --- | --- | --- |
| 383 | 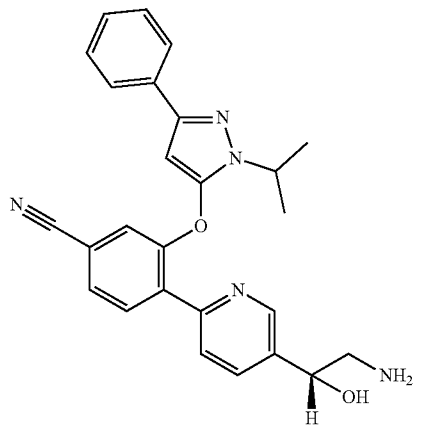 [SMILES: CC(C)n1nc(-c2ccccc2)cc1Oc1cc(C#N)ccc1-c1ccc([C@@H](O)CN)cn1] | 4-[5-[(1R)-2-amino-1-hydroxyethyl]pyridin-2-yl]-3-(5-phenyl-2-propan-2-ylpyrazol-3-yl)oxybenzonitrile |
| 384 | 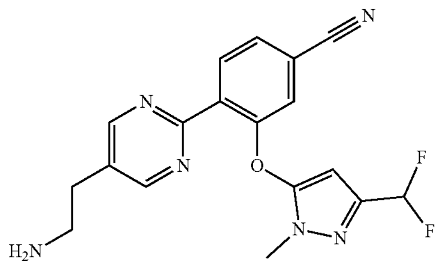 [SMILES: Cn1nc(C(F)F)cc1Oc1cc(C#N)ccc1-c1ncc(CCN)cn1] | 4-[5-(2-aminoethyl)pyrimidin-2-yl]-3-[5-(difluoromethyl)-2-methylpyrazol-3-yl]oxybenzonitrile |
| 385 | 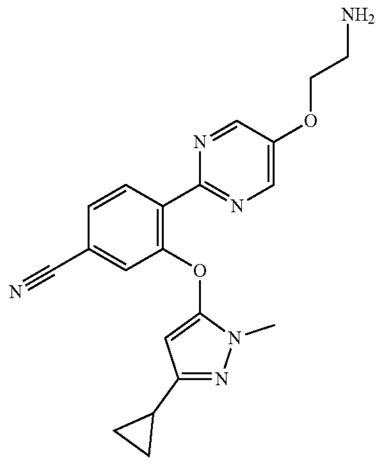 [SMILES: Cn1nc(C2CC2)cc1Oc1cc(C#N)ccc1-c1ncc(OCCN)cn1] | 4-[5-(2-aminoethoxy)pyrimidin-2-yl]-3-(5-cyclopropyl-2-methylpyrazol-3-yl)oxybenzonitrile |

TABLE 1-continued
| Compound number | Structural formula | Compound name |
|---|---|---|
| 386 | 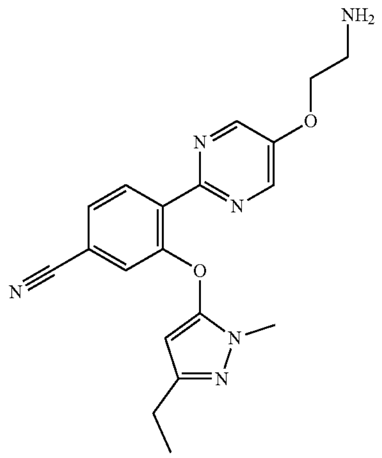 [SMILES: CCc1cc(Oc2cc(C#N)ccc2-c2ncc(OCCN)cn2)n(C)n1] | 4-[5-(2-aminoethoxy)pyrimidin-2-yl]-3-(5-ethyl-2-methylpyrazol-3-yl)oxybenzonitrile |
| 387 | 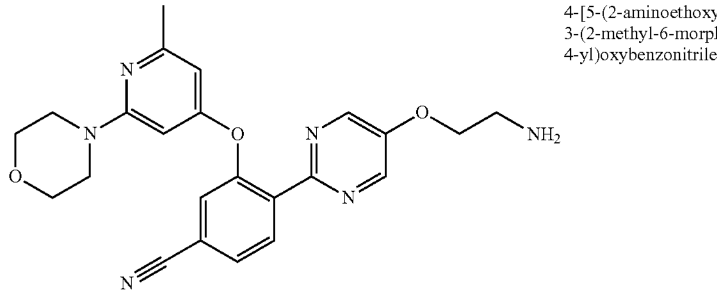 | 4-[5-(2-aminoethoxy)pyrimidin-2-yl]-3-(2-methyl-6-morpholin-4-ylpyridin-4-yl)oxybenzonitrile |
| 388 | 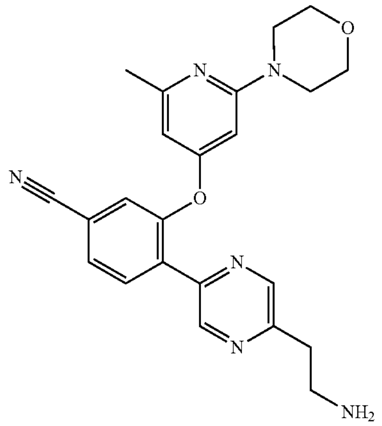 [SMILES: Cc1cc(Oc2cc(C#N)ccc2-c2cnc(CCN)cn2)cc(N2CCOCC2)n1] | 4-[5-(2-aminoethyl)pyrazin-2-yl]-3-(2-methyl-6-morpholin-4-ylpyridin-4-yl)oxybenzonitrile |

TABLE 1-continued
| Compound number | Structural formula | Compound name |
|---|---|---|
| 389 | 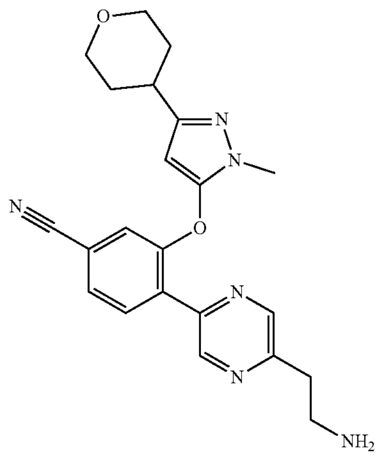 [SMILES: Cn1nc(C2CCOCC2)cc1Oc1cc(C#N)ccc1-c1cnc(CCN)cn1] | 4-[5-(2-aminoethyl)pyrazin-2-yl]-3-[2-methyl-5-(oxan-4-yl)pyrazol-3-yl]oxybenzonitrile |
| 390 | 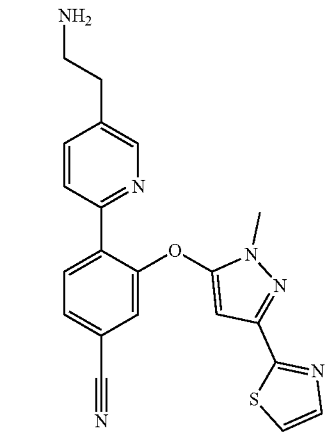 [SMILES: Cn1nc(-c2nccs2)cc1Oc1cc(C#N)ccc1-c1ccc(CCN)cn1] | 4-[5-(2-aminoethyl)pyridin-2-yl]-3-[2-methyl-5-(1,3-thiazol-2-yl)pyrazol-3-yl]oxybenzonitrile |
| 391 | 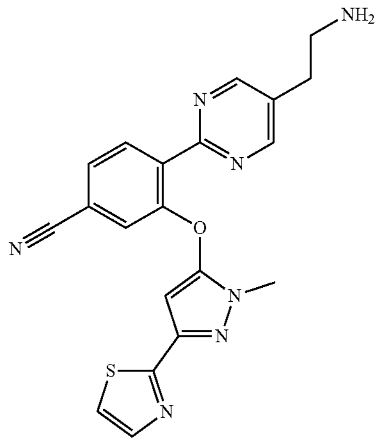 [SMILES: Cn1nc(-c2nccs2)cc1Oc1cc(C#N)ccc1-c1ncc(CCN)cn1] | 4-[5-(2-aminoethyl)pyrimidin-2-yl]-3-[2-methyl-5-(1,3-thiazol-2-yl)pyrazol-3-yl]oxybenzonitrile |

TABLE 1-continued

| Compound number | Structural formula | Compound name |
|---|---|---|
| 392 | 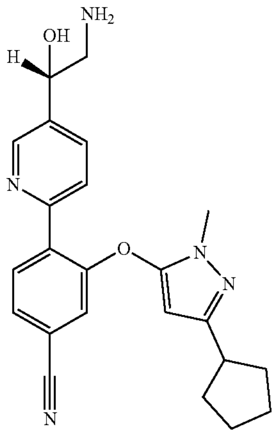 [SMILES: Cn1nc(C2CCCC2)cc1Oc1cc(C#N)ccc1-c1ccc([C@H](O)CN)cn1] | 4-[5-[(1S)-2-amino-1-hydroxyethyl]pyridin-2-yl]-3-(5-cyclopentyl-2-methylpyrazol-3-yl)oxybenzonitrile |
| 393 | 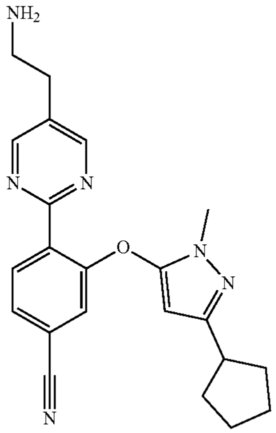 [SMILES: Cn1nc(C2CCCC2)cc1Oc1cc(C#N)ccc1-c1ncc(CCN)cn1] | 4-[5-(2-aminoethyl)pyrimidin-2-yl]-3-(5-cyclopentyl-2-methylpyrazol-3-yl)oxybenzonitrile |
| 394 | 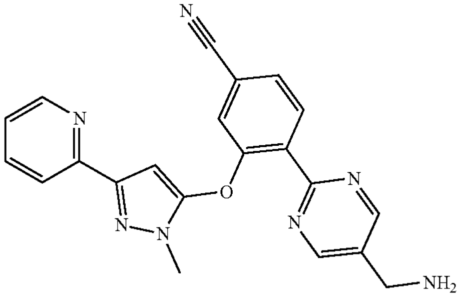 [SMILES: Cn1nc(-c2ccccn2)cc1Oc1cc(C#N)ccc1-c1ncc(CN)cn1] | 4-[5-(aminomethyl)pyrimidin-2-yl]-3-(2-methyl-5-pyridin-2-ylpyrazol-3-yl)oxybenzonitrile |
| 395 | 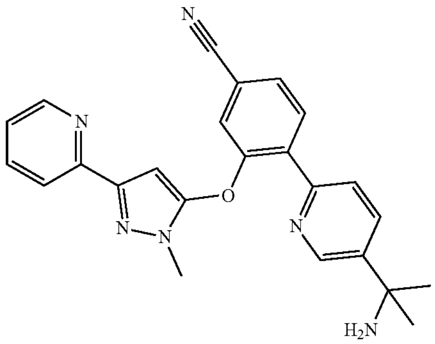 [SMILES: Cn1nc(-c2ccccn2)cc1Oc1cc(C#N)ccc1-c1ccc(C(C)(C)N)cn1] | 4-[5-(2-aminopropan-2-yl)pyridin-2-yl]-3-(2-methyl-5-pyridin-2-ylpyrazol-3-yl)oxybenzonitrile |

TABLE 1-continued

| Compound number | Structural formula | Compound name |
| --- | --- | --- |
| 396 | 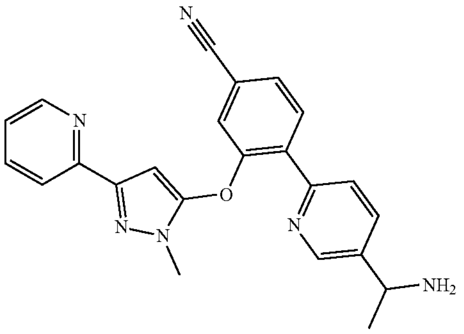 [SMILES: CC(N)c1ccc(-c2ccc(C#N)cc2Oc2cc(-c3ccccn3)nn2C)nc1] | 4-[5-(1-aminoethyl)pyridin-2-yl]-3-(2-methyl-5-pyridin-2-ylpyrazol-3-yl)oxybenzonitrile |
| 397 | 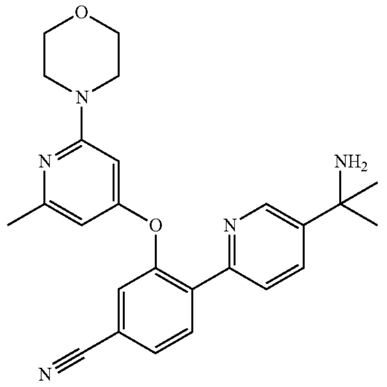 [SMILES: Cc1cc(Oc2cc(C#N)ccc2-c2ccc(C(C)(C)N)cn2)cc(N2CCOCC2)n1] | 4-[5-(2-aminopropan-2-yl)pyridin-2-yl]-3-(2-methyl-6-morpholin-4-ylpyridin-4-yl)oxybenzonitrile |
| 398 | 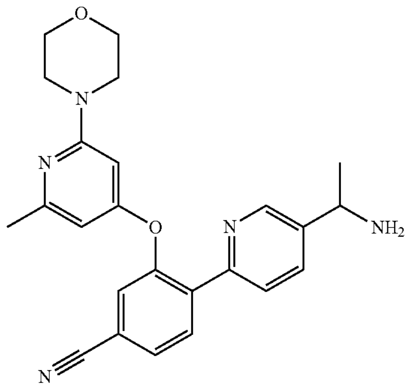 [SMILES: Cc1cc(Oc2cc(C#N)ccc2-c2ccc(C(C)N)cn2)cc(N2CCOCC2)n1] | 4-[5-(1-aminoethyl)pyridin-2-yl]-3-(2-methyl-6-morpholin-4-ylpyridin-4-yl)oxybenzonitrile |
| 399 | 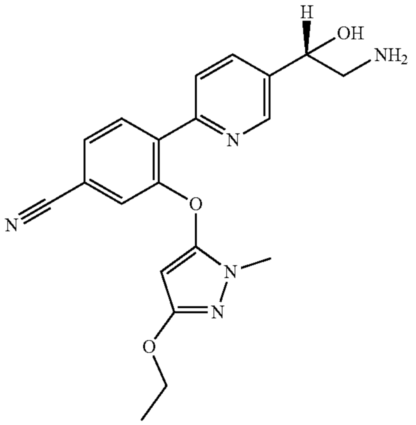 [SMILES: CCOc1cc(Oc2cc(C#N)ccc2-c2ccc([C@H](O)CN)cn2)n(C)n1] | 4-[5-[(1S)-2-amino-1-hydroxyethyl]pyridin-2-yl]-3-(5-ethoxy-2-methylpyrazol-3-yl)oxybenzonitrile |

TABLE 1-continued

| Compound number | Structural formula | Compound name |
|---|---|---|
| 400 | 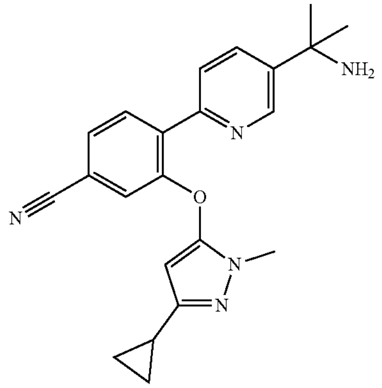 [SMILES: Cn1nc(C2CC2)cc1Oc1cc(C#N)ccc1-c1ccc(C(C)(C)N)cn1] | 4-[5-(2-aminopropan-2-yl)pyridin-2-yl]-3-(5-cyclopropyl-2-methylpyrazol-3-yl)oxybenzonitrile |
| 401 | 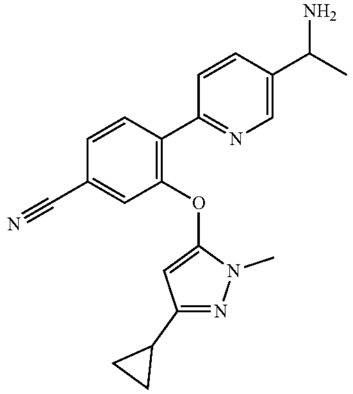 [SMILES: CC(N)c1ccc(-c2ccc(C#N)cc2Oc2cc(C3CC3)nn2C)nc1] | 4-[5-(1-aminoethyl)pyridin-2-yl]-3-(5-cyclopropyl-2-methylpyrazol-3-yl)oxybenzonitrile |
| 402 | 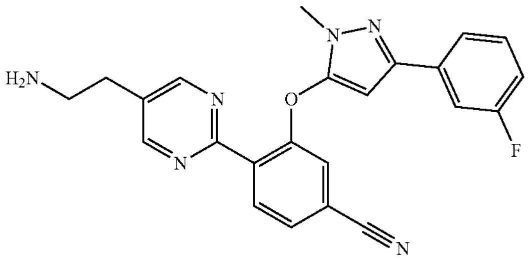 [SMILES: Cn1nc(-c2cccc(F)c2)cc1Oc1cc(C#N)ccc1-c1ncc(CCN)cn1] | 4-[5-(2-aminoethyl)pyrimidin-2-yl]-3-[5-(3-fluorophenyl)-2-methylpyrazol-3-yl]oxybenzonitrile |
| 403 | 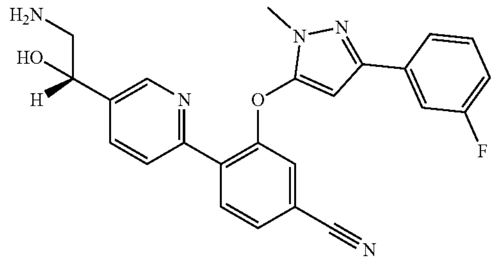 [SMILES: Cn1nc(-c2cccc(F)c2)cc1Oc1cc(C#N)ccc1-c1ccc([C@H](O)CN)cn1] | 4-[5-[(1S)-2-amino-1-hydroxyethyl]pyridin-2-yl]-3-[5-(3-fluorophenyl)-2-methylpyrazol-3-yl]oxybenzonitrile |
| 404 | 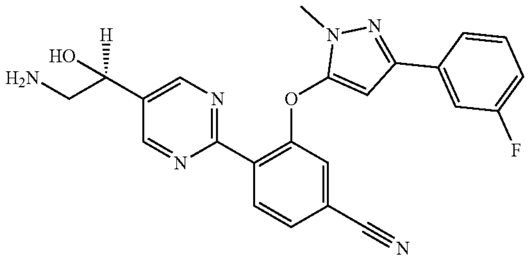 [SMILES: Cn1nc(-c2cccc(F)c2)cc1Oc1cc(C#N)ccc1-c1ncc([C@H](O)CN)cn1] | 4-[5-(2-amino-1-hydroxyethyl)pyrimidin-2-yl]-3-[5-(3-fluorophenyl)-2-methylpyrazol-3 yl]oxybenzonitrile |

TABLE 1-continued
| Compound number | Structural formula | Compound name |
|---|---|---|
| 405 | 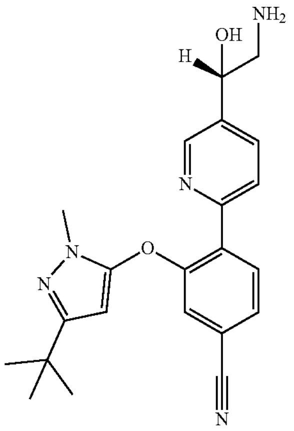 [SMILES: Cn1nc(C(C)(C)C)cc1Oc1cc(C#N)ccc1-c1ccc([C@H](O)CN)cn1] | 4-[5-[(1S)-2-amino-1-hydroxyethyl]pyridin-2-yl]-3-(5-tert-butyl-2-methylpyrazol-3-yl)oxybenzonitrile |
| 406 | 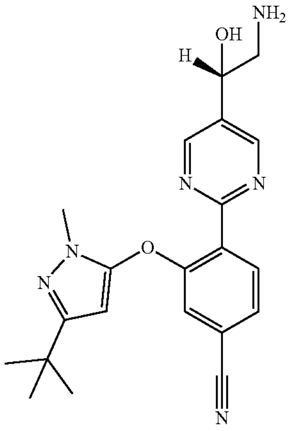 [SMILES: Cn1nc(C(C)(C)C)cc1Oc1cc(C#N)ccc1-c1ncc([C@H](O)CN)cn1] | 4-[5-[(1S)-2-amino-1-hydroxyethyl]pyrimidin-2-yl]-3-(5-tert-butyl-2-methylpyrazol-3-yl)oxybenzonitrile |
| 407 | 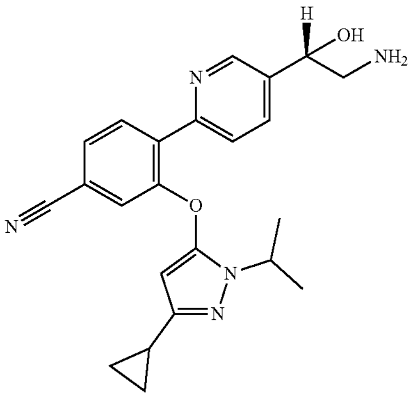 [SMILES: CC(C)n1nc(C2CC2)cc1Oc1cc(C#N)ccc1-c1ccc([C@H](O)CN)cn1] | 4-[5-[(1S)-2-amino-1-hydroxyethyl]pyridin-2-yl]-3-(5-cyclopropyl-2-propan-2-ylpyrazol-3-yl)oxybenzonitrile |

TABLE 1-continued

| Compound number | Structural formula | Compound name |
|---|---|---|
| 408 | 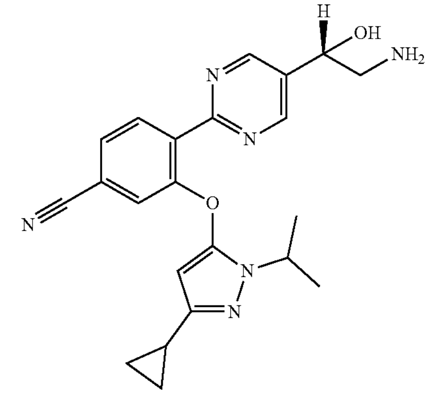 [SMILES: CC(C)n1nc(C2CC2)cc1Oc1cc(C#N)ccc1-c1ncc([C@H](O)CN)cn1] | 4-[5-[(1S)-2-amino-1-hydroxyethyl]pyrimidin-2-yl]-3-(5-cyclopropyl-2-propan-2-ylpyrazol-3-yl)oxybenzonitrile |
| 409 | 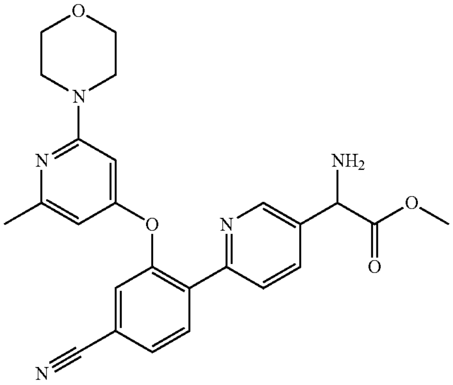 | methyl 2-amino-2-[6-[4-cyano-2-(2-methyl-6-morpholin-4-ylpyridin-4-yl)oxyphenyl]pyridin-3-yl]acetate |
| 410 | 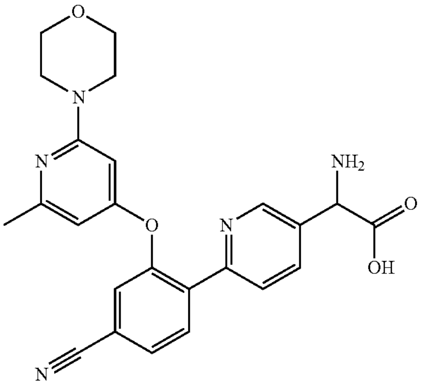 [SMILES: Cc1cc(Oc2cc(C#N)ccc2-c2ccc(C(N)C(=O)O)cn2)cc(N2CCOCC2)n1] | 2-amino-2-[6-[4-cyano-2-(2-methyl-6-morpholin-4-ylpyridin-4-yl)oxyphenyl]pyridin-3-yl]acetic acid |
| 411 | 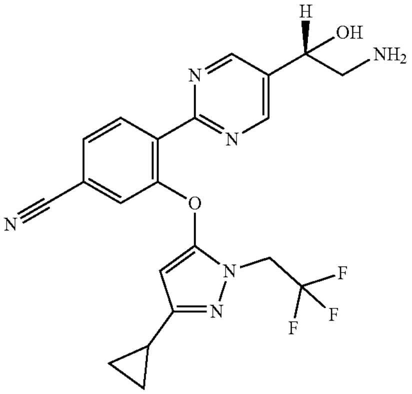 [SMILES: N#Cc1ccc(-c2ncc([C@H](O)CN)cn2)c(Oc2cc(C3CC3)nn2CC(F)(F)F)c1] | 4-[5-[(1S)-2-amino-1-hydroxyethyl]pyrimidin-2-yl]-3-[5-cyclopropyl-2-(2,2,2-trifluoroethyl)pyrazol-3-yl]oxybenzonitrile |

TABLE 1-continued

| Compound number | Structural formula | Compound name |
| --- | --- | --- |
| 412 | 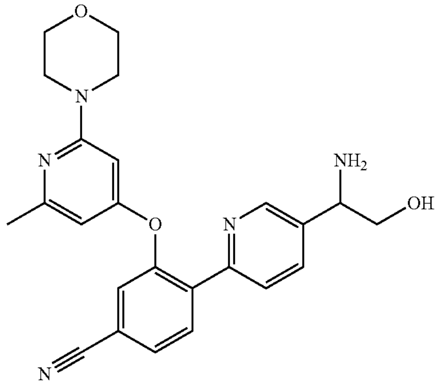 [SMILES: Cc1cc(Oc2cc(C#N)ccc2-c2ccc(C(N)CO)cn2)cc(N2CCOCC2)n1] | 4-[5-(1-amino-2-hydroxyethyl)pyridin-2-yl]-3-(2-methyl-6-morpholin-4-ylpyridin-4-yl)oxybenzonitrile |
| 413 | 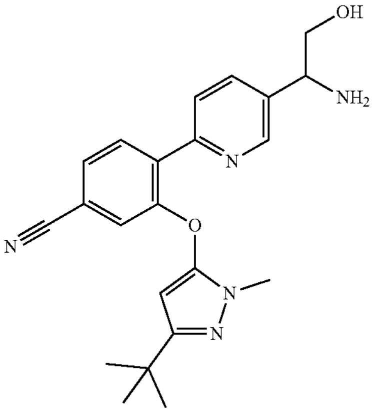 [SMILES: Cn1nc(C(C)(C)C)cc1Oc1cc(C#N)ccc1-c1ccc(C(N)CO)cn1] | 4-[5-(1-amino-2-hydroxyethyl)pyridin-2-yl]-3-(5-tert-butyl-2-methylpyrazol-3-yl)oxybenzonitrile |
| 414 | 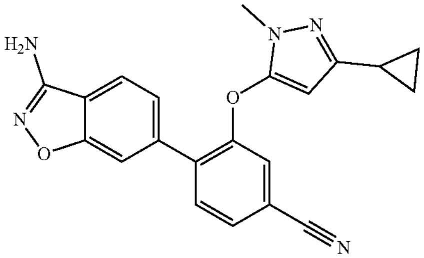 [SMILES: Cn1nc(C2CC2)cc1Oc1cc(C#N)ccc1-c1ccc2c(N)noc2c1] | 4-(3-amino-1,2-benzoxazol-6-yl)-3-(5-cyclopropyl-2-methylpyrazol-3-yl)oxybenzonitrile |
| 415 | 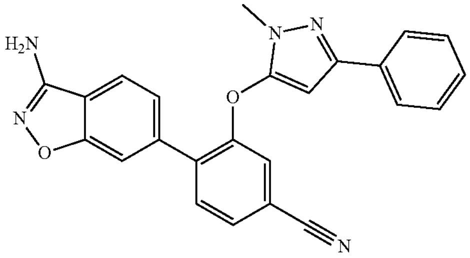 [SMILES: Cn1nc(-c2ccccc2)cc1Oc1cc(C#N)ccc1-c1ccc2c(N)noc2c1] | 4-(3-amino-1,2-benzoxazol-6-yl)-3-(2-methyl-5-phenylpyrazol-3-yl)oxybenzonitrile |

TABLE 1-continued

| Compound number | Structural formula | Compound name |
|---|---|---|
| 416 | 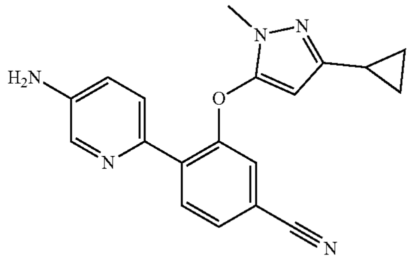 [SMILES: Cn1nc(C2CC2)cc1Oc1cc(C#N)ccc1-c1ccc(N)cn1] | 4-(5-aminopyridin-2-yl)-3-(5-cyclopropyl-2-methylpyrazol-3-yl)oxybenzonitrile |
| 417 | 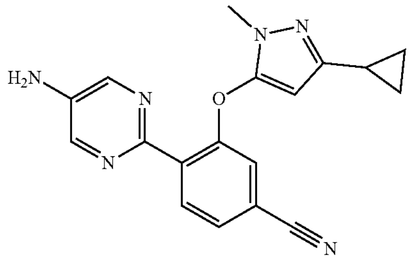 [SMILES: Cn1nc(C2CC2)cc1Oc1cc(C#N)ccc1-c1ncc(N)cn1] | 4-(5-aminopyrimidin-2-yl)-3-(5-cyclopropyl-2-methylpyrazol-3-yl)oxybenzonitrile |
| 418 | 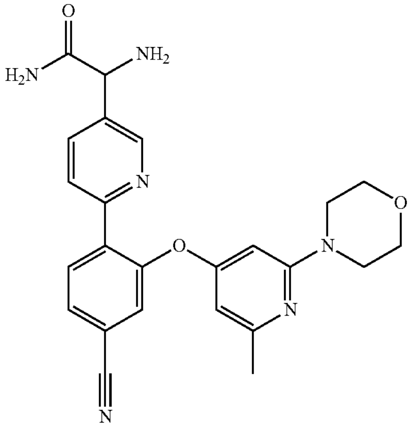 [SMILES: Cc1cc(Oc2cc(C#N)ccc2-c2ccc(C(N)C(N)=O)cn2)cc(N2CCOCC2)n1] | 2-amino-2-[6-[4-cyano-2-(2-methyl-6-morpholin-4-ylpyridin-4-yl)oxyphenyl]pyridin-3-yl]acetamide |
| 419 | 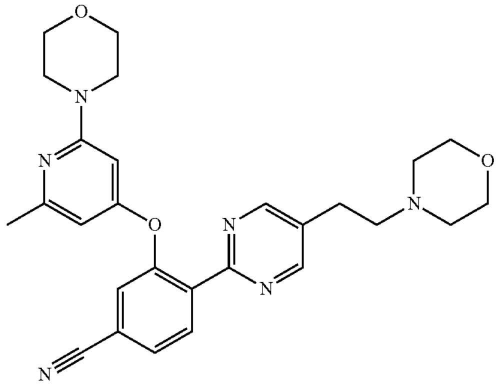 [SMILES: Cc1cc(Oc2cc(C#N)ccc2-c2ncc(CCN3CCOCC3)cn2)cc(N2CCOCC2)n1] | 3-(2-methyl-6-morpholin-4-ylpyridin-4-yl)oxy-4-[5-(2-morpholin-4-ylethyl)pyrimidin-2-yl]benzonitrile |

TABLE 1-continued
| Compound number | Structural formula | Compound name |
| --- | --- | --- |
| 420 | 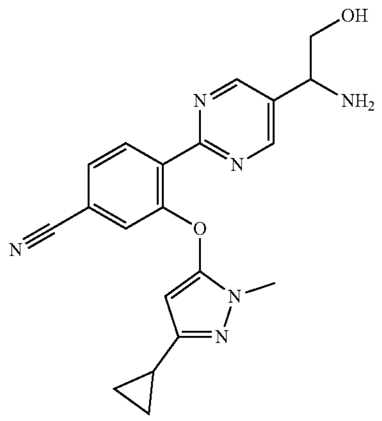 [SMILES: Cn1nc(C2CC2)cc1Oc1cc(C#N)ccc1-c1ncc(C(N)CO)cn1] | 4-[5-(1-amino-2-hydroxyethyl)pyrimidin-2-yl]-3-(5-cyclopropyl-2-methylpyrazol-3-yl)oxybenzonitrile |
| 421 | 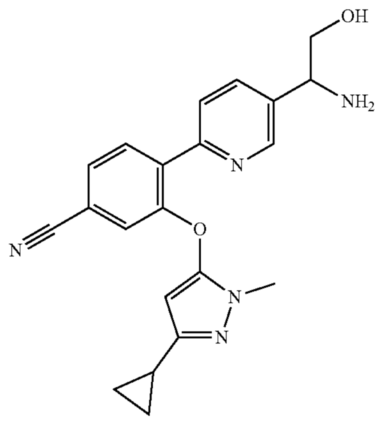 [SMILES: Cn1nc(C2CC2)cc1Oc1cc(C#N)ccc1-c1ccc(C(N)CO)cn1] | 4-[5-(1-amino-2-hydroxyethyl)pyridin-2-yl]-3-(5-cyclopropyl-2-methylpyrazol-3-yl)oxybenzonitrile |
| 422 | 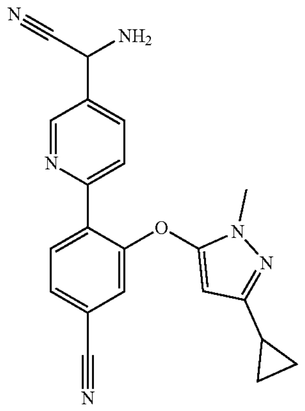 [SMILES: Cn1nc(C2CC2)cc1Oc1cc(C#N)ccc1-c1ccc(C(N)C#N)cn1] | 4-[5-[amino(cyano)methyl]pyridin-2-yl]-3-(5-cyclopropyl-2-methylpyrazol-3-yl)oxybenzonitrile |

TABLE 1-continued
| Compound number | Structural formula | Compound name |
| --- | --- | --- |
| 423 | 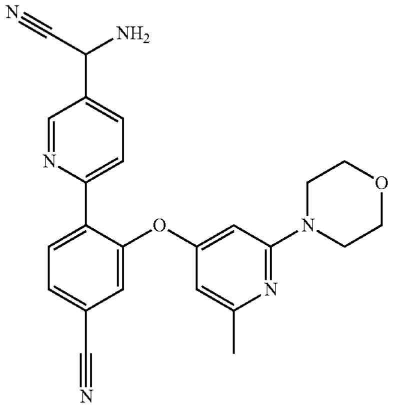 [SMILES: Cc1cc(Oc2cc(C#N)ccc2-c2ccc(C(N)C#N)cn2)cc(N2CCOCC2)n1] | 4-[5-[amino(cyano)methyl]pyridin-2-yl]-3-(2-methyl-6-morpholin-4-ylpyridin-4-yl)oxybenzonitrile |
| 424 | 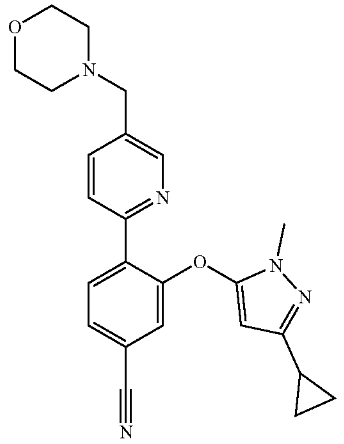 [SMILES: Cn1nc(C2CC2)cc1Oc1cc(C#N)ccc1-c1ccc(CN2CCOCC2)cn1] | 3-(5-cyclopropyl-2-methylpyrazol-3-yl)oxy-4-[5-(morpholin-4-ylmethyl)pyridin-2-yl]benzonitrile |
| 425 | 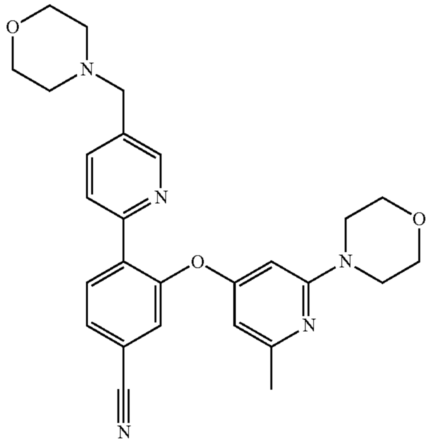 [SMILES: Cc1cc(Oc2cc(C#N)ccc2-c2ccc(CN3CCOCC3)cn2)cc(N2CCOCC2)n1] | 3-(2-methyl-6-morpholin-4-ylpyridin-4-yl)oxy-4-[5-(morpholin-4-ylmethyl)pyridin-2-yl]benzonitrile |

TABLE 1-continued
| Compound number | Structural formula | Compound name |
|---|---|---|
| 426 | 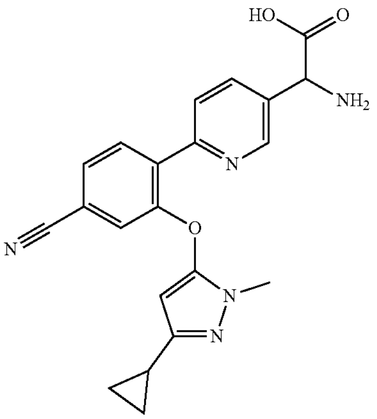 [SMILES: Cn1nc(C2CC2)cc1Oc1cc(C#N)ccc1-c1ccc(C(N)C(=O)O)cn1] | 2-amino-2-[6-[4-cyano-2-(5-cyclopropyl-2-methylpyrazol-3-yl)oxyphenyl]pyridin-3-yl]acetic acid |
| 427 | 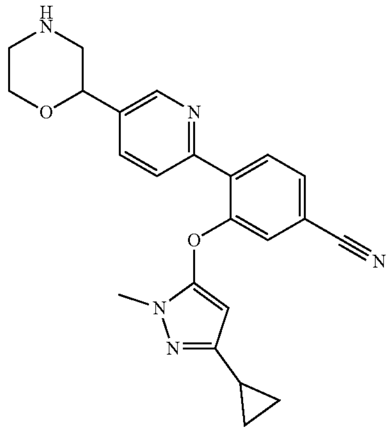 [SMILES: Cn1nc(C2CC2)cc1Oc1cc(C#N)ccc1-c1ccc(C2CNCCO2)cn1] | 3-(5-cyclopropyl-2-methylpyrazol-3-yl)oxy-4-(5-morpholin-2-ylpyridin-2-yl)benzonitrile |
| 428 | 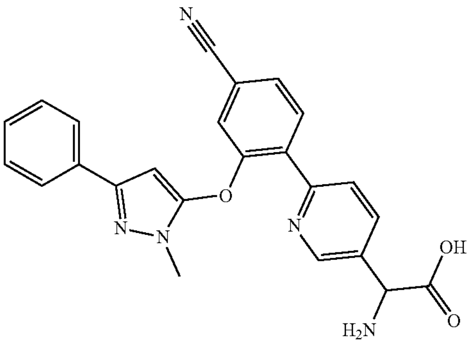 [SMILES: Cn1nc(-c2ccccc2)cc1Oc1cc(C#N)ccc1-c1ccc(C(N)C(=O)O)cn1] | 2-amino-2-[6-[4-cyano-2-(2-methyl-5-phenylpyrazol-3-yl)oxyphenyl]pyridin-3-yl]acetic acid |

TABLE 1-continued
| Compound number | Structural formula | Compound name |
|---|---|---|
| 429 | 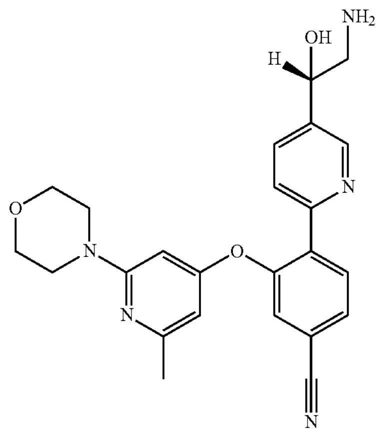 [SMILES: Cc1cc(Oc2cc(C#N)ccc2-c2ccc([C@H](O)CN)cn2)cc(N2CCOCC2)n1] | 4-[5-[(1S)-2-amino-1-hydroxyethyl]pyridin-2-yl]-3-(2-methyl-6-morpholin-4-ylpyridin-4-yl)oxybenzonitrile |
| 430 | 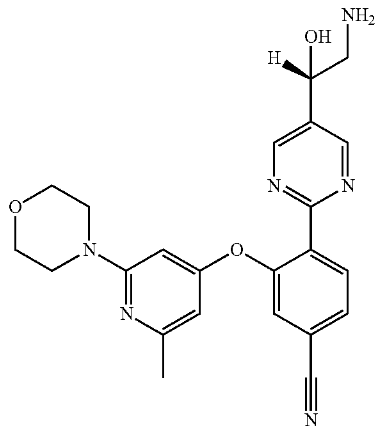 [SMILES: Cc1cc(Oc2cc(C#N)ccc2-c2ncc([C@H](O)CN)cn2)cc(N2CCOCC2)n1] | 4-[5-[(1S)-2-amino-1-hydroxyethyl]pyrimidin-2-yl]-3-(2-methyl-6-morpholin-4-ylpyridin-4-yl)oxybenzonitrile |
| 431 | 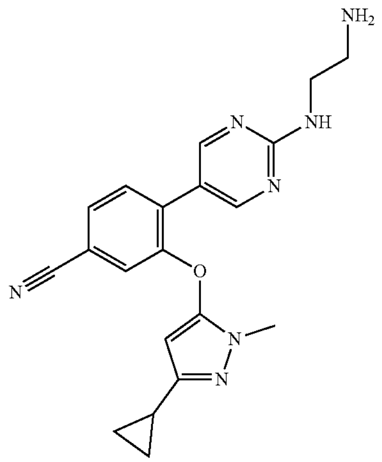 [SMILES: Cn1nc(C2CC2)cc1Oc1cc(C#N)ccc1-c1cnc(NCCN)nc1] | 4-[2-(2-aminoethylamino)pyrimidin-5-yl]-3-(5-cyclopropyl-2-methylpyrazol-3-yl)oxybenzonitrile |

TABLE 1-continued
| Compound number | Structural formula | Compound name |
|---|---|---|
| 432 | 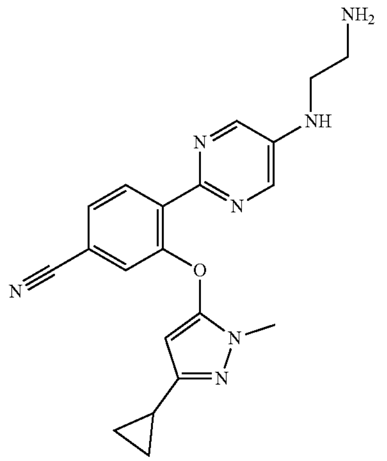 [SMILES: Cn1nc(C2CC2)cc1Oc1cc(C#N)ccc1-c1ncc(NCCN)cn1] | 4-[5-(2-aminoethylamino)pyrimidin-2-yl]-3-(5-cyclopropyl-2-methylpyrazol-3-yl)oxybenzonitrile |
| 433 | 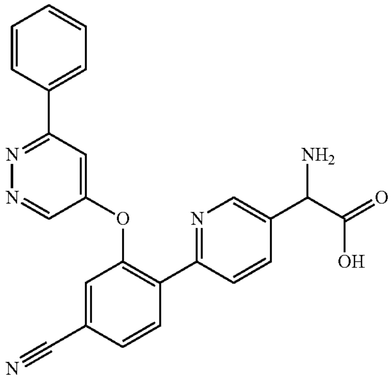 [SMILES: N#Cc1ccc(-c2ccc(C(N)C(=O)O)cn2)c(Oc2cnnc(-c3ccccc3)c2)c1] | 2-amino-2-[6-[4-cyano-2-(6-phenylpyridazin-4-yl)oxyphenyl]pyridin-3-yl]acetic acid |
| 434 | 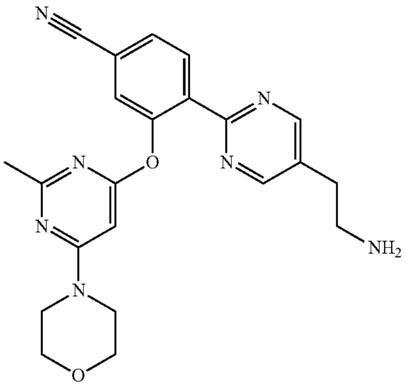 [SMILES: Cc1nc(Oc2cc(C#N)ccc2-c2ncc(CCN)cn2)cc(N2CCOCC2)n1] | 4-[5-(2-aminoethyl)pyrimidin-2-yl]-3-(2-methyl-6-morpholin-4-ylpyrimidin-4-yl)oxybenzonitrile |

TABLE 1-continued
| Compound number | Structural formula | Compound name |
|---|---|---|
| 435 | 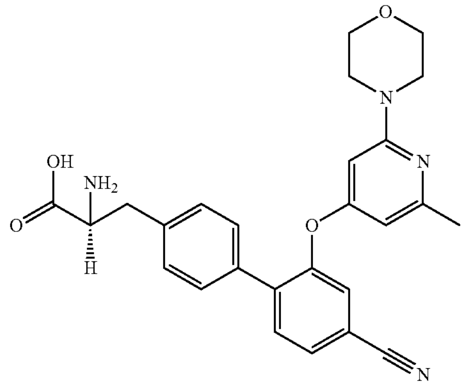 [SMILES: Cc1cc(Oc2cc(C#N)ccc2-c2ccc(C[C@H](N)C(=O)O)cc2)cc(N2CCOCC2)n1] | (2S)-2-amino-3-[4-[4-cyano-2-(2-methyl-6-morpholin-4-ylpyridin-4-yl)oxyphenyl]phenyl]propanoic acid |
| 436 | 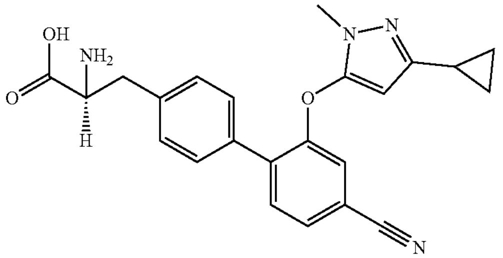 [SMILES: Cn1nc(C2CC2)cc1Oc1cc(C#N)ccc1-c1ccc(C[C@H](N)C(=O)O)cc1] | (2S)-2-amino-3-[4-[4-cyano-2-(5-cyclopropyl-2-methylpyrazol-3-yl)oxyphenyl]phenyl]propanoic acid |
| 437 | 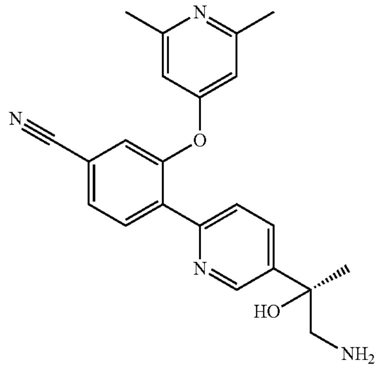 [SMILES: Cc1cc(Oc2cc(C#N)ccc2-c2ccc([C@](C)(O)CN)cn2)cc(C)n1] | 4-[5-[(1S)-2-amino-1-hydroxyethyl]pyridin-2-yl]-3-(2,6-dimethylpyridin-4-yl)oxybenzonitrile |
| 438 | 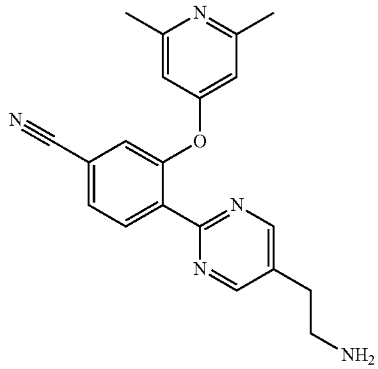 [SMILES: Cc1cc(Oc2cc(C#N)ccc2-c2ncc(CCN)cn2)cc(C)n1] | 4-[5-(2-aminoethyl)pyrimidin-2-yl]-3-(2,6-dimethylpyridin-4-yl)oxybenzonitrile |

TABLE 1-continued
| Compound number | Structural formula | Compound name |
|---|---|---|
| 439 | 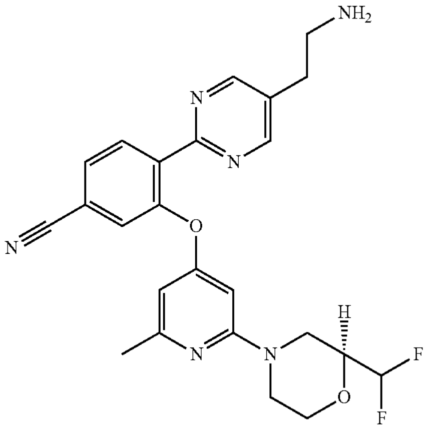 [SMILES: Cc1cc(Oc2cc(C#N)ccc2-c2ncc(CCN)cn2)cc(N2CCO[C@H](C(F)F)C2)n1] | 4-[5-(2-aminoethyl)pyrimidin-2-yl]-3-[2-[(2S)-2-(difluoromethyl)morpholin-4-yl]-6-methylpyridin-4-yl]oxybenzonitrile |
| 440 | 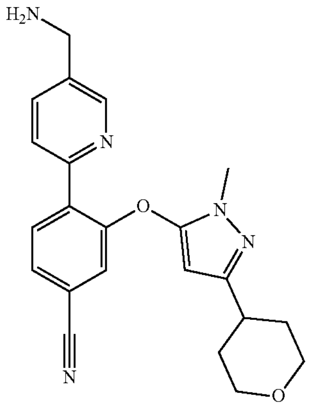 [SMILES: Cn1nc(C2CCOCC2)cc1Oc1cc(C#N)ccc1-c1ccc(CN)cn1] | 4-[5-(aminomethyl)pyridin-2-yl]-3-[2-methyl-5-(oxan-4-yl)pyrazol-3-yl]oxybenzonitrile |
| 441 | 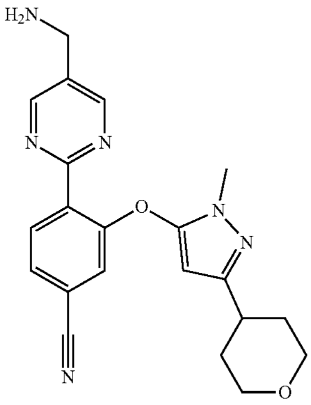 [SMILES: Cn1nc(C2CCOCC2)cc1Oc1cc(C#N)ccc1-c1ncc(CN)cn1] | 4-[5-(aminomethyl)pyrimidin-2-yl]-3-[2-methyl-5-(oxan-4-yl)pyrazol-3-yl]oxybenzonitrile |

TABLE 1-continued
| Compound number | Structural formula | Compound name |
|---|---|---|
| 442 | 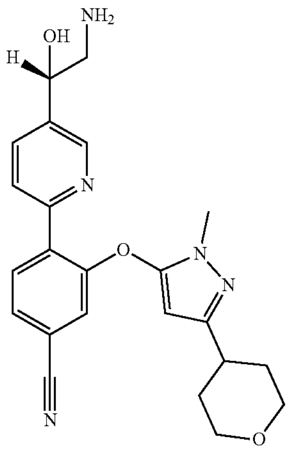 [SMILES: Cn1nc(C2CCOCC2)cc1Oc1cc(C#N)ccc1-c1ccc([C@H](O)CN)cn1] | 4-[5-[(1S)-2-amino-1-hydroxyethyl]pyridin-2-yl]-3-[2-methyl-5-(oxan-4-yl)pyrazol-3-yl]oxybenzonitrile |
| 443 | 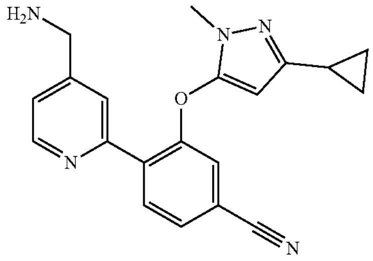 [SMILES: Cn1nc(C2CC2)cc1Oc1cc(C#N)ccc1-c1cc(CN)ccn1] | 4-[4-(aminomethyl)pyridin-2-yl]-3-(5-cyclopropyl-2-methylpyrazol-3-yl)oxybenzonitrile |
| 444 | 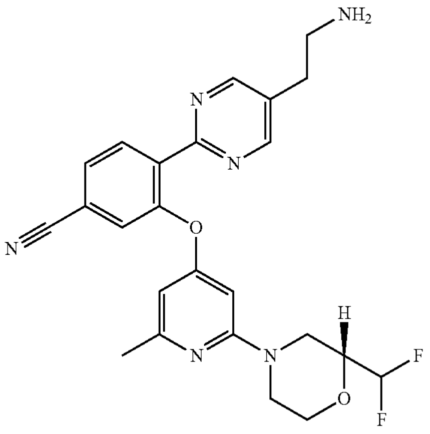 [SMILES: Cc1cc(Oc2cc(C#N)ccc2-c2ncc(CCN)cn2)cc(N2CCO[C@@H](C(F)F)C2)n1] | 4-[5-(2-aminoethyl)pyrimidin-2-yl]-3-[2-[(2R)-2-(difluoromethyl)morpholin-4-yl]-6-methylpyridin-4-yl]oxybenzonitrile |

TABLE 1-continued

| Compound number | Structural formula | Compound name |
|---|---|---|
| 445 | 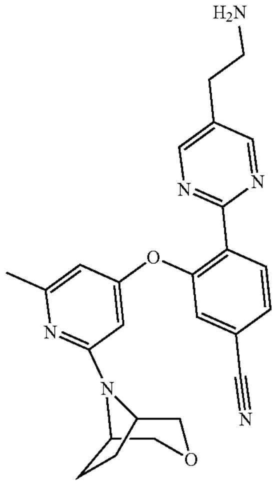 [SMILES: Cc1cc(Oc2cc(C#N)ccc2-c2ncc(CCN)cn2)cc(N2C3CCC2COC3)n1] | 4-[5-(2-aminoethyl)pyrimidin-2-yl]-3-[2-methyl-6-(3-oxa-8-azabicyclo[3.2.1]octan-8-yl)pyridin-4-yl]oxybenzonitrile |
| 446 | 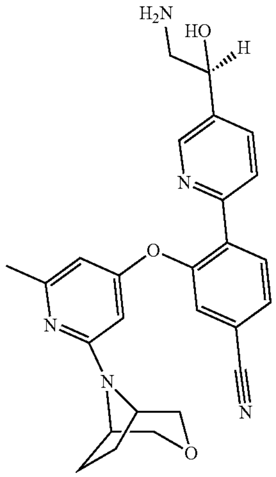 [SMILES: Cc1cc(Oc2cc(C#N)ccc2-c2ccc([C@H](O)CN)cn2)cc(N2C3CCC2COC3)n1] | 4-[5-[(1S)-2-amino-1-hydroxyethyl]pyridin-2-yl]-3-[2-methyl-6-(3-oxa-8-azabicyclo[3.2.1]octan-8-yl)pyridin-4-yl]oxybenzonitrile |
| 447 | 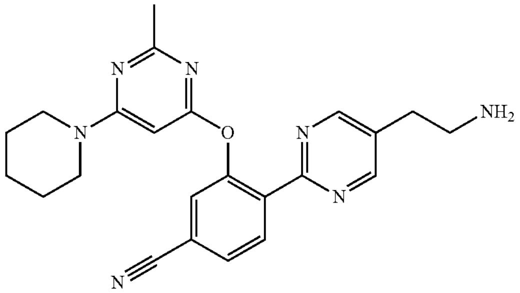 | 4-[5-(2-aminoethyl)pyrimidin-2-yl]-3-(2-methyl-6-piperidin-1-ylpyrimidin-4-yl)oxybenzonitrile |
| 448 | 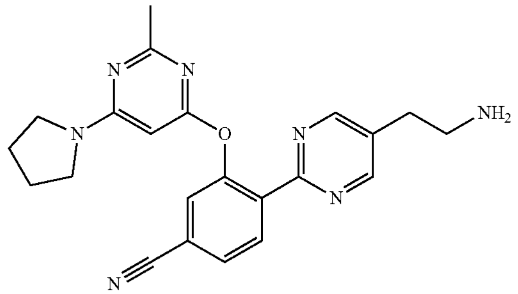 [SMILES: Cc1nc(Oc2cc(C#N)ccc2-c2ncc(CCN)cn2)cc(N2CCCC2)n1] | 4-[5-(2-aminoethyl)pyrimidin-2-yl]-3-(2-methyl-6-pyrrolidin-1-ylpyrimidin-4-yl)oxybenzonitrile |

TABLE 1-continued
| Compound number | Structural formula | Compound name |
| --- | --- | --- |
| 449 | 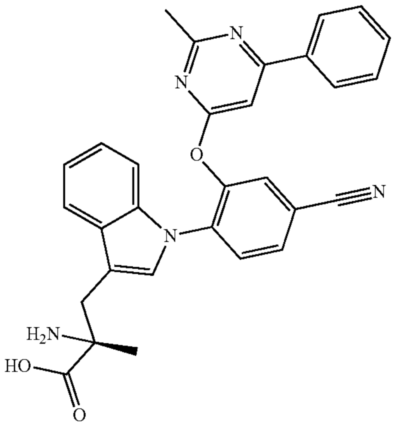 [SMILES: Cc1nc(Oc2cc(C#N)ccc2-n2cc(C[C@@](C)(N)C(=O)O)c3ccccc32)cc(-c2ccccc2)n1] | 2-amino-3-[1-[4-cyano-2-(2-methyl-6-phenylpyrimidin-4-yl)oxyphenyl]indol-3-yl]propanoic acid |
| 450 | 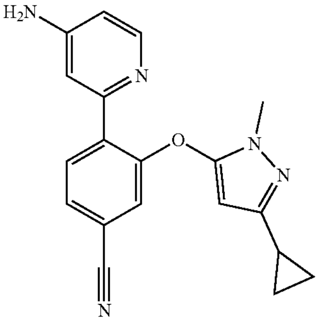 [SMILES: Cn1nc(C2CC2)cc1Oc1cc(C#N)ccc1-c1cc(N)ccn1] | 4-(4-aminopyridin-2-yl)-3-(5-cyclopropyl-2-methylpyrazol-3-yl)oxybenzonitrile |
| 451 | 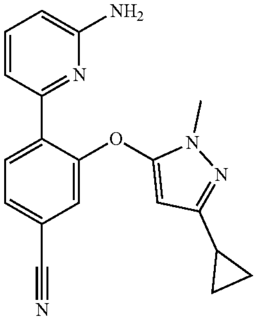 [SMILES: Cn1nc(C2CC2)cc1Oc1cc(C#N)ccc1-c1cccc(N)n1] | 4-(6-aminopyridin-2-yl)-3-(5-cyclopropyl-2-methylpyrazol-3-yl)oxybenzonitrile |
| 452 | 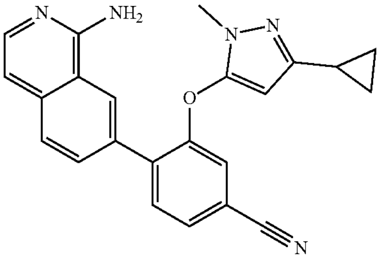 [SMILES: Cn1nc(C2CC2)cc1Oc1cc(C#N)ccc1-c1ccc2ccnc(N)c2c1] | 4-(1-aminoisoquinolin-7-yl)-3-(5-cyclopropyl-2-methylpyrazol-3-yl)oxybenzonitrile |

TABLE 1-continued

| Compound number | Structural formula | Compound name |
|---|---|---|
| 453 | 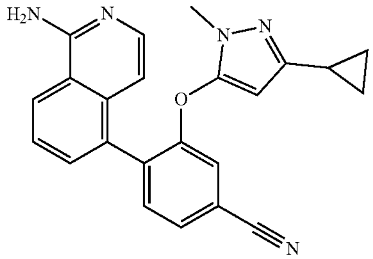 [SMILES: Cn1nc(C2CC2)cc1Oc1cc(C#N)ccc1-c1cccc2c(N)nccc12] | 4-(1-aminoisoquinolin-5-yl)-3-(5-cyclopropyl-2-methylpyrazol-3-yl)oxybenzonitrile |
| 454 | 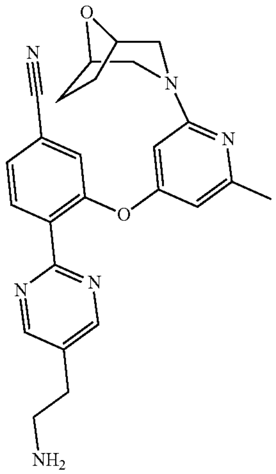 [SMILES: Cc1cc(Oc2cc(C#N)ccc2-c2ncc(CCN)cn2)cc(N2CC3CCC(C2)O3)n1] | 4-[5-(2-aminoethyl)pyrimidin-2-yl]-3-[2-methyl-6-(8-oxa-3-azabicyclo[3.2.1]octan-3-yl)pyridin-4-yl]oxybenzonitrile |
| 455 | 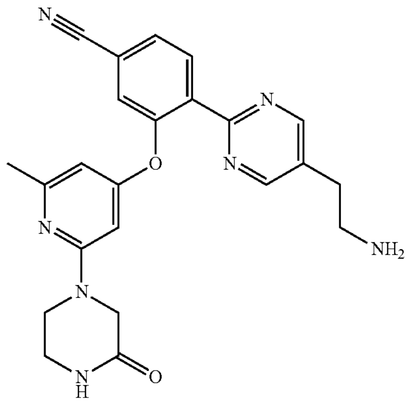 [SMILES: Cc1cc(Oc2cc(C#N)ccc2-c2ncc(CCN)cn2)cc(N2CCNC(=O)C2)n1] | 4-[5-(2-aminoethyl)pyrimidin-2-yl]-3-[2-methyl-6-(3-oxopiperazin-1-yl)pyridin-4-yl]oxybenzonitrile |
| 456 | 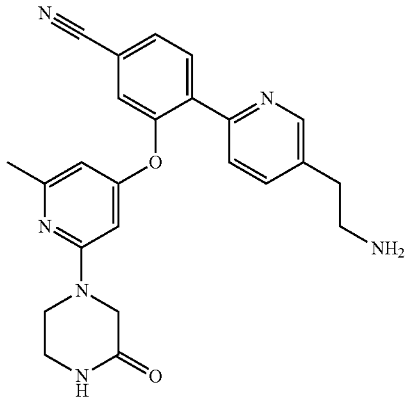 [SMILES: Cc1cc(Oc2cc(C#N)ccc2-c2ccc(CCN)cn2)cc(N2CCNC(=O)C2)n1] | 4-[5-(2-aminoethyl)pyridin-2-yl]-3-[2-methyl-6-(3-oxopiperazin-1-yl)pyridin-4-yl]oxybenzonitrile |

TABLE 1-continued

| Compound number | Structural formula | Compound name |
|---|---|---|
| 457 | 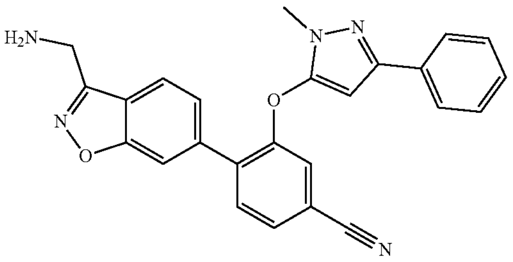 [SMILES: Cn1nc(-c2ccccc2)cc1Oc1cc(C#N)ccc1-c1ccc2c(CN)noc2c1] | 4-[3-(aminomethyl)-1,2-benzoxazol-6-yl]-3-(2-methyl-5-phenylpyrazol-3-yl)oxybenzonitrile |
| 458 | 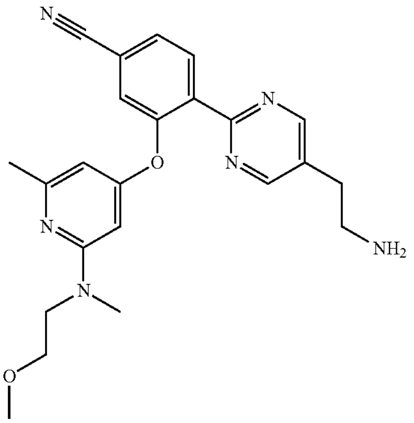 [SMILES: COCCN(C)c1cc(Oc2cc(C#N)ccc2-c2ncc(CCN)cn2)cc(C)n1] | 4-[5-(2-aminoethyl)pyrimidin-2-yl]-3-[2-[2-methoxyethyl(methyl)amino]-6-methylpyridin-4-yl]oxybenzonitrile |
| 459 | 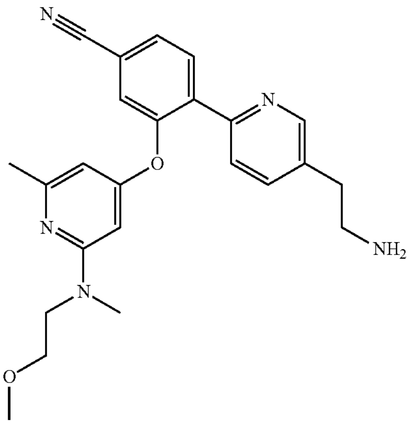 [SMILES: COCCN(C)c1cc(Oc2cc(C#N)ccc2-c2ccc(CCN)cn2)cc(C)n1] | 4-[5-(2-aminoethyl)pyridin-2-yl]-3-[2-[2-methoxyethyl(methyl)amino]-6-methylpyridin-4-yl]oxybenzonitrile |
| 460 | 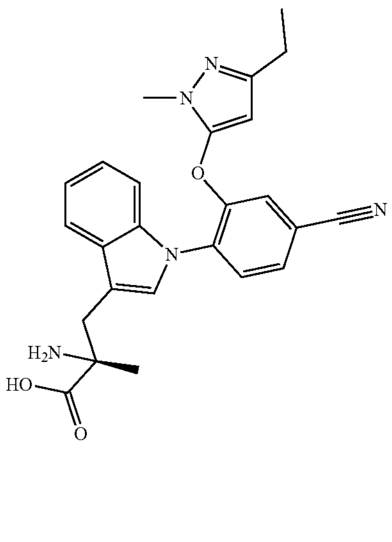 [SMILES: CCc1cc(Oc2cc(C#N)ccc2-n2cc(C[C@@](C)(N)C(=O)O)c3ccccc32)n(C)n1] | 2-amino-3-[1-[4-cyano-2-(5-ethyl-2-methylpyrazol-3-yl)oxyphenyl]indol-3-yl]propanoic acid |

TABLE 1-continued

| Compound number | Structural formula | Compound name |
|---|---|---|
| 461 | 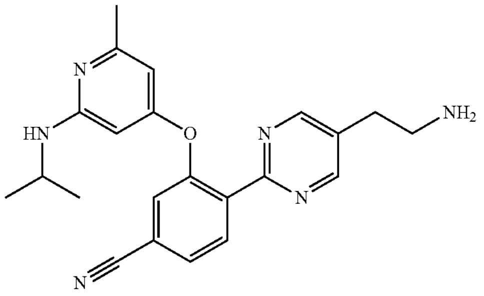 [SMILES: Cc1cc(Oc2cc(C#N)ccc2-c2ncc(CCN)cn2)cc(NC(C)C)n1] | 4-[5-(2-aminoethyl)pyrimidin-2-yl]-3-[2-methyl-6-(propan-2-ylamino)pyridin-4-yl]oxybenzonitrile |
| 462 | 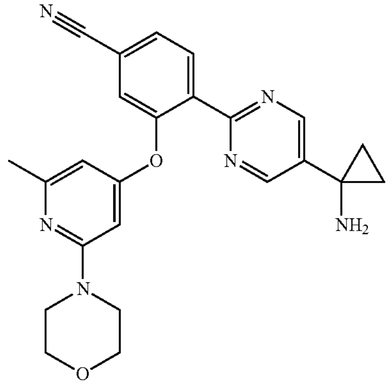 [SMILES: Cc1cc(Oc2cc(C#N)ccc2-c2ncc(C3(N)CC3)cn2)cc(N2CCOCC2)n1] | 4-[5-(1-aminocyclopropyl)pyrimidin-2-yl]-3-(2-methyl-6-morpholin-4-ylpyridin-4-yl)oxybenzonitrile |
| 463 | 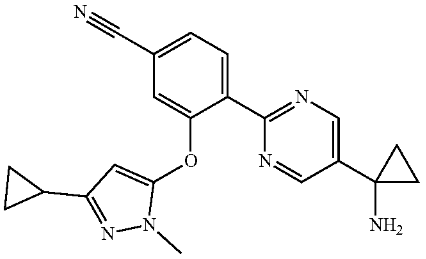 [SMILES: Cn1nc(C2CC2)cc1Oc1cc(C#N)ccc1-c1ncc(C2(N)CC2)cn1] | 4-[5-(1-aminocyclopropyl)pyrimidin-2-yl]-3-(5-cyclopropyl-2-methylpyrazol-3-yl)oxybenzonitrile |
| 464 | 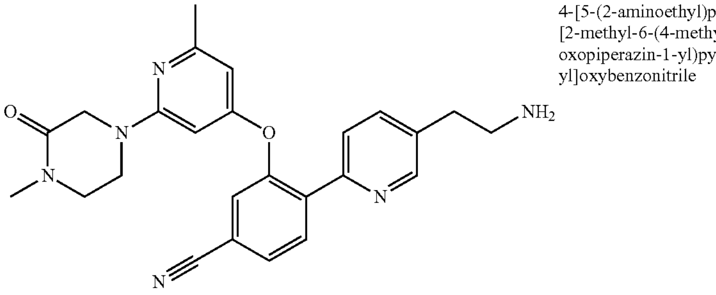 | 4-[5-(2-aminoethyl)pyridin-2-yl]-3-[2-methyl-6-(4-methyl-3-oxopiperazin-1-yl)pyridin-4-yl]oxybenzonitrile |
| 465 | 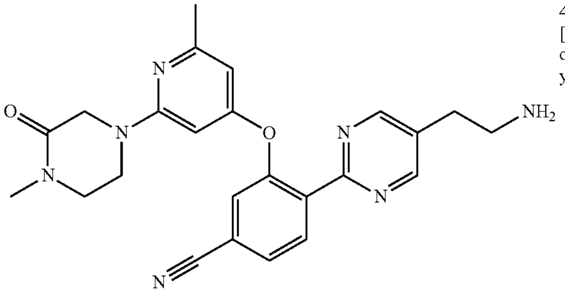 | 4-[5-(2-aminoethyl)pyrimidin-2-yl]-3-[2-methyl-6-(4-methyl-3-oxopiperazin-1-yl)pyridin-4-yl]oxybenzonitrile |

TABLE 1-continued

| Compound number | Structural formula | Compound name |
|---|---|---|
| 466 | 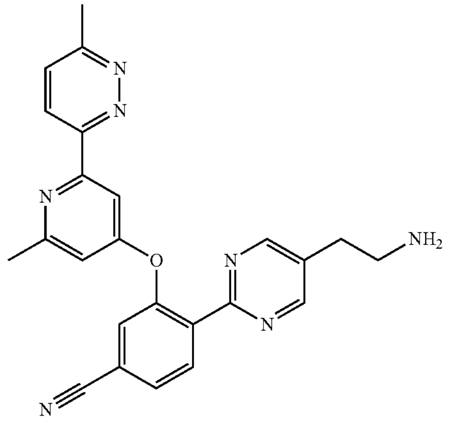 [SMILES: Cc1ccc(-c2cc(Oc3cc(C#N)ccc3-c3ncc(CCN)cn3)cc(C)n2)nn1] | 4-[5-(2-aminoethyl)pyrimidin-2-yl]-3-[2-methyl-6-(6-methylpyridazin-3-yl)pyridin-4-yl]oxybenzonitrile |
| 467 | 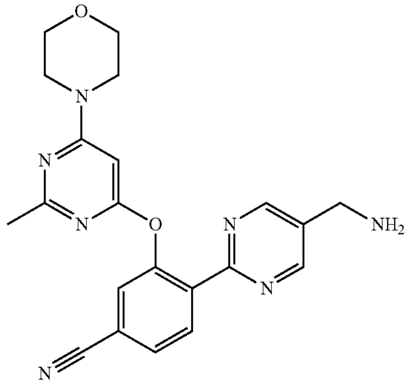 [SMILES: Cc1nc(Oc2cc(C#N)ccc2-c2ncc(CN)cn2)cc(N2CCOCC2)n1] | 4-[5-(aminomethyl)pyrimidin-2-yl]-3-(2-methyl-6-morpholin-4-ylpyrimidin-4-yl)oxybenzonitrile |
| 468 | 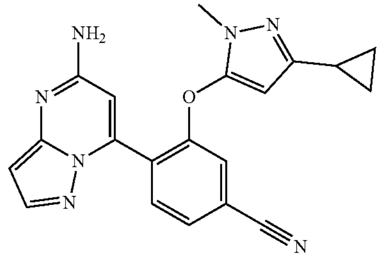 [SMILES: Cn1nc(C2CC2)cc1Oc1cc(C#N)ccc1-c1cc(N)nc2ccnn12] | 4-(5-aminopyrazolo[1,5-a]pyrimidin-7-yl)-3-(5-cyclopropyl-2-methylpyrazol-3-yl)oxybenzonitrile |
| 469 | 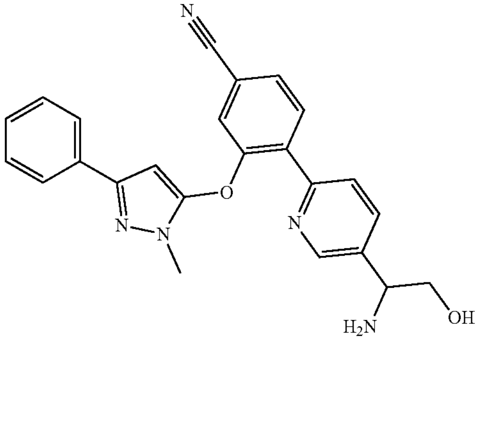 [SMILES: Cn1nc(-c2ccccc2)cc1Oc1cc(C#N)ccc1-c1ccc(C(N)CO)cn1] | 4-[5-(1-amino-2-hydroxyethyl)pyridin-2-yl]-3-(2-methyl-5-phenylpyrazol-3-yl)oxybenzonitrile |

TABLE 1-continued

| Compound number | Structural formula | Compound name |
| --- | --- | --- |
| 470 | 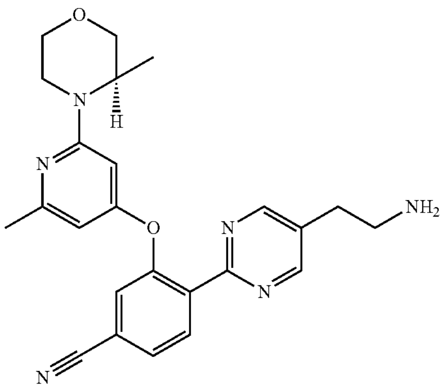 [SMILES: Cc1cc(Oc2cc(C#N)ccc2-c2ncc(CCN)cn2)cc(N2CCOC[C@H]2C)n1] | 4-[5-(2-aminoethyl)pyrimidin-2-yl]-3-[2-methyl-6-[(3R)-3-methylmorpholin-4-yl]pyridin-4-yl]oxybenzonitrile |
| 471 | 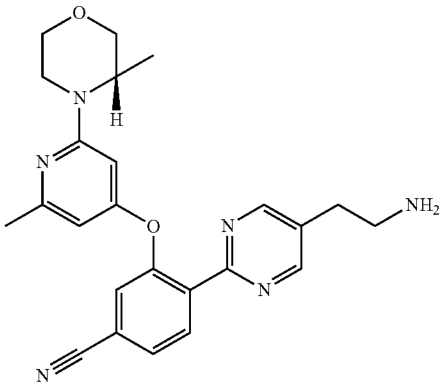 [SMILES: Cc1cc(Oc2cc(C#N)ccc2-c2ncc(CCN)cn2)cc(N2CCOC[C@@H]2C)n1] | 4-[5-(2-aminoethyl)pyrimidin-2-yl]-3-[2-methyl-6-[(3S)-3-methylmorpholin-4-yl]pyridin-4-yl]oxybenzonitrile |
| 472 | 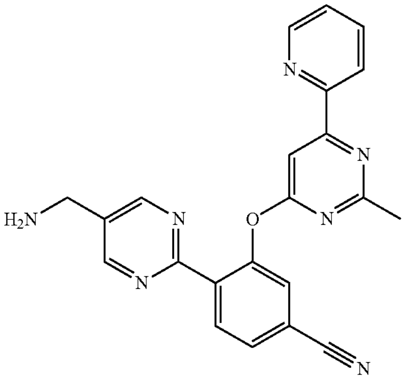 [SMILES: Cc1nc(Oc2cc(C#N)ccc2-c2ncc(CN)cn2)cc(-c2ccccn2)n1] | 4-[5-(aminomethyl)pyrimidin-2-yl]-3-(2-methyl-6-pyridin-2-ylpyrimidin-4-yl)oxybenzonitrile |
| 473 | 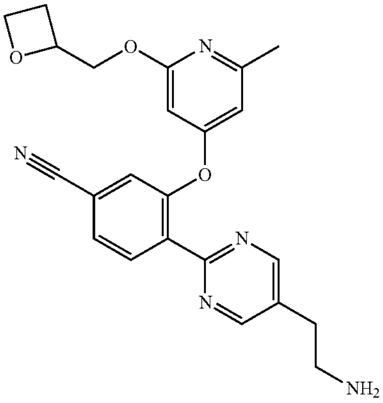 [SMILES: Cc1cc(Oc2cc(C#N)ccc2-c2ncc(CCN)cn2)cc(OCC2CCO2)n1] | 4-[5-(2-aminoethyl)pyrimidin-2-yl]-3-[2-methyl-6-(oxetan-2-ylmethoxy)pyridin-4-yl]oxybenzonitrile |

TABLE 1-continued

| Compound number | Structural formula | Compound name |
|---|---|---|
| 474 | 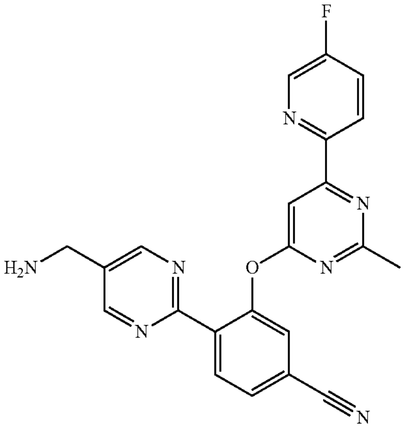 [SMILES: Cc1nc(Oc2cc(C#N)ccc2-c2ncc(CN)cn2)cc(-c2ccc(F)cn2)n1] | 4-[5-(aminomethyl)pyrimidin-2-yl]-3-[6-(5-fluoropyridin-2-yl)-2-methylpyrimidin-4-yl]oxybenzonitrile |
| 475 | 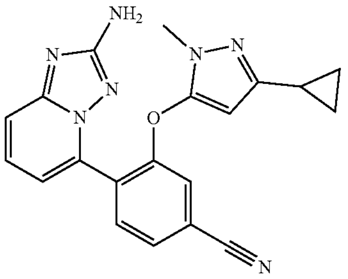 [SMILES: Cn1nc(C2CC2)cc1Oc1cc(C#N)ccc1-c1cccc2nc(N)nn12] | 4-(2-amino-[1,2,4]triazolo[1,5-a]pyridin-5-yl)-3-(5-cyclopropyl-2-methylpyrazol-3-yl)oxybenzonitrile |
| 476 | 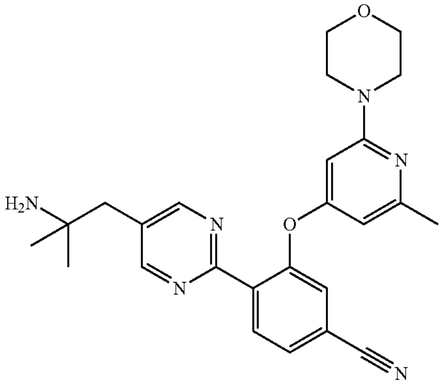 [SMILES: Cc1cc(Oc2cc(C#N)ccc2-c2ncc(CC(C)(C)N)cn2)cc(N2CCOCC2)n1] | 4-[5-(2-amino-2-methylpropyl)pyrimidin-2-yl]-3-(2-methyl-6-morpholin-4-ylpyridin-4-yl)oxybenzonitrile |
| 477 | 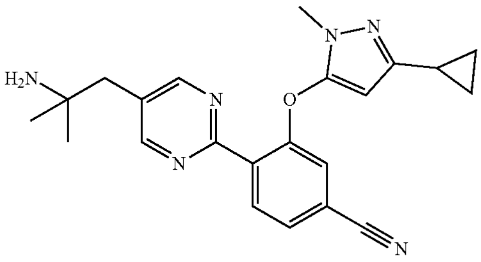 [SMILES: Cn1nc(C2CC2)cc1Oc1cc(C#N)ccc1-c1ncc(CC(C)(C)N)cn1] | 4-[5-(2-amino-2-methylpropyl)pyrimidin-2-yl]-3-(5-cyclopropyl-2-methylpyrazol-3-yl)oxybenzonitrile |

TABLE 1-continued

| Compound number | Structural formula | Compound name |
|---|---|---|
| 478 | 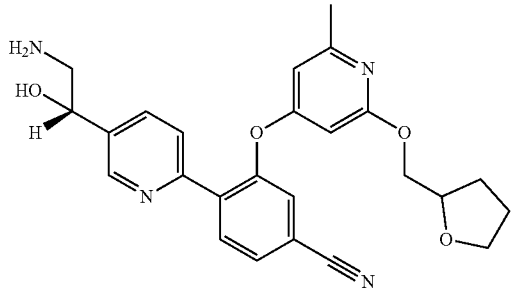 [SMILES: Cc1cc(Oc2cc(C#N)ccc2-c2ccc([C@H](O)CN)cn2)cc(OCC2CCCO2)n1] | 4-[5-[(1S)-2-amino-1-hydroxyethyl]pyridin-2-yl]-3-[2-methyl-6-(oxolan-2-ylmethoxy)pyridin-4-yl]oxybenzonitrile |
| 479 | 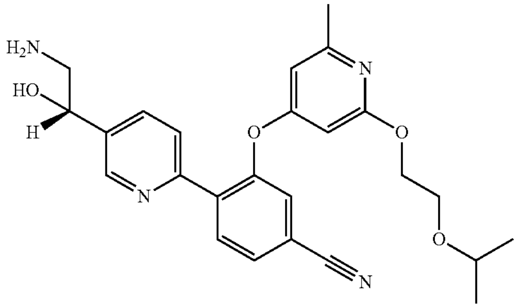 [SMILES: Cc1cc(Oc2cc(C#N)ccc2-c2ccc([C@H](O)CN)cn2)cc(OCCOC(C)C)n1] | 4-[5-[(1S)-2-amino-1-hydroxyethyl]pyridin-2-yl]-3-[2-methyl-6-(2-propan-2-yloxyethoxy)pyridin-4-yl]oxybenzonitrile |
| 480 | 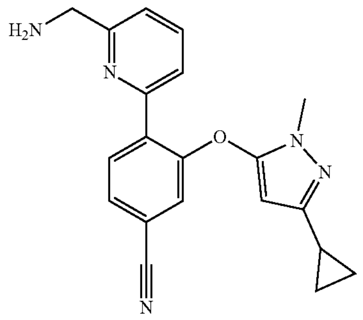 [SMILES: Cn1nc(C2CC2)cc1Oc1cc(C#N)ccc1-c1cccc(CN)n1] | 4-[6-(aminomethyl)pyridin-2-yl]-3-(5-cyclopropyl-2-methylpyrazol-3-yl)oxybenzonitrile |
| 481 | 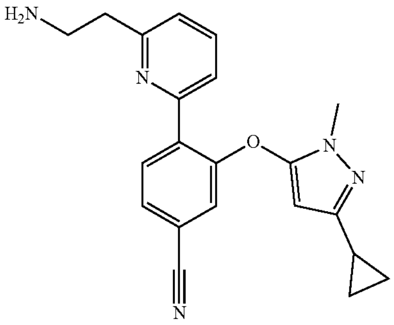 [SMILES: Cn1nc(C2CC2)cc1Oc1cc(C#N)ccc1-c1cccc(CCN)n1] | 4-[6-(2-aminoethyl)pyridin-2-yl]-3-(5-cyclopropyl-2-methylpyrazol-3-yl)oxybenzonitrile |

TABLE 1-continued
| Compound number | Structural formula | Compound name |
|---|---|---|
| 482 | 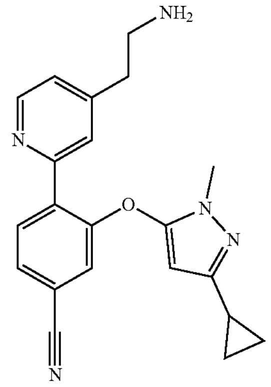 [SMILES: Cn1nc(C2CC2)cc1Oc1cc(C#N)ccc1-c1cc(CCN)ccn1] | 4-[4-(2-aminoethyl)pyridin-2-yl]-3-(5-cyclopropyl-2-methylpyrazol-3-yl)oxybenzonitrile |
| 483 | 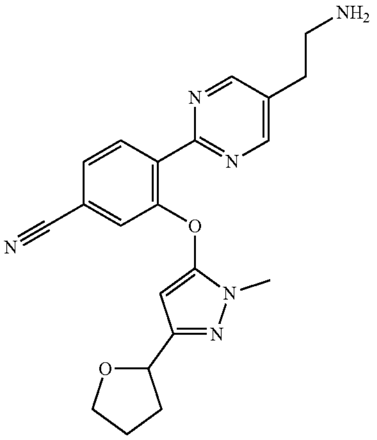 | 4-[5-(2-aminoethyl)pyrimidin-2-yl]-3-[2-methyl-5-(oxolan-2-yl)pyrazol-3-yl]oxybenzonitrile |
| 484 | 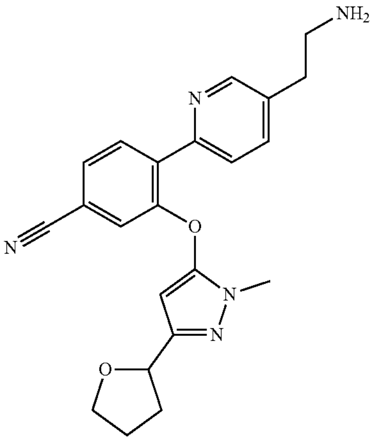 [SMILES: Cn1nc(C2CCCO2)cc1Oc1cc(C#N)ccc1-c1ccc(CCN)cn1] | 4-[5-(2-aminoethyl)pyridin-2-yl]-3-[2-methyl-5-(oxolan-2-yl)pyrazol-3-yl]oxybenzonitrile |
| 485 | 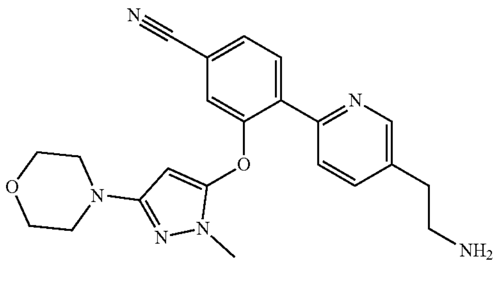 | 4-[5-(2-aminoethyl)pyridin-2-yl]-3-(2-methyl-5-morpholin-4-ylpyrazol-3-yl)oxybenzonitrile |

TABLE 1-continued
| Compound number | Structural formula | Compound name |
|---|---|---|
| 486 | 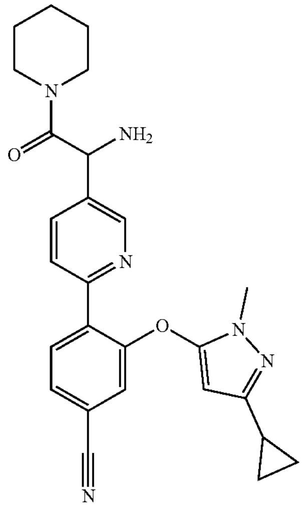 [SMILES: Cn1nc(C2CC2)cc1Oc1cc(C#N)ccc1-c1ccc(C(N)C(=O)N2CCCCC2)cn1] | 4-[5-(1-amino-2-oxo-2-piperidin-1-ylethyl)pyridin-2-yl]-3-(5-cyclopropyl-2-methylpyrazol-3-yl)oxybenzonitrile |
| 487 | 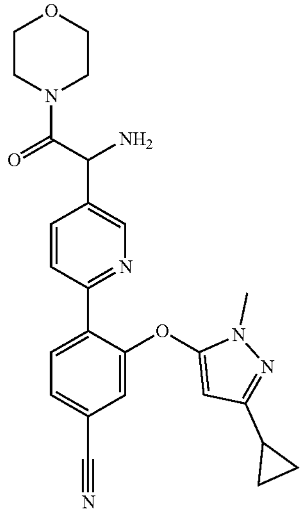 [SMILES: Cn1nc(C2CC2)cc1Oc1cc(C#N)ccc1-c1ccc(C(N)C(=O)N2CCOCC2)cn1] | 4-[5-(1-amino-2-morpholin-4-yl-2-oxoethyl)pyridin-2-yl]-3-(5-cyclopropyl-2-methylpyrazol-3-yl)oxybenzonitrile |
| 488 | 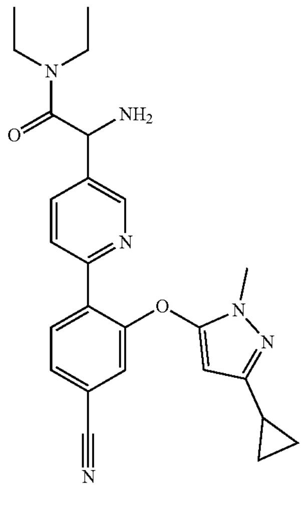 [SMILES: CCN(CC)C(=O)C(N)c1ccc(-c2ccc(C#N)cc2Oc2cc(C3CC3)nn2C)nc1] | 2-amino-2-[6-[4-cyano-2-(5-cyclopropyl-2-methylpyrazol-3-yl)oxyphenyl]pyridin-3-yl]-N,N-diethylacetamide |

TABLE 1-continued
| Compound number | Structural formula | Compound name |
|---|---|---|
| 489 | 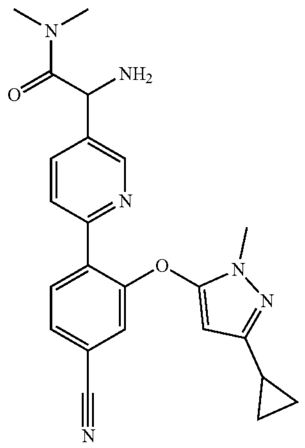 [SMILES: CN(C)C(=O)C(N)c1ccc(-c2ccc(C#N)cc2Oc2cc(C3CC3)nn2C)nc1] | 2-amino-2-[6-[4-cyano-2-(5-cyclopropyl-2-methylpyrazol-3-yl)oxyphenyl]pyridin-3-yl]-N,N-dimethylacetamide |
| 490 | 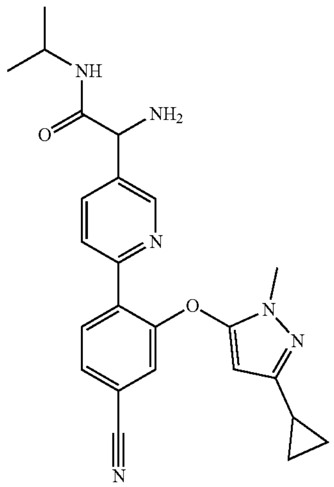 [SMILES: CC(C)NC(=O)C(N)c1ccc(-c2ccc(C#N)cc2Oc2cc(C3CC3)nn2C)nc1] | 2-amino-2-[6-[4-cyano-2-(5-cyclopropyl-2-methylpyrazol-3-yl)oxyphenyl]pyridin-3-yl]-N-propan-2-ylacetamide |
| 491 | 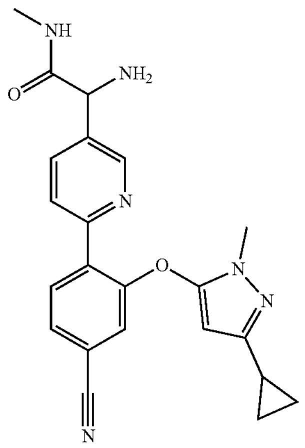 [SMILES: CNC(=O)C(N)c1ccc(-c2ccc(C#N)cc2Oc2cc(C3CC3)nn2C)nc1] | 2-amino-2-[6-[4-cyano-2-(5-cyclopropyl-2-methylpyrazol-3-yl)oxyphenyl]pyridin-3-yl]-N-methylacetamide |

TABLE 1-continued

| Compound number | Structural formula | Compound name |
|---|---|---|
| 492 | 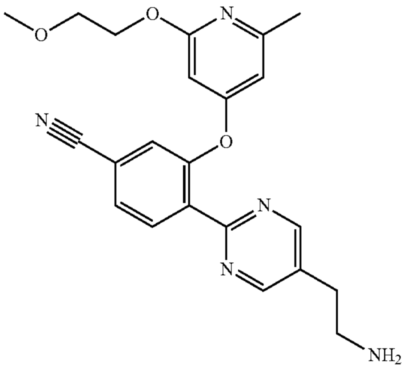 [SMILES: COCCOc1cc(Oc2cc(CN)ccc2-c2ncc(CCN)cn2)cc(C)n1] | 4-[5-(2-aminoethyl)pyrimidin-2-yl]-3-[2-(2-methoxyethoxy)-6-methylpyridin-4-yl]oxybenzonitrile |
| 493 | 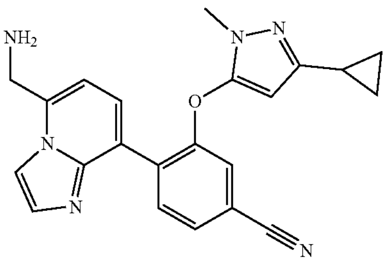 [SMILES: Cn1nc(C2CC2)cc1Oc1cc(C#N)ccc1-c1ccc(CN)n2ccnc12] | 4-[5-(aminomethyl)imidazo[1,2-a]pyridin-8-yl]-3-(5-cyclopropyl-2-methylpyrazol-3-yl)oxybenzonitrile |
| 494 | 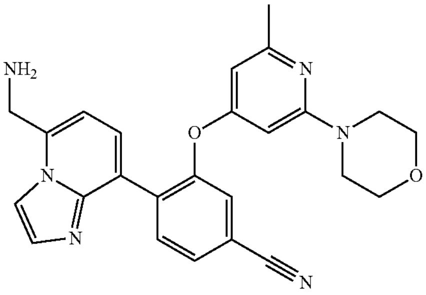 [SMILES: Cc1cc(Oc2cc(C#N)ccc2-c2ccc(CN)n3ccnc23)cc(N2CCOCC2)n1] | 4-[5-(aminomethyl)imidazo[1,2-a]pyridin-8-yl]-3-(2-methyl-6-morpholin-4-ylpyridin-4-yl)oxybenzonitrile |
| 495 | 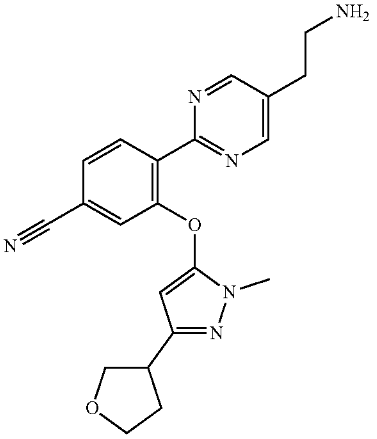 [SMILES: Cn1nc(C2CCOC2)cc1Oc1cc(C#N)ccc1-c1ncc(CCN)cn1] | 4-[5-(2-aminoethyl)pyrimidin-2-yl]-3-[2-methyl-5-(oxolan-3-yl)pyrazol-3-yl]oxybenzonitrile |

TABLE 1-continued
| Compound number | Structural formula | Compound name |
|---|---|---|
| 496 | 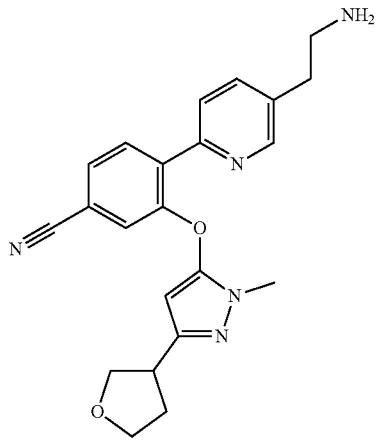 [SMILES: Cn1nc(C2CCOC2)cc1Oc1cc(C#N)ccc1-c1ccc(CCN)cn1] | 4-[5-(2-aminoethyl)pyridin-2-yl]-3-[2-methyl-5-(oxolan-3-yl)pyrazol-3-yl]oxybenzonitrile |
| 497 | 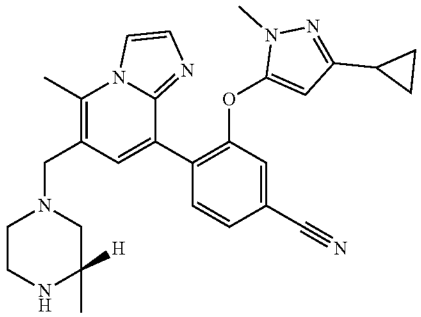 [SMILES: Cc1c(CN2CCN[C@@H](C)C2)cc(-c2ccc(C#N)cc2Oc2cc(C3CC3)nn2C)c2nccn12] | 3-(5-cyclopropyl-2-methylpyrazol-3-yl)oxy-4-[5-methyl-6-[[(3S)-3-methylpiperazin-1-yl]methyl]imidazo[1,2-a]pyridin-8-yl]benzonitrile |
| 498 | 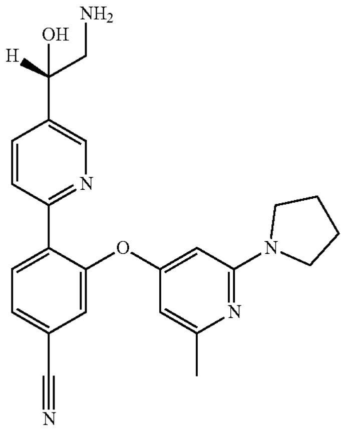 | 4-[5-[(1S)-2-amino-1-hydroxyethyl]pyridin-2-yl]-3-(2-methyl-6-pyrrolidin-1-ylpyridin-4-yl)oxybenzonitrile |

TABLE 1-continued
| Compound number | Structural formula | Compound name |
|---|---|---|
| 499 | 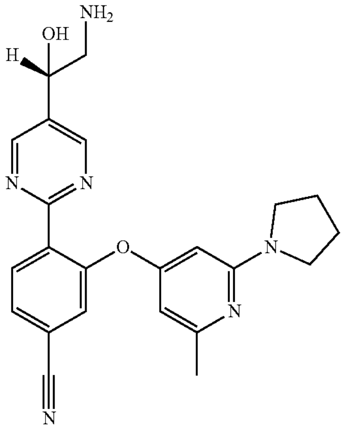 [SMILES: Cc1cc(Oc2cc(C#N)ccc2-c2ncc([C@H](O)CN)cn2)cc(N2CCCC2)n1] | 4-[5-[(1S)-2-amino-1-hydroxyethyl]pyrimidin-2-yl]-3-(2-methyl-6-pyrrolidin-1-ylpyridin-4-yl)oxybenzonitrile |
| 500 | 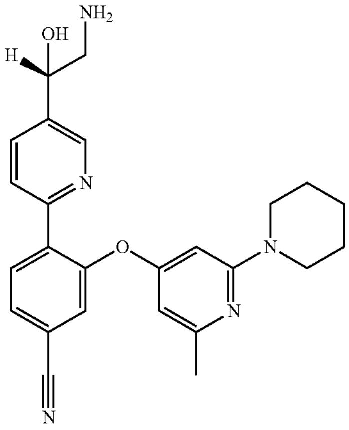 [SMILES: Cc1cc(Oc2cc(C#N)ccc2-c2ccc([C@H](O)CN)cn2)cc(N2CCCCC2)n1] | 4-[5-[(1S)-2-amino-1-hydroxyethyl]pyridin-2-yl]-3-(2-methyl-6-piperidin-1-ylpyridin-4-yl)oxybenzonitrile |
| 501 | 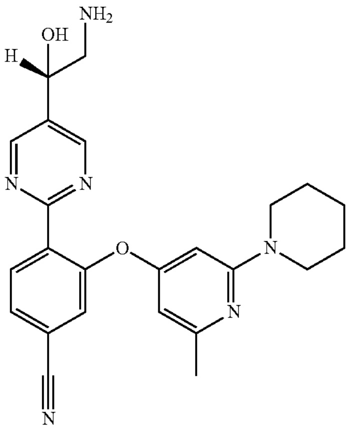 [SMILES: Cc1cc(Oc2cc(C#N)ccc2-c2ncc([C@H](O)CN)cn2)cc(N2CCCCC2)n1] | 4-[5-[(1S)-2-amino-1-hydroxyethyl]pyrimidin-2-yl]-3-(2-methyl-6-piperidin-1-ylpyridin-4-yl)oxybenzonitrile |

TABLE 1-continued
| Compound number | Structural formula | Compound name |
|---|---|---|
| 502 | 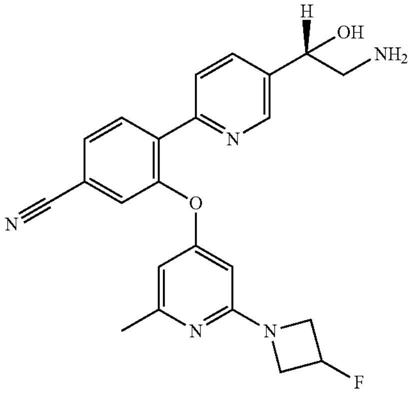 [SMILES: Cc1cc(Oc2cc(C#N)ccc2-c2ccc([C@H](O)CN)cn2)cc(N2CC(F)C2)n1] | 4-[5-[(1S)-2-amino-1-hydroxyethyl]pyridin-2-yl]-3-[2-(3-fluoroazetidin-1-yl)-6-methylpyridin-4-yl]oxybenzonitrile |
| 503 | 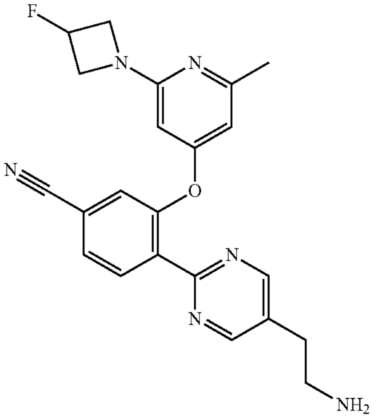 [SMILES: Cc1cc(Oc2cc(C#N)ccc2-c2ncc(CCN)cn2)cc(N2CC(F)C2)n1] | 4-[5-(2-aminoethyl)pyrimidin-2-yl]-3-[2-(3-fluoroazetidin-1-yl)-6-methylpyridin-4-yl]oxybenzonitrile |
| 504 | 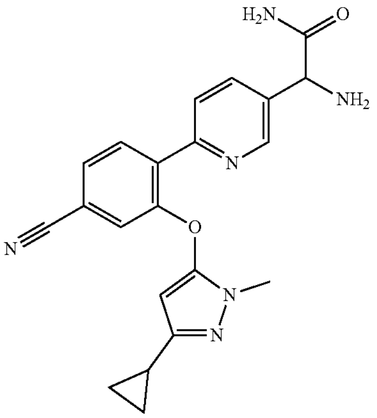 | 2-amino-2-[6-[4-cyano-2-(5-cyclopropyl-2-methylpyrazol-3-yl)oxyphenyl]pyridin-3-yl]acetamide |

TABLE 1-continued
| Compound number | Structural formula | Compound name |
| --- | --- | --- |
| 505 | 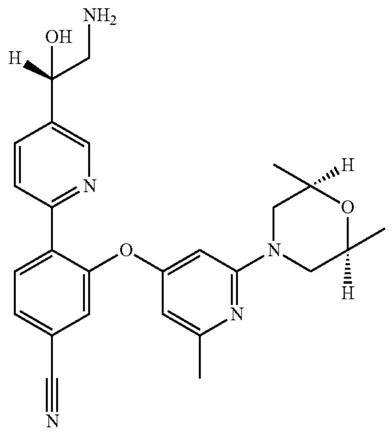 [SMILES: Cc1cc(Oc2cc(C#N)ccc2-c2ccc([C@H](O)CN)cn2)cc(N2C[C@@H](C)O[C@@H](C)C2)n1] | 4-[5-[(1S)-2-amino-1-hydroxyethyl]pyridin-2-yl]-3-[2-[(2S,6R)-2,6-dimethylmorpholin-4-yl]-6-methylpyridin-4-yl]oxybenzonitrile |
| 506 | 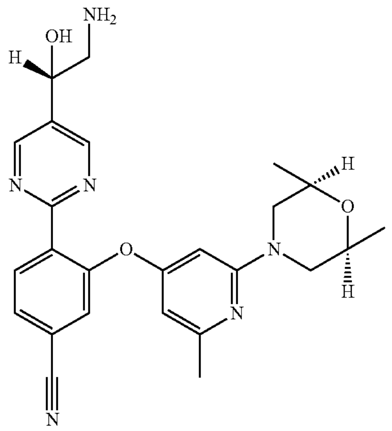 [SMILES: Cc1cc(Oc2cc(C#N)ccc2-c2ncc([C@H](O)CN)cn2)cc(N2C[C@@H](C)O[C@@H](C)C2)n1] | 4-[5-[(1S)-2-amino-1-hydroxyethyl]pyrimidin-2-yl]-3-[2-[(2S,6R)-2,6-dimethylmorpholin-4-yl]-6-methylpyridin-4-yl]oxybenzonitrile |
| 507 | 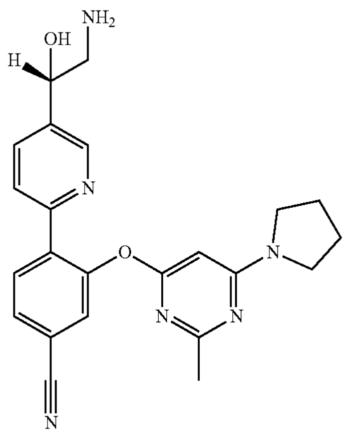 | 4-[5-[(1S)-2-amino-1-hydroxyethyl]pyridin-2-yl]-3-(2-methyl-6-pyrrolidin-1-ylpyrimidin-4-yl)oxybenzonitrile |

TABLE 1-continued
| Compound number | Structural formula | Compound name |
| --- | --- | --- |
| 508 | 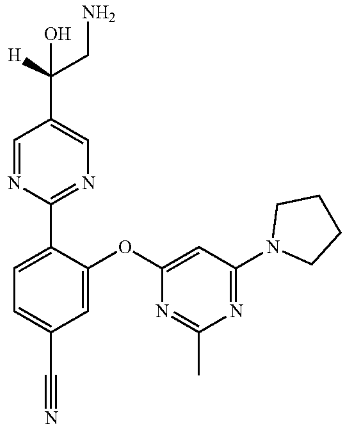 [SMILES: Cc1nc(Oc2cc(C#N)ccc2-c2ncc([C@H](O)CN)cn2)cc(N2CCCC2)n1] | 4-[5-[(1S)-2-amino-1-hydroxyethyl]pyrimidin-2-yl]-3-(2-methyl-6-pyrrolidin-1-ylpyrimidin-4-yl)oxybenzonitrile |
| 509 | 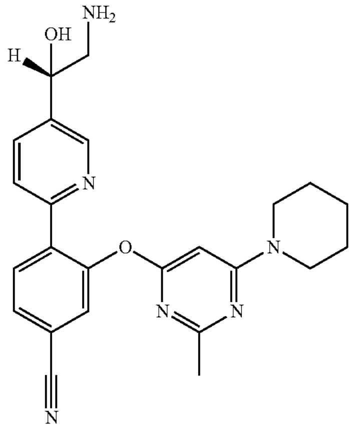 [SMILES: Cc1nc(Oc2cc(C#N)ccc2-c2ccc([C@H](O)CN)cn2)cc(N2CCCCC2)n1] | 4-[5-[(1S)-2-amino-1-hydroxyethyl]pyridin-2-yl]-3-(2-methyl-6-piperidin-1-ylpyrimidin-4-yl)oxybenzonitrile |
| 510 | 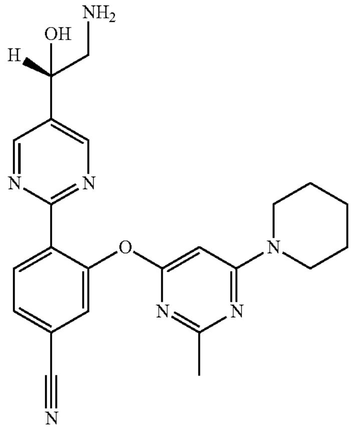 [SMILES: Cc1nc(Oc2cc(C#N)ccc2-c2ncc([C@H](O)CN)cn2)cc(N2CCCCC2)n1] | 4-[5-[(1S)-2-amino-1-hydroxyethyl]pyrimidin-2-yl]-3-(2-methyl-6-piperidin-1-ylpyrimidin-4-yl)oxybenzonitrile |

TABLE 1-continued

| Compound number | Structural formula | Compound name |
|---|---|---|
| 511 | 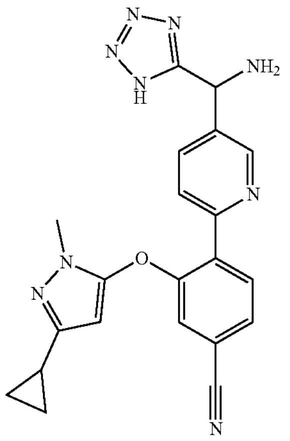 [SMILES: Cn1nc(C2CC2)cc1Oc1cc(C#N)ccc1-c1ccc(C(N)c2nnn[nH]2)cn1] | 4-[5-[amino(1H-tetrazol-5-yl)methyl]pyridin-2-yl]-3-(5-cyclopropyl-2-methylpyrazol-3-yl)oxybenzonitrile |
| 512 | 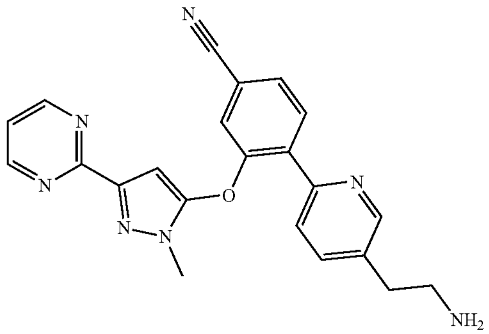 [SMILES: Cn1nc(-c2ncccn2)cc1Oc1cc(C#N)ccc1-c1ccc(CCN)cn1] | 4-[5-(2-aminoethyl)pyridin-2-yl]-3-(2-methyl-5-pyrimidin-2-ylpyrazol-3-yl)oxybenzonitrile |
| 513 | 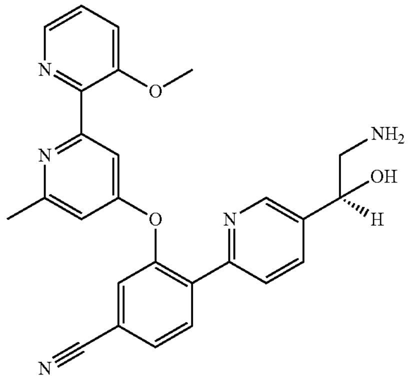 [SMILES: COc1cccnc1-c1cc(Oc2cc(C#N)ccc2-c2ccc([C@H](O)CN)cn2)cc(C)n1] | 4-[5-[(1S)-2-amino-1-hydroxyethyl]pyridin-2-yl]-3-[2-(3-methoxypyridin-2-yl)-6-methylpyridin-4-yl]oxybenzonitrile |
| 514 | 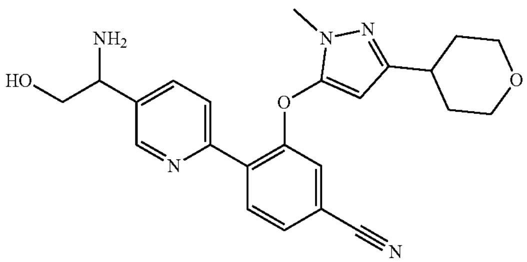 [SMILES: Cn1nc(C2CCOCC2)cc1Oc1cc(C#N)ccc1-c1ccc(C(N)CO)cn1] | 4-[5-(1-amino-2-hydroxyethyl)pyridin-2-yl]-3-[2-methyl-5-(oxan-4-yl)pyrazol-3-yl]oxybenzonitrile |

TABLE 1-continued

| Compound number | Structural formula | Compound name |
|---|---|---|
| 515 | 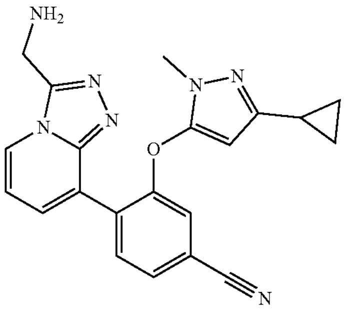 [SMILES: Cn1nc(C2CC2)cc1Oc1cc(C#N)ccc1-c1cccn2c(CN)nnc12] | 4-[3-(aminomethyl)-[1,2,4]triazolo[4,3-a]pyridin-8-yl]-3-(5-cyclopropyl-2-methylpyrazol-3-yl)oxybenzonitrile |
| 516 | 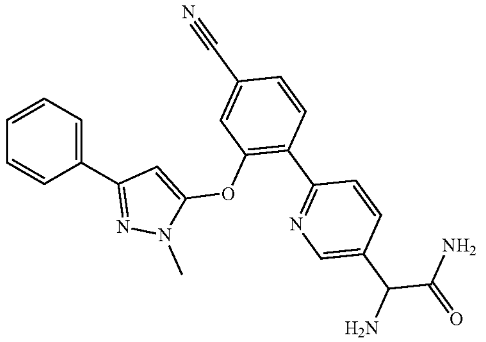 [SMILES: Cn1nc(-c2ccccc2)cc1Oc1cc(C#N)ccc1-c1ccc(C(N)C(N)=O)cn1] | 2-amino-2-[6-[4-cyano-2-(2-methyl-5-phenylpyrazol-3-yl)oxyphenyl]pyridin-3-yl]acetamide |
| 517 | 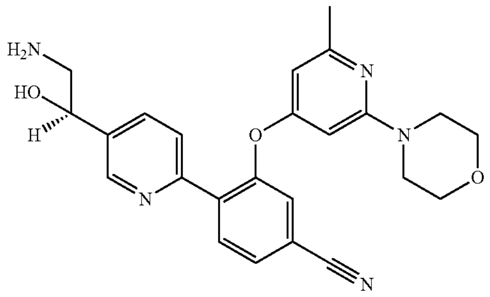 [SMILES: Cc1cc(Oc2cc(C#N)ccc2-c2ccc([C@@H](O)CN)cn2)cc(N2CCOCC2)n1] | 4-[5-[(1R)-2-amino-1-hydroxyethyl]pyridin-2-yl]-3-(2-methyl-6-morpholin-4-ylpyridin-4-yl)oxybenzonitrile |
| 518 | 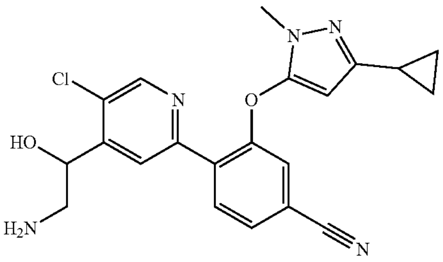 [SMILES: Cn1nc(C2CC2)cc1Oc1cc(C#N)ccc1-c1cc(C(O)CN)c(Cl)cn1] | 4-[4-(2-amino-1-hydroxyethyl)-5-chloropyridin-2-yl]-3-(5-cyclopropyl-2-methylpyrazol-3-yl)oxybenzonitrile |
| 519 | 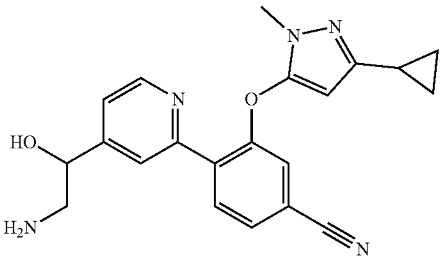 [SMILES: Cn1nc(C2CC2)cc1Oc1cc(C#N)ccc1-c1cc(C(O)CN)ccn1] | 4-[4-(2-amino-1-hydroxyethyl)pyridin-2-yl]-3-(5-cyclopropyl-2-methylpyrazol-3-yl)oxybenzonitrile |

TABLE 1-continued

| Compound number | Structural formula | Compound name |
|---|---|---|
| 520 | 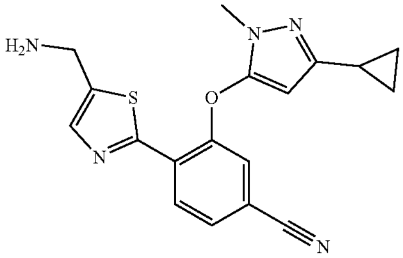 [SMILES: Cn1nc(C2CC2)cc1Oc1cc(C#N)ccc1-c1ncc(CN)s1] | 4-[5-(aminomethyl)-1,3-thiazol-2-yl]-3-(5-cyclopropyl-2-methylpyrazol-3-yl)oxybenzonitrile |
| 521 | 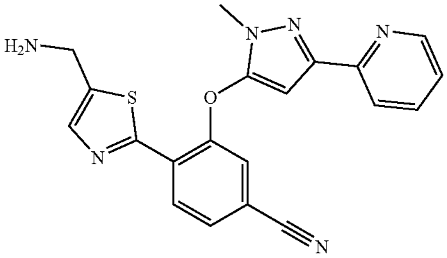 [SMILES: Cn1nc(-c2ccccn2)cc1Oc1cc(C#N)ccc1-c1ncc(CN)s1] | 4-[5-(aminomethyl)-1,3-thiazol-2-yl]-3-(2-methyl-5-pyridin-2-ylpyrazol-3-yl)oxybenzonitrile |
| 522 | 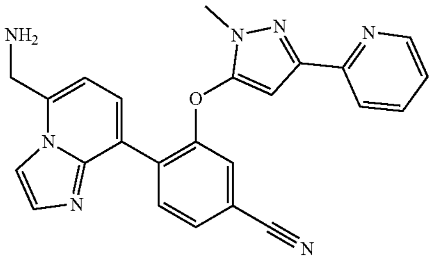 [SMILES: Cn1nc(-c2ccccn2)cc1Oc1cc(C#N)ccc1-c1ccc(CN)n2ccnc12] | 4-[5-(aminomethyl)imidazo[1,2-a]pyridin-8-yl]-3-(2-methyl-5-pyridin-2-ylpyrazol-3-yl)oxybenzonitrile |
| 523 | 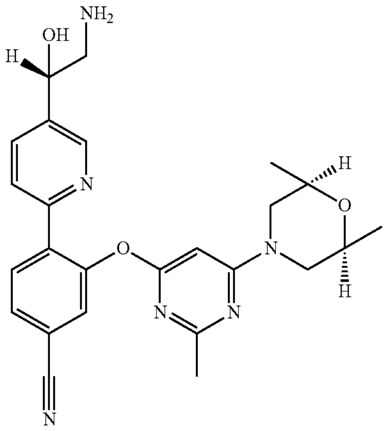 [SMILES: Cc1nc(Oc2cc(C#N)ccc2-c2ccc([C@H](O)CN)cn2)cc(N2C[C@@H](C)O[C@@H](C)C2)n1] | 4-[5-[(1S)-2-amino-1-hydroxyethyl]pyridin-2-yl]-3-[6-[(2S,6R)-2,6-dimethylmorpholin-4-yl]-2-methylpyrimidin-4-yl]oxybenzonitrile |

TABLE 1-continued

| Compound number | Structural formula | Compound name |
|---|---|---|
| 524 | 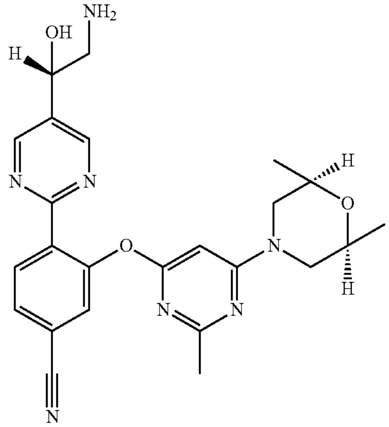 [SMILES: Cc1nc(Oc2cc(C#N)ccc2-c2ncc([C@H](O)CN)cn2)cc(N2C[C@@H](C)O[C@@H](C)C2)n1] | 4-[5-[(1S)-2-amino-1-hydroxyethyl]pyrimidin-2-yl]-3-[6-[(2S,6R)-2,6-dimethylmorpholin-4-yl]-2-methylpyrimidin-4-yl]oxybenzonitrile |
| 525 | 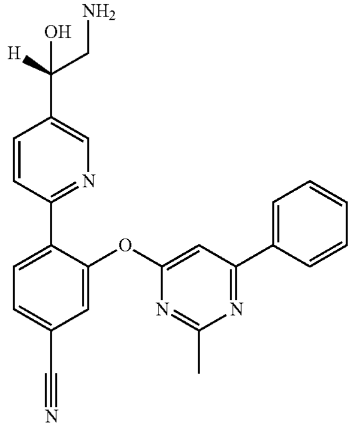 [SMILES: Cc1nc(Oc2cc(C#N)ccc2-c2ccc([C@H](O)CN)cn2)cc(-c2ccccc2)n1] | 4-[5-[(1S)-2-amino-1-hydroxyethyl]pyridin-2-yl]-3-(2-methyl-6-phenylpyrimidin-4-yl)oxybenzonitrile |
| 526 | 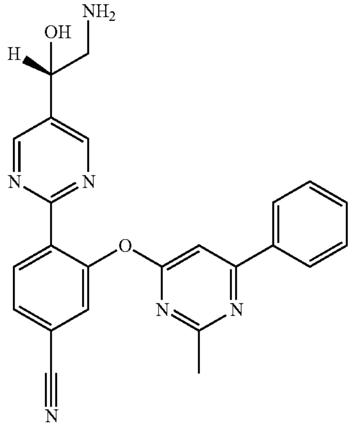 [SMILES: Cc1nc(Oc2cc(C#N)ccc2-c2ncc([C@H](O)CN)cn2)cc(-c2ccccc2)n1] | 4-[5-[(1S)-2-amino-1-hydroxyethyl]pyrimidin-2-yl]-3-(2-methyl-6-phenylpyrimidin-4-yl)oxybenzonitrile |
| 527 | 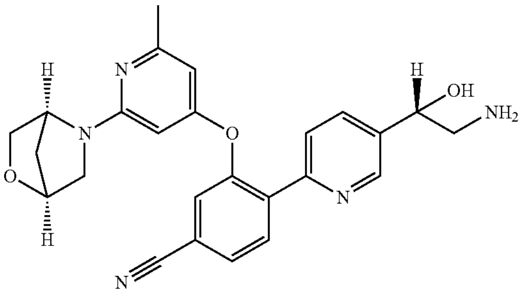 [SMILES: Cc1cc(Oc2cc(C#N)ccc2-c2ccc([C@H](O)CN)cn2)cc(N2C[C@@H]3C[C@H]2CO3)n1] | 4-[5-[(1S)-2-amino-1-hydroxyethyl]pyridin-2-yl]-3-[2-methyl-6-[(1S,4S)-2-oxa-5-azabicyclo[2.2.1]heptan-5-yl]pyridin-4-yl]oxybenzonitrile |

TABLE 1-continued

| Compound number | Structural formula | Compound name |
| --- | --- | --- |
| 528 | 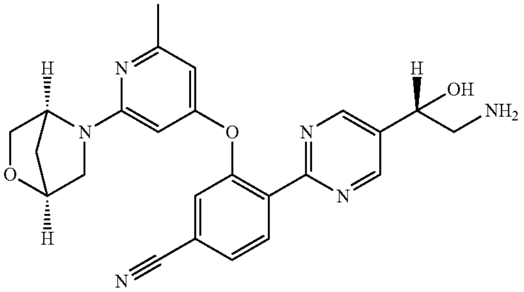 [SMILES: Cc1cc(Oc2cc(C#N)ccc2-c2ncc([C@H](O)CN)cn2)cc(N2C[C@@H]3C[C@H]2CO3)n1] | 4-[5-[(1S)-2-amino-1-hydroxyethyl]pyrimidin-2-yl]-3-[2-methyl-6-[(1S,4S)-2-oxa-5-azabicyclo[2.2.1]heptan-5-yl]pyridin-4-yl]oxybenzonitrile |
| 529 | 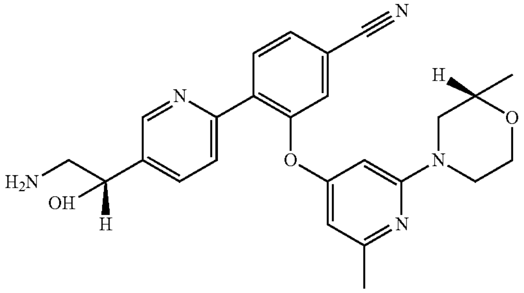 [SMILES: Cc1cc(Oc2cc(C#N)ccc2-c2ccc([C@H](O)CN)cn2)cc(N2CCO[C@@H](C)C2)n1] | 4-[5-[(1S)-2-amino-1-hydroxyethyl]pyridin-2-yl]-3-[2-methyl-6-[(2S)-2-methylmorpholin-4-yl]pyridin-4-yl]oxybenzonitrile |
| 530 | 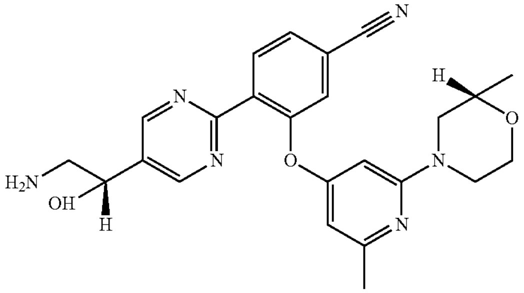 [SMILES: Cc1cc(Oc2cc(C#N)ccc2-c2ncc([C@H](O)CN)cn2)cc(N2CCO[C@@H](C)C2)n1] | 4-[5-[(1S)-2-amino-1-hydroxyethyl]pyrimidin-2-yl]-3-[2-methyl-6-[(2S)-2-methylmorpholin-4-yl]pyridin-4-yl]oxybenzonitrile |
| 531 | 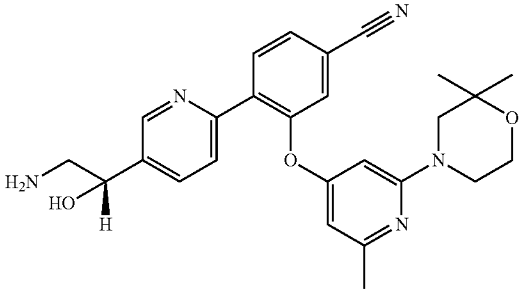 [SMILES: Cc1cc(Oc2cc(C#N)ccc2-c2ccc([C@H](O)CN)cn2)cc(N2CCOC(C)(C)C2)n1] | 4-[5-[(1S)-2-amino-1-hydroxyethyl]pyridin-2-yl]-3-[2-(2,2-dimethylmorpholin-4-yl)-6-methylpyridin-4-yl]oxybenzonitrile |
| 532 | 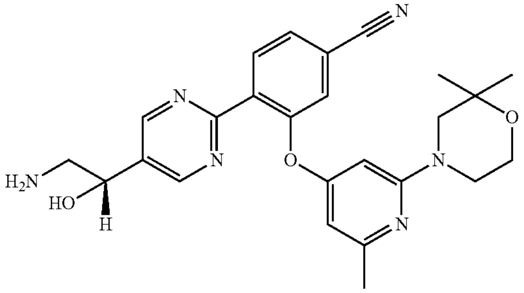 [SMILES: Cc1cc(Oc2cc(C#N)ccc2-c2ncc([C@H](O)CN)cn2)cc(N2CCOC(C)(C)C2)n1] | 4-[5-[(1S)-2-amino-1-hydroxyethyl]pyrimidin-2-yl]-3-[2-(2,2-dimethylmorpholin-4-yl)-6-methylpyridin-4-yl]oxybenzonitrile |

TABLE 1-continued

| Compound number | Structural formula | Compound name |
|---|---|---|
| 533 | 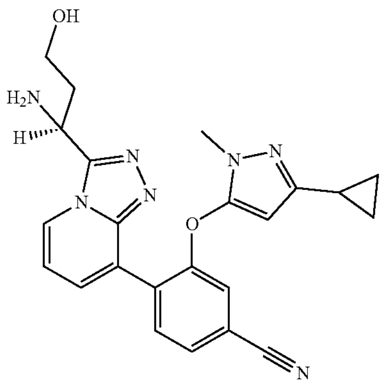 [SMILES: Cn1nc(C2CC2)cc1Oc1cc(C#N)ccc1-c1cccn2c([C@@H](N)CCO)nnc12] | 4-[3-(1-amino-3-hydroxypropyl)-[1,2,4]triazolo[4,3-a]pyridin-8-yl]-3-(5-cyclopropyl-2-methylpyrazol-3-yl)oxybenzonitrile |
| 534 | 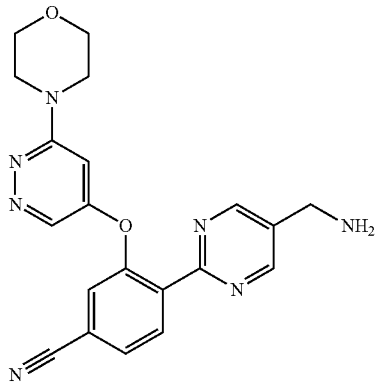 [SMILES: N#Cc1ccc(-c2ncc(CN)cn2)c(Oc2cnnc(N3CCOCC3)c2)c1] | 4-[5-(aminomethyl)pyrimidin-2-yl]-3-(6-morpholin-4-ylpyridazin-4-yl)oxybenzonitrile |
| 535 | 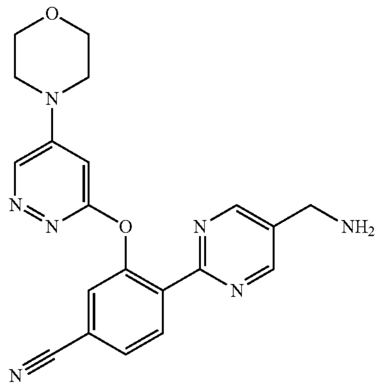 [SMILES: N#Cc1ccc(-c2ncc(CN)cn2)c(Oc2cc(N3CCOCC3)cnn2)c1] | 4-[5-(aminomethyl)pyrimidin-2-yl]-3-(5-morpholin-4-ylpyridazin-3-yl)oxybenzonitrile |
| 536 | 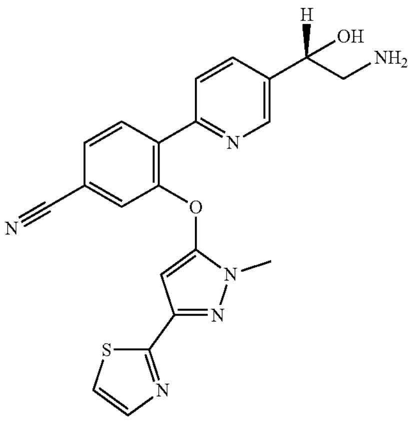 | 4-[5-[(1S)-2-amino-1-hydroxyethyl]pyridin-2-yl]-3-[2-methyl-5-(1,3-thiazol-2-yl)pyrazol-3-yl]oxybenzonitrile |

TABLE 1-continued
| Compound number | Structural formula | Compound name |
|---|---|---|
| 537 | 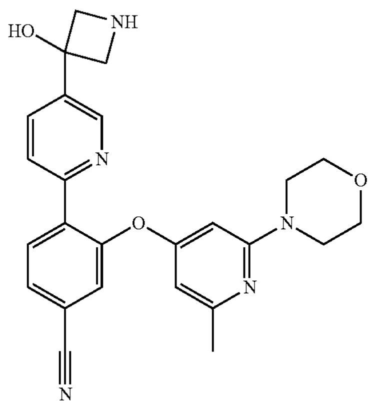 [SMILES: Cc1cc(Oc2cc(C#N)ccc2-c2ccc(C3(O)CNC3)cn2)cc(N2CCOCC2)n1] | 4-[5-(3-hydroxyazetidin-3-yl)pyridin-2-yl]-3-(2-methyl-6-morpholin-4-ylpyridin-4-yl)oxybenzonitrile |
| 538 | 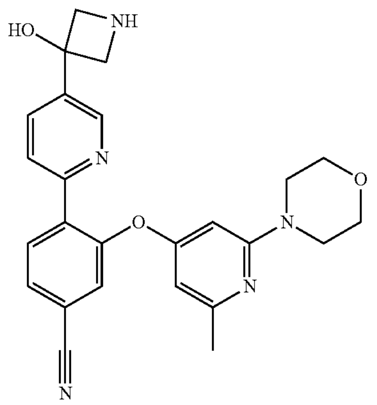 [SMILES: Cc1cc(Oc2cc(C#N)ccc2-c2ccc(C3(O)CNC3)cn2)cc(N2CCOCC2)n1] | 4-[5-(3-fluoroazetidin-3-yl)pyridin-2-yl]-3-(2-methyl-6-morpholin-4-ylpyridin-4-yl)oxybenzonitrile |
| 539 | 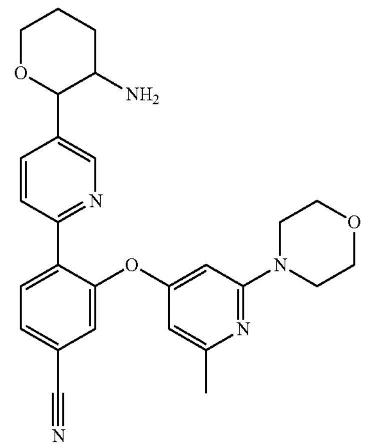 [SMILES: Cc1cc(Oc2cc(C#N)ccc2-c2ccc(C3OCCCC3N)cn2)cc(N2CCOCC2)n1] | 4-[5-(3-aminooxan-2-yl)pyridin-2-yl]-3-(2-methyl-6-morpholin-4-ylpyridin-4-yl)oxybenzonitrile |

TABLE 1-continued

| Compound number | Structural formula | Compound name |
| --- | --- | --- |
| 540 | 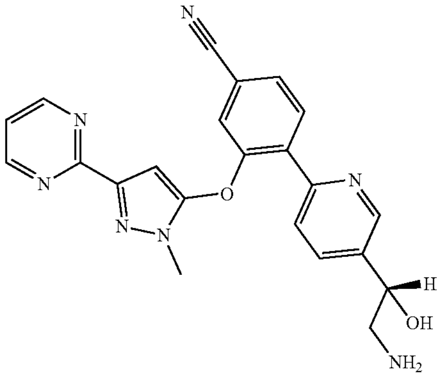 [SMILES: Cn1nc(-c2ncccn2)cc1Oc1cc(C#N)ccc1-c1ccc([C@H](O)CN)cn1] | 4-[5-[(1S)-2-amino-1-hydroxyethyl]pyridin-2-yl]-3-(2-methyl-5-pyrimidin-2-ylpyrazol-3-yl)oxybenzonitrile |
| 541 | 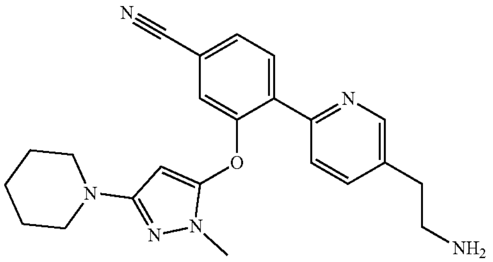 [SMILES: Cn1nc(N2CCCCC2)cc1Oc1cc(C#N)ccc1-c1ccc(CCN)cn1] | 4-[5-(2-aminoethyl)pyridin-2-yl]-3-(2-methyl-5-piperidin-1-ylpyrazol-3-yl)oxybenzonitrile |
| 542 | 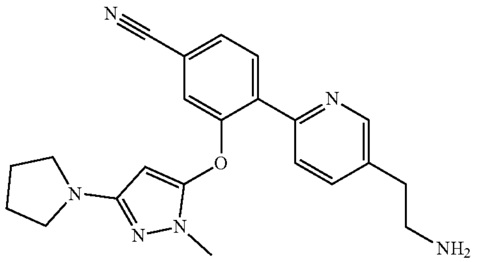 [SMILES: Cn1nc(N2CCCC2)cc1Oc1cc(C#N)ccc1-c1ccc(CCN)cn1] | 4-[5-(2-aminoethyl)pyridin-2-yl]-3-(2-methyl-5-pyrrolidin-1-ylpyrazol-3-yl)oxybenzonitrile |
| 543 | 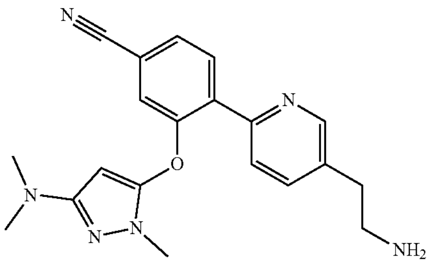 [SMILES: CN(C)c1cc(Oc2cc(C#N)ccc2-c2ccc(CCN)cn2)n(C)n1] | 4-[5-(2-aminoethyl)pyridin-2-yl]-3-[5-(dimethylamino)-2-methylpyrazol-3-yl]oxybenzonitrile |
| 544 | 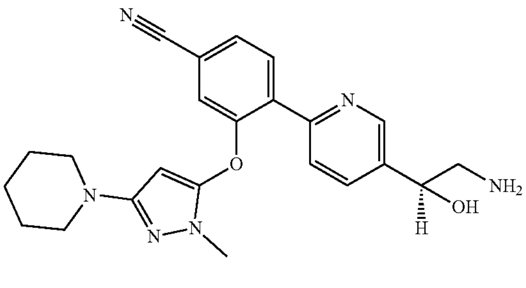 [SMILES: Cn1nc(N2CCCCC2)cc1Oc1cc(C#N)ccc1-c1ccc([C@H](O)CN)cn1] | 4-[5-[(1S)-2-amino-1-hydroxyethyl]pyridin-2-yl]-3-(2-methyl-5-pipeddin-1-ylpyrazol-3-yl)oxybenzonitrile |

TABLE 1-continued

| Compound number | Structural formula | Compound name |
| --- | --- | --- |
| 545 | 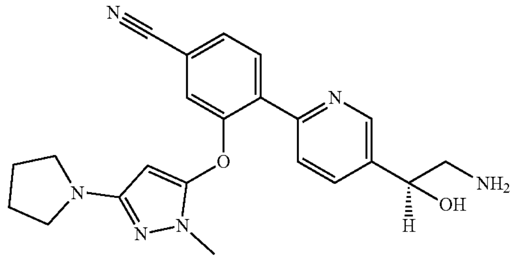 [SMILES: Cn1nc(N2CCCC2)cc1Oc1cc(C#N)ccc1-c1ccc([C@H](O)CN)cn1] | 4-[5-[(1S)-2-amino-1-hydroxyethyl]pyridin-2-yl]-3-(2-methyl-5-pyrrolidin-1-ylpyrazol-3-yl)oxybenzonitrile |
| 546 | 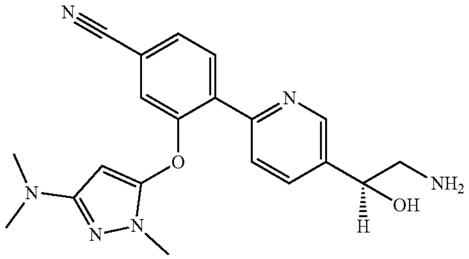 [SMILES: CN(C)c1cc(Oc2cc(C#N)ccc2-c2ccc([C@H](O)CN)cn2)n(C)n1] | 4-[5-[(1S)-2-amino-1-hydroxyethyl]pyridin-2-yl]-3-[5-(dimethylamino)-2-methylpyrazol-3-yl]oxybenzonitrile |
| 547 | 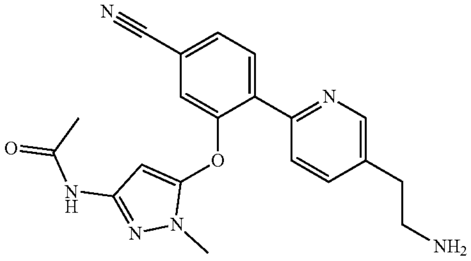 [SMILES: CC(=O)Nc1cc(Oc2cc(C#N)ccc2-c2ccc(CCN)cn2)n(C)n1] | N-[5-[2-[5-(2-aminoethyl)pyridin-2-yl]-5-cyanophenoxy]-1-methylpyrazol-3-yl]acetamide |
| 548 | 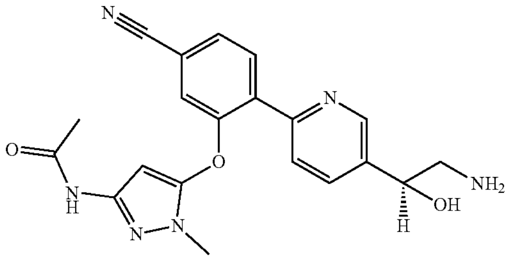 [SMILES: CC(=O)Nc1cc(Oc2cc(C#N)ccc2-c2ccc([C@H](O)CN)cn2)n(C)n1] | N-[5-[2-[5-[(1S)-2-amino-1-hydroxyethyl]pyridin-2-yl]-5-cyanophenoxy]-1-methylpyrazol-3-yl]acetamide |
| 549 | 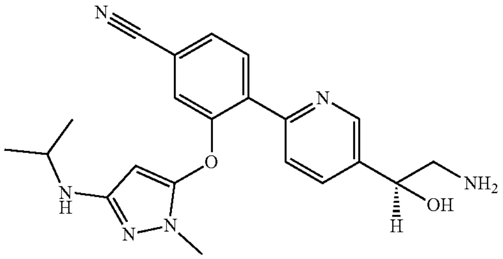 [SMILES: CC(C)Nc1cc(Oc2cc(C#N)ccc2-c2ccc([C@H](O)CN)cn2)n(C)n1] | 4-[5-[(1S)-2-amino-1-hydroxyethyl]pyridin-2-yl]-3-[2-methyl-5-(propan-2-ylamino)pyrazol-3-yl]oxybenzonitrile |

TABLE 1-continued
| Compound number | Structural formula | Compound name |
| --- | --- | --- |
| 550 | 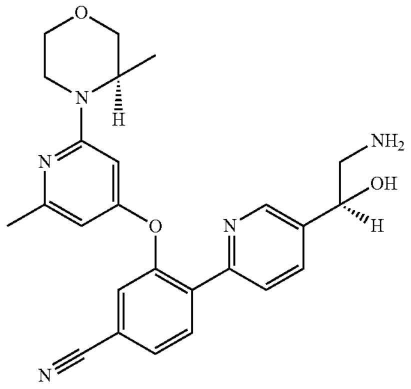 [SMILES: Cc1cc(Oc2cc(C#N)ccc2-c2ccc([C@H](O)CN)cn2)cc(N2CCOC[C@H]2C)n1] | 4-[5-[(1S)-2-amino-1-hydroxyethyl]pyridin-2-yl]-3-[2-methyl-6-[(3R)-3-methylmorpholin-4-yl]pyridin-4-yl]oxybenzonitrile |
| 551 | 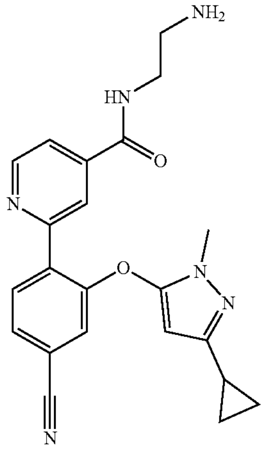 [SMILES: Cn1nc(C2CC2)cc1Oc1cc(C#N)ccc1-c1cc(C(=O)NCCN)ccn1] | N-(2-aminoethyl)-2-[4-cyano-2-(5-cyclopropyl-2-methylpyrazol-3-yl)oxyphenyl]pyridine-4-carboxamide |
| 552 | 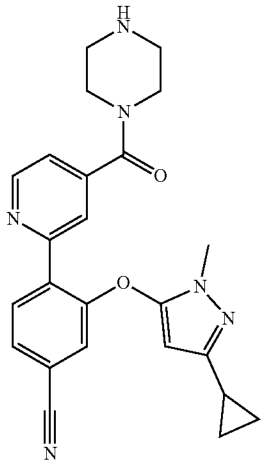 [SMILES: Cn1nc(C2CC2)cc1Oc1cc(C#N)ccc1-c1cc(C(=O)N2CCNCC2)ccn1] | 3-(5-cyclopropyl-2-methylpyrazol-3-yl)oxy-4-[4-(piperazine-1-carbonyl)pyridin-2-yl]benzonitrile |

TABLE 1-continued
| Compound number | Structural formula | Compound name |
|---|---|---|
| 553 | 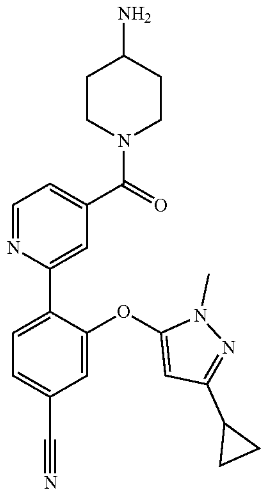 [SMILES: Cn1nc(C2CC2)cc1Oc1cc(C#N)ccc1-c1cc(C(=O)N2CCC(N)CC2)ccn1] | 4-[4-(4-aminopiperidine-1-carbonyl)pyridin-2-yl]-3-(5-cyclopropyl-2-methylpyrazol-3-yl)oxybenzonitrile |
| 554 | 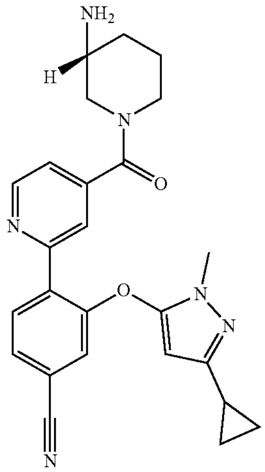 [SMILES: Cn1nc(C2CC2)cc1Oc1cc(C#N)ccc1-c1cc(C(=O)N2CCC[C@@H](N)C2)ccn1] | 4-[4-[(3R)-3-aminopiperidine-1-carbonyl]pyridin-2-yl]-3-(5-cyclopropyl-2-methylpyrazol-3-yl)oxybenzonitrile |
| 555 | 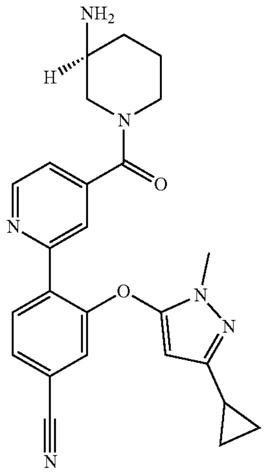 [SMILES: Cn1nc(C2CC2)cc1Oc1cc(C#N)ccc1-c1cc(C(=O)N2CCC[C@H](N)C2)ccn1] | 4-[4-[(3S)-3-aminopiperidine-1-carbonyl]pyridin-2-yl]-3-(5-cyclopropyl-2-methylpyrazol-3-yl)oxybenzonitrile |

TABLE 1-continued

| Compound number | Structural formula | Compound name |
|---|---|---|
| 556 | 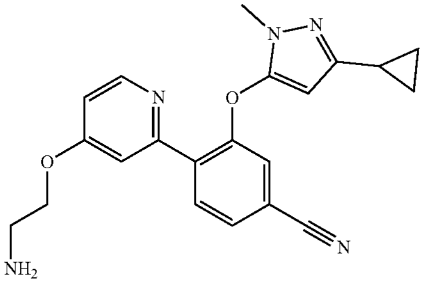 [SMILES: Cn1nc(C2CC2)cc1Oc1cc(C#N)ccc1-c1cc(OCCN)ccn1] | 4-[4-(2-aminoethoxy)pyridin-2-yl]-3-(5-cyclopropyl-2-methylpyrazol-3-yl)oxybenzonitrile |
| 557 | 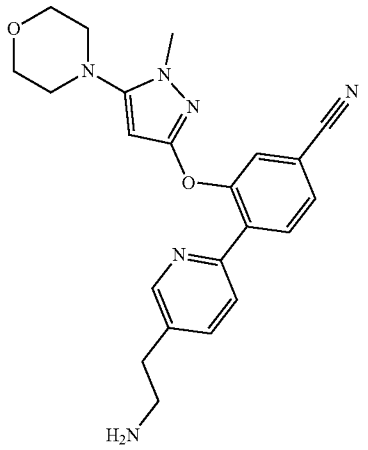 [SMILES: Cn1nc(Oc2cc(C#N)ccc2-c2ccc(CCN)cn2)cc1N1CCOCC1] | 4-[5-(2-aminoethyl)pyridin-2-yl]-3-(1-methyl-5-morpholin-4-ylpyrazol-3-yl)oxybenzonitrile |
| 558 | 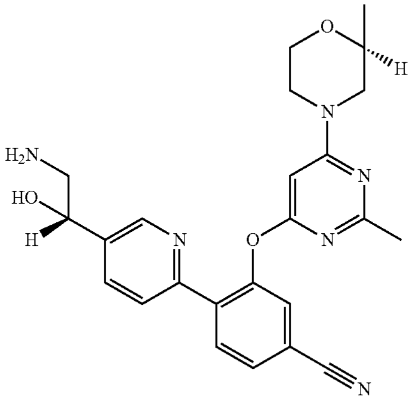 [SMILES: Cc1nc(Oc2cc(C#N)ccc2-c2ccc([C@H](O)CN)cn2)cc(N2CCO[C@@H](C)C2)n1] | 4-[5-[(1S)-2-amino-1-hydroxyethyl]pyridin-2-yl]-3-[2-methyl-6-[(2S)-2-methylmorpholin-4-yl]pyrimidin-4-yl]oxybenzonitrile |
| 559 | 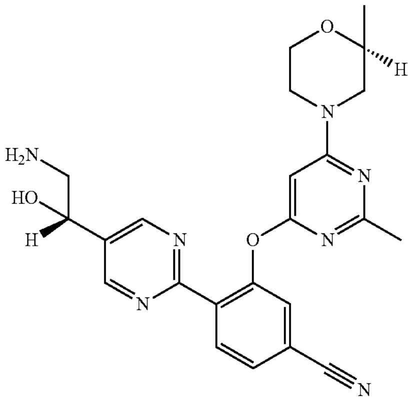 [SMILES: Cc1nc(Oc2cc(C#N)ccc2-c2ncc([C@H](O)CN)cn2)cc(N2CCO[C@@H](C)C2)n1] | 4-[5-[(1S)-2-amino-1-hydroxyethyl]pyrimidin-2-yl]-3-[2-methyl-6-[(2S)-2-methylmorpholin-4-yl]pyrimidin-4-yl]oxybenzonitrile |

TABLE 1-continued
| Compound number | Structural formula | Compound name |
|---|---|---|
| 560 | 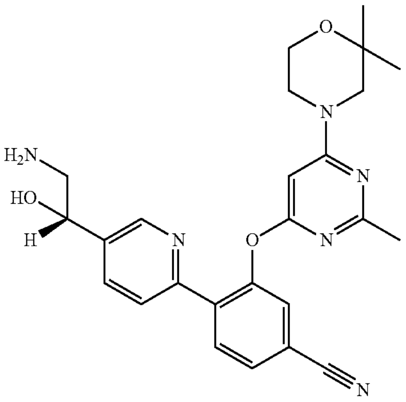 [SMILES: Cc1nc(Oc2cc(C#N)ccc2-c2ccc([C@H](O)CN)cn2)cc(N2CCOC(C)(C)C2)n1] | 4-[5-[(1S)-2-amino-1-hydroxyethyl]pyridin-2-yl]-3-[6-(2,2-dimethylmorpholin-4-yl)-2-methylpyrimidin-4-yl]oxybenzonitrile |
| 561 | 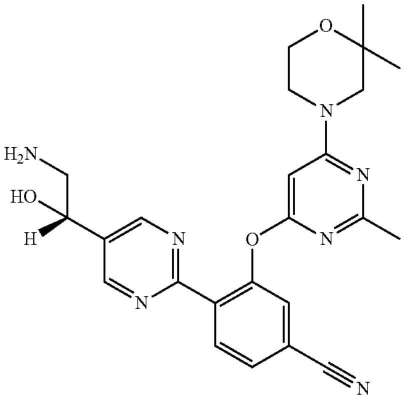 [SMILES: Cc1nc(Oc2cc(C#N)ccc2-c2ncc([C@H](O)CN)cn2)cc(N2CCOC(C)(C)C2)n1] | 4-[5-[(1S)-2-amino-1-hydroxyethyl]pyrimidin-2-yl]-3-[6-(2,2-dimethylmorpholin-4-yl)-2-methylpyrimidin-4-yl]oxybenzonitrile |
| 562 | 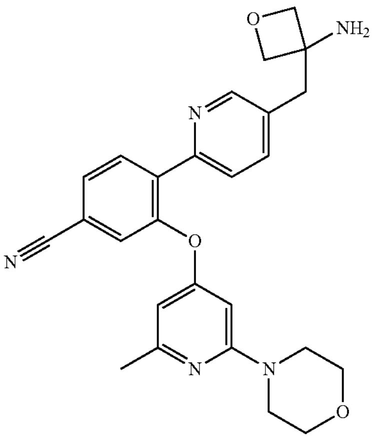 [SMILES: Cc1cc(Oc2cc(C#N)ccc2-c2ccc(CC3(N)COC3)cn2)cc(N2CCOCC2)n1] | 4-[5-[(3-aminooxetan-3-yl)methyl]pyridin-2-yl]-3-(2-methyl-6-morpholin-4-ylpyridin-4-yl)oxybenzonitrile |

TABLE 1-continued
| Compound number | Structural formula | Compound name |
|---|---|---|
| 563 | 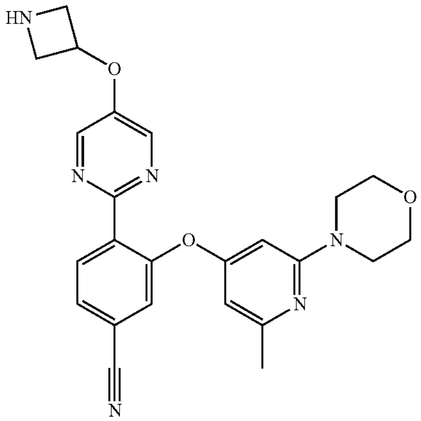 [SMILES: Cc1cc(Oc2cc(C#N)ccc2-c2ncc(OC3CNC3)cn2)cc(N2CCOCC2)n1] | 4-[5-(azetidin-3-yloxy)pyrimidin-2-yl]-3-(2-methyl-6-morpholin-4 ylpyridin-4-yl)oxybenzonitrile |
| 564 | 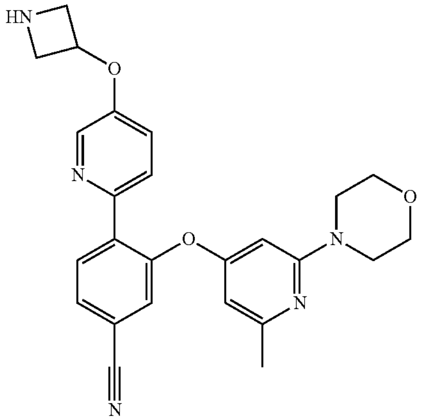 [SMILES: Cc1cc(Oc2cc(C#N)ccc2-c2ccc(OC3CNC3)cn2)cc(N2CCOCC2)n1] | 4-[5-(azetidin-3-yloxy)pyridin-2-yl]-3-(2-methyl-6-morpholin-4-ylpyridin-4-yl)oxybenzonitrile |
| 565 | 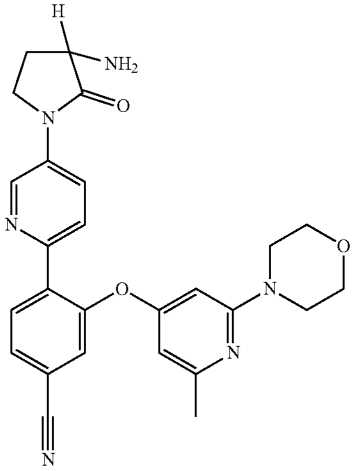 [SMILES: Cc1cc(Oc2cc(C#N)ccc2-c2ccc(N3CCC(N)C3=O)cn2)cc(N2CCOCC2)n1] | 4-[5-[(3S)-3-amino-2-oxopyrrolidin-1-yl]pyridin-2-yl]-3-(2-methyl-6-morpholin-4-ylpyridin-4-yl)oxybenzonitrile |

TABLE 1-continued
| Compound number | Structural formula | Compound name |
|---|---|---|
| 566 | 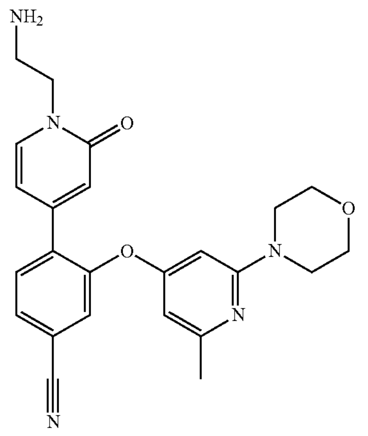 [SMILES: Cc1cc(Oc2cc(C#N)ccc2-c2ccn(CCN)c(=O)c2)cc(N2CCOCC2)n1] | 4-[1-(2-aminoethyl)-2-oxopyridin-4-yl]-3-(2-methyl-6-morpholin-4-ylpyridin-4-yl)oxybenzonitrile |
| 567 | 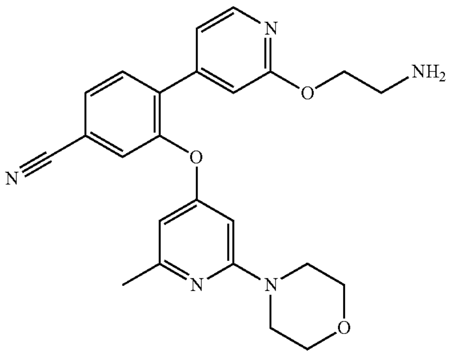 [SMILES: Cc1cc(Oc2cc(C#N)ccc2-c2ccnc(OCCN)c2)cc(N2CCOCC2)n1] | 4-[2-(2-aminoethoxy)pyridin-4-yl]-3-(2-methyl-6-morpholin-4-ylpyridin-4-yl)oxybenzonitrile |
| 568 | 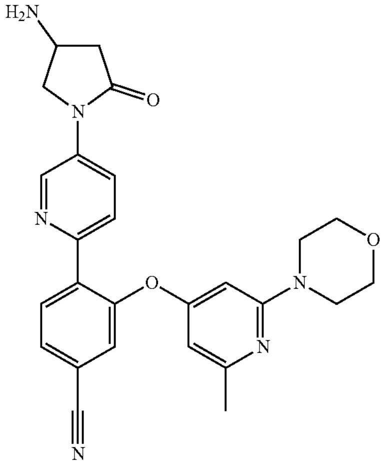 [SMILES: Cc1cc(Oc2cc(C#N)ccc2-c2ccc(N3CC(N)CC3=O)cn2)cc(N2CCOCC2)n1] | 4-[5-(4-amino-2-oxopyrrolidin-1-yl)pyridin-2-yl]-3-(2-methyl-6-morpholin-4-ylpyridin-4-yl)oxybenzonitrile |

TABLE 1-continued

| Compound number | Structural formula | Compound name |
|---|---|---|
| 569 | 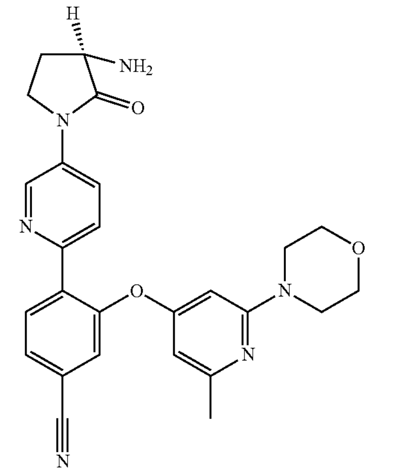 [SMILES: Cc1cc(Oc2cc(C#N)ccc2-c2ccc(N3CC[C@@H](N)C3=O)cn2)cc(N2CCOCC2)n1] | 4-[5-[(3R)-3-amino-2-oxopyrrolidin-1-yl]pyridin-2-yl]-3-(2-methyl-6-morpholin-4-ylpyridin-4-yl)oxybenzonitrile |
| 570 | 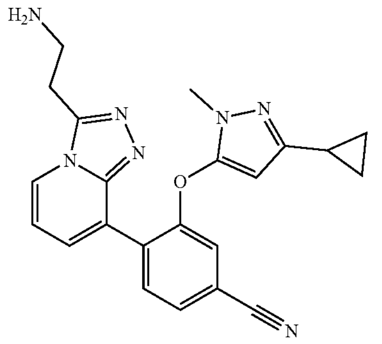 [SMILES: Cn1nc(C2CC2)cc1Oc1cc(C#N)ccc1-c1cccn2c(CCN)nnc12] | 4-[3-(2-aminoethyl)-[1,2,4]triazolo[4,3-a]pyridin-8-yl]-3-(5-cyclopropyl-2-methylpyrazol-3-yl)oxybenzonitrile |
| 571 | 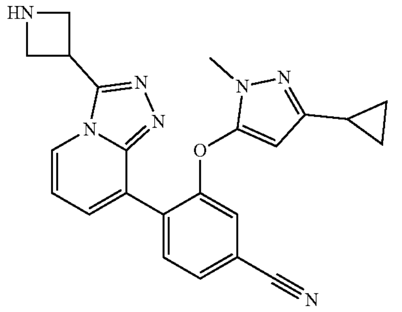 [SMILES: Cn1nc(C2CC2)cc1Oc1cc(C#N)ccc1-c1cccn2c(C3CNC3)nnc12] | 4-[3-(azetidin-3-yl)-[1,2,4]triazolo[4,3-a]pyridin-8-yl]-3-(5-cyclopropyl-2-methylpyrazol-3-yl)oxybenzonitrile |
| 572 | 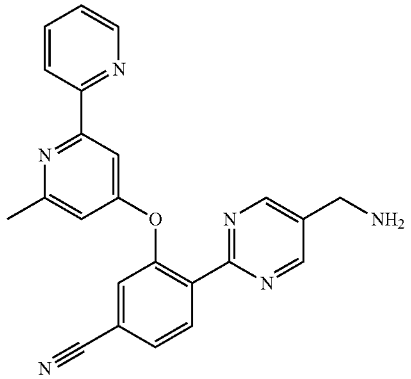 [SMILES: Cc1cc(Oc2cc(C#N)ccc2-c2ncc(CN)cn2)cc(-c2ccccn2)n1] | 4-[5-(aminomethyl)pyrimidin-2-yl]-3-(2-methyl-6-pyridin-2-ylpyridin-4-yl)oxybenzonitrile |

TABLE 1-continued

| Compound number | Structural formula | Compound name |
|---|---|---|
| 573 | 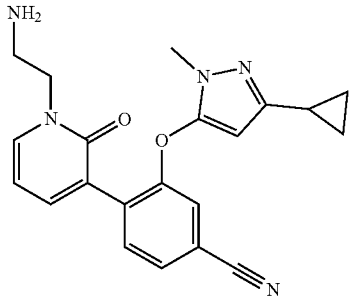 [SMILES: Cn1nc(C2CC2)cc1Oc1cc(C#N)ccc1-c1cccn(CCN)c1=O] | 4-[1-(2-aminoethyl)-2-oxopyridin-3-yl]-3-(5-cyclopropyl-2-methylpyrazol-3-yl)oxybenzonitrile |
| 574 | 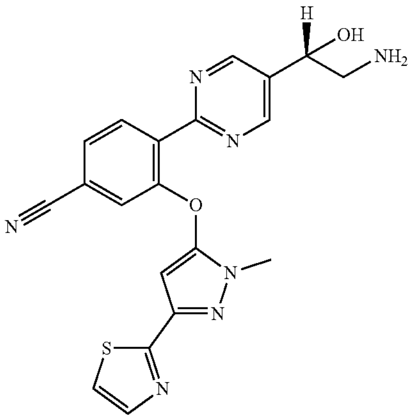 | 4-[5-[(1S)-2-amino-1-hydroxyethyl]pyrimidin-2-yl]-3-[2-methyl-5-(1,3-thiazol-2-yl)pyrazol-3-yl]oxybenzonitrile |
| 575 | 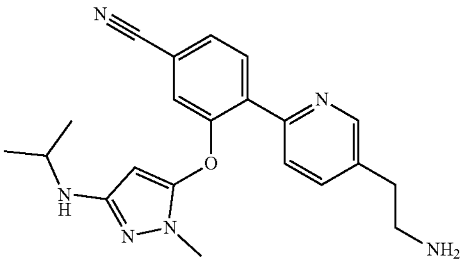 | 4-[5-(2-aminoethyl)pyridin-2-yl]-3-[2-methyl-5-(propan-2-ylamino)pyrazol-3-yl]oxybenzonitrile |
| 576 | 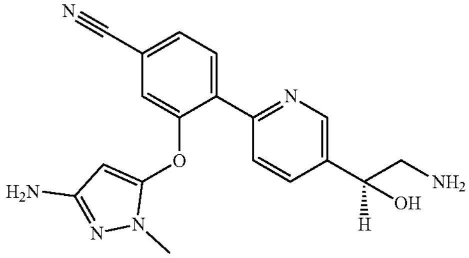 [SMILES: Cn1nc(N)cc1Oc1cc(C#N)ccc1-c1ccc([C@H](O)CN)cn1] | 4-[5-[(1S)-2-amino-1-hydroxyethyl]pyridin-2-yl]-3-(5-amino-2-methylpyrazol-3-yl)oxybenzonitrile |
| 577 | 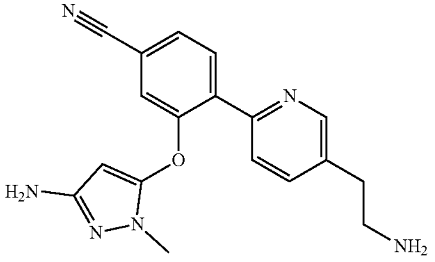 | 4-[5-(2-aminoethyl)pyridin-2-yl]-3-(5-amino-2-methylpyrazol-3-yl)oxybenzonitrile |

TABLE 1-continued

| Compound number | Structural formula | Compound name |
|---|---|---|
| 578 | 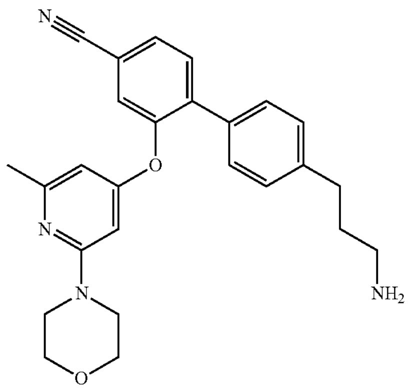 [SMILES: Cc1cc(Oc2cc(C#N)ccc2-c2ccc(CCCN)cc2)cc(N2CCOCC2)n1] | 4-[4-(3-aminopropyl)phenyl]-3-(2-methyl-6-morpholin-4-ylpyridin-4-yl)oxybenzonitrile |
| 579 | 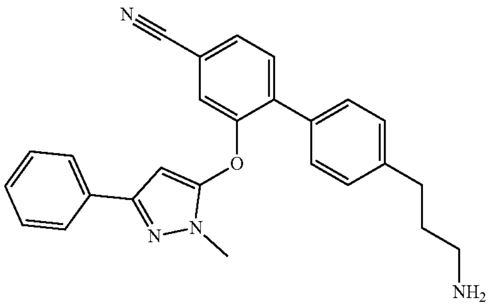 [SMILES: Cn1nc(-c2ccccc2)cc1Oc1cc(C#N)ccc1-c1ccc(CCCN)cc1] | 4-[4-(3-aminopropyl)phenyl]-3-(2-methyl-5-phenylpyrazol-3-yl)oxybenzonitrile |
| 580 | 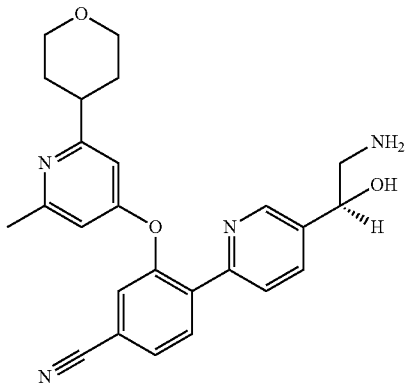 [SMILES: Cc1cc(Oc2cc(C#N)ccc2-c2ccc([C@H](O)CN)cn2)cc(C2CCOCC2)n1] | 4-[5-[(1S)-2-amino-1-hydroxyethyl]pyridin-2-yl]-3-[2-methyl-6-(oxan-4-yl)pyridin-4-yl]oxybenzonitrile |
| 581 | 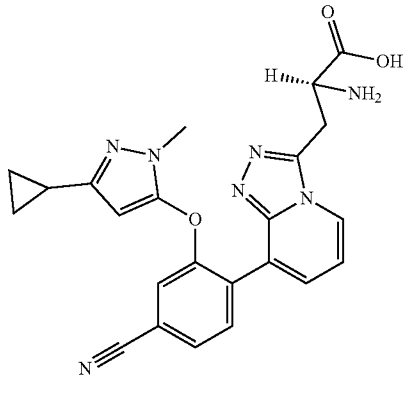 [SMILES: Cn1nc(C2CC2)cc1Oc1cc(C#N)ccc1-c1cccn2c(C[C@H](N)C(=O)O)nnc12] | 2-amino-3-[8-[4-cyano-2-(5-cyclopropyl-2-methylpyrazol-3-yl)oxyphenyl]-[1,2,4]triazolo[4,3-a]pyridin-3-yl]propanoic acid |

TABLE 1-continued

| Compound number | Structural formula | Compound name |
|---|---|---|
| 582 | 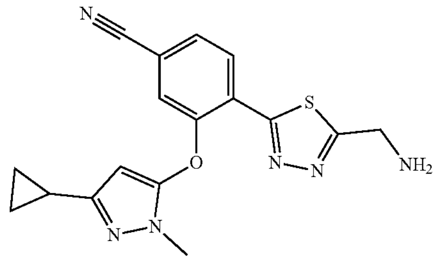 [SMILES: Cn1nc(C2CC2)cc1Oc1cc(C#N)ccc1-c1nnc(CN)s1] | 4-[5-(aminomethyl)-1,3,4-thiadiazol-2-yl]-3-(5-cyclopropyl-2-methylpyrazol-3-yl)oxybenzonitrile |
| 583 | 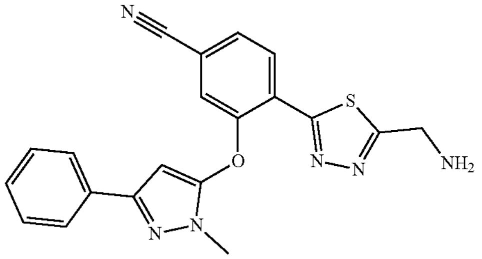 [SMILES: Cn1nc(-c2ccccc2)cc1Oc1cc(C#N)ccc1-c1nnc(CN)s1] | 4-[5-(aminomethyl)-1,3,4-thiadiazol-2-yl]-3-(2-methyl-5-phenylpyrazol-3-yl)oxybenzonitrile |
| 584 | 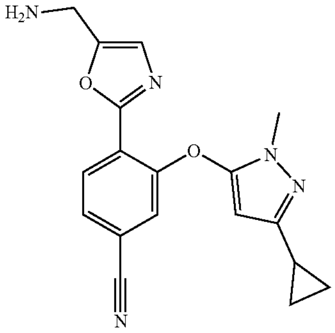 [SMILES: Cn1nc(C2CC2)cc1Oc1cc(C#N)ccc1-c1ncc(CN)o1] | 4-[5-(aminomethyl)-1,3-oxazol-2-yl]-3-(5-cyclopropyl-2-methylpyrazol-3-yl)oxybenzonitrile |
| 585 | 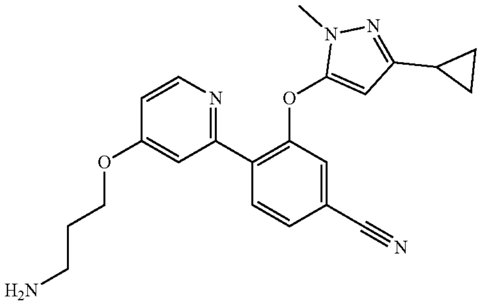 [SMILES: Cn1nc(C2CC2)cc1Oc1cc(C#N)ccc1-c1cc(OCCCN)ccn1] | 4-[4-(3-aminopropoxy)pyridin-2-yl]-3-(5-cyclopropyl-2-methylpyrazol-3-yl)oxybenzonitrile |
| 586 | 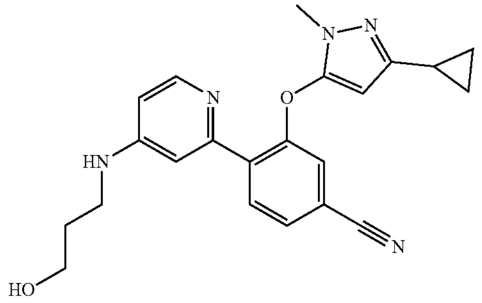 [SMILES: Cn1nc(C2CC2)cc1Oc1cc(C#N)ccc1-c1cc(NCCCO)ccn1] | 3-(5-cyclopropyl-2-methylpyrazol-3-yl)oxy-4-[4-(3-hydroxypropylamino)pyridin-2-yl]benzonitrile |

TABLE 1-continued

| Compound number | Structural formula | Compound name |
|---|---|---|
| 587 | 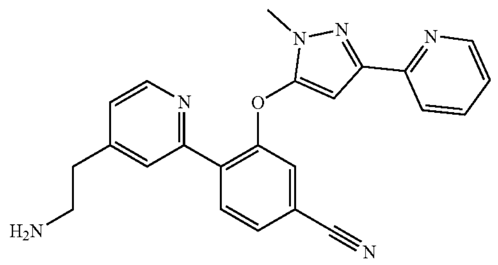 [SMILES: Cn1nc(-c2ccccn2)cc1Oc1cc(C#N)ccc1-c1cc(CCN)ccn1] | 4-[4-(2-aminoethyl)pyridin-2-yl]-3-(2-methyl-5-pyridin-2-ylpyrazol-3-yl)oxybenzonitrile |
| 588 | 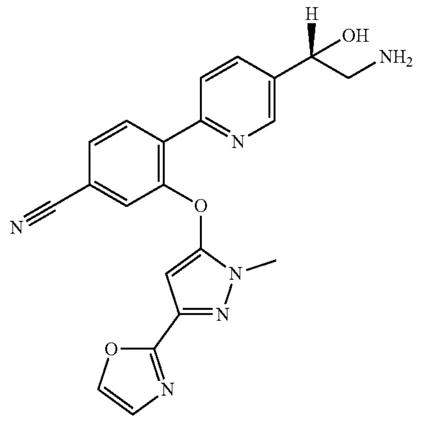 [SMILES: Cn1nc(-c2ncco2)cc1Oc1cc(C#N)ccc1-c1ccc([C@H](O)CN)cn1] | 4-[5-[(1S)-2-amino-1-hydroxyethyl]pyridin-2-yl]-3-[2-methyl-5-(1,3-oxazol-2-yl)pyrazol-3-yl]oxybenzonitrile |
| 589 | 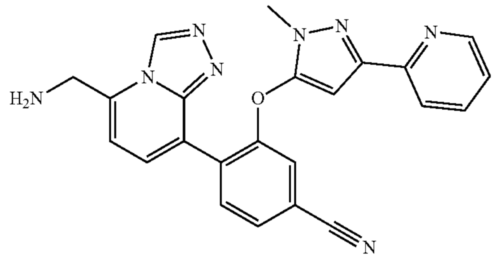 [SMILES: Cn1nc(-c2ccccn2)cc1Oc1cc(C#N)ccc1-c1ccc(CN)n2cnnc12] | 4-[5-(aminomethyl)-[1,2,4]triazolo[4,3-a]pyridin-8-yl]-3-(2-methyl-5-pyridin-2-ylpyrazol-3-yl)oxybenzonitrile |
| 590 | 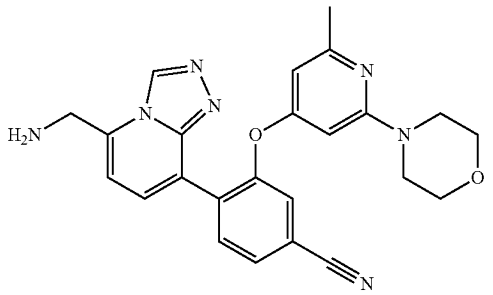 [SMILES: Cc1cc(Oc2cc(C#N)ccc2-c2ccc(CN)n3cnnc23)cc(N2CCOCC2)n1] | 4-[5-(aminomethyl)-[1,2,4]triazolo[4,3-a]pyridin-8-yl]-3-(2-methyl-6-morpholin-4-ylpyridin-4-yl)oxybenzonitrile |

TABLE 1-continued

| Compound number | Structural formula | Compound name |
|---|---|---|
| 591 | 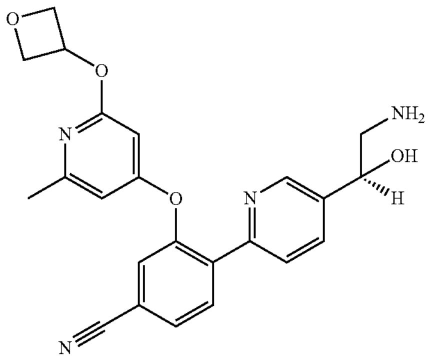 [SMILES: Cc1cc(Oc2cc(C#N)ccc2-c2ccc([C@H](O)CN)cn2)cc(OC2COC2)n1] | 4-[5-[(1S)-2-amino-1-hydroxyethyl]pyridin-2-yl]-3-[2-methyl-6-(oxetan-3-yloxy)pyridin-4-yl]oxybenzonitrile |
| 592 | 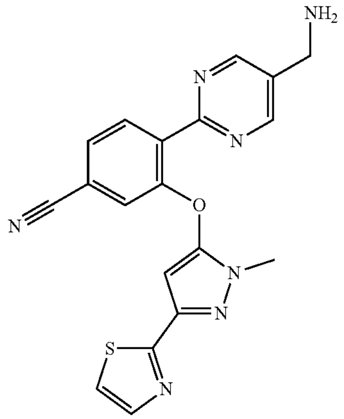 [SMILES: Cn1nc(-c2nccs2)cc1Oc1cc(C#N)ccc1-c1ncc(CN)cn1] | 4-[5-(aminomethyl)pyrimidin-2-yl]-3-[2-methyl-5-(1,3-thiazol-2-yl)pyrazol-3-yl]oxybenzonitrile |
| 593 | 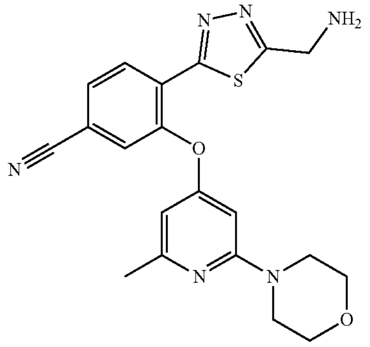 [SMILES: Cc1cc(Oc2cc(C#N)ccc2-c2nnc(CN)s2)cc(N2CCOCC2)n1] | 4-[5-(aminomethyl)-1,3,4-thiazol-2-yl]-3-(2-methyl-6-morpholin-4-ylpyridin-4-yl)oxybenzonitrile |
| 594 | 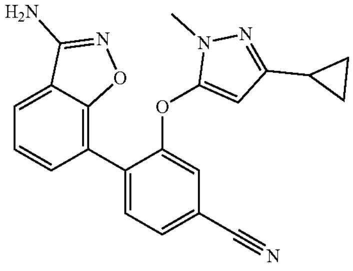 [SMILES: Cn1nc(C2CC2)cc1Oc1cc(C#N)ccc1-c1cccc2c(N)noc12] | 4-(3-amino-1,2-benzoxazol-7-yl)-3-(5-cyclopropyl-2-methylpyrazol-3-yl)oxybenzonitrile |

TABLE 1-continued
| Compound number | Structural formula | Compound name |
|---|---|---|
| 595 | 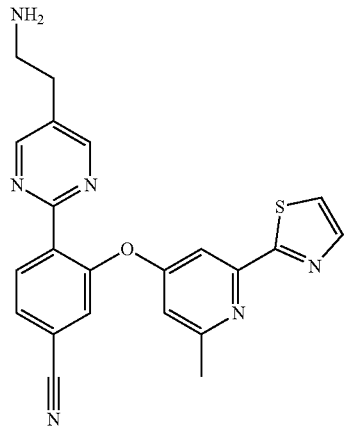 [SMILES: Cc1cc(Oc2cc(C#N)ccc2-c2ncc(CCN)cn2)cc(-c2nccs2)n1] | 4-[5-(2-aminoethyl)pyrimidin-2-yl]-3-[2-methyl-6-(1,3-thiazol-2-yl)pyridin-4-yl]oxybenzonitrile |
| 596 | 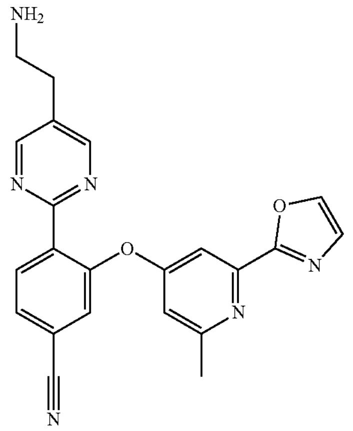 [SMILES: Cc1cc(Oc2cc(C#N)ccc2-c2ncc(CCN)cn2)cc(-c2ncco2)n1] | 4-[5-(2-aminoethyl)pyrimidin-2-yl]-3-[2-methyl-6-(1,3-oxazol-2-yl)pyridin-4-yl]oxybenzonitrile |
| 597 | 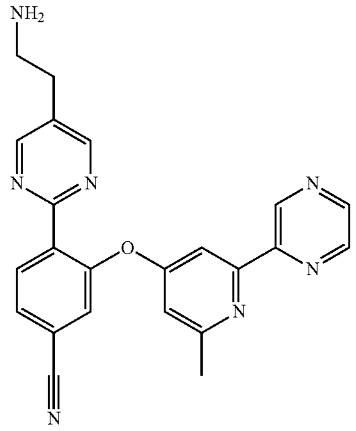 [SMILES: Cc1cc(Oc2cc(C#N)ccc2-c2ncc(CCN)cn2)cc(-c2cnccn2)n1] | 4-[5-(2-aminoethyl)pyrimidin-2-yl]-3-(2-methyl-6-pyrazin-2-ylpyridin-4-yl)oxybenzonitrile |

TABLE 1-continued
| Compound number | Structural formula | Compound name |
| --- | --- | --- |
| 598 | 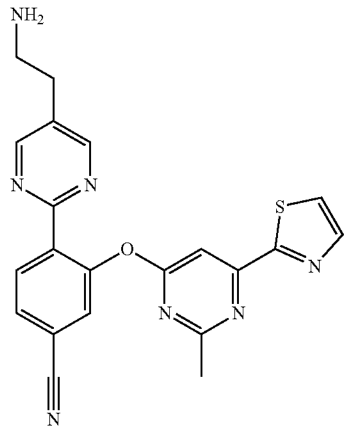 [SMILES: Cc1nc(Oc2cc(C#N)ccc2-c2ncc(CCN)cn2)cc(-c2nccs2)n1] | 4-[5-(2-aminoethyl)pyrimidin-2-yl]-3-[2-methyl-6-(1,3-thiazol-2-yl)pyrimidin-4-yl]oxybenzonitrile |
| 599 | 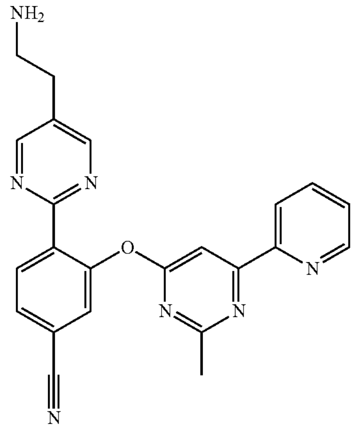 [SMILES: Cc1nc(Oc2cc(C#N)ccc2-c2ncc(CCN)cn2)cc(-c2ccccn2)n1] | 4-[5-(2-aminoethyl)pyrimidin-2-yl]-3-(2-methyl-6-pyridin-2-ylpyrimidin-4-yl)oxybenzonitrile |
| 600 | 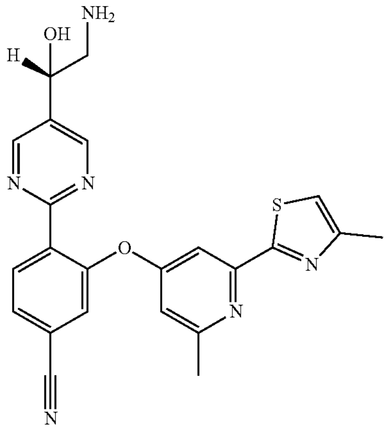 [SMILES: Cc1cc(Oc2cc(C#N)ccc2-c2ncc([C@H](O)CN)cn2)cc(-c2nc(C)cs2)n1] | 4-[5-[(1S)-2-amino-1-hydroxyethyl]pyrimidin-2-yl]-3-[2-methyl-6-(4-methyl-1,3-thiazol-2-yl)pyridin-4-yl]oxybenzonitrile |

TABLE 1-continued
| Compound number | Structural formula | Compound name |
|---|---|---|
| 601 | 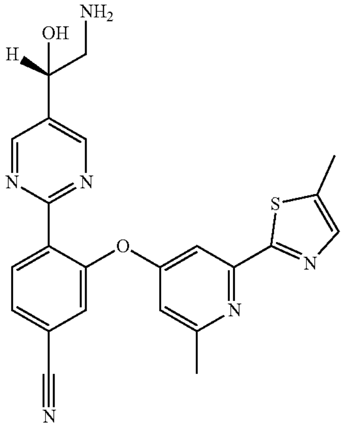 [SMILES: Cc1cc(Oc2cc(C#N)ccc2-c2ncc([C@H](O)CN)cn2)cc(-c2ncc(C)s2)n1] | 4-[5-[(1S)-2-amino-1-hydroxyethyl]pyrimidin-2-yl]-3-[2-methyl-6-(5-methyl-1,3-thiazol-2-yl)pyridin-4-yl]oxybenzonitrile |
| 602 | 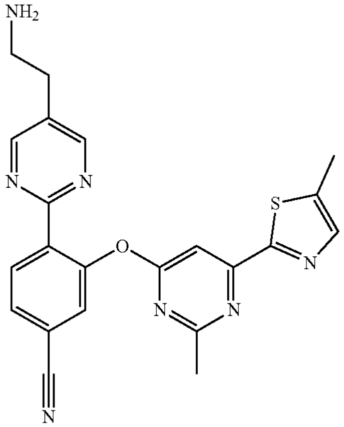 [SMILES: Cc1nc(Oc2cc(C#N)ccc2-c2ncc(CCN)cn2)cc(-c2ncc(C)s2)n1] | 4-[5-(2-aminoethyl)pyrimidin-2-yl]-3-[2-methyl-6-(5-methyl-1,3-thiazol-2-yl)pyrimidm-4-yl]oxybenzonitrile |
| 603 | 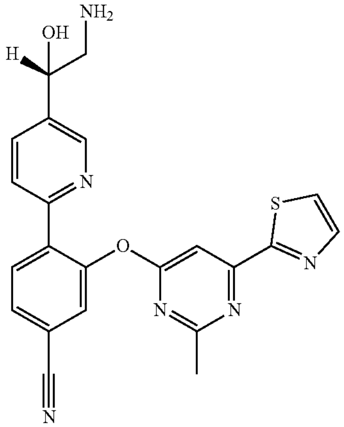 [SMILES: Cc1nc(Oc2cc(C#N)ccc2-c2ccc([C@H](O)CN)cn2)cc(-c2nccs2)n1] | 4-[5-[(1S)-2-amino-1-hydroxyethyl]pyridin-2-yl]-3-[2-methyl-6-(1,3-thiazol-2-yl)pyrimidin-4-yl]oxybenzonitrile |

TABLE 1-continued
| Compound number | Structural formula | Compound name |
| --- | --- | --- |
| 604 | 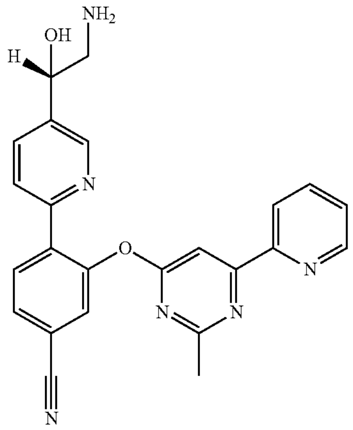 [SMILES: Cc1nc(Oc2cc(C#N)ccc2-c2ccc([C@H](O)CN)cn2)cc(-c2ccccn2)n1] | 4-[5-[(1S)-2-amino-1-hydroxyethyl]pyridin-2-yl]-3-(2-methyl-6-pyridin-2-ylpyrimidin-4-yl)oxybenzonitrile |
| 605 | 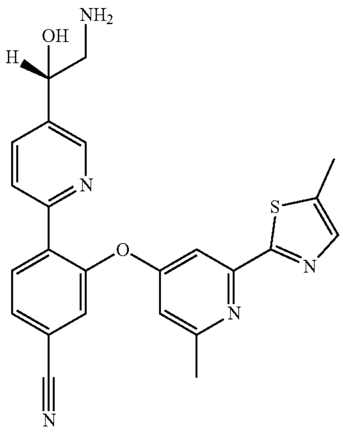 [SMILES: Cc1cc(Oc2cc(C#N)ccc2-c2ccc([C@H](O)CN)cn2)cc(-c2ncc(C)s2)n1] | 4-[5-[(1S)-2-amino-1-hydroxyethyl]pyridin-2-yl]-3-[2-methyl-6-(5-methyl-1,3-thiazol-2-yl)pyridin-4-yl]oxybenzonitrile |
| 606 | 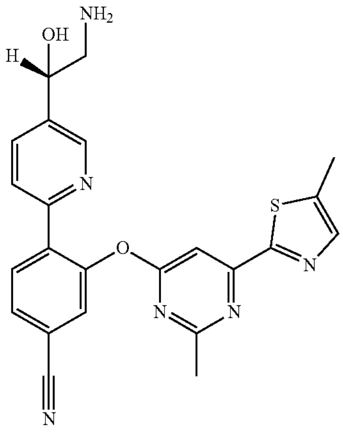 [SMILES: Cc1nc(Oc2cc(C#N)ccc2-c2ccc([C@H](O)CN)cn2)cc(-c2ncc(C)s2)n1] | 4-[5-[(1S)-2-amino-1-hydroxyethyl]pyridin-2-yl]-3-[2-methyl-6-(5-methyl-1,3-thiazol-2-yl)pyrimidin-4-yl]oxybenzonitrile |

TABLE 1-continued

| Compound number | Structural formula | Compound name |
|---|---|---|
| 607 | 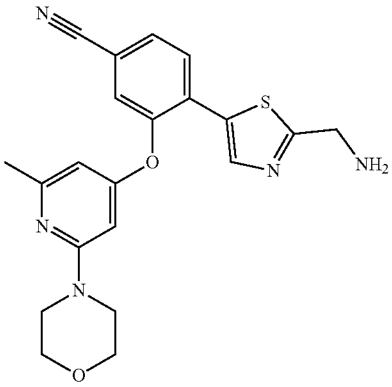 [SMILES: Cc1cc(Oc2cc(C#N)ccc2-c2cnc(CN)s2)cc(N2CCOCC2)n1] | 4-[2-(aminomethyl)-1,3-thiazol-5-yl]-3-(2-methyl-6-morpholin-4-ylpyridin-4-yl)oxybenzonitrile |
| 608 | 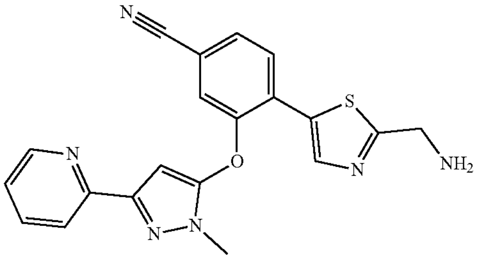 [SMILES: Cn1nc(-c2ccccn2)cc1Oc1cc(C#N)ccc1-c1cnc(CN)s1] | 4-[2-(aminomethyl)-1,3-thiazol-5-yl]-3-(2-methyl-5-pyridin-2-ylpyrazol-3-yl)oxybenzonitrile |
| 609 | 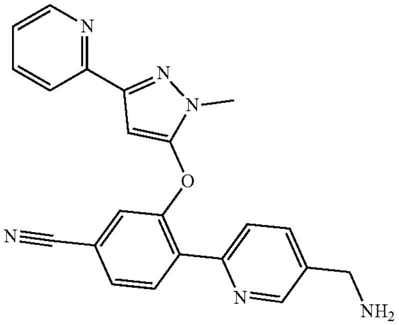 [SMILES: Cn1nc(-c2ccccn2)cc1Oc1cc(C#N)ccc1-c1ccc(CN)cn1] | 4-[5-(aminomethyl)pyridin-2-yl]-3-(2-methyl-5-pyridin-2-ylpyrazol-3-yl)oxybenzonitrile |
| 610 | 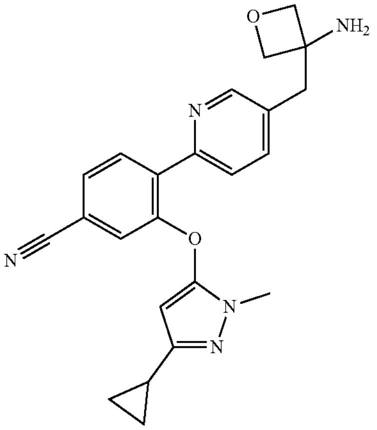 [SMILES: Cn1nc(C2CC2)cc1Oc1cc(C#N)ccc1-c1ccc(CC2(N)COC2)cn1] | 4-[5-[(3-aminooxetan-3-yl)methyl]pyridin-2-yl]-3-(5-cyclopropyl-2-methylpyrazol-3-yl)oxybenzonitrile |

TABLE 1-continued
| Compound number | Structural formula | Compound name |
|---|---|---|
| 611 | 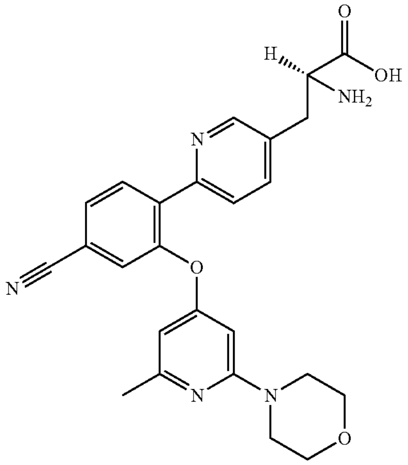 [SMILES: Cc1cc(Oc2cc(C#N)ccc2-c2ccc(C[C@H](N)C(=O)O)cn2)cc(N2CCOCC2)n1] | (2S)-2-amino-3-[6-[4-cyano-2-(2-methyl-6-morpholin-4-ylpyridin-4-yl)oxyphenyl]pyridin-3-yl]propanoic acid |
| 612 | 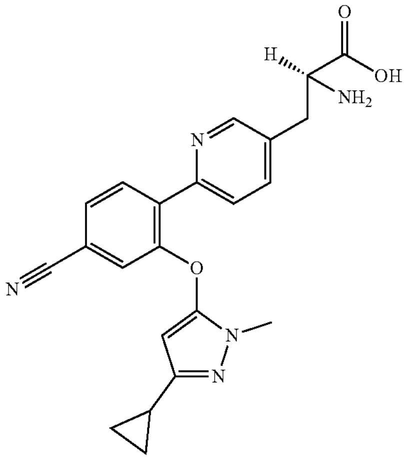 [SMILES: Cn1nc(C2CC2)cc1Oc1cc(C#N)ccc1-c1ccc(C[C@H](N)C(=O)O)cn1] | (2S)-2-amino-3-[6-[4-cyano-2-(5-cyclopropyl-2-methylpyrazol-3-yl)oxyphenyl]pyridin-3-yl]propanoic acid |
| 613 | 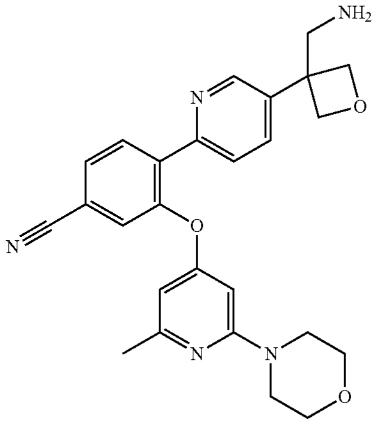 [SMILES: Cc1cc(Oc2cc(C#N)ccc2-c2ccc(C3(CN)COC3)cn2)cc(N2CCOCC2)n1] | 4-[5-[3-(aminomethyl)oxetan-3-yl]pyridin-2-yl]-3-(2-methyl-6-morpholin-4-ylpyridin-4-yl)oxybenzonitrile |

TABLE 1-continued

| Compound number | Structural formula | Compound name |
|---|---|---|
| 614 | 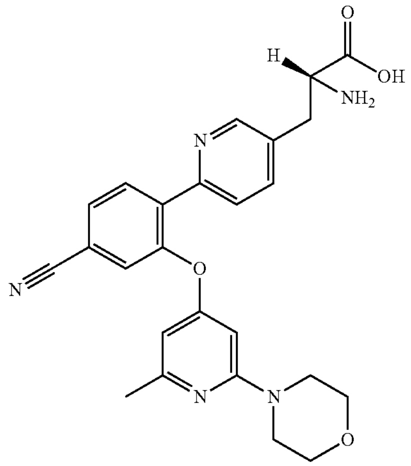 [SMILES: Cc1cc(Oc2cc(C#N)ccc2-c2ccc(C[C@@H](N)C(=O)O)cn2)cc(N2CCOCC2)n1] | (2R)-2-amino-3-[6-[4-cyano-2-(2-methyl-6-morpholin-4-ylpyridin-4-yl)oxyphenyl]pyridin-3-yl]propanoic acid |
| 615 | 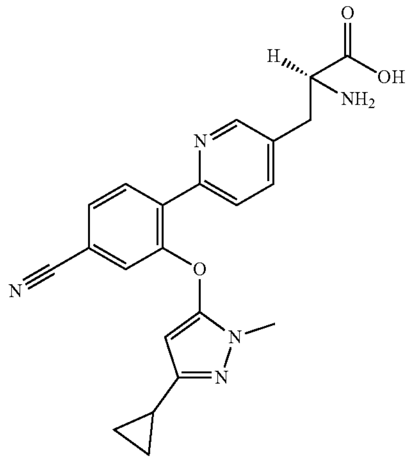 [SMILES: Cn1nc(C2CC2)cc1Oc1cc(C#N)ccc1-c1ccc(C[C@H](N)C(=O)O)cn1] | (2R)-2-amino-3-[6-[4-cyano-2-(5-cyclopropyl-2-methylpyrazol-3-yl)oxyphenyl]pyridin-3-yl]propanoic acid |
| 616 | 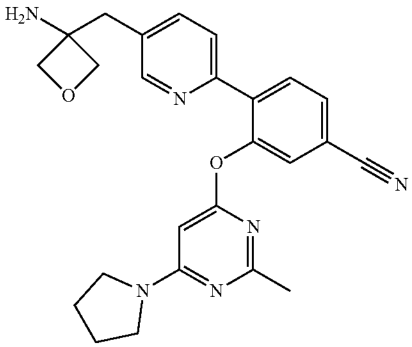 [SMILES: Cc1nc(Oc2cc(C#N)ccc2-c2ccc(CC3(N)COC3)cn2)cc(N2CCCC2)n1] | 4-[5-[(3-aminooxetan-3-yl)methyl]pyridin-2-yl]-3-(2-methyl-6-pyrrolidin-1-ylpyrimidin-4-yl)oxybenzonitrile |
| 617 | 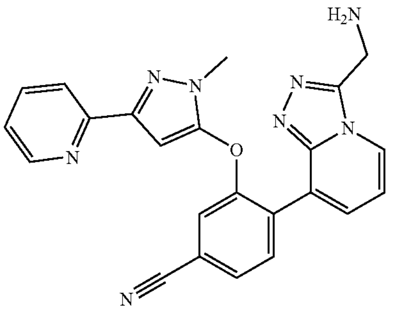 [SMILES: Cn1nc(-c2ccccn2)cc1Oc1cc(C#N)ccc1-c1cccn2c(CN)nnc12] | 4-[3-(aminomethyl)-[1,2,4]triazolo[4,3-a]pyridin-8-yl]-3-(2-methyl-5-pyridin-2-ylpyrazol-3-yl)oxybenzonitrile |

TABLE 1-continued

| Compound number | Structural formula | Compound name |
|---|---|---|
| 618 | 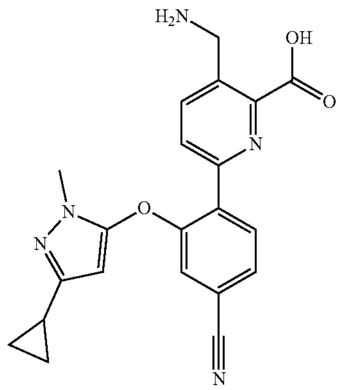 [SMILES: Cn1nc(C2CC2)cc1Oc1cc(C#N)ccc1-c1ccc(CN)c(C(=O)O)n1] | 3-(aminomethyl)-6-[4-cyano-2-(5-cyclopropyl-2-methylpyrazol-3-yl)oxyphenyl]pyridine-2-carboxylic acid |
| 619 | 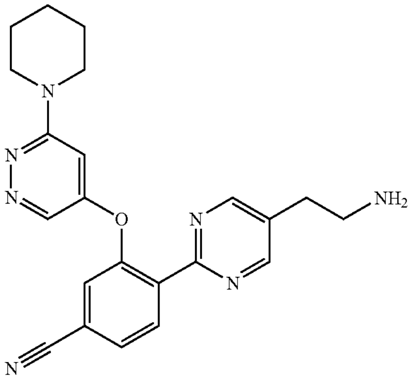 [SMILES: N#Cc1ccc(-c2ncc(CCN)cn2)c(Oc2cnnc(N3CCCCC3)c2)c1] | 4-[5-(2-aminoethyl)pyrimidin-2-yl]-3-(6-piperidin-1-ylpyridazin-4-yl)oxybenzonitrile |
| 620 | 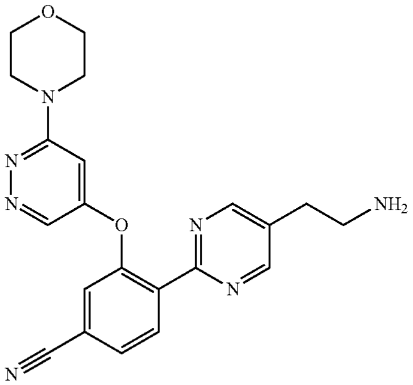 [SMILES: N#Cc1ccc(-c2ncc(CCN)cn2)c(Oc2cnnc(N3CCOCC3)c2)c1] | 4-[5-(2-aminoethyl)pyrimidin-2-yl]-3-(6-morpholin-4-ylpyridazin-4-yl)oxybenzonitrile |
| 621 | 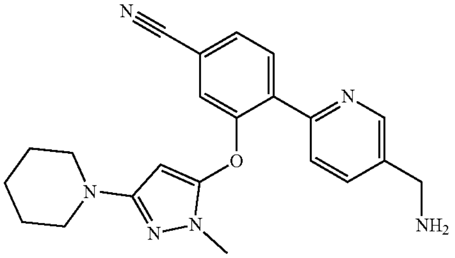 [SMILES: Cn1nc(N2CCCCC2)cc1Oc1cc(C#N)ccc1-c1ccc(CN)cn1] | 4-[5-(aminomethyl)pyridin-2-yl]-3-(2-methyl-5-piperidin-1-ylpyrazol-3-yl)oxybenzonitrile |

TABLE 1-continued

| Compound number | Structural formula | Compound name |
|---|---|---|
| 622 | 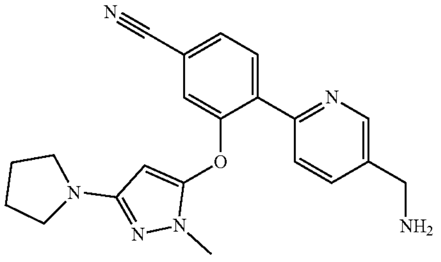 [SMILES: Cn1nc(N2CCCC2)cc1Oc1cc(C#N)ccc1-c1ccc(CN)cn1] | 4-[5-(aminomethyl)pyridin-2-yl]-3-(2-methyl-5-pyrrolidin-1-ylpyrazol-3-yl)oxybenzonitrile |
| 623 | 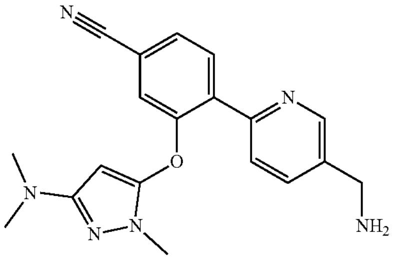 [SMILES: CN(C)c1cc(Oc2cc(C#N)ccc2-c2ccc(CN)cn2)n(C)n1] | 4-[5-(aminomethyl)pyridin-2-yl]-3-[5-(dimethylamino)-2-methylpyrazol-3-yl]oxybenzonitrile |
| 624 | 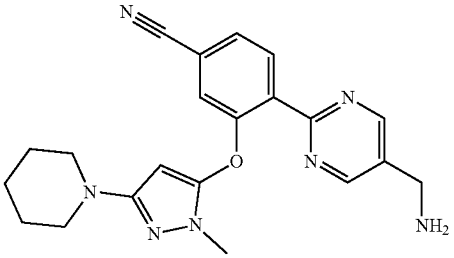 [SMILES: Cn1nc(N2CCCCC2)cc1Oc1cc(C#N)ccc1-c1ncc(CN)cn1] | 4-[5-(aminomethyl)pyrimidin-2-yl]-3-(2-methyl-5-piperidin-1-ylpyrazol-3-yl)oxybenzonitrile |
| 625 | 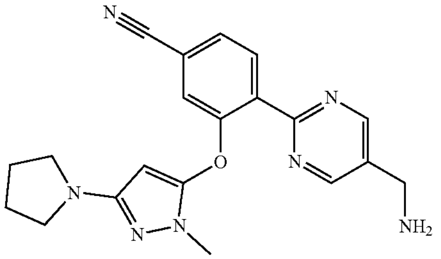 | 4-[5-(aminomethyl)pyrimidin-2-yl]-3-(2-methyl-5-pyrrolidin-1-ylpyrazol-3-yl)oxybenzonitrile |
| 626 | 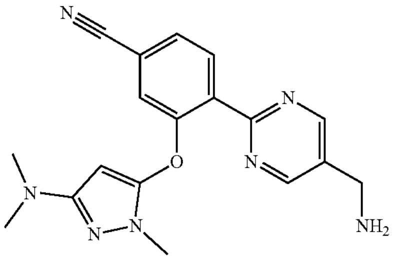 [SMILES: CN(C)c1cc(Oc2cc(C#N)ccc2-c2ncc(CN)cn2)n(C)n1] | 4-[5-(aminomethyl)pyrimidin-2-yl]-3-[5-(dimethylamino)-2-methylpyrazol-3-yl]oxybenzonitrile |

TABLE 1-continued

| Compound number | Structural formula | Compound name |
|---|---|---|
| 627 | 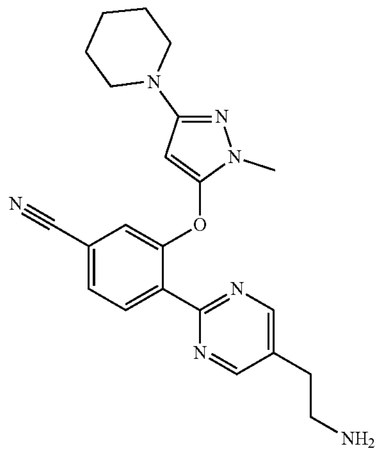 [SMILES: Cn1nc(N2CCCCC2)cc1Oc1cc(C#N)ccc1-c1ncc(CCN)cn1] | 4-[5-(2-aminoethyl)pyrimidin-2-yl]-3-(2-methyl-5-piperidin-1-ylpyrazol-3-yl)oxybenzonitrile |
| 628 | 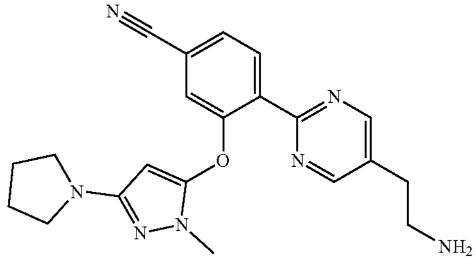 | 4-[5-(2-aminoethyl)pyrimidin-2-yl]-3-(2-methyl-5-pyrrolidin-1-ylpyrazol-3-yl)oxybenzonitrile |
| 629 | 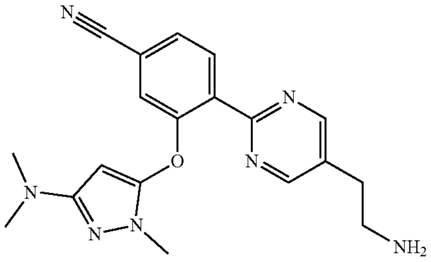 [SMILES: CN(C)c1cc(Oc2cc(C#N)ccc2-c2ncc(CCN)cn2)n(C)n1] | 4-[5-(2-aminoethyl)pyrimidin-2-yl]-3-[5-(dimethylamino)-2-methylpyrazol-3-yl]oxybenzonitrile |
| 630 | 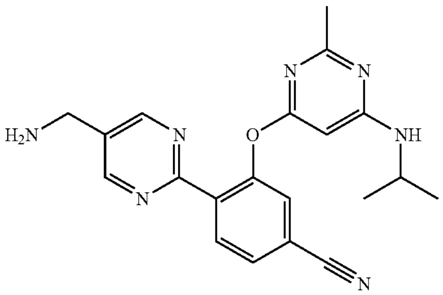 [SMILES: Cc1nc(NC(C)C)cc(Oc2cc(C#N)ccc2-c2ncc(CN)cn2)n1] | 4-[5-(aminomethyl)pyrimidin-2-yl]-3-[2-methyl-6-(propan-2-ylamino)pyrimidin-4 yl]oxybenzonitrile |
| 631 | 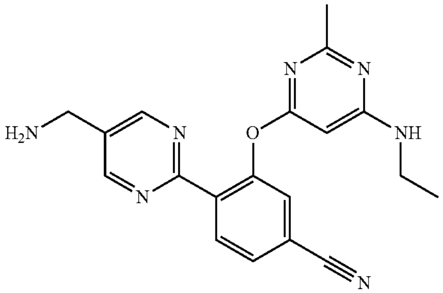 [SMILES: CCNc1cc(Oc2cc(C#N)ccc2-c2ncc(CN)cn2)nc(C)n1] | 4-[5-(aminomethyl)pyrimidin-2-yl]-3-[6-(ethylamino)-2-methylpyrimidin-4-yl]oxybenzonitrile |

TABLE 1-continued

| Compound number | Structural formula | Compound name |
| --- | --- | --- |
| 632 | 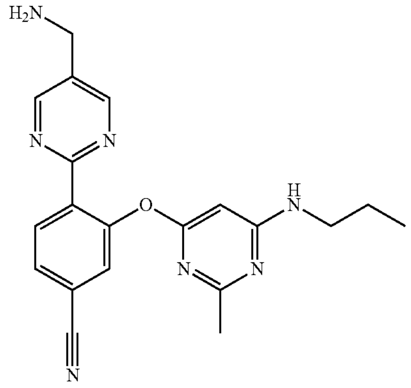 [SMILES: CCCNc1cc(Oc2cc(C#N)ccc2-c2ncc(CN)cn2)nc(C)n1] | 4-[5-(aminomethyl)pyrimidin-2-yl]-3-[2-methyl-6-(propylamino)pyrimidin-4-yl]oxybenzonitrile |
| 633 | 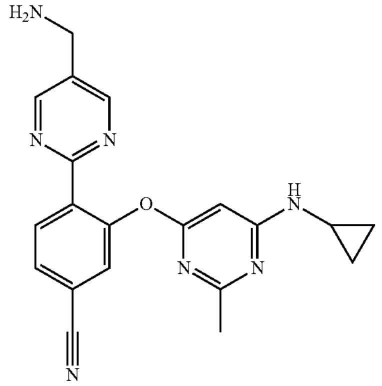 [SMILES: Cc1nc(NC2CC2)cc(Oc2cc(C#N)ccc2-c2ncc(CN)cn2)n1] | 4-[5-(aminomethyl)pyrimidin-2-yl]-3-[6-(cyclopropylamino)-2-methylpyrimidin-4-yl]oxybenzonitrile |
| 634 | 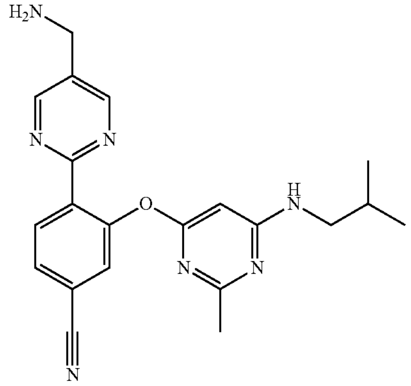 [SMILES: Cc1nc(NCC(C)C)cc(Oc2cc(C#N)ccc2-c2ncc(CN)cn2)n1] | 4-[5-(aminomethyl)pyrimidin-2-yl]-3-[2-methyl-6-(2-methylpropylamino)pyrimidin-4-yl]oxybenzonitrile |
| 635 | 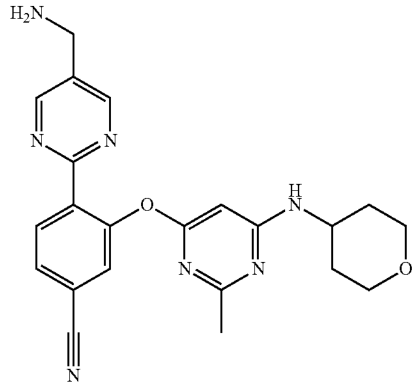 [SMILES: Cc1nc(NC2CCOCC2)cc(Oc2cc(C#N)ccc2-c2ncc(CN)cn2)n1] | 4-[5-(aminomethyl)pyrimidin-2-yl]-3-[2-methyl-6-(oxan-4 ylamino)pyrimidin-4-yl]oxybenzonitrile |

TABLE 1-continued

| Compound number | Structural formula | Compound name |
|---|---|---|
| 636 | 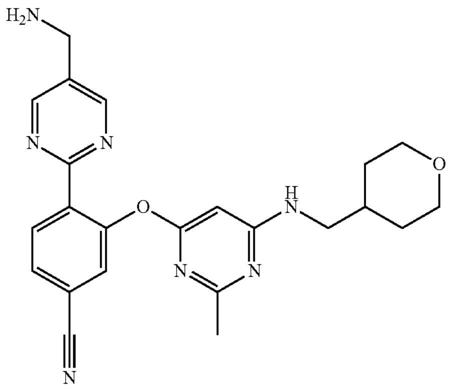 [SMILES: Cc1nc(NCC2CCOCC2)cc(Oc2cc(C#N)ccc2-c2ncc(CN)cn2)n1] | 4-[5-(aminomethyl)pyrimidin-2-yl]-3-[2-methyl-6-(oxan-4-ylmethylamino)pyrimidin-4-yl]oxybenzonitrile |
| 637 | 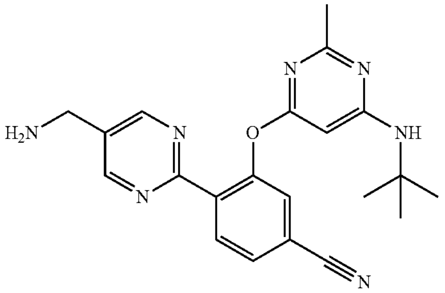 [SMILES: Cc1nc(NC(C)(C)C)cc(Oc2cc(C#N)ccc2-c2ncc(CN)cn2)n1] | 4-[5-(aminomethyl)pyrimidin-2-yl]-3-[6-(tert-butylamino)-2-methylpyrimidin-4-yl]oxybenzonitrile |
| 638 | 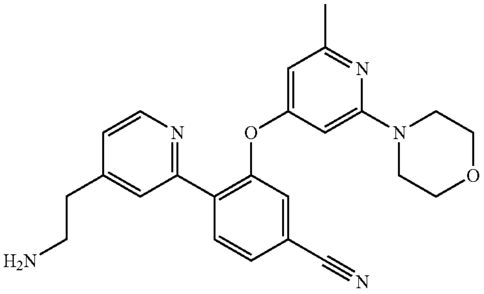 [SMILES: Cc1cc(Oc2cc(C#N)ccc2-c2cc(CCN)ccn2)cc(N2CCOCC2)n1] | 4-[4-(2-aminoethyl)pyridin-2-yl]-3-(2-methyl-6-morpholin-4-ylpyridin-4-yl)oxybenzonitrile |
| 639 | 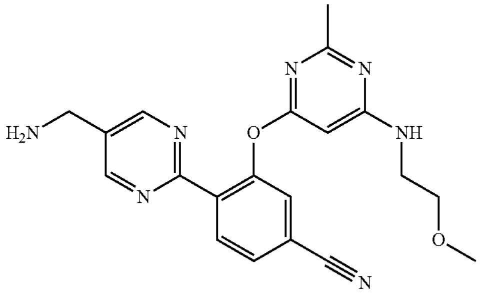 [SMILES: COCCNc1cc(Oc2cc(C#N)ccc2-c2ncc(CN)cn2)nc(C)n1] | 4-[5-(aminomethyl)pyrimidin-2-yl]-3-[6-(2-methoxyethylamino)-2-methylpyrimidin-4-yl]oxybenzonitrile |
| 640 | 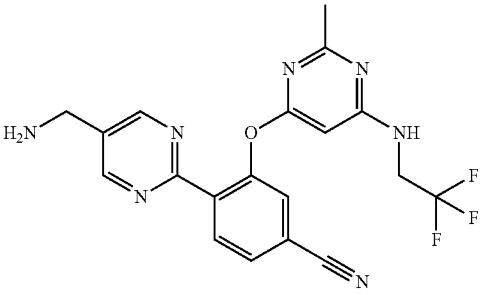 [SMILES: Cc1nc(NCC(F)(F)F)cc(Oc2cc(C#N)ccc2-c2ncc(CN)cn2)n1] | 4-[5-(aminomethyl)pyrimidin-2-yl]-3-[2-methyl-6-(2,2,2-trifluoroethylamino)pyrimidin-4-yl]oxybenzonitrile |

TABLE 1-continued

| Compound number | Structural formula | Compound name |
|---|---|---|
| 641 | 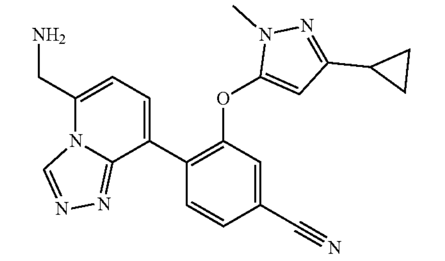 [SMILES: Cn1nc(C2CC2)cc1Oc1cc(C#N)ccc1-c1ccc(CN)n2cnnc12] | 4-[5-(aminomethyl)-[1,2,4]triazolo[4,3-a]pyridin-8-yl]-3-(5-cyclopropyl-2-methylpyrazol-3-yl)oxybenzonitrile |
| 642 | 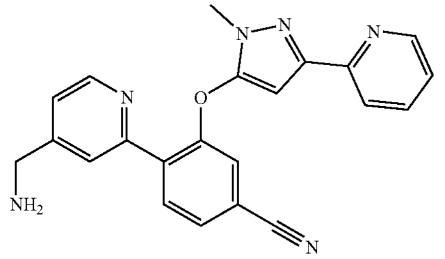 [SMILES: Cn1nc(-c2ccccn2)cc1Oc1cc(C#N)ccc1-c1cc(CN)ccn1] | 4-[4-(aminomethyl)pyridin-2-yl]-3-(2-methyl-5-pyridin-2-ylpyrazol-3-yl)oxybenzonitrile |
| 643 | 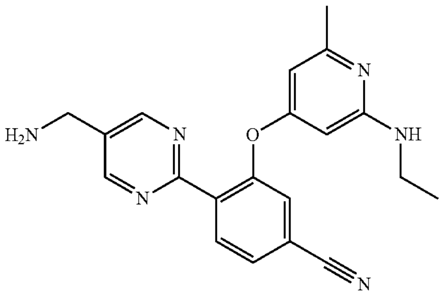 [SMILES: CCNc1cc(Oc2cc(C#N)ccc2-c2ncc(CN)cn2)cc(C)n1] | 4-[5-(aminomethyl)pyrimidin-2-yl]-3-[2-(ethylamino)-6-methylpyridin-4-yl]oxybenzonitrile |
| 644 | 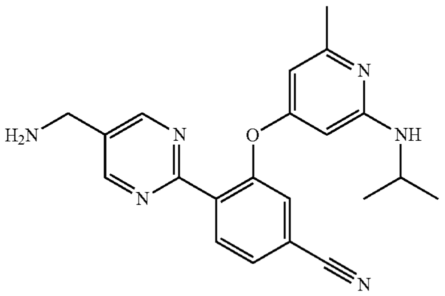 [SMILES: Cc1cc(Oc2cc(C#N)ccc2-c2ncc(CN)cn2)cc(NC(C)C)n1] | 4-[5-(aminomethyl)pyrimidin-2-yl]-3-[2-methyl-6-(propan-2-ylamino)pyridin-4-yl]oxybenzonitrile |
| 645 | 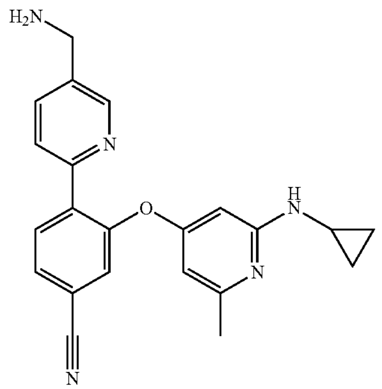 | 4-[5-(aminomethyl)pyridin-2-yl]-3-[2-(cyclopropylamino)-6-methylpyridin-4-yl]oxybenzonitrile |

TABLE 1-continued

| Compound number | Structural formula | Compound name |
|---|---|---|
| 646 | 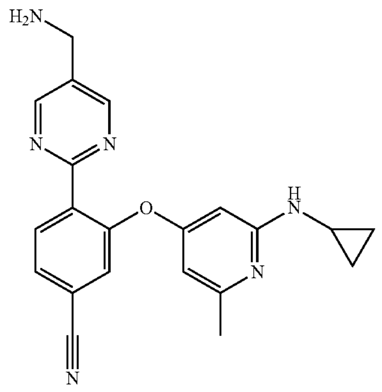 [SMILES: Cc1cc(Oc2cc(C#N)ccc2-c2ncc(CN)cn2)cc(NC2CC2)n1] | 4-[5-(aminomethyl)pyrimidin-2-yl]-3-[2-(cyclopropylamino)-6-methylpyridin-4-yl]oxybenzonitrile |
| 647 | 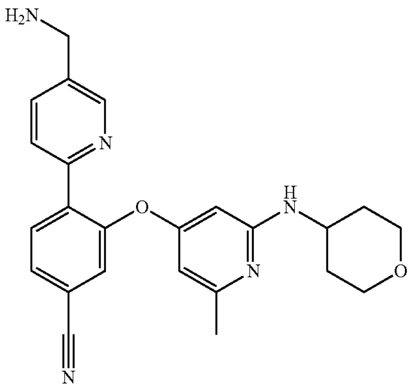 [SMILES: Cc1cc(Oc2cc(C#N)ccc2-c2ccc(CN)cn2)cc(NC2CCOCC2)n1] | 4-[5-(aminomethyl)pyridin-2-yl]-3-[2-methyl-6-(oxan-4-ylamino)pyridin-4-yl]oxybenzonitrile |
| 648 | 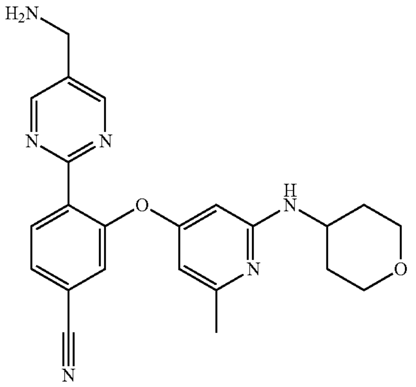 [SMILES: Cc1cc(Oc2cc(C#N)ccc2-c2ncc(CN)cn2)cc(NC2CCOCC2)n1] | 4-[5-(aminomethyl)pyrimidin-2-yl]-3-[2-methyl-6-(oxan-4-ylamino)pyridin-4-yl]oxybenzonitrile |
| 649 | 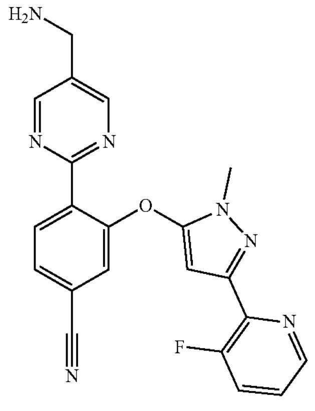 [SMILES: Cn1nc(-c2ncccc2F)cc1Oc1cc(C#N)ccc1-c1ncc(CN)cn1] | 4-[5-(aminomethyl)pyrimidin-2-yl]-3-[5-(3-fluoropyridin-2-yl)-2-methylpyrazol-3-yl]oxybenzonitrile |

TABLE 1-continued
| Compound number | Structural formula | Compound name |
|---|---|---|
| 650 | 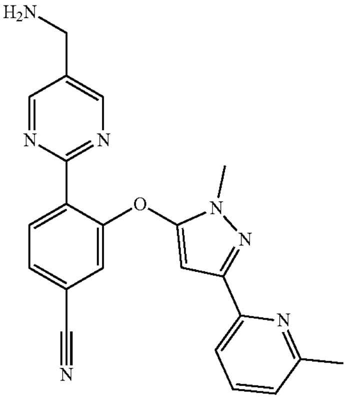 [SMILES: Cc1cccc(-c2cc(Oc3cc(C#N)ccc3-c3ncc(CN)cn3)n(C)n2)n1] | 4-[5-(aminomethyl)pyrimidin-2-yl]-3-[2-methyl-5-(6-methylpyridin-2-yl)pyrazol-3-yl]oxybenzonitrile |
| 651 | 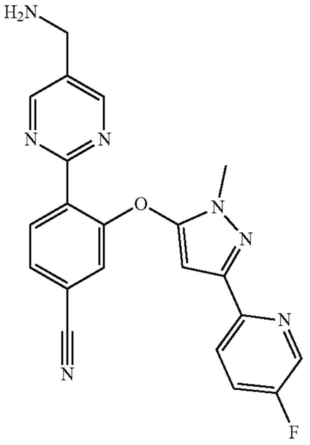 [SMILES: Cn1nc(-c2ccc(F)cn2)cc1Oc1cc(C#N)ccc1-c1ncc(CN)cn1] | 4-[5-(aminomethyl)pyrimidin-2-yl]-3-[5-(5-fluoropyridin-2-yl)-2-methylpyrazol-3-yl]oxybenzonitrile |
| 652 | 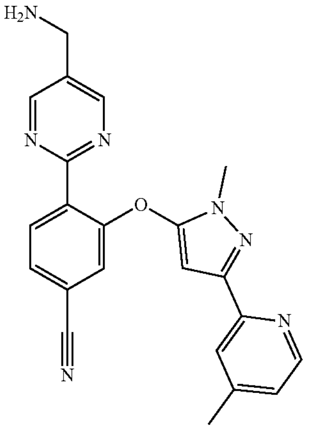 [SMILES: Cc1ccnc(-c2cc(Oc3cc(C#N)ccc3-c3ncc(CN)cn3)n(C)n2)c1] | 4-[5-(aminomethyl)pyrimidin-2-yl]-3-[2-methyl-5-(4-methylpyridin-2-yl)pyrazol-3-yl]oxybenzonitrile |

TABLE 1-continued

| Compound number | Structural formula | Compound name |
|---|---|---|
| 653 | 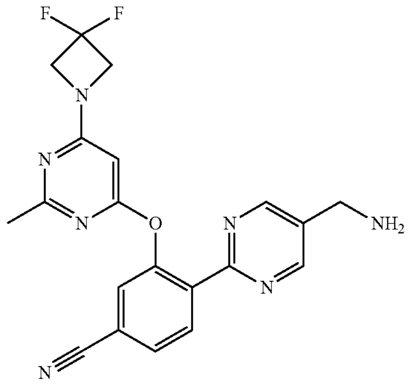 [SMILES: Cc1nc(Oc2cc(C#N)ccc2-c2ncc(CN)cn2)cc(N2CC(F)(F)C2)n1] | 4-[5-(aminomethyl)pyrimidin-2-yl]-3-[6-(3,3-difluoroazetidin-1-yl)-2-methylpyrimidin-4-yl]oxybenzonitrile |
| 654 | 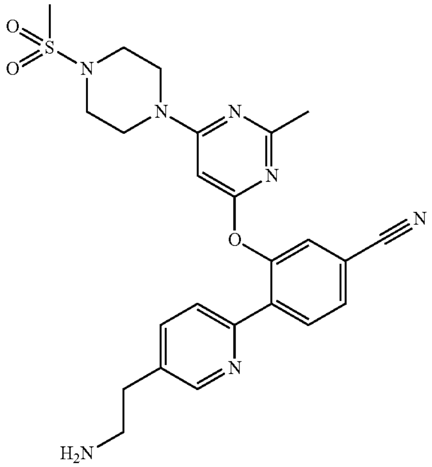 [SMILES: Cc1nc(Oc2cc(C#N)ccc2-c2ccc(CCN)cn2)cc(N2CCN(S(C)(=O)=O)CC2)n1] | 4-[5-(2-aminoethyl)pyridin-2-yl]-3-[2-methyl-6-(4-methylsulfonylpiperazin-1-yl)pyrimidin-4-yl]oxybenzonitrile |
| 655 | 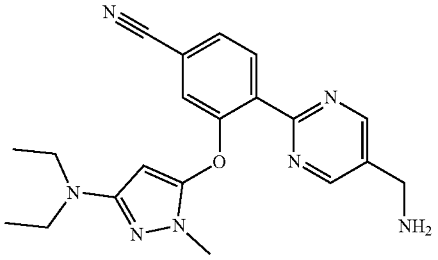 [SMILES: CCN(CC)c1cc(Oc2cc(C#N)ccc2-c2ncc(CN)cn2)n(C)n1] | 4-[5-(aminomethyl)pyrimidin-2-yl]-3-[5-(diethylamino)-2-methylpyrazol-3-yl]oxybenzonitrile |
| 656 | 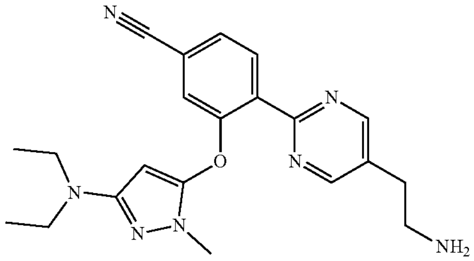 | 4-[5-(2-aminoethyl)pyrimidin-2-yl]-3-[5-(diethylamino)-2-methylpyrazol-3-yl]oxybenzonitrile |

TABLE 1-continued

| Compound number | Structural formula | Compound name |
|---|---|---|
| 657 | 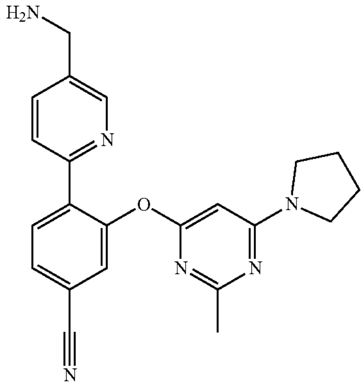 | 4-[5-(aminomethyl)pyridin-2-yl]-3-(2-methyl-6-pyrrolidin-1-ylpyrimidin-4-yl)oxybenzonitrile |
| 658 | 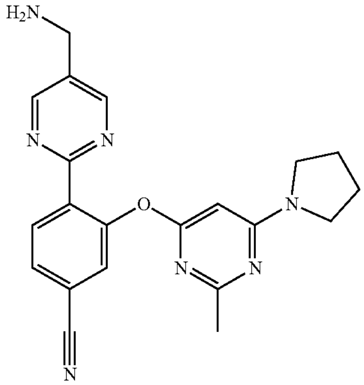 [SMILES: Cc1nc(Oc2cc(C#N)ccc2-c2ncc(CN)cn2)cc(N2CCCC2)n1] | 4-[5-(aminomethyl)pyrimidin-2-yl]-3-(2-methyl-6-pyrrolidin-1-ylpyrimidin-4-yl)oxybenzonitrile |
| 659 | 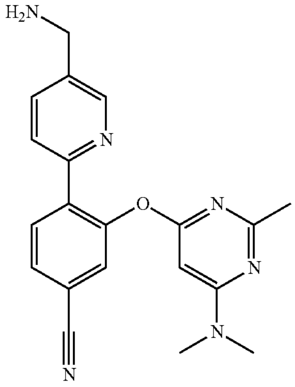 [SMILES: Cc1nc(Oc2cc(C#N)ccc2-c2ccc(CN)cn2)cc(N(C)C)n1] | 4-[5-(aminomethyl)pyridin-2-yl]-3-[6-(dimethylamino)-2-methylpyrimidin-4-yl]oxybenzonitrile |
| 660 | 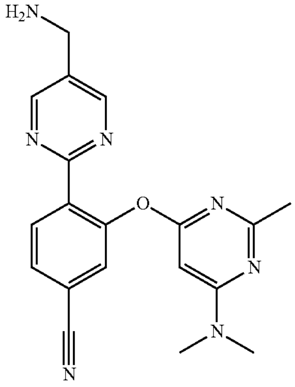 [SMILES: Cc1nc(Oc2cc(C#N)ccc2-c2ncc(CN)cn2)cc(N(C)C)n1] | 4-[5-(aminomethyl)pyrimidin-2-yl]-3-[6-(dimethylamino)-2-methylpyrimidin-4-yl]oxybenzonitrile |

TABLE 1-continued
| Compound number | Structural formula | Compound name |
|---|---|---|
| 661 | 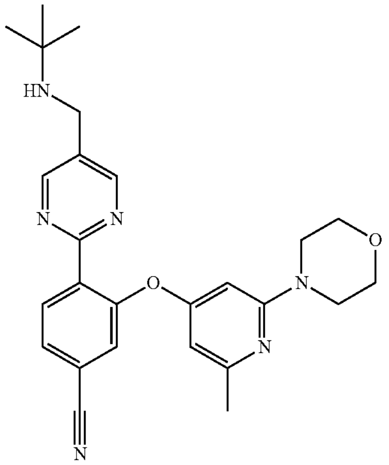 [SMILES: Cc1cc(Oc2cc(C#N)ccc2-c2ncc(CNC(C)(C)C)cn2)cc(N2CCOCC2)n1] | 4-[5-[(tert-butylamino)methyl]pyrimidin-2-yl]-3-(2-methyl-6-morpholin-4-ylpyridin-4-yl)oxybenzonitrile |
| 662 | 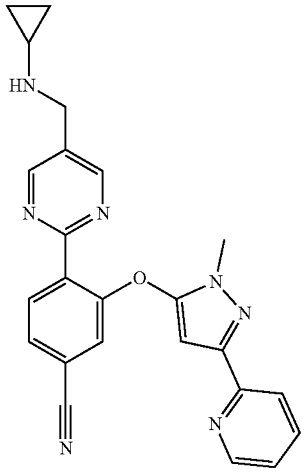 [SMILES: Cn1nc(-c2ccccn2)cc1Oc1cc(C#N)ccc1-c1ncc(CNC2CC2)cn1] | 4-[5-[(cyclopropylamino)methyl]pyrimidin-2-yl]-3-(2-methyl-5-pyridin-2-ylpyrazol-3-yl)oxybenzonitrile |
| 663 | 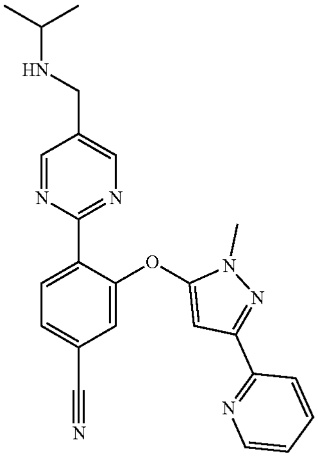 [SMILES: CC(C)NCc1cnc(-c2ccc(C#N)cc2Oc2cc(-c3ccccn3)nn2C)nc1] | 3-(2-methyl-5-pyridin-2-ylpyrazol-3-yl)oxy-4-[5-[(propan-2-ylamino)methyl]pyrimidin-2-yl]benzonitrile |

TABLE 1-continued
| Compound number | Structural formula | Compound name |
|---|---|---|
| 664 | 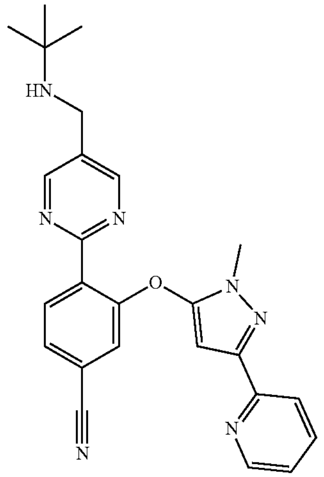 [SMILES: Cn1nc(-c2ccccn2)cc1Oc1cc(C#N)ccc1-c1ncc(CNC(C)(C)C)cn1] | 4-[5-[(tert-butylamino)methyl]pyrimidin-2-yl]-3-(2-methyl-5-pyridin-2-ylpyrazol-3-yl)oxybenzonitrile |
| 665 | 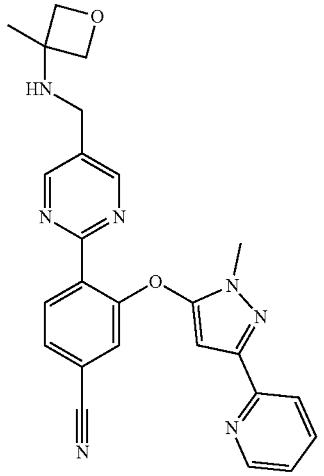 [SMILES: Cn1nc(-c2ccccn2)cc1Oc1cc(C#N)ccc1-c1ncc(CNC2(C)COC2)cn1] | 4-[5-[[(3-methyloxetan-3-yl)amino]methyl]pyrimidin-2-yl]-3-(2-methyl-5-pyridin-2-ylpyrazol-3-yl)oxybenzonitrile |
| 666 | 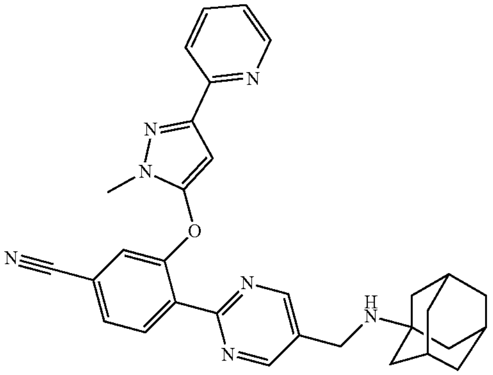 [SMILES: Cn1nc(-c2ccccn2)cc1Oc1cc(C#N)ccc1-c1ncc(CNC23CC4CC(CC(C4)C2)C3)cn1] | 4-[5-[(1-adamantylamino)methyl]pyrimidin-2-yl]-3-(2-methyl-5-pyridin-2-ylpyrazol-3-yl)oxybenzonitrile |

TABLE 1-continued
| Compound number | Structural formula | Compound name |
|---|---|---|
| 667 | 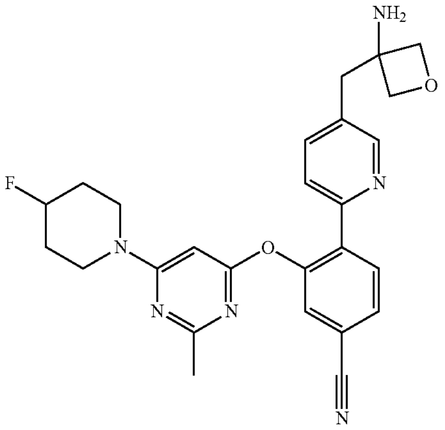 [SMILES: Cc1nc(Oc2cc(C#N)ccc2-c2ccc(CC3(N)COC3)cn2)cc(N2CCC(F)CC2)n1] | 4-[5-[(3-aminooxetan-3-yl)methyl]pyridin-2-yl]-3-[6-(4-fluoropiperidin-1-yl)-2-methylpyrimidin-4-yl]oxybenzonitrile |
| 668 | 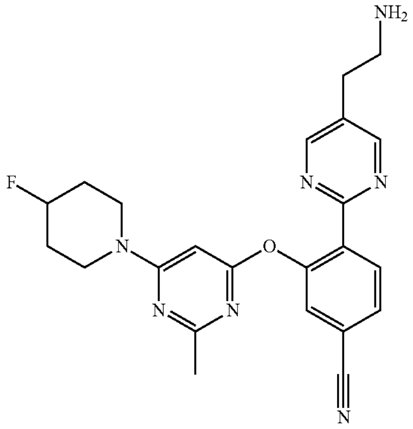 [SMILES: Cc1nc(Oc2cc(C#N)ccc2-c2ncc(CCN)cn2)cc(N2CCC(F)CC2)n1] | 4-[5-(2-aminoethyl)pyrimidin-2-yl]-3-[6-(4-fluoropiperidin-1-yl)-2-methylpyrimidin-4-yl]oxybenzonitrile |
| 669 | 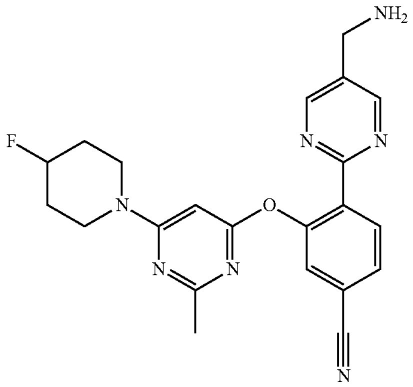 [SMILES: Cc1nc(Oc2cc(C#N)ccc2-c2ncc(CN)cn2)cc(N2CCC(F)CC2)n1] | 4-[5-(aminomethyl)pyrimidin-2-yl]-3-[6-(4-fluoropiperidin-1-yl)-2-methylpyrimidin-4-yl]oxybenzonitrile |

TABLE 1-continued
| Compound number | Structural formula | Compound name |
|---|---|---|
| 670 | 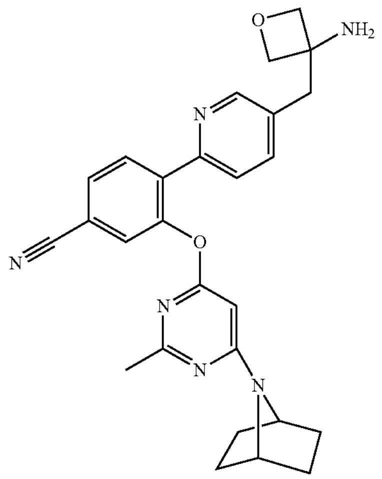 [SMILES: Cc1nc(Oc2cc(C#N)ccc2-c2ccc(CC3(N)COC3)cn2)cc(N2C3CCC2CC3)n1] | 4-[5-[(3-aminooxetan-3-yl)methyl]pyridin-2-yl]-3-[6-(7-azabicyclo[2.2.1]heptan-7-yl)-2-methylpyrimidin-4-yl]oxybenzonitrile |
| 671 | 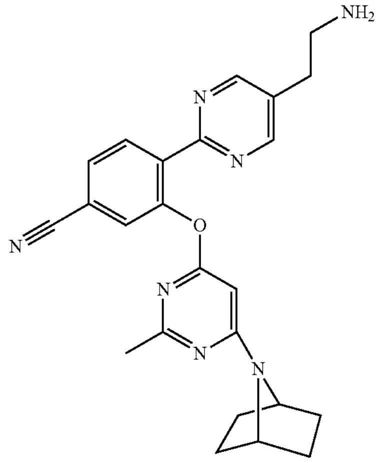 [SMILES: Cc1nc(Oc2cc(C#N)ccc2-c2ncc(CCN)cn2)cc(N2C3CCC2CC3)n1] | 4-[5-(2-aminoethyl)pyrimidin-2-yl]-3-[6-(7-azabicyclo[2.2.1]heptan-7-yl)-2-methylpyrimidin-4-yl]oxybenzonitrile |
| 672 | 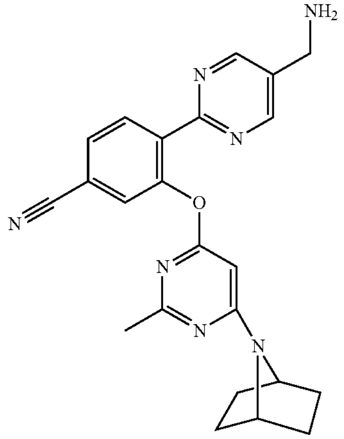 [SMILES: Cc1nc(Oc2cc(C#N)ccc2-c2ncc(CN)cn2)cc(N2C3CCC2CC3)n1] | 4-[5-(aminomethyl)pyrimidin-2-yl]-3-[6-(7-azabicyclo[2.2.1]heptan-7-yl)-2-methylpyrimidin-4-yl]oxybenzonitrile |

TABLE 1-continued

| Compound number | Structural formula | Compound name |
|---|---|---|
| 673 | 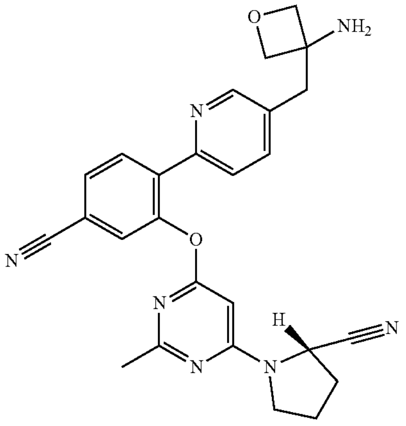 [SMILES: Cc1nc(Oc2cc(C#N)ccc2-c2ccc(CC3(N)COC3)cn2)cc(N2CCC[C@H]2C#N)n1] | (2S)-1-[6-[2-[5-[(3-aminooxetan-3-yl)methyl]pyridin-2-yl]-5-cyanophenoxy]-2-methylpyrimidin-4-yl]pyrrolidine-2-carbonitrile |
| 674 | 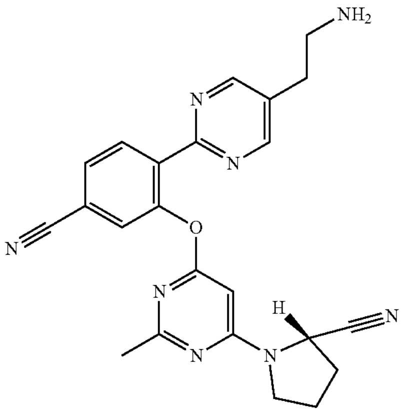 [SMILES: Cc1nc(Oc2cc(C#N)ccc2-c2ncc(CCN)cn2)cc(N2CCC[C@H]2C#N)n1] | (2S)-1-[6-[2-[5-(2-aminoethyl)pyrimidin-2-yl]-5-cyanophenoxy]-2-methylpyrimidin-4-yl]pyrrolidine-2-carbonitrile |
| 675 | 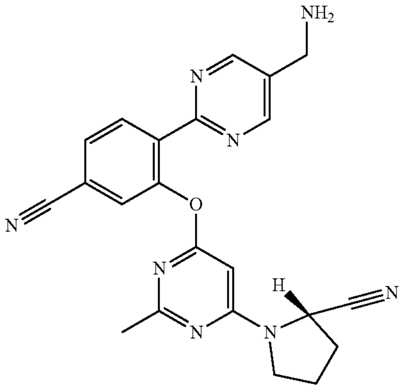 [SMILES: Cc1nc(Oc2cc(C#N)ccc2-c2ncc(CN)cn2)cc(N2CCC[C@H]2C#N)n1] | (2S)-1-[6-[2-[5-(aminomethyl)pyrimidin-2-yl]-5-cyanophenoxy]-2-methylpyrimidin-4-yl]pyrrolidine-2-carbonitrile |
| 676 | 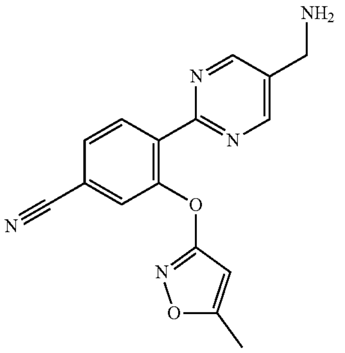 [SMILES: Cc1cc(Oc2cc(C#N)ccc2-c2ncc(CN)cn2)no1] | 4-[5-(aminomethyl)pyrimidin-2-yl]-3-[(5-methyl-1,2-oxazol-3-yl)oxy]benzonitrile |

TABLE 1-continued

| Compound number | Structural formula | Compound name |
| --- | --- | --- |
| 677 | 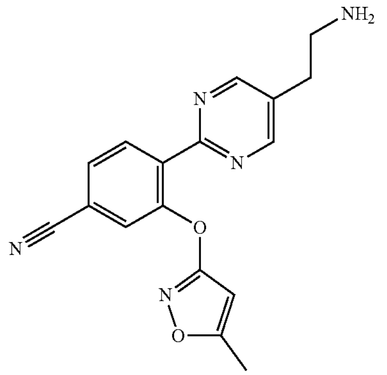 [SMILES: Cc1cc(Oc2cc(C#N)ccc2-c2ncc(CCN)cn2)no1] | 4-[5-(2-aminoethyl)pyrimidin-2-yl]-3-[(5-methyl-1,2-oxazol-3-yl)oxy]benzonitrile |
| 678 | 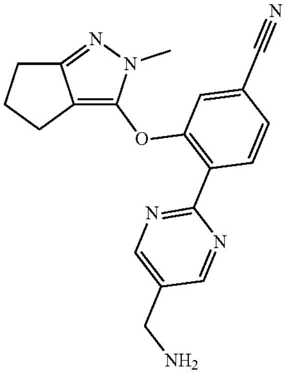 [SMILES: Cn1nc2c(c1Oc1cc(C#N)ccc1-c1ncc(CN)cn1)CCC2] | 4-[5-(aminomethyl)pyrimidin-2-yl]-3-[(2-methyl-5,6-dihydro-4H-cyclopenta[c]pyrazol-3-yl)oxy]benzonitrile |
| 679 | 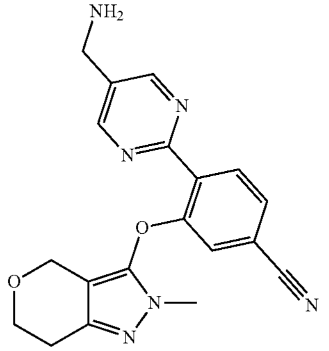 [SMILES: Cn1nc2c(c1Oc1cc(C#N)ccc1-c1ncc(CN)cn1)COCC2] | 4-[5-(aminomethyl)pyrimidin-2-yl]-3-[(2-methyl-6,7-dihydro-4H-pyrano[4,3-c]pyrazol-3-yl)oxy]benzonitrile |
| 680 | 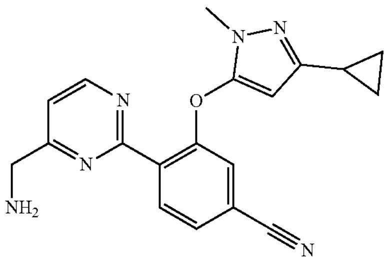 [SMILES: Cn1nc(C2CC2)cc1Oc1cc(C#N)ccc1-c1nccc(CN)n1] | 4-[4-(aminomethyl)pyrimidin-2-yl]-3-(5-cyclopropyl-2-methylpyrazol-3-yl)oxybenzonitrile |

TABLE 1-continued

| Compound number | Structural formula | Compound name |
|---|---|---|
| 681 | 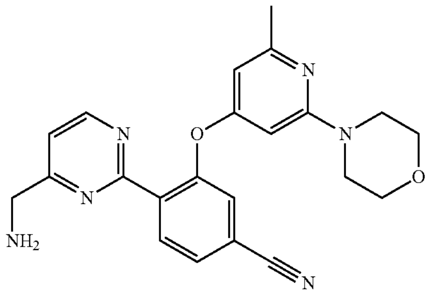 [SMILES: Cc1cc(Oc2cc(C#N)ccc2-c2nccc(CN)n2)cc(N2CCOCC2)n1] | 4-[4-(aminomethyl)pyrimidin-2-yl]-3-(2-methyl-6-morpholin-4-ylpyridin-4-yl)oxybenzonitrile |
| 682 | 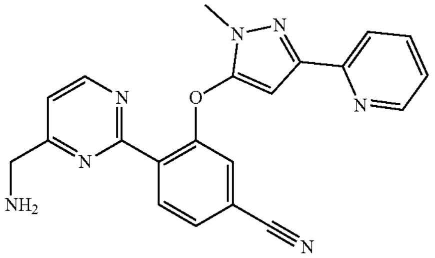 [SMILES: Cn1nc(-c2ccccn2)cc1Oc1cc(C#N)ccc1-c1nccc(CN)n1] | 4-[4-(aminomethyl)pyrimidin-2-yl]-3-(2-methyl-5-pyridin-2-ylpyrazol-3-yl)oxybenzonitrile |
| 683 | 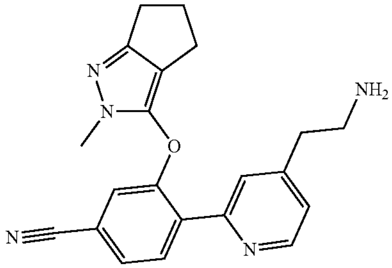 [SMILES: Cn1nc2c(c1Oc1cc(C#N)ccc1-c1cc(CCN)ccn1)CCC2] | 4-[4-(2-aminoethyl)pyridin-2-yl]-3-[(2-methyl-5,6-dihydro-4H-cyclopenta[c]pyrazol-3-yl)oxy]benzonitrile |
| 684 | 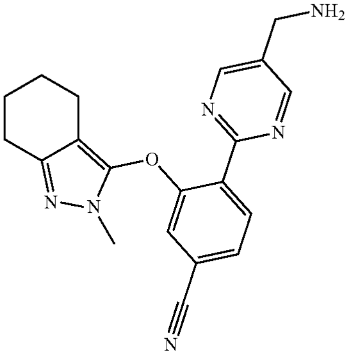 [SMILES: Cn1nc2c(c1Oc1cc(C#N)ccc1-c1ncc(CN)cn1)CCCC2] | 4-[5-(aminomethyl)pyrimidin-2-yl]-3-[(2-methyl-4,5.6,7-tetrahydroindazol-3-yl)oxy]benzonitrile |
| 685 | 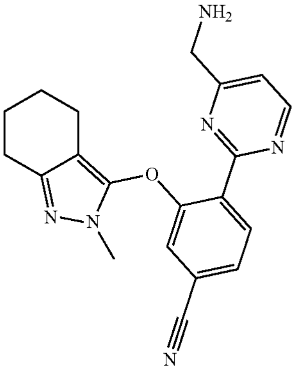 [SMILES: Cn1nc2c(c1Oc1cc(C#N)ccc1-c1nccc(CN)n1)CCCC2] | 4-[4-(aminomethyl)pyrimidin-2-yl]-3-[(2-methyl-4,5,6,7-tetrahydroindazol-3-yl)oxy]benzonitrile |

TABLE 1-continued
| Compound number | Structural formula | Compound name |
|---|---|---|
| 686 | 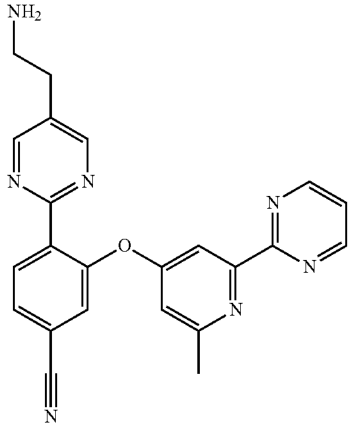 [SMILES: Cc1cc(Oc2cc(C#N)ccc2-c2ncc(CCN)cn2)cc(-c2ncccn2)n1] | 4-[5-(2-aminoethyl)pyrimidin-2-yl]-3-(2-methyl-6-pyrimidin-2-ylpyridin-4-yl)oxybenzonitrile |
| 687 | 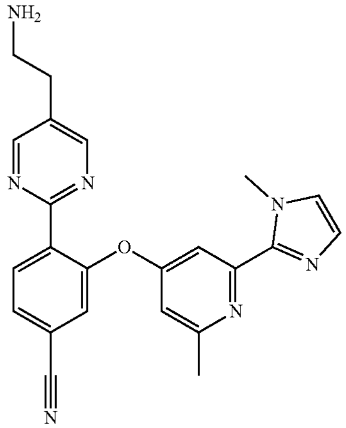 [SMILES: Cc1cc(Oc2cc(C#N)ccc2-c2ncc(CCN)cn2)cc(-c2nccn2C)n1] | 4-[5-(2-aminoethyl)pyrimidin-2-yl]-3-[2-methyl-6-(1-methylimidazol-2-yl)pyridin-4-yl]oxybenzonitrile |
| 688 | 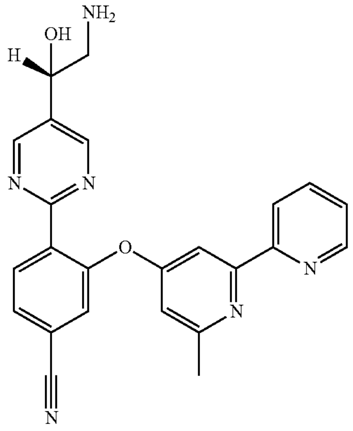 [SMILES: Cc1cc(Oc2cc(C#N)ccc2-c2ncc([C@H](O)CN)cn2)cc(-c2ccccn2)n1] | 4-[5-[(1S)-2-amino-1-hydroxyethyl]pyrimidin-2-yl]-3-(2-methyl-6-pyridin-2-ylpyridin-4-yl)oxybenzonitrile |

TABLE 1-continued
| Compound number | Structural formula | Compound name |
|---|---|---|
| 689 | 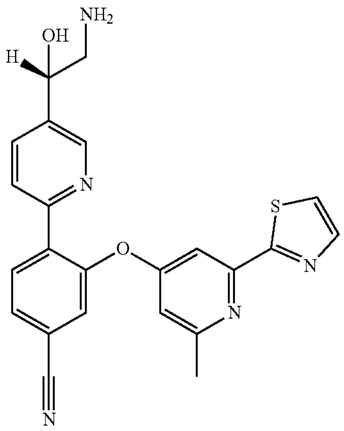 | 4-[5-[(1S)-2-amino-1-hydroxyethyl]pyridin-2-yl]-3-[2-methyl-6-(1,3-thiazol-2-yl)pyridin-4-yl]oxybenzonitrile |
| 690 | 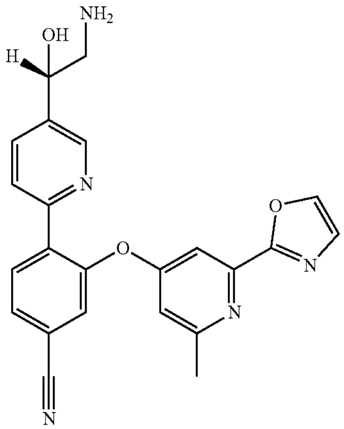 [SMILES: Cc1cc(Oc2cc(C#N)ccc2-c2ccc([C@H](O)CN)cn2)cc(-c2ncco2)n1] | 4-[5-[(1S)-2-amino-1-hydroxyethyl]pyridin-2-yl]-3-[2-methyl-6-(1,3-oxazol-2-yl)pyridin-4-yl]oxybenzonitrile |
| 691 | 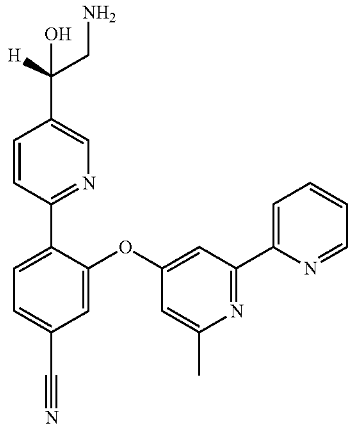 [SMILES: Cc1cc(Oc2cc(C#N)ccc2-c2ccc([C@H](O)CN)cn2)cc(-c2ccccn2)n1] | 4-[5-[(1S)-2-amino-1-hydroxyethyl]pyridin-2-yl]-3-(2-methyl-6-pyridin-2-ylpyridin-4-yl)oxybenzonitrile |

TABLE 1-continued
| Compound number | Structural formula | Compound name |
|---|---|---|
| 692 | 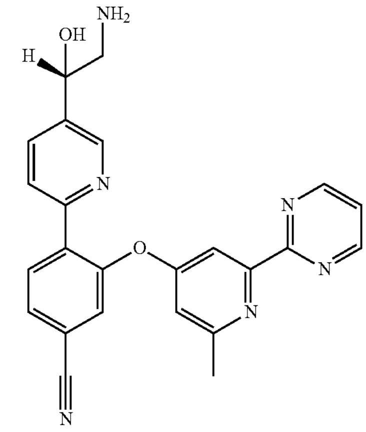 [SMILES: Cc1cc(Oc2cc(C#N)ccc2-c2ccc([C@H](O)CN)cn2)cc(-c2ncccn2)n1] | 4-[5-[(1S)-2-amino-1-hydroxyethyl]pyridin-2-yl]-3-(2-methyl-6-pyrimidin-2-ylpyridin-4-yl)oxybenzonitrile |
| 693 | 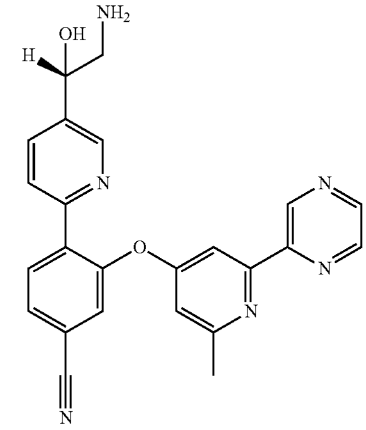 [SMILES: Cc1cc(Oc2cc(C#N)ccc2-c2ccc([C@H](O)CN)cn2)cc(-c2cnccn2)n1] | 4-[5-[(1S)-2-amino-1-hydroxyethyl]pyridin-2-yl]-3-(2-methyl-6-pyrazin-2-ylpyridin-4-yl)oxybenzonitrile |
| 694 | 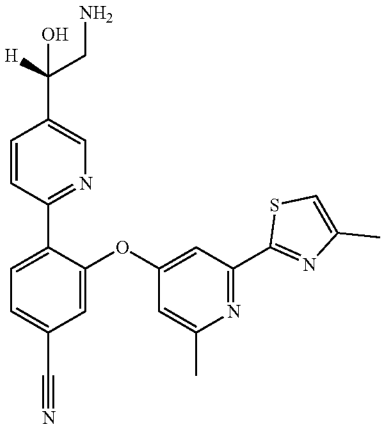 [SMILES: Cc1cc(Oc2cc(C#N)ccc2-c2ccc([C@H](O)CN)cn2)cc(-c2nc(C)cs2)n1] | 4-[5-[(1S)-2-amino-1-hydroxyethyl]pyridin-2-yl]-3-[2-methyl-6-(4-methyl-1,3-thiazol-2-yl)pyridin-4-yl]oxybenzonitrile |

TABLE 1-continued
| Compound number | Structural formula | Compound name |
|---|---|---|
| 695 | 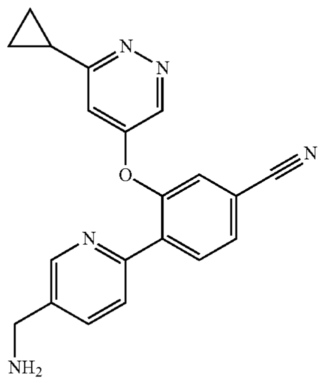 | 4-[5-(aminomethyl)pyridin-2-yl]-3-(6-cyclopropylpyridazin-4-yl)oxybenzonitrile |
| 696 | 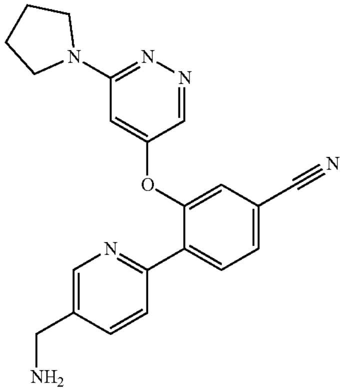 [SMILES: N#Cc1ccc(-c2ccc(CN)cn2)c(Oc2cnnc(N3CCCC3)c2)c1] | 4-[5-(aminomethyl)pyridin-2-yl]-3-(6-pyrrolidin-1-ylpyridazin-4-yl)oxybenzonitrile |
| 697 | 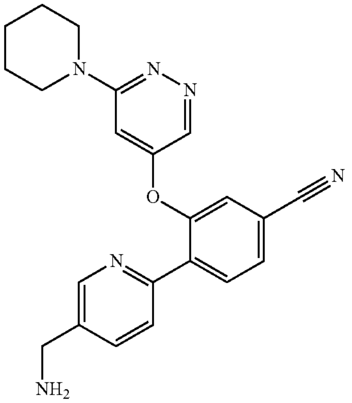 [SMILES: N#Cc1ccc(-c2ccc(CN)cn2)c(Oc2cnnc(N3CCCCC3)c2)c1] | 4-[5-(aminomethyl)pyridin-2-yl]-3-(6-piperidin-1-ylpyridazin-4-yl)oxybenzonitrile |
| 698 | 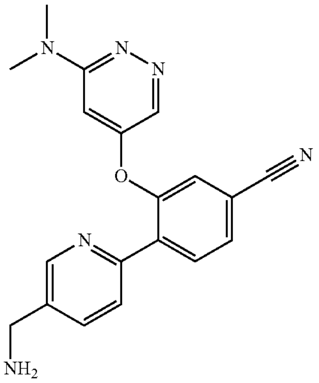 [SMILES: CN(C)c1cc(Oc2cc(C#N)ccc2-c2ccc(CN)cn2)cnn1] | 4-[5-(aminomethyl)pyridin-2-yl]-3-[6-(dimethylamino)pyridazin-4-yl]oxybenzonitrile |

TABLE 1-continued
| Compound number | Structural formula | Compound name |
|---|---|---|
| 699 | 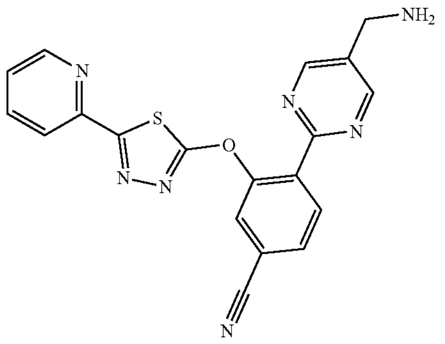 [SMILES: N#Cc1ccc(-c2ncc(CN)cn2)c(Oc2nnc(-c3ccccn3)s2)c1] | 4-[5-(aminomethyl)pyrimidin-2-yl]-3-[(5-pyridin-2-yl-1,3,4-thiadiazol-2-yl)oxy]benzonitrile |
| 700 | 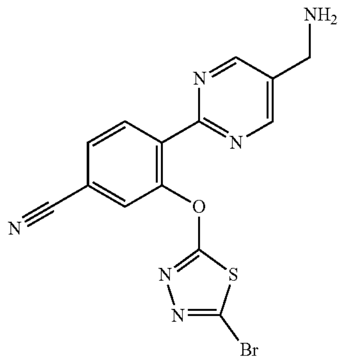 [SMILES: N#Cc1ccc(-c2ncc(CN)cn2)c(Oc2nnc(Br)s2)c1] | 4-[5-(aminomethyl)pyrimidin-2-yl]-3-[(5-bromo-1,3,4-thiadiazol-2-yl)oxy]benzonitrile |
| 701 | 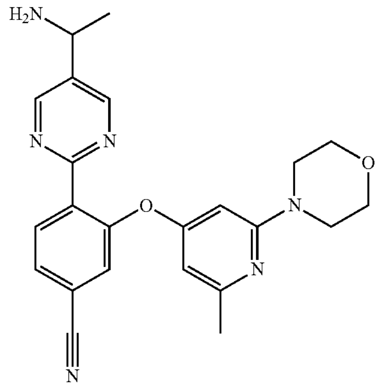 [SMILES: Cc1cc(Oc2cc(C#N)ccc2-c2ncc(C(C)N)cn2)cc(N2CCOCC2)n1] | 4-[5-(1-aminoethypyrimidin-2-yl]-3-(2-methyl-6-morpholin-4-ylpyridin-4-yl)oxybenzonitrile |
| 702 | 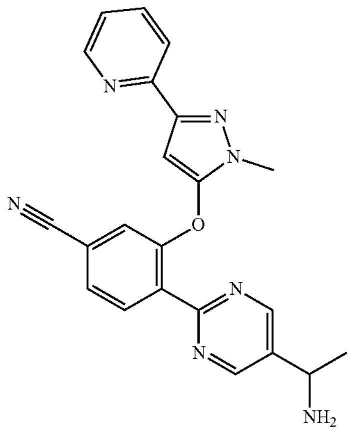 [SMILES: CC(N)c1cnc(-c2ccc(C#N)cc2Oc2cc(-c3ccccn3)nn2C)nc1] | 4-[5-(1-aminoethyl)pyrimidin-2-yl]-3-(2-methyl-5-pyridin-2-ylpyrazol-3-yl)oxybenzonitrile |

TABLE 1-continued
| Compound number | Structural formula | Compound name |
|---|---|---|
| 703 | 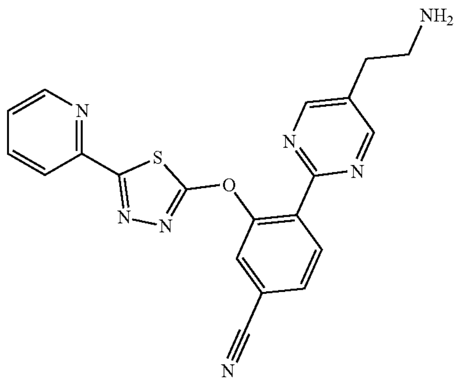 [SMILES: N#Cc1ccc(-c2ncc(CCN)cn2)c(Oc2nnc(-c3ccccn3)s2)c1] | 4-[5-(2-aminoethyl)pyrimidin-2-yl]-3-[(5-pyridin-2-yl-1,3,4-thiadiazol-2-yl)oxy]benzonitrile |
| 704 | 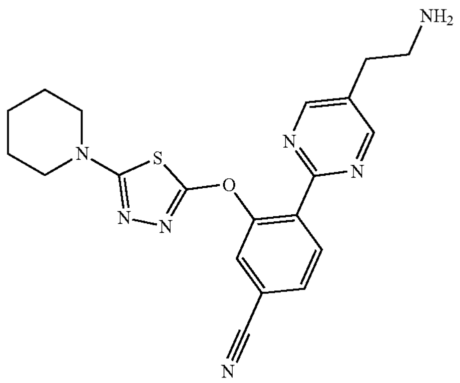 [SMILES: N#Cc1ccc(-c2ncc(CCN)cn2)c(Oc2nnc(N3CCCCC3)s2)c1] | 4-[5-(2-aminoethyl)pyrimidin-2-yl]-3-[(5-piperidin-1-yl-1,3,4-thiadiazol-2-yl)oxy]benzonitrile |
| 705 | 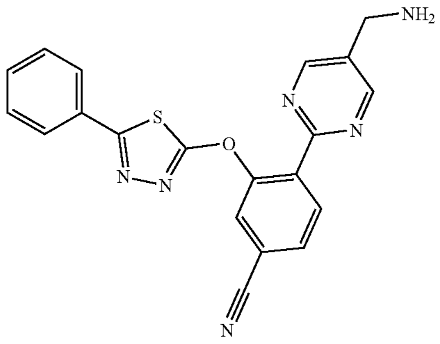 [SMILES: N#Cc1ccc(-c2ncc(CN)cn2)c(Oc2nnc(-c3ccccc3)s2)c1] | 4-[5-(aminomethyl)pyrimidin-2-yl]-3-[(5-phenyl-1,3,4-thiadiazol-2-yl)oxy]benzonitrile |
| 706 | 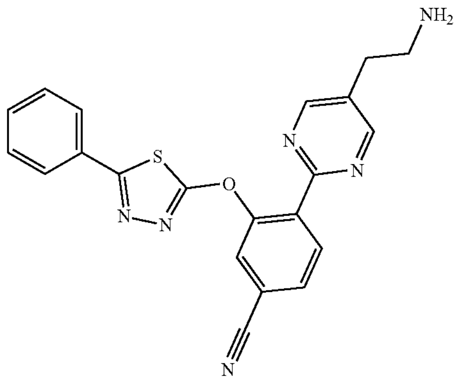 [SMILES: N#Cc1ccc(-c2ncc(CCN)cn2)c(Oc2nnc(-c3ccccc3)s2)c1] | 4-[5-(2-aminoethyl)pyrimidin-2-yl]-3-[(5-phenyl-1,3,4-thiadiazol-2-yl)oxy]benzonitrile |

TABLE 1-continued

| Compound number | Structural formula | Compound name |
|---|---|---|
| 707 | 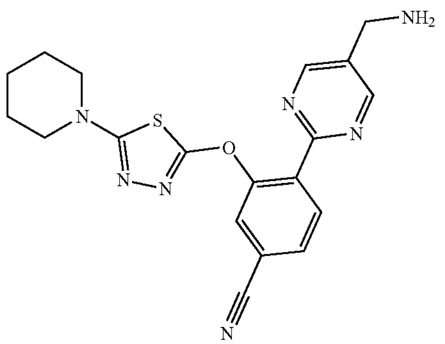 [SMILES: N#Cc1ccc(-c2ncc(CN)cn2)c(Oc2nnc(N3CCCCC3)s2)c1] | 4-[5-(aminomethyl)pyrimidin-2-yl]-3-[(5-piperidin-1-yl-1,3,4-thiadiazol-2-yl)oxy]benzonitrile |
| 708 | 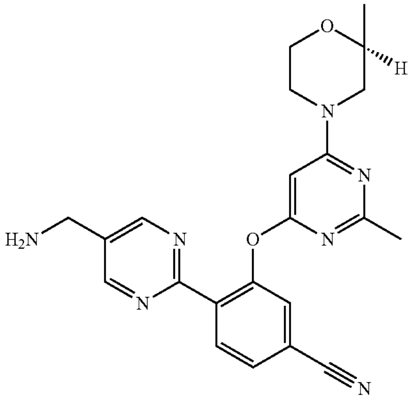 [SMILES: Cc1nc(Oc2cc(C#N)ccc2-c2ncc(CN)cn2)cc(N2CCO[C@@H](C)C2)n1] | 4-[5-(aminomethyl)pyrimidin-2-yl]-3-[2-methyl-6-[(2S)-2-methylmorpholin-4-yl]pyrimidin-4-yl]oxybenzonitrile |
| 709 | 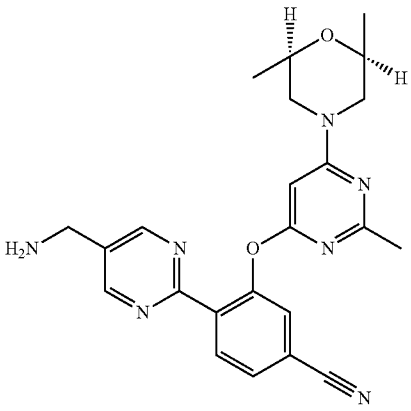 [SMILES: Cc1nc(Oc2cc(C#N)ccc2-c2ncc(CN)cn2)cc(N2C[C@@H](C)O[C@@H](C)C2)n1] | 4-[5-(aminomethyl)pyrimidin-2-yl]-3-[6-[(2R,6S)-2,6-dimethylmorpholin-4-yl]-2-methylpyrimidin-4-yl]oxybenzonitrile |
| 710 | 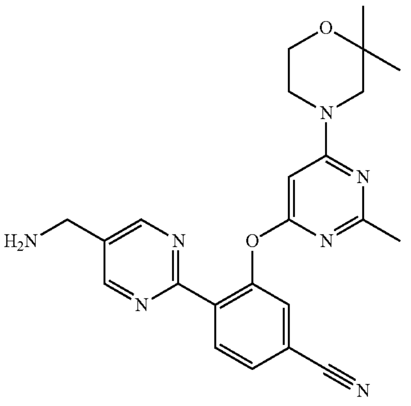 [SMILES: Cc1nc(Oc2cc(C#N)ccc2-c2ncc(CN)cn2)cc(N2CCOC(C)(C)C2)n1] | 4-[5-(aminomethyl)pyrimidin-2-yl]-3-[6-(2,2-dimethylmorpholin-4-yl)-2-methylpyrimidin-4-yl]oxybenzonitrile |

TABLE 1-continued

| Compound number | Structural formula | Compound name |
|---|---|---|
| 711 | 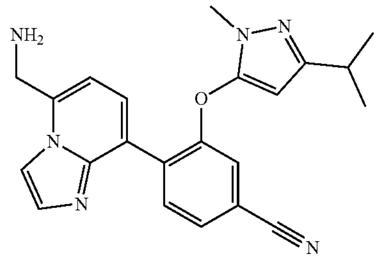 [SMILES: CC(C)c1cc(Oc2cc(C#N)ccc2-c2ccc(CN)n3ccnc23)n(C)n1] | 4-[5-(aminomethyl)imidazo[1,2-a]pyridin-8-yl]-3-(2-methyl-5-propan-2-ylpyrazol-3-yl)oxybenzonitrile |
| 712 | 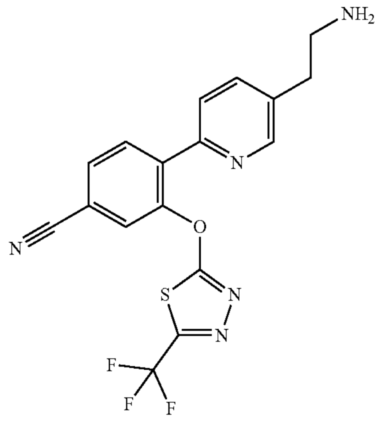 [SMILES: N#Cc1ccc(-c2ccc(CCN)cn2)c(Oc2nnc(C(F)(F)F)s2)c1] | 4-[5-(2-aminoethyl)pyridin-2-yl]-3-[[5-(trifluoromethyl)-1,3,4-thiadiazol-2-yl]oxy]benzonitrile |
| 713 | 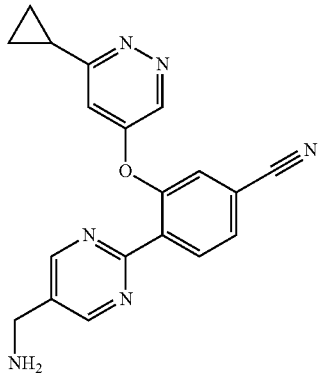 [SMILES: N#Cc1ccc(-c2ncc(CN)cn2)c(Oc2cnnc(C3CC3)c2)c1] | 4-[5-(aminomethyl)pyrimidin-2-yl]-3-(6-cyclopropylpyridazin-4-yl)oxybenzonitrile |
| 714 | 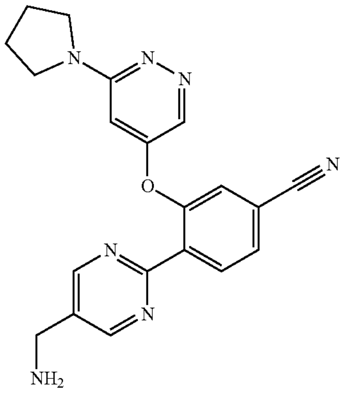 | 4-[5-(aminomethyl)pyrimidin-2-yl]-3-(6-pyrrolidin-1-ylpyridazin-4-yl)oxybenzonitrile |

TABLE 1-continued
| Compound number | Structural formula | Compound name |
| --- | --- | --- |
| 715 | 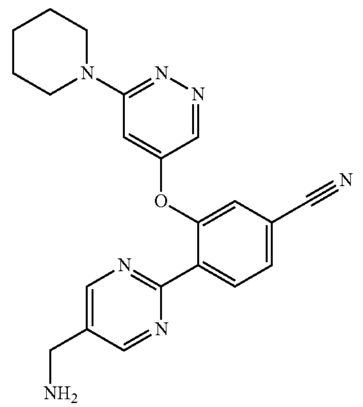 [SMILES: N#Cc1ccc(-c2ncc(CN)cn2)c(Oc2cnnc(N3CCCCC3)c2)c1] | 4-[5-(aminomethyl)pyrimidin-2-yl]-3-(6-piperidin-1-ylpyridazin-4-yl)oxybenzonitrile |
| 716 | 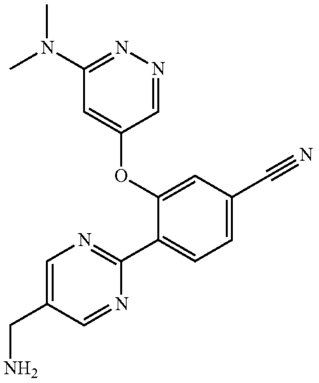 [SMILES: CN(C)c1cc(Oc2cc(C#N)ccc2-c2ncc(CN)cn2)cnn1] | 4-[5-(aminomethyl)pyrimidin-2-yl]-3-[6-(dimethylamino)pyridazin-4-yl]oxybenzonitrile |
| 717 | 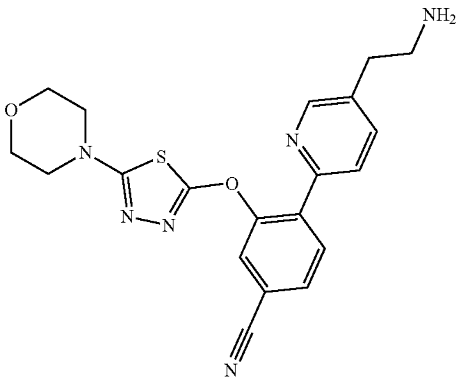 [SMILES: N#Cc1ccc(-c2ccc(CCN)cn2)c(Oc2nnc(N3CCOCC3)s2)c1] | 4-[5-(2-aminoethyl)pyridin-2-yl]-3-[(5-morpholin-4-yl-1,3,4-thiadiazol-2-yl)oxy]benzonitrile |
| 718 | 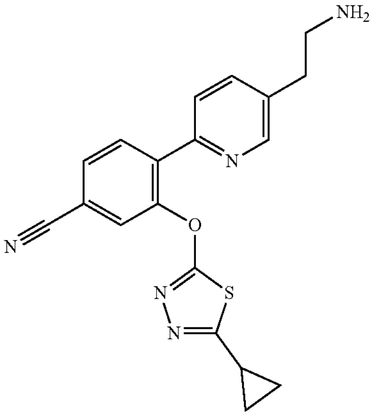 [SMILES: N#Cc1ccc(-c2ccc(CCN)cn2)c(Oc2nnc(C3CC3)s2)c1] | 4-[5-(2-aminoethyl)pyridin-2-yl]-3-[(5-cyclopropyl-1,3,4-thiadiazol-2-yl)oxy]benzonitrile |

TABLE 1-continued
| Compound number | Structural formula | Compound name |
| --- | --- | --- |
| 719 | 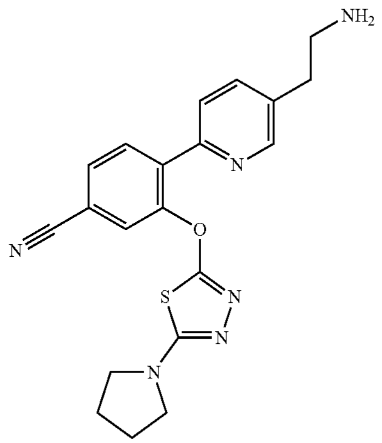 [SMILES: N#Cc1ccc(-c2ccc(CCN)cn2)c(Oc2nnc(N3CCCC3)s2)c1] | 4-[5-(2-aminoethyl)pyridin-2-yl]-3-[(5-pyrrolidin-1-yl-1,3,4-thiadiazol-2-yl)oxy]benzonitrile |
| 720 | 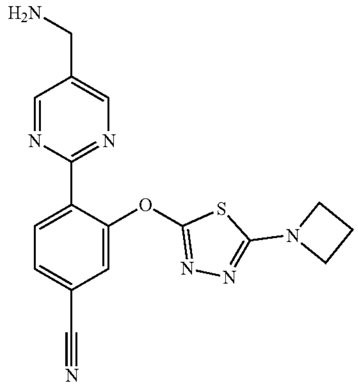 [SMILES: N#Cc1ccc(-c2ncc(CN)cn2)c(Oc2nnc(N3CCC3)s2)c1] | 4-[5-(aminomethyl)pyrimidin-2-yl]-3-[[5-(azetidin-1-yl)-1,3,4-thiadiazol-2-yl]oxy]benzonitrile |
| 721 | 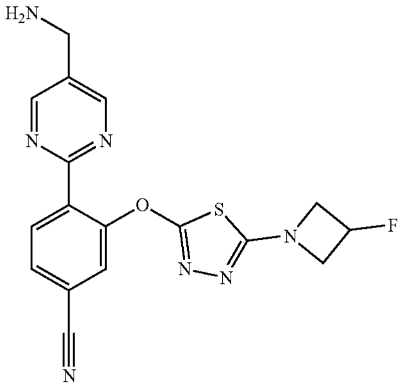 [SMILES: N#Cc1ccc(-c2ncc(CN)cn2)c(Oc2nnc(N3CC(F)C3)s2)c1] | 4-[5-(aminomethyl)pyrimidin-2-yl]-3-[[5-(3-fluoroazetidin-1-yl)-1,3,4-thiadiazol-2-yl]oxy]benzonitrile |

TABLE 1-continued
| Compound number | Structural formula | Compound name |
|---|---|---|
| 722 | 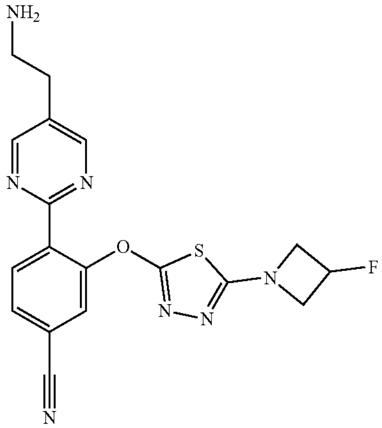 [SMILES: N#Cc1ccc(-c2ncc(CCN)cn2)c(Oc2nnc(N3CC(F)C3)s2)c1] | 4-[5-(2-aminoethyl)pyrimidin-2-yl]-3-[[5-(3-fluoroazetidin-1-yl)-1,3,4-thiadiazol-2-yl]oxy]benzonitrile |
| 723 | 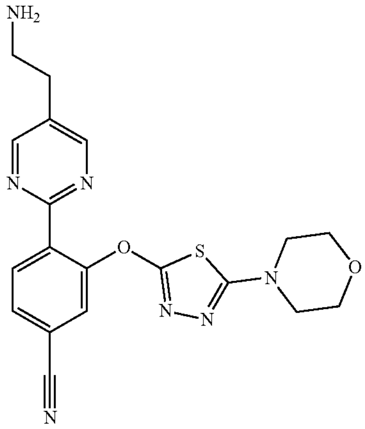 [SMILES: N#Cc1ccc(-c2ncc(CCN)cn2)c(Oc2nnc(N3CCOCC3)s2)c1] | 4-[5-(2-aminoethyl)pyrimidin-2-yl]-3-[(5-morpholin-4-yl-1,3,4-thiadiazol-2-yl)oxy]benzonitrile |
| 724 | 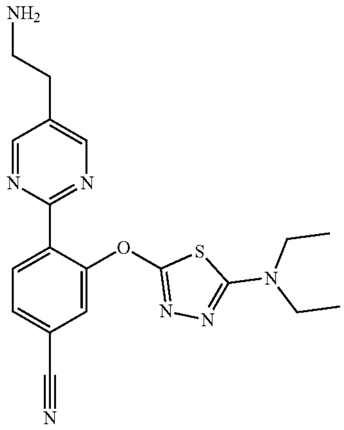 [SMILES: CCN(CC)c1nnc(Oc2cc(C#N)ccc2-c2ncc(CCN)cn2)s1] | 4-[5-(2-aminoethyl)pyrimidin-2-yl]-3-[[5-(diethylamino)-1,3,4-thiadiazol-2-yl]oxy]benzonitrile |

TABLE 1-continued
| Compound number | Structural formula | Compound name |
|---|---|---|
| 725 | 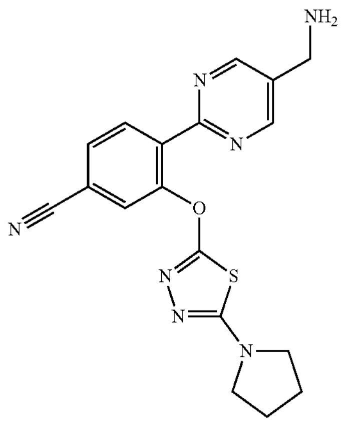 [SMILES: N#Cc1ccc(-c2ncc(CN)cn2)c(Oc2nnc(N3CCCC3)s2)c1] | 4-[5-(aminomethyl)pyrimidin-2-yl]-3-[(5-pyrrolidin-1-yl-1,3,4-thiadiazol-2-yl)oxy]benzonitrile |
| 726 | 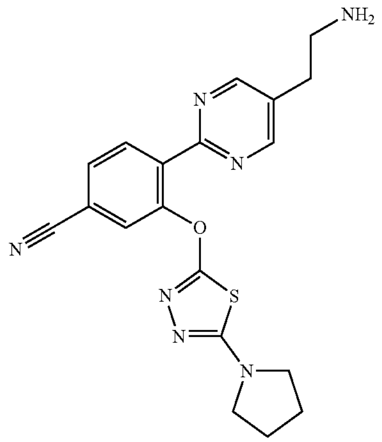 [SMILES: N#Cc1ccc(-c2ncc(CCN)cn2)c(Oc2nnc(N3CCCC3)s2)c1] | 4-[5-(2-aminoethyl)pyrimidin-2-yl]-3-[(5-pyrrolidin-1-yl-1,3,4-thiadiazol-2-yl)oxy]benzonitrile |
| 727 | 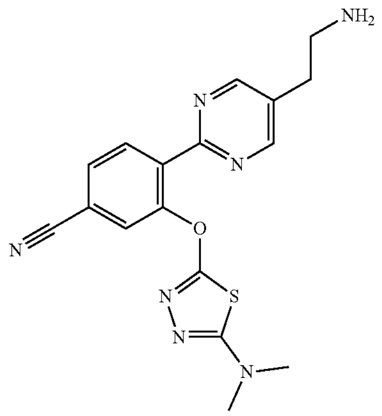 [SMILES: CN(C)c1nnc(Oc2cc(C#N)ccc2-c2ncc(CCN)cn2)s1] | 4-[5-(2-aminoethyl)pyrimidin-2-yl]-3-[[5-(dimethylamino)-1,3,4-thiadiazol-2-yl]oxy]benzonitrile |

TABLE 1-continued

| Compound number | Structural formula | Compound name |
| --- | --- | --- |
| 728 | 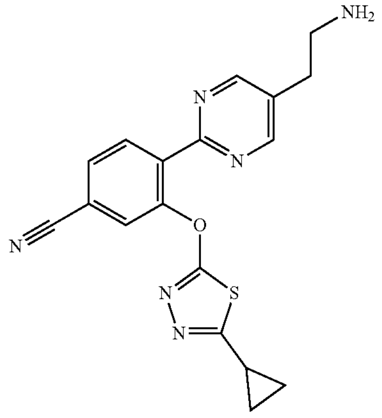 | 4-[5-(2-aminoethyl)pyrimidin-2-yl]-3-[(5-cyclopropyl-1,3,4-thiadiazol-2-yl)oxy]benzonitrile |
| 729 | 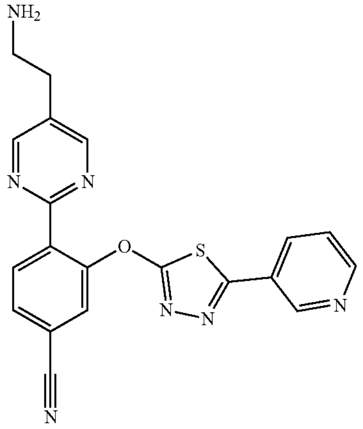 [SMILES: N#Cc1ccc(-c2ncc(CCN)cn2)c(Oc2nnc(-c3cccnc3)s2)c1] | 4-[5-(2-aminoethyl)pyrimidin-2-yl]-3-[(5-pyridin-3-yl-1,3,4-thiadiazol-2-yl)oxy]benzonitrile |
| 730 | 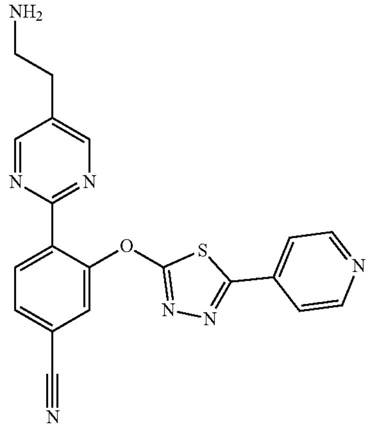 [SMILES: N#Cc1ccc(-c2ncc(CCN)cn2)c(Oc2nnc(-c3ccncc3)s2)c1] | 4-[5-(2-aminoethyl)pyrimidin-2-yl]-3-[(5-pyridin-4-yl-1,3,4-thiadiazol-2-yl)oxy]benzonitrile |
| 731 | 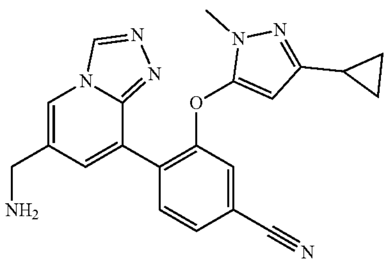 [SMILES: Cn1nc(C2CC2)cc1Oc1cc(C#N)ccc1-c1cc(CN)cn2cnnc12] | 4-[6-(aminomethyl)-[1,2,4]triazolo[4,3-a]pyridin-8-yl]-3-(5-cyclopropyl-2-methylpyrazol-3-yl)oxybenzonitrile |

TABLE 1-continued

| Compound number | Structural formula | Compound name |
|---|---|---|
| 732 | 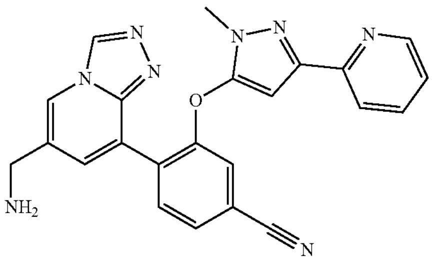 | 4-[6-(aminomethyl)-[1,2,4]triazolo[4,3-a]pyridin-8-yl]-3-(2-methyl-5-pyridin-2-ylpyrazol-3-yl)oxybenzonitrile |
| 733 | 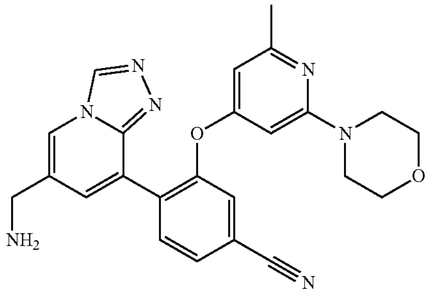 [SMILES: Cc1cc(Oc2cc(C#N)ccc2-c2cc(CN)cn3cnnc23)cc(N2CCOCC2)n1] | 4-[6-(aminomethyl)-[1,2,4]triazolo[4,3-a]pyridin-8-yl]-3-(2-methyl-6-morpholin-4-ylpyridin-4-yl)oxybenzonitrile |
| 734 | 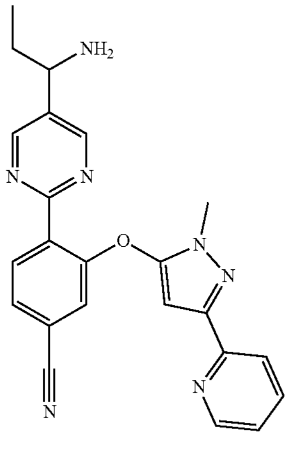 [SMILES: CCC(N)c1cnc(-c2ccc(C#N)cc2Oc2cc(-c3ccccn3)nn2C)nc1] | 4-[5-(1-aminopropyl)pyrimidin-2-yl]-3-(2-methyl-5-pyridin-2-ylpyrazol-3-yl)oxybenzonitrile |
| 735 | 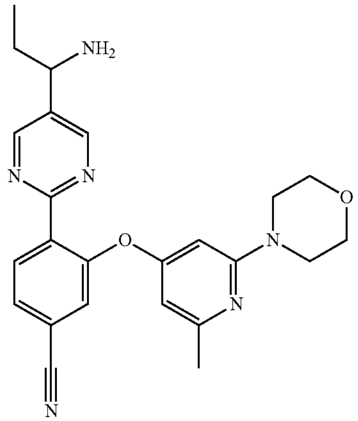 [SMILES: CCC(N)c1cnc(-c2ccc(C#N)cc2Oc2cc(C)nc(N3CCOCC3)c2)nc1] | 4-[5-(1-aminopropyl)pyrimidin-2-yl]-3-(2-methyl-6-morpholin-4-ylpyridin-4-yl)oxybenzonitrile |

TABLE 1-continued

| Compound number | Structural formula | Compound name |
|---|---|---|
| 736 | 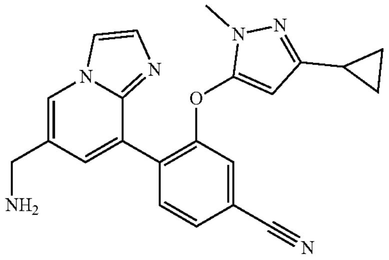 [SMILES: Cn1nc(C2CC2)cc1Oc1cc(C#N)ccc1-c1cc(CN)cn2ccnc12] | 4-[6-(aminomethyl)imidazo[1,2-a]pyridin-8-yl]-3-(5-cyclopropyl-2-methylpyrazol-3-yl)oxybenzonitrile |
| 737 | 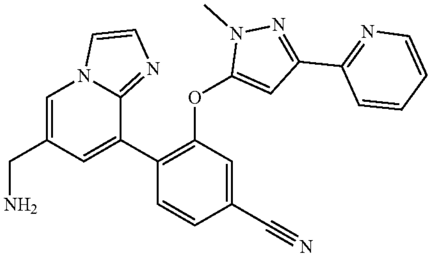 [SMILES: Cn1nc(-c2ccccn2)cc1Oc1cc(C#N)ccc1-c1cc(CN)cn2ccnc12] | 4-[6-(aminomethyl)imidazo[1,2-a]pyridin-8-yl]-3-(2-methyl-5-pyridin-2-ylpyrazol-3-yl)oxybenzonitrile |
| 738 | 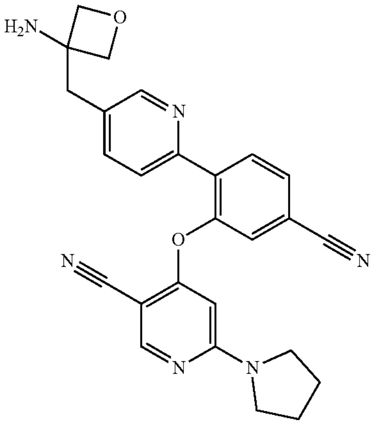 [SMILES: N#Cc1ccc(-c2ccc(CC3(N)COC3)cn2)c(Oc2cc(N3CCCC3)ncc2C#N)c1] | 4-[2-[5-[(3-aminooxetan-3-yl)methyl]pyridin-2-yl]-5-cyanophenoxy]-6-pyrrolidin-1-ylpyridine-3-carbonitrile |
| 739 | 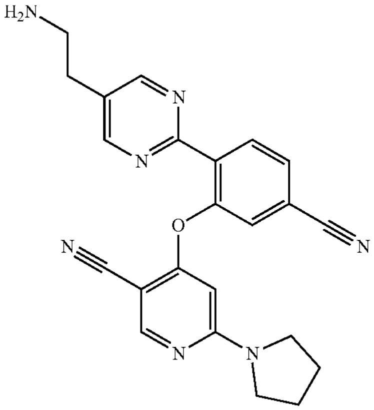 [SMILES: N#Cc1ccc(-c2ncc(CCN)cn2)c(Oc2cc(N3CCCC3)ncc2C#N)c1] | 4-[2-[5-(2-aminoethyl)pyrimidin-2-yl]-5-cyanophenoxy]-6-pyrrolidin-1-ylpyridine-3-carbonitrile |

TABLE 1-continued
| Compound number | Structural formula | Compound name |
|---|---|---|
| 740 | 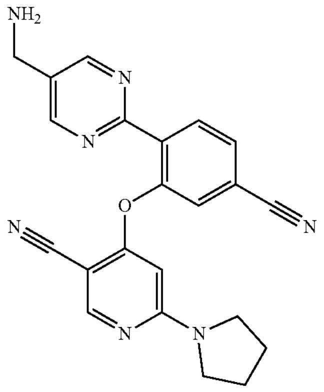 [SMILES: N#Cc1ccc(-c2ncc(CN)cn2)c(Oc2cc(N3CCCC3)ncc2C#N)c1] | 4-[2-[5-(aminomethyl)pyrimidin-2-yl]-5-cyanophenoxy]-6-pyrrolidin-1-ylpyridine-3-carbonitrile |
| 741 | 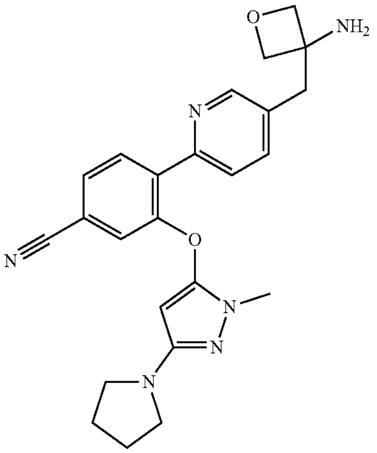 [SMILES: Cn1nc(N2CCCC2)cc1Oc1cc(C#N)ccc1-c1ccc(CC2(N)COC2)cn1] | 4-[5-[(3-aminooxetan-3-yl)methyl]pyridin-2-yl]-3-(2-methyl-5-pyrrolidin-1-ylpyrazol-3-yl)oxybenzonitrile |
| 742 | 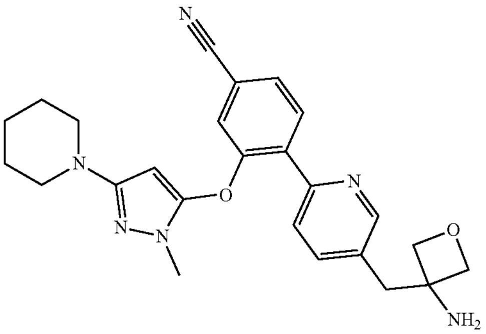 [SMILES: Cn1nc(N2CCCCC2)cc1Oc1cc(C#N)ccc1-c1ccc(CC2(N)COC2)cn1] | 4-[5-[(3-aminooxetan-3-yl)methyl]pyridin-2-yl]-3-(2-methyl-5-piperidin-1-ylpyrazol-3-yl)oxybenzonitrile |

TABLE 1-continued

| Compound number | Structural formula | Compound name |
| --- | --- | --- |
| 743 | 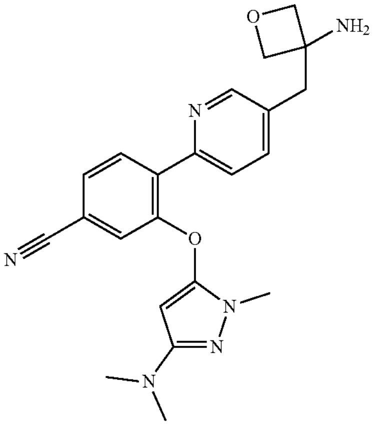 [SMILES: CN(C)c1cc(Oc2cc(C#N)ccc2-c2ccc(CC3(N)COC3)cn2)n(C)n1] | 4-[5-[(3-aminooxetan-3-yl)methyl]pyridin-2-yl]-3-[5-(dimethylamino)-2-methylpyrazol-3-yl]oxybenzonitrile |
| 744 | 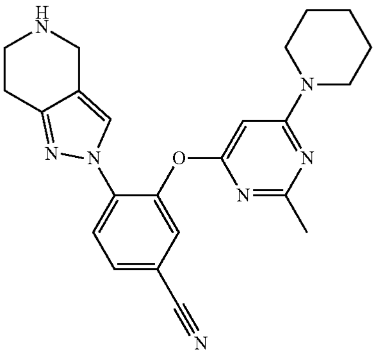 [SMILES: Cc1nc(Oc2cc(C#N)ccc2-n2cc3c(n2)CCNC3)cc(N2CCCCC2)n1] | 3-(2-methyl-6-piperidin-1-ylpyrimidin-4-yl)oxy-4-(4,5,6,7-tetrahydropyrazolo[4,3-c]pyridin-2-yl)benzonitrile |
| 745 | 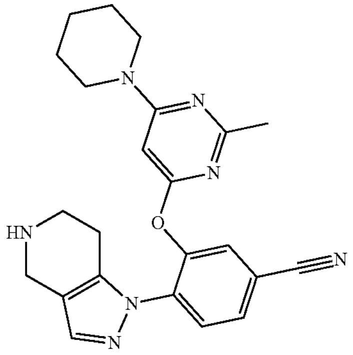 [SMILES: Cc1nc(Oc2cc(C#N)ccc2-n2ncc3c2CCNC3)cc(N2CCCCC2)n1] | 3-(2-methyl-6-piperidin-1-ylpyrimidin-4-yl)oxy-4-(4,5,6,7-tetrahydropyrazolo[4,3-c]pyridin-1-yl)benzonitrile |
| 746 | 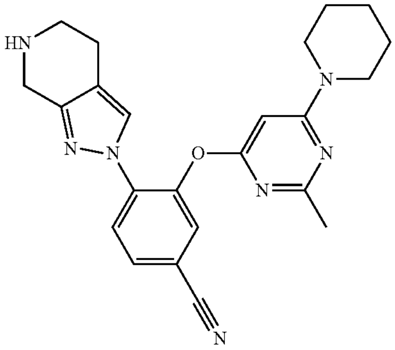 [SMILES: Cc1nc(Oc2cc(C#N)ccc2-n2cc3c(n2)CNCC3)cc(N2CCCCC2)n1] | 3-(2-methyl-6-piperidin-1-ylpyrimidin-4-yl)oxy-4-(4,5,6,7-tetrahydropyrazolo[3,4-c]pyridin-2-yl)benzonitrile |

TABLE 1-continued

| Compound number | Structural formula | Compound name |
|---|---|---|
| 747 | 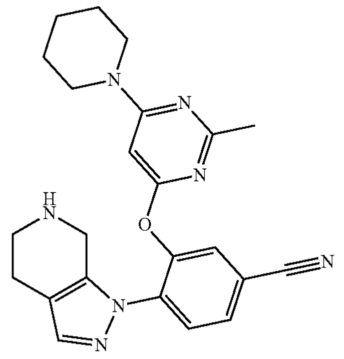 [SMILES: Cc1nc(Oc2cc(C#N)ccc2-n2ncc3c2CNCC3)cc(N2CCCCC2)n1] | 3-(2-methyl-6-piperidin-1-ylpyrimidin-4-yl)oxy-4-(4,5,6,7-tetrahydropyrazolo[3,4-c]pyridin-1-yl)benzonitrile |
| 748 | 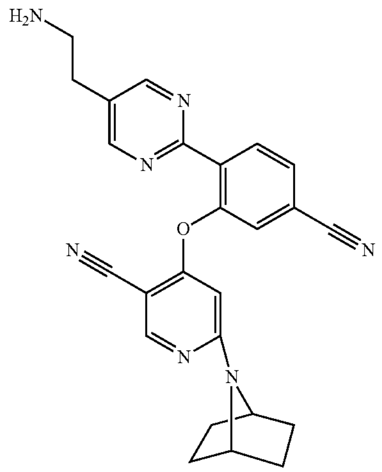 [SMILES: N#Cc1ccc(-c2ncc(CCN)cn2)c(Oc2cc(N3C4CCC3CC4)ncc2C#N)c1] | 4-[2-[5-(2-aminoethyl)pyrimidin-2-yl]-5-cyanophenoxy]-6-(7-azabicyclo[2.2.1]heptan-7-yl)pyridine-3-carbomtrile |
| 749 | 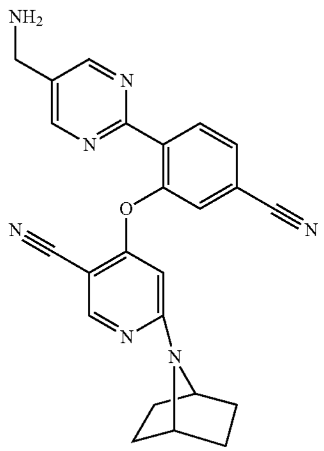 [SMILES: N#Cc1ccc(-c2ncc(CN)cn2)c(Oc2cc(N3C4CCC3CC4)ncc2C#N)c1] | 4-[2-[5-(aminomethyl)pyrimidin-2-yl]-5-cyanophenoxy]-6-(7-azabicyclo[2.2.1]heptan-7-yl)pyridine-3-carbonitrile |
| 750 | 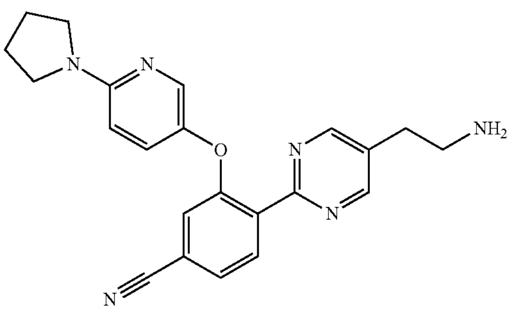 [SMILES: N#Cc1ccc(-c2ncc(CCN)cn2)c(Oc2ccc(N3CCCC3)nc2)c1] | 4-[5-(2-aminoethyl)pyrimidin-2-yl]-3-(6-pyrrolidin-1-ylpyridin-3-yl)oxybenzonitrile |

TABLE 1-continued

| Compound number | Structural formula | Compound name |
|---|---|---|
| 751 | 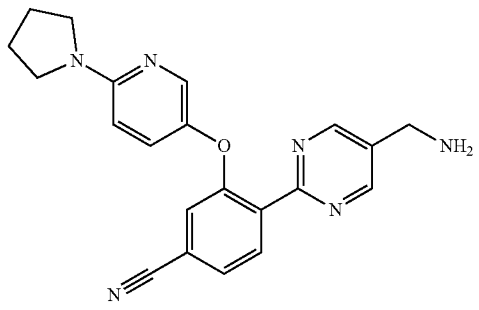 [SMILES: N#Cc1ccc(-c2ncc(CN)cn2)c(Oc2ccc(N3CCCC3)nc2)c1] | 4-[5-(aminomethyl)pyrimidin-2-yl]-3-(6-pyrrolidin-1-ylpyridin-3-yl)oxybenzonitrile |
| 752 | 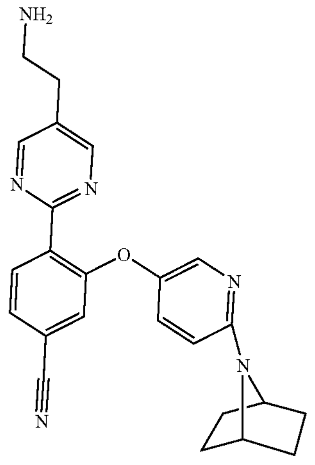 [SMILES: N#Cc1ccc(-c2ncc(CCN)cn2)c(Oc2ccc(N3C4CCC3CC4)nc2)c1] | 4-[5-(2-aminoethyl)pyrimidin-2-yl]-3-[6-(7-azabicyclo[2.2.1]heptan-7-yl)pyridin-3-yl]oxybenzonitrile |
| 753 | 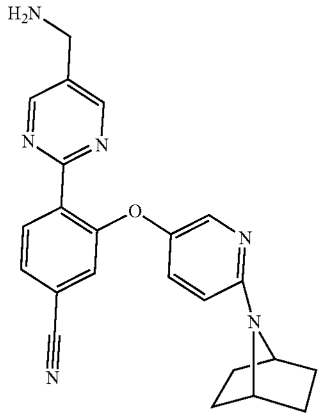 [SMILES: N#Cc1ccc(-c2ncc(CN)cn2)c(Oc2ccc(N3C4CCC3CC4)nc2)c1] | 4-[5-(aminomethyl)pyrimidin-2-yl]-3-[6-(7-azabicyclo[2.2.1]heptan-7-yl)pyridin-3-yl]oxybenzonitrile |
| 754 | 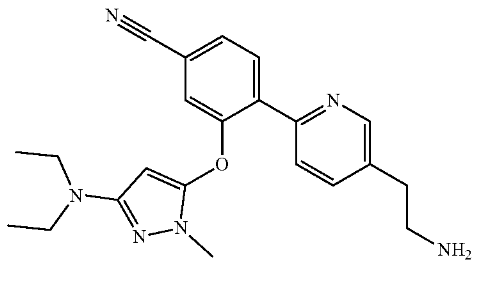 [SMILES: CCN(CC)c1cc(Oc2cc(C#N)ccc2-c2ccc(CCN)cn2)n(C)n1] | 4-[5-(2-aminoethyl)pyridin-2-yl]-3-[5-(diethylamino)-2-methylpyrazol-3-yl]oxybenzonitrile |

TABLE 1-continued

| Compound number | Structural formula | Compound name |
|---|---|---|
| 755 | 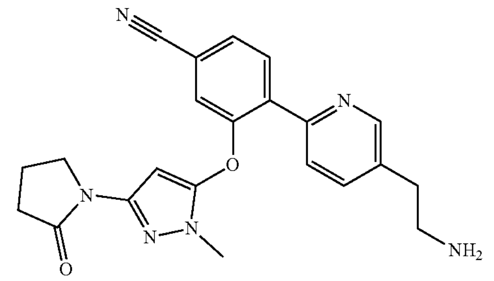 [SMILES: Cn1nc(N2CCCC2=O)cc1Oc1cc(C#N)ccc1-c1ccc(CCN)cn1] | 4-[5-(2-aminoethyl)pyridin-2-yl]-3-[2-methyl-5-(2-oxopyrrolidin-1-yl)pyrazol-3-yl]oxybenzonitrile |
| 756 | 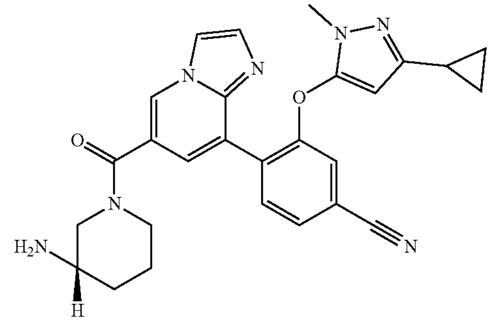 [SMILES: Cn1nc(C2CC2)cc1Oc1cc(C#N)ccc1-c1cc(C(=O)N2CCC[C@H](N)C2)cn2ccnc12] | 4-[6-[(3S)-3-aminopiperidine-1-carbonyl]imidazo[1,2-a]pyridin-8-yl]-3-(5-cyclopropyl-2-methylpyrazol-3-yl)oxybenzonitrile |
| 757 | 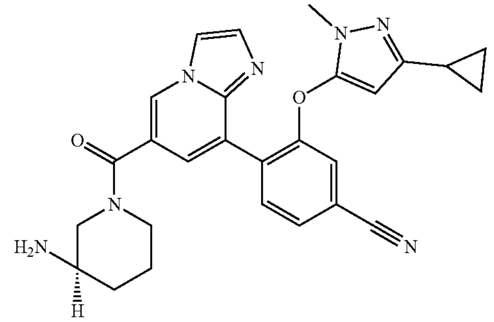 [SMILES: Cn1nc(C2CC2)cc1Oc1cc(C#N)ccc1-c1cc(C(=O)N2CCC[C@@H](N)C2)cn2ccnc12] | 4-[6-[(3R)-3-aminopiperidine-1-carbonyl]imidazo[1,2-a]pyridin-8-yl]-3-(5-cyclopropyl-2-methylpyrazol-3-yl)oxybenzonitrile |
| 758 | 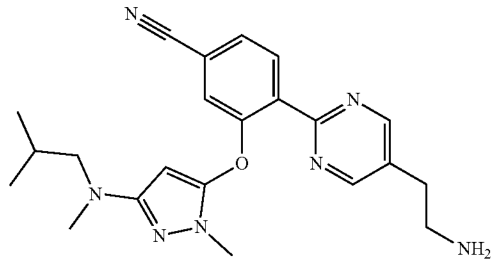 [SMILES: CC(C)CN(C)c1cc(Oc2cc(C#N)ccc2-c2ncc(CCN)cn2)n(C)n1] | 4-[5-(2-aminoethyl)pyrimidin-2-yl]-3-[2-methyl-5-[methyl(2-methylpropyl)amino]pyrazol-3-yl]oxybenzonitrile |
| 759 | 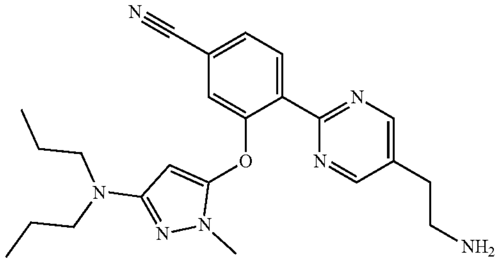 [SMILES: CCCN(CCC)c1cc(Oc2cc(C#N)ccc2-c2ncc(CCN)cn2)n(C)n1] | 4-[5-(2-aminoethyl)pyrimidin-2-yl]-3-[5-(dipropylamino)-2-methylpyrazol-3-yl]oxybenzonitrile |

TABLE 1-continued

| Compound number | Structural formula | Compound name |
| --- | --- | --- |
| 760 | 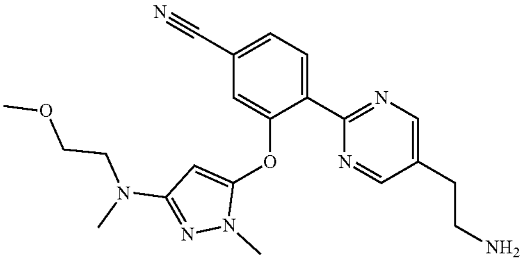 [SMILES: COCCN(C)c1cc(Oc2cc(C#N)ccc2-c2ncc(CCN)cn2)n(C)n1] | 4-[5-(2-aminoethyl)pyrimidin-2-yl]-3-[5-[2-methoxyethyl(methyl)amino]-2-methylpyrazol-3-yl]oxybenzonitrile |
| 761 | 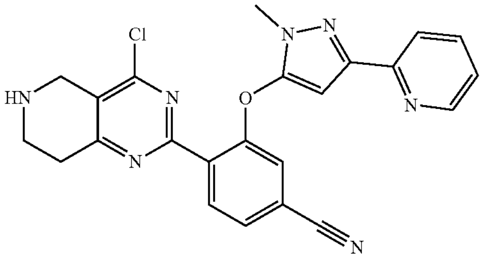 [SMILES: Cn1nc(-c2ccccn2)cc1Oc1cc(C#N)ccc1-c1nc(Cl)c2c(n1)CCNC2] | 4-(4-chloro-5,6,7,8-tetrahydropyrido[4,3-d]pyrimidin-2-yl)-3-(2-methyl-5-pyridin-2-ylpyrazol-3-yl))oxybenzonitrile |
| 762 | 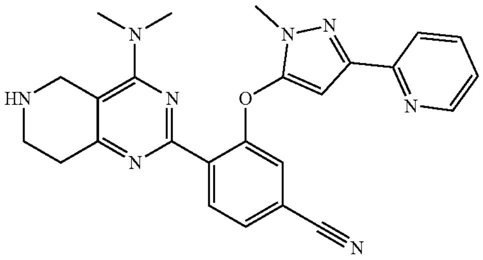 [SMILES: CN(C)c1nc(-c2ccc(C#N)cc2Oc2cc(-c3ccccn3)nn2C)nc2c1CNCC2] | 4-[4-(dimethylamino)-5,6,7,8-tetrahydropyrido[4,3-d]pyrimidin-2-yl]-3-(2-methyl-5-pyridin-2-ylpyrazol-3-yl)oxybenzonitrile |
| 763 | 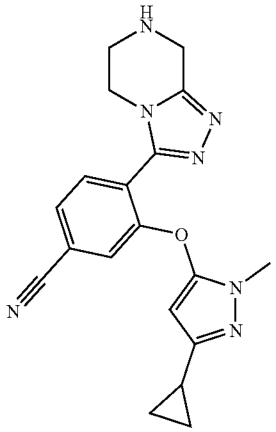 [SMILES: Cn1nc(C2CC2)cc1Oc1cc(C#N)ccc1-c1nnc2n1CCNC2] | 3-(5-cyclopropyl-2-methylpyrazol-3-yl)oxy-4(5,6,7,8-tetrahydro-[1,2,4]triazolo[4,3-a]pyrazin-3-yl)benzonitrile |

TABLE 1-continued
| Compound number | Structural formula | Compound name |
| --- | --- | --- |
| 764 | 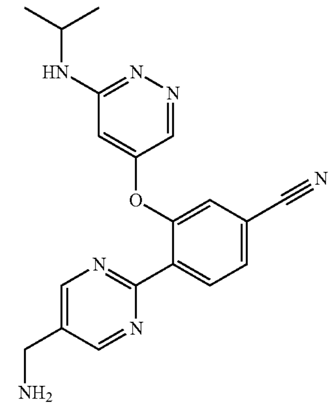 [SMILES: CC(C)Nc1cc(Oc2cc(C#N)ccc2-c2ncc(CN)cn2)cnn1] | 4-[5-(aminomethyl)pyrimidin-2-yl]-3-[6-(propan-2-ylamino)pyridazin-4-yl]oxybenzonitrile |
| 765 | 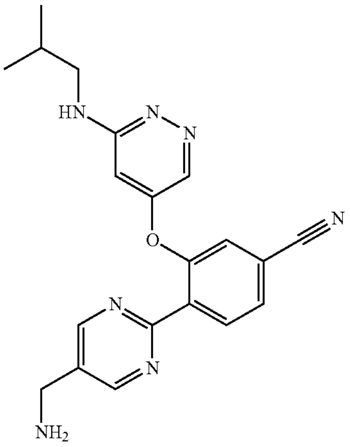 [SMILES: CC(C)CNc1cc(Oc2cc(C#N)ccc2-c2ncc(CN)cn2)cnn1] | 4-[5-(aminomethyl)pyrimidin-2-yl]-3-[6-(2-methylpropylamino)pyridazin-4-yl]oxybenzonitrile |
| 766 | 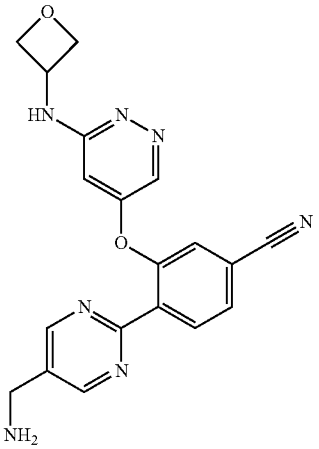 [SMILES: N#Cc1ccc(-c2ncc(CN)cn2)c(Oc2cnnc(NC3COC3)c2)c1] | 4-[5-(aminomethyl)pyrimidin-2-yl]-3-[6-(oxetan-3-ylamino)pyridazin-4-yl]oxybenzonitrile |

TABLE 1-continued

| Compound number | Structural formula | Compound name |
|---|---|---|
| 767 | 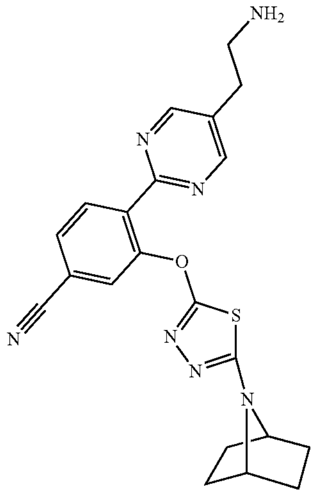 [SMILES: N#Cc1ccc(-c2ncc(CCN)cn2)c(Oc2nnc(N3C4CCC3CC4)s2)c1] | 4-[5-(2-aminoethyl)pyrimidin-2-yl]-3-[[5-(7-azabicyclo[2.2.1]heptan-7-yl)-1,3,4-thiadiazol-2-yl]oxy]benzonitrile |
| 768 | 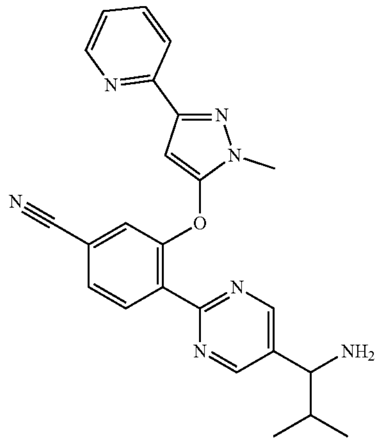 [SMILES: CC(C)C(N)c1cnc(-c2ccc(C#N)cc2Oc2cc(-c3ccccn3)nn2C)nc1] | 4-[5-(1-amino-2-methylpropyl)pyrimidin-2-yl]-3-(2-methyl-5-pyridin-2-ylpyrazol-3-yl)oxybenzonitrile |
| 769 | 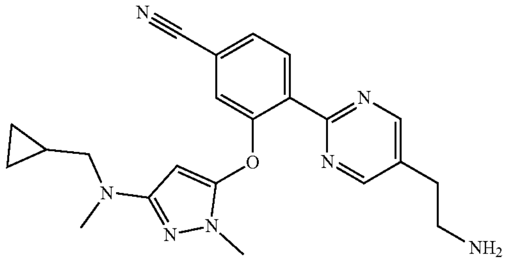 [SMILES: CN(CC1CC1)c1cc(Oc2cc(C#N)ccc2-c2ncc(CCN)cn2)n(C)n1] | 4-[5-(2-aminoethyl)pyrimidin-2-yl]-3-[5-[cyclopropylmethyl(methyl)amino]-2-methylpyrazol-3-yl]oxybenzonitrile |
| 770 | 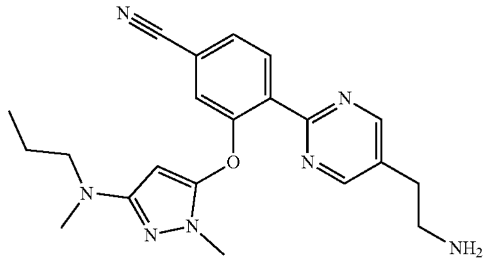 [SMILES: CCCN(C)c1cc(Oc2cc(C#N)ccc2-c2ncc(CCN)cn2)n(C)n1] | 4-[5-(2-aminoethyl)pyrimidin-2-yl]-3-[2-methyl-5-[methyl(propyl)amino]pyrazol-3-yl]oxybenzonitrile |

TABLE 1-continued

| Compound number | Structural formula | Compound name |
|---|---|---|
| 771 | 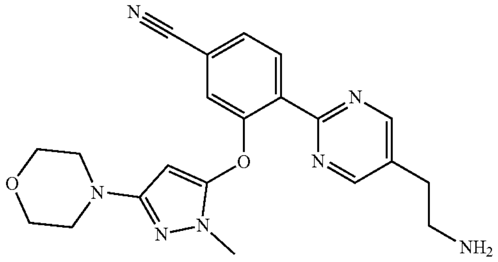 | 4-[5-(2-aminoethyl)pyrimidin-2-yl]-3-(2-methyl-5-morpholin-4-ylpyrazol-3-yl)oxybenzonitrile |
| 772 | 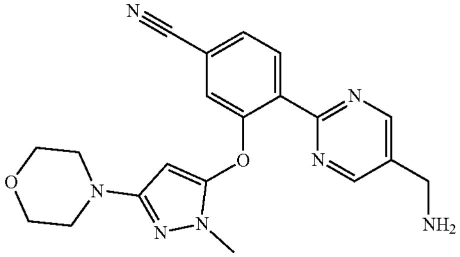 [SMILES: Cn1nc(N2CCOCC2)cc1Oc1cc(C#N)ccc1-c1ncc(CN)cn1] | 4-[5-(aminomethyl)pyrimidin-2-yl]-3-(2-methyl-5-morpholin-4-ylpyrazol-3-yl)oxybenzonitrile |
| 773 | 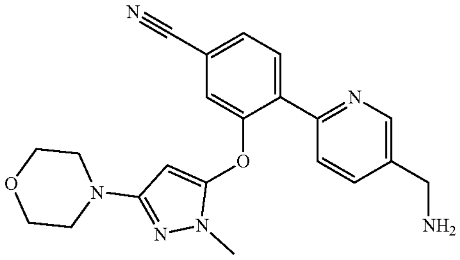 [SMILES: Cn1nc(N2CCOCC2)cc1Oc1cc(C#N)ccc1-c1ccc(CN)cn1] | 4-[5-(aminomethyl)pyridin-2-yl]-3-(2-methyl-5-morpholin-4-ylpyrazol-3-yl)oxybenzonitrile |
| 774 | 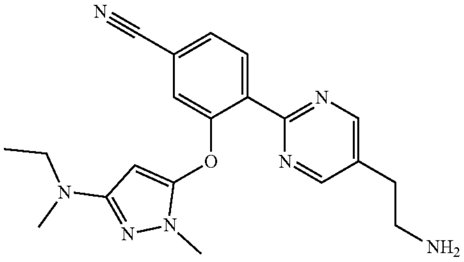 [SMILES: CCN(C)c1cc(Oc2cc(C#N)ccc2-c2ncc(CCN)cn2)n(C)n1] | 4-[5-(2-aminoethyl)pyrimidin-2-yl]-3-[5-[ethyl(methyl)amino]-2-methylpyrazol-3-yl]oxybenzonitrile |
| 775 | 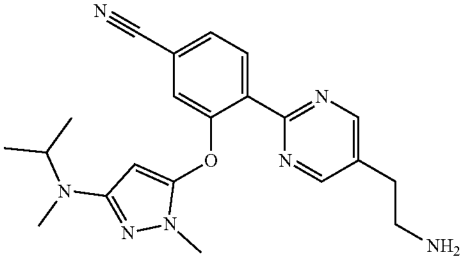 [SMILES: CC(C)N(C)c1cc(Oc2cc(C#N)ccc2-c2ncc(CCN)cn2)n(C)n1] | 4-[5-(2-aminoethyl)pyrimidin-2-yl]-3-[2-methyl-5-[methyl(propan-2-yl)amino]pyrazol-3-yl]oxybenzonitrile |

TABLE 1-continued

| Compound number | Structural formula | Compound name |
|---|---|---|
| 776 | 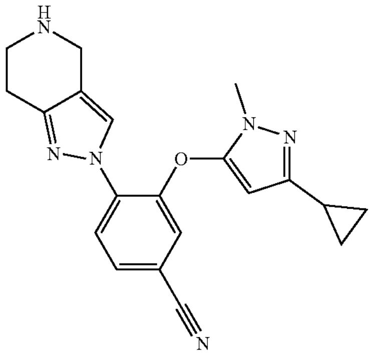 [SMILES: Cn1nc(C2CC2)cc1Oc1cc(C#N)ccc1-n1cc2c(n1)CCNC2] | 3-(5-cyclopropyl-2-methylpyrazol-3-yl)oxy-4-(4,5,6,7-tetrahydropyrazolo[4,3-c]pyridin-2-yl)benzonitrile |
| 777 | 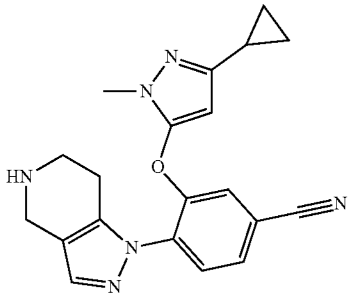 [SMILES: Cn1nc(C2CC2)cc1Oc1cc(C#N)ccc1-n1ncc2c1CCNC2] | 3-(5-cyclopropyl-2-methylpyrazol-3-yl)oxy-4-(4,5,6,7-tetrahydropyrazolo[4,3-c]pyridin-1-yl)benzonitrile |
| 778 | 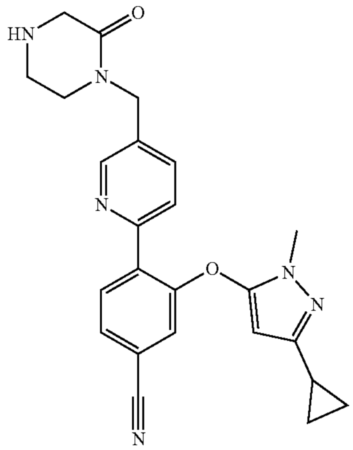 [SMILES: Cn1nc(C2CC2)cc1Oc1cc(C#N)ccc1-c1ccc(CN2CCNCC2=O)cn1] | 3-(5-cyclopropyl-2-methylpyrazol-3-yl)oxy-4-[5-[(2-oxopiperazin-1-yl)methyl]pyridin-2-yl]benzonitrile |
| 779 | 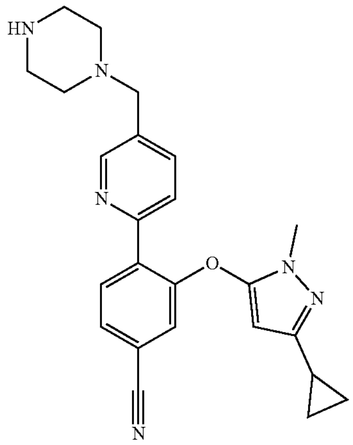 [SMILES: Cn1nc(C2CC2)cc1Oc1cc(C#N)ccc1-c1ccc(CN2CCNCC2)cn1] | 3-(5-cyclopropyl-2-methylpyrazol-3-yl)oxy-4-[5-(piperazin-1-ylmethyl)pyridin-2-yl]benzonitrile |

TABLE 1-continued
| Compound number | Structural formula | Compound name |
| --- | --- | --- |
| 780 | 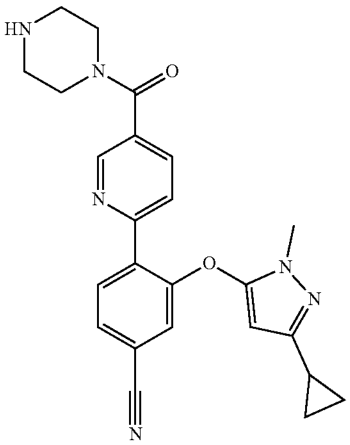 [SMILES: Cn1nc(C2CC2)cc1Oc1cc(C#N)ccc1-c1ccc(C(=O)N2CCNCC2)cn1] | 3-(5-cyclopropyl-2-methylpyrazol-3-yl)oxy-4-[5-(piperazine-1-carbonyl)pyridin-2-yl]benzonitrile |
| 781 | 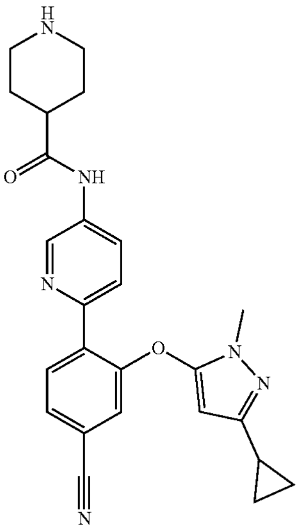 [SMILES: Cn1nc(C2CC2)cc1Oc1cc(C#N)ccc1-c1ccc(NC(=O)C2CCNCC2)cn1] | N-[6-[4-cyano-2-(5-cyclopropyl-2-methylpyrazol-3-yl)oxyphenyl]pyridin-3-yl]piperidine-4-carboxamide |
| 782 | 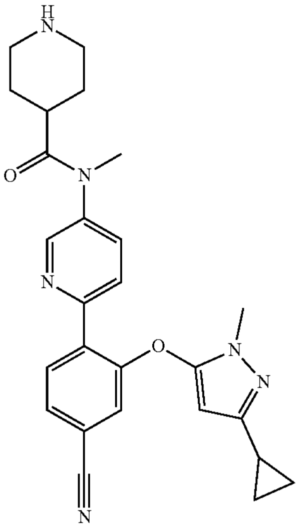 [SMILES: CN(C(=O)C1CCNCC1)c1ccc(-c2ccc(C#N)cc2Oc2cc(C3CC3)nn2C)nc1] | N-[6-[4-cyano-2-(5-cyclopropyl-2-methylpyrazol-3-yl)oxyphenyl]pyridin-3-yl]-N-methylpiperidine-4-carboxamide |

TABLE 1-continued
| Compound number | Structural formula | Compound name |
|---|---|---|
| 783 | 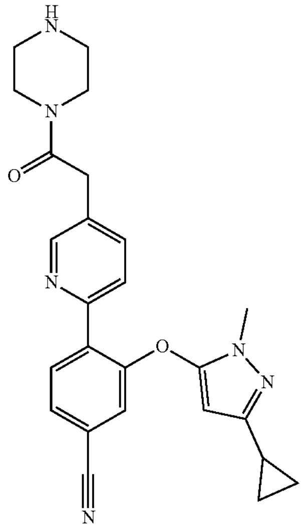 [SMILES: Cn1nc(C2CC2)cc1Oc1cc(C#N)ccc1-c1ccc(CC(=O)N2CCNCC2)cn1] | 3-(5-cyclopropyl-2-methylpyrazol-3-yl)oxy-4-[5-(2-oxo-2-piperazin-1-ylethyl)pyridin-2-yl]benzonitrile |
| 784 | 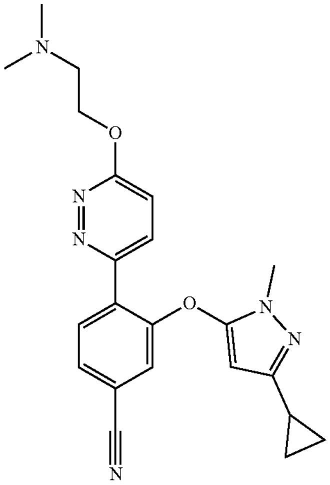 [SMILES: CN(C)CCOc1ccc(-c2ccc(C#N)cc2Oc2cc(C3CC3)nn2C)nn1] | 3-(5-cyclopropyl-2-methylpyrazol-3-yl)oxy-4-[6-[2-(dimethylamino)ethoxy]pyridazin-3-yl]benzonitrile |
| 785 | 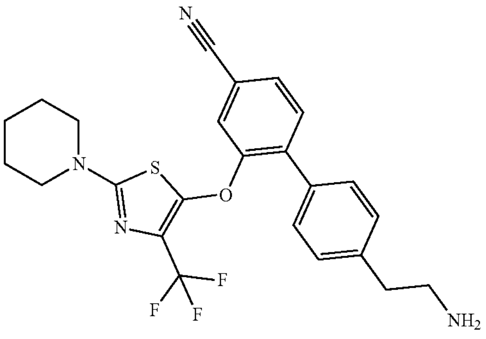 [SMILES: N#Cc1ccc(-c2ccc(CCN)cc2)c(Oc2sc(N3CCCCC3)nc2C(F)(F)F)c1] | 4-[4-(2-aminoethyl)phenyl]-3-[[2-piperidin-1-yl-4(trifluoromethyl)-1,3-thiazol-5-yl]oxy]benzonitrile |

TABLE 1-continued

| Compound number | Structural formula | Compound name |
| --- | --- | --- |
| 786 | 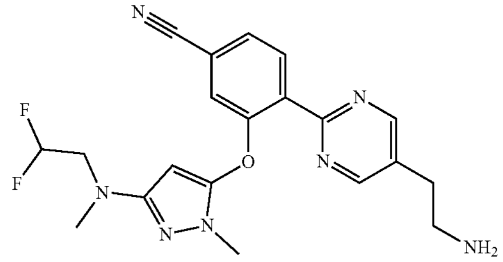 [SMILES: CN(CC(F)F)c1cc(Oc2cc(C#N)ccc2-c2ncc(CCN)cn2)n(C)n1] | 4-[5-(2-aminoethyl)pyrimidin-2-yl]-3-[5-[2,2-difluoroethyl(methyl)amino]-2-methylpyrazol-3-yl]oxybenzonitrile |
| 787 | 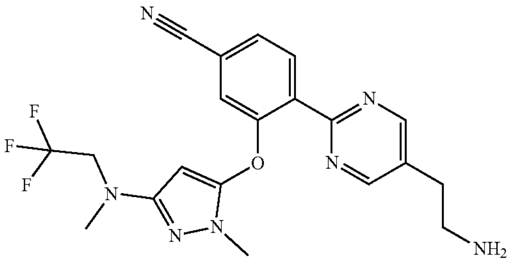 [SMILES: CN(CC(F)(F)F)c1cc(Oc2cc(C#N)ccc2-c2ncc(CCN)cn2)n(C)n1] | 4-[5-(2-aminoethyl)pyrimidin-2-yl]-3-[2-methyl-5-[methyl(2,2,2-trifluoroethyl)amino]pyrazol-3-yl]oxybenzonitrile |
| 788 | 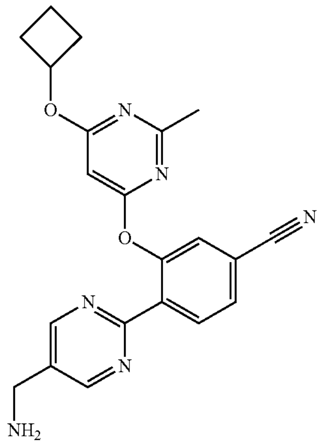 [SMILES: Cc1nc(Oc2cc(C#N)ccc2-c2ncc(CN)cn2)cc(OC2CCC2)n1] | 4-[5-(aminomethyl)pyrimidin-2-yl]-3-(6-cyclobutyloxy-2-methylpyrimidin-4-yl)oxybenzonitrile |
| 789 | 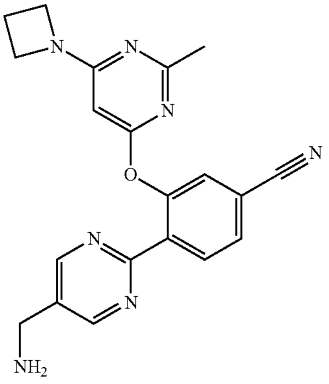 [SMILES: Cc1nc(Oc2cc(C#N)ccc2-c2ncc(CN)cn2)cc(N2CCC2)n1] | 4-[5-(aminomethyl)pyrimidin-2-yl]-3-[6-(azetidin-1-yl)-2-methylpyrimidin-4-yl]oxybenzonitrile |

TABLE 1-continued
| Compound number | Structural formula | Compound name |
| --- | --- | --- |
| 790 | 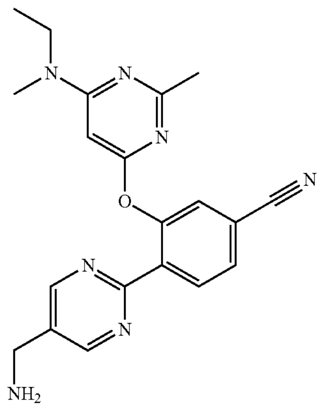 [SMILES: CCN(C)c1cc(Oc2cc(C#N)ccc2-c2ncc(CN)cn2)nc(C)n1] | 4-[5-(aminomethyl)pyrimidin-2-yl]-3-[6-[ethyl(methyl)amino]-2-methylpyrimidin-4-yl]oxybenzonitrile |
| 791 | 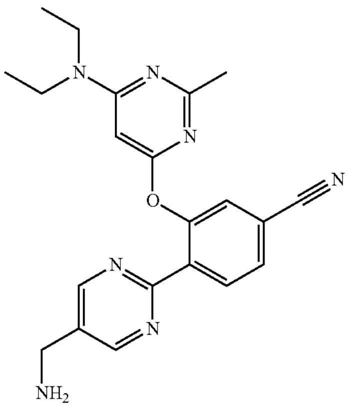 [SMILES: CCN(CC)c1cc(Oc2cc(C#N)ccc2-c2ncc(CN)cn2)nc(C)n1] | 4-[5-(aminomethyl)pyrimidin-2-yl]-3-[6-(diethylamino)-2-methylpyrimidin-4-yl]oxybenzonitrile |
| 792 | 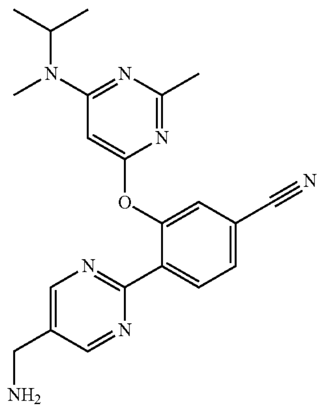 [SMILES: Cc1nc(Oc2cc(C#N)ccc2-c2ncc(CN)cn2)cc(N(C)C(C)C)n1] | 4-[5-(aminomethyl)pyrimidin-2-yl]-3-[2-methyl-6-[methyl(propan-2-yl)amino]pyrimidin-4-yl]oxybenzonitrile |

TABLE 1-continued
| Compound number | Structural formula | Compound name |
|---|---|---|
| 793 | 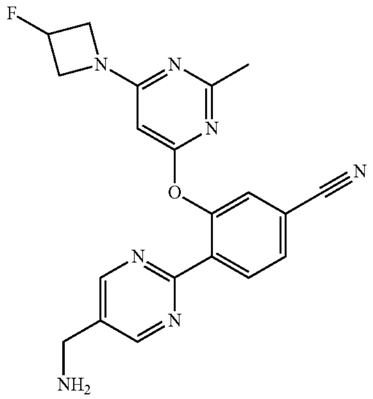 [SMILES: Cc1nc(Oc2cc(C#N)ccc2-c2ncc(CN)cn2)cc(N2CC(F)C2)n1] | 4-[5-(aminomethyl)pyrimidin-2-yl]-3-[6-(3-fluoroazetidin-1-yl)-2-methylpyrimidin-4-yl]oxybenzonitrile |
| 794 | 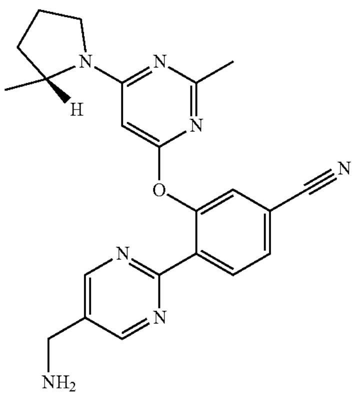 [SMILES: Cc1nc(Oc2cc(C#N)ccc2-c2ncc(CN)cn2)cc(N2CCC[C@H]2C)n1] | 4-[5-(aminomethyl)pyrimidin-2-yl]-3-[2-methyl-6-[(2R)-2-methylpyrrolidin-1-yl]pyrimidin-4-yl]oxybenzonitrile |
| 795 | 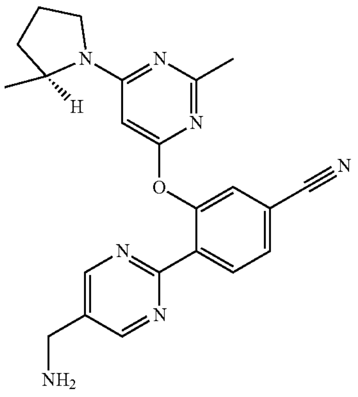 [SMILES: Cc1nc(Oc2cc(C#N)ccc2-c2ncc(CN)cn2)cc(N2CCC[C@@H]2C)n1] | 4-[5-(aminomethyl)pyrimidin-2-yl]-3-[2-methyl-6-[(2S)-2-methylpyrrolidin-1-yl]pyrimidin-4-yl]oxybenzonitrile |

TABLE 1-continued

| Compound number | Structural formula | Compound name |
|---|---|---|
| 796 | 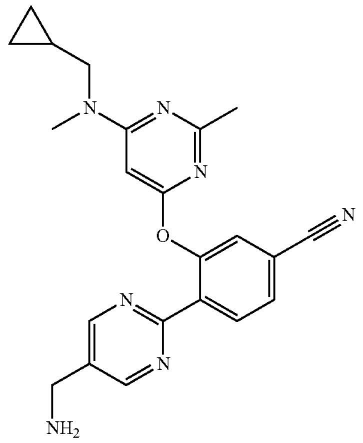 [SMILES: Cc1nc(Oc2cc(C#N)ccc2-c2ncc(CN)cn2)cc(N(C)CC2CC2)n1] | 4-[5-(aminomethyl)pyrimidin-2-yl]-3-[6-[cyclopropylmethyl(methyl)amino]-2-methylpyrimidin-4-yl]oxybenzonitrile |
| 797 | 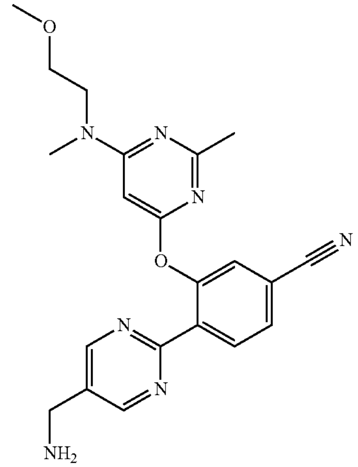 [SMILES: COCCN(C)c1cc(Oc2cc(C#N)ccc2-c2ncc(CN)cn2)nc(C)n1] | 4-[5-(aminomethyl)pyrimidin-2-yl]-3-[6-[2-methoxyethyl(methyl)amino]-2-methylpyrimidin-4-yl]oxybenzonitrile |
| 798 | 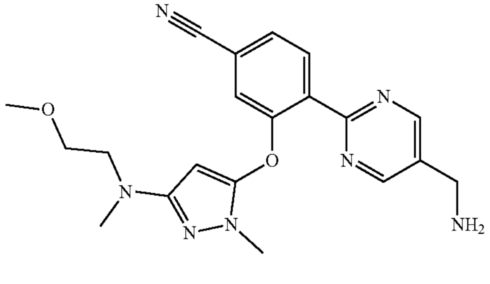 [SMILES: COCCN(C)c1cc(Oc2cc(C#N)ccc2-c2ncc(CN)cn2)n(C)n1] | 4-[5-(aminomethyl)pyrimidin-2-yl]-3-[5-[2-methoxyethyl(methyl)amino]-2-methylpyrazol-3-yl]oxybenzonitrile |
| 799 | 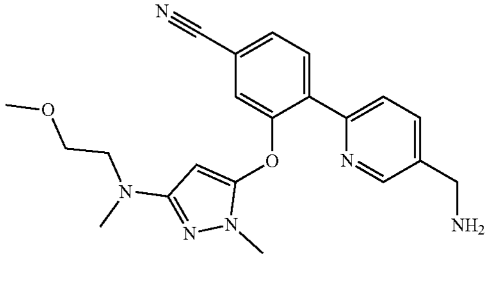 [SMILES: COCCN(C)c1cc(Oc2cc(C#N)ccc2-c2ccc(CN)cn2)n(C)n1] | 4-[5-(aminomethyl)pyridin-2-yl]-3-[5-[2-methoxyethyl(methyl)amino]-2-methylpyrazol-3-yl]oxybenzonitrile |

TABLE 1-continued

| Compound number | Structural formula | Compound name |
| --- | --- | --- |
| 800 | 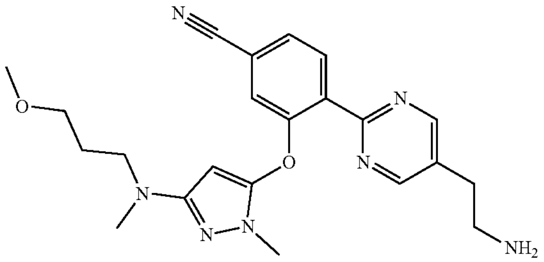 [SMILES: COCCCN(C)c1cc(Oc2cc(C#N)ccc2-c2ncc(CCN)cn2)n(C)n1] | 4-[5-(2-aminoethyl)pyrimidin-2-yl]-3-[5-[3-methoxypropyl(methyl)amino]-2-methylpyrazol-3-yl]oxybenzonitrile |
| 801 | 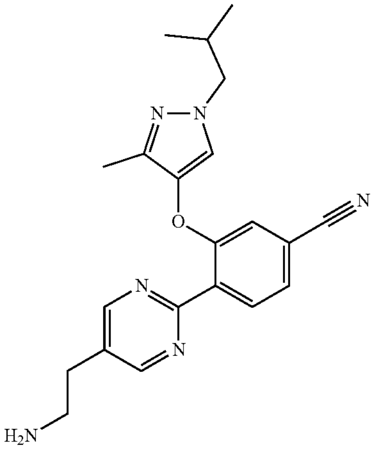 [SMILES: Cc1nn(CC(C)C)cc1Oc1cc(C#N)ccc1-c1ncc(CCN)cn1] | 4-[5-(2-aminoethyl)pyrimidin-2-yl]-3-[3-methyl-1-(2-methylpropyl)pyrazol-4-yl]oxybenzonitrile |
| 802 | 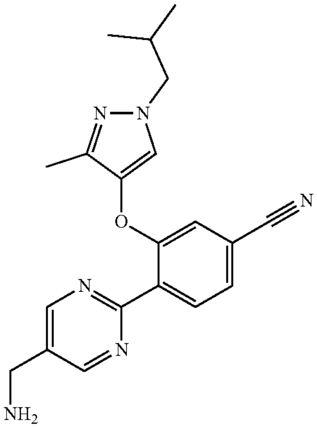 [SMILES: Cc1nn(CC(C)C)cc1Oc1cc(C#N)ccc1-c1ncc(CN)cn1] | 4-[5-(aminomethyl)pyrimidin-2-yl]-3-[3-methyl-1-(2-methylpropyl)pyrazol-4-yl]oxybenzonitrile |
| 803 | 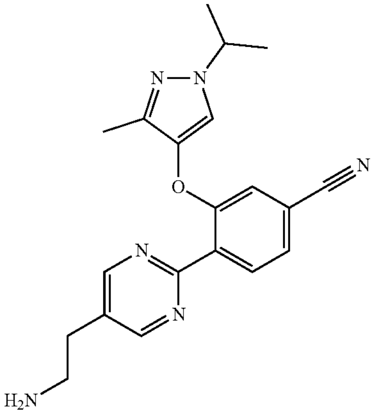 [SMILES: Cc1nn(C(C)C)cc1Oc1cc(C#N)ccc1-c1ncc(CCN)cn1] | 4-[5-(2-aminoethyl)pyrimidin-2-yl]-3-(3-methyl-1-propan-2-ylpyrazol-4-yl)oxybenzonitrile |

TABLE 1-continued
| Compound number | Structural formula | Compound name |
|---|---|---|
| 804 | 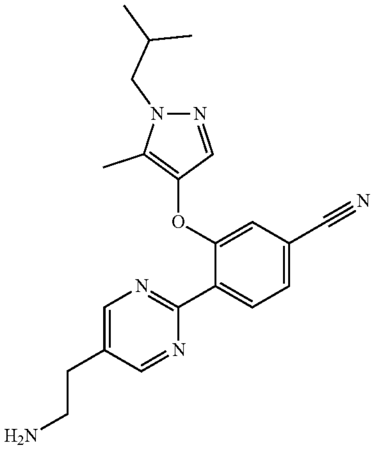 [SMILES: Cc1c(Oc2cc(C#N)ccc2-c2ncc(CCN)cn2)cnn1CC(C)C] | 4-[5-(2-aminoethyl)pyrimidin-2-yl]-3-[5-methyl-1-(2-methylpropyl)pyrazol-4-yl]oxybenzonitrile |
| 805 | 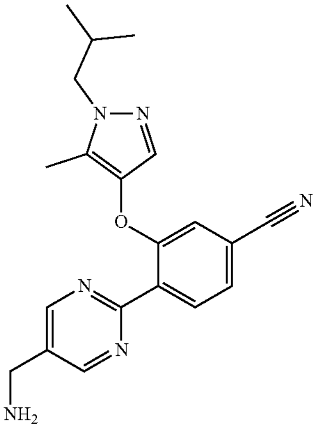 [SMILES: Cc1c(Oc2cc(C#N)ccc2-c2ncc(CN)cn2)cnn1CC(C)C] | 4-[5-(aminomethyl)pyrimidin-2-yl]-3-[5-methyl-1-(2-methylpropyl)pyrazol-4-yl]oxybenzonitrile |
| 806 | 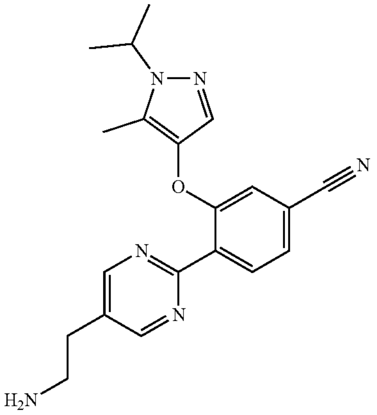 [SMILES: Cc1c(Oc2cc(C#N)ccc2-c2ncc(CCN)cn2)cnn1C(C)C] | 4-[5-(2-aminoethyl)pyrimidin-2-yl]-3-(5-methyl-1-propan-2-ylpyrazol-4-yl)oxybenzonitrile |

TABLE 1-continued
| Compound number | Structural formula | Compound name |
|---|---|---|
| 807 | 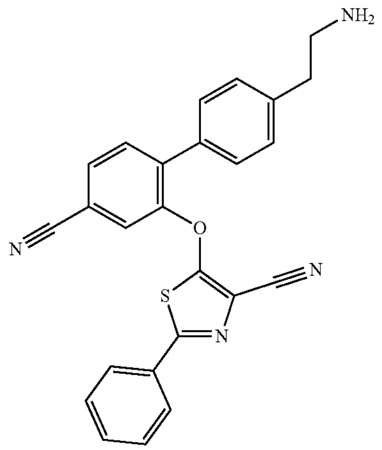 [SMILES: N#Cc1ccc(-c2ccc(CCN)cc2)c(Oc2sc(-c3ccccc3)nc2C#N)c1] | 5-[2-[4-(2-aminoethyl)phenyl]-5-cyanophenoxy]-2-phenyl-1,3-thiazole-4-carbonitrile |
| 808 | 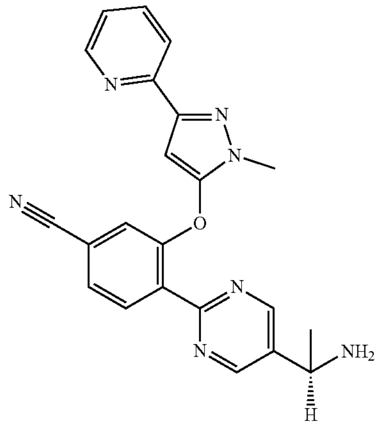 [SMILES: C[C@@H](N)c1cnc(-c2ccc(C#N)cc2Oc2cc(-c3ccccn3)nn2C)nc1] | 4-[5-[(1R)-1-aminoethyl]pyrimidin-2-yl]-3-(2-methyl-5-pyridin-2-ylpyrazol-3-yl)oxybenzonitrile |
| 809 | 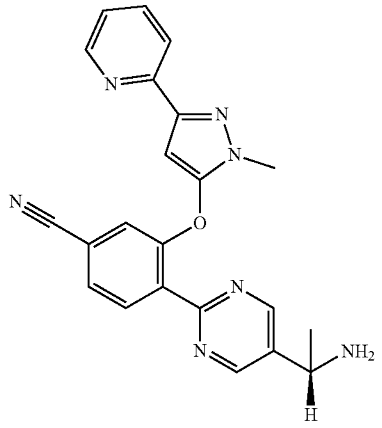 [SMILES: C[C@H](N)c1cnc(-c2ccc(C#N)cc2Oc2cc(-c3ccccn3)nn2C)nc1] | 4-[5-[(1S)-1-aminoethyl]pyrimidin-2-yl]-3-(2-methyl-5-pyridin-2-ylpyrazol-3-yl)oxybenzonitrile |

TABLE 1-continued

| Compound number | Structural formula | Compound name |
|---|---|---|
| 810 | 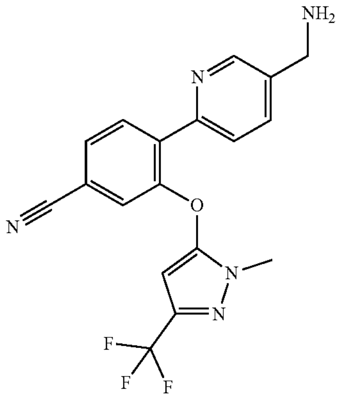 [SMILES: Cn1nc(C(F)(F)F)cc1Oc1cc(C#N)ccc1-c1ccc(CN)cn1] | 4-[5-(aminomethyl)pyridin-2-yl]-3-[2-methyl-5-(trifluoromethyl)pyrazol-3-yl]oxybenzonitrile |
| 811 | 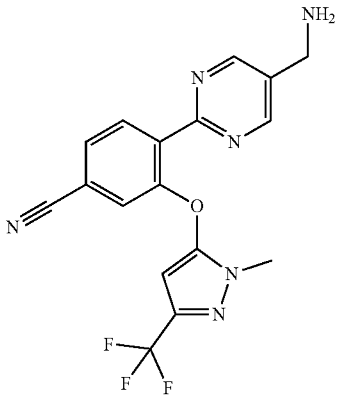 [SMILES: Cn1nc(C(F)(F)F)cc1Oc1cc(C#N)ccc1-c1ncc(CN)cn1] | 4-[5-(aminomethyl)pyrimidin-2-yl]-3-[2-methyl-5-(trifluoromethyl)pyrazol-3-yl]oxybenzonitrile |
| 812 | 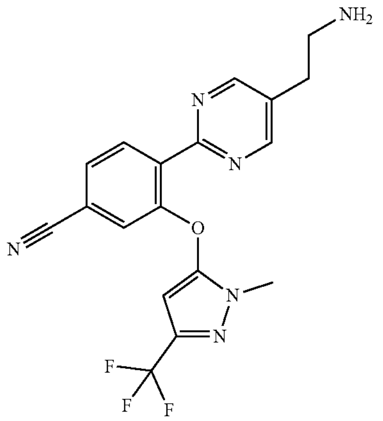 [SMILES: Cn1nc(C(F)(F)F)cc1Oc1cc(C#N)ccc1-c1ncc(CCN)cn1] | 4-[5-(2-aminoethyl)pyrimidin-2-yl]-3-[2-methyl-5-(tritluoromethyl)pyrazol-3-yl]oxybenzonitrile |
| 813 | 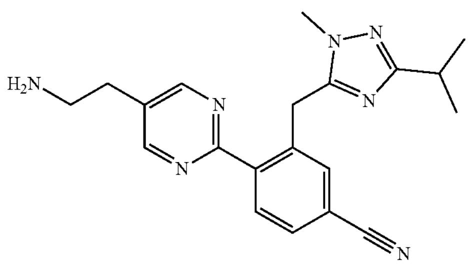 [SMILES: CC(C)c1nc(Cc2cc(C#N)ccc2-c2ncc(CCN)cn2)n(C)n1] | 4-[5-(2-aminoethyl)pyrimidin-2-yl]-3-[(2-methyl-5-propan-2-yl-1,2,4-triazol-3-yl)oxy]benzonitrile |

TABLE 1-continued

| Compound number | Structural formula | Compound name |
|---|---|---|
| 814 | 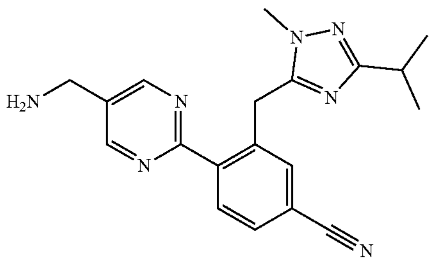 [SMILES: CC(C)c1nc(Cc2cc(C#N)ccc2-c2ncc(CN)cn2)n(C)n1] | 4-[5-(aminomethyl)pyrimidin-2-yl]-3-[(2-methyl-5-propan-2-yl-1,2,4-triazol-3-yl)oxy]benzonitrile |
| 815 | 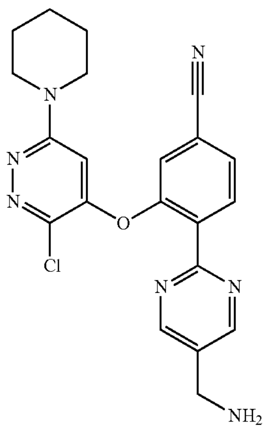 [SMILES: N#Cc1ccc(-c2ncc(CN)cn2)c(Oc2cc(N3CCCCC3)nnc2Cl)c1] | 4-[5-(aminomethyl)pyrimidin-2-yl]-3-(3-chloro-6-piperidin-1-ylpyridazin-4-yl)oxybenzonitrile |
| 816 | 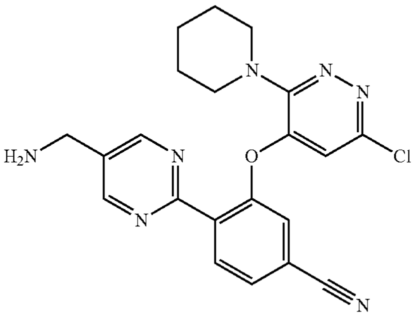 [SMILES: N#Cc1ccc(-c2ncc(CN)cn2)c(Oc2cc(Cl)nnc2N2CCCCC2)c1] | 4-[5-(aminomethyl)pyrimidin-2-yl]-3-(6-chloro-3-piperidin-1-ylpyridazin-4-yl)oxybenzonitrile |
| 817 | 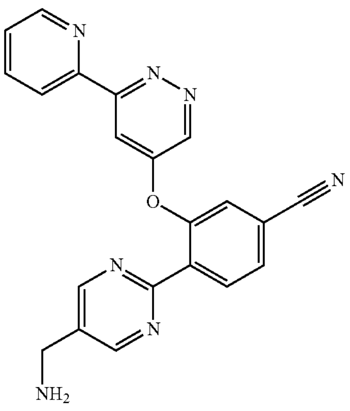 [SMILES: N#Cc1ccc(-c2ncc(CN)cn2)c(Oc2cnnc(-c3ccccn3)c2)c1] | 4-[5-(aminomethyl)pyrimidin-2-yl]-3-(6-pyridin-2-ylpyridazin-4 yl)oxybenzonitrile |

TABLE 1-continued
| Compound number | Structural formula | Compound name |
|---|---|---|
| 818 | 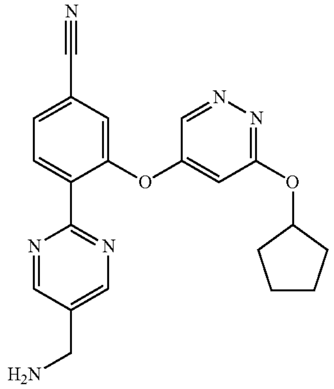 [SMILES: N#Cc1ccc(-c2ncc(CN)cn2)c(Oc2cnnc(OC3CCCC3)c2)c1] | 4-[5-(aminomethyl)pyrimidin-2-yl]-3-(6-cyclopentyloxypyridazin-4-yl)oxybenzonitrile |
| 819 | 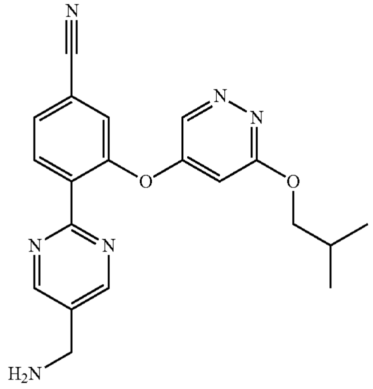 [SMILES: CC(C)COc1cc(Oc2cc(C#N)ccc2-c2ncc(CN)cn2)cnn1] | 4-[5-(aminomethyl)pyrimidin-2-yl]-3-[6-(2-methylpropoxy)pyridazin-4-yl]oxybenzonitrile |
| 820 | 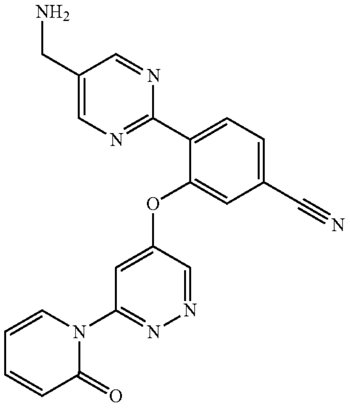 [SMILES: N#Cc1ccc(-c2ncc(CN)cn2)c(Oc2cnnc(-n3ccccc3=O)c2)c1] | 4-[5-(aminomethyl)pyrimidin-2-yl]-3-[6-(2-oxopyridin-1-yl)pyridazin-4-yl]oxybenzonitrile |

TABLE 1-continued

| Compound number | Structural formula | Compound name |
|---|---|---|
| 821 | 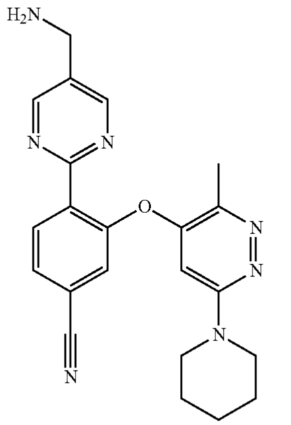 [SMILES: Cc1nnc(N2CCCCC2)cc1Oc1cc(C#N)ccc1-c1ncc(CN)cn1] | 4-[5-(aminomethyl)pyrimidin-2-yl]-3-(3-methyl-6-piperidin-1-ylpyridazin-4-yl)oxybenzonitrile |
| 822 | 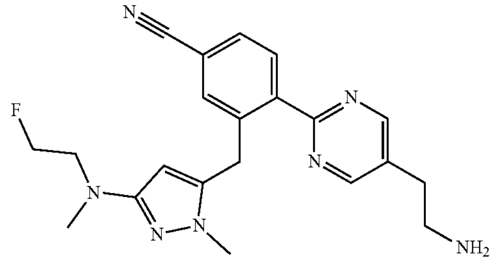 [SMILES: CN(CCF)c1cc(Cc2cc(C#N)ccc2-c2ncc(CCN)cn2)n(C)n1] | 4-[5-(2-aminoethyl)pyrimidin-2-yl]-3-[5-[2-fluoroethyl(methyl)amino]-2-methylpyrazol-3-yl]oxybenzonitrile |
| 823 | 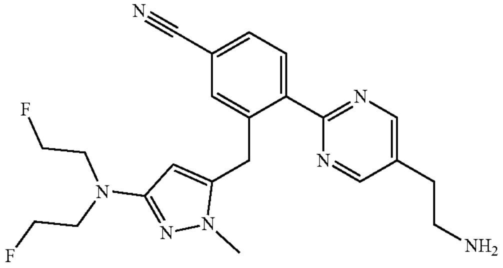 [SMILES: Cn1nc(N(CCF)CCF)cc1Cc1cc(C#N)ccc1-c1ncc(CCN)cn1] | 4-[5-(2-aminoethyl)pyrimidin-2-yl]-3-[5-[bis(2-fluoroethyl)amino]-2-methylpyrazol-3-yl]oxybenzonitrile |
| 824 | 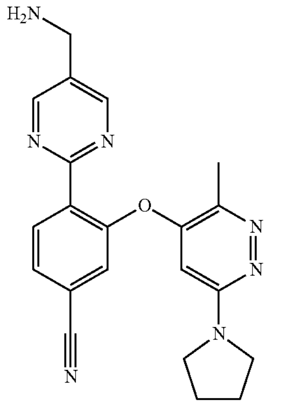 [SMILES: Cc1nnc(N2CCCC2)cc1Oc1cc(C#N)ccc1-c1ncc(CN)cn1] | 4-[5-(aminomethyl)pyrimidin-2-yl]-3-(3-methyl-6-pyrrolidin-1-ylpyridazin-4-yl)oxybenzonitrile |

TABLE 1-continued

| Compound number | Structural formula | Compound name |
|---|---|---|
| 825 | 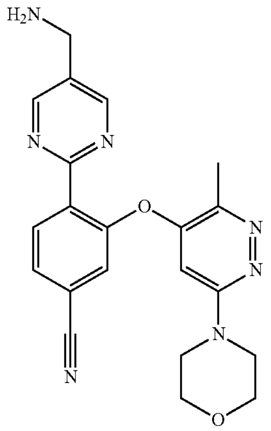 [SMILES: Cc1nnc(N2CCOCC2)cc1Oc1cc(C#N)ccc1-c1ncc(CN)cn1] | 4-[5-(aminomethyl)pyrimidin-2-yl]-3-(3-methyl-6-morpholin-4-ylpyridazin-4-yl)oxybenzonitrile |
| 826 | 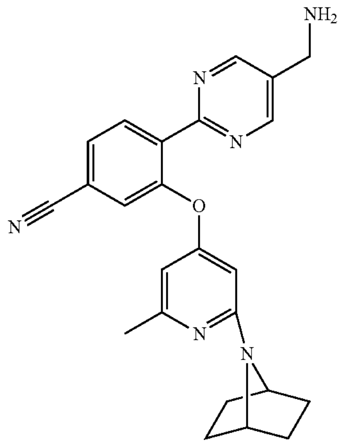 [SMILES: Cc1cc(Oc2cc(C#N)ccc2-c2ncc(CN)cn2)cc(N2C3CCC2CC3)n1] | 4-[5-(aminomethyl)pyrimidin-2-yl]-3-[2-(7-azabicyclo[2.2.1]heptan-7-yl)-6-methylpyridin-4-yl]oxybenzonitrile |
| 827 | 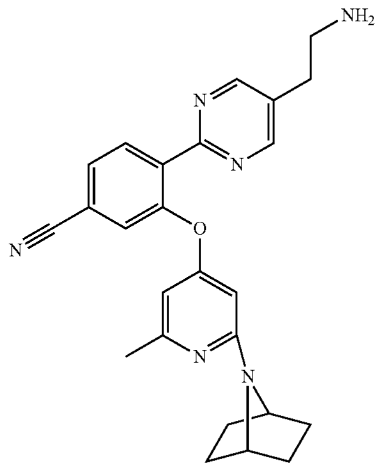 [SMILES: Cc1cc(Oc2cc(C#N)ccc2-c2ncc(CCN)cn2)cc(N2C3CCC2CC3)n1] | 4-[5-(2-aminoethyl)pyrimidin-2-yl]-3-[2-(7-azabicyclo[2.2.1]heptan-7-yl)-6-methylpyridin-4-yl]oxybenzonitrile |
| 828 | 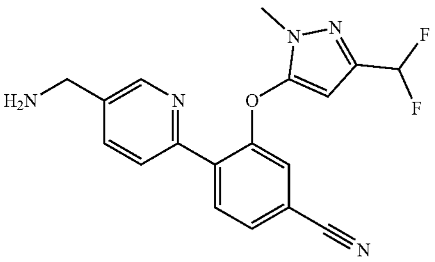 [SMILES: Cn1nc(C(F)F)cc1Oc1cc(C#N)ccc1-c1ccc(CN)cn1] | 4-[5-(aminomethyl)pyridin-2-yl]-3-[5-(difluoromethyl)-2-methylpyrazol-3-yl]oxybenzonitrile |

TABLE 1-continued
| Compound number | Structural formula | Compound name |
|---|---|---|
| 829 | 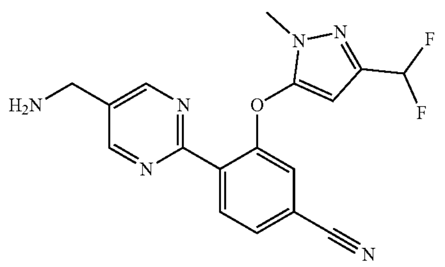 [SMILES: Cn1nc(C(F)F)cc1Oc1cc(C#N)ccc1-c1ncc(CN)cn1] | 4-[5-(aminomethyl)pyrimidin-2-yl]-3-[5-(difluoromethyl)-2-methylpyrazol-3-yl]oxybenzonitrile |
| 830 | 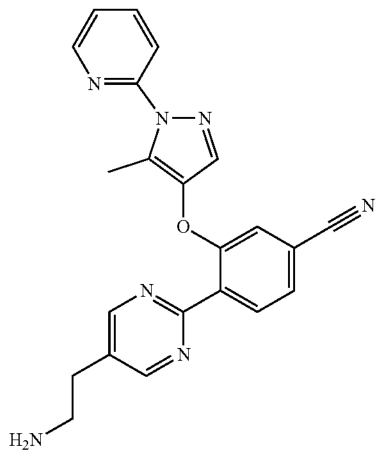 [SMILES: Cc1c(Oc2cc(C#N)ccc2-c2ncc(CCN)cn2)cnn1-c1ccccn1] | 4-[5-(2-aminoethyl)pyrimidin-2-yl]-3-(5-methyl-1-pyridin-2-ylpyrazol-4-yl)oxybenzonitrile |
| 831 | 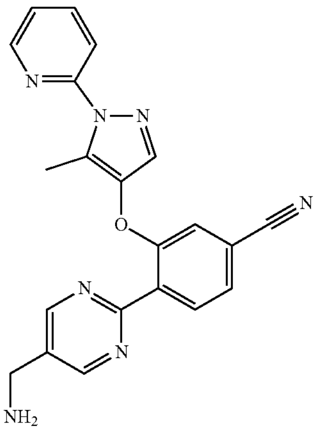 [SMILES: Cc1c(Oc2cc(C#N)ccc2-c2ncc(CN)cn2)cnn1-c1ccccn1] | 4-[5-(aminomethyl)pyrimidin-2-yl]-3-(5-methyl-1-pyridin-2-ylpyrazol-4-yl)oxybenzonitrile |

TABLE 1-continued
| Compound number | Structural formula | Compound name |
|---|---|---|
| 832 | 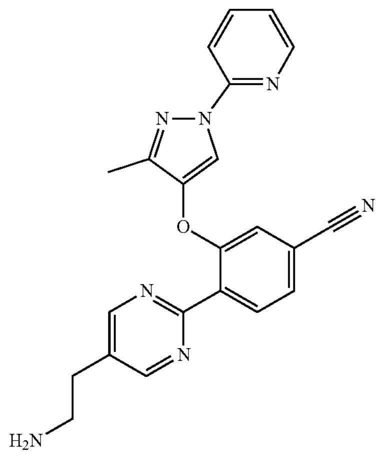 [SMILES: Cc1nn(-c2ccccn2)cc1Oc1cc(C#N)ccc1-c1ncc(CCN)cn1] | 4-[5-(2-aminoethyl)pyrimidin-2-yl]-3-(3-methyl-1-pyridin-2-ylpyrazol-4-yl)oxybenzonitrile |
| 833 | 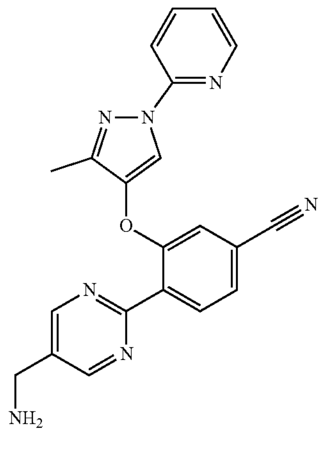 [SMILES: Cc1nn(-c2ccccn2)cc1Oc1cc(C#N)ccc1-c1ncc(CN)cn1] | 4-[5-(aminomethyl)pyrimidin-2-yl]-3-(3-methyl-1-pyridin-2-ylpyrazol-4 yl)oxybenzonitrile |
| 834 | 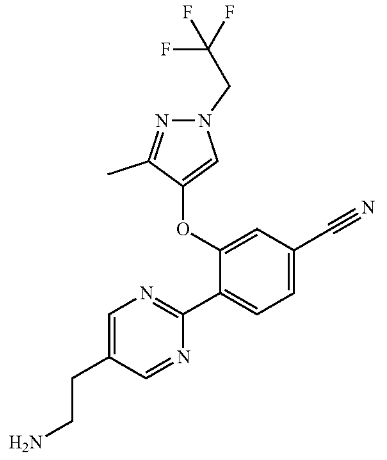 [SMILES: Cc1nn(CC(F)(F)F)cc1Oc1cc(C#N)ccc1-c1ncc(CCN)cn1] | 4-[5-(2-aminoethyl)pyrimidin-2-yl]-3-[3-methyl-1-(2,2,2-trifluoroethyl)pyrazol-4-yl]oxybenzonitrile |

TABLE 1-continued

| Compound number | Structural formula | Compound name |
|---|---|---|
| 835 | 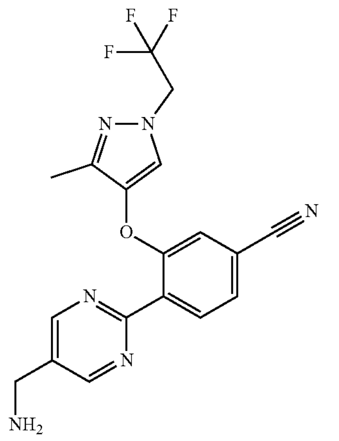 [SMILES: Cc1nn(CC(F)(F)F)cc1Oc1cc(C#N)ccc1-c1ncc(CN)cn1] | 4-[5-(aminomethyl)pyrimidin-2-yl]-3-[3-methyl-1-(2,2,2-trifluoroethyl)pyrazol-4-yl]oxybenzonitrile |
| 836 | 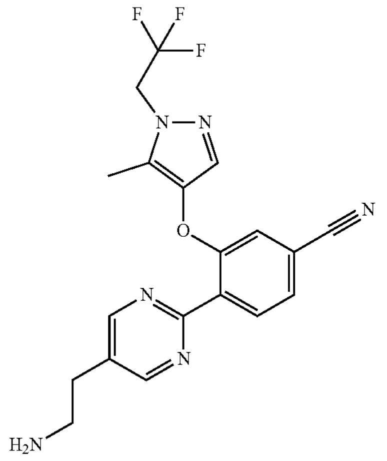 [SMILES: Cc1c(Oc2cc(C#N)ccc2-c2ncc(CCN)cn2)cnn1CC(F)(F)F] | 4-[5-(2-aminoethyl)pyrimidin-2-yl]-3-[5-methyl-1-(2,2,2-trifluoroethyl)pyrazol-4-yl]oxybenzonitrile |
| 837 | 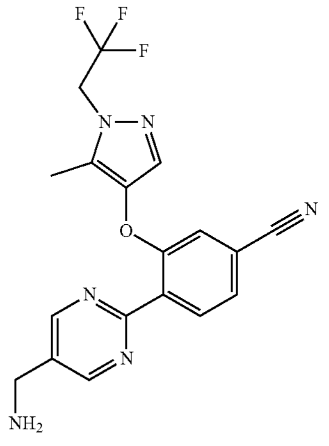 [SMILES: Cc1c(Oc2cc(C#N)ccc2-c2ncc(CN)cn2)cnn1CC(F)(F)F] | 4-[5-(aminomethyl)pyrimidin-2-yl]-3-[5-methyl-1-(2,2,2-trifluoroethyl)pyrazol-4-yl]oxybenzonitrile |
| 838 | 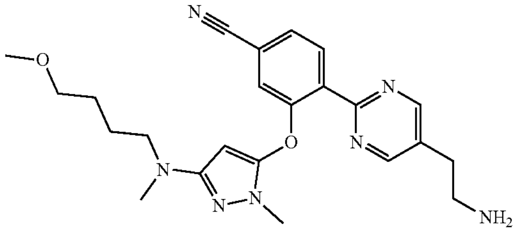 [SMILES: COCCCCN(C)c1cc(Oc2cc(C#N)ccc2-c2ncc(CCN)cn2)n(C)n1] | 4-[5-(2-aminoethyl)pyrimidin-2-yl]-3-[5-[4-methoxybutyl(methyl)amino]-2-methylpyrazol-3-yl]oxybenzonitrile |

TABLE 1-continued
| Compound number | Structural formula | Compound name |
|---|---|---|
| 839 | 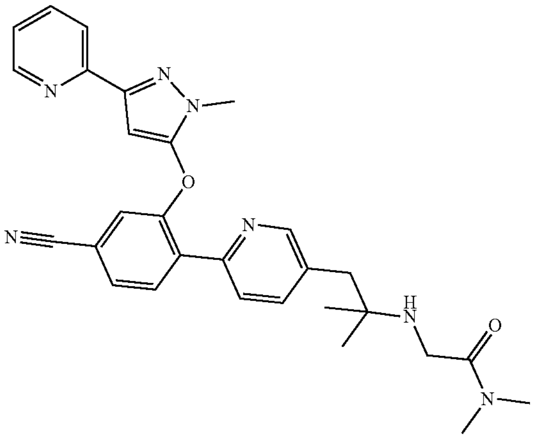 [SMILES: CN(C)C(=O)CNC(C)(C)Cc1ccc(-c2ccc(C#N)cc2Oc2cc(-c3ccccn3)nn2C)nc1] | 2-[[1-[6-[4-cyano-2-(2-methyl-5-pyridin-2-ylpyrazol-3-yl)oxyphenyl]pyridin-3-yl]-2-methylpropan-2-yl]amino]-N,N-dimethylacetamide |
| 840 | 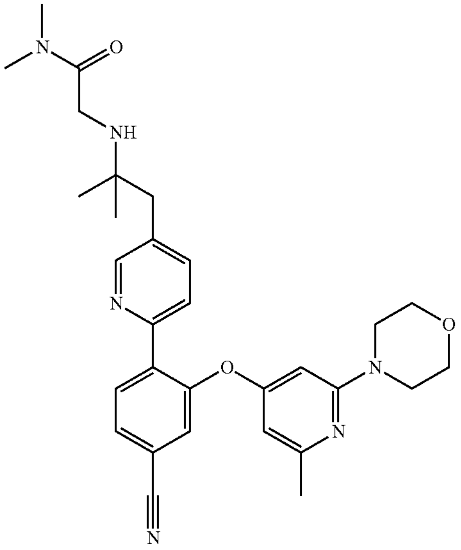 [SMILES: Cc1cc(Oc2cc(C#N)ccc2-c2ccc(CC(C)(C)NCC(=O)N(C)C)cn2)cc(N2CCOCC2)n1] | 2-[[1-[6-[4-cyano-2-(2-methyl-6-morpholin-4-ylpyridin-4-yl)oxyphenyl]pyridin-3-yl]-2-methylpropan-2-yl]amino]-N,N-dimethylacetamide |
| 841 | 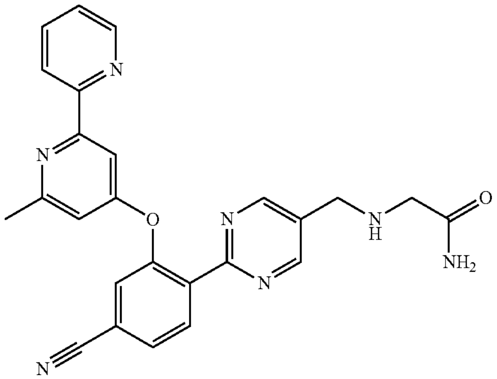 [SMILES: Cc1cc(Oc2cc(C#N)ccc2-c2ncc(CNCC(N)=O)cn2)cc(-c2ccccn2)n1] | 2-[[2-[4-cyano-2-(2-methyl-6-pyridin-2-ylpyridin-4-yl)oxyphenyl]pyrimidin-5-yl]methylamino]acetamide |

TABLE 1-continued
| Compound number | Structural formula | Compound name |
|---|---|---|
| 842 | 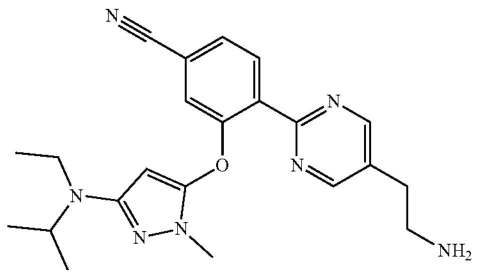 [SMILES: CCN(c1cc(Oc2cc(C#N)ccc2-c2ncc(CCN)cn2)n(C)n1)C(C)C] | 4-[5-(2-aminoethyl)pyrimidin-2-yl]-3-[5-[ethyl(propan-2-yl)amino]-2-methylpyrazol-3-yl]oxybenzonitrile |
| 843 | 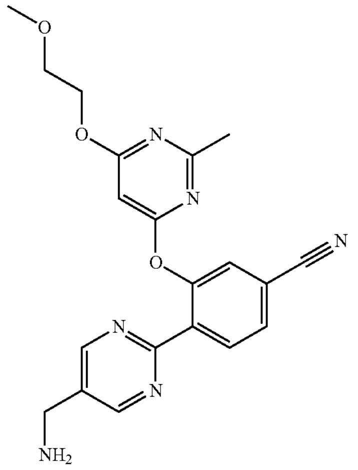 [SMILES: COCCOc1cc(Oc2cc(C#N)ccc2-c2ncc(CN)cn2)nc(C)n1] | 4-[5-(aminomethyl)pyrimidin-2-yl]-3-[6-(2-methoxyethoxy)-2-methylpyrimidin-4-yl]oxybenzonitrile |
| 844 | 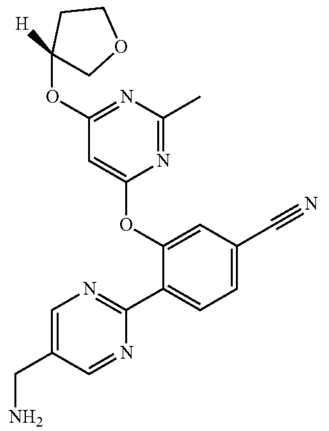 [SMILES: Cc1nc(Oc2cc(C#N)ccc2-c2ncc(CN)cn2)cc(O[C@@H]2CCOC2)n1] | 4-[5-(aminomethyl)pyrimidin-2-yl]-3-[2-methyl-6-[(3R)-oxolan-3-yl]oxypyrimidin-4-yl]oxybenzonitrile |

TABLE 1-continued
| Compound number | Structural formula | Compound name |
|---|---|---|
| 845 | 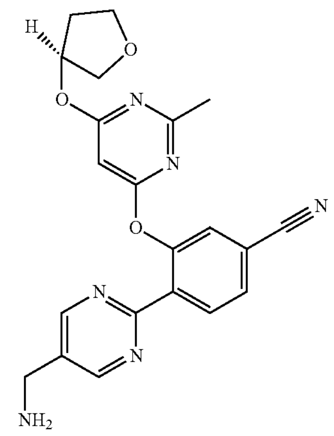 [SMILES: Cc1nc(Oc2cc(C#N)ccc2-c2ncc(CN)cn2)cc(O[C@H]2CCOC2)n1] | 4-[5-(aminomethyl)pyrimidin-2-yl]-3-[2-methyl-6-[(3S)-oxolan-3-yl]oxypyrimidin-4-yl]oxybenzonitrile |
| 846 | 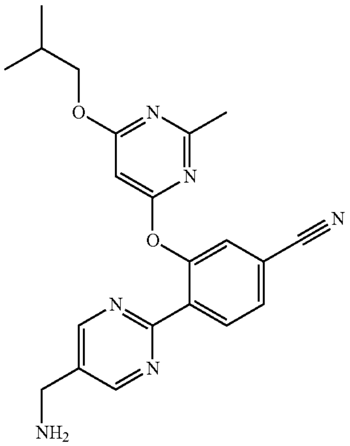 [SMILES: Cc1nc(OCC(C)C)cc(Oc2cc(C#N)ccc2-c2ncc(CN)cn2)n1] | 4-[5-(aminomethyl)pyrimidin-2-yl]-3-[2-methyl-6-(2-methylpropoxy)pyrimidin-4-yl]oxybenzonitrile |
| 847 | 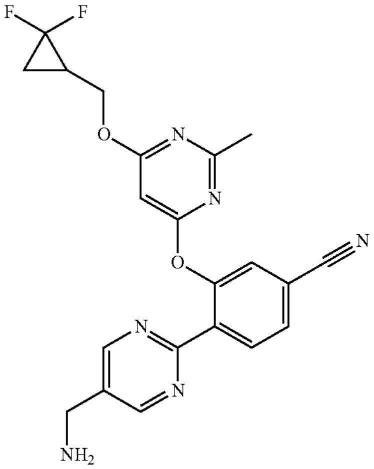 [SMILES: Cc1nc(OCC2CC2(F)F)cc(Oc2cc(C#N)ccc2-c2ncc(CN)cn2)n1] | 4-[5-(aminomethyl)pyrimidin-2-yl]-3-[6-[(2,2-difluorocyclopropyl)methoxy]-2-methylpyrimidin-4-yl]oxybenzonitrile |

TABLE 1-continued
| Compound number | Structural formula | Compound name |
|---|---|---|
| 848 | 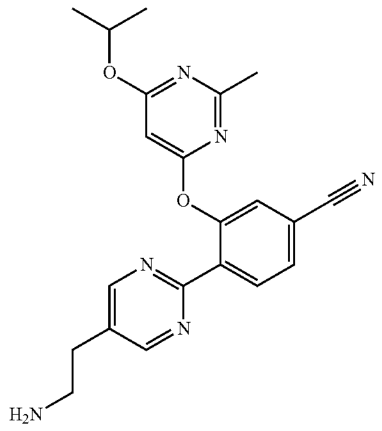 [SMILES: Cc1nc(Oc2cc(C#N)ccc2-c2ncc(CCN)cn2)cc(OC(C)C)n1] | 4-[5-(2-aminoethyl)pyrimidin-2-yl]-3-(2-methyl-6-propan-2-yloxypyrimidin-4-yl)oxybenzonitrile |
| 849 | 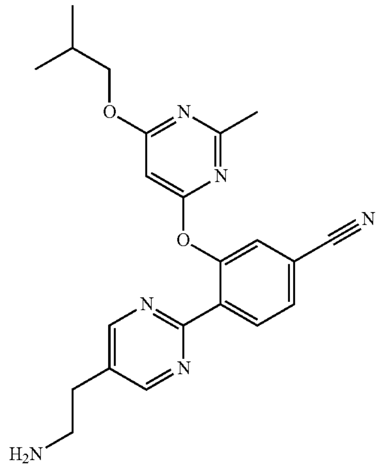 [SMILES: Cc1nc(OCC(C)C)cc(Oc2cc(C#N)ccc2-c2ncc(CCN)cn2)n1] | 4-[5-(2-aminoethyl)pyrimidin-2-yl]-3-[2-methyl-6-(2-methylpropoxy)pyrimidin-4-yl]oxybenzonitrile |
| 850 | 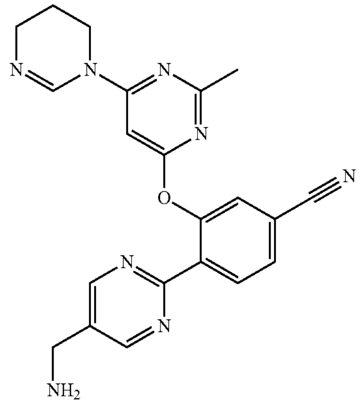 [SMILES: Cc1nc(Oc2cc(C#N)ccc2-c2ncc(CN)cn2)cc(N2C=NCCC2)n1] | 4-[5-(aminomethyl)pyrimidin-2-yl]-3-[6-(5,6-dihydro-4H-pyrimidin-1-yl)-2-methylpyrimidin-4-yl]oxybenzonitrile |

TABLE 1-continued
| Compound number | Structural formula | Compound name |
|---|---|---|
| 851 | 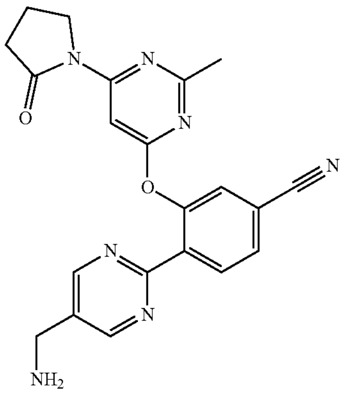 [SMILES: Cc1nc(Oc2cc(C#N)ccc2-c2ncc(CN)cn2)cc(N2CCCC2=O)n1] | 4-[5-(aminomethyl)pyrimidin-2-yl]-3-[2-methyl-6-(2-oxopyrrolidin-1-yl)pyrimidin-4-yl]oxybenzonitrile |
| 852 | 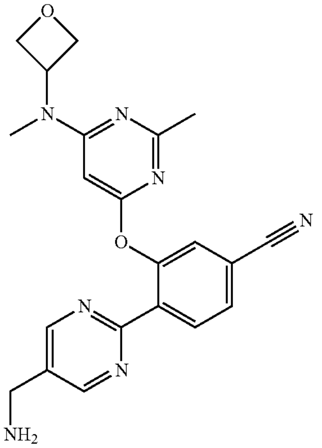 [SMILES: Cc1nc(Oc2cc(C#N)ccc2-c2ncc(CN)cn2)cc(N(C)C2COC2)n1] | 4-[5-(aminomethyl)pyrimidin-2-yl]-3-[2-methyl-6-[methyl(oxetan-3-yl)amino]pyrimidin-4-yl]oxybenzonitrile |
| 853 | 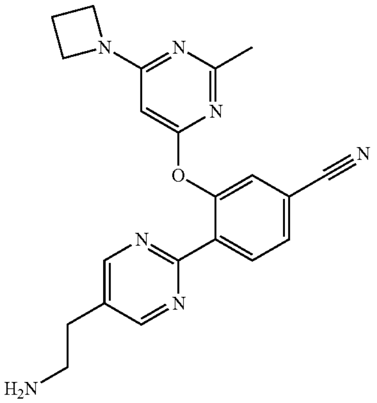 [SMILES: Cc1nc(Oc2cc(C#N)ccc2-c2ncc(CCN)cn2)cc(N2CCC2)n1] | 4-[5-(2-aminoethyl)pyrimidin-2-yl]-3-[6-(azetidin-1-yl)-2-methylpyrimidin-4-yl]oxybenzonitrile |

TABLE 1-continued
| Compound number | Structural formula | Compound name |
| --- | --- | --- |
| 854 | 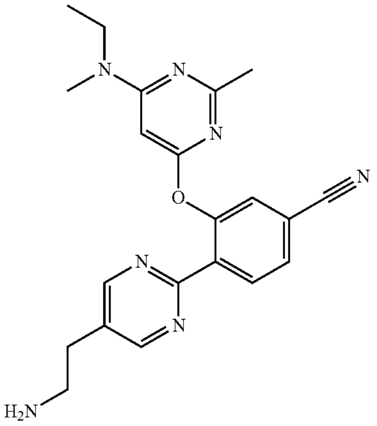 [SMILES: CCN(C)c1cc(Oc2cc(C#N)ccc2-c2ncc(CCN)cn2)nc(C)n1] | 4-[5-(2-aminoethyl)pyrimidin-2-yl]-3-[6-[ethyl(methyl)amino]-2-methylpyrimidin-4-yl]oxybenzonitrile |
| 855 | 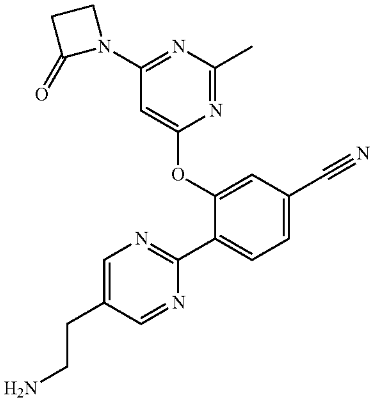 [SMILES: Cc1nc(Oc2cc(C#N)ccc2-c2ncc(CCN)cn2)cc(N2CCC2=O)n1] | 4-[5-(2-aminoethyl)pyrimidin-2-yl]-3-[2-methyl-6-(2-oxoazetidin-1-yl)pyrimidin-4-yl]oxybenzonitrile |
| 856 | 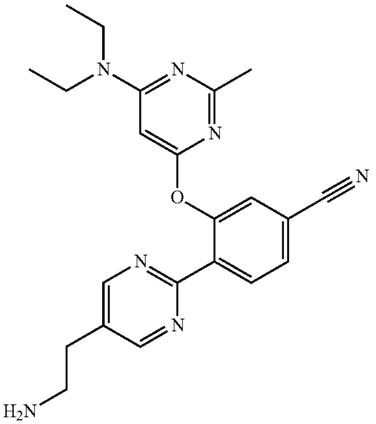 [SMILES: CCN(CC)c1cc(Oc2cc(C#N)ccc2-c2ncc(CCN)cn2)nc(C)n1] | 4-[5-(2-aminoethyl)pyrimidin-2-yl]-3-[6-(diethylamino)-2-methylpyrimidin-4-yl]oxybenzonitrile |

TABLE 1-continued
| Compound number | Structural formula | Compound name |
|---|---|---|
| 857 | 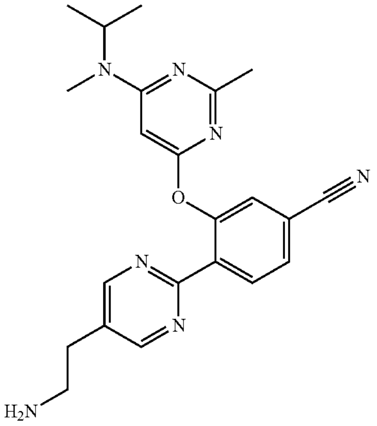 [SMILES: Cc1nc(Oc2cc(C#N)ccc2-c2ncc(CCN)cn2)cc(N(C)C(C)C)n1] | 4-[5-(2-aminoethyl)pyrimidin-2-yl]-3-[2-methyl-6-[methyl(propan-2-yl)amino]pyrimidin-4-yl]oxybenzonitrile |
| 858 | 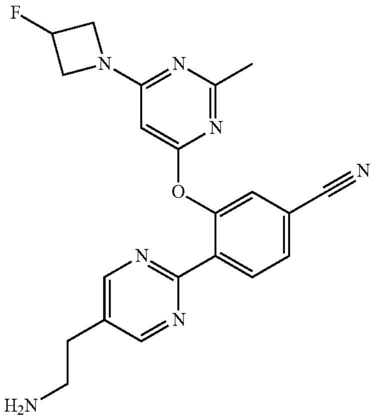 [SMILES: Cc1nc(Oc2cc(C#N)ccc2-c2ncc(CCN)cn2)cc(N2CC(F)C2)n1] | 4-[5-(2-aminoethyl)pyrimidin-2-yl]-3-[6-(3-fluoroazetidin-1-yl)-2-methylpyrimidin-4-yl]oxybenzonitrile |
| 859 | 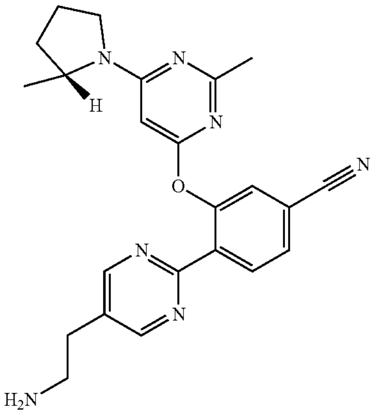 [SMILES: Cc1nc(Oc2cc(C#N)ccc2-c2ncc(CCN)cn2)cc(N2CCC[C@H]2C)n1] | 4-[5-(2-aminoethyl)pyrimidin-2-yl]-3-[2-methyl-6-[(2R)-2-methylpyrrolidin-1-yl]pyrimidin-4-yl]oxybenzonitrile |

TABLE 1-continued
| Compound number | Structural formula | Compound name |
| --- | --- | --- |
| 860 | 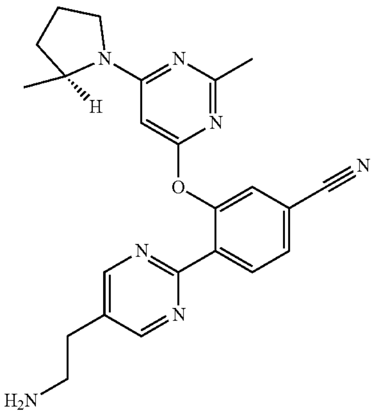 [SMILES: Cc1nc(Oc2cc(C#N)ccc2-c2ncc(CCN)cn2)cc(N2CCC[C@@H]2C)n1] | 4-[5-(2-aminoethyl)pyrimidin-2-yl]-3-[2-methyl-6-[(2S)-2-methylpyrrolidin-1-yl]pyrimidin-4-yl]oxybenzonitrile |
| 861 | 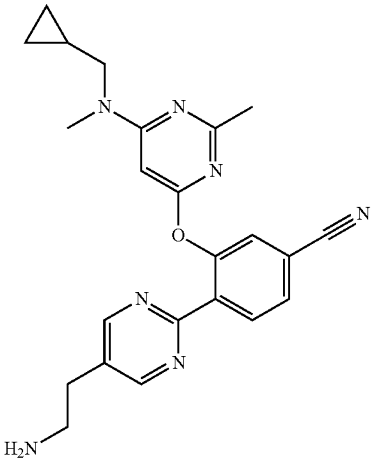 [SMILES: Cc1nc(Oc2cc(C#N)ccc2-c2ncc(CCN)cn2)cc(N(C)CC2CC2)n1] | 4-[5-(2-aminoethyl)pyrimidin-2-yl]-3-[6-[cyclopropylmethyl(methyl)amino]-2-methylpyrimidin-4-yl]oxybenzonitrile |
| 862 | 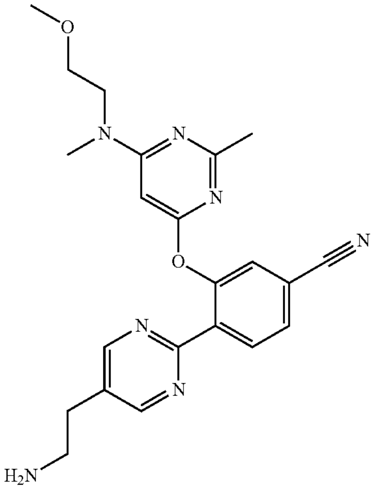 [SMILES: COCCN(C)c1cc(Oc2cc(C#N)ccc2-c2ncc(CCN)cn2)nc(C)n1] | 4-[5-(2-aminoethyl)pyrimidin-2-yl]-3-[6-[2-methoxyethyl(methyl)amino]-2-methylpyrimidin-4-yl]oxybenzonitrile |

TABLE 1-continued
| Compound number | Structural formula | Compound name |
| --- | --- | --- |
| 863 | 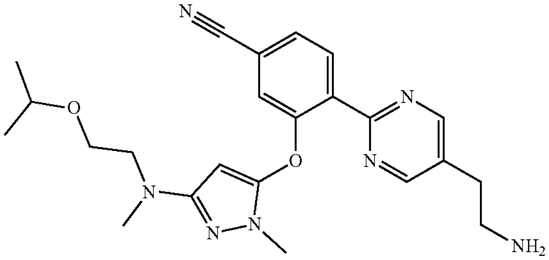 [SMILES: CC(C)OCCN(C)c1cc(Oc2cc(C#N)ccc2-c2ncc(CCN)cn2)n(C)n1] | 4-[5-(2-aminoethyl)pyrimidin-2-yl]-3-[2-methyl-5-[methyl(2-propan-2-yloxyethyl)amino]pyrazol-3-yl]oxybenzonitrile |
| 864 | 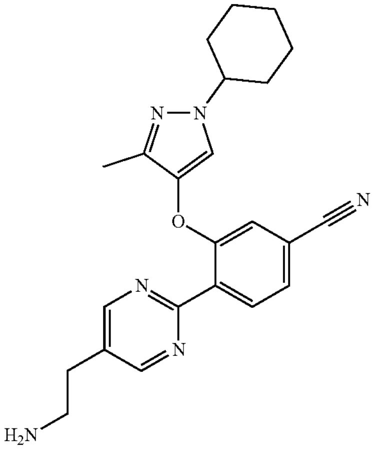 [SMILES: Cc1nn(C2CCCCC2)cc1Oc1cc(C#N)ccc1-c1ncc(CCN)cn1] | 4-[5-(2-aminoethyl)pyrimidin-2-yl]-3-(1-cyclohexyl-3-methylpyrazol-4-yl)oxybenzonitrile |
| 865 | 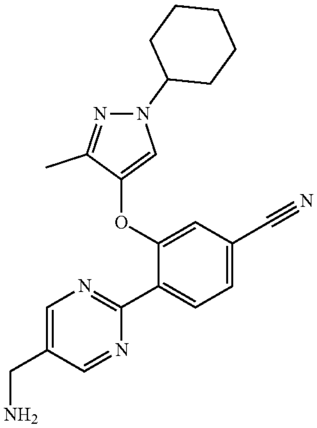 [SMILES: Cc1nn(C2CCCCC2)cc1Oc1cc(C#N)ccc1-c1ncc(CN)cn1] | 4-[5-(aminomethyl)pyrimidin-2-yl]-3-(1-cyclohexyl-3-methylpyrazol-4-yl)oxybenzonitrile |

TABLE 1-continued

| Compound number | Structural formula | Compound name |
|---|---|---|
| 866 | 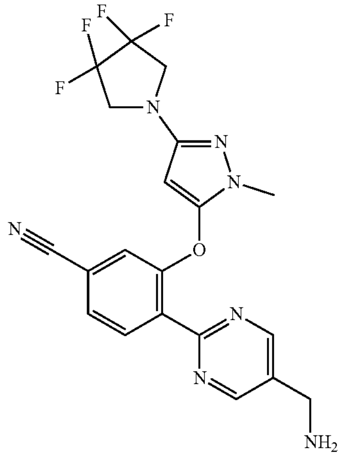 [SMILES: Cn1nc(N2CC(F)(F)C(F)(F)C2)cc1Oc1cc(C#N)ccc1-c1ncc(CN)cn1] | 4-[5-(aminomethyl)pyrimidin-2-yl]-3-[2-methyl-5-(3,3,4,4-tetrafluoropyrrolidin-1-yl)pyrazol-3-yl]oxybenzonitrile |
| 867 | 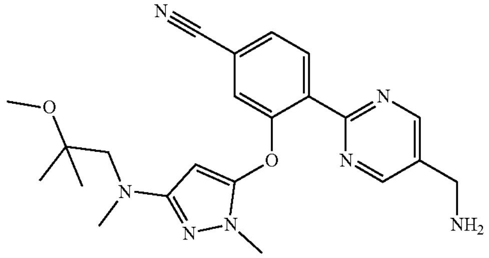 [SMILES: COC(C)(C)CN(C)c1cc(Oc2cc(C#N)ccc2-c2ncc(CN)cn2)n(C)n1] | 4-[5-(aminomethyl)pyrimidin-2-yl]-3-[5-[(2-methoxy-2-methylpropyl)-methylamino]-2-methylpyrazol-3-yl]oxybenzonitrile |
| 868 | 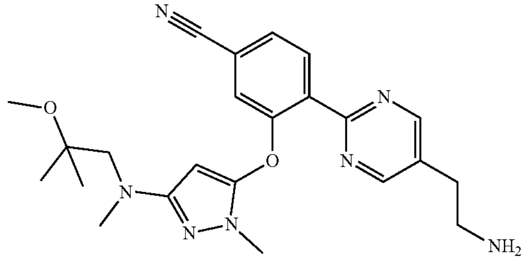 [SMILES: COC(C)(C)CN(C)c1cc(Oc2cc(C#N)ccc2-c2ncc(CCN)cn2)n(C)n1] | 4-[5-(2-aminoethyl)pyrimidin-2-yl]-3-[5-[(2-methoxy-2-methylpropyl)-methylamino]-2-methylpyrazol-3-yl]oxybenzonitrile |
| 869 | 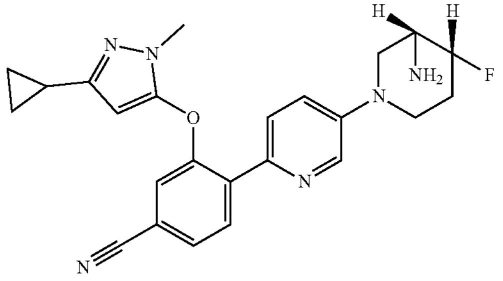 | 4-[5-[(4R)-3-amino-4-fluoropiperidin-1-yl]pyridin-2-yl]-3-(5-cyclopropyl-2-methylpyrazol-3-yl)oxybenzonitrile |

TABLE 1-continued

| Compound number | Structural formula | Compound name |
|---|---|---|
| 870 | 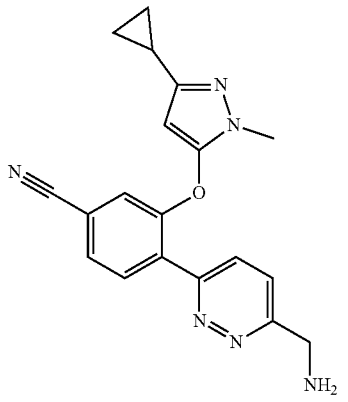 [SMILES: Cn1nc(C2CC2)cc1Oc1cc(C#N)ccc1-c1ccc(CN)nn1] | 4-[6-(aminomethyl)pyridazin-3-yl]-3-(5-cyclopropyl-2-methylpyrazol-3-yl)oxybenzonitrile |
| 871 | 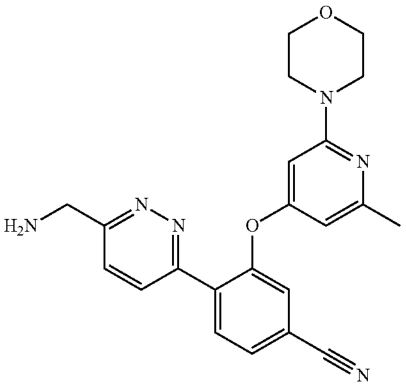 [SMILES: Cc1cc(Oc2cc(C#N)ccc2-c2ccc(CN)nn2)cc(N2CCOCC2)n1] | 4-[6-(aminomethyl)pyridazin-3-yl]-3-(2-methyl-6-morpholin-4-ylpyridin-4-yl)oxybenzonitrile |
| 872 | 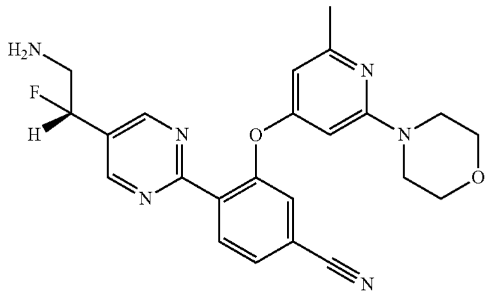 [SMILES: Cc1cc(Oc2cc(C#N)ccc2-c2ncc([C@H](F)CN)cn2)cc(N2CCOCC2)n1] | 4-[5-[(1S)-2-amino-1-fluoroethyl]pyrimidin-2-yl]-3-(2-methyl-6-morpholin-4-ylpyridin-4-yl)oxybenzonitrile |
| 873 | 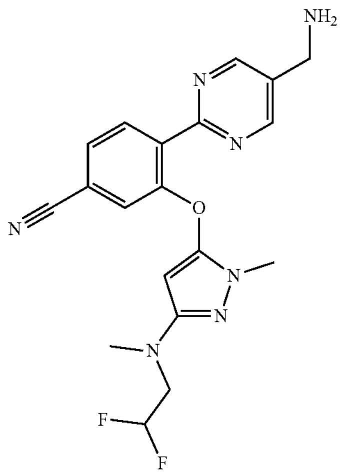 [SMILES: CN(CC(F)F)c1cc(Oc2cc(C#N)ccc2-c2ncc(CN)cn2)n(C)n1] | 4-[5-(aminomethyl)pyrimidin-2-yl]-3-[5-[2,2-difluoroethyl(methyl)amino]-2-methylpyrazol-3-yl]oxybenzonitrile |

TABLE 1-continued
| Compound number | Structural formula | Compound name |
|---|---|---|
| 874 | 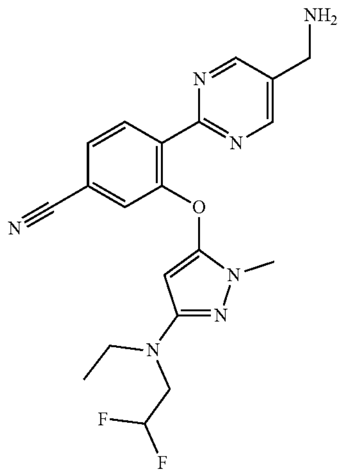 [SMILES: CCN(CC(F)F)c1cc(Oc2cc(C#N)ccc2-c2ncc(CN)cn2)n(C)n1] | 4-[5-(aminomethyl)pyrimidin-2-yl]-3-[5-[2,2-difluoroethyl(ethyl)amino]-2-methylpyrazol-3-yl]oxybenzonitrile |
| 875 | 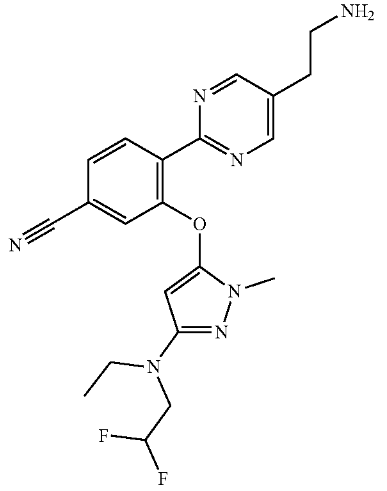 [SMILES: CCN(CC(F)F)c1cc(Oc2cc(C#N)ccc2-c2ncc(CCN)cn2)n(C)n1] | 4-[5-(2-aminoethyl)pyrimidin-2-yl]-3-[5-[2,2-difluoroethyl(ethyl)amino]-2 methylpyrazol-3-yl]oxybenzonitrile |
| 876 | 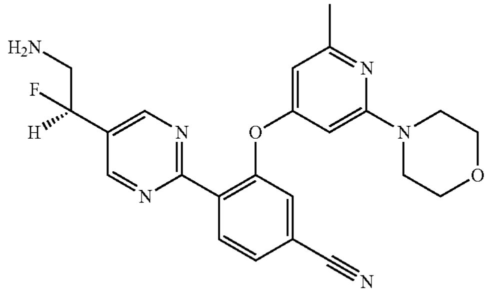 [SMILES: Cc1cc(Oc2cc(C#N)ccc2-c2ncc([C@@H](F)CN)cn2)cc(N2CCOCC2)n1] | 4-[5-[(1R)-2-amino-1-fluoroethyl]pyrimidin-2-yl]-3-(2-methyl-6-morpholin-4-ylpyridin-4-yl)oxybenzonitrile |

TABLE 1-continued
| Compound number | Structural formula | Compound name |
|---|---|---|
| 877 | 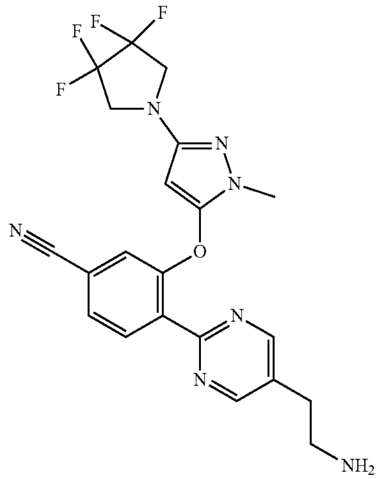 [SMILES: Cn1nc(N2CC(F)(F)C(F)(F)C2)cc1Oc1cc(C#N)ccc1-c1ncc(CCN)cn1] | 4-[5-(2-aminoethyl)pyrimidin-2-yl]-3-[2-methyl-5-(3,3,4,4-tetrafluoropyrrolidin-1-yl)pyrazol-3-yl]oxybenzonitrile |
| 878 | 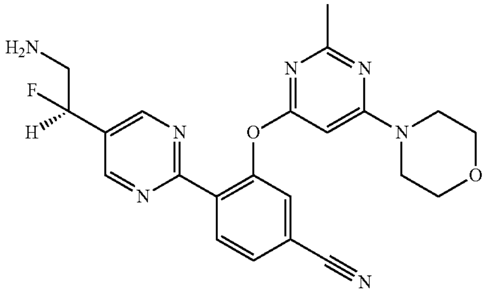 [SMILES: Cc1nc(Oc2cc(C#N)ccc2-c2ncc([C@@H](F)CN)cn2)cc(N2CCOCC2)n1] | 4-[5-[(1R)-2-amino-1-fluoroethyl]pyrimidin-2-yl]-3-(2-methyl-6-morpholin-4-ylpyrimidin-4-yl)oxybenzonitrile |
| 879 | 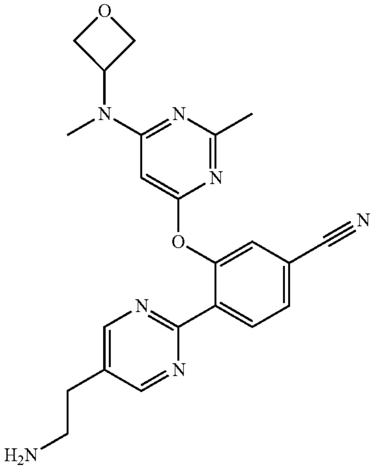 [SMILES: Cc1nc(Oc2cc(C#N)ccc2-c2ncc(CCN)cn2)cc(N(C)C2COC2)n1] | 4-[5-(2-aminoethyl)pyrimidm-2-yl]-3-[2-methyl-6-[methyl(oxetan-3-yl)amino]pyrimidin-4-yl]oxybenzonitrile |

TABLE 1-continued
| Compound number | Structural formula | Compound name |
| --- | --- | --- |
| 880 | 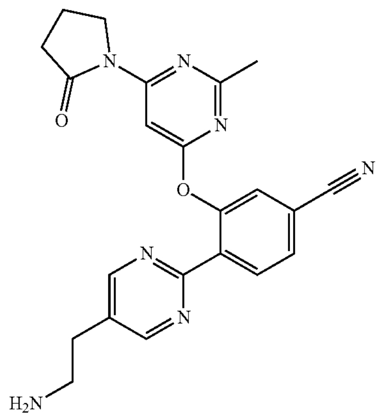 [SMILES: Cc1nc(Oc2cc(C#N)ccc2-c2ncc(CCN)cn2)cc(N2CCCC2=O)n1] | 4-[5-(2-aminoethyl)pyrimidin-2-yl]-3-[2-methyl-6-(2-oxopyrrolidin-1-yl)pyrimidin-4-yl]oxybenzonitrile |
| 881 | 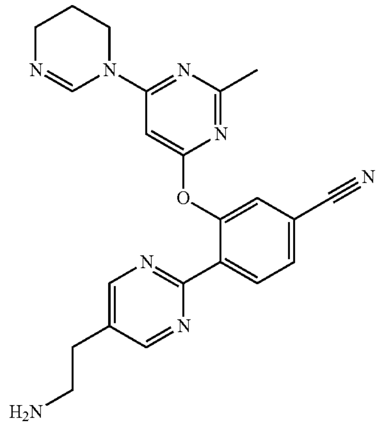 [SMILES: Cc1nc(Oc2cc(C#N)ccc2-c2ncc(CCN)cn2)cc(N2C=NCCC2)n1] | 4-[5-(2-aminoethyl)pyrimidin-2-yl]-3-[6-(5,6-dihydro-4H-pyrimidin-1-yl)-2-methylpyrimidin-4-yl]oxybenzonitrile |
| 882 | 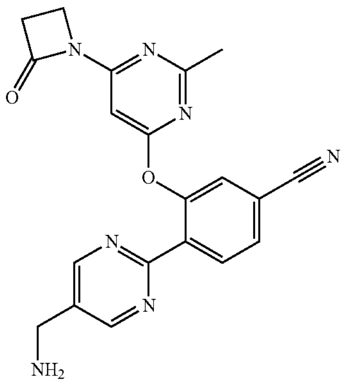 [SMILES: Cc1nc(Oc2cc(C#N)ccc2-c2ncc(CN)cn2)cc(N2CCC2=O)n1] | 4-[5-(aminomethyl)pyrimidin-2-yl]-3-[2-methyl-6-(2-oxoazetidin-1-yl)pyrimidin-4-yl]oxybenzonitrile |

TABLE 1-continued
| Compound number | Structural formula | Compound name |
|---|---|---|
| 883 | 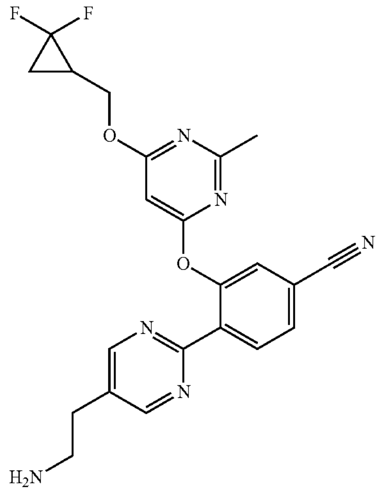 [SMILES: Cc1nc(OCC2CC2(F)F)cc(Oc2cc(C#N)ccc2-c2ncc(CCN)cn2)n1] | 4-[5-(2-aminoethyl)pyrimidin-2-yl]-3-[6-[(2,2-difluorocyclopropyl)methoxy]-2-methylpyrimidin-4-yl]oxybenzonitrile |
| 884 | 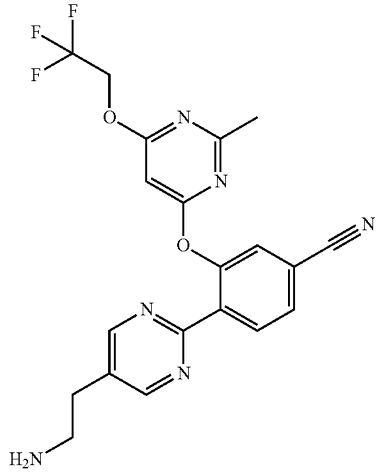 [SMILES: Cc1nc(OCC(F)(F)F)cc(Oc2cc(C#N)ccc2-c2ncc(CCN)cn2)n1] | 4-[5-(2-aminoethyl)pyrimidin-2-yl]-3-[2-methyl-6-(2,2,2-trifluoroethoxy)pyrimidin-4-yl]oxybenzonitrile |
| 885 | 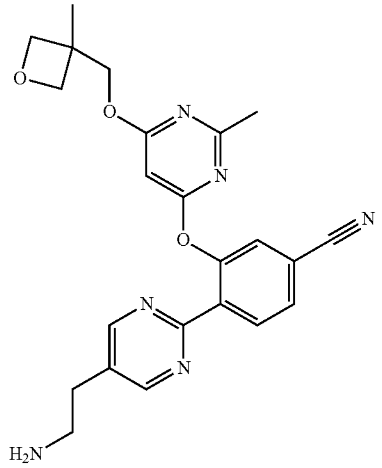 [SMILES: Cc1nc(OCC2(C)COC2)cc(Oc2cc(C#N)ccc2-c2ncc(CCN)cn2)n1] | 4-[5-(2-aminoethyl)pyrimidin-2-yl]-3-[2-methyl-6-[(3-methyloxetan-3-yl)methoxy]pyrimidin-4-yl]oxybenzonitrile |

TABLE 1-continued
| Compound number | Structural formula | Compound name |
|---|---|---|
| 886 | 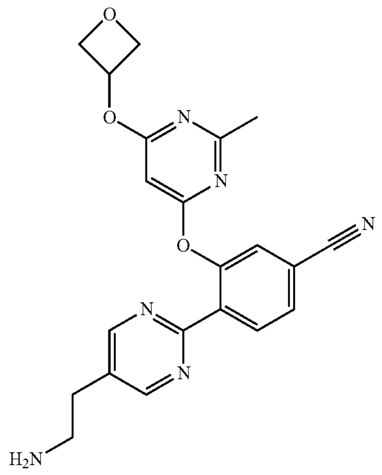 [SMILES: Cc1nc(Oc2cc(C#N)ccc2-c2ncc(CCN)cn2)cc(OC2COC2)n1] | 4-[5-(2-aminoethyl)pyrimidin-2-yl]-3-[2-methyl-6-(oxetan-3-yloxy)pyrimidin-4-yl]oxybenzonitrile |
| 887 | 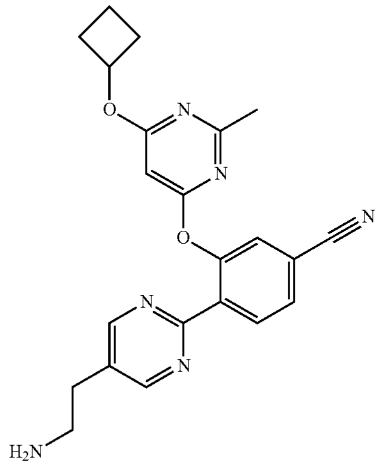 [SMILES: Cc1nc(Oc2cc(C#N)ccc2-c2ncc(CCN)cn2)cc(OC2CCC2)n1] | 4-[5-(2-aminoethyl)pyrimidin-2-yl]-3-(6-cyclobutyloxy-2-methylpyrimidin-4-yl)oxybenzonitrile |
| 888 | 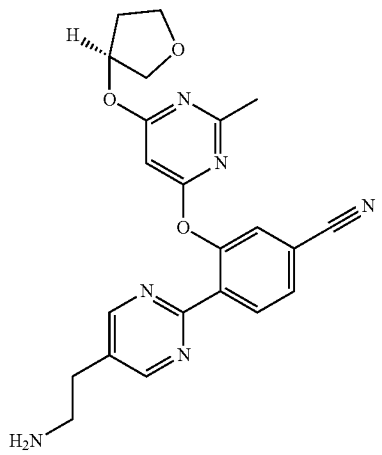 [SMILES: Cc1nc(Oc2cc(C#N)ccc2-c2ncc(CCN)cn2)cc(O[C@H]2CCOC2)n1] | 4-[5-(2-aminoethyl)pyrimidin-2-yl]-3-[2-methyl-6-[(3S)-oxolan-3-yl]oxypyrimidin-4-yl]oxybenzonitrile |

TABLE 1-continued
| Compound number | Structural formula | Compound name |
|---|---|---|
| 889 | 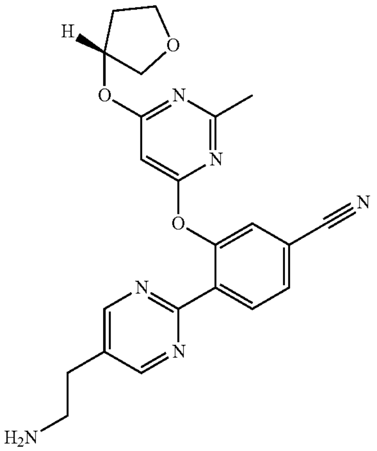 [SMILES: Cc1nc(Oc2cc(C#N)ccc2-c2ncc(CCN)cn2)cc(O[C@@H]2CCOC2)n1] | 4-[5-(2-aminoethyl)pyrimidin-2-yl]-3-[2-methyl-6-[(3R)-oxolan-3-yl]oxypyrimidin-4-yl]oxybenzonitrile |
| 890 | 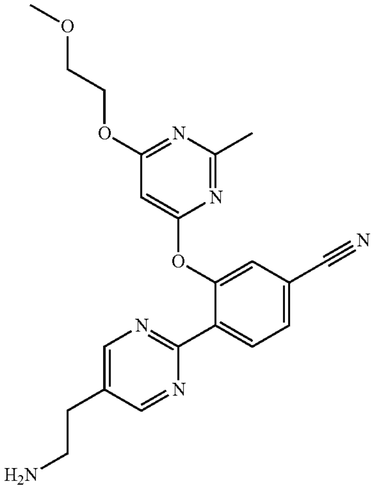 [SMILES: COCCOc1cc(Oc2cc(C#N)ccc2-c2ncc(CCN)cn2)nc(C)n1] | 4-[5-(2-aminoethyl)pyrimidin-2-yl]-3-[6-(2-methoxyethoxy)-2-methylpyrimidin-4-yl]oxybenzonitrile |
| 891 | 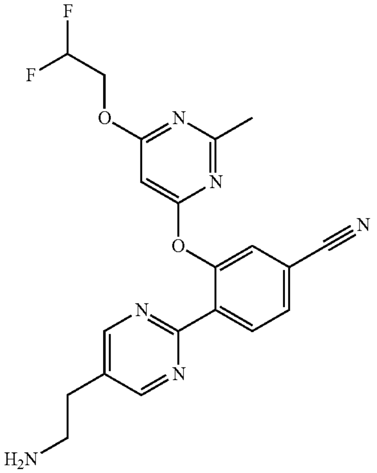 [SMILES: Cc1nc(OCC(F)F)cc(Oc2cc(C#N)ccc2-c2ncc(CCN)cn2)n1] | 4-[5-(2-aminoethyl)pyrimidin-2-yl]-3-[6-(2,2-difluoroethoxy)-2-methylpyrimidin-4-yl]oxybenzonitrile |

TABLE 1-continued
| Compound number | Structural formula | Compound name |
|---|---|---|
| 892 | 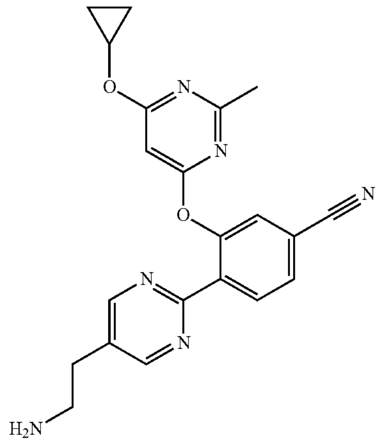 [SMILES: Cc1nc(Oc2cc(C#N)ccc2-c2ncc(CCN)cn2)cc(OC2CC2)n1] | 4-[5-(2-aminoethyl)pyrimidin-2-yl]-3-(6-cyclopropyloxy-2-methylpyrimidin-4-yl)oxybenzonitrile |
| 893 | 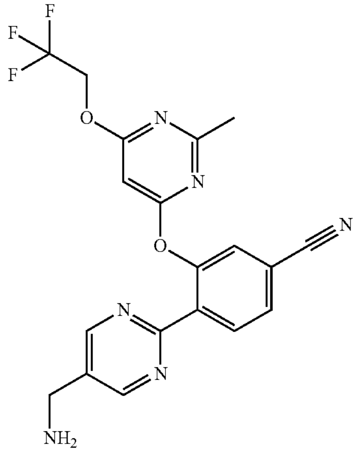 [SMILES: Cc1nc(OCC(F)(F)F)cc(Oc2cc(C#N)ccc2-c2ncc(CN)cn2)n1] | 4-[5-(aminomethyl)pyrimidin-2-yl]-3-[2-methyl-6-(2,2,2-trifluoroethoxy)pyrimidin-4-yl]oxybenzonitrile |
| 894 | 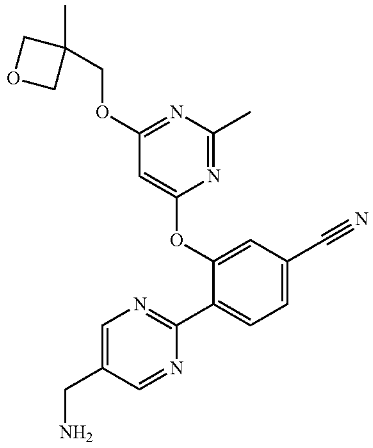 [SMILES: Cc1nc(OCC2(C)COC2)cc(Oc2cc(C#N)ccc2-c2ncc(CN)cn2)n1] | 4-[5-(aminomethyl)pyrimidin-2-yl]-3-[2-methyl-6-[(3-methyloxetan-3-yl)methoxy]pyrimidin-4-yl]oxybenzonitrile |

TABLE 1-continued
| Compound number | Structural formula | Compound name |
| --- | --- | --- |
| 895 | 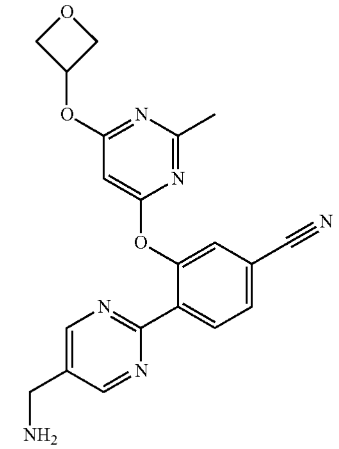 [SMILES: Cc1nc(Oc2cc(C#N)ccc2-c2ncc(CN)cn2)cc(OC2COC2)n1] | 4-[5-(aminomethyl)pyrimidin-2-yl]-3-[2-methyl-6-(oxetan-3-yloxy)pyrimidin-4-yl]oxybenzonitrile |
| 896 | 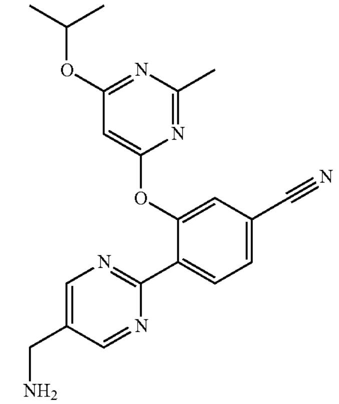 [SMILES: Cc1nc(Oc2cc(C#N)ccc2-c2ncc(CN)cn2)cc(OC(C)C)n1] | 4-[5-(aminomethyl)pyrimidin-2-yl]-3-(2-methyl-6-propan-2-yloxypyrimidin-4-yl)oxybenzonitrile |
| 897 | 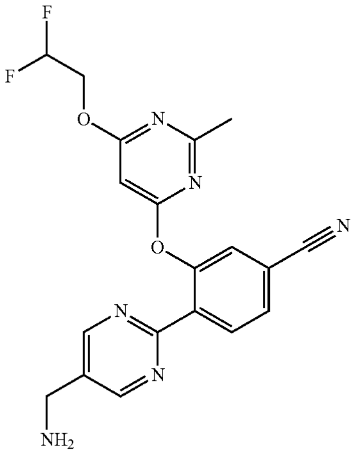 [SMILES: Cc1nc(OCC(F)F)cc(Oc2cc(C#N)ccc2-c2ncc(CN)cn2)n1] | 4-[5-(aminomethyl)pyrimidin-2-yl]-3-[6-(2,2-difluoroethoxy)-2-methylpyrimidin-4-yl]oxybenzonitrile |

TABLE 1-continued

| Compound number | Structural formula | Compound name |
|---|---|---|
| 898 | 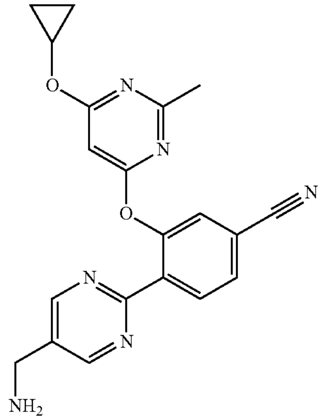 [SMILES: Cc1nc(Oc2cc(C#N)ccc2-c2ncc(CN)cn2)cc(OC2CC2)n1] | 4-[5-(aminomethyl)pyrimidin-2-yl]-3-(6-cyclopropyloxy-2-methylpyrimidin-4-yl)oxybenzonitrile |
| 899 | 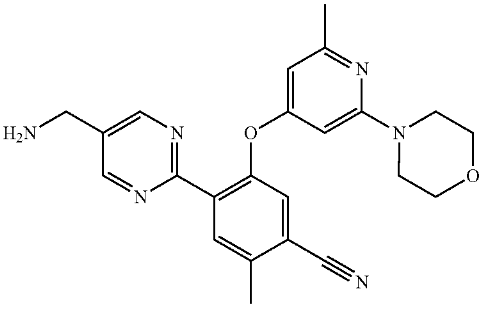 [SMILES: Cc1cc(Oc2cc(C#N)c(C)cc2-c2ncc(CN)cn2)cc(N2CCOCC2)n1] | 4-[5-(aminomethyl)pyrimidin-2-yl]-2-methyl-5-(2-methyl-6-morpholin-4-ylpyridin-4-yl)oxybenzonitrile |
| 900 | 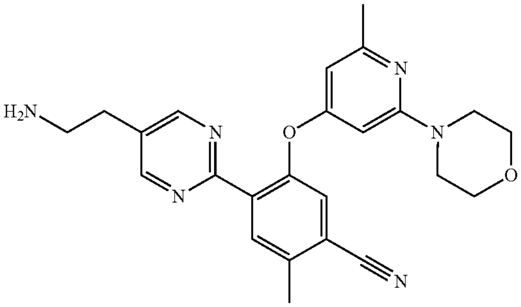 [SMILES: Cc1cc(Oc2cc(C#N)c(C)cc2-c2ncc(CCN)cn2)cc(N2CCOCC2)n1] | 4-[5-(2-aminoethyl)pyrimidin-2-yl]-2-methyl-5-(2-methyl-6-morpholin-4-ylpyridin-4-yl)oxybenzonitrile |
| 901 | 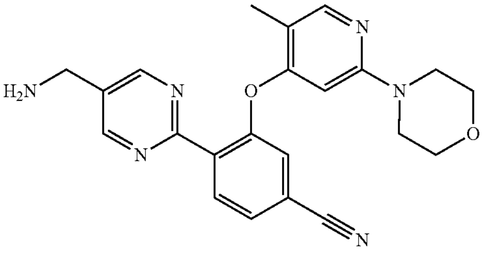 [SMILES: Cc1cnc(N2CCOCC2)cc1Oc1cc(C#N)ccc1-c1ncc(CN)cn1] | 4-[5-(aminomethyl)pyrimidin-2-yl]-3-(5-methyl-2-morpholin-4-ylpyridin-4-yl)oxybenzonitrile |
| 902 | 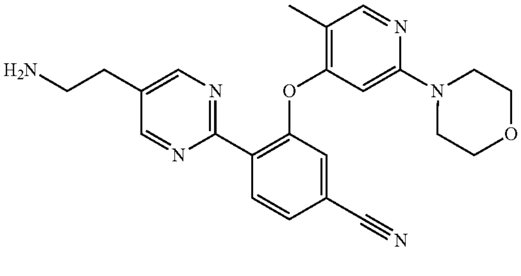 [SMILES: Cc1cnc(N2CCOCC2)cc1Oc1cc(C#N)ccc1-c1ncc(CCN)cn1] | 4-[5-(2-aminoethyl)pyrimidin-2-yl]-3-(5-methyl-2-morpholin-4-ylpyridin-4-yl)oxybenzonitrile |

TABLE 1-continued

| Compound number | Structural formula | Compound name |
|---|---|---|
| 903 | 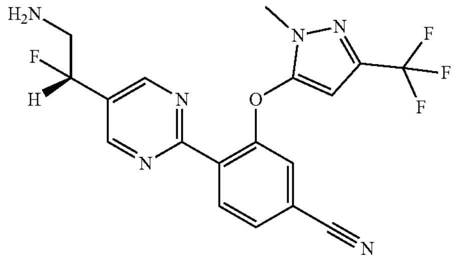 [SMILES: Cn1nc(C(F)(F)F)cc1Oc1cc(C#N)ccc1-c1ncc([C@H](F)CN)cn1] | 4-[5-[(1S)-2-amino-1-fluoroethyl]pyrimidin-2-yl]-3-[2-methyl-5-(trifluoromethyl)pyrazol-3-yl]oxybenzonitrile |
| 904 | 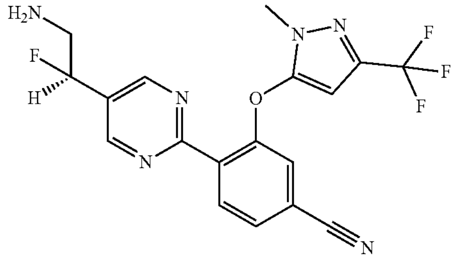 [SMILES: Cn1nc(C(F)(F)F)cc1Oc1cc(C#N)ccc1-c1ncc([C@@H](F)CN)cn1] | 4-[5-[(1R)-2-amino-1-fluoroethyl]pyrimidin-2-yl]-3-[2-methyl-5-(trifluoromethyl)pyrazol-3-yl]oxybenzonitrile |
| 905 | 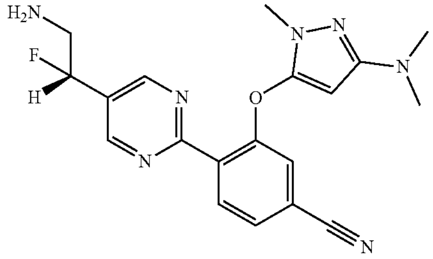 [SMILES: CN(C)c1cc(Oc2cc(C#N)ccc2-c2ncc([C@H](F)CN)cn2)n(C)n1] | 4-[5-[(1S)-2-amino-1-fluoroethyl]pyrimidin-2-yl]-3-[5-(dimethylamino)-2-methylpyrazol-3-yl]oxybenzonitrile |
| 906 | 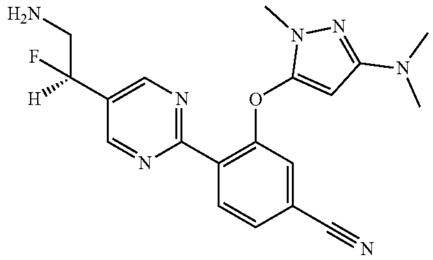 [SMILES: CN(C)c1cc(Oc2cc(C#N)ccc2-c2ncc([C@@H](F)CN)cn2)n(C)n1] | 4-[5-[(1R)-2-amino-1-fluoroethyl]pyrimidin-2-yl]-3-[5-(dimethylamino)-2-methylpyrazol-3-yl]oxybenzonitrile |
| 907 | 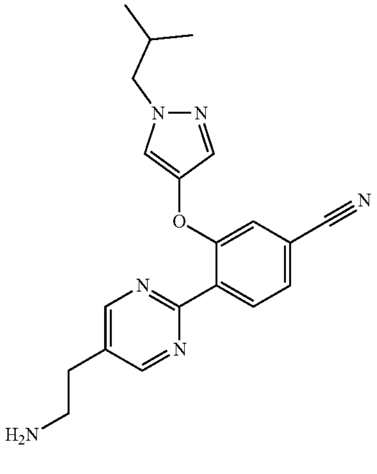 [SMILES: CC(C)Cn1cc(Oc2cc(C#N)ccc2-c2ncc(CCN)cn2)cn1] | 4-[5-(2-aminoethyl)pyrimidin-2-yl]-3-[1-(2-methylpropyl)pyrazol-4-yl]oxybenzonitrile |

TABLE 1-continued

| Compound number | Structural formula | Compound name |
| --- | --- | --- |
| 908 | 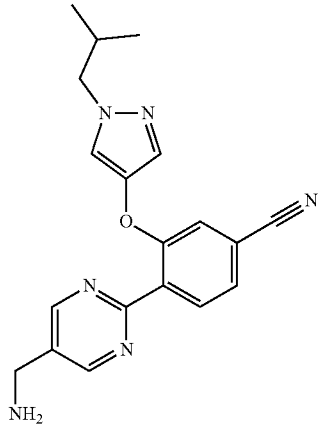 [SMILES: CC(C)Cn1cc(Oc2cc(C#N)ccc2-c2ncc(CN)cn2)cn1] | 4-[5-(aminomethyl)pyrimidin-2-yl]-3-[1-(2-methylpropyl)pyrazol-4-yl]oxybenzonitrile |
| 909 | 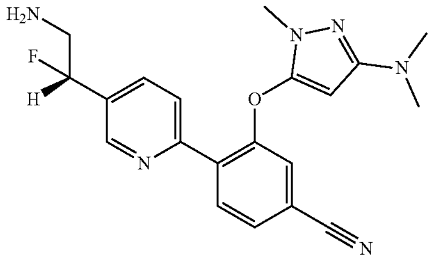 | 4-[5-[(1S)-2-amino-1-fluoroethyl]pyridin-2-yl]-3-[5-(dimethylamino)-2-methylpyrazol-3-yl]oxybenzonitrile |
| 910 | 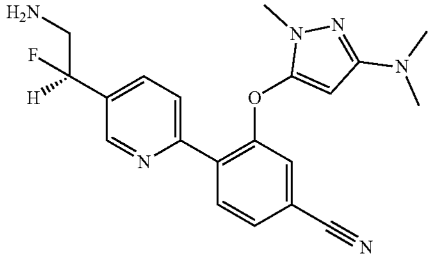 | 4-[5-[(1R)-2-amino-1-fluoroethyl]pyridin-2-yl]-3-[5-(dimethylamino)-2-methylpyrazol-3-yl]oxybenzonitrile |
| 911 | 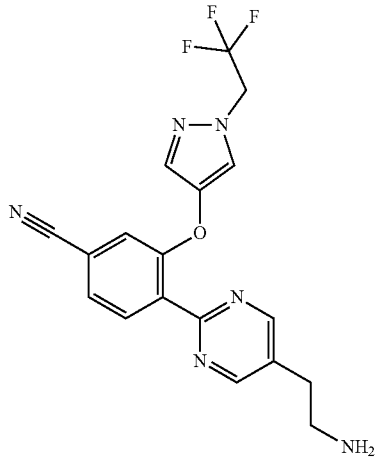 [SMILES: N#Cc1ccc(-c2ncc(CCN)cn2)c(Oc2cnn(CC(F)(F)F)c2)c1] | 4-[5-(2-aminoethyl)pyrimidin-2-yl]-3-[1-(2,2,2-trifluoroethyl)pyrazol-4-yl]oxybenzonitrile |

TABLE 1-continued

| Compound number | Structural formula | Compound name |
|---|---|---|
| 912 | 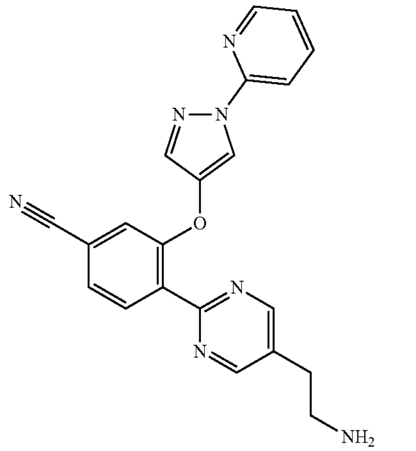 [SMILES: N#Cc1ccc(-c2ncc(CCN)cn2)c(Oc2cnn(-c3ccccn3)c2)c1] | 4-[5-(2-aminoethyl)pyrimidin-2-yl]-3-(1-pyridin-2-ylpyrazol-4-yl)oxybenzonitrile |
| 913 | 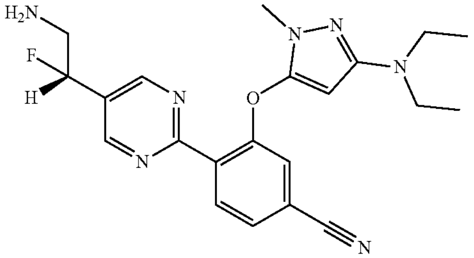 [SMILES: CCN(CC)c1cc(Oc2cc(C#N)ccc2-c2ncc([C@H](F)CN)cn2)n(C)n1] | 4-[5-[(1S)-2-amino-1-fluoroethyl]pyrimidin-2-yl]-3-[5-(diethylamino)-2-methylpyrazol-3-yl]oxybenzonitrile |
| 914 | 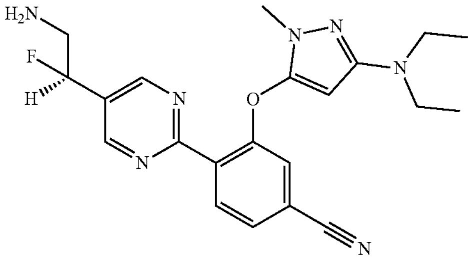 [SMILES: CCN(CC)c1cc(Oc2cc(C#N)ccc2-c2ncc([C@@H](F)CN)cn2)n(C)n1] | 4-[5-[(1R)-2-amino-1-fluoroethyl]pyrimidin-2-yl]-3-[5-(diethylamino)-2-methylpyrazol-3-yl]oxybenzonitrile |
| 915 | 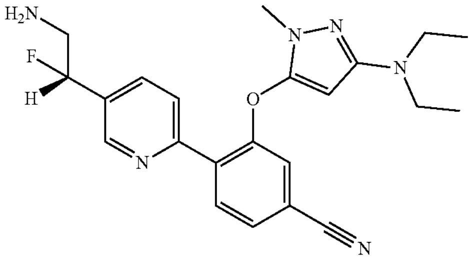 [SMILES: CCN(CC)c1cc(Oc2cc(C#N)ccc2-c2ccc([C@H](F)CN)cn2)n(C)n1] | 4-[5-[(1S)-2-amino-1-fluoroethyl]pyridin-2-yl]-3-[5-(diethylamino)-2-methylpyrazol-3-yl]oxybenzonitrile |
| 916 | 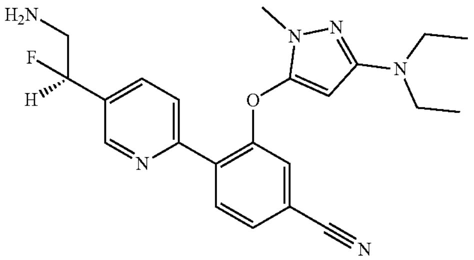 [SMILES: CCN(CC)c1cc(Oc2cc(C#N)ccc2-c2ccc([C@@H](F)CN)cn2)n(C)n1] | 4-[5-[(1R)-2-amino-1-fluoroethyl]pyridin-2-yl]-3-[5-(diethylamino)-2-methylpyrazol-3-yl]oxybenzonitrile |

TABLE 1-continued

| Compound number | Structural formula | Compound name |
|---|---|---|
| 917 | 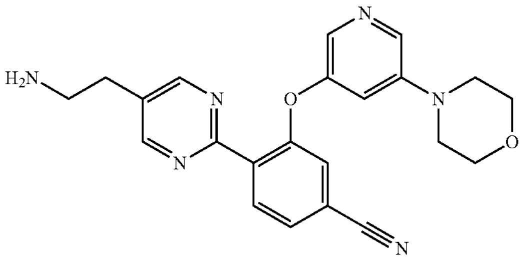 [SMILES: N#Cc1ccc(-c2ncc(CCN)cn2)c(Oc2cncc(N3CCOCC3)c2)c1] | 4-[5-(2-aminoethyl)pyrimidin-2-yl]-3-(5-morpholin-4-ylpyridin-3-yl)oxybenzonitrile |
| 918 | 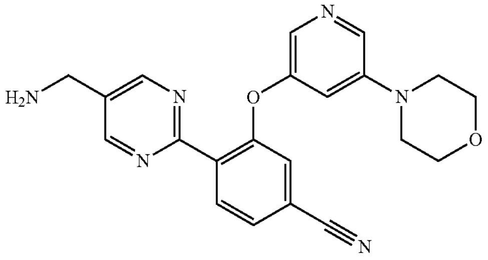 [SMILES: N#Cc1ccc(-c2ncc(CN)cn2)c(Oc2cncc(N3CCOCC3)c2)c1] | 4-[5-(aminomethyl)pyrimidin-2-yl]-3-(5-morpholin-4-ylpyridin-3-yl)oxybenzonitrile |
| 919 | 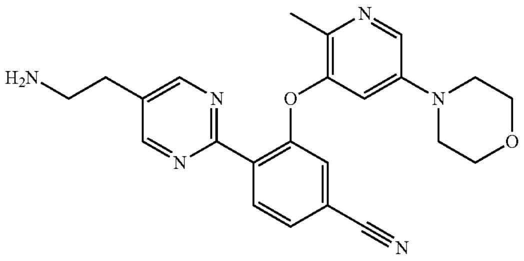 [SMILES: Cc1ncc(N2CCOCC2)cc1Oc1cc(C#N)ccc1-c1ncc(CCN)cn1] | 4-[5-(2-aminoethyl)pyrimidin-2-yl]-3-(2-methyl-5-morpholin-4-ylpyridin-3-yl)oxybenzonitrile |
| 920 | 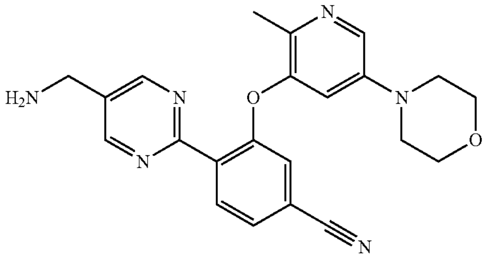 [SMILES: Cc1ncc(N2CCOCC2)cc1Oc1cc(C#N)ccc1-c1ncc(CN)cn1] | 4-[5-(aminomethyl)pyrimidin-2-yl]-3-(2-methyl-5-morpholin-4-ylpyridin-3-yl)oxybenzonitrile |
| 921 | 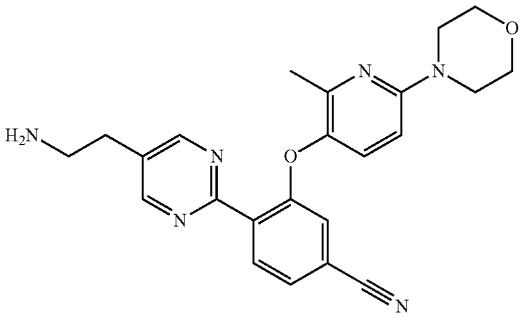 [SMILES: Cc1nc(N2CCOCC2)ccc1Oc1cc(C#N)ccc1-c1ncc(CCN)cn1] | 4-[5-(2-aminoethyl)pyrimidin-2-yl]-3-(2-methyl-6-morpholin-4-ylpyridin-3-yl)oxybenzonitrile |

TABLE 1-continued
| Compound number | Structural formula | Compound name |
| --- | --- | --- |
| 922 | 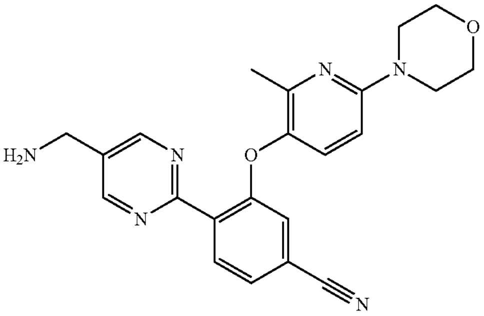 [SMILES: Cc1nc(N2CCOCC2)ccc1Oc1cc(C#N)ccc1-c1ncc(CN)cn1] | 4-[5-(aminomethyl)pyrimidin-2-yl]-3-(2-methyl-6-morpholin-4-ylpyridin-3-yl)oxybenzonitrile |
| 923 | 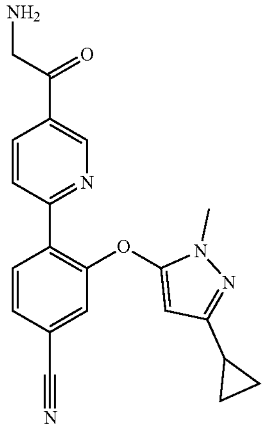 [SMILES: Cn1nc(C2CC2)cc1Oc1cc(C#N)ccc1-c1ccc(C(=O)CN)cn1] | 4-[5-(2-aminoacetyl)pyridin-2-yl]-3-(5-cyclopropyl-2-methylpyrazol-3-yl)oxybenzonitrile |
| 924 | 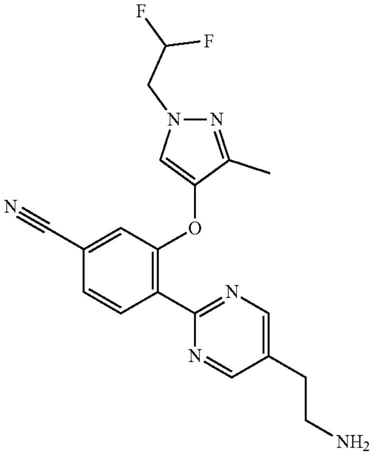 [SMILES: Cc1nn(CC(F)F)cc1Oc1cc(C#N)ccc1-c1ncc(CCN)cn1] | 4-[5-(2-aminoethyl)pyrimidin-2-yl]-3-[1-(2,2-difluoroethyl)-3-methylpyrazol-4-yl]oxybenzonitrile |

TABLE 1-continued
| Compound number | Structural formula | Compound name |
|---|---|---|
| 925 | 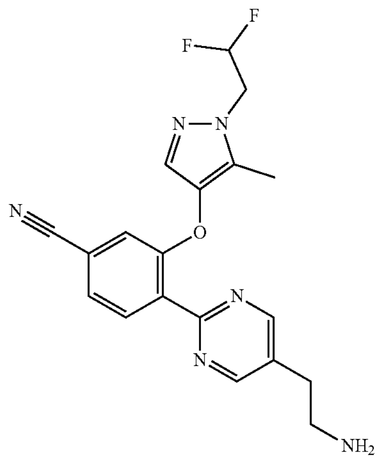 [SMILES: Cc1c(Oc2cc(C#N)ccc2-c2ncc(CCN)cn2)cnn1CC(F)F] | 4-[5-(2-aminoethyl)pyrimidin-2-yl]-3-[1-(2,2-difluoroethyl)-5-methylpyrazol-4-yl]oxybenzonitrile |
| 926 | 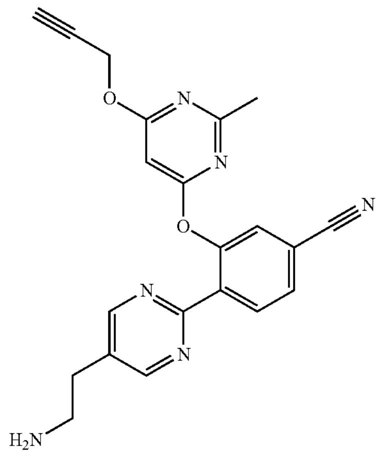 [SMILES: C#CCOc1cc(Oc2cc(C#N)ccc2-c2ncc(CCN)cn2)nc(C)n1] | 4-[5-(2-aminoethyl)pyrimidin-2-yl]-3-(2-methyl-6-prop-2-ynoxypyrimidin-4-yl)oxybenzonitrile |
| 927 | 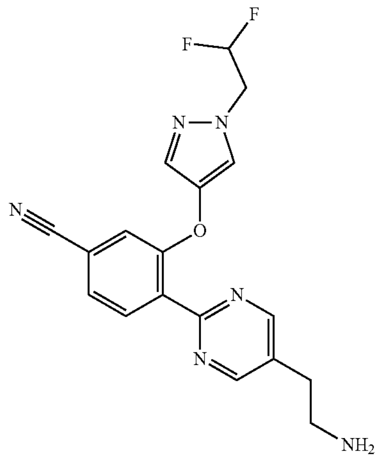 [SMILES: N#Cc1ccc(-c2ncc(CCN)cn2)c(Oc2cnn(CC(F)F)c2)c1] | 4-[5-(2-aminoethyl)pyrimidin-2-yl]-3-[1-(2,2-difluoroethyl)pyrazol-4-yl]oxybenzonitrile |

TABLE 1-continued

| Compound number | Structural formula | Compound name |
|---|---|---|
| 928 | 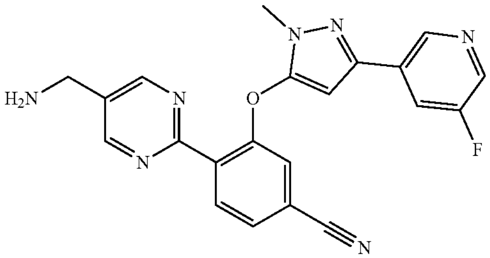 [SMILES: Cn1nc(-c2cncc(F)c2)cc1Oc1cc(C#N)ccc1-c1ncc(CN)cn1] | 4-[5-(aminomethyl)pyrimidin-2-yl]-3-[5-(5-fluoropyridin-3-yl)-2-methylpyrazol-3-yl]oxybenzonitrile |
| 929 | 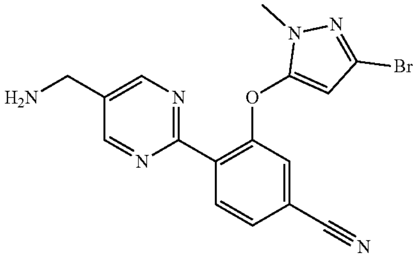 [SMILES: Cn1nc(Br)cc1Oc1cc(C#N)ccc1-c1ncc(CN)cn1] | 4-[5-(aminomethyl)pyrimidin-2-yl]-3-(5-bromo-2-methylpyrazol-3-yl)oxybenzonitrile |
| 930 | 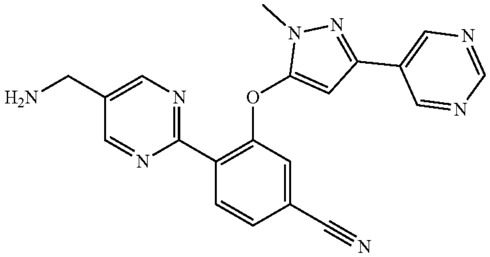 [SMILES: Cn1nc(-c2cncnc2)cc1Oc1cc(C#N)ccc1-c1ncc(CN)cn1] | 4-[5-(aminomethyl)pyrimidin-2-yl]-3-(2-methyl-5-pyrimidin-5-ylpyrazol-3-yl)oxybenzonitrile |
| 931 | 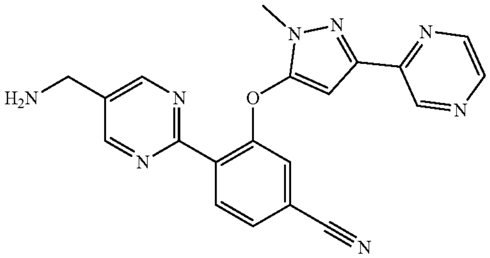 [SMILES: Cn1nc(-c2cnccn2)cc1Oc1cc(C#N)ccc1-c1ncc(CN)cn1] | 4-[5-(aminomethyl)pyrimidin-2-yl]-3-(2-methyl-5-pyrazin-2-ylpyrazol-3-yl)oxybenzonitrile |
| 932 | 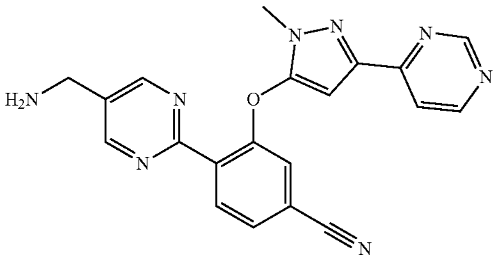 [SMILES: Cn1nc(-c2ccncn2)cc1Oc1cc(C#N)ccc1-c1ncc(CN)cn1] | 4-[5-(aminomethyl)pyrimidin-2-yl]-3-(2-methyl-5-pyrimidin-4-ylpyrazol-3-yl)oxybenzonitrile |

TABLE 1-continued

| Compound number | Structural formula | Compound name |
|---|---|---|
| 933 | 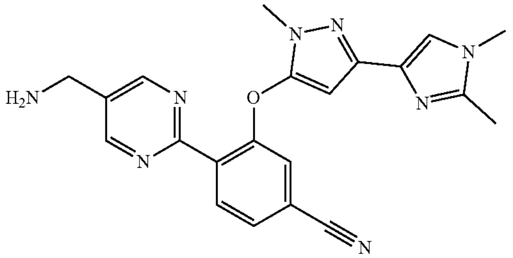 [SMILES: Cc1nc(-c2cc(Oc3cc(C#N)ccc3-c3ncc(CN)cn3)n(C)n2)cn1C] | 4-[5-(aminomethyl)pyrimidin-2-yl]-3-[5-(1,2-dimethylimidazol-4-yl)-2-methylpyrazol-3-yl]oxybenzonitrile |
| 934 | 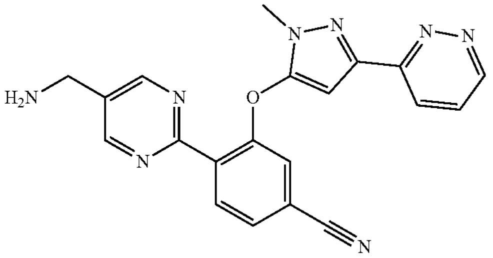 [SMILES: Cn1nc(-c2cccnn2)cc1Oc1cc(C#N)ccc1-c1ncc(CN)cn1] | 4-[5-(aminomethyl)pyrimidin-2-yl]-3-(2-methyl-5-pyridazin-3-ylpyrazol-3-yl)oxybenzonitrile |
| 935 | 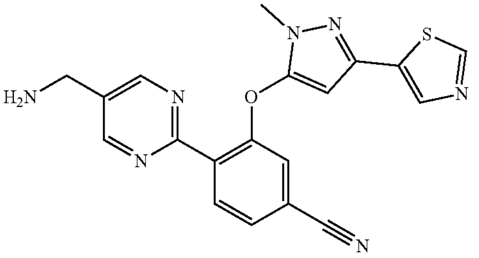 [SMILES: Cn1nc(-c2cncs2)cc1Oc1cc(C#N)ccc1-c1ncc(CN)cn1] | 4-[5-(aminomethyl)pyrimidin-2-yl]-3-[2-methyl-5-(1,3-thiazol-5-yl)pyrazol-3-yl]oxybenzonitrile |
| 936 | 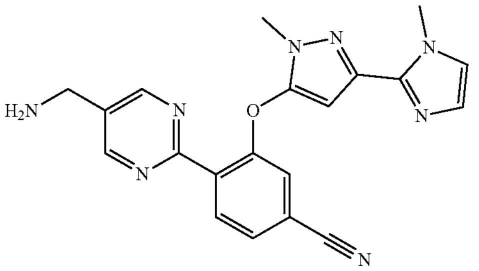 [SMILES: Cn1ccnc1-c1cc(Oc2cc(C#N)ccc2-c2ncc(CN)cn2)n(C)n1] | 4-[5-(aminomethyl)pyrimidin-2-yl]-3-[2-methyl-5-(1-methylimidazol-2-yl)pyrazol-3-yl]oxybenzonitrile |
| 937 | 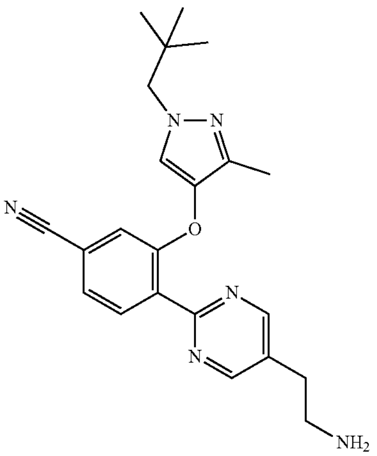 [SMILES: Cc1nn(CC(C)(C)C)cc1Oc1cc(C#N)ccc1-c1ncc(CCN)cn1] | 4-[5-(2-aminoethyl)pyrimidin-2-yl]-3-[1-(2,2-dimethylpropyl)-3-methylpyrazol-4-yl]oxybenzonitrile |

TABLE 1-continued
| Compound number | Structural formula | Compound name |
| --- | --- | --- |
| 938 | 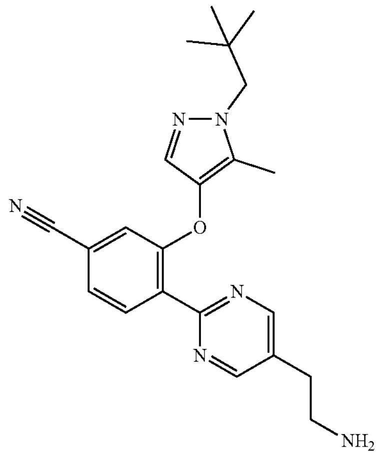 [SMILES: Cc1c(Oc2cc(C#N)ccc2-c2ncc(CCN)cn2)cnn1CC(C)(C)C] | 4-[5-(2-aminoethyl)pyrimidin-2-yl]-3-[1-(2,2-dimethylpropyl)-5-methylpyrazol-4-yl]oxybenzonitrile |
| 939 | 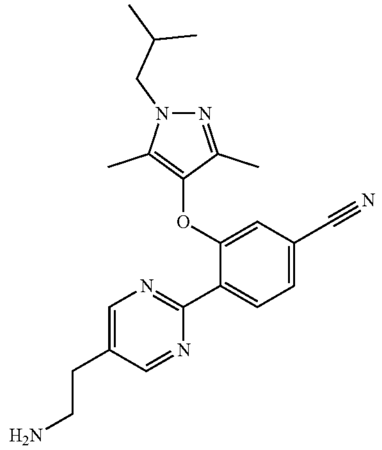 [SMILES: Cc1nn(CC(C)C)c(C)c1Oc1cc(C#N)ccc1-c1ncc(CCN)cn1] | 4-[5-(2-aminoethyl)pyrimidin-2-yl]-3-[3,5-dimethyl-1-(2-methylpropyl)pyrazol-4-yl]oxybenzonitrile |
| 940 | 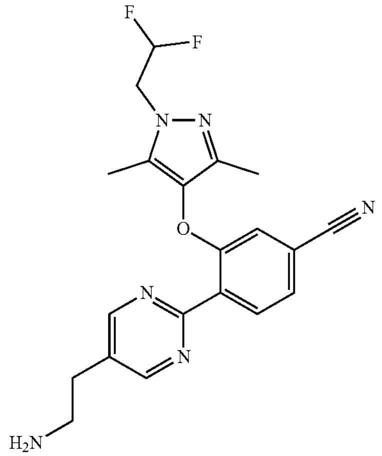 [SMILES: Cc1nn(CC(F)F)c(C)c1Oc1cc(C#N)ccc1-c1ncc(CCN)cn1] | 4-[5-(2-aminoethyl)pyrimidin-2-yl]-3-[1-(2,2-difluoroethyl)-3,5-dimethylpyrazol-4-yl]oxybenzonitrile |

TABLE 1-continued
| Compound number | Structural formula | Compound name |
|---|---|---|
| 941 | 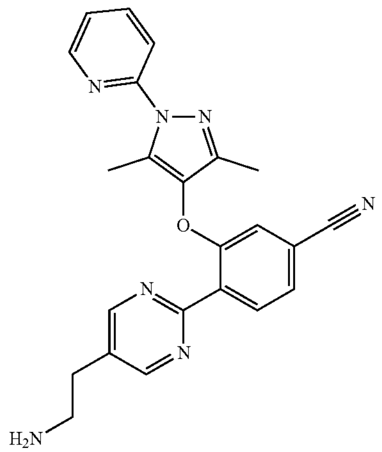 [SMILES: Cc1nn(-c2ccccn2)c(C)c1Oc1cc(C#N)ccc1-c1ncc(CCN)cn1] | 4-[5-(2-aminoethyl)pyrimidin-2-yl]-3-(3,5-dimethyl-1-pyridin-2-ylpyrazol-4-yl)oxybenzonitrile |
| 942 | 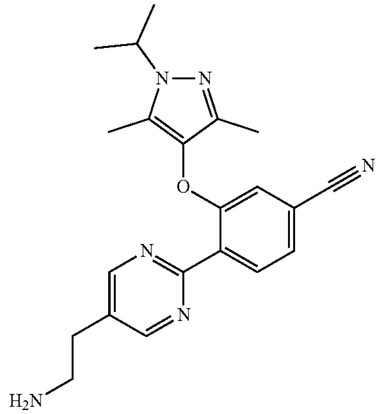 [SMILES: Cc1nn(C(C)C)c(C)c1Oc1cc(C#N)ccc1-c1ncc(CCN)cn1] | 4-[5-(2-aminoethyl)pyrimidin-2-yl]-3-(3,5-dimethyl-1-propan-2-ylpyrazol-4-yl)oxybenzonitrile |
| 943 | 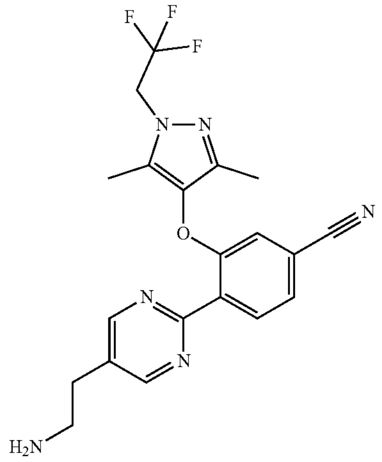 [SMILES: Cc1nn(CC(F)(F)F)c(C)c1Oc1cc(C#N)ccc1-c1ncc(CCN)cn1] | 4-[5-(2-aminoethyl)pyrimidin-2-yl]-3-[3,5-dimethyl-1-(2,2,2-trifluoroethyl)pyrazol-4-yl]oxybenzonitrile |

TABLE 1-continued

| Compound number | Structural formula | Compound name |
| --- | --- | --- |
| 944 | 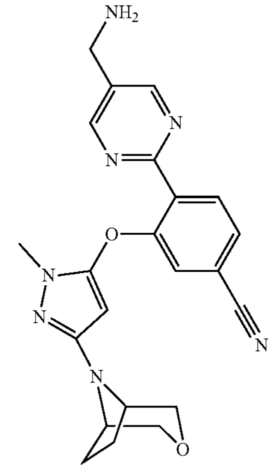 [SMILES: Cn1nc(N2C3CCC2COC3)cc1Oc1cc(C#N)ccc1-c1ncc(CN)cn1] | 4-[5-(aminomethyl)pyrimidin-2-yl]-3-[2-methyl-5-(3-oxa-8-azabicyclo[3.2.1]octan-8-yl)pyrazol-3-yl]oxybenzonitrile |
| 945 | 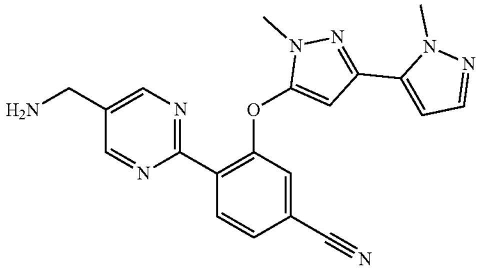 [SMILES: Cn1nc(-c2ccnn2C)cc1Oc1cc(C#N)ccc1-c1ncc(CN)cn1] | 4-[5-(aminomethyl)pyrimidin-2-yl]-3-[2-methyl-5-(2-methylpyrazol-3-yl)pyrazol-3-yl]oxybenzonitrile |
| 946 | 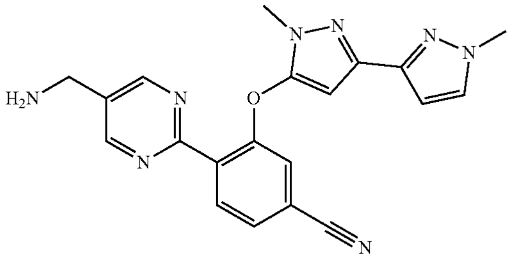 [SMILES: Cn1ccc(-c2cc(Oc3cc(C#N)ccc3-c3ncc(CN)cn3)n(C)n2)n1] | 4-[5-(aminomethyl)pyrimidin-2-yl]-3-[2-methyl-5-(1-methylpyrazol-3-yl)pyrazol-3-yl]oxybenzonitrile |
| 947 | 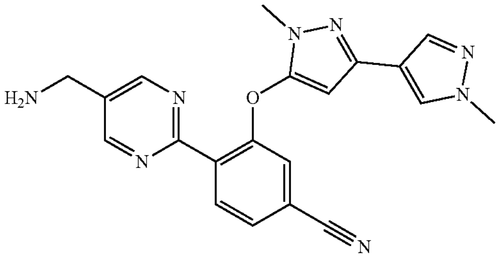 [SMILES: Cn1cc(-c2cc(Oc3cc(C#N)ccc3-c3ncc(CN)cn3)n(C)n2)cn1] | 4-[5-(aminomethyl)pyrimidin-2-yl]-3-[2-methyl-5-(1-methylpyrazol-4-yl)pyrazol-3-yl]oxybenzonitrile |
| 948 | 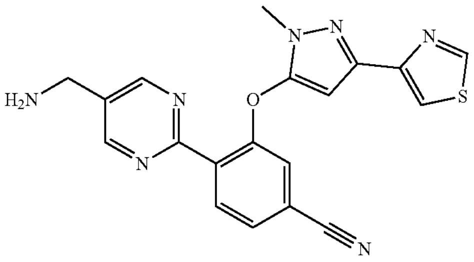 [SMILES: Cn1nc(-c2cscn2)cc1Oc1cc(C#N)ccc1-c1ncc(CN)cn1] | 4-[5-(aminomethyl)pyrimidin-2-yl]-3-[2-methyl-5-(1,3-thiazol-4-yl)pyrazol-3-yl]oxybenzonitrile |

TABLE 1-continued

| Compound number | Structural formula | Compound name |
|---|---|---|
| 949 | 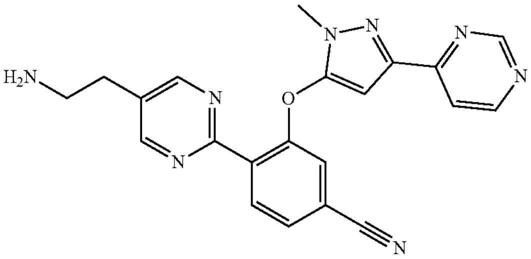 [SMILES: Cn1nc(-c2ccncn2)cc1Oc1cc(C#N)ccc1-c1ncc(CCN)cn1] | 4-[5-(2-aminoethyl)pyrimidin-2-yl]-3-(2-methyl-5-pyrimidin-4-ylpyrazol-3-yl)oxybenzonitrile |
| 950 | 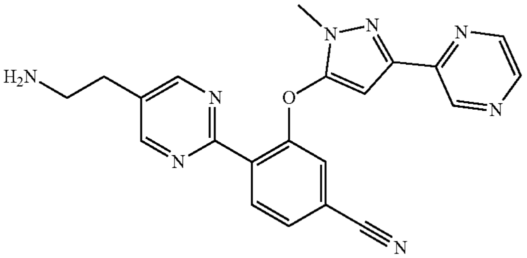 [SMILES: Cn1nc(-c2cnccn2)cc1Oc1cc(C#N)ccc1-c1ncc(CCN)cn1] | 4-[5-(2-aminoethyl)pyrimidin-2-yl]-3-(2-methyl-5-pyrazin-2-ylpyrazol-3-yl)oxybenzonitrile |
| 951 | 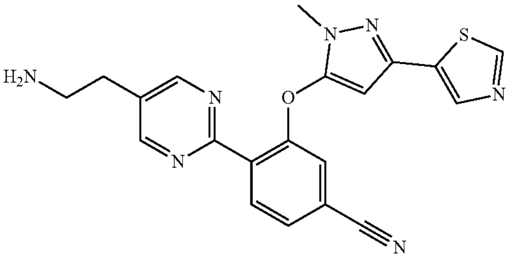 [SMILES: Cn1nc(-c2cncs2)cc1Oc1cc(C#N)ccc1-c1ncc(CCN)cn1] | 4-[5-(2-aminoethyl)pyrimidin-2-yl]-3-[2-methyl-5-(1,3-thiazol-5-yl)pyrazol-3-yl]oxybenzonitrile |
| 952 | 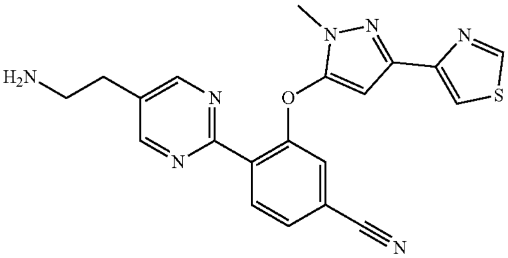 [SMILES: Cn1nc(-c2cscn2)cc1Oc1cc(C#N)ccc1-c1ncc(CCN)cn1] | 4-[5-(2-aminoethyl)pyrimidin-2-yl]-3-[2-methyl-5-(1,3-thiazol-4-yl)pyrazol-3-yl]oxybenzonitrile |
| 953 | 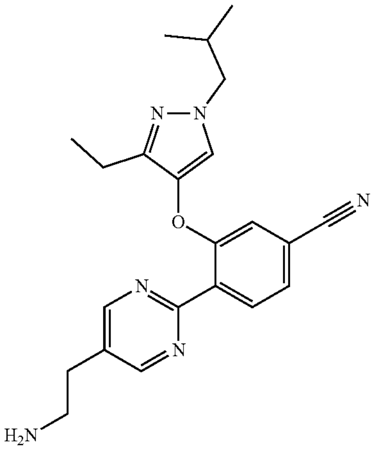 [SMILES: CCc1nn(CC(C)C)cc1Oc1cc(C#N)ccc1-c1ncc(CCN)cn1] | 4-[5-(2-aminoethyl)pyrimidin-2-yl]-3-[3-ethyl-1-(2-methylpropyl)pyrazol-4-yl]oxybenzonitrile |

TABLE 1-continued

| Compound number | Structural formula | Compound name |
|---|---|---|
| 954 | 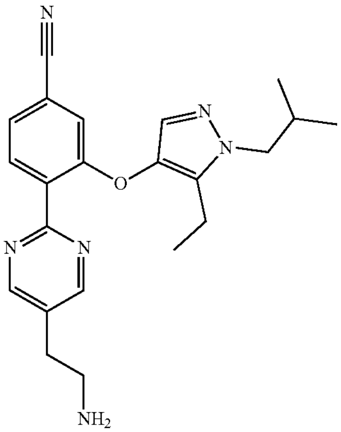 [SMILES: CCc1c(Oc2cc(C#N)ccc2-c2ncc(CCN)cn2)cnn1CC(C)C] | 4-[5-(2-aminoethyl)pyrimidin-2-yl]-3-[5-ethyl-1-(2-methylpropyl)pyrazol-4-yl]oxybenzonitrile |
| 955 | 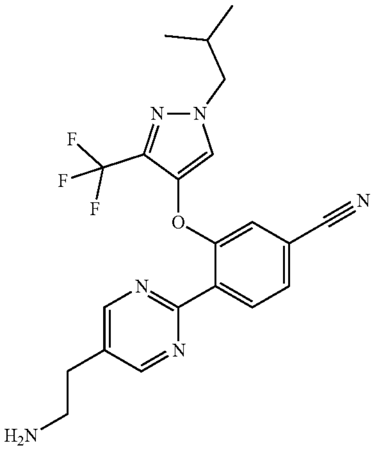 [SMILES: CC(C)Cn1cc(Oc2cc(C#N)ccc2-c2ncc(CCN)cn2)c(C(F)(F)F)n1] | 4-[5-(2-aminoethyl)pyrimidin-2-yl]-3-[1-(2-methylpropyl)-3-(trifluoromethyl)pyrazol-4-yl]oxybenzonitrile |
| 956 | 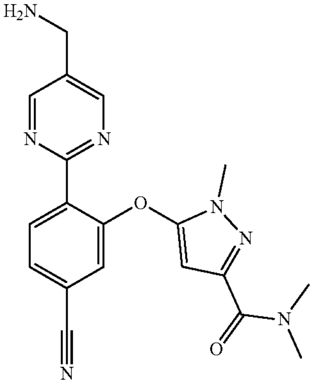 [SMILES: CN(C)C(=O)c1cc(Oc2cc(C#N)ccc2-c2ncc(CN)cn2)n(C)n1] | 5-[2-[5-(aminomethyl)pyrimidin-2-yl]-5-cyanophenoxy]-N,N,1-trimethylpyrazole-3-carboxamide |
| 957 | 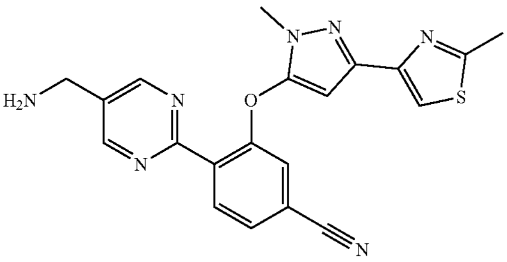 [SMILES: Cc1nc(-c2cc(Oc3cc(C#N)ccc3-c3ncc(CN)cn3)n(C)n2)cs1] | 4-[5-(aminomethyl)pyrimidin-2-yl]-3-[2-methyl-5-(2-methyl-1,3-thiazol-4-yl)pyrazol-3-yl]oxybenzonitrile |

TABLE 1-continued
| Compound number | Structural formula | Compound name |
|---|---|---|
| 958 | 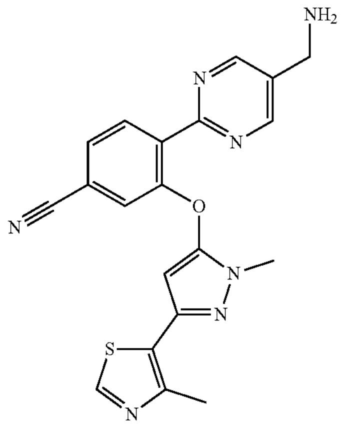 [SMILES: Cc1ncsc1-c1cc(Oc2cc(C#N)ccc2-c2ncc(CN)cn2)n(C)n1] | 4-[5-(aminomethyl)pyrimidin-2-yl]-3-[2-methyl-5-(4-methyl-1,3-thiazol-5-y)pyrazol-3-yl]oxybenzonitrile |
| 959 | 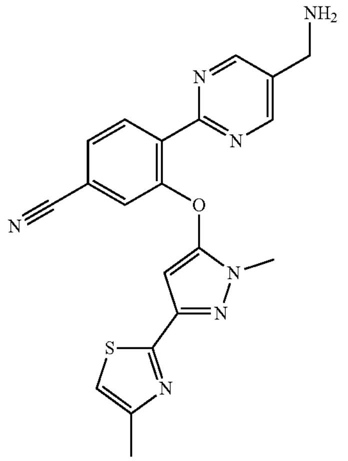 [SMILES: Cc1csc(-c2cc(Oc3cc(C#N)ccc3-c3ncc(CN)cn3)n(C)n2)n1] | 4-[5-(aminomethyl)pyrimidin-2-yl]-3-[2-methyl-5-(4-methyl-1,3-thiazol-2-yl)pyrazol-3-yl]oxybenzonitrile |
| 960 | 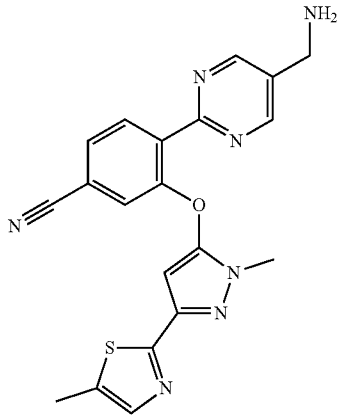 [SMILES: Cc1cnc(-c2cc(Oc3cc(C#N)ccc3-c3ncc(CN)cn3)n(C)n2)s1] | 4-[5-(aminomethyl)pyrimidin-2-yl]-3-[2-methyl-5-(5-methyl-1,3-thiazol-2-yl)pyrazol-3-yl]oxybenzonitrile |

TABLE 1-continued
| Compound number | Structural formula | Compound name |
|---|---|---|
| 961 | 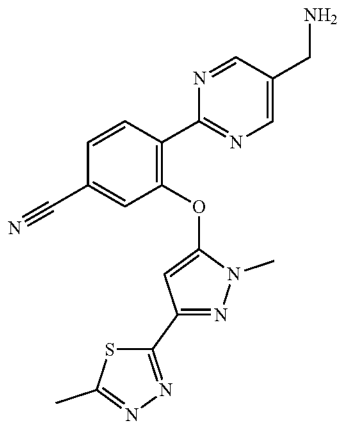 [SMILES: Cc1nnc(-c2cc(Oc3cc(C#N)ccc3-c3ncc(CN)cn3)n(C)n2)s1] | 4-[5-(aminomethyl)pyrimidin-2-yl]-3-[2-methyl-5-(5-methyl-1,3,4-thiadiazol-2-yl)pyrazol-3-yl]oxybenzonitrile |
| 962 | 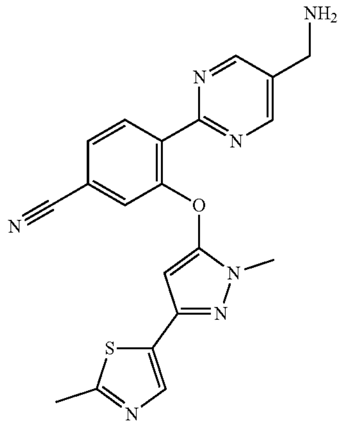 [SMILES: Cc1ncc(-c2cc(Oc3cc(C#N)ccc3-c3ncc(CN)cn3)n(C)n2)s1] | 4-[5-(aminomethyl)pyrimidin-2-yl]-3-[2-methyl-5-(2-methyl-1,3-thiazol-5-yl)pyrazol-3-yl]oxybenzonitrile |
| 963 | 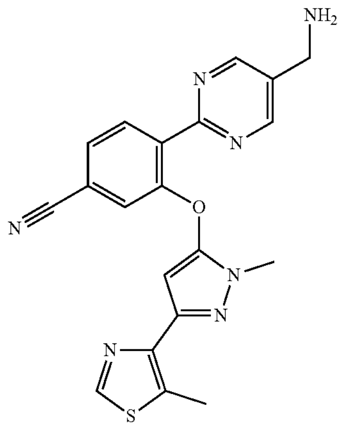 [SMILES: Cc1scnc1-c1cc(Oc2cc(C#N)ccc2-c2ncc(CN)cn2)n(C)n1] | 4-[5-(aminomethyl)pyrimidin-2-yl]-3-[2-methyl-5-(5-methyl-1,3-thiazol-4-yl)pyrazol-3-yl]oxybenzonitrile |

TABLE 1-continued
| Compound number | Structural formula | Compound name |
|---|---|---|
| 964 | 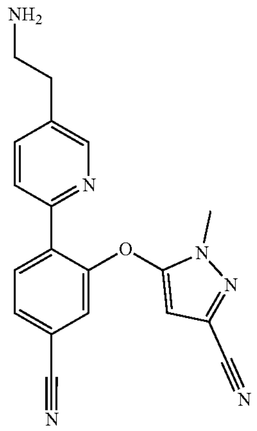 [SMILES: Cn1nc(C#N)cc1Oc1cc(C#N)ccc1-c1ccc(CCN)cn1] | 5-[2-[5-(2-aminoethyl)pyridin-2-yl]-5-cyanophenoxy]-1-methylpyrazole-3-carbonitrile |
| 965 | 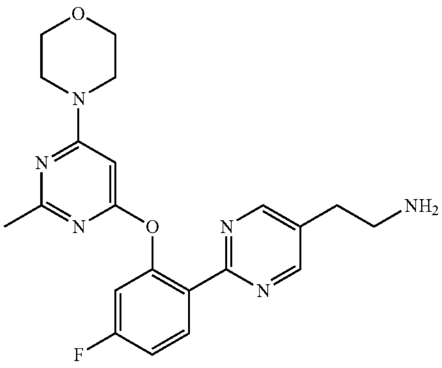 [SMILES: Cc1nc(Oc2cc(F)ccc2-c2ncc(CCN)cn2)cc(N2CCOCC2)n1] | 2-[2-[4-fluoro-2-(2-methyl-6-morpholin-4-ylpyrimidin-4-yl)oxyphenyl]pyrimidin-5-yl]ethanamine |
| 966 | 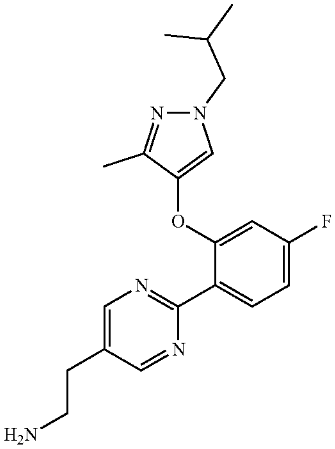 [SMILES: Cc1nn(CC(C)C)cc1Oc1cc(F)ccc1-c1ncc(CCN)cn1] | 2-[2-[4-fluoro-2-[3-methyl-1-(2-methylpropyl)pyrazol-4-yl]oxyphenyl]pyrimidin-5-yl]ethanamine |

TABLE 1-continued
| Compound number | Structural formula | Compound name |
| --- | --- | --- |
| 967 | 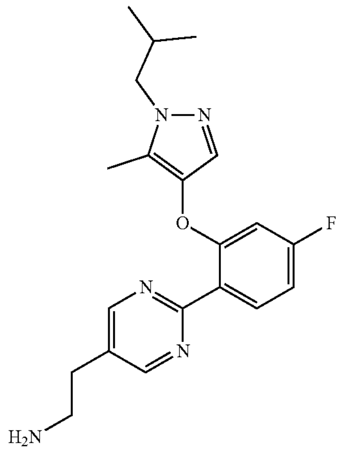 [SMILES: Cc1c(Oc2cc(F)ccc2-c2ncc(CCN)cn2)cnn1CC(C)C] | 2-[2-[4-fluoro-2-[5-methyl-1-(2-methylpropyl)pyrazol-4-yl]oxyphenyl]pyrimidin-5-yl]ethanamine |
| 968 | 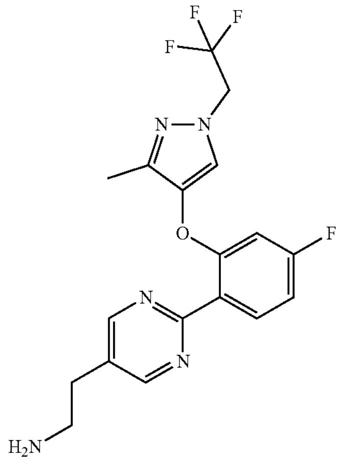 [SMILES: Cc1nn(CC(F)(F)F)cc1Oc1cc(F)ccc1-c1ncc(CCN)cn1] | 2-[2-[4-fluoro-2-[3-methyl-1-(2,2,2-trifluoroethyl)pyrazol-4-yl]oxyphenyl]pyrimidin-5-yl]ethanamine |
| 969 | 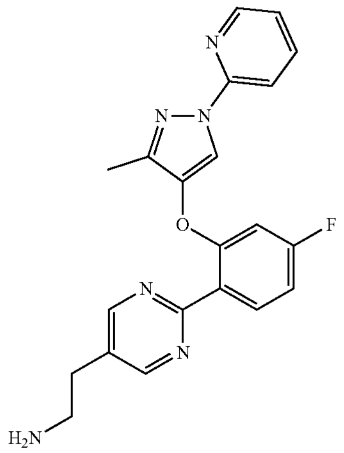 [SMILES: Cc1nn(-c2ccccn2)cc1Oc1cc(F)ccc1-c1ncc(CCN)cn1] | 2-[2-[4-fluoro-2-(3-methyl-1-pyridin-2-ylpyrazol-4-yl)oxyphenyl]pyrimidin-5-yl]ethanamine |

TABLE 1-continued

| Compound number | Structural formula | Compound name |
|---|---|---|
| 970 | 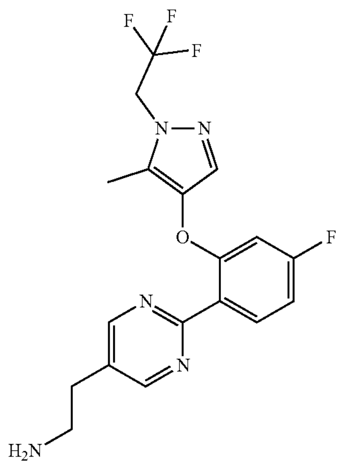 [SMILES: Cc1c(Oc2cc(F)ccc2-c2ncc(CCN)cn2)cnn1CC(F)(F)F] | 2-[2-[4-fluoro-2-[5-methyl-1-(2,2,2-trifluoroethyl)pyrazol-4-yl]oxyphenyl]pyrimidin-5-yl]ethanamine |
| 971 | 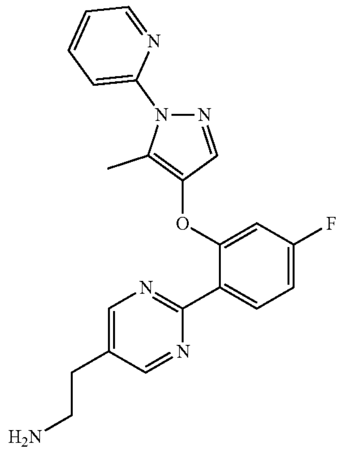 [SMILES: Cc1c(Oc2cc(F)ccc2-c2ncc(CCN)cn2)cnn1-c1ccccn1] | 2-[2-[4-fluoro-2-(5-methyl-1-pyridin-2-ylpyrazol-4-yl)oxyphenyl]pyrimidin-5-yl]ethanamine |
| 972 | 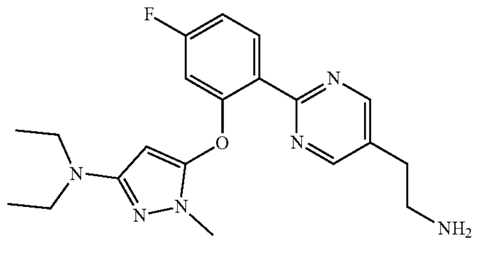 [SMILES: CCN(CC)c1cc(Oc2cc(F)ccc2-c2ncc(CCN)cn2)n(C)n1] | 5-[2-[5-(2-aminoethyl)pyrimidin-2-yl]-5-fluorophenoxy]-N,N-diethyl-1-methylpyrazole-3-amine |
| 973 | 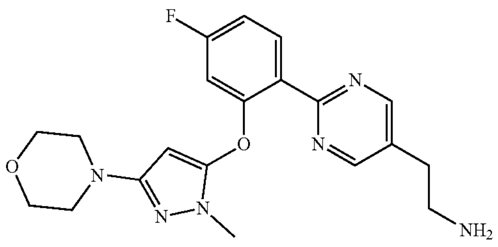 [SMILES: Cn1nc(N2CCOCC2)cc1Oc1cc(F)ccc1-c1ncc(CCN)cn1] | 2-[2-[4-fluoro-2-(2-methyl-5-morpholin-4-ylpyrazol-3-yl)oxyphenyl]pyrimidin-5-yl]ethanamine |

TABLE 1-continued

| Compound number | Structural formula | Compound name |
|---|---|---|
| 974 | 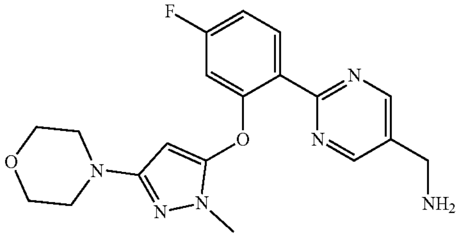 [SMILES: Cn1nc(N2CCOCC2)cc1Oc1cc(F)ccc1-c1ncc(CN)cn1] | [2-[4-fluoro-2-(2-methyl-5-morpholin-4-ylpyrazol-3-yl)oxyphenyl]pyrimidin-5-yl]methanamine |
| 975 | 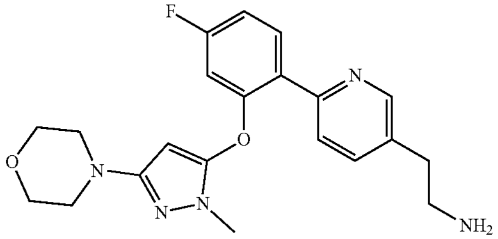 [SMILES: Cn1nc(N2CCOCC2)cc1Oc1cc(F)ccc1-c1ccc(CCN)cn1] | 2-[6-[4-fluoro-2-(2-methyl-5-morpholin-4-ylpyrazol-3-yl)oxyphenyl]pyridin-3-yl]ethanamine |
| 976 | 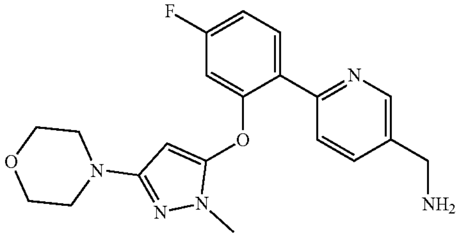 [SMILES: Cn1nc(N2CCOCC2)cc1Oc1cc(F)ccc1-c1ccc(CN)cn1] | [6-[4-fluoro-2-(2-methyl-5-morpholin-4-ylpyrazo1-3-yl)oxyphenyl]pyridin-3-yl]methanamine |
| 977 | 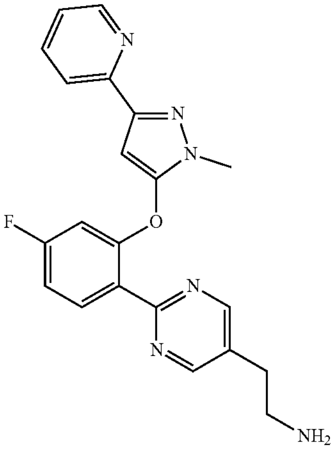 [SMILES: Cn1nc(-c2ccccn2)cc1Oc1cc(F)ccc1-c1ncc(CCN)cn1] | 2-[2-[4-fluoro-2-(2-methyl-5-pyridin-2-ylpyrazol-3-yl)oxyphenyl]pyrimidin-5-yl]ethanamine |

TABLE 1-continued
| Compound number | Structural formula | Compound name |
|---|---|---|
| 978 | 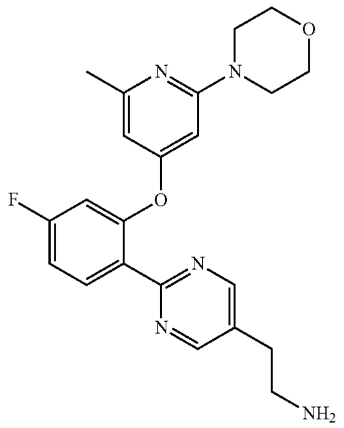 [SMILES: Cc1cc(Oc2cc(F)ccc2-c2ncc(CCN)cn2)cc(N2CCOCC2)n1] | 2-[2-[4-fluoro-2-(2-methyl-6-morpholin-4-ylpyridin-4-yl)oxyphenyl]pyrimidin-5-yl]ethanamine |
| 979 | 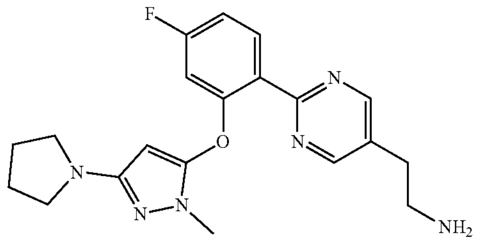 [SMILES: Cn1nc(N2CCCC2)cc1Oc1cc(F)ccc1-c1ncc(CCN)cn1] | 2-[2-[4-fluoro-2-(2-methyl-5-pyrrolidin-1-ylpyrazol-3-yl)oxyphenyl]pyrimidin-5-yl]ethanamine |
| 980 | 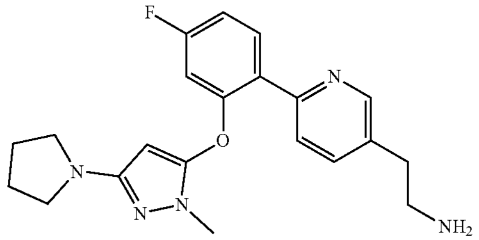 [SMILES: Cn1nc(N2CCCC2)cc1Oc1cc(F)ccc1-c1ccc(CCN)cn1] | 2-[6-[4-fluoro-2-(2-methyl-5-pyrrolidin-1-ylpyrazol-3-yl)oxyphenyl]pyridin-3-yl]ethanamine |
| 981 | 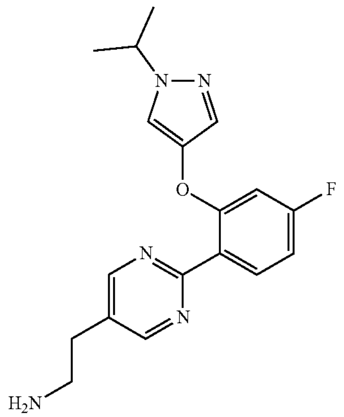 [SMILES: CC(C)n1cc(Oc2cc(F)ccc2-c2ncc(CCN)cn2)cn1] | 2-[2-[4-fluoro-2-(1-propan-2-ylpyrazol-4-yl)oxyphenyl]pyrimidin-5-yl]ethanamine |

TABLE 1-continued
| Compound number | Structural formula | Compound name |
|---|---|---|
| 982 | 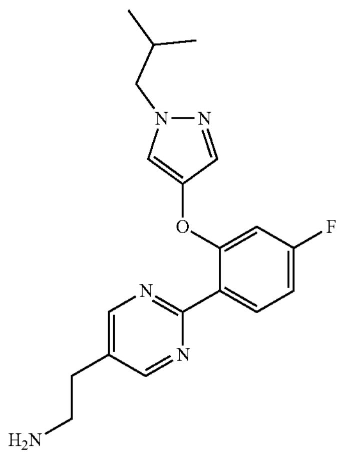 [SMILES: CC(C)Cn1cc(Oc2cc(F)ccc2-c2ncc(CCN)cn2)cn1] | 2-[2-[4-fluoro-2-[1-(2-methylpropyl)pyrazol-4-yl]oxyphenyl]pyrimidin-5-yl]ethanamine |
| 983 | 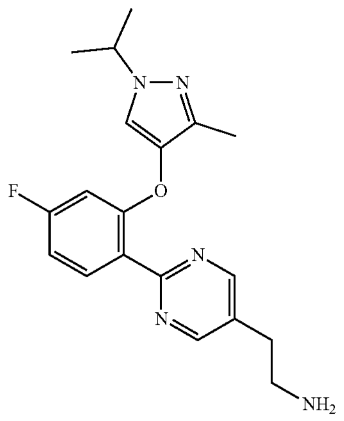 [SMILES: Cc1nn(C(C)C)cc1Oc1cc(F)ccc1-c1ncc(CCN)cn1] | 2-[2-[4-fluoro-2-(3-methyl-1-propan-2-ylpyrazol-4-yl)oxyphenyl]pyrimidin-5-yl]ethanamine |
| 984 | 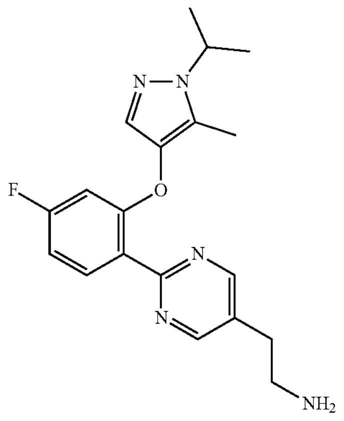 [SMILES: Cc1c(Oc2cc(F)ccc2-c2ncc(CCN)cn2)cnn1C(C)C] | 2-[2-[4-fluoro-2-(5-methyl-1-propan-2-ylpyrazol-4-yl)oxyphenyl]pyrimidin-5-yl]ethanamine |

TABLE 1-continued

| Compound number | Structural formula | Compound name |
|---|---|---|
| 985 | 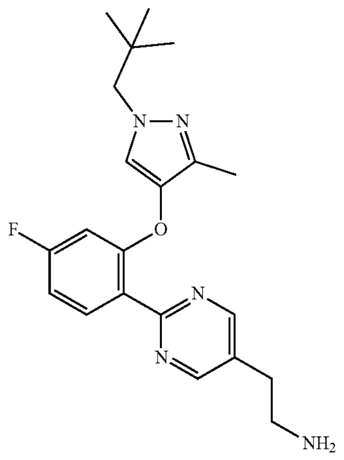 [SMILES: Cc1nn(CC(C)(C)C)cc1Oc1cc(F)ccc1-c1ncc(CCN)cn1] | 2-[2-[2-[1-(2,2-dimethylpropyl)-3-methylpyrazol-4-yl]oxy-4-fluorophenyl]pyrimidin-5-yl]ethanamine |
| 986 | 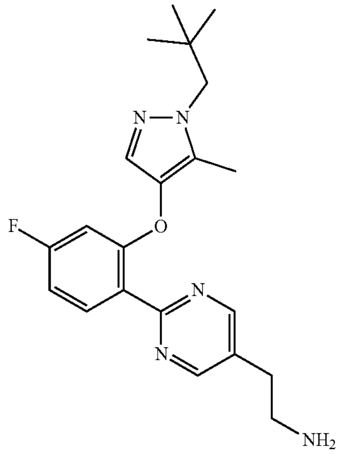 [SMILES: Cc1c(Oc2cc(F)ccc2-c2ncc(CCN)cn2)cnn1CC(C)(C)C] | 2-[2-[2-[1-(2,2-dimethylpropyl)-5-methylpyrazol-4-yl]oxy-4-fluorophenyl]pyrimidin-5-yl]ethanamine |
| 987 | 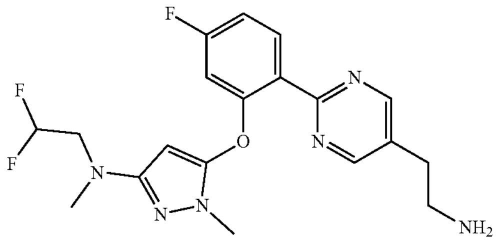 [SMILES: CN(CC(F)F)c1cc(Oc2cc(F)ccc2-c2ncc(CCN)cn2)n(C)n1] | 5-[2-[5-(2-aminoethyl)pyrimidin-2-yl]-5-fluorophenoxy]-N-(2,2-difluoroethyl)-N,1-dimethylpyrazole-3-amine |
| 988 | 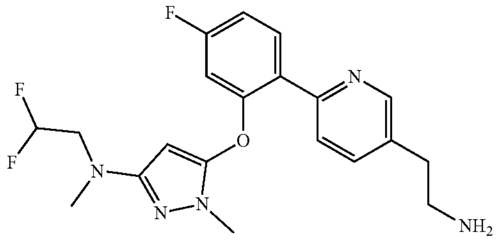 [SMILES: CN(CC(F)F)c1cc(Oc2cc(F)ccc2-c2ccc(CCN)cn2)n(C)n1] | 5-[2-[5-(2-aminoethyl)pyridin-2-yl]-5-fluorophenoxy]-N-(2,2-difluoroethyl)-N,1-dimethylpyrazole-3-amine |

TABLE 1-continued

| Compound number | Structural formula | Compound name |
|---|---|---|
| 989 | 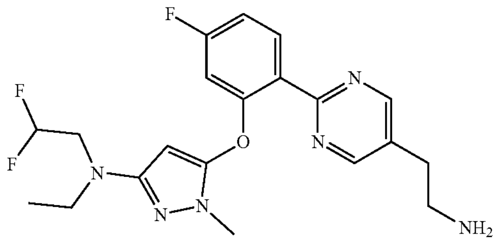 [SMILES: CCN(CC(F)F)c1cc(Oc2cc(F)ccc2-c2ncc(CCN)cn2)n(C)n1] | 5-[2-[5-(2-aminoethyl)pyrimidin-2-yl]-5-fluorophenoxy]-N-(2,2-difluoroethyl)-N-ethyl-1-methylpyrazole-3-amine |
| 990 | 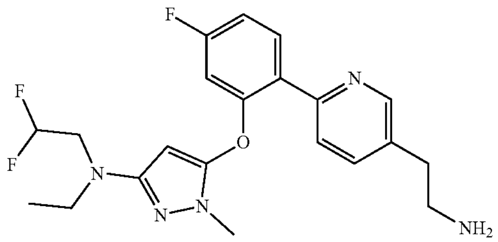 [SMILES: CCN(CC(F)F)c1cc(Oc2cc(F)ccc2-c2ccc(CCN)cn2)n(C)n1] | 5-[2-[5-(2-aminoethyl)pyridin-2-yl]-5-fluorophenoxy]-N-(2,2-difluoroethyl)-N-ethyl-1-methylpyrazole-3-amine |
| 991 | 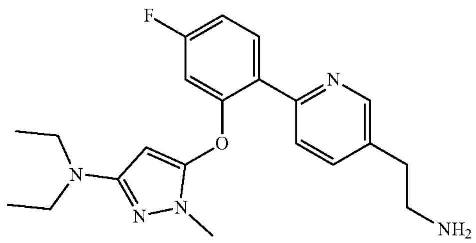 | 5-[2-[5-(2-aminoethyl)pyridin-2-yl]-5-fluorophenoxy]-N,N-diethyl-1-methylpyrazole-3-amine |
| 992 | 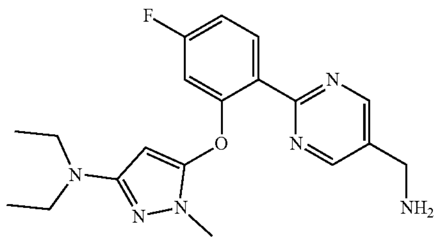 [SMILES: CCN(CC)c1cc(Oc2cc(F)ccc2-c2ncc(CN)cn2)n(C)n1] | 5-[2-[5-(aminomethyl)pyrimidin-2-yl]-5-fluorophenoxy]-N,N-diethyl-1-methylpyrazole-3-amine |
| 993 | 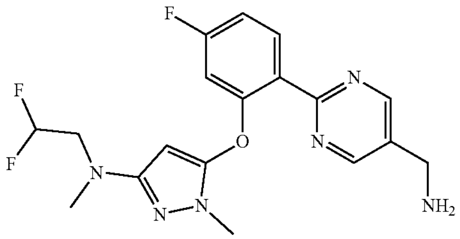 [SMILES: CN(CC(F)F)c1cc(Oc2cc(F)ccc2-c2ncc(CN)cn2)n(C)n1] | 5-[2-[5-(aminomethyl)pyrimidin-2-yl]-5-fluorophenoxy]-N-(2,2-difluoroethyl)-N,1-dimethylpyrazole-3-amine |
| 994 | 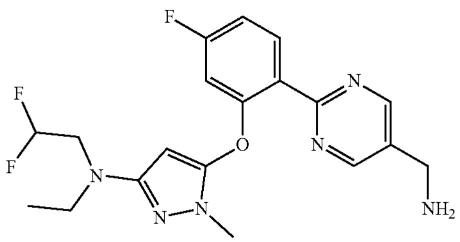 [SMILES: CCN(CC(F)F)c1cc(Oc2cc(F)ccc2-c2ncc(CN)cn2)n(C)n1] | 5-[2-[5-(aminomethyl)pyrimidin-2-yl]-5-fluorophenoxy]-N-(2,2-difluoroethyl)-N-ethyl-1 methylpyrazole-3-amine |

TABLE 1-continued

| Compound number | Structural formula | Compound name |
|---|---|---|
| 995 | 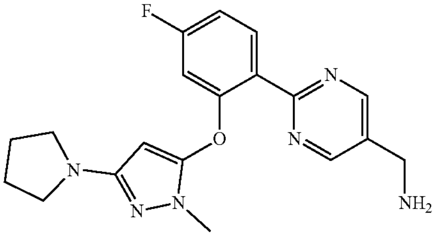 [SMILES: Cn1nc(N2CCCC2)cc1Oc1cc(F)ccc1-c1ncc(CN)cn1] | [2-[4-fluoro-2-(2-methyl-5-pyrrolidin-1-ylpyrazol-3-yl)oxyphenyl]pyrimidin-5-yl]methanamine |
| 996 | 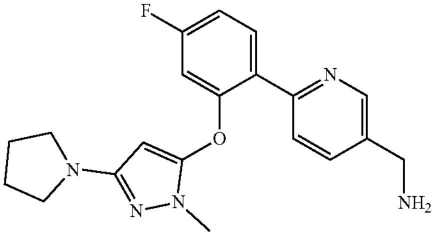 | [6-[4-fluoro-2-(2-methyl-5-pyrrolidin-1-ylpyrazol-3-yl)oxyphenyl]pyridin-3-yl]methanamine |
| 997 | 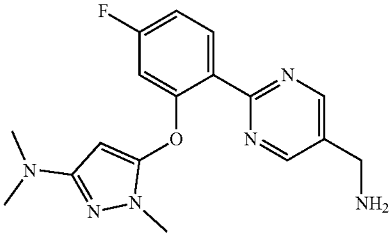 [SMILES: CN(C)c1cc(Oc2cc(F)ccc2-c2ncc(CN)cn2)n(C)n1] | 5-[2-[5-(aminomethyl)pyrimidin-2-yl]-5-fluorophenoxy]-N,N,1 trimethylpyrazole-3-amine |
| 998 | 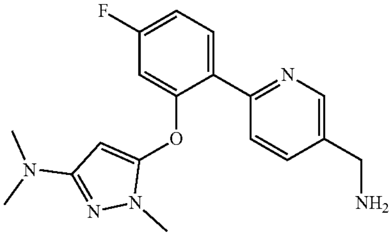 [SMILES: CN(C)c1cc(Oc2cc(F)ccc2-c2ccc(CN)cn2)n(C)n1] | 5-[2-[5-(aminomethyl)pyridin-2-yl]-5-fluorophenoxy]-N,N,1-trimethylpyrazole-3-amine |
| 999 | 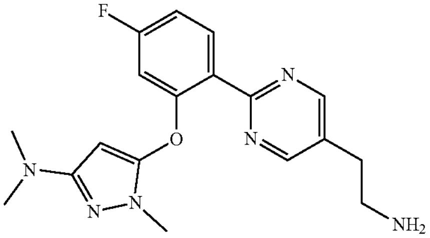 | 5-[2-[5-(2-aminoethyl)pyrimidin-2-yl]-5-fluorophenoxy]-N,N,1-trimethylpyrazole-3-amine |
| 1000 | 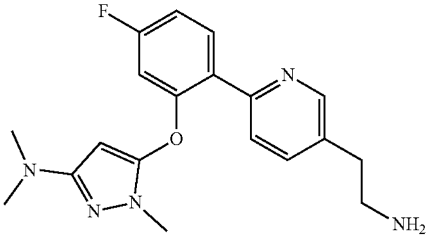 [SMILES: CN(C)c1cc(Oc2cc(F)ccc2-c2ccc(CCN)cn2)n(C)n1] | 5-[2-[5-(2-aminoethyl)pyridin-2-yl]-5-fluorophenoxy]-N,N,1-trimethylpyrazole-3-amine |

TABLE 1-continued

| Compound number | Structural formula | Compound name |
|---|---|---|
| 1001 | 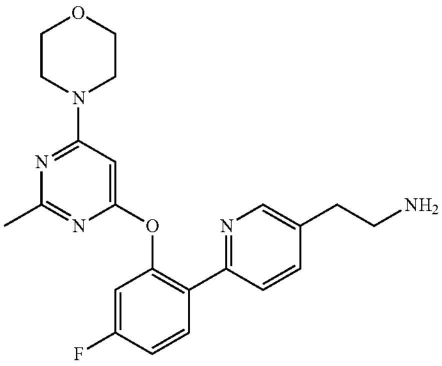 [SMILES: Cc1nc(Oc2cc(F)ccc2-c2ccc(CCN)cn2)cc(N2CCOCC2)n1] | 2-[6-[4-fluoro-2-(2-methyl-6-morpholin-4-ylpyrimidin-4-yl)oxyphenyl]pyridin-3-yl]ethanamine |
| 1002 | 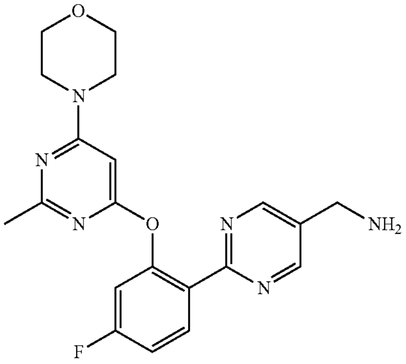 [SMILES: Cc1nc(Oc2cc(F)ccc2-c2ncc(CN)cn2)cc(N2CCOCC2)n1] | [2-[4-fluoro-2-(2-methyl-6-morpholin-4-ylpyrimidin-4-yl)oxyphenyl]pyrimidin-5-yl]methanamine |
| 1003 | 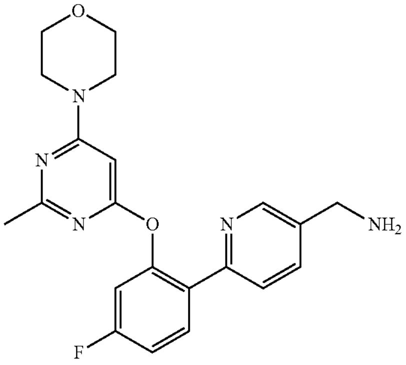 [SMILES: Cc1nc(Oc2cc(F)ccc2-c2ccc(CN)cn2)cc(N2CCOCC2)n1] | [6-[4-fluoro-2-(2-methyl-6-morpholin-4-ylpyrimidin-4-yl)oxyphenyl]pyridin-3-yl]methanamine |
| 1004 | 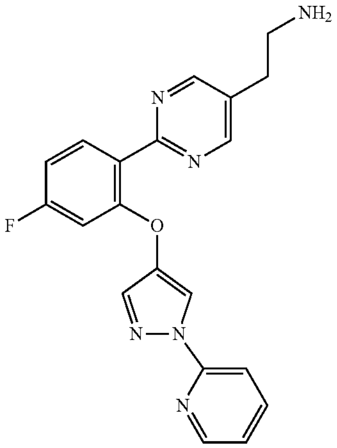 [SMILES: NCCc1cnc(-c2ccc(F)cc2Oc2cnn(-c3ccccn3)c2)nc1] | 2-[2-[4-fluoro-2-(1-pyridin-2-ylpyrazol-4-yl)oxyphenyl]pyrimidin-5-yl]ethanamine |

TABLE 1-continued

| Compound number | Structural formula | Compound name |
|---|---|---|
| 1005 | 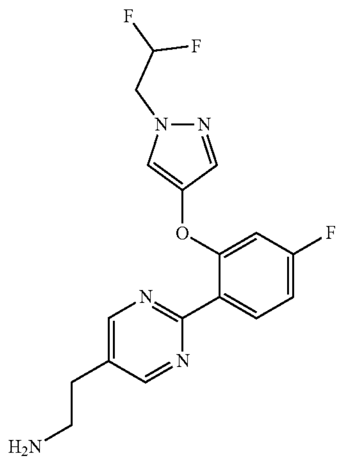 [SMILES: NCCc1cnc(-c2ccc(F)cc2Oc2cnn(CC(F)F)c2)nc1] | 2-[2-[2-[1-(2,2-difluoroethyl)pyrazol-4-yl]oxy-4-fluorophenyl]pyrimidin-5-yl]ethanamine |
| 1006 | 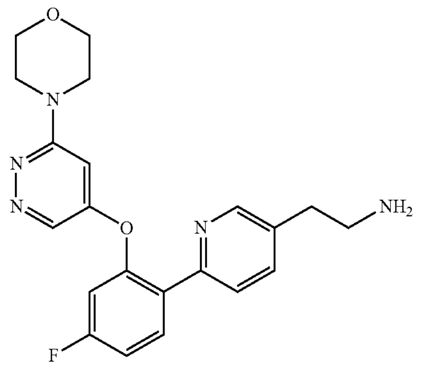 [SMILES: NCCc1ccc(-c2ccc(F)cc2Oc2cnnc(N3CCOCC3)c2)nc1] | 2-[6-[4-fluoro-2-(6-morpholin-4-ylpyridazin-4-yl)oxyphenyl]pyridin-3-yl]ethanamine |
| 1007 | 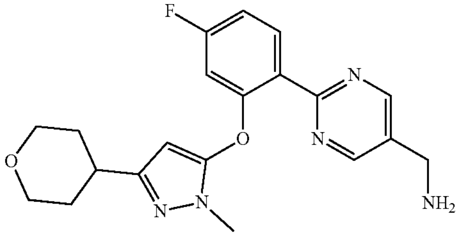 | [2-[4-fluoro-2-[2-methyl-5-(oxan-4-yl)pyrazol-3-yl]oxyphenyl]pyrimidin-5-yl]methanamine |
| 1008 | 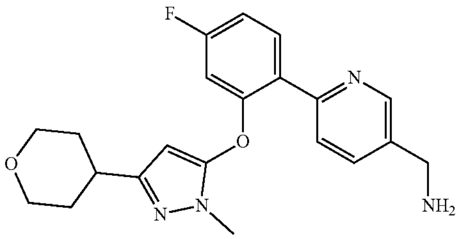 [SMILES: Cn1nc(C2CCOCC2)cc1Oc1cc(F)ccc1-c1ccc(CN)cn1] | [6-[4-fluoro-2-[2-methyl-5-(oxan-4-yl)pyrazol-3-yl]oxyphenyl]pyridin-3-yl]methanamine |
| 1009 | 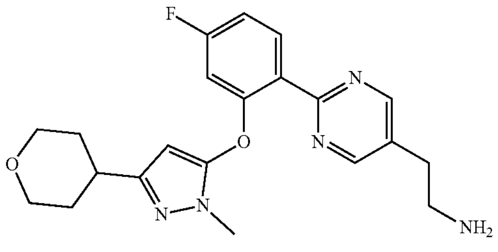 | 2-[2-[4-fluoro-2-[2-methyl-5-(oxan-4-yl)pyrazol-3-yl]oxyphenyl]pyrimidin-5-yl]ethanamine |

TABLE 1-continued

| Compound number | Structural formula | Compound name |
|---|---|---|
| 1010 | 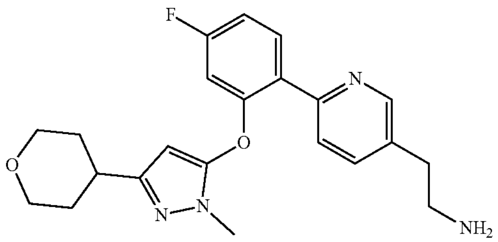 [SMILES: Cn1nc(C2CCOCC2)cc1Oc1cc(F)ccc1-c1ccc(CCN)cn1] | 2-[6-[4-fluoro-2-[2-methyl-5-(oxan-4-yl)pyrazol-3-yl]oxyphenyl]pyridin-3-yl]ethanamine |
| 1011 | 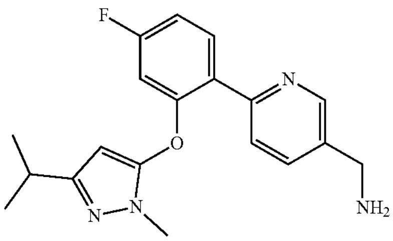 [SMILES: CC(C)c1cc(Oc2cc(F)ccc2-c2ccc(CN)cn2)n(C)n1] | [6-[4-fluoro-2-(2-methyl-5-propan-2-ylpyrazol-3-yl)oxyphenyl]pyridin-3-yl]methanamine |
| 1012 | 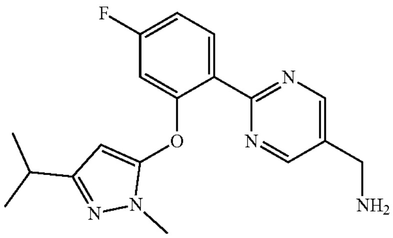 [SMILES: CC(C)c1cc(Oc2cc(F)ccc2-c2ncc(CN)cn2)n(C)n1] | [2-[4-fluoro-2-(2-methyl-5-propan-2-ylpyrazol-3-yl)oxyphenyl]pyrimidin-5-yl]methanamine |
| 1013 | 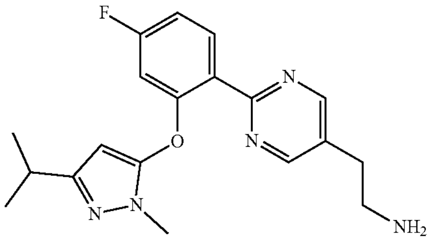 | 2-[2-[4-fluoro-2-(2-methyl-5-propan-2-ylpyrazol-3-yl)oxyphenyl]pyrimidin-5-yl]ethanamine |
| 1014 | 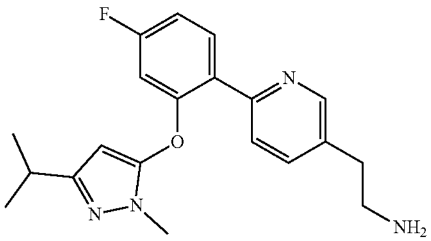 | 2-[6-[4-fluoro-2-(2-methyl-5-propan-2-ylpyrazol-3-yl)oxyphenyl]pyridin-3-yl]ethanamine |
| 1015 | 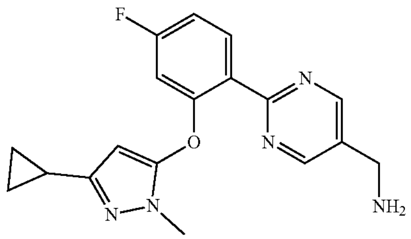 [SMILES: Cn1nc(C2CC2)cc1Oc1cc(F)ccc1-c1ncc(CN)cn1] | [2-[2-(5-cyclopropyl-2-methylpyrazol-3-yl)oxy-4-fluorophenyl]pyrimidin-5-yl]methanamine |

TABLE 1-continued
| Compound number | Structural formula | Compound name |
|---|---|---|
| 1016 | 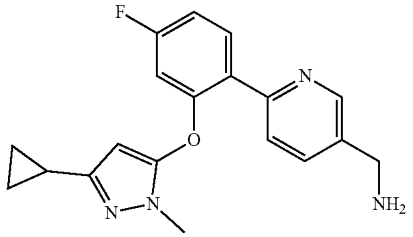 [SMILES: Cn1nc(C2CC2)cc1Oc1cc(F)ccc1-c1ccc(CN)cn1] | [6-[2-(5-cyclopropyl-2-methylpyrazol-3-yl)oxy-4-fluorophenyl]pyridin- 3 -yl]methanamine |
| 1017 | 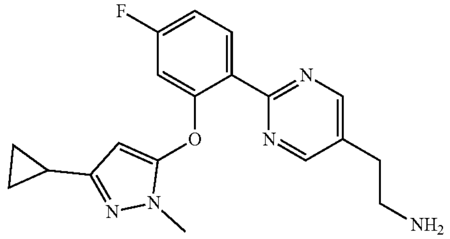 [SMILES: Cn1nc(C2CC2)cc1Oc1cc(F)ccc1-c1ncc(CCN)cn1] | 2-[2-[2-(5-cyclopropyl-2-methylpyrazol-3-yl)oxy-4-fluorophenyl]pyrimidin-5-yl]ethanamine |
| 1018 | 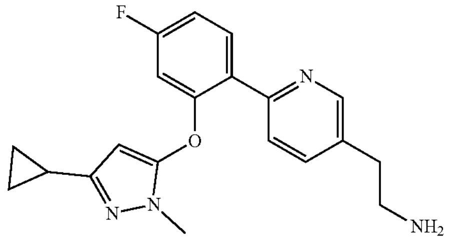 [SMILES: Cn1nc(C2CC2)cc1Oc1cc(F)ccc1-c1ccc(CCN)cn1] | 2-[6-[2-(5-cyclopropyl-2-methylpyrazol-3-yl)oxy-4-fluorophenyl]pyridin-3-yl]ethanamine |
| 1019 | 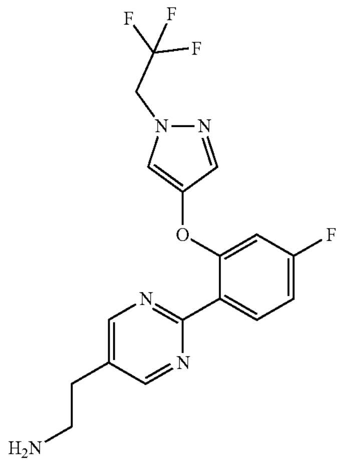 [SMILES: NCCc1cnc(-c2ccc(F)cc2Oc2cnn(CC(F)(F)F)c2)nc1] | 2-[2-[4-fluoro-2-[1-(2,2,2-trifluoroethyl)pyrazol-4-yl]oxyphenyl]pyrimidin-5-yl]ethanamine |

TABLE 1-continued
| Compound number | Structural formula | Compound name |
| --- | --- | --- |
| 1020 | 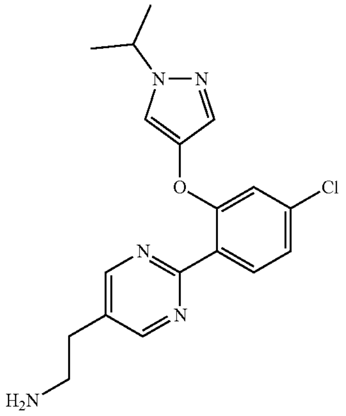 [SMILES: CC(C)n1cc(Oc2cc(Cl)ccc2-c2ncc(CCN)cn2)cn1] | 2-[2-[4-chloro-2-(1-propan-2-ylpyrazol-4-yl)oxyphenyl]pyrimidin-5-yl]ethanamine |
| 1021 | 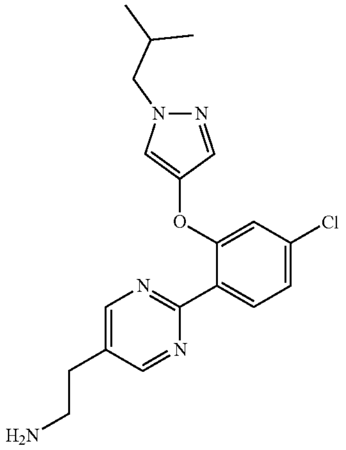 [SMILES: CC(C)Cn1cc(Oc2cc(Cl)ccc2-c2ncc(CCN)cn2)cn1] | 2-[2-[4-chloro-2-[1-(2-methylpropyl)pyrazol-4-yl]oxyphenyl]pyrimidin-5-yl]ethanamine |
| 1022 | 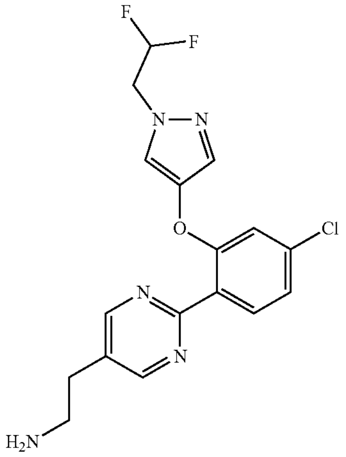 [SMILES: NCCc1cnc(-c2ccc(Cl)cc2Oc2cnn(CC(F)F)c2)nc1] | 2-[2-[4-chloro-2-[1-(2,2-difluoroethyl)pyrazol-4-yl]oxyphenyl]pyrimidin-5-yl]ethanamine |

TABLE 1-continued
| Compound number | Structural formula | Compound name |
| --- | --- | --- |
| 1023 | 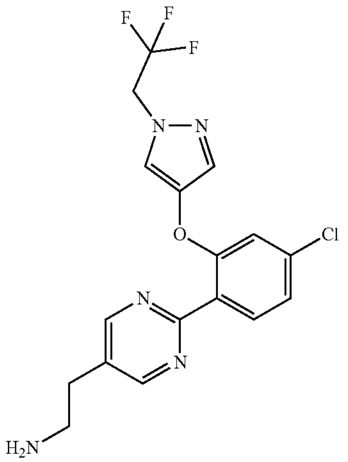 [SMILES: NCCc1cnc(-c2ccc(Cl)cc2Oc2cnn(CC(F)(F)F)c2)nc1] | 2-[2-[4-chloro-2-[1-(2,2,2-trifluoroethyl)pyrazol-4-yl]oxyphenyl]pyrimidin-5-yl]ethanamine |
| 1024 | 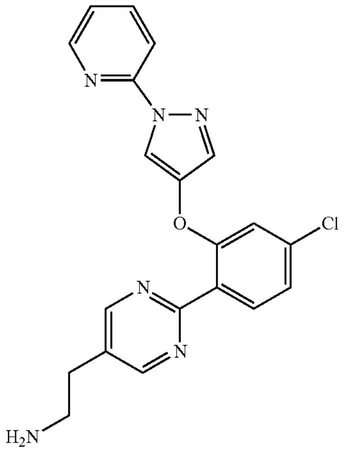 [SMILES: NCCc1cnc(-c2ccc(Cl)cc2Oc2cnn(-c3ccccn3)c2)nc1] | 2-[2-[4-chloro-2-(1-pyridin-2-ylpyrazol-4-yl)oxyphenyl]pyrimidin-5-yl]ethanamine |
| 1025 | 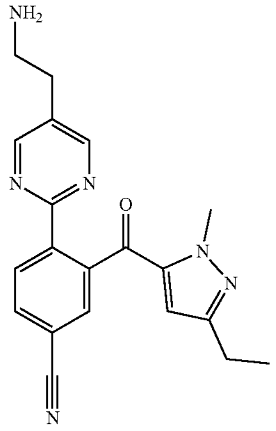 [SMILES: CCc1cc(C(=O)c2cc(C#N)ccc2-c2ncc(CCN)cn2)n(C)n1] | 4-[5-(2-aminoethyl)pyrimidin-2-yl]-3-(5-ethyl-2-methylpyrazole-3-carbonyl)benzonitrile |

TABLE 1-continued

| Compound number | Structural formula | Compound name |
|---|---|---|
| 1026 | 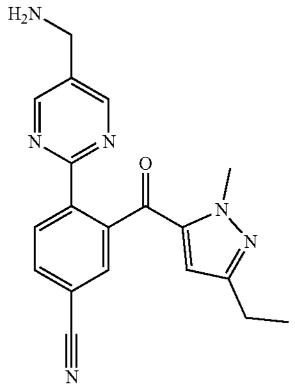 [SMILES: CCc1cc(C(=O)c2cc(C#N)ccc2-c2ncc(CN)cn2)n(C)n1] | 4-[5-(aminomethyl)pyrimidin-2-yl]-3-(5-ethyl-2-methylpyrazole-3-carbonyl)benzonitrile |
| 1027 | 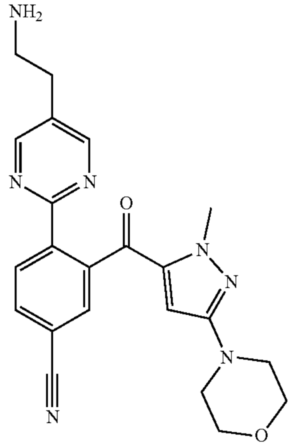 [SMILES: Cn1nc(N2CCOCC2)cc1C(=O)c1cc(C#N)ccc1-c1ncc(CCN)cn1] | 4-[5-(2-aminoethyl)pyrimidin-2-yl]-3-(2-methyl-5-morpholin-4-ylpyrazole-3-carbonyl)benzonitrile |
| 1028 | 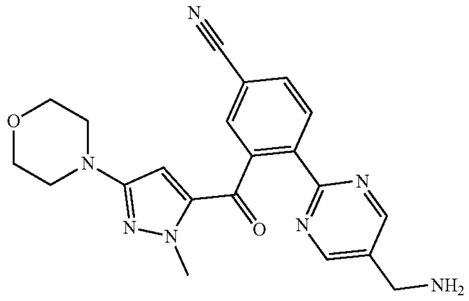 [SMILES: Cn1nc(N2CCOCC2)cc1C(=O)c1cc(C#N)ccc1-c1ncc(CN)cn1] | 4-[5-(aminomethyl)pyrimidin-2-yl]-3-(2-methyl-5-morpholin-4-ylpyrazole-3-carbonyl)benzonitrile |
| 1029 | 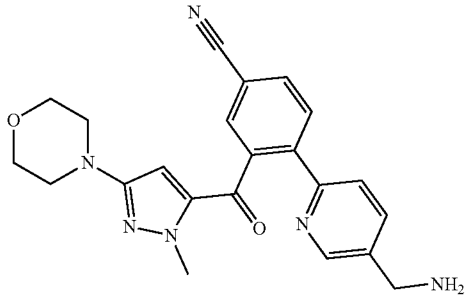 [SMILES: Cn1nc(N2CCOCC2)cc1C(=O)c1cc(C#N)ccc1-c1ccc(CN)cn1] | 4-[5-(aminomethyl)pyridin-2-yl]-3-(2-methyl-5-morpholin-4-ylpyrazole-3-carbonyl)benzonitrile |

TABLE 1-continued
| Compound number | Structural formula | Compound name |
| --- | --- | --- |
| 1030 | 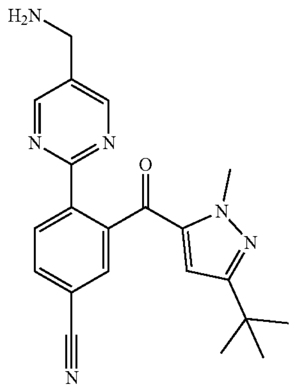 [SMILES: Cn1nc(C(C)(C)C)cc1C(=O)c1cc(C#N)ccc1-c1ncc(CN)cn1] | 4-[5-(aminomethyl)pyrimidin-2-yl]-3-(5-tert-butyl-2-methylpyrazole-3-carbonyl)benzonitrile |
| 1031 | 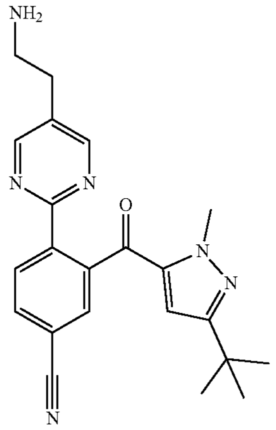 [SMILES: Cn1nc(C(C)(C)C)cc1C(=O)c1cc(C#N)ccc1-c1ncc(CCN)cn1] | 4-[5-(2-aminoethyl)pyrimidin-2-yl]-3-(5-tert-butyl-2-methylpyrazole-3-carbonyl)benzonitrile |
| 1032 | 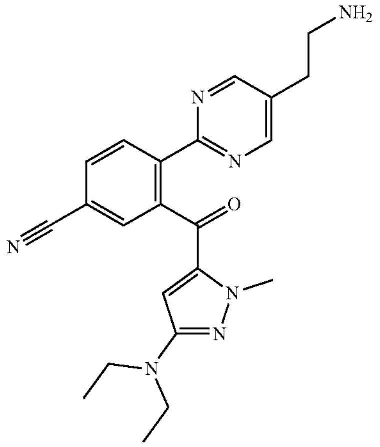 [SMILES: CCN(CC)c1cc(C(=O)c2cc(C#N)ccc2-c2ncc(CCN)cn2)n(C)n1] | 4-[5-(2-aminoethyl)pyrimidin-2-yl]-3-[5-(diethylamino)-2-methylpyrazole-3-carbonyl]benzonitrile |

TABLE 1-continued
| Compound number | Structural formula | Compound name |
| --- | --- | --- |
| 1033 | 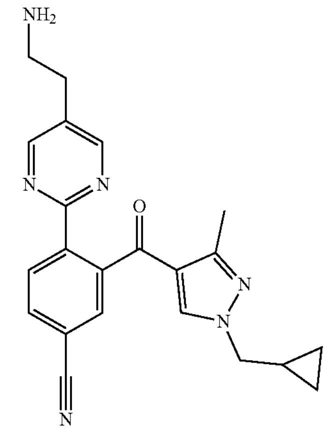 [SMILES: Cc1nn(CC2CC2)cc1C(=O)c1cc(C#N)ccc1-c1ncc(CCN)cn1] | 4-[5-(2-aminoethyl)pyrimidin-2-yl]-3-[1-(cyclopropylmethyl)-3-methylpyrazole-4-carbonyl]benzonitrile |
| 1034 | 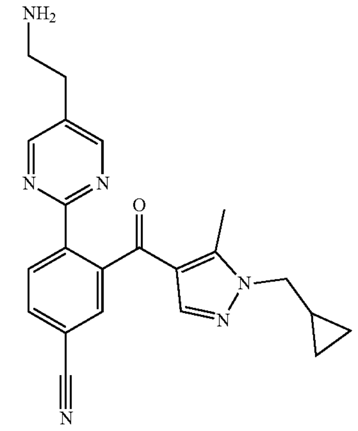 [SMILES: Cc1c(C(=O)c2cc(C#N)ccc2-c2ncc(CCN)cn2)cnn1CC1CC1] | 4-[5-(2-aminoethyl)pyrimidin-2-yl]-3-[1-(cyclopropylmethyl)-5-methylpyrazole-4-carbonyl]benzonitrile |
| 1035 | 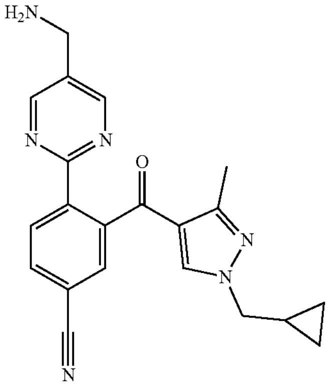 [SMILES: Cc1nn(CC2CC2)cc1C(=O)c1cc(C#N)ccc1-c1ncc(CN)cn1] | 4-[5-(aminomethyl)pyrimidin-2-yl]-3-[1-(cyclopropylmethyl)-3-methylpyrazole-4-carbonyl]benzonitrile |

TABLE 1-continued
| Compound number | Structural formula | Compound name |
|---|---|---|
| 1036 | 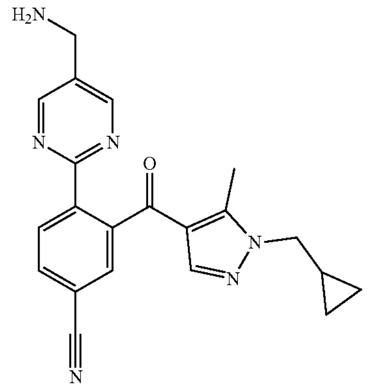 [SMILES: Cc1c(C(=O)c2cc(C#N)ccc2-c2ncc(CN)cn2)cnn1CC1CC1] | 4-[5-(aminomethyl)pyrimidin-2-yl]-3-[1-(cyclopropylmethyl)-5-methylpyrazole-4-carbonyl]benzonitrile |
| 1037 | 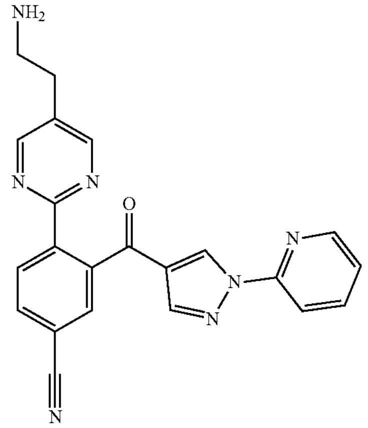 [SMILES: N#Cc1ccc(-c2ncc(CCN)cn2)c(C(=O)c2cnn(-c3ccccn3)c2)c1] | 4-[5-(2-aminoethyl)pyrimidin-2-yl]-3-(1-pyridin-2-ylpyrazole-4-carbonyl)benzonitrile |
| 1038 | 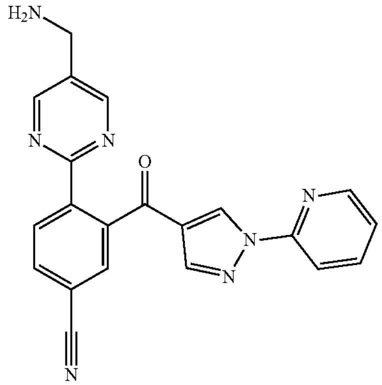 [SMILES: N#Cc1ccc(-c2ncc(CN)cn2)c(C(=O)c2cnn(-c3ccccn3)c2)c1] | 4-[5-(aminomethyl)pyrimidin-2-yl]-3-(1-pyridin-2-ylpyrazole-4-carbonyl)benzonitrile |

TABLE 1-continued
| Compound number | Structural formula | Compound name |
|---|---|---|
| 1039 | 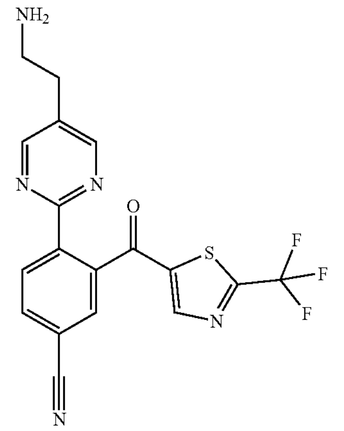 [SMILES: N#Cc1ccc(-c2ncc(CCN)cn2)c(C(=O)c2cnc(C(F)(F)F)s2)c1] | 4-[5-(2-aminoethyl)pyrimidin-2-yl]-3-[2-(trifluoromethyl)-1,3-thiazole-5-carbonyl]benzonitrile |
| 1040 | 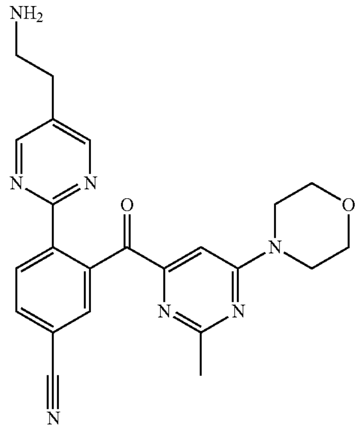 [SMILES: Cc1nc(C(=O)c2cc(C#N)ccc2-c2ncc(CCN)cn2)cc(N2CCOCC2)n1] | 4-[5-(2-aminoethyl)pyrimidin-2-yl]-3-(2-methyl-6-morpholin-4-ylpyrimidine-4-carbonyl)benzonitrile |
| 1041 | 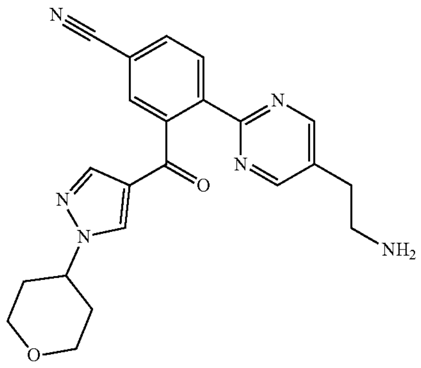 [SMILES: N#Cc1ccc(-c2ncc(CCN)cn2)c(C(=O)c2cnn(C3CCOCC3)c2)c1] | 4-[5-(2-aminoethyl)pyrimidin-2-yl]-3-[1-(oxan-4-yl)pyrazole-4-carbonyl]benzonitrile |

TABLE 1-continued
| Compound number | Structural formula | Compound name |
|---|---|---|
| 1042 | 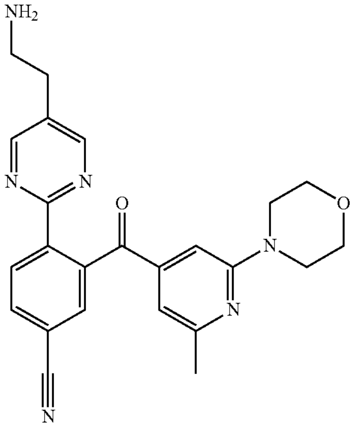 [SMILES: Cc1cc(C(=O)c2cc(C#N)ccc2-c2ncc(CCN)cn2)cc(N2CCOCC2)n1] | 4-[5-(2-aminoethyl)pyrimidin-2-yl]-3-(2-methyl-6-morpholin-4-ylpyridine-4-carbonyl)benzonitrile |
| 1043 | 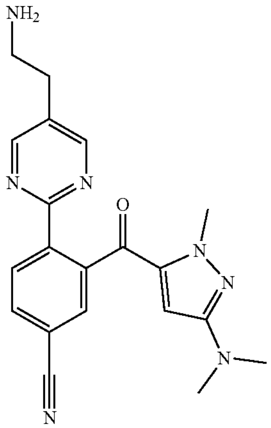 [SMILES: CN(C)c1cc(C(=O)c2cc(C#N)ccc2-c2ncc(CCN)cn2)n(C)n1] | 4-[5-(2-aminoethyl)pyrimidin-2-yl]-3-[5-(dimethylamino)-2-methylpyrazole-3-carbonyl]benzonitrile |
| 1044 | 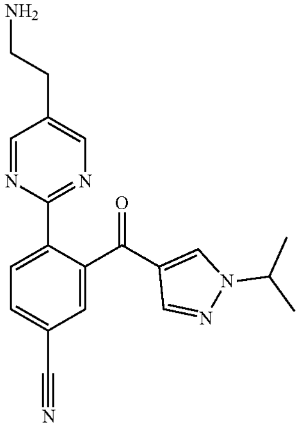 [SMILES: CC(C)n1cc(C(=O)c2cc(C#N)ccc2-c2ncc(CCN)cn2)cn1] | 4-[5-(2-aminoethyl)pyrimidin-2-yl]-3-(1-propan-2-ylpyrazole-4-carbonyl)benzonitrile |

TABLE 1-continued
| Compound number | Structural formula | Compound name |
|---|---|---|
| 1045 | 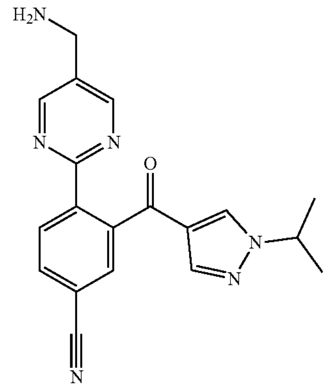 [SMILES: CC(C)n1cc(C(=O)c2cc(C#N)ccc2-c2ncc(CN)cn2)cn1] | 4-[5-(aminomethyl)pyrimidin-2-yl]-3-(1-propan-2-ylpyrazole-4-carbonyl)benzonitrile |
| 1046 | 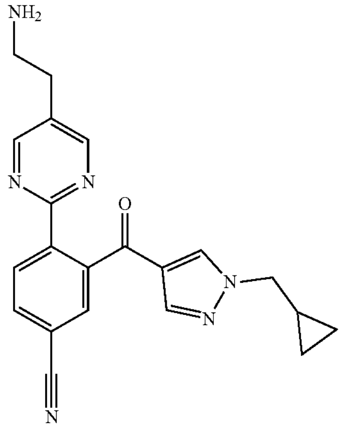 [SMILES: N#Cc1ccc(-c2ncc(CCN)cn2)c(C(=O)c2cnn(CC3CC3)c2)c1] | 4-[5-(2-aminoethyl)pyrimidin-2-yl]-3-[1-(cyclopropylmethyl)pyrazole-4-carbonyl]benzonitrile |
| 1047 | 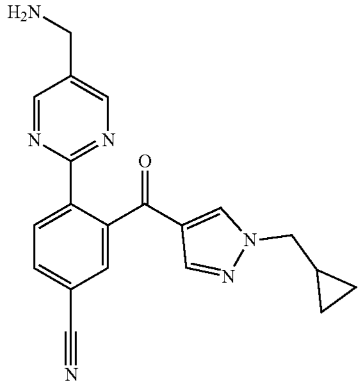 [SMILES: N#Cc1ccc(-c2ncc(CN)cn2)c(C(=O)c2cnn(CC3CC3)c2)c1] | 4-[5-(aminomethyl)pyrimidin-2-yl]-3-[1-(cyclopropylmethyl)pyrazole-4-carbonyl]benzonitrile |

TABLE 1-continued

| Compound number | Structural formula | Compound name |
|---|---|---|
| 1048 | 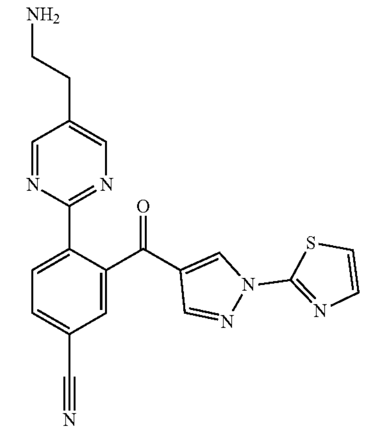 [SMILES: N#Cc1ccc(-c2ncc(CCN)cn2)c(C(=O)c2cnn(-c3nccs3)c2)c1] | 4-[5-(2-aminoethyl)pyrimidin-2-yl]-3-[1-(1,3-thiazol-2-yl)pyrazole-4-carbonyl]benzonitrile |
| 1049 | 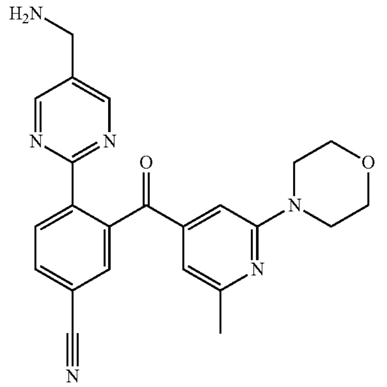 [SMILES: Cc1cc(C(=O)c2cc(C#N)ccc2-c2ncc(CN)cn2)cc(N2CCOCC2)n1] | 4-[5-(aminomethyl)pyrimidin-2-yl]-3-(2-methyl-6-morpholin-4-ylpyridine-4-carbonyl)benzonitrile |
| 1050 | 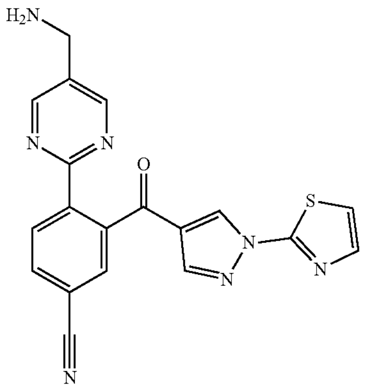 [SMILES: N#Cc1ccc(-c2ncc(CN)cn2)c(C(=O)c2cnn(-c3nccs3)c2)c1] | 4-[5-(aminomethyl)pyrimidin-2-yl]-3-[1-(1,3-thiazol-2-yl)pyrazole-4-carbonyl]benzonitrile |
| 1051 | 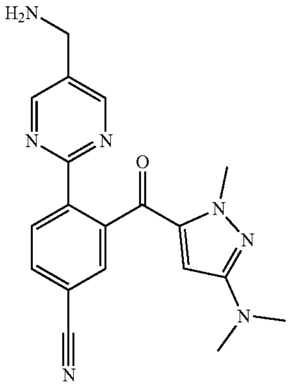 [SMILES: CN(C)c1cc(C(=O)c2cc(C#N)ccc2-c2ncc(CN)cn2)n(C)n1] | 4-[5-(aminomethyl)pyrimidin-2-yl]-3-[5-(dimethylamino)-2-methylpyrazole-3-carbonyl]benzonitrile |

TABLE 1-continued
| Compound number | Structural formula | Compound name |
| --- | --- | --- |
| 1052 | 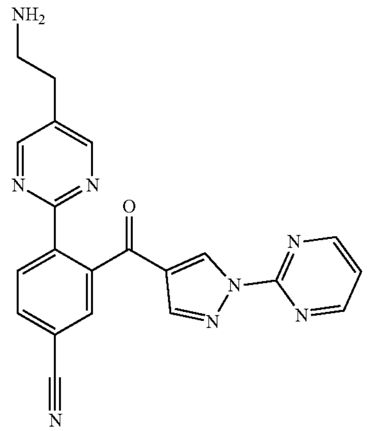 [SMILES: N#Cc1ccc(-c2ncc(CCN)cn2)c(C(=O)c2cnn(-c3ncccn3)c2)c1] | 4-[5-(2-aminoethyl)pyrimidin-2-yl]-3-(1-pyrimidin-2-ylpyrazole-4-carbonyl)benzonitrile |
| 1053 | 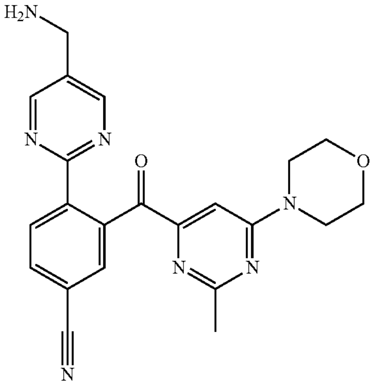 [SMILES: Cc1nc(C(=O)c2cc(C#N)ccc2-c2ncc(CN)cn2)cc(N2CCOCC2)n1] | 4-[5-(aminomethyl)pyrimidin-2-yl]-3-(2-methyl-6-morpholin-4-ylpyrimidine-4-carbonyl)benzonitrile |
| 1054 | 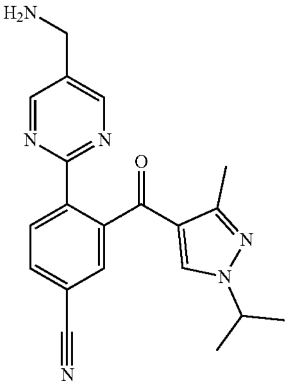 [SMILES: Cc1nn(C(C)C)cc1C(=O)c1cc(C#N)ccc1-c1ncc(CN)cn1] | 4-[5-(aminomethyl)pyrimidin-2-yl]-3-(3-methyl-1-propan-2-ylpyrazole-4-carbonyl)benzonitrile |

TABLE 1-continued
| Compound number | Structural formula | Compound name |
|---|---|---|
| 1055 | 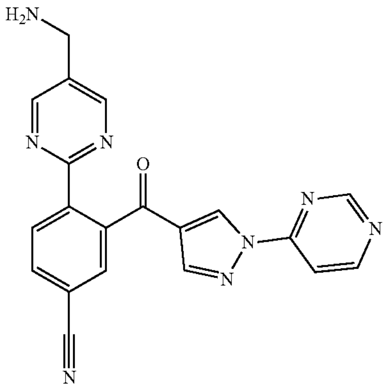 [SMILES: N#Cc1ccc(-c2ncc(CN)cn2)c(C(=O)c2cnn(-c3ccncn3)c2)c1] | 4-[5-(aminomethyl)pyrimidin-2-yl]-3-(1-pyrimidin-4-ylpyrazole-4-carbonyl)benzonitrile |
| 1056 | 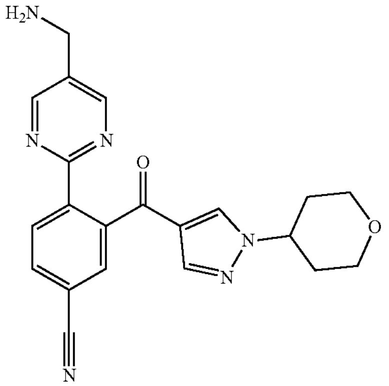 [SMILES: N#Cc1ccc(-c2ncc(CN)cn2)c(C(=O)c2cnn(C3CCOCC3)c2)c1] | 4-[5-(aminomethyl)pyrimidin-2-yl]-3-[1-(oxan-4-yl)pyrazole-4-carbonyl]benzonitrile |
| 1057 | 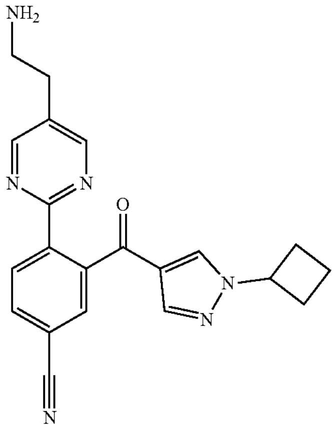 [SMILES: N#Cc1ccc(-c2ncc(CCN)cn2)c(C(=O)c2cnn(C3CCC3)c2)c1] | 4-[5-(2-aminoethyl)pyrimidin-2-yl]-3-(1-cyclobutylpyrazole-4-carbonyl)benzonitrile |
| 1058 | 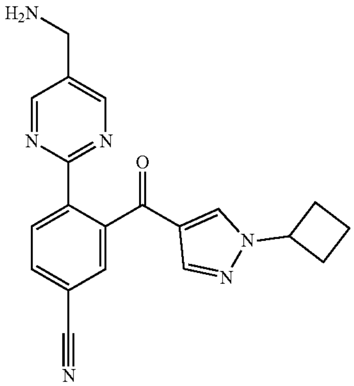 [SMILES: N#Cc1ccc(-c2ncc(CN)cn2)c(C(=O)c2cnn(C3CCC3)c2)c1] | 4-[5-(aminomethyl)pyrimidin-2-yl]-3-(1-cyclobutylpyrazole-4-carbonyl)benzonitrile |

TABLE 1-continued
| Compound number | Structural formula | Compound name |
|---|---|---|
| 1059 | 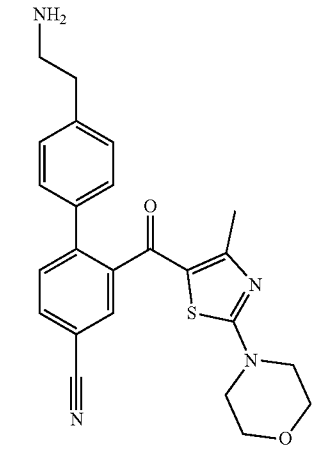 [SMILES: Cc1nc(N2CCOCC2)sc1C(=O)c1cc(C#N)ccc1-c1ccc(CCN)cc1] | 4-[4-(2-aminoethyl)phenyl]-3-(4-methyl-2-morpholin-4-yl-1,3-thiazole-5-carbonyl)benzonitrile |
| 1060 | 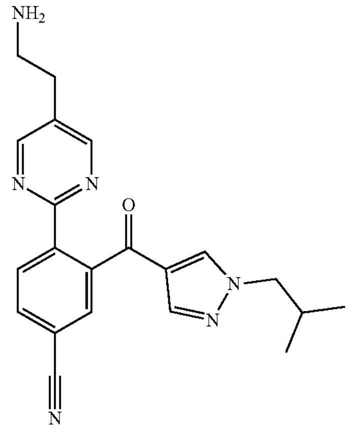 [SMILES: CC(C)Cn1cc(C(=O)c2cc(C#N)ccc2-c2ncc(CCN)cn2)cn1] | 4-[5-(2-aminoethyl)pyrimidin-2-yl]-3-[1-(2-methylpropyl)pyrazole-4-carbonyl]benzonitrile |
| 1061 | 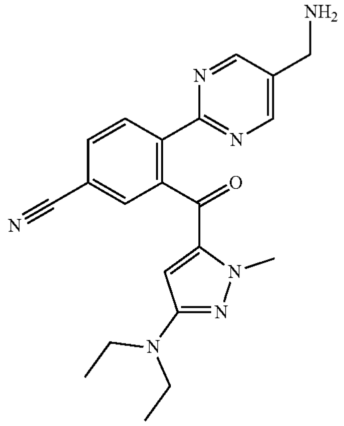 [SMILES: CCN(CC)c1cc(C(=O)c2cc(C#N)ccc2-c2ncc(CN)cn2)n(C)n1] | 4-[5-(aminomethyl)pyrimidin-2-yl]-3-[5-(diethylamino)-2-methylpyrazole-3-carbonyl]benzonitrile |

TABLE 1-continued
| Compound number | Structural formula | Compound name |
|---|---|---|
| 1062 | 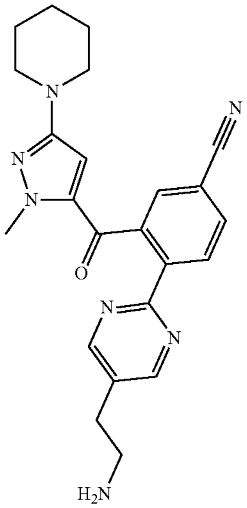 [SMILES: Cn1nc(N2CCCCC2)cc1C(=O)c1cc(C#N)ccc1-c1ncc(CCN)cn1] | 4-[5-(2-aminoethyl)pyrimidin-2-yl]-3-(2-methyl-5-piperidin-1-ylpyrazole-3-carbonyl)benzonitrile |
| 1063 | 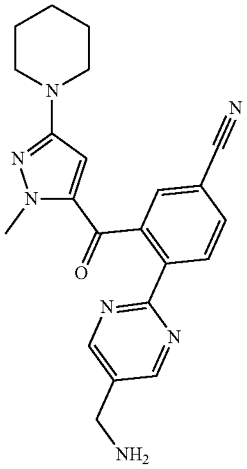 [SMILES: Cn1nc(N2CCCCC2)cc1C(=O)c1cc(C#N)ccc1-c1ncc(CN)cn1] | 4-[5-(aminomethyl)pyrimidin-2-yl]-3-(2-methyl-5-piperidin-1-ylpyrazole-3-carbonyl)benzonitrile |
| 1064 | 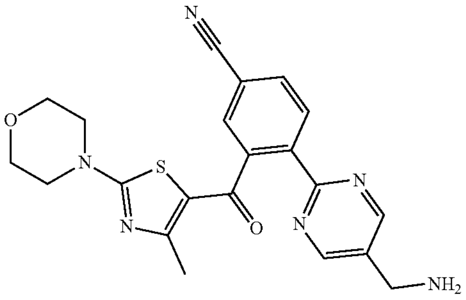 [SMILES: Cc1nc(N2CCOCC2)sc1C(=O)c1cc(C#N)ccc1-c1ncc(CN)cn1] | 4-[5-(aminomethyl)pyrimidin-2-yl]-3-(4-methyl-2-morpholin-4-yl-1,3-thiazole-5-carbonyl)benzonitrile |

TABLE 1-continued

| Compound number | Structural formula | Compound name |
|---|---|---|
| 1065 | 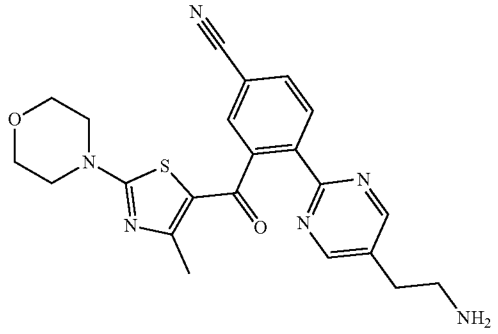 [SMILES: Cc1nc(N2CCOCC2)sc1C(=O)c1cc(C#N)ccc1-c1ncc(CCN)cn1] | 4-[5-(2-aminoethyl)pyrimidin-2-yl]-3-(4-methyl-2-morpholin-4-yl-1,3-thiazole-5-carbonyl)benzonitrile |
| 1066 | 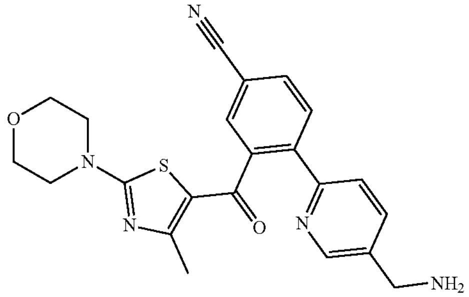 [SMILES: Cc1nc(N2CCOCC2)sc1C(=O)c1cc(C#N)ccc1-c1ccc(CN)cn1] | 4-[5-(aminomethyl)pyridin-2-yl]-3-(4-methyl-2-morpholin-4-yl-1,3-thiazole-5-carbonyl)benzonitrile |
| 1067 | 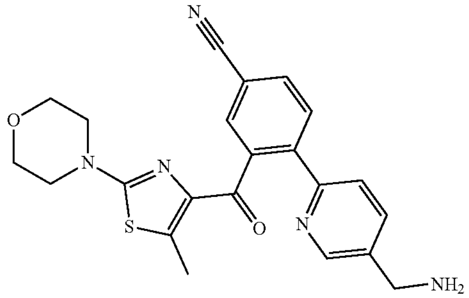 [SMILES: Cc1sc(N2CCOCC2)nc1C(=O)c1cc(C#N)ccc1-c1ccc(CN)cn1] | 4-[5-(aminomethyl)pyridin-2-yl]-3-(5-methyl-2-morpholin-4-yl-1,3-thiazole-4-carbonyl)benzonitrile |
| 1068 | 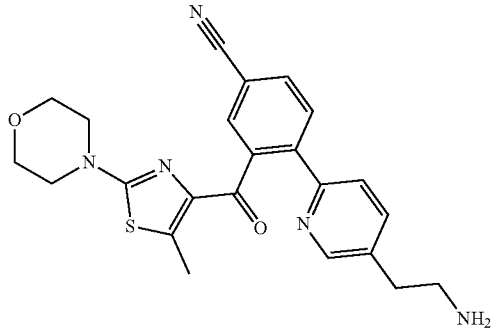 [SMILES: Cc1sc(N2CCOCC2)nc1C(=O)c1cc(C#N)ccc1-c1ccc(CCN)cn1] | 4-[5-(2-aminoethyl)pyridin-2-yl]-3-(5-methyl-2-morpholin-4-yl-1,3-thiazole-4-carbonyl)benzonitrile |

TABLE 1-continued

| Compound number | Structural formula | Compound name |
|---|---|---|
| 1069 | 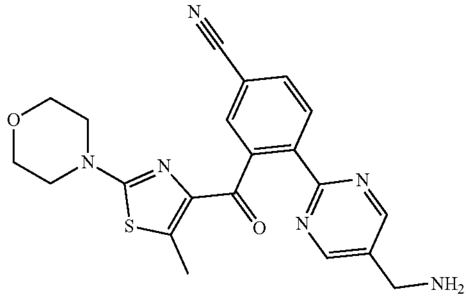 [SMILES: Cc1sc(N2CCOCC2)nc1C(=O)c1cc(C#N)ccc1-c1ncc(CN)cn1] | 4-[5-(aminomethyl)pyrimidin-2-yl]-3-(5-methyl-2-morpholin-4-yl-1,3-thiazole-4-carbonyl)benzonitrile |
| 1070 | 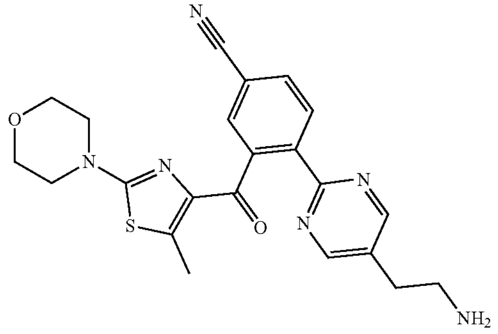 [SMILES: Cc1sc(N2CCOCC2)nc1C(=O)c1cc(C#N)ccc1-c1ncc(CCN)cn1] | 4-[5-(2-aminoethyl)pyrimidin-2-yl]-3-(5-methyl-2-morpholin-4-yl-1,3-thiazole-4-carbonyl)benzonitrile |
| 1071 | 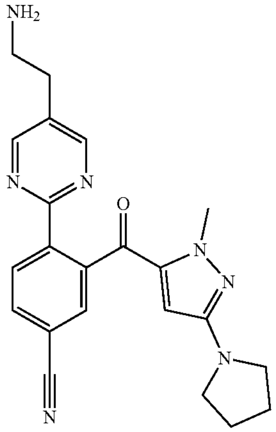 [SMILES: Cn1nc(N2CCCC2)cc1C(=O)c1cc(C#N)ccc1-c1ncc(CCN)cn1] | 4-[5-(2-aminoethyl)pyrimidin-2-yl]-3-(2-methyl-5-pyrrolidin-1-ylpyrazole-3-carbonyl)benzonitrile |
| 1072 | 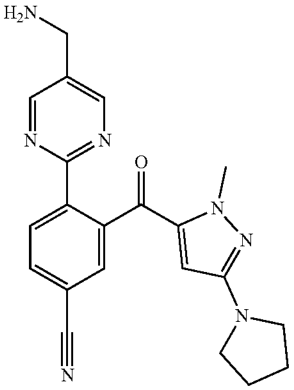 [SMILES: Cn1nc(N2CCCC2)cc1C(=O)c1cc(C#N)ccc1-c1ncc(CN)cn1] | 4-[5-(aminomethyl)pyrimidin-2-yl]-3-(2-methyl-5-pyrrolidin-1-ylpyrazole-3-carbonyl)benzonitrile |

TABLE 1-continued
| Compound number | Structural formula | Compound name |
|---|---|---|
| 1073 | 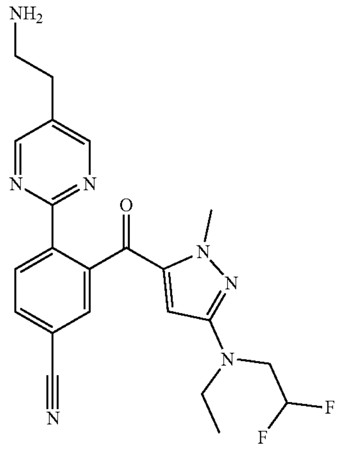 [SMILES: CCN(CC(F)F)c1cc(C(=O)c2cc(C#N)ccc2-c2ncc(CCN)cn2)n(C)n1] | 4-[5-(2-aminoethyl)pyrimidin-2-yl]-3-[5-[2,2-difluoroethyl(ethyl)amino]-2-methylpyrazole-3-carbonyl]benzonitrile |
| 1074 | 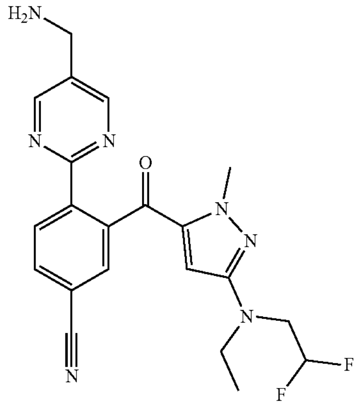 [SMILES: CCN(CC(F)F)c1cc(C(=O)c2cc(C#N)ccc2-c2ncc(CN)cn2)n(C)n1] | 4-[5-(aminomethyl)pyrimidin-2-yl]-3-[5-[2,2-difluoroethyl(ethyl)amino]-2-methylpyrazole-3-carbonyl]benzonitrile |
| 1075 | 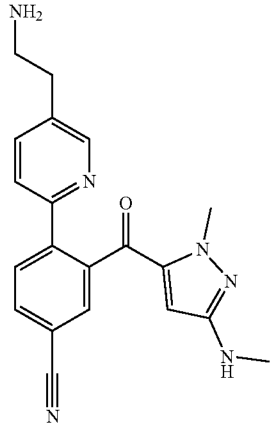 [SMILES: CNc1cc(C(=O)c2cc(C#N)ccc2-c2ccc(CCN)cn2)n(C)n1] | 4-[5-(2-aminoethyl)pyridin-2-yl]-3-[2-methyl-5-(methylamino)pyrazole-3-carbonyl]benzonitrile |

TABLE 1-continued

| Compound number | Structural formula | Compound name |
|---|---|---|
| 1076 | 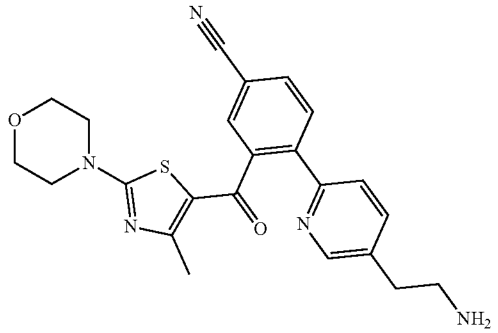 [SMILES: Cc1nc(N2CCOCC2)sc1C(=O)c1cc(C#N)ccc1-c1ccc(CCN)cn1] | 4-[5-(2-aminoethyl)pyridin-2-yl]-3-(4-methyl-2-morpholin-4-yl-1,3-thiazole-5-carbonyl)benzonitrile |
| 1077 | 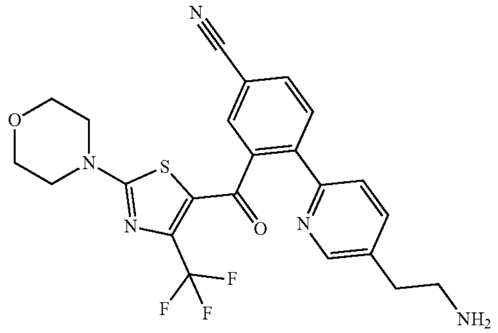 [SMILES: N#Cc1ccc(-c2ccc(CCN)cn2)c(C(=O)c2sc(N3CCOCC3)nc2C(F)(F)F)c1] | 4-[5-(2-aminoethyl)pyridin-2-yl]-3-[2-morpholin-4-yl-4-(trifluoromethyl)-1,3-thiazole-5-carbonyl]benzonitrile |
| 1078 | 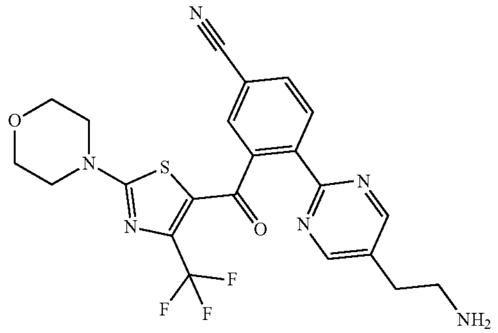 [SMILES: N#Cc1ccc(-c2ncc(CCN)cn2)c(C(=O)c2sc(N3CCOCC3)nc2C(F)(F)F)c1] | 4-[5-(2-aminoethyl)pyrimidin-2-yl]-3-[2-morpholin-4-yl-4-(trifluoromethyl)-1,3-thiazole-5-carbonyl]benzonitrile |
| 1079 | 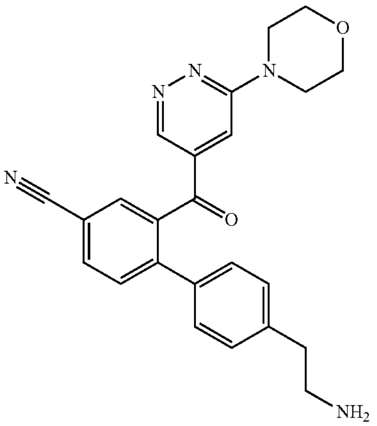 [SMILES: N#Cc1ccc(-c2ccc(CCN)cc2)c(C(=O)c2cnnc(N3CCOCC3)c2)c1] | 4-[4-(2-aminoethyl)phenyl]-3-(6-morpholin-4-ylpyridazine-4-carbonyl)benzonitrile |

TABLE 1-continued

| Compound number | Structural formula | Compound name |
| --- | --- | --- |
| 1080 | 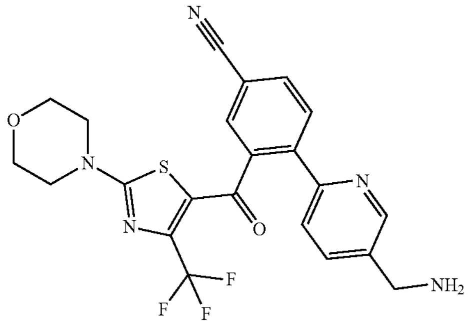 [SMILES: N#Cc1ccc(-c2ccc(CN)cn2)c(C(=O)c2sc(N3CCOCC3)nc2C(F)(F)F)c1] | 4-[5-(aminomethyl)pyridin-2-yl]-3-[2-morpholin-4-yl-4-(trifluoromethyl)-1,3-thiazole-5-carbonyl]benzonitrile |
| 1081 | 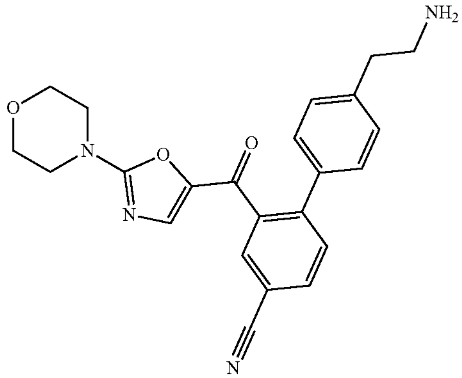 [SMILES: N#Cc1ccc(-c2ccc(CCN)cc2)c(C(=O)c2cnc(N3CCOCC3)o2)c1] | 4-[4-(2-aminoethyl)phenyl]-3-(2-morpholin-4-yl-1,3-oxazole-5-carbonyl)benzonitrile |
| 1082 | 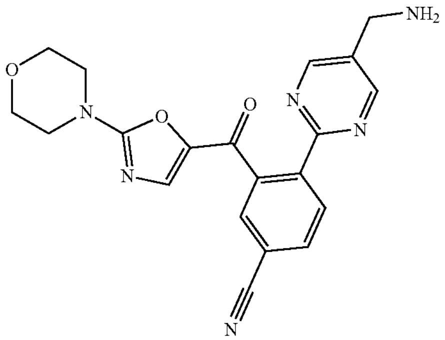 [SMILES: N#Cc1ccc(-c2ncc(CN)cn2)c(C(=O)c2cnc(N3CCOCC3)o2)c1] | 4-[5-(aminomethyl)pyrimidin-2-yl]-3-(2-morpholin-4-yl-1,3-oxazole-5-carbonyl)benzonitrile |
| 1083 | 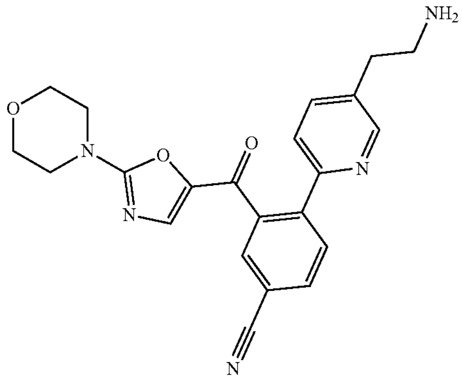 | 4-[5-(2-aminoethyl)pyridin-2-yl]-3-(2-morpholin-4-yl-1,3-oxazole-5-carbonyl)benzonitrile |

TABLE 1-continued

| Compound number | Structural formula | Compound name |
|---|---|---|
| 1084 | 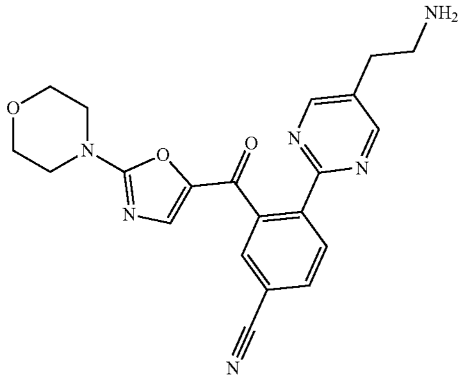 [SMILES: N#Cc1ccc(-c2ncc(CCN)cn2)c(C(=O)c2cnc(N3CCOCC3)o2)c1] | 4-[5-(2-aminoethyl)pyrimidin-2-yl]-3-(2-morpholin-4-yl-1,3-oxazole-5-carbonyl)benzonitrile |
| 1085 | 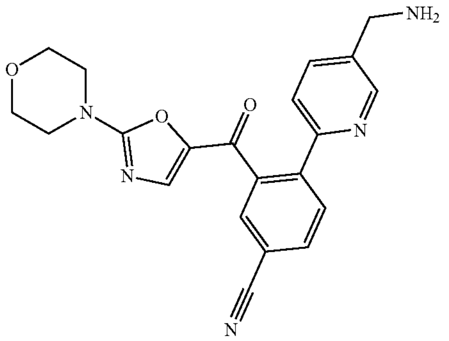 [SMILES: N#Cc1ccc(-c2ccc(CN)cn2)c(C(=O)c2cnc(N3CCOCC3)o2)c1] | 4-[5-(aminomethyl)pyridin-2-yl]-3-(2-morpholin-4-yl-1,3-oxazole-5-carbonyl)benzonitrile |
| 1086 | 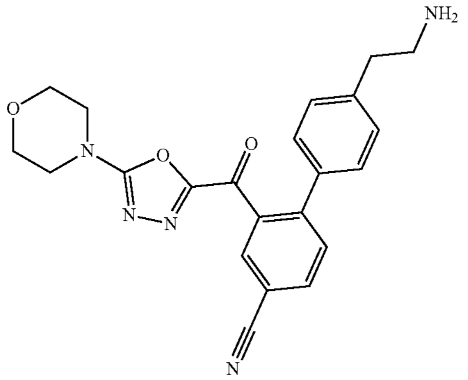 [SMILES: N#Cc1ccc(-c2ccc(CCN)cc2)c(C(=O)c2nnc(N3CCOCC3)o2)c1] | 4-[4-(2-aminoethyl)phenyl]-3-(5-morpholin-4-yl-1,3,4-oxadiazole-2-carbonyl)benzonitrile |
| 1087 | 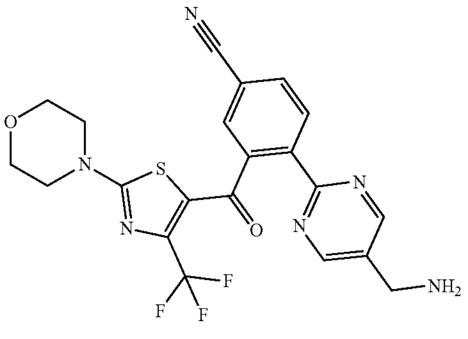 [SMILES: N#Cc1ccc(-c2ncc(CN)cn2)c(C(=O)c2sc(N3CCOCC3)nc2C(F)(F)F)c1] | 4-[5-(aminomethyl)pyrimidin-2-yl]-3-[2-morpholin-4-yl-4-(trifluoromethyl)-1,3-thiazole-5-carbonyl]benzonitrile |

TABLE 1-continued
| Compound number | Structural formula | Compound name |
|---|---|---|
| 1088 | 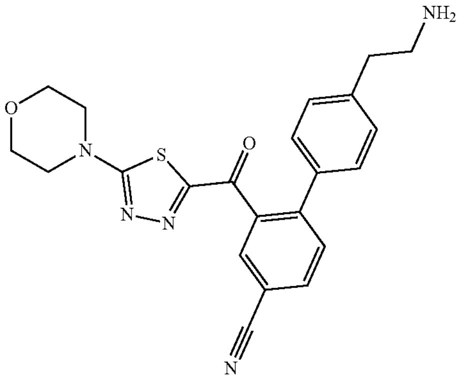 | 4-[4-(2-aminoethyl)phenyl]-3-(5-morpholin-4-yl-1,3,4-thiadiazole-2-carbonyl)benzonitrile |
| 1089 | 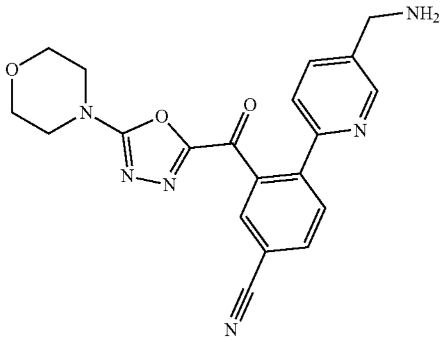 [SMILES: N#Cc1ccc(-c2ccc(CN)cn2)c(C(=O)c2nnc(N3CCOCC3)o2)c1] | 4-[5-(aminomethyl)pyridin-2-yl]-3-(5-morpholin-4-yl-1,3,4-oxadiazole-2-carbonyl)benzonitrile |
| 1090 | 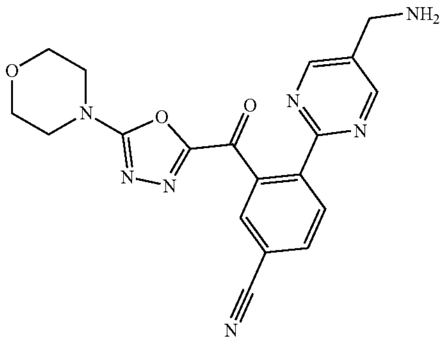 [SMILES: N#Cc1ccc(-c2ncc(CN)cn2)c(C(=O)c2nnc(N3CCOCC3)o2)c1] | 4-[5-(aminomethyl)pyrimidin-2-yl]-3-(5-morpholin-4-yl-1,3,4-oxadiazole-2-carbonyl)benzonitrile |
| 1091 | 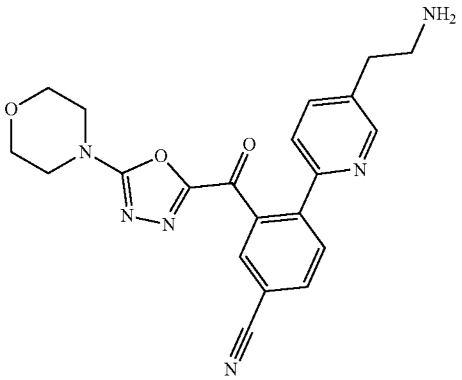 | 4-[5-(2-aminoethyl)pyridin-2-yl]-3-(5-morpholin-4-yl-1,3,4-oxadiazole-2-carbonyl)benzonitrile |

TABLE 1-continued

| Compound number | Structural formula | Compound name |
|---|---|---|
| 1092 | 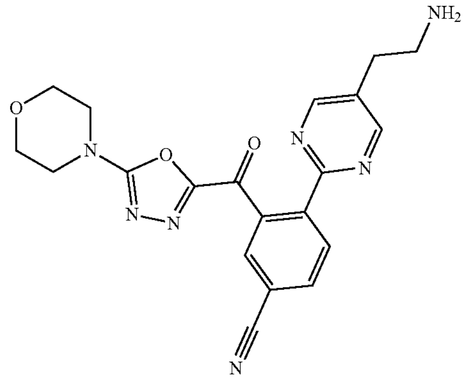 | 4-[5-(2-aminoethyl)pyrimidin-2-yl]-3-(5-morpholin-4-yl-1,3,4-oxadiazole-2-carbonyl)benzonitrile |
| 1093 | 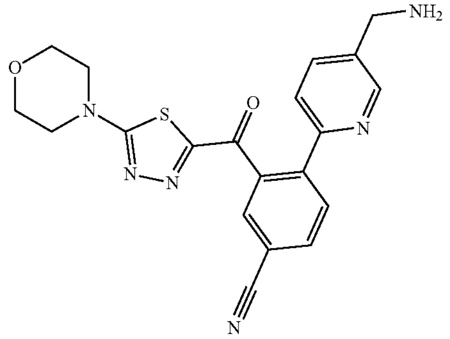 | 4-[5-(aminomethyl)pyridin-2-yl]-3-(5-morpholin-4-yl-1,3,4-thiadiazole-2-carbonyl)benzonitrile |
| 1094 | 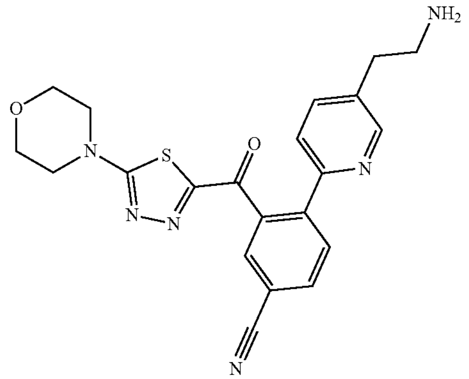 [SMILES: N#Cc1ccc(-c2ccc(CCN)cn2)c(C(=O)c2nnc(N3CCOCC3)o2)c1] | 4-[5-(2-aminoethyl)pyridin-2-yl]-3-(5-morpholin-4-yl-1,3,4-thiadiazole-2-carbonyl)benzonitrile |
| 1095 | 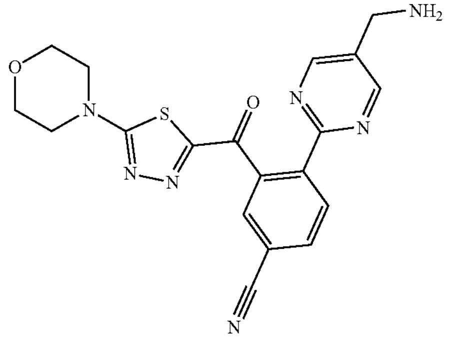 | 4-[5-(aminomethyl)pyrimidin-2-yl]-3-(5-morpholin-4-yl-1,3,4-thiadiazole-2-carbonyl)benzonitrile |

TABLE 1-continued

| Compound number | Structural formula | Compound name |
| --- | --- | --- |
| 1096 | 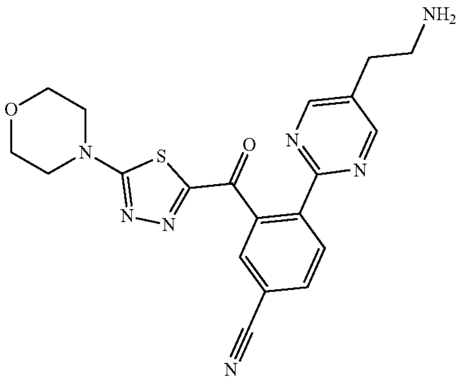 [SMILES: N#Cc1ccc(-c2ncc(CCN)cn2)c(C(=O)c2nnc(N3CCOCC3)o2)c1] | 4-[5-(2-aminoethyl)pyrimidin-2-yl]-3-(5-morpholin-4-yl-1,3,4-thiadiazole-2-carbonyl)benzonitrile |
| 1097 | 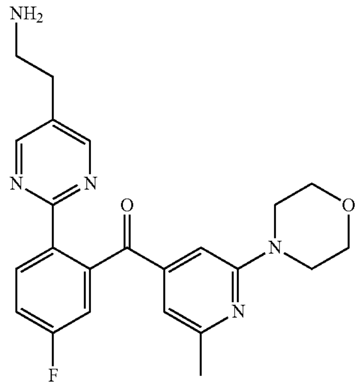 [SMILES: Cc1cc(C(=O)c2cc(F)ccc2-c2ncc(CCN)cn2)cc(N2CCOCC2)n1] | [2-[5-(2-aminoethyl)pyrimidin-2-yl]-5-fluorophenyl]-(2-methyl-6-morpholin-4-ylpyridin-4-yl)methanone |
| 1098 | 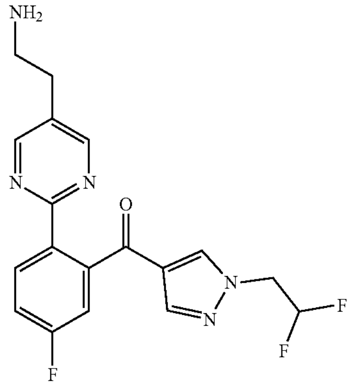 [SMILES: NCCc1cnc(-c2ccc(F)cc2C(=O)c2cnn(CC(F)F)c2)nc1] | [2-[5-(2-aminoethyl)pyrimidin-2-yl]-5-fluorophenyl]-[1-(2,2-difluoroethyl)pyrazol-4-yl]methanone |
| 1099 | 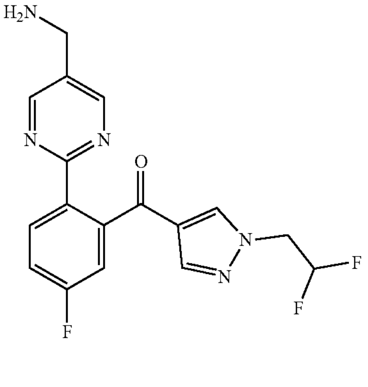 [SMILES: NCc1cnc(-c2ccc(F)cc2C(=O)c2cnn(CC(F)F)c2)nc1] | [2-[5-(aminomethyl)pyrimidin-2-yl]-5-fluorophenyl]-[1-(2,2-difluoroethyl)pyrazol-4-yl]methanone |

TABLE 1-continued

| Compound number | Structural formula | Compound name |
|---|---|---|
| 1100 | 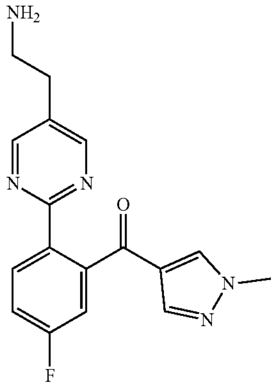 [SMILES: Cn1cc(C(=O)c2cc(F)ccc2-c2ncc(CCN)cn2)cn1] | [2-[5-(2-aminoethyl)pyrimidin-2-yl]-5-fluorophenyl]-(1-methylpyrazol-4-yl)methanone |
| 1101 | 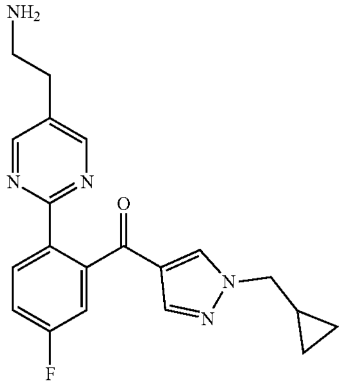 [SMILES: NCCc1cnc(-c2ccc(F)cc2C(=O)c2cnn(CC3CC3)c2)nc1] | [2-[5-(2-aminoethyl)pyrimidin-2-yl]-5-fluorophenyl]-[1-(cyclopropylmethyl)pyrazol-4-yl]methanone |
| 1102 | 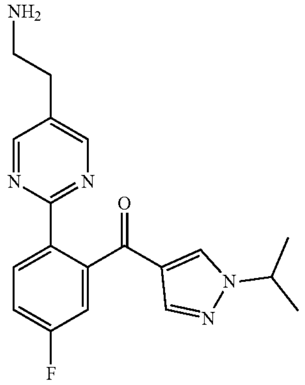 [SMILES: CC(C)n1cc(C(=O)c2cc(F)ccc2-c2ncc(CCN)cn2)cn1] | [2-[5-(2-aminoethyl)pyrimidin-2-yl]-5-fluorophenyl]-(1-propan-2-ylpyrazol-4-yl)methanone |
| 1103 | 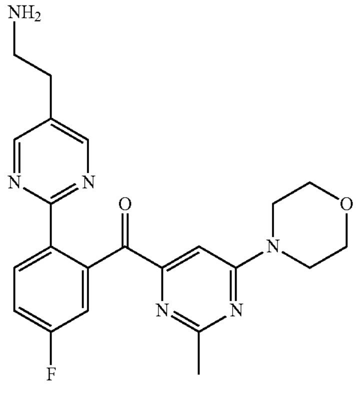 [SMILES: Cc1nc(C(=O)c2cc(F)ccc2-c2ncc(CCN)cn2)cc(N2CCOCC2)n1] | [2-[5-(2-aminoethyl)pyrimidin-2-yl]-5-fluorophenyl]-(2-methyl-6-morpholin-4-ylpyrimidin-4-yl)methanone |

TABLE 1-continued

| Compound number | Structural formula | Compound name |
|---|---|---|
| 1104 | 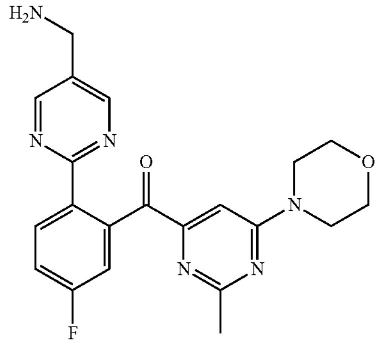 [SMILES: Cc1nc(C(=O)c2cc(F)ccc2-c2ncc(CN)cn2)cc(N2CCOCC2)n1] | [2-[5-(aminomethyl)pyrimidin-2-yl]-5-fluorophenyl]-(2-methyl-6-morpholin-4-ylpyrimidin-4-yl)methanone |
| 1105 | 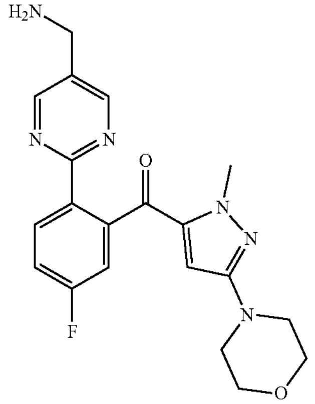 [SMILES: Cn1nc(N2CCOCC2)cc1C(=O)c1cc(F)ccc1-c1ncc(CN)cn1] | [2-[5-(aminomethyl)pyrimidin-2-yl]-5-fluorophenyl]-(2-methyl-5-morpholin-4-ylpyrazol-3-yl)methanone |
| 1106 | 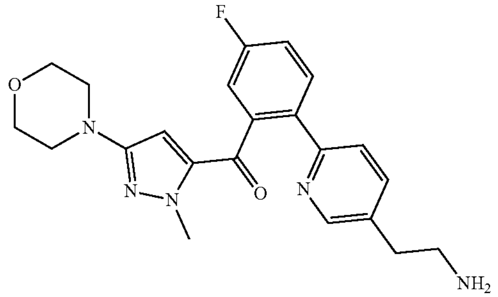 [SMILES: Cn1nc(N2CCOCC2)cc1C(=O)c1cc(F)ccc1-c1ccc(CCN)cn1] | [2-[5-(2-aminoethyl)pyridin-2-yl]-5-fluorophenyl]-(2-methyl-5-morpholin-4-ylpyrazol-3-yl)methanone |
| 1107 | 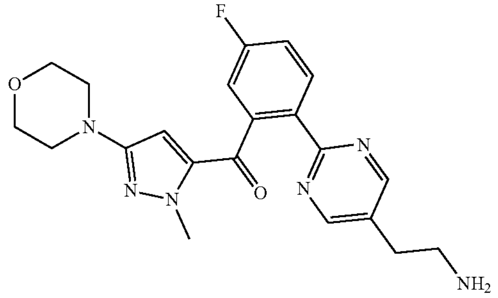 [SMILES: Cn1nc(N2CCOCC2)cc1C(=O)c1cc(F)ccc1-c1ncc(CCN)cn1] | [2-[5-(2-aminoethyl)pyrimidin-2-yl]-5-fluorophenyl]-(2-methyl-5-morpholin-4-ylpyrazol-3-yl)methanone |

TABLE 1-continued
| Compound number | Structural formula | Compound name |
|---|---|---|
| 1108 | 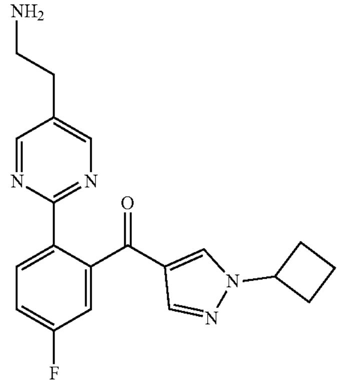 [SMILES: NCCc1cnc(-c2ccc(F)cc2C(=O)c2cnn(C3CCC3)c2)nc1] | [2-[5-(2-aminoethyl)pyrimidin-2-yl]-5-fluorophenyl]-(1-cyclobutylpyrazol-4-yl)methanone |
| 1109 | 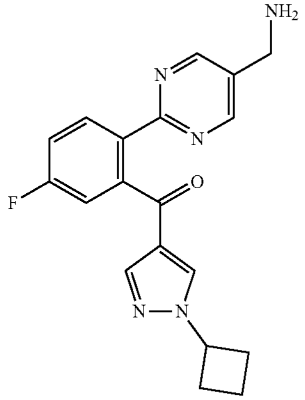 [SMILES: NCc1cnc(-c2ccc(F)cc2C(=O)c2cnn(C3CCC3)c2)nc1] | [2-[5-(aminomethyl)pyrimidin-2-yl]-5-fluorophenyl]-(1-cyclobutylpyrazol-4-yl)methanone |
| 1110 | 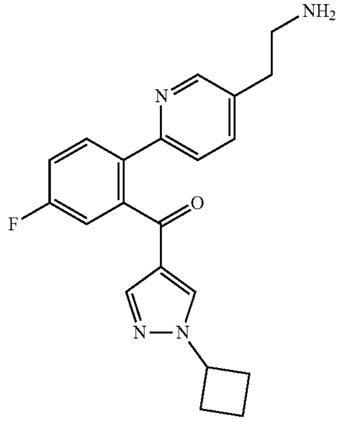 [SMILES: NCCc1ccc(-c2ccc(F)cc2C(=O)c2cnn(C3CCC3)c2)nc1] | [2-[5-(2-aminoethyl)pyridin-2-yl]-5-fluorophenyl]-(1-cyclobutylpyrazol-4-yl)methanone |
| 1111 | 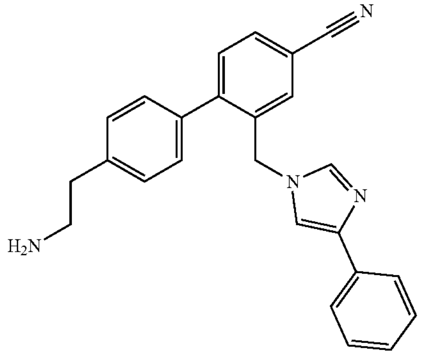 [SMILES: N#Cc1ccc(-c2ccc(CCN)cc2)c(Cn2cnc(-c3ccccc3)c2)c1] | 4-[4-(2-aminoethyl)phenyl]-3-[(4-phenylimidazol-1-yl)methyl]benzonitrile |

TABLE 1-continued

| Compound number | Structural formula | Compound name |
|---|---|---|
| 1112 | 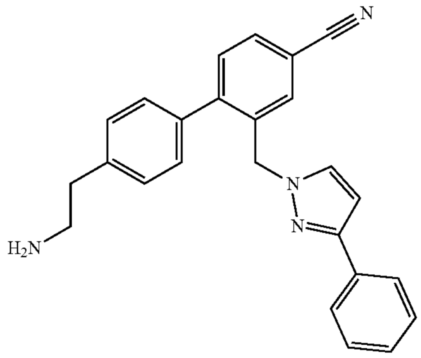 [SMILES: N#Cc1ccc(-c2ccc(CCN)cc2)c(Cn2ccc(-c3ccccc3)n2)c1] | 4-[4-(2-aminoethyl)phenyl]-3-[(3-phenylpyrazol-1-yl)methyl]benzonitrile |
| 1113 | 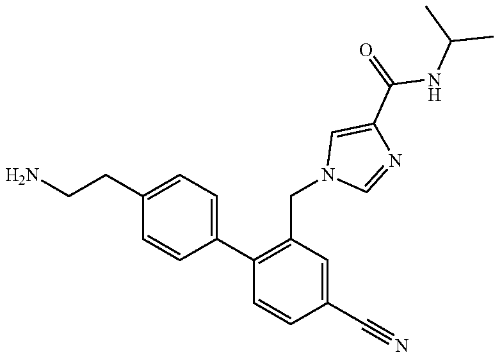 [SMILES: CC(C)NC(=O)c1cn(Cc2cc(C#N)ccc2-c2ccc(CCN)cc2)cn1] | 1-[[2-[4-(2-aminoethyl)phenyl]-5-cyanophenyl]methyl]-N-propan-2-ylimidazole-4-carboxamide |
| 1114 | 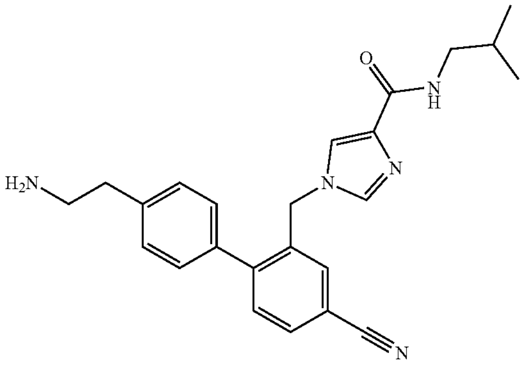 [SMILES: CC(C)CNC(=O)c1cn(Cc2cc(C#N)ccc2-c2ccc(CCN)cc2)cn1] | 1-[[2-[4-(2-aminoethyl)phenyl]-5-cyanophenyl]methyl]-N-(2-methylpropyl)imidazole-4-carboxamide |
| 1115 | 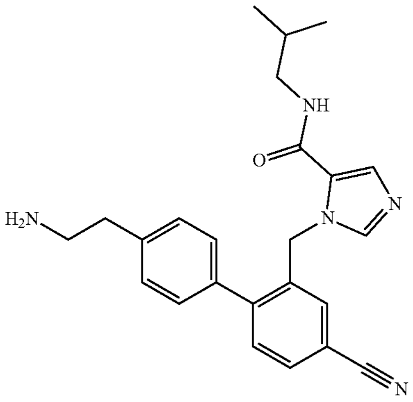 [SMILES: CC(C)CNC(=O)c1cncn1Cc1cc(C#N)ccc1-c1ccc(CCN)cc1] | 3-[[2-[4-(2-aminoethyl)phenyl]-5-cyanophenyl]methyl]-N-(2-methylpropyl)imidazole-4-carboxamide |

TABLE 1-continued
| Compound number | Structural formula | Compound name |
|---|---|---|
| 1116 | 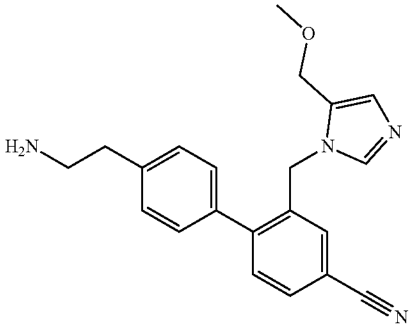 [SMILES: COCc1cncn1Cc1cc(C#N)ccc1-c1ccc(CCN)cc1] | 4-[4-(2-aminoethyl)phenyl]-3-[[5-(methoxymethyl)imidazol-1-yl]methyl]benzonitrile |
| 1117 | 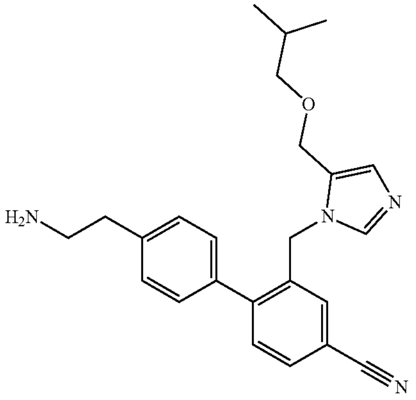 [SMILES: CC(C)COCc1cncn1Cc1cc(C#N)ccc1-c1ccc(CCN)cc1] | 4-[4-(2-aminoethyl)phenyl]-3-[[5-(2-methylpropoxymethyl)imidazol-1-yl]methyl]benzonitrile |
| 1118 | 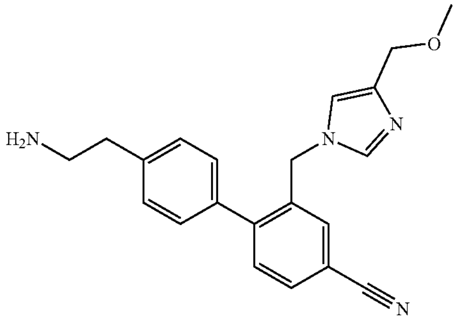 [SMILES: COCc1cn(Cc2cc(C#N)ccc2-c2ccc(CCN)cc2)cn1] | 4-[4-(2-aminoethyl)phenyl]-3-[[4-(methoxymethyl)imidazol-1-yl]methyl]benzonitrile |
| 1119 | 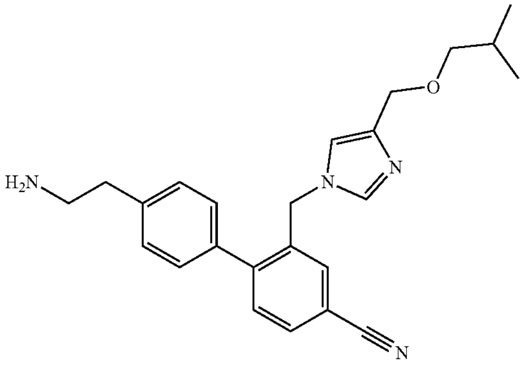 [SMILES: CC(C)COCc1cn(Cc2cc(C#N)ccc2-c2ccc(CCN)cc2)cn1] | 4-[4-(2-aminoethyl)phenyl]-3-[[4-(2-methylpropoxymethyl)imidazol-1-yl]methyl]benzonitrile |

TABLE 1-continued
| Compound number | Structural formula | Compound name |
|---|---|---|
| 1120 | 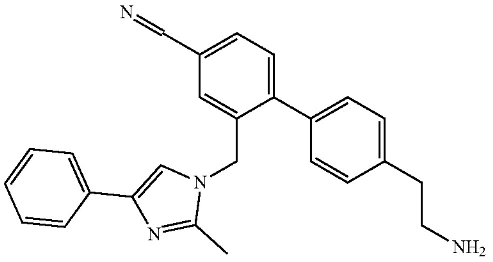 [SMILES: Cc1nc(-c2ccccc2)cn1Cc1cc(C=N)ccc1-c1ccc(CCN)cc1] | 4-[4-(2-aminoethyl)phenyl]-3-[(2-methyl-4-phenylimidazol-1-yl)methyl]benzonitrile |
| 1121 | 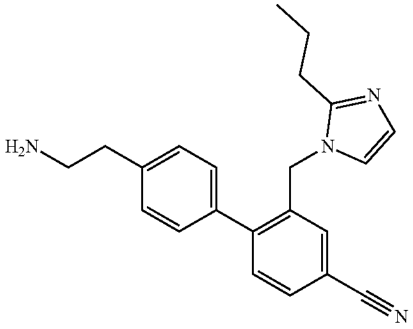 [SMILES: CCCc1nccn1Cc1cc(C#N)ccc1-c1ccc(CCN)cc1] | 4-[4-(2-aminoethyl)phenyl]-3-[(2-propylimidazol-1-yl)methyl]benzonitrile |
| 1122 | 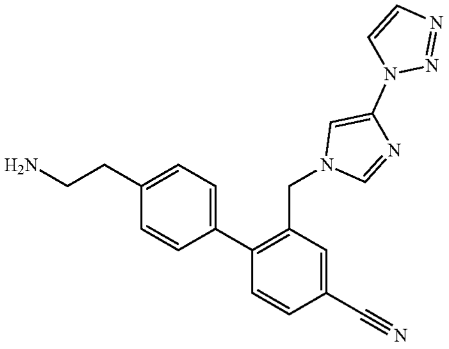 [SMILES: N#Cc1ccc(-c2ccc(CCN)cc2)c(Cn2cnc(-n3ccnn3)c2)c1] | 4-[4-(2-aminoethyl)phenyl]-3-[[4-(triazol-1-yl)imidazol-1-yl]methyl]benzonitrile |
| 1123 | 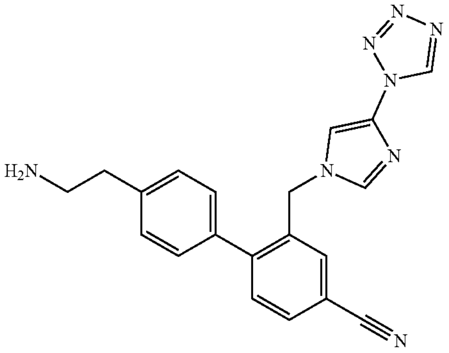 [SMILES: N#Cc1ccc(-c2ccc(CCN)cc2)c(Cn2cnc(-n3cnnn3)c2)c1] | 4-[4-(2-aminoethyl)phenyl]-3-[[4-(tetrazol-1-yl)imidazol-1-yl]methyl]benzonitrile |

TABLE 1-continued

| Compound number | Structural formula | Compound name |
|---|---|---|
| 1124 | 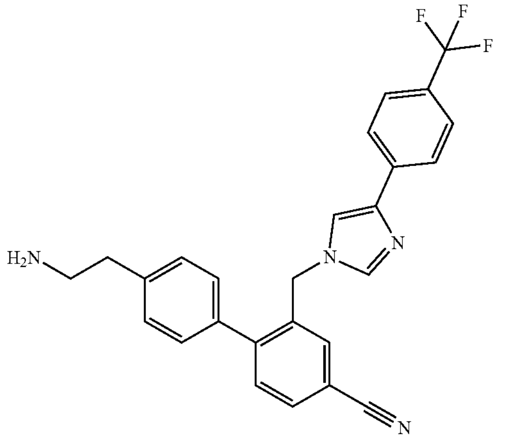 [SMILES: N#Cc1ccc(-c2ccc(CCN)cc2)c(Cn2cnc(-c3ccc(C(F)(F)F)cc3)c2)c1] | 4-[4-(2-aminoethyl)phenyl]-3-[[4-[4-(trifluoromethyl)phenyl]imidazol-1-yl]methyl]benzonitrile |
| 1125 | 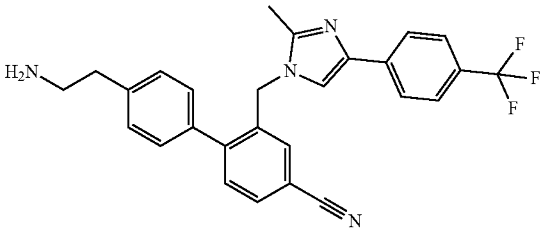 [SMILES: Cc1nc(-c2ccc(C(F)(F)F)cc2)cn1Cc1cc(C#N)ccc1-c1ccc(CCN)cc1] | 4-[4-(2-aminoethyl)phenyl]-3-[[2-methyl-4-[4-(trifluoromethyl)phenyl]imidazol-1-yl]methyl]benzonitrile |
| 1126 | 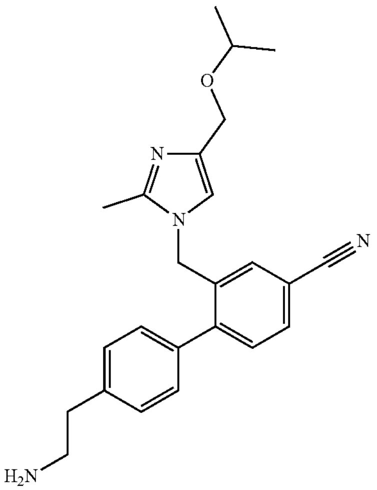 [SMILES: Cc1nc(COC(C)C)cn1Cc1cc(C#N)ccc1-c1ccc(CCN)cc1] | 4-[4-(2-aminoethyl)phenyl]-3-[[2-methyl-4-(propan-2-yloxymethyl)imidazol-1-yl]methyl]benzonitrile |
| 1127 | 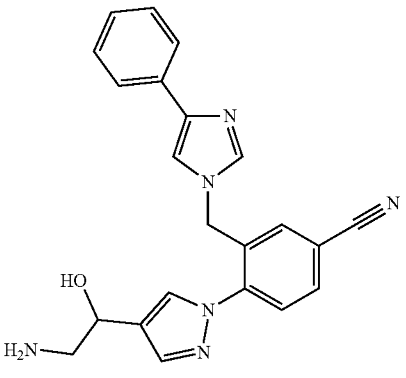 [SMILES: N#Cc1ccc(-n2cc(C(O)CN)cn2)c(Cn2cnc(-c3ccccc3)c2)c1] | 4-[4-(2-amino-1-hydroxyethyl)pyrazol-1-yl]-3-[(4-phenylimidazol-1 yl)methyl]benzonitrile |

TABLE 1-continued
| Compound number | Structural formula | Compound name |
| --- | --- | --- |
| 1128 | 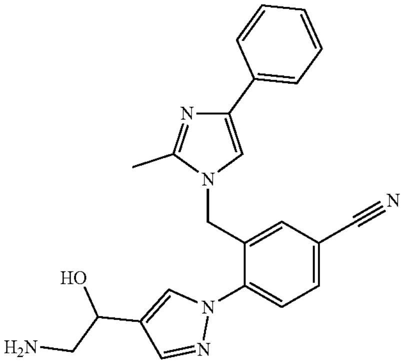 [SMILES: Cc1nc(-c2ccccc2)cn1Cc1cc(C#N)ccc1-n1cc(C(O)CN)cn1] | 4-[4-(2-amino-1-hydroxyethyl)pyrazol-1-yl]-3-[(2-methyl-4-phenylimidazol-1-yl)methyl]benzonitrile |
| 1129 | 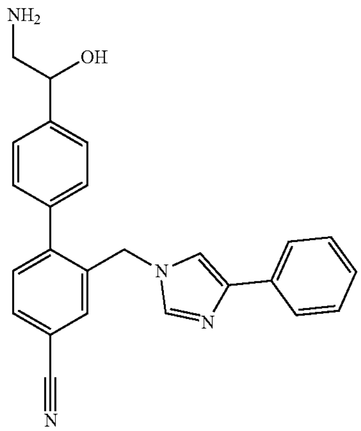 [SMILES: N#Cc1ccc(-c2ccc(C(O)CN)cc2)c(Cn2cnc(-c3ccccc3)c2)c1] | 4-[4-(2-amino-1-hydroxyethyl)phenyl]-3-[(4-phenylimidazol-1-yl)methyl]benzonitrile |
| 1130 | 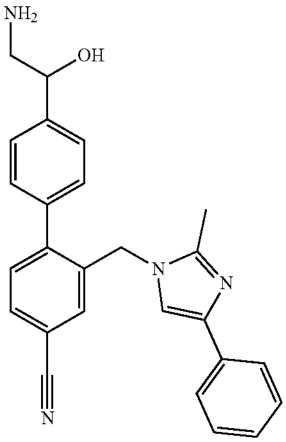 [SMILES: Cc1nc(-c2ccccc2)cn1Cc1cc(C#N)ccc1-c1ccc(C(O)CN)cc1] | 4-[4-(2-amino-1-hydroxyethyl)phenyl]-3-[(2-methyl-4-phenylimidazol-1-yl)methyl]benzonitrile |

TABLE 1-continued
| Compound number | Structural formula | Compound name |
|---|---|---|
| 1131 | 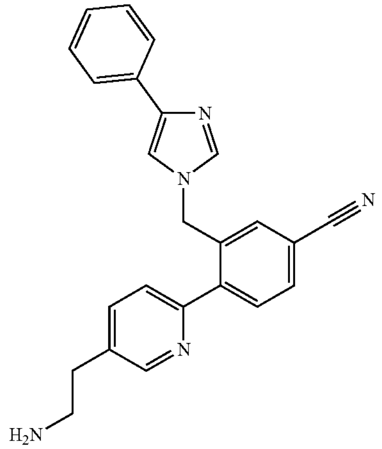 [SMILES: N#Cc1ccc(-c2ccc(CCN)cn2)c(Cn2cnc(-c3ccccc3)c2)c1] | 4-[5-(2-aminoethyl)pyridin-2-yl]-3-[(4-phenylimidazol-1-yl)methyl]benzonitrile |
| 1132 | 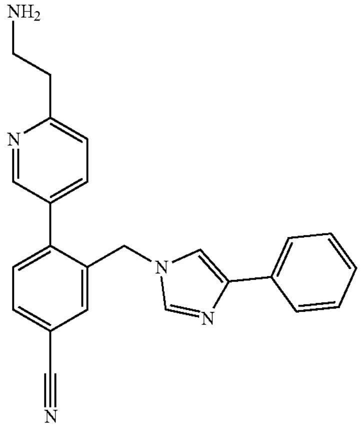 [SMILES: N#Cc1ccc(-c2ccc(CCN)nc2)c(Cn2cnc(-c3ccccc3)c2)c1] | 4-[6-(2-aminoethyl)pyridin-3-yl]-3-[(4-phenylimidazol-1-yl)methyl]benzonitrile |
| 1133 | 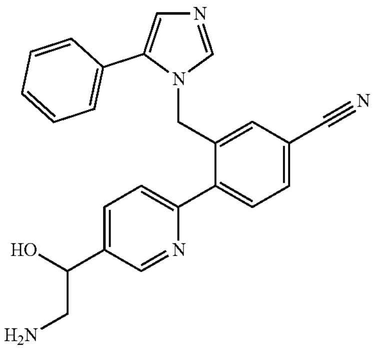 [SMILES: N#Cc1ccc(-c2ccc(C(O)CN)cn2)c(Cn2cncc2-c2ccccc2)c1] | 4-[5-(2-amino-1-hydroxyethyl)pyridin-2-yl]-3-[(5-phenylimidazol-1-yl)methyl]benzonitrile |
| 1134 | 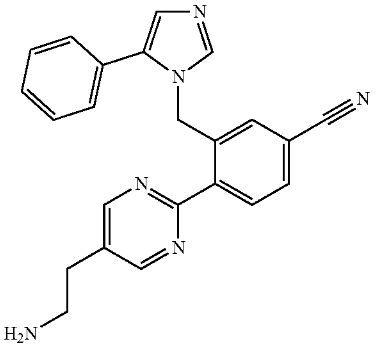 [SMILES: N#Cc1ccc(-c2ncc(CCN)cn2)c(Cn2cncc2-c2ccccc2)c1] | 4-[5-(2-aminoethyl)pyrimidin-2-yl]-3-[(5-phenylimidazol-1-yl)methyl]benzonitrile |

TABLE 1-continued
| Compound number | Structural formula | Compound name |
|---|---|---|
| 1135 | 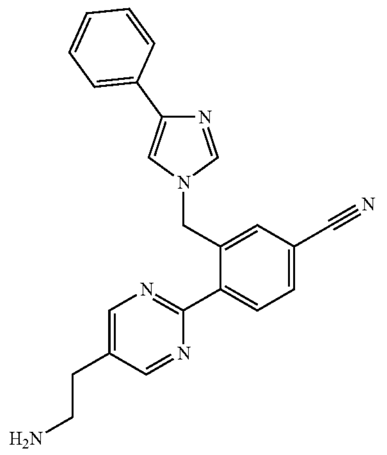 [SMILES: N#Cc1ccc(-c2ncc(CCN)cn2)c(Cn2cnc(-c3ccccc3)c2)c1] | 4-[5-(2-aminoethyl)pyrimidin-2-yl]-3-[(4-phenylimidazol-1-yl)methyl]benzonitrile |
| 1136 | 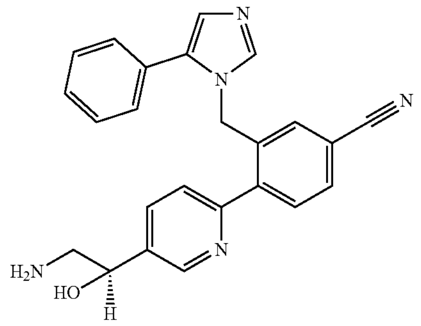 [SMILES: N#Cc1ccc(-c2ccc([C@@H](O)CN)cn2)c(Cn2cncc2-c2ccccc2)c1] | 4-[5-[(1R)-2-amino-1-hydroxyethyl]pyridin-2-yl]-3-[(5-phenylimidazol-1-yl)methyl]benzonitrile |
| 1137 | 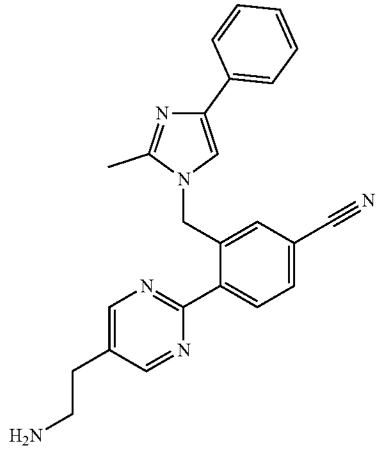 [SMILES: Cc1nc(-c2ccccc2)cn1Cc1cc(C#N)ccc1-c1ncc(CCN)cn1] | 4-[5-(2-aminoethyl)pyrimidin-2-yl]-3-[(2-methyl-4-phenylimidazol-1-yl)methyl]benzonitrile |

TABLE 1-continued
| Compound number | Structural formula | Compound name |
|---|---|---|
| 1138 | 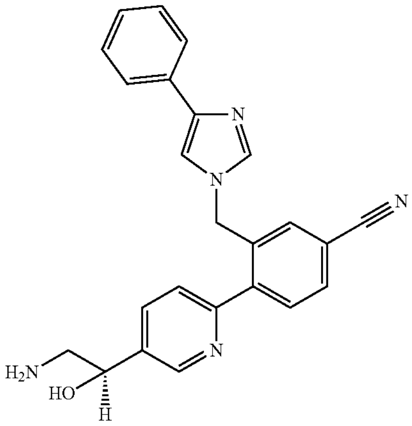 [SMILES: N#Cc1ccc(-c2ccc([C@@H](O)CN)cn2)c(Cn2cnc(-c3ccccc3)c2)c1] | 4-[5-[(1R)-2-amino-1-hydroxyethyl]pyridin-2-yl]-3-[(4-phenylimidazol-1-yl)methyl]benzonitrile |
| 1139 | 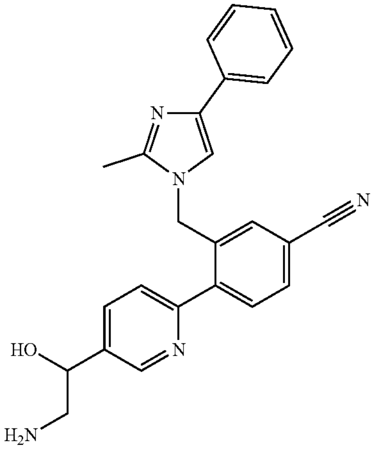 [SMILES: Cc1nc(-c2ccccc2)cn1Cc1cc(C#N)ccc1-c1ccc(C(O)CN)cn1] | 4-[5-(2-amino-1-hydroxyethyl)pyridin-2-yl]-3-[(2-methyl-4-phenylimidazol-1-yl)methyl]benzonitrile |
| 1140 | 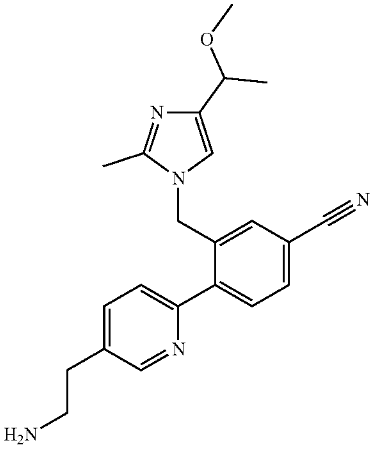 [SMILES: COC(C)c1cn(Cc2cc(C#N)ccc2-c2ccc(CCN)cn2)c(C)n1] | 4-[5-(2-aminoethyl)pyridin-2-yl]-3-[[4-(1-methoxyethyl)-2-methylimidazol-1-yl]methyl]benzonitrile |

TABLE 1-continued
| Compound number | Structural formula | Compound name |
|---|---|---|
| 1141 | 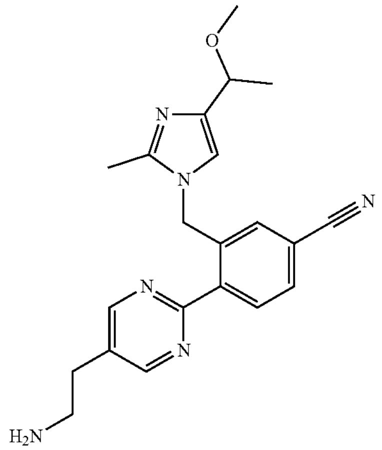 [SMILES: COC(C)c1cn(Cc2cc(C#N)ccc2-c2ncc(CCN)cn2)c(C)n1] | 4-[5-(2-aminoethyl)pyrimidin-2-yl]-3-[[4-(1-methoxyethyl)-2-methylimidazol-1-yl]methyl]benzonitrile |
| 1142 | 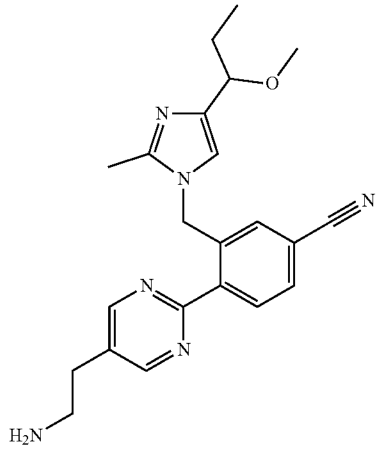 [SMILES: CCC(OC)c1cn(Cc2cc(C#N)ccc2-c2ncc(CCN)cn2)c(C)n1] | 4-[5-(2-aminoethyl)pyrimidin-2-yl]-3-[[4-(1-methoxypropyl)-2-methylimidazol-1-yl]methyl]benzonitrile |
| 1143 | 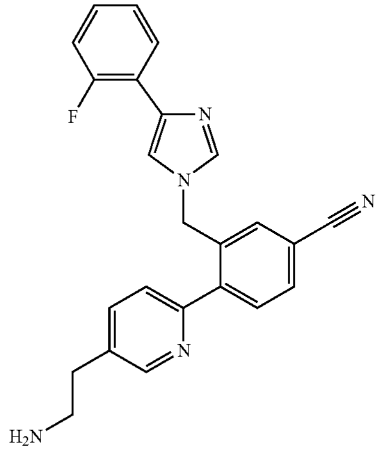 [SMILES: N#Cc1ccc(-c2ccc(CCN)cn2)c(Cn2cnc(-c3ccccc3F)c2)c1] | 4-[5-(2-aminoethyl)pyridin-2-yl]-3-[[4-(2-fluorophenyl)imidazol-1-yl]methyl]benzonitrile |

TABLE 1-continued
| Compound number | Structural formula | Compound name |
|---|---|---|
| 1144 | 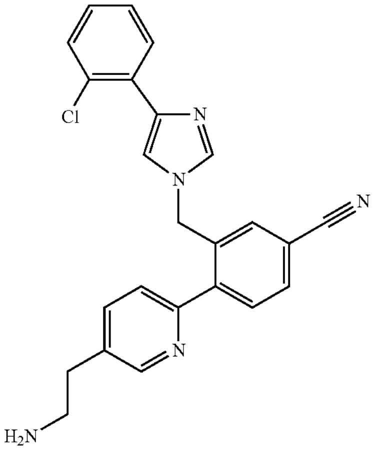 [SMILES: N#Cc1ccc(-c2ccc(CCN)cn2)c(Cn2cnc(-c3ccccc3Cl)c2)c1] | 4-[5-(2-aminoethyl)pyridin-2-yl]-3-[[4-(2-chlorophenyl)imidazol-1-yl]methyl]benzonitrile |
| 1145 | 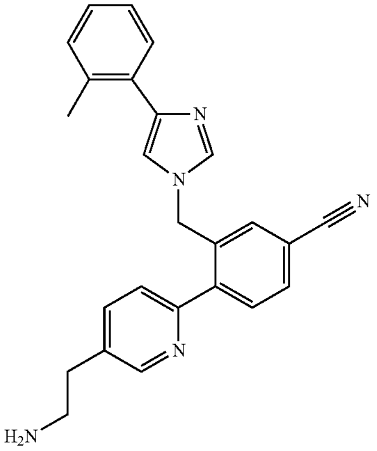 [SMILES: Cc1ccccc1-c1cn(Cc2cc(C#N)ccc2-c2ccc(CCN)cn2)cn1] | 4-[5-(2-aminoethyl)pyridin-2-yl]-3-[[4-(2-methylphenyl)imidazol-1-yl]methyl]benzonitrile |
| 1146 | 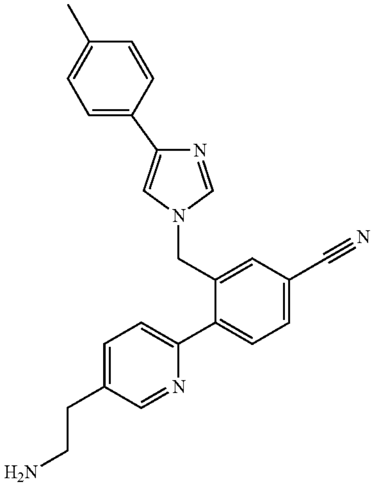 [SMILES: Cc1ccc(-c2cn(Cc3cc(C#N)ccc3-c3ccc(CCN)cn3)cn2)cc1] | 4-[5-(2-aminoethyl)pyridin-2-yl]-3-[[4-(4-methylphenyl)imidazol-1-yl]methyl]benzonitrile |

TABLE 1-continued
| Compound number | Structural formula | Compound name |
|---|---|---|
| 1147 | 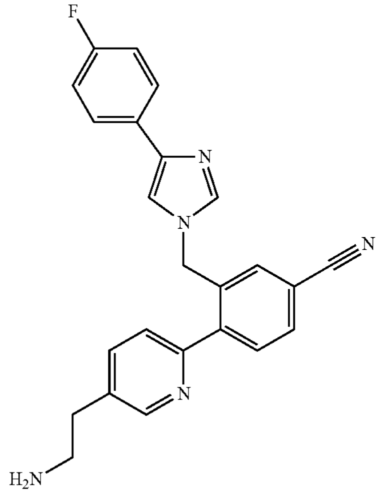 [SMILES: N#Cc1ccc(-c2ccc(CCN)cn2)c(Cn2cnc(-c3ccc(F)cc3)c2)c1] | 4-[5-(2-aminoethyl)pyridin-2-yl]-3-[[4-(4-fluorophenyl)imidazol-1-yl]methyl]benzonitrile |
| 1148 | 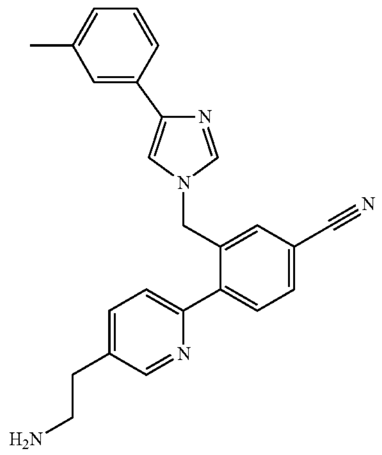 [SMILES: Cc1cccc(-c2cn(Cc3cc(C#N)ccc3-c3ccc(CCN)cn3)cn2)c1] | 4-[5-(2-aminoethyl)pyridin-2-yl]-3-[[4-(3-methylphenyl)imidazol-1-yl]methyl]benzonitrile |
| 1149 | 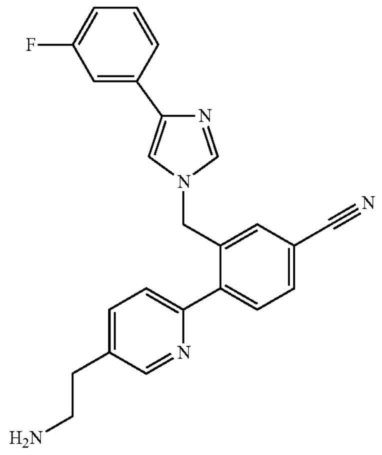 [SMILES: N#Cc1ccc(-c2ccc(CCN)cn2)c(Cn2cnc(-c3cccc(F)c3)c2)c1] | 4-[5-(2-aminoethyl)pyridin-2-yl]-3-[[4-(3-fluorophenyl)imidazol-1-yl]methyl]benzonitrile |

TABLE 1-continued
| Compound number | Structural formula | Compound name |
| --- | --- | --- |
| 1150 | 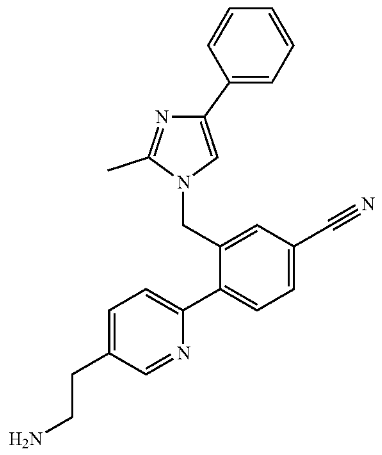 [SMILES: Cc1nc(-c2ccccc2)cn1Cc1cc(C#N)ccc1-c1ccc(CCN)cn1] | 4-[5-(2-aminoethyl)pyridin-2-yl]-3-[(2-methyl-4-phenylimidazol-1-yl)methyl]benzonitrile |
| 1151 | 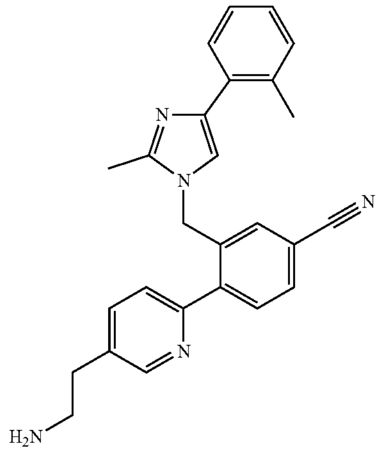 [SMILES: Cc1ccccc1-c1cn(Cc2cc(C#N)ccc2-c2ccc(CCN)cn2)c(C)n1] | 4-[5-(2-aminoethyl)pyridin-2-yl]-3-[[2-methyl-4-(2-methylphenyl)imidazol-1-yl]methyl]benzonitrile |
| 1152 | 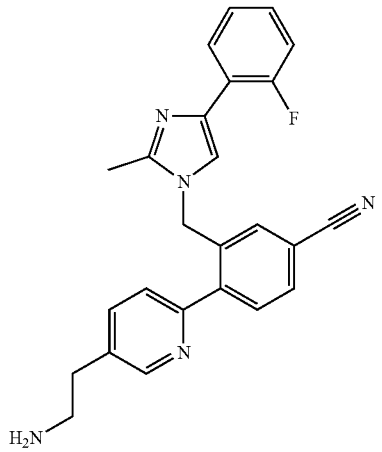 | 4-[5-(2-aminoethyl)pyridin-2-yl]-3-[[4-(2-fluorophenyl)-2-methylimidazol-1-yl]methyl]benzonitrile |

TABLE 1-continued
| Compound number | Structural formula | Compound name |
| --- | --- | --- |
| 1153 | 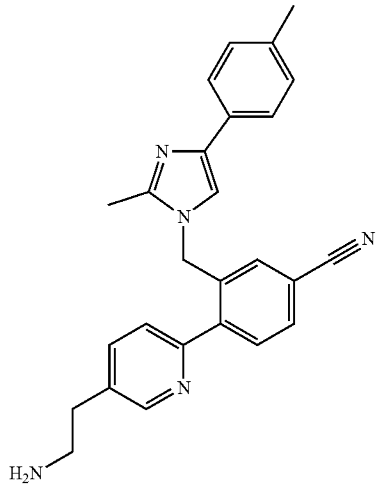 [SMILES: Cc1ccc(-c2cn(Cc3cc(C#N)ccc3-c3ccc(CCN)cn3)c(C)n2)cc1] | 4-[5-(2-aminoethyl)pyridin-2-yl]-3-[[2-methyl-4-(4-methylphenyl)imidazol-1-yl]methyl]benzonitrile |
| 1154 | 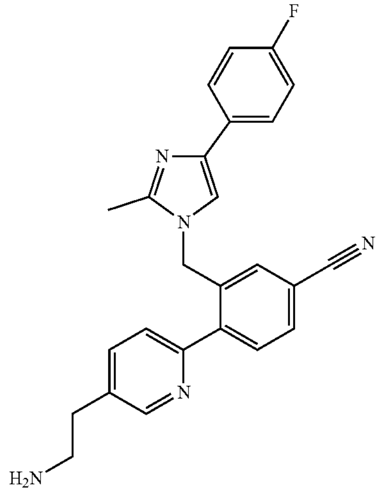 [SMILES: Cc1nc(-c2ccc(F)cc2)cn1Cc1cc(C#N)ccc1-c1ccc(CCN)cn1] | 4-[5-(2-aminoethyl)pyridin-2-yl]-3-[[4-(4-fluorophenyl)-2-methylimidazol-1-yl]methyl]benzonitrile |
| 1155 | 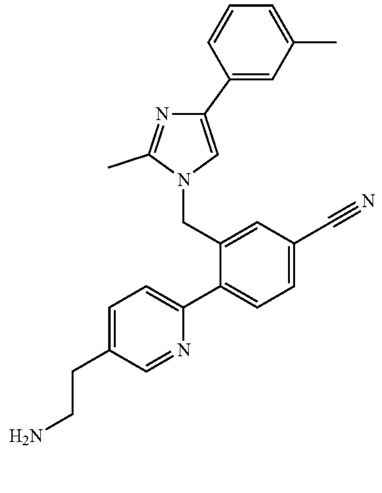 | 4-[5-(2-aminoethyl)pyridin-2-yl]-3-[[2-methyl-4-(3-methylphenyl)imidazol-1-yl]methyl]benzonitrile |

TABLE 1-continued
| Compound number | Structural formula | Compound name |
|---|---|---|
| 1156 | 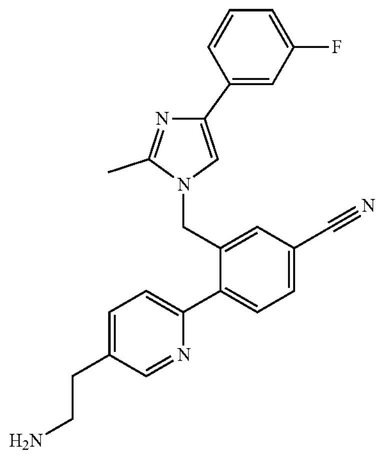 [SMILES: Cc1nc(-c2cccc(F)c2)cn1Cc1cc(C#N)ccc1-c1ccc(CCN)cn1] | 4-[5-(2-aminoethyl)pyridin-2-yl]-3-[[4-(3-fluorophenyl)-2-methylimidazol-1-yl]methyl]benzonitrile |
| 1157 | 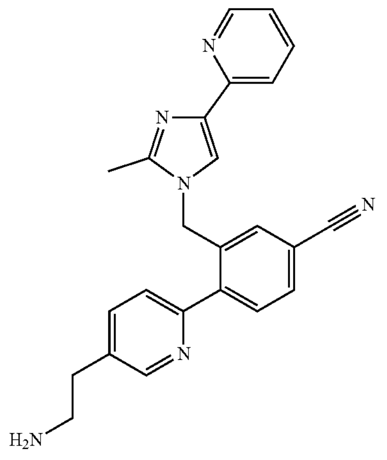 | 4-[5-(2-aminoethyl)pyridin-2-yl]-3-[(2-methyl-4-pyridin-2-ylimidazol-1-yl)methyl]benzonitrile |
| 1158 | 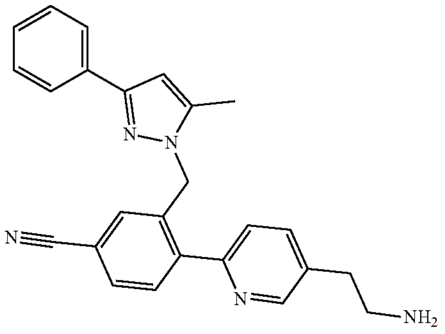 [SMILES: Cc1cc(-c2ccccc2)nn1Cc1cc(C#N)ccc1-c1ccc(CCN)cn1] | 4-[5-(2-aminoethyl)pyridin-2-yl]-3-[(5-methyl-3-phenylpyrazol-1-yl)methyl]benzonitrile |

TABLE 1-continued

| Compound number | Structural formula | Compound name |
|---|---|---|
| 1159 | 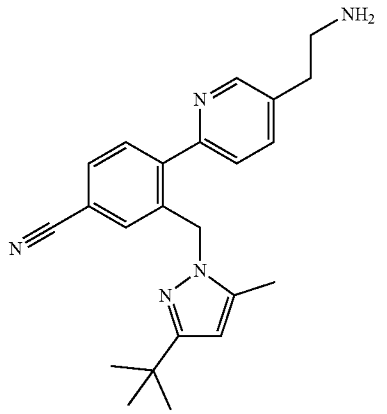 [SMILES: Cc1cc(C(C)(C)C)nn1Cc1cc(C#N)ccc1-c1ccc(CCN)cn1] | 4-[5-(2-aminoethyl)pyridin-2-yl]-3-[(3-tert-butyl-5-methylpyrazol-1-yl)methyl]benzonitrile |
| 1160 | 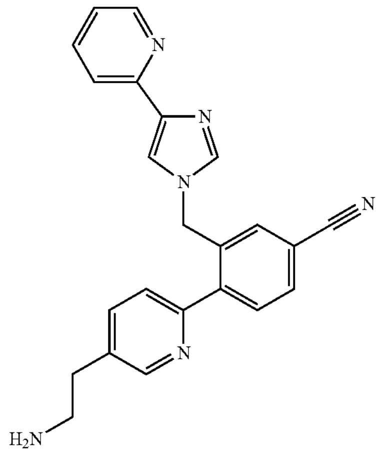 [SMILES: N#Cc1ccc(-c2ccc(CCN)cn2)c(Cn2cnc(-c3ccccn3)c2)c1] | 4-[5-(2-aminoethyl)pyridin-2-yl]-3-[(4-pyridin-2-ylimidazol-1-yl)methyl]benzonitrile |
| 1161 | 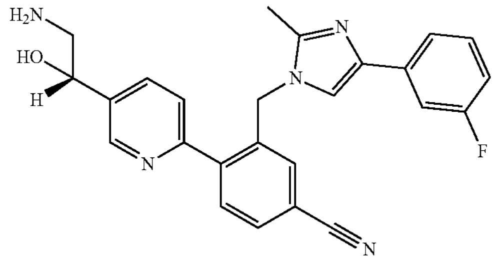 [SMILES: Cc1nc(-c2cccc(F)c2)cn1Cc1cc(C#N)ccc1-c1ccc([C@H](O)CN)cn1] | 4-[5-[(1S)-2-amino-1-hydroxyethyl]pyridin-2-yl]-3-[[4-(3-fluorophenyl)-2-methylimidazol-1-yl]methyl]benzonitrile |
| 1162 | 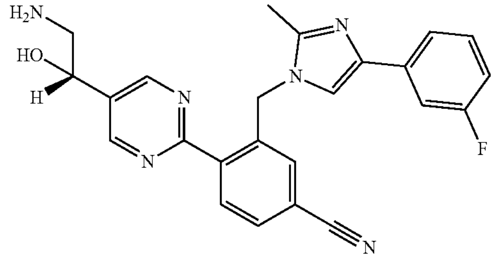 [SMILES: Cc1nc(-c2cccc(F)c2)cn1Cc1cc(C#N)ccc1-c1ncc([C@H](O)CN)cn1] | 4-[5-[(1S)-2-amino-1-hydroxyethyl]pyrimidin-2-yl]-3-[[4-(3-fluorophenyl)-2-methylimidazol-1-yl]methyl]benzonitrile |

TABLE 1-continued
| Compound number | Structural formula | Compound name |
|---|---|---|
| 1163 | 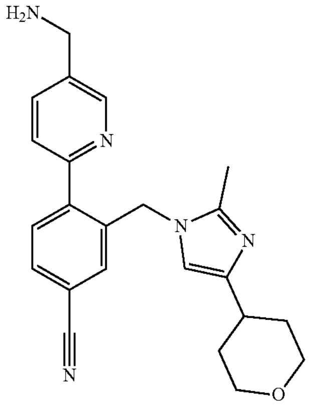 | 4-[5-(aminomethyl)pyridin-2-yl]-3-[[2-methyl-4-(oxan-4-yl)imidazol-1-yl]methyl]benzonitrile |
| 1164 | 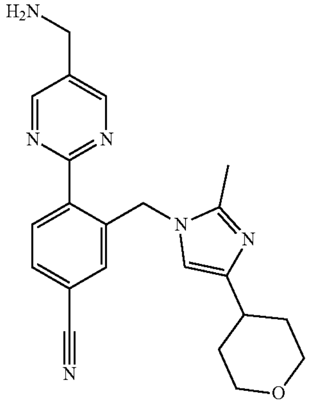 [SMILES: Cc1nc(C2CCOCC2)cn1Cc1cc(C#N)ccc1-c1ncc(CN)cn1] | 4-[5-(aminomethyl)pyrimidin-2-yl]-3-[[2-methyl-4-(oxan-4-yl)imidazol-1-yl]methyl]benzonitrile |
| 1165 | 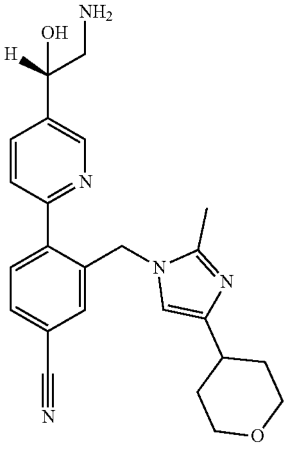 [SMILES: Cc1nc(C2CCOCC2)cn1Cc1cc(C#N)ccc1-c1ccc([C@H](O)CN)cn1] | 4-[5-[(1S)-2-amino-1-hydroxyethyl]pyridin-2-yl]-3-[[2-methyl-4-(oxan-4-yl)imidazol-1-yl]methyl]]benzonitrile |

TABLE 1-continued
| Compound number | Structural formula | Compound name |
|---|---|---|
| 1166 | 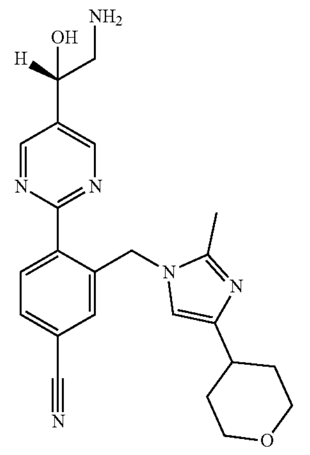 [SMILES: Cc1nc(C2CCOCC2)cn1Cc1cc(C#N)ccc1-c1ncc([C@H](O)CN)cn1] | 4-[5-[(1S)-2-amino-1-hydroxyethyl]pyrimidin-2-yl]-3-[[2-methyl-4-(oxan-4-yl)imidazol-1-yl]methyl]]benzonitrile |
| 1167 | 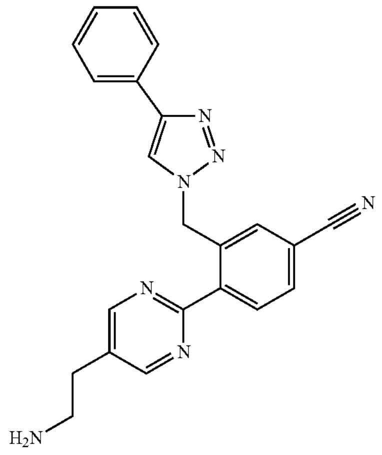 [SMILES: N#Cc1ccc(-c2ncc(CCN)cn2)c(Cn2cc(-c3ccccc3)nn2)c1] | 4-[5-(2-aminoethyl)pyrimidin-2-yl]-3-[(4-phenyltriazol-1-yl)methyl]benzonitrile |
| 1168 | 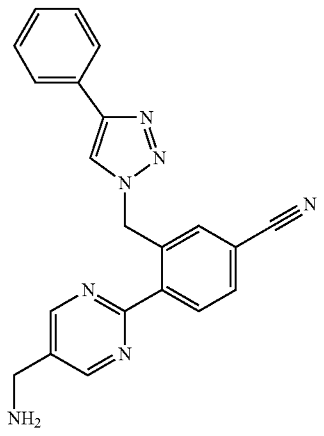 [SMILES: N#Cc1ccc(-c2ncc(CN)cn2)c(Cn2cc(-c3ccccc3)nn2)c1] | 4-[5-(aminomethyl)pyrimidin-2-yl]-3-[(4-phenyltriazol-1-yl)methyl]benzonitrile |

TABLE 1-continued
| Compound number | Structural formula | Compound name |
|---|---|---|
| 1169 | 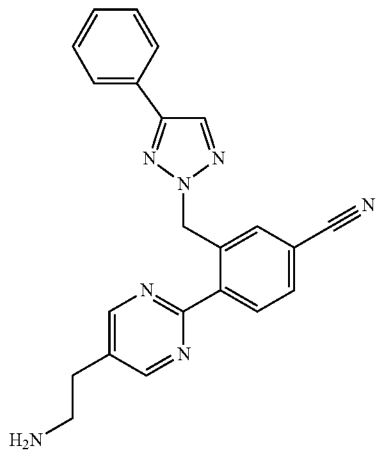 [SMILES: N#Cc1ccc(-c2ncc(CCN)cn2)c(Cn2ncc(-c3ccccc3)n2)c1] | 4-[5-(2-aminoethyl)pyrimidin-2-yl]-3-[(4-phenyltriazol-2-yl)methyl]benzonitrile |
| 1170 | 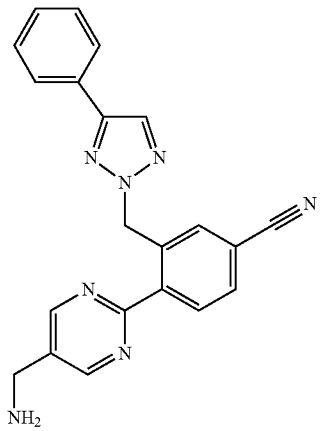 [SMILES: N#Cc1ccc(-c2ncc(CN)cn2)c(Cn2ncc(-c3ccccc3)n2)c1] | 4-[5-(aminomethyl)pyrimidin-2-yl]-3-[(4-phenyltriazol-2-yl)methyl]benzonitrile |
| 1171 | 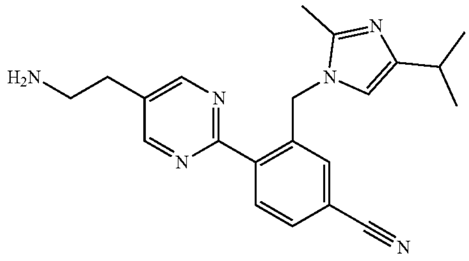 [SMILES: Cc1nc(C(C)C)cn1Cc1cc(C#N)ccc1-c1ncc(CCN)cn1] | 4-[5-(2-aminoethyl)pyrimidin-2-yl]-3-[(2-methyl-4-propan-2-ylimidazol-1-yl)methyl]benzonitrile |
| 1172 | 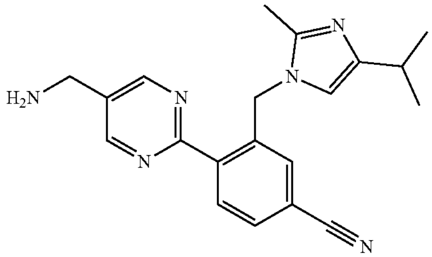 [SMILES: Cc1nc(C(C)C)cn1Cc1cc(C#N)ccc1-c1ncc(CN)cn1] | 4-[5-(aminomethyl)pyrimidin-2-yl]-3-[(2-methyl-4-propan-2-ylimidazol-1-yl)methyl]benzonitrile |

TABLE 1-continued

| Compound number | Structural formula | Compound name |
| --- | --- | --- |
| 1173 | 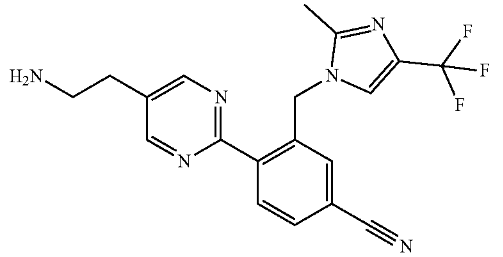 [SMILES: Cc1nc(C(F)(F)F)cn1Cc1cc(C#N)ccc1-c1ncc(CCN)cn1] | 4-[5-(2-aminoethyl)pyrimidin-2-yl]-3-[[2-methyl-4-(trifluoromethyl)imidazol-1-yl]methyl]benzonitrile |
| 1174 | 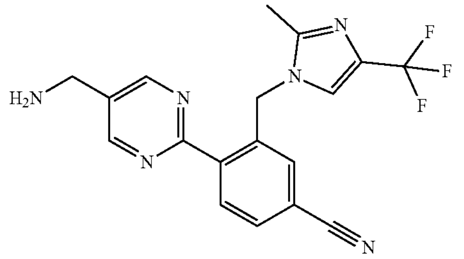 [SMILES: Cc1nc(C(F)(F)F)cn1Cc1cc(C#N)ccc1-c1ncc(CN)cn1] | 4-[5-(aminomethyl)pyrimidin-2-yl]-3-[[2-methyl-4-(trifluoromethyl)imidazol-1-yl]methyl]benzonitrile |
| 1175 | 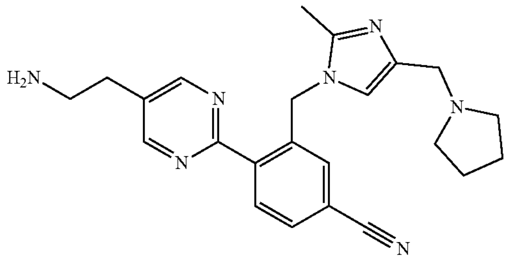 [SMILES: Cc1nc(CN2CCCC2)cn1Cc1cc(C#N)ccc1-c1ncc(CCN)cn1] | 4-[5-(2-aminoethyl)pyrimidin-2-yl]-3-[[2-methyl-4-(pyrrolidin-1-ylmethyl)imidazol-1-yl]methyl]benzonitrile |
| 1176 | 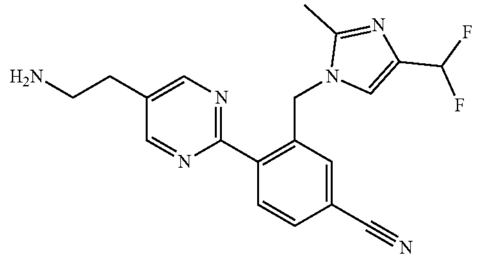 [SMILES: Cc1nc(C(F)F)cn1Cc1cc(C#N)ccc1-c1ncc(CCN)cn1] | 4-[5-(2-aminoethyl)pyrimidin-2-yl]-3-[[4-(difluoromethyl)-2-methylimidazol-1-yl]methyl]benzonitrile |
| 1177 | 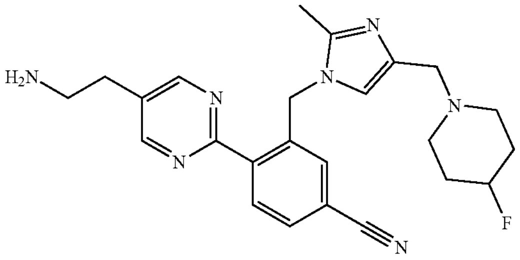 [SMILES: Cc1nc(CN2CCC(F)CC2)cn1Cc1cc(C#N)ccc1-c1ncc(CCN)cn1] | 4-[5-(2-aminoethyl)pyrimidin-2-yl]-3-[[4-[(4-fluoropiperidin-1-yl)methyl]-2-methylimidazol-1-yl]methyl]benzonitrile |

TABLE 1-continued

| Compound number | Structural formula | Compound name |
|---|---|---|
| 1178 | 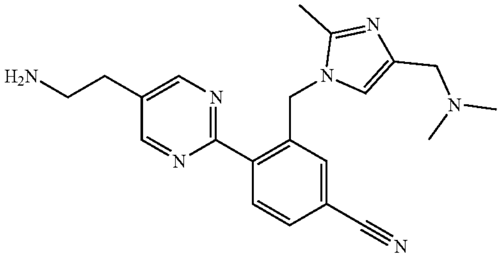 [SMILES: Cc1nc(CN(C)C)cn1Cc1cc(C#N)ccc1-c1ncc(CCN)cn1] | 4-[5-(2-aminoethyl)pyrimidin-2-yl]-3-[[4-[(dimethylamino)methyl]-2-methylimidazol-1-yl]methyl]benzonitrile |
| 1179 | 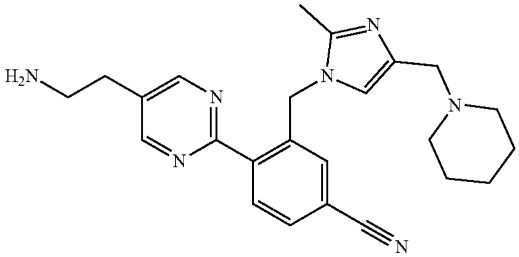 [SMILES: Cc1nc(CN2CCCCC2)cn1Cc1cc(C#N)ccc1-c1ncc(CCN)cn1] | 4-[5-(2-aminoethyl)pyrimidin-2-yl]-3-[[2-methyl-4-(piperidin-1-ylmethyl)imidazol-1-yl]methyl]benzonitrile |
| 1180 | 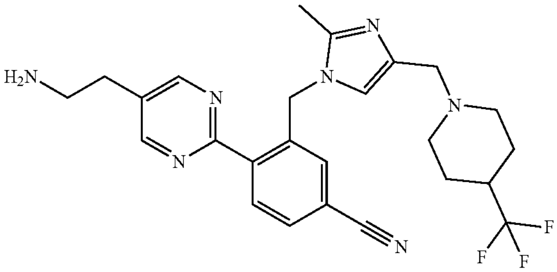 [SMILES: Cc1nc(CN2CCC(C(F)(F)F)CC2)cn1Cc1cc(C#N)ccc1-c1ncc(CCN)cn1] | 4-[5-(2-aminoethyl)pyrimidin-2-yl]-3-[[2-methyl-4-[[4-(trifluoromethyl)piperidin-1-yl]methyl]imidazol-1-yl]methyl]benzonitrile |
| 1181 | 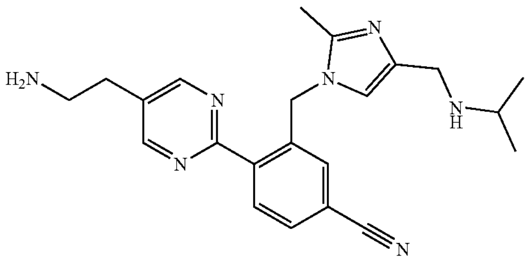 [SMILES: Cc1nc(CNC(C)C)cn1Cc1cc(C#N)ccc1-c1ncc(CCN)cn1] | 4-[5-(2-aminoethyl)pyrimidin-2-yl]-3-[[2-methyl-4-[(propan-2-ylamino)methyl]imidazol-1-yl]methyl]benzonitrile |
| 1182 | 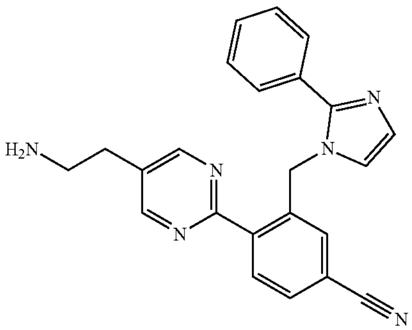 [SMILES: N#Cc1ccc(-c2ncc(CCN)cn2)c(Cn2ccnc2-c2ccccc2)c1] | 4-[5-(2-aminoethyl)pyrimidin-2-yl]-3-[(2-phenylimidazol-1-yl)methyl]benzonitrile |

TABLE 1-continued
| Compound number | Structural formula | Compound name |
|---|---|---|
| 1183 | 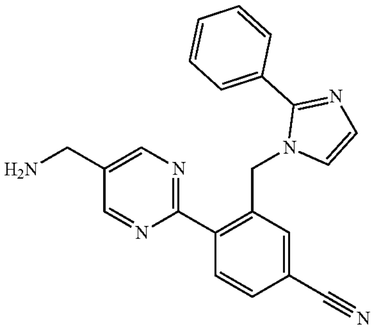 [SMILES: N#Cc1ccc(-c2ncc(CN)cn2)c(Cn2ccnc2-c2ccccc2)c1] | 4-[5-(2-aminoethyl)pyrimidin-2-yl]-3-[(2-phenylimidazol-1-yl)methyl]benzonitrile |
| 1184 | 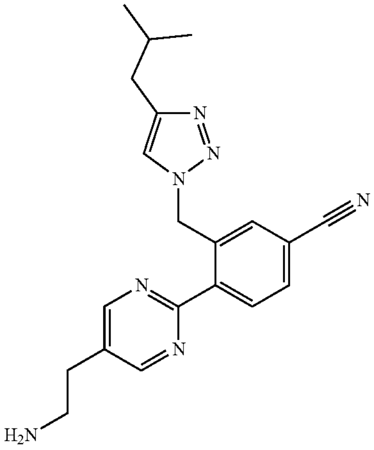 [SMILES: CC(C)Cc1cn(Cc2cc(C#N)ccc2-c2ncc(CCN)cn2)nn1] | 4-[5-(2-aminoethyl)pyrimidin-2-yl]-3-[[4-(2-methylpropyl)triazol-1-yl]methyl]benzonitrile |
| 1185 | 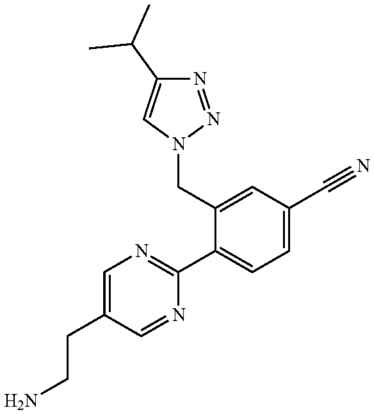 [SMILES: CC(C)c1cn(Cc2cc(C#N)ccc2-c2ncc(CCN)cn2)nn1] | 4-[5-(2-aminoethyl)pyrimidin-2-yl]-3-[(4-propan-2-yltriazol-1-yl)methyl]benzonitrile |

TABLE 1-continued
| Compound number | Structural formula | Compound name |
|---|---|---|
| 1186 | 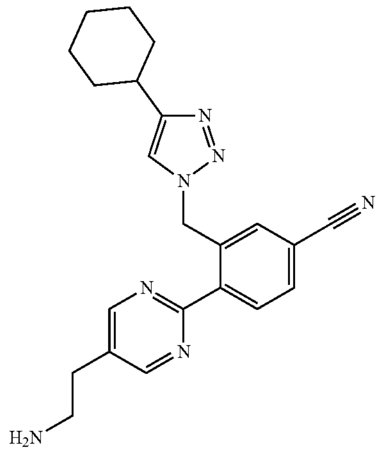 [SMILES: N#Cc1ccc(-c2ncc(CCN)cn2)c(Cn2cc(C3CCCCC3)nn2)c1] | 4-[5-(2-aminoethyl)pyrimidin-2-yl]-3-[(4-cyclohexyltriazol-1-yl)methyl]benzonitrile |
| 1187 | 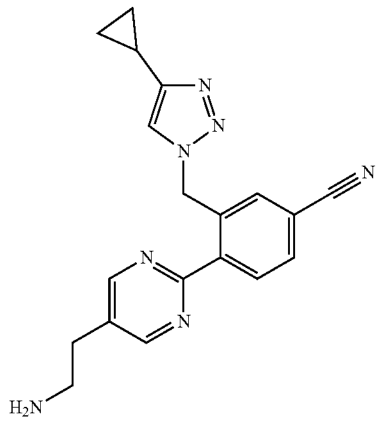 [SMILES: N#Cc1ccc(-c2ncc(CCN)cn2)c(Cn2cc(C3CC3)nn2)c1] | 4-[5-(2-aminoethyl)pyrimidin-2-yl]-3-[(4-cyclopropyltriazol-1-yl)methyl]benzonitrile |
| 1188 | 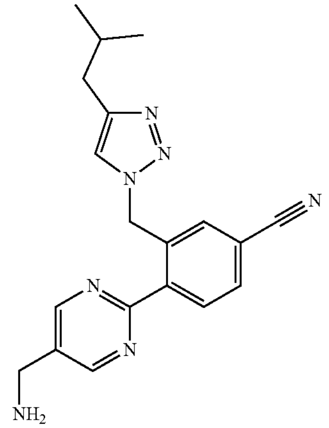 [SMILES: CC(C)Cc1cn(Cc2cc(C#N)ccc2-c2ncc(CN)cn2)nn1] | 4-[5-(aminomethyl)pyrimidin-2-yl]-3-[[4-(2-methylpropyl)triazol-1-yl]methyl]benzonitrile |

TABLE 1-continued
| Compound number | Structural formula | Compound name |
|---|---|---|
| 1189 | 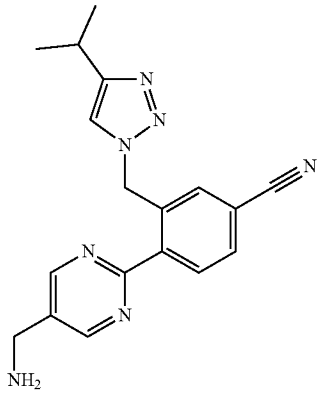 [SMILES: CC(C)c1cn(Cc2cc(C#N)ccc2-c2ncc(CN)cn2)nn1] | 4-[5-(aminomethyl)pyrimidin-2-yl]-3-[(4-propan-2-yltriazol-1-yl)methyl]benzonitrile |
| 1190 | 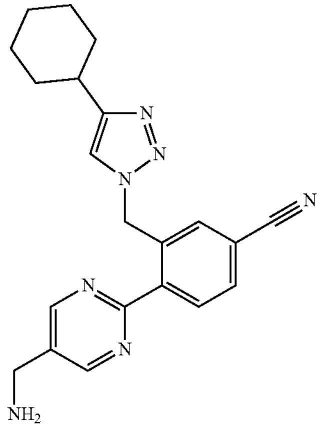 [SMILES: N#Cc1ccc(-c2ncc(CN)cn2)c(Cn2cc(C3CCCCC3)nn2)c1] | 4-[5-(aminomethyl)pyrimidin-2-yl]-3-[(4-cyclohexyltriazol-1-yl)methyl]benzonitrile |
| 1191 | 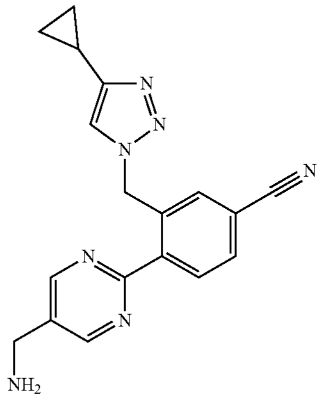 [SMILES: N#Cc1ccc(-c2ncc(CN)cn2)c(Cn2cc(C3CC3)nn2)c1] | 4-[5-(aminomethyl)pyrimidin-2-yl]-3-[(4-cyclopropyltriazol-1-yl)methyl]benzonitrile |

TABLE 1-continued
| Compound number | Structural formula | Compound name |
|---|---|---|
| 1192 | 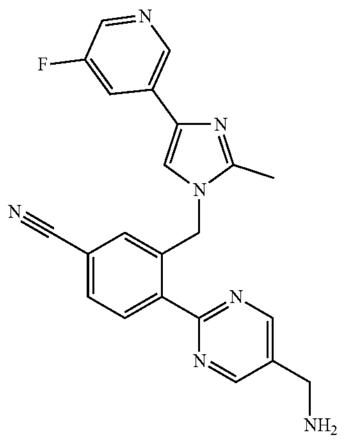 [SMILES: Cc1nc(-c2cncc(F)c2)cn1Cc1cc(C#N)ccc1-c1ncc(CN)cn1] | 4-[5-(aminomethyl)pyrimidin-2-yl]-3-[[4-(5-fluoropyridin-3-yl)-2-methylimidazol-1-yl]methyl]benzonitrile |
| 1193 | 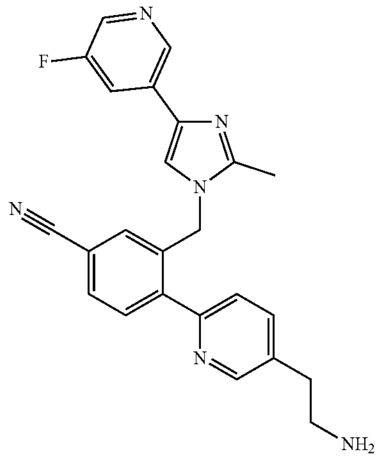 [SMILES: Cc1nc(-c2cncc(F)c2)cn1Cc1cc(C#N)ccc1-c1ccc(CCN)cn1] | 4-[5-(2-aminoethyl)pyridin-2-yl]-3-[[4-(5-fluoropyridin-3-yl)-2-methylimidazol-1-yl]methyl]benzonitrile |
| 1194 | 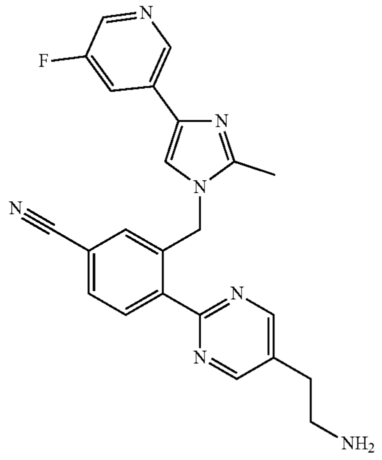 [SMILES: Cc1nc(-c2cncc(F)c2)cn1Cc1cc(C#N)ccc1-c1ncc(CCN)cn1] | 4-[5-(2-aminoethyl)pyrimidin-2-yl]-3-[[4-(5-fluoropyridin-3-yl)-2-methylimidazol-1-yl]methyl]benzonitrile |

TABLE 1-continued
| Compound number | Structural formula | Compound name |
|---|---|---|
| 1195 | 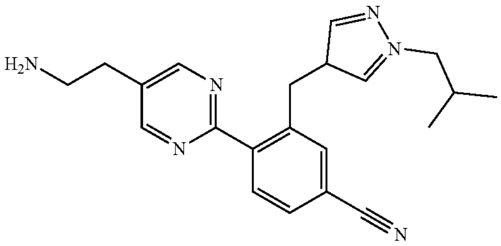 | 4-[5-(2-aminoethyl)pyrimidin-2-yl]-3-[[1-(2-methylpropyl)pyrazol-4-yl]methyl]benzonitrile |
| 1196 | 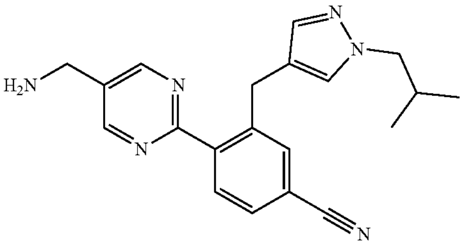 [SMILES: CC(C)Cn1cc(Cc2cc(C#N)ccc2-c2ncc(CN)cn2)cn1] | 4-[5-(aminomethyl)pyrimidin-2-yl]-3-[[1-(2-methylpropyl)pyrazol-4-yl]methyl]benzonitrile |
| 1197 | 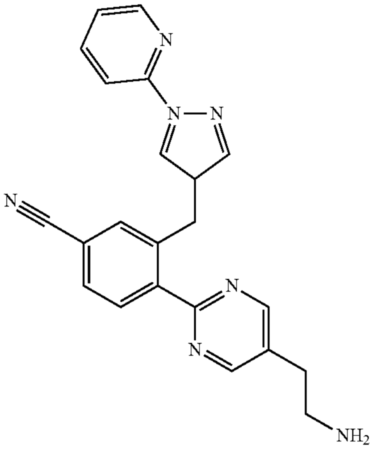 | 4-[5-(2-aminoethyl)pyrimidin-2-yl]-3-[(1-pyridin-2-ylpyrazol-4-yl)methyl]benzonitrile |
| 1198 | 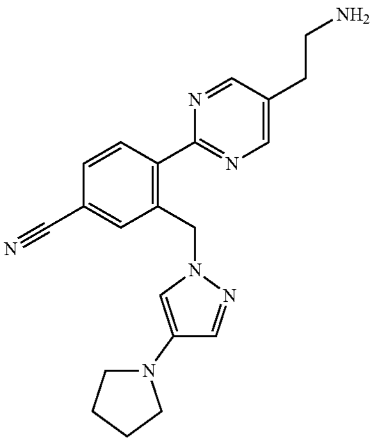 [SMILES: N#Cc1ccc(-c2ncc(CCN)cn2)c(Cn2cc(N3CCCC3)cn2)c1] | 4-[5-(2-aminoethyl)pyrimidin-2-yl]-3-[(4-pyrrolidin-1-ylpyrazol-1-yl)methyl]benzonitrile |

TABLE 1-continued
| Compound number | Structural formula | Compound name |
| --- | --- | --- |
| 1199 | 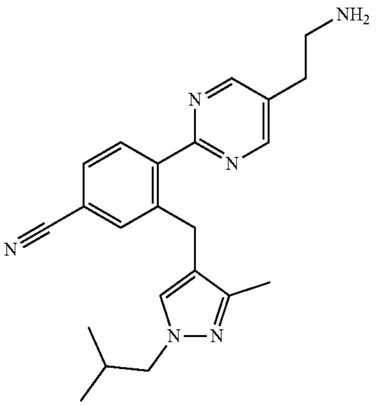 [SMILES: Cc1nn(CC(C)C)cc1Cc1cc(C#N)ccc1-c1ncc(CCN)cn1] | 4-[5-(2-aminoethyl)pyrimidin-2-yl]-3-[[3-methyl-1-(2-methylpropyl)pyrazol-4-yl]methyl]benzonitrile |
| 1200 | 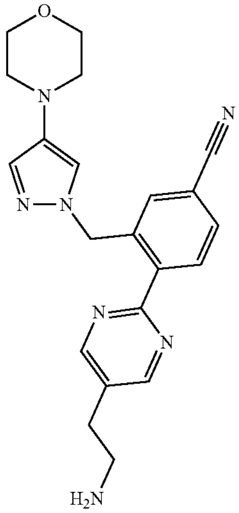 [SMILES: N#Cc1ccc(-c2ncc(CCN)cn2)c(Cn2cc(N3CCOCC3)cn2)c1] | 4-[5-(2-aminoethyl)pyrimidin-2-yl]-3-[(4-morpholin-4-ylpyrazol-1-yl)methyl]benzonitrile |
| 1201 | 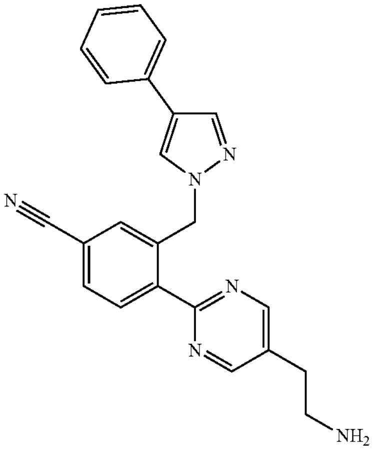 [SMILES: N#Cc1ccc(-c2ncc(CCN)cn2)c(Cn2cc(-c3ccccc3)cn2)c1] | 4-[5-(2-aminoethyl)pyrimidin-2-yl]-3-[(4-phenylpyrazol-1-yl)methyl]benzonitrile |

TABLE 1-continued

| Compound number | Structural formula | Compound name |
|---|---|---|
| 1202 | 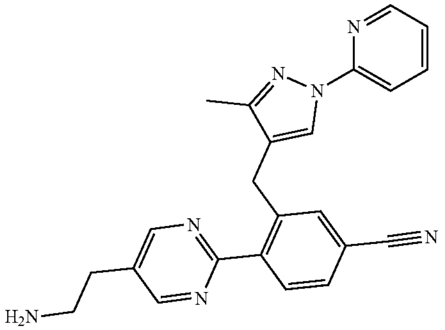 [SMILES: Cc1nn(-c2ccccn2)cc1Cc1cc(C#N)ccc1-c1ncc(CCN)cn1] | 4-[5-(2-aminoethyl)pyrimidin-2-yl]-3-[(3-methyl-1-pyridin-2-ylpyrazol-4-yl)methyl]benzonitrile |
| 1203 | 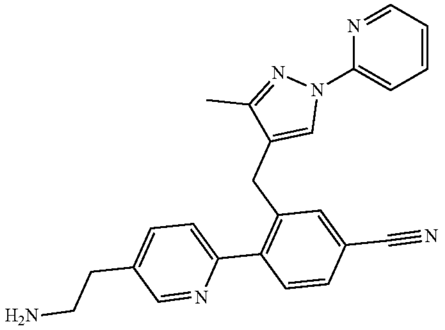 [SMILES: Cc1nn(-c2ccccn2)cc1Cc1cc(C#N)ccc1-c1ccc(CCN)cn1] | 4-[5-(2-aminoethyl)pyridin-2-yl]-3-[(3-methyl-1-pyridin-2-ylpyrazol-4-yl)methyl]benzonitrile |
| 1204 | 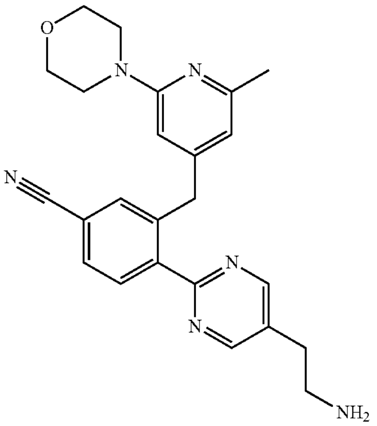 [SMILES: Cc1cc(Cc2cc(C#N)ccc2-c2ncc(CCN)cn2)cc(N2CCOCC2)n1] | 4-[5-(2-aminoethyl)pyrimidin-2-yl]-3-[(2-methyl-6-morpholin-4-ylpyridin-4-yl)methyl]benzonitrile |
| 1205 | 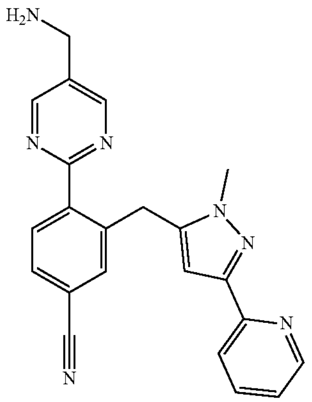 [SMILES: Cn1nc(-c2ccccn2)cc1Cc1cc(C#N)ccc1-c1ncc(CN)cn1] | 4-[5-(aminomethyl)pyrimidin-2-yl]-3-[(2-methyl-5-pyridin-2-ylpyrazol-3-yl)methyl]benzonitrile |

TABLE 1-continued
| Compound number | Structural formula | Compound name |
|---|---|---|
| 1206 | 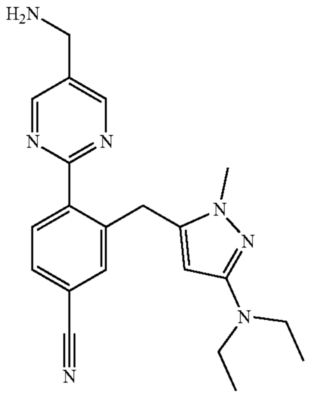 [SMILES: CCN(CC)c1cc(Cc2cc(C#N)ccc2-c2ncc(CN)cn2)n(C)n1] | 4-[5-(aminomethyl)pyrimidin-2-yl]-3-[[5-(diethylamino)-2-methylpyrazol-3-yl]methyl]benzonitrile |
| 1207 | 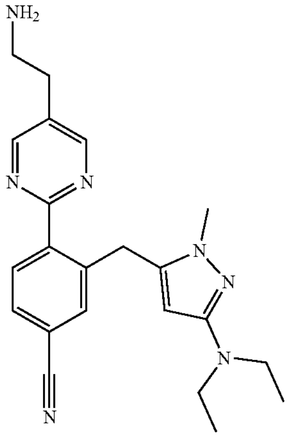 [SMILES: CCN(CC)c1cc(Cc2cc(C#N)ccc2-c2ncc(CCN)cn2)n(C)n1] | 4-[5-(2-aminoethyl)pyrimidin-2-yl]-3-[[5-(diethylamino)-2-methylpyrazol-3-yl]methyl]benzonitrile |
| 1208 | 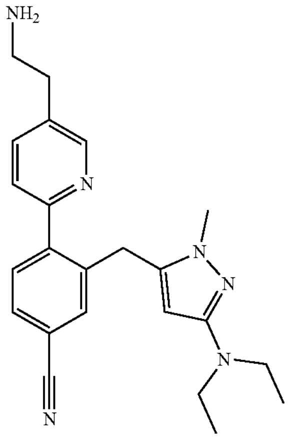 [SMILES: CCN(CC)c1cc(Cc2cc(C#N)ccc2-c2ccc(CCN)cn2)n(C)n1] | 4-[5-(2-aminoethyl)pyridin-2-yl]-3-[[5-(diethylamino)-2-methylpyrazol-3-yl]methyl]benzonitrile |

TABLE 1-continued
| Compound number | Structural formula | Compound name |
|---|---|---|
| 1209 | 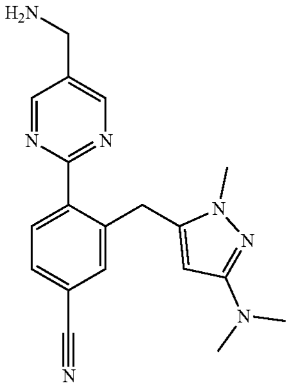 [SMILES: CN(C)c1cc(Cc2cc(C#N)ccc2-c2ncc(CN)cn2)n(C)n1] | 4-[5-(aminomethyl)pyrimidin-2-yl]-3-[[5-(dimethylamino)-2-methylpyrazol-3-yl]methyl]benzonitrile |
| 1210 | 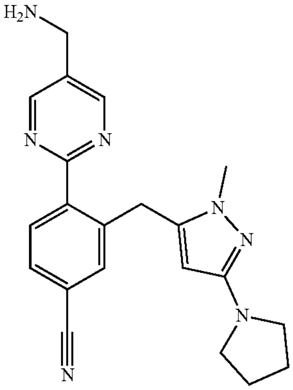 [SMILES: Cn1nc(N2CCCC2)cc1Cc1cc(C#N)ccc1-c1ncc(CN)cn1] | 4-[5-(aminomethyl)pyrimidin-2-yl]-3-[(2-methyl-5-pyrrolidin-1-ylpyrazol-3-yl)methyl]benzonitrile |
| 1211 | 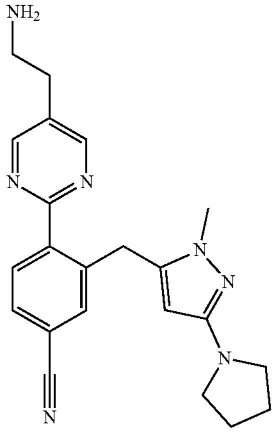 [SMILES: Cn1nc(N2CCCC2)cc1Cc1cc(C#N)ccc1-c1ncc(CCN)cn1] | 4-[5-(2-aminoethyl)pyrimidin-2-yl]-3-[(2-methyl-5-pyrrolidin-1-ylpyrazol-3-yl)methyl]benzonitrile |

TABLE 1-continued
| Compound number | Structural formula | Compound name |
|---|---|---|
| 1212 | 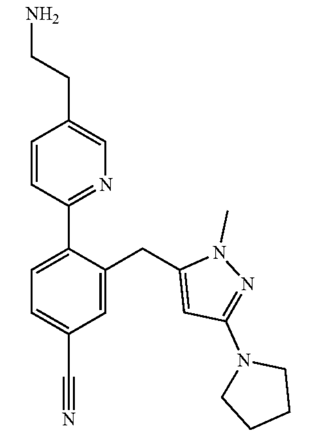 [SMILES: Cn1nc(N2CCCC2)cc1Cc1cc(C#N)ccc1-c1ccc(CCN)cn1] | 4-[5-(2-aminoethyl)pyridin-2-yl]-3-[(2-methyl-5-pyrrolidin-1-ylpyrazol-3-yl)methyl]benzonitrile |
| 1213 | 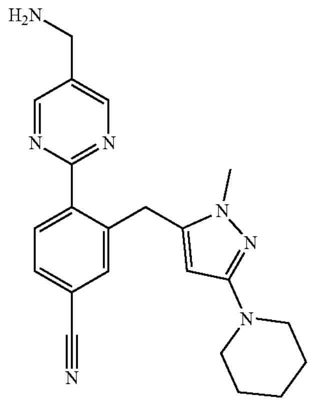 [SMILES: Cn1nc(N2CCCCC2)cc1Cc1cc(C#N)ccc1-c1ncc(CN)cn1] | 4-[5-(aminomethyl)pyrimidin-2-yl]-3-[(2-methyl-5-piperidin-1-ylpyrazol-3-yl)methyl]benzonitrile |
| 1214 | 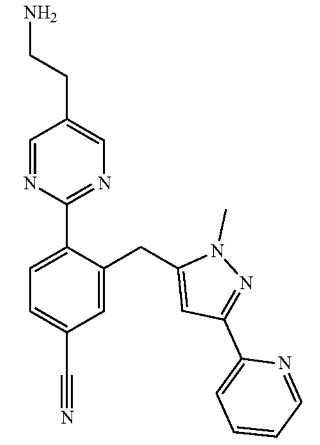 [SMILES: Cn1nc(-c2ccccn2)cc1Cc1cc(C#N)ccc1-c1ncc(CCN)cn1] | 4-[5-(2-aminoethyl)pyrimidin-2-yl]-3-[(2-methyl-5-pyridin-2-ylpyrazol-3-yl)methyl]benzonitrile |

TABLE 1-continued
| Compound number | Structural formula | Compound name |
| --- | --- | --- |
| 1215 | 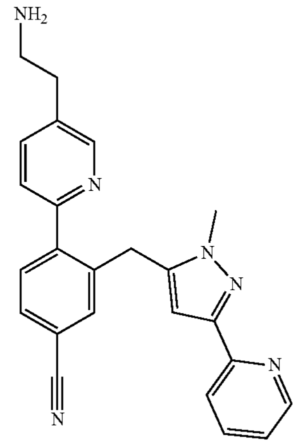 [SMILES: Cn1nc(-c2ccccn2)cc1Cc1cc(C#N)ccc1-c1ccc(CCN)cn1] | 4-[5-(2-aminoethyl)pyridin-2-yl]-3-[(2-methyl-5-pyridin-2-ylpyrazol-3-yl)methyl]benzonitrile |
| 1216 | 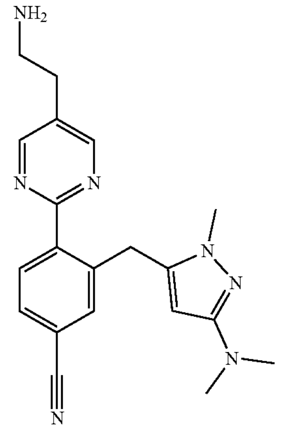 [SMILES: CN(C)c1cc(Cc2cc(C#N)ccc2-c2ncc(CCN)cn2)n(C)n1] | 4-[5-(2-aminoethyl)pyrimidin-2-yl]-3-[[5-(dimethylamino)-2-methylpyrazol-3-yl]methyl]benzonitrile |
| 1217 | 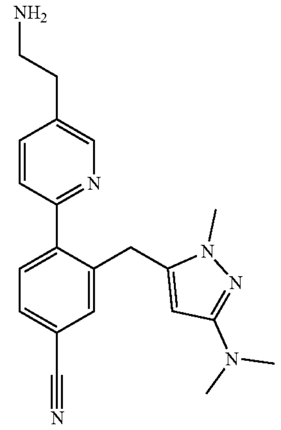 [SMILES: CN(C)c1cc(Cc2cc(C#N)ccc2-c2ccc(CCN)cn2)n(C)n1] | 4-[5-(2-aminoethyl)pyridin-2-yl]-3-[[5-(dimethylamino)-2-methylpyrazol-3-yl]methyl]benzonitrile |

TABLE 1-continued
| Compound number | Structural formula | Compound name |
|---|---|---|
| 1218 | 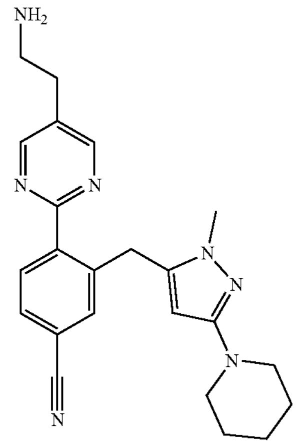 [SMILES: Cn1nc(N2CCCCC2)cc1Cc1cc(C#N)ccc1-c1ncc(CCN)cn1] | 4-[5-(2-aminoethyl)pyrimidin-2-yl]-3-[(2-methyl-5-piperidin-1-ylpyrazol-3-yl)methyl]benzonitrile |
| 1219 | 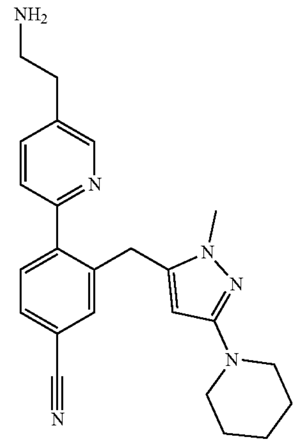 [SMILES: Cn1nc(N2CCCCC2)cc1Cc1cc(C#N)ccc1-c1ccc(CCN)cn1] | 4-[5-(2-aminoethyl)pyridin-2-yl]-3-[(2-methyl-5-piperidin-1-ylpyrazol-3-yl)methyl]benzonitrile |
| 1220 | 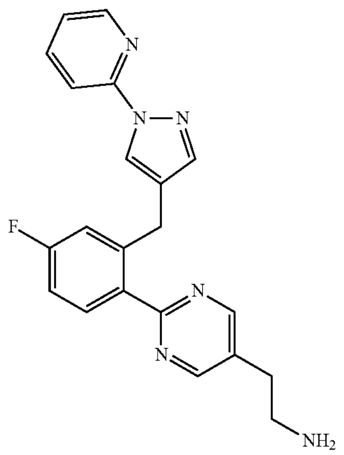 [SMILES: NCCc1cnc(-c2ccc(F)cc2Cc2cnn(-c3ccccn3)c2)nc1] | 2-[2-[4-fluoro-2-[(1-pyridin-2-ylpyrazol-4-yl)methyl]phenyl]pyrimidin-5-yl]ethanamine |

TABLE 1-continued
| Compound number | Structural formula | Compound name |
|---|---|---|
| 1221 | 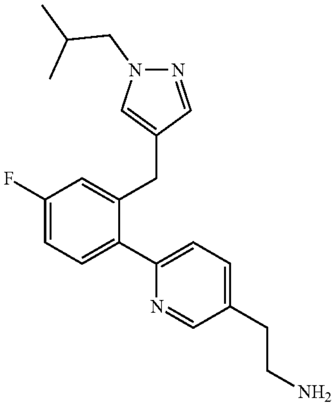 [SMILES: CC(C)Cn1cc(Cc2cc(F)ccc2-c2ccc(CCN)cn2)cn1] | 2-[6-[4-fluoro-2-[[1-(2-methylpropyl)pyrazol-4-yl]methyl]phenyl]pyridin-3-yl]ethanamine |
| 1222 | 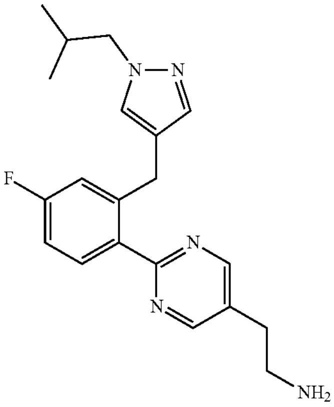 [SMILES: CC(C)Cn1cc(Cc2cc(F)ccc2-c2ncc(CCN)cn2)cn1] | 2-[2-[4-fluoro-2-[[1-(2-methylpropyl)pyrazol-4-yl]methyl]phenyl]pyrimidin-5-yl]ethanamine |
| 1223 | 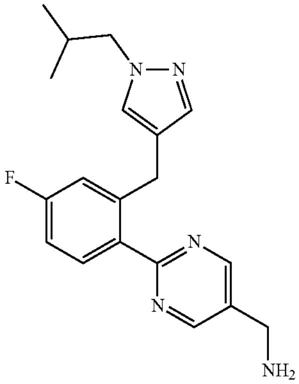 [SMILES: CC(C)Cn1cc(Cc2cc(F)ccc2-c2ncc(CN)cn2)cn1] | [2-[4-fluoro-2-[[1-(2-methylpropyl)pyrazol-4-yl]methyl]phenyl]pyrimidin-5-yl]methanamine |

TABLE 1-continued
| Compound number | Structural formula | Compound name |
|---|---|---|
| 1224 | 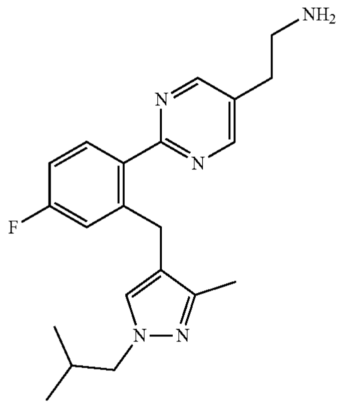 [SMILES: Cc1nn(CC(C)C)cc1Cc1cc(F)ccc1-c1ncc(CCN)cn1] | 2-[2-[4-fluoro-2-[[3-methyl-1-(2-methylpropyl)pyrazol-4-yl]methyl]phenyl]pyrimidin-5-yl]ethanamine |
| 1225 | 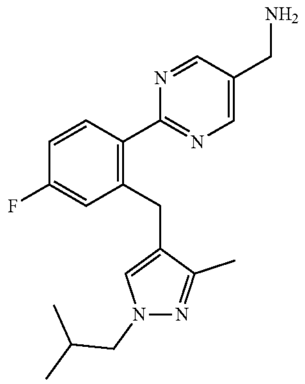 [SMILES: Cc1nn(CC(C)C)cc1Cc1cc(F)ccc1-c1ncc(CN)cn1] | [2-[4-fluoro-2-[[3-methyl-1-(2-methylpropyl)pyrazol-4-yl]methyl]phenyl]pyrimidin-5-yl]methanamine |
| 1226 | 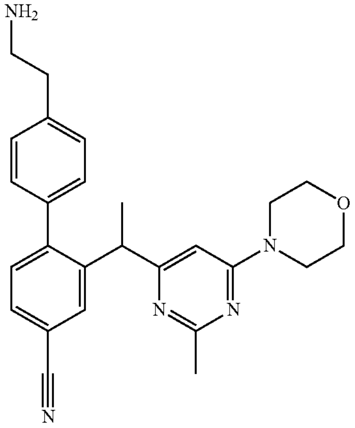 [SMILES: Cc1nc(C(C)c2cc(C#N)ccc2-c2ccc(CCN)cc2)cc(N2CCOCC2)n1] | 4-[4-(2-aminoethyl)phenyl]-3-[1-(2-methyl-6-morpholin-4-ylpyrimidin-4-yl)ethyl]benzonitrile |

TABLE 1-continued
| Compound number | Structural formula | Compound name |
| --- | --- | --- |
| 1227 | 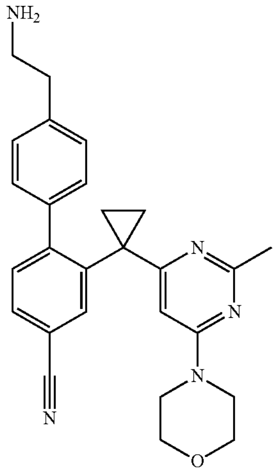 [SMILES: Cc1nc(N2CCOCC2)cc(C2(c3cc(C#N)ccc3-c3ccc(CCN)cc3)CC2)n1] | 4-[4-(2-aminoethyl)phenyl]-3-[1-(2-methyl-6-morpholin-4-ylpyrimidin-4-yl)cyclopropyl]benzonitrile |
| 1228 | 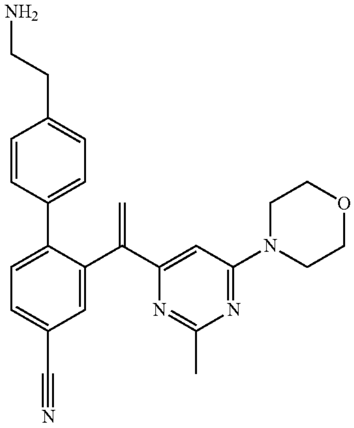 [SMILES: C=C(c1cc(N2CCOCC2)nc(C)n1)c1cc(C#N)ccc1-c1ccc(CCN)cc1] | 4-[4-(2-aminoethyl)phenyl]-3-[1-(2-methyl-6-morpholin-4-ylpyrimidin-4-yl)ethenyl]benzonitrile |
| 1229 | 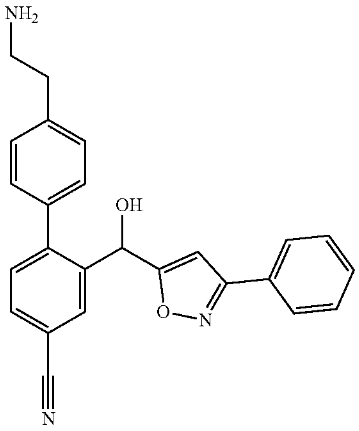 [SMILES: N#Cc1ccc(-c2ccc(CCN)cc2)c(C(O)c2cc(-c3ccccc3)no2)c1] | 4-[4-(2-aminoethyl)phenyl]-3-[hydroxy-(3-phenyl-1,2-oxazol-5-yl)methyl]benzonitrile |

TABLE 1-continued
| Compound number | Structural formula | Compound name |
|---|---|---|
| 1230 | 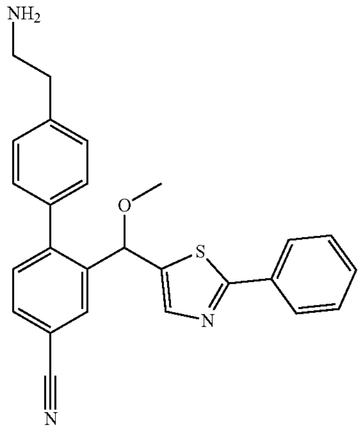 [SMILES: COC(c1cnc(-c2ccccc2)s1)c1cc(C#N)ccc1-c1ccc(CCN)cc1] | 4-[4-(2-aminoethyl)phenyl]-3-[methoxy-(2-phenyl-1,3-thiazol-5-yl)methyl]benzonitrile |
| 1231 | 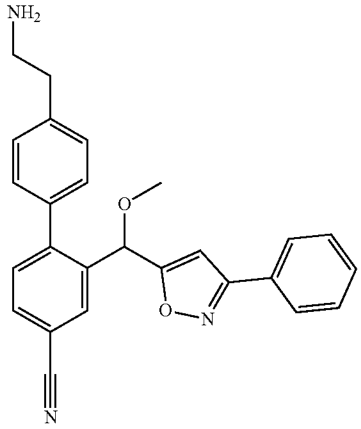 [SMILES: COC(c1cc(-c2ccccc2)no1)c1cc(C#N)ccc1-c1ccc(CCN)cc1] | 4-[4-(2-aminoethyl)phenyl]-3-[methoxy-(3-phenyl-1,2-oxazol-5-yl)methyl]benzonitrile |
| 1232 | 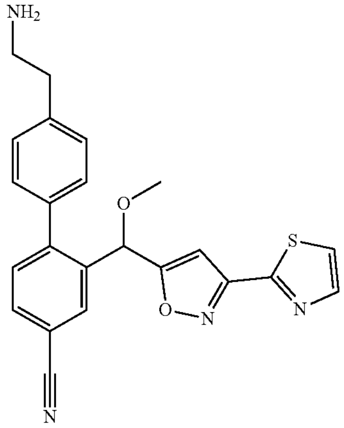 [SMILES: COC(c1cc(-c2nccs2)no1)c1cc(C#N)ccc1-c1ccc(CCN)cc1] | 4-[4-(2-aminoethyl)phenyl]-3-[methoxy-[3-(1,3-thiazol-2-yl)-1,2-oxazol-5-yl]methyl]benzonitrile |

TABLE 1-continued
| Compound number | Structural formula | Compound name |
| --- | --- | --- |
| 1233 | 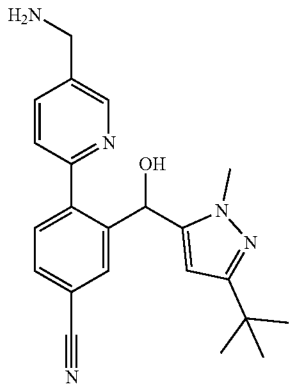 [SMILES: Cn1nc(C(C)(C)C)cc1C(O)c1cc(C#N)ccc1-c1ccc(CN)cn1] | 4-[5-(aminomethyl)pyridin-2-yl]-3-[(5-tert-butyl-2-methylpyrazol-3-yl)-hydroxymethyl]benzonitrile |
| 1234 | 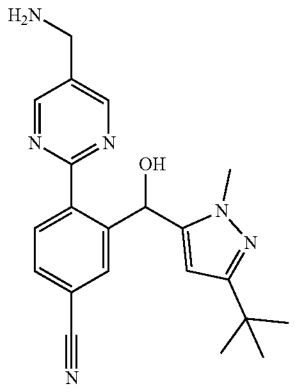 [SMILES: Cn1nc(C(C)(C)C)cc1C(O)c1cc(C#N)ccc1-c1ncc(CN)cn1] | 4-[5-(aminomethyl)pyrimidin-2-yl]-3-[(5-tert-butyl-2-methylpyrazol-3-yl)-hydroxymethyl]benzonitrile |
| 1235 | 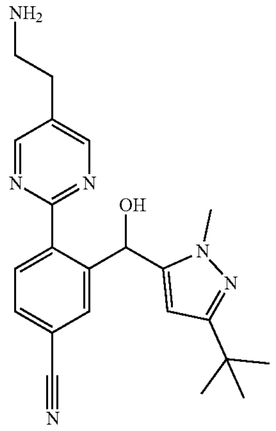 [SMILES: Cn1nc(C(C)(C)C)cc1C(O)c1cc(C#N)ccc1-c1ncc(CCN)cn1] | 4-[5-(2-aminoethyl)pyrimidin-2-yl]-3-[(5-tert-butyl-2-methylpyrazol-3-yl)-hydroxymethyl]benzonitrile |

TABLE 1-continued
| Compound number | Structural formula | Compound name |
|---|---|---|
| 1236 | 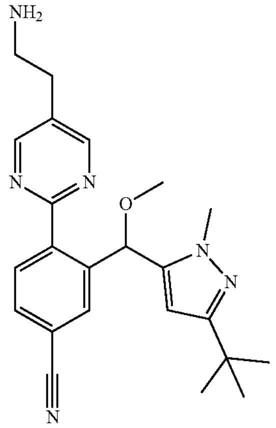 [SMILES: COC(c1cc(C#N)ccc1-c1ncc(CCN)cn1)c1cc(C(C)(C)C)nn1C] | 4-[5-(2-aminoethyl)pyrimidin-2-yl]-3-[(5-tert-butyl-2-methylpyrazol-3-yl)-methoxymethyl]benzonitrile |
| 1237 | 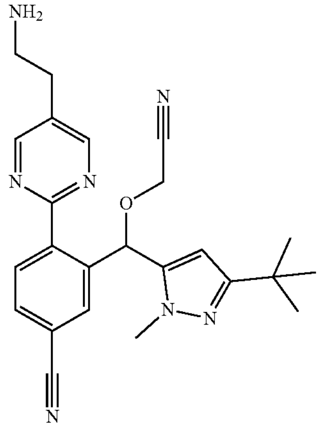 [SMILES: Cn1nc(C(C)(C)C)cc1C(OCC#N)c1cc(C#N)ccc1-c1ncc(CCN)cn1] | 4-[5-(2-aminoethyl)pyrimidin-2-yl]-3-[(5-tert-butyl-2-methylpyrazol-3-yl)-(cyanomethoxy)methyl]benzonitrile |
| 1238 | 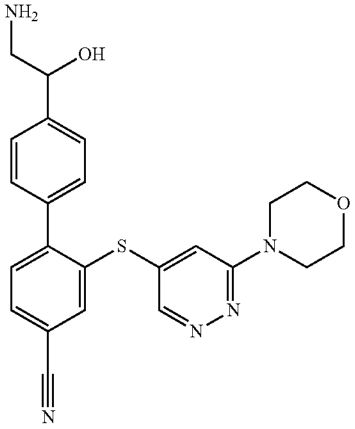 [SMILES: N#Cc1ccc(-c2ccc(C(O)CN)cc2)c(Sc2cnnc(N3CCOCC3)c2)c1] | 4-[4-(2-amino-1-hydroxyethyl)phenyl]-3-(6-morpholin-4-ylpyridazin-4-yl)sulfanylbenzonitrile |

TABLE 1-continued
| Compound number | Structural formula | Compound name |
|---|---|---|
| 1239 | 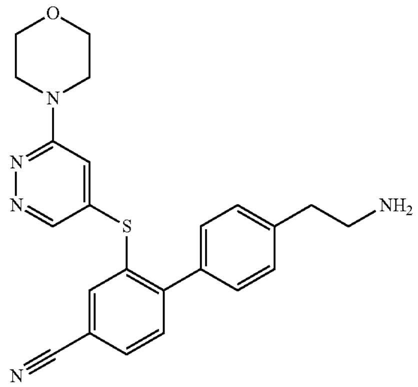 [SMILES: N#Cc1ccc(-c2ccc(CCN)cc2)c(Sc2cnnc(N3CCOCC3)c2)c1] | 4-[4-(2-aminoethyl)phenyl]-3-(6-morpholin-4-ylpyridazin-4-yl)sulfanylbenzonitrile |
| 1240 | 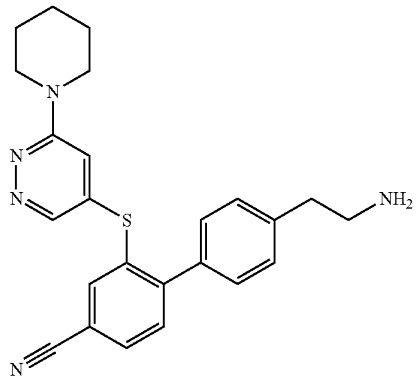 [SMILES: N#Cc1ccc(-c2ccc(CCN)cc2)c(Sc2cnnc(N3CCCCC3)c2)c1] | 4-[4-(2-aminoethyl)phenyl]-3-(6-piperidin-1-ylpyridazin-4-yl)sulfanylbenzonitrile |
| 1241 | 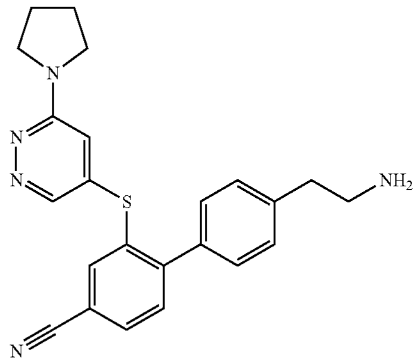 [SMILES: N#Cc1ccc(-c2ccc(CCN)cc2)c(Sc2cnnc(N3CCCC3)c2)c1] | 4-[4-(2-aminoethyl)phenyl]-3-(6-pyrrolidin-1-ylpyridazin-4-yl)sulfanylbenzonitrile |
| 1242 | 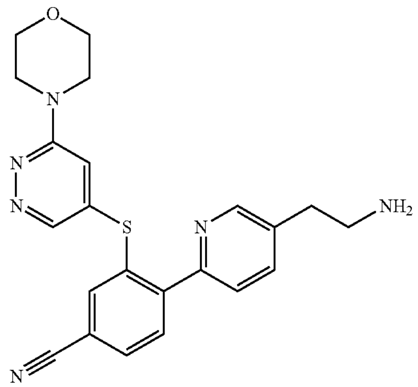 [SMILES: N#Cc1ccc(-c2ccc(CCN)cn2)c(Sc2cnnc(N3CCOCC3)c2)c1] | 4-[5-(2-aminoethyl)pyridin-2-yl]-3-(6-morpholin-4-ylpyridazin-4-yl)sulfanylbenzonitrile |

TABLE 1-continued

| Compound number | Structural formula | Compound name |
|---|---|---|
| 1243 | 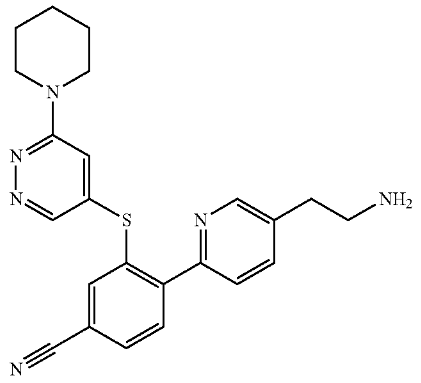 [SMILES: N#Cc1ccc(-c2ccc(CCN)cn2)c(Sc2cnnc(N3CCCCC3)c2)c1] | 4-[5-(2-aminoethyl)pyridin-2-yl]-3-(6-piperidin-1-ylpyridazin-4-yl)sulfanylbenzonitrile |
| 1244 | 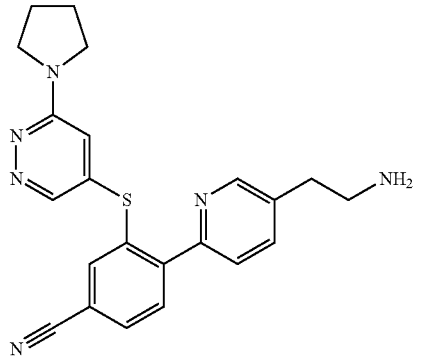 [SMILES: N#Cc1ccc(-c2ccc(CCN)cn2)c(Sc2cnnc(N3CCCC3)c2)c1] | 4-[5-(2-aminoethyl)pyridin-2-yl]-3-(6-pyrrolidin-1-ylpyridazin-4-yl)sulfanylbenzonitrile |
| 1245 | 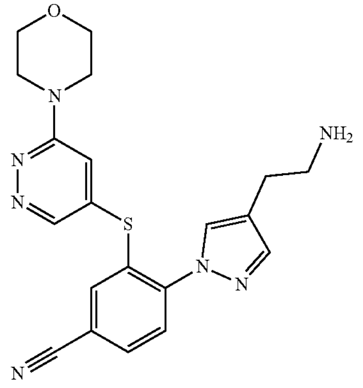 [SMILES: N#Cc1ccc(-n2cc(CCN)cn2)c(Sc2cnnc(N3CCOCC3)c2)c1] | 4-[4-(2-aminoethyl)pyrazol-1-yl]-3-(6-morpholin-4-ylpyridazin-4-yl)sulfanylbenzonitrile |
| 1246 | 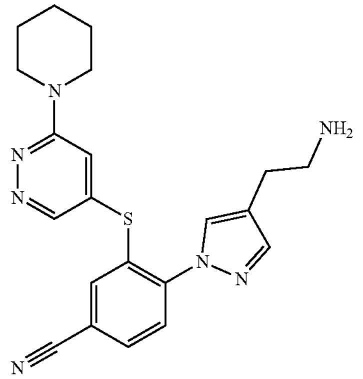 [SMILES: N#Cc1ccc(-n2cc(CCN)cn2)c(Sc2cnnc(N3CCCCC3)c2)c1] | 4-[4-(2-aminoethyl)pyrazol-1-yl]-3-(6-piperidin-1-ylpyridazin-4-yl)sulfanylbenzonitrile |

TABLE 1-continued

| Compound number | Structural formula | Compound name |
|---|---|---|
| 1247 | 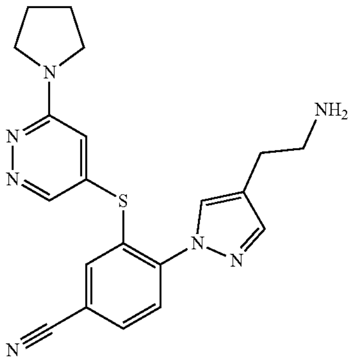 | 4-[4-(2-aminoethyl)pyrazol-1-yl]-3-(6-pyrrolidin-1-ylpyridazin-4-yl)sulfanylbenzonitrile |
| 1248 | 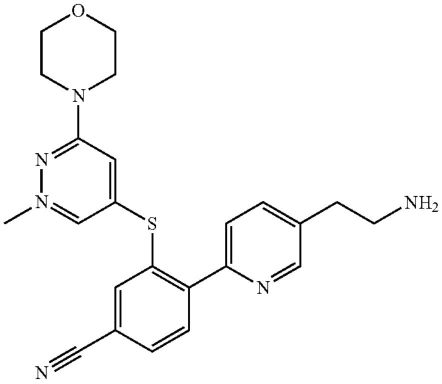 | 4-[5-(2-aminoethyl)pyridin-2-yl]-3-(2-methyl-6-morpholin-4-ylpyrimidin-4-yl)sulfanylbenzonitrile |
| 1249 | 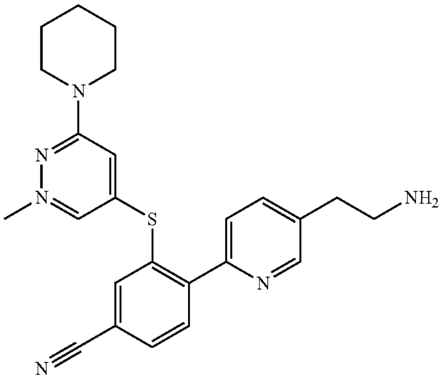 | 4-[5-(2-aminoethyl)pyridin-2-yl]-3-(2-methyl-6-piperidin-1-ylpyrimidin-4-yl)sulfanylbenzonitrile |
| 1250 | 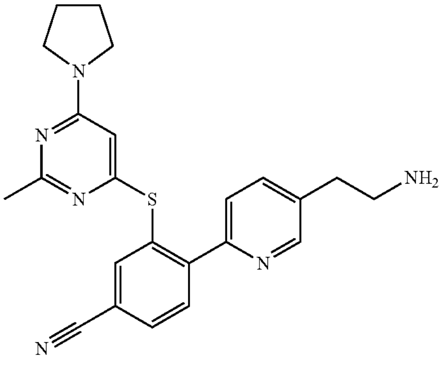 [SMILES: Cc1nc(Sc2cc(C#N)ccc2-c2ccc(CCN)cn2)cc(N2CCCC2)n1] | 4-[5-(2-aminoethyl)pyridin-2-yl]-3-(2-methyl-6-pyrrolidin-1-ylpyrimidin-4-yl)sulfanylbenzonitrile |

TABLE 1-continued

| Compound number | Structural formula | Compound name |
| --- | --- | --- |
| 1251 | 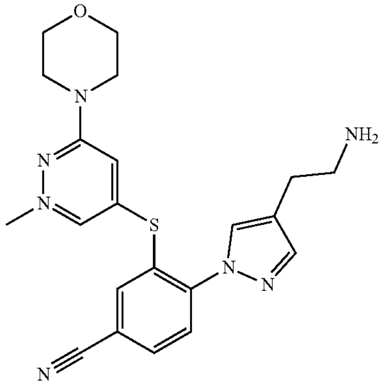 | 4-[4-(2-aminoethyl)pyrazol-1-yl]-3-(2-methyl-6-morpholin-4-ylpyrimidin-4-yl)sulfanylbenzonitrile |
| 1252 | 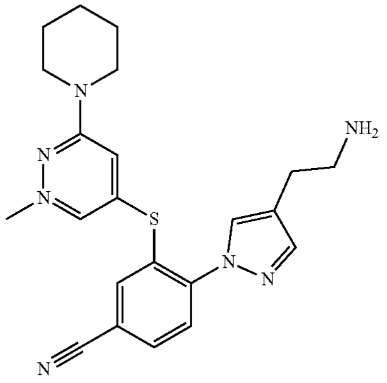 | 4-[4-(2-aminoethyl)pyrazol-1-yl]-3-(2-methyl-6-piperidin-1-ylpyrimidin-4-yl)sulfanylbenzonitrile |
| 1253 | 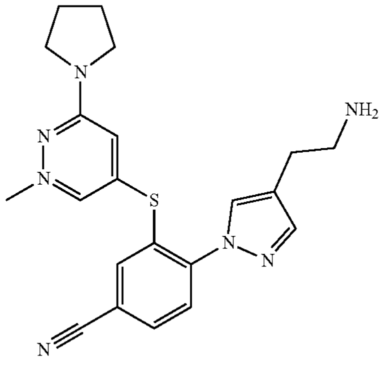 | 4-[4-(2-aminoethyl)pyrazol-1-yl]-3-(2-methyl-6-pyrrolidin-1-ylpyrimidin-4-yl)sulfanylbenzonitrile |
| 1254 | 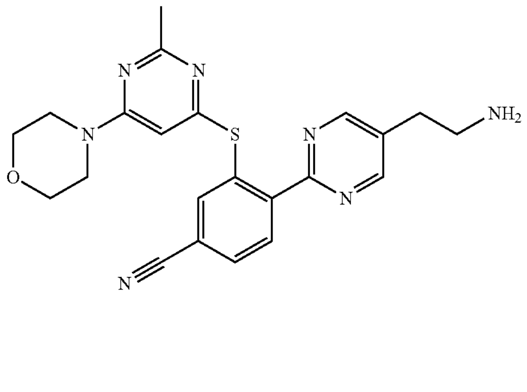 [SMILES: Cc1nc(Sc2cc(C#N)ccc2-c2ncc(CCN)cn2)cc(N2CCOCC2)n1] | 4-[5-(2-aminoethyl)pyrimidin-2-yl]-3-(2-methyl-6-morpholin-4-ylpyrimidin-4-yl)sulfanylbenzonitrile |

TABLE 1-continued

| Compound number | Structural formula | Compound name |
|---|---|---|
| 1255 | 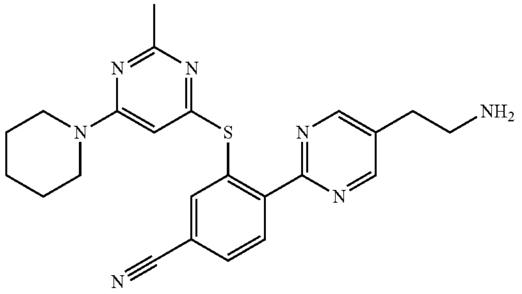 | 4-[5-(2-aminoethyl)pyrimidin-2-yl]-3-(2-methyl-6-piperidin-1-ylpyrimidin-4-yl)sulfanylbenzonitrile |
| 1256 | 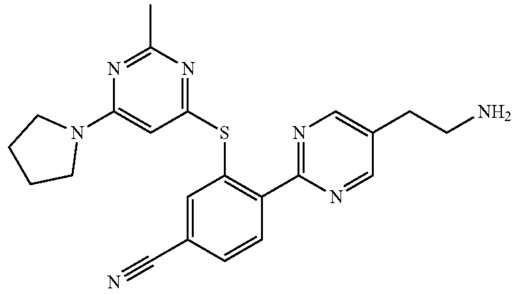 | 4-[5-(2-aminoethyl)pyrimidin-2-yl]-3-(2-methyl-6-pyrrolidin-1-ylpyrimidin-4-yl)sulfanylbenzonitrile |
| 1257 | 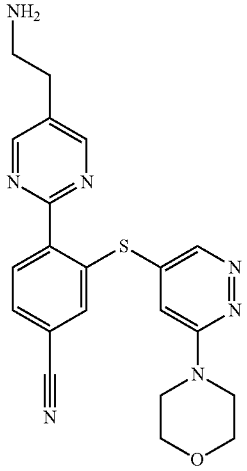 [SMILES: N#Cc1ccc(-c2ncc(CCN)cn2)c(Sc2cnnc(N3CCOCC3)c2)c1] | 4-[5-(2-aminoethyl)pyrimidin-2-yl]-3-(6-morpholin-4-ylpyridazin-4-yl)sulfanylbenzonitrile |
| 1258 | 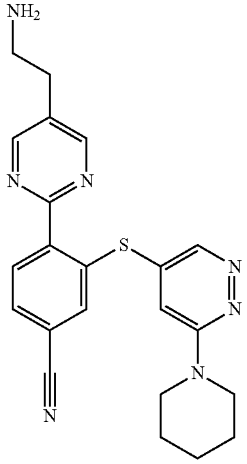 [SMILES: N#Cc1ccc(-c2ncc(CCN)cn2)c(Sc2cnnc(N3CCCCC3)c2)c1] | 4-[5-(2-aminoethyl)pyrimidin-2-yl]-3-(6-piperidin-1-ylpyridazin-4-yl)sulfanylbenzonitrile |

TABLE 1-continued
| Compound number | Structural formula | Compound name |
|---|---|---|
| 1259 | 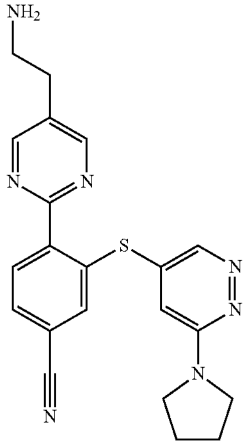 [SMILES: N#Cc1ccc(-c2ncc(CCN)cn2)c(Sc2cnnc(N3CCCC3)c2)c1] | 4-[5-(2-aminoethyl)pyrimidin-2-yl]-3-(6-pyrrolidin-1-ylpyridazin-4-yl)sulfanylbenzonitrile |
| 1260 | 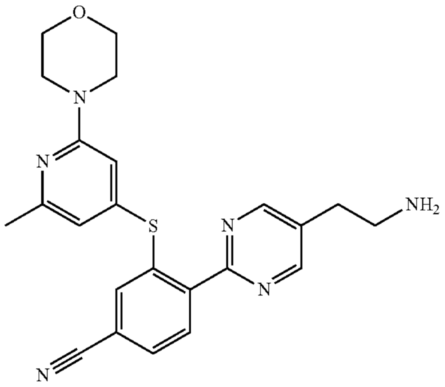 [SMILES: Cc1cc(Sc2cc(C#N)ccc2-c2ncc(CCN)cn2)cc(N2CCOCC2)n1] | 4-[5-(2-aminoethyl)pyrimidin-2-yl]-3-(2-methyl-6-morpholin-4-ylpyridin-4-yl)sulfanylbenzonitrile |
| 1261 | 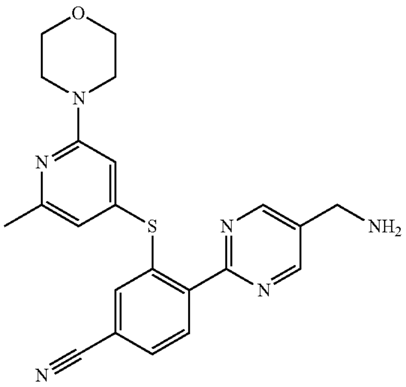 [SMILES: Cc1cc(Sc2cc(C#N)ccc2-c2ncc(CN)cn2)cc(N2CCOCC2)n1] | 4-[5-(aminomethyl)pyrimidin-2-yl]-3-(2-methyl-6-morpholin-4-ylpyridin-4-yl)sulfanylbenzonitrile |

TABLE 1-continued

| Compound number | Structural formula | Compound name |
|---|---|---|
| 1262 | 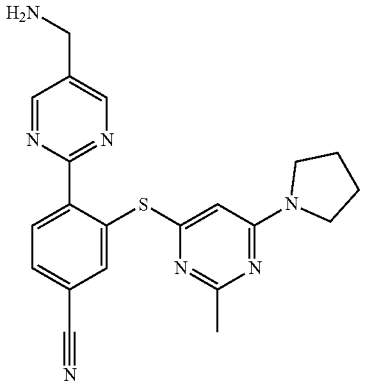 | 4-[5-(aminomethyl)pyrimidin-2-yl]-3-(2-methyl-6-pyrrolidin-1-ylpyrimidin-4-yl)sulfanylbenzonitrile |
| 1263 | 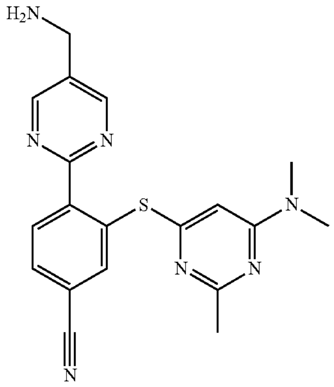 [SMILES: Cc1nc(Sc2cc(C#N)ccc2-c2ncc(CN)cn2)cc(N(C)C)n1] | 4-[5-(aminomethyl)pyrimidin-2-yl]-3-[6-(dimethylamino)-2-methylpyrimidin-4-yl]sulfanylbenzonitrile |
| 1264 | 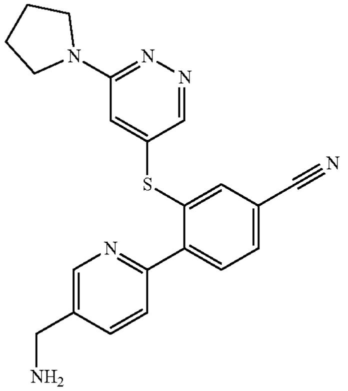 | 4-[5-(aminomethyl)pyridin-2-yl]-3-(6-pyrrolidin-1-ylpyridazin-4-yl)sulfanylbenzonitrile |
| 1265 | 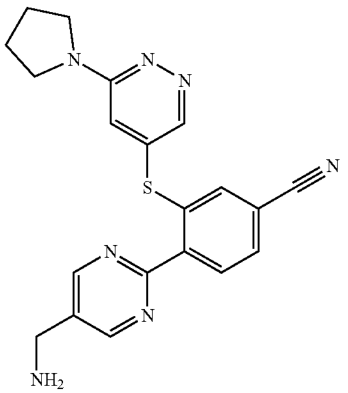 [SMILES: N#Cc1ccc(-c2ncc(CN)cn2)c(Sc2cnnc(N3CCCC3)c2)c1] | 4-[5-(aminomethyl)pyrimidin-2-yl]-3-(6-pyrrolidin-1-ylpyridazin-4-yl)sulfanylbenzonitrile |

TABLE 1-continued

| Compound number | Structural formula | Compound name |
| --- | --- | --- |
| 1266 | 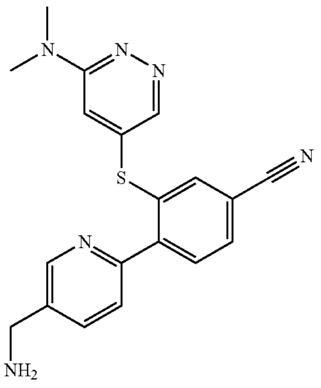 | 4-[5-(aminomethyl)pyridin-2-yl]-3-[6-(dimethylamino)pyridazin-4-yl]sulfanylbenzonitrile |
| 1267 | 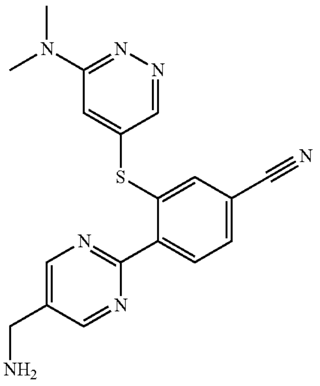 [SMILES: CN(C)c1cc(Sc2cc(C#N)ccc2-c2ncc(CN)cn2)cnn1] | 4-[5-(aminomethyl)pyrimidin-2-yl]-3-[6-(dimethylamino)pyridazin-4-yl]sulfanylbenzonitrile |
| 1268 | 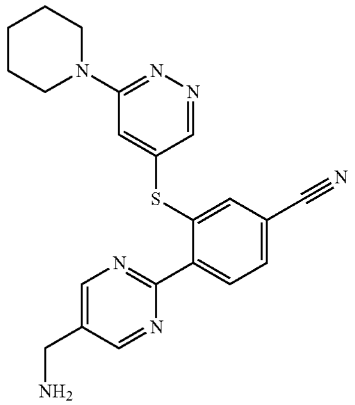 [SMILES: N#Cc1ccc(-c2ncc(CN)cn2)c(Sc2cnnc(N3CCCCC3)c2)c1] | 4-[5-(aminomethyl)pyrimidin-2-yl]-3-(6-piperidin-1-ylpyridazin-4-yl)sulfanylbenzonitrile |
| 1269 | 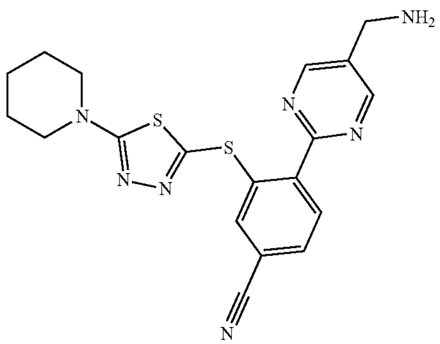 [SMILES: N#Cc1ccc(-c2ncc(CN)cn2)c(Sc2nnc(N3CCCCC3)s2)c1] | 4-[5-(aminomethyl)pyrimidin-2-yl]-3-[(5-piperidin-1-yl-1,3,4-thiadiazol-2-yl)sulfanyl]benzonitrile |

TABLE 1-continued

| Compound number | Structural formula | Compound name |
|---|---|---|
| 1270 | 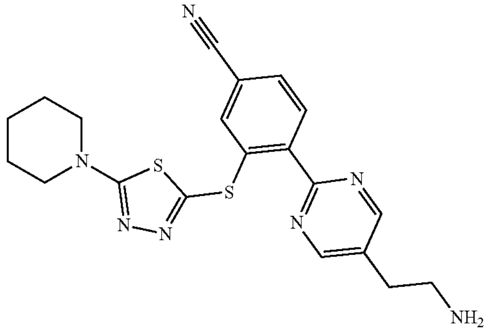 [SMILES: N#Cc1ccc(-c2ncc(CCN)cn2)c(Sc2nnc(N3CCCCC3)s2)c1] | 4-[5-(2-aminoethyl)pyrimidin-2-yl]-3-[(5-piperidin-1-yl-1,3,4-thiadiazol-2-yl)sulfanyl]benzonitrile |
| 1271 | 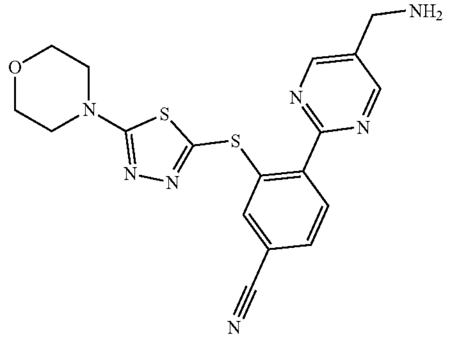 [SMILES: N#Cc1ccc(-c2ncc(CN)cn2)c(Sc2nnc(N3CCOCC3)s2)c1] | 4-[5-(aminomethyl)pyrimidin-2-yl]-3-[(5-morpholin-4-yl-1,3,4-thiadiazol-2-yl)sulfanyl]benzonitrile |
| 1272 | 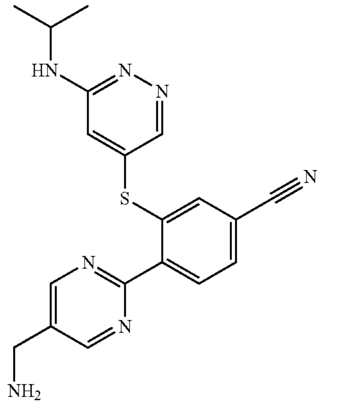 | 4-[5-(aminomethyl)pyrimidin-2-yl]-3-[6-(propan-2-ylamino)pyridazin-4-yl]sulfanylbenzonitrile |
| 1273 | 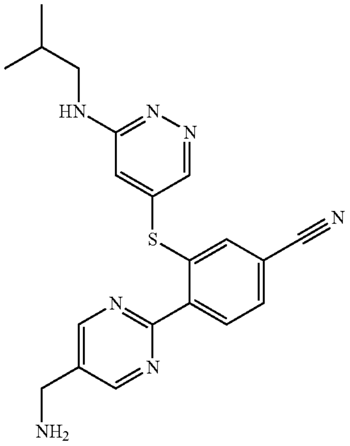 | 4-[5-(aminomethyl)pyrimidin-2-yl]-3-[6-(2-methylpropylamino)pyridazin-4-yl]sulfanylbenzonitrile |

TABLE 1-continued
| Compound number | Structural formula | Compound name |
|---|---|---|
| 1274 | 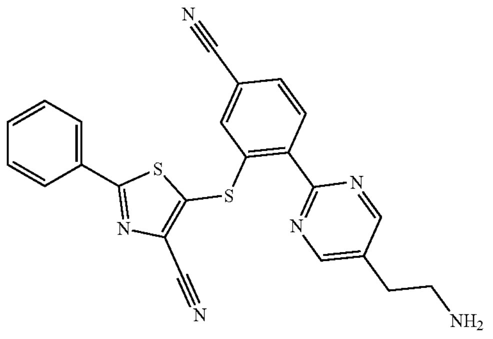 [SMILES: N#Cc1ccc(-c2ncc(CCN)cn2)c(Sc2sc(-c3ccccc3)nc2C#N)c1] | 5-[2-[5-(2-aminoethyl)pyrimidin-2-yl]-5-cyanophenyl]sulfanyl-2-phenyl-1,3-thiazole-4-carbonitrile |
| 1275 | 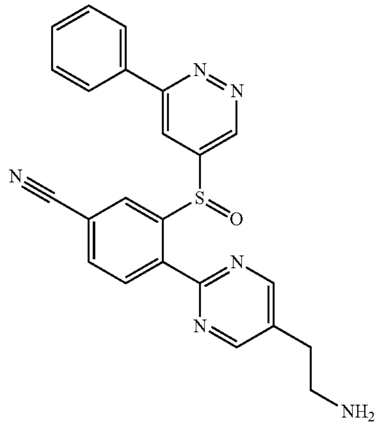 [SMILES: N#Cc1ccc(-c2ncc(CCN)cn2)c(S(=O)c2cnnc(-c3ccccc3)c2)c1] | 4-[5-(2-aminoethyl)pyrimidin-2-yl]-3-(6-phenylpyridazin-4-yl)sulfinylbenzonitrile |
| 1276 | 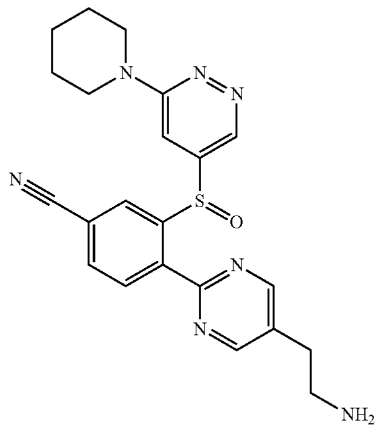 [SMILES: N#Cc1ccc(-c2ncc(CCN)cn2)c(S(=O)c2cnnc(N3CCCCC3)c2)c1] | 4-[5-(2-aminoethyl)pyrimidin-2-yl]-3-(6-piperidin-1-ylpyridazin-4-yl)sulfinylbenzonitrile |

TABLE 1-continued

| Compound number | Structural formula | Compound name |
|---|---|---|
| 1277 | 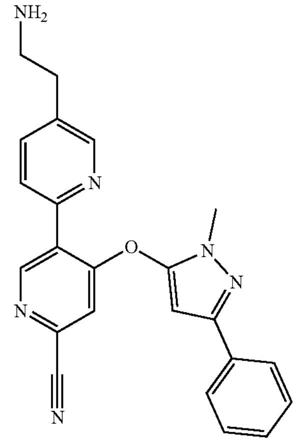 [SMILES: Cn1nc(-c2ccccc2)cc1Oc1cc(C#N)ncc1-c1ccc(CCN)cn1] | 5-[5-(2-aminoethyl)pyridin-2-yl]-4-(2-methyl-5-phenylpyrazol-3-yl)oxypyridine-2-carbonitrile |
| 1278 | 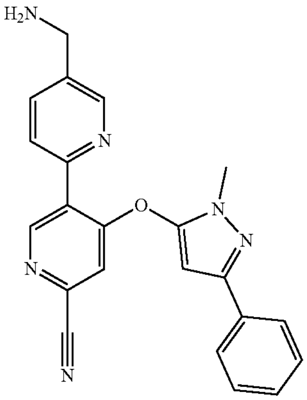 [SMILES: Cn1nc(-c2ccccc2)cc1Oc1cc(C#N)ncc1-c1ccc(CN)cn1] | 5-[5-(aminomethyl)pyridin-2-yl]-4-(2-methyl-5-phenylpyrazol-3-yl)oxypyridine-2-carbonitrile |
| 1279 | 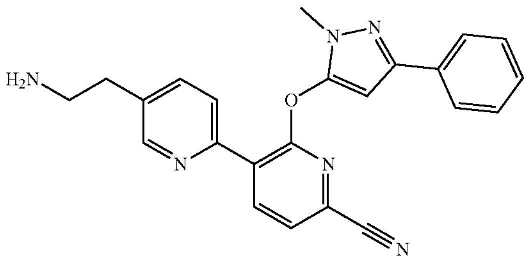 [SMILES: Cn1nc(-c2ccccc2)cc1Oc1nc(C#N)ccc1-c1ccc(CCN)cn1] | 5-[5-(2-aminoethyl)pyridin-2-yl]-6-(2-methyl-5-phenylpyrazol-3-yl)oxypyridine-2-carbonitrile |
| 1280 | 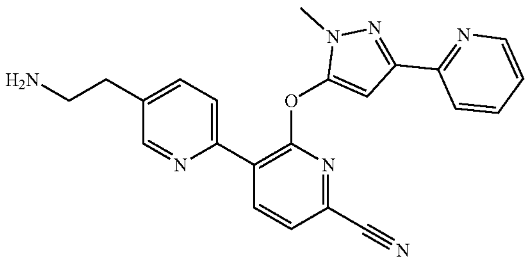 [SMILES: Cn1nc(-c2ccccn2)cc1Oc1nc(C#N)ccc1-c1ccc(CCN)cn1] | 5-[5-(2-aminoethyl)pyridin-2-yl]-6-(2-methyl-5-pyridin-2-ylpyrazol-3-yl)oxypyridine-2-carbonitrile |

TABLE 1-continued

| Compound number | Structural formula | Compound name |
|---|---|---|
| 1281 | 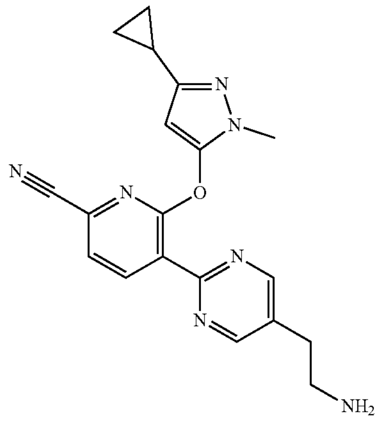 [SMILES: Cn1nc(C2CC2)cc1Oc1nc(C#N)ccc1-c1ncc(CCN)cn1] | 5-[5-(2-aminoethyl)pyrimidin-2-yl]-6-(5-cyclopropyl-2-methylpyrazol-3-yl)oxypyridine-2-carbonitrile |
| 1282 | 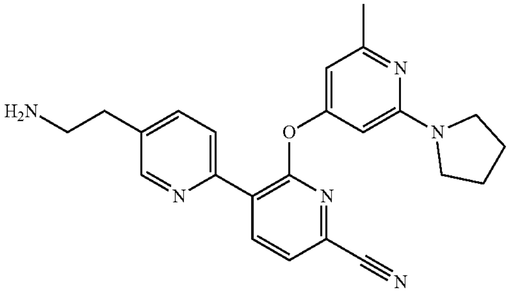 [SMILES: Cc1cc(Oc2nc(C#N)ccc2-c2ccc(CCN)cn2)cc(N2CCCC2)n1] | 5-[5-(2-aminoethyl)pyridin-2-yl]-6-(2-methyl-6-pyrrolidin-1-ylpyridin-4-yl)oxypyridine-2-carbonitrile |
| 1283 | 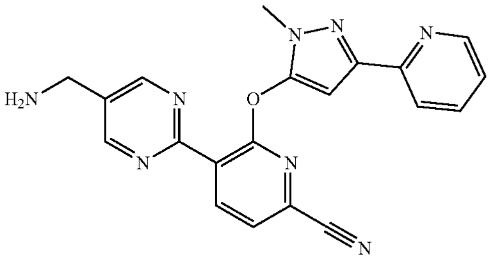 [SMILES: Cn1nc(-c2ccccn2)cc1Oc1nc(C#N)ccc1-c1ncc(CN)cn1] | 5-[5-(aminomethyl)pyrimidin-2-yl]-6-(2-methyl-5-pyridin-2-ylpyrazol-3-yl)oxypyridine-2-carbonitrile |
| 1284 | 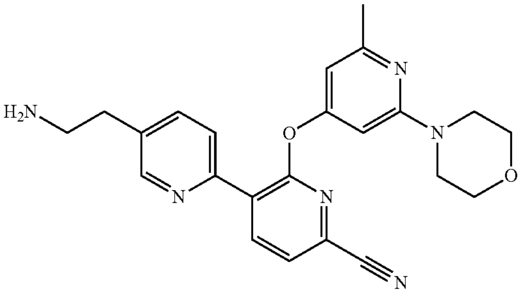 [SMILES: Cc1cc(Oc2nc(C#N)ccc2-c2ccc(CCN)cn2)cc(N2CCOCC2)n1] | 5-[5-(2-aminoethyl)pyridin-2-yl]-6-(2-methyl-6-morpholin-4-ylpyridin-4-yl)oxypyridine-2-carbonitrile |
| 1285 | 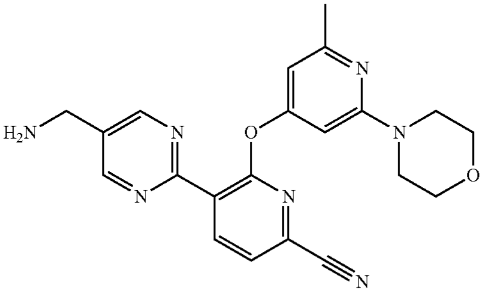 [SMILES: Cc1cc(Oc2nc(C#N)ccc2-c2ncc(CN)cn2)cc(N2CCOCC2)n1] | 5-[5-(aminomethyl)pyrimidin-2-yl]-6-(2-methyl-6-morpholin-4-ylpyridin-4-yl)oxypyridine-2-carbonitrile |

TABLE 1-continued

| Compound number | Structural formula | Compound name |
|---|---|---|
| 1286 | 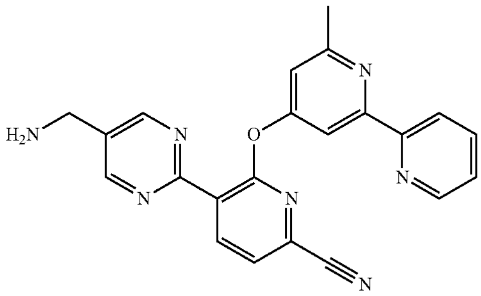 [SMILES: Cc1cc(Oc2nc(C#N)ccc2-c2ncc(CN)cn2)cc(-c2ccccn2)n1] | 5-[5-(aminomethyl)pyrimidin-2-yl]-6-(2-methyl-6-pyridin-2-ylpyridin-4-yl)oxypyridine-2-carbonitrile |
| 1287 | 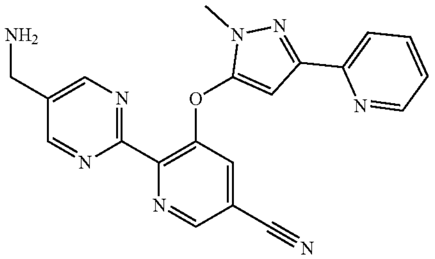 [SMILES: Cn1nc(-c2ccccn2)cc1Oc1cc(C#N)cnc1-c1ncc(CN)cn1] | 6-[5-(aminomethyl)pyrimidin-2-yl]-5-(2-methyl-5-pyridin-2-ylpyrazol-3-yl)oxypyridine-3-carbonitrile |
| 1288 | 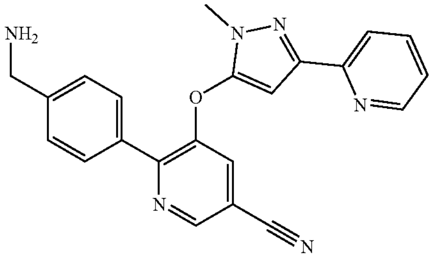 [SMILES: Cn1nc(-c2ccccn2)cc1Oc1cc(C#N)cnc1-c1ccc(CN)cc1] | 6-[4-(aminomethyl)phenyl]-5-(2-methyl-5-pyridin-2-ylpyrazol-3-yl)oxypyridine-3-carbonitrile |
| 1289 | 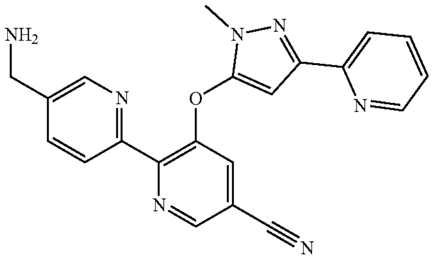 [SMILES: Cn1nc(-c2ccccn2)cc1Oc1cc(C#N)cnc1-c1ccc(CN)cn1] | 6-[5-(aminomethyl)pyridin-2-yl]-5-(2-methyl-5-pyridin-2-ylpyrazol-3-yl)oxypyridine-3-carbonitrile |
| 1290 | 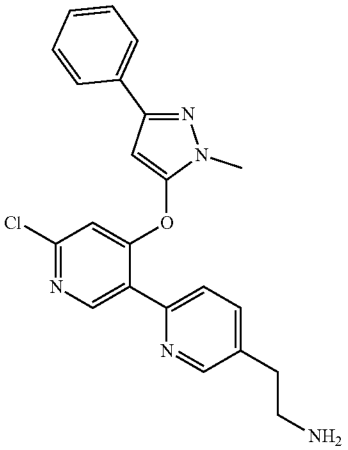 [SMILES: Cn1nc(-c2ccccc2)cc1Oc1cc(Cl)ncc1-c1ccc(CCN)cn1] | 2-[6-[6-chloro-4-(2-methyl-5-phenylpyrazol-3-yl)oxypyridin-3-yl]pyridin-3-yl]ethanamine |

TABLE 1-continued
| Compound number | Structural formula | Compound name |
|---|---|---|
| 1291 | 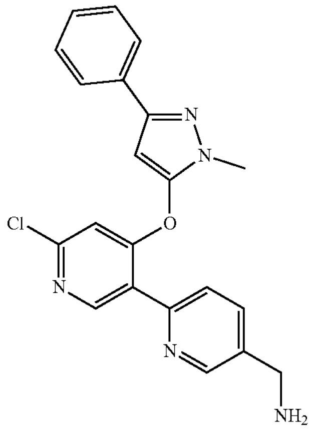 [SMILES: Cn1nc(-c2ccccc2)cc1Oc1cc(Cl)ncc1-c1ccc(CN)cn1] | [6-[6-chloro-4-(2-methyl-5-phenylpyrazol-3-yl)oxypyridin-3-yl]pyridin-3-yl]methanamine |
| 1292 | 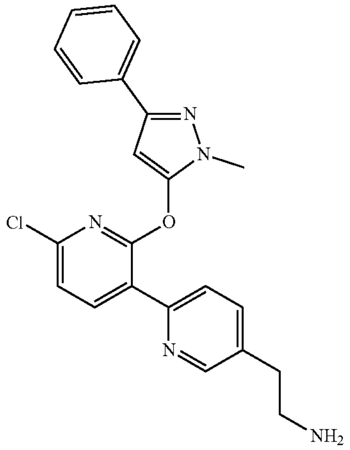 [SMILES: Cn1nc(-c2ccccc2)cc1Oc1nc(Cl)ccc1-c1ccc(CCN)cn1] | 2-[6-[6-chloro-2-(2-methyl-5-phenylpyrazol-3-yl)oxypyridin-3-yl]pyridin-3-yl]ethanamine |
| 1293 | 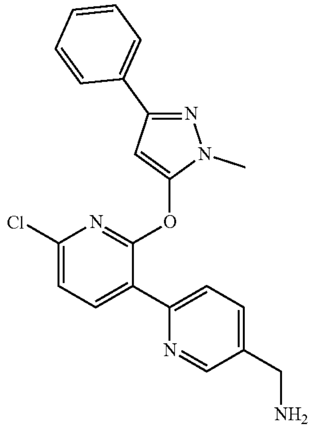 [SMILES: Cn1nc(-c2ccccc2)cc1Oc1nc(Cl)ccc1-c1ccc(CN)cn1] | [6-[6-chloro-2-(2-methyl-5-phenylpyrazol-3-yl)oxypyridin-3-yl]pyridin-3-yl]methanamine |

TABLE 1-continued
| Compound number | Structural formula | Compound name |
| --- | --- | --- |
| 1294 | 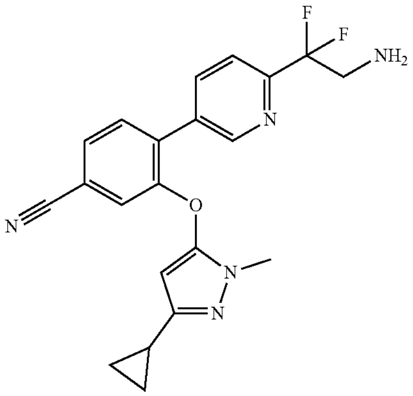 [SMILES: Cn1nc(C2CC2)cc1Oc1cc(C#N)ccc1-c1ccc(C(F)(F)CN)nc1] | 4-[6-(2-amino-1,1-difluoroethyl)pyridin-3-yl]-3-(5-cyclopropyl-2-methylpyrazol-3-yl)oxybenzonitrile |
| 1295 | 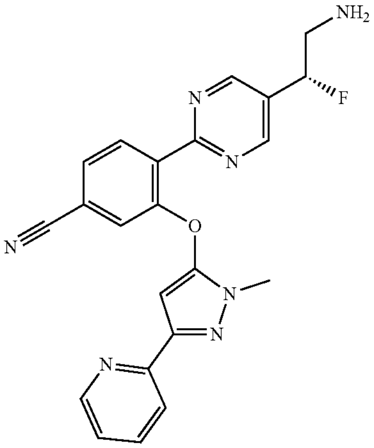 [SMILES: Cn1nc(-c2ccccn2)cc1Oc1cc(C#N)ccc1-c1ncc([C@@H](F)CN)cn1] | 4-[5-[(1R)-2-amino-1-fluoroethyl]pyrimidin-2-yl]-3-(2-methyl-5-pyridin-2-ylpyrazol-3-yl)oxybenzonitrile |
| 1296 | 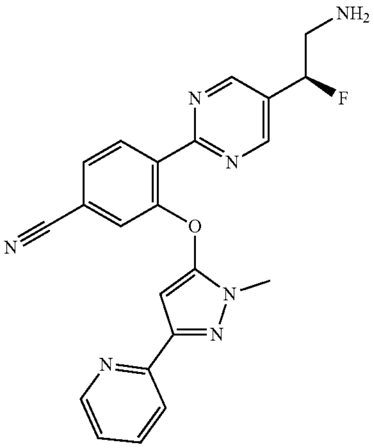 [SMILES: Cn1nc(-c2ccccn2)cc1Oc1cc(C#N)ccc1-c1ncc([C@H](F)CN)cn1] | 4-[5-[(1S)-2-amino-1-fluoroethyl]pyrimidin-2-yl]-3-(2-methyl-5-pyridin-2-ylpyrazol-3-yl)oxybenzonitrile |

TABLE 1-continued

| Compound number | Structural formula | Compound name |
|---|---|---|
| 1297 | 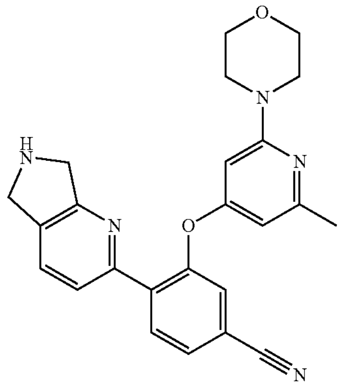 [SMILES: Cc1cc(Oc2cc(C#N)ccc2-c2ccc3c(n2)CNC3)cc(N2CCOCC2)n1] | 4-(6,7-dihydro-5H-pyrrolo[3,4-b]pyridin-2-yl)-3-(2-methyl-6-morpholin-4-ylpyridin-4-yl)oxybenzonitrile |
| 1298 | 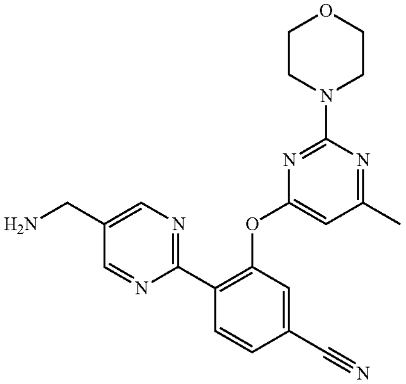 [SMILES: Cc1cc(Oc2cc(C#N)ccc2-c2ncc(CN)cn2)nc(N2CCOCC2)n1] | 4-[5-(aminomethyl)pyrimidin-2-yl]-3-(6-methyl-2-morpholin-4-ylpyrimidin-4-yl)oxybenzonitrile |
| 1299 | 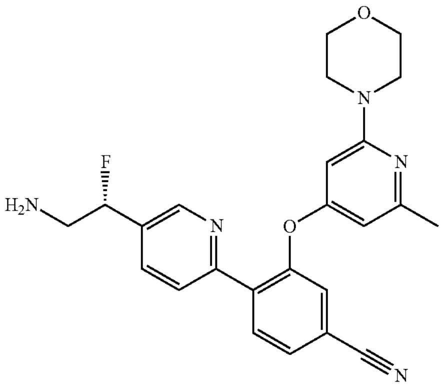 [SMILES: Cc1cc(Oc2cc(C#N)ccc2-c2ccc([C@@H](F)CN)cn2)cc(N2CCOCC2)n1] | 4-[5-[(1R)-2-amino-1-fluoroethyl]pyridin-2-yl]-3-(2-methyl-6-morpholin-4-ylpyridin-4-yl)oxybenzonitrile |
| 1300 | 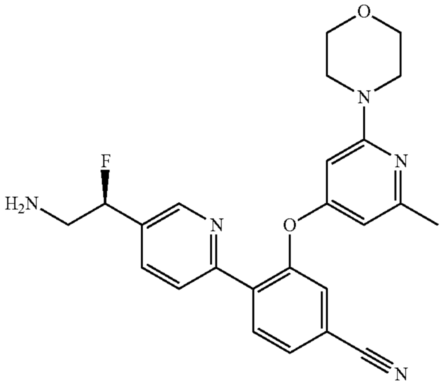 [SMILES: Cc1cc(Oc2cc(C#N)ccc2-c2ccc([C@H](F)CN)cn2)cc(N2CCOCC2)n1] | 4-[5-[(1S)-2-amino-1-fluoroethyl]pyridin-2-yl]-3-(2-methyl-6-morpholin-4-ylpyridin-4-yl)oxybenzonitrile |

TABLE 1-continued
| Compound number | Structural formula | Compound name |
|---|---|---|
| 1301 | 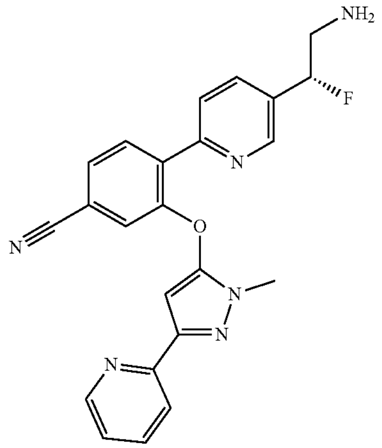 | 4-[5-[(1R)-2-amino-1-fluoroethyl]pyridin-2-yl]-3-(2-methyl-5-pyridin-2-ylpyrazol-3-yl)oxybenzonitrile |
| 1302 | 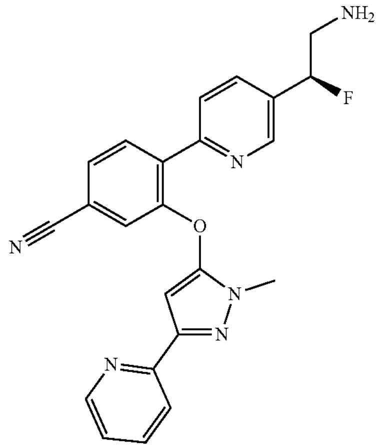 [SMILES: Cn1nc(-c2ccccn2)cc1Oc1cc(C#N)ccc1-c1ccc([C@H](F)CN)cn1] | 4-[5-[(1S)-2-amino-1-fluoroethyl]pyridin-2-yl]-3-(2-methyl-5-pyridin-2-ylpyrazol-3-yl)oxybenzonitrile |
| 1303 | 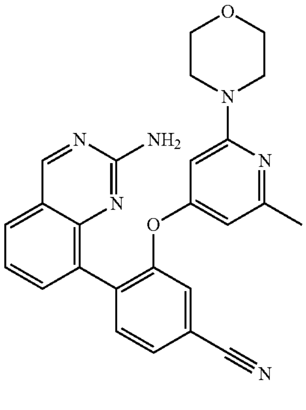 [SMILES: Cc1cc(Oc2cc(C#N)ccc2-c2cccc3cnc(N)nc23)cc(N2CCOCC2)n1] | 4-(2-aminoquinazolin-8-yl)-3-(2-methyl-6-morpholin-4-ylpyridin-4-yl)oxybenzonitrile |

TABLE 1-continued

| Compound number | Structural formula | Compound name |
| --- | --- | --- |
| 1304 | 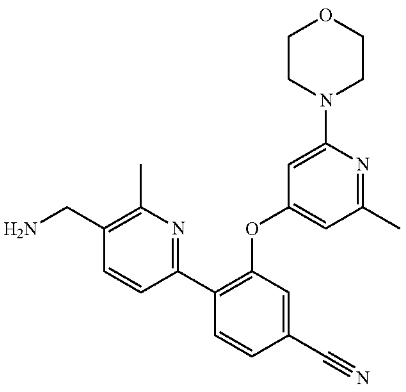 [SMILES: Cc1cc(Oc2cc(C#N)ccc2-c2ccc(CN)c(C)n2)cc(N2CCOCC2)n1] | 4-[5-(aminomethyl)-6-methylpyridin-2-yl]-3-(2-methyl-6-morpholin-4-ylpyridin-4-yl)oxybenzonitrile |
| 1305 | 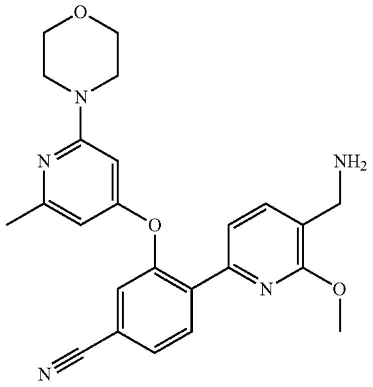 | 4-[5-(aminomethyl)-6-methoxypyridin-2-yl]-3-(2-methyl-6-morpholin-4-ylpyridin-4-yl)oxybenzonitrile |
| 1306 | 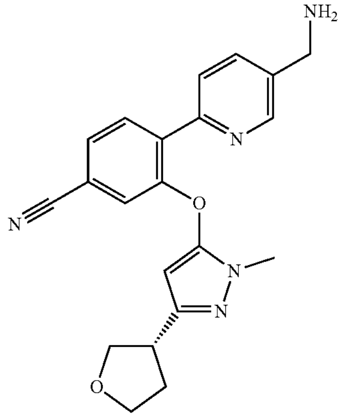 [SMILES: Cn1nc([C@@H]2CCOC2)cc1Oc1cc(C#N)ccc1-c1ccc(CN)cn1] | 4-[5-(aminomethyl)pyridin-2-yl]-3-[2-methyl-5-[(3S)-oxolan-3-yl]pyrazol-3-yl]oxybenzonitrile |
| 1307 | 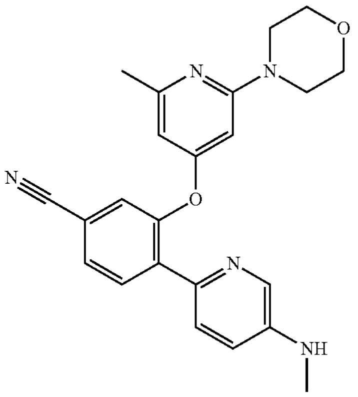 [SMILES: CNc1ccc(-c2ccc(C#N)cc2Oc2cc(C)nc(N3CCOCC3)c2)nc1] | 4-[5-(methylamino)pyridin-2-yl]-3-(2-methyl-6-morpholin-4-ylpyridin-4-yl)oxybenzonitrile |

TABLE 1-continued

| Compound number | Structural formula | Compound name |
|---|---|---|
| 1308 | 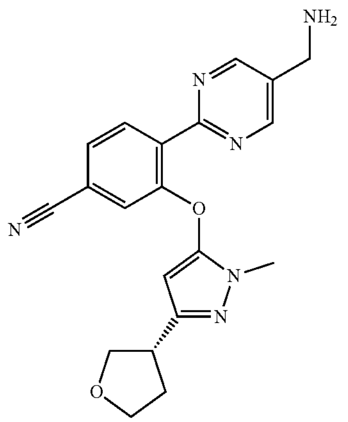 [SMILES: Cn1nc([C@@H]2CCOC2)cc1Oc1cc(C#N)ccc1-c1ncc(CN)cn1] | 4-[5-(aminomethyl)pyrimidin-2-yl]-3-[2-methyl-5-[(3S)-oxolan-3-yl]pyrazol-3-yl]oxybenzonitrile |
| 1309 | 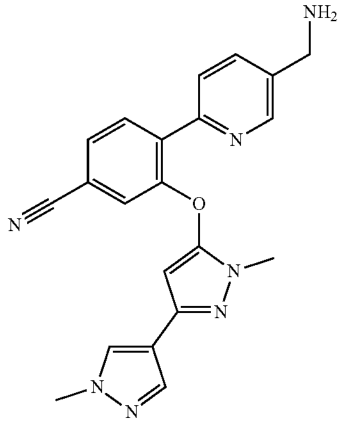 [SMILES: Cn1cc(-c2cc(Oc3cc(C#N)ccc3-c3ccc(CN)cn3)n(C)n2)cn1] | 4-[5-(aminomethyl)pyridin-2-yl]-3-[2-methyl-5-(1-methylpyrazol-4-yl)pyrazol-3-yl]oxybenzonitrile |
| 1310 | 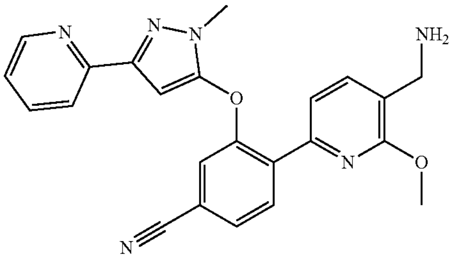 [SMILES: COc1nc(-c2ccc(C#N)cc2Oc2cc(-c3ccccn3)nn2C)ccc1CN] | 4-[5-(aminomethyl)-6-methoxypyridin-2-yl]-3-(2-methyl-5-pyridin-2-ylpyrazol-3-yl)oxybenzonitrile |
| 1311 | 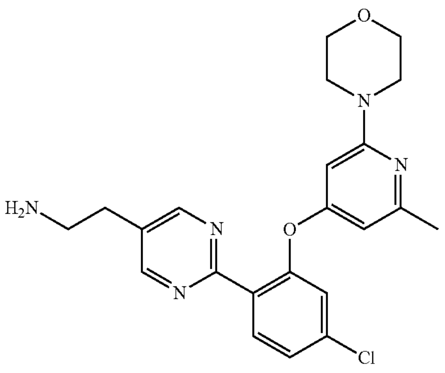 [SMILES: Cc1cc(Oc2cc(Cl)ccc2-c2ncc(CCN)cn2)cc(N2CCOCC2)n1] | 2-[2-[4-chloro-2-(2-methyl-6-morpholin-4-ylpyridin-4-yl)oxyphenyl]pyrimidin-5-yl]ethanamine |

TABLE 1-continued
| Compound number | Structural formula | Compound name |
| --- | --- | --- |
| 1312 | 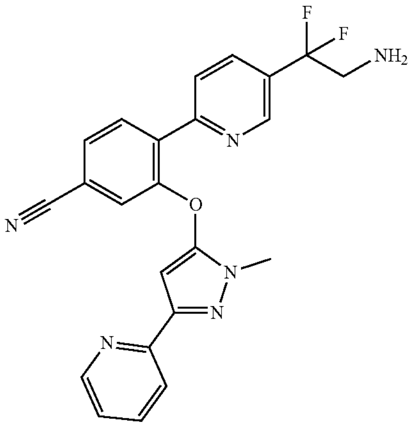 [SMILES: Cn1nc(-c2ccccn2)cc1Oc1cc(C#N)ccc1-c1ccc(C(F)(F)CN)cn1] | 4-[5-(2-amino-1,1-difluoroethyl)pyridin-2-yl]-3-(2-methyl-5-pyridin-2-ylpyrazol-3-yl)oxybenzonitrile |
| 1313 | 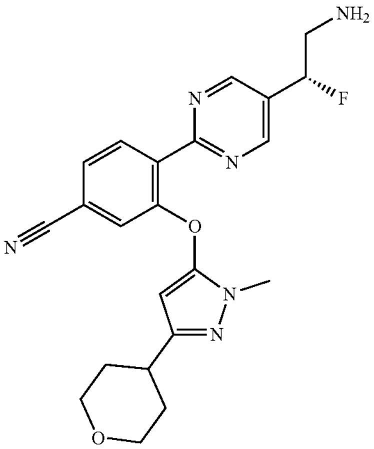 | 4-[5-[(1R)-2-amino-1-fluoroethyl]pyrimidin-2-yl]-3-[2-methyl-5-(oxan-4-yl)pyrazol-3-yl]oxybenzonitrile |
| 1314 | 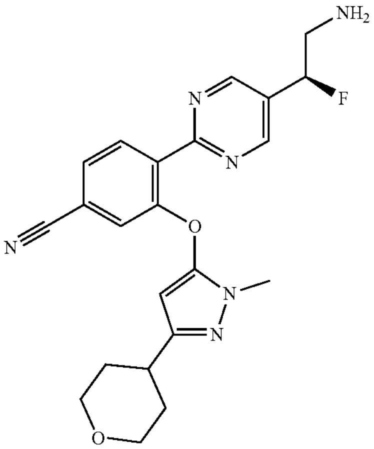 | 4-[5-[(1S)-2-amino-1-fluoroethyl]pyrimidin-2-yl]-3-[2-methyl-5-(oxan-4-yl)pyrazol-3-yl]oxybenzonitrile |

TABLE 1-continued
| Compound number | Structural formula | Compound name |
|---|---|---|
| 1315 | 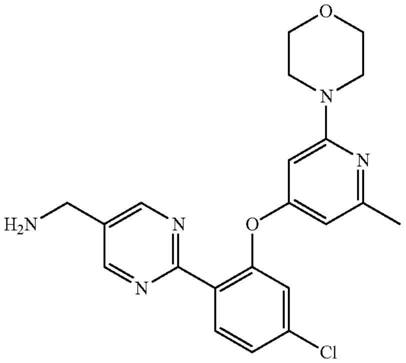 [SMILES: Cc1cc(Oc2cc(Cl)ccc2-c2ncc(CN)cn2)cc(N2CCOCC2)n1] | [2-[4-chloro-2-(2-methyl-6-morpholin-4-ylpyridin-4-yl)oxyphenyl]pyrimidin-5-yl]methanamine |
| 1316 | 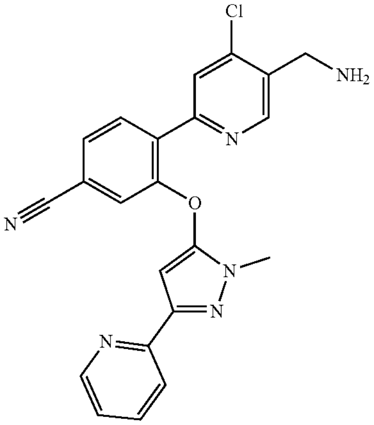 [SMILES: Cn1nc(-c2ccccn2)cc1Oc1cc(C#N)ccc1-c1cc(Cl)c(CN)cn1] | 4-[5-(aminomethyl)-4-chloropyridin-2-yl]-3-(2-methyl-5-pyridin-2-ylpyrazol-3-yl)oxybenzonitrile |
| 1317 | 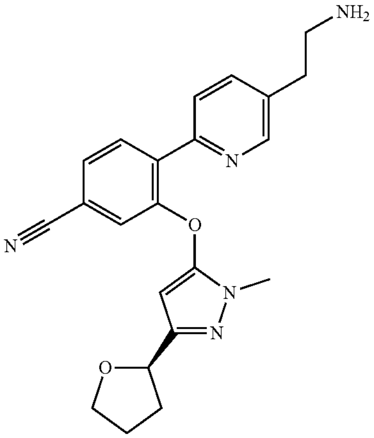 [SMILES: Cn1nc([C@H]2CCCO2)cc1Oc1cc(C#N)ccc1-c1ccc(CCN)cn1] | 4-[5-(aminomethyl)pyrldin-2-yl]-3-[2-methyl-5-[(2R)-oxolan-2-yl]pyrazol-3-yl]oxybenzonitrile |

TABLE 1-continued
| Compound number | Structural formula | Compound name |
|---|---|---|
| 1318 | 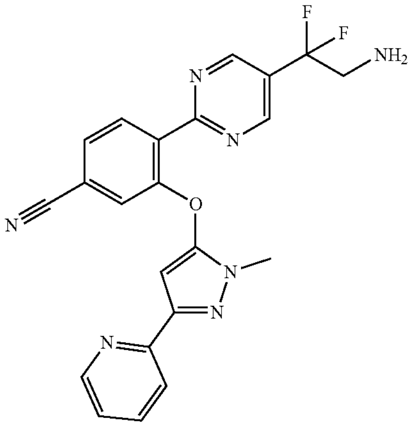 | 4-[5-(2-amino-1,1-difluoroethyl)pyrimidin-2-yl]-3-(2-methyl-5-pyridin-2-ylpyrazol-3-yl)oxybenzonitrile |
| 1319 | 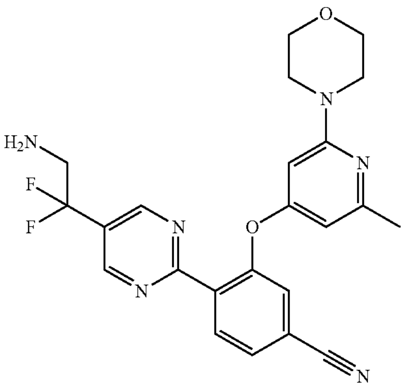 [SMILES: Cc1cc(Oc2cc(C#N)ccc2-c2ncc(C(F)(F)CN)cn2)cc(N2CCOCC2)n1] | 4-[5-(2-amino-1,1-difluoroethyl)pyrimidin-2-yl]-3-(2-methyl-6-morpholin-4-ylpyridin-4-yl)oxybenzonitrile |
| 1320 | 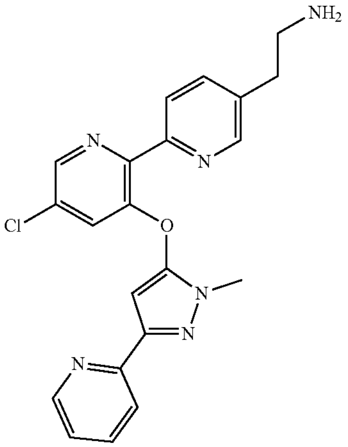 [SMILES: Cn1nc(-c2ccccn2)cc1Oc1cc(Cl)cnc1-c1ccc(CCN)cn1] | 2-[4-[5-chloro-3-(2-methyl-5-pyridin-2-ylpyrazol-3-yl)oxypyridin-2-yl]phenyl]ethanamine |

TABLE 1-continued
| Compound number | Structural formula | Compound name |
|---|---|---|
| 1321 | 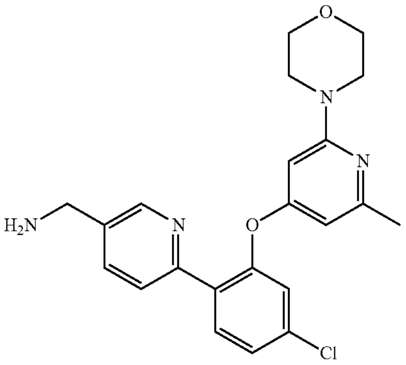 [SMILES: Cc1cc(Oc2cc(Cl)ccc2-c2ccc(CN)cn2)cc(N2CCOCC2)n1] | [6-[4-chloro-2-(2-methyl-6-morpholin-4-ylpyridin-4-yl)oxyphenyl]pyridin-3-yl]methanamine |
| 1322 | 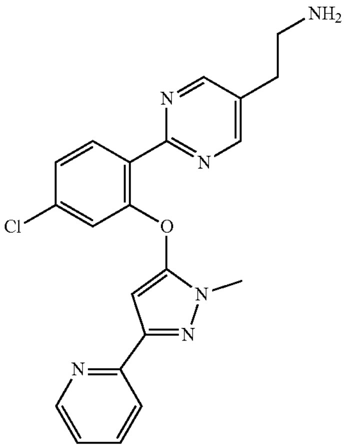 [SMILES: Cn1nc(-c2ccccn2)cc1Oc1cc(Cl)ccc1-c1ncc(CCN)cn1] | 2-[2-[4-chloro-2-(2-methyl-5-pyridin-2-ylpyrazol-3-yl)oxyphenyl]pyrimidin-5-yl]ethanamine |
| 1323 | 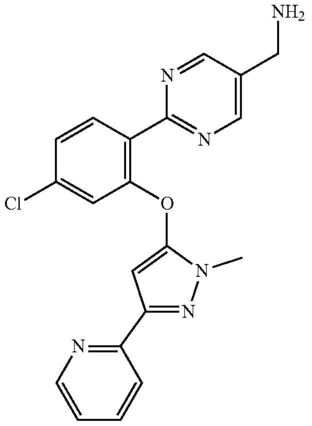 [SMILES: Cn1nc(-c2ccccn2)cc1Oc1cc(Cl)ccc1-c1ncc(CN)cn1] | [2-[4-chloro-2-(2-methyl-5-pyridin-2-ylpyrazol-3-yl)oxyphenyl]pyrimidin-5-yl]methanamine |

TABLE 1-continued

| Compound number | Structural formula | Compound name |
|---|---|---|
| 1324 | 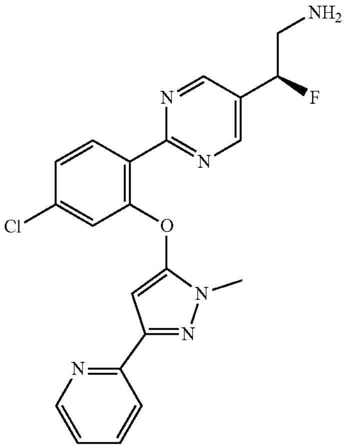 [SMILES: Cn1nc(-c2ccccn2)cc1Oc1cc(Cl)ccc1-c1ncc([C@H](F)CN)cn1] | (2S)-2-[2-[4-chloro-2-(2-methyl-5-pyridin-2-ylpyrazol-3 yl)oxyphenyl]pyrimidin-5-yl]-2-fluoroethanamine |
| 1325 | 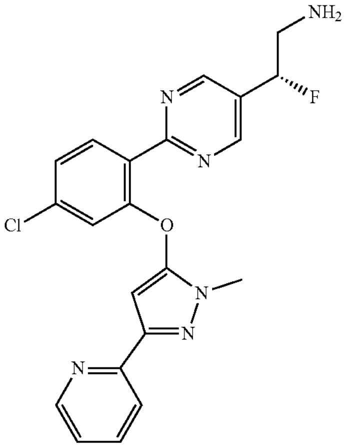 [SMILES: Cn1nc(-c2ccccn2)cc1Oc1cc(Cl)ccc1-c1ncc([C@@H](F)CN)cn1] | (2R)-2-[2-[4-chloro-2-(2-methyl-5-pyridin-2-ylpyrazol-3-yl)oxyphenyl]pyrimidin-5-yl]-2-fluoroethanamine |
| 1326 | 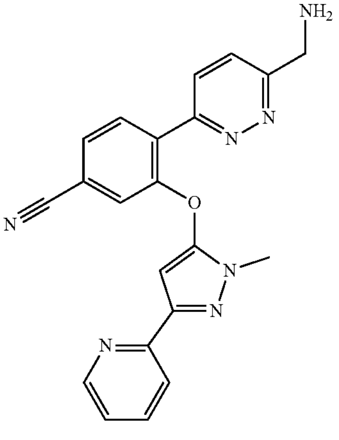 [SMILES: Cn1nc(-c2ccccn2)cc1Oc1cc(C#N)ccc1-c1ccc(CN)nn1] | 4-[6-(aminomethyl)pyridazin-3-yl]-3-(2-methyl-5-pyridin-2-ylpyrazol-3-yl)oxybenzonitrile |
| 1327 | 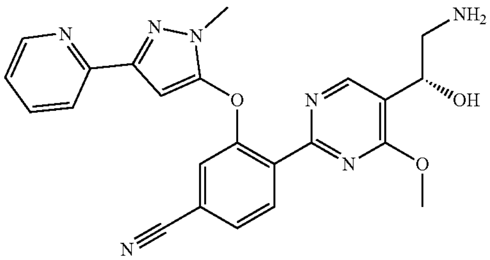 [SMILES: COc1nc(-c2ccc(C#N)cc2Oc2cc(-c3ccccn3)nn2C)ncc1[C@@H](O)CN] | 4-[5-[(1R)-2-amino-1-hydroxyethyl]-4-methoxypyrimidin-2-yl]-3-(2-methyl-5-pyridin-2-ylpyrazol-3-yl)oxybenzonitrile |

TABLE 1-continued

| Compound number | Structural formula | Compound name |
|---|---|---|
| 1328 | 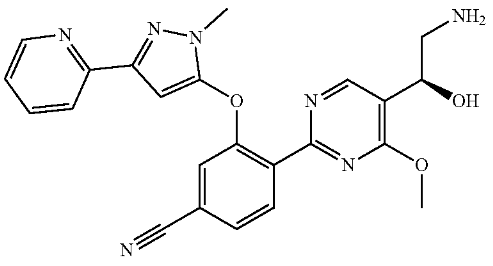 [SMILES: COc1nc(-c2ccc(C#N)cc2Oc2cc(-c3ccccn3)nn2C)ncc1[C@H](O)CN] | 4-[5-[(1S)-2-amino-1-hydroxyethyl]-4-methoxypyrimidin-2-yl]-3-(2-methyl-5-pyridin-2-ylpyrazol-3-yl)oxybenzonitrile |
| 1329 | 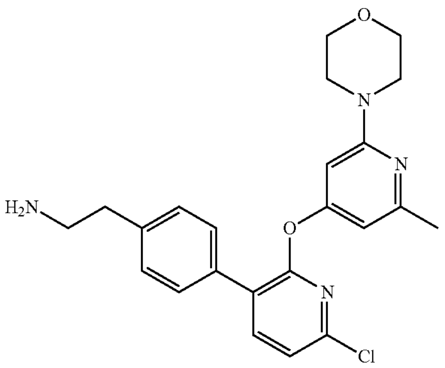 [SMILES: Cc1cc(Oc2nc(Cl)ccc2-c2ccc(CCN)cc2)cc(N2CCOCC2)n1] | 2-[4-[6-chloro-2-(2-methyl-6-morpholin-4-ylpyridin-4-yl)oxypyridin-3-yl]phenyl]ethanamine |
| 1330 | 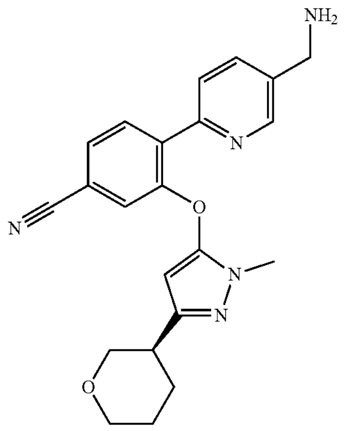 [SMILES: Cn1nc([C@H]2CCCOC2)cc1Oc1cc(C#N)ccc1-c1ccc(CN)cn1] | 4-[5-(aminomethyl)pyridin-2-yl]-3-[2-methyl-5-[(3R)-oxan-3-yl]pyrazol-3-yl]oxybenzonitrile |
| 1331 | 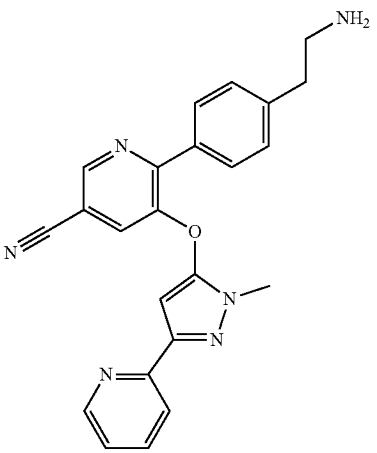 [SMILES: Cn1nc(-c2ccccn2)cc1Oc1cc(C#N)cnc1-c1ccc(CCN)cc1] | 6-[4-(2-aminoethyl)phenyl]-5-(2-methyl-5-pyridin-2-ylpyrazol-3-yl)oxypyridine-3-carbonitrile |

TABLE 1-continued
| Compound number | Structural formula | Compound name |
|---|---|---|
| 1332 | 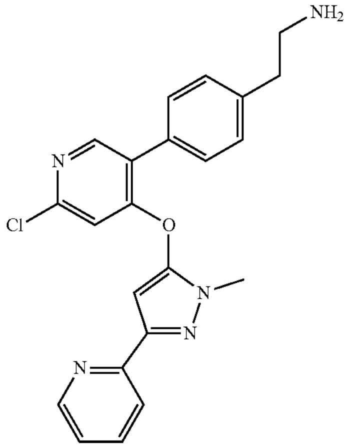 [SMILES: Cn1nc(-c2ccccn2)cc1Oc1cc(Cl)ncc1-c1ccc(CCN)cc1] | 2-[4-[6-chloro-4-(2-methyl-5-pyridin-2-ylpyrazol-3-yl)oxypyridin-3-yl]phenyl]ethanamine |
| 1333 | 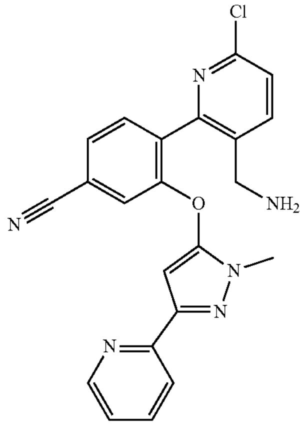 [SMILES: Cn1nc(-c2ccccn2)cc1Oc1cc(C#N)ccc1-c1nc(Cl)ccc1CN] | 4-[3-(aminomethyl)-6-chloropyridin-2-yl]-3-(2-methyl-5-pyridin-2-ylpyrazol-3-yl)oxybenzonitrile |
| 1334 | 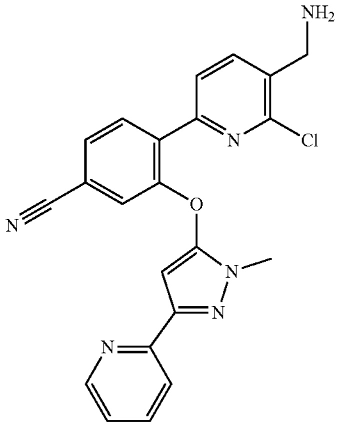 [SMILES: Cn1nc(-c2ccccn2)cc1Oc1cc(C#N)ccc1-c1ccc(CN)c(Cl)n1] | 4-[5-(aminomethyl)-6-chloropyridin-2-yl]-3-(2-methyl-5-pyridin-2-ylpyrazol-3-yl)oxybenzonitrile |

TABLE 1-continued
| Compound number | Structural formula | Compound name |
|---|---|---|
| 1335 | 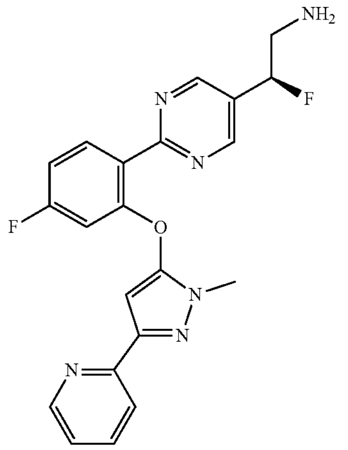 [SMILES: Cn1nc(-c2ccccn2)cc1Oc1cc(F)ccc1-c1ncc([C@H](F)CN)cn1] | (2S)-2-fluoro-2-[2-[4-fluoro-2-(2-methyl-5-pyridin-2-ylpyrazol-3-yl)oxyphenyl]pyrimidin-5-yl]ethanamine |
| 1336 | 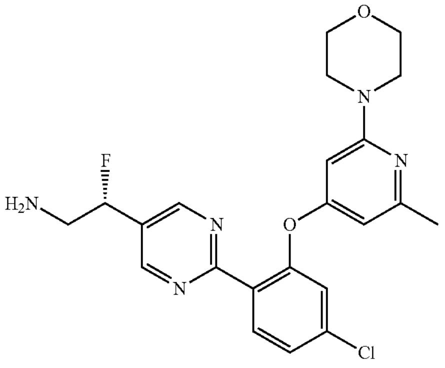 [SMILES: Cc1cc(Oc2cc(Cl)ccc2-c2ncc([C@@H](F)CN)cn2)cc(N2CCOCC2)n1] | (2R)-2-[2-[4-chloro-2-(2-methyl-6-morpholin-4-ylpyridin-4-yl)oxyphenyl]pyrimidin-5-yl]-2-fluoroethanamine |
| 1337 | 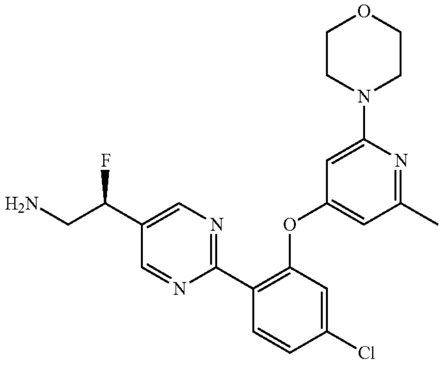 [SMILES: Cc1cc(Oc2cc(Cl)ccc2-c2ncc([C@H](F)CN)cn2)cc(N2CCOCC2)n1] | (2S)-2-[2-[4-chloro-2-(2-methyl-6-morpholin-4-ylpyridin-4-yl)oxyphenyl]pyrimidin-5-yl]-2-fluoroethanamine |

TABLE 1-continued
| Compound number | Structural formula | Compound name |
|---|---|---|
| 1338 | 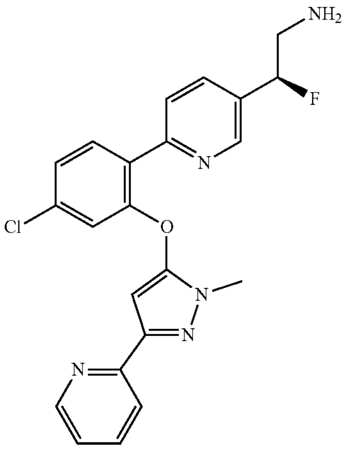 [SMILES: Cn1nc(-c2ccccn2)cc1Oc1cc(Cl)ccc1-c1ccc([C@H](F)CN)cn1] | (2S)-2-[6-[4-chloro-2-(2-methyl-5-pyridin-2-ylpyrazol-3-yl)oxyphenyl]pyridin-3-yl]-2-fluoroethanamine |
| 1339 | 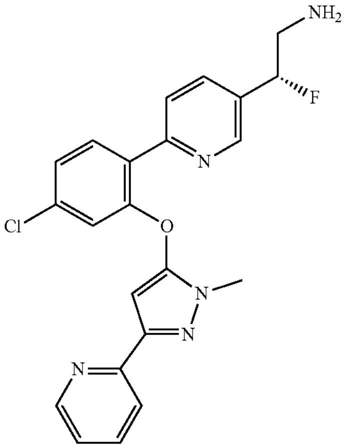 [SMILES: Cn1nc(-c2ccccn2)cc1Oc1cc(Cl)ccc1-c1ccc([C@@H](F)CN)cn1] | (2R)-2-[6-[4-chloro-2-(2-methyl-5-pyridin-2-ylpyrazol-3-yl)oxyphenyl]pyridin-3-yl]-2-fluoroethanamine |
| 1340 | 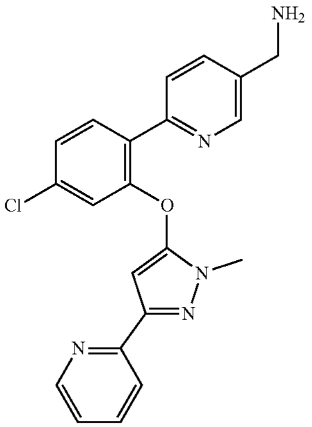 [SMILES: Cn1nc(-c2ccccn2)cc1Oc1cc(Cl)ccc1-c1ccc(CN)cn1] | [6-[4-chloro-2-(2-methyl-5-pyridin-2-ylpyrazol-3-yl)oxyphenyl]pyridin-3-yl]methanamine |

TABLE 1-continued
| Compound number | Structural formula | Compound name |
|---|---|---|
| 1341 | 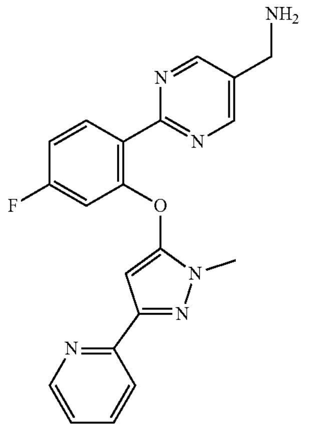 [SMILES: Cn1nc(-c2ccccn2)cc1Oc1cc(F)ccc1-c1ncc(CN)cn1] | [2-[4-fluoro-2-(2-methyl-5-pyridin-2-ylpyrazol-3-yl)oxyphenyl]pyrimidin-5-yl]methanamine |
| 1342 | 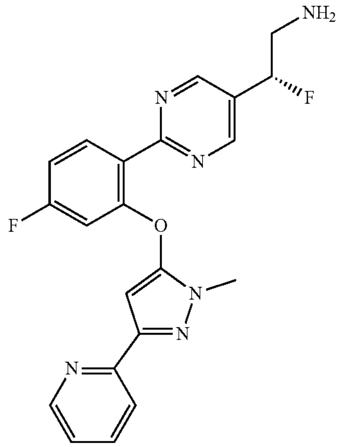 [SMILES: Cn1nc(-c2ccccn2)cc1Oc1cc(F)ccc1-c1ncc([C@@H](F)CN)cn1] | (2R)-2-fluoro-2-[2-[4-fluoro-2-(2-methyl-5-pyridin-2-ylpyrazol-3-yl)oxyphenyl]pyrimidin-5-yl]ethanamine |
| 1343 | 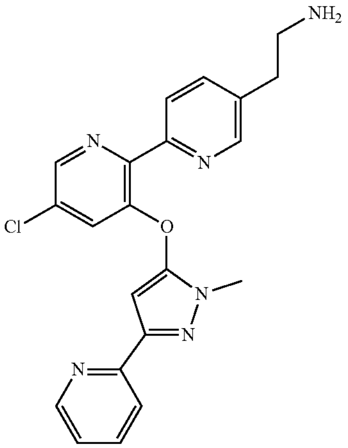 [SMILES: Cn1nc(-c2ccccn2)cc1Oc1cc(Cl)cnc1-c1ccc(CCN)cn1] | [6-[5-chloro-3-(2-methyl-5-pyridin-2-ylpyrazol-3-yl)oxypyridin-2-yl]pyridin-3-yl]methanamine |

TABLE 1-continued
| Compound number | Structural formula | Compound name |
|---|---|---|
| 1344 | 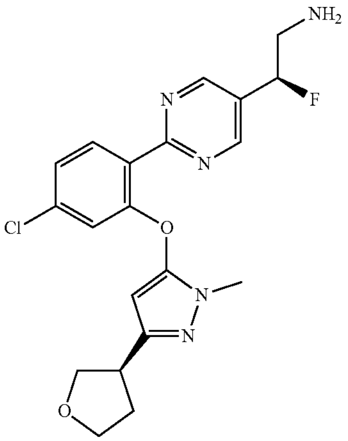 [SMILES: Cn1nc([C@H]2CCOC2)cc1Oc1cc(Cl)ccc1-c1ncc([C@H](F)CN)cn1] | (2S)-2-[2-[4-chloro-2-[2-methyl-5-[(3R)-oxolan-3-yl]pyrazol-3-yl]oxyphenyl]pyrimidin-5-yl]-2-fluoroethanamine |
| 1345 | 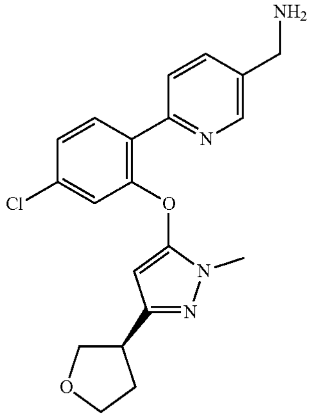 [SMILES: Cn1nc([C@H]2CCOC2)cc1Oc1cc(Cl)ccc1-c1ccc(CN)cn1] | [6-[4-chloro-2-[2-methyl-5-[(3R)-oxolan-3-yl]pyrazol-3-yl]oxyphenyl]pyridin-3-yl]methanamine |
| 1346 | 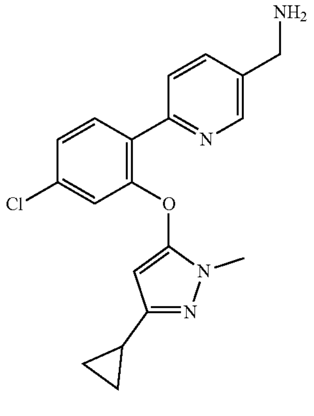 [SMILES: Cn1nc(C2CC2)cc1Oc1cc(Cl)ccc1-c1ccc(CN)cn1] | [6-[4-chloro-2-(5-cyclopropyl-2-methylpyrazol-3-yl)oxyphenyl]pyridin-3-yl]methanamine |

TABLE 1-continued

| Compound number | Structural formula | Compound name |
| --- | --- | --- |
| 1347 | 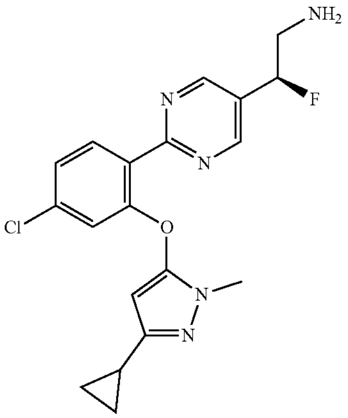 [SMILES: Cn1nc(C2CC2)cc1Oc1cc(Cl)ccc1-c1ncc([C@H](F)CN)cn1] | (2S)-2-[2-[4-chloro-2-(5-cyclopropyl-2-methylpyrazol-3-yl)oxyphenyl]pyrimidin-5-yl]-2-fluoroethanamine |
| 1348 | 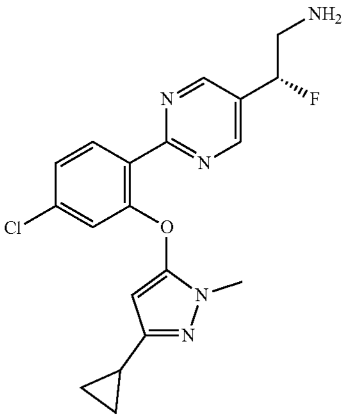 [SMILES: Cn1nc(C2CC2)cc1Oc1cc(Cl)ccc1-c1ncc([C@@H](F)CN)cn1] | (2R)-2-[2-[4-chloro-2-(5-cyclopropyl-2-methylpyrazol-3-yl)oxyphenyl]pyrimidin-5-yl]-2-fluoroethanamine |
| 1349 | 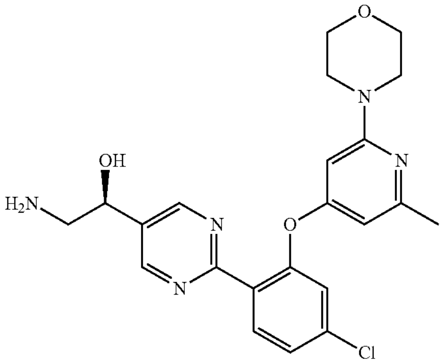 [SMILES: Cc1cc(Oc2cc(Cl)ccc2-c2ncc([C@H](O)CN)cn2)cc(N2CCOCC2)n1] | (1S)-2-amino-1-[2-[4-chloro-2-(2-methyl-6-morpholin-4-ylpyridin-4-yl)oxyphenyl]pyrimidin-5-yl]ethanol |
| 1350 | 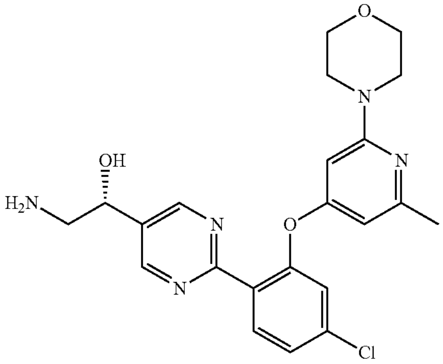 [SMILES: Cc1cc(Oc2cc(Cl)ccc2-c2ncc([C@@H](O)CN)cn2)cc(N2CCOCC2)n1] | (1R)-2-amino-1-[2-[4-chloro-2-(2-methyl-6-morpholin-4-ylpyridin-4-yl)oxyphenyl]pyrimidin-5-yl]ethanol |

TABLE 1-continued
| Compound number | Structural formula | Compound name |
|---|---|---|
| 1351 | 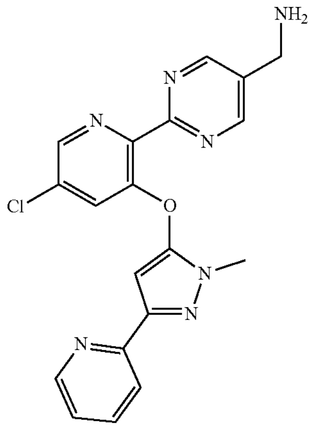 [SMILES: Cn1nc(-c2ccccn2)cc1Oc1cc(Cl)cnc1-c1ncc(CN)cn1] | [2-[5-chloro-3-(2-methyl-5-pyridin-2-ylpyrazol-3-yl)oxypyridin-2-yl]pyrimidin-5-yl]methanamine |
| 1352 | 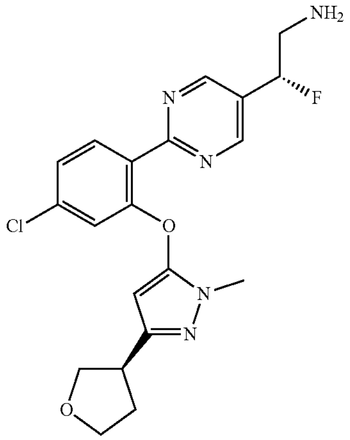 [SMILES: Cn1nc([C@H]2CCOC2)cc1Oc1cc(Cl)ccc1-c1ncc([C@@H](F)CN)cn1] | (2R)-2-[2-[4-chloro-2-[2-methyl-5-[(3R)-oxolan-3-yl]pyrazol-3-yl]oxyphenyl]pyrimidin-5-yl]-2-fluoroethanamine |
| 1353 | 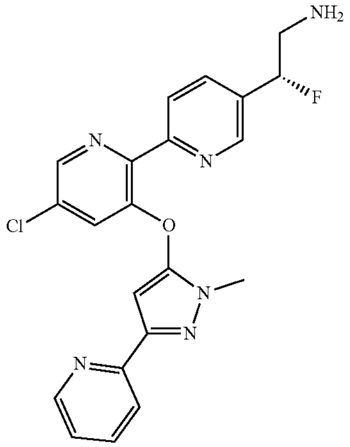 [SMILES: Cn1nc(-c2ccccn2)cc1Oc1cc(Cl)cnc1-c1ccc([C@@H](F)CN)cn1] | (2R)-2-[6-[5-chloro-3-(2-methyl-5-pyridin-2-ylpyrazol-3-yl)oxypyridin-2-yl]pyridin-3-yl]-2-fluoroethanamme |

TABLE 1-continued
| Compound number | Structural formula | Compound name |
|---|---|---|
| 1354 | 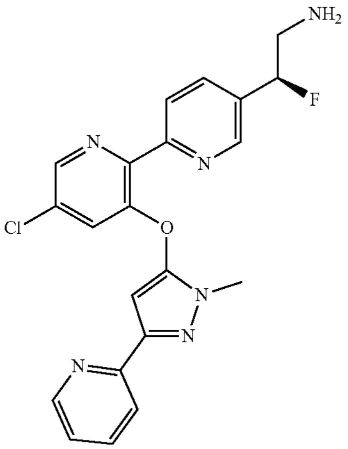 [SMILES: Cn1nc(-c2ccccn2)cc1Oc1cc(Cl)cnc1-c1ccc([C@H](F)CN)cn1] | (2S)-2-[6-[5-chloro-3-(2-methyl-5-pyridin-2-ylpyrazol-3-yl)oxypyridin-2-yl]pyridin-3-yl]-2-fluoroethanamine |
| 1355 | 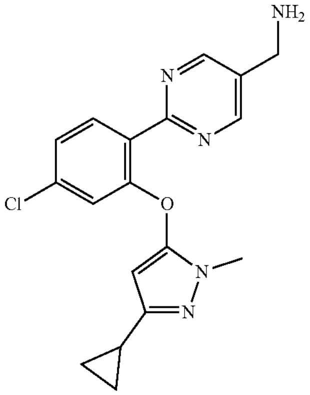 [SMILES: Cn1nc(C2CC2)cc1Oc1cc(Cl)ccc1-c1ncc(CN)cn1] | [2-[4-chloro-2-(5-cyclopropyl-2-methylpyrazol-3-yl)oxyphenyl]pyrimidin-5-yl]methanamine |
| 1356 | 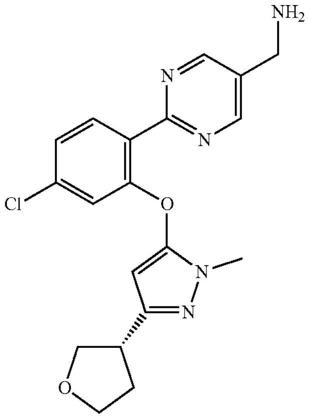 [SMILES: Cn1nc([C@@H]2CCOC2)cc1Oc1cc(Cl)ccc1-c1ncc(CN)cn1] | [2-[4-chloro-2-[2-methyl-5-[(3S)-oxolan-3-yl]pyrazol-3-yl]oxyphenyl]pyrimidin-5-yl]methanamine |

TABLE 1-continued
| Compound number | Structural formula | Compound name |
| --- | --- | --- |
| 1357 | 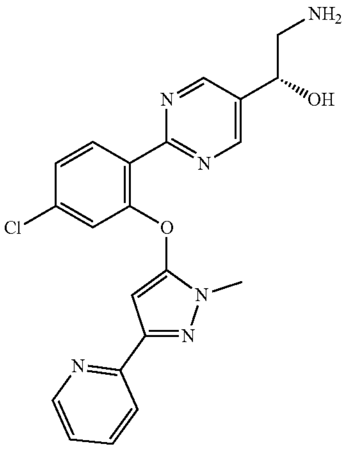 [SMILES: Cn1nc(-c2ccccn2)cc1Oc1cc(Cl)ccc1-c1ncc([C@@H](O)CN)cn1] | (1R)-2-amino-1-[2-[4-chloro-2-(2-methyl-5-pyridin-2-ylpyrazol-3-yl)oxyphenyl]pyrimidin-5-yl]ethanol |
| 1358 | 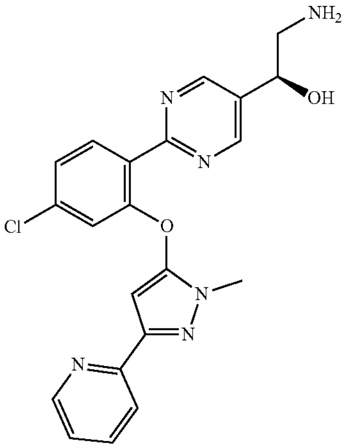 [SMILES: Cn1nc(-c2ccccn2)cc1Oc1cc(Cl)ccc1-c1ncc([C@H](O)CN)cn1] | (1S)-2-amino-1-[2-[4-chloro-2-(2-methyl-5-pyridin-2-ylpyrazol-3-yl)oxyphenyl]pyrimidin-5-yl]ethanol |
| 1359 | 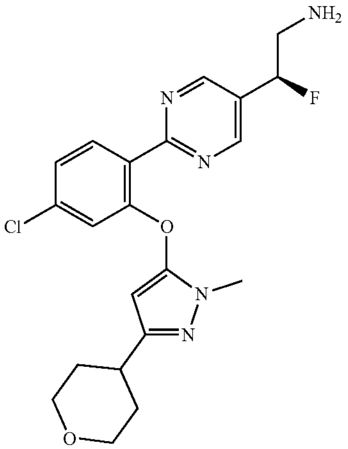 [SMILES: Cn1nc(C2CCOCC2)cc1Oc1cc(Cl)ccc1-c1ncc([C@H](F)CN)cn1] | (2S)-2-[2-[4-chloro-2-[2-methyl-5-(oxan-4-yl)pyrazol-3-yl]oxyphenyl]pyrimidin-5-yl]-2-fluoroethanamine |

TABLE 1-continued
| Compound number | Structural formula | Compound name |
|---|---|---|
| 1360 | 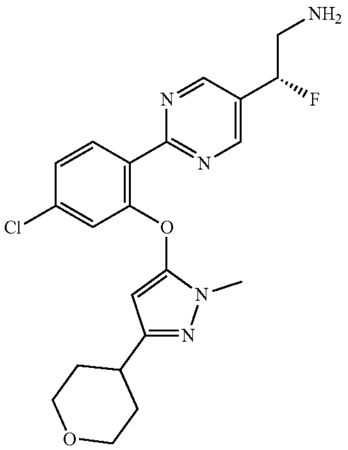 [SMILES: Cn1nc(C2CCOCC2)cc1Oc1cc(Cl)ccc1-c1ncc([C@@H](F)CN)cn1] | (2R)-2-[2-[4-chloro-2-[2-methyl-5-(oxan-4-yl)pyrazol-3-yl]oxyphenyl]pyrimidin-5-yl]-2-fluoroethanamine |
| 1361 | 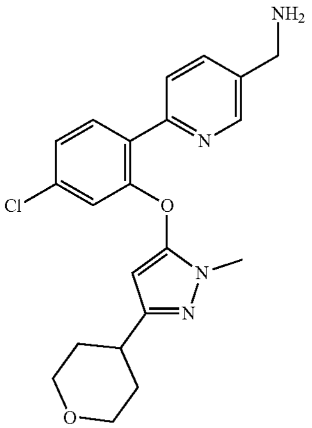 [SMILES: Cn1nc(C2CCOCC2)cc1Oc1cc(Cl)ccc1-c1ccc(CN)cn1] | [6-[4-chloro-2-[2-methyl-5-(oxan-4-yl)pyrazol-3-yl]oxyphenyl]pyridin-3-yl]methanamine |
| 1362 | 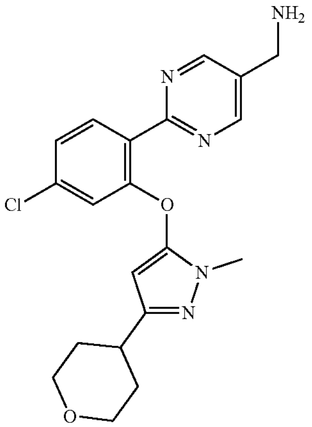 [SMILES: Cn1nc(C2CCOCC2)cc1Oc1cc(Cl)ccc1-c1ncc(CN)cn1] | [2-[4-chloro-2-[2-methyl-5-(oxan-4-yl)pyrazol-3-yl]oxyphenyl]pyrimidin-5-yl]methanamine |

TABLE 1-continued
| Compound number | Structural formula | Compound name |
| --- | --- | --- |
| 1363 | 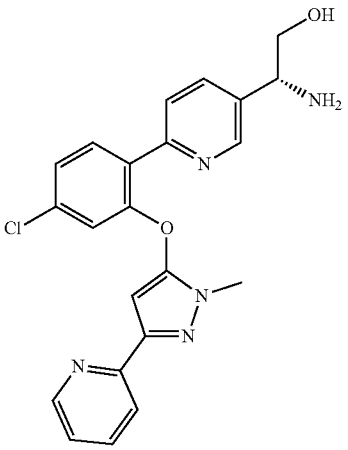 [SMILES: Cn1nc(-c2ccccn2)cc1Oc1cc(Cl)ccc1-c1ccc([C@@H](N)CO)cn1] | (2R)-2-amino-2-[6-[4-chloro-2-(2-methyl-5-pyridin-2-ylpyrazol-3-yl)oxyphenyl]pyridin-3-yl]ethanol |
| 1364 | 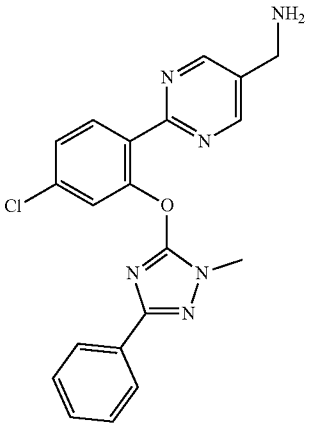 [SMILES: Cn1nc(-c2ccccc2)nc1Oc1cc(Cl)ccc1-c1ncc(CN)cn1] | [2-[4-chloro-2-[(2-methyl-5-phenyl 1,2,4-triazol-3-yl)oxy]phenyl]pyrimidin-5-yl]methanamine |
| 1365 | 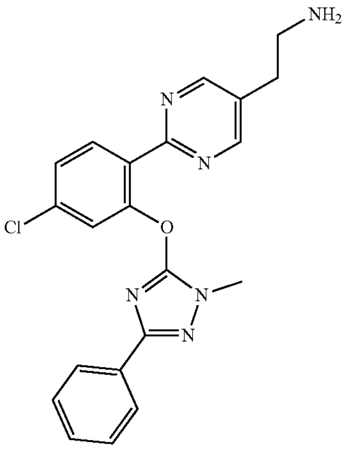 [SMILES: Cn1nc(-c2ccccc2)nc1Oc1cc(Cl)ccc1-c1ncc(CCN)cn1] | 2-[2-[4-chloro-2-[(2-methyl-5-phenyl-1,2,4-triazol-3-yl)oxy]phenyl]pyrimidin-5-yl]ethanamine |

TABLE 1-continued
| Compound number | Structural formula | Compound name |
|---|---|---|
| 1366 | 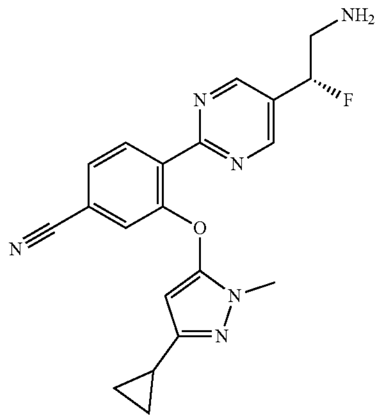 [SMILES: Cn1nc(C2CC2)cc1Oc1cc(C#N)ccc1-c1ncc([C@@H](F)CN)cn1] | 4-[5-[(1R)-2-amino-1-fluoroethyl]pyrimidin-2-yl]-3-(5-cyclopropyl-2-methylpyrazol-3-yl)oxybenzonitrile |
| 1367 | 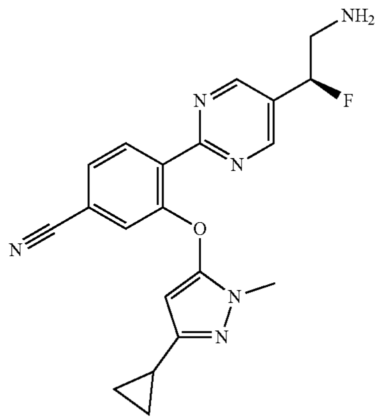 [SMILES: Cn1nc(C2CC2)cc1Oc1cc(C#N)ccc1-c1ncc([C@H](F)CN)cn1] | 4-[5-[(1S)-2-amino-1-fluoroethyl]pyrimidin-2-yl]-3-(5-cyclopropyl-2-methylpyrazol-3-yl)oxybenzonitrile |
| 1368 | 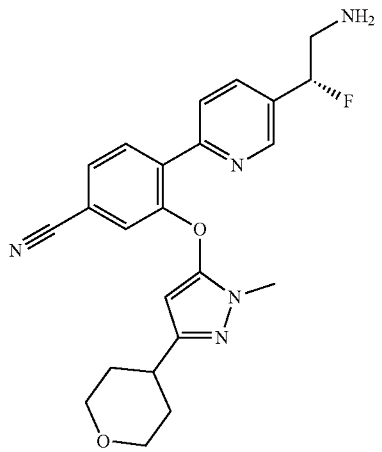 [SMILES: Cn1nc(C2CCOCC2)cc1Oc1cc(C#N)ccc1-c1ccc([C@@H](F)CN)cn1] | 4-[5-[(1R)-2-amino-1-fluoroethyl]pyridin-2-yl]-3-[2-methyl-5-(oxan-4-yl)pyrazol-3-yl]oxybenzonitrile |

TABLE 1-continued
| Compound number | Structural formula | Compound name |
|---|---|---|
| 1369 | 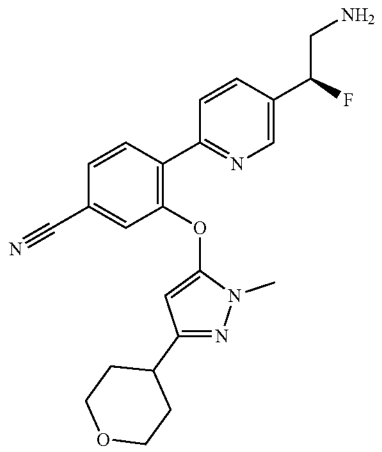 [SMILES: Cn1nc(C2CCOCC2)cc1Oc1cc(C#N)ccc1-c1ccc([C@H](F)CN)cn1] | 4-[5-[(1S)-2-amino-1-fluoroethyl]pyridin-2-yl]-3-[2-methyl-5-(oxan-4-yl)pyrazol-3-yl]oxybenzonitrile |
| 1370 | 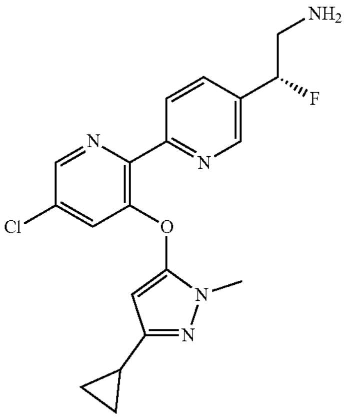 [SMILES: Cn1nc(C2CC2)cc1Oc1cc(Cl)cnc1-c1ccc([C@@H](F)CN)cn1] | (2R)-2-[6-[5-chloro-3-(5-cyclopropyl-2-methylpyrazol-3-yl)oxypyridin-2-yl]pyridin-3-yl]-2-fluoroethanamine |
| 1371 | 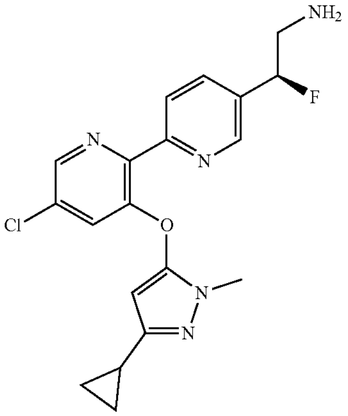 [SMILES: Cn1nc(C2CC2)cc1Oc1cc(Cl)cnc1-c1ccc([C@H](F)CN)cn1] | (2S)-2-[6-[5-chloro-3-(5-cyclopropyl-2-methylpyrazol-3-yl)oxypyridin-2-yl]pyridin-3-yl]-2-fluoroethanamine |

TABLE 1-continued
| Compound number | Structural formula | Compound name |
|---|---|---|
| 1372 | 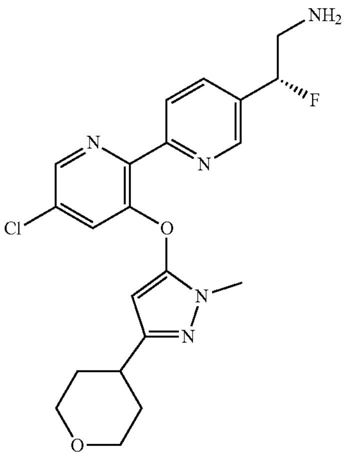 [SMILES: Cn1nc(C2CCOCC2)cc1Oc1cc(Cl)cnc1-c1ccc([C@@H](F)CN)cn1] | (2R)-2-[6-[5-chloro-3-[2-methyl-5-(oxan-4-yl)pyrazol-3-yl]oxypyridin-2-yl]pyridin-3-yl]-2-fluoroethanamine |
| 1373 | 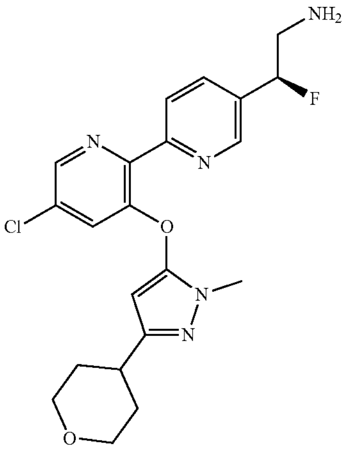 [SMILES: Cn1nc(C2CCOCC2)cc1Oc1cc(Cl)cnc1-c1ccc([C@H](F)CN)cn1] | (2S)-2-[6-[5-chloro-3-[2-methyl-5-(oxan-4-yl)pyrazol-3-yl]oxypyridin-2-yl]pyridin-3-yl]-2-fluoroethanamine |
| 1374 | 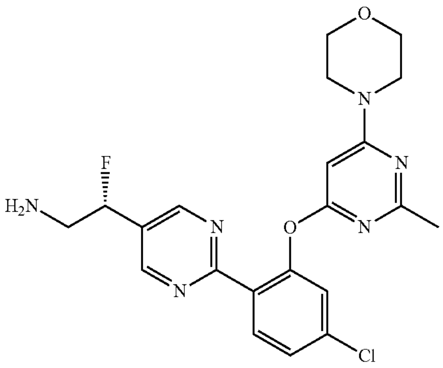 [SMILES: Cc1nc(Oc2cc(Cl)ccc2-c2ncc([C@@H](F)CN)cn2)cc(N2CCOCC2)n1] | (2R)-2-[2-[4-chloro-2-(2-methyl-6-morpholin-4-ylpyrimidin-4-yl)oxyphenyl]pyrimidin-5-yl]-2-fluoroethanamine |

TABLE 1-continued

| Compound number | Structural formula | Compound name |
|---|---|---|
| 1375 | 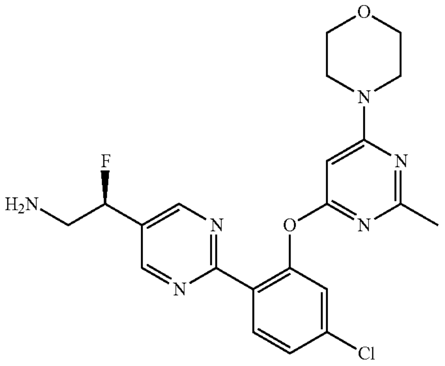 [SMILES: Cc1nc(Oc2cc(Cl)ccc2-c2ncc([C@H](F)CN)cn2)cc(N2CCOCC2)n1] | (2S)-2-[2-[4-chloro-2-(2-methyl-6-morpholin-4-ylpyrimidin-4-yl)oxyphenyl]pyrimidin-5-yl]-2-fluoroethanamine |
| 1376 | 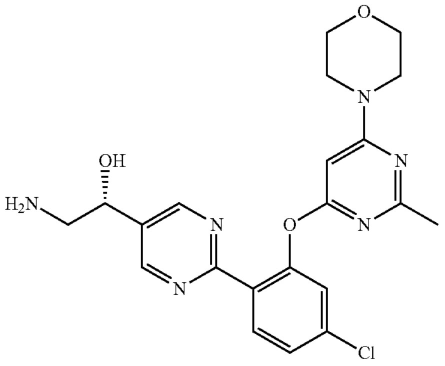 [SMILES: Cc1nc(Oc2cc(Cl)ccc2-c2ncc([C@@H](O)CN)cn2)cc(N2CCOCC2)n1] | (1R)-2-amino-1-[2-[4-chloro-2-(2-methyl-6-morpholin-4-ylpyrimidin-4-yl)oxyphenyl]pyrimidin-5-yl]ethanol |
| 1377 | 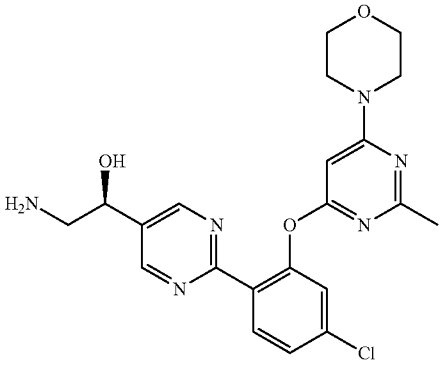 [SMILES: Cc1nc(Oc2cc(Cl)ccc2-c2ncc([C@H](O)CN)cn2)cc(N2CCOCC2)n1] | (1S)-2-amino-1-[2-[4-chloro-2-(2-methyl-6-morpholin-4-ylpyrimidin-4-yl)oxyphenyl]pyrimidin-5-yl]ethanol |
| 1378 | 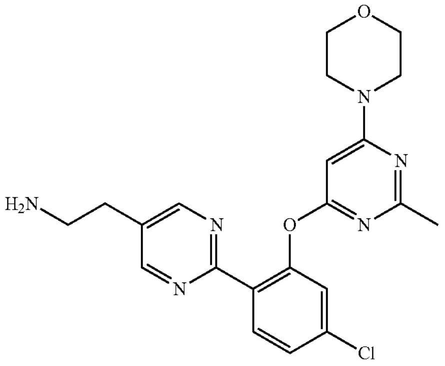 [SMILES: Cc1nc(Oc2cc(Cl)ccc2-c2ncc(CCN)cn2)cc(N2CCOCC2)n1] | 2-[2-[4-chloro-2-(2-methyl-6-morpholin-4-ylpyrimidin-4-yl)oxyphenyl]pyrimidin-5-yl]ethanamine |

TABLE 1-continued
| Compound number | Structural formula | Compound name |
| --- | --- | --- |
| 1379 | 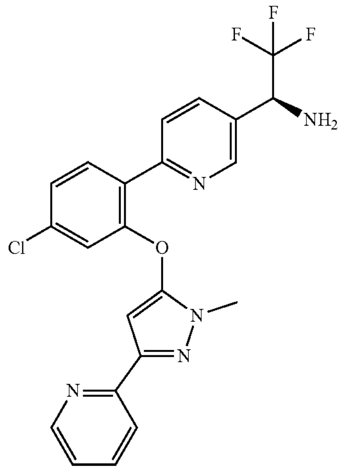 [SMILES: Cn1nc(-c2ccccn2)cc1Oc1cc(Cl)ccc1-c1ccc([C@H](N)C(F)(F)F)cn1] | (1S)-1-[6-[4-chloro-2-(2-methyl-5-pyridin-2-ylpyrazol-3-yl)oxyphenyl]pyridin-3-yl]-2,2,2-trifluoroethanamine |
| 1380 | 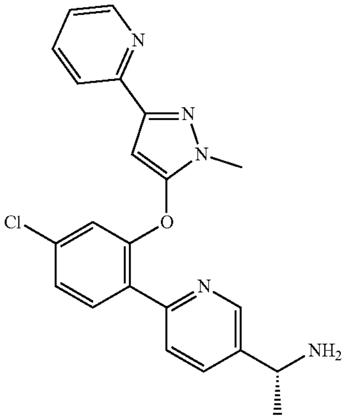 [SMILES: C[C@@H](N)c1ccc(-c2ccc(Cl)cc2Oc2cc(-c3ccccn3)nn2C)nc1] | (1R)-1-[6-[4-chloro-2-(2-methyl-5-pyridin-2-ylpyrazol-3-yl)oxyphenyl]pyridin-3-yl]ethanamine |
| 1381 | 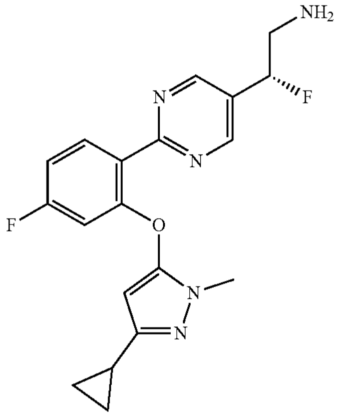 [SMILES: Cn1nc(C2CC2)cc1Oc1cc(F)ccc1-c1ncc([C@@H](F)CN)cn1] | (2S)-2-[2-[2-(5-cyclopropyl-2-methylpyrazol-3-yl)oxy-4-fluorophenyl]pyrimidin-5-yl]-2-fluoroethanamine |

TABLE 1-continued
| Compound number | Structural formula | Compound name |
|---|---|---|
| 1382 | 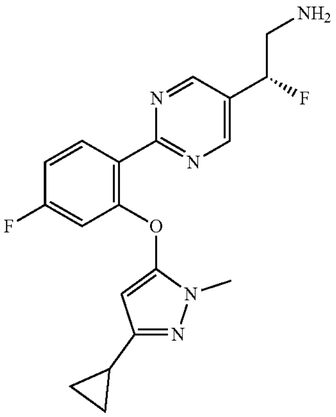 [SMILES: Cn1nc(C2CC2)cc1Oc1cc(F)ccc1-c1ncc([C@@H](F)CN)cn1] | (2R)-2-[2-[2-(5-cyclopropyl-2-methylpyrazol-3-yl)oxy-4-fluorophenyl]pyrimidin-5-yl]-2-fluoroethanamine |
| 1383 | 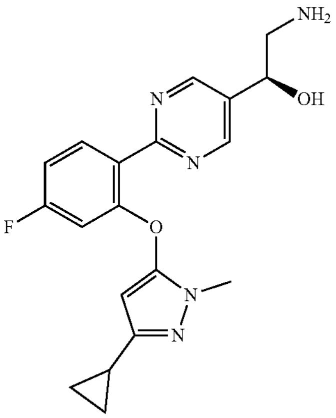 [SMILES: Cn1nc(C2CC2)cc1Oc1cc(F)ccc1-c1ncc([C@H](O)CN)cn1] | (1S)-2-amino-1-[2-[2-(5-cyclopropyl-2-methylpyrazol-3-yl)oxy-4-fluorophenyl]pyrimidin-5-yl]ethanol |
| 1384 | 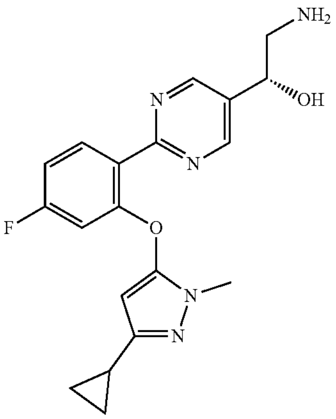 [SMILES: Cn1nc(C2CC2)cc1Oc1cc(F)ccc1-c1ncc([C@@H](O)CN)cn1] | (1R)-2-amino-1-[2-[2-(5-cyclopropyl-2-methylpyrazol-3-yl)oxy-4-fluorophenyl]pyrimidin-5-yl]ethanol |

TABLE 1-continued
| Compound number | Structural formula | Compound name |
|---|---|---|
| 1385 | 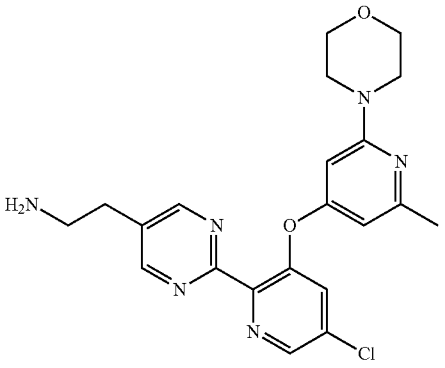 [SMILES: Cc1cc(Oc2cc(Cl)cnc2-c2ncc(CCN)cn2)cc(N2CCOCC2)n1] | 2-[2-[5-chloro-3-(2-methyl-6-morpholin-4-ylpyridin-4-yl)oxypyridin-2-yl]pyrimidin-5-yl]ethanamine |
| 1386 | 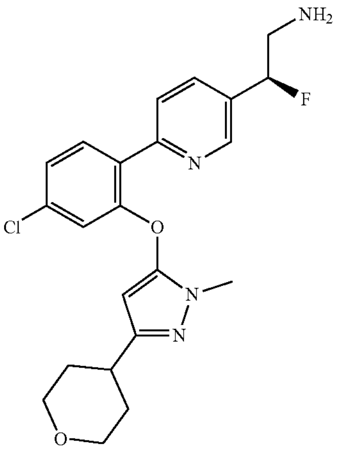 [SMILES: Cn1nc(C2CCOCC2)cc1Oc1cc(Cl)ccc1-c1ccc([C@H](F)CN)cn1] | (2S)-2-[6-[4-chloro-2-[2-methyl-5-(oxan-4-yl)pyrazol-3-yl]oxyphenyl]pyridin-3-yl]-2-fluoroethanamine |
| 1387 | 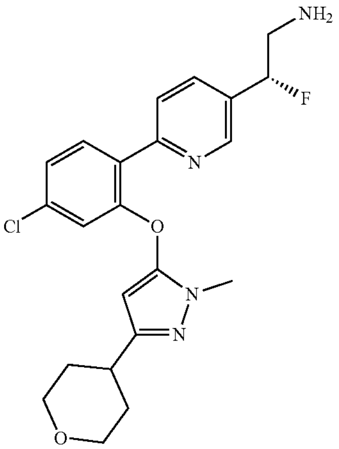 [SMILES: Cn1nc(C2CCOCC2)cc1Oc1cc(Cl)ccc1-c1ccc([C@@H](F)CN)cn1] | (2R)-2-[6-[4-chloro-2-[2-methyl-5-(oxan-4-yl)pyrazol-3-yl]oxyphenyl]pyridin-3-yl]-2-fluoroethanamine |

TABLE 1-continued
| Compound number | Structural formula | Compound name |
|---|---|---|
| 1388 | 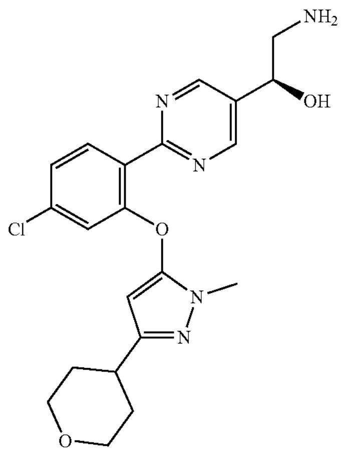 [SMILES: Cn1nc(C2CCOCC2)cc1Oc1cc(Cl)ccc1-c1ncc([C@H](O)CN)cn1] | (1S)-2-amino-1-[2-[4-chloro-2-[2-methyl-5-(oxan-4-yl)pyrazol-3-yl]oxyphenyl]pyrimidin-5-yl]ethanol |
| 1389 | 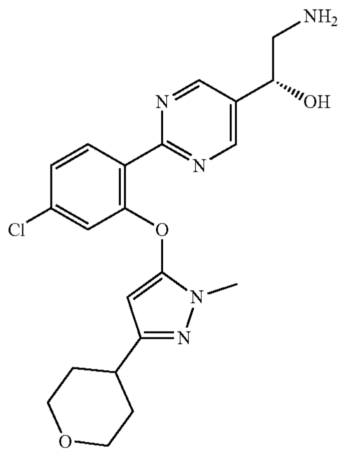 [SMILES: Cn1nc(C2CCOCC2)cc1Oc1cc(Cl)ccc1-c1ncc([C@@H](O)CN)cn1] | (1R)-2-amino-1-[2-[4-chloro-2-[2-methyl-5-(oxan-4-yl)pyrazol-3-yl]oxyphenyl]pyrimidin-5-yl]ethanol |
| 1390 | 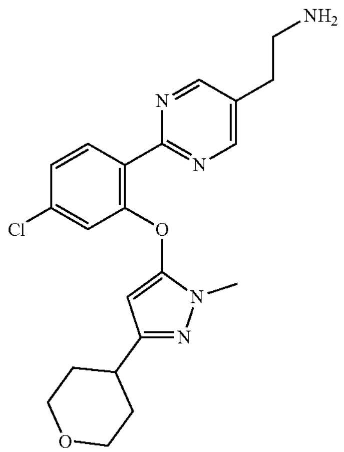 [SMILES: Cn1nc(C2CCOCC2)cc1Oc1cc(Cl)ccc1-c1ncc(CCN)cn1] | 2-[2-[4-chloro-2-[2-methyl-5-(oxan-4-yl)pyrazol-3-yl]oxyphenyl]pyrimidin-5-yl]ethanamine |

TABLE 1-continued

| Compound number | Structural formula | Compound name |
|---|---|---|
| 1391 | 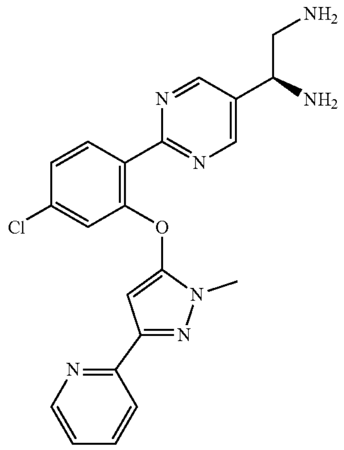 | (2S)-2-amino-2-[2-[4-chloro-2-(2-methyl-5-pyridin-2-ylpyrazol-3-yl)oxyphenyl]pyrimidin-5-yl]ethanol |
| 1392 | 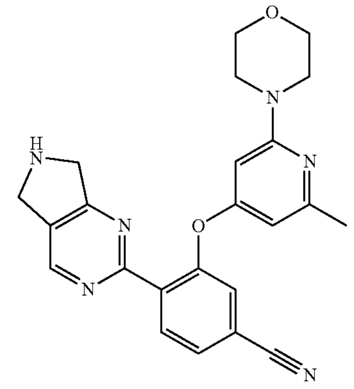 [SMILES: Cc1cc(Oc2cc(C#N)ccc2-c2ncc3c(n2)CNC3)cc(N2CCOCC2)n1] | 4-(6,7-dihydro-5H-pyrrolo[3,4-d]pyrimidin-2-yl)-3-(2-methyl-6-morpholin-4-ylpyridin-4-yl)oxybenzonitrile |
| 1393 | 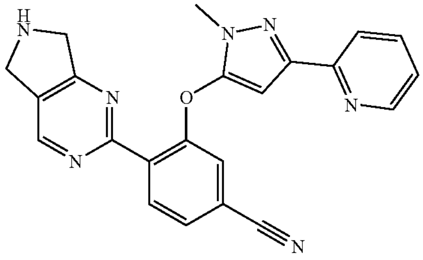 [SMILES: Cn1nc(-c2ccccn2)cc1Oc1cc(C#N)ccc1-c1ncc2c(n1)CNC2] | 4-(6,7-dihydro-5H-pyrrolo[3,4-d]pyrimidin-2-yl)-3-(2-methyl-5-pyridin-2-ylpyrazol-3-yl)oxybenzonitrile |
| 1394 | 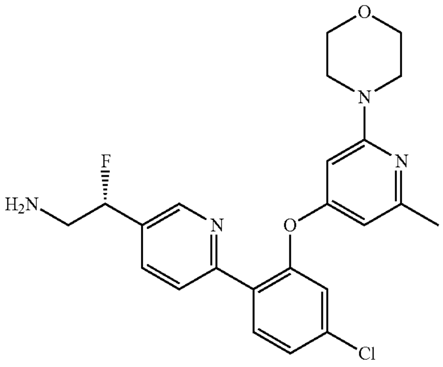 [SMILES: Cc1cc(Oc2cc(Cl)ccc2-c2ccc([C@@H](F)CN)cn2)cc(N2CCOCC2)n1] | (2R)-2-[6-[4-chloro-2-(2-methyl-6-morpholin-4-ylpyridin-4-yl)oxyphenyl]pyridin-3-yl]-2-fluoroethanamine |

TABLE 1-continued

| Compound number | Structural formula | Compound name |
| --- | --- | --- |
| 1395 | 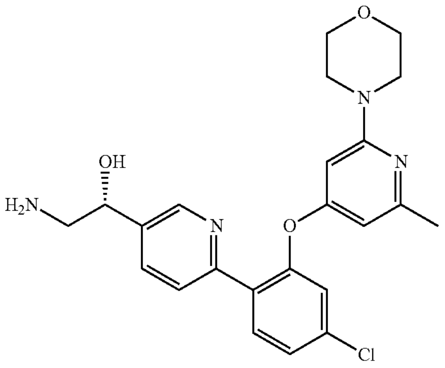 [SMILES: Cc1cc(Oc2cc(Cl)ccc2-c2ccc([C@@H](O)CN)cn2)cc(N2CCOCC2)n1] | (1R)-2-amino-1-[6-[4-chloro-2-(2-methyl-6-morpholin-4-ylpyridin-4-yl)oxyphenyl]pyridin-3-yl]ethanol |
| 1396 | 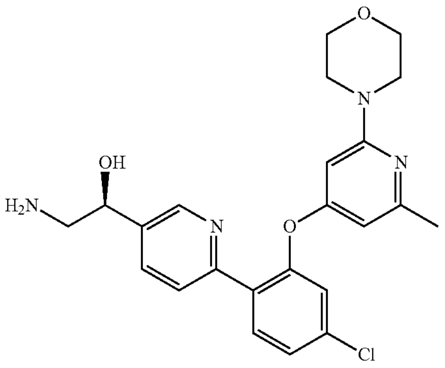 [SMILES: Cc1cc(Oc2cc(Cl)ccc2-c2ccc([C@H](O)CN)cn2)cc(N2CCOCC2)n1] | (1S)-2-amino-1-[6-[4-chloro-2-(2-methyl-6-morpholin-4-ylpyridin-4-yl)oxyphenyl]pyridin-3-yl]ethanol |
| 1397 | 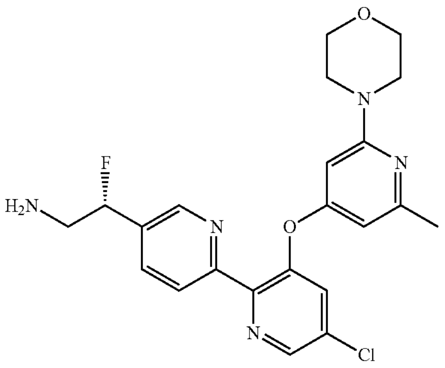 [SMILES: Cc1cc(Oc2cc(Cl)cnc2-c2ccc([C@@H](F)CN)cn2)cc(N2CCOCC2)n1] | (2R)-2-[6-[5-chloro-3-(2-methyl-6-morpholin-4-ylpyridin-4 yl)oxypyridin-2-yl]pyridin-3-yl]-2-fluoroethanamine |
| 1398 | 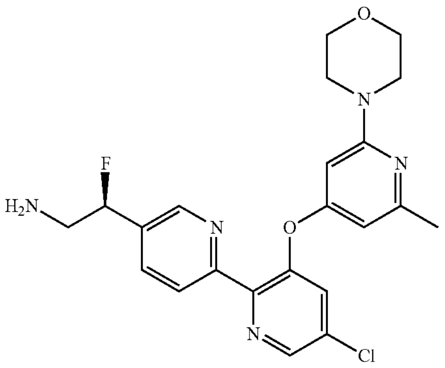 [SMILES: Cc1cc(Oc2cc(Cl)cnc2-c2ccc([C@H](F)CN)cn2)cc(N2CCOCC2)n1] | (2S)-2-[6-[5-chloro-3-(2-methyl-6-morpholin-4-ylpyridin-4-yl)oxypyridin-2-yl]pyridin-3-yl-2-fluoroethanamine |

TABLE 1-continued
| Compound number | Structural formula | Compound name |
| --- | --- | --- |
| 1399 | 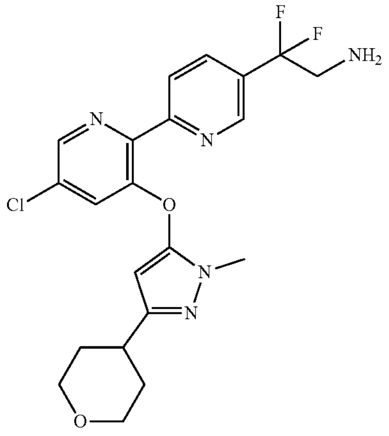 [SMILES: Cn1nc(C2CCOCC2)cc1Oc1cc(Cl)cnc1-c1ccc(C(F)(F)CN)cn1] | 2-[6-[5-chloro-3-[2-methyl-5-(oxan-4-yl)pyrazol-3-yl]oxypyridin-2-yl]pyridin-3-yl]-2,2-difluoroethanamine |
| 1400 | 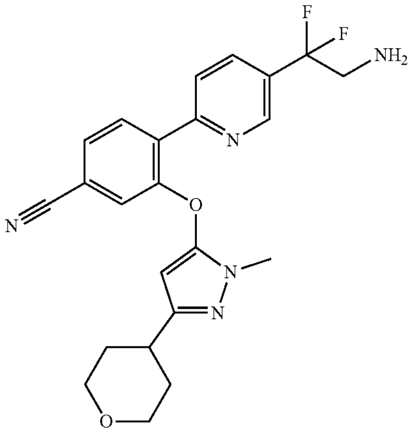 [SMILES: Cn1nc(C2CCOCC2)cc1Oc1cc(C#N)ccc1-c1ccc(C(F)(F)CN)cn1] | 4-[5-(2-amino-1,1-difluoroethyl)pyridin-2-yl]-3-[2-methyl-5-(oxan-4-yl)pyrazol-3-yl]oxybenzonitrile |
| 1401 | 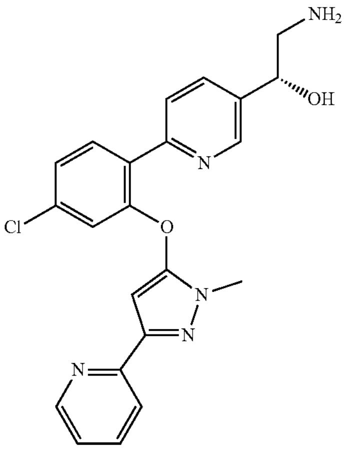 [SMILES: Cn1nc(-c2ccccn2)cc1Oc1cc(Cl)ccc1-c1ccc([C@@H](O)CN)cn1] | (1R)-2-amino-1-[6-[4-chloro-2-(2-methyl-5-pyridin-2-ylpyrazol-3-yl)oxyphenyl]pyridin-3-yl]ethanol |

TABLE 1-continued
| Compound number | Structural formula | Compound name |
| --- | --- | --- |
| 1402 | 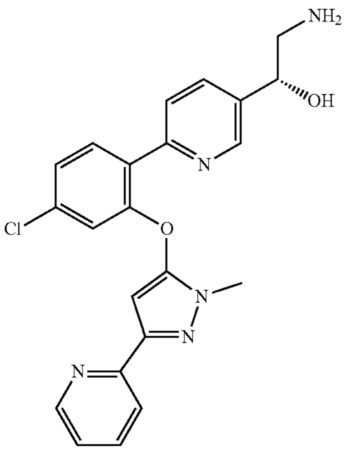 [SMILES: Cn1nc(-c2ccccn2)cc1Oc1cc(Cl)ccc1-c1ccc([C@@H](O)CN)cn1] | (1S)-2-amino-1-6-[4-chloro-2-(2-methyl-5-pyridin-2-ylpyrazol-3-yl)oxyphenyl]pyridin-3-yl]ethanol |
| 1403 | 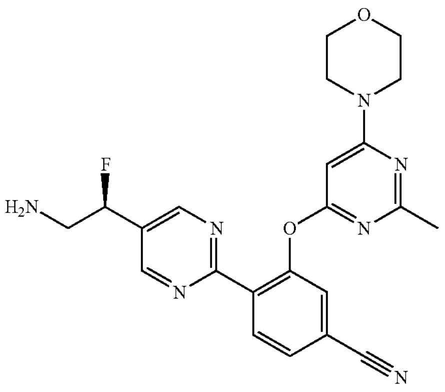 [SMILES: Cc1nc(Oc2cc(C#N)ccc2-c2ncc([C@H](F)CN)cn2)cc(N2CCOCC2)n1] | 4-[5-[(1S)-2-amino-1-fluoroethyl]pyrimidin-2-yl]-3-(2-methyl-6-morpholin-4-ylpyrimidin-4-yl)oxybenzonitrile |
| 1404 | 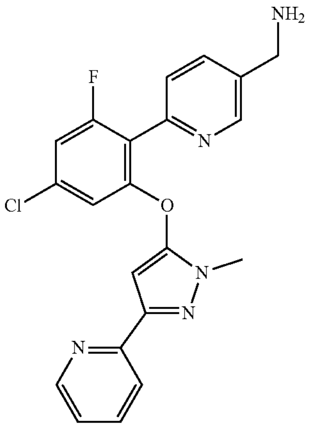 [SMILES: Cn1nc(-c2ccccn2)cc1Oc1cc(Cl)cc(F)c1-c1ccc(CN)cn1] | [6-[4-chloro-2-fluoro-6-(2-methyl-5-pyridin-2-ylpyrazol-3-yl)oxyphenyl]pyridin-3-yl]methanamine |

TABLE 1-continued

| Compound number | Structural formula | Compound name |
| --- | --- | --- |
| 1405 | 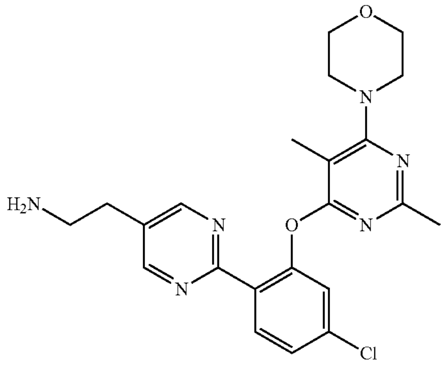 [SMILES: Cc1nc(Oc2cc(Cl)ccc2-c2ncc(CCN)cn2)c(C)c(N2CCOCC2)n1] | 2-[2-[4-chloro-2-(2,5-dimethyl-6-morpholin-4-ylpyrimidin-4-yl)oxyphenyl]pyrimidin-5-yl]ethanamine |

Among these, preferable compounds are those of compound number 2, 6, 7, 9, 11, 17, 21, 25, 26, 30, 32, 33, 46, 50, 62, 65, 66, 69, 70, 82, 93, 100, 101, 112, 113, 115, 120, 130, 133, 137, 138, 149, 150, 153, 157, 159-162, 164, 170-177, 179, 180, 182, 183, 185-187, 197-199, 202, 204-206, 211-213, 215, 225-233, 237, 238, 241, 246-250, 253, 254, 258, 260-262, 264, 266, 267, 272-278, 285, 287-289, 293-296, 299, 301, 306, 310, 312-315, 317-321, 324-329, 333-338, 341, 344, 346, 348, 360-367, 370-376, 378, 379, 381-384, 388, 390-394, 396, 398, 399, 401-407, 413, 426, 429, 430, 432, 434, 439-441, 444-448, 454, 458, 459, 461, 467, 469-471, 477, 482-485, 493, 496, 498-503, 505-510, 517, 521, 522, 525-527, 529-532, 536, 541-544, 550, 562, 575, 587, 592, 599, 604, 609, 610, 619, 621-629, 634, 637, 642, 644, 651, 652, 655-657, 668, 670-672, 691, 695-697, 701, 702, 704, 706, 708, 711, 714, 715, 718, 724, 734, 735, 737, 742, 743, 748, 754, 758-760, 765, 767-770, 772-775, 786, 787, 795, 799, 801-803, 808-812, 822, 823, 826-828, 832-835, 842, 848-850, 854, 856, 857, 859-861, 866, 872-878, 900, 903-910, 912-916, 932, 935, 937, 945, 948-953, 955, 957, 958, 963, 966, 968, 969, 972, 975, 977-980, 983, 985, 987-992, 996, 1000, 1001, 1010-1014, 1017, 1018, 1025-1033, 1035, 1037, 1042-1049, 1051, 1054, 1057-1063, 1065, 1066, 1071-1080, 1086, 1087, 1097, 1106, 1107, 1110, 1120, 1129-1131, 1135, 1137, 1143-1145, 1147-1156, 1167, 1173, 1184-1187, 1195, 1199, 1202, 1203, 1205-1208, 1210-1212, 1214, 1215, 1217-1219, 1233, 1234, 1237, 1239-1241, 1243, 1244, 1249, 1255, 1258, 1259, 1279, 1280, 1295, 1296, 1299-1302, 1304, 1306, 1312, 1316, 1317, 1322-1325, 1330, 1334, 1335, 1337-1340, 1346, 1348, 1350, 1354, 1357, 1360, 1361, 1366-1369, 1371, 1373, 1380, 1387, 1395, 1398 and 1404, more preferably those of compound number 173, 175, 176, 182, 185, 199, 202, 228-230, 237, 250, 254, 258, 260-262, 264, 272, 274, 275, 277, 285, 288, 289, 293, 295, 299, 310, 317, 319, 324-329, 361-364, 367, 371, 390, 391, 393, 394, 402, 439, 440, 444, 445, 447, 448, 454, 459, 461, 470, 471, 541-543, 592, 599, 609, 621-623, 652, 655-658, 671, 672, 697, 706, 754, 758, 769, 770, 773, 775, 786, 787, 795, 801, 802, 810, 811, 812, 826, 827, 832, 833, 835, 842, 849, 856, 857, 859, 860, 866, 874, 875, 877, 907, 912, 937, 948, 953, 955, 958, 963, 966, 972, 975, 977, 979, 980, 987-991, 1000, 1010, 1012-1014, 1018, 1025-1032, 1037, 1042, 1043, 1051, 1061-1063, 1071-1074.

<General Synthesis Method>

The compound represented by the formula (I) of the present invention and a pharmaceutically acceptable salt thereof (hereinafter, these are collectively referred to as the compound of the present invention) can be synthesized by a combination of known methods in the art including the synthesis methods described below. Reagents or solvents described as conditions in the chemical formula are merely examples as described in the description. Each substituent may be protected with a suitable protecting group, if necessary, and may be protected or deprotected at an appropriate step. As a suitable protecting group and a removal method of the protecting group, a protecting group for each substituent and a known method, widely used in this field, can be adopted, and are described, for example, in PROTECTIVE GROUPS in ORGANIC SYNTHESIS, THIRD EDITION, John Wiley & Sons, Inc. Further, the intermediate produced in the following synthesis method may be isolated and purified by a method such as column chromatography, recrystallization, or distillation, or may be used in the next step without isolation.

Typical synthesis methods of the compound of the present invention represented by the general formula (I) will be described below. The synthesis method of the compound of the present invention is not limited to these. The symbols in each formula are defined in the formula (I).

The compound of the present invention can be produced by several synthesis methods. Hereinafter, a typical synthesis method will be described for each structure of $L^1$ of the formula (I).

When $L^1$ in the formula (I) is —$NR^{12}$— in the compound of the present invention, the synthesis can be performed by the method, for example as shown in the following reaction scheme, of constructing a biaryl structure with $Ar^2$ ring and then bonding with $Ar^1$ ring. That is, (A-I) is converted to a boronic acid ester (A-II), then converted to (A-III) by a Suzuki-Miyaura coupling reaction, and then (A-IV) is obtained by a Buchwald-Hartwig amination reaction. The target compound can be synthesized by deprotecting this compound. The target compound can be also synthesized by modifying the amino group after deprotection.

In the following reaction scheme, PG is a protecting group for the amino group (the same applies hereinafter).

[Chem. 8]

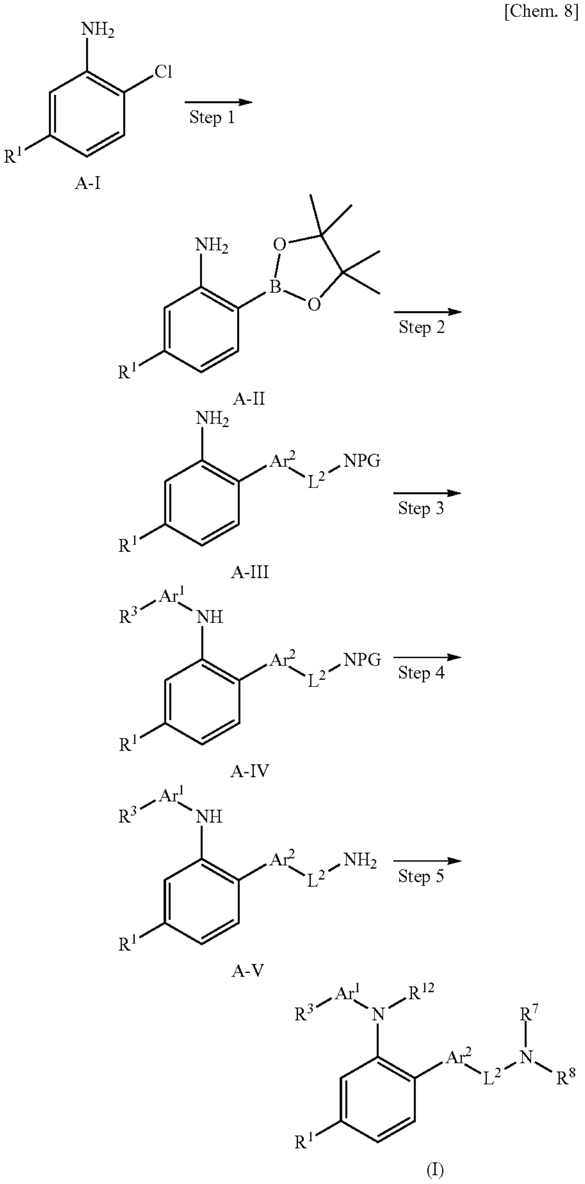

Step 1: Bis(pinacolato)diboron is preferable as the borylation reagent, and tris(dibenzylideneacetone)dipalladium, palladium acetate, tetrakis(triphenylphosphine)palladium, bis(triphenylphosphine)palladium dichloride, [1,1-bis(diphenylphosphino)ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. As the base to be used, potassium acetate or the like is preferable. Here, the solvent is not particularly limited and includes, for example, ethers such as tetrahydrofuran, 1,4-dioxane, 1,2-dimethoxyethane, 1,2-diethoxyethane, and the like, N,N-dimethylformamide, N-methylpyrrolidone, dimethyl sulfoxide, a mixed solvent thereof, and the like. The reaction temperature is preferably from 50° C. to 150° C., and particularly preferably from 70° C. to 120° C.

Step 2: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 3: Tris(dibenzylideneacetone)dipalladium, palladium acetate or the like is preferable as the palladium catalyst. 4,5-Bis(diphenylphosphino)-9,9-dimethylxanthene, 2-dicyclohexylphosphino-2',6'-dimethoxybiphenyl, 2-dicyclohexylphosphino-2',4',6'-triisopropylbiphenyl or the like is preferable as the ligand. The base includes inorganic salts such as sodium hydroxide, potassium hydroxide, lithium hydroxide, sodium carbonate, potassium carbonate, cesium carbonate, tripotassium phosphate, and the like, potassium tert-butoxide, sodium tert-butoxide and the like. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, N,N-dimethylformamide, N-methylpyrrolidone, dimethyl sulfoxide and the like. The reaction temperature is preferably from 50° C. to 150° C., and particularly preferably from 80° C. to 150° C.

Step 4: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine, ethylenediamine or the like is preferable. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide and the like. The reaction temperature is preferably from 0° C. to 100° C.

Step 5: The reaction can be performed using an alkyl halide or the like as a reagent having a leaving group. The base includes organic bases such as triethylamine, N,N-diisopropylethylamine, and the like, and inorganic bases such as potassium carbonate, cesium carbonate, and the like. Tetrahydrofuran, N,N-dimethylformamide, dimethyl sulfoxide or the like is preferable as the solvent. The reaction temperature is preferably from 0° C. to 120° C., and particularly preferable from 0° C. to room temperature. When $X^1$, $X^2$ and $X^3$ in the formula (I) are CH, the synthesis is performed in the above reaction scheme, while even the compound wherein at least one of $X^1$, $X^2$ and $X^3$ is N or CY (wherein Y is a halogen atom or a methyl group) can be synthesized in the same method.

When $L^1$ in the formula (I) is $—NR^{12}—$ in the compound of the present invention, synthesis can be performed by the method, for example as shown in the following reaction scheme, of reacting with $Ar^1$ ring having an amino group and constructing the $L^1$ linker moiety, and then forming a biaryl bond with $Ar^2$ ring.

[Chem. 9]

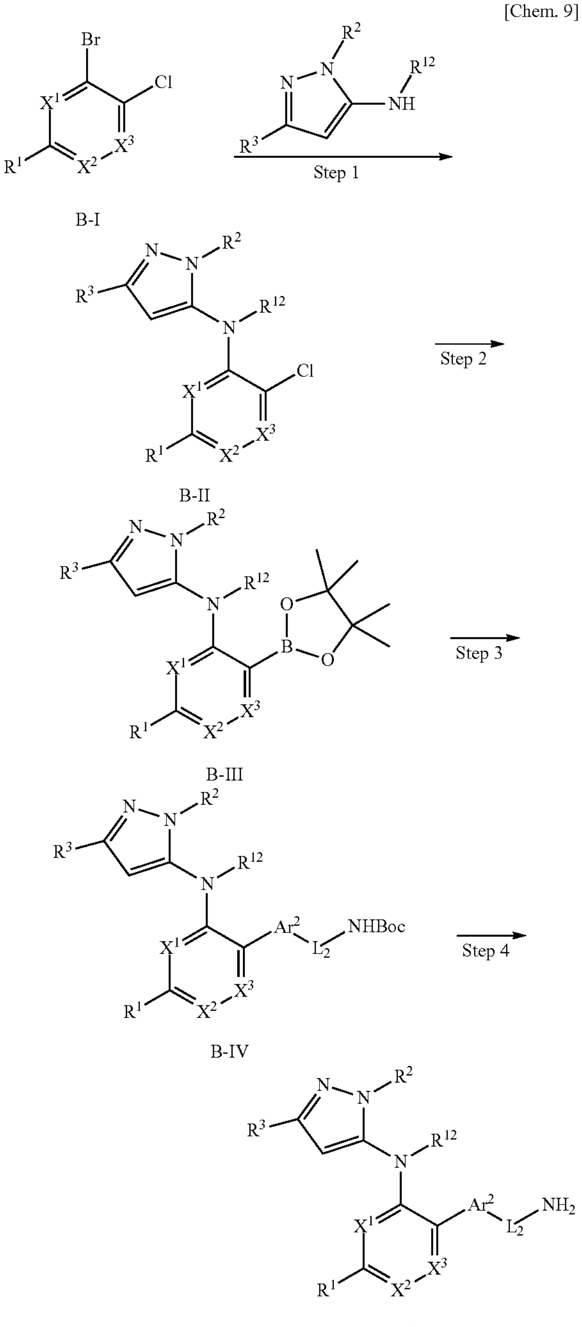

B-I

B-II

B-III

B-IV (I)

Step 1: Tris(dibenzylideneacetone)dipalladium, palladium acetate or the like is preferable as the palladium catalyst. 4,5-Bis(diphenylphosphino)-9,9-dimethylxanthene, 2-dicyclohexylphosphino-2',6'-dimethoxybiphenyl, 2-dicyclohexylphosphino-2',4',6'-triisopropylbiphenyl or the like is preferable as the ligand. The base includes inorganic salts such as sodium hydroxide, potassium hydroxide, lithium hydroxide, sodium carbonate, potassium carbonate, cesium carbonate, tripotassium phosphate, and the like, potassium tert-butoxide, sodium tert-butoxide and the like. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, N,N-dimethylformamide, N-methylpyrrolidone, dimethyl sulfoxide and the like. The reaction temperature is preferably from 50° C. to 150° C., and particularly preferably from 80° C. to 150° C.

Step 2: Bis(pinacolato)diboron is preferable as the borylation reagent and tris(dibenzylideneacetone)dipalladium, palladium acetate, tetrakis(triphenylphosphine)palladium, bis(triphenylphosphine)palladium dichloride, [1,1-bis(diphenylphosphino)ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. The base to be used include potassium acetate and the like. Here, the solvent is not particularly limited, and include, for example, ethers such as tetrahydrofuran, 1,4-dioxane, 1,2-dimethoxyethane, 1,2-diethoxyethane, and the like, N,N-dimethylformamide, N-methylpyrrolidone, dimethyl sulfoxide, a mixed solvent thereof, and the like. The reaction temperature is preferably from 50° C. to 150° C., and particularly preferably from 70° C. to 120° C.

Step 3: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N, N-dimethylformamide, N-methylpyrrolidone, dimethyl sulfoxide, water a mixed solvent thereof, and the like. The reaction temperature is preferably from 50° C. to 150° C., and particularly preferably from 80° C. to 120° C.

Step 4: A strong acid such as trifluoroacetic acid, hydrochloric acid, sulfuric acid, or the like is preferable as the reagent, and a solvent such as dichloromethane, tetrahydrofuran, ethyl acetate or the like is preferable as the solvent. The reaction temperature is preferably from 0° C. to 50° C., and particularly preferably from 0° C. to room temperature.

When $L^1$ in the formula (I) is —O— in the compound of the present invention, synthesis can be performed by using the following synthesis methods.

For example, the synthesis can be performed by the method shown in the following reaction scheme. That is, by obtaining (C—II) bonding with $Ar^1$ ring via an oxygen atom by nucleophilic aromatic substitution reaction, converting (C—II) into a boron compound, a tin compound, or the like, and by performing the cross-coupling reaction with the corresponding $Ar^2$ ring compound, the biaryl form (C—IV) can be synthesized. After that, if the amino group is protected, the deprotection thereof can be performed, and if necessary, the target compound can be synthesized by modification of a free amino group. On the other hand, (C—II) can be directly used to perform cross-coupling reaction or the like with $Ar^2$ ring compounds having suitable reactive substituents without an operation of step 2. Further, substituent $R^3$ can be converted at an appropriate timing in the following reaction scheme by methods known to those skilled in the art, depending on a target structure.

[Chem. 10]

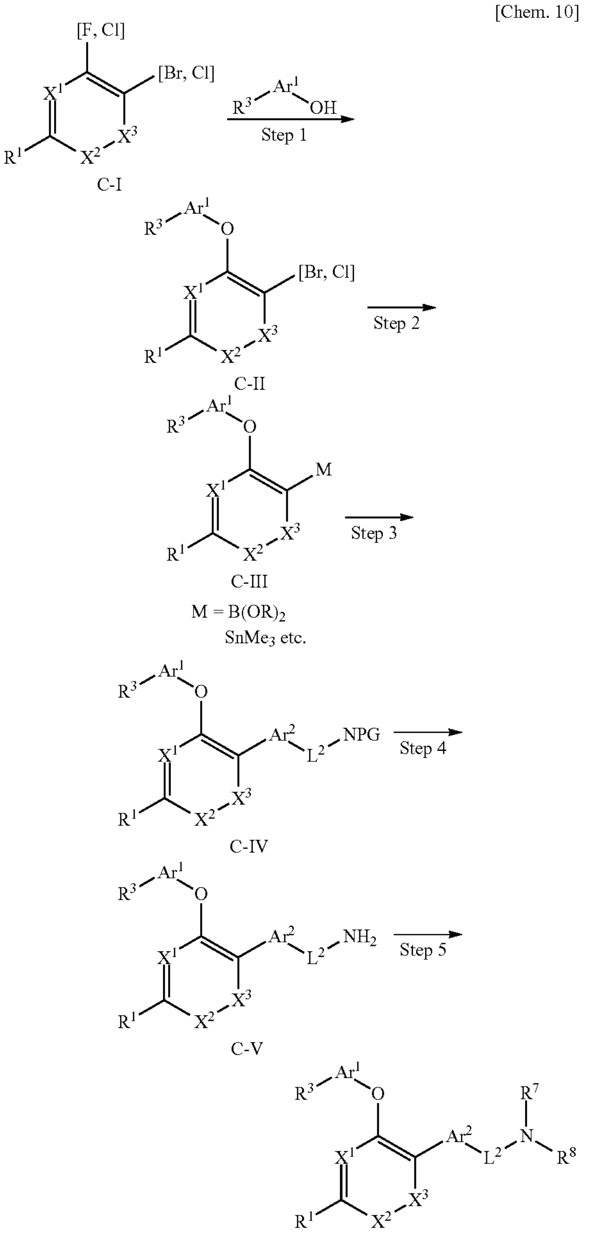

Step 1: Potassium carbonate, sodium carbonate, cesium carbonate, potassium tert-butoxide, sodium tert-butoxide or the like is preferable as the base to be used. Preferred solvents include, for example, N,N-dimethylformamide, N,N-dimethylacetamide, N-methylpyrrolidone, dimethyl sulfoxide and the like. The reaction temperature is preferably from room temperature to 150° C.

Step 2: The borylation reagent to be used includes, for example, bis(pinacolato)diboron and the like, and the tin reagent includes, for example, hexamethylditin and the like. Tris(dibenzylideneacetone)dipalladium, palladium acetate, tetrakis(triphenylphosphine)palladium, bis(triphenylphosphine)palladium dichloride, [1,1'-bis(diphenylphosphino) ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. Potassium acetate or the like is preferable as the base for borylation. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide and the like. The reaction temperature is preferably from 50° C. to 150° C., and particularly preferably from 70° C. to 120° C.

Step 3: Tetrakis(triphenylphosphine)palladium(0), bis(triphenylphosphine)palladium(II) dichloride, [1,1'-bis(diphenylphosphino)ferrocene]palladium(II) dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 4: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine or ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide and the like. The reaction temperature is preferably from 0° C. to 100° C.

Step 5: Alkyl halide or the like can be used for the reaction as a reaction reagent having a leaving group. The base includes, for example, organic bases such as triethylamine, N,N-diisopropylethylamine and the like, and inorganic bases such as potassium carbonate, cesium carbonate and the like. Tetrahydrofuran, N,N-dimethylformamide, N-methylpyrrolidone, dimethyl sulfoxide or the like is preferable as the solvent. The reaction temperature is preferably from 0° C. to 120° C.

When $L^1$ in the formula (I) is —O— in the compound of the present invention, the target compound can be also synthesized using the intermediate pyrazole (D-I) as shown in the following reaction scheme. That is, after reacting (D-I) with a reagent having a leaving group and modifying the amino group to obtain (D-II), the target compound can be synthesized by the same method as described above.

[Chem. 11]

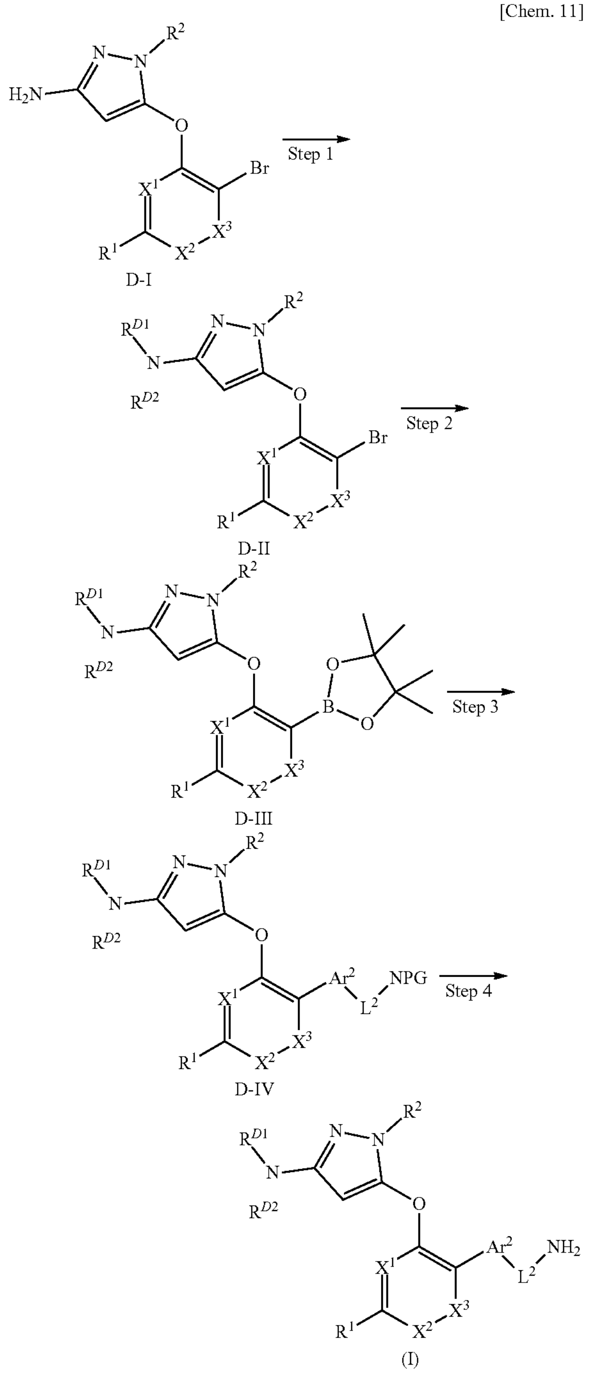

(Wherein, $R^{D1}$ and $R^{D2}$ are substituents that form $—NR^{D1}R^{D2}$ to satisfy $R^3$ in the formula (I).)

Step 1: Reaction reagent having a leaving group includes, for example, alkyl halides and alkyl triflate and the like. Organic bases such as triethylamine and N,N-diisopropylethylamine, inorganic bases such as potassium carbonate and cesium carbonate or the like is preferable as the base. If necessary, an additive such as potassium iodide may be added. 1,4-Dioxane, N,N-dimethylformamide, N,N-dimethylacetamide, N-methylpyrrolidone or the like is preferable as the solvent. The reaction temperature is preferably from room temperature to 150° C., and particularly preferably from 50° C. to 120° C.

Step 2: The borylation reagent includes, for example, bis(pinacolato)diboron and the like. Tris(dibenzylideneacetone)dipalladium, palladium acetate, tetrakis(triphenylphosphine)palladium, bis(triphenylphosphine)palladium dichloride, [1,1'-bis(diphenylphosphino)ferrocene] palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. Potassium acetate or the like is preferable as the base to be used. Here, the solvent is not particularly limited and includes, for example, ethers such as tetrahydrofuran, 1,4-dioxane, 1,2-dimethoxyethane, 1,2-diethoxyethane, and the like, N,N-dimethylformamide, N-methylpyrrolidone, dimethyl sulfoxide, a mixed solvent thereof, and the like. The reaction temperature is preferably from 50° C. to 150° C., and particularly preferably from 70° C. to 120° C.

Step 3: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 4: As a removal method of the protecting group, a known method widely used in this field can be adopted. For example, when the protecting group is a Boc group, a strong acid such as trifluoroacetic acid, hydrochloric acid, sulfuric acid, or the like is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide and the like. The reaction temperature is preferably from 0° C. to 100° C.

When $L^1$ in the formula (I) is —O— in the compound of the present invention, the target compound can be also synthesized, as shown in the following reaction scheme, by constructing a biaryl bond with $Ar^2$ ring, then converting the amino group in (E-III) to a bromine atom, and introducing $R^3$ substituent by, for example, cross-coupling reaction.

[Chem. 12]

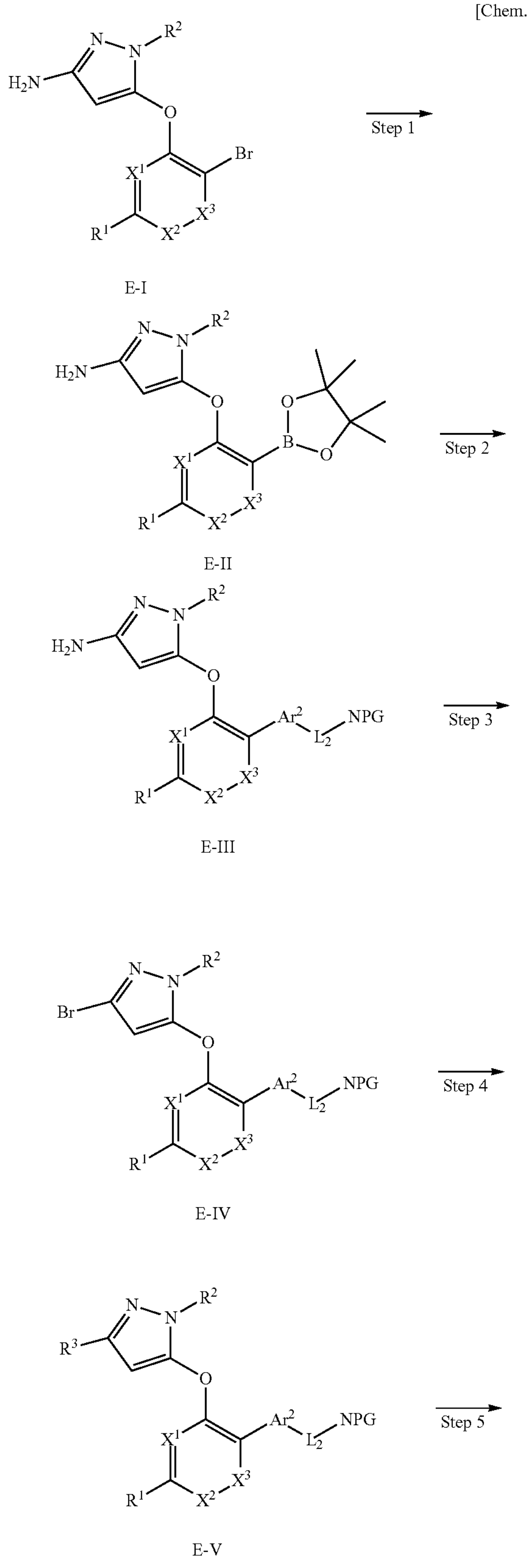

E-I

E-II

E-III

E-IV

E-V

-continued

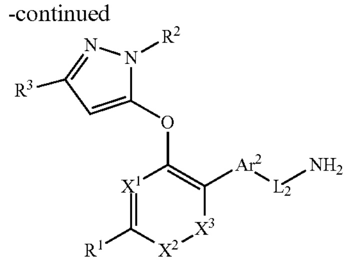

(I)

Step 1: Bis(pinacolato)diboron is preferable as the borylation reagent, and tris(dibenzylideneacetone)dipalladium, palladium acetate, tetrakis(triphenylphosphine)palladium, bis(triphenylphosphine)palladium dichloride, [1,1'-bis(diphenylphosphino)ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. Potassium acetate or the like is preferable as the base to be used. Here, the solvent is not particularly limited and includes, for example, ethers such as tetrahydrofuran, 1,4-dioxane, 1,2-dimethoxyethane, 1,2-diethoxyethane, and the like, N,N-dimethylformamide, N-methylpyrrolidone, dimethyl sulfoxide, a mixed solvent thereof, and the like. The reaction temperature is preferably from 50° C. to 150° C., and particularly preferably from 70° C. to 120° C.

Step 2: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 3: Isoamyl nitrite is preferable as the reagent to be used, and copper bromide or the like is preferable as the bromination reagent. Preferred solvents include acetonitrile, toluene, and the like. The reaction temperature is preferably from 0° C. to 50° C.

Step 4: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 5: As a removal method of the protecting group, a known method widely used in this field can be adopted. For example, when the protecting group is a Boc group, a strong acid such as trifluoroacetic acid, hydrochloric acid, sulfuric acid, or the like is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide and the like. The reaction temperature is preferably from 0° C. to 100° C.

When $L^1$ in the formula (I) is —O— in the compound of the present invention, the target compound can be also synthesized, as shown in the following reaction scheme, by performing an aromatic nucleophilic substitution reaction using a raw material (F-I) having a nitro group, then converting the functional group of the nitro group, followed by a biaryl bond formation with $Ar^2$ ring.

[Chem. 13]

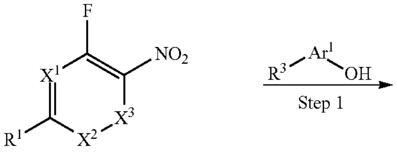

F-I

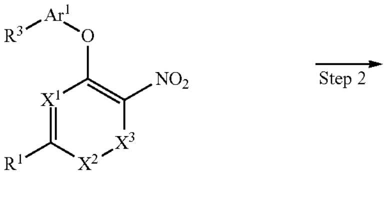

F-II

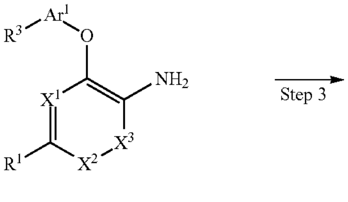

F-III

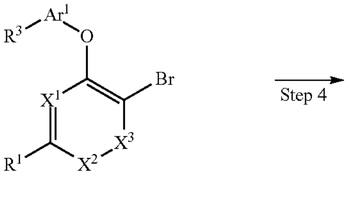

F-IV

-continued

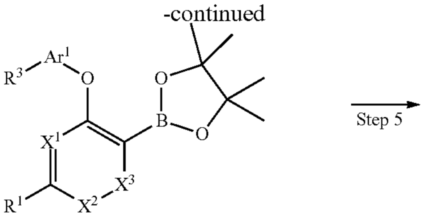

F-V

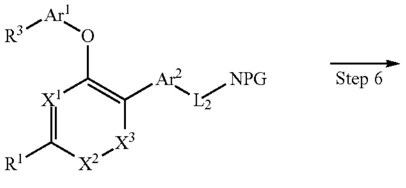

F-VI

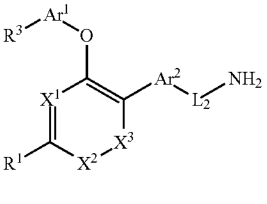

(I)

Step 1: Potassium carbonate, sodium carbonate, cesium carbonate, potassium tert-butoxide, sodium tert-butoxide or the like is preferable as the base to be used. Preferred solvents include N,N-dimethylformamide, N,N-dimethylacetamide, N-methylpyrrolidone, dimethyl sulfoxide and the like. The reaction temperature is preferably from room temperature to 100° C.

Step 2: Iron, zinc, or the like is preferable as the metal reagent to be used, and is preferably used in combination with a reagent such as ammonium chloride, acetic acid, or the like. Preferred solvents include organic solvents such as ethanol, methanol, tetrahydrofuran, and the like, mixed solvents obtained by adding water thereto, and the like. The reaction temperature is preferably from room temperature to 100° C.

Step 3: Isoamyl nitrite is preferable as the reagent to be used, and copper bromide or the like is preferable as the bromination reagent. Preferred solvents include acetonitrile, toluene, and the like. The reaction temperature is preferably from 0° C. to 50° C.

Step 4: Bis(pinacolato)diboron is preferable as the borylation reagent, and tris(dibenzylideneacetone)dipalladium, palladium acetate, tetrakis(triphenylphosphine)palladium, bis(triphenylphosphine)palladium dichloride, [1,1'-bis(diphenylphosphino)ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. Potassium acetate or the like is preferable as the base to be used. Here, the solvent is not particularly limited and includes, for example, ethers such as tetrahydrofuran, 1,4-dioxane, 1,2-dimethoxyethane, 1,2-diethoxyethane, and the like, N,N-dimethylformamide, N-methylpyrrolidone, dimethyl sulfoxide, a mixed solvent thereof, and the like. The reaction temperature is preferably from 50° C. to 150° C., and particularly preferably from 70° C. to 120° C.

Step 5: Tetrakis(triphenylphosphine)palladium, bis(triphenylphosphine)palladium dichloride, [1,1'-bis(diphenylphosphino)ferrocene]palladium dichloride or the like is preferable as the palladium catalyst and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 6: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is —O— in the compound of the present invention, the target compound can be also synthesized, using the intermediate pyrazole (G-IV) obtained through the cyclization reaction, as shown in the following reaction scheme. That is, after reacting a reagent having a leaving group with pyrazole (G-IV) obtained in three steps from the starting material (G-I) to introduce $R^3$ substituent, the target compound can be synthesized by the same method as described above.

[Chem. 14]

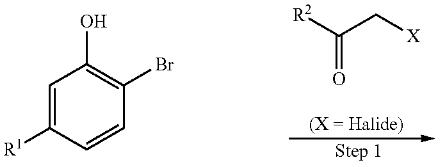

G-I

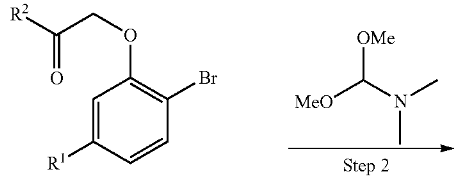

G-II

-continued

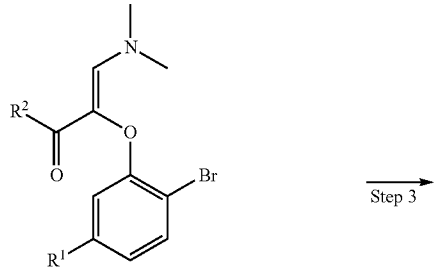

G-III

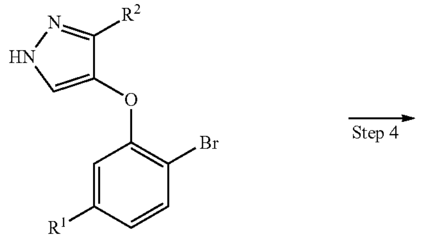

G-IV

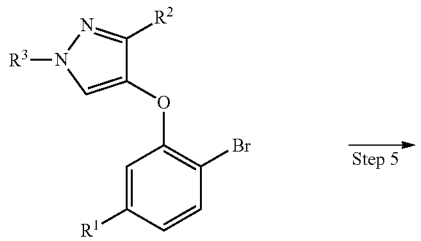

G-V

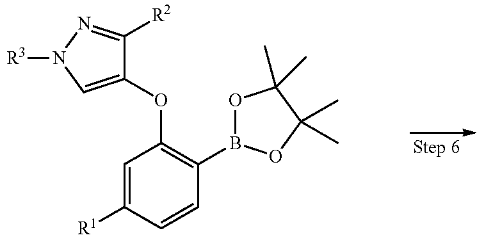

G-VI

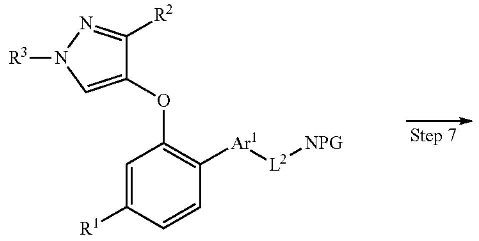

G-VII

-continued

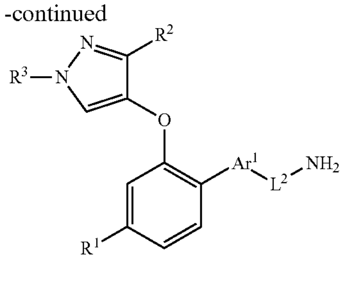

(I)

Step 1: Potassium carbonate, sodium carbonate, cesium carbonate, potassium tert-butoxide, sodium tert-butoxide or the like is preferable as the base to be used. Preferred solvents include N,N-dimethylformamide, N,N-dimethylacetamide, N-methylpyrrolidone, dimethyl sulfoxide and the like. The reaction temperature is preferably from room temperature to 100° C.

Step 2: This reaction is preferably performed without solvent. The reaction temperature is preferably from 50° C. to 100° C.

Step 3: The reaction is performed using hydrazine monohydrate as a reagent. Acetic acid or the like is preferable as the solvent. The reaction temperature is preferably from 70° C. to 120° C.

Step 4: The reaction reagent having a leaving group includes, for example, alkyl halides, aryl halides, and the like. Organic bases such as triethylamine and N,N-diisopropylethylamine, and the like, inorganic bases such as potassium carbonate and cesium carbonate, and the like are preferable as the base. Here, the solvent is not particularly limited and includes, for example, ethers such as diethyl ether, tetrahydrofuran, 1,4-dioxane, 1,2-dimethoxyethane, 1,2-diethoxyethane, and the like, N,N-dimethylformamide, N-methylpyrrolidone, dimethyl sulfoxide, and the like. The reaction temperature is preferably from room temperature to 150° C.

Step 5: Bis(pinacolato)diboron is preferable as the borylation reagent, and tris(dibenzylideneacetone)dipalladium, palladium acetate, tetrakis(triphenylphosphine)palladium, bis(triphenylphosphine)palladium dichloride, [1,1'-bis(diphenylphosphino)ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. Potassium acetate or the like is preferable as the base to be used. Here, the solvent is not particularly limited and includes, for example, ethers such as tetrahydrofuran, 1,4-dioxane, 1,2-dimethoxyethane, 1,2-diethoxyethane, and the like, N,N-dimethylformamide, N-methylpyrrolidone, dimethyl sulfoxide, a mixed solvent thereof, and the like. The reaction temperature is preferably from 50° C. to 150° C., and particularly preferably from 70° C. to 120° C.

Step 6: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, mixed solvent thereof, and the like. The reaction temperature is preferably from 50° C. to 150° C., and particularly preferably from 80° C. to 120° C.

Step 7: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is —O— in the compound of the present invention, an aromatic nucleophilic substitution reaction or the like can be also performed using a substrate having a leaving group in $Ar^1$ ring as shown in the following reaction scheme. (H—IV) can be synthesized by reacting (H—II) directly with $Ar^2$ ring compounds having suitable reactive substituents without an operation of step 2. Substituent $R^3$ (e.g., a halogen atom) can be converted to a target structure at an appropriate timing in the following reaction scheme by a method known to those skilled in the art, depending on a target structure.

[Chem. 15]

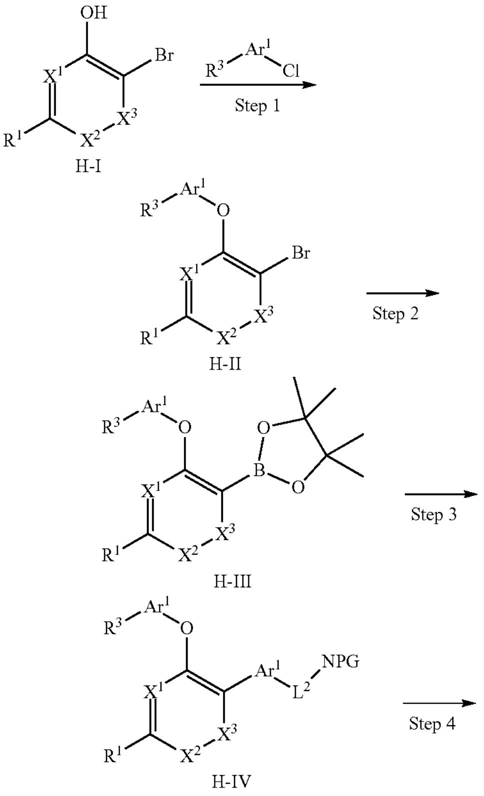

-continued

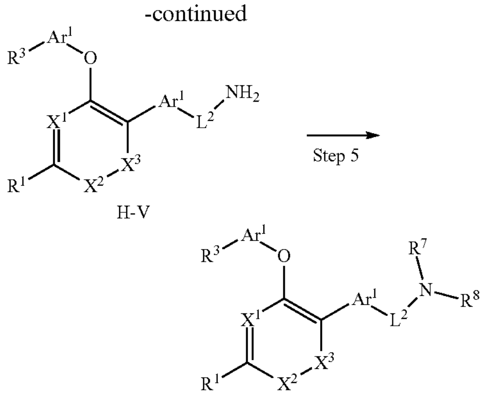

H-V (I)

Step 1: Potassium carbonate, sodium carbonate, cesium carbonate, potassium tert-butoxide, sodium tert-butoxide or the like is preferable as the base to be used. Preferred solvents include N,N-dimethylformamide, N,N-dimethylacetamide, N-methylpyrrolidone, dimethyl sulfoxide and the like. The reaction temperature is preferably from room temperature to 150° C.

Step 2: Bis(pinacolato)diboron is preferable as the borylation reagent, and tris(dibenzylideneacetone)dipalladium, palladium acetate, tetrakis(triphenylphosphine)palladium, bis(triphenylphosphine)palladium dichloride, [1,1-bis(diphenylphosphino)ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. Potassium acetate or the like is preferable as the base to be used. Here, the solvent is not particularly limited and includes, for example, ethers such as tetrahydrofuran, 1,4-dioxane, 1,2-dimethoxyethane, 1,2-diethoxyethane, and the like, N, N-dimethylformamide, N-methylpyrrolidone, dimethyl sulfoxide, a mixed solvent thereof, and the like. The reaction temperature is preferably 50° C. to 150° C., and particularly preferably from 70° C. to 120° C.

Step 3: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, mixed solvent thereof, and the like. The reaction temperature is preferably from 50° C. to 150° C., and particularly preferably from 80° C. to 120° C.

Step 4: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

Step 5: The reaction reagent having a leaving group includes, for example, alkyl halides and aryl triflate, and the like. The base includes, for example, organic bases such as triethylamine, N,N-diisopropylethylamine and the like, and inorganic bases such as potassium carbonate, cesium carbonate and the like. Tetrahydrofuran, N,N-dimethylformamide, N-methylpyrrolidone, dimethyl sulfoxide or the like is preferable as the solvent. The reaction temperature is preferably from 0° C. to 120° C.

When $L^1$ in the formula (I) is —O— in the compound of the present invention, the target compound can be synthesized by modifying the compound (I-I) having an alcohol as shown in the following reaction scheme.

[Chem. 16]

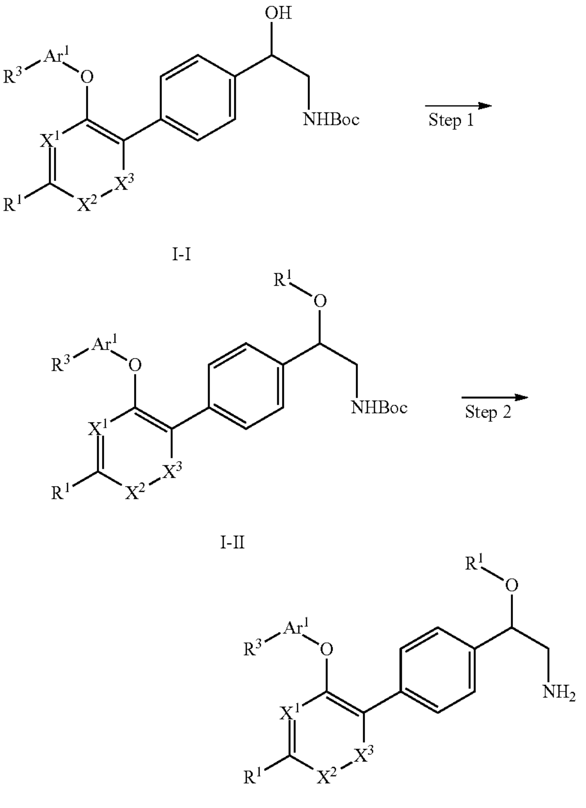

I-I

I-II (I)

(Wherein, $R^1$ is a substituent which forms —$OR^1$ to satisfy $R^{21}$ in the formula (I).)

Step 1: The reaction reagent having a leaving group includes, for example, alkyl halides and alkyl triflate and the like. Sodium hydride, potassium carbonate, cesium carbonate or the like is preferable as the base. Here, the solvent is not particularly limited and includes, for example, ethers such as diethyl ether, tetrahydrofuran, 1,4-dioxane, 1,2-dimethoxyethane, 1,2-diethoxyethane, and the like, N,N-dimethylformamide, N-methylpyrrolidone, dimethyl sulfoxide, and the like. The reaction temperature is preferably from 0° C. to 120° C.

Step 2: Trifluoroacetic acid, hydrochloric acid, sulfuric acid, or the like is preferable as the strong acid to be used, and a solvent such as dichloromethane, tetrahydrofuran, ethyl acetate and the like is preferable as the solvent. The reaction temperature is preferably from 0° C. to 50° C., and particularly preferably from 0° C. to room temperature.

When $L^1$ in the formula (I) is —O— in the compound of the present invention, after converting the alcohol in (J-I) to a leaving group to introduce an alkoxy group as shown in the following reaction scheme, the target compound can also be synthesized by the same method as described above.

[Chem. 17]

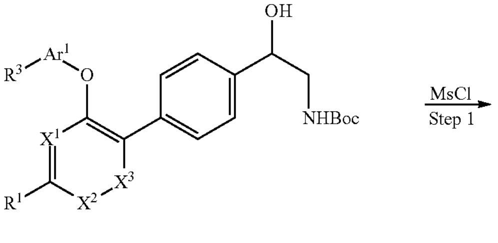

J-I

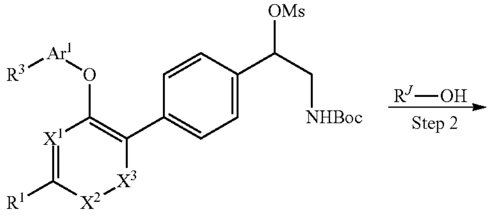

J-II

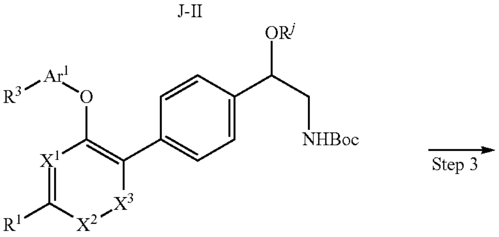

J-III

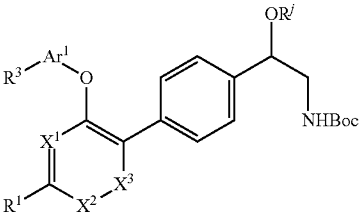

(I)

(Wherein,
Ms is a methanesulfonyl group;
$R^J$ is a substituent which forms —$OR^J$ to satisfy $R^{21}$ in the formula (I).)

Step 1: As the mesylation reagent, methanesulfonyl chloride can be used to perform the reaction. Triethylamine, potassium carbonate, cesium carbonate or the like is preferable as the base. The solvent is not particularly limited in this reaction and includes, for example, organic solvents such as tetrahydrofuran, dichloromethane, and the like. This reaction is performed preferably at 0° C. to 60° C., and particularly preferably at 0° C. to room temperature.

Step 2: An alcohol ($R^J$—OH) corresponding to the target compound can be used to perform the reaction. As preferred bases, inorganic bases such as sodium hydride, potassium carbonate, cesium carbonate, and the like can be used. The solvent in this reaction includes, for example, organic solvents such as tetrahydrofuran, N,N-dimethylformamide, N,N-dimethylacetamide, N-methylpyrrolidone, and the like, or a mixed solvent thereof. This reaction is performed preferably at room temperature to 150° C., and particularly preferably at room temperature to 100° C.

Step 3: Trifluoroacetic acid, hydrochloric acid, sulfuric acid, or the like is preferable as the strong acid to be used, and a solvent such as dichloromethane, tetrahydrofuran, ethyl acetate or the like is preferable as the solvent. The reaction temperature is preferably from 0° C. to 50° C., and particularly preferably from 0° C. to room temperature.

When $L^1$ in the formula (I) is —O— in the compound of the present invention, after introducing the target substituent via tosylhydrazone (K-II) as described in the following reaction scheme, synthesis can be performed by the same method as described above.

[Chem. 18]

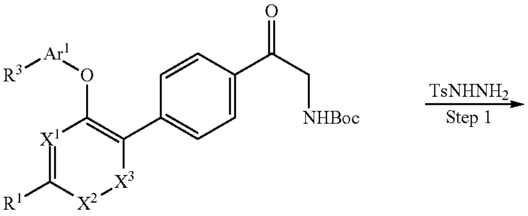

K-I

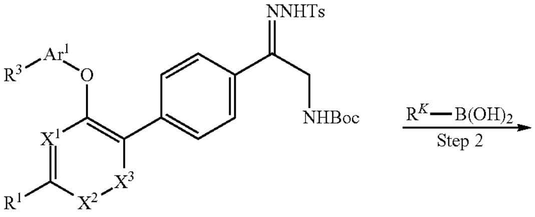

K-II

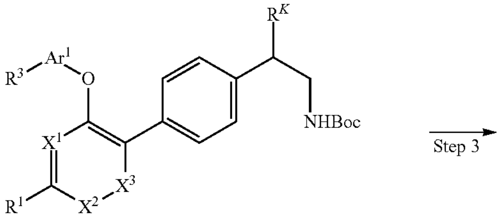

K-III

-continued

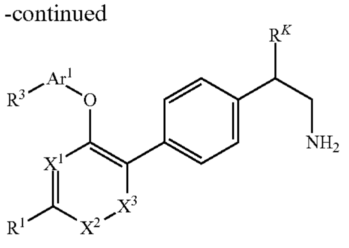

(I)

(Wherein,

Ts is a p-toluenesulfonyl group;

$R^K$ is a $C_{1-3}$ alkoxy-$C_{1-3}$ alkyl group, a hydroxy($C_{1-6}$ alkyl) group, a hydroxycarbonyl-($C_{1-3}$ alkyl) group, a ($C_{1-3}$ alkoxy) carbonyl-($C_{1-3}$ alkyl) group, or a phenyl group optionally substituted with 1 to 3 halogen atoms.)

Step 1: Tosylhydrazine is used as a reagent in this reaction. Preferred solvents include toluene, methanol, ethanol, and the like. The reaction temperature is preferably from room temperature to 120° C., and particularly preferably from 50° C. to 120° C.

Step 2: Potassium carbonate, cesium carbonate, cesium fluoride or the like is preferable as the base to be used. Here, the solvent is not particularly limited and includes, for example, ethers such as diethyl ether, tetrahydrofuran, 1,4-dioxane, 1,2-dimethoxyethane, 1,2-diethoxyethane and the like. The reaction temperature is preferably from room temperature to 150° C., and particularly preferably from 80° C. to 120° C.

Step 3: Trifluoroacetic acid, hydrochloric acid, sulfuric acid, or the like is preferable as the strong acid to be used, and a solvent such as dichloromethane, tetrahydrofuran, ethyl acetate or the like is preferable as the solvent. The reaction temperature is preferably from 0° C. to 50° C., and particularly preferably from 0° C. to room temperature.

When $L^1$ in the formula (I) is —O— in the compound of the present invention, synthesis can be performed also by a method described in the following reaction scheme. That is, the target compound can be synthesized by the following steps: the raw material (L-I) is reacted with paramethoxybenzyl alcohol to obtain compound (L-II); subsequently, the biaryl compound (L-IV) is obtained through functional group conversion of the bromine atom in (L-II), and then the PMB group is deprotected to lead to phenol (L-V); after linking this phenol (L-V) with $Ar^1$ compound having a reactive substituent by an appropriate reaction, an amino group is deprotected.

[Chem. 19]

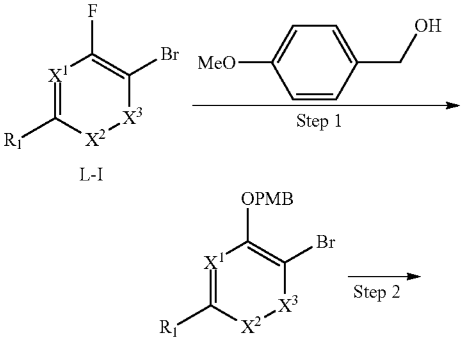

L-I

L-II

-continued

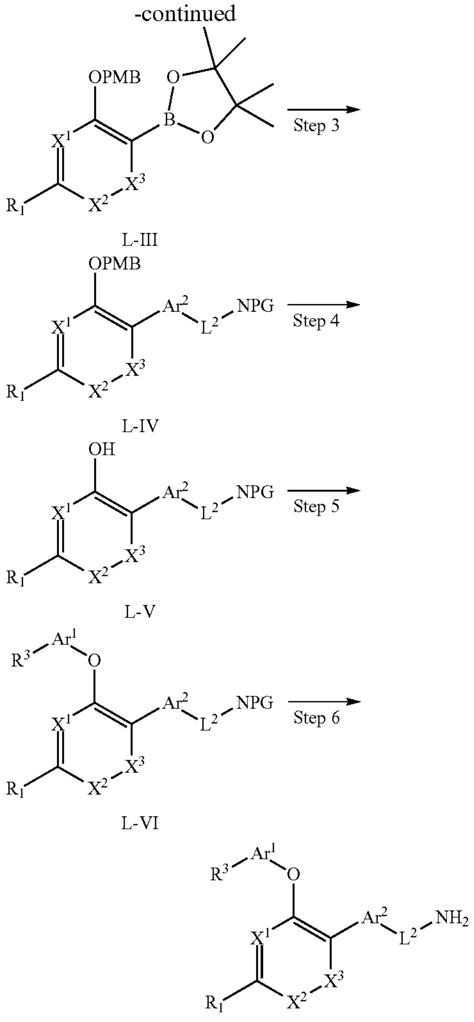

L-III

L-IV

L-V

L-VI (I)

Step 1: Potassium carbonate, sodium carbonate, cesium carbonate, potassium tert-butoxide, sodium tert-butoxide or the like is preferable as the base to be used. Preferred solvents include N,N-dimethylformamide, N,N-dimethylacetamide, N-methylpyrrolidone, dimethyl sulfoxide, and the like. The reaction temperature is preferably from room temperature to 100° C.

Step 2: Bis(pinacolato)diboron is preferable as the borylation reagent to be used, and tris(dibenzylideneacetone) dipalladium, palladium acetate, tetrakis(triphenylphosphine) palladium, bis(triphenylphosphine)palladium dichloride, [1,1'-bis(diphenylphosphino)ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. Potassium acetate or the like is preferable as the base to be used. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, and the like. The reaction temperature is preferably from 50° C. to 150° C., and particularly preferably from 70° C. to 120° C.

Step 3: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 4: As a removal method of the paramethoxybenzyl group, a known method can be adopted. For example, strong acids include such as trifluoroacetic acid, hydrochloric acid, sulfuric acid, and the like, and the solvent is not particularly limited and includes, for example, tetrahydrofuran, 1,4-dioxane, dichloromethane and the like. The reaction temperature is preferably from 0° C. to 100° C.

Step 5: Potassium carbonate, sodium carbonate, cesium carbonate, potassium tert-butoxide, sodium tert-butoxide or the like is preferable as the base to be used. Preferred solvents include N,N-dimethylformamide, N,N-dimethylacetamide, N-methylpyrrolidone, dimethyl sulfoxide and the like. The reaction temperature is preferably from room temperature to 150° C.

Step 6: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide and the like. The reaction temperature is preferably from 0° C. to 100° C.

When $L^1$ in the formula (I) is —O— in the compound of the present invention, synthesis can be performed also by a method described in the following reaction scheme. That is, the target compound can be synthesized by the following steps: 2,4-dihydroxy-6-methylpyridine is reacted with the raw material (M-I) to obtain compound (M-II); subsequently, (M-II) is triflated, and then the target $R^3$ substituents is introduced thereto to give (M-IV); subsequently, the biaryl compound (M-VI) is obtained through functional group conversion of the bromine atom in (M-IV), and then the amino group is deprotected.

[Chem. 20]

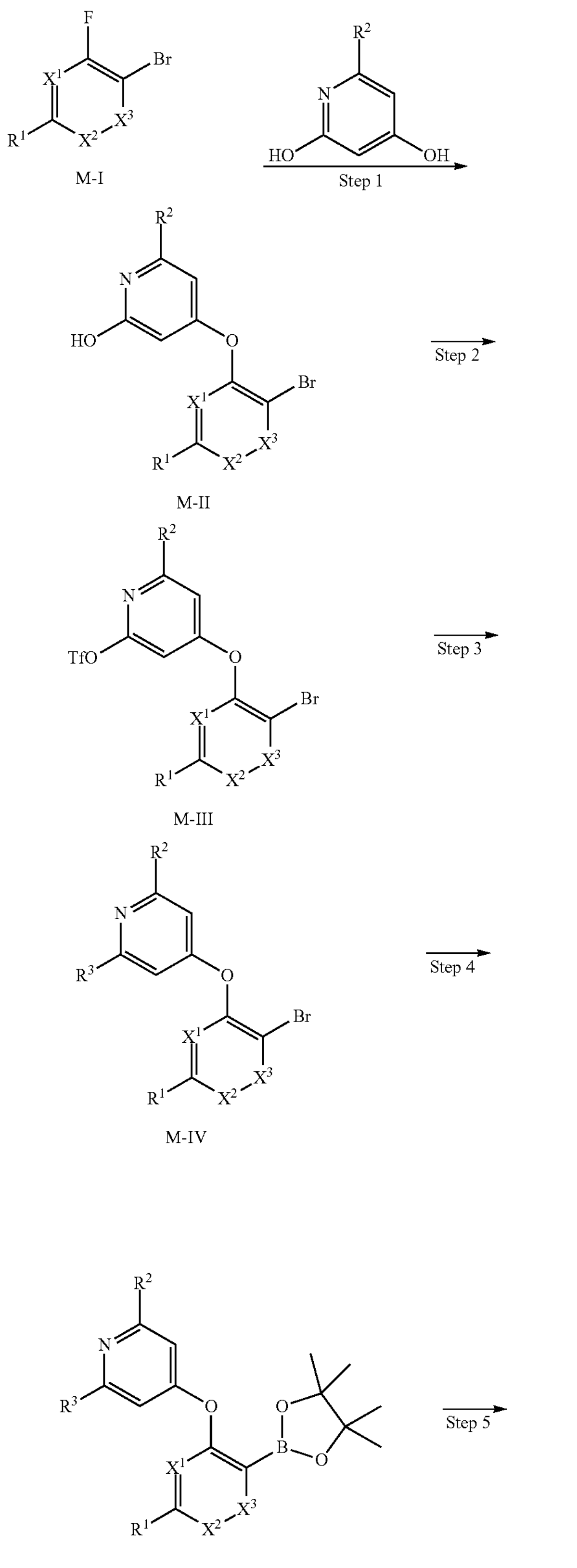

M-I
M-II
M-III
M-IV
M-V

-continued

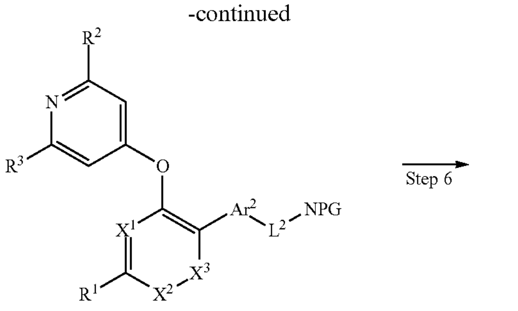

M-VI

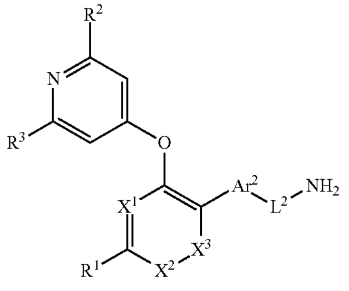

(I)

Step 1: Potassium carbonate, sodium carbonate, cesium carbonate, potassium tert-butoxide, sodium tert-butoxide or the like is preferable as the base to be used. Preferred solvents include N,N-dimethylformamide, N,N-dimethylacetamide, N-methylpyrrolidone, dimethyl sulfoxide and the like. The reaction temperature is preferably from room temperature to 160° C.

Step 2: The triflation agent to be used includes trifluoromethanesulfonic anhydride ($Tf_2O$) and the like, and pyridine, triethylamine, N,N-diisopropylethylamine or the like is preferable as the base. Preferred solvents include tetrahydrofuran, dichloromethane, 1,2-dichloroethane and the like. The reaction temperature is preferably from 0° C. to 100° C.

Step 3: As a method for introducing $R^3$ substituent, a known method commonly used in the art can be adopted. For example, in the case of introducing $R^3$ substituent using boronic acid derivatives, tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Further, for example, in the case of reacting with an alcohol or an amine corresponding to $R^3$ substituent, preferred base includes, for example, organic bases such as triethylamine and N,N-diisopropylethylamine, an inorganic base such as potassium carbonate and cesium carbonate and the like. Here, the solvent is not particularly limited and includes, for example, ethers such as tetrahydrofuran, 1,4-dioxane, 1,2-dimethoxyethane, 1,2-diethoxyethane, and the like, N,N-dimethylformamide, N-methylpyrrolidone, dimethyl sulfoxide and the like. The reaction temperature is preferably from room temperature to 150° C.

Step 4: Bis(pinacolato)diboron is preferable as the borylation reagent to be used, and tris(dibenzylideneacetone) dipalladium, palladium acetate, tetrakis(triphenylphosphine) palladium, bis(triphenylphosphine)palladium dichloride, [1,1'-bis(diphenylphosphino)ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. The base to be used includes potassium acetate and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide and the like. The reaction temperature is preferably from 50° C. to 150° C., and particularly preferably from 70° C. to 120° C.

Step 5: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 6: As a removal method of the protecting group, a known method widely used in this field can be adopted. For example, when the protecting group is a Boc group, a strong acid such as trifluoroacetic acid, hydrochloric acid, sulfuric acid, or the like is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is —CO— in the compound of the present invention, the synthesis can be performed by using the following synthesis methods.

For example, the synthesis can be performed by the method shown in the following reaction scheme. That is, an $Ar^1$ ring compound having an aldehyde is reacted with an anionic reagent prepared from the compound (N-I) to synthesize a corresponding alcohol (N-II), which is further oxidized to give a ketone (N-III). Subsequently, a biaryl bond can be formed to synthesize (N-V). Further, $R^3$ substituent can be converted at an appropriate timing in the following reaction scheme by a method known to those skilled in the art, depending on a target structure.

[Chem. 21]

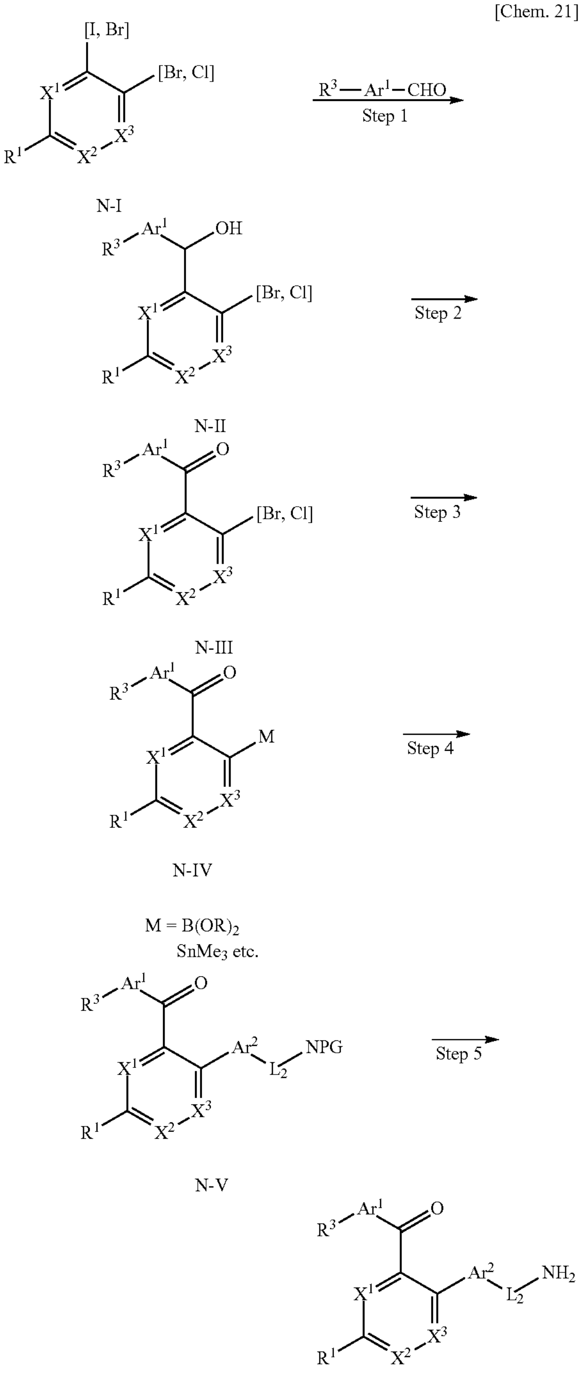

N-I, N-II, N-III, N-IV, N-V, (I)

Step 1: The reagent for preparing an anion by reacting with (N-I) includes, for example, n-butyllithium, isopropylmagnesium chloride-lithium chloride complex solution, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, and halogenated hydrocarbons such as dichloromethane, 1,2-dichloroethane, chloroform, and the like. The reaction temperature is preferably from −78° C. to 50° C., and particularly preferably from −40° C. to room temperature.

Step 2: Dess-Martin periodinane, 2-iodoxybenzoic acid, pyridinium chlorochromate or the like is preferable as the oxidizing agent to be used. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, and halogenated hydrocarbons such as dichloromethane, 1,2-dichloroethane, chloroform, and the like. The reaction temperature is preferably from 0° C. to 100° C.

Step 3: The borylation reagent to be used includes bis(pinacolato)diboron and the like, and the tin reagent includes hexamethylditin and the like. Tris(dibenzylideneacetone)dipalladium, palladium acetate, tetrakis(triphenylphosphine)palladium, bis(triphenylphosphine)palladium dichloride, [1,1'-bis(diphenylphosphino)ferrocene]palladium dichloride or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. The base to be used for borylation includes potassium acetate and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide and the like. The reaction temperature is preferably from 50° C. to 150° C., and particularly preferably from 70° C. to 120° C.

Step 4: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 5: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide and the like. The reaction temperature is preferably from 0° C. to 100° C.

When $L^1$ in the formula (I) is —CO— in the compound of the present invention, the target compound can be synthesized also by utilizing the intermediate pyrazole (O-II) as shown in the following reaction scheme. That is, after the amino group in (O-II) obtained by reducing (O-I) was modified with a reagent having a leaving group to obtain (O-III), the target compound can be synthesized by the same method as described above.

[Chem. 22]

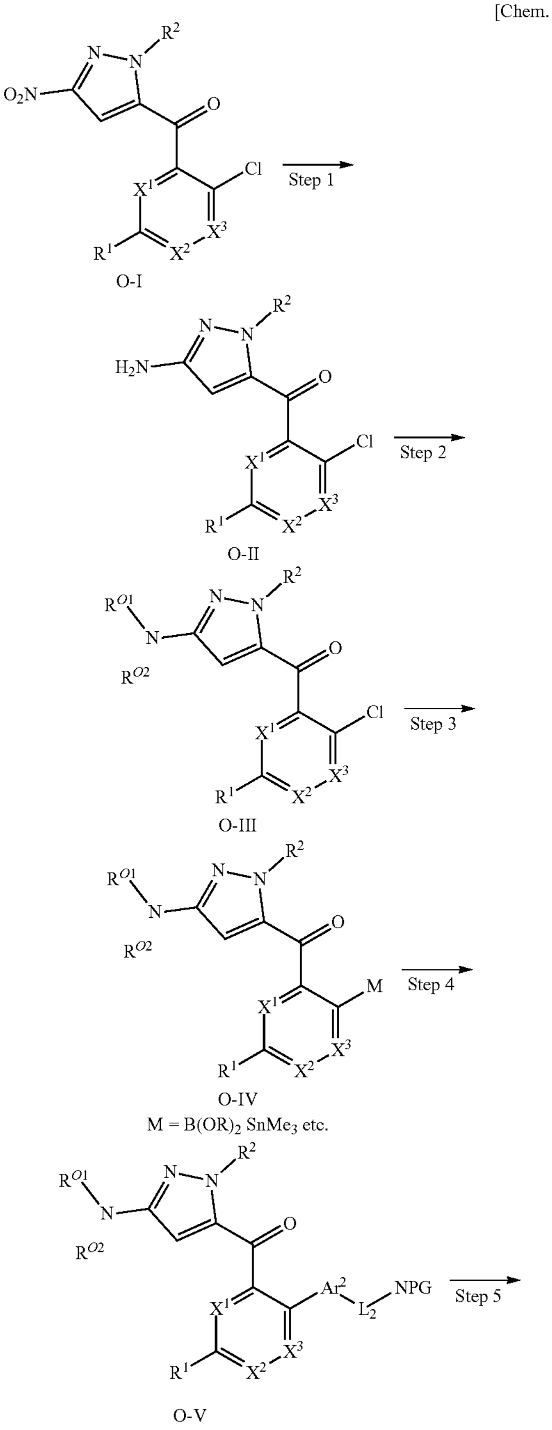

-continued

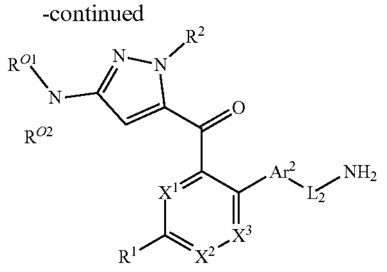

(I)

(Wherein, $R^{O1}$, $R^{O2}$ are substituents that form —$NR^{O1}R^{O2}$ which may be included in $R^3$ of formula (I).)

Step 1: Iron, zinc or the like is preferable as the metal reagent to be used, and the metal reagent is preferably used in combination with a reagent such as ammonium chloride and acetic acid. Preferred solvents include organic solvents such as ethanol, methanol, tetrahydrofuran and the like, mixed solvents obtained by adding water thereto, and the like. The reaction temperature is preferably from room temperature to 100° C.

Step 2: The reaction reagent having a leaving group includes, for example, alkyl halides, alkyl triflate and the like. Organic bases such as triethylamine, N,N-diisopropylethylamine, and the like and inorganic bases such as potassium carbonate, cesium carbonate and the like are preferable as the base. 1,4-Dioxane, N,N-dimethylformamide, N,N-dimethylacetamide, N-methylpyrrolidone, dimethyl sulfoxide or the like is preferable as the solvent. The reaction temperature is preferably from room temperature to 150° C.

Step 3: The borylation reagent to be used includes bis(pinacolato)diboron, and the tin reagent includes hexamethylditin and the like. The preferred palladium catalyst includes, for example, tris(dibenzylideneacetone)dipalladium, palladium acetate, tetrakis(triphenylphosphine)palladium, bis(triphenylphosphine)palladium dichloride, [1,1'-bis(diphenylphosphino)ferrocene]palladium dichloride and the like. If necessary, tricyclohexylphosphine, tricyclohexylphosphonium tetrafluoroborate, 4,5-bis(diphenylphosphino)-9,9-dimethylxanthene or the like is used as the ligand. The base used for borylation includes, for example, potassium acetate and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, and the like. The reaction temperature is preferably from 50° C. to 150° C., and particularly preferably from 70° C. to 120° C.

Step 4: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 5: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is —CO— in the compound of the present invention, as shown in the following reaction scheme, after reacting the anionic reagent prepared from $Ar^1$ ring with aldehyde (P-I) to obtain a corresponding alcohol (P-II), the synthesis can be performed by the same method as described above.

[Chem. 23]

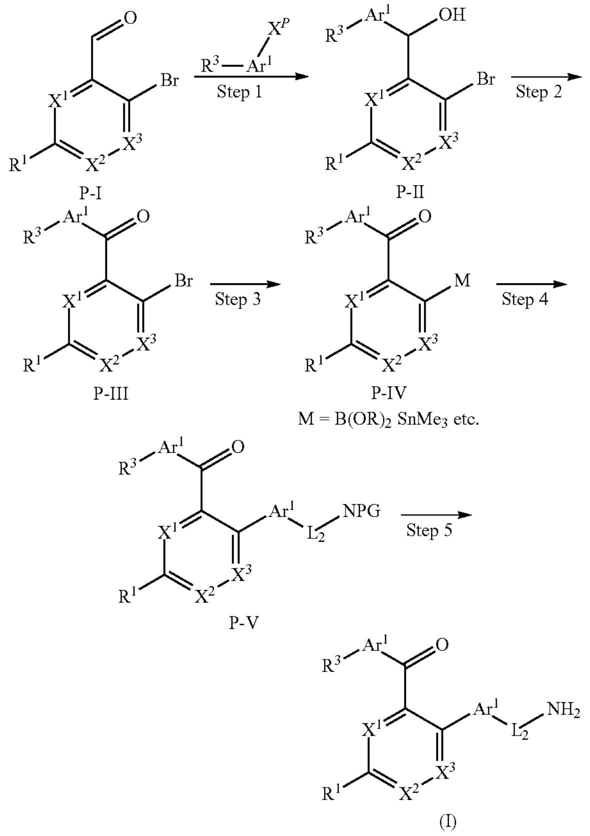

(Wherein, $X^P$ is H or a halogen atom.)

Step 1: The reagent for preparing an anion in the reaction system includes, for example, n-butyllithium, isopropylmagnesium chloride-lithium chloride complex solution and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, and halogenated hydrocarbons such as dichloromethane, 1,2-dichloroethane, chloroform, and the like. The reaction temperature is preferably from −78° C. to 50° C., and particularly preferably from −40° C. to room temperature.

Step 2: Dess-Martin periodinane, 2-iodoxybenzoic acid, pyridinium chlorochromate or the like is preferable as the oxidizing agent to be used. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, and halogenated hydrocarbons such as dichloromethane, 1,2-dichloroethane, chloroform, and the like. The reaction temperature is preferably from 0° C. to 100° C.

Step 3: The borylation reagent to be used includes, for example, bis(pinacolato)diboron, and the tin reagent includes, for example, hexamethylditin, and the like. Tris(dibenzylideneacetone)dipalladium, palladium acetate, tetrakis(triphenylphosphine)palladium, bis(triphenylphosphine)palladium dichloride, [1,1'-bis(diphenylphosphino)ferrocene]palladium dichloride or the like is preferable as the preferred palladium catalyst. If necessary, tricyclohexylphosphine, tricyclohexylphosphonium tetrafluoroborate, 4,5-bis(diphenylphosphino)-9,9-dimethylxanthene or the like is used as the ligand. The base to be used for borylation includes, for example, potassium acetate and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, and the like. The reaction temperature is preferably from 50° C. to 150° C., and particularly preferably from 70° C. to 120° C.

Step 4: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 5: As a removal method of the protecting group, a known method widely used in this field can be adopted. For example, when the protecting group is a Boc group, a strong acid such as trifluoroacetic acid, hydrochloric acid, sulfuric acid, or the like is preferable, and when the protecting group is phthalimide, hydrazine, ethylenediamine or the like is preferable. The solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is —CO— in the compound of the present invention, after synthesizing the corresponding ketone (Q-II) using $Ar^1$ ring having the Weinreb amide (Q-II) as shown in the following reaction scheme, the synthesis can be performed by the same method as described above.

[Chem. 24]

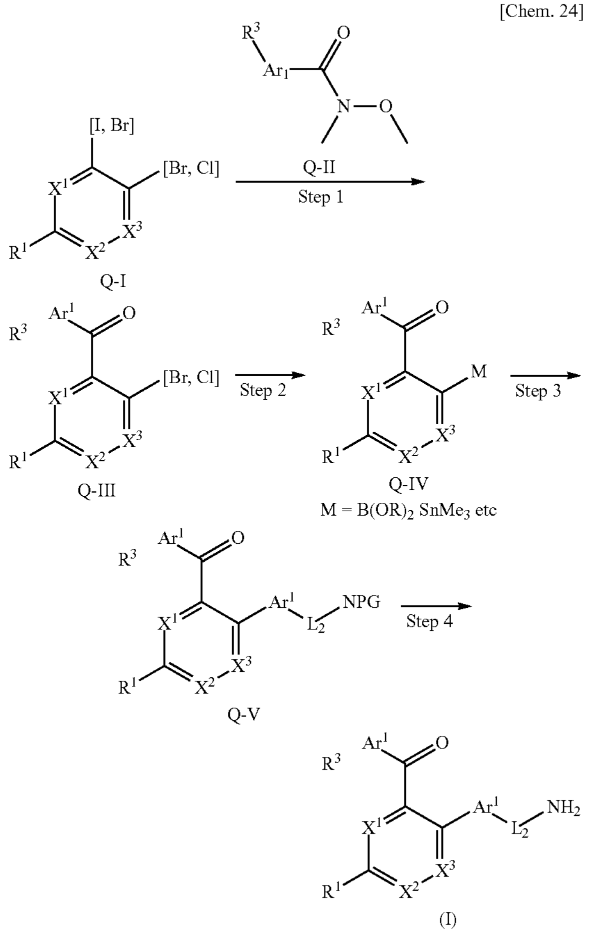

Step 1: The reagent for preparing an anion in the reaction system includes, for example, n-butyllithium, isopropylmagnesium chloride-lithium chloride complex solution, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like. The reaction temperature is preferably from −78° C. to 50° C., and particularly preferably from −40° C. to room temperature.

Step 2: The borylation reagent to be used includes, for example, bis(pinacolato)diboron, and the tin reagent includes, for example, hexamethylditin and the like. Tris(dibenzylideneacetone)dipalladium, palladium acetate, tetrakis(triphenylphosphine)palladium, bis(triphenylphosphine)palladium dichloride, [1,1'-bis(diphenylphosphino)ferrocene]palladium dichloride, or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. The base to be used for borylation includes, for example, potassium acetate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, and the like. The reaction temperature is preferably from 50° C. to 150° C., and particularly preferably from 70° C. to 120° C.

Step 3: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 4: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is —$CH_2$— in the compound of the present invention, synthesis can be performed by using the following synthesis methods.

For example, synthesis can be performed as shown in the following reaction scheme. That is, after bonding $Ar^1$ ring compound (R-II) having a reactive substituent such as a boronic acid derivative with benzyl bromide (R-I) by a cross-coupling reaction, by converting (R-III) to a boron compound, tin compound, or the like, then performing the cross-coupling reaction with the corresponding $Ar^2$ ring compounds, a biaryl bond can be formed to complete the synthesis. On the other hand, (R-III) can be directly used to perform cross-coupling reaction or the like with $Ar^2$ ring compounds having suitable reactive substituents without an operation of step 2.

[Chem. 25]

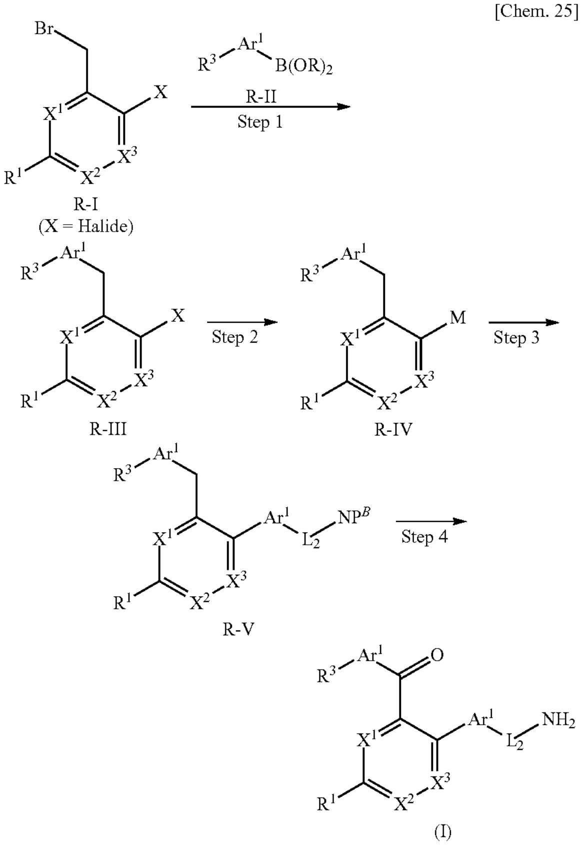

Step 1: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 2: The borylation reagent to be used includes, for example, bis(pinacolato)diboron, and the tin reagent includes, for example, hexamethylditin and the like. Tris(dibenzylideneacetone)dipalladium, palladium acetate, tetrakis(triphenylphosphine)palladium, bis(triphenylphosphine)palladium dichloride, [1,1'-bis(diphenylphosphino)ferrocene]palladium dichloride, or the like is preferable as the palladium catalyst. If necessary, tricyclohexylphosphine, tricyclohexylphosphonium tetrafluoroborate, 4,5-bis(diphenylphosphino)-9,9-dimethylxanthene or the like is used as the ligand. The base to be used for borylation includes, for example, potassium acetate and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, and the like. The reaction temperature is preferably from 50° C. to 150° C., and particularly from preferably 70° C. to 120° C.

Step 3: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, mixed solvent thereof, and the like. The reaction temperature is preferably from 50° C. to 150° C., and particularly preferably from 80° C. to 120° C.

Step 4: As a removal method of the protecting group, a known method widely used in this field can be adopted. For example, when the protecting group is a Boc group, a strong acid such as trifluoroacetic acid, hydrochloric acid or sulfuric acid is preferable, and when the protecting group is phthalimide, hydrazine or ethylenediamine is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol butanol, and the like, N,N-dimethylformamide, N-methylpyrrolidone, dimethyl sulfoxide, and the like. The reaction temperature is preferably from 0° C. to 100° C.

When $L^1$ in the formula (I) is $—CH_2—$ in the compound of the present invention, as shown in the following reaction scheme, after obtaining (S-II) by bonding to $Ar^1$ ring through an alkylation reaction using a nitrogen atom in the $Ar^1$ ring, the synthesis can be performed by the same method as described above.

[Chem. 26]

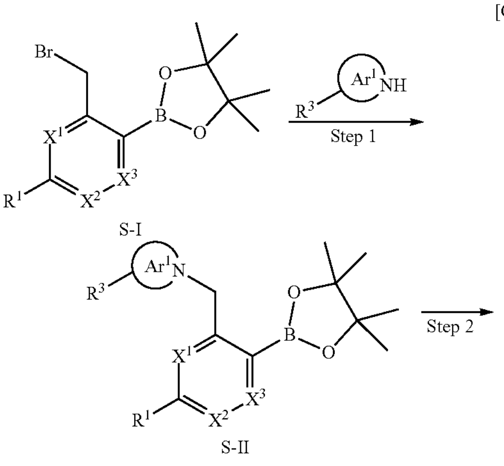

-continued

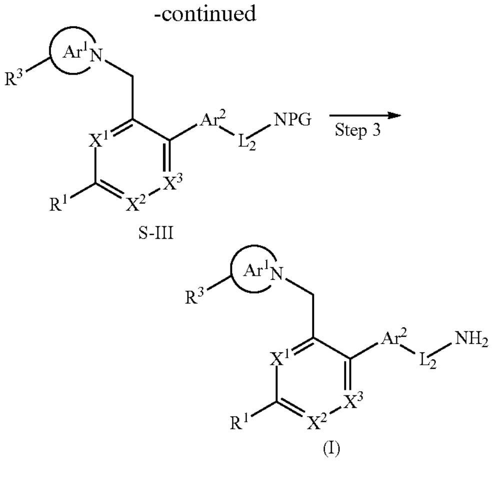

Step 1: Triethylamine, N,N-diisopropylethylamine, potassium carbonate, cesium carbonate or the like is preferable as the base. Here, the solvent is not particularly limited and includes, for example, ethers such as tetrahydrofuran, 1,4-dioxane, 1,2-dimethoxyethane, 1,2-diethoxyethane, and the like, N,N-dimethylformamide, N-methylpyrrolidone, dimethyl sulfoxide, and the like. The reaction temperature is preferably from room temperature to 120° C., and particularly preferably from 40° C. to 100° C.

Step 2: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 3: As a removal method of the protecting group, a known method widely used in this field can be adopted. For example, when the protecting group is a Boc group, a strong acid such as trifluoroacetic acid, hydrochloric acid, sulfuric acid, or the like is preferable, and when the protecting group is phthalimide, hydrazine, ethylenediamine or the like is preferable. Here, the solvent is not particularly limited and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is —$CH_2$— in the compound of the present invention, as shown in the following reaction scheme, a target compound in which amino group or alkoxy group is introduced can be synthesized using the aldehyde of intermediate (T-I) as a foothold.

[Chem. 27]

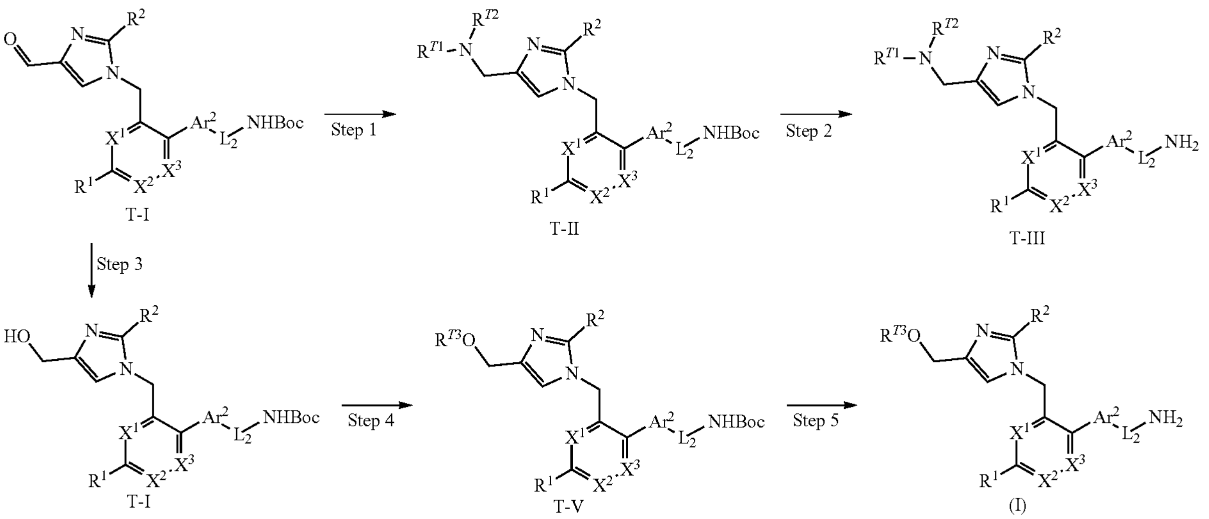

(Wherein, $R^{T1}$, $R^{T2}$, $R^{T3}$ are H atoms or $C_{1-6}$ alkyl groups.)

Step 1: A reductive amination reaction is performed using an amine suitable for the target compound. The imine reducing agent includes, for example, sodium triacetoxyborohydride, sodium cyanoborohydride, and the like. Preferred solvents include, for example, toluene, dichloromethane, dichloroethane, and the like. The reaction temperature is preferably from room temperature to 80° C.

Step 2: Trifluoroacetic acid, hydrochloric acid, sulfuric acid, or the like, is preferable as the strong acid to be used, and dichloromethane, tetrahydrofuran, ethyl acetate or the like, is preferable as the solvent. The reaction temperature is preferably from 0° C. to 50° C., and particularly preferably from 0° C. to room temperature.

Step 3: The reducing agent to be used includes, for example, sodium borohydride, lithium borohydride, and the like. Preferred solvents include tetrahydrofuran, methanol, a mixed solvent thereof, and the like. The reaction temperature is preferably from 0° C. to room temperature.

Step 4: Alkyl halide, alkyl triflate or the like is used as a reagent having a leaving group. The base includes, for example, sodium hydride, potassium carbonate, cesium carbonate. Tetrahydrofuran, N,N-dimethylformamide, dimethyl sulfoxide or the like is preferable as the solvent. The reaction temperature is preferably from 0° C. to 80° C.

Step 5: Trifluoroacetic acid, hydrochloric acid, sulfuric acid, or the like is preferable as the strong acid to be used, and dichloromethane, tetrahydrofuran, ethyl acetate or the like is preferable as the solvent. The reaction temperature is preferably from 0° C. to 50° C., and particularly preferably from 0° C. to room temperature.

When $L^1$ in the formula (I) is —$CH_2$— in the compound of the present invention, as shown in the following reaction scheme, a target compound having an amide group can be synthesized via functional group conversion of the ester group in intermediate (U-I).

[Chem. 28]

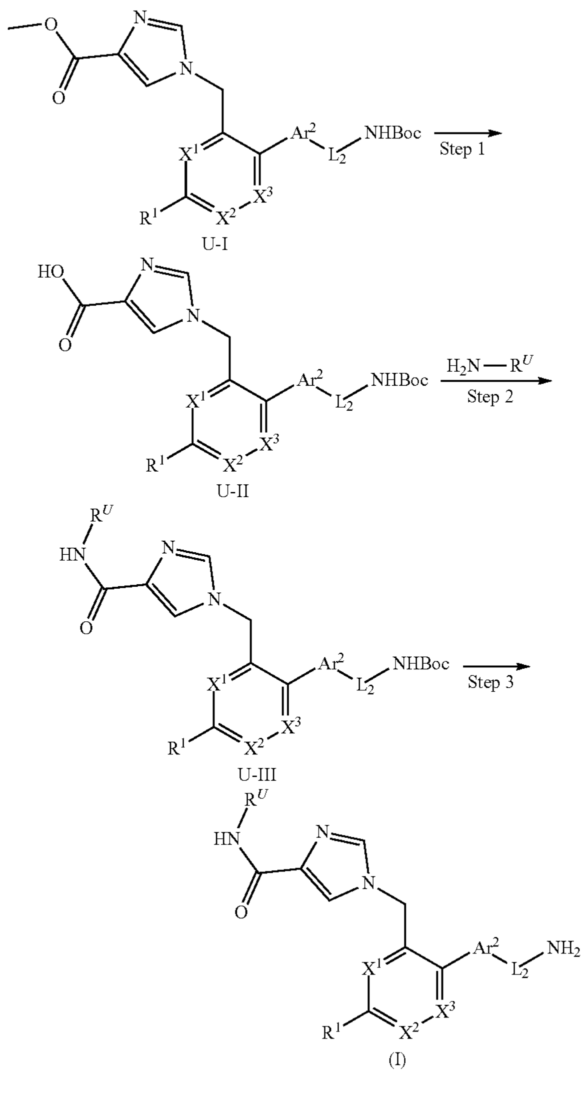

U-I
U-II
U-III
(I)

(Wherein, $R^U$ is a $C_{1-6}$ alkyl group.)

Step 1: The base includes, for example, inorganic salts such as sodium hydroxide, potassium hydroxide, lithium hydroxide, sodium carbonate, potassium carbonate, and the like, metal alkoxides such as sodium ethoxide, sodium methoxide, and the like, a solution thereof diluted with water, and the like. Here, the solvent is not particularly limited, and includes, for example, tetrahydrofuran, methanol, ethanol, water, a mixed solvent thereof, and the like. The reaction temperature is preferably from 0° C. to 60° C.

Step 2: The condensing agent to be used includes, for example, HATU, HOBt, HOAt, EDCI, and the like. The reaction is performed in the presence of no base or a base such as triethylamine, N,N-diisopropylethylamine, and the like. Tetrahydrofuran, dichloromethane, N,N-dimethylformamide or the like is preferable as the solvent. The reaction temperature is preferably from 0° C. to 100° C.

Step 3: Trifluoroacetic acid, hydrochloric acid, sulfuric acid, or the like is preferable as the strong acid to be used, and a solvent such as dichloromethane, tetrahydrofuran, ethyl acetate or the like is preferable as the solvent. The reaction temperature is preferably from 0° C. to 50° C., and particularly preferably from 0° C. to room temperature.

When L in the formula (I) is —$CH_2$— in the compound of the present invention, the synthesis can also be performed by the method shown in the following reaction scheme. That is, after obtaining triazole (V-IV) by reacting the acetylene compound (V-III) with the (V-II) into which an azide group is introduced, the synthesis can be performed by the same method as described above.

[Chem. 29]

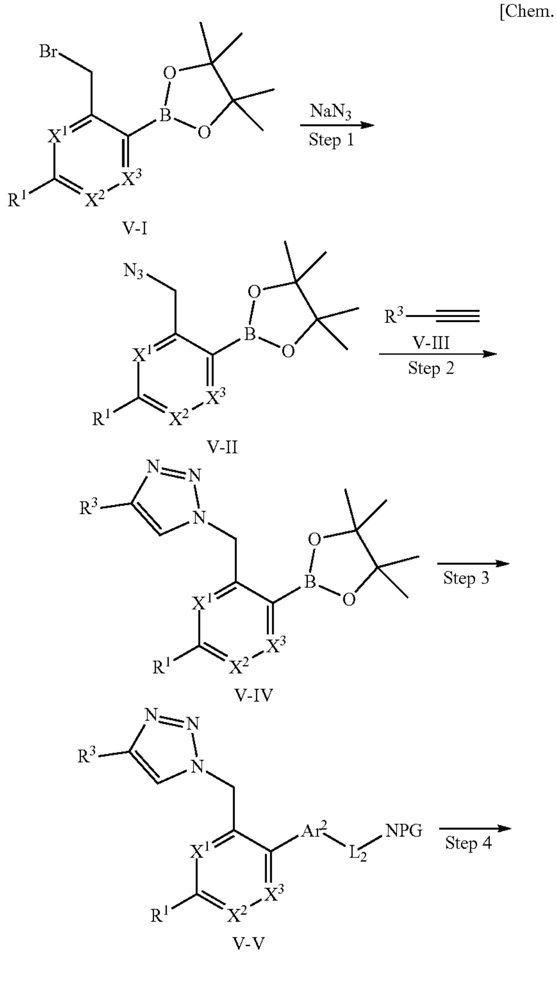

V-I
V-II
V-IV
V-V

-continued

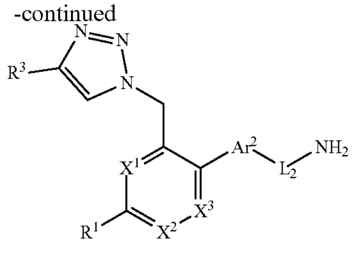

(I)

Step 1: This reaction is a reaction of introducing an azido group using sodium azide. The solvent includes, for example, N,N-dimethylformamide, N-methylpyrrolidone, dimethyl sulfoxide, and the like. The reaction temperature is preferably from room temperature to 100° C.

Step 2: This reaction is a reaction of performing triazole ring synthesis using an alkyne compound corresponding to the target compound. Copper(I) iodide, copper(I) bromide or the like is preferable as the metal reagent, and if necessary, a ligand such as tris[(1-benzyl-1H-1,2,3-triazol-4-yl) methyl]amine (TBTA) is also added. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from room temperature to 80° C.

Step 3: Preferred palladium catalyst includes, for example, tetrakis(triphenylphosphine)palladium, bis(triphenylphosphine)palladium dichloride, [1,1'-bis(diphenylphosphino)ferrocene]palladium dichloride, and the like, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 4: As a removal method of the protecting group, a known method widely used in this field can be adopted. For example, when the protecting group is a Boc group, a strong acid such as trifluoroacetic acid, hydrochloric acid, sulfuric acid, or the like is preferable, and when the protecting group is phthalimide, hydrazine, ethylenediamine or the like is preferable. The solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is $—CH_2—$ in the compound of the present invention, the synthesis can be performed also by the method shown in the following reaction scheme. That is, after obtaining (W-V) by a coupling reaction between boronic acid (W-I) and nitropyrazole ring (W-II), reducing a nitro group, and modifying an amino group, the target compound can be synthesized by the same method as described above.

[Chem. 30]

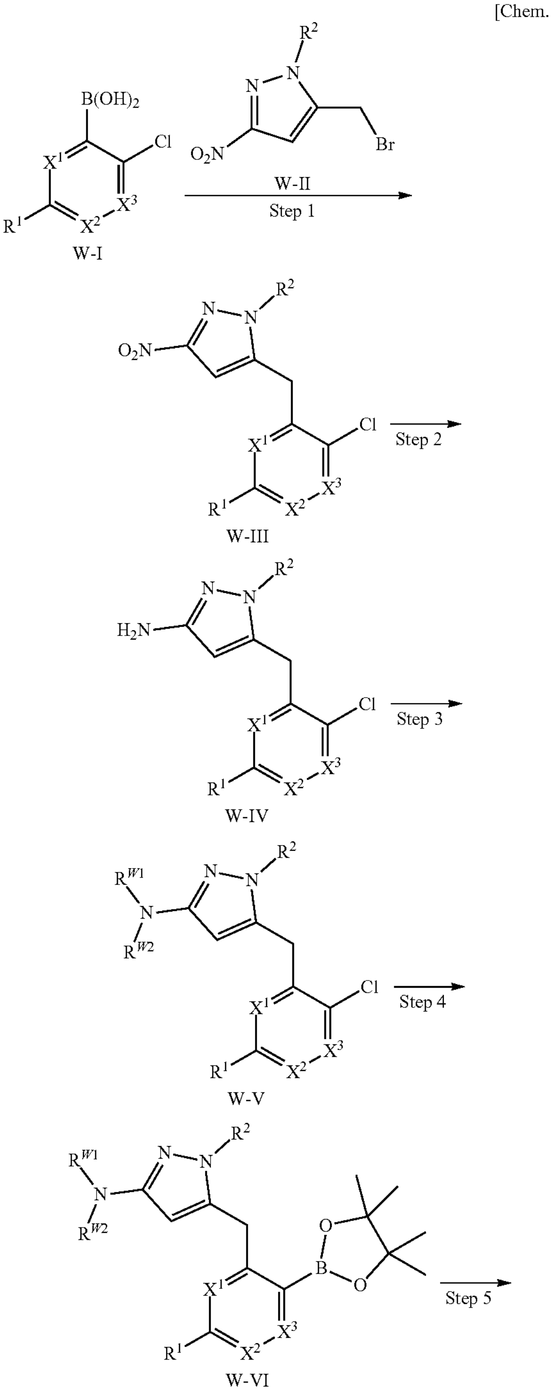

-continued

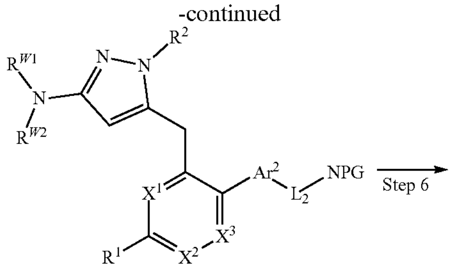

W-VII

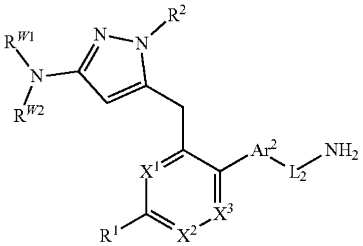

(I)

(Wherein, $R^{W1}$ and $R^{W2}$ are substituents which form —$NR^{W1}R^{W2}$ which may be included in $R^3$ of the formula (I).)

Step 1: Tetrakis(triphenylphosphine)palladium, bis(triphenylphosphine)palladium dichloride, [1,1'-bis(diphenylphosphino)ferrocene]palladium dichloride, or the like is preferable as the palladium catalyst and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 2: Iron, zinc, or the like is preferable as the metal reagent to be used, and is preferably used in combination with a reagent such as ammonium chloride, acetic acid, and the like. Preferred solvents include, for example, organic solvents such as ethanol, methanol and tetrahydrofuran, and mixed solvents obtained by adding water thereto, and the like. The reaction temperature is preferably from room temperature to 100° C.

Step 3: The reaction reagent having a leaving group includes, for example, alkyl halides, alkyl triflate, and the like. Organic bases such as triethylamine, N,N-diisopropylethylamine, or the like, or inorganic bases such as potassium carbonate, cesium carbonate, or the like is preferable as the base. 1,4-Dioxane, N,N-dimethylformamide, N,N-dimethylacetamide, N-methylpyrrolidone, dimethyl sulfoxide or the like is preferable as the solvent. The reaction temperature is preferably from room temperature to 150° C.

Step 4: The borylation reagent includes, for example, bis(pinacolato)diboron, and the like. Tetrakis(triphenylphosphine)palladium, bis(triphenylphosphine)palladium dichloride, [1,1'-bis(diphenylphosphino)ferrocene]palladium dichloride, tris(dibenzylideneacetone)dipalladium, palladium acetate, XPhos-Pd-G2, or the like is preferable as the catalyst. If necessary, the ligand such as tricyclohexylphosphine, 2-dicyclohexylphosphino-2',4',6'-triisopropylbiphenyl, 2-dicyclohexylphosphino-2',6'-dimethoxybiphenyl, or the like can be used. Potassium acetate or the like is preferable as the base. Preferred solvents include, for example, 1,4-dioxane, dimethyl sulfoxide, and the like. The reaction temperature is preferably from 50° C. to 150° C., and particularly preferably from 70° C. to 120° C.

Step 5: Tetrakis(triphenylphosphine)palladium, bis(triphenylphosphine)palladium dichloride, [1,1'-bis(diphenylphosphino)ferrocene]palladium dichloride, or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 6: As a removal method of the protecting group, a known method widely used in this field can be adopted. For example, when the protecting group is a Boc group, a strong acid such as trifluoroacetic acid, hydrochloric acid, sulfuric acid, or the like is preferable, and when the protecting group is phthalimide, hydrazine, ethylenediamine or the like is preferable. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is —CHMe-, —C(=$CH_2$)—, or a 1,1-cyclopropropylidene group in the compound of the present invention, synthesis can be performed as shown in the following reaction scheme. That is, after reacting tosylhydrazone (X-III) with an $Ar^1$ ring compound having a halogen atom to obtain an exoolefin (X-IV), the target compound can be synthesized by reducing or cyclopropanating the olefin, and then deprotecting. The compound represented by formula (I) in which $L^1$ is —C(=$CH_2$)— can be synthesized by deprotecting (X-IV).

[Chem. 31]

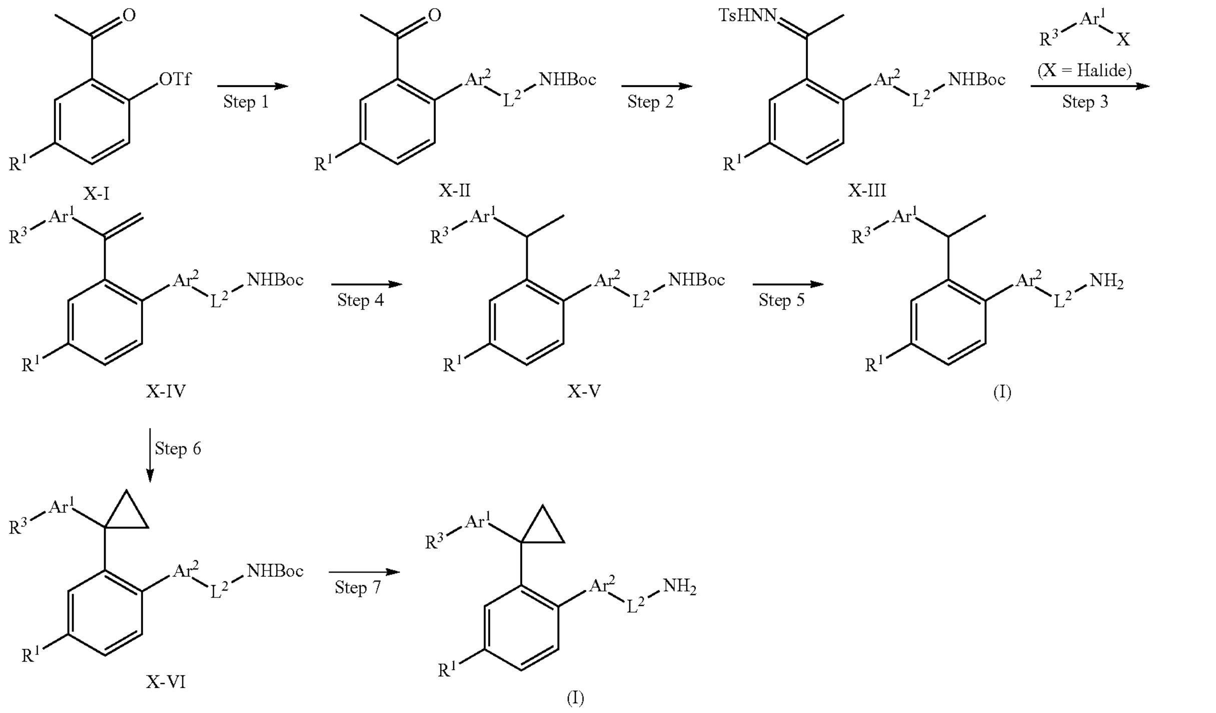

X-I X-II X-III X-IV X-V (I) X-VI (I)

Step 1: Tetrakis(triphenylphosphine)palladium, bis(triphenylphosphine)palladium dichloride, [1,1'-bis(diphenylphosphino)ferrocene]palladium dichloride, or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 2: This reaction is a reaction of forming tosylhydrazone using tosylhydrazine as a reagent. Preferred solvents include toluene, methanol, ethanol, and the like. The reaction temperature is preferably from room temperature to 120° C.

Step 3: This reaction is a reaction of synthesizing an exoolefin by performing a coupling reaction between tosylhydrazone and aryl halide. Tetrakis(triphenylphosphine)palladium, bis(triphenylphosphine)palladium dichloride, [1,1'-bis(diphenylphosphino)ferrocene]palladium dichloride, tris (dibenzylideneacetone)dipalladium, palladium acetate, or the like is preferable as the catalyst. If necessary, a ligand such as 4,5-bis(diphenylphosphino)-9,9-dimethylxanthene, 2-(dicyclohexylphosphino)-2',4',6'-tri-isopropyl-1,1'-biphenyl, 2-dicyclohexylphosphino-2',6'-dimethoxybiphenyl, or the like can be used. Preferred bases include cesium carbonate, lithium tert-butoxide, tripotassium phosphate. Preferred solvents include 1,4-dioxane, toluene, fluorobenzene, and the like. The reaction temperature is preferably from 50° C. to 150° C.

Step 4: This reaction is a reaction of reducing an olefin by combining a metal reagent such as palladium carbon (Pd/C) and a hydrogen source such as hydrogen gas. Ethanol, methanol, ethyl acetate or the like is preferable as the solvent. The reaction temperature is preferably from 0° C. to 100° C.

Step 5: Trifluoroacetic acid, hydrochloric acid, sulfuric acid, or the like is preferable as the strong acid to be used, and dichloromethane, tetrahydrofuran, ethyl acetate or the like is preferable as the solvent. The reaction temperature is preferably from 0° C. to 50° C., and particularly preferably from 0° C. to room temperature.

Step 6: This reaction is a reaction of converting an olefin to cyclopropane using trimethylsulfoxonium iodide. Preferred bases include, for example, sodium hydride, potassium tert-butoxide, and the like. Dimethyl sulfoxide, tetrahydrofuran or the like is preferable as the solvent. The reaction temperature is preferably from 0° C. to 100° C.

Step 7: Trifluoroacetic acid, hydrochloric acid, sulfuric acid, or the like is preferable as the strong acid to be used, and dichloromethane, tetrahydrofuran, ethyl acetate, or the like is preferable as the solvent. The reaction temperature is preferably from 0° C. to 50° C., and particularly preferably from 0° C. to room temperature.

When L in the formula (I) is —CH($R^{11}$)— in the compound of the present invention, synthesis can be performed by using the following methods.

For example, synthesis can be performed as shown in the following reaction scheme. That is, after reducing the ketone of (Y-I) prepared by the synthesis method described above, the target compound can be synthesized by deprotecting the amino group. It is also possible to modify the hydroxy group in intermediate (Y-II) by an alkylation reaction or the like.

[Chem. 32]

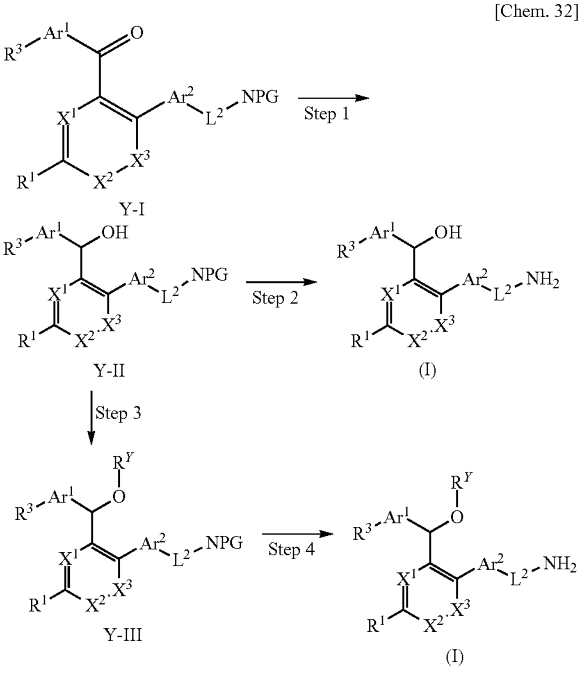

Y-I, Y-II, (I), Y-III, (I)

(Wherein, $R^Y$ is a substituent which forms —$OR^Y$ which satisfies $R^{11}$ in the formula (I).)

Step 1: The reducing reagent includes, for example, sodium borohydride, lithium borohydride, and the like. Preferred solvents include, for example, tetrahydrofuran, methanol, ethanol, a mixed solvent thereof, and the like. The reaction temperature is preferably from 0° C. to 50° C.

Step 2: As a removal method of the protecting group, a known method widely used in this field can be adopted. For example, when the protecting group is a Boc group, a strong acid such as trifluoroacetic acid, hydrochloric acid, sulfuric acid, or the like is preferable, and when the protecting group is phthalimide, hydrazine, ethylenediamine or the like is preferable. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

Step 3: Alkyl halide, alkyl triflate or the like is used as the reagent having a leaving group. The base includes, for example, sodium hydride, potassium carbonate, cesium carbonate, and the like. Tetrahydrofuran, N,N-dimethylformamide, dimethyl sulfoxide, or the like is preferable as the solvent. The reaction temperature is preferably from 0° C. to 80° C.

Step 4: As a removal method of the protecting group, a known method widely used in this field can be adopted. For example, when the protecting group is a Boc group, a strong acid such as trifluoroacetic acid, hydrochloric acid, sulfuric acid, or the like is preferable, and when the protecting group is phthalimide, hydrazine, ethylenediamine or the like is preferable. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, halogenated hydrocarbons such as dichloromethane, 1,2-dichloroethane, chloroform, and the like, alcohols such as methanol, ethanol, 2-propanol, butanol, and the like, N,N-dimethylformamide, N-methylpyrrolidone, dimethyl sulfoxide, and the like. The reaction temperature is preferably from 0° C. to 100° C.

When $L^1$ in the formula (I) is —$CH(R^{11})$— in the compound of the present invention, the synthesis can be performed also as shown in the following reaction scheme. That is, after introducing an ethynyl group on the raw material aldehyde (Z-I), cyclization reaction is performed using (Z-IV) to obtain target isoxazole (Z-V) having $R^3$ substituent. After modifying the hydroxy group of (Z-V) by an alkylation reaction or the like, the target compound can be synthesized by deprotecting the amino group.

[Chem. 33]

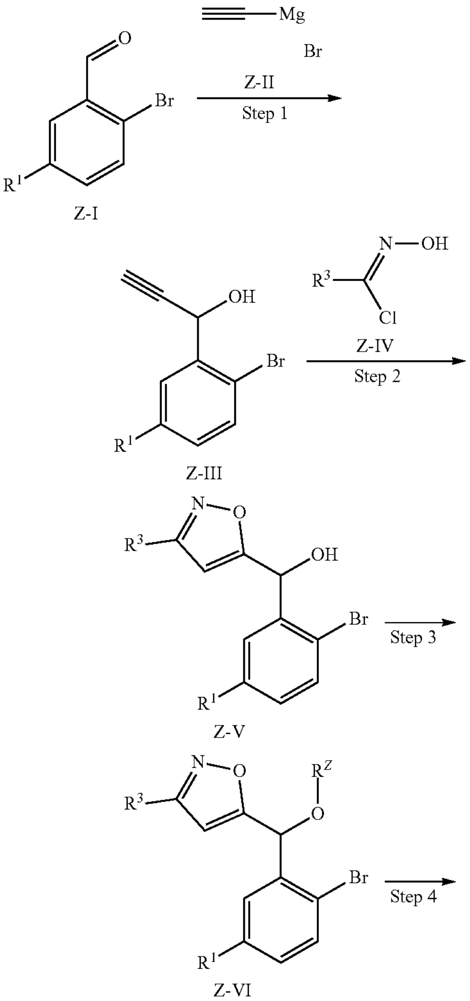

Z-I, Z-II, Z-III, Z-IV, Z-V, Z-VI

-continued

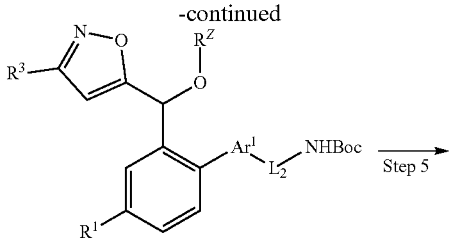

Z-VII

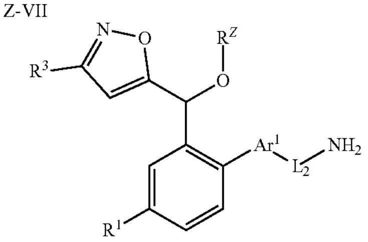

(I)

(Wherein, $R^Z$ is a substituent which forms —$OR^Z$ which satisfies $R^{11}$ in the formula (I).)

Step 1: This reaction is an addition reaction of ethynylmagnesium bromide (Z-II) to aldehyde (Z-I). Tetrahydrofuran, dichloromethane, or the like is preferable as the solvent to be used. The reaction temperature is preferably from −78° C. to room temperature.

Step 2: This reaction is a reaction of constructing an isoxazole ring using an oxime reagent (Z-IV) corresponding to the target compound. Potassium carbonate, sodium carbonate, cesium carbonate, or the like is preferable as the base, and 1,4-dioxane, toluene, or the like is preferable as the solvent. The reaction temperature is preferably from 50° C. to 120° C.

Step 3: Alkyl halide, alkyl triflate or the like is used as the reagent having a leaving group. The base includes, for example, sodium hydride, potassium carbonate, cesium carbonate, and the like. Tetrahydrofuran, N,N-dimethylformamide, dimethyl sulfoxide or the like is preferable as the solvent. The reaction temperature is preferably from 0° C. to 80° C.

Step 4: Tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, a mixed solvent thereof, and the like. The reaction temperature is preferably from 50° C. to 150° C., and particularly preferably from 80° C. to 120° C.

Step 5: Trifluoroacetic acid, hydrochloric acid, sulfuric acid, or the like is preferable as the strong acid to be used, and dichloromethane, tetrahydrofuran, ethyl acetate or the like is preferable as the solvent. The reaction temperature is preferably from 0° C. to 50° C., and particularly preferably from 0° C. to room temperature.

When $L^1$ in the formula (I) is —S— or —SO— in the compound of the present invention, the synthesis can be performed using the following methods.

For example, synthesis can be performed as shown in the following reaction scheme. That is, after converting the intermediate (A'-I) obtained by the above-mentioned synthesis method into triflate (A'-II), a thiol side chain is introduced by a coupling reaction, and this compound (A'-III) is treated with a suitable base and subjected to an aromatic nucleophilic substitution reaction to be bonded with $Ar^1$ ring. If necessary, after this, the target compound can be synthesized by introducing the target side chain substituent using a halogen atom in $Ar^1$ as a foothold. If the $Ar^1$ compound used in step 3 has already been modified with $R^3$, the operation in step 4 can be omitted.

[Chem. 34]

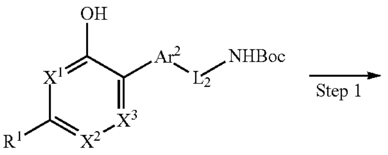

A'-I

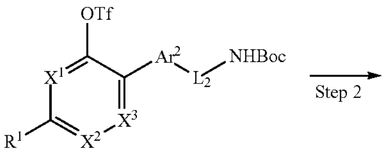

A'-II

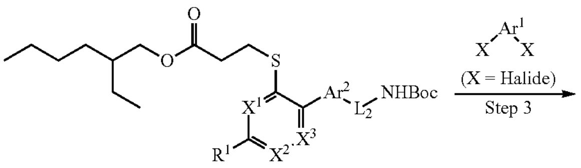

A'-III

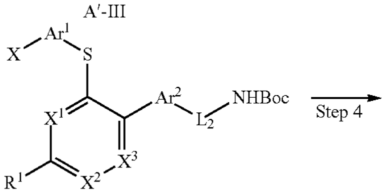

A'-IV

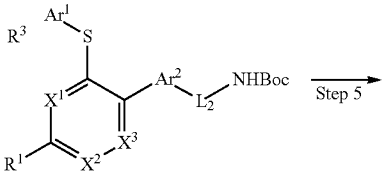

A'-V

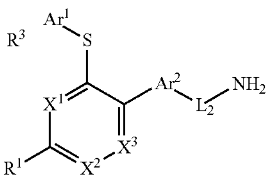

(I)

Step 1: The triflation agent to be used include trifluoromethanesulfonic anhydride ($Tf_2O$), and the like and pyridine, triethylamine, N,N-diisopropylethylamine or the like is preferable as the base. Preferred solvents include, for example, tetrahydrofuran, dichloromethane, 1,2-dichloroethane, and the like. The reaction temperature is preferably from −20° C. to 50° C.

Step 2: Tetrakis(triphenylphosphine)palladium, bis(triphenylphosphine)palladium dichloride, [1,1'-bis(diphenylphosphino)ferrocene]palladium dichloride, tris(dibenzylideneacetone)dipalladium, palladium acetate, or the like is preferable as the catalyst. If necessary, the ligand such as 4,5-bis(diphenylphosphino)-9,9-dimethylxanthene, 2-(dicyclohexylphosphino)-2',4',6'-tri-isopropyl-1,1'-biphenyl and 2-dicyclohexylphosphino-2',6'-dimethoxybiphenyl, or the like can be used. Preferred bases include, for example, N,N-diisopropylethylamine, triethylamine, potassium carbonate, cesium carbonate, and the like. The solvent includes, for example, 1,4-dioxane, tetrahydrofuran, N,N-dimethylformamide, and the like. The reaction temperature is preferably from 50° C. to 150° C.

Step 3: Potassium carbonate, cesium carbonate, 1,8-diazabicyclo[5.4.0]-7-undecene (DBU) or the like is preferable as the base. Preferred solvents include, for example, 1,4-dioxane, tetrahydrofuran, N,N-dimethylformamide, N-methylpyrrolidone, dimethyl sulfoxide, and the like. The reaction temperature is preferably from 0° C. to 150° C.

Step 4: For introduction of the $R^3$ substituent, a known method commonly used in the art can be adopted. For example, when the $R^3$ substituent is introduced using boronic acid derivatives, tetrakis(triphenylphosphine)palladium, bis(triphenylphosphine)palladium dichloride, [1,1'-bis(diphenylphosphino)ferrocene]palladium dichloride or the like is preferable as the palladium catalyst, and the base includes, for example, inorganic salts such as sodium hydroxide, potassium hydroxide, lithium hydroxide, sodium carbonate, potassium carbonate, cesium carbonate, tripotassium phosphate, and the like. Here, the solvent is not particularly limited, and includes, for example, aromatic hydrocarbons such as benzene, toluene, xylene, and the like, ethers such as diethyl ether, tetrahydrofuran, 1,4-dioxane, 1,2-dimethoxyethane, 1,2-diethoxyethane, and the like, alcohols such as methanol, ethanol, 2-propanol, butanol, and the like, N,N-dimethylformamide, N-methylpyrrolidone, dimethyl sulfoxide, water, mixed solvent thereof, and the like. The reaction temperature is preferably form 50° C. to 150° C., and particularly preferably from 80° C. to 120° C.

Further, for example, when an alcohol or an amine corresponding to the $R^3$ substituent is reacted, preferred bases include, for example, organic bases such as triethylamine, N,N-diisopropylethylamine, and the like, and inorganic bases such as potassium carbonate, cesium carbonate, and the like. Here, the solvent is not particularly limited, and includes, for example, ethers such as tetrahydrofuran, 1,4-dioxane, 1,2-dimethoxyethane, 1,2-diethoxyethane, and the like, N,N-dimethylformamide, N-methylpyrrolidone, dimethyl sulfoxide, and the like. The reaction temperature is preferably from room temperature to 150° C.

Step 5: Trifluoroacetic acid, hydrochloric acid, sulfuric acid, or the like is preferable as the strong acid to be used, and dichloromethane, tetrahydrofuran, ethyl acetate or the like is preferable as the solvent. The reaction temperature is preferably from 0° C. to 50° C., and particularly preferably 0° C. to room temperature.

When $L^1$ in the formula (I) is —S— in the compound of the present invention, synthesis can be performed also as shown in the following reaction scheme. That is, since an aromatic nucleophilic substitution reaction can be used as a method for bonding with an $Ar^2$ ring such as pyrazole or the like, after the formation of a biaryl bond, the synthesis can be performed in the same manner as in the above scheme.

[Chem. 35]

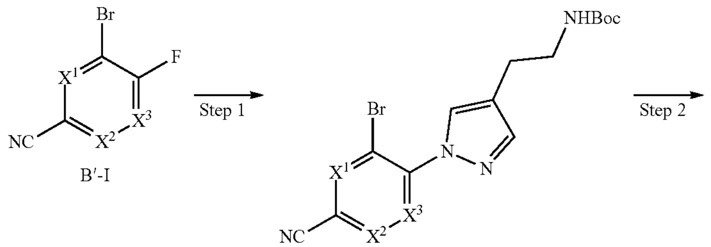

B'-I

B'-II

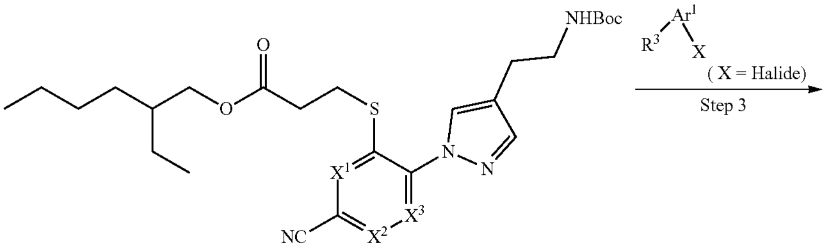

B'-III

-continued

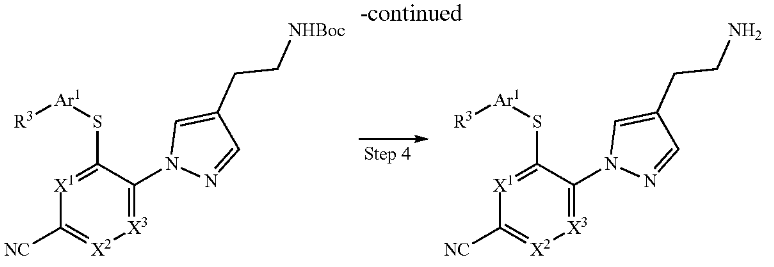

B'-IV (I)

Step 1: Triethylamine, N,N-diisopropylethylamine, potassium carbonate, cesium carbonate, or the like is preferable as the base to be used. Preferred solvents include, for example, 1,4-dioxane, tetrahydrofuran, N,N-dimethylformamide, N-methylpyrrolidone, dimethyl sulfoxide, and the like. The reaction temperature is preferably from room temperature to 150° C.

Step 2: Tetrakis(triphenylphosphine)palladium, bis(triphenylphosphine)palladium dichloride, [1,1'-bis(diphenylphosphino)ferrocene]palladium dichloride, tris(dibenzylideneacetone)dipalladium, palladium acetate, or the like is preferable as the catalyst. If necessary, the ligand such as 4,5-bis(diphenylphosphino)-9,9-dimethylxanthene, 2-(dicyclohexylphosphino)-2',4',6'-tri-isopropyl-1,1'-biphenyl, 2-dicyclohexylphosphino-2',6'-dimethoxybiphenyl, or the like can be used. Preferred bases include N,N-diisopropylethylamine, triethylamine, potassium carbonate, cesium carbonate, and the like. The solvent includes, for example, 1,4-dioxane, tetrahydrofuran, N,N-dimethylformamide, and the like. The reaction temperature is preferably from 50° C. to 150° C.

Step 3: Potassium carbonate, cesium carbonate, 1,8-diazabicyclo[5.4.0]-7-undecene (DBU) or the like is preferable as the base. Preferred solvents include, for example, 1,4-dioxane, tetrahydrofuran, N,N-dimethylformamide, N-methylpyrrolidone, dimethyl sulfoxide, and the like. The reaction temperature is preferably from 0° C. to 150° C.

Step 4: Trifluoroacetic acid, hydrochloric acid, sulfuric acid, or the like is preferable as the strong acid to be used, and dichloromethane, tetrahydrofuran, ethyl acetate or the like is preferable as the solvent. The reaction temperature is preferably from 0° C. to 50° C., and particularly preferably from 0° C. to room temperature.

When $L^1$ in the formula (I) is —SO— in the compound of the present invention, as shown in the following reaction scheme, the target compound can be synthesized by oxidizing sulfide (C'—I) to convert to sulfoxide (C'—II), and then performing deprotection.

[Chem. 36]

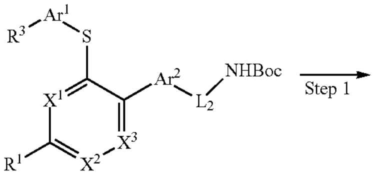

C'-I

-continued

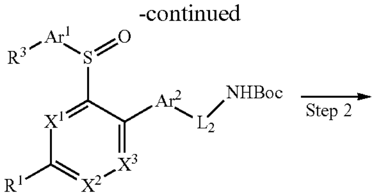

C'-I

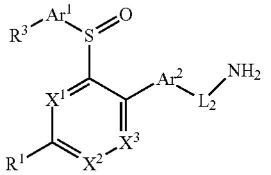

(I)

Step 1: The oxidizing agent to be used includes, for example, 3-chloroperbenzoic acid and the like. The solvent includes, for example, 1,4-dioxane, tetrahydrofuran, N,N-dimethylformamide, dimethyl sulfoxide, and the like. The reaction temperature is preferably from 0° C. to 100° C.

Step 2: Trifluoroacetic acid, hydrochloric acid, sulfuric acid, or the like is preferable as the strong acid to be used, and dichloromethane, tetrahydrofuran, ethyl acetate, or the like is preferable as the solvent. The reaction temperature is preferably from 0° C. to 50° C., and particularly preferably from 0° C. to room temperature.

Pharmaceutically acceptable salts of the compounds represented by formula (I) are not particularly limited as long as they are pharmaceutically acceptable salts, and include, for example, salts with inorganic acids such as hydrogen chloride, hydrogen bromide, sulfuric acid, nitric acid, phosphoric acid, carbonic acid, and the like, salts with organic acids such as maleic acid, fumaric acid, citric acid, malic acid, tartaric acid, lactic acid, succinic acid, benzoic acid, oxalic acid, methanesulfonic acid, benzenesulfonic acid, p-toluenesulfonic acid, acetic acid, trifluoroacetic acid, formic acid, and the like, salts with amino acids such as glycine, lysine, arginine, histidine, ornithine, glutamic acid, aspartic acid, and the like, salts with alkali metals such as sodium, potassium, lithium, and the like, salts with alkaline earth metals such as calcium, magnesium, and the like, salts with metals such as aluminum, zinc, iron, and the like, salts with organic oniums such as tetramethylammonium, choline, and the like, and salts with organic bases such as ammonia, propanediamine, pyrrolidine, piperidine, pyridine, ethanolamine, N,N-dimethylethanolamine, 4-hydroxypiperidine, t-octylamine, dibenzylamine, morpholine, glucosamine, phenylglycyl alkyl ester, ethylenediamine, N-methylglucamine, guanidine, diethylamine, triethylamine, dicyclohexylamine, N,N'-dibenzylethylenediamine, chloroprocaine, procaine, diethanolamine, N-benzylphenylamine, piperazine, tris(hydroxymethyl)aminomethane, and the like.

Further, the compounds represented by formula (I) or pharmaceutically acceptable salts thereof include various hydrates and solvates. The solvents of the solvates include, though not particularly limited, for example, methanol, ethanol, 1-propanol, 2-propanol, butanol, t-butanol, acetonitrile, acetone, methyl ethyl ketone, chloroform, ethyl acetate, diethyl ether, t-butylmethyl ether, tetrahydrofuran, 1,4-dioxane, 1,2-dimethoxyethane, 1,2-diethoxyethane, benzene, toluene, N,N-dimethylformamide, dimethyl sulfoxide, and the like.

The medically acceptable salts of the compound represented by the formula (I) may be appropriately produced based on conventional knowledge in the art.

The compounds represented by formula (I) or pharmaceutically acceptable salts thereof include stereoisomers, racemates and all possible optically active substances thereof.

The compound represented by formula (I) of the present invention or the pharmaceutically acceptable salt thereof can be used in any formulation such as solid preparation, semi-solid preparation and liquid preparation, or any application such as oral and non-oral preparations (injections, percutaneous absorption agents, eye drops, suppositories, transnasal absorption agents, inhalants, and the like).

The pharmaceutical composition containing a compound represented by formula (I) of the present invention or a pharmaceutically acceptable salt thereof is prepared using additives usually used for formulation. The additives for a solid preparation includes, for example, an excipient such as lactose, saccharose, glucose, corn starch, potato starch, crystalline cellulose, light anhydrous silicic acid, synthetic aluminum silicate, magnesium aluminometasilicate, calcium hydrogen phosphate, and the like, a binder such as crystalline cellulose, carboxymethyl cellulose, hydroxypropyl cellulose, carboxymethylcellulose sodium, polyvinyl pyrrolidone, and the like, a disintegrating agent such as starch, carboxymethylcellulose sodium, carboxymethylcellulose calcium, croscarmellose sodium and sodium carboxy methyl starch, and the like, a lubricant such as talc, stearic acids, and the like, a coating agent such as hydroxymethylpropylcellulose, hydroxypropylmethylcellulose phthalate, ethylcellulose, and the like, and a coloring agent; the additives for a semisolid preparation include, for example, a substrate such as white petrolatum and the like; and the additives for a liquid preparation includes, for example, a solvent such as ethanol, and the like, a solubilizing agent such as ethanol, and the like, a preservative such as para-hydroxybenzoate, and the like, a isotonizing agent such as glucose, and the like, a buffer such as citric acid, and the like, an antioxidant such as L-ascorbic acid, and the like, a chelating agent such as EDTA, and the like, and a suspending agent and an emulsifying agent such as polysorbate 80 and the like.

The therapeutically effective amount of the active ingredient in the therapeutic agent or prophylactic agent in the present invention, which depends on the route of administration, the age and sex of the patient, and the severity of the disease, is usually of the order of 0.1 to 1000 mg/day, and the frequency of administration is usually one to three times/day to one to seven times/week. The preparation is preferably prepared so as to satisfy such conditions.

In the present invention, the term "prevention" means to prevent incidence or onset of diseases in an individual who is not affected by diseases or has not yet developed diseases and the term "treatment" means to cure, suppress, or remedy diseases or symptoms in an individual who has already been affected by diseases or has developed diseases.

EXAMPLES

Hereinafter, the present invention will be described in greater detail by way of working examples, but not limited thereto. Abbreviations in the present invention are as follows:

BINAP=2,2'-bis(diphenylphosphino)-1,1'-binaphthyl
DBU=1,8-diazabicyclo[5.4.0]-7-undecene
DMA=N,N-dimethylacetamide
DMF=N,N-dimethylformamide
DMSO=dimethyl sulfoxide
HATU=1-[bis(dimethylamino)methylene]-1H-1,2,3-triazolo[4,5-b]pyridinium 3-oxide hexafluorophosphate
NMP=1-methyl-2-pyrrolidone
TFA=trifluoroacetic acid
THF=tetrahydrofuran The structure of the novel compound isolated was identified by $^1$H-NMR and/or mass spectrometry using a single quadrupole instrumentation equipped with an electron spray source, or by other suitable analytical methods.

For the measurement of $^1$H-NMR spectrum (400 MHz, DMSO-$d_6$, $CDCl_3$, or $CD_3OD$), the chemical shift (δ: ppm) and coupling constant (J: Hz) are shown. As for the result of mass spectrometry, the measured value observed as $M^+$+H, that is, the value obtained by adding the mass of a proton ($H^+$) to the molecular mass of a compound (M) is shown. The abbreviations used are as follows:

s=singlet, d=doublet, t=triplet, q=quartet, quin=quintet, brs=broad singlet, m=multiplet.

Reference Example 1

Tert-Butyl (2-hydroxy-2-(4-(4,4,5,5-tetramethyl-1,3,2-dioxaboran-2-yl)phenyl)ethyl)carbamate

[Chem. 37]

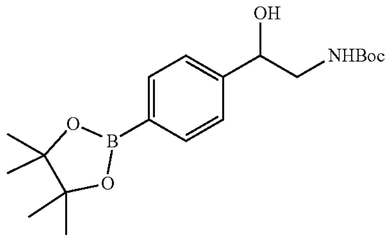

tert-Butyl (2-(4-bromophenyl)-2-hydroxyethyl)carbamate (503 mg, 1.59 mmol) was dissolved in 1,4-dioxane (10 mL), then to the solution, bis(pinacolato)diboron (404 mg, 1.59 mmol), [1,1'-bis(diphenylphosphino)ferrocene]dichloropalladium (61 mg, 0.084 mmol) and potassium acetate (469 mg, 4.78 mmol) were added, and the mixture was stirred at 90° C. for 15 hours. The reaction mixture was cooled to room temperature, filtered through Celite, and then concentrated under reduced pressure. The crude product was purified by silica gel column chromatography to obtain the title compound (412 mg, 71%).

$^1$H-NMR ($CDCl_3$) δ: 7.81 (2H, d, J=7.8 Hz), 7.38 (2H, d, J=7.8 Hz), 4.90-4.86 (2H, m), 3.53-3.45 (1H, m)), 3.27-3.20 (1H, m), 1.45 (9H, s), 1.34 (12H, s).

Reference Example 2

Tert-Butyl N-[3,3-difluoro-2-[4-(4,4,5,5-tetramethyl-1,3,2-dioxaborolan-2-yl)phenyl]propyl]carbamate

[Chem. 38]

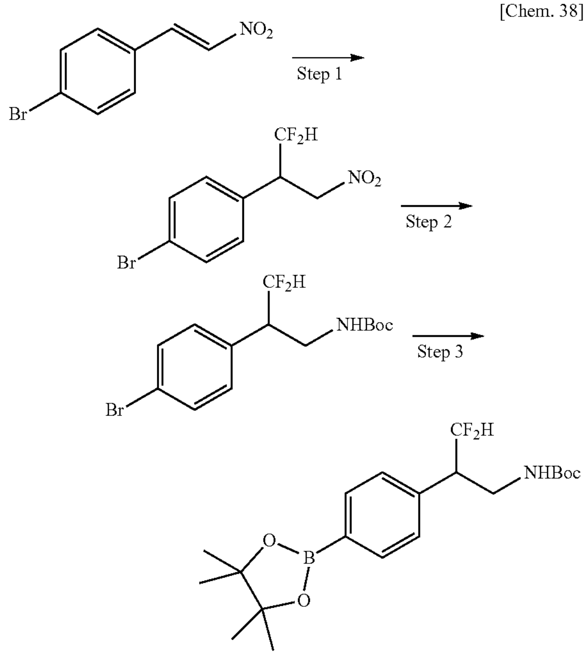

Step 1: 1-Bromo-4-(1,1-difluoro-3-nitropropan-2-yl)benzene

1-Bromo-4-[(E)-2-nitroethenyl]benzene (1 g) was dissolved in acetonitrile (4.4 mL), the solution was cooled to 0° C., then to the solution, (bromodifluoromethyl)trimethylsilane (1.03 mL), triphenylphosphine (1.38 g), and 1,3-dimethyl-3,4,5,6-tetrahydro-2(1H)-pyrimidinone (1.06 mL) were added, and the mixture was stirred at room temperature for 30 minutes. The reaction mixture was cooled to −20° C., then to the mixture, chlorotrimethylsilane (0.11 mL) and methanol (0.89 mL) were added, and the mixture was stirred at the same temperature for 15 minutes and then heated to room temperature. Water (4 mL) and pyridine (0.42 mL) were added to the reaction mixture, and the mixture was stirred at 80° C. for 1.5 hours, and extracted with ethyl acetate. The organic layer was dried over anhydrous sodium sulfate, and the solution was concentrated under reduced pressure. The crude product was purified by silica gel column chromatography to obtain the target compound (785 mg).

$^1$H-NMR ($CDCl_3$) δ: 7.54 (2H, d, J=9.0 Hz), 7.18 (2H, d, J=8.2 Hz), 6.01 (1H, td, J=55.3, 2.7 Hz), 4.94 (1H, dd, J=13.7, 5.5 Hz), 4.83 (1H, ddd, J=71.4, 13.7, 7.3 Hz), 4.06-3.93 (OH, m).

Step, 2: tert-Butyl N-[2-(4-bromophenyl)-3,3-difluoropropyl]carbamate

1-Bromo-4-(1,1-difluoro-3-nitropropan-2-yl)benzene (785 mg) was suspended in a mixed solvent of ethanol (7 mL) and water (2 mL), then to the suspension, iron powder (470 mg) and ammonium chloride (450 mg) were added, and the mixture was stirred at 80° C. for 2 hours. The reaction mixture was cooled to room temperature, filtered through Celite, the mother liquor was dried over anhydrous magnesium sulfate, and the solution was concentrated under reduced pressure. This crude product was dissolved in dichloromethane (14 mL), then to the solution, di-tert-butyl dicarbonate (612 mg) and N,N-diisopropylethylamine (0.39 mL) were added, and the mixture was stirred at room temperature for 1 hour. Water was added to the reaction solution, the mixture was extracted with ethyl acetate, the organic layer was dried over anhydrous magnesium sulfate, and the solution was concentrated under reduced pressure. The crude product was purified by silica gel column chromatography to obtain the target compound (667 mg).

MS: m/z 294.1 (M−tBu+H)$^+$.

Step 3: tert-Butyl N-[3,3-difluoro-2-[4-(4,4,5,5-tetramethyl-1,3,2-dioxaborolan-2-yl)phenyl]propyl]carbamate tert-Butyl N-[2-(4-bromophenyl)-3,3-difluoropropyl]carbamate (667 mg) was dissolved in 1,4-dioxane (19 mL), then to the solution, bis(pinacolato)diboron (629 mg), [1,1'-bis(diphenylphosphino)ferrocene]dichloropalladium (139 mg) and potassium acetate (561 mg) were added, and the mixture was stirred at 100° C. for 3 hours. The reaction mixture was cooled to room temperature, filtered through Celite, and concentrated under reduced pressure to obtain a crude product of the title compound.

Reference Example 3

Tert-Butyl N-[2-(6-chloropyridin-3-yl)-2-hydroxyethyl]carbamate

[Chem. 39]

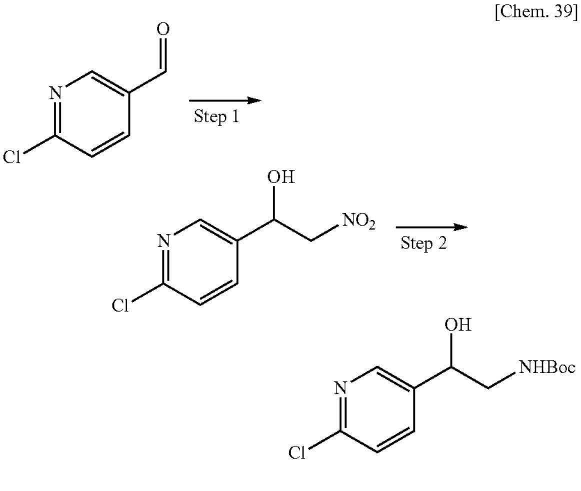

Step 1: 1-(6-Chloropyridin-3-yl)-2-nitroethanol

Nitromethane (3 mL) and triethylamine (3 mL) were added to 6-chloropyridin-3-carbaldehyde (1 g), and the mixture was stirred at room temperature for 1 hour. The reaction mixture was concentrated under reduced pressure, and the crude product was used in the next reaction without further purification.

Step 2: tert-Butyl N-[2-(6-chloropyridin-3-yl)-2-hydroxyethyl]carbamate

The crude product obtained in Step 1 was dissolved in THF (10 mL), then to the solution, zinc powder (2.31 g) and acetic acid (3 mL) were added, and the mixture was stirred at room temperature for 1 hour. The reaction mixture was filtered through Celite and then concentrated under reduced pressure. This crude product was dissolved in dichloromethane (14 mL), then to the solution, di-tert-butyl dicarbonate (1.54 g) and N,N-diisopropylethylamine (2 mL) were added, and the mixture was stirred at room temperature for 16 hours. The reaction mixture was concentrated under reduced pressure, and the crude product was purified by silica gel column chromatography to obtain the title compound (651 mg).

MS: m/z 273.2 $(M+H)^+$.

Reference Example 4

Tert-Butyl N-[2-(2-chloropyrimidin-5-yl)-2-hydroxyethyl]carbamate

[Chem. 40]

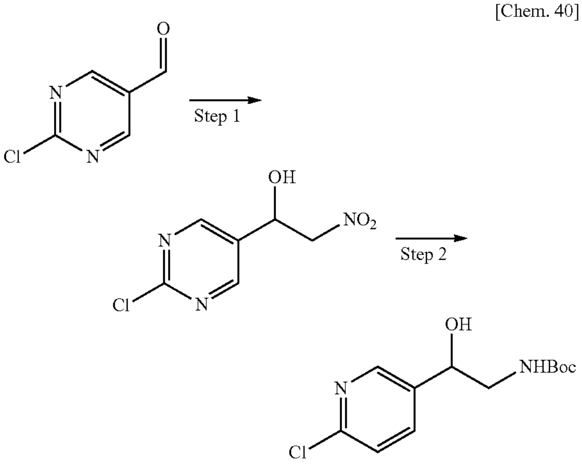

Step 1: 1-(2-Chloropyrimidin-5-yl)-2-nitroethanol

Nitromethane (1 mL) and triethylamine (2 mL) were added to 2-chloropyrimidine-5-carbaldehyde (428 mg), and the mixture was stirred at room temperature for 2 hours. The reaction mixture was concentrated under reduced pressure, and the crude product was used in the next reaction without further purification.

Step 2: tert-Butyl N-[2-(2-chloropyrimidin-5-yl)-2-hydroxyethyl]carbamate

The crude product obtained in Step 1 was dissolved in THF (5 mL), then to the solution, zinc powder (981 mg) and acetic acid (0.86 mL) were added, and the mixture was stirred at room temperature for 2 hours. The reaction mixture was filtered through Celite and then concentrated under reduced pressure. This crude product was dissolved in dichloromethane (5 mL), then to the solution, di-tert-butyl dicarbonate (1.31 g) and N,N-diisopropylethylamine (1.6 mL) were added, and the mixture was stirred at room temperature for 2 hours. Water was added to the reaction mixture, the mixture was extracted with ethyl acetate. The organic layer was dried over anhydrous magnesium sulfate, and the solution was concentrated under reduced pressure. The crude product was purified by silica gel column chromatography to obtain the title compound (208 mg).

MS: m/z 274.1 $(M+H)^+$.

$^1$H-NMR ($CDCl_3$) δ: 8.64 (2H, s), 4.96-4.94 (2H, m), 3.55-3.51 (1H, m), 3.34-3.27 (1H, m), 1.45 (9H, s).

Reference Example 5

Tert-Butyl N-[2-(5-chloropyrazin-2-yl)-2-hydroxyethyl]carbamate

[Chem. 41]

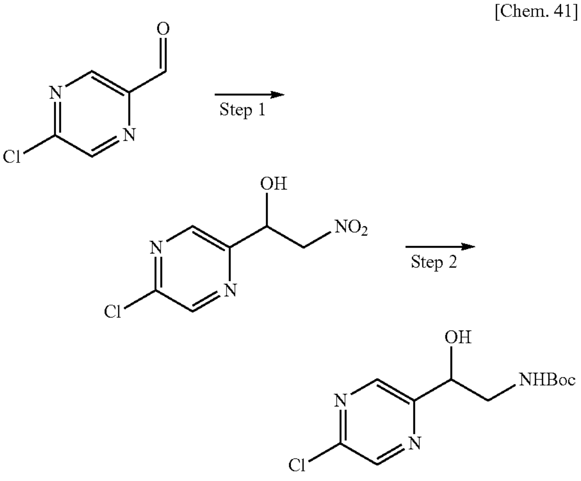

Step 1: 1-(5-Chloropyrazin-2-yl)-2-nitroethanol

Nitromethane (1 mL) and triethylamine (1 mL) were added to 5-chloropyrazine-2-carbaldehyde (826 mg), and the mixture was stirred at room temperature for 1 hour. The reaction mixture was concentrated under reduced pressure, and the crude product was used in the next reaction without further purification.

Step 2: tert-Butyl N-[2-(5-chloropyrazin-2-yl)-2-hydroxyethyl]carbamate

The crude product obtained in Step 1 was dissolved in THF (5 mL), the solution was cooled to 0° C., then to the solution, di-tert-butyl dicarbonate (1.06 g), zinc powder (792 mg) and acetic acid (0.7 mL) were added, and then the mixture was stirred at room temperature for 16 hours. The reaction mixture was filtered through Celite, water was added to the filtrate, and the mixture was extracted with ethyl acetate. The organic layer was dried over anhydrous magnesium sulfate, and the solution was concentrated under reduced pressure. The crude product was purified by silica gel column chromatography to obtain the title compound (57.5 mg).

MS: m/z 218.1 $(M-tBu+H)^-$.

Reference Example 6

Tert-Butyl 3-(6-chloropyridin-3-yl)-3-fluoroazetidine-1-carboxylate

[Chem. 42]

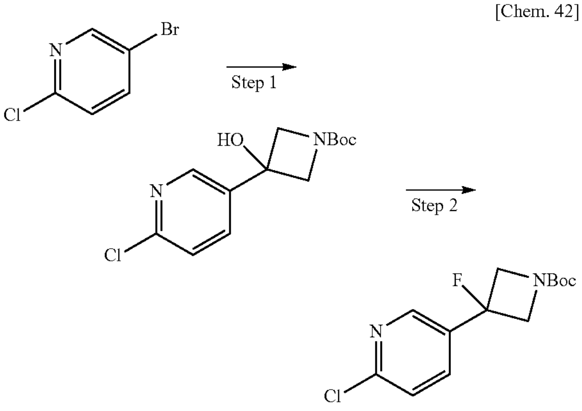

Step 1: tert-Butyl 3-(6-chloropyridin-3-yl)-3-hydroxyazetidine-1-carboxylate

5-Bromo-2-chloropyridine (385 mg) was dissolved in THF (10 mL), the solution was cooled to −78° C., and to the solution, n-butyllithium (1.2 mL) was added dropwise. After stirring at the same temperature for 1 hour, then to the solution, a solution (2 mL) of 1-(tert-butoxycarbonyl)-3-azetidinone (342 mg) in THF was added, and the temperature of the solution was raised to room temperature over 4 hours. A saturated aqueous solution of ammonium chloride was added to the reaction mixture, the mixture was extracted with ethyl acetate, the organic layer was dried over anhydrous magnesium sulfate, and the solution was concentrated under reduced pressure. The crude product was purified by silica gel column chromatography to obtain the target compound (209 mg).

MS: m/z 285.0 $(M+H)^+$.

Step 2: tert-Butyl 3-(6-chloropyridin-3-yl)-3-fluoroazetidine-1-carboxylate tert-Butyl 3-(6-chloropyridin-3-yl)-3-hydroxyazetidine-1-carboxylate (100 mg) was dissolved in dichloromethane (1.8 mL), the solution was cool to −78° C., then to the solution bis(2-methoxyethyl)aminosulfur trifluoride (0.078 mL) was added, and the mixture was stirred at the same temperature for 2 hours. The reaction mixture was heated to room temperature, then to the solution, saturated aqueous sodium hydrogen carbonate was added, and the mixture was extracted with ethyl acetate. The organic layer was dried over anhydrous magnesium sulfate and the solution was concentrated under reduced pressure to obtain a crude product of the title compound (40 mg).

MS: m/z 287.0 $(M+H)^+$.

Reference Example 7

N-[3-[(6-Chloropyridin-3-yl)methyl]oxetan-3-yl]-2-methylpropane-2-sulfinamide

[Chem. 43]

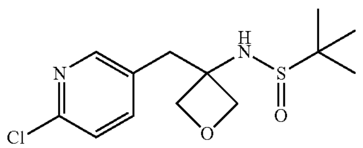

2-Chloro-5-iodopyridine (479 mg) was dissolved in THF (10 mL) and to the solution, isopropylmagnesium bromide (1 M solution in THF, 2.0 mL) was added dropwise at 0° C. After stirring the solution at the same temperature for 1 hour, then to the solution, copper(I) iodide (38.1 mg) was added, and the mixture was cooled to −30° C. A solution (2 mL) of 1-tert-butylsulfinyl-5-oxa-1-azaspiro[2.3]hexane (189 mg) in THF was added dropwise to the reaction mixture, the mixture was heated to room temperature, and the mixture was stirred for 2 hours. A saturated aqueous solution of ammonium chloride was added to the reaction mixture, the mixture was extracted with ethyl acetate, the organic layer was dried over anhydrous sodium sulfate, and the solution was concentrated under reduced pressure. The crude product was purified by silica gel column chromatography to obtain the title compound (108 mg).

MS: m/z 303.1 $(M+H)^+$.

$^1$H-NMR ($CDCl_3$) δ: 8.33 (1H, s), 7.71 (1H, d, J=7.3 Hz), 7.30 (1H, d, J=8.2 Hz), 4.83 (1H, d, J=6.4 Hz), 4.66-4.56 (3H, m), 3.59 (1H, s), 3.41 (2H, q, J=14.5 Hz), 1.22 (9H, s).

Reference Example 8

Tert-Butyl N-[(2R)-2-(6-chloropyridin-3-yl)-2-fluoroethyl]carbamate

[Chem. 44]

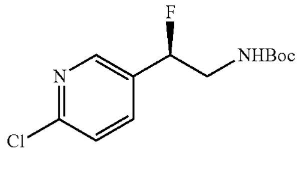

tert-Butyl N-[(2S)-2-(6-chloropyridin-3-yl)-2-hydroxyethyl]carbamate (164 mg) obtained by chiral separation of the racemic compound of Reference Example 3 was added to dichloromethane (3 mL), and to the mixture, bis(2-methoxyethyl)aminosulfur trifluoride (0.13 mL) was added dropwise at 0° C. After stirring the mixture at the same temperature for 1 hour, the reaction mixture was directly purified by silica gel column chromatography to obtain the title compound (37.5 mg).

MS: m/z 275.1 $(M+H)^+$.

Reference Example 9

Tert-Butyl N-[(2R)-2-(2-chloropyrimidin-5-yl)-2-fluoroethyl]carbamate

[Chem. 45]

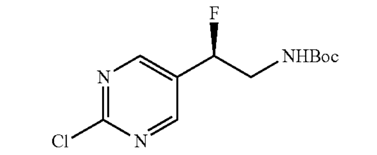

tert-Butyl N-[(2S)-2-(2-chloropyrimidin-5-yl)-2-hydroxyethyl]carbamate (547 mg) obtained by chiral separation of the racemic compound of Example 4 was dissolved in dichloromethane (10 mL), and to the solution, bis(2-methoxyethyl)aminosulfur trifluoride (0.44 mL) was added dropwise at 0° C. After stirring the mixture at the same temperature for 1 hour, the reaction mixture was directly purified by silica gel column chromatography to obtain the title compound (83.3 mg).

MS: m/z 276.2 $(M+H)^+$.

Reference Example 10

2-[2-(6-Chloropyridin-3-yl)-2,2-difluoroethyl]isoindole-1,3-dione

[Chem. 46]

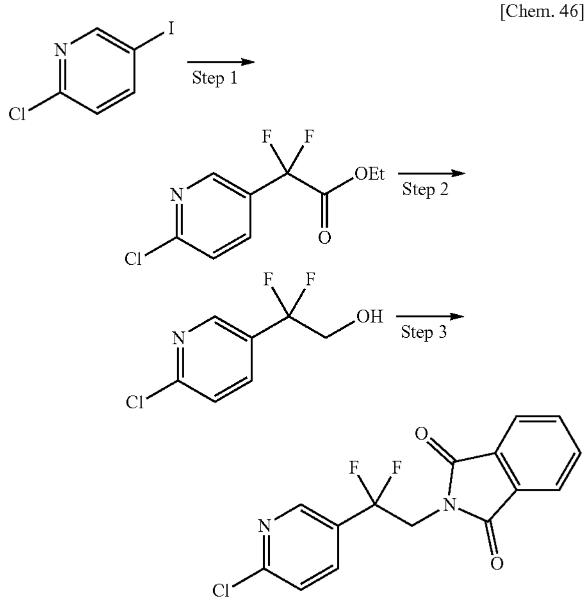

Step 1: Ethyl 2-(6-chloropyridin-3-yl)-2,2-difluoroacetate

2-Chloro-5-iodopyridine (2 g) was dissolved in DMSO (33 mL), then to the solution, ethyl bromodifluoroacetate (1.87 g) and copper powder (1.33 g) were added, and the mixture was stirred at 80° C. for 16 hours. The reaction mixture was cooled to room temperature, an aqueous disodium hydrogen phosphate solution was added to the solution, the mixture was extracted with ethyl acetate, the organic layer was dried over anhydrous sodium sulfate, and the solution was concentrated under reduced pressure. The crude product was purified by silica gel column chromatography to obtain the target compound (958 mg).

MS: m/z 236.1 $(M+H)^+$.

Step 2: 2-(6-Chloropyridin-3-yl)-2,2-difluoroethanol

Ethyl 2-(6-chloropyridin-3-yl)-2,2-difluoroacetate (958 mg) was dissolved in methanol (20 mL), the solution was cooled to 0° C., and to the solution, sodium borohydride (308 mg) was added. The mixture was stirred at room temperature for 1 hour. Water was added to the reaction mixture, the mixture was extracted with ethyl acetate, the organic layer was dried over anhydrous sodium sulfate, and the solution was concentrated under reduced pressure. The crude product was purified by silica gel column chromatography to obtain the target compound (493 mg).

MS: m/z 194.1 $(M+H)^+$.

Step 3: 2-[2-(6-Chloropyridin-3-yl)-2,2-difluoroethyl]isoindole-1,3-dione 2-(6-Chloropyridin-3-yl)-2,2-difluoroethanol (493 mg), phthalimide (487 mg) and triphenylphosphine (1 g) were suspended in THF (5 mL), then to the suspension, diisopropyl azodicarboxylate (0.74 mL) was added dropwise, and the mixture was stirred at room temperature for 16 hours. Water was added to the reaction mixture, the mixture was extracted with ethyl acetate, the organic layer was dried over anhydrous magnesium sulfate, and the solution was concentrated under reduced pressure. The crude product was purified by silica gel column chromatography to obtain the title compound (395 mg).

MS: m/z 323.1 $(M+H)^+$.

Example 1

4-[4-(2-Aminoacetyl)phenyl]-3-[(2-methyl-6-morpholin-4-ylpyrimidin-4-yl)amino]benzonitrile (Compound No. 4)

[Chem. 47]

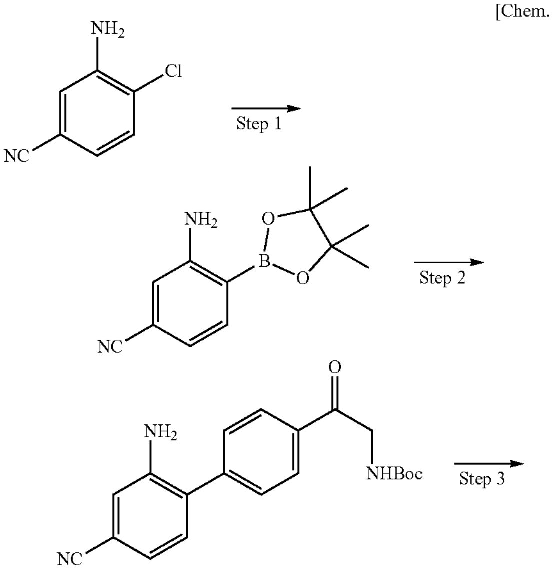

-continued

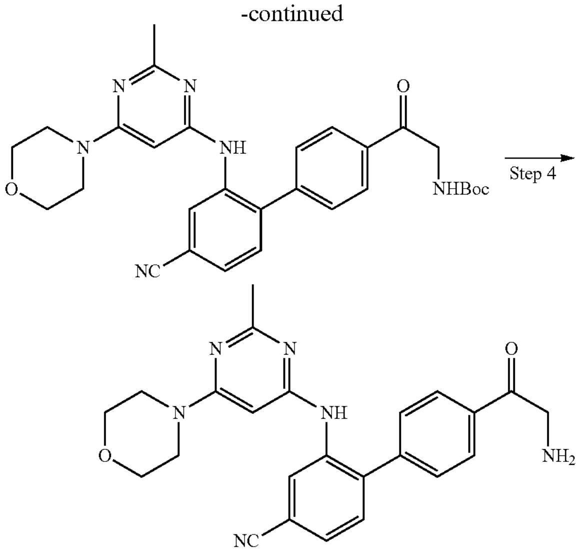

Step 1: 3-Amino-4-(4,4,5,5-tetramethyl-1,3,2-dioxaboran-2-yl)benzonitrile

3-Amino-4-chlorobenzonitrile (700 mg, 4.59 mmol) was dissolved in 1,4-dioxane (23 mL), then to the solution, bis(pinacolato)diboron (1.28 g, 5.05 mmol), tris(dibenzylideneacetone)dipalladium (126 mg, 0.14 mmol), tricyclohexylphosphonium tetrafluoroborate (101 mg, 0.28 mmol) and potassium acetate (1.35 g, 13.8 mmol) were added, and the mixture was stirred at 100° C. for 15 hours. The reaction mixture was cooled to room temperature and filtered through Celite, then the mother liquor was extracted with ethyl acetate, the organic layer was dried over anhydrous magnesium sulfate, and the solution was concentrated under reduced pressure. The crude product was purified by silica gel column chromatography to obtain the target compound (541 mg, 48%).

$^1$H-NMR ($CDCl_3$) δ: 7.65 (1H, d, J=7.3 Hz), 6.89 (1H, d, J=7.8 Hz), 6.81 (1H, s), 4.93 (2H, brs), 1.35 (12H, s).

Step 2: tert-Butyl (2-(2'-amino-4'-cyano-[1,1'-biphenyl]-4-yl)-2-oxoethyl)carbamate To a solution of 3-amino-4-(4,4,5,5-tetramethyl-1,3,2-dioxaboran-2-yl)benzonitrile (245 mg, 1.00 mmol) in toluene/water (=4/1, 5 mL), tert-butyl N-[2-(4-bromophenyl)-2-oxo-ethyl]carbamate (315 mg, 1.00 mmol), tetrakis(triphenylphosphine)palladium (57.9 mg, 0.050 mmol) and potassium carbonate (416 mg, 3.00 mmol) were added, and the mixture was stirred at 80° C. for 2 hours. The reaction mixture was cooled to room temperature and filtered through Celite. Water was added to the mother liquor, the mixture was extracted with ethyl acetate, the organic layer was dried over anhydrous magnesium sulfate, and the solution was concentrated under reduced pressure. The crude product was purified by silica gel column chromatography to obtain the target compound (280 mg, 80%).

MS: m/z 296.1 (M−tBu+H)$^+$.

Step 3: tert-Butyl (2-(4'-cyano-2'-((2-methyl-6-morpholinopyrimidin-4-yl)amino)-[1,1'-biphenyl]-4-yl)-2-oxoethyl)carbamate tert-Butyl (2-(2'-amino-4'-cyano-[1,1'-biphenyl]-4-yl)-2-oxoethyl)carbamate (50.8 mg, 0.145 mmol) was dissolved in toluene (2 mL), then to the solution, 4-(6-chloro-2-methylpyrimidin-4-yl)morpholine (30.9 mg, 0.145 mmol), tris(dibenzylideneacetone)dipalladium (6.6 mg, 0.072 mmol), 4,5-bis(diphenylphosphino)-9,9-dimethylxanthene (8.4 mg, 0.015 mmol) and sodium tert-butoxide (27.8 mg, 0.289 mmol) were added, and the mixture was stirred at 150° C. under microwave irradiation for 1.5 hours. The reaction mixture was cooled to room temperature and filtered through Celite, and then the solution was concentrated under reduced pressure. The crude product was used in the next reaction without further purification.

Step 4: 4-[4-(2-Aminoacetyl)phenyl]-3-[(2-methyl-6-morpholin-4-ylpyrimidin-4-yl)amino]benzonitrile Dichloromethane (2 mL) and TFA (0.5 mL) were added to the crude product obtained in Step 3, and the mixture was stirred at room temperature for 30 minutes. The reaction mixture was concentrated under reduced pressure, and the crude product was purified by HPLC to obtain the target compound (2.09 mg).

Exact MS: 428.2

Obs. MS (M+H)$^+$: 429.4

Example 2

4-[5-(2-Aminoethyl)pyrimidin-2-yl]-3-[methyl-(2-methyl-5-phenylpyrazol-3-yl)amino]benzonitrile (Compound No. 6)

[Chem. 48]

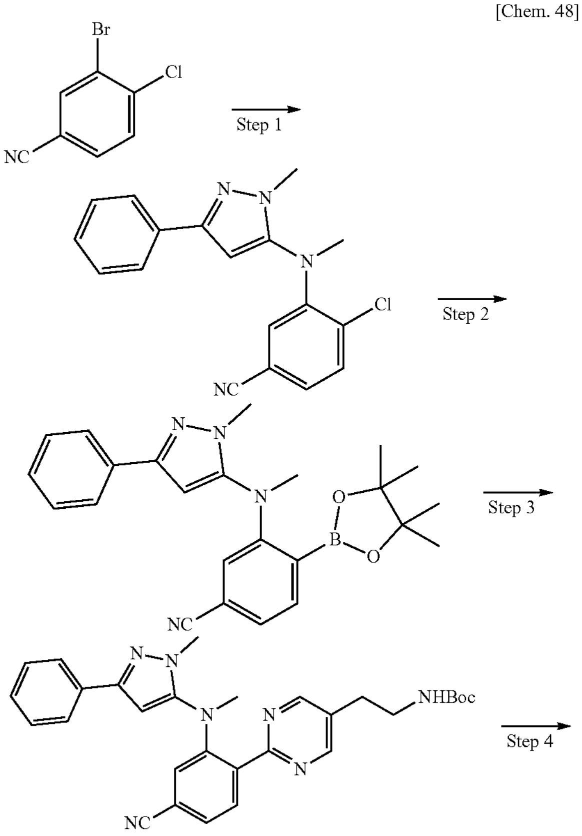

-continued

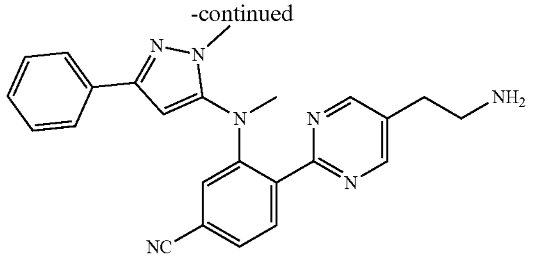

Step 1: 4-Chloro-3-[methyl-(2-methyl-5-phenylpyrazol-3-yl)amino]benzonitrile 1,4-Dioxane (6.7 mL) was added to 3-bromo-4-chlorobenzonitrile (578 mg, 2.67 mmol) and N,2-dimethyl-5-phenylpyrazole-3-amine (500 mg, 2.67 mmol), and to the mixture, tris(dibenzylideneacetone)dipalladium (122 mg, 0.134 mmol), 4,5-bis(diphenylphosphino)-9,9-dimethylxanthene (232 mg, 0.401 mmol), and cesium carbonate (2.18 g, 6.68 mmol) were added, and the mixture was stirred at 100° C. for 16 hours. The reaction mixture was cooled to room temperature, and filtered through Celite, and then the solution was concentrated under reduced pressure. The crude product was purified by silica gel column chromatography to obtain the target compound (512 mg, 59%).

MS: m/z 323.1 $(M+H)^+$.

Step 2: 3-[Methyl-(2-methyl-5-phenylpyrazol-3-yl)amino]-4-(4,4,5,5-tetramethyl-1,3,2-dioxaborolan-2-yl)benzonitrile 4-Chloro-3-[methyl-(2-methyl-5-phenylpyrazol-3-yl)amino]benzonitrile (256 mg, 0.792 mmol) was dissolved in 1,4-dioxane (2.6 mL), then to the solution, bis(pinacolato)diboron (302 mg, 1.19 mmol), bis(tricyclohexylphosphine)palladium dichloride (58.5 mg, 0.0792 mmol), and potassium acetate (233 mg, 2.38 mmol) were added, and the mixture was stirred at 100° C. for 2 hours. The reaction mixture was cooled to room temperature, and filtered through Celite, and then the solution was concentrated under reduced pressure. The obtained crude product was used in the next reaction without further purification.

MS: m/z 415.0 $(M+H)^+$.

Step 3: tert-Butyl N-[2-[2-[4-cyano-2-[methyl-(2-methyl-5-phenylpyrazol-3-yl)amino]phenyl]pyrimidin-5-yl]ethyl]carbamate The crude product obtained in Step 2 was dissolved in 1,4-dioxane (2.6 mL), then to the solution, tert-butyl N-[2-(2-chloropyrimidin-5-yl)ethyl]carbamate (50.0 mg, 0.194 mmol), tetrakis(triphenylphosphine)palladium (22.4 mg, 0.0194 mmol), potassium carbonate (80.4 mg, 0.582 mmol) and water (0.1 mL) were added, and the mixture was stirred at 100° C. for 1 hour. The reaction mixture was cooled to room temperature, ethyl acetate and water were added to the mixture, and the mixture was extracted. The organic layer was washed with saturated brine, dried over anhydrous magnesium sulfate, and the solution was concentrated under reduced pressure. The crude product was used in the next reaction without further purification.

MS: m/z 510.0 $(M+H)^+$.

Step 4: 4-[5-(2-Aminoethyl)pyrimidin-2-yl]-3-[methyl-(2-methyl-5-phenylpyrazol-3-yl)amino]benzonitrile Dichloromethane (1 mL) and TFA (0.5 mL) were added to the crude product obtained in Step 3, and the mixture was stirred at room temperature for 30 minutes. The reaction mixture was concentrated under reduced pressure, and the crude product was purified by HPLC to obtain the target compound (48.3 mg).

Exact MS: 409.2

Obs. MS $(M+H)^+$: 410.4

Example 3

4-[4-(2-Aminoethyl)phenyl]-3-(2-methyl-6-morpholin-4-ylpyrimidin-4-yl)oxybenzonitrile (Compound No. 7)

[Chem. 49]

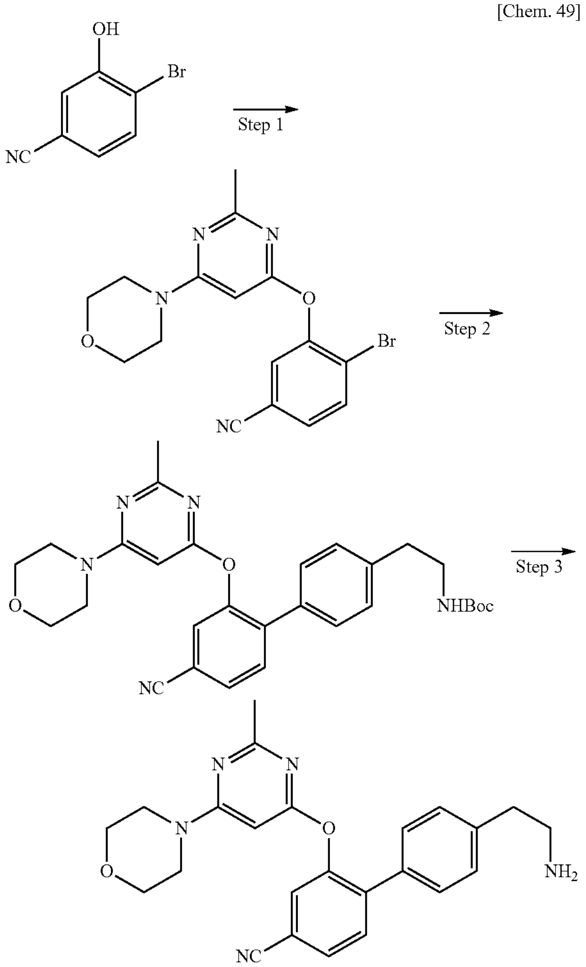

Step 1: 4-Bromo-3-((2-methyl-6-morpholinopyrimidin-4-yl)oxy)benzonitrile

4-Bromo-3-hydroxybenzonitrile (1.19 g, 6.0 mmol) was dissolved in DMF (10 mL), then to the solution, 4-(6-chloro-2-methylpyrimidin-4-yl)morpholine (1.28 g, 6.0 mmol) and potassium carbonate (2.49 g, 18 mmol) were added to the mixture, and the mixture was stirred at 150° C. for 23 hours. The reaction mixture was cooled to room temperature, water was added, and the mixture was extracted with ethyl acetate. The organic layer was washed with saturated brine, dried over anhydrous magnesium sulfate, and the solution was concentrated under reduced pressure. The crude product was purified on a silica gel column to obtain the target compound (1.23 g, 54%).

Step 2: tert-Butyl (2-(4'-cyano-2'-((2-methyl-6-morpholinopyrimidin-4-yloxy)-[1,1'-biphenyl]-4-ylethyl) carbamate 4-Bromo-3-((2-methyl-6-morpholinopyrimidin-4-yl)oxy) benzonitrile (110 mg, 0.29 mmol) was dissolved in toluene/ water (=4/1) mixed solution (2.5 mL), then to the solution, tert-butyl 4-(4,4,5,5-tetramethyl-1,3,2-dioxaboran-2-yl) phenethylcarbamate (132 mg, 0.38 mmol), tetrakistriphenylphosphine palladium (16.9 mg, 0.015 mmol) and potassium carbonate (121 mg, 0.88 mmol) were added, and the mixture was stirred at 110° C. for 10 hours. The reaction mixture was cooled to room temperature, water was added to the solution, and the mixture was extracted with ethyl acetate. The organic layer was dried over anhydrous magnesium sulfate and the solution was concentrated under reduced pressure. The crude product was purified by silica gel column chromatography to obtain the target compound (140 mg, 93%).

MS: m/z 516.3 $(M+H)^+$.

Step 3: 4-[4-(2-Aminoethyl)phenyl]-3-(2-methyl-6-morpholin-4-ylpyrimidin-4-yl)oxybenzonitrile tert-Butyl (2-(4'-cyano-2'-((2-methyl-6-morpholinopyrimidin-4-yl)oxy)-[1,1'-biphenyl]-4-yl)ethyl)carbamate (140 mg, 0.27 mmol) was dissolved in 1,4-dioxane (2 mL), then to the solution, a 4 M (=mol/L) hydrochloric acid/1,4-dioxane solution (2 mL) was added dropwise, and the mixture was stirred at room temperature for 1 hour. The reaction mixture was concentrated under reduced pressure, the crude product was dissolved in a mixed solution of ethyl acetate (50 mL) and 2 M hydrochloric acid (20 mL), and the target compound was back-extracted into an aqueous layer. Then, methanol/dichloromethane (=1/4) mixed solution (50 mL) and a 2 M aqueous sodium hydroxide solution (22 mL) were added to the mixture and the target compound was extracted into an organic phase. The organic layer was dried over anhydrous sodium sulfate and the solution was concentrated under reduced pressure. The crude product was purified by silica gel column chromatography to obtain the target compound (84.1 mg).

Exact MS: 415.2

Obs. MS $(M+H)^+$: 416.2

Example 4

4-[4-(2-Amino-1-methoxyethyl)phenyl]-3-(2-methyl-6-morpholin-4-ylpyrimidin-4-yl)oxybenzonitrile (Compound No. 11)

[Chem. 50]

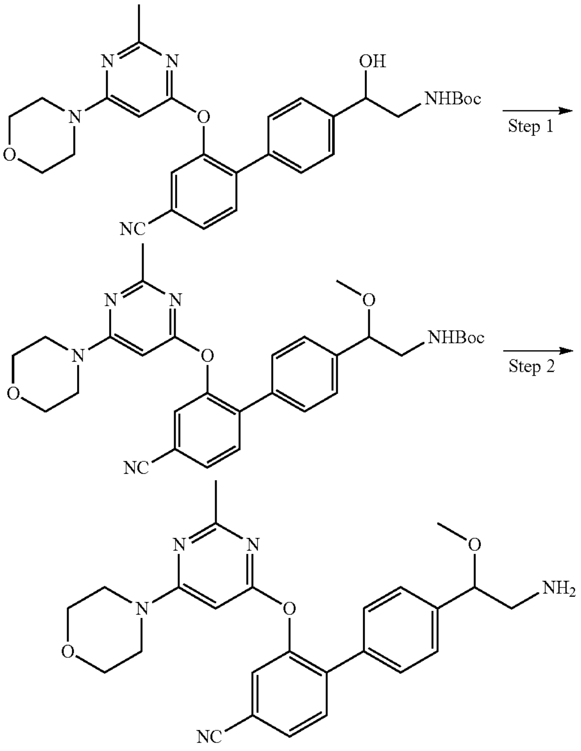

Step 1: tert-Butyl (2-(4'-cyano-2'-((2-methyl-6-morpholinopyrimidin-4-yl)oxy)-[1,1'-biphenyl]-4-yl)-2-methoxyethyl)carbamate tert-Butyl (2-(4'-cyano-2'-((2-methyl-6-morpholinopyrimidin-4-yl)oxy)-[1,1'-biphenyl]-4-yl)-2-hydroxyethyl)carbamate (29 mg, 0.055 mmol) synthesized by the same method as in Example 3 was dissolved in DMF (1 mL), then to the solution, sodium hydride (2.7 mg) was added, and the mixture was stirred at room temperature for 5 minutes. Iodomethane (4.2 μL, 0.066 mmol) was added to this reaction mixture, and the mixture was stirred at room temperature for 1 hour. Water was added to the reaction mixture, the mixture was stirred, and the mixture was extracted with ethyl acetate. The organic layer was washed with saturated brine and dried over anhydrous magnesium sulfate, and the solution was concentrated under reduced pressure. The crude product was used in the next reaction without further purification.

Step 2: 4-[4-(2-Amino-1-methoxyethyl)phenyl]-3-(2-methyl-6-morpholin-4-ylpyrimidin-4-yl)oxybenzonitrile The crude product obtained in Step 1 was dissolved in dichloromethane (2 mL), then to the solution, TFA (0.5 mL) was added, and the mixture was stirred at room temperature for 30 minutes. The reaction mixture was concentrated under reduced pressure, and the crude product was purified by HPLC to obtain the target compound (8.7 mg).

Exact MS: 445.2

Obs. MS $(M+H)^+$: 446.2

Example 5

4-[4-(2-Amino-1-phenoxyethyl)phenyl]-3-(2-methyl-6-morpholin-4-ylpyrimidin-4-yl)oxybenzonitrile (Compound No. 13)

[Chem. 51]

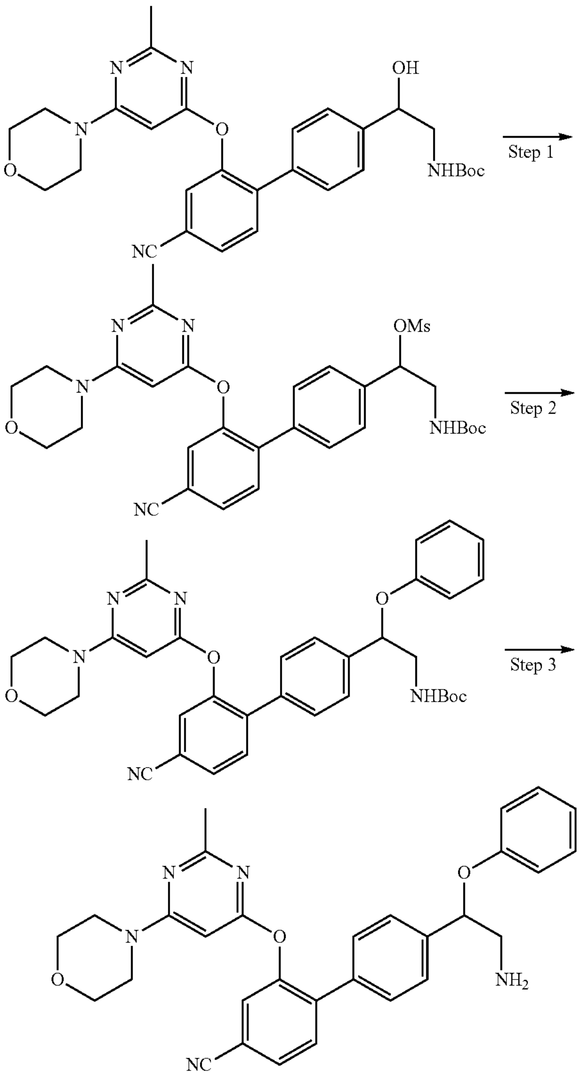

Step 1: 2-((tert-Butoxycarbonyl)amino)-1-(4'-cyano-2'-((2-methyl-6-morpholinopyrimidin-4-yl)oxy)-[1,1'-biphenyl]-4-yl)ethylmethanesulfonate tert-Butyl (2-(4'-cyano-2'-((2-methyl-6-morpholinopyrimidin-4-yl)oxy)-[1,1'-biphenyl]-4-yl)-2-hydroxyethyl)carbamate (60.9 g, 0.115 mmol) synthesized by the same method as in Example 3 was dissolved in THF (2 mL), then to the solution, triethylamine (48 μL, 0.34 mmol) and methanesulfonyl chloride (11 μL, 0.14 mmol) were added, and the mixture was stirred at room temperature for 1 hour. The reaction mixture was diluted with water and ethyl acetate, and extracted with ethyl acetate. The organic layer was washed with saturated brine, dried over anhydrous magnesium sulfate, and concentrated under reduced pressure. The crude product was used in the next reaction without further purification.

MS: m/z 610.3 $(M+H)^+$.

Step 2: tert-Butyl (2-(4'-cyano-2'-((2-methyl-6-morpholinopyrimidin-4-yl)oxy)-[1,1'-biphenyl]-4-yl)-2-phenoxyethyl)carbamate The crude product obtained in Step 1 was dissolved in DMF (2 mL), then to the solution, phenol (10.8 mg, 0.115 mmol) and potassium carbonate (47.5 mg, 0.34 mmol) were added, and the mixture was stirred at 100° C. for 16 hours. Water was added to the reaction mixture, and the mixture was extracted with ethyl acetate. The organic layer was washed with saturated brine, dried over anhydrous magnesium sulfate, and concentrated under reduced pressure. The crude product was used in the next reaction without further purification.

MS: m/z 608.3 $(M+H)^+$.

Step 3: 4-[4-(2-Amino-1-phenoxyethyl)phenyl]-3-(2-methyl-6-morpholin-4-ylpyrimidin-4-yl)oxybenzonitrile The crude product obtained in Step 2 was dissolved in dichloromethane (2 mL), then to the solution, TFA (0.5 mL) was added, and the mixture was stirred at room temperature for 30 minutes. The reaction mixture was concentrated under reduced pressure, and the crude product was purified by HPLC to obtain the target compound (5.5 mg).

Exact MS: 507.2

Obs. MS $(M+H)^+$: 508.2

Example 6

4-[4-(2-Aminoethyl)phenyl]-3-(2-methyl-6-piperidin-1-ylpyrimidin-4-yl)oxybenzonitrile (Compound No. 17)

[Chem. 52]

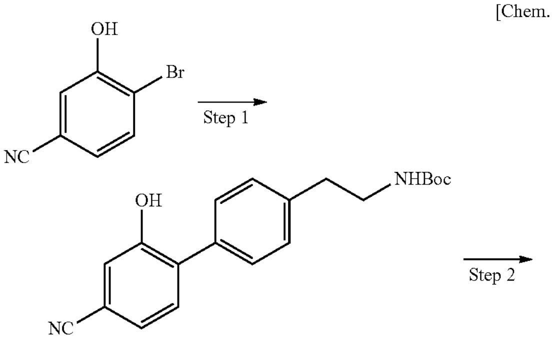

-continued

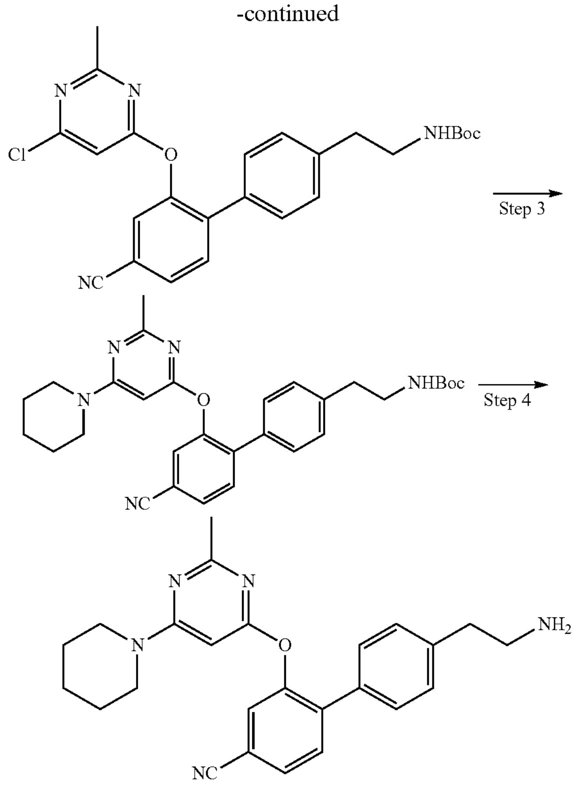

Step 1: tert-Butyl (2-(4'-cyano-2'-hydroxy-[1,1'-biphenyl]-4-yl)ethyl)carbamate

To a solution (50 mL) of 4-bromo-3-hydroxybenzonitrile (8.6 g, 43.4 mmol) in toluene/water (=9/1), tert-butyl 4-(4,4,5,5-tetramethyl-1,3,2-dioxaboran-2-yl)phenethylcarbamate (22.7 g, 65.1 mmol), tetrakistriphenylphosphine palladium (5.0 g, 4.34 mmol), and potassium carbonate (11.9 g, 86.1 mmol) were added, and the mixture was stirred at 90° C. for 16 hours. The reaction mixture was cooled to room temperature, filtered through Celite, the mother liquor was extracted with ethyl acetate, the organic layer was dried over anhydrous sodium sulfate, and the solution was concentrated under reduced pressure. The crude product was purified by silica gel column chromatography to obtain the target compound (5.0 g, 35%).

Step 2: tert-Butyl (2-(2'-((6-chloro-2-methylpyrimidin-4-yl)oxy)-4'-cyano-[1,1'-biphenyl]-4-yl)ethyl)carbamate To a solution of tert-butyl (2-(4'-cyano-2'-hydroxy-[1,1'-biphenyl]-4-yl)ethyl)carbamate (2.8 g, 8.3 mmol) in DMF (15 mL), 4,6-dichloro-2-methylpyrimidine (1.35 g, 8.28 mmol) and cesium carbonate (5.38 g, 16.6 mmol) were added, and the mixture was stirred overnight at room temperature. Water and ethyl acetate were added to the reaction mixture, the mixture was extracted with ethyl acetate, the organic layer was dried over anhydrous magnesium sulfate, and the solution was concentrated under reduced pressure. The crude product was purified by silica gel column chromatography to obtain the target compound (1.8 g, 46%).

MS: m/z 464.8 $(M+H)^+$.

Step 3: tert-Butyl (2-(4'-cyano-2'-((2-methyl-6-(piperidin-1-ylpyrimidin-4-yl)oxy)-[1,1'-biphenyl]-4-yl)ethyl)carbamate tert-Butyl (2-(2'-((6-chloro-2-methylpyrimidin-4-yl)oxy)-4'-cyano-[1,1'-biphenyl]-4-yl)ethyl)carbamate (100 mg, 0.216 mmol) was dissolved in DMF (3 mL), then to the solution, piperidine (0.043 mL, 0.432 mmol) and cesium carbonate (140 mg, 0.431 mmol) were added, and the mixture was stirred at room temperature for 16 hours. Water was added to the reaction mixture, the mixture was extracted with dichloromethane, the organic layer was dried over anhydrous sodium sulfate, and the solution was concentrated under reduced pressure. The crude product was used in the next reaction without further purification.

MS: m/z 514.3 $(M+H)^+$.

Step 4: 4-[4-(2-Aminoethyl)phenyl]-3-(2-methyl-6-piperidin-1-ylpyrimidin-4-yl)oxybenzonitrile TFA (0.5 mL) was added to a solution of the crude product obtained in Step 3 in dichloromethane (2 mL), and the mixture was stirred at room temperature for 2 hours. The reaction mixture was concentrated under reduced pressure, and the crude product was purified by HPLC to obtain the target compound (57.2 mg).

Exact MS: 413.2

Obs. MS $(M+H)^+$: 414.0

$^1$H-NMR (DMSO-$d_6$) δ: 7.73 (1H, d, J=8.4 Hz), 7.68 (1H, s), 7.61 (1H, d, J=8.0 Hz), 7.35 (2H, d, J=7.6 Hz), 7.21 (2H, d, J=7.6 Hz), 6.03 (1H, s), 3.52 (4H, bs), 2.75-2.78 (2H, m), 2.64 (2H, s), 2.15 (3H, s), 1.59 (2H, s), 1.45 (4H, bs).

Example 7

4-[4-(2-Aminoethyl)phenyl]-3-[6-(2-cyanophenyl)-2-methylpyrimidin-4-yl]oxybenzonitrile (Compound No. 21)

[Chem. 53]

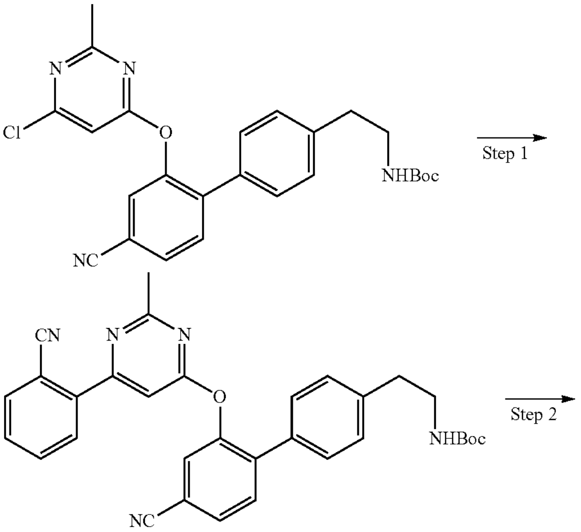

-continued

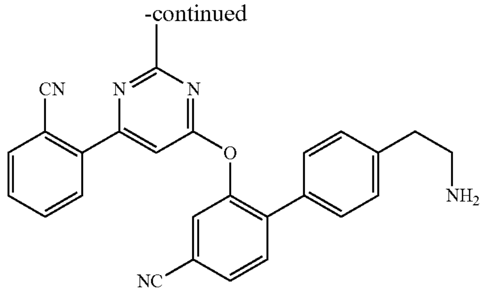

Step 1: tert-Butyl (2-(4'-cyano-2'-((6-(2-cyanophenyl)-2-methylpyrimidin-4-yl)oxy)-[1,1'-biphenyl]-4-yl)ethyl)carbamate An intermediate of tert-butyl (2-(2'-((6-chloro-2-methylpyrimidin-4-yl)oxy)-4'-cyano-[1,1'-biphenyl]-4-yl)ethyl) carbamate (100 mg, 0.215 mmol) obtained in Example 6 was dissolved in 1,4-dioxane (2 mL), then to the solution, potassium carbonate (59 mg, 0.43 mmol), 2-cyanophenylboronic acid (47 mg, 0.32 mmol), and tetrakistriphenylphosphine palladium (20 mg, 0.017 mmol) were added, and the mixture was stirred overnight at 100° C. under a nitrogen atmosphere. The reaction mixture was cooled to room temperature and filtered through Celite, water was added to the mixture, and the mixture was extracted with ethyl acetate. The organic layer was dried over anhydrous sodium sulfate and the solution was concentrated under reduced pressure. The crude product was used in the next reaction without further purification.

Step 2: 4-[4-(2-Aminoethyl)phenyl]-3-[6-(2-cyanophenyl)-2-methylpyrimidin-4-yl]oxybenzonitrile The crude product obtained in Step 1 was dissolved in dichloromethane (2 mL), then to the solution, TFA (0.5 mL) was added, and the mixture was stirred at room temperature for 2 hours. The reaction mixture was concentrated under reduced pressure, and the crude product was purified by HPLC to obtain the target compound (15.4 mg).

Exact MS: 431.2

Obs. MS $(M+H)^+$: 431.9

$^1$H-NMR (DMSO-$d_6$) δ: 8.01-7.99 (2H, m), 7.95-7.93 (1H, m), 7.89-7.82 (2H, m), 7.74-7.70 (2H, m), 7.44-7.39 (3H, m), 7.28-7.23 (2H, m), 3.23 (2H, s), 1.90 (3H, s), 1.23 (2H, s).

Example 8

4-[4-(2-Aminoethyl)phenyl]-3-[6-(2,2-dimethylpropoxy)-2-methylpyrimidin-4-yl]oxybenzonitrile (Compound No. 47)

[Chem. 54]

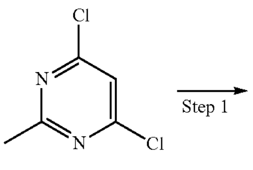

-continued

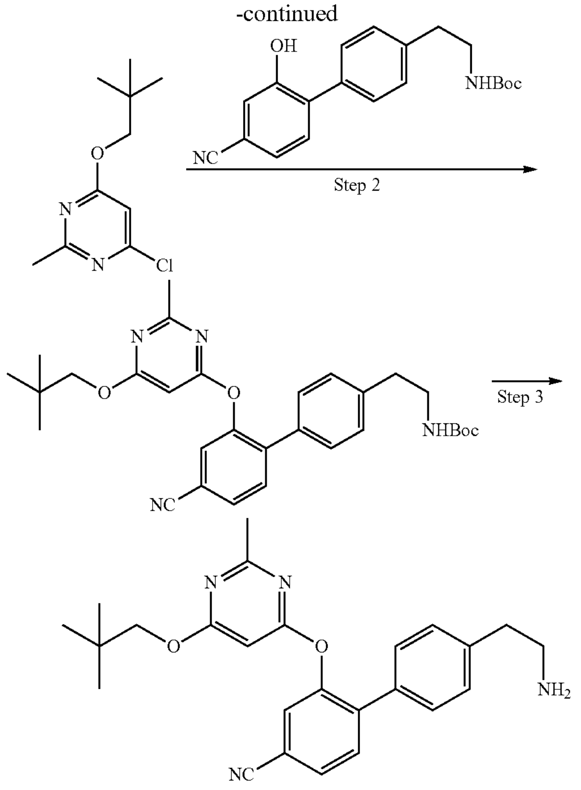

Step 1: 4-Chloro-2-methyl-6-(neopentyloxy)pyrimidine

To a stirred mixture of sodium hydride (82 mg, 3.4 mmol) suspended in THF (4 mL), a solution of 2,2-dimethylpropan-1-ol (323 mg, 3.68 mmol) in THF (0.5 mL) was added dropwise at room temperature and the mixture was stirred at the same temperature for 15 minutes. The reaction mixture was cooled to 0° C., a solution of 4,6-dichloro-2-methylpyrimidine (400 mg, 2.45 mmol) in THF (0.5 mL) was added dropwise to the mixture, and the mixture was stirred at 0° C. for 4 hours. A saturated aqueous ammonium chloride solution was added to the reaction mixture, and the mixture was extracted with diethyl ether. The organic layer was dried over anhydrous sodium sulfate and the solution was concentrated under reduced pressure. The crude product was purified on a silica gel column to obtain the target compound (245 mg, 47%).

Step 2: tert-Butyl (2-(4'-cyano-2'-((2-methyl-6-(neopentyloxy)pyrimidin-4-yloxy)-[1,1'-biphenyl]-4-yl) ethyl)carbamate tert-Butyl (2-(4'-cyano-2'-hydroxy-[1,1'-biphenyl]-4-yl) ethyl)carbamate (50 mg, 0.148 mmol) was dissolved in DMF (1 mL), then to the solution, 4-chloro-2-methyl-6-(neopentyloxy)pyrimidine (63.5 mg, 0.296 mmol) and cesium carbonate (96.4 mg, 0.296 mmol) were added, and the mixture was stirred at 70° C. overnight. Water was added to the reaction mixture, the mixture was extracted with ethyl acetate, the organic layer was dried over anhydrous sodium sulfate, and the solution was concentrated under reduced pressure. The crude product was used in the next reaction without further purification.

MS: m/z 517.0 $(M+H)^+$.

Step 3: 4-[4-(2-Aminoethyl)phenyl]-3-[6-(2,2-dimethylpropoxy)-2-methylpyrimidin-4-yl]oxybenzonitrile Dichloromethane (2 mL) and TFA (0.5 mL) were added to the crude product obtained in Step 2, and the mixture was stirred at room temperature for 3 hours. The reaction mixture was concentrated under reduced pressure, and the crude product was purified by HPLC to obtain the target compound (21.4 mg).

Exact MS: 416.2

Obs. MS $(M+H)^+$: 417.3

Example 9

4-[4-[2-(3-Hydroxypropylamino)ethyl]phenyl]-3-(2-methyl-6-morpholin-4-ylpyrimidin-4-yl)oxybenzonitrile (Compound No. 58)

[Chem. 55]

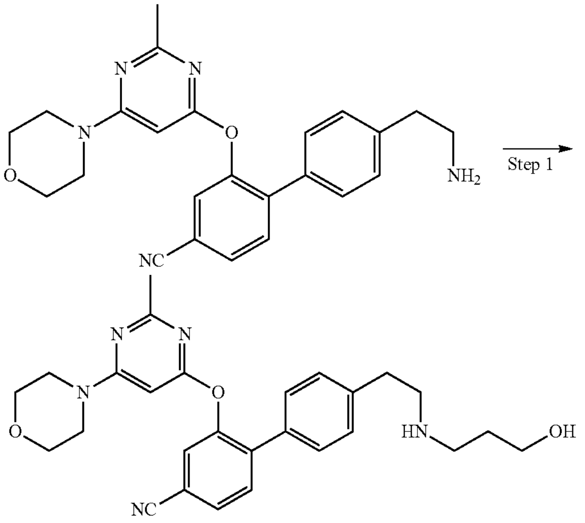

Step 1: 4-[4-[2-(3-Hydroxypropylamino)ethyl]phenyl]-3-(2-methyl-6-morpholin-4-ylpyrimidin-4-yl)oxybenzonitrile 4-[4-(2-Aminoethyl)phenyl]-3-(2-methyl-6-morpholin-4-ylpyrimidin-4-yl)oxybenzonitrile (54 mg, 0.13 mmol) obtained in Example 3 was dissolved in DMF (1 mL), then to the solution, 3-bromopropan-1-ol (0.014 ml, 0.16 mmol) and triethylamine (0.055 mL, 0.39 mmol) were added, and the mixture was stirred at 60° C. for 3 hours. The reaction mixture was cooled to room temperature, water was added to the mixture, and the mixture was extracted with ethyl acetate. The organic layer was washed with saturated brine and dried over anhydrous magnesium sulfate, and the solution was concentrated under reduced pressure. The crude product was purified by HPLC to obtain the target compound (11.3 mg).

Exact MS: 473.2

Obs. MS $(M+H)^+$: 474.5

Example 10

4-[4-(2-Amino-1-phenylethyl)phenyl]-3-(2-methyl-6-morpholin-4-ylpyrimidin-4-yl)oxybenzonitrile (Compound No. 59)

[Chem. 56]

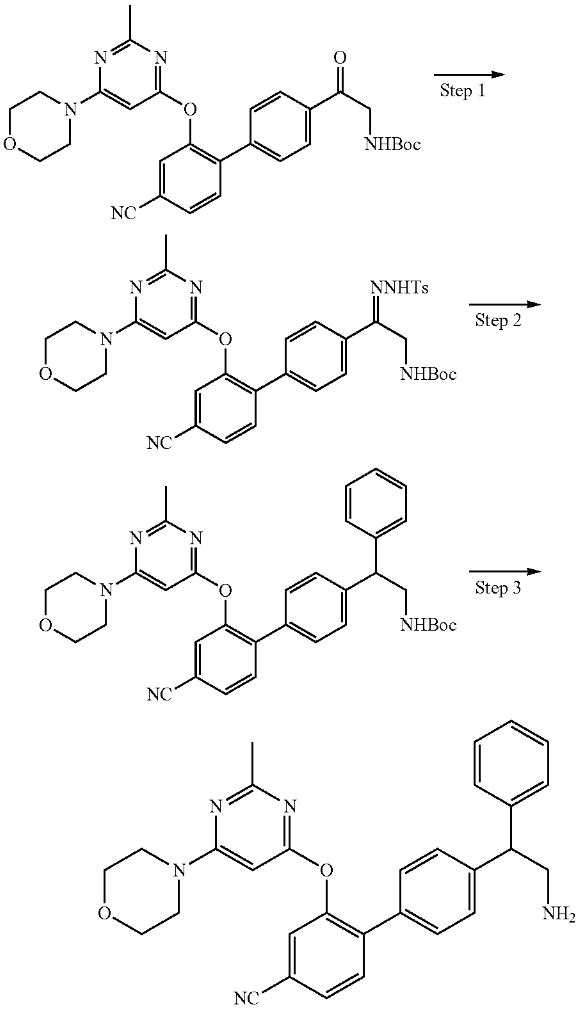

Step 1: tert-Butyl (2-(4'-cyano-2'-((2-methyl-6-morpholinopyrimidin-4-yl)oxy)-[1,1'-biphenyl]-4-yl)-2-(2-tosylhydrazono)ethyl)carbamate tert-Butyl (2-(4'-cyano-2'-((2-methyl-6-morpholinopyrimidin-4-yl)oxy)-[1,1'-biphenyl]-4-yl)-2-oxoethyl)carbamate (855.8 mg, 1.62 mmol) synthesized by the same method in Example 3 was dissolved in toluene (8 mL), then to the solution, p-toluenesulfonyl hydrazide (301 mg, 1.62 mmol) was added, and the mixture was stirred at 110° C. for 4 hours. The reaction mixture was concentrated under reduced pressure, and the crude product was used in the next reaction without further purification.

MS: m/z 698.2 $(M+H)^+$.

Step 2: tert-Butyl (2-(4'-cyano-2'-((2-methyl-6-morpholinopyrimidin-4-yl)oxy)-[1,1'-biphenyl]-4-yl)-2-phenylethyl)carbamate An aliquot (30 mg) of the crude product obtained in Step 1 was dissolved in 1,4-dioxane (1 mL), then to the solution, phenylboronic acid (11 mg, 0.086 mmol) and potassium carbonate (24 mg, 0.17 mmol) were added, and the mixture was stirred at 110° C. for 15 hours. Water was added to the reaction mixture, and the mixture was extracted with ethyl acetate. The organic layer was washed with saturated brine and dried over anhydrous magnesium sulfate, and the solution was concentrated under reduced pressure. The crude product was used in the next reaction without further purification.

MS: m/z 592.3 $(M+H)^+$.

Step 3: 4-[4-(2-Amino-1-phenylethyl)phenyl]-3-(2-methyl-6-morpholin-4-ylpyrimidin-4-yl)oxybenzonitrile The crude product obtained in Step 2 was dissolved in dichloromethane (2 mL), then to the solution, TFA (0.5 mL) was added, and the mixture was stirred at room temperature for 30 minutes. The reaction mixture was concentrated under reduced pressure, and the crude product was purified by HPLC to obtain the target compound (3.1 mg).

Exact MS: 491.2

Obs. MS $(M+H)^+$: 492.5

Example 11

4-(2-Amino-1-oxo-2,3-dihydroinden-5-yl)-3-(2-methyl-6-morpholin-4-ylpyrimidin-4-yl)oxybenzonitrile (Compound No. 131)

[Chem. 57]

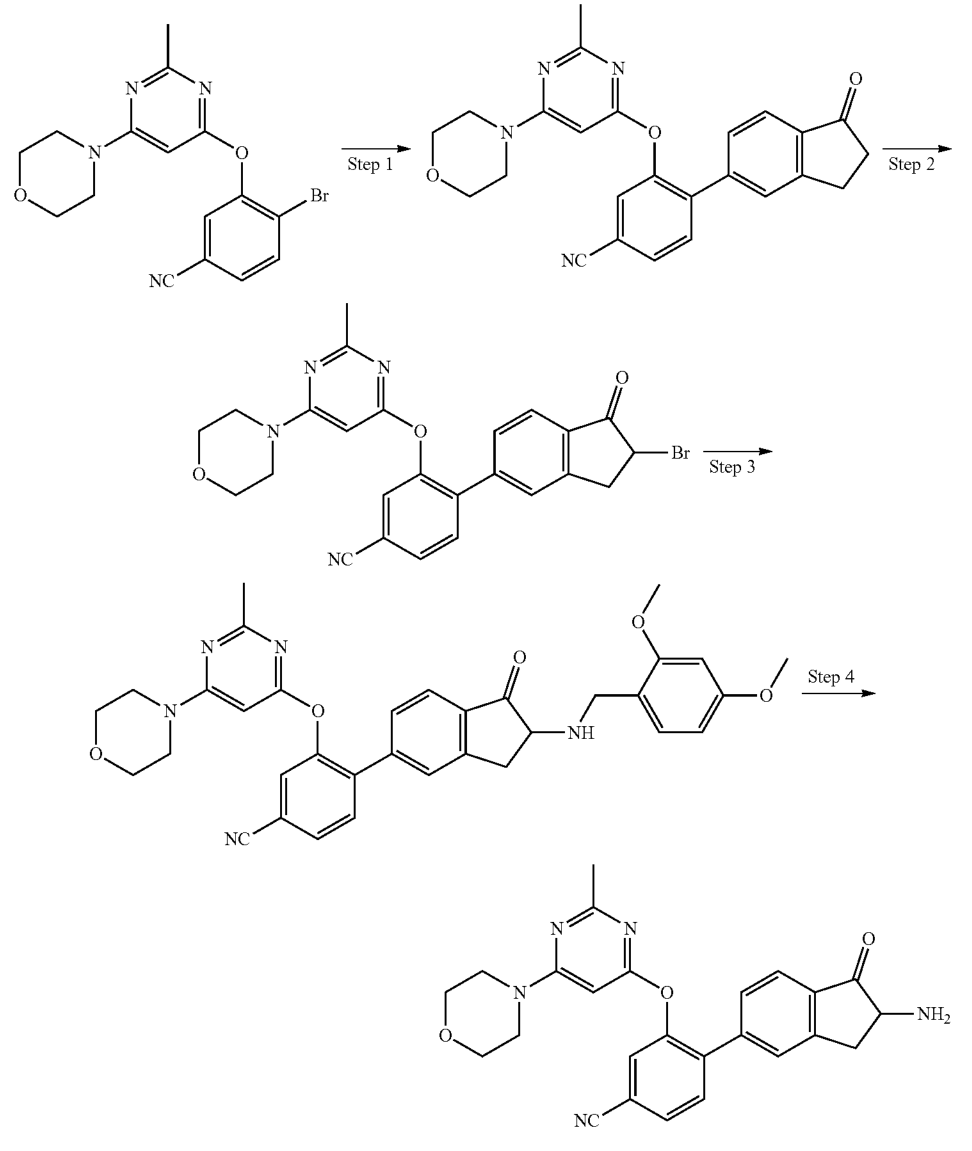

Step 1: 3-(2-Methyl-6-morpholin-4-ylpyrimidin-4-yl)oxy-4-(1-oxo-2,3-dihydroinden-5-yl)benzonitrile 4-Bromo-3-(2-methyl-6-morpholin-4-ylpyrimidin-4-yl)oxybenzonitrile (300 mg, 0.800 mmol) was dissolved in 1,4-dioxane (2 mL), then to the solution, 5-(4,4,5,5-tetramethyl-1,3,2-dioxaborolan-2-yl)-2,3-dihydroinden-1-one (289 mg, 1.12 mmol), tetrakis(triphenylphosphine)palladium (46.2 mg, 0.0400 mmol), potassium carbonate (332 mg, 2.40 mmol) and water (0.5 mL) were added, and the mixture was stirred at 100° C. for 4 hours. The reaction mixture was cooled to room temperature, water was added to the mixture, and the mixture was extracted with ethyl acetate. The organic layer was washed with saturated brine and dried over anhydrous magnesium sulfate, and the solution was concentrated under reduced pressure. The crude product was purified by silica gel column chromatography to obtain the target compound (290 mg, 85%).

MS: m/z 427.2 $(M+H)^+$.

Step 2: 4-(2-Bromo-1-oxo-2,3-dihydroinden-5-yl)-3-(2-methyl-6-morpholin-4-ylpyrimidin-4-yl)oxybenzonitrile 3-(2-Methyl-6-morpholin-4-ylpyrimidin-4-yl)oxy-4-(1-oxo-2,3-dihydroinden-5-yl)benzonitrile (290 mg, 0.680 mmol) was dissolved in a mixed solvent (6 mL) of chloroform/ethyl acetate (=1/1), then to the solution, copper(II) bromide (304 mg, 1.36 mmol) was added, and the mixture was stirred at 90° C. for 7 hours. The reaction mixture was cooled to room temperature and filtered through Celite, and then the solution was concentrated under reduced pressure. The crude product was purified by silica gel column chromatography to obtain the target compound (26.0 mg, 8%).

MS: m/z 505.1 $(M+H)^+$.

Step 3: 4-[2-[(2,4-Dimethoxyphenyl)methylamino]-1-oxo-2,3-dihydroinden-5-yl]-3-(2-methyl-6-morpholin-4-ylpyrimidin-4-yl)oxybenzonitrile 4-(2-Bromo-1-oxo-2,3-dihydroinden-5-yl)-3-(2-methyl-6-morpholin-4-ylpyrimidin-4-yl)oxybenzonitrile (26.0 mg, 0.0514 mmol) was dissolved in DMF (I mL), then to the solution, 2,4-dimethoxybenzenemethanamine (12.9 mg, 0.0772 mmol) and triethylamine (0.022 mL, 0.154 mmol) were added, and the mixture was stirred at room temperature for 1 hour. Water was added to the reaction mixture, and the mixture was extracted with ethyl acetate. The organic layer was washed with saturated brine and dried over anhydrous magnesium sulfate, and the solution was concentrated under reduced pressure. The crude product was used in the next reaction without further purification.

Step 4: 4-(2-Amino-1-oxo-2,3-dihydroinden-5-yl)-3-(2-methyl-6-morpholin-4-ylpyrimidin-4-yl)oxybenzonitrile TFA (1 mL) was added to the crude product obtained in Step 3, and the mixture was stirred at 120° C. for 10 minutes. The reaction mixture was concentrated under reduced pressure, and the crude product was purified by HPLC to obtain the target compound (6.00 mg).

Exact MS: 441.2

Obs. MS $(M+H)^+$: 442.2

Example 12

4-[4-(2-Amino-1-hydroxyethyl)-3-fluorophenyl]-3-(2-methyl-6-morpholin-4-ylpyrimidin-4-yl)oxybenzonitrile (Compound No. 149)

[Chem. 58]

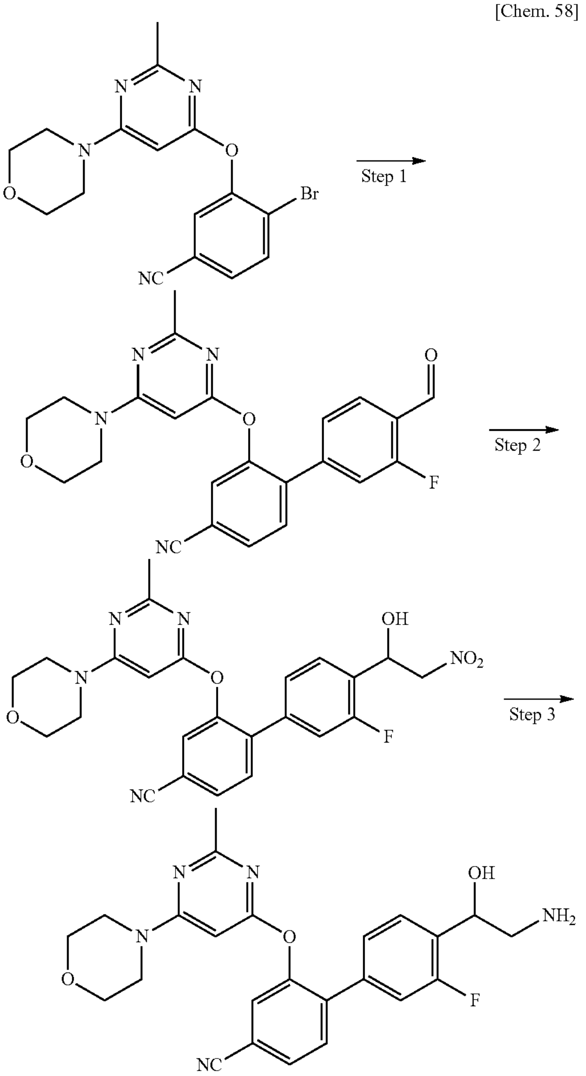

Step 1: 4-(3-fluoro-4-formylphenyl)-3-(2-methyl-6-morpholin-4-ylpyrimidin-4-yl)oxybenzonitrile 4-Bromo-3-(2-methyl-6-morpholin-4-ylpyrimidin-4-yl)oxybenzonitrile (188 mg, 0.500 mmol) was dissolved in 1,4-dioxane (4 mL), then to the solution, 2-fluoro-4-(4,4,5,5-tetramethyl-1,3,2-dioxaborolan-2-yl)benzaldehyde (250 mg, 1.00 mmol), [1,1'-bis(diphenylphosphino)ferrocene] palladium dichloride (36.6 mg, 0.0500 mmol), potassium carbonate (415 mg, 3.00 mmol) and water (1 mL) were added, and the mixture was stirred at 100° C. for 30 minutes. The reaction mixture was cooled to room temperature, water was added to the mixture, and the mixture was extracted with ethyl acetate. The organic layer was washed with saturated brine and dried over anhydrous magnesium sulfate, and the solution was concentrated under reduced pressure. The crude product was purified by silica gel column chromatography to obtain the target compound (174 mg, 83%).

MS: m/z 419.2 $(M+H)^+$.

Step 2: 4-[3-Fluoro-4-(1-hydroxy-2-nitroethyl)phenyl]-3-(2-methyl-6-morpholin-4-ylpyrimidin-4-yl)oxybenzonitrile 4-(3-Fluoro-4-formylphenyl)-3-(2-methyl-6-morpholin-4-ylpyrimidin-4-yl)oxybenzonitrile (174 mg, 0.416 mmol) was dissolved in THF (4 mL), then to the solution, nitromethane (0.5 mL) and triethylamine (1 mL) were added, and the mixture was stirred at room temperature for 2 hours. The reaction solution was concentrated under reduced pressure, and the crude product was used in the next reaction without further purification.

MS: m/z 480.2 $(M+H)^+$.

Step 3: 4-[4-(2-Amino-1-hydroxyethyl)-3-fluorophenyl]-3-(2-methyl-6-morpholin-4-ylpyrimidin-4-yl)oxybenzonitrile Zinc powder (500 mg, 7.64 mmol) and acetic acid (4 mL) were added to the crude product obtained in Step 2, and the mixture was stirred for 30 minutes. The reaction mixture was filtered through Celite and concentrated under reduced pressure, and the crude product was purified by HPLC to obtain the target compound (15.7 mg).

Exact MS: 449.2

Obs. MS $(M+H)^+$: 450.2

Example 13

4-[4-[(1R)-2-Amino-1-hydroxyethyl]pyrazol-1-yl]-3-(2-methyl-6-phenylpyrimidin-4-yl)oxybenzonitrile (Compound No. 170)

[Chem. 59]

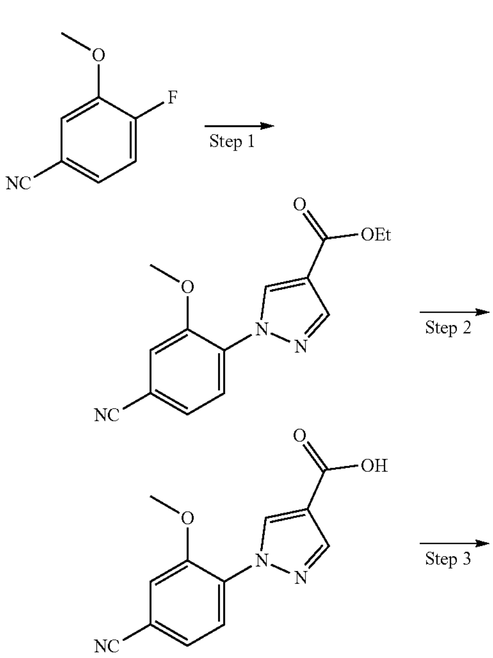

-continued

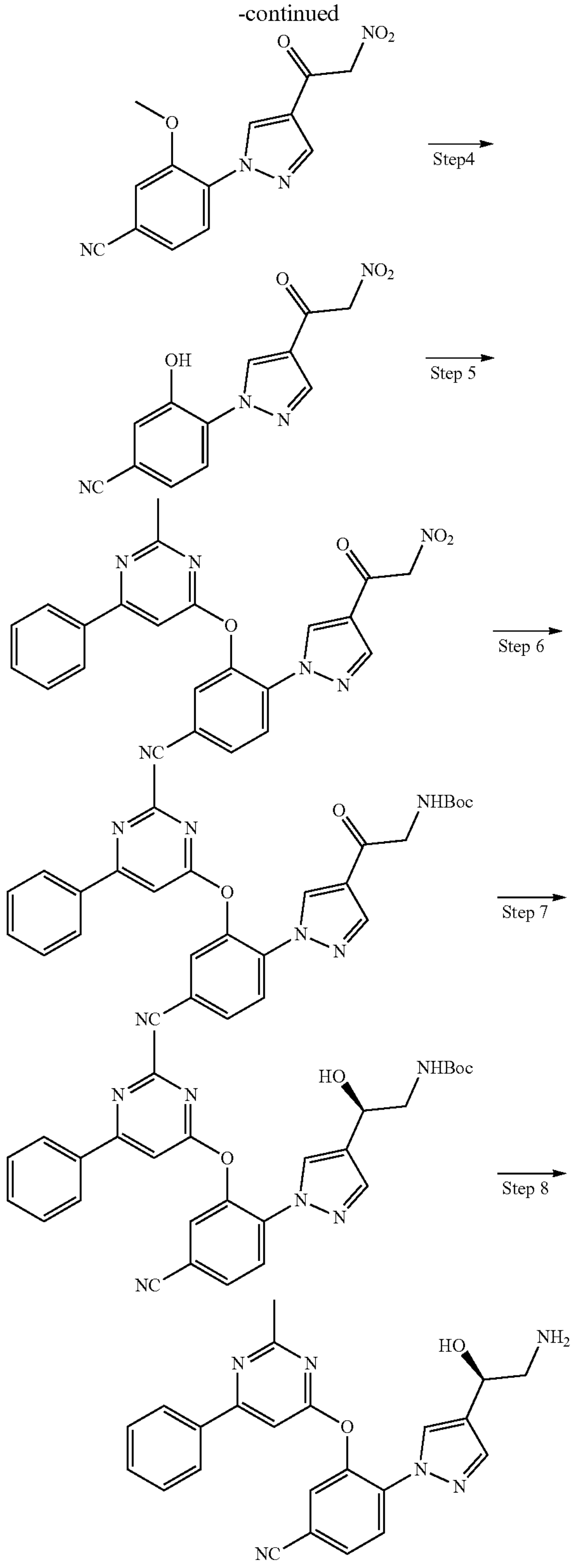

Step 1: Ethyl 1-(4-cyano-2-methoxyphenyl)pyrazole-4-carboxylate

DMSO (120 mL) was added to 4-fluoro-3-methoxybenzonitrile (15.1 g, 100 mmol), ethyl 1H-pyrazole-4-carboxylate (15.4 g, 110 mmol), and potassium carbonate (27.6 g, 200 mmol), and the mixture was stirred at 60° C. for 3 hours. The reaction mixture was cooled to room temperature, water was added to the mixture, and the mixture was stirred. The precipitated solid was collected by filtration through a glass filter and dried to obtain the target compound (22.8 g, 84%).

MS: m/z 272.0 $(M+H)^+$.

Step 2: 1-(4-Cyano-2-methoxyphenyl)pyrazole-4-carboxylic acid

Ethyl 1-(4-cyano-2-methoxyphenyl)pyrazole-4-carboxylate (11.0 g, 40.5 mmol) was dissolved in a mixed solvent of THF (40 mL)/methanol (40 mL), then to the solution, a 2 M aqueous sodium hydroxide solution (40.5 mL, 81.1 mmol) was added, and the mixture was stirred at room temperature for 2 hours. After adding 2 M hydrochloric acid to the reaction mixture and stirring the mixture, water was further added to the solution to precipitate the target compound. The target compound was collected by filtration with a glass filter and dried to obtain the target compound (7.38 g, 75%).

MS: m/z 244.0 $(M+H)^+$.

Step 3: 3-Methoxy-4-[4-(2-nitroacetyl)pyrazol-1-yl] benzonitrile

To 1-(4-cyano-2-methoxyphenyl)pyrazole-4-carboxylic acid (7.38 g, 30.3 mmol), DMF (40 mL) and 1,1'-carbonyldime (5.90 g, 36.4 mmol) were added and the mixture was stirred for 2 hours (reaction mixture A). Nitromethane (2.78 g, 45.5 mmol) and DMF (40 mL) were added to another reaction vessel, sodium hydride (1.59 g, 36.4 mmol) was further added, and the mixture was stirred for 2 hours to separately prepare another solution (reaction mixture B). The reaction mixture B was cooled to 0° C., the reaction mixture A was added dropwise to the reaction mixture B, and then the mixture was heated to 100° C. and stirred for 3 hours. The reaction mixture was cooled to room temperature, water was added to the mixture, and the target compound was precipitated. The precipitate was collected by filtration with a glass filter and dried to obtain the target compound (8.70 g, quant.).

MS: m/z 287.0 $(M+H)^+$.

Step 4: 3-Hydroxy-4-[4-(2-nitroacetyl)pyrazol-1-yl] benzonitrile

3-Methoxy-4-[4-(2-nitroacetyl)pyrazol-1-yl]benzonitrile (4.50 g, 15.7 mmol) was dissolved in DMF (40 mL), then to the solution, lithium chloride (6.67 g, 157 mmol) was added, and the mixture was stirred at 150° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was used in the next reaction without further purification.

MS: m/z 273.0 $(M+H)^+$.

Step 5: 3-(2-Methyl-6-phenylpyrimidin-4-yl)oxy-4-[4-(2-nitroacetyl)pyrazol-1-yl]benzonitrile The crude product obtained in Step 4 was dissolved in DMF (40 mL), then to the solution, 4-chloro-2-methyl-6-phenylpyrimidine (3.54 g, 17.3 mmol) and potassium carbonate (4.35 g, 31.4 mmol) were added, and the mixture was stirred at 100° C. overnight. Water was added to the reaction mixture, and the mixture was extracted with ethyl acetate. The organic layer was washed with saturated brine and dried over anhydrous sodium sulfate, and the solution was concentrated under reduced pressure to obtain the target compound (2.69 g, 39%).

MS: m/z 441.1 $(M+H)^+$.

Step 6: tert-Butyl N-[2-[1-[4-cyano-2-(2-methyl-6-phenylpyrimidin-4-yl)oxyphenyl]pyrazol-4-yl]-2-oxoethyl]carbamate THF (40 mL) and acetic acid (1.83 g, 30.5 mmol) were added to 3-(2-methyl-6-phenylpyrimidin-4-yl)oxy-4-[4-(2-nitroacetyl)pyrazol-1-yl]benzonitrile (2.69 g, 6.11 mmol), di-tert-butyl dicarbonate (4.00 g, 18.3 mmol) and zinc powder (2.00 g, 30.5 mmol), and the mixture was stirred at room temperature overnight. The reaction mixture was filtered through Celite, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (540 mg, 17%).

MS: m/z 511.2 $(M+H)^+$.

Step 7: tert-Butyl N-[(2R)-2-[I-[4-cyano-2-(2-methyl-6-phenylpyrimidin-4-yl)oxyphenyl]pyrazol-4-yl]-2-hydroxyethyl]carbamate tert-Butyl N-[2-[1-[4-cyano-2-(2-methyl-6-phenylpyrimidin-4-yl)oxyphenyl]pyrazol-4-yl]-2-oxoethyl]carbamate (106 mg, 0.208 mmol) and (S)-5,5-diphenyl-2-methyl-3,4-propano-1,3,2-oxazaborolidine (5.8 mg, 0.021 mmol) were dissolved in dichloromethane (1 mL) and the solution was cooled to 0° C. Dimethyl sulfide borane (47.3 mg, 0.633 mmol) was added to the reaction mixture, and the mixture was stirred at the same temperature for 10 hours. Methanol and water were added to the reaction mixture, and the mixture was extracted with ethyl acetate. The organic layer was washed with saturated brine and dried over anhydrous sodium sulfate, and the solution was concentrated under reduced pressure. The crude product was used in the next reaction without further purification.

MS: m/z 513.2 $(M+H)^+$.

Step 8: 4-[4-[(1R)-2-Amino-1-hydroxyethyl]pyrazol-1-yl]-3-(2-methyl-6-phenylpyrimidin-4-yl)oxybenzonitrile The crude product obtained in Step 7 was dissolved in dichloromethane (1 mL), TFA (1 mL) was added to the solution, and the mixture was stirred at room temperature for 1 hour. The reaction mixture was concentrated under reduced pressure, and the crude product was purified by HPLC to obtain the target compound (18.6 mg).

Exact MS: 412.2

Obs. MS $(M+H)^+$: 413.2

Example 14

3-(6-Cyclopentyl-2-methylpyrimidin-4-yl)oxy-4-[4-(2-oxopiperazin-1-yl)pyrazol-1-yl]benzonitrile (Compound No. 208)

[Chem. 60]

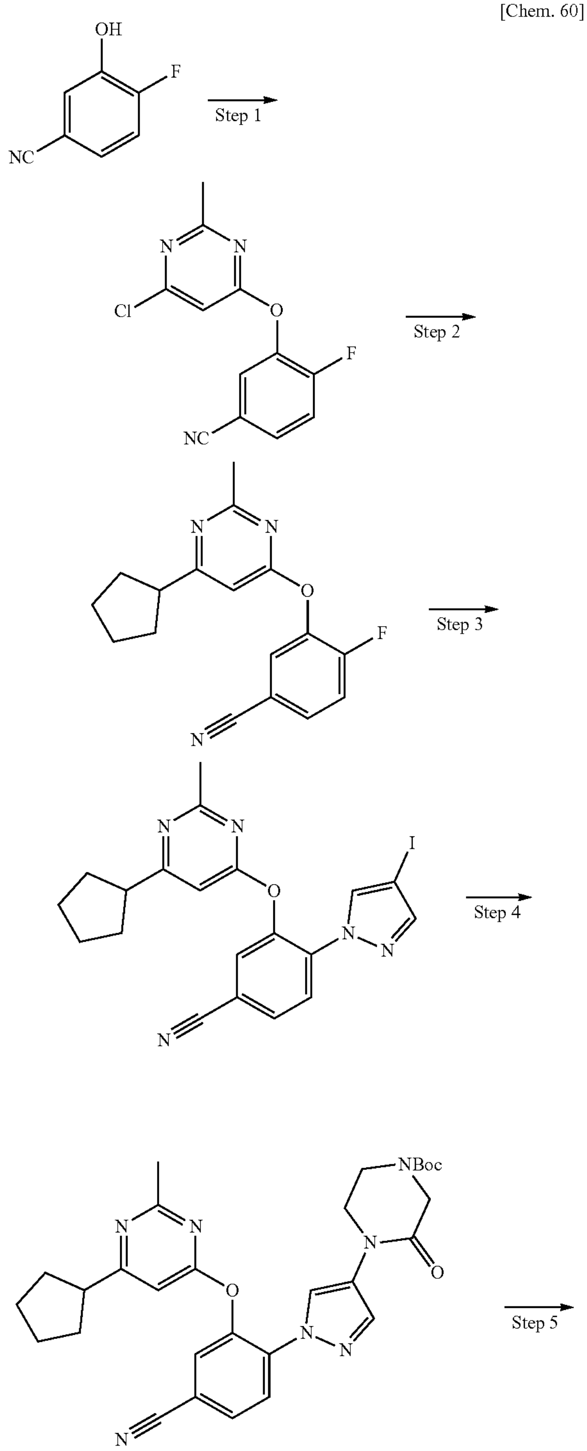

-continued

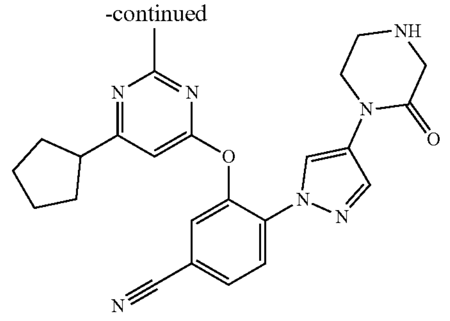

Step 1: 3-(6-Chloro-2-methylpyrimidin-4-yl)oxy-4-fluorobenzonitrile

4-Fluoro-3-hydroxybenzonitrile (3.7 g, 27 mmol) was dissolved in DMF (90 mL), then to the solution, 4,6-dichloro-2-methylpyrimidine (6.6 g, 40 mmol) and potassium carbonate (7.5 g, 54 mmol) were added, and the mixture was stirred at 100° C. for 2 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified on a silica gel column to obtain the target compound (6.5 g).

MS: m/z 264.1 $(M+H)^+$.

$^1$H-NMR ($CDCl_3$) δ: 7.61 (1H, dq, J=8.7, 2.1 Hz), 7.56 (1H, dd, J=7.1, 2.2 Hz), 7.32 (1H, dd, J=9.5, 8.5 Hz), 6.90 (1H, s), 2.51 (3H, s).

Step 2: 3-(6-Cyclopentyl-2-methylpyrimidin-4-yl)oxy-4-fluorobenzonitrile

THF (12.6 mL) was added to 3-(6-chloro-2-methylpyrimidin-4-yl)oxy-4-fluorobenzonitrile (1.0 g, 3.79 mmol) and [1,1'-bis(diphenylphosphino)ferrocene]palladium dichloride (557 mg, 0.759 mmol), then to the mixture, cyclopentyl zinc bromide (1.22 g, 5.69 mmol) was added dropwise, and the mixture was stirred at 70° C. for 1 hour. The reaction mixture was cooled to room temperature, water was added to the mixture, and the mixture was extracted with ethyl acetate. The organic layer was washed with saturated brine, dried over anhydrous sodium sulfate, and the solution was concentrated under reduced pressure. The crude product was purified on a silica gel column to obtain the target compound (888 mg).

MS: m/z 298.1 $(M+H)^+$.

Step 3: 3-(6-Cyclopentyl-2-methylpyrimidin-4-yl)oxy-4-(4-iodopyrazol-1-yl)benzonitrile 3-(6-Cyclopentyl-2-methylpyrimidin-4-yl)oxy-4-fluorobenzonitrile (100 mg, 0.336 mmol) was dissolved in DMSO (0.5 mL), then to the solution, 4-iodo-1H-pyrazole (65.2 mg, 0.336 mmol) and potassium carbonate (93.0 mg, 0.673 mmol) were added, and the mixture was stirred at 120° C. for 2 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified on a silica gel column to obtain the target compound (78.9 mg).

MS: m/z 472.1 $(M+H)^+$.

Step 4: 3-(6-Cyclopentyl-2-methylpyrimidin-1-yloxy-4-(4-iodopyrazol-1-yl)benzonitrile 3-(6-Cyclopentyl-2-methylpyrimidin-4-yl)oxy-4-(4-iodopyrazol-1-yl)benzonitrile (34.2 mg, 0.0726 mmol) was added to 1,4-dioxane (0.4 mL), then to the solution, tert-butyl 3-oxopiperazine-1-carboxylate (16 mg, 0.080 mmol), copper(I) iodide (2.8 mg, 0.015 mmol), trans-1,2-cyclohexanediamine (1.7 mg, 0.015 mmol) and tripotassium phosphate (46.2 mg, 0.218 mmol) were added, and the mixture was stirred at 110° C. for 2 hours. The reaction mixture was cooled to room temperature and filtered through Celite, water was added to the mixture, and the mixture was extracted with ethyl acetate. The organic layer was washed with saturated brine, dried over anhydrous sodium sulfate, and the solution was concentrated under reduced pressure. The crude product was used in the next reaction without further purification.

Step 5: 3-(6-Cyclopentyl-2-methylpyrimidin-4-yl)oxy-4-[4-(2-oxopiperazin-1-yl)pyrazol-1-yl]benzonitrile Dichloromethane (1 mL) and TFA (1 mL) were added to the crude product obtained in Step 4, and the mixture was stirred at room temperature for 1 hour. The reaction mixture was concentrated under reduced pressure, and the crude product was purified by HPLC to obtain the target compound (7.3 mg).

Exact MS: 443.2

Obs. MS $(M+H)^+$: 444.3

Example 15

3-(2-Methyl-5-phenylpyrazol-3-yl)oxy-4-[4-(7-oxo-1,4-diazepan-1-yl)pyrazol-1-yl]benzonitrile (Compound No. 219)

[Chem. 61]

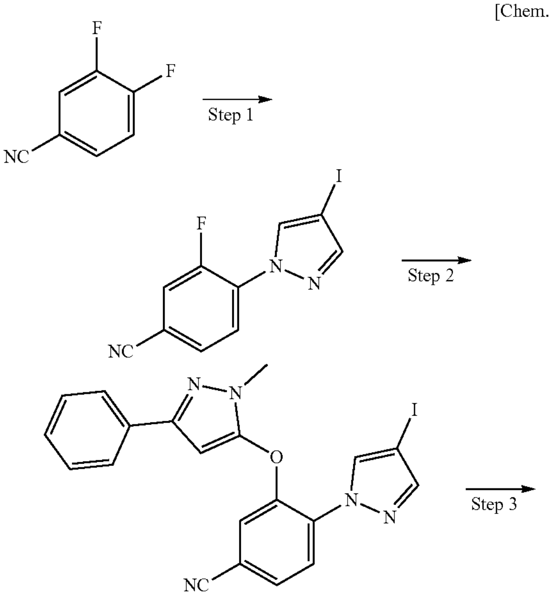

-continued

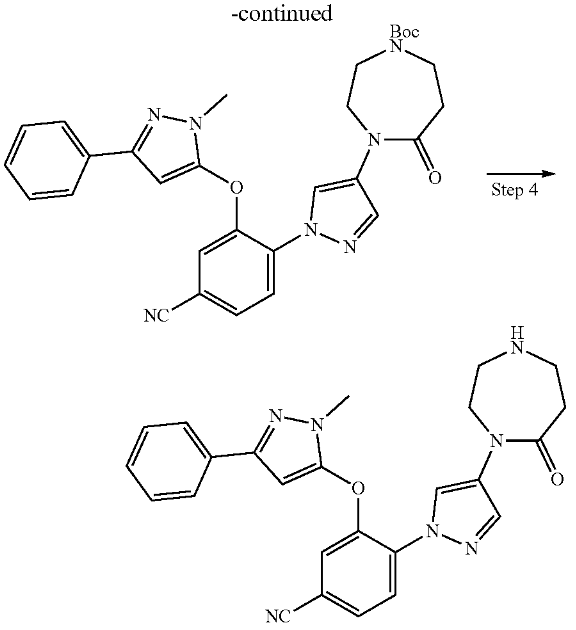

Step 1: 3-Fluoro-4-(4-iodopyrazol-1-yl)benzonitrile

DMF (8.6 mL) was added to 3,4-difluorobenzonitrile (430 mg, 3.09 mmol), 4-iodo-1H-pyrazole (500 mg, 2.58 mmol), and cesium carbonate (1.68 g, 5.16 mmol), and the mixture was stirred at 120° C. for 3 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (428 mg, 53%).

$^1$H-NMR ($CDCl_3$) δ: 8.18 (1H, d, J=2.7 Hz), 8.15 (1H, t, J=8.2 Hz), 7.79 (1H, s), 7.60-7.55 (2H, m).

Step 2: 4-(4-Iodopyrazol-1-yl)-3-(2-methyl-5-phenylpyrazol-3-yl)oxybenzonitrile

NMP (2.6 mL) was added to 3-fluoro-4-(4-iodopyrazol-1-yl)benzonitrile (201 mg, 0.642 mmol), 2-methyl-5-phenyl-4H-pyrazol-3-one (123 mg, 0.706 mmol), and potassium carbonate (177 mg, 1.28 mmol), and the mixture was stirred at 120° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (198 mg, 66%).

MS: m/z 468.1 $(M+H)^+$.

Step 3: tert-Butyl 4-[1-[4-cyano-2-(2-methyl-5-phenylpyrazol-3-yl)oxyphenyl]pyrazol-4-yl]-5-oxo-1,4-diazepane-1-carboxylate tert-Butyl 5-oxo-1,4-diazepane-1-carboxylate (24 mg, 0.11 mmol), copper(I) iodide (3.7 mg, 0.020 mmol), trans-1,2-cyclohexanediamine (2.2 mg, 0.020 mmol) and tripotassium phosphate (62.7 mg, 0.295 mmol) were added to a solution (0.5 mL) of 4-(4-Iodopyrazol-1-yl)-3-(2-methyl-5-phenylpyrazol-3-yl)oxybenzonitrile (46 mg, 0.098 mmol) in 1,4-dioxane, and the mixture was stirred at 100° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was used in the next reaction without further purification.

Step 4: 3-(2-Methyl-5-phenylpyrazol-3-yl)oxy-4-[4-(7-oxo-1,4-diazepan-1-yl)pyrazol-1-yl]benzonitrile The crude product obtained in Step 3 was dissolved in dichloromethane (1 mL), TFA (1 mL) was added to the solution, and the mixture was stirred at room temperature for 2 hours. The reaction mixture was concentrated under reduced pressure, and the crude product was purified by HPLC to obtain the target compound (15.7 mg).

Exact MS: 453.2

Obs. MS $(M+H)^+$: 454.3

Example 16

4-[5-(2-aminoethyl)pyrimidin-2-yl]-3-(2-methyl-6-morpholin-4-ylpyridin-4-yl)oxybenzonitrile (Compound No. 250)

[Chem. 62]

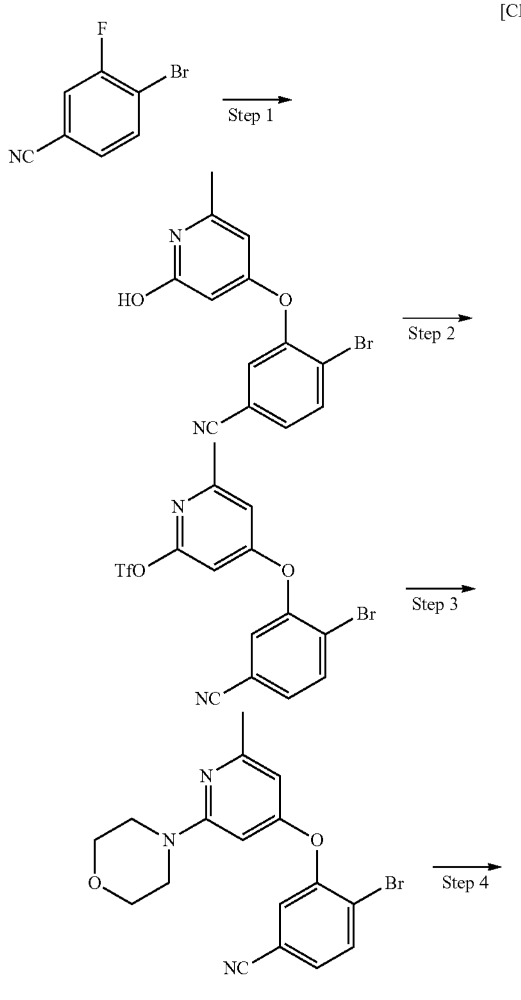

-continued

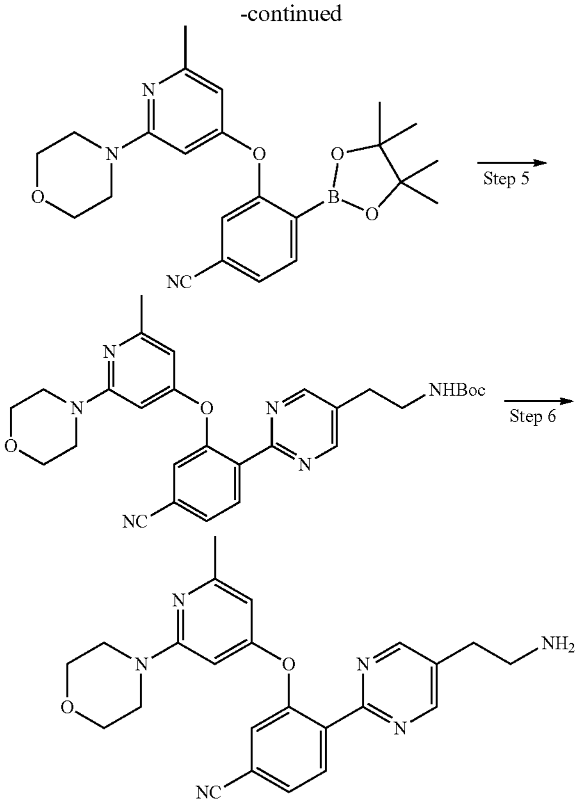

Step 1: 4-Bromo-3-(2-hydroxy-6-methylpyridin-4-yl)oxybenzonitrile

NMP (400 mL) was added to 4-bromo-3-fluorobenzonitrile (40.0 g, 200 mmol), 6-methylpyridine-2,4-diol (30.0 g, 240 mmol), and sodium carbonate (53.0 g, 500 mmol), and the mixture was stirred at 160° C. for 5 hours. Water was added to the reaction mixture, and the mixture was extracted with ethyl acetate. The organic layer was washed with saturated brine and dried over anhydrous magnesium sulfate, and the solution was concentrated under reduced pressure. Ethyl acetate was added to the concentrated crude product to prepare a suspension, heptane was further added to the suspension, and the precipitated solid was collected by filtration through a glass filter. The solid was vacuum dried to obtain the target compound (20.3 g, 33%).

MS: m/z 305.0 $(M+H)^+$.

$^1$H-NMR (DMSO-$d_6$) δ: 11.47 (1H, s), 8.00 (1H, d, J=8.2 Hz), 7.92 (1H, d, J=1.8 Hz), 7.73 (1H, dd, J=8.2, 2.3 Hz), 5.89 (1H, d, J=1.8 Hz), 5.15 (1H, d, J=2.7 Hz), 2.15 (3H, s).

Step 2: [4-(2-Bromo-5-cyanophenoxy)-6-methylpyridin-2-yl]trifluoromethanesulfonate Dichloromethane (22 mL) was added to 4-bromo-3-(2-hydroxy-6-methylpyridin-4-yl)oxybenzonitrile (2.7 g, 8.85 mmol), the mixture was cooled to 0° C., and then trifluoromethanesulfonic anhydride (3.25 g, 11.5 mmol) was added to the mixture. Pyridine (2.1 mL, 26.5 mmol) was added dropwise to this reaction mixture at the same temperature, then the temperature was raised to room temperature, and the mixture was stirred for 2 hours. Water was added to the reaction mixture, and the mixture was extracted with dichloromethane. The organic layer was washed with saturated brine and dried over anhydrous magnesium sulfate, and the solution was concentrated under reduced pressure. The crude product was used in the next reaction without further purification.

MS: m/z 436.9 $(M+H)^+$.

Step 3: 4-Bromo-3-(2-methyl-6-morpholin-4-ylpyridin-4-yl)oxybenzonitrile

The crude product obtained in Step 2 was dissolved in DMSO (18 mL), then to the solution, morpholine (1.16 g, 13.3 mmol) and N, N-diisopropylethylamine (4.73 mL, 26.5 mmol) were added, and the mixture was stirred at 70° C. for 2 hours. Water was added to the reaction mixture, and the mixture was extracted with ethyl acetate. The organic layer was washed with saturated brine and dried over anhydrous magnesium sulfate, and the solution was concentrated under reduced pressure. Ethanol was added to the concentrated crude product and dried overnight. The precipitated target compound was collected by filtration through a glass filter and dried to obtain the target compound (1.87 g, 57%).

MS: m/z 374.0 $(M+H)^+$.

$^1$H-NMR ($CDCl_3$) δ: 7.77 (1H, d, J=8.2 Hz), 7.35 (1H, dd, J=8.2, 1.8 Hz), 7.29 (1H, d, J=1.8 Hz), 6.02 (1H, d, J=1.4 Hz), 6.00 (1H, d, J=1.4 Hz), 3.80 (4H, t, J=5.0 Hz), 3.48 (4H, t, J=4.8 Hz), 2.36 (3H, s).

Step 4: 3-(2-methyl-6-morpholin-4-ylpyridin-4-yloxy-4-(4,4,5,5-tetramethyl-1,3,2-dioxaborolan-2-yl)benzonitrile 4-Bromo-3-(2-methyl-6-morpholin-4-ylpyridin-4-yl)oxybenzonitrile (790 mg, 2.11 mmol) was dissolved in 1,4-dioxane (11 mL), then to the solution, bis(pinacolato)diboron (804 mg, 3.17 mmol), [1,1'-bis(diphenylphosphino)ferrocene]palladium dichloride (76.4 mg, 0.106 mmol), and potassium acetate (415 mg, 4.22 mmol) were added, and the mixture was stirred at 90° C. overnight. The reaction mixture was cooled to room temperature, water was added to the mixture, and the mixture was extracted with ethyl acetate. The organic layer was washed with saturated brine, dried over anhydrous sodium sulfate, and the solution was concentrated under reduced pressure. The crude product was purified by silica gel column chromatography to obtain the target compound (567 mg).

MS: m/z 422.3 $(M+H)^+$.

Step 5: tert-Butyl N-[2-[2-[4-cyano-2-(2-methyl-6-morpholin-4-ylpyridin-4-yl)oxyphenyl]pyrimidin-5-yl]ethyl]carbamate 3-(2-Methyl-6-morpholin-4-ylpyridin-4-yl)oxy-4-(4,4,5,5-tetramethyl-1,3,2-dioxaborolan-2-yl)benzonitrile (222 mg, 0.527 mmol) was dissolved in 1,4-dioxane (1.8 mL), then to the solution, tert-butyl N-[2-(2-chloropyrimidin-5-yl)ethyl]carbamate (90.5 mg, 0.351 mmol), [1,1'-bis(diphenylphosphino)ferrocene]palladium dichloride (12.8 mg, 0.0176 mmol), potassium carbonate (97.1 mg, 0.702 mmol), and water (0.4 mL) were added, and the mixture was stirred at 90° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (71.9 mg, 40%).

MS: m/z 517.3 $(M+H)^+$.

$^1$H-NMR ($CDCl_3$) δ: 8.61 (2H, s), 8.05 (1H, d, J=8.2 Hz), 7.61 (11H, dd, J=8.2, 1.4 Hz), 7.44 (1H, d, J=1.4 Hz), 6.01 (1H, d, J=1.4 Hz), 5.94 (1H, d, J=1.8 Hz), 4.70 (1H, brs), 3.78 (4H, t, J=4.8 Hz), 3.41 (4H, t, J=4.8 Hz), 3.36 (2H, q, J=6.6 Hz), 2.82 (2H, t, J=6.6 Hz), 2.29 (3H, s), 1.43 (9H, s).

Step 6: 4-[5-(2-Aminoethyl)pyrimidin-2-yl]-3-(2-methyl-6-morpholin-4-ylpyridin-4-yl)oxybenzonitrile tert-Butyl N-[2-[2-[4-cyano-2-(2-methyl-6-morpholin-4-ylpyridin-4-yl)oxyphenyl]pyrimidin-5-yl]ethyl]carbamate (71.9 mg, 0.139 mmol) was dissolved in dichloromethane (1 mL), then TFA (1 mL) was added to the solution, and the mixture was stirred at room temperature for 1 hour. The reaction mixture was concentrated under reduced pressure, and the crude product was purified by HPLC to obtain the target compound (63.62 mg).

Exact MS: 416.2

Obs. MS $(M+H)^+$: 417.4

$^1$H-NMR ($CD_3OD$) δ: 8.79 (2H, s), 8.33 (1H, d, J=8.2 Hz), 7.90 (1H, dd, J=8.0, 1.6 Hz), 7.79 (1H, d, J=1.4 Hz), 6.46 (1H, d, J=1.8 Hz), 6.39 (1H, d, J=1.8 Hz), 3.79 (4H, t, J=5.0 Hz), 3.55 (4H, t, J=5.0 Hz), 3.25 (2H, t, J=7.8 Hz), 3.04 (2H, t, J=7.8 Hz), 2.50 (3H, s).

Example 17

4-[5-(2-Aminoethyl)pyrimidin-2-yl]-3-(2-methyl-5-propan-2-ylpyrazol-3-yl)oxybenzonitrile (Compound No. 261)

[Chem. 63]

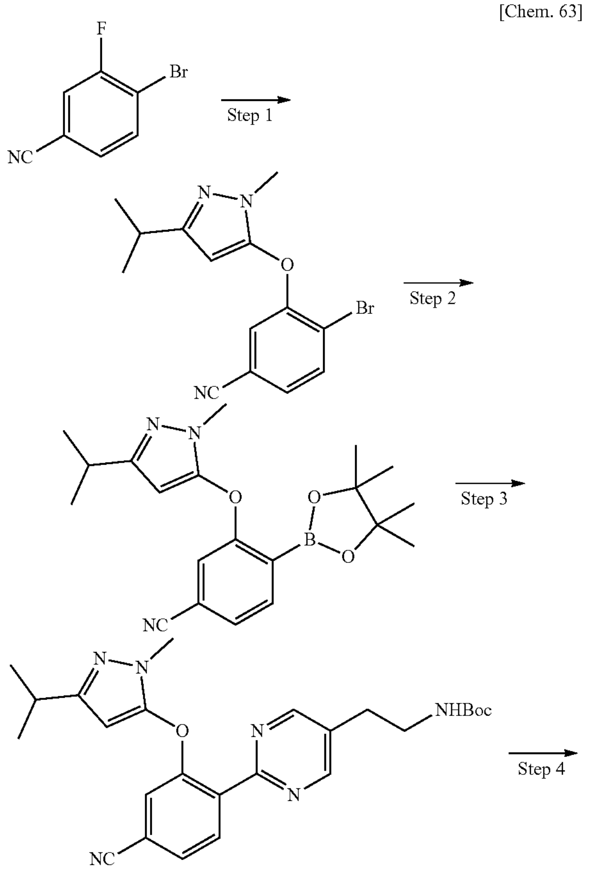

-continued

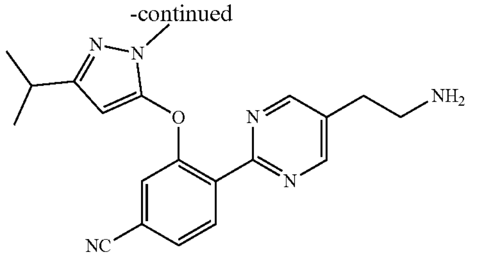

Step 1: 4-Bromo-3-(2-methyl-5-propan-2-ylpyrazol-3-yl)oxybenzonitrile

4-Bromo-3-fluorobenzonitrile (2.14 g, 10.7 mmol) and 2-methyl-5-propan-2-ylpyrazole-3-ol (1.50 g, 10.7 mmol) were dissolved in DMA (21 mL), then potassium carbonate (4.44 g, 32.1 mmol) was added to the solution, and the mixture was stirred at 130° C. for 3 hours. The reaction mixture was cooled to room temperature, water was added to the mixture, and the mixture was extracted with ethyl acetate. The organic layer was washed with saturated brine and dried over anhydrous magnesium sulfate, and the solution was concentrated under reduced pressure. The crude product was purified by silica gel column chromatography to obtain the target compound (1.06 g, 31%).

MS: m/z 322.1 $(M+H)^+$.

$^1$H-NMR ($CDCl_3$) δ: 7.77 (1H, d, J=8.2 Hz), 7.34-7.32 (2H, m), 5.52 (1H, s), 3.70 (3H, s), 2.94-2.87 (1H, m), 1.25 (6H, d, J=6.9 Hz).

Step 2: 3-(2-Methyl-5-propan-2-ylpyrazol-3-yloxy-4-(4,4,5,5-tetramethyl-1,3,2-dioxaborolan-2-yl)benzonitrile 4-Bromo-3-(2-methyl-5-propan-2-ylpyrazol-3-yl)oxybenzonitrile (646 mg, 2.02 mmol) was dissolved in 1,4-dioxane (10 mL), then to the solution, bis(pinacolato)diboron (615 mg, 2.42 mmol), bis(triphenylphosphine)palladium dichloride (70.8 mg, 0.101 mmol) and potassium acetate (396 mg, 4.03 mmol) were added, and the mixture was stirred at 100° C. for 2 hours. The reaction solution was cooled to room temperature and filtered through Celite, and then the solution was concentrated under reduced pressure. The crude product was used in the next reaction without further purification.

MS: m/z 368.2 $(M+H)^+$.

Step 3: tert-Butyl N-[2-[2-[4-cyano-2-(2-methyl-5-propan-2-ylpyrazol-3-yl)oxyphenyl]pyrimidin-5-yl]ethyl]carbamate To a solution (13.5 mL) of the crude product in 1,4-dioxane obtained in Step 2, tert-butyl N-[2-(2-chloropyrimidin-5-yl)ethyl]carbamate (520 mg, 2.02 mmol), tetrakis(triphenylphosphine)palladium (117 mg, 0.101 mmol), potassium carbonate (697 mg, 5.04 mmol) and water (3.4 mL) were added, and the mixture was stirred at 100° C. for 2 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (946 mg, containing impurities).

MS: m/z 463.2 $(M+H)^+$.

Step 4: 4-[5-(2-Aminoethyl)pyrimidin-2-yl]-3-(2-methyl-5-propan-2-ylpyrazol-3-yl)oxybenzonitrile tert-Butyl N-[2-[2-[4-cyano-2-(2-methyl-5-propan-2-ylpyrazol-3-yl)oxyphenyl]pyrimidin-5-yl]ethyl]carbamate (946 mg, 1.23 mmol) was dissolved in 1,4-dioxane (5.1 mL), then to the solution, a 4 M hydrochloric acid/1,4-dioxane solution (5.1 mL) was added dropwise at 0° C., the temperature of the mixture was raised to room temperature, and the mixture was stirred for 5 hours. The reaction mixture was concentrated under reduced pressure, ethyl acetate was added to the concentrated crude product, and the mixture was concentrated under reduced pressure again. The mixture was vacuum dried to obtain the hydrochloride salt of the target compound (681 mg, 76%).

Exact MS: 362.2

Obs. MS $(M+H)^+$: 363.3

Example 18

4-[4-(2-Aminoethyl)pyrazol-1-yl]-3-(6-pyrrolidin-1-ylpyridazin-4-yl)oxybenzonitrile (Compound No. 284)

[Chem. 64]

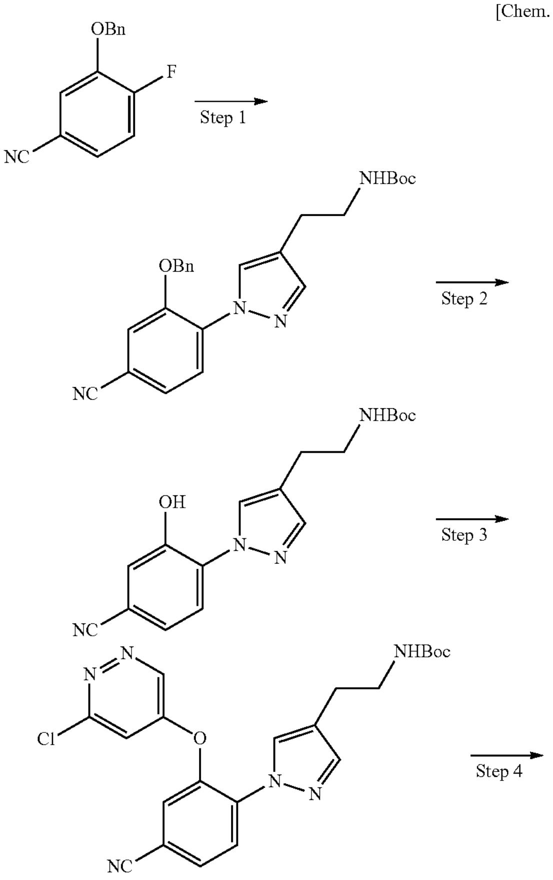

-continued

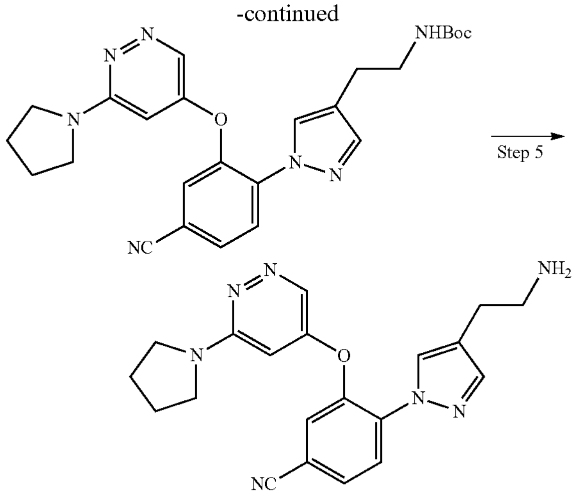

Step 1: tert-Butyl N-[2-[1-(4-cyano-2-phenylmethoxyphenyl)pyrazol-4-yl]ethyl]carbamate DMA (2 mL) was added to 4-fluoro-3-phenylmethoxybenzonitrile (307 mg, 1.35 mmol), tert-butyl N-[2-(1H-pyrazol-4-yl)ethyl]carbamate (190 mg, 0.900 mmol), and potassium carbonate (373 mg, 2.70 mmol), and the mixture was stirred at 150° C. for 2 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (263 mg, 70%).

MS: m/z 419.2 $(M+H)^+$.

Step 2: tert-Butyl N-[2-[1-(4-cyano-2-hydroxyphenyl)pyrazol-4-yl]ethyl]carbamate tert-Butyl N-[2-[1-(4-cyano-2-phenylmethoxyphenyl) pyrazol-4-yl]ethyl]carbamate (263 mg, 0.628 mmol) was dissolved in methanol (5 mL)/ethyl acetate (5 mL) and palladium-activated carbon (100 mg) was added to the solution under a nitrogen atmosphere. A hydrogen gas balloon was attached to the reaction vessel, and after the inside of the vessel was replaced with hydrogen gas, the mixture was stirred at room temperature for 30 minutes. The reaction mixture was filtered through Celite, the filtrate was concentrated under reduced pressure, and the crude product was purified by silica gel column chromatography to obtain the target compound (172 mg, 83%).

MS: m/z 273.0 $(M-tBu+H)^+$.

Step 3: tert-Butyl N-[2-[1-[2-(6-chloropyridazin-4-yl)oxy-4-cyanophenyl]pyrazol-4-yl]ethyl]carbamate DMF (1.3 mL) was added to tert-butyl N-[2-[1-(4-cyano-2-hydroxyphenyl)pyrazol-4-yl]ethyl]carbamate (172 mg, 0.524 mmol), 3,5-dichloropyridazine (101 mg, 0.681 mmol), and potassium carbonate (217 mg, 1.57 mmol), and the mixture was stirred at 100° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (218 mg, 94%).

MS: m/z 385.0 $(M-tBu+H)^+$.

Step 4: tert-Butyl N-[2-[1-[4-cyano-2-(6-pyrrolidin-1-ylpyridazin-4-yl)oxyphenyl]pyrazol-4-yl]ethyl]carbamate tert-Butyl N-[2-[1-[2-(6-chloropyridazin-4-yl)oxy-4-cyanophenyl]pyrazol-4-yl]ethyl]carbamate (70.0 mg, 0.159 mmol) was dissolved in toluene (0.8 mL), then to the solution, pyrrolidine (33.9 mg, 0.476 mmol), tris(dibenzylideneacetone)dipalladium (7.3 mg, 7.9 μmol), (±)-BINAP (9.9 mg, 16 μmol)), and cesium carbonate (220 mg, 2.25 mmol) were added, and the mixture was stirred at 100° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (51.0 mg, 68%).

Step 5: 4-[4-(2-Aminoethyl)pyrazol-1-yl]-3-(6-pyrrolidin-1-ylpyridazin-4-yl)oxybenzonitrile tert-Butyl N-[2-[1-[4-cyano-2-(6-pyrrolidin-1-ylpyridazin-4-yl)oxyphenyl]pyrazol-4-yl]ethyl]carbamate (51.0 mg, 0.107 mmol) was dissolved in dichloromethane (2 mL), then TFA (0.5 mL) was added to the solution, and the mixture was stirred at room temperature for 30 minutes. The reaction mixture was concentrated under reduced pressure, and the crude product was purified by HPLC to obtain the target compound (9.71 mg).

Exact MS: 375.2

Obs. MS $(M+H)^+$: 376.2

Example 19

4-[5-(1-Amino-2-morpholin-4-yl-2-oxoethyl)pyridin-2-yl]-3-(5-cyclopropyl-2-methylpyrazol-3-yl) oxybenzonitrile (Compound No. 487)

[Chem. 65]

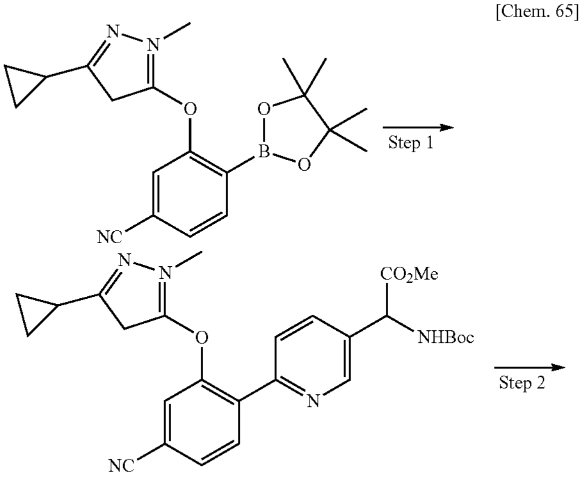

-continued

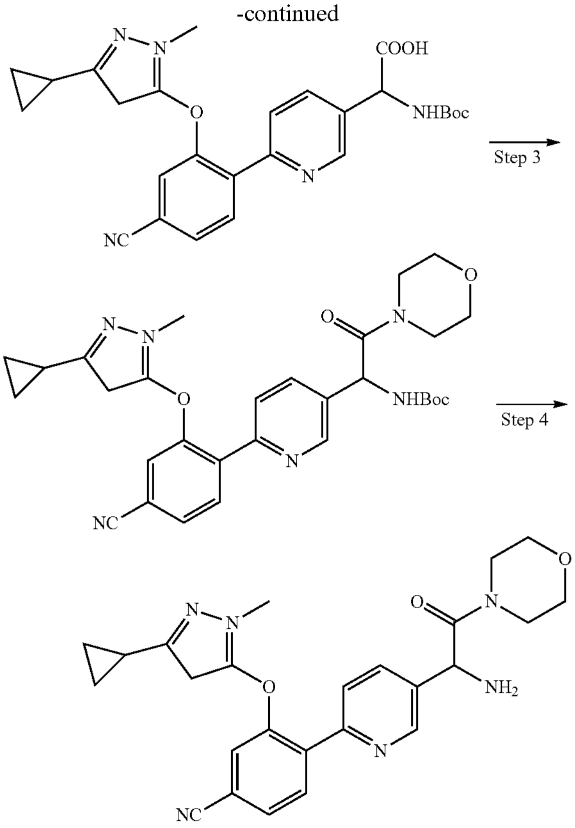

Step 1: Methyl 2-[6-[4-cyano-2-(5-cyclopropyl-2-methylpyrazol-3-yl)oxyphenyl]pyridin-3-yl]-2-[(2-methylpropan-2-yl)oxycarbonylamino]acetate 3-(5-Cyclopropyl-2-methylpyrazol-3-yl)oxy-4-(4,4,5,5-tetramethyl-1,3,2-dioxaborolan-2-yl)benzonitrile (881 mg, 2.41 mmol) synthesized in the same method as in Example 17 was dissolved in 1,4-dioxane (12 mL), then to the solution, methyl 2-(6-chloropyridin-3-yl)-2-[(2-methylpropan-2-yl)oxycarbonylamino]acetate (725 mg, 2.41 mmol), [1,1'-bis(diphenylphosphino)ferrocene]palladium dichloride (176.5 mg, 0.241 mmol), potassium carbonate (1.00 g, 7.24 mmol) and water (3 mL) were added, and the mixture was stirred at 100° C. for 2 hours. The reaction mixture was cooled to room temperature, water was added to the mixture, and the mixture was extracted with ethyl acetate. The organic layer was washed with saturated brine and dried over anhydrous magnesium sulfate, and the solution was concentrated under reduced pressure. The crude product was purified by silica gel column chromatography to obtain the target compound (976 mg, 80%).

MS: m/z 504.4 $(M+H)^+$.

Step 2: 2-[6-[4-Cyano-2-(5-cyclopropyl-2-methylpyrazol-3-yl)oxyphenyl]pyridin-3-yl]-2-[(2-methylpropan-2-yl)oxycarbonylamino]acetic acid Methyl 2-[6-[4-cyano-2-(5-cyclopropyl-2-methylpyrazol-3-yl)oxyphenyl]pyridin-3-yl]-2-[(2-methylpropan-2-yl)oxycarbonylamino]acetate (976 mg, 1.94 mmol) was dissolved in methanol (10 mL), then a 2 M aqueous sodium hydroxide solution (2 mL) was added to the solution, and the mixture was stirred at room temperature for 15 minutes. After adding 1 M hydrochloric acid (4 mL) to the reaction mixture and stirring the mixture, the mixture was extracted by adding ethyl acetate. The organic layer was washed with saturated brine and dried over anhydrous magnesium sulfate, and concentrated under reduced pressure. The crude product was used in the next reaction without further purification.

MS: m/z 490.3 $(M+H)^+$.

Step 3: tert-Butyl N-[1-[6-[4-cyano-2-(5-cyclopropyl-2-methylpyrazol-3-yl)oxyphenyl]pyridin-3-yl]-2-morpholin-4-yl-2-oxoethyl]carbamate An aliquot (160 mg, 0.320 mmol) of the crude product obtained in Step 2 was dissolved in DMF (1 mL), then to the solution, morpholine (0.041 mL, 0.48 mmol), HATU (160 mg, 0.420 mmol), and triethylamine (0.130 mL, 0.960 mmol) were added, and the mixture was stirred at room temperature for 3 hours. Water was added to the reaction mixture, and the mixture was extracted with ethyl acetate. The organic layer was washed with saturated brine and dried over anhydrous magnesium sulfate, and the solution was concentrated under reduced pressure. The crude product was used in the next reaction without further purification.

MS: m/z 559.4 $(M+H)^+$.

Step 4: 4-[5-(1-Amino-2-morpholin-4-yl-2-oxoethyl)pyridin-2-yl]-3-(5-cyclopropyl-2-methylpyrazol-3-yl)oxybenzonitrile The crude product obtained in Step 3 was dissolved in dichloromethane (1 mL), then TFA (0.5 mL) was added to the solution, and the mixture was stirred at room temperature for 30 minutes. The reaction mixture was concentrated under reduced pressure, and the crude product was purified by HPLC to obtain the target compound (39.7 mg).

Exact MS: 458.2

Obs. MS $(M+H)^+$: 459.3

Example 20

4-[5-[(3-Aminooxetan-3-yl)methyl]pyridin-2-yl]-3-[6-(7-azabicyclo[2.2.1]heptan-7-yl)-2-methylpyrimidin-4-yl]oxybenzonitrile (Compound No. 670)

[Chem. 66]

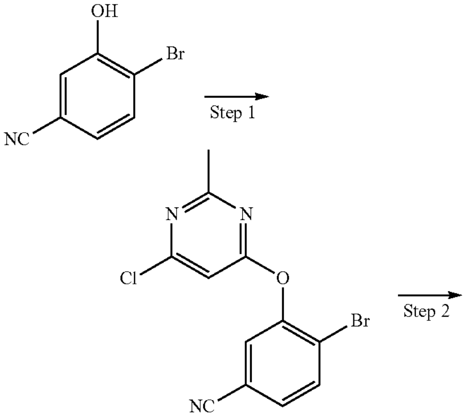

-continued

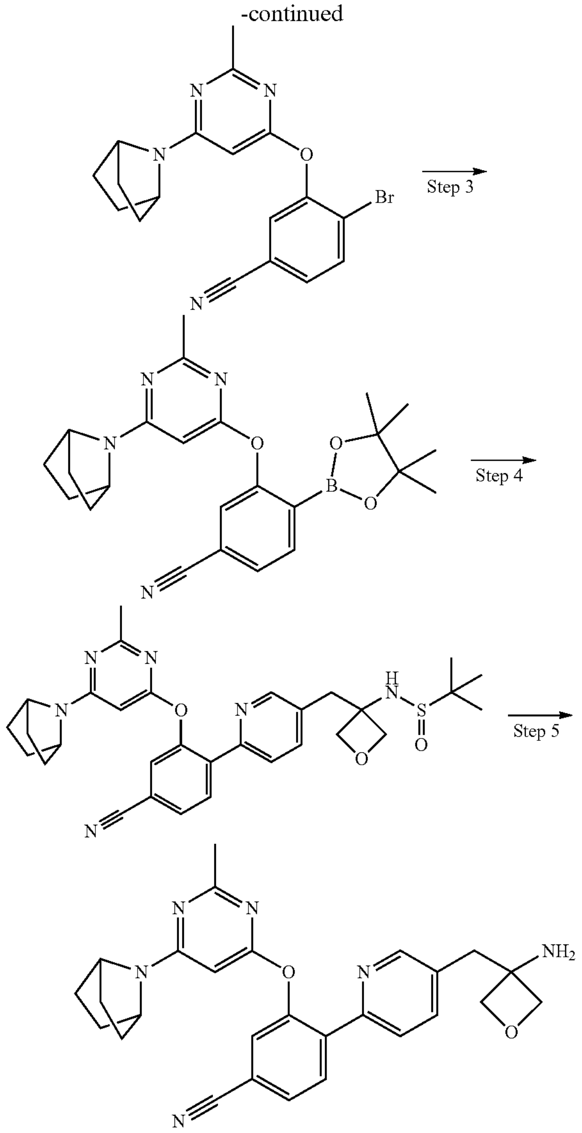

Step 1: 4-Bromo-3-(6-chloro-2-methylpyrimidin-4-yl)oxybenzonitrile

4-Bromo-3-hydroxybenzonitrile (1.78 g, 9.00 mmol) was dissolved in DMSO (30 mL), then to the solution, 4,6-dichloro-2-methylpyrimidine (1.28 g, 6.0 mmol) and potassium carbonate (2.49 g, 18.0 mmol) were added, and the mixture was stirred at 80° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (1.16 g, 60%).

MS: m/z 324.0 $(M+H)^+$.

Step 2: 3-[6-(7-azabicyclo[2.2.1]heptan-7-yl)-2-methylpyrimidin-4-yl]oxy-4-bromobenzonitrile 4-Bromo-3-(6-chloro-2-methylpyrimidin-4-yl)oxybenzonitrile (325 mg, 1.00 mmol) was dissolved in DMF (5 mL), then to the solution, 7-azabicyclo[2.2.1]heptane hydrochloride (200 mg, 1.50 mmol) and potassium carbonate (415 mg, 3.00 mmol) were added, and the mixture was stirred at 80° C. overnight. The reaction mixture was cooled to room temperature, water was added to the mixture, and the mixture was extracted with a mixed solution of ethyl acetate/heptane (=1/1). The organic layer was washed with saturated brine and dried over anhydrous sodium sulfate, and the solution was concentrated under reduced pressure. The crude product was purified by silica gel column chromatography to obtain the target compound (235 mg, 61%).

MS: m/z 385.1 $(M+H)^+$.

$^1$H-NMR ($CDCl_3$) δ: 7.73 (1H, d, J=8.2 Hz), 7.47 (1H, d, J=2.3 Hz), 7.36 (1H, dd, J=8.2, 1.8 Hz), 5.89 (1H, s), 4.51 (2H, brs), 2.36 (3H, s), 1.82-1.80 (4H, m), 1.57-1.50 (4H, m).

Step 3: 3-[6-(7-Azabicyclo[2.2.1]heptan-7-yl)-2-methylpyrimidin-4-yl]oxy-4-(4,4,5,5-tetramethyl-1,3,2-dioxaborolan-2-yl)benzonitrile 3-[6-(7-Azabicyclo[2.2.1]heptan-7-yl)-2-methylpyrimidin-4-yl]oxy-4-bromobenzonitrile (231 mg, 0.600 mmol) was dissolved in 1,4-dioxane (3 mL), then to the solution, bis(pinacolato)diboron (305 mg, 1.20 mmol), [1,1'-bis(diphenylphosphino)ferrocene]palladium dichloride (43.9 mg, 0.0600 mmol), and potassium acetate (177 mg, 1.80 mmol) were added, and the mixture was stirred at 100° C. overnight. The reaction solution was cooled to room temperature and filtered through Celite, and then the solution was concentrated under reduced pressure. The concentrated crude product was used in the next reaction without further purification.

Step 4: N-[3-[[6-[2-[6-(7-Azabicyclo[2.2.1]heptan-7-yl)-2-methylpyrimidin-4-yl]oxy-4-cyanophenyl]pyridin-3-yl]methyl]oxetan-3-yl]-2-methylpropane-2-sulfinamide An aliquot (64.8 mg) of the crude product obtained in Step 3 was dissolved in 1,4-dioxane (1 mL), then to the solution, N-[3-[(6-chloropyridin-3-yl)methyl]oxetan-3-yl]-2-methylpropane-2-sulfinamide (30.3 mg, 0.100 mmol), [1,1'-bis(diphenylphosphino)ferrocene]palladium dichloride (7.3 mg, 0.010 mmol), potassium carbonate (41.5 mg, 0.300 mmol) and water (0.2 mL) were added, and the mixture was stirred at 100° C. overnight. The reaction solution was cooled to room temperature and filtered through Celite, and then the solution was concentrated under reduced pressure. The concentrated crude product was used in the next reaction without further purification.

Step 5: 4-[5-[(3-Aminooxetan-3-yl)methyl]pyridin-2-yl]-3-[6-(7-azabicyclo[2.2.1]heptan-7-yl)-2-methylpyrimidin-4-yl]oxybenzonitrile The crude product obtained in Step 4 was dissolved in methanol (1 mL), then to the solution, a 4 M hydrochloric acid/1,4-dioxane solution (0.15 mL) was added at 0° C., and the mixture was stirred at the same temperature for 2 hours. Saturated aqueous sodium hydrogen carbonate (5 mL) was added to the reaction mixture, and the mixture was extracted with dichloromethane. The organic layer was dried over anhydrous sodium sulfate and the solution was concentrated under reduced pressure. The crude product was purified by silica gel column chromatography to obtain the target compound (8.2 mg).

Exact MS: 468.2

Obs. MS $(M+H)^+$: 469.2

Example 21

4-[5-(2-Aminoethyl)pyridin-2-yl]-3-[[5-(trifluoromethyl)-1,3,4-thiadiazol-2-yl]oxy]benzonitrile (Compound No. 712)

[Chem. 67]

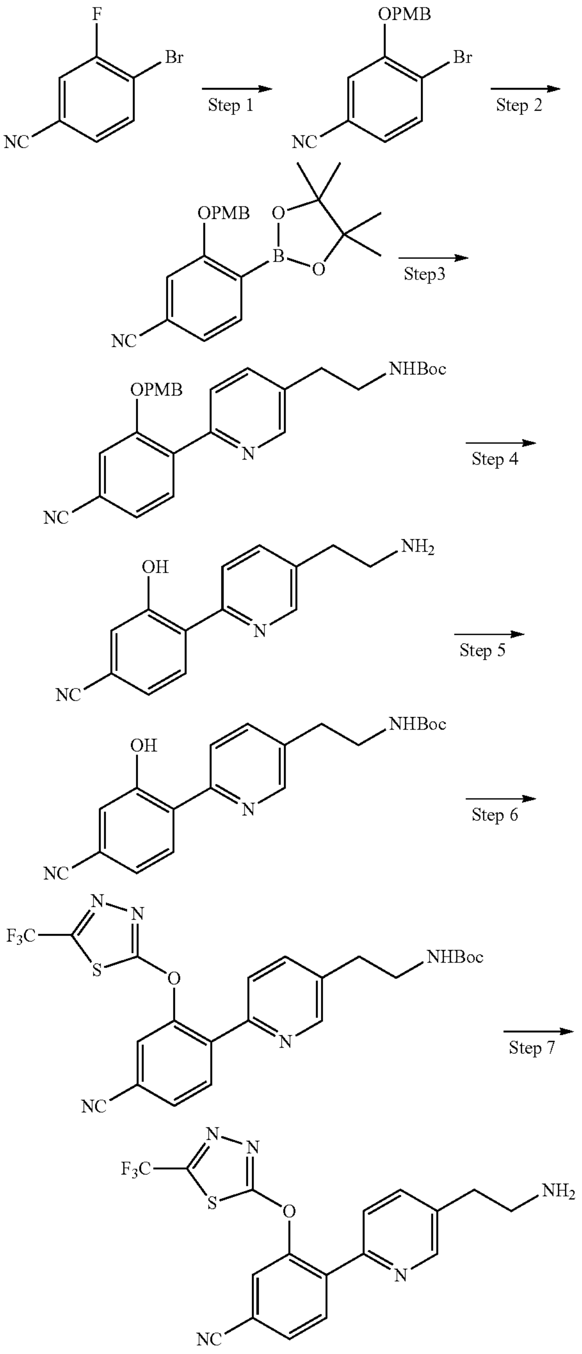

Step 1: 4-Bromo-3-[(4-methoxyphenyl)methoxy]benzonitrile

4-Bromo-3-fluorobenzonitrile (6.00 g, 30.0 mmol) was added to a solution of 4-methoxybenzyl alcohol (4.97 g, 36.0 mmol) and potassium tert-butoxide (4.04 g, 36.0 mmol) in DMF (100 mL), and the mixture was stirred at room temperature for 2.5 hours. Water was added to the reaction mixture, the mixture was stirred, and the precipitated solid was collected by filtration through a glass filter and vacuum dried to obtain the target compound (8.04 g, 84%).

$^1$H-NMR ($CDCl_3$) δ: 7.65 (1H, d, J=7.8 Hz), 7.37 (2H, d, J=8.7 Hz), 7.13 (2H, dd, J=9.8, 1.1 Hz), 6.93 (2H, d, J=8.2 Hz), 5.11 (2H, s), 3.83 (3H, s).

Step 2: 3-[(4-Methoxyphenyl]methoxyl-4-(4,4,5,5-tetramethyl-1,3,2-dioxaborolan-2-ylbenzonitrile 4-Bromo-3-[(4-methoxyphenyl)methoxy]benzonitrile (1.0 g, 3.14 mmol) was dissolved in 1,4-dioxane (16 mL), then to the solution, bis(pinacolato)diboron (1.20 g, 4.71 mmol), [1,1'-bis(diphenylphosphino)ferrocene]palladium dichloride (115 mg, 0.157 mmol) and potassium acetate (617 mg, 6.29 mmol) were added, and the mixture was stirred at 100° C. for 2 hours. The reaction mixture was cooled to room temperature, filtered through Celite, and then concentrated under reduced pressure. The concentrated crude product was used in the next reaction without further purification.

MS: m/z 433.2 $(M+H)^+$.

Step 3: tert-Butyl N-[2-[6-[4-cyano-2-[(4-methoxyphenyl)methoxy]phenyl]pyridin-3-yl]ethyl]carbamate tert-Butyl N-[2-(6-chloropyridin-3-yl)ethyl]carbamate (807 mg, 3.14 mmol), [1,1'-bis(diphenylphosphino)ferrocene]palladium dichloride (231 mg, 0.314 mmol), potassium carbonate (2.05 g, 6.29 mmol) and water (1 mL) were added to a solution of the crude product in 1,4-dioxane (6 mL) obtained in Step 2, and the mixture was stirred at 100° C. for 4 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (1.17 g, 81%).

MS: m/z 460.2 $(M+H)^+$.

Step 4: 4-[5-(2-Aminoethyl)pyridin-2-yl]-3-hydroxybenzonitrile tert-Butyl N-[2-[6-[4-cyano-2-[(4-methoxyphenyl)methoxy]phenyl]pyridin-3-yl]ethyl]carbamate (1.05 g, 1.60 mmol) was dissolved in dichloromethane (10 mL), then TFA (2 mL) was added to the solution, and the mixture was stirred at room temperature for 2 hours. The reaction solution was concentrated under reduced pressure, and the concentrated crude product was used in the next reaction without further purification.

Step 5: tert-Butyl N-[2-[6-(4-cyano-2-hydroxyphenyl)pyridin-3-yl]ethyl]carbamate The crude product obtained in Step 4 was dissolved in dichloromethane (5 mL), then to the solution, di-tert-butyl dicarbonate (698 mg, 3.20 mmol) and triethylamine (1.00 mL) were added, and the mixture was stirred at room temperature for 1 hour. Water was added to the reaction mixture, and the mixture was extracted with dichloromethane. The organic layer was washed with saturated brine and dried over anhydrous sodium sulfate, and the solution was concentrated under reduced pressure. The crude product was purified by silica gel column chromatography to obtain the target compound (526 mg, 97%).

MS: m/z 340.1 $(M+H)^+$.

Step 6: tert-Butyl N-[2-[6-[4-cyano-2-[[5-(trifluoromethyl)-1,3,4-thiadiazol-2-yl]oxy]phenyl]pyridin-3-yl]ethyl]carbamate tert-Butyl N-[2-[6-(4-cyano-2-hydroxyphenyl)pyridin-3-yl]ethyl]carbamate (30 mg, 0.088 mmol) was dissolved in NMP (1 mL), then to the solution, 2-bromo-5-(trifluoromethyl)-1,3,4-thiadiazole (24.7 mg, 0.106 mmol) and potassium carbonate (36.7 mg, 0.265 mmol) were added, and the mixture was stirred at 80° C. for 1 hour. Water was added to the reaction mixture, and the mixture was extracted with ethyl acetate. The organic layer was washed with saturated brine and dried over anhydrous magnesium sulfate, and the solution was concentrated under reduced pressure. The obtained crude product was used in the next reaction without further purification.

MS: m/z 492.1 $(M+H)^+$.

Step 7: 4-[5-(2-Aminoethyl)pyridin-2-yl]-3-[[5-(trifluoromethyl)-1,3,4-thiadiazol-2-yl]oxy]benzonitrile The crude product obtained in Step 6 was dissolved in dichloromethane (1 mL), TFA (0.5 mL) was added to the solution, and the mixture was stirred at room temperature for 30 minutes. The reaction mixture was concentrated under reduced pressure, and the crude product was purified by HPLC to obtain the target compound (35.9 mg).

Exact MS: 391.1

Obs. MS $(M+H)^+$: 392.2

Example 22

4-[5-(Aminomethyl)pyrimidin-2-yl]-3-[2-methyl-5-(trifluoromethyl)pyrazol-3-yl]oxybenzonitrile (Compound No. 811)

[Chem. 68]

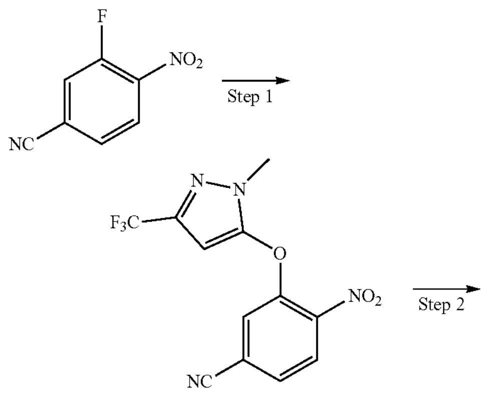

-continued

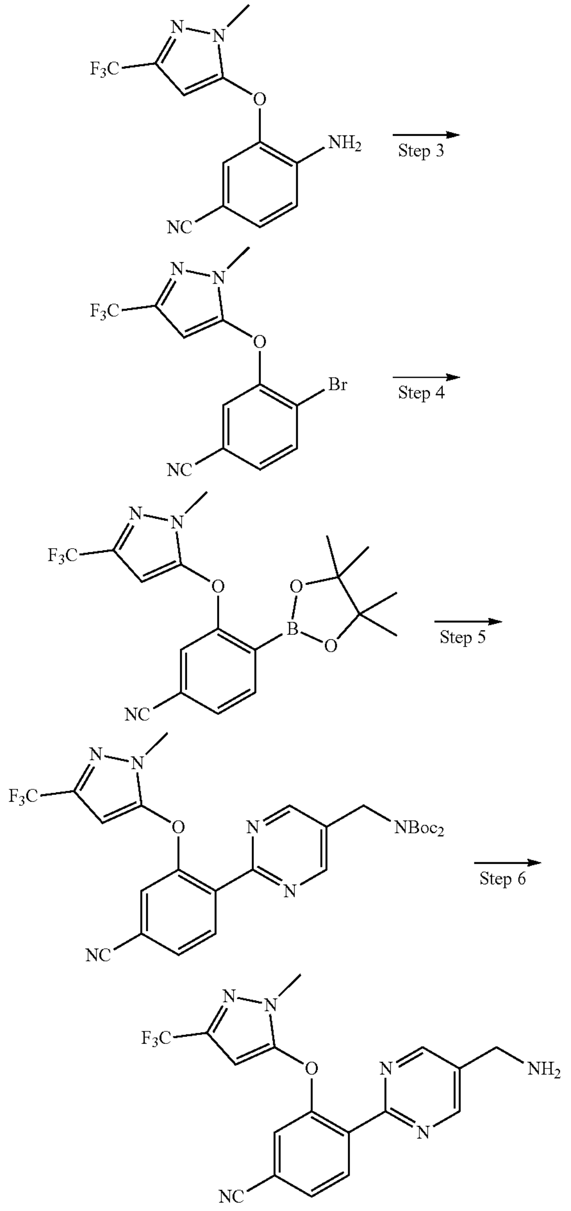

Step 1: 3-[2-methyl-5-(trifluoromethyl)pyrazol-3-yl]oxy-4-nitrobenzonitrile

3-Fluoro-4-nitrobenzonitrile (664 mg, 4.00 mmol) and 2-methyl-5-(trifluoromethyl)-4H-pyrazol-3-one (731 mg, 4.40 mmol) were dissolved in DMF (6 mL), then potassium carbonate (663 mg, 4.80 mmol) was added to the solution, and the mixture was stirred at room temperature for 5 hours. Water was added to the reaction mixture, and the mixture was extracted with ethyl acetate. The organic layer was washed with saturated brine and dried over anhydrous sodium sulfate, and the solution was concentrated under reduced pressure. The obtained solid was washed with a small amount of ethyl acetate to obtain the target compound (417 mg).

MS: m/z 313.1 $(M+H)^+$.

Step 2: 4-Amino-3-[2-methyl-5-(trifluoromethyl)pyrazol-3-yl]oxybenzonitrile

Iron powder (224 mg, 4.01 mmol), ammonium chloride (214 mg, 4.01 mmol), ethanol (1.3 mL) and water (1.3 mL) were added to 3-[2-methyl-5-(trifluoromethyl)pyrazol-3-yl]oxy-4-nitrobenzonitrile (417 mg, 1.34 mmol), and the mixture was stirred at 70° C. for 1.5 hours. The reaction mixture was cooled to room temperature, filtered through Celite, and then extracted by adding ethyl acetate and water to the mother liquor. The organic layer was washed with saturated brine, dried over anhydrous magnesium sulfate, and concentrated under reduced pressure. The concentrated crude product was used in the next reaction without further purification.

MS: m/z 283.1 $(M+H)^+$.

Step 3: 4-Bromo-3-[2-methyl-5-(trifluoromethyl)pyrazol-3-yl]oxybenzonitrile

The crude product obtained in Step 2 was dissolved in acetonitrile (6.5 mL), then isoamyl nitrite (224 mg, 1.92 mmol) and copper(II) bromide (341 mg, 1.53 mmol) were added to the solution, and the mixture was stirred at 65° C. for 16 hours. The reaction mixture was cooled to room temperature, 20% hydrochloric acid was added to the mixture, and the mixture was extracted with ethyl acetate. The organic layer was washed with saturated brine and dried over anhydrous magnesium sulfate, and the solution was concentrated under reduced pressure. The crude product was purified by silica gel column chromatography to obtain the target compound (389 mg).

MS: m/z 346.0 $(M+H)^+$.

Step 4: 3-[2-Methyl-5-(trifluoromethyl)pyrazol-3-yl]oxy-4-(4,4,5,5-tetramethyl-1,3,2-dioxaborolan-2-yl)benzonitrile 4-Bromo-3-[2-methyl-5-(trifluoromethyl)pyrazol-3-yl]oxybenzonitrile (389 mg, 1.12 mmol) was dissolved in 1,4-dioxane (5.6 mL), then to the solution, bis(pinacolato)diboron (428 mg, 1.68 mmol), bis(triphenylphosphine)palladium dichloride (78.8 mg, 0.112 mmol) and potassium acetate (220 mg, 2.25 mmol) were added, and the mixture was stirred at 110° C. for 1 hour. The reaction solution was cooled to room temperature and used in the next reaction without further purification.

MS: m/z 394.2 $(M+H)^+$.

Step 5: tert-Butyl N-[[2-[4-cyano-2-[2-methyl-5-(trifluoromethyl)pyrazol-3-yl]oxyphenyl]pyrimidin-5-yl]methyl]-N-[(2-methylpropan-2-yl)oxycarbonyl]carbamate tert-Butyl N-[(2-chloropyrimidin-5-yl)methyl]-N-[(2-methylpropan-2-yl)oxycarbonyl]carbamate (107 mg, 0.31 mmol), [1,1'-bis(diphenylphosphino)ferrocene]palladium dichloride (21 mg, 0.028 mmol), potassium carbonate (120 mg, 0.840 mmol), and water (0.3 mL) were added to an aliquot (1.2 mL) of the reaction mixture obtained in Step 4, and the mixture was stirred at 100° C. for 1 hour. The reaction mixture was cooled to room temperature, water was added, and the mixture was extracted with ethyl acetate. The organic layer was washed with saturated brine and dried over anhydrous sodium sulfate, and the solution was concentrated under reduced pressure. The concentrated crude product was used in the next reaction without further purification.

Step 6: 4-[5-(Aminomethyl)pyrimidin-2-yl]-3-[2-methyl-5-(trifluoromethyl)pyrazol-3-yl]oxybenzonitrile Dichloromethane (0.5 mL) and TFA (0.5 mL) were added to the crude product obtained in Step 5, and the mixture was stirred at room temperature for 1 hour. The reaction mixture was concentrated under reduced pressure, and the crude product was purified by HPLC to obtain the target compound (88.7 mg).

Exact MS: 374.1

Obs. MS $(M+H)^+$: 375.3

Example 23

4-[5-(2-Aminoethyl)pyrimidin-2-yl]-3-[5-[2,2-difluoroethyl(ethyl)amino]-2-methylpyrazol-3-yl]oxybenzonitrile (Compound No. 875)

[Chem. 69]

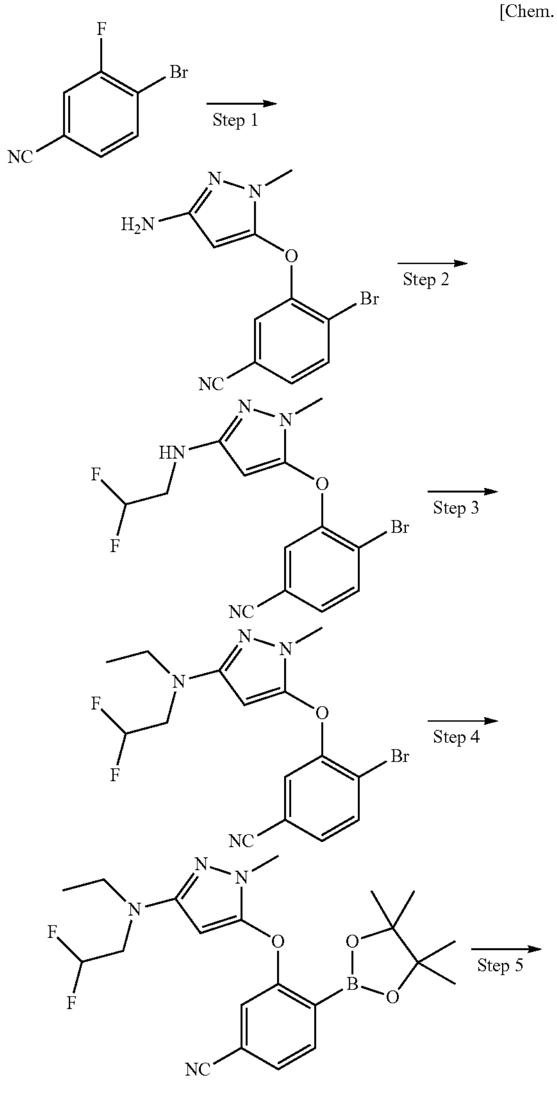

-continued

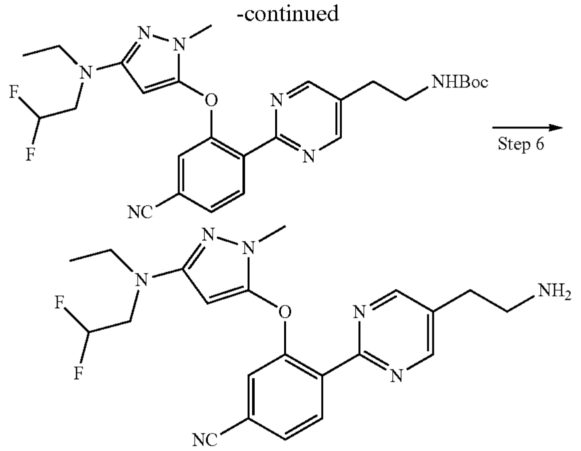

Step 1: 3-(5-Amino-2-methylpyrazol-3-yl)oxy-4-bromobenzonitrile

4-Bromo-3-fluorobenzonitrile (3.0 g, 15 mmol) and 5-amino-2-methyl-4H-pyrazol-3-one (1.7 g, 15 mmol) were dissolved in DMA (40 mL), and potassium carbonate (4.14 g, 30.0 mmol) was added to the solution, and the mixture was stirred at 120° C. for 2 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (444 mg, 10%).

MS: m/z 292.9 $(M+H)^+$.

$^1$H-NMR ($CDCl_3$) δ: 7.76 (1H, d, J=8.2 Hz), 7.36 (1H, d, J=1.8 Hz), 7.32 (1H, dd, J=8.0, 1.6 Hz), 5.11 (1H, s), 3.63 (2H, brs), 3.57 (3H, s).

Step 2: 4-Bromo-3-[5-(2,2-difluoroethylamino)-2-methylpyrazol-3-yl]oxybenzonitrile 3-(5-Amino-2-methylpyrazol-3-yl)oxy-4-bromobenzonitrile (1.47 g, 5.00 mmol) was dissolved in DMA (10 mL), then to the solution, 1,1-difluoro-2-iodoethane (1.44 g, 7.50 mmol) and N,N-diisopropylethylamine (1.74 mL, 10.0 mmol) were added, and the mixture was stirred at 140° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (1.10 g, 62%).

MS: m/z 359.0 $(M+H)^+$.

Step 3: 4-Bromo-3-[5-[2,2-difluoroethyl(ethyl)amino]-2-methylpyrazol-3-yl]oxybenzonitrile 4-Bromo-3-[5-(2,2-difluoroethylamino)-2-methylpyrazol-3-yl]oxybenzonitrile (1.10 g, 3.09 mmol) was dissolved in DMA (10 mL), then to the solution, iodoethane (963 mg, 6.17 mmol) and N,N-diisopropylethylamine (1.08 mL, 6.17 mmol) were added, and the mixture was stirred at 120° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (766 mg, 64%).

MS: m/z 385.0 $(M+H)^+$.

Step 4: 3-[5-[2,2-Difluoroethyl(ethyl)amino]-2-methylpyrazol-3-yl]oxy-4-(4,4,5,5-tetramethyl-1,3,2-dioxaborolan-2-yl)benzonitrile 4-Bromo-3-[5-[2,2-difluoroethyl(ethyl)amino]-2-methylpyrazol-3-yl]oxybenzonitrile (766 mg, 1.99 mmol) was dissolved in 1,4-dioxane (10 mL), then to the solution, bis(pinacolato)diboron (758 mg, 2.98 mmol), [1,1'-bis(diphenylphosphino)ferrocene]palladium dichloride (72.8 mg, 0.0995 mmol), and potassium acetate (391 mg, 3.98 mmol) were added, and the mixture was stirred at 100° C. for 2 hours. The reaction mixture was cooled to room temperature, filtered through Celite, and then the solution was concentrated under reduced pressure. The crude product was used in the next reaction without further purification.

MS: m/z 433.2 $(M+H)^+$.

Step 5: tert-Butyl N-[2-[2-[4-cyano-2-[5-[2,2-difluoroethyl(ethyl)amino]-2-methylpyrazol-3-yl]oxyphenyl]pyrimidin-5-yl]ethyl]carbamate The crude product obtained in Step 4 was dissolved in 1,4-dioxane (10 mL), then to the solution, tert-butyl N-[2-(2-chloropyrimidin-5-yl)ethyl]carbamate (462 mg, 1.79 mmol), tetrakis(triphenylphosphine)palladium (115 mg, 0.0995 mmol), potassium carbonate (550 mg, 3.98 mmol) and water (3 mL) were added, and the mixture was stirred at 100° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (648 mg, 62%).

MS: m/z 528.2 $(M+H)^+$.

Step 6: 4-[5-(2-Aminoethyl)pyrimidin-2-yl]-3-[5-[2,2-difluoroethyl(ethyl)amino]-2-methylpyrazol-3-yl]oxybenzonitrile tert-Butyl N-[2-[2-[4-cyano-2-[5-[2,2-difluoroethyl(ethyl)amino]-2-methylpyrazol-3-yl]oxyphenyl]pyrimidin-5-yl]ethyl]carbamate (648 mg, 1.23 mmol) was dissolved in 1,4-dioxane (4 mL), then a 4 M hydrochloric acid/1,4-dioxane solution (2 mL) was added dropwise at 0° C. to the mixture, then the temperature of the mixture was raised to room temperature, and the mixture was stirred for 2 hours. The reaction mixture was concentrated under reduced pressure, and the solid obtained was vacuum dried to obtain a hydrochloride of the target compound (642 mg).

Exact MS: 427.2

Obs. MS $(M+H)^+$: 428.3

Example 24

4-[5-(Aminomethyl)pyrimidin-2-yl]-3-(2-methyl-5-pyrazin-2-ylpyrazol-3-yl)oxybenzonitrile (Compound No. 931)

[Chem. 70]

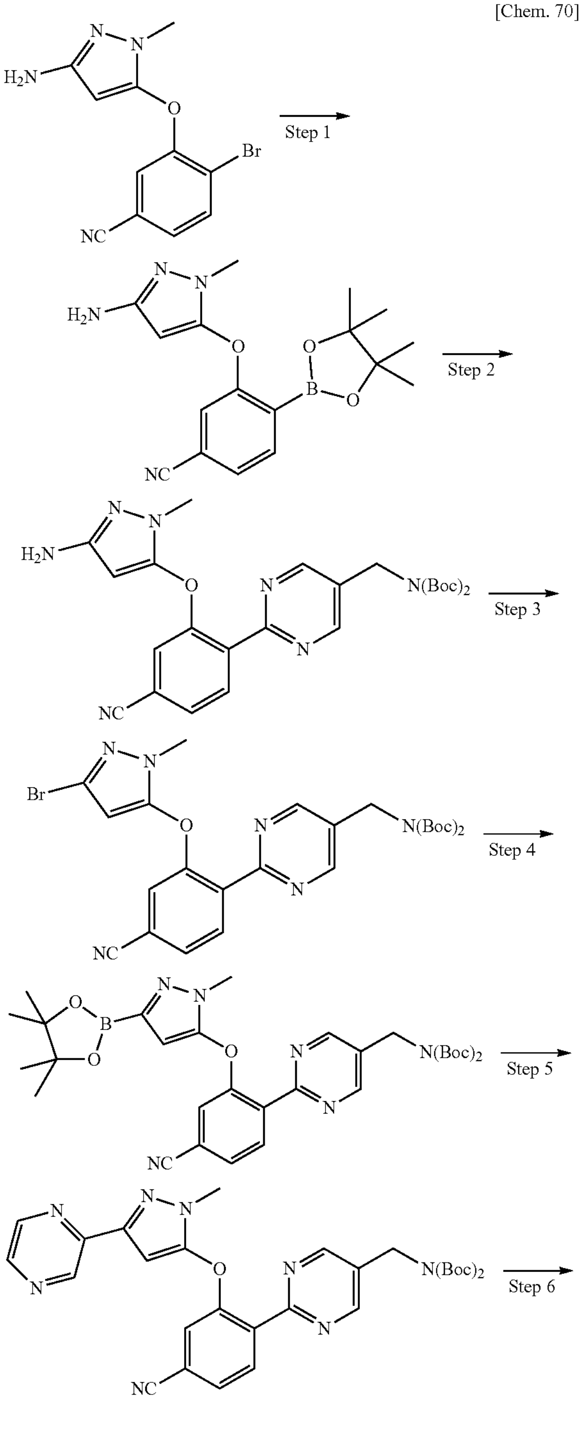

-continued

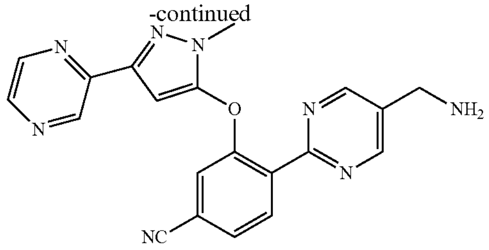

Step 1: 3-(5-Amino-2-methylpyrazol-3-yl)oxy-4-(4,4,5,5-tetramethyl-1,3,2-dioxaborolan-2-yl)benzonitrile The intermediate of 3-(5-amino-2-methylpyrazol-3-yl)oxy-4-bromobenzonitrile (879 mg, 3.00 mmol) obtained in Example 23 was dissolved in 1,4-dioxane (7.5 mL), then to the solution, bis(pinacolato)diboron (1.52 g, 6.00 mmol), bis(triphenylphosphine)palladium dichloride (211 mg, 0.300 mmol), and potassium acetate (589 mg, 6.00 mmol) were added, and the mixture was stirred at 110° C. for 2 hours. The reaction mixture was cooled to room temperature, filtered through Celite, and the filtrate was concentrated under reduced pressure. The concentrated crude product was used in the next reaction without further purification.

Step 2: tert-Butyl N-[[2-[2-(5-amino-2-methylpyrazol-3-yl)oxy-4-cyanophenyl]pyrimidin-5-yl]methyl]-N-[(2-methylpropan-2-yl)oxycarbonyl]carbamate To a solution of the crude product in 1,4-dioxane (15 mL) obtained in Step 1, tert-butyl N-[(2-chloropyrimidin-5-yl)methyl]-N-[(2-methylpropan-2-yl)oxycarbonyl]carbamate (1.03 g, 3.00 mmol), [1,1'-bis(diphenylphosphino)ferrocene] palladium dichloride (220 mg, 0.300 mmol), potassium carbonate (1.24 g, 9.00 mmol), and water (3 mL) were added, and the mixture was stirred at 100° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (1.48 g, containing impurities).

MS: m/z 522.3 $(M+H)^+$.

Step 3: tert-Butyl N-[[2-[2-(5-bromo-2-methylpyrazol-3-yl)oxy-4-cyanophenyl]pyrimidin-5-yl]methyl]-N-[(2-methylpropan-2-yl)oxycarbonyl]carbamate tert-Butyl N-[[2-[2-(5-amino-2-methylpyrazol-3-yl)oxy-4-cyanophenyl]pyrimidin-5-yl]methyl]-N-[(2-methylpropan-2-yl)oxycarbonyl]carbamate (1.48 g, 2.83 mmol) was dissolved in acetonitrile (28 mL), then isoamyl nitrite (488 mg, 4.17 mmol) and copper(I) bromide (476 mg, 3.32 mmol) were added to the solution, and the mixture was stirred at room temperature overnight. Water was added to the reaction mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (289 mg).

MS: m/z 585.2 $(M+H)^+$.

Step 4: tert-Butyl N-[[2-[4-cyano-2-[2-methyl-5-(4,4,5,5-tetramethyl-1,3,2-dioxaborolan-2-yl)pyrazol-3-yl]oxyphenyl]pyrimidin-5-yl]methyl]-N-[(2-methylpropan-2-yl)oxycarbonyl]carbamate tert-Butyl N-[[2-[2-(5-bromo-2-methylpyrazol-3-yl)oxy-4-cyanophenyl]pyrimidin-5-yl]methyl]-N-[(2-methylpropan-2-yl)oxycarbonyl]carbamate (40 mg, 0.068 mmol) was dissolved in 1,4-dioxane (0.2 mL), then to the solution, bis(pinacolato)diboron (26.0 mg, 0.102 mmol), [1,1'-bis(diphenylphosphino)ferrocene]palladium dichloride (5.0 mg, 6.8 μmol) and potassium acetate (20.1 mg, 0.205 mmol) were added, and the mixture was stirred at 110° C. for 2 hours. The reaction mixture was cooled to room temperature, filtered through Celite, and then concentrated under reduced pressure. The crude product obtained was used in the next reaction without further purification.

Step 5: tert-Butyl N-[[2-[4-cyano-2-(2-methyl-5-pyrazin-2-ylpyrazol-3-yl)oxyphenyl]pyrimidin-5-yl]methyl]-N-[(2-methylpropan-2-yl)oxycarbonyl]carbamate An aliquot (24 mg) of the crude product obtained in Step 4 was dissolved in 1,4-dioxane (0.19 mL), then to the solution, 2-chloropyrazine (25.7 mg, 0.076 mmol), [1,1'-bis(diphenylphosphino)ferrocene]palladium dichloride (2.8 mg, 3.8 μmol), potassium carbonate (16 mg, 0.11 mmol) and water (0.038 mL) were added, and the mixture was stirred at 100° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was used in the next reaction without further purification.

Step 6: 4-[5-(Aminomethyl)pyrimidin-2-yl]-3-(2-methyl-5-pyrazin-2-ylpyrazol-3-yl)oxybenzonitrile TFA (0.5 mL) was added to the crude product obtained in Step 5, and the mixture was stirred at room temperature for 1 hour. The reaction mixture was concentrated under reduced pressure, and the crude product was purified by HPLC to obtain the target compound (5.25 mg).

Exact MS: 384.1

Obs. MS $(M+H)^+$: 385.2

Example 25

2-[2-[4-Fluoro-2-[3-methyl-1-(2-methylpropyl)pyrazol-4-yl]oxyphenyl]pyrimidin-5-yl]ethanamine (Compound No. 966) (Target compound) and 2-[2-[4-fluoro-2-[5-methyl-1-(2-methylpropyl)pyrazol-4-yl]oxyphenyl]pyrimidin-5-yl]ethanamine (Compound No. 967) (Regioisomer)

[Chem. 71]

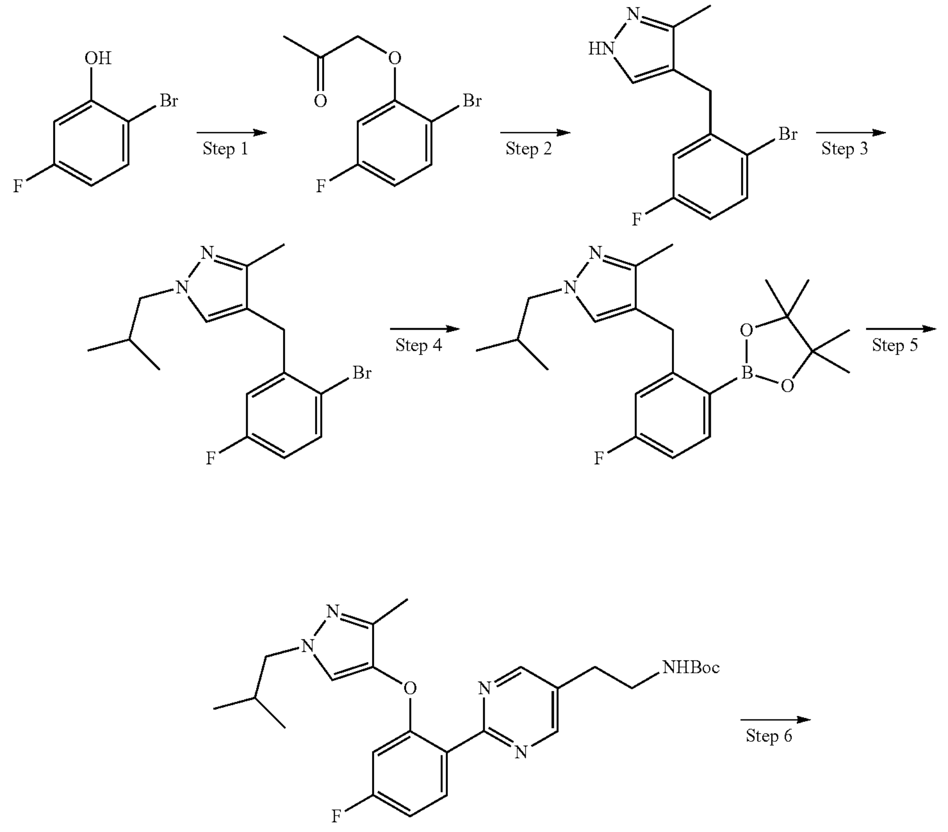

-continued

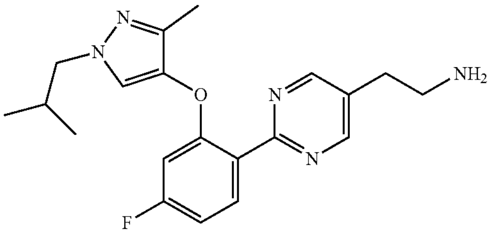

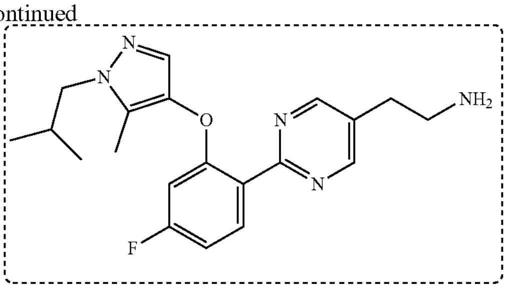

Step 1: 1-(2-Bromo-5-fluorophenoxy)propan-2-one

2-Bromo-5-fluorophenol (2.29 g, 12.0 mmol) and 1-bromopropan-2-one (1.97 g, 14.4 mmol) were dissolved in DMF (20 mL), potassium carbonate (3.32 g, 24.0 mmol) was added to the solution, and the mixture was heated and stirred at 100° C. After completion of the reaction, the reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (2.51 g, 85%).

Step 2: 3-(2-Bromo-5-fluorophenoxy)-4-(dimethylamino)but-3-en-2-one

To 1-(2-bromo-5-fluorophenoxy)propan-2-one (2.73 g, 11.0 mmol), N,N-dimethylformamide dimethylacetal (1.58 g, 13.2 mmol) was added, the mixture was stirred at 80° C. overnight. After cooling the reaction mixture to room temperature, acetic acid (20 mL) and hydrazine monohydrate (826 mg, 16.5 mmol) were added to the mixture, and the mixture was stirred at 100° C. for 3 hours. The reaction mixture was cooled to room temperature, water was added to the mixture, and the mixture was extracted with ethyl acetate. The organic layer was washed with saturated aqueous sodium hydrogen carbonate and saturated brine and dried over anhydrous sodium sulfate, and the solution was concentrated under reduced pressure. The crude product was purified by silica gel column chromatography to obtain the target compound (2.41 g, 81%).

MS: m/z 271.0 $(M+H)^+$.

Step 3: 4-(2-Bromo-5-fluorophenoxy)-3-methyl-1-(2-methylpropyl)pyrazole

To 4-(2-bromo-5-fluorophenoxy)-3-methyl-1H-pyrazole (270 mg, 1.0 mmol), DMSO (2 mL), 1-bromo-2-methylpropane (160 mg, 1.2 mmol), and potassium carbonate (280 mg, 2.0 mmol) were added, and the mixture was stirred at 100° C. for 5 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain a mixture (185 mg) of the target compound and its regioisomer. Regioisomers were separated by HPLC purification after the last step.

MS: m/z 327.1 $(M+H)^+$.

$^1$H-NMR (DMSO-$d_6$) δ: 7.80 (1H, s), 7.72 (1H, dd, J=9.2, 2.8 Hz), 6.93-6.88 (I H, m), 6.60 (1H, dd, J=10.4, 2.8 Hz), 3.81 (1H, d, J=7.2 Hz), 2.14-2.07 (1H, m), 1.98 (3H, s), 0.85 (6H, d, J=6.8 Hz).

Step 4: 4-[5-Fluoro-2-(4,4,5,5-tetramethyl-1,3,2-dioxaborolan-2-yl) phenoxy]-3-methyl-1-(2-methylpropyl)pyrazole The isomer mixture (185 mg, 0.565 mmol) obtained in Step 3 was dissolved in 1,4-dioxane (1.1 mL), then to the solution, bis(pinacolato)diboron (215 mg, 0.848 mmol), [1,1'-bis(diphenylphosphino)ferrocene]palladium dichloride (20.7 mg, 0.0283 mmol) and potassium acetate (111 mg, 1.13 mmol) were added, and the mixture was stirred at 100° C. for 2 hours. The reaction mixture was cooled to room temperature, filtered through Celite, and then concentrated under reduced pressure. The crude product was used in the next reaction without further purification.

Step 5: tert-Butyl N-[2-[2-[4-fluoro-2-[3-methyl-1-(2-methylpropyl)pyrazol-4-yl]oxyphenyl]pyrimidin-5-yl]ethyl]carbamate An aliquot (106 mg) of the crude product obtained in Step 4 was dissolved in 1,4-dioxane (1 mL), then to the solution, tert-butyl N-[2-(2-chloropyrimidin-5-yl)ethyl]carbamate (87.6 mg, 0.340 mmol), tetrakis(triphenylphosphine)palladium (16.4 mg, 0.0142 mmol), potassium carbonate (78.3 mg, 0.566 mmol), and water (0.3 mL) were added, and the mixture was stirred at 100° C. for 2 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was used in the next reaction without further purification.

Step 6: 2-[2-[4-Fluoro-2-[3-methyl-1-(2-methylpropyl)pyrazol-4-yl]oxyphenyl]pyrimidin-5-yl] ethanamine (Target compound) and 2-[2-[4-fluoro-2-[5-methyl-1-(2-methylpropyl)pyrazol-4-yl] oxyphenyl]pyrimidin-5-yl]ethanamine (Regioisomer)

The crude product obtained in Step 5 was dissolved in dichloromethane (1 mL), TFA (0.5 mL) was added to the solution, and the mixture was stirred at room temperature for 1 hour. The reaction mixture was concentrated under reduced pressure, and the crude product was purified by HPLC to obtain the target compound (11.82 mg) and its regioisomer (10.77 mg).

Exact MS: 369.2

Obs. MS $(M+H)^+$: 370.4 (Compound No. 966), 370.3 (Compound No. 967)

Example 26

4-[5-(Aminomethyl)pyrimidin-2-yl]-3-(2-methyl-5-morpholin-4-ylpyrazole-3-carbonyl)benzonitrile (Compound No. 1028)

[Chem. 72]

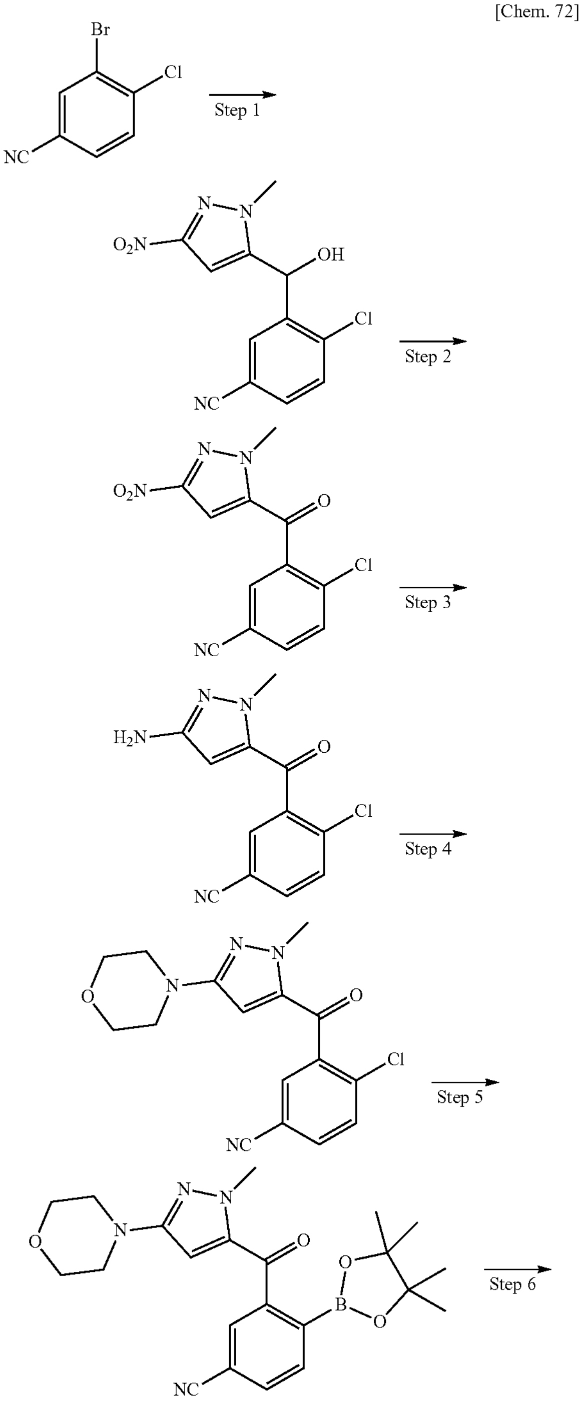

-continued

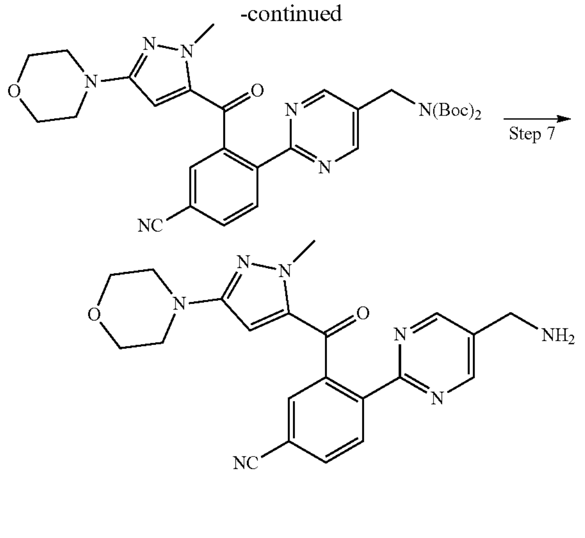

Step 1: 4-Chloro-3-[hydroxy-(2-methyl-5-nitropyrazol-3-yl)methyl]benzonitrile 3-Bromo-4-chlorobenzonitrile (5.69 g, 26.3 mmol) was dissolved in THF (50 mL), then to the solution, isopropylmagnesium chloride lithium chloride complex (14% solution in THF, 20 mL, 26.27 mmol) was added dropwise at 0° C., and the mixture was stirred at the same temperature for 30 minutes. A solution (5 mL) of 2-methyl-5-nitropyrazole-3-carbaldehyde (3.13 g, 20.2 mmol) in THF was added dropwise to this reaction mixture, the temperature of the mixture was raised to room temperature, and the mixture was stirred for 1 hour. 1 M hydrochloric acid was added to the reaction mixture, the mixture was stirred, and then the mixture was extracted with ethyl acetate. The organic layer was washed with saturated brine and dried over anhydrous magnesium sulfate, and the solution was concentrated under reduced pressure. The crude product was purified by silica gel column chromatography to obtain the target compound (4.85 g, 82%).

MS: m/z 293.1 $(M+H)^+$.

$^1$H-NMR ($CDCl_3$) δ: 8.06 (1H, s), 7.67 (1H, dd, J=8.2, 1.8 Hz), 7.56 (1H, d, J=8.2 Hz), 6.39 (1H, s), 6.23 (1H, s), 4.10 (3H, s), 2.97 (1H, s).

Step 2: 4-Chloro-3-(2-methyl-5-nitropyrazole-3-carbonyl)benzonitrile

Dess-Martin reagent (7.73 g, 18.2 mmol) was added to a solution (83 mL) of 4-chloro-3-[hydroxy-(2-methyl-5-nitropyrazol-3-yl)methyl]benzonitrile (4.85 g, 16.6 mmol) in dichloromethane, and the mixture was stirred at room temperature for 2 hours. A saturated aqueous sodium thiosulfate solution and a saturated aqueous sodium hydrogen carbonate solution were added to the reaction mixture, and the mixture was stirred and then extracted with dichloromethane. The organic layer was washed with saturated brine and dried over anhydrous magnesium sulfate, and the solution was concentrated under reduced pressure. The crude product was used in the next reaction without further purification.

MS: m/z 291.0 $(M+H)^+$.

$^1$H-NMR ($DMSO-d_6$) δ: 8.21 (1H, d, J=2.3 Hz), 8.11 (1H, dd, J=8.5, 2.1 Hz), 7.88 (1H, d, J=8.2 Hz), 7.58 (1H, s), 4.27 (3H, s).

Step 3: 3-(5-Amino-2-methylpyrazole-3-carbonyl)-4-chlorobenzonitrile

The crude product obtained in Step 2 was suspended in a mixed solvent (66 mL) of ethanol/water (=1/1), then to the suspension, iron powder (2.78 g, 49.7 mmol) and ammonium chloride (2.66 g, 49.74 mol) were added, and the mixture was stirred at 80° C. for 2 hours. The reaction mixture was cooled to room temperature and filtered through Celite, and then most of the ethanol was evaporated under reduced pressure. The residue was extracted by adding ethyl acetate, the organic layer was washed with saturated brine and dried over anhydrous magnesium sulfate, and the solution was concentrated under reduced pressure. The crude product was purified by silica gel column chromatography to obtain the target compound (3.76 g, 87%).

MS: m/z 261.1 $(M+H)^+$.

$^1$H-NMR ($CDCl_3$) δ: 7.72-7.70 (2H, m), 7.60 (1H, d, J=9.1 Hz), 5.67 (1H, s), 4.11 (3H, s), 3.73 (2H, brs).

Step 4: 4-Chloro-3-(2-methyl-5-morpholin-4-ylpyrazole-3-carbonyl)benzonitrile 3-(5-Amino-2-methylpyrazole-3-carbonyl)-4-chlorobenzonitrile (449 mg, 1.72 mmol) was dissolved in NMP (4.3 mL), then to the solution, bis(2-bromoethyl)ether (439 mg, 1.89 mmol) and potassium iodide (28.6 mg, 0.172 mmol) were added, and the mixture was stirred at 110° C. for 16 hours. The reaction mixture was cooled to room temperature, ethyl acetate and water were added to the mixture, and the mixture was extracted. The organic layer was washed with saturated brine and dried over anhydrous magnesium sulfate, and the solution was concentrated under reduced pressure. The crude product was purified by silica gel column chromatography to obtain the target compound (391 mg, 69%).

MS: m/z 331.1 $(M+H)^+$.

$^1$H-NMR ($CDCl_3$) δ: 7.73-7.71 (2H, m), 7.61 (1H, dd, J=7.5, 1.6 Hz), 5.68 (1H, s), 4.15 (3H, s), 3.80 (4H, t, J=4.8 Hz), 3.14 (4H, t, J=4.8 Hz).

Step 5: 3-(2-Methyl-5-morpholin-4-ylpyrazole-3-carbonyl)-4-(4,4,5,5-tetramethyl-1,3,2-dioxaborolan-2-yl)benzonitrile 4-Chloro-3-(2-methyl-5-morpholin-4-ylpyrazole-3-carbonyl)benzonitrile (391 mg, 1.18 mmol) was dissolved in 1,4-dioxane (4 mL), then to the solution, bis(pinacolato) diboron (451 mg, 1.78 mmol), bis(tricyclohexylphosphine) palladium dichloride (87.3 mg, 0.118 mmol) and potassium acetate (348 mg, 3.55 mmol) were added, and the mixture was stirred at 110° C. for 2 hours. The reaction mixture was cooled to room temperature and filtered through Celite, and then the solution was concentrated under reduced pressure. The crude product was used in the next reaction without further purification.

MS: m/z 423.2 $(M+H)^+$.

Step 6: tert-Butyl N-[[2-[4-cyano-2-(2-methyl-5-morpholin-4-ylpyrazole-3-carbonyl)phenyl]pyrimidin-5-yl]methyl]-N-[(2-methylpropan-2-yl)oxycarbonyl]carbamate An aliquot (166 mg) of the crude product obtained in Step 5 was dissolved in 1,4-dioxane (1 mL), then to the solution, tert-butyl N-[(2-chloropyrimidin-5-yl)methyl]-N-[(2-methylpropan-2-yl)oxycarbonyl]carbamate (50.0 mg, 0.145 mmol), tetrakis(triphenylphosphine)palladium (16.8 mg, 0.0145 mmol), potassium carbonate (60.3 mg, 0.436 mmol), and water (0.1 mL) were added, and the mixture was stirred at 100° C. for 1 hour. The reaction mixture was cooled to room temperature and filtered through Celite, and then the solution was concentrated under reduced pressure. The crude product was used in the next reaction without further purification.

MS: m/z 604.3 $(M+H)^+$.

$^1$H-NMR ($CDCl_3$) δ: 8.70 (2H, s), 8.51 (1H, d, J=8.2 Hz), 7.90 (1H, d, J=8.2 Hz), 7.79 (1H, s), 5.38 (1H, S), 4.73 (2H, s), 4.14 (3H, s), 3.72 (4H, t, J=4.8 Hz), 3.00 (4H, t, J=4.8 Hz), 1.48 (18H, s).

Step 7: 4-[5-(Aminomethyl)pyrimidin-2-yl]-3-(2-methyl-5-morpholin-4-ylpyrazole-3-carbonyl)benzonitrile Dichloromethane (1 mL) and TFA (0.5 mL) were added to the crude product obtained in Step 6, and the mixture was stirred at room temperature for 30 minutes. The reaction mixture was concentrated under reduced pressure, and the crude product was purified by HPLC to obtain the target compound (34.2 mg).

Exact MS: 403.2

Obs. MS $(M+H)^+$: 404.3 $^1$H-NMR (DMSO-$d_6$) δ: 8.93 (2H, s), 8.49 (1H, d, J=7.8 Hz), 8.32 (3H, brs), 8.18 (1H, dd, J=8.2, 1.8 Hz), 8.10 (1H, d, J=1.8H), 5.72 (1H, S), 4.10 (2H, d, J=5.9 Hz), 4.02 (3H, S), 3.57 (4H, t, J=4.8 Hz), 2.92 (4H, t, J=4.6 Hz).

Example 27

4-[5-(Aminomethyl)pyrimidin-2-yl]-3-(5-tert-butyl-2-methylpyrazole-3-carbonyl)benzonitrile (Compound No. 1030)

[Chem. 73]

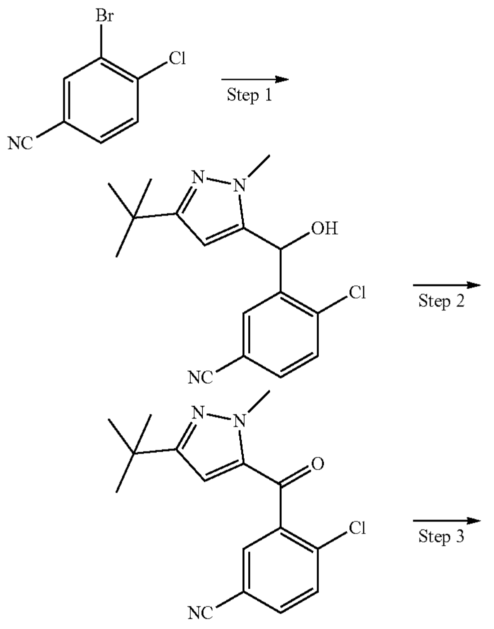

-continued

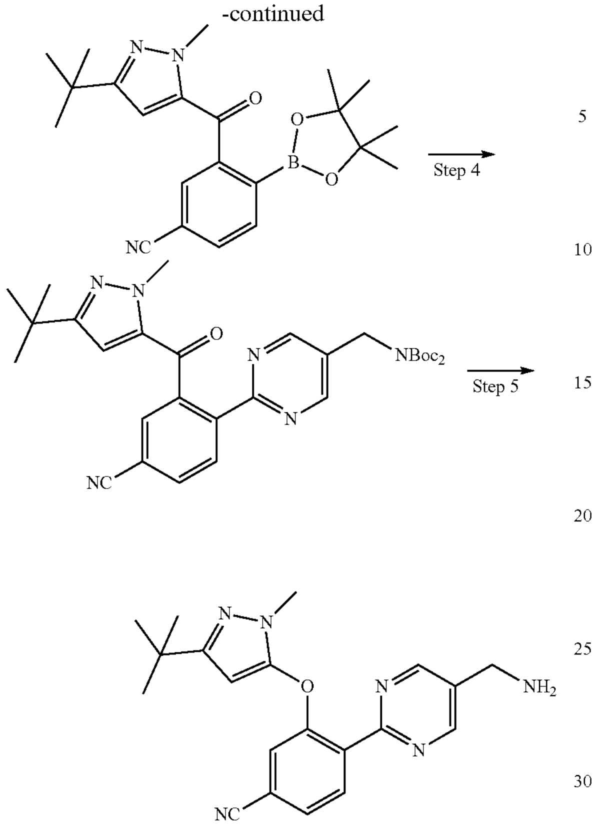

Step 1: 3-[(5-tert-Butyl-2-methylpyrazol-3-yl)-hydroxymethyl]-4-chlorobenzonitrile 3-Bromo-4-chlorobenzonitrile (3.28 g, 15.2 mmol) was dissolved in THF (50 mL), and isopropylmagnesium chloride lithium chloride complex (14% solution in THF, 13 mL, 16.7 mmol) was added dropwise to the solution at 0° C., and the mixture was stirred at the same temperature for 15 minutes. A solution (5 mL) of 5-tert-butyl-2-methylpyrazole-3-carbaldehyde (2.52 g, 15.2 mmol) in THF was added dropwise to the reaction solution, then the temperature of the mixture was raised to room temperature, and the mixture was stirred for 1.5 hours. 1 M Hydrochloric acid was added to the reaction mixture, the mixture was stirred, and the mixture was extracted with ethyl acetate. The organic layer was washed with saturated brine and dried over anhydrous magnesium sulfate, and the solution was concentrated under reduced pressure. Ethanol was added to the crude product, the mixture was stirred, and then the precipitated solid was collected by filtration through a glass filter, and vacuum dried to obtain the target compound (2.22 g, 48%).

MS: m/z 304.2 $(M+H)^+$.

$^1H$-NMR ($CDCl_3$) δ: 8.02 (1H, d, J=1.8 Hz), 7.60 (1H, dd, J=8.2, 1.8 Hz), 7.49 (1H, d, J=8.2 Hz), 6.15 (1H, d, J=5.0 Hz), 5.62 (1H, s), 3.90 (3H, s), 2.49 (1H, d, J=5.0 Hz), 1.23 (9H, s).

Step 2: 3-(5-tert-Butyl-2-methylpyrazole-3-carbonyl)-4-chlorobenzonitrile

Dess-Martin reagent (768 mg, 1.81 mmol) was added to a solution (16 mL) of 3-[(5-tert-butyl-2-methylpyrazol-3-yl)-hydroxymethyl]-4-chlorobenzonitrile (500 mg, 1.65 mmol) in dichloromethane, and the mixture was stirred at room temperature for 1.5 hours. A saturated aqueous sodium thiosulfate solution and a saturated aqueous sodium hydrogen carbonate solution were added to the reaction mixture, and the mixture was stirred and then extracted with ethyl acetate. The organic layer was washed with saturated brine and dried over anhydrous magnesium sulfate, and the solution was concentrated under reduced pressure. The crude product was purified by silica gel column chromatography to obtain the target compound (440 mg, 89%).

MS: m/z 302.1 $(M+H)^+$.

Step 3: 3-(5-tert-Butyl-2-methylpyrazole-3-carbonyl)-4-(4,4,5,5-tetramethyl-1,3,2-dioxaborolan-2-yl) benzonitrile 3-(5-tert-Butyl-2-methylpyrazole-3-carbonyl)-4-chlorobenzonitrile (440 mg, 1.46 mmol) was dissolved in 1,4-dioxane (4.9 mL), then to the solution, bis(pinacolato) diboron (556 mg, 2.19 mmol), bis(tricyclohexylphosphine) palladium dichloride (53.9 mg, 0.073 mmol) and potassium acetate (430 mg, 4.38 mmol) were added, and the mixture was stirred at 110° C. for 3 hours. The reaction mixture was cooled to room temperature and filtered through Celite, and then the solution was concentrated under reduced pressure. The crude product was used in the next reaction without further purification.

MS: m/z 394.3 $(M+H)^+$.

Step 4: tert-Butyl N-[[2-[2-(5-tert-butyl-2-methylpyrazole-3-carbonyl)-4-cyanophenyl]pyrimidin-5-yl]methyl]-N-[(2-methylpropan-2-yl)oxycarbonyl] carbamate An aliquot (115 mg) of the crude product obtained in Step 3 was dissolved in 1,4-dioxane (1 mL), then to the solution, tert-butyl N-[(2-chloropyrimidin-5-yl)methyl]-N-[(2-methylpropan-2-yl)oxycarbonyl]carbamate (50.0 mg, 0.145 mmol), tetrakis(triphenylphosphine)palladium (16.8 mg, 0.0145 mmol), potassium carbonate (60.3 mg, 0.436 mmol), and water (0.1 mL) was added, and the mixture was stirred at 100° C. for 1 hour. The reaction solution was cooled to room temperature and filtered through Celite, and then the solution was concentrated under reduced pressure. The crude product was used in the next reaction without further purification.

MS: m/z 575.4 $(M+H)^+$.

Step 5: 4-[5-(Aminomethyl)pyrimidin-2-yl]-3-(5-tert-butyl-2-methylpyrazole-3-carbonyl)benzonitrile Dichloromethane (1 mL) and TFA (0.5 mL) were added to the crude product obtained in Step 4, and the mixture was stirred at room temperature for 30 minutes. The reaction mixture was concentrated under reduced pressure, and the crude product was purified by HPLC to obtain the target compound (9.7 mg).

Exact MS: 374.2

Obs. MS $(M+H)^+$: 375.4

Example 28

4-[5-(2-Aminoethyl)pyrimidin-2-yl]-3-(2-methyl-6-morpholin-4-ylpyridine-4-carbonyl)benzonitrile (Compound No. 1042)

[Chem. 74]

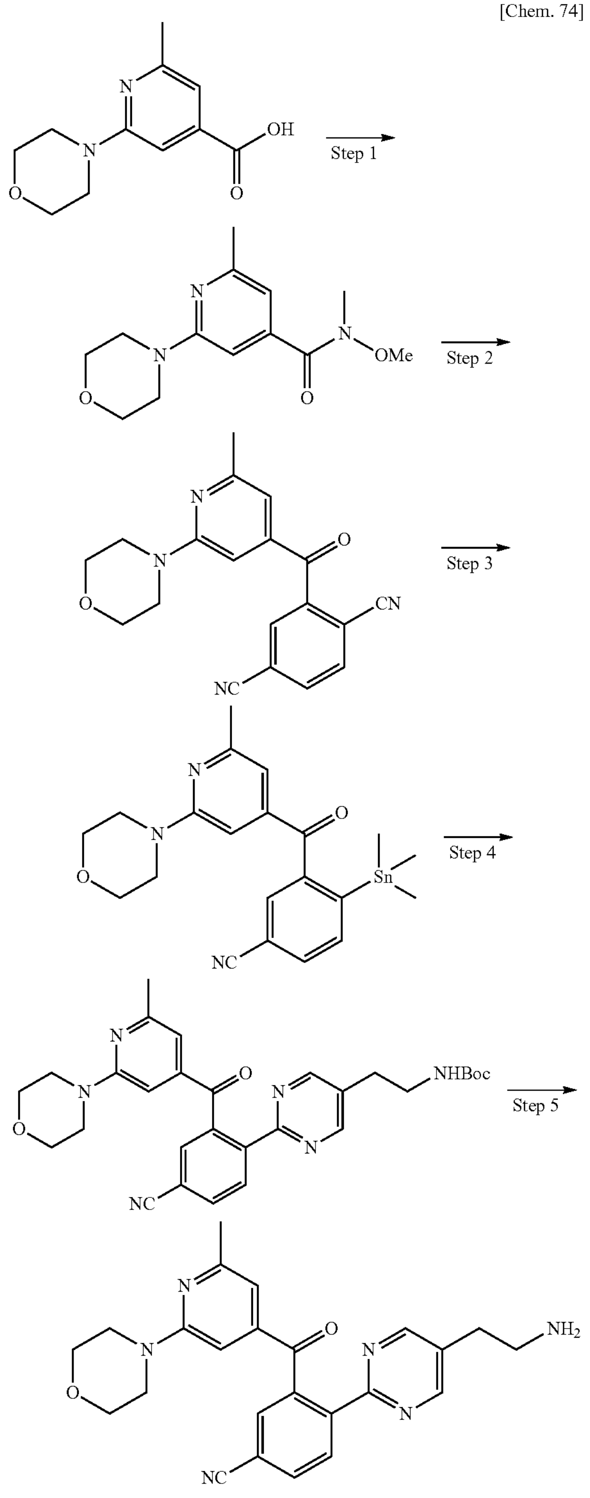

Step 1: N-Methoxy-N,2-dimethyl-6-morpholin-4-ylpyridine-4-carboxamide

2-Methyl-6-morpholin-4-ylpyridine-4-carboxylic acid (235 mg, 1.43 mmol) was dissolved in DMF (5.3 mL), then to the solution, N,O-dimethylhydroxylamine hydrochloride (124 mg, 1.27 mmol), HATU (524 mg, 1.38 mmol) and triethylamine (0.45 mL, 3.18 mmol) were added, and the mixture was stirred at room temperature for 1 hour. Water was added to the reaction mixture, and the mixture was extracted with ethyl acetate. The organic layer was dried over anhydrous magnesium sulfate and the solution was concentrated under reduced pressure. Then, the crude product was purified by silica gel column chromatography to obtain the target compound (174 mg, 62%).

MS: m/z 266.1 $(M+H)^+$.

Step 2: 4-Chloro-3-(2-methyl-6-morpholin-4-ylpyridine-4-carbonyl)benzonitrile

3-Bromo-4-chlorobenzonitrile (284 g, 1.31 mmol) was dissolved in THF (3.3 mL), and isopropylmagnesium chloride lithium chloride complex (14% solution in THF, 1.0 mL, 1.31 mmol) was added dropwise to the solution at 0° C., and the mixture was stirred at the same temperature for 30 minutes. A solution (1 mL) of N-methoxy-N,2-dimethyl-6-morpholin-4-ylpyridine-4-carboxamide (174 mg, 0.656 mmol) in THF was added dropwise to the reaction mixture, and then the temperature of the mixture was raised to room temperature, and the mixture was stirred for 1.5 hours. A saturated aqueous ammonium chloride solution was added to the reaction mixture, and the mixture was stirred, and then extracted with ethyl acetate. The organic layer was washed with saturated brine and dried over anhydrous magnesium sulfate, and the solution was concentrated under reduced pressure. The crude product was purified by silica gel column chromatography to obtain the target compound (67.1 mg, 30%).

MS: m/z 342.1 $(M+H)^+$.

Step 3: 3-(2-Methyl-6-morpholin-4-ylpyridine-4-carbonyl)-4-trimethylstannylbenzonitrile 4-Chloro-3-(2-methyl-6-morpholin-4-ylpyridine-4-carbonyl)benzonitrile (67.1 mg, 0.196 mmol) was dissolved in 1,4-dioxane (1 mL), then to the solution, hexamethylditin (96.5 mg, 0.294 mmol) and tetrakis(triphenylphosphine)palladium (22.7 mg, 0.0196 mmol) were added, and the mixture was stirred at 110° C. for 3 hours. The reaction solution was cooled to room temperature and filtered through Celite, and then the solution was concentrated under reduced pressure. The crude product was purified by silica gel column chromatography to obtain the target compound (21.3 mg, 23%).

MS: m/z 472.1 $(M+H)^+$.

Step 4: tert-Butyl N-[2-[2-[4-cyano-2-(2-methyl-6-morpholin-4-ylpyridine-4-carbonyl)phenyl]pyrimidin-5-yl]ethyl]carbamate 3-(2-Methyl-6-morpholin-4-ylpyridine-4-carbonyl)-4-trimethylstannylbenzonitrile (21.3 mg, 0.0453 mmol) was dissolved in 1,4-dioxane (1 mL), then to the solution, tert-butyl N-[2-(2-chloropyrimidin-5-yl)ethyl]carbamate (30.0 mg, 0.116 mmol), tetrakis(triphenylphosphine)palladium (5.2 mg, 4.53 μmol), and copper(I) iodide (1.7 mg, 9.06 μmol) was added, and the mixture was stirred at 110°

C. for 2 hours. The reaction mixture was cooled to room temperature and filtered through Celite, and then the solution was concentrated under reduced pressure. The crude product was used in the next reaction without further purification.

MS: m/z 529.3 $(M+H)^+$.

Step 5: 4-[5-(2-Aminoethyl)pyrimidin-2-yl]-3-(2-methyl-6-morpholin-4-ylpyridine-4-carbonyl)benzonitrile Dichloromethane (1.0 mL) and TFA (0.5 mL) were added to the crude product obtained in Step 4, and the mixture was stirred at room temperature for 30 minutes. The reaction mixture was concentrated under reduced pressure, and the crude product was purified by HPLC to obtain the target compound (5.0 mg, 26%).

Exact MS: 428.2

Obs. MS $((M+H)^+$: 429.3

Example 29

4-[5-(Aminomethyl)pyrimidin-2-yl]-3-(4-methyl-2-morpholin-4-yl-1,3-thiazole-5-carbonyl)benzonitrile (Compound No. 1064)

[Chem. 75]

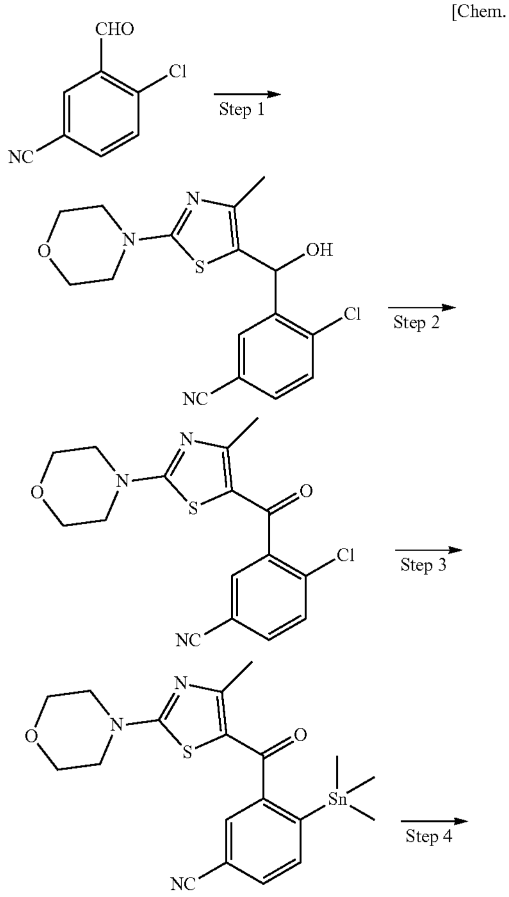

-continued

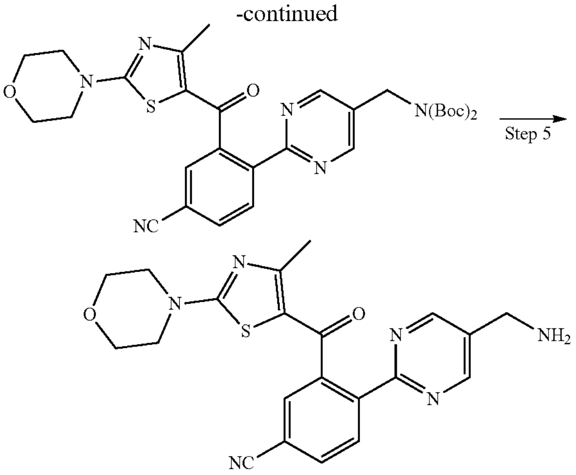

Step 1: 4-Chloro-3-[hydroxy-(4-methyl-2-morpholin-4-yl-1,3-thiazol-5-yl)methyl]benzonitrile 4-(4-Methyl-1,3-thiazol-2-yl)morpholine (1.25 g, 6.78 mmol) was dissolved in THF (34 mL), the solution was cooled to −78° C., then to the solution, an n-butyllithium hexane solution (2.76 M, 2.7 mL, 7.46 mmol) was added dropwise, and the mixture was stirred at the same temperature for 30 minutes. To the reaction mixture, 4-chloro-3-formylbenzonitrile (1.24 g, 7.46 mmol) was added, and the mixture was stirred at −78° C. for 1 hour. Then, the temperature of the mixture was raised to room temperature, a saturated aqueous ammonium chloride solution was added to the mixture, the mixture was stirred, and then extracted with ethyl acetate. The organic layer was washed with saturated brine, dried over anhydrous sodium sulfate, and the solution was concentrated under reduced pressure. The crude product was purified by silica gel column chromatography to obtain the target compound (1.30 g, 55%).

MS: m/z 350.0 $(M+H)^+$.

Step 2: 4-Chloro-3-(4-methyl-2-morpholin-4-yl-1,3-thiazole-5-carbonyl)benzonitrile 4-Chloro-3-[hydroxy-(4-methyl-2-morpholin-4-yl-1,3-thiazol-5-yl)methyl]benzonitrile (500 mg, 1.43 mmol) was dissolved in THF (15 mL), then to the solution, 2-iodoxybenzoic acid (801 mg, 2.86 mmol) was added, and the mixture was stirred at 50° C. for 2 hours. The reaction mixture was cooled to room temperature, a saturated aqueous sodium thiosulfate solution was added, and the mixture was extracted with ethyl acetate. The organic layer was dried over anhydrous sodium sulfate and the solution was concentrated under reduced pressure. Then, the crude product was purified by silica gel column chromatography to obtain the target compound (310 mg, 62%).

MS: m/z 348.0 $(M+H)^+$.

Step 3: 3-(4-Methyl-2-morpholin-4-yl-1,3-thiazole-5-carbonyl)-4-trimethylstannylbenzonitrile 4-Chloro-3-(4-methyl-2-morpholin-4-yl-1,3-thiazole-5-carbonyl)benzonitrile (170 mg, 0.489 mmol) was dissolved in 1,4-dioxane (1.2 mL), then to the solution, hexamethylditin (240 mg, 0.733 mmol) and tetrakis(triphenylphosphine)palladium (56.5 mg, 0.0489 mmol) were added, and the mixture was stirred at 110° C. for 4 hours. The reaction mixture was cooled to room temperature and purified directly by silica gel column chromatography to obtain the target compound (138 mg, 59%).

MS: m/z 478.0 $(M+H)^+$.

Step 4: tert-Butyl N-[[2-[4-cyano-2-(4-methyl-2-morpholin-4-yl-1,3-thiazole-5-carbonyl)phenyl]pyrimidin-5-yl]methyl]-N-[(2-methylpropan-2-yl)oxycarbonyl]carbamate 3-(4-Methyl-2-morpholin-4-yl-1,3-thiazole-5-carbonyl)-4-trimethylstannylbenzonitrile (46.0 mg, 0.0966 mmol) was dissolved in 1,4-dioxane (1 mL), then to the solution, tert-butyl N-[(2-chloropyrimidin-5-yl)methyl]-N-[(2-methylpropan-2-yl)oxycarbonyl]carbamate (66.0 mg, 0.193 mmol), tetrakis(triphenylphosphine)palladium (11.2 mg, 9.66 μmol) and copper(I) iodide (3.68 mg, 0.0193 mmol) were added, and the mixture was stirred at 110° C. for 16 hours. The reaction mixture was concentrated under reduced pressure, and the crude product was used in the next reaction without further purification.

Step 5: 4-[5-(Aminomethyl)pyrimidin-2-yl]-3-(4-methyl-2-morpholin-4-yl-1,3-thiazole-5-carbonyl)benzonitrile Dichloromethane (0.5 mL) and TFA (0.5 mL) were added to the crude product obtained in Step 4, and the mixture was stirred at room temperature for 2 hours. The reaction mixture was concentrated under reduced pressure, and the crude product was purified by HPLC to obtain the target compound (10.8 mg).

Exact MS: 420.1

Obs. MS $(M+H)^+$: 421.2

Example 30

4-[5-(2-Aminoethyl)pyridin-2-yl]-3-[(4-phenylimidazol-1-yl)methyl]benzonitrile (Compound No. 1131)

[Chem. 76]

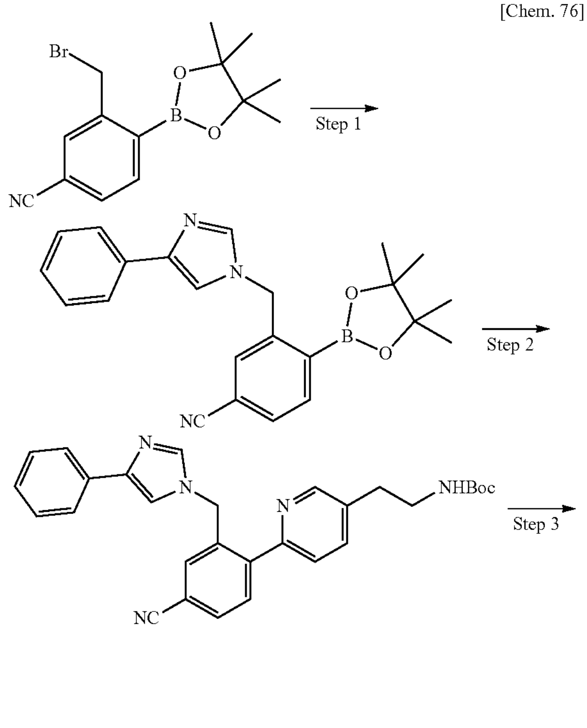

-continued

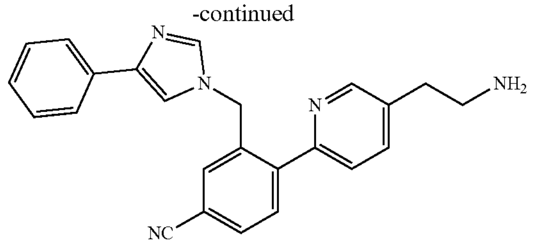

Step 1: 3-[(4-Phenylimidazol-1-yl)methyl]-4-(4,4,5,5-tetramethyl-1,3,2-dioxaborolan-2-yl)benzonitrile 3-(Bromomethyl)-4-(4,4,5,5-tetramethyl-1,3,2-dioxaborolan-2-yl)benzonitrile (6.00 g, 18.6 mmol) was dissolved in DMF (80 mL), then to the solution, 4-phenyl-1H-imidazole (2.69 g, 18.6 mmol) and potassium carbonate (5.15 g, 37.3 mmol) were added, and the mixture was stirred at 80° C. for 3 hours. The reaction mixture was cooled to room temperature, water was added to the mixture, and the mixture was extracted with ethyl acetate. The organic layer was washed with saturated brine and dried over anhydrous sodium sulfate, and concentrated under reduced pressure. The obtained crude product was used in the next reaction without further purification.

MS: m/z 386.2 $(M+H)^+$.

Step 2: tert-Butyl N-[2-[6-[4-cyano-2-[(4-phenylimidazol-1-yl)methyl]phenyl]pyridin-3-yl]ethyl]carbamate The crude product obtained in Step 1 was dissolved in 1,4-dioxane (80 mL), then to the solution, tert-butyl N-[2-(6-chloropyridin-3-yl)ethyl]carbamate (3.87 g, 15.1 mmol), [1,1'-bis(diphenylphosphino)ferrocene]palladium dichloride (552 mg, 0.754 mmol), potassium carbonate (4.17 g, 30.2 mmol) and water (20 mL) were added, and the mixture was stirred at 100° C. for 2 hours. The reaction mixture was cooled to room temperature, water was added to the mixture, and the mixture was extracted with ethyl acetate. The extract was dried over anhydrous sodium sulfate and concentrated under reduced pressure. The crude product was purified by silica gel column chromatography to obtain the target compound (1.41 g, 20%).

MS: m/z 480.2 $(M+H)^+$.

Step 3: 4-[5-(2-Aminoethyl(pyridin-2-yl]-3-[(4-phenylimidazol-1-yl)methyl]benzonitrile 1,4-Dioxane (20 mL) was added to tert-butyl N-[2-[6-[4-cyano-2-[(4-phenylimidazol-1-yl)methyl]phenyl]pyridin-3-yl]ethyl]carbamate (1.19 g, 2.49 mmol), then to the mixture, a 4 M hydrochloric acid/dioxane solution (20 mL) was added dropwise at 0° C., the temperature of the mixture was raised to room temperature, and the mixture was stirred for 3 hours. The reaction solution was concentrated under reduced pressure, and the crude product was purified by HPLC to obtain the target compound (678 mg, 72%).

Exact MS: 379.2

Obs. MS $(M+H)^+$: 380.3

Example 31

4-[5-(2-Aminoethyl)pyrimidin-2-yl]-3-[[2-methyl-4-(piperidin-1-ylmethyl)imidazol-1-yl]methyl]benzonitrile (Compound No. 1179)

[Chem. 77]

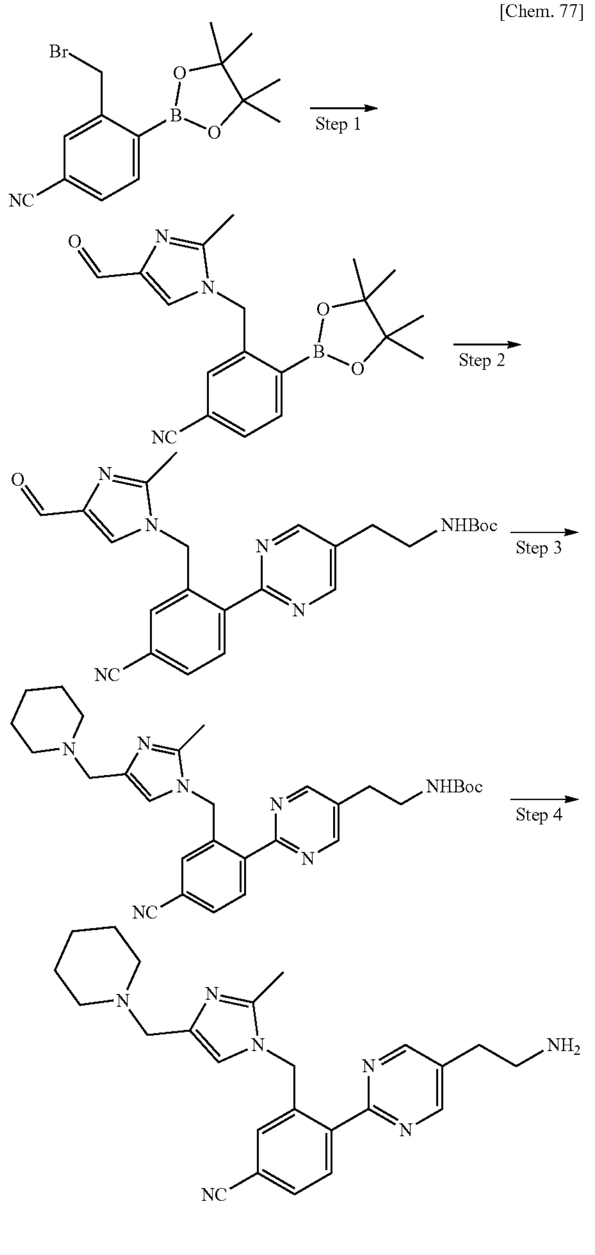

Step 1: 3-[(4-Formyl-2-methylimidazol-1-yl)methyl]-4-(4,4,5,5-tetramethyl-1,3,2-dioxaborolan-2-yl)benzonitrile 3-(Bromomethyl)-4-(4,4,5,5-tetramethyl-1,3,2-dioxaborolan-2-yl)benzonitrile (354 mg, 1.10 mmol) was dissolved in acetonitrile (5 mL), then to the solution, 2-methyl-1H-imidazole-4-carbaldehyde (110 mg, 1.00 mmol) and triethylamine (0.356 mL, 2.00 mmol) were added, and the mixture was stirred at 80° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product obtained was used in the next reaction without further purification.

Step 2: tert-Butyl N-[2-[2-[4-cyano-2-[(4-formyl-2-methylimidazol-1-yl)methyl]phenyl]pyrimidin-5-yl]ethyl]carbamate The crude product obtained in Step 1 was dissolved in 1,4-dioxane (5 mL), then to the solution, tert-butyl N-[2-(2-chloropyrimidin-5-yl)ethyl]carbamate (283 mg, 1.10 mmol), [1,1'-bis(diphenylphosphino)ferrocene]palladium dichloride (73.4 mg, 0.100 mmol), potassium carbonate (415 mg, 3.00 mmol) and water (1 mL) were added, and the mixture was stirred at 100° C. for 1 hour. The reaction mixture was cooled to room temperature, water was added to the mixture, and the mixture was extracted with ethyl acetate. The extract was dried over anhydrous sodium sulfate and the solution was concentrated under reduced pressure. The crude product was purified by silica gel column chromatography to obtain the target compound (446 mg, quant.).

MS: m/z 447.3 $(M+H)^+$.

Step 3: tert-Butyl N-[2-[2-[4-cyano-2-[[2-methyl-4-(piperidin-1-ylmethyl)imidazol-1-yl]methyl]phenyl]pyrimidin-5-yl]ethyl]carbamate tert-Butyl N-[2-[2-[4-cyano-2-[(4-formyl-2-methylimidazol-1-yl)methyl]phenyl]pyrimidin-5-yl]ethyl]carbamate (31.0 mg, 0.070 mmol) was dissolved in dichloromethane (0.7 mL), then to the solution, piperidine (7.2 mg, 0.084 mmol) and sodium triacetoxyborohydride (37.0 mg, 0.180 mmol) were added, and the mixture was stirred at room temperature for 5 hours. Water was added to the reaction mixture, and the mixture was extracted with ethyl acetate. The organic layer was washed with saturated brine and dried over anhydrous sodium sulfate, and the solution was concentrated under reduced pressure. The obtained crude product was used in the next reaction without further purification.

Step 4: 4-[5-(2-Aminoethyl)pyrimidin-2-yl]-3-[[2-methyl-4-(piperidin-1-ylmethyl)imidazol-1-yl]methyl]benzonitrile Dichloromethane (0.5 mL) and TFA (0.5 mL) were added to the crude product obtained in Step 3, and the mixture was stirred at room temperature for 1 hour. The mixture was concentrated under reduced pressure, and the crude product was purified by HPLC to obtain the target compound (12.2 mg).

Exact MS: 415.3

Obs. MS $(M+H)^+$: 416.4

Example 32

4-[5-(2-Aminoethyl)pyrimidin-2-yl]-3-[(4-cyclopropyltriazol-1-yl)methyl]benzonitrile (Compound No. 1187)

[Chem. 78]

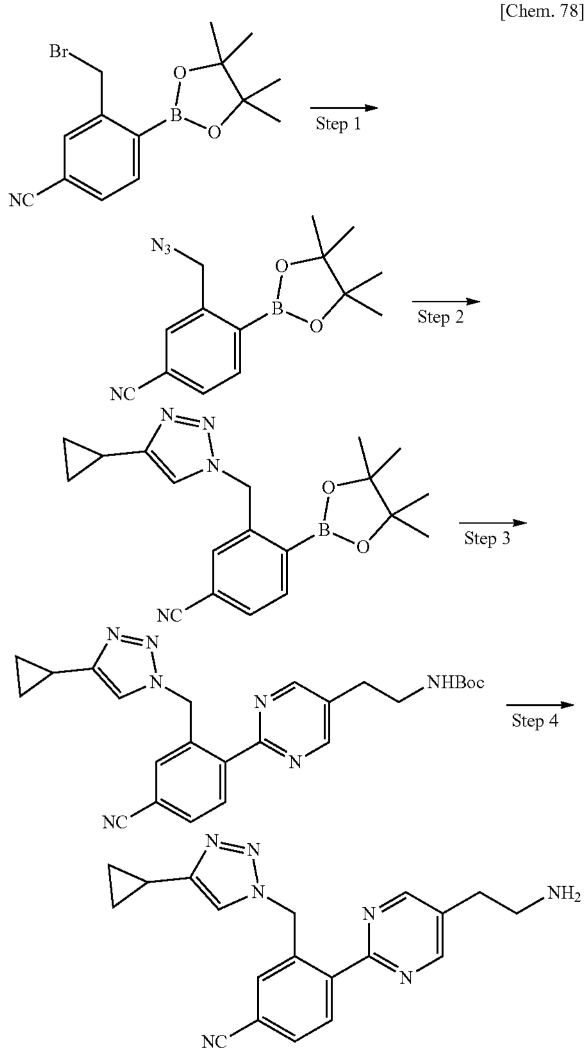

Step 1: 3-(Azidomethyl)-4-(4,4,5,5-tetramethyl-1,3,2-dioxaborolan-2-yl)benzonitrile 3-(Bromomethyl)-4-(4,4,5,5-tetramethyl-1,3,2-dioxaborolan-2-yl)benzonitrile (3.50 g, 10.9 mmol) was dissolved in DMSO (22 mL), then to the solution, sodium azide (777 mg, 12.0 mmol) was added, and the mixture was stirred at 70° C. for 3 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (2.80 g, 91%).

Step 2: 3-[(4-Cyclopropyltriazol-1-yl)methyl]-4-(4,4,5,5-tetramethyl-1,3,2-dioxaborolan-2-yl)benzonitrile 3-(Azidomethyl)-4-(4,4,5,5-tetramethyl-1,3,2-dioxaborolan-2-yl)benzonitrile (1.10 g, 3.87 mmol) was dissolve in DMSO (10 mL), then to the solution, ethynylcyclopropane (307 mg, 4.65 mmol), copper(I) iodide (36.9 mg, 0.194 mmol) and TBTA (103 mg, 0.194 mmol) were added, and the mixture was stirred at room temperature overnight. Water was added to the reaction mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (416 mg, 31%).

Step 3: tert-Butyl N-[2-[2-[4-cyano-2-[(4-cyclopropyltriazol-1-yl)methyl]phenyl]pyrimidin-5-yl]ethyl]carbamate 3-[(4-Cyclopropyltriazol-1-yl)methyl]-4-(4,4,5,5-tetramethyl-1,3,2-dioxaborolan-2-yl)benzonitrile (208 mg, 0.594 mmol) was dissolved in 1,4-dioxane (3 mL), then to the solution, tert-butyl N-[2-(2-chloropyrimidin-5-yl)ethyl]carbamate (168 mg, 0.653 mmol), tetrakis(triphenylphosphine) palladium (34 mg, 0.030 mmol), sodium carbonate (126 mg, 1.19 mmol) and water (1 mL) were added, and the mixture was stirred at 80° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (120 mg, 45%).

Step 4: 4-[5-(2-Aminoethyl)pyrimidin-2-yl]-3-[(4-cyclopropyltriazol-1-yl)methyl]benzonitrile Dichloromethane (1 mL) and TFA (0.5 mL) were added to tert-butyl N-[2-[2-[4-cyano-2-[(4-cyclopropyltriazol-1-yl)methyl]phenyl]pyrimidin-5-yl]ethyl]carbamate (120 mg, 0.269 mmol), and the mixture was stirred at room temperature for 1 hour. The mixture was concentrated under reduced pressure, and the crude product was purified by HPLC to obtain the target compound (12.8 mg).

Exact MS: 345.2

Obs. MS $(M+H)^+$: 346.2

Example 33

4-[5-(2-Aminoethyl)pyrimidin-2-yl]-3-[[I-(2-methylpropyl)pyrazol-4-yl]methyl]benzonitrile (Compound No. 1195)

[Chem. 79]

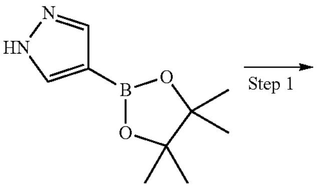

-continued

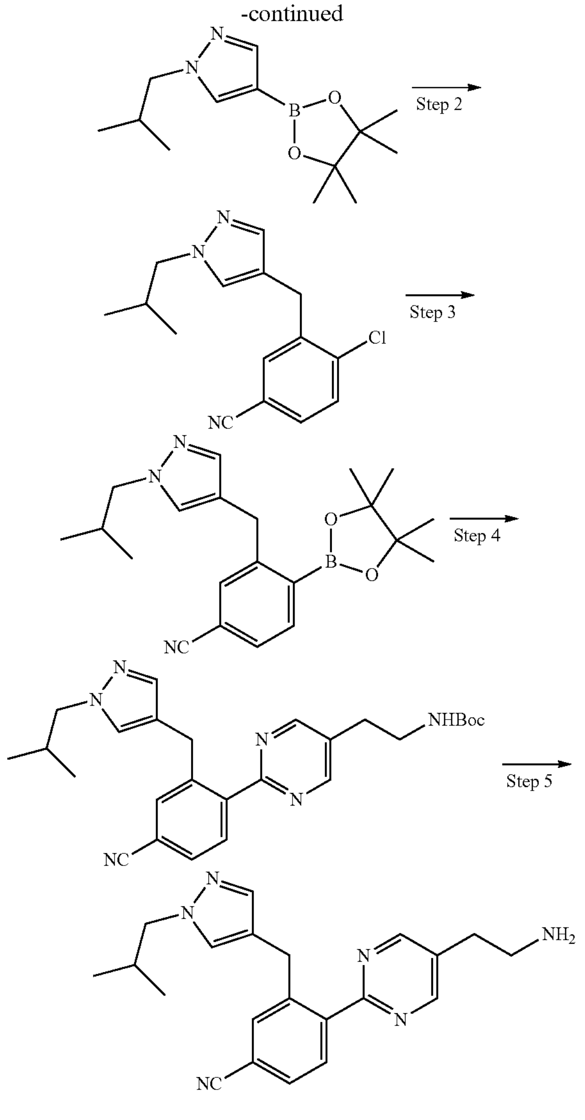

Step 1: 1-(2-Methylpropyl-4-(4,4,5,5-tetramethyl-1,3,2-dioxaborolan-2-yl)pyrazole 4-(4,4,5,5-tetramethyl-1,3,2-dioxaborolan-2-yl)-1H-pyrazole (1.94 g, 10.0 mmol) was dissolved in DMF (10 mL), then to the solution, 1-bromo-2-methylpropane (1.64 g, 12.0 mmol) and potassium carbonate (4.14 g, 30.0 mmol) were added, and the mixture was stirred at 100° C. for 2 hours. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The obtained crude product was used in the next reaction without further purification.

MS: m/z 251.2 $(M+H)^+$.

Step 2: 4-Chloro-3-[[1-(2-methylpropyl)pyrazol-4-yl]methyl]benzonitrile

An aliquot (500 mg, 2.00 mmol) of the crude product obtained in Step 1 was dissolved in 1,4-dioxane (10 mL), then to the solution, 3-(bromomethyl)-4-chlorobenzonitrile (461 mg, 2.00 mmol), tetrakis(triphenylphosphine)palladium (162 mg, 0.140 mmol), cesium carbonate (1.95 g, 6.00 mmol) and water (2 mL) were added, and the mixture was stirred at 100° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (548 mg, containing impurities).

MS: m/z 274.1 $(M+H)^+$.

Step 3: 3-[[1-(2-Methylpropyl)pyrazol-4-yl]methyl]-4-(4,4,5,5-tetramethyl-1,3,2-dioxaborolan-2-yl)benzonitrile 4-Chloro-3-[[1-(2-methylpropyl)pyrazol-4-yl]methyl]benzonitrile (274 mg, 1.00 mmol) was dissolved in 1,4-dioxane (3.3 mL), then to the solution, bis(pinacolato)diboron (381 mg, 1.50 mmol), bis(tricyclohexylphosphine)palladium dichloride (73.8 mg, 0.100 mmol), and potassium acetate (294 mg, 3.00 mmol) were added, and the mixture was stirred at 110° C. for 2 hours. The reaction mixture was cooled to room temperature, filtered through Celite, and then concentrated under reduced pressure. The crude product was used in the next reaction without further purification.

MS: m/z 366.3 $(M+H)^+$.

Step 4: tert-Butyl N-[2-[2-[4-cyano-2-[[1-(2-methylpropyl)pyrazol-4-yl]methyl]phenyl]pyrimidin-5-yl]ethyl]carbamate An aliquot (37 mg) of the crude product obtained in Step 3 was dissolved in 1,4-dioxane (0.5 mL), then to the solution, tert-butyl N-[2-(2-chloropyrimidin-5-yl)ethyl]carbamate (25.8 mg, 0.100 mmol), [1,1'-bis(diphenylphosphino)ferrocene]palladium dichloride (7.3 mg, 0.01 mmol), potassium carbonate (41.0 mg, 0.300 mmol), and water (0.1 mL) were added, and the mixture was stirred at 100° C. for 1 hour. The reaction mixture was cooled to room temperature, water was added to the mixture, and the mixture was extracted with ethyl acetate. The solution was dried over anhydrous sodium sulfate, the solution was concentrated under reduced pressure, and the crude product was used in the next reaction without further purification.

Step 5: 4-[5-(2-Aminoethyl)pyrimidin-2-yl]-3-[[1-(2-methylpropyl)pyrazol-4-yl]methyl]benzonitrile TFA (0.5 mL) was added to the crude product obtained in Step 4, and the mixture was stirred at room temperature for 1 hour. The reaction mixture was concentrated under reduced pressure, and the crude product was purified by HPLC to obtain the target compound (26.0 mg).

Exact MS: 360.2

Obs. MS $(M+H)^+$: 361.0

Example 34

4-[5-(2-Aminoethyl)pyrimidin-2-yl]-3-[(4-pyrrolidin-1-ylpyrazol-1-yl)methyl]benzonitrile (Compound No. 1198)

[Chem. 80]

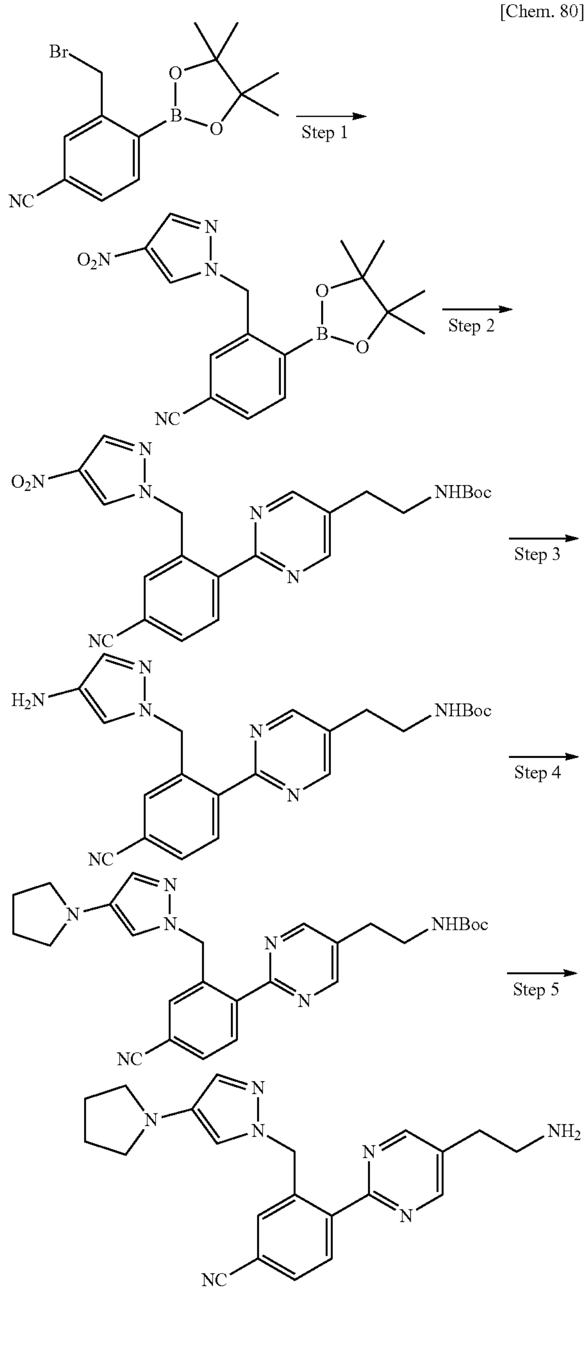

Step 1: 3-[(4-Nitropyrazol-1-yl)methyl]-4-(4,4,5,5-tetramethyl-1,3,2-dioxaborolan-2-yl)benzonitrile 3-(bromomethyl)-4-(4,4,5,5-tetramethyl-1,3,2-dioxaborolan-2-yl)benzonitrile (230 mg, 0.700 mmol) was dissolved in DMF (0.7 mL), then to the solution, 4-nitro-1H-pyrazole (95 mg, 0.84 mmol) and potassium carbonate (190 mg, 1.40 mmol) were added, and the mixture was stirred at room temperature for 2 hours. Water was added to the reaction mixture, and the mixture was extracted with ethyl acetate. The organic layer was washed with saturated brine and dried over anhydrous sodium sulfate, the solvent was evaporated under reduced pressure, and the crude product was used in the next reaction without further purification.

MS: m/z 355.2 $(M+H)^+$.

Step 2: tert-Butyl N-[2-[2-[4-cyano-2-[(4-nitropyrazol-1-yl)methyl]phenyl]pyrimidin-5-yl]ethyl]carbamate The crude product obtained in Step 1 was dissolved in 1,4-dioxane (3.5 mL), then to the solution, tert-butyl N-[2-(2-chloropyrimidin-5-yl)ethyl]carbamate (180 mg, 0.700 mmol), [1,1'-bis(diphenylphosphino)ferrocene]palladium dichloride (51.2 mg, 0.0700 mmol), potassium carbonate (290 mg, 2.10 mmol), and water (0.7 mL) were added, and the mixture was stirred at 100° C. for 1 hours. The reaction mixture was cooled to room temperature, water was added to the mixture, and the mixture was extracted with ethyl acetate. The solution was dried over anhydrous sodium sulfate and the solution was concentrated under reduced pressure. The crude product was purified by silica gel column chromatography to obtain the target compound (310 mg, 99%).

MS: m/z 450.2 $(M+H)^+$.

Step 3: tert-Butyl N-[2-[2-[2-[(4-aminopyrazol-1-yl)methyl]-4-cyanophenyl]pyrimidin-5-yl]ethyl]carbamate tert-Butyl N-[2-[2-[4-cyano-2-[(4-nitropyrazol-1-yl)methyl]phenyl]pyrimidin-5-yl]ethyl]carbamate (310 mg, 0.690 mmol) was dissolved in methanol (0.7 mL) and palladium-active carbon ethylenediamine complex (50 mg) was added to the mixture. A hydrogen gas balloon was attached to the reaction vessel, and after the inside of the vessel was replaced with hydrogen gas, the mixture was stirred at room temperature overnight. After filtering the reaction mixture with Celite, the solution was concentrated under reduced pressure, and the crude product was used in the next reaction without further purification.

MS: m/z 420.3 $(M+H)^+$.

Step 4: tert-Butyl N-[2-[2-[4-cyano-2-[(4-pyrrolidin-1-ylpyrazol-1-yl)methyl]phenyl]pyrimidin-5-yl]ethyl]carbamate An aliquot (45.2 mg) of the crude product obtained in Step 3 was dissolved in DMA (0.5 mL), then to the solution, 1,4-dibromobutane (25.6 mg, 0.119 mmol) and N,N-diisopropylethylamine (0.054 mL, 0.323 mmol) were added, and the mixture was stirred at 110° C. overnight. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was used in the next reaction without further purification.

MS: m/z 474.3 $(M+H)^+$.

Step 5: 4-[5-(2-Aminoethyl)pyrimidin-2-yl]-3-[(4-pyrrolidin-1-ylpyrazol-1-yl)methyl]benzonitrile TFA (0.5 mL) was added to the crude product obtained in Step 4, and the mixture was stirred at room temperature for 1 hour. The mixture was concentrated under reduced pressure, and the crude product was purified by HPLC to obtain the target compound (7.4 mg).

Exact MS: 373.2

Obs. MS $(M+H)^+$: 374.2

Example 35

4-[4-(2-Aminoethyl)phenyl]-3-[1-(2-methyl-6-morpholin-4-ylpyrimidin-4-yl)ethyl]benzonitrile (Compound No. 1226))

[Chem. 81]

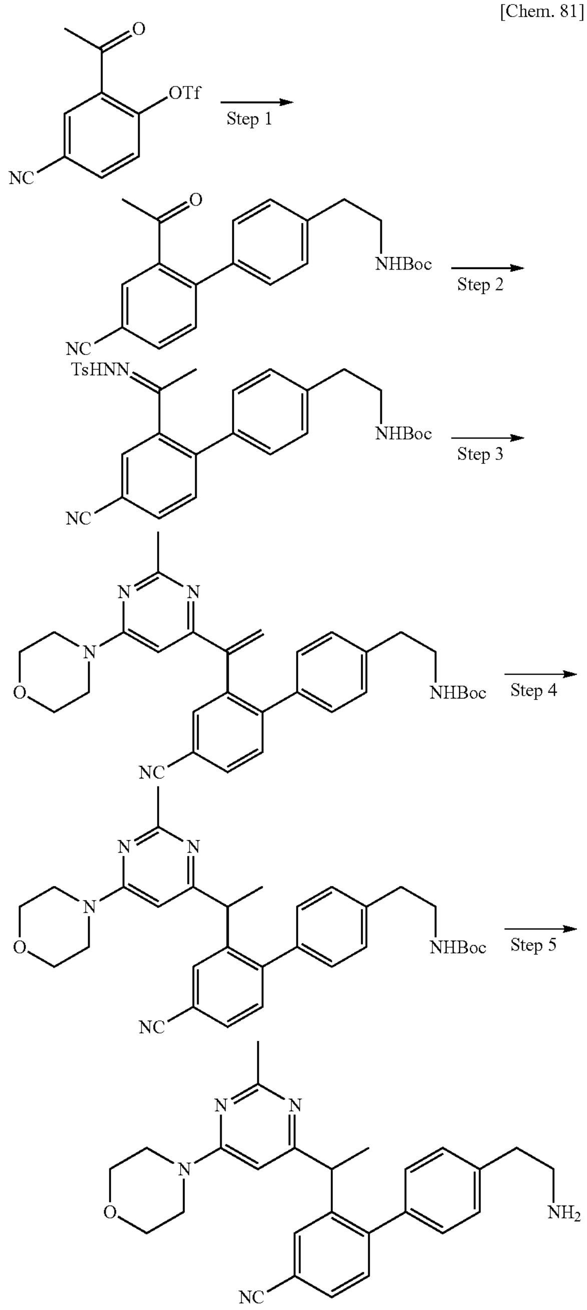

Step 1: tert-Butyl (2-(2'-acetyl-4'-cyano-[1,1'-biphenyl]-4-yl)ethyl)carbamate

To a mixed solution (5 mL) of 2-acetyl-4-cyanophenyl-trifluoromethanesulfonate (250 mg, 0.85 mmol) in toluene/water (=4/1), tert-butyl 4-(4,4,5,5-tetramethyl-1,3,2-dioxaboran-2-yl)phenethylcarbamate (355 mg, 1.02 mmol), [1,1'-bis(diphenylphosphino)ferrocene]dichloropalladium (62.4 mg, 0.085 mmol), and potassium carbonate (354 mg, 2.56 mmol) were added, and the mixture was stirred at 110° C. for 30 minutes. The reaction mixture was cooled to room temperature, and water and ethyl acetate were added to the mixture. The mixture was extracted with ethyl acetate, the organic layer was dried over anhydrous magnesium sulfate, and the solution was concentrated under reduced pressure. The crude product was purified by silica gel column chromatography to obtain the target compound (328 mg, quant.).

MS: m/z 309.1 $(M+H-tBu)^+$.

Step 2: tert-Butyl (2-(4'-cyano-2'-(1-(2-tosylhydrazono)ethyl)-[1,1'-biphenyl]-4-yl)ethyl)carbamate p-Toluene sulfonyl hydrazide (167 mg, 0.899 mmol) was added to a solution (3 mL) of tert-butyl (2-(2'-acetyl-4'-cyano-[1,1'-biphenyl]-4-yl)ethyl)carbamate (328 mg, 0.899 mmol) in toluene, and the mixture was stirred at 110° C. for 3 hours. The reaction solution was concentrated under reduced pressure, and the crude product was used in the next reaction without further purification.

MS: m/z 477.2 $(M+H-tBu)^+$.

Step 3: tert-Butyl (2-(4'-cyano-2'-(1-(2-methyl-6-morpholinopyrimidin-4-yl)vinyl)-[1,1'-biphenyl]-4-ylethylcarbamate The crude product obtained in Step 2 was dissolved in 1,4-dioxane (4.5 mL), then to the solution, 4-(6-chloro-2-methylpyrimidin-4-yl)morpholine (192 mg, 0.899 mmol), tris(dibenzylideneacetone)dipalladium (32.9 mg, 0.036 mmol), 2-(dicyclohexylphosphino)-2',4',6'-tri-1-propyl-1,1'-biphenyl (68.6 mg, 0.14 mmol) and lithium tert-butoxide (166 mg, 2.07 mmol) were added, and the mixture was stirred at 110° C. for 3 hours. The reaction mixture was cooled to room temperature and filtered through Celite, and then the solution was concentrated under reduced pressure. The crude product was purified by silica gel column chromatography to obtain the target compound (96.1 mg, 20%).

MS: m/z 526.3 $(M+H)^+$.

Step 4: tert-Butyl (2-(4'-cyano-2'-(1-(2-methyl-6-morpholinopyrimidin-4-yl)ethyl)-[1,1'-biphenyl]-4-yl)ethyl carbamate Ethyl acetate (4 mL) was added to tert-butyl (2-(4'-cyano-2'-(1-(2-methyl-6-morpholinopyrimidin-4-yl)vinyl)-[1,1'-biphenyl]-4-yl)ethyl)carbamate (79 mg, 0.15 mmol), and 10% palladium-activated carbon (20 mg) was added to the mixture under a nitrogen atmosphere. A hydrogen gas balloon was attached to the reaction vessel, the inside of the vessel was replaced with hydrogen gas, and the mixture was stirred at room temperature for 1 hour. After replacing the reaction system with nitrogen, the reaction mixture was filtered through Celite and concentrated under reduced pressure. The obtained crude product was used in the next reaction without further purification.

MS: m/z 528.3 $(M+H)^+$.

Step 5: 4-[4-(2-Aminoethyl)phenyl]-3-[1-(2-methyl-6-morpholin-4-ylpyrimidin-4-yl)ethyl]benzonitrile The crude product obtained in Step 4 was dissolved in dichloromethane (1 mL), TFA (0.5 mL) was added to the mixture, and the mixture was stirred at room temperature for 30 minutes. The reaction mixture was concentrated under reduced pressure, and the crude product was purified by HPLC to obtain the target compound (30.8 mg).

Exact MS: 427.2

Obs. MS $(M+H)^+$: 428.5

Example 36

4-[4-(2-Aminoethyl)phenyl]-3-[1-(2-methyl-6-morpholin-4-ylpyrimidin-4-yl)cyclopropyl]benzonitrile (Compound No. 1227)

[Chem. 82]

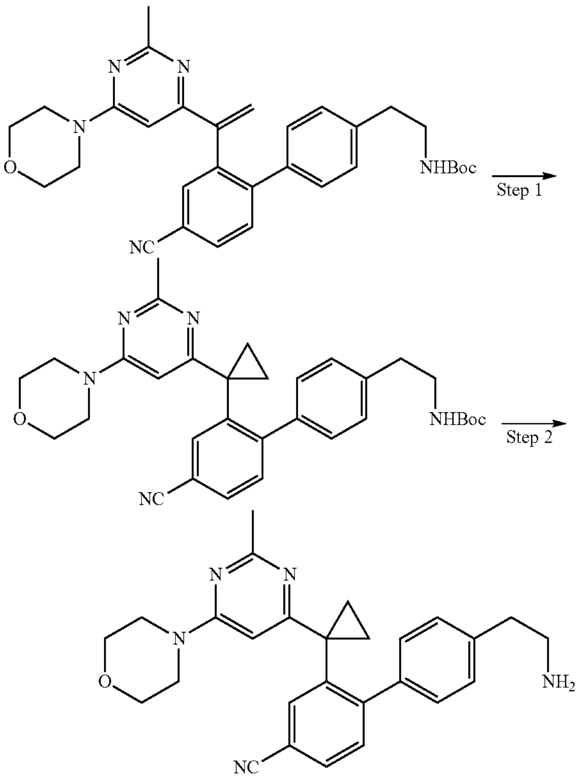

Step 1: tert-Butyl (2-(4'-cyano-2'-(1-(2-methyl-6-morpholinopyrimidin-4-yl)cyclopropyl)-[1,1'-biphenyl]-4-yl)ethyl)carbamate DMSO (0.5 mL) and sodium hydride (1.3 mg) were added to trimethyl sulfoxonium iodide (7.1 mg, 0.032 mmol), the mixture was stirred at room temperature for 40 minutes, then to the mixture, a solution (0.5 mL) of tert-butyl (2-(4'-cyano-2'-(1-(2-methyl-6-morpholinopyrimidin-4-yl)vinyl)-[1,1'-biphenyl]-4-yl)ethyl)carbamate (16.9 mg, 0.032 mmol) in DMSO obtained in Example 35 was added, and the mixture was stirred at room temperature for 1 hour. Water was added to the reaction mixture, the mixture was extracted with ethyl acetate, and the organic layer was dried over anhydrous magnesium sulfate, and concentrated under reduced pressure. The crude product was used in the next reaction without further purification.

MS: m/z 540.3 $(M+H)^+$.

Step 2: 4-[4-(2-Aminoethyl)phenyl]-3-[1-(2-methyl-6-morpholin-4-ylpyrimidin-4-yl)cyclopropyl]benzonitrile The crude product obtained in Step 1 was dissolved in dichloromethane (1 mL), TFA (0.5 mL) was added to the solution, and the mixture was stirred at room temperature for 30 minutes. The reaction mixture was concentrated under reduced pressure, and the crude product was purified by silica gel column chromatography to obtain the target compound (11.6 mg).

Exact MS: 439.2

Obs. MS $(M+H)^+$: 440.5

Example 37

4-[4-(2-Aminoethyl)phenyl]-3-[methoxy-[3-(1,3-thiazol-2-yl)-1,2-oxazol-5-yl]methyl]benzonitrile (Compound No. 1232)

[Chem. 83]

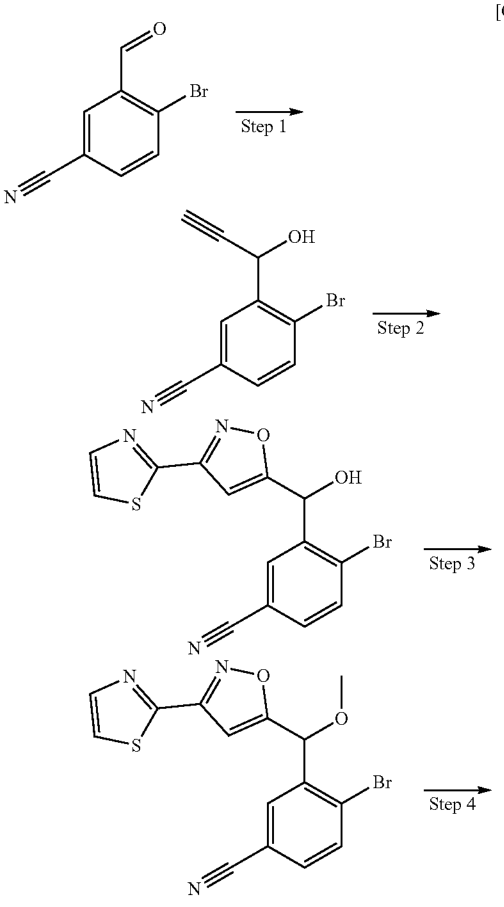

-continued

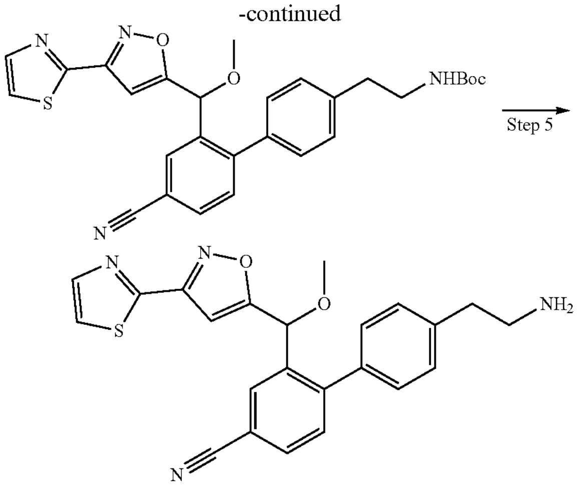

Step 1: 4-Bromo-3-(1-hydroxyprop-2-ynyl)benzonitrile

THF (40 mL) was added to 4-bromo-3-formylbenzonitrile (1.38 g, 6.57 mmol), then to the mixture, a 0.5 M ethynylmagnesium bromide solution (14.5 mL, 7.23 mmol) in THF was added dropwise at 0° C., and the mixture was stirred at the same temperature for 1 hour. After completion of the reaction, 2 M hydrochloric acid was added to the mixture and the mixture was extracted with ethyl acetate. The organic layer was washed with saturated brine and dried over anhydrous sodium sulfate, and the solution was concentrated under reduced pressure. The crude product obtained was used in the next reaction.

Step 2: 4-Bromo-3-[hydroxy-[3-(1,3-thiazol-2-yl)-1,2-oxazol-5-yl]methyl]benzonitrile To an aliquot (283 mg) of the crude product obtained in Step 1, (2Z)—N-hydroxy-1,3-thiazole-2-carboximidoyl chloride (163 mg, 1.00 mmol), potassium carbonate (276 mg, 2.00 mmol) and toluene (1 mL) were added, and the mixture was stirred at 100° C. overnight. The reaction mixture was cooled to room temperature, water was added to the mixture, and the mixture was extracted with ethyl acetate. The organic layer was washed with saturated brine and dried over anhydrous magnesium sulfate, and the solution was concentrated under reduced pressure. The crude product was purified by silica gel column chromatography to obtain the target compound (65.6 mg, 18%).

MS: m/z 362.0 $(M+H)^+$.

Step 3: 4-Bromo-3-[methoxy-[3-(1,3-thiazol-2-yl)-1,2-oxazol-5-yl]methyl]benzonitrile 4-Bromo-3-[hydroxy-[3-(1,3-thiazol-2-yl)-1,2-oxazol-5-yl]methyl]benzonitrile (65.6 mg, 0.181 mmol) was dissolved in DMF (1 mL), then sodium hydride (9.5 mg, 0.217 mmol) was added to the mixture, and the mixture was stirred at room temperature for 10 minutes. Iodomethane (38.8 mg, 0.272 mmol) was added to the reaction mixture, and the mixture was stirred at room temperature overnight. After completion of the reaction, water was added to the mixture, and the mixture was extracted with ethyl acetate. The organic layer was washed with saturated brine and dried over anhydrous magnesium sulfate, and the solution was concentrated under reduced pressure. The crude product obtained was used in the next reaction.

MS: m/z 377.9 $(M+H)^+$.

Step 4: tert-Butyl N-[2-[4-[4-cyano-2-[methoxy-[3-(1,3-thiazol-2-yl-1,2-oxazol-5-yl]methyl]phenyl]phenyl]ethyl]carbamate The crude product obtained in Step 3 was dissolved in 1,4-dioxane (0.8 mL), then to the solution, tert-butyl N-[2-[4-(4,4,5,5-tetramethyl-1,3,2-dioxaborolan-2-yl)phenyl]ethyl]carbamate (75.4 mg, 0.217 mmol), [1,1'-bis(diphenylphosphino)ferrocene]palladium dichloride (6.6 mg, 9.0 μmol), potassium carbonate (50.0 mg, 0.362 mmol) and water (0.2 mL) were added, and the mixture was stirred at 100° C. for 1 hour. The reaction mixture was cooled to room temperature, water was added to the mixture, and the mixture was extracted with ethyl acetate. The solution was dried over anhydrous sodium sulfate, the solution was concentrated under reduced pressure, and the crude product was used in the next reaction without further purification.

MS: m/z 517.2 $(M+H)^+$.

Step 5: 4-[4-(2-aminoethyl)phenyl]-3-[methoxy-[3-(1,3-thiazol-2-yl)-1,2-oxazol-5-yl]methyl]benzonitrile Dichloromethane (1 mL) and TFA (0.5 mL) were added to the crude product obtained in Step 4, and the mixture was stirred at room temperature for 30 minutes. The mixture was concentrated under reduced pressure, and the crude product was purified by HPLC to obtain the target compound (48.3 mg).

Exact MS: 416.1

Obs. MS $(M+H)^+$: 417.2

Example 38

4-[5-(2-Aminoethyl)pyrimidin-2-yl]-3-[(5-tert-butyl-2-methylpyrazol-3-yl)-(cyanomethoxy)methyl]benzonitrile (Compound No. 1237)

[Chem. 84]

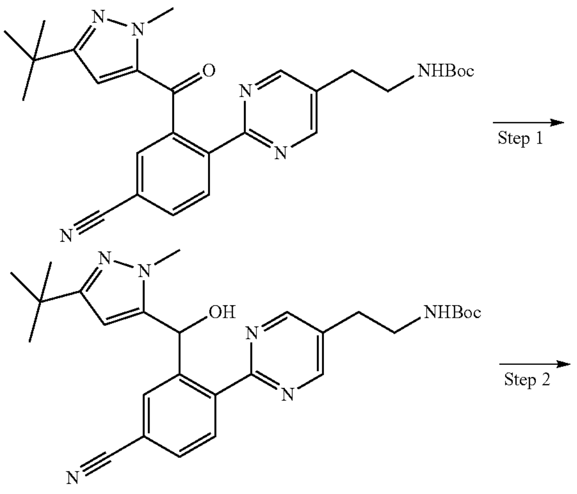

-continued

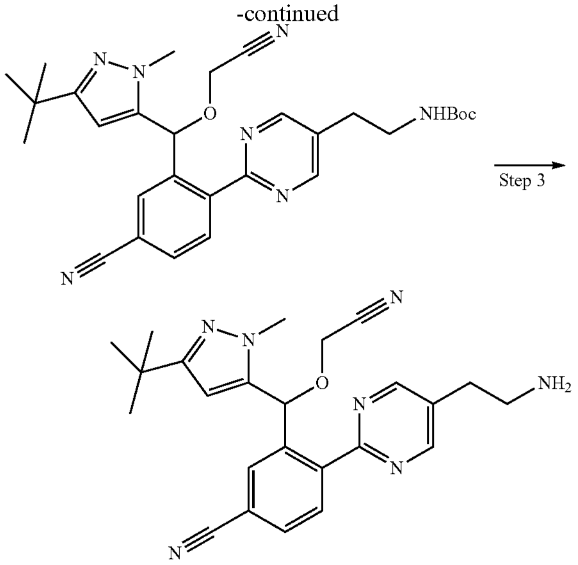

Step 1: tert-Butyl N-[2-[2-[2-[(5-tert-butyl-2-methylpyrazol-3-yl)-hydroxymethyl]-4-cyanophenyl]pyrimidin-5-yl]ethyl]carbamate THF (7.8 mL) was added to tert-butyl N-[2-[2-[2-(5-tert-butyl-2-methylpyrazole-3-carbonyl)-4-cyanophenyl]pyrimidin-5-yl]ethyl]carbamate (379 mg, 0.776 mmol), which can be synthesized in the same method as in Example 27, and a 4 M lithium borohydride solution (0.776 mL, 2.33 mmol) in THF was added dropwise to the mixture. After stirring the mixture at room temperature for 1 hour, water was added to the reaction mixture, and the mixture was extracted with ethyl acetate. The organic layer was washed with saturated brine and dried over anhydrous magnesium sulfate, and the solution was concentrated under reduced pressure. The crude product obtained was used in the next reaction.

MS: m/z 491.3 $(M+H)^+$.

Step 2: tert-Butyl N-[2-[2-[2-[(5-tert-butyl-2-methylpyrazol-3-yl)-(cyanomethoxy)methyl]-4-cyanophenyl]pyrimidin-5-yl]ethyl]carbamate An aliquot (127 mg) of the crude product obtained in Step 1 was dissolved in DMF (1 mL), then to the solution, chloroacetonitrile (23.4 mg, 0.310 mmol) and cesium carbonate (169 mg, 0.517 mmol) were added, and the mixture was stirred at 60° C. for 16 hours. The reaction mixture was cooled to room temperature, water was added to the mixture, and the mixture was extracted with ethyl acetate. The organic layer was washed with saturated brine and dried over anhydrous magnesium sulfate, and the solution was concentrated under reduced pressure. The crude product obtained was used in the next reaction.

MS: m/z 530.3 $(M+H)^+$.

Step 3: 4-[5-(2-Aminoethyl)pyrimidin-2-yl]-3-[(5-tert-butyl-2-methylpyrazol-3-yl)-(cyanomethoxy)methyl]benzonitrile Dichloromethane (1 mL) and TFA (0.5 mL) were added to the crude product obtained in Step 2, and the mixture was stirred at room temperature for 30 minutes. The reaction mixture was concentrated under reduced pressure, and the crude product was purified by HPLC to obtain the target compound (10.2 mg).

Exact MS: 429.2

Obs. MS $(M+H)^+$: 430.2

Example 39

4-[4-(2-Aminoethyl)phenyl]-3-(6-piperidin-1-ylpyridazin-4-yl)sulfanylbenzonitrile (Compound No. 1240)

[Chem. 85]

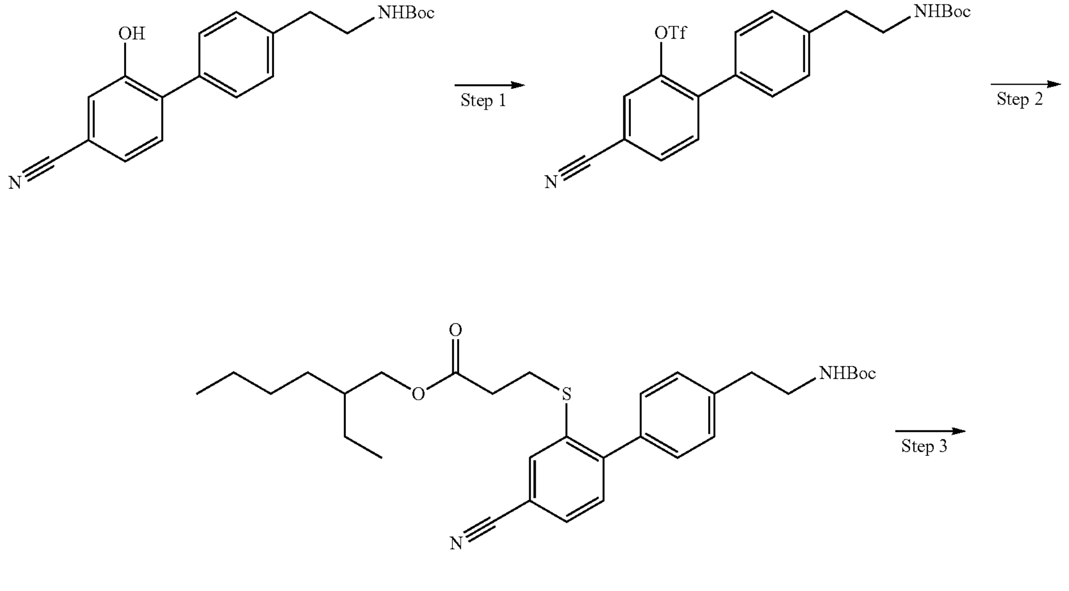

-continued

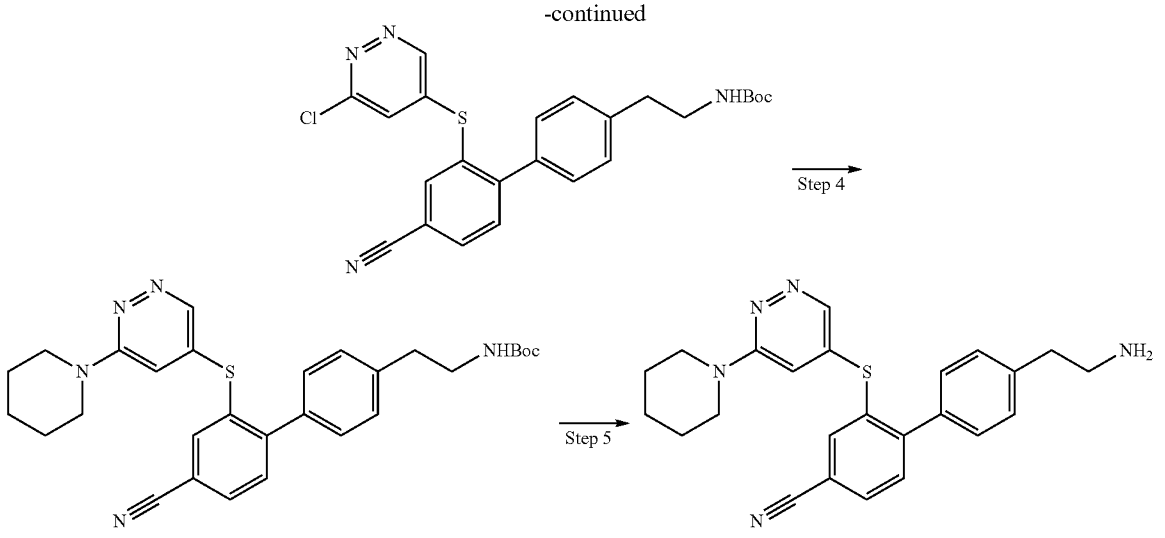

Step 1: [5-Cyano-2-[5-[2-[(2-methylpropan-2-yl)oxycarbonylamino]ethyl]pyridin-2-yl]phenyl]trifluoromethanesulfonate Dichloromethane (5 mL), and pyridine (172 mg, 2.17 mmol) were added to the intermediate of tert-butyl N-[2-[4-(4-cyano-2-hydroxyphenyl)phenyl]ethyl]carbamate (245 mg, 0.724 mmol) obtained in Example 6, the mixture was cooled to 0° C., and trifluoromethanesulfonic anhydride (306 mg, 1.09 mmol) was added dropwise to the mixture. After stirring the mixture at the same temperature for 30 minutes, water was added to the reaction mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (301 mg, 88%).

MS: m/z 415.0 (M−tBu+H)$^+$.

Step 2: 2-Ethylhexyl 3-[5-cyano-2-[4-[2-[(2-methylpropan-2-yl)oxycarbonylamino]ethyl]phenyl]phenyl]sulfanylpropanoate

[5-Cyano-2-[5-[2-[(2-methylpropan-2-yl)oxycarbonylamino]ethyl]pyridin-2-yl]phenyl]trifluoromethanesulfonate (301 mg, 0.640 mmol) was dissolved in 1,4-dioxane (2.6 mL), then to the solution, 2-ethylhexyl 3-mercaptopropionate (168 mg, 0.768 mmol), tris(dibenzylideneacetone)dipalladium (29 mg, 0.032 mmol), 4,5-bis(diphenylphosphino)-9,9-dimethylxanthene (37 mg, 0.064 mmol) and N,N-diisopropylethylamine (0.223 mL, 1.28 mmol) were added, and the mixture was stirred at 100° C. for 2 hours. The reaction mixture was cooled to room temperature, filtered through Celite, and then concentrated under reduced pressure. The crude product was purified by silica gel column chromatography to obtain the target compound (479 mg, containing impurities).

MS: m/z 439.2 (M-Boc+H)$^+$.

Step 3: tert-Butyl N-[2-[4-[2-(6-chloropyridazin-4-ylsulfanyl-4-cyanophenyl]phenyl]ethyl]carbamate 2-Ethylhexyl 3-[5-cyano-2-[4-[2-[(2-methylpropan-2-yl)oxycarbonylamino]ethyl]phenyl]phenyl]sulfanylpropanoate (479 mg) was dissolved in DMF (5 mL), then to the solution, 3,5-dichloropyridazine (265 mg, 1.78 mmol) and DBU (0.5 mL) were added, and the mixture was stirred at 50° C. for 30 minutes. The reaction mixture was cooled to room temperature, water was added to the mixture, and the mixture was extracted with ethyl acetate. The solution was dried over anhydrous sodium sulfate and the solution was concentrated under reduced pressure. The crude product was purified by silica gel column chromatography to obtain the target compound (340 mg).

MS: m/z 411.0 (M−tBu+H)$^+$.

$^1$H-NMR ($CDCl_3$) δ: 8.58 (1H, d, J=2.3 Hz), 7.98 (1H, d, J=1.4 Hz), 7.86 (1H, dd, J=8.0, 1.6 Hz), 7.61 (1H, d, J=7.8 Hz), 7.22-7.17 (4H, m), 6.83 (1H, d, J=2.3 Hz), 4.65 (1H, brs), 3.36 (2H, q, J=6.6 Hz), 2.80 (2H, t, J=6.9 Hz), 1.45 (9H, s).

Step 4: tert-Butyl N-[2-[4-[4-cyano-2-(6-piperidin-1-ylpyridazin-4-yl)sulfanylphenyl]phenyl]ethyl]carbamate DMF (1 mL) was added to tert-butyl N-[2-[4-[2-(6-chloropyridazin-4-yl)sulfanyl-4-cyanophenyl]phenyl]ethyl]carbamate (50.0 mg, 0.107 mmol), then to the solution, piperidine (27.4 mg, 0.321 mmol) and N,N-diisopropylethylamine (0.15 mL) were added, and the mixture was stirred at 100° C. overnight. The reaction mixture was cooled to room temperature, water was added to the mixture, and the mixture was extracted with ethyl acetate. The solution was dried over anhydrous sodium sulfate, the solution was concentrated under reduced pressure, and the crude product was used in the next reaction without further purification.

Step 5: 4-[4-(2-Aminoethyl)phenyl]-3-(6-piperidin-1-ylpyridazin-4-yl)sulfanylbenzonitrile Dichloromethane (1 mL) and TFA (0.5 mL) were added to the crude product obtained in Step 4, and the mixture was stirred at room temperature for 30 minutes. The reaction mixture was concentrated under reduced pressure, and the crude product was purified by HPLC to obtain the target compound (41.7 mg).

Exact MS: 415.2

Obs. MS (M+H)$^+$: 416.4

Example 40

4-[4-(2-Aminoethyl)pyrazol-1-yl]-3-(6-piperidin-1-ylpyridazin-4-yl)sulfanylbenzonitrile (Compound No. 1246)

[Chem. 86]

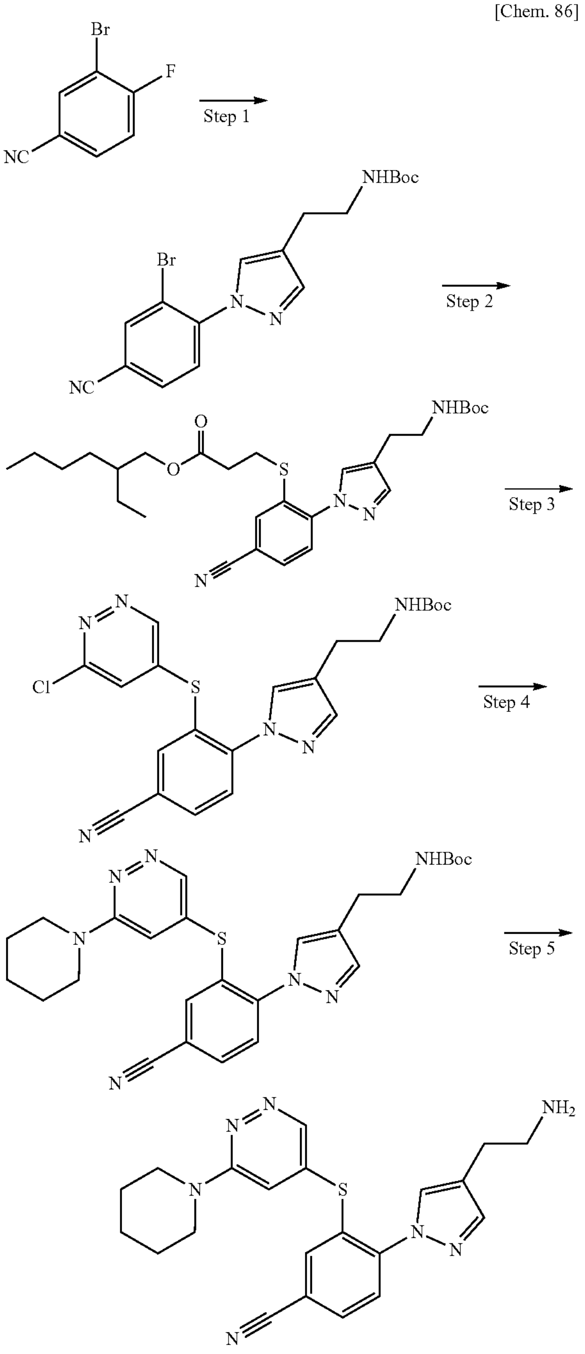

Step 1: tert-Butyl N-[2-[1-(2-bromo-4-cyanophenyl) pyrazol-4-yl]ethyl]carbamate

DMF (15 mL) was added to 3-bromo-4-fluorobenzonitrile (1.80 g, 9.00 mmol), tert-butyl N-[2-(1H-pyrazol-4-yl)ethyl] carbamate (950 mg, 4.50 mmol) and potassium carbonate (1.87 g, 13.5 mmol), and the mixture was stirred at 150° C. for 1 hour. The reaction mixture was cooled to room temperature, water was added to the mixture, and the mixture was extracted with ethyl acetate. The solution was dried over anhydrous sodium sulfate and concentrated under reduced pressure. The crude product was purified by silica gel column chromatography to obtain the target compound (1.86 g, containing impurities).

MS: m/z 391.0 $(M+H)^+$.

Step 2: 2-Ethylhexyl 3-[5-cyano-2-[4-[2-[(2-methyl-propan-2-yl)oxycarbonylamino]ethyl]pyrazol-1-yl] phenyl]sulfanylpropanoate tert-Butyl N-[2-[1-(2-bromo-4-cyanophenyl)pyrazol-4-yl]ethyl]carbamate (500 mg, 1.28 mmol) was dissolved in 1,4-dioxane (5.11 mL), then to the solution, 2-ethylhexyl 3-mercaptopropionate (335 mg, 1.53 mmol), tris(dibenzylideneacetone)dipalladium (58.5 mg, 0.0639 mmol), 4,5-bis(diphenylphosphino)-9,9-dimethylxanthene (73.9 mg, 0.128 mmol) and N,N-diisopropylethylamine (0.445 mL, 2.56 mmol) were added, and the mixture was stirred at 100° C. for 1 hour. The reaction solution was cooled to room temperature and filtered through Celite, and then the solution was concentrated under reduced pressure. The crude product was purified by silica gel column chromatography to obtain the target compound (723 mg, 96%).

MS: m/z 529.3 $(M+H)^+$.

Step 3: tert-Butyl N-[2-[l-[2-(6-chloropyridazin-4-yl)sulfanyl-4-cyanophenyl]pyrazol-4-yl]ethyl]carbamate 2-Ethylhexyl 3-[5-cyano-2-[4-[2-[(2-methylpropan-2-yl) oxycarbonylamino]ethyl]pyrazol-1-yl]phenyl]sulfanylpropanoate (723 mg, 1.37 mmol) was dissolved in DMF (2 mL), then to the solution, 3,5-dichloropyridazine (408 mg, 2.74 mmol) and DBU (0.5 mL) were added, and the mixture was stirred at 50° C. for 30 minutes. The reaction mixture was cooled to room temperature, water was added to the mixture, and the mixture was extracted with ethyl acetate. The solution was dried over anhydrous sodium sulfate and concentrated under reduced pressure. The crude product was purified by silica gel column chromatography to obtain the target compound (543 mg, 87%).

MS: m/z 401.1 $(M-tBu+H)^+$.

$^1$H-NMR ($CDCl_3$) δ: 8.78 (1H, d, J=1.8 Hz), 7.95 (1H, d, J=1.8 Hz), 7.88 (1H, dd, J=8.5, 2.1 Hz), 7.77 (1H, d, J=8.2 Hz), 7.72 (1H, s), 7.52 (1H, s), 7.00 (1H, d, J=1.8 Hz), 4.61 (1H, brs), 3.29 (2H, q, J=6.6 Hz), 2.66 (2H, t, J=7.1 Hz), 1.44 (9H, s).

Step 4: tert-Butyl N-[2-[1-[4-cyano-2-(6-piperidin-1-ylpyridazin-4-yl)sulfanylphenyl]pyrazol-4-yl] ethyl]carbamate DMF (1 mL) was added to tert-butyl N-[2-[1-[2-(6-chloropyridazin-4-yl)sulfanyl-4-cyanophenyl]pyrazol-4-yl] ethyl]carbamate (60 mg, 0.131 mmol), then to the mixture, piperidine (33.5 mg, 0.394 mmol) and N,N-diisopropylethylamine (0.15 mL) were added, and the mixture was stirred at 100° C. for 5 hours. The reaction mixture was cooled to room temperature, water was added to the mixture, and the mixture was extracted with ethyl acetate. The solution was dried over anhydrous sodium sulfate, concentrated under reduced pressure, and the crude product was used in the next reaction without further purification.

Step 5: 4-[4-(2-Aminoethyl)pyrazol-1-yl]-3-(6-piperidin-1-ylpyridazin-4-yl)sulfanylbenzonitrile Dichloromethane (1 mL) and TFA (0.5 mL) were added to the crude product obtained in Step 4, and the mixture was stirred at room temperature for 30 minutes. The reaction mixture was concentrated under reduced pressure, and the crude product was purified by HPLC to obtain the target compound (50.3 mg, 95%).

Exact MS: 405.2

Obs. MS $(M+H)^+$: 406.4

Example 41

4-[5-(2-Aminoethyl)pyrimidin-2-yl]-3-(6-piperidin-1-ylpyridazin-4-yl)sulfanylbenzonitrile (Compound No. 1276)

[Chem. 87]

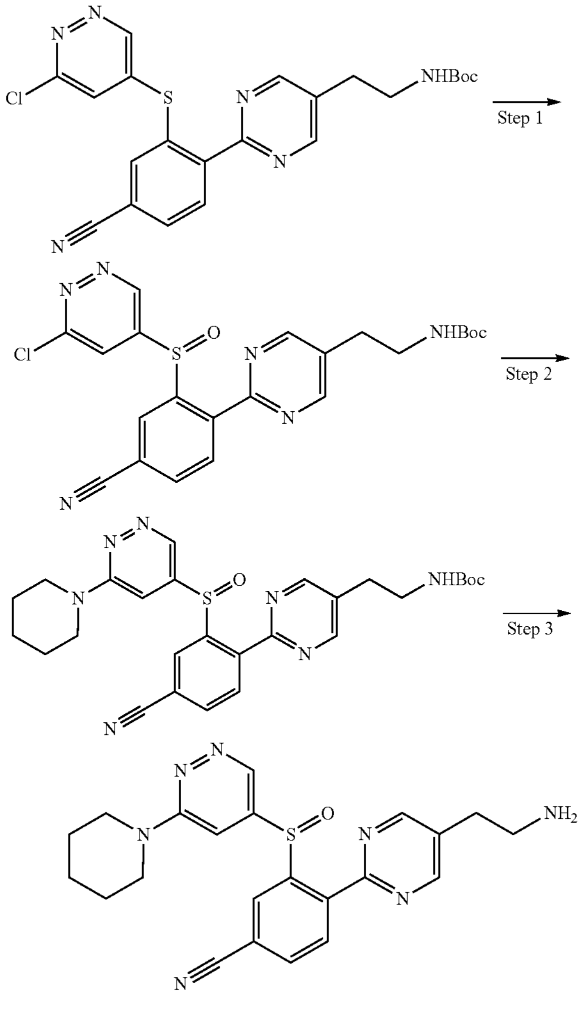

Step 1: tert-Butyl N-[2-[2-[2-(6-chloropyridazin-4-yl)sulfinyl-4-cyanophenyl]pyrimidin-5-yl]ethyl]carbamate Dichloromethane (3.3 mL) was added to tert-butyl N-[2-[2-[2-(6-chloropyridazin-4-yl)sulfanyl-4-cyanophenyl]pyrimidin-5-yl]ethyl]carbamate (154 mg, 0.328 mmol), then to the mixture, 3-chloroperbenzoic acid (75.4 mg, 0.328 mmol) was added at 0° C., and then the reaction mixture was heated to room temperature and stirred for 2 hours. The reaction solution was concentrated under reduced pressure, and the crude product obtained was used in the next reaction.

MS: m/z 485.1 $(M+H)^+$.

Step 2: tert-Butyl N-[2-[2-[4-cyano-2-(6-piperidin-1-ylpyridazin-4-yl)sulfanylphenyl]pyrimidin-5-yl]ethyl]carbamate An aliquot (79.1 mg) of the crude product obtained in Step 1 was dissolved in 1,4-dioxane (1 mL), then to the solution, piperidine (27.8 mg, 0.326 mmol), tris(dibenzylideneacetone)dipalladium (14.9 mg, 0.0163 mmol), 4,5-bis(diphenylphosphino)-9,9-dimethylxanthene (18.9 mg, 0.0326 mmol), and cesium carbonate (159 mg, 0.489 mmol) were added, and the mixture was stirred at 100° C. for 1 hour. The reaction mixture was cooled to room temperature and filtered through Celite, and then the solution was concentrated under reduced pressure. The crude was used in the next reaction.

MS: m/z 534.2 $(M+H)^+$.

Step 3: 4-[5-(2-Aminoethyl)pyrimidin-2-yl]-3-(6-piperidin-1-ylpyridazin-4-yl)sulfanylbenzonitrile Dichloromethane (1 mL) and TFA (0.5 mL) were added to the crude product obtained in Step 2, and the mixture was stirred at room temperature for 30 minutes. The reaction mixture was concentrated under reduced pressure, and the crude product was purified by HPLC to obtain the target compound (1.72 mg).

Exact MS: 433.2

Obs. MS $(M+H)^+$: 434.3

Example 42

5-[5-(2-Aminoethyl)pyridin-2-yl]-4-(2-methyl-5-phenylpyrazol-3-yl)oxypyridine-2-carbonitrile (Compound No. 1277)

[Chem. 88]

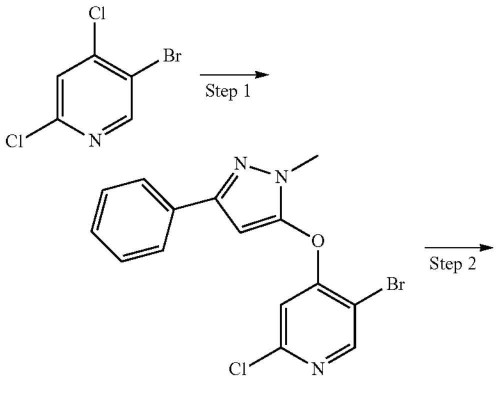

-continued

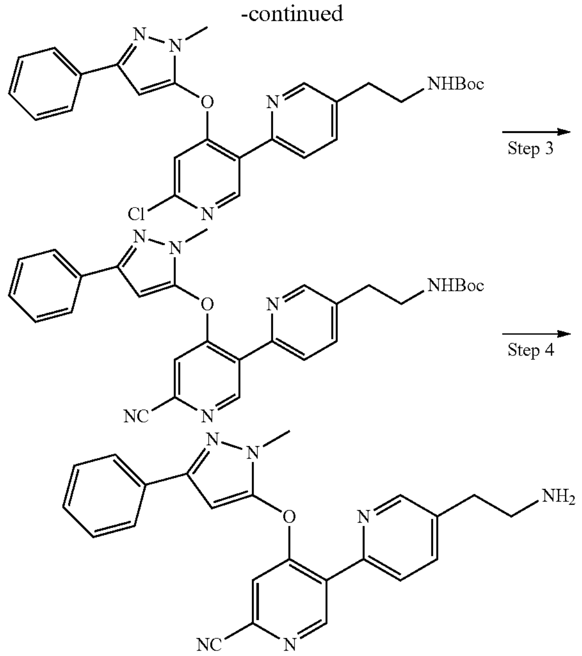

Step 1: 5-Bromo-2-chloro-4-(2-methyl-5-phenylpyrazol-3-yl)oxypyridine

5-Bromo-2,4-dichloropyridine (230 mug, 1.00 mmol) and 2-methyl-5-phenyl-4H-pyrazol-3-one (170 mg, 1.00 mmol) were dissolved in NMP (4 mL), then to the solution, potassium carbonate (280 mg, 2.00 mmol) was added, and the mixture was stirred at 130° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (279 mg, 77%).

MS: m/z 364.0 $(M+H)^+$.

Step 2: tert-Butyl N-[2-[6-[6-chloro-4-(2-methyl-5-phenylpyrazol-3-yl)oxypyridin-3-yl]pyridin-3-yl]ethyl]carbamate tert-Butyl N-[2-(6-chloropyridin-3-yl)ethyl]carbamate (77 mg, 0.30 mmol) was dissolved in 1,4-dioxane (1.5 mL), then to the solution, hexamethylditin (128 mg, 0.390 mmol) and tetrakis(triphenylphosphine)palladium (34.7 mg, 0.030 mmol) were added, and the mixture was stirred at 130° C. for 1.5 hours. To the reaction mixture, 5-bromo-2-chloro-4-(2-methyl-5-phenylpyrazol-3-yl)oxypyridine (109 mg, 0.300 mmol) and copper(I) iodide (5.7 mg, 0.030 mmol) were added, and the mixture was stirred at 130° C. for 2 hours. The reaction solution was cooled to room temperature and filtered through Celite, and then the solution was concentrated under reduced pressure. The crude product was purified by silica gel column chromatography to obtain the target compound (47.2 mg, 31%).

MS: m/z 506.2 $(M+H)^+$.

Step 3: tert-Butyl N-[2-[6-[6-cyano-4-(2-methyl-5-phenylpyrazol-3-yl)oxypyridin-3-yl]pyridin-3-yl]ethyl]carbamate tert-Butyl N-[2-[6-[6-chloro-4-(2-methyl-5-phenylpyrazol-3-yl)oxypyridin-3-yl]pyridin-3-yl]ethyl]carbamate (32.2 mg, 0.0636 mmol) was dissolved in DMF (0.13 mL), then to the solution, zinc cyanide (4.5 mg, 0.038 mmol), zinc powder (0.4 mg, 6.4 μmol), [1,1'-bis(diphenylphosphino)ferrocene]palladium dichloride-dichloromethane adduct (2.6 mg, 3.2 μmol) were added, and the mixture was stirred at 130° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was used in the next reaction without further purification.

Step 4: 5-[5-(2-Aminoethyl)pyridin-2-yl]-4-(2-methyl-5-phenylpyrazol-3-yl)oxypyridine-2-carbonitrile Dichloromethane (0.5 mL) and TFA (0.5 mL) were added to the crude product obtained in Step 3, and the mixture was stirred at room temperature for 1 hour. The reaction mixture was concentrated under reduced pressure, and the crude product was purified by HPLC to obtain the target compound (3.6 mg).

Exact MS: 396.2

Obs. MS $(M+H)^+$: 397.2

Example 43

5-[5-(2-Aminoethyl)pyridin-2-yl]-6-(2-methyl-5-phenylpyrazol-3-yl)oxypyridine-2-carbonitrile (Compound No. 1279)

[Chem. 89]

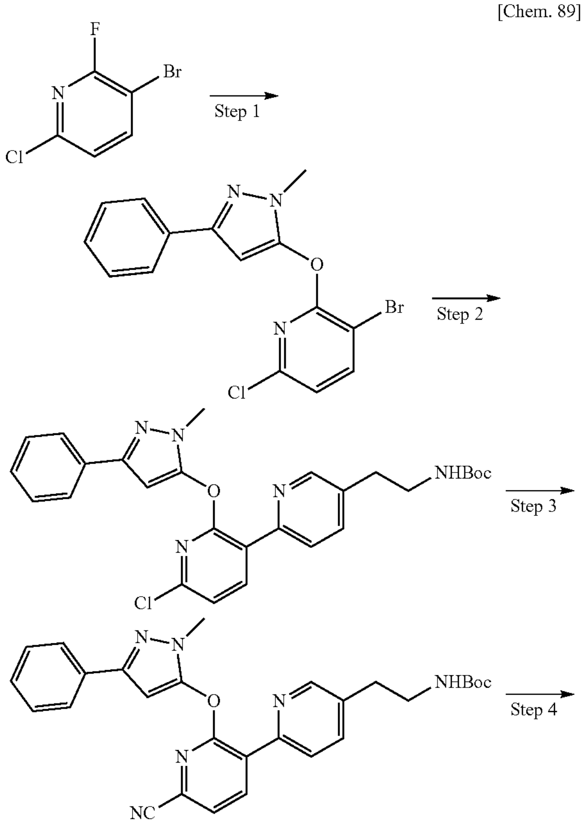

-continued

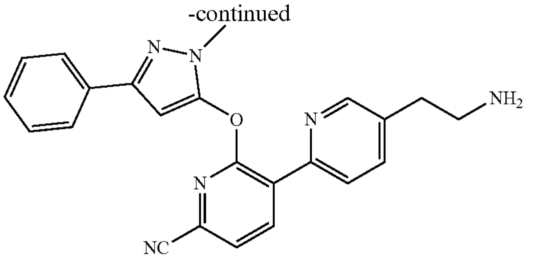

Step 1: 3-Bromo-6-chloro-2-(2-methyl-5-phenylpyrazol-3-yl)oxypyridine

3-Bromo-6-chloro-2-fluoropyridine (420 mg, 2.00 mmol) and 2-methyl-5-phenyl-4H-pyrazol-3-one (348 mg, 2.00 mmol) were dissolved in NMP (8 mL), then to the solution, potassium carbonate (552 mg, 3.99 mmol) was added, and the mixture was stirred at 130° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was purified by silica gel column chromatography to obtain the target compound (495 mg, 68%).

MS: m/z 364.0 $(M+H)^+$.

Step 2: tert-Butyl N-[2-[6-[6-cyano-2-(2-methyl-5-phenylpyrazol-3-yl)oxypyridin-3-yl]pyridin-3-yl]ethyl]carbamate tert-Butyl N-[2-(6-chloropyridin-3-yl)ethyl]carbamate (77 mg, 0.30 mmol) was dissolved in 1,4-dioxane (1.5 mL), then to the solution, hexamethylditin (128 mg, 0.390 mmol) and tetrakis(triphenylphosphine)palladium (34.7 mg, 0.030 mmol) were added, and the mixture was stirred at 130° C. for 1.5 hours. To the reaction mixture, 3-bromo-6-chloro-2-(2-methyl-5-phenylpyrazol-3-yl)oxypyridine (109 mg, 0.300 mmol) and copper(I) iodide (5.7 mg, 0.030 mmol) were added, and the mixture was stirred at 130° C. for 2 hours. The reaction mixture was cooled to room temperature and filtered through Celite, and then the solution was concentrated under reduced pressure. The crude product was purified by silica gel column chromatography to obtain the target compound (32.9 mg, 22%).

MS: m/z 506.2 $(M+H)^+$.

Step 3: tert-Butyl N-[2-[6-[6-cyano-2-(2-methyl-5-phenylpyrazol-3-yl)oxypyridin-3-yl]pyridin-3-yl]ethyl]carbamate tert-Butyl N-[2-[6-[6-cyano-2-(2-methyl-5-phenylpyrazol-3-yl)oxypyridin-3-yl]pyridin-3-yl]ethyl]carbamate (20 mg, 0.0395 mmol) was dissolved in DMF (0.13 mL), then to the solution, zinc cyanide (2.8 mg, 0.024 mmol), zinc powder (0.3 mg, 4 μmol), and [1,1'-bis(diphenylphosphino)ferrocene]palladium dichloride-dichloromethane adduct (1.6 mg, 2 μmol) were added, and the mixture was stirred at 130° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was used in the next reaction without further purification.

MS: m/z 497.3 $(M+H)^+$.

Step 4: 5-[5-(2-Aminoethyl)pyridin-2-yl]-6-(2-methyl-5-phenylpyrazol-3-yl)oxypyridine-2-carbonitrile Dichloromethane (0.5 mL) and TFA (0.5 mL) were added to the crude product obtained in Step 3, and the mixture was stirred at room temperature for 1 hour. The reaction mixture was concentrated under reduced pressure, and the crude product was purified by HPLC to obtain the target compound (8.6 mg).

Exact MS: 396.2

Obs. MS $(M+H)^+$: 397.4

Example 44

6-[5-(Aminomethyl)pyridin-2-yl]-5-(2-methyl-5-pyridin-2-ylpyrazol-3-yl)oxypyridine-3-carbonitrile (Compound No. 1289)

[Chem. 90]

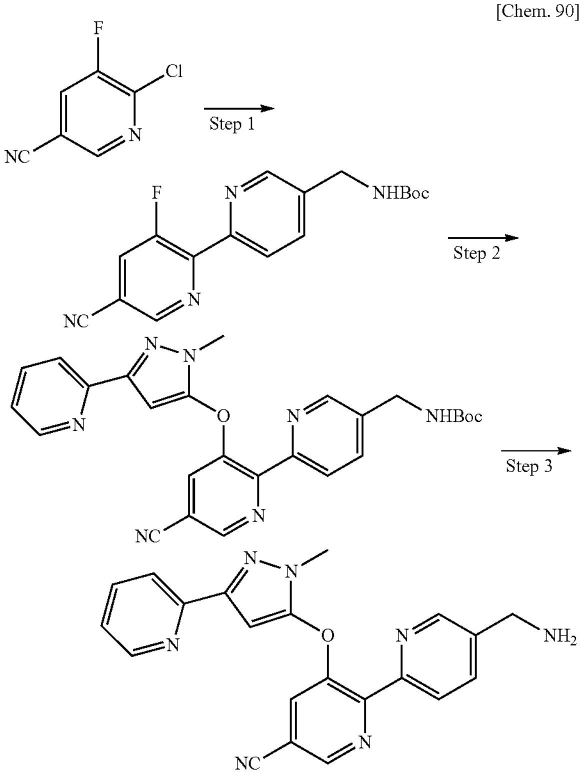

Step 1: tert-Butyl N-[[6-(5-cyano-3-fluoropyridin-2-yl)pyridin-3-yl]methyl]carbamate tert-Butyl N-[(6-chloropyridin-3-yl)methyl]carbamate (72.8 mg, 0.300 mmol) was dissolved in 1,4-dioxane (1.5 mL), then to the solution, hexamethylditin (128 mg, 0.390 mmol) and tetrakis(triphenylphosphine)palladium (34.7 mg, 0.030 mmol) were added, and the mixture was stirred at 130° C. for 1.5 hours. To the reaction mixture, 6-chloro-5-fluoropyridine-3-carbonitrile (51.7 mg, 0.330 mmol) and copper (I) iodide (5.7 mg, 0.030 mmol) were added, and the mixture was stirred at 130° C. for 2 hours. The reaction mixture was cooled to room temperature and filtered through Celite, and then the solution was concentrated under reduced pressure. The crude product was purified by silica gel column chromatography to obtain the target compound (77.9 mg, 79%).

MS: m/z 329.2 $(M+H)^+$.

Step, 2: tert-Butyl N-[[6-[5-cyano-3-(2-methyl-5-pyridin-2-ylpyrazol-3-yl)oxypyridin-2-yl]pyridin-3-yl]methyl]carbamate tert-Butyl N-[[6-(5-cyano-3-fluoropyridin-2-yl)pyridin-3-yl]methyl]carbamate (77.9 mg, 0.237 mmol) and 2-methyl-5-pyridin-2-yl-4H-pyrazol-3-one (41.6 mg, 0.237 mmol) were dissolved in NMP (0.95 mL), then to the solution, potassium carbonate (65.6 mg, 0.475 mmol) was added, and the mixture was stirred at 130° C. for 1 hour. The reaction mixture was cooled to room temperature, water was added to the mixture, and the mixture was extracted with ethyl acetate. The organic layer was washed with saturated brine and dried over anhydrous sodium sulfate, and the solution was concentrated under reduced pressure. The crude product was used in the next reaction without further purification.

Step 3: 6-[5-(Aminomethyl)pyridin-2-yl]-5-(2-methyl-5-pyridin-2-ylpyrazol-3-yl)oxypyridine-3-carbonitrile Dichloromethane (0.5 mL) and TFA (0.5 mL) were added to the crude product obtained in Step 2, and the mixture was stirred at room temperature for 1 hour. The reaction mixture was concentrated under reduced pressure, and the crude product was purified by HPLC to obtain the target compound (6.9 mg).

Exact MS: 383.2

Obs. MS $(M+H)^+$: 384.2

Example 45

Compounds 1 to 1405 shown in Table 1 above were synthesized by protection, deprotection and the like as necessary according to the synthesis methods described in Examples 1 to 44. The MS data is shown in Table 2 below.

TABLE 2

| Compound number | Exact MS | Obs MS $(M + H)^+$ |
|---|---|---|
| 1 | 377.2 | 378.1 |
| 2 | 414.2 | 415.2 |
| 3 | 454.2 | 455.2 |
| 4 | 428.2 | 429.4 |
| 5 | 482.2 | 483.4 |
| 6 | 409.2 | 410.4 |
| 7 | 415.2 | 416.2 |
| 8 | 429.2 | 430.2 |
| 9 | 431.2 | 432.2 |
| 10 | 470.2 | 471.3 |
| 11 | 445.2 | 446.2 |
| 12 | 456.2 | 457.3 |
| 13 | 507.2 | 508.2 |
| 14 | 389.2 | 390.2 |
| 15 | 401.2 | 402.4 |
| 16 | 429.3 | 430.5 |
| 17 | 413.2 | 414.0 |
| 18 | 449.2 | 450.4 |
| 19 | 449.2 | 450.4 |
| 20 | 410.2 | 411.4 |

TABLE 2-continued

| Compound number | Exact MS | Obs MS $(M + H)^+$ |
|---|---|---|
| 21 | 431.2 | 431.9 |
| 22 | 422.2 | 422.9 |
| 23 | 474.2 | 474.9 |
| 24 | 421.2 | 422.4 |
| 25 | 399.2 | 400.2 |
| 26 | 471.2 | 471.9 |
| 27 | 427.2 | 428.0 |
| 28 | 409.2 | 409.9 |
| 29 | 409.2 | 409.9 |
| 30 | 413.1 | 413.9 |
| 31 | 429.2 | 430.0 |
| 32 | 412.1 | 412.9 |
| 33 | 412.1 | 412.9 |
| 34 | 397.2 | 398.4 |
| 35 | 428.1 | 428.9 |
| 36 | 406.2 | 406.9 |
| 37 | 442.2 | 443.4 |
| 38 | 402.2 | 402.9 |
| 39 | 442.2 | 443.0 |
| 40 | 413.1 | 413.8 |
| 41 | 416.2 | 417.3 |
| 42 | 430.2 | 431.3 |
| 43 | 414.2 | 415.3 |
| 44 | 428.2 | 429.3 |
| 45 | 414.2 | 415.3 |
| 46 | 398.2 | 399.2 |
| 47 | 416.2 | 417.3 |
| 48 | 404.2 | 405.2 |
| 49 | 414.2 | 415.3 |
| 50 | 401.2 | 402.4 |
| 51 | 417.2 | 418.5 |
| 52 | 427.2 | 428.5 |
| 53 | 441.2 | 442.5 |
| 54 | 515.3 | 516.5 |
| 55 | 499.2 | 500.5 |
| 56 | 487.2 | 488.5 |
| 57 | 487.3 | 488.6 |
| 58 | 473.2 | 474.5 |
| 59 | 491.2 | 492.5 |
| 60 | 509.2 | 510.4 |
| 61 | 509.2 | 510.5 |
| 62 | 429.2 | 430.5 |
| 63 | 489.2 | 490.4 |
| 64 | 489.2 | 490.2 |
| 65 | 385.2 | 386.2 |
| 66 | 399.2 | 400.4 |
| 67 | 441.2 | 442.3 |
| 68 | 445.2 | 446.4 |
| 69 | 392.2 | 393.3 |
| 70 | 408.2 | 409.0 |
| 71 | 443.1 | 444.1 |
| 72 | 497.2 | 498.3 |
| 73 | 481.2 | 482.3 |
| 74 | 416.2 | 417.3 |
| 75 | 407.2 | 408.3 |
| 76 | 351.1 | 352.2 |
| 77 | 402.2 | 403.1 |
| 78 | 400.2 | 401.2 |
| 79 | 351.1 | 352.2 |
| 80 | 402.2 | 403.1 |
| 81 | 400.2 | 401.1 |
| 82 | 408.2 | 409.3 |
| 83 | 418.2 | 419.3 |
| 84 | 435.1 | 436.2 |
| 85 | 416.2 | 417.3 |
| 86 | 407.2 | 408.3 |
| 87 | 351.1 | 352.2 |
| 88 | 351.1 | 352.0 |
| 89 | 402.2 | 403.3 |
| 90 | 400.2 | 401.3 |
| 91 | 402.2 | 403.3 |
| 92 | 400.2 | 401.1 |
| 93 | 417.2 | 418.3 |
| 94 | 435.2 | 436.3 |
| 95 | 427.2 | 428.3 |
| 96 | 450.2 | 451.3 |
| 97 | 476.2 | 477.2 |

TABLE 2-continued

| Compound number | Exact MS | Obs MS (M + H)+ |
|---|---|---|
| 98 | 471.2 | 472.2 |
| 99 | 468.2 | 469.3 |
| 100 | 459.2 | 460.2 |
| 101 | 483.2 | 484.2 |
| 102 | 393.2 | 394.3 |
| 103 | 393.2 | 394.3 |
| 104 | 440.2 | 441.3 |
| 105 | 449.2 | 450.3 |
| 106 | 459.2 | 460.3 |
| 107 | 400.2 | 401.3 |
| 108 | 402.2 | 403.3 |
| 109 | 414.1 | 415.2 |
| 110 | 411.2 | 412.3 |
| 111 | 464.2 | 465.2 |
| 112 | 424.2 | 425.3 |
| 113 | 469.2 | 470.2 |
| 114 | 393.2 | 394.3 |
| 115 | 394.2 | 395.3 |
| 116 | 410.2 | 411.2 |
| 117 | 476.1 | 477.2 |
| 118 | 422.2 | 423.2 |
| 119 | 449.2 | 450.2 |
| 120 | 450.2 | 451.2 |
| 121 | 436.2 | 437.2 |
| 122 | 469.2 | 470.1 |
| 123 | 416.2 | 417.1 |
| 124 | 416.2 | 417.1 |
| 125 | 402.2 | 403.3 |
| 126 | 416.2 | 417.3 |
| 127 | 432.2 | 433.2 |
| 128 | 414.2 | 415.2 |
| 129 | 452.2 | 453.1 |
| 130 | 424.2 | 425.2 |
| 131 | 441.2 | 442.2 |
| 132 | 427.2 | 428.2 |
| 133 | 465.2 | 466.2 |
| 134 | 443.2 | 444.2 |
| 135 | 368.1 | 369.1 |
| 136 | 421.2 | 422.1 |
| 137 | 384.2 | 385.1 |
| 138 | 414.2 | 415.3 |
| 139 | 451.2 | 452.2 |
| 140 | 430.2 | 431.2 |
| 141 | 430.2 | 431.2 |
| 142 | 426.2 | 427.2 |
| 143 | 441.2 | 442.2 |
| 144 | 421.2 | 422.1 |
| 145 | 401.2 | 402.2 |
| 146 | 410.1 | 411.1 |
| 147 | 470.2 | 471.2 |
| 148 | 470.2 | 471.2 |
| 149 | 449.2 | 450.2 |
| 150 | 465.2 | 466.2 |
| 151 | 499.2 | 500.2 |
| 152 | 447.2 | 448.2 |
| 153 | 467.2 | 468.2 |
| 154 | 398.1 | 399.1 |
| 155 | 475.2 | 476.1 |
| 156 | 461.2 | 462.2 |
| 157 | 445.2 | 446.2 |
| 158 | 470.2 | 471.2 |
| 159 | 446.1 | 447.1 |
| 160 | 395.2 | 396.3 |
| 161 | 411.2 | 412.3 |
| 162 | 396.2 | 397.3 |
| 163 | 395.2 | 396.3 |
| 164 | 409.2 | 410.3 |
| 165 | 412.2 | 413.3 |
| 166 | 408.2 | 409.3 |
| 167 | 425.2 | 426.2 |
| 168 | 438.1 | 439.2 |
| 169 | 421.2 | 422.3 |
| 170 | 412.2 | 413.2 |
| 171 | 412.2 | 413.2 |
| 172 | 415.2 | 416.3 |
| 173 | 415.2 | 416.2 |
| 174 | 395.2 | 396.3 |

TABLE 2-continued

| Compound number | Exact MS | Obs MS (M + H)+ |
|---|---|---|
| 175 | 395.2 | 396.3 |
| 176 | 396.2 | 397.3 |
| 177 | 411.2 | 412.2 |
| 178 | 396.2 | 397.3 |
| 179 | 396.2 | 397.2 |
| 180 | 425.2 | 426.3 |
| 181 | 410.2 | 411.3 |
| 182 | 410.2 | 411.3 |
| 183 | 428.2 | 429.2 |
| 184 | 413.2 | 414.3 |
| 185 | 413.2 | 414.2 |
| 186 | 412.2 | 413.3 |
| 187 | 413.2 | 414.3 |
| 188 | 408.2 | 409.3 |
| 189 | 422.2 | 423.3 |
| 190 | 425.2 | 426.2 |
| 191 | 448.2 | 449.1 |
| 192 | 438.2 | 439.2 |
| 193 | 438.2 | 439.2 |
| 194 | 415.2 | 416.3 |
| 195 | 429.1 | 430.2 |
| 196 | 387.1 | 388.3 |
| 197 | 430.2 | 431.3 |
| 198 | 428.2 | 429.3 |
| 199 | 413.2 | 414.3 |
| 200 | 412.2 | 413.1 |
| 201 | 419.2 | 420.3 |
| 202 | 359.2 | 360.4 |
| 203 | 411.2 | 412.3 |
| 204 | 400.2 | 401.1 |
| 205 | 426.2 | 427.3 |
| 206 | 426.2 | 427.3 |
| 207 | 451.2 | 452.3 |
| 208 | 443.2 | 444.3 |
| 209 | 457.2 | 458.4 |
| 210 | 457.2 | 458.3 |
| 211 | 374.2 | 375.3 |
| 212 | 390.2 | 391.3 |
| 213 | 358.2 | 359.3 |
| 214 | 372.2 | 373.3 |
| 215 | 374.2 | 375.3 |
| 216 | 381.1 | 382.1 |
| 217 | 439.2 | 440.3 |
| 218 | 453.2 | 454.3 |
| 219 | 453.2 | 454.3 |
| 220 | 431.1 | 432.3 |
| 221 | 426.2 | 427.4 |
| 222 | 429.1 | 430.1 |
| 223 | 429.1 | 430.1 |
| 224 | 429.1 | 430.3 |
| 225 | 417.1 | 418.1 |
| 226 | 411.2 | 412.1 |
| 227 | 403.2 | 404.3 |
| 228 | 375.2 | 376.0 |
| 229 | 361.2 | 362.0 |
| 230 | 361.2 | 362.0 |
| 231 | 426.2 | 427.2 |
| 232 | 405.2 | 406.2 |
| 233 | 419.2 | 420.2 |
| 234 | 461.3 | 462.1 |
| 235 | 447.2 | 448.2 |
| 236 | 427.2 | 428.1 |
| 237 | 373.2 | 374.0 |
| 238 | 395.1 | 396.0 |
| 239 | 445.2 | 446.1 |
| 240 | 449.2 | 450.0 |
| 241 | 420.2 | 421.2 |
| 242 | 376.2 | 377.1 |
| 243 | 416.3 | 417.1 |
| 244 | 468.2 | 469.0 |
| 245 | 417.2 | 418.2 |
| 246 | 415.1 | 416.1 |
| 247 | 443.2 | 444.1 |
| 248 | 412.2 | 413.0 |
| 249 | 412.2 | 413.1 |
| 250 | 416.2 | 417.4 |
| 251 | 449.2 | 450.3 |

TABLE 2-continued

| Compound number | Exact MS | Obs MS (M + H)+ |
|---|---|---|
| 252 | 441.2 | 442.0 |
| 253 | 487.2 | 488.0 |
| 254 | 399.2 | 400.1 |
| 255 | 391.2 | 392.2 |
| 256 | 455.2 | 456.3 |
| 257 | 455.2 | 456.3 |
| 258 | 407.2 | 408.2 |
| 259 | 405.2 | 406.3 |
| 260 | 362.2 | 363.3 |
| 261 | 362.2 | 363.3 |
| 262 | 400.2 | 401.1 |
| 263 | 429.1 | 430.3 |
| 264 | 387.1 | 388.4 |
| 265 | 420.2 | 421.3 |
| 266 | 434.2 | 435.2 |
| 267 | 408.2 | 409.3 |
| 268 | 434.1 | 435.3 |
| 269 | 406.2 | 407.3 |
| 270 | 420.2 | 421.3 |
| 271 | 442.2 | 443.3 |
| 272 | 374.2 | 375.3 |
| 273 | 404.2 | 405.3 |
| 274 | 396.2 | 397.3 |
| 275 | 408.2 | 409.3 |
| 276 | 389.2 | 390.4 |
| 277 | 394.2 | 395.3 |
| 278 | 390.2 | 391.4 |
| 279 | 451.2 | 452.4 |
| 280 | 428.2 | 429.2 |
| 281 | 429.2 | 430.4 |
| 282 | 391.2 | 392.2 |
| 283 | 389.2 | 390.2 |
| 284 | 375.2 | 376.2 |
| 285 | 397.2 | 398.4 |
| 286 | 398.2 | 399.4 |
| 287 | 390.2 | 391.4 |
| 288 | 347.2 | 348.4 |
| 289 | 381.2 | 382.3 |
| 290 | 382.2 | 383.3 |
| 291 | 407.2 | 408.4 |
| 292 | 408.2 | 409.4 |
| 293 | 348.2 | 349.2 |
| 294 | 409.2 | 410.4 |
| 295 | 433.2 | 434.2 |
| 296 | 423.2 | 424.2 |
| 297 | 429.2 | 430.3 |
| 298 | 391.2 | 392.2 |
| 299 | 333.2 | 334.2 |
| 300 | 319.1 | 320.3 |
| 301 | 439.2 | 440.3 |
| 302 | 449.2 | 450.3 |
| 303 | 459.2 | 460.3 |
| 304 | 322.2 | 323.2 |
| 305 | 334.2 | 335.2 |
| 306 | 381.1 | 382.3 |
| 307 | 451.2 | 452.4 |
| 308 | 431.2 | 432.3 |
| 309 | 391.2 | 392.3 |
| 310 | 382.2 | 383.2 |
| 311 | 320.1 | 321.3 |
| 312 | 396.2 | 397.2 |
| 313 | 396.2 | 397.2 |
| 314 | 412.2 | 413.3 |
| 315 | 371.2 | 372.3 |
| 316 | 363.1 | 364.3 |
| 317 | 360.2 | 361.3 |
| 318 | 391.2 | 392.4 |
| 319 | 376.2 | 377.4 |
| 320 | 441.2 | 442.4 |
| 321 | 427.2 | 428.4 |
| 322 | 517.2 | 518.4 |
| 323 | 319.1 | 320.3 |
| 324 | 334.2 | 335.3 |
| 325 | 346.2 | 347.3 |
| 326 | 333.2 | 334.3 |
| 327 | 345.2 | 346.3 |
| 328 | 402.2 | 403.4 |

TABLE 2-continued

| Compound number | Exact MS | Obs MS (M + H)+ |
|---|---|---|
| 329 | 401.2 | 402.4 |
| 330 | 333.2 | 334.3 |
| 331 | 345.2 | 346.3 |
| 332 | 402.2 | 403.4 |
| 333 | 443.2 | 444.4 |
| 334 | 387.2 | 388.4 |
| 335 | 403.2 | 404.3 |
| 336 | 419.2 | 420.4 |
| 337 | 392.2 | 393.3 |
| 338 | 424.2 | 425.4 |
| 339 | 430.2 | 431.3 |
| 340 | 446.1 | 447.3 |
| 341 | 437.2 | 438.4 |
| 342 | 430.2 | 431.3 |
| 343 | 446.1 | 447.3 |
| 344 | 437.2 | 438.4 |
| 345 | 363.2 | 364.4 |
| 346 | 396.2 | 397.4 |
| 347 | 360.2 | 361.4 |
| 348 | 375.2 | 376.4 |
| 349 | 349.2 | 350.3 |
| 350 | 431.2 | 432.4 |
| 351 | 480.2 | 481.4 |
| 352 | 413.2 | 414.4 |
| 353 | 480.2 | 481.4 |
| 354 | 426.2 | 427.4 |
| 355 | 480.2 | 481.4 |
| 356 | 413.2 | 414.4 |
| 357 | 480.2 | 481.4 |
| 358 | 426.2 | 427.4 |
| 359 | 378.2 | 379.3 |
| 360 | 414.2 | 415.3 |
| 361 | 347.2 | 384.4 |
| 362 | 347.2 | 348.4 |
| 363 | 348.2 | 349.3 |
| 364 | 348.2 | 349.3 |
| 365 | 411.2 | 412.3 |
| 366 | 411.2 | 412.4 |
| 367 | 376.2 | 377.4 |
| 368 | 417.2 | 418.3 |
| 369 | 402.2 | 403.4 |
| 370 | 443.2 | 444.3 |
| 371 | 408.2 | 409.2 |
| 372 | 376.2 | 377.3 |
| 373 | 376.2 | 377.3 |
| 374 | 375.2 | 376.3 |
| 375 | 375.2 | 376.3 |
| 376 | 438.1 | 439.2 |
| 377 | 445.1 | 446.2 |
| 378 | 425.2 | 426.4 |
| 379 | 428.2 | 429.3 |
| 380 | 388.2 | 389.3 |
| 381 | 424.2 | 425.4 |
| 382 | 403.2 | 404.4 |
| 383 | 439.2 | 440.4 |
| 384 | 370.1 | 371.3 |
| 385 | 376.2 | 377.3 |
| 386 | 364.2 | 365.3 |
| 387 | 432.2 | 433.3 |
| 388 | 416.2 | 417.4 |
| 389 | 404.2 | 405.4 |
| 390 | 402.1 | 403.2 |
| 391 | 403.1 | 404.3 |
| 392 | 403.2 | 404.3 |
| 393 | 388.2 | 389.4 |
| 394 | 383.1 | 384.3 |
| 395 | 410.2 | 411.3 |
| 396 | 396.2 | 397.2 |
| 397 | 429.2 | 430.4 |
| 398 | 415.2 | 416.4 |
| 399 | 379.2 | 380.2 |
| 400 | 373.2 | 374.3 |
| 401 | 359.2 | 360.3 |
| 402 | 414.2 | 415.3 |
| 403 | 429.2 | 430.3 |
| 404 | 430.2 | 431.3 |
| 405 | 391.2 | 392.4 |

TABLE 2-continued

| Compound number | Exact MS | Obs MS (M + H)+ |
|---|---|---|
| 406 | 392.2 | 393.4 |
| 407 | 403.2 | 404.4 |
| 408 | 404.2 | 405.4 |
| 409 | 459.2 | 460.3 |
| 410 | 445.2 | 446.3 |
| 411 | 444.2 | 445.3 |
| 412 | 431.2 | 432.3 |
| 413 | 391.2 | 392.4 |
| 414 | 371.1 | 372.3 |
| 415 | 407.1 | 408.3 |
| 416 | 331.1 | 332.2 |
| 417 | 332.1 | 333.2 |
| 418 | 444.2 | 445.3 |
| 419 | 486.2 | 487.4 |
| 420 | 376.2 | 377.3 |
| 421 | 375.2 | 376.3 |
| 422 | 370.2 | 371.2 |
| 423 | 426.2 | 427.3 |
| 424 | 415.2 | 416.3 |
| 425 | 471.2 | 472.4 |
| 426 | 389.1 | 390.3 |
| 427 | 401.2 | 402.3 |
| 428 | 425.1 | 426.3 |
| 429 | 431.2 | 432.3 |
| 430 | 432.2 | 433.3 |
| 431 | 375.2 | 376.3 |
| 432 | 375.2 | 376.3 |
| 433 | 423.1 | 424.2 |
| 434 | 417.2 | 418.2 |
| 435 | 458.2 | 459.3 |
| 436 | 402.2 | 403.2 |
| 437 | 360.2 | 361.2 |
| 438 | 345.2 | 346.2 |
| 439 | 466.2 | 467.3 |
| 440 | 389.2 | 390.3 |
| 441 | 390.2 | 391.2 |
| 442 | 419.2 | 420.3 |
| 443 | 345.2 | 346.2 |
| 444 | 466.2 | 467.3 |
| 445 | 442.2 | 443.3 |
| 446 | 457.2 | 458.3 |
| 447 | 415.2 | 416.3 |
| 448 | 401.2 | 402.3 |
| 449 | 489.2 | 490.3 |
| 450 | 331.1 | 332.2 |
| 451 | 331.1 | 332.2 |
| 452 | 381.2 | 382.2 |
| 453 | 381.2 | 382.2 |
| 454 | 442.2 | 443.3 |
| 455 | 429.2 | 430.3 |
| 456 | 428.2 | 429.3 |
| 457 | 421.2 | 422.2 |
| 458 | 418.2 | 419.3 |
| 459 | 417.2 | 418.3 |
| 460 | 429.2 | 430.3 |
| 461 | 388.2 | 389.3 |
| 462 | 428.2 | 429.3 |
| 463 | 372.2 | 373.3 |
| 464 | 442.2 | 443.2 |
| 465 | 443.2 | 444.3 |
| 466 | 423.2 | 424.3 |
| 467 | 403.2 | 404.2 |
| 468 | 371.1 | 372.2 |
| 469 | 411.2 | 412.2 |
| 470 | 430.2 | 431.3 |
| 471 | 430.2 | 431.3 |
| 472 | 395.1 | 396.2 |
| 473 | 417.2 | 418.2 |
| 474 | 413.1 | 414.2 |
| 475 | 371.1 | 372.2 |
| 476 | 444.2 | 445.3 |
| 477 | 388.2 | 389.3 |
| 478 | 446.2 | 447.3 |
| 479 | 448.2 | 449.3 |
| 480 | 345.2 | 346.2 |
| 481 | 359.2 | 360.2 |
| 482 | 359.2 | 360.2 |

TABLE 2-continued

| Compound number | Exact MS | Obs MS (M + H)+ |
|---|---|---|
| 483 | 390.2 | 391.2 |
| 484 | 389.2 | 390.2 |
| 485 | 404.2 | 405.3 |
| 486 | 456.2 | 457.3 |
| 487 | 458.2 | 459.3 |
| 488 | 444.2 | 445.3 |
| 489 | 416.2 | 417.2 |
| 490 | 430.2 | 431.3 |
| 491 | 402.2 | 403.2 |
| 492 | 405.2 | 406.2 |
| 493 | 384.2 | 385.3 |
| 494 | 440.2 | 441.2 |
| 495 | 390.2 | 391.2 |
| 496 | 389.2 | 390.2 |
| 497 | 481.3 | 482.2 |
| 498 | 415.2 | 416.2 |
| 499 | 416.2 | 417.2 |
| 500 | 429.2 | 430.2 |
| 501 | 430.2 | 431.2 |
| 502 | 419.2 | 420.2 |
| 503 | 404.2 | 405.2 |
| 504 | 388.2 | 389.2 |
| 505 | 459.2 | 460.2 |
| 506 | 460.2 | 416.2 |
| 507 | 416.2 | 417.2 |
| 508 | 417.2 | 418.2 |
| 509 | 430.2 | 431.2 |
| 510 | 431.2 | 432.2 |
| 511 | 413.2 | 414.2 |
| 512 | 397.2 | 398.2 |
| 513 | 453.2 | 454.2 |
| 514 | 419.2 | 420.2 |
| 515 | 385.2 | 386.2 |
| 516 | 424.2 | 425.2 |
| 517 | 431.2 | 432.2 |
| 518 | 409.1 | 352.1 |
| 519 | 375.2 | 376.2 |
| 520 | 351.1 | 352.1 |
| 521 | 388.1 | 389.1 |
| 522 | 421.2 | 422.2 |
| 523 | 460.2 | 461.2 |
| 524 | 461.2 | 462.2 |
| 525 | 423.2 | 424.2 |
| 526 | 424.2 | 425.2 |
| 527 | 443.2 | 444.2 |
| 528 | 444.2 | 445.2 |
| 529 | 445.2 | 446.2 |
| 530 | 446.2 | 447.2 |
| 531 | 459.2 | 460.2 |
| 532 | 460.2 | 461.2 |
| 533 | 429.2 | 430.2 |
| 534 | 389.2 | 390.2 |
| 535 | 389.2 | 390.2 |
| 536 | 418.1 | 419.1 |
| 537 | 443.2 | 444.2 |
| 538 | 445.2 | 446.2 |
| 539 | 471.2 | 472.2 |
| 540 | 413.2 | 414.2 |
| 541 | 402.2 | 403.2 |
| 542 | 388.2 | 389.2 |
| 543 | 362.2 | 363.2 |
| 544 | 418.2 | 419.2 |
| 545 | 404.2 | 405.2 |
| 546 | 378.2 | 379.2 |
| 547 | 376.2 | 377.2 |
| 548 | 392.2 | 393.2 |
| 549 | 392.2 | 393.2 |
| 550 | 445.2 | 446.2 |
| 551 | 402.2 | 403.2 |
| 552 | 428.2 | 429.2 |
| 553 | 442.2 | 443.2 |
| 554 | 442.2 | 443.2 |
| 555 | 442.2 | 443.2 |
| 556 | 375.2 | 376.2 |
| 557 | 404.2 | 405.2 |
| 558 | 446.2 | 447.2 |
| 559 | 447.2 | 448.2 |

TABLE 2-continued

| Compound number | Exact MS | Obs MS $(M + H)^+$ |
|---|---|---|
| 560 | 460.2 | 461.2 |
| 561 | 461.2 | 462.2 |
| 562 | 457.2 | 458.2 |
| 563 | 444.2 | 445.2 |
| 564 | 443.2 | 444.2 |
| 565 | 470.2 | 471.3 |
| 566 | 431.2 | 432.3 |
| 567 | 431.2 | 432.2 |
| 568 | 470.2 | 471.2 |
| 569 | 470.2 | 471.2 |
| 570 | 399.2 | 400.2 |
| 571 | 411.2 | 412.3 |
| 572 | 394.2 | 395.2 |
| 573 | 375.2 | 376.2 |
| 574 | 419.1 | 420.1 |
| 575 | 376.2 | 377.2 |
| 576 | 350.1 | 351.2 |
| 577 | 334.2 | 335.2 |
| 578 | 428.2 | 429.2 |
| 579 | 408.2 | 409.2 |
| 580 | 430.2 | 431.2 |
| 581 | 443.2 | 444.2 |
| 582 | 352.1 | 353.1 |
| 583 | 388.1 | 389.1 |
| 584 | 335.1 | 336.1 |
| 585 | 389.2 | 390.2 |
| 586 | 389.2 | 390.2 |
| 587 | 396.2 | 397.2 |
| 588 | 402.1 | 403.2 |
| 589 | 422.2 | 423.2 |
| 590 | 441.2 | 442.2 |
| 591 | 418.2 | 419.2 |
| 592 | 389.1 | 390.1 |
| 593 | 408.1 | 409.1 |
| 594 | 371.1 | 372.2 |
| 595 | 414.1 | 415.1 |
| 596 | 398.1 | 399.2 |
| 597 | 409.2 | 410.2 |
| 598 | 415.1 | 416.1 |
| 599 | 409.2 | 410.2 |
| 600 | 444.1 | 445.1 |
| 601 | 444.1 | 445.1 |
| 602 | 429.1 | 430.1 |
| 603 | 430.1 | 431.1 |
| 604 | 424.2 | 425.2 |
| 605 | 443.1 | 444.1 |
| 606 | 444.1 | 445.1 |
| 607 | 407.1 | 408.2 |
| 608 | 388.1 | 389.2 |
| 609 | 382.2 | 383.2 |
| 610 | 401.2 | 402.2 |
| 611 | 459.2 | 460.2 |
| 612 | 403.2 | 404.2 |
| 613 | 457.2 | 458.2 |
| 614 | 459.2 | 460.2 |
| 615 | 403.2 | 404.2 |
| 616 | 442.2 | 443.2 |
| 617 | 422.2 | 423.1 |
| 618 | 389.1 | 390.2 |
| 619 | 401.2 | 402.2 |
| 620 | 403.2 | 404.2 |
| 621 | 388.2 | 389.2 |
| 622 | 374.2 | 375.2 |
| 623 | 348.2 | 349.2 |
| 624 | 389.2 | 390.2 |
| 625 | 375.2 | 376.2 |
| 626 | 349.2 | 350.1 |
| 627 | 403.2 | 404.2 |
| 628 | 389.2 | 390.2 |
| 629 | 363.2 | 364.2 |
| 630 | 375.2 | 376.1 |
| 631 | 361.2 | 362.1 |
| 632 | 375.2 | 376.1 |
| 633 | 373.2 | 374.1 |
| 634 | 389.2 | 390.2 |
| 635 | 417.2 | 418.1 |
| 636 | 431.2 | 432.1 |

TABLE 2-continued

| Compound number | Exact MS | Obs MS $(M + H)^+$ |
|---|---|---|
| 637 | 389.2 | 390.2 |
| 638 | 415.2 | 416.2 |
| 639 | 391.2 | 392.1 |
| 640 | 415.1 | 416.2 |
| 641 | 385.2 | 386.1 |
| 642 | 382.2 | 383.1 |
| 643 | 360.2 | 361.2 |
| 644 | 374.2 | 375.2 |
| 645 | 371.2 | 372.2 |
| 646 | 372.2 | 373.2 |
| 647 | 415.2 | 416.2 |
| 648 | 416.2 | 417.2 |
| 649 | 401.1 | 402.2 |
| 650 | 397.2 | 398.2 |
| 651 | 401.1 | 402.2 |
| 652 | 397.2 | 398.1 |
| 653 | 409.1 | 410.3 |
| 654 | 493.2 | 494.3 |
| 655 | 377.2 | 378.2 |
| 656 | 391.2 | 392.2 |
| 657 | 386.2 | 387.2 |
| 658 | 387.2 | 388.2 |
| 659 | 360.2 | 361.2 |
| 660 | 361.2 | 362.2 |
| 661 | 458.2 | 459.2 |
| 662 | 423.2 | 424.2 |
| 663 | 425.2 | 426.2 |
| 664 | 439.2 | 440.2 |
| 665 | 453.2 | 454.2 |
| 666 | 517.3 | 518.3 |
| 667 | 474.2 | 475.2 |
| 668 | 433.2 | 434.2 |
| 669 | 419.2 | 420.2 |
| 670 | 468.2 | 469.2 |
| 671 | 427.2 | 428.2 |
| 672 | 413.2 | 414.2 |
| 673 | 467.2 | 468.2 |
| 674 | 426.2 | 427.2 |
| 675 | 412.2 | 413.2 |
| 676 | 307.1 | 308.1 |
| 677 | 321.1 | 322.1 |
| 678 | 346.2 | 347.1 |
| 679 | 362.1 | 363.1 |
| 680 | 346.2 | 347.1 |
| 681 | 402.2 | 403.2 |
| 682 | 383.1 | 384.2 |
| 683 | 359.2 | 360.3 |
| 684 | 360.2 | 361.3 |
| 685 | 360.2 | 361.3 |
| 686 | 409.2 | 410.3 |
| 687 | 411.2 | 412.3 |
| 688 | 424.2 | 425.3 |
| 689 | 429.1 | 430.2 |
| 690 | 413.1 | 414.3 |
| 691 | 423.2 | 424.3 |
| 692 | 424.2 | 425.3 |
| 693 | 424.2 | 425.3 |
| 694 | 443.1 | 444.3 |
| 695 | 343.1 | 344.2 |
| 696 | 372.2 | 373.3 |
| 697 | 386.2 | 387.3 |
| 698 | 346.2 | 347.3 |
| 699 | 387.1 | 388.1 |
| 700 | 388.0 | 389.1 |
| 701 | 416.2 | 417.3 |
| 702 | 397.2 | 398.3 |
| 703 | 401.1 | 402.3 |
| 704 | 407.2 | 408.3 |
| 705 | 386.1 | 387.2 |
| 706 | 400.1 | 401.2 |
| 707 | 393.1 | 394.2 |
| 708 | 417.2 | 418.3 |
| 709 | 431.2 | 432.3 |
| 710 | 431.2 | 432.3 |
| 711 | 386.2 | 387.3 |
| 712 | 391.1 | 392.2 |
| 713 | 344.1 | 345.2 |

TABLE 2-continued

| Compound number | Exact MS | Obs MS (M + H)+ |
|---|---|---|
| 714 | 373.2 | 374.2 |
| 715 | 387.2 | 388.2 |
| 716 | 347.1 | 348.2 |
| 717 | 408.1 | 409.2 |
| 718 | 363.1 | 364.1 |
| 719 | 392.1 | 393.2 |
| 720 | 365.1 | 366.1 |
| 721 | 383.1 | 384.1 |
| 722 | 397.1 | 398.2 |
| 723 | 409.1 | 410.2 |
| 724 | 395.2 | 396.2 |
| 725 | 379.1 | 380.2 |
| 726 | 393.1 | 394.2 |
| 727 | 367.1 | 368.1 |
| 728 | 364.1 | 365.1 |
| 729 | 401.1 | 402.1 |
| 730 | 401.1 | 402.1 |
| 731 | 385.2 | 386.2 |
| 732 | 422.2 | 423.2 |
| 733 | 441.2 | 442.2 |
| 734 | 411.2 | 412.2 |
| 735 | 430.2 | 431.2 |
| 736 | 384.2 | 385.2 |
| 737 | 421.2 | 422.2 |
| 738 | 452.2 | 453.3 |
| 739 | 411.2 | 412.2 |
| 740 | 397.2 | 398.2 |
| 741 | 430.2 | 431.3 |
| 742 | 444.2 | 445.3 |
| 743 | 404.2 | 405.3 |
| 744 | 415.2 | 416.2 |
| 745 | 415.2 | 416.3 |
| 746 | 415.2 | 416.3 |
| 747 | 415.2 | 416.3 |
| 748 | 437.2 | 438.3 |
| 749 | 423.2 | 424.2 |
| 750 | 386.2 | 387.2 |
| 751 | 372.2 | 373.3 |
| 752 | 412.2 | 413.3 |
| 753 | 398.2 | 399.2 |
| 754 | 390.2 | 391.3 |
| 755 | 402.2 | 403.2 |
| 756 | 481.2 | 482.3 |
| 757 | 481.2 | 482.3 |
| 758 | 405.2 | 406.3 |
| 759 | 419.2 | 420.3 |
| 760 | 407.2 | 408.2 |
| 761 | 443.1 | 444.2 |
| 762 | 452.2 | 453.3 |
| 763 | 361.2 | 362.2 |
| 764 | 361.2 | 362.3 |
| 765 | 375.2 | 376.3 |
| 766 | 375.1 | 376.3 |
| 767 | 419.2 | 420.2 |
| 768 | 425.2 | 426.3 |
| 769 | 403.2 | 404.3 |
| 770 | 391.2 | 392.3 |
| 771 | 405.2 | 406.3 |
| 772 | 391.2 | 392.3 |
| 773 | 390.2 | 391.3 |
| 774 | 377.2 | 378.3 |
| 775 | 391.2 | 392.3 |
| 776 | 360.2 | 361.3 |
| 777 | 360.2 | 361.2 |
| 778 | 428.2 | 429.3 |
| 779 | 414.2 | 415.3 |
| 780 | 428.2 | 429.3 |
| 781 | 442.2 | 443.3 |
| 782 | 456.2 | 457.3 |
| 783 | 442.2 | 443.3 |
| 784 | 404.2 | 405.3 |
| 785 | 472.2 | 473.3 |
| 786 | 413.2 | 414.3 |
| 787 | 431.2 | 432.3 |
| 788 | 388.2 | 389.3 |
| 789 | 373.2 | 374.3 |
| 790 | 375.2 | 376.4 |

TABLE 2-continued

| Compound number | Exact MS | Obs MS (M + H)+ |
|---|---|---|
| 791 | 389.2 | 390.4 |
| 792 | 389.2 | 390.4 |
| 793 | 391.2 | 392.1 |
| 794 | 401.2 | 402.4 |
| 795 | 401.2 | 402.4 |
| 796 | 401.2 | 402.4 |
| 797 | 405.2 | 406.4 |
| 798 | 393.2 | 394.3 |
| 799 | 392.2 | 393.2 |
| 800 | 421.2 | 422.3 |
| 801 | 376.2 | 377.3 |
| 802 | 362.2 | 363.2 |
| 803 | 362.2 | 363.1 |
| 804 | 376.2 | 377.3 |
| 805 | 362.2 | 363.2 |
| 806 | 362.2 | 363.2 |
| 807 | 422.1 | 423.3 |
| 808 | 397.2 | 398.3 |
| 809 | 397.2 | 398.3 |
| 810 | 373.1 | 374.3 |
| 811 | 374.1 | 375.3 |
| 812 | 388.1 | 389.3 |
| 813 | 363.2 | 364.3 |
| 814 | 349.2 | 350.2 |
| 815 | 421.1 | 422.3 |
| 816 | 421.1 | 422.3 |
| 817 | 381.1 | 382.3 |
| 818 | 388.2 | 389.3 |
| 819 | 376.2 | 377.3 |
| 820 | 397.1 | 398.2 |
| 821 | 401.2 | 402.4 |
| 822 | 395.2 | 396.4 |
| 823 | 427.2 | 428.3 |
| 824 | 387.2 | 388.4 |
| 825 | 403.2 | 404.4 |
| 826 | 412.2 | 413.4 |
| 827 | 426.2 | 427.3 |
| 828 | 355.1 | 356.3 |
| 829 | 356.1 | 357.3 |
| 830 | 397.2 | 398.2 |
| 831 | 383.1 | 384.2 |
| 832 | 397.2 | 398.2 |
| 833 | 383.1 | 384.2 |
| 834 | 402.1 | 403.2 |
| 835 | 388.1 | 389.2 |
| 836 | 402.1 | 403.2 |
| 837 | 388.1 | 389.2 |
| 838 | 435.2 | 436.5 |
| 839 | 509.3 | 510.4 |
| 840 | 528.3 | 529.4 |
| 841 | 451.2 | 452.2 |
| 842 | 405.2 | 406.4 |
| 843 | 392.2 | 393.4 |
| 844 | 404.2 | 405.4 |
| 845 | 404.2 | 405.4 |
| 846 | 390.2 | 391.4 |
| 847 | 424.1 | 425.4 |
| 848 | 390.2 | 391.4 |
| 849 | 404.2 | 405.4 |
| 850 | 400.2 | 401.4 |
| 851 | 401.2 | 402.4 |
| 852 | 403.2 | 404.4 |
| 853 | 387.2 | 388.4 |
| 854 | 389.2 | 390.4 |
| 855 | 401.2 | 402.4 |
| 856 | 403.2 | 404.4 |
| 857 | 403.2 | 404.4 |
| 858 | 405.2 | 406.4 |
| 859 | 415.2 | 416.4 |
| 860 | 415.2 | 416.4 |
| 861 | 415.2 | 416.4 |
| 862 | 419.2 | 420.4 |
| 863 | 435.2 | 436.4 |
| 864 | 402.2 | 403.4 |
| 865 | 388.2 | 389.4 |
| 866 | 447.1 | 448.3 |
| 867 | 421.2 | 422.4 |

TABLE 2-continued

| Compound number | Exact MS | Obs MS (M + H)+ |
|---|---|---|
| 868 | 435.2 | 436.3 |
| 869 | 432.2 | 433.4 |
| 870 | 346.2 | 347.3 |
| 871 | 402.2 | 403.3 |
| 872 | 434.2 | 435.3 |
| 873 | 399.2 | 400.2 |
| 874 | 413.2 | 414.3 |
| 875 | 427.2 | 428.3 |
| 876 | 434.2 | 435.4 |
| 877 | 461.2 | 462.3 |
| 878 | 435.2 | 436.4 |
| 879 | 417.2 | 418.4 |
| 880 | 415.2 | 416.2 |
| 881 | 414.2 | 415.4 |
| 882 | 387.1 | 388.3 |
| 883 | 438.2 | 439.3 |
| 884 | 430.1 | 431.4 |
| 885 | 432.2 | 433.2 |
| 886 | 404.2 | 405.3 |
| 887 | 402.2 | 403.4 |
| 888 | 418.2 | 419.4 |
| 889 | 418.2 | 419.3 |
| 890 | 406.2 | 407.4 |
| 891 | 412.1 | 413.3 |
| 892 | 388.2 | 389.3 |
| 893 | 416.1 | 417.3 |
| 894 | 418.2 | 419.4 |
| 895 | 390.1 | 391.3 |
| 896 | 376.2 | 377.3 |
| 897 | 398.1 | 399.3 |
| 898 | 374.1 | 375.3 |
| 899 | 416.2 | 417.3 |
| 900 | 430.2 | 431.3 |
| 901 | 402.2 | 403.4 |
| 902 | 416.2 | 417.4 |
| 903 | 406.1 | 407.3 |
| 904 | 406.1 | 407.3 |
| 905 | 381.2 | 382.4 |
| 906 | 381.2 | 382.3 |
| 907 | 362.2 | 363.3 |
| 908 | 348.2 | 349.3 |
| 909 | 380.2 | 381.2 |
| 910 | 380.2 | 381.2 |
| 911 | 388.1 | 389.2 |
| 912 | 383.1 | 384.2 |
| 913 | 409.2 | 410.4 |
| 914 | 409.2 | 410.4 |
| 915 | 408.2 | 409.4 |
| 916 | 408.2 | 409.4 |
| 917 | 402.2 | 403.3 |
| 918 | 388.2 | 389.3 |
| 919 | 416.2 | 417.3 |
| 920 | 402.2 | 403.3 |
| 921 | 416.2 | 417.3 |
| 922 | 402.2 | 403.3 |
| 923 | 373.2 | 374.2 |
| 924 | 384.2 | 385.4 |
| 925 | 384.2 | 385.4 |
| 926 | 386.1 | 387.0 |
| 927 | 370.1 | 371.3 |
| 928 | 401.1 | 402.2 |
| 929 | 384.0 | 385.1 |
| 930 | 384.1 | 385.2 |
| 931 | 384.1 | 385.2 |
| 932 | 384.1 | 385.2 |
| 933 | 400.2 | 401.2 |
| 934 | 384.1 | 385.2 |
| 935 | 389.1 | 390.2 |
| 936 | 386.2 | 387.2 |
| 937 | 390.2 | 391.2 |
| 938 | 390.2 | 391.2 |
| 939 | 390.2 | 391.2 |
| 940 | 398.2 | 399.2 |
| 941 | 411.2 | 412.2 |
| 942 | 376.2 | 377.2 |
| 943 | 416.2 | 417.2 |
| 944 | 417.2 | 418.3 |

TABLE 2-continued

| Compound number | Exact MS | Obs MS (M + H)+ |
|---|---|---|
| 945 | 386.2 | 387.2 |
| 946 | 386.2 | 387.2 |
| 947 | 386.2 | 387.2 |
| 948 | 389.1 | 390.0 |
| 949 | 398.2 | 399.0 |
| 950 | 398.2 | 399.2 |
| 951 | 403.1 | 404.0 |
| 952 | 403.1 | 404.0 |
| 953 | 390.2 | 391.1 |
| 954 | 390.2 | 391.2 |
| 955 | 430.2 | 431.1 |
| 956 | 377.2 | 378.2 |
| 957 | 403.1 | 404.2 |
| 958 | 403.1 | 404.1 |
| 959 | 403.1 | 404.1 |
| 960 | 403.1 | 404.1 |
| 961 | 404.1 | 405.2 |
| 962 | 403.1 | 404.2 |
| 963 | 403.1 | 404.1 |
| 964 | 344.1 | 345.2 |
| 965 | 410.2 | 411.4 |
| 966 | 369.2 | 370.4 |
| 967 | 369.2 | 370.3 |
| 968 | 395.1 | 396.5 |
| 969 | 390.2 | 391.2 |
| 970 | 395.1 | 396.5 |
| 971 | 390.2 | 391.5 |
| 972 | 384.2 | 385.2 |
| 973 | 398.2 | 399.2 |
| 974 | 384.2 | 385.2 |
| 975 | 397.2 | 398.3 |
| 976 | 383.2 | 384.2 |
| 977 | 390.2 | 391.4 |
| 978 | 409.2 | 410.2 |
| 979 | 382.2 | 383.2 |
| 980 | 381.2 | 382.2 |
| 981 | 341.2 | 342.2 |
| 982 | 355.2 | 356.2 |
| 983 | 355.2 | 356.2 |
| 984 | 355.2 | 356.2 |
| 985 | 383.2 | 384.2 |
| 986 | 383.2 | 384.2 |
| 987 | 406.2 | 407.2 |
| 988 | 405.2 | 406.2 |
| 989 | 420.2 | 421.2 |
| 990 | 419.2 | 420.3 |
| 991 | 383.2 | 384.2 |
| 992 | 370.2 | 371.2 |
| 993 | 392.2 | 393.2 |
| 994 | 406.2 | 407.2 |
| 995 | 368.2 | 369.2 |
| 996 | 367.2 | 368.2 |
| 997 | 342.2 | 343.0 |
| 998 | 341.2 | 342.0 |
| 999 | 356.2 | 357.0 |
| 1000 | 355.2 | 356.0 |
| 1001 | 409.2 | 410.0 |
| 1002 | 396.2 | 397.0 |
| 1003 | 395.2 | 396.0 |
| 1004 | 376.1 | 377.0 |
| 1005 | 363.1 | 364.0 |
| 1006 | 395.2 | 396.0 |
| 1007 | 383.2 | 384.2 |
| 1008 | 382.2 | 383.2 |
| 1009 | 397.2 | 398.2 |
| 1010 | 396.2 | 397.1 |
| 1011 | 340.2 | 342.1 |
| 1012 | 341.2 | 341.1 |
| 1013 | 355.2 | 356.2 |
| 1014 | 354.2 | 355.2 |
| 1015 | 339.1 | 340.1 |
| 1016 | 338.2 | 339.1 |
| 1017 | 353.2 | 354.1 |
| 1018 | 352.2 | 353.1 |
| 1019 | 381.1 | 382.1 |
| 1020 | 357.1 | 358.2 |
| 1021 | 371.2 | 372.2 |

TABLE 2-continued

| Compound number | Exact MS | Obs MS $(M + H)^+$ |
|---|---|---|
| 1022 | 379.1 | 380.1 |
| 1023 | 397.1 | 398.2 |
| 1024 | 392.1 | 393.2 |
| 1025 | 360.2 | 361.3 |
| 1026 | 346.2 | 347.3 |
| 1027 | 417.2 | 418.4 |
| 1028 | 403.2 | 404.3 |
| 1029 | 402.2 | 403.3 |
| 1030 | 374.2 | 375.4 |
| 1031 | 388.2 | 389.4 |
| 1032 | 403.2 | 404.4 |
| 1033 | 386.2 | 387.5 |
| 1034 | 386.2 | 387.5 |
| 1035 | 372.2 | 373.4 |
| 1036 | 372.2 | 373.4 |
| 1037 | 395.1 | 396.3 |
| 1038 | 381.1 | 382.2 |
| 1039 | 403.1 | 404.1 |
| 1040 | 429.2 | 430.2 |
| 1041 | 402.2 | 403.3 |
| 1042 | 428.2 | 429.3 |
| 1043 | 375.2 | 376.1 |
| 1044 | 360.2 | 361.2 |
| 1045 | 346.2 | 347.2 |
| 1046 | 372.2 | 373.2 |
| 1047 | 358.2 | 359.2 |
| 1048 | 401.1 | 402.1 |
| 1049 | 414.2 | 415.2 |
| 1050 | 387.1 | 388.1 |
| 1051 | 361.2 | 362.2 |
| 1052 | 396.1 | 397.0 |
| 1053 | 415.2 | 416.3 |
| 1054 | 360.2 | 361.2 |
| 1055 | 382.1 | 383.0 |
| 1056 | 388.2 | 389.2 |
| 1057 | 372.2 | 373.1 |
| 1058 | 358.2 | 359.1 |
| 1059 | 432.2 | 433.2 |
| 1060 | 374.2 | 375.2 |
| 1061 | 389.2 | 390.1 |
| 1062 | 415.2 | 416.2 |
| 1063 | 401.2 | 402.1 |
| 1064 | 420.1 | 421.2 |
| 1065 | 434.2 | 435.2 |
| 1066 | 419.1 | 420.1 |
| 1067 | 419.1 | 420.2 |
| 1068 | 433.2 | 434.2 |
| 1069 | 420.1 | 421.1 |
| 1070 | 434.2 | 435.1 |
| 1071 | 401.2 | 402.2 |
| 1072 | 387.2 | 388.2 |
| 1073 | 439.2 | 440.1 |
| 1074 | 425.2 | 426.1 |
| 1075 | 360.2 | 361.1 |
| 1076 | 433.2 | 434.1 |
| 1077 | 487.1 | 488.1 |
| 1078 | 488.1 | 489.1 |
| 1079 | 413.2 | 414.1 |
| 1080 | 473.1 | 474.0 |
| 1081 | 402.2 | 403.1 |
| 1082 | 390.1 | 391.1 |
| 1083 | 403.2 | 404.1 |
| 1084 | 404.2 | 405.1 |
| 1085 | 389.1 | 390.1 |
| 1086 | 403.2 | 404.1 |
| 1087 | 474.1 | 475.1 |
| 1088 | 419.1 | 420.1 |
| 1089 | 390.1 | 391.1 |
| 1090 | 391.1 | 392.1 |
| 1091 | 404.2 | 407.1 |
| 1092 | 405.2 | 406.1 |
| 1093 | 406.1 | 408.1 |
| 1094 | 420.1 | 421.1 |
| 1095 | 407.1 | 408.1 |
| 1096 | 421.1 | 422.1 |
| 1097 | 421.2 | 422.3 |
| 1098 | 375.1 | 376.2 |

TABLE 2-continued

| Compound number | Exact MS | Obs MS $(M + H)^+$ |
|---|---|---|
| 1099 | 361.1 | 362.2 |
| 1100 | 325.1 | 326.1 |
| 1101 | 365.2 | 366.2 |
| 1102 | 353.2 | 354.2 |
| 1103 | 422.2 | 423.0 |
| 1104 | 408.2 | 409.2 |
| 1105 | 396.2 | 397.0 |
| 1106 | 409.2 | 410.0 |
| 1107 | 410.2 | 411.0 |
| 1108 | 365.2 | 366.2 |
| 1109 | 351.1 | 352.1 |
| 1110 | 364.2 | 365.2 |
| 1111 | 378.2 | 379.3 |
| 1112 | 378.2 | 379.3 |
| 1113 | 387.2 | 388.3 |
| 1114 | 401.2 | 402.3 |
| 1115 | 401.2 | 402.2 |
| 1116 | 346.2 | 347.1 |
| 1117 | 388.2 | 389.2 |
| 1118 | 346.2 | 347.3 |
| 1119 | 388.2 | 389.3 |
| 1120 | 392.2 | 393.2 |
| 1121 | 344.2 | 345.3 |
| 1122 | 369.2 | 370.3 |
| 1123 | 370.2 | 371.3 |
| 1124 | 446.2 | 447.2 |
| 1125 | 460.2 | 461.3 |
| 1126 | 388.2 | 389.2 |
| 1127 | 384.2 | 384.9 |
| 1128 | 398.2 | 399.1 |
| 1129 | 394.2 | 395.2 |
| 1130 | 408.2 | 409.2 |
| 1131 | 379.2 | 380.3 |
| 1132 | 379.2 | 380.3 |
| 1133 | 395.2 | 396.4 |
| 1134 | 380.2 | 381.3 |
| 1135 | 380.2 | 381.2 |
| 1136 | 395.2 | 396.4 |
| 1137 | 394.2 | 395.4 |
| 1138 | 395.2 | 396.4 |
| 1139 | 409.2 | 410.3 |
| 1140 | 375.2 | 376.4 |
| 1141 | 376.2 | 377.4 |
| 1142 | 390.2 | 391.4 |
| 1143 | 397.2 | 398.4 |
| 1144 | 413.1 | 414.3 |
| 1145 | 393.2 | 394.4 |
| 1146 | 393.2 | 394.4 |
| 1147 | 397.2 | 398.4 |
| 1148 | 393.2 | 394.4 |
| 1149 | 397.2 | 398.4 |
| 1150 | 393.2 | 394.4 |
| 1151 | 407.2 | 408.4 |
| 1152 | 411.2 | 412.4 |
| 1153 | 407.2 | 408.4 |
| 1154 | 411.2 | 412.4 |
| 1155 | 407.2 | 408.4 |
| 1156 | 411.2 | 412.4 |
| 1157 | 394.2 | 395.3 |
| 1158 | 393.2 | 394.3 |
| 1159 | 373.2 | 374.3 |
| 1160 | 380.2 | 381.3 |
| 1161 | 427.2 | 428.2 |
| 1162 | 428.2 | 429.2 |
| 1163 | 387.2 | 388.2 |
| 1164 | 388.2 | 389.2 |
| 1165 | 417.2 | 418.3 |
| 1166 | 418.2 | 419.2 |
| 1167 | 381.2 | 382.3 |
| 1168 | 367.2 | 368.2 |
| 1169 | 381.2 | 382.3 |
| 1170 | 367.2 | 368.2 |
| 1171 | 360.2 | 361.3 |
| 1172 | 346.2 | 347.3 |
| 1173 | 386.1 | 387.2 |
| 1174 | 372.1 | 373.2 |
| 1175 | 401.2 | 402.3 |

TABLE 2-continued

| Compound number | Exact MS | Obs MS $(M + H)^+$ |
|---|---|---|
| 1176 | 368.2 | 369.2 |
| 1177 | 433.2 | 434.3 |
| 1178 | 375.2 | 376.4 |
| 1179 | 415.2 | 416.4 |
| 1180 | 483.2 | 484.4 |
| 1181 | 389.2 | 390.4 |
| 1182 | 380.2 | 381.3 |
| 1183 | 366.2 | 367.2 |
| 1184 | 361.2 | 362.3 |
| 1185 | 347.2 | 348.3 |
| 1186 | 387.2 | 388.3 |
| 1187 | 345.2 | 346.2 |
| 1188 | 347.2 | 348.3 |
| 1189 | 333.2 | 334.2 |
| 1190 | 373.2 | 374.3 |
| 1191 | 331.2 | 332.2 |
| 1192 | 399.2 | 400.2 |
| 1193 | 412.2 | 413.2 |
| 1194 | 413.2 | 414.3 |
| 1195 | 360.2 | 361.0 |
| 1196 | 346.2 | 347.0 |
| 1197 | 381.2 | 382.2 |
| 1198 | 373.2 | 374.2 |
| 1199 | 374.2 | 375.2 |
| 1200 | 389.2 | 390.2 |
| 1201 | 380.2 | 381.1 |
| 1202 | 395.2 | 396.2 |
| 1203 | 394.2 | 395.2 |
| 1204 | 414.2 | 415.3 |
| 1205 | 381.2 | 382.1 |
| 1206 | 375.2 | 376.2 |
| 1207 | 389.2 | 390.2 |
| 1208 | 388.2 | 389.2 |
| 1209 | 347.2 | 348.1 |
| 1210 | 373.2 | 374.2 |
| 1211 | 387.2 | 388.2 |
| 1212 | 386.2 | 387.2 |
| 1213 | 387.2 | 388.2 |
| 1214 | 395.2 | 396.3 |
| 1215 | 394.2 | 395.3 |
| 1216 | 361.2 | 363.3 |
| 1217 | 360.2 | 361.2 |
| 1218 | 401.2 | 402.4 |
| 1219 | 400.2 | 401.4 |
| 1220 | 374.2 | 375.0 |
| 1221 | 352.2 | 353.0 |
| 1222 | 353.2 | 354.1 |
| 1223 | 339.2 | 340.0 |
| 1224 | 367.2 | 368.3 |
| 1225 | 353.2 | 354.3 |
| 1226 | 427.2 | 428.5 |
| 1227 | 439.2 | 440.5 |
| 1228 | 425.2 | 426.2 |
| 1229 | 395.2 | 396.3 |
| 1230 | 425.2 | 426.3 |
| 1231 | 409.2 | 410.3 |
| 1232 | 416.1 | 417.2 |
| 1233 | 375.2 | 376.4 |
| 1234 | 376.2 | 377.2 |
| 1235 | 390.2 | 391.1 |
| 1236 | 404.2 | 405.2 |
| 1237 | 429.2 | 430.2 |
| 1238 | 433.2 | 434.1 |
| 1239 | 417.2 | 418.4 |
| 1240 | 415.2 | 416.4 |
| 1241 | 401.2 | 402.4 |
| 1242 | 418.2 | 419.4 |
| 1243 | 416.2 | 417.4 |
| 1244 | 402.2 | 403.4 |
| 1245 | 407.2 | 408.3 |
| 1246 | 405.2 | 406.4 |
| 1247 | 391.2 | 392.4 |
| 1248 | 432.2 | 433.2 |
| 1249 | 430.2 | 431.3 |
| 1250 | 416.2 | 417.4 |
| 1251 | 421.2 | 422.4 |
| 1252 | 419.2 | 420.3 |

TABLE 2-continued

| Compound number | Exact MS | Obs MS $(M + H)^+$ |
|---|---|---|
| 1253 | 405.2 | 406.4 |
| 1254 | 433.2 | 434.3 |
| 1255 | 431.2 | 432.4 |
| 1256 | 417.2 | 418.4 |
| 1257 | 419.2 | 420.3 |
| 1258 | 417.2 | 418.3 |
| 1259 | 403.2 | 404.3 |
| 1260 | 432.2 | 433.2 |
| 1261 | 418.2 | 419.2 |
| 1262 | 403.2 | 404.2 |
| 1263 | 377.1 | 378.3 |
| 1264 | 388.1 | 389.2 |
| 1265 | 389.1 | 390.2 |
| 1266 | 362.1 | 363.2 |
| 1267 | 363.1 | 364.2 |
| 1268 | 403.2 | 404.2 |
| 1269 | 409.1 | 410.1 |
| 1270 | 423.1 | 424.2 |
| 1271 | 411.1 | 412.2 |
| 1272 | 377.1 | 378.2 |
| 1273 | 391.2 | 392.3 |
| 1274 | 440.1 | 441.3 |
| 1275 | 426.1 | 427.2 |
| 1276 | 433.2 | 434.3 |
| 1277 | 396.2 | 397.2 |
| 1278 | 382.2 | 383.2 |
| 1279 | 396.2 | 397.4 |
| 1280 | 397.2 | 398.3 |
| 1281 | 361.2 | 362.2 |
| 1282 | 400.2 | 401.5 |
| 1283 | 384.1 | 385.4 |
| 1284 | 416.2 | 417.4 |
| 1285 | 403.2 | 404.2 |
| 1286 | 395.1 | 396.2 |
| 1287 | 384.1 | 385.2 |
| 1288 | 382.2 | 383.3 |
| 1289 | 383.1 | 384.2 |
| 1290 | 405.1 | 406.3 |
| 1291 | 391.1 | 392.2 |
| 1292 | 405.1 | 406.2 |
| 1293 | 391.1 | 392.3 |

Example 46

Evaluation of TRPC6 Channel Inhibitory Activity (1) (Compound Nos. 1-1293)

In order to investigate TRPC6 channel inhibitory activity of the compounds, evaluation was conducted using FLIPR® Calcium 5 Assay Kit (Molecular Devices) in accordance with the following procedure. Human TRPC6 stably-expressing cells were seeded in a 384-well black clear bottom plate at a density of $5\times10^3$/well and cultured in an incubator at 37° C. 5% $CO_2$ for 24 hours. Thereafter, 25 μL of a Non Wash Dye Solution, prepared using Component A, 20 mM HEPES-HBSS and 250 mM probenecid, all of which are included in the kit, was added to each well, and the plate was incubated for 30 minutes. A volume of 12.5 μL of a compound solution was added into each well while the fluorescence was measured with FLIPR tetra. After 20 minutes, 12.5 μL of a 1-oleoyl-2-acetyl glycerol (OAG) solution was added at a final concentration of 30 μM. The difference between the minimum fluorescence intensity before the addition of the compound and the maximum fluorescence intensity after the addition of OAG was defined as a signal. An inhibition rate was calculated, assuming the average signal of wells without the compound as the inhibition rate of 0% and the average signal of wells without the compound and OAG as the inhibition rate of 100%. The calculated inhibition rate was analyzed by a four-parameter logistic regression to quantify the inhibition rate in the logarithm of the inverse of the effective concentration which gives a 50% inhibition rate ($pIC_{50}$). The results are shown in the following Table 3. The intensity was expressed by the following symbols (+, ++, +++).

+: $pIC_{50}<6.0$

++: $6.0\leq pIC_{50}<8.0$

+++: $8.0\leq pIC_{50}$

Example 47

Evaluation of TRPC6 Channel Inhibitory Activity (2) (Compound Nos. 1293 to 1405)

The activity of the TRPC6 inhibitor was measured by stimulating HEK293 cells, in which human TRPC6 was stably introduced, with OAG (1-Oleoyl-2-acetyl-sn-glycerol, Milipore Sigma, 06754), using the FLIPR tetra system. The cells were proliferated in a humid environment at 37° C. 5% $CO_2$ using a growth medium (DMEM (Dulbecco's Modified Eagle's Medium) high glucose containing 10% fetal bovine serum, 1×PSGlu (penicillin-streptomycin glutamine), 1×NEAA (Non-essential amino acid), sodium pyruvate and 200 μg/mL hyglomycin. For cell subculture, the cells were proliferated to 70-90% confluence, and gently washed twice with PBS (phosphate-buffered saline) free of calcium and magnesium after removing the medium. Then, the cells were incubated at 37° C. for 5 minutes after adding trypsin (3 mL), peeled off by tapping the flask at the base of the hand, 7 mL of growth medium was added to inactivate trypsin, and then the cells were resuspended. Usually, the cells were separated every 2-3 days to become a cell density of ⅕. The day before evaluation, the cells were seeded in a poly-D-lysine (PDL) coated 384-well plate using a multichannel pipette or multidrop at a cell density of $1.0\text{-}1.5\times10^4$ cells/25 μL/well. After culturing overnight in a PDL-coated 384 Blackwell plate, a fluorescent dye buffer was added first to the cells and the cells were cultured at room temperature for 90-120 minutes. For preparing 10 mL of fluorescent dye buffer, 9 mL of assay buffer, 1 mL of 10×PBX signal enhancer, and 10 μL of calcium indicator were mixed. Cells treated with the compounds of each level 25 minutes before the stimulation with OAG of TRPC6 agonist were incubated. OAG solution was prepared by adding OAG to assay buffer (Ca ringer solution base: 10 mM HEPES (4-(2-hydroxyethyl)-1-piperazine-ethanesulfonic acid), 4 mM $MgCl_2$, 120 mM NaCl, 5 mM KCl, pH=7.2 (25° C.)+0.1% BSA+2 mM $CaCl_2$)) to give an OAG concentration of 0.2 mM/2% DMSO. The final concentration of OAG added to the cells is 50 μM/0.5% DMSO. A volume of 12.5 μL of OAG solution was added, and activation of TRPC6 channel was measured using the FLIPR tetra system assaying the change in intracellular calcium level as an index. The 180 seconds imaging frame was defined as the background signal, and the subtraction of the background signal from the raw data was used as the fluorescence peak signal. Each fluorescence peak signal is standardized using an OAG-induced signal and buffer-induced signal as 100% and 0%, respectively. The inhibition rate obtained by plotting the peak signal after the addition of the compounds of each level was analyzed by a four-parameter logistic regression to quantify the inhibition rate in the logarithm of the inverse of the effective concentration which gives a 50% inhibition rate ($pIC_{50}$). The results are shown in the following Table 3. The intensity was expressed by the above-mentioned symbols (+, ++, +++).

TABLE 3

| Compound number | Inhibitory activity |
|---|---|
| 1 | ++ |
| 2 | +++ |
| 3 | ++ |
| 4 | + |
| 5 | + |
| 6 | +++ |
| 7 | +++ |
| 8 | + |
| 9 | +++ |
| 10 | + |
| 11 | +++ |
| 12 | + |
| 13 | ++ |
| 14 | + |
| 15 | ++ |
| 16 | ++ |
| 17 | +++ |
| 18 | ++ |
| 19 | ++ |
| 20 | ++ |
| 21 | +++ |
| 22 | ++ |
| 23 | ++ |
| 24 | ++ |
| 25 | +++ |
| 26 | +++ |
| 27 | ++ |
| 28 | ++ |
| 29 | ++ |
| 30 | +++ |
| 31 | ++ |
| 32 | +++ |
| 33 | +++ |
| 34 | ++ |
| 35 | ++ |
| 36 | ++ |
| 37 | + |
| 38 | + |
| 39 | + |
| 40 | + |
| 41 | + |
| 42 | + |
| 43 | ++ |
| 44 | + |
| 45 | ++ |
| 46 | +++ |
| 47 | ++ |
| 48 | ++ |
| 49 | ++ |
| 50 | +++ |
| 51 | + |
| 52 | ++ |
| 53 | ++ |
| 54 | + |
| 55 | + |
| 56 | + |
| 57 | + |
| 58 | ++ |
| 59 | ++ |
| 60 | ++ |
| 61 | + |
| 62 | +++ |
| 63 | + |
| 64 | + |
| 65 | +++ |
| 66 | +++ |
| 67 | ++ |
| 68 | ++ |
| 69 | +++ |
| 70 | +++ |
| 71 | ++ |
| 72 | ++ |
| 73 | ++ |
| 74 | ++ |
| 75 | ++ |
| 76 | + |
| 77 | + |

TABLE 3-continued

| Compound number | Inhibitory activity |
|---|---|
| 78 | ++ |
| 79 | + |
| 80 | + |
| 81 | + |
| 82 | +++ |
| 83 | + |
| 84 | ++ |
| 85 | ++ |
| 86 | ++ |
| 87 | + |
| 88 | + |
| 89 | + |
| 90 | ++ |
| 91 | + |
| 92 | + |
| 93 | +++ |
| 94 | + |
| 95 | + |
| 96 | + |
| 97 | + |
| 98 | + |
| 99 | + |
| 100 | +++ |
| 101 | +++ |
| 102 | ++ |
| 103 | ++ |
| 104 | + |
| 105 | + |
| 106 | + |
| 107 | ++ |
| 108 | ++ |
| 109 | + |
| 110 | + |
| 111 | ++ |
| 112 | +++ |
| 113 | +++ |
| 114 | ++ |
| 115 | +++ |
| 116 | ++ |
| 117 | ++ |
| 118 | ++ |
| 119 | + |
| 120 | +++ |
| 121 | + |
| 122 | ++ |
| 123 | ++ |
| 124 | ++ |
| 125 | ++ |
| 126 | + |
| 127 | + |
| 128 | + |
| 129 | + |
| 130 | +++ |
| 131 | + |
| 132 | ++ |
| 133 | +++ |
| 134 | ++ |
| 135 | + |
| 136 | ++ |
| 137 | +++ |
| 138 | +++ |
| 139 | ++ |
| 140 | ++ |
| 141 | ++ |
| 142 | ++ |
| 143 | + |
| 144 | ++ |
| 145 | ++ |
| 146 | + |
| 147 | ++ |
| 148 | ++ |
| 149 | +++ |
| 150 | +++ |
| 151 | ++ |
| 152 | ++ |
| 153 | +++ |
| 154 | ++ |

TABLE 3-continued

| Compound number | Inhibitory activity |
|---|---|
| 155 | ++ |
| 156 | ++ |
| 157 | +++ |
| 158 | ++ |
| 159 | +++ |
| 160 | +++ |
| 161 | +++ |
| 162 | +++ |
| 163 | ++ |
| 164 | +++ |
| 165 | ++ |
| 166 | ++ |
| 167 | ++ |
| 168 | ++ |
| 169 | + |
| 170 | +++ |
| 171 | +++ |
| 172 | +++ |
| 173 | +++ |
| 174 | +++ |
| 175 | +++ |
| 176 | +++ |
| 177 | +++ |
| 178 | ++ |
| 179 | +++ |
| 180 | +++ |
| 181 | ++ |
| 182 | +++ |
| 183 | +++ |
| 184 | ++ |
| 185 | +++ |
| 186 | +++ |
| 187 | +++ |
| 188 | + |
| 189 | + |
| 190 | ++ |
| 191 | + |
| 192 | ++ |
| 193 | + |
| 194 | + |
| 195 | ++ |
| 196 | ++ |
| 197 | +++ |
| 198 | +++ |
| 199 | +++ |
| 200 | + |
| 201 | + |
| 202 | +++ |
| 203 | ++ |
| 204 | +++ |
| 205 | +++ |
| 206 | +++ |
| 207 | ++ |
| 208 | + |
| 209 | + |
| 210 | + |
| 211 | +++ |
| 212 | +++ |
| 213 | +++ |
| 214 | ++ |
| 215 | +++ |
| 216 | ++ |
| 217 | + |
| 218 | + |
| 219 | ++ |
| 220 | + |
| 221 | ++ |
| 222 | ++ |
| 223 | ++ |
| 224 | ++ |
| 225 | +++ |
| 226 | +++ |
| 227 | +++ |
| 228 | +++ |
| 229 | +++ |
| 230 | +++ |
| 231 | +++ |

TABLE 3-continued

| Compound number | Inhibitory activity |
|---|---|
| 232 | +++ |
| 233 | +++ |
| 234 | + |
| 235 | ++ |
| 236 | ++ |
| 237 | +++ |
| 238 | +++ |
| 239 | + |
| 240 | ++ |
| 241 | +++ |
| 242 | + |
| 243 | + |
| 244 | ++ |
| 245 | ++ |
| 246 | +++ |
| 247 | +++ |
| 248 | +++ |
| 249 | +++ |
| 250 | +++ |
| 251 | + |
| 252 | + |
| 253 | +++ |
| 254 | +++ |
| 255 | ++ |
| 256 | ++ |
| 257 | ++ |
| 258 | +++ |
| 259 | ++ |
| 260 | +++ |
| 261 | +++ |
| 262 | +++ |
| 263 | ++ |
| 264 | +++ |
| 265 | ++ |
| 266 | +++ |
| 267 | +++ |
| 268 | ++ |
| 269 | ++ |
| 270 | ++ |
| 271 | ++ |
| 272 | +++ |
| 273 | +++ |
| 274 | +++ |
| 275 | +++ |
| 276 | +++ |
| 277 | +++ |
| 278 | +++ |
| 279 | + |
| 280 | ++ |
| 281 | + |
| 282 | ++ |
| 283 | ++ |
| 284 | ++ |
| 285 | +++ |
| 286 | ++ |
| 287 | +++ |
| 288 | +++ |
| 289 | +++ |
| 290 | ++ |
| 291 | + |
| 292 | ++ |
| 293 | +++ |
| 294 | +++ |
| 295 | +++ |
| 296 | +++ |
| 297 | ++ |
| 298 | ++ |
| 299 | +++ |
| 300 | ++ |
| 301 | +++ |
| 302 | ++ |
| 303 | ++ |
| 304 | + |
| 305 | ++ |
| 306 | +++ |
| 307 | ++ |
| 308 | ++ |

TABLE 3-continued

| Compound number | Inhibitory activity |
|---|---|
| 309 | ++ |
| 310 | +++ |
| 311 | + |
| 312 | +++ |
| 313 | +++ |
| 314 | +++ |
| 315 | +++ |
| 316 | + |
| 317 | +++ |
| 318 | +++ |
| 319 | +++ |
| 320 | +++ |
| 321 | +++ |
| 322 | ++ |
| 323 | ++ |
| 324 | +++ |
| 325 | +++ |
| 326 | +++ |
| 327 | +++ |
| 328 | +++ |
| 329 | +++ |
| 330 | + |
| 331 | ++ |
| 332 | ++ |
| 333 | +++ |
| 334 | +++ |
| 335 | +++ |
| 336 | +++ |
| 337 | +++ |
| 338 | +++ |
| 339 | ++ |
| 340 | ++ |
| 341 | +++ |
| 342 | ++ |
| 343 | ++ |
| 344 | +++ |
| 345 | ++ |
| 346 | +++ |
| 347 | + |
| 348 | +++ |
| 349 | + |
| 350 | ++ |
| 351 | ++ |
| 352 | ++ |
| 353 | ++ |
| 354 | ++ |
| 355 | + |
| 356 | ++ |
| 357 | ++ |
| 358 | ++ |
| 359 | ++ |
| 360 | +++ |
| 361 | +++ |
| 362 | +++ |
| 363 | +++ |
| 364 | +++ |
| 365 | +++ |
| 366 | +++ |
| 367 | +++ |
| 368 | ++ |
| 369 | ++ |
| 370 | +++ |
| 371 | +++ |
| 372 | +++ |
| 373 | +++ |
| 374 | +++ |
| 375 | +++ |
| 376 | +++ |
| 377 | ++ |
| 378 | +++ |
| 379 | +++ |
| 380 | ++ |
| 381 | +++ |
| 382 | +++ |
| 383 | +++ |
| 384 | +++ |
| 385 | ++ |

TABLE 3-continued

| Compound number | Inhibitory activity |
|---|---|
| 386 | ++ |
| 387 | ++ |
| 388 | +++ |
| 389 | ++ |
| 390 | +++ |
| 391 | +++ |
| 392 | +++ |
| 393 | +++ |
| 394 | +++ |
| 395 | ++ |
| 396 | +++ |
| 397 | ++ |
| 398 | +++ |
| 399 | +++ |
| 400 | ++ |
| 401 | +++ |
| 402 | +++ |
| 403 | +++ |
| 404 | +++ |
| 405 | +++ |
| 406 | +++ |
| 407 | +++ |
| 408 | ++ |
| 409 | ++ |
| 410 | ++ |
| 411 | ++ |
| 412 | ++ |
| 413 | +++ |
| 414 | + |
| 415 | + |
| 416 | + |
| 417 | + |
| 418 | ++ |
| 419 | + |
| 420 | ++ |
| 421 | ++ |
| 422 | ++ |
| 423 | ++ |
| 424 | + |
| 425 | + |
| 426 | +++ |
| 427 | ++ |
| 428 | ++ |
| 429 | +++ |
| 430 | +++ |
| 431 | ++ |
| 432 | +++ |
| 433 | ++ |
| 434 | +++ |
| 435 | + |
| 436 | + |
| 437 | ++ |
| 438 | ++ |
| 439 | +++ |
| 440 | +++ |
| 441 | +++ |
| 442 | ++ |
| 443 | ++ |
| 444 | +++ |
| 445 | +++ |
| 446 | +++ |
| 447 | +++ |
| 448 | +++ |
| 449 | + |
| 450 | + |
| 451 | + |
| 452 | + |
| 453 | + |
| 454 | +++ |
| 455 | + |
| 456 | + |
| 457 | + |
| 458 | +++ |
| 459 | +++ |
| 460 | + |
| 461 | +++ |
| 462 | + |

TABLE 3-continued

| Compound number | Inhibitory activity |
|---|---|
| 463 | + |
| 464 | + |
| 465 | + |
| 466 | + |
| 467 | +++ |
| 468 | + |
| 469 | +++ |
| 470 | +++ |
| 471 | +++ |
| 472 | ++ |
| 473 | ++ |
| 474 | + |
| 475 | + |
| 476 | ++ |
| 477 | +++ |
| 478 | ++ |
| 479 | + |
| 480 | + |
| 481 | + |
| 482 | +++ |
| 483 | +++ |
| 484 | +++ |
| 485 | +++ |
| 486 | + |
| 487 | + |
| 488 | + |
| 489 | + |
| 490 | + |
| 491 | ++ |
| 492 | ++ |
| 493 | +++ |
| 494 | ++ |
| 495 | ++ |
| 496 | +++ |
| 497 | + |
| 498 | +++ |
| 499 | +++ |
| 500 | +++ |
| 501 | +++ |
| 502 | +++ |
| 503 | +++ |
| 504 | + |
| 505 | +++ |
| 506 | +++ |
| 507 | +++ |
| 508 | +++ |
| 509 | +++ |
| 510 | +++ |
| 511 | + |
| 512 | ++ |
| 513 | ++ |
| 514 | ++ |
| 515 | ++ |
| 516 | + |
| 517 | +++ |
| 518 | ++ |
| 519 | ++ |
| 520 | ++ |
| 521 | +++ |
| 522 | +++ |
| 523 | ++ |
| 524 | ++ |
| 525 | +++ |
| 526 | +++ |
| 527 | +++ |
| 528 | ++ |
| 529 | +++ |
| 530 | +++ |
| 531 | +++ |
| 532 | +++ |
| 533 | + |
| 534 | ++ |
| 535 | + |
| 536 | +++ |
| 537 | + |
| 538 | ++ |
| 539 | ++ |

TABLE 3-continued

| Compound number | Inhibitory activity |
|---|---|
| 540 | + |
| 541 | +++ |
| 542 | +++ |
| 543 | +++ |
| 544 | +++ |
| 545 | ++ |
| 546 | ++ |
| 547 | ++ |
| 548 | + |
| 549 | ++ |
| 550 | +++ |
| 551 | ++ |
| 552 | + |
| 553 | + |
| 554 | + |
| 555 | + |
| 556 | ++ |
| 557 | ++ |
| 558 | ++ |
| 559 | ++ |
| 560 | ++ |
| 561 | ++ |
| 562 | +++ |
| 563 | + |
| 564 | ++ |
| 565 | + |
| 566 | ++ |
| 567 | ++ |
| 568 | + |
| 569 | + |
| 570 | ++ |
| 571 | + |
| 572 | ++ |
| 573 | ++ |
| 574 | ++ |
| 575 | +++ |
| 576 | + |
| 577 | ++ |
| 578 | ++ |
| 579 | ++ |
| 580 | ++ |
| 581 | + |
| 582 | + |
| 583 | + |
| 584 | + |
| 585 | + |
| 586 | + |
| 587 | +++ |
| 588 | ++ |
| 589 | ++ |
| 590 | + |
| 591 | + |
| 592 | +++ |
| 593 | + |
| 594 | + |
| 595 | ++ |
| 596 | ++ |
| 597 | ++ |
| 598 | ++ |
| 599 | +++ |
| 600 | ++ |
| 601 | ++ |
| 602 | ++ |
| 603 | ++ |
| 604 | +++ |
| 605 | ++ |
| 606 | ++ |
| 607 | + |
| 608 | + |
| 609 | +++ |
| 610 | +++ |
| 611 | + |
| 612 | + |
| 613 | ++ |
| 614 | + |
| 615 | + |
| 616 | ++ |

TABLE 3-continued

| Compound number | Inhibitory activity |
|---|---|
| 617 | ++ |
| 618 | ++ |
| 619 | +++ |
| 620 | ++ |
| 621 | +++ |
| 622 | +++ |
| 623 | +++ |
| 624 | +++ |
| 625 | +++ |
| 626 | +++ |
| 627 | +++ |
| 628 | +++ |
| 629 | +++ |
| 630 | ++ |
| 631 | ++ |
| 632 | ++ |
| 633 | ++ |
| 634 | +++ |
| 635 | + |
| 636 | + |
| 637 | +++ |
| 638 | ++ |
| 639 | + |
| 640 | ++ |
| 641 | ++ |
| 642 | +++ |
| 643 | ++ |
| 644 | +++ |
| 645 | ++ |
| 646 | ++ |
| 647 | + |
| 648 | + |
| 649 | ++ |
| 650 | ++ |
| 651 | +++ |
| 652 | +++ |
| 653 | ++ |
| 654 | + |
| 655 | +++ |
| 656 | +++ |
| 657 | +++ |
| 658 | ++ |
| 659 | ++ |
| 660 | + |
| 661 | + |
| 662 | ++ |
| 663 | ++ |
| 664 | ++ |
| 665 | + |
| 666 | + |
| 667 | ++ |
| 668 | +++ |
| 669 | ++ |
| 670 | +++ |
| 671 | +++ |
| 672 | +++ |
| 673 | + |
| 674 | ++ |
| 675 | ++ |
| 676 | + |
| 677 | + |
| 678 | + |
| 679 | + |
| 680 | + |
| 681 | + |
| 682 | ++ |
| 683 | + |
| 684 | + |
| 685 | + |
| 686 | + |
| 687 | + |
| 688 | ++ |
| 689 | ++ |
| 690 | ++ |
| 691 | +++ |
| 692 | + |
| 693 | ++ |

TABLE 3-continued

| Compound number | Inhibitory activity |
|---|---|
| 694 | ++ |
| 695 | +++ |
| 696 | +++ |
| 697 | +++ |
| 698 | ++ |
| 699 | + |
| 700 | + |
| 701 | +++ |
| 702 | +++ |
| 703 | ++ |
| 704 | +++ |
| 705 | ++ |
| 706 | +++ |
| 707 | ++ |
| 708 | +++ |
| 709 | ++ |
| 710 | ++ |
| 711 | +++ |
| 712 | ++ |
| 713 | ++ |
| 714 | +++ |
| 715 | +++ |
| 716 | ++ |
| 717 | ++ |
| 718 | +++ |
| 719 | ++ |
| 720 | + |
| 721 | + |
| 722 | ++ |
| 723 | ++ |
| 724 | +++ |
| 725 | + |
| 726 | ++ |
| 727 | ++ |
| 728 | ++ |
| 729 | ++ |
| 730 | ++ |
| 731 | + |
| 732 | ++ |
| 733 | + |
| 734 | +++ |
| 735 | +++ |
| 736 | ++ |
| 737 | +++ |
| 738 | ++ |
| 739 | ++ |
| 740 | + |
| 741 | ++ |
| 742 | +++ |
| 743 | +++ |
| 744 | ++ |
| 745 | + |
| 746 | + |
| 747 | + |
| 748 | +++ |
| 749 | ++ |
| 750 | ++ |
| 751 | + |
| 752 | ++ |
| 753 | + |
| 754 | +++ |
| 755 | ++ |
| 756 | + |
| 757 | + |
| 758 | +++ |
| 759 | +++ |
| 760 | +++ |
| 761 | + |
| 762 | + |
| 763 | + |
| 764 | ++ |
| 765 | +++ |
| 766 | + |
| 767 | +++ |
| 768 | +++ |
| 769 | +++ |
| 770 | +++ |

TABLE 3-continued

| Compound number | Inhibitory activity |
|---|---|
| 771 | ++ |
| 772 | +++ |
| 773 | +++ |
| 774 | +++ |
| 775 | +++ |
| 776 | + |
| 777 | + |
| 778 | + |
| 779 | + |
| 780 | + |
| 781 | + |
| 782 | + |
| 783 | + |
| 784 | + |
| 785 | ++ |
| 786 | +++ |
| 787 | +++ |
| 788 | + |
| 789 | ++ |
| 790 | ++ |
| 791 | ++ |
| 792 | ++ |
| 793 | + |
| 794 | ++ |
| 795 | +++ |
| 796 | ++ |
| 797 | + |
| 798 | ++ |
| 799 | +++ |
| 800 | ++ |
| 801 | +++ |
| 802 | +++ |
| 803 | +++ |
| 804 | ++ |
| 805 | ++ |
| 806 | ++ |
| 807 | ++ |
| 808 | +++ |
| 809 | +++ |
| 810 | +++ |
| 811 | +++ |
| 812 | +++ |
| 813 | + |
| 814 | + |
| 815 | ++ |
| 816 | + |
| 817 | + |
| 818 | ++ |
| 819 | ++ |
| 820 | + |
| 821 | ++ |
| 822 | +++ |
| 823 | +++ |
| 824 | ++ |
| 825 | ++ |
| 826 | +++ |
| 827 | +++ |
| 828 | +++ |
| 829 | ++ |
| 830 | ++ |
| 831 | + |
| 832 | +++ |
| 833 | +++ |
| 834 | +++ |
| 835 | +++ |
| 836 | ++ |
| 837 | ++ |
| 838 | ++ |
| 839 | + |
| 840 | + |
| 841 | + |
| 842 | +++ |
| 843 | + |
| 844 | + |
| 845 | + |
| 846 | ++ |
| 847 | + |

TABLE 3-continued

| Compound number | Inhibitory activity |
|---|---|
| 848 | +++ |
| 849 | +++ |
| 850 | +++ |
| 851 | + |
| 852 | + |
| 853 | ++ |
| 854 | +++ |
| 855 | ++ |
| 856 | +++ |
| 857 | +++ |
| 858 | ++ |
| 859 | +++ |
| 860 | +++ |
| 861 | +++ |
| 862 | ++ |
| 863 | + |
| 864 | ++ |
| 865 | + |
| 866 | +++ |
| 867 | + |
| 868 | ++ |
| 869 | + |
| 870 | ++ |
| 871 | + |
| 872 | +++ |
| 873 | +++ |
| 874 | +++ |
| 875 | +++ |
| 876 | +++ |
| 877 | +++ |
| 878 | +++ |
| 879 | + |
| 880 | ++ |
| 881 | + |
| 882 | + |
| 883 | ++ |
| 884 | ++ |
| 885 | + |
| 886 | + |
| 887 | ++ |
| 888 | ++ |
| 889 | + |
| 890 | ++ |
| 891 | ++ |
| 892 | ++ |
| 893 | + |
| 894 | + |
| 895 | + |
| 896 | ++ |
| 897 | + |
| 898 | + |
| 899 | ++ |
| 900 | +++ |
| 901 | + |
| 902 | ++ |
| 903 | +++ |
| 904 | +++ |
| 905 | +++ |
| 906 | +++ |
| 907 | +++ |
| 908 | +++ |
| 909 | +++ |
| 910 | +++ |
| 911 | ++ |
| 912 | +++ |
| 913 | +++ |
| 914 | +++ |
| 915 | +++ |
| 916 | +++ |
| 917 | ++ |
| 918 | + |
| 919 | ++ |
| 920 | + |
| 921 | + |
| 922 | + |
| 923 | ++ |
| 924 | ++ |

TABLE 3-continued

| Compound number | Inhibitory activity |
|---|---|
| 925 | + |
| 926 | + |
| 927 | ++ |
| 928 | ++ |
| 929 | + |
| 930 | ++ |
| 931 | ++ |
| 932 | +++ |
| 933 | + |
| 934 | ++ |
| 935 | +++ |
| 936 | ++ |
| 937 | +++ |
| 938 | ++ |
| 939 | ++ |
| 940 | + |
| 941 | + |
| 942 | + |
| 943 | + |
| 944 | ++ |
| 945 | +++ |
| 946 | ++ |
| 947 | + |
| 948 | +++ |
| 949 | +++ |
| 950 | +++ |
| 951 | +++ |
| 952 | +++ |
| 953 | +++ |
| 954 | ++ |
| 955 | +++ |
| 956 | ++ |
| 957 | +++ |
| 958 | +++ |
| 959 | ++ |
| 960 | ++ |
| 961 | + |
| 962 | ++ |
| 963 | +++ |
| 964 | ++ |
| 965 | ++ |
| 966 | +++ |
| 967 | ++ |
| 968 | +++ |
| 969 | +++ |
| 970 | + |
| 971 | + |
| 972 | +++ |
| 973 | ++ |
| 974 | ++ |
| 975 | +++ |
| 976 | ++ |
| 977 | +++ |
| 978 | +++ |
| 979 | +++ |
| 980 | +++ |
| 981 | ++ |
| 982 | ++ |
| 983 | +++ |
| 984 | ++ |
| 985 | +++ |
| 986 | ++ |
| 987 | +++ |
| 988 | +++ |
| 989 | +++ |
| 990 | +++ |
| 991 | +++ |
| 992 | +++ |
| 993 | ++ |
| 994 | ++ |
| 995 | ++ |
| 996 | +++ |
| 997 | ++ |
| 998 | ++ |
| 999 | ++ |
| 1000 | +++ |
| 1001 | +++ |

TABLE 3-continued

| Compound number | Inhibitory activity |
|---|---|
| 1002 | + |
| 1003 | ++ |
| 1004 | ++ |
| 1005 | + |
| 1006 | ++ |
| 1007 | ++ |
| 1008 | ++ |
| 1009 | ++ |
| 1010 | +++ |
| 1011 | +++ |
| 1012 | +++ |
| 1013 | +++ |
| 1014 | +++ |
| 1015 | ++ |
| 1016 | ++ |
| 1017 | +++ |
| 1018 | +++ |
| 1019 | ++ |
| 1020 | ++ |
| 1021 | ++ |
| 1022 | + |
| 1023 | ++ |
| 1024 | ++ |
| 1025 | +++ |
| 1026 | +++ |
| 1027 | +++ |
| 1028 | +++ |
| 1029 | +++ |
| 1030 | +++ |
| 1031 | +++ |
| 1032 | +++ |
| 1033 | +++ |
| 1034 | ++ |
| 1035 | +++ |
| 1036 | + |
| 1037 | +++ |
| 1038 | ++ |
| 1039 | ++ |
| 1040 | ++ |
| 1041 | ++ |
| 1042 | +++ |
| 1043 | +++ |
| 1044 | +++ |
| 1045 | +++ |
| 1046 | +++ |
| 1047 | +++ |
| 1048 | +++ |
| 1049 | +++ |
| 1050 | ++ |
| 1051 | +++ |
| 1052 | ++ |
| 1053 | + |
| 1054 | +++ |
| 1055 | + |
| 1056 | ++ |
| 1057 | +++ |
| 1058 | +++ |
| 1059 | +++ |
| 1060 | +++ |
| 1061 | +++ |
| 1062 | +++ |
| 1063 | +++ |
| 1064 | ++ |
| 1065 | +++ |
| 1066 | +++ |
| 1067 | + |
| 1068 | ++ |
| 1069 | + |
| 1070 | + |
| 1071 | +++ |
| 1072 | +++ |
| 1073 | +++ |
| 1074 | +++ |
| 1075 | +++ |
| 1076 | +++ |
| 1077 | +++ |
| 1078 | +++ |

TABLE 3-continued

| Compound number | Inhibitory activity |
|---|---|
| 1079 | +++ |
| 1080 | +++ |
| 1081 | ++ |
| 1082 | + |
| 1083 | ++ |
| 1084 | ++ |
| 1085 | ++ |
| 1086 | +++ |
| 1087 | +++ |
| 1088 | ++ |
| 1089 | ++ |
| 1090 | + |
| 1091 | ++ |
| 1092 | ++ |
| 1093 | + |
| 1094 | ++ |
| 1095 | + |
| 1096 | ++ |
| 1097 | +++ |
| 1098 | + |
| 1099 | + |
| 1100 | + |
| 1101 | ++ |
| 1102 | ++ |
| 1103 | ++ |
| 1104 | + |
| 1105 | ++ |
| 1106 | +++ |
| 1107 | +++ |
| 1108 | ++ |
| 1109 | ++ |
| 1110 | +++ |
| 1111 | ++ |
| 1112 | + |
| 1113 | + |
| 1114 | + |
| 1115 | + |
| 1116 | + |
| 1117 | ++ |
| 1118 | + |
| 1119 | ++ |
| 1120 | +++ |
| 1121 | + |
| 1122 | + |
| 1123 | + |
| 1124 | + |
| 1125 | + |
| 1126 | + |
| 1127 | + |
| 1128 | + |
| 1129 | +++ |
| 1130 | +++ |
| 1131 | +++ |
| 1132 | ++ |
| 1133 | + |
| 1134 | + |
| 1135 | +++ |
| 1136 | + |
| 1137 | +++ |
| 1138 | ++ |
| 1139 | ++ |
| 1140 | ++ |
| 1141 | ++ |
| 1142 | ++ |
| 1143 | +++ |
| 1144 | +++ |
| 1145 | +++ |
| 1146 | ++ |
| 1147 | +++ |
| 1148 | +++ |
| 1149 | +++ |
| 1150 | +++ |
| 1151 | +++ |
| 1152 | +++ |
| 1153 | +++ |
| 1154 | +++ |
| 1155 | +++ |

TABLE 3-continued

| Compound number | Inhibitory activity |
|---|---|
| 1156 | +++ |
| 1157 | ++ |
| 1158 | + |
| 1159 | ++ |
| 1160 | + |
| 1161 | ++ |
| 1162 | ++ |
| 1163 | ++ |
| 1164 | ++ |
| 1165 | + |
| 1166 | + |
| 1167 | +++ |
| 1168 | ++ |
| 1169 | + |
| 1170 | + |
| 1171 | ++ |
| 1172 | ++ |
| 1173 | +++ |
| 1174 | ++ |
| 1175 | + |
| 1176 | ++ |
| 1177 | + |
| 1178 | + |
| 1179 | + |
| 1180 | + |
| 1181 | + |
| 1182 | + |
| 1183 | + |
| 1184 | +++ |
| 1185 | +++ |
| 1186 | +++ |
| 1187 | +++ |
| 1188 | ++ |
| 1189 | ++ |
| 1190 | ++ |
| 1191 | ++ |
| 1192 | + |
| 1193 | ++ |
| 1194 | + |
| 1195 | +++ |
| 1196 | ++ |
| 1197 | ++ |
| 1198 | ++ |
| 1199 | +++ |
| 1200 | ++ |
| 1201 | ++ |
| 1202 | +++ |
| 1203 | +++ |
| 1204 | ++ |
| 1205 | +++ |
| 1206 | +++ |
| 1207 | +++ |
| 1208 | +++ |
| 1209 | ++ |
| 1210 | +++ |
| 1211 | +++ |
| 1212 | +++ |
| 1213 | ++ |
| 1214 | +++ |
| 1215 | +++ |
| 1216 | ++ |
| 1217 | +++ |
| 1218 | +++ |
| 1219 | +++ |
| 1220 | + |
| 1221 | ++ |
| 1222 | ++ |
| 1223 | + |
| 1224 | ++ |
| 1225 | ++ |
| 1226 | ++ |
| 1227 | ++ |
| 1228 | ++ |
| 1229 | ++ |
| 1230 | + |
| 1231 | ++ |
| 1232 | + |

TABLE 3-continued

| Compound number | Inhibitory activity |
|---|---|
| 1233 | +++ |
| 1234 | +++ |
| 1235 | ++ |
| 1236 | ++ |
| 1237 | +++ |
| 1238 | + |
| 1239 | +++ |
| 1240 | +++ |
| 1241 | +++ |
| 1242 | ++ |
| 1243 | +++ |
| 1244 | +++ |
| 1245 | ++ |
| 1246 | ++ |
| 1247 | ++ |
| 1248 | ++ |
| 1249 | +++ |
| 1250 | ++ |
| 1251 | ++ |
| 1252 | ++ |
| 1253 | ++ |
| 1254 | ++ |
| 1255 | +++ |
| 1256 | ++ |
| 1257 | ++ |
| 1258 | +++ |
| 1259 | +++ |
| 1260 | ++ |
| 1261 | + |
| 1262 | + |
| 1263 | + |
| 1264 | ++ |
| 1265 | ++ |
| 1266 | ++ |
| 1267 | + |
| 1268 | ++ |
| 1269 | + |
| 1270 | ++ |
| 1271 | + |
| 1272 | ++ |
| 1273 | ++ |
| 1274 | ++ |
| 1275 | + |
| 1276 | + |
| 1277 | ++ |
| 1278 | ++ |
| 1279 | +++ |
| 1280 | +++ |
| 1281 | ++ |
| 1282 | ++ |
| 1283 | + |
| 1284 | ++ |
| 1285 | + |
| 1286 | + |
| 1287 | + |
| 1288 | + |
| 1289 | + |
| 1290 | ++ |
| 1291 | + |
| 1292 | ++ |
| 1293 | ++ |
| 1294 | + |
| 1295 | +++ |
| 1296 | +++ |
| 1297 | ++ |
| 1298 | ++ |
| 1299 | +++ |
| 1300 | +++ |
| 1301 | +++ |
| 1302 | +++ |
| 1303 | + |
| 1304 | +++ |
| 1305 | ++ |
| 1306 | +++ |
| 1307 | + |
| 1308 | ++ |
| 1309 | ++ |

TABLE 3-continued

| Compound number | Inhibitory activity |
|---|---|
| 1310 | ++ |
| 1311 | ++ |
| 1312 | +++ |
| 1313 | ++ |
| 1314 | ++ |
| 1315 | ++ |
| 1316 | +++ |
| 1317 | +++ |
| 1318 | ++ |
| 1319 | ++ |
| 1320 | ++ |
| 1321 | ++ |
| 1322 | +++ |
| 1323 | +++ |
| 1324 | +++ |
| 1325 | +++ |
| 1326 | ++ |
| 1327 | ++ |
| 1328 | ++ |
| 1329 | + |
| 1330 | +++ |
| 1331 | + |
| 1332 | + |
| 1333 | ++ |
| 1334 | +++ |
| 1335 | +++ |
| 1336 | ++ |
| 1337 | +++ |
| 1338 | +++ |
| 1339 | +++ |
| 1340 | +++ |
| 1341 | ++ |
| 1342 | ++ |
| 1343 | ++ |
| 1344 | + |
| 1345 | ++ |
| 1346 | +++ |
| 1347 | ++ |
| 1348 | +++ |
| 1349 | ++ |
| 1350 | +++ |
| 1351 | + |
| 1352 | ++ |
| 1353 | ++ |
| 1354 | +++ |
| 1355 | ++ |
| 1356 | ++ |
| 1357 | +++ |
| 1358 | ++ |
| 1359 | ++ |
| 1360 | +++ |
| 1361 | +++ |
| 1362 | ++ |
| 1363 | + |
| 1364 | + |
| 1365 | + |
| 1366 | +++ |
| 1367 | +++ |
| 1368 | +++ |
| 1369 | +++ |
| 1370 | ++ |
| 1371 | +++ |
| 1372 | + |
| 1373 | +++ |
| 1374 | ++ |
| 1375 | ++ |
| 1376 | ++ |
| 1377 | ++ |
| 1378 | ++ |
| 1379 | + |
| 1380 | +++ |
| 1381 | + |
| 1382 | ++ |
| 1383 | ++ |
| 1384 | ++ |
| 1385 | ++ |
| 1386 | ++ |
| 1387 | +++ |
| 1388 | ++ |
| 1389 | ++ |
| 1390 | ++ |
| 1391 | ++ |
| 1392 | + |
| 1393 | ++ |
| 1394 | ++ |
| 1395 | +++ |
| 1396 | ++ |
| 1397 | ++ |
| 1398 | +++ |
| 1399 | + |
| 1400 | ++ |
| 1401 | ++ |
| 1402 | ++ |
| 1403 | ++ |
| 1404 | +++ |
| 1405 | + |

INDUSTRIAL APPLICABILITY

The compound of the present invention is used as a pharmaceutical product.

The invention claimed is:

1. A compound represented by the formula (I) or a pharmaceutically acceptable salt thereof:

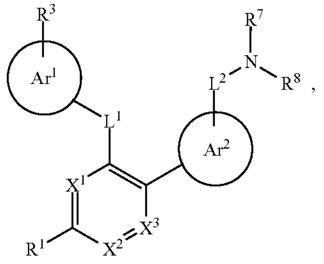

(I)

wherein, $X^1$, $X^2$, and $X^3$ are independently CH, N, or CY;

At least one of $X^1$, $X^2$, and $X^3$ is CH or CY;

Y is a halogen atom, or a $C_{1-3}$ alkyl group optionally substituted with 1 to 3 halogen atoms;

$R^1$ is a cyano group, a fluorine atom, or a chlorine atom;

$L^1$ is —O—, —S—, —SO—, —CH($R^{11}$)—, —C(=$CH_2$)—, —CO—, 1,1-cyclopropylidene group, or —$NR^{12}$—;

$R^{11}$ is a hydrogen atom, a hydroxy group, a $C_{1-3}$ alkyl group optionally substituted with 1 to 3 halogen atoms, or a $C_{1-3}$ alkoxy group optionally substituted with 1 to 2 cyano groups;

$R^{12}$ is a hydrogen atom, or a $C_{1-3}$ alkyl group optionally substituted with 1 to 3 halogen atoms;

$Ar^1$ is a nitrogen-containing heteroaryl ring optionally substituted with 1 to 3 $R^2$ selected from:

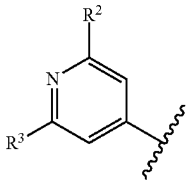
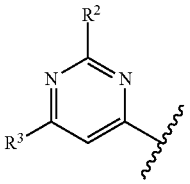
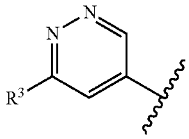
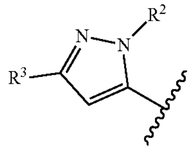
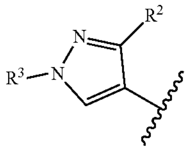
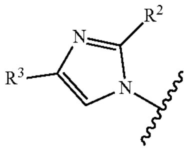
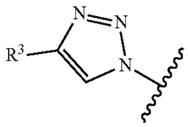
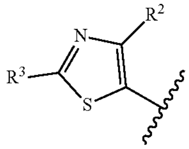
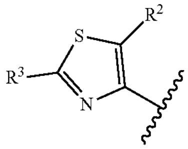
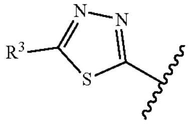
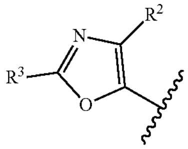
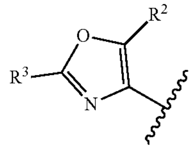
or
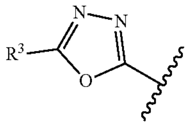
;

$R^2$ is independently a halogen atom, a cyano group, or a $C_{1-4}$ alkyl group optionally substituted with 1 to 3 halogen atoms;

$R^3$ is a hydrogen atom, a halogen atom, an amino group, a cyano group, a carboxy group, a ($C_{1-3}$ alkylcarbonyl) amino group, a ($C_{1-6}$ alkylamino) carbonyl group, a di($C_{1-3}$ alkyl)aminocarbonyl group, a ($C_{1-3}$ alkoxy) carbonyl group, a ($C_{3-8}$ cycloalkyl)amino group, a ($C_{3-8}$ heterocycloalkyl)amino group, a $C_{3-8}$ cycloalkyl group, a 3- to 8-membered heterocycloalkyloxy group, a $C_{3-8}$ cycloalkyloxy group optionally substituted with 1 to 6 $R^{31}$, a $C_{1-6}$ alkyl group optionally substituted with 1 to 6 $R^{31}$, a $C_{1-6}$ alkoxy group optionally substituted with 1 to 6 $R^{31}$, a di($C_{1-6}$ alkyl)amino group optionally substituted with 1 to 6 $R^{31}$, a ($C_{1-6}$ alkyl)amino group optionally substituted with 1 to 6 $R^{31}$, a 3- to 8-membered heterocycloalkyl group optionally substituted with 1 to 4 $R^{32}$, an aryl group optionally substituted with 1 to 4 $R^{32}$, or a heteroaryl group optionally substituted with 1 to 4 $R^{32}$;

$R^{31}$ is independently a halogen atom, a hydroxy group, a cyclopropylidene group, a $C_{3-8}$ cycloalkyl group optionally substituted with 1 to 3 halogen atoms, a 3- to 8-membered heterocycloalkyl group, an oxetanylidene group, a $C_{1-4}$ alkoxy group, or a 3- to 8-membered cycloalkyloxy group;

$R^{32}$ is independently a halogen atom, a hydroxy group, an acetylamino group, a $C_{1-3}$ alkyl group optionally substituted with 1 to 3 halogen atoms, a $C_{1-3}$ alkoxy group optionally substituted with 1 to 3 halogen atoms, an oxo group, a cyano group, a carboxy group, a ($C_{1-3}$ alkoxy) carbonyl group, a ($C_{1-3}$ alkyl) sulfonyl group, a carboxamide group, or a benzyloxy group;

$Ar^2$ is an aryl ring optionally substituted with 1 to 4 $R^4$, or a heteroaryl ring optionally substituted with 1 to 4 $R^4$;

$R^4$ is independently a halogen atom, a hydroxy group, a carboxy group, a cyano group, a cyanomethyl group, an amino group, a di($C_{1-3}$ alkyl)amino group, a $C_{1-3}$ alkyl group optionally substituted with 1 to 3 halogen atoms, or $C_{1-3}$ alkoxy group;

$L^2$ is a single bond, a $C_{1-6}$ alkylene group optionally substituted with 1 to 3 $R^{21}$, a $C_{3-8}$ cycloalkylene group optionally substituted with 1 to 3 $R^{21}$, or a 4- to 8-membered heterocycloalkylene group optionally substituted with 1 to 3 $R^{21}$;

$L^2$ may be bonded at any position to $Ar^2$ or —$NR^7R^8$ which is located at either end thereof;

One $sp^3$ carbon atom at any position of $L^2$ may be replaced by a structure of —O— or —$NR^{22}$—;

$R^{21}$ is independently a halogen atom, a hydroxy group, an oxo group, a cyano group, a 1,1-cyclopropylidene group, an oxetanylidene group, a carboxy group, a carboxamide group, a $C_{1-6}$ alkyl group optionally substituted with 1 to 3 halogen atoms, a $C_{3-8}$ cycloalkyl group, a $C_{1-6}$ alkoxy group, a ($C_{1-3}$ alkoxy) $C_{1-3}$ alkyl group, a ($C_{1-3}$ alkoxy) $C_{1-3}$ alkoxy group, a (hydroxy) $C_{1-6}$ alkyl group, a (carboxy) $C_{1-3}$ alkyl group, a (carboxy) $C_{1-3}$ alkoxy group, a ($C_{1-3}$ alkoxy) carbonyl group, a ($C_{1-3}$ alkoxycarbonyl) $C_{1-3}$ alkyl group, a ($C_{1-6}$ alkylamino) carbonyl group, a di($C_{1-3}$ alkyl)aminocarbonyl group, a phenyl group optionally substituted with 1 to 3 halogen atoms, a heteroaryl group optionally substituted with 1 to 3 halogen atoms, or a phenoxy group optionally substituted with 1 to 3 halogen atoms;

$R^{22}$ is a hydrogen atom or a $C_{1-3}$ alkyl group;

$L^2$ and $R^7$ may be bonded via a single bond, —O—, —S(=O)$_n$—, or —$NR^{23}$—, to form a 4- to 8-membered ring containing a nitrogen atom to which $L^2$ and $R^7$ are bonded, and the ring is optionally substituted with 1 to 3 halogen atoms or 1 to 2 hydroxy groups;

n represents an integer from 0 to 2;

$R^{23}$ is a hydrogen atom or a $C_{1-3}$ alkyl group;

when $L^2$ and $R^4$ are bonded to atoms adjacent to each other on $Ar^2$, they may be bonded via a single-bond or —O— to form a 5- to 8-membered ring together with the atoms of $Ar^2$ to which they are bonded;

$R^7$ is a hydrogen atom, or $C_{1-3}$ alkyl group;

$R^7$ and an atom of $Ar^2$ may be bonded via a single bond to form a 5- to 8-membered ring;

$R^8$ is a hydrogen atom, a $C_{1-6}$ alkyl group, an adamantyl group, a $C_{3-6}$ cycloalkyl group, a cyanomethyl group, an oxetanyl group, a ($C_{1-3}$ alkylamino) carbonylmethyl group, a di($C_{1-3}$ alkyl)aminocarbonylmethyl group, a ($C_{1-3}$ alkylamino) $C_{1-8}$ alkyl group, a di($C_{1-3}$ alkyl) amino$C_{1-8}$ alkyl group, a (hydroxy) $C_{1-8}$ alkyl group, a (carboxy) $C_{1-3}$ alkyl group, a ($C_{1-3}$ alkoxycarbonyl) $C_{1-3}$ alkyl group, or a ($C_{1-3}$ alkoxy) $C_{1-3}$ alkyl group;

$R^7$ and $R^8$ may be bonded each other via a single bond, —O—, —S(—O)$_m$—, or —$NR^{41}$— to form a 3- to 8-membered ring, and further, the ring is optionally substituted with an amino group, an oxo group, or a $C_{1-3}$ alkyl group;

m represents an integer from 0 to 2;

$R^{41}$ is a hydrogen atom or a $C_{1-3}$ alkyl group.

2. The compound according to claim 1 or a pharmaceutically acceptable salt thereof, wherein $X^1$, $X^2$, and $X^3$ are CH.

3. The compound according to claim 1 or a pharmaceutically acceptable salt thereof, wherein $R^1$ is a cyano group.

4. The compound according to claim 1 or a pharmaceutically acceptable salt thereof, wherein $R^1$ is a fluorine atom.

5. The compound according to claim 1 or a pharmaceutically acceptable salt thereof, wherein $L^1$ is —O—.

6. The compound according to claim 1 or a pharmaceutically acceptable salt thereof, wherein $L^1$ is —CO—.

7. The compound according to claim 1 or a pharmaceutically acceptable salt thereof, wherein $L^1$ is —$CH_2$—.

8. The compound according to claim 1 or a pharmaceutically acceptable salt thereof, wherein $R^2$ is a methyl group.

9. The compound according to claim 1 or a pharmaceutically acceptable salt thereof, wherein $R^3$ is a $C_{3-8}$ cycloalkyl group, a 3- to 8-membered heterocycloalkyloxy group, a $C_{3-8}$ cycloalkyloxy group optionally substituted with 1 to 6 $R^{31}$, a $C_{1-6}$ alkyl group optionally substituted with 1 to 6 $R^{31}$, a $C_{1-6}$ alkoxy group optionally substituted with 1 to 6 $R^{31}$, a di($C_{1-6}$ alkyl)amino group optionally substituted with 1 to 6 $R^{31}$, a ($C_{1-6}$ alkyl)amino group optionally substituted with 1 to 6 $R^{31}$, a 3- to 8-membered heterocycloalkyl group optionally substituted with 1 to 4 $R^{32}$, an aryl group optionally substituted with 1 to 4 $R^{32}$, or a heteroaryl group optionally substituted with 1 to 4 $R^{32}$.

10. The compound according to claim 1 or a pharmaceutically acceptable salt thereof, wherein $R^{31}$ is a halogen atom, a cyclopropylidene group, or a $C_{1-4}$ alkoxy group.

11. The compound according to claim 1 or a pharmaceutically acceptable salt thereof, wherein $R^{32}$ is a halogen atom, a $C_{1-3}$ alkyl group optionally substituted with 1 to 3 halogen atoms, a $C_{1-3}$ alkoxy group optionally substituted with 1 to 3 halogen atoms, an oxo group or a cyano group.

12. The compound according to claim 1 or a pharmaceutically acceptable salt thereof, wherein the heteroaryl ring of $Ar^2$ is

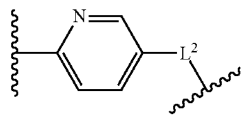

or

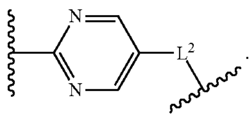

.

13. The compound according to claim 1 or a pharmaceutically acceptable salt thereof, wherein $L^2$ is a $C_{1-3}$ alkylene group optionally substituted with 1 to 2 $R^{21}$.

14. The compound according to claim 1 or a pharmaceutically acceptable salt thereof, wherein $L^2$ is —$CH_2$—.

15. The compound according to claim 1 or a pharmaceutically acceptable salt thereof, wherein $L^2$ is —$CH_2CH_2$—.

16. The compound according to claim 1 or a pharmaceutically acceptable salt thereof, wherein $R^7$ is a hydrogen atom.

17. The compound according to claim 1 or a pharmaceutically acceptable salt thereof, wherein $R^8$ is a hydrogen atom.

18. The compound according to claim 1 or a pharmaceutically acceptable salt thereof, wherein the compound represented by the formula (I) is selected from:

(1) 4-[5-(2-aminoethyl)pyridin-2-yl]-3-(2-methyl-6-morpholin-4-ylpyridin-4-yl)oxybenzonitrile;

(2) 4-[5-(2-aminoethyl)pyridin-2-yl]-3-(2-methyl-5-phenylpyrazol-3-yl)oxybenzonitrile;

(3) 4-[5-(2-aminoethyl)pyridin-2-yl]-3-(2-methyl-5-pyridin-2-ylpyrazol-3-yl)oxybenzonitrile;

(4) 4-[5-(2-aminoethyl)pyridin-2-yl]-3-[2-methyl-5-(5-methylpyridin-2-yl) pyrazol-3-yl]oxybenzonitrile;

(5) 4-[5-(2-aminoethyl)pyridin-2-yl]-3-[5-(4-fluorophenyl)-2-methylpyrazol-3-yl]oxybenzonitrile;

(6) 4-[5-(2-aminoethyl)pyridin-2-yl]-3-[5-(3-fluorophenyl)-2-methylpyrazol-3-yl]oxybenzonitrile;

(7) 4-[5-(2-aminoethyl)pyridin-2-yl]-3-(5-cyclopropyl-2-methylpyrazol-3-yl)oxybenzonitrile;

(8) 4-[5-(2-aminoethyl)pyridin-2-yl]-3-[2-methyl-5-(2-methylpropyl) pyrazol-3-yl]oxybenzonitrile;

(9) 4-[5-(2-aminoethyl)pyridin-2-yl]-3-(2-methyl-5-propan-2-ylpyrazol-3-yl)oxybenzonitrile;

(10) 4-[5-(2-aminoethyl)pyridin-2-yl]-3-(2-methyl-5-propylpyrazol-3-yl)oxybenzonitrile;

(11) 4-[5-(2-aminoethyl)pyridin-2-yl]-3-(5-cyclobutyl-2-methylpyrazol-3-yl)oxybenzonitrile;

(12) 4-[5-(2-aminoethyl)pyrimidin-2-yl]-3-(2-methyl-6-morpholin-4-ylpyridin-4-yl)oxybenzonitrile;

(13) 4-[5-(2-aminoethyl)pyridin-2-yl]-3-(2-methyl-6-pyrrolidin-1-ylpyridin-4-yl)oxybenzonitrile;

(14) 4-[5-(2-aminoethyl)pyridin-2-yl]-3-(2-methyl-6-pyridin-2-ylpyridin-4-yl)oxybenzonitrile;

(15) 4-[5-(2-aminoethyl)pyrimidin-2-yl]-3-(2-methyl-5-propylpyrazol-3-yl)oxybenzonitrile;

(16) 4-[5-(2-aminoethyl)pyrimidin-2-yl]-3-(2-methyl-5-propan-2-ylpyrazol-3-yl)oxybenzonitrile;

(17) 4-[5-(2-aminoethyl)pyrimidin-2-yl]-3-(2-methyl-6-pyrrolidin-1-ylpyridin-4-yl)oxybenzonitrile;

(18) 4-[5-(2-aminoethyl)pyridin-2-yl]-3-[2-methyl-5-(trifluoromethyl) pyrazol-3-yl]oxybenzonitrile;

(19) 4-[5-(2-aminoethyl)pyrimidin-2-yl]-3-(5-cyclobutyl-2-methylpyrazol-3-yl)oxybenzonitrile;

(20) 4-[5-(2-aminoethyl)pyrimidin-2-yl]-3-(2-methyl-5-phenylpyrazol-3-yl)oxybenzonitrile;

(21) 4-[5-(2-aminoethyl)pyrimidin-2-yl]-3-(2-methyl-6-phenylpyrimidin-4-yl)oxybenzonitrile;

(22) 4-[5-(2-aminoethyl)pyrimidin-2-yl]-3-(6-phenylpyridazin-4-yl)oxybenzonitrile;

(23) 4-[5-(2-aminoethyl)pyrimidin-2-yl]-3-(2-methyl-5-pyridin-2-ylpyrazol-3-yl)oxybenzonitrile;

(24) 4-[5-(2-aminoethyl)pyridin-2-yl]-3-(5-ethyl-2-methylpyrazol-3-yl)oxybenzonitrile;

(25) 4-[5-(aminomethyl)pyridin-2-yl]-3-(2-methyl-5-phenylpyrazol-3-yl)oxybenzonitrile;

(26) 4-[5-(2-aminoethyl)pyrimidin-2-yl]-3-(5-ethyl-2-methylpyrazol-3-yl)oxybenzonitrile;

(27) 4-[5-(2-aminoethyl)pyrimidin-2-yl]-3-[6-(2-cyanophenyl)-2-methylpyrimidin-4-yl]oxybenzonitrile;

(28) 4-[5-(2-aminoethyl)pyridin-2-yl]-3-(2,5-dimethylpyrazol-3-yl)oxybenzonitrile;

(29) 4-[5-(aminomethyl)pyrimidin-2-yl]-3-(2-methyl-5-phenylpyrazol-3-yl)oxybenzonitrile;

(30) 4-[5-(2-aminoethyl)pyrimidin-2-yl]-3-(5-cyclopropyl-2-methylpyrazol-3-yl)oxybenzonitrile;

(31) 4-[5-(2-aminoethyl)pyrimidin-2-yl]-3-(5-butyl-2-methylpyrazol-3-yl)oxybenzonitrile;

(32) 4-[5-(aminomethyl)pyrimidin-2-yl]-3-(5-ethyl-2-methylpyrazol-3-yl)oxybenzonitrile;

(33) 4-[5-(aminomethyl)pyrimidin-2-yl]-3-(5-cyclopropyl-2-methylpyrazol-3-yl)oxybenzonitrile;

(34) 4-[5-(aminomethyl)pyridin-2-yl]-3-(5-ethyl-2-methylpyrazol-3-yl)oxybenzonitrile;

(35) 4-[5-(aminomethyl)pyridin-2-yl]-3-(5-cyclopropyl-2-methylpyrazol-3-yl)oxybenzonitrile;

(36) 4-[5-(aminomethyl)pyrimidin-2-yl]-3-(2-methyl-6-morpholin-4-ylpyridin-4-yl)oxybenzonitrile;

(37) 4-[5-(aminomethyl)pyridin-2-yl]-3-(2-methyl-6-morpholin-4-ylpyridin-4-yl)oxybenzonitrile;

(38) 4-[5-(aminomethyl)pyridin-2-yl]-3-(2-methyl-5-propylpyrazol-3-yl)oxybenzonitrile;

(39) 4-[5-(aminomethyl)pyridin-2-yl]-3-(2-methyl-5-propan-2-ylpyrazol-3-yl)oxybenzonitrile;

(40) 4-[5-(aminomethyl)pyrimidin-2-yl]-3-(2-methyl-5-propylpyrazol-3-yl)oxybenzonitrile;

(41) 4-[5-(aminomethyl)pyrimidin-2-yl]-3-(2-methyl-5-propan-2-ylpyrazol-3-yl)oxybenzonitrile;

(42) 4-[5-(2-aminoethyl)pyrimidin-2-yl]-3-(5-tert-butyl-2-methylpyrazol-3-yl)oxybenzonitrile;

(43) 4-[5-(2-aminoethyl)pyrimidin-2-yl]-3-(2-methyl-6-pyridin-2-ylpyridin-4-yl)oxybenzonitrile;

(44) 4-[5-(2-aminoethyl)pyridin-2-yl]-3-[2-methyl-5-(1,3-thiazol-2-yl) pyrazol-3-yl]oxybenzonitrile;

(45) 4-[5-(2-aminoethyl)pyrimidin-2-yl]-3-[2-methyl-5-(1,3-thiazol-2-yl) pyrazol-3-yl]oxybenzonitrile;

(46) 4-[5-(2-aminoethyl)pyrimidin-2-yl]-3-(5-cyclopentyl-2-methylpyrazol-3-yl)oxybenzonitrile;

(47) 4-[5-(aminomethyl)pyrimidin-2-yl]-3-(2-methyl-5-pyridin-2-ylpyrazol-3-yl)oxybenzonitrile;

(48) 4-[5-(2-aminoethyl)pyrimidin-2-yl]-3-[5-(3-fluorophenyl)-2-methylpyrazol-3-yl]oxybenzonitrile;

(49) 4-[5-(2-aminoethyl)pyrimidin-2-yl]-3-[2-[(2S)-2-(difluoromethyl) morpholin-4-yl]-6-methylpyridin-4-yl]oxybenzonitrile;

(50) 4-[5-(aminomethyl)pyridin-2-yl]-3-[2-methyl-5-(oxan-4-yl) pyrazol-3-yl]oxybenzonitrile;

(51) 4-[5-(2-aminoethyl)pyrimidin-2-yl]-3-[2-[(2R)-2-(difluoromethyl) morpholin-4-yl]-6-methylpyridin-4-yl]oxybenzonitrile;

(52) 4-[5-(2-aminoethyl)pyrimidin-2-yl]-3-[2-methyl-6-(3-oxa-8-azabicyclo[3.2.1]octan-8-yl)pyridin-4-yl] oxybenzonitrile;

(53) 4-[5-(2-aminoethyl)pyrimidin-2-yl]-3-(2-methyl-6-piperidin-1-ylpyrimidin-4-yl)oxybenzonitrile;

(54) 4-[5-(2-aminoethyl)pyrimidin-2-yl]-3-(2-methyl-6-pyrrolidin-1-ylpyrimidin-4-yl)oxybenzonitrile;

(55) 4-[5-(2-aminoethyl)pyrimidin-2-yl]-3-[2-methyl-6-(8-oxa-3-azabicyclo[3.2.1]octan-3-yl)pyridin-4-yl] oxybenzonitrile;

(56) 4-[5-(2-aminoethyl)pyridin-2-yl]-3-[2-[2-methoxyethyl(methyl)amino]-6-methylpyridin-4-yl]oxybenzonitrile;

(57) 4-[5-(2-aminoethyl)pyrimidin-2-yl]-3-[2-methyl-6-(propan-2-ylamino)pyridin-4-yl]oxybenzonitrile;

(58) 4-[5-(2-aminoethyl)pyrimidin-2-yl]-3-[2-methyl-6-[(3R)-3-methylmorpholin-4-yl]pyridin-4-yl]oxybenzonitrile;

(59) 4-[5-(2-aminoethyl)pyrimidin-2-yl]-3-[2-methyl-6-[(3S)-3-methylmorpholin-4-yl]pyridin-4-yl]oxybenzonitrile;

(60) 4-[5-(2-aminoethyl)pyridin-2-yl]-3-(2-methyl-5-piperidin-1-ylpyrazol-3-yl)oxybenzonitrile;

(61) 4-[5-(2-aminoethyl)pyridin-2-yl]-3-(2-methyl-5-pyrrolidin-1-ylpyrazol-3-yl)oxybenzonitrile;

(62) 4-[5-(2-aminoethyl)pyridin-2-yl]-3-[5-(dimethylamino)-2-methylpyrazol-3-yl]oxybenzonitrile;

(63) 4-[5-(aminomethyl)pyrimidin-2-yl]-3-[2-methyl-5-(1,3-thiazol-2-yl) pyrazol-3-yl]oxybenzonitrile;

(64) 4-[5-(2-aminoethyl)pyrimidin-2-yl]-3-(2-methyl-6-pyridin-2-ylpyrimidin-4-yl)oxybenzonitrile;

(65) 4-[5-(aminomethyl)pyridin-2-yl]-3-(2-methyl-5-pyridin-2-ylpyrazol-3-yl)oxybenzonitrile;

(66) 4-[5-(aminomethyl)pyridin-2-yl]-3-(2-methyl-5-piperidin-1-ylpyrazol-3-yl)oxybenzonitrile;

(67) 4-[5-(aminomethyl)pyridin-2-yl]-3-(2-methyl-5-pyrrolidin-1-ylpyrazol-3-yl)oxybenzonitrile;

(68) 4-[5-(aminomethyl)pyridin-2-yl]-3-[5-(dimethylamino)-2-methylpyrazol-3-yl]oxybenzonitrile;

(69) 4-[5-(aminomethyl)pyrimidin-2-yl]-3-[2-methyl-5-(4-methylpyridin-2-yl) pyrazol-3-yl]oxybenzonitrile;

(70) 4-[5-(aminomethyl)pyrimidin-2-yl]-3-[5-(diethylamino)-2-methylpyrazol-3-yl]oxybenzonitrile;

(71) 4-[5-(2-aminoethyl)pyrimidin-2-yl]-3-[5-(diethylamino)-2-methylpyrazol-3-yl]oxybenzonitrile;

(72) 4-[5-(aminomethyl)pyridin-2-yl]-3-(2-methyl-6-pyrrolidin-1-ylpyrimidin-4-yl)oxybenzonitrile;

(73) 4-[5-(aminoethyl)pyrimidin-2-yl]-3-[2-methyl-6-pyrrolidin-1-ylpyrimidin-4-yl]oxybenzonitrile;

(74) 4-[5-(2-aminoethyl)pyrimidin-2-yl]-3-[6-(7-azabicyclo[2.2.1]heptan-7-yl)-2-methylpyrimidin-4-yl]oxybenzonitrile;

(75) 4-[5-(aminomethyl)pyrimidin-2-yl]-3-[6-(7-azabicyclo[2.2.1]heptan-7-yl)-2-methylpyrimidin-4-yl]oxybenzonitrile;

(76) 4-[5-(aminomethyl)pyridin-2-yl]-3-(6-piperidin-1-ylpyridazin-4-yl)oxybenzonitrile;

(77) 4-[5-(2-aminoethyl)pyrimidin-2-yl]-3-[(5-phenyl-1,3,4-thiadiazol-2-yl)oxy]benzonitrile;

(78) 4-[5-(2-aminoethyl)pyridin-2-yl]-3-[5-(diethylamino)-2-methylpyrazol-3-yl]oxybenzonitrile;

(79) 4-[5-(2-aminoethyl)pyrimidin-2-yl]-3-[2-methyl-5-[methyl (2-methylpropyl)amino]pyrazol-3-yl]oxybenzonitrile;

(80) 4-[5-(2-aminoethyl)pyrimidin-2-yl]-3-[5-[cyclopropylmethyl(methyl)amino]-2-methylpyrazol-3-yl]oxybenzonitrile;

(81) 4-[5-(2-aminoethyl)pyrimidin-2-yl]-3-[2-methyl-5-[methyl(propyl)amino]pyrazol-3-yl]oxybenzonitrile;

(82) 4-[5-(aminomethyl)pyridin-2-yl]-3-(2-methyl-5-morpholin-4-ylpyrazol-3-yl)oxybenzonitrile;

(83) 4-[5-(2-aminoethyl)pyrimidin-2-yl]-3-[2-methyl-5-[methyl(propan-2-yl)amino]pyrazol-3-yl]oxybenzonitrile;

(84) 4-[5-(2-aminoethyl)pyrimidin-2-yl]-3-[5-[2,2-difluoroethyl(methyl)amino]-2-methylpyrazol-3-yl]oxybenzonitrile;

(85) 4-[5-(2-aminoethyl)pyrimidin-2-yl]-3-[2-methyl-5-[methyl (2,2,2-trifluoroethyl)amino]pyrazol-3-yl]oxybenzonitrile;

(86) 4-[5-(aminomethyl)pyrimidin-2-yl]-3-[2-methyl-6-[(2S)-2-methylpyrrolidin-1-yl]pyrimidin-4-yl]oxybenzonitrile;

(87) 4-[5-(2-aminoethyl)pyrimidin-2-yl]-3-[3-methyl-1-(2-methylpropyl) pyrazol-4-yl]oxybenzonitrile;

(88) 4-[5-(aminomethyl)pyrimidin-2-yl]-3-[3-methyl-1-(2-methylpropyl) pyrazol-4-yl]oxybenzonitrile;

(89) 4-[5-(aminomethyl)pyridin-2-yl]-3-[2-methyl-5-(trifluoromethyl) pyrazol-3-yl]oxybenzonitrile;

(90) 4-[5-(aminomethyl)pyrimidin-2-yl]-3-[2-methyl-5-(trifluoromethyl) pyrazol-3-yl]oxybenzonitrile;

(91) 4-[5-(2-aminoethyl)pyrimidin-2-yl]-3-[2-methyl-5-(trifluoromethyl) pyrazol-3-yl]oxybenzonitrile;

(92) 4-[5-(aminomethyl)pyrimidin-2-yl]-3-[2-(7-azabicyclo[2.2.1]heptan-7-yl)-6-methylpyridin-4-yl]oxybenzonitrile;

(93) 4-[5-(2-aminoethyl)pyrimidin-2-yl]-3-[2-(7-azabicyclo[2.2.1]heptan-7-yl)-6-methylpyridin-4-yl]oxybenzonitrile;

(94) 4-[5-(2-aminoethyl)pyrimidin-2-yl]-3-(3-methyl-1-pyridin-2-ylpyrazol-4-yl)oxybenzonitrile;

(95) 4-[5-(aminomethyl)pyrimidin-2-yl]-3-(3-methyl-1-pyridin-2-ylpyrazol-4-yl)oxybenzonitrile;

(96) 4-[5-(aminomethyl)pyrimidin-2-yl]-3-[3-methyl-1-(2,2,2-trifluoroethyl) pyrazol-4-yl]oxybenzonitrile;

(97) 4-[5-(2-aminoethyl)pyrimidin-2-yl]-3-[5-[ethyl(propan-2-yl)amino]-2-methylpyrazol-3-yl]oxybenzonitrile;

(98) 4-[5-(2-aminoethyl)pyrimidin-2-yl]-3-[2-methyl-6-(2-methylpropoxy)pyrimidin-4-yl]oxybenzonitrile;

(99) 4-[5-(2-aminoethyl)pyrimidin-2-yl]-3-[6-(diethylamino)-2-methylpyrimidin-4-yl]oxybenzonitrile;

(100) 4-[5-(2-aminoethyl)pyrimidin-2-yl]-3-[2-methyl-6-[methyl(propan-2-yl)amino]pyrimidin-4-yl]oxybenzonitrile;

(101) 4-[5-(2-aminoethyl)pyrimidin-2-yl]-3-[2-methyl-6-[(2R)-2-methylpyrrolidin-1-yl]pyrimidin-4-yl]oxybenzonitrile;

(102) 4-[5-(2-aminoethyl)pyrimidin-2-yl]-3-[2-methyl-6-[(2S)-2-methylpyrrolidin-1-yl]pyrimidin-4-yl]oxybenzonitrile;

(103) 4-[5-(aminomethyl)pyrimidin-2-yl]-3-[2-methyl-5-(3,3,4,5-tetrafluoropyrrolidin-1-yl) pyrazol-3-yl]oxybenzonitrile;

(104) 4-[5-(aminomethyl)pyrimidin-2-yl]-3-[5-[2,2-difluoroethyl(ethyl)amino]-2-methylpyrazol-3-yl]oxybenzonitrile;

(105) 4-[5-(2-aminoethyl)pyrimidin-2-yl]-3-[5-[2,2-difluoroethyl(ethyl)amino]-2-methylpyrazol-3-yl]oxybenzonitrile;

(106) 4-[5-(2-aminoethyl)pyrimidin-2-yl]-3-[2-methyl-5-(3,3,4,4-tetrafluoropyrrolidin-1-yl) pyrazol-3-yl]oxybenzonitrile;

(107) 4-[5-(2-aminoethyl)pyrimidin-2-yl]-3-[1-(2-methylpropyl) pyrazol-4-yl]oxybenzonitrile;

(108) 4-[5-(2-aminoethyl)pyrimidin-2-yl]-3-(1-pyridin-2-ylpyrazol-4-yl)oxybenzonitrile;

(109) 4-[5-(2-aminoethyl)pyrimidin-2-yl]-3-[1-(2,2-dimethylpropyl)-3-methylpyrazol-4-yl]oxybenzonitrile;

(110) 4-[5-(aminomethyl)pyrimidin-2-yl]-3-[2-methyl-5-(1,3-thiazol-4-yl) pyrazol-3-yl]oxybenzonitrile;

(111) 4-[5-(2-aminoethyl)pyrimidin-2-yl]-3-[3-ethyl-1-(2-methylpropyl) pyrazol-4-yl]oxybenzonitrile;

(112) 4-[5-(2-aminoethyl)pyrimidin-2-yl]-3-[1-(2-methylpropyl)-3-(trifluoromethyl) pyrazol-4-yl]oxybenzonitrile;

(113) 4-[5-(aminomethyl)pyrimidin-2-yl]-3-[2-methyl-5-(4-methyl-1,3-thiazol-5-yl) pyrazol-3-yl]oxybenzonitrile;

(114) 4-[5-(aminomethyl)pyrimidin-2-yl]-3-[2-methyl-5-(5-methyl-1,3-thiazol-4-yl) pyrazol-3-yl]oxybenzonitrile;

(115) 2-[2-[4-fluoro-2-[3-methyl-1-(2-methylpropyl) pyrazol-4-yl]oxyphenyl]pyrimidin-5-yl]ethanamine;

(116) 5-[2-[5-(2-aminoethyl)pyrimidin-2-yl]-5-fluorophenoxy]-N,N-diethyl-1-methylpyrazole-3-amine;

(117) 2-[6-[4-fluoro-2-(2-methyl-5-morpholin-4-ylpyrazol-3-yl)oxyphenyl]pyridin-3-yl]ethanamine;

(118) 2-[2-[4-fluoro-2-(2-methyl-5-pyridin-2-ylpyrazol-3-yl)oxyphenyl]pyrimidin-5-yl]ethanamine;

(119) 2-[2-[4-fluoro-2-(2-methyl-5-pyrrolidin-1-ylpyrazol-3-yl)oxyphenyl]pyrimidin-5-yl]ethanamine;

(120) 2-[6-[4-fluoro-2-(2-methyl-5-pyrrolidin-1-ylpyrazol-3-yl)oxyphenyl]pyridin-3-yl]ethanamine;

(121) 5-[2-[5-(2-aminoethyl)pyrimidin-2-yl]-5-fluorophenoxy]-N-(2,2-difluoroethyl)-N,1-dimethylpyrazole-3-amine;

(122) 5-[2-[5-(2-aminoethyl)pyridin-2-yl]-5-fluorophenoxy]-N-(2,2-difluoroethyl)-N, 1-dimethylpyrazole-3-amine;

(123) 5-[2-[5-(2-aminoethyl)pyrimidin-2-yl]-5-fluorophenoxy]-N-(2,2-difluoroethyl)-N-ethyl-1-methylpyrazole-3-amine;

(124) 5-[2-[5-(2-aminoethyl)pyridin-2-yl]-5-fluorophenoxy]-N-(2,2-difluoroethyl)-N-ethyl-1-methylpyrazole-3-amine;

(125) 5-[2-[5-(2-aminoethyl)pyridin-2-yl]-5-fluorophenoxy]-N,N-diethyl-1-methylpyrazole-3-amine;

(126) 5-[2-[5-(2-aminoethyl)pyridin-2-yl]-5-fluorophenoxy]-N,N,1-trimethylpyrazole-3-amine;

(127) 2-[6-[4-fluoro-2-[2-methyl-5-(oxan-4-yl) pyrazol-3-yl]oxyphenyl]pyridin-3-yl]ethanamine;

(128) [2-[4-fluoro-2-(2-methyl-5-propan-2-ylpyrazol-3-yl)oxyphenyl]pyrimidin-5-yl]methanamine;

(129) 2-[2-[4-fluoro-2-(2-methyl-5-propan-2-ylpyrazol-3-yl)oxyphenyl]pyrimidin-5-yl]ethanamine;

(130) 2-[6-[4-fluoro-2-(2-methyl-5-propan-2-ylpyrazol-3-yl)oxyphenyl]pyridin-3-yl]ethanamine;

(131) 2-[6-[2-(5-cyclopropyl-2-methylpyrazol-3-yl)oxy-4-fluorophenyl]pyridin-3-yl]ethanamine;

(132) 4-[5-(2-aminoethyl)pyrimidin-2-yl]-3-(5-ethyl-2-methylpyrazole-3-carbonyl)benzonitrile;

(133) 4-[5-(aminomethyl)pyrimidin-2-yl]-3-(5-ethyl-2-methylpyrazole-3-carbonyl)benzonitrile;

(134) 4-[5-(2-aminoethyl)pyrimidin-2-yl]-3-(2-methyl-5-morpholin-4-ylpyrazole-3-carbonyl)benzonitrile;

(135) 4-[5-(aminomethyl)pyrimidin-2-yl]-3-(2-methyl-5-morpholin-4-ylpyrazole-3-carbonyl)benzonitrile;

(136) 4-[5-(aminomethyl)pyridin-2-yl]-3-(2-methyl-5-morpholin-4-ylpyrazole-3-carbonyl)benzonitrile;

(137) 4-[5-(aminomethyl)pyrimidin-2-yl]-3-(5-tert-butyl-2-methylpyrazole-3-carbonyl)benzonitrile;

(138) 4-[5-(2-aminoethyl)pyrimidin-2-yl]-3-(5-tert-butyl-2-methylpyrazole-3-carbonyl)benzonitrile;

(139) 4-[5-(2-aminoethyl)pyrimidin-2-yl]-3-[5-(diethylamino)-2-methylpyrazole-3-carbonyl]benzonitrile;

(140) 4-[5-(2-aminoethyl)pyrimidin-2-yl]-3-(1-pyridin-2-ylpyrazole-4-carbonyl)benzonitrile;

(141) 4-[5-(2-aminoethyl)pyrimidin-2-yl]-3-(2-methyl-6-morpholin-4-ylpyridine-4-carbonyl)benzonitrile;

(142) 4-[5-(2-aminoethyl)pyrimidin-2-yl]-3-[5-(dimethylamino)-2-methylpyrazole-3-carbonyl]benzonitrile;

(143) 4-[5-(aminomethyl)pyrimidin-2-yl]-3-[5-(dimethylamino)-2-methylpyrazole-3-carbonyl]benzonitrile;

(144) 4-[5-(aminomethyl)pyrimidin-2-yl]-3-[5-(diethylamino)-2-methylpyrazole-3-carbonyl]benzonitrile;

(145) 4-[5-(2-aminoethyl)pyrimidin-2-yl]-3-(2-methyl-5-piperidin-1-ylpyrazole-3-carbonyl)benzonitrile;

(146) 4-[5-(aminomethyl)pyrimidin-2-yl]-3-(2-methyl-5-piperidin-1-ylpyrazole-3-carbonyl)benzonitrile;

(147) 4-[5-(2-aminoethyl)pyrimidin-2-yl]-3-(2-methyl-5-pyrrolidin-1-ylpyrazole-3-carbonyl)benzonitrile;

(148) 4-[5-(aminomethyl)pyrimidin-2-yl]-3-(2-methyl-5-pyrrolidin-1-ylpyrazole-3-carbonyl)benzonitrile;

(149) 4-[5-(2-aminoethyl)pyrimidin-2-yl]-3-[5-[2,2-difluoroethyl(ethyl)amino]-2-methylpyrazole-3-carbonyl] benzonitrile; and (150) 4-[5-(aminomethyl)pyrimidin-2-yl]-3-[5-[2,2-difluoroethyl(ethyl)amino]-2-methylpyrazole-3-carbonyl]benzonitrile.

19. A pharmaceutical composition comprising the compound according to claim 1 or a pharmaceutically acceptable salt thereof.

20. A pharmaceutical composition having TRPC6 channel inhibitory activity, comprising the compound according to claim 1 or a pharmaceutically acceptable salt thereof.

21. A therapeutic or prophylactic agent for nephrotic syndrome, membranous nephropathy, acute renal failure, sepsis, chronic renal failure, diabetic nephropathy, pulmonary hypertension, acute lung injury, heart failure, malignant tumor, or muscular dystrophy, comprising the compound according to claim 1 or a pharmaceutically acceptable salt thereof.

* * * * *